US009139604B2

(12) United States Patent

Boojamra et al.

(10) Patent No.: US 9,139,604 B2
(45) Date of Patent: *Sep. 22, 2015

(54) ANTIVIRAL PHOSPHONATE ANALOGS

(71) Applicant: Gilead Sciences, Inc., Foster City, CA (US)

(72) Inventors: Constantine G. Boojamra, San Francisco, CA (US); Carina E. Cannizzaro, Foster City, CA (US); James M. Chen, San Ramon, CA (US); Xiaowu Chen, Hillsborough, CA (US); Aesop Cho, Mountain View, CA (US); Lee S. Chong, Newark, CA (US); Maria Fardis, San Carlos, CA (US); Haolun Jin, Foster City, CA (US); Ralph Hirschmann, Lansdale, PA (US); Alan X. Huang, San Mateo, CA (US); Choung U. Kim, San Carlos, CA (US); Thorsten A. Kirschberg, Redwood City, CA (US); Christopher P. Lee, San Francisco, CA (US); William A. Lee, Los Altos, CA (US); Richard L. Mackman, Millbrae, CA (US); David Y. Markevitch, San Jose, CA (US); David A. Oare, Belmont, CA (US); Vidya K. Prasad, Munich (DE); Hyung-Jung Pyun, Fremont, CA (US); Adrian S. Ray, Redwood City, CA (US); Rosemarie O'Shea, San Carlos, CA (US); Sundaramoorthi Swaminathan, Burlingame, CA (US); William J. Watkins, Saratoga, CA (US); Jennifer R. Zhang, Union City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/309,790

(22) Filed: Jun. 19, 2014

(65) Prior Publication Data

US 2015/0025039 A1 Jan. 22, 2015

Related U.S. Application Data

(60) Continuation of application No. 13/848,593, filed on Mar. 21, 2013, now Pat. No. 8,871,785, which is a continuation of application No. 13/187,293, filed on Jul. 20, 2011, now abandoned, which is a division of application No. 12/166,076, filed on Jul. 1, 2008, now Pat. No. 8,022,083, which is a division of application No. 10/832,815, filed on Apr. 26, 2004, now Pat. No. 7,429,565.

(60) Provisional application No. 60/465,630, filed on Apr. 25, 2003, provisional application No. 60/465,400, (Continued)

(51) Int. Cl.

| | |
|---|---|
| *A61K 31/44* | (2006.01) |
| *C07F 9/6561* | (2006.01) |
| *A61K 31/662* | (2006.01) |
| *A61K 31/7072* | (2006.01) |
| *A61K 31/7076* | (2006.01) |
| *A61K 47/48* | (2006.01) |
| *C07D 205/04* | (2006.01) |
| *C07D 211/58* | (2006.01) |
| *C07D 409/06* | (2006.01) |
| *C07D 409/14* | (2006.01) |
| *C07D 413/14* | (2006.01) |

(Continued)

(52) U.S. Cl.

CPC ........... *C07F 9/65616* (2013.01); *A61K 31/662* (2013.01); *A61K 31/7072* (2013.01); *A61K 31/7076* (2013.01); *A61K 47/48084* (2013.01); *C07D 205/04* (2013.01); *C07D 211/58* (2013.01); *C07D 409/06* (2013.01); *C07D 409/14* (2013.01); *C07D 413/14* (2013.01); *C07D 475/00* (2013.01); *C07F 9/4075* (2013.01); *C07F 9/5728* (2013.01); *C07F 9/582* (2013.01); *C07F 9/588* (2013.01); *C07F 9/60* (2013.01); *C07F 9/653* (2013.01); *C07F 9/65037* (2013.01); *C07F 9/6539* (2013.01); *C07F 9/6561* (2013.01); *C07F 9/65515* (2013.01); *C07F 9/650941* (2013.01); *C07F 9/655354* (2013.01); *C07H 15/00* (2013.01); *C07H 17/00* (2013.01); *C07H 19/056* (2013.01); *C07H 19/10* (2013.01); *C07H 19/20* (2013.01); *C07H 21/00* (2013.01)

(58) Field of Classification Search

USPC .......................................... 544/254; 514/300

See application file for complete search history.

(56) References Cited

U.S. PATENT DOCUMENTS

| | | | |
|---|---|---|---|
| 4,649,041 | A | 3/1987 | Peters et al. |
| 4,665,074 | A | 5/1987 | Amschler |

(Continued)

FOREIGN PATENT DOCUMENTS

| | | | |
|---|---|---|---|
| AU | 779816 | B2 | 2/2005 |
| CN | 101031306 | A | 9/2007 |

(Continued)

OTHER PUBLICATIONS

Abdel-Meguid, S.S. et al. (1993). "Inhibition of Human Immunodeficiency Virus-1 Protease by a C2-Symmetric Phosphinate. Synthesis and Crystallographic Analysis," *Biochemistry* 32(31):7972-7980.

(Continued)

*Primary Examiner* — Rei-Tsang Shiao

(74) *Attorney, Agent, or Firm* — Timothy A. Marquart

(57) ABSTRACT

The invention is related to phosphorus substituted compounds with antiviral activity, compositions containing such compounds, and therapeutic methods that include the administration of such compounds, as well as to processes and intermediates useful for preparing such compounds.

9 Claims, No Drawings

Related U.S. Application Data filed on Apr. 25, 2003, provisional application No. 60/465,587, filed on Apr. 25, 2003, provisional application No. 60/465,463, filed on Apr. 25, 2003, provisional application No. 60/465,602, filed on Apr. 25, 2003, provisional application No. 60/465,598, filed on Apr. 25, 2003, provisional application No. 60/465,633, filed on Apr. 25, 2003, provisional application No. 60/465,550, filed on Apr. 25, 2003, provisional application No. 60/465,610, filed on Apr. 25, 2003, provisional application No. 60/465,720, filed on Apr. 25, 2003, provisional application No. 60/465,634, filed on Apr. 25, 2003, provisional application No. 60/465,537, filed on Apr. 25, 2003, provisional application No. 60/465,698, filed on Apr. 25, 2003, provisional application No. 60/465,667, filed on Apr. 25, 2003, provisional application No. 60/465,554, filed on Apr. 25, 2003, provisional application No. 60/465,553, filed on Apr. 25, 2003, provisional application No. 60/465,561, filed on Apr. 25, 2003, provisional application No. 60/465,548, filed on Apr. 25, 2003, provisional application No. 60/465,696, filed on Apr. 25, 2003, provisional application No. 60/465,347, filed on Apr. 25, 2003, provisional application No. 60/465,289, filed on Apr. 25, 2003, provisional application No. 60/465,478, filed on Apr. 25, 2003, provisional application No. 60/465,600, filed on Apr. 25, 2003, provisional application No. 60/465,591, filed on Apr. 25, 2003, provisional application No. 60/465,684, filed on Apr. 25, 2003, provisional application No. 60/465,821, filed on Apr. 25, 2003, provisional application No. 60/465,647, filed on Apr. 25, 2003, provisional application No. 60/465,742, filed on Apr. 25, 2003, provisional application No. 60/465,649, filed on Apr. 25, 2003, provisional application No. 60/465,690, filed on Apr. 25, 2003, provisional application No. 60/465,469, filed on Apr. 25, 2003, provisional application No. 60/465,408, filed on Apr. 25, 2003, provisional application No. 60/465,608, filed on Apr. 25, 2003, provisional application No. 60/465,584, filed on Apr. 25, 2003, provisional application No. 60/465,687, filed on Apr. 25, 2003, provisional application No. 60/465,759, filed on Apr. 25, 2003, provisional application No. 60/465,559, filed on Apr. 25, 2003, provisional application No. 60/465,322, filed on Apr. 25, 2003, provisional application No. 60/465,377, filed on Apr. 25, 2003, provisional application No. 60/465,844, filed on Apr. 25, 2003, provisional application No. 60/465,544, filed on Apr. 25, 2003, provisional application No. 60/490,799, filed on Jul. 29, 2003, provisional application No. 60/495,687, filed on Aug. 15, 2003, provisional application No. 60/495,490, filed on Aug. 15, 2003, provisional application No. 60/495,805, filed on Aug. 15, 2003, provisional application No. 60/495,684, filed on Aug. 15, 2003, provisional application No. 60/495,600, filed on Aug. 15, 2003, provisional application No. 60/495,342, filed on Aug. 15, 2003, provisional application No. 60/495,564, filed on Aug. 15, 2003, provisional application No. 60/495,772, filed on Aug. 15, 2003, provisional application No. 60/495,592, filed on Aug. 15, 2003, provisional application No. 60/495,453, filed on Aug. 15, 2003, provisional application No. 60/495,491, filed on Aug. 15, 2003, provisional application No. 60/495,964, filed on Aug. 15, 2003, provisional application No. 60/495,317, filed on Aug. 15, 2003, provisional application No. 60/495,696, filed on Aug. 15, 2003, provisional application No. 60/495,760, filed on Aug. 15, 2003, provisional application No. 60/495,334, filed on Aug. 15, 2003, provisional application No. 60/495,671, filed on Aug. 15, 2003, provisional application No. 60/495,349, filed on Aug. 15, 2003, provisional application No. 60/495,273, filed on Aug. 15, 2003, provisional application No. 60/495,763, filed on Aug. 15, 2003, provisional application No. 60/495,345, filed on Aug. 15, 2003, provisional application No. 60/495,602, filed on Aug. 15, 2003, provisional application No. 60/495,343, filed on Aug. 15, 2003, provisional application No. 60/495,344, filed on Aug. 15, 2003, provisional application No. 60/495,278, filed on Aug. 15, 2003, provisional application No. 60/495,277, filed on Aug. 15, 2003, provisional application No. 60/495,275, filed on Aug. 15, 2003, provisional application No. 60/495,630, filed on Aug. 15, 2003, provisional application No. 60/495,485, filed on Aug. 15, 2003, provisional application No. 60/495,430, filed on Aug. 15, 2003, provisional application No. 60/495,388, filed on Aug. 15, 2003, provisional application No. 60/495,341, filed on Aug. 15, 2003, provisional application No. 60/495,631, filed on Aug. 15, 2003, provisional application No. 60/495,633, filed on Aug. 15, 2003, provisional application No. 60/495,632, filed on Aug. 15, 2003, provisional application No. 60/495,539, filed on Aug. 15, 2003, provisional application No. 60/495,387, filed on Aug. 15, 2003, provisional application No. 60/495,392, filed on Aug. 15, 2003, provisional application No. 60/495,425, filed on Aug. 15, 2003, provisional application No. 60/495,393, filed on Aug. 15, 2003, provisional application No. 60/495,616, filed on Aug. 15, 2003, provisional application No. 60/510,245, filed on Oct. 10, 2003, provisional application No. 60/514,202, filed on Oct. 24, 2003, provisional application No. 60/513,948, filed on Oct. 24, 2003, provisional application No. 60/514,258, filed on Oct. 24, 2003, provisional application No. 60/515,266, filed on Oct. 29, 2003, provisional application No. 60/519,476, filed on Nov. 12, 2003, provisional application No. 60/524,340, filed on Nov. 20, 2003, provisional application No. 60/532,591, filed on Dec. 23, 2003.

(51) Int. Cl.

| | |
|---|---|
| *C07D 475/00* | (2006.01) |
| *C07F 9/40* | (2006.01) |
| *C07F 9/572* | (2006.01) |
| *C07F 9/58* | (2006.01) |
| *C07F 9/60* | (2006.01) |
| *C07F 9/6503* | (2006.01) |
| *C07F 9/6509* | (2006.01) |
| *C07F 9/653* | (2006.01) |
| *C07F 9/6539* | (2006.01) |
| *C07F 9/655* | (2006.01) |
| *C07F 9/6553* | (2006.01) |
| *C07H 15/00* | (2006.01) |
| *C07H 17/00* | (2006.01) |
| *C07H 21/00* | (2006.01) |
| *C07H 19/056* | (2006.01) |
| *C07H 19/10* | (2006.01) |
| *C07H 19/20* | (2006.01) |

(56) References Cited

U.S. PATENT DOCUMENTS 4,816,570 A 3/1989 Farquhar
4,968,788 A 11/1990 Farquhar

(56) References Cited

U.S. PATENT DOCUMENTS

| | | | |
|---|---|---|---|
| 5,260,440 | A | 11/1993 | Hirai et al. |
| 5,378,474 | A | 1/1995 | Morella et al. |
| 5,413,996 | A | 5/1995 | Bodor |
| 5,455,339 | A | 10/1995 | Chu |
| 5,466,793 | A | 11/1995 | Honda et al. |
| 5,493,030 | A | 2/1996 | Morgans, Jr. et al. |
| 5,585,397 | A | 12/1996 | Tung et al. |
| 5,633,279 | A | 5/1997 | Morgans, Jr. et al. |
| 5,654,286 | A | 8/1997 | Hostetler |
| 5,656,745 | A | 8/1997 | Bischofberger et al. |
| 5,663,159 | A | 9/1997 | Starrett, Jr. et al. |
| 5,670,497 | A | 9/1997 | Bold et al. |
| 5,744,600 | A | 4/1998 | Mansuri et al. |
| 5,747,498 | A | 5/1998 | Schnur et al. |
| 5,750,343 | A | 5/1998 | Maag et al. |
| 5,750,493 | A | 5/1998 | Schinazi et al. |
| 5,792,756 | A | 8/1998 | Starrett, Jr. et al. |
| 5,795,909 | A | 8/1998 | Shashoua et al. |
| 5,804,559 | A | 9/1998 | Budt et al. |
| 5,811,422 | A | 9/1998 | Lam et al. |
| 5,874,577 | A | 2/1999 | Chen et al. |
| 5,914,332 | A | 6/1999 | Sham et al. |
| 5,962,684 | A | 10/1999 | Vince et al. |
| 6,018,049 | A | 1/2000 | Hajima et al. |
| 6,072,053 | A | 6/2000 | Vince et al. |
| 6,174,888 | B1 | 1/2001 | McQuire et al. |
| 6,290,994 | B1 | 9/2001 | Lazaro Flores et al. |
| 6,312,662 | B1 | 11/2001 | Erion et al. |
| 6,319,946 | B1 | 11/2001 | Hale et al. |
| 6,395,763 | B1 | 5/2002 | Stamos et al. |
| 6,555,676 | B2 | 4/2003 | Gosselin et al. |
| 6,581,606 | B2 | 6/2003 | Kutzko et al. |
| 6,602,902 | B2 | 8/2003 | Shashoua et al. |
| 6,608,027 | B1 | 8/2003 | Tsantrizos et al. |
| 6,761,903 | B2 | 7/2004 | Chen et al. |
| 6,767,900 | B2 | 7/2004 | Ubasawa et al. |
| 6,844,349 | B2 | 1/2005 | Kath et al. |
| 6,858,618 | B2 | 2/2005 | Raza et al. |
| 6,872,827 | B2 | 3/2005 | Webb et al. |
| 6,962,684 | B2 | 11/2005 | Kawazu et al. |
| 7,084,123 | B2 | 8/2006 | Fujikura et al. |
| 7,169,766 | B2 | 1/2007 | Sommadossi et al. |
| 7,273,715 | B2 | 9/2007 | McDermott |
| 7,273,716 | B2 | 9/2007 | McDermott |
| 7,273,717 | B2 | 9/2007 | McDermott |
| 7,300,924 | B2 | 11/2007 | Boojamra et al. |
| 7,319,148 | B2 | 1/2008 | Marliere et al. |
| 7,358,261 | B2 | 4/2008 | Carson et al. |
| 7,407,965 | B2 | 8/2008 | Chen et al. |
| 7,417,055 | B2 | 8/2008 | Cannizzaro et al. |
| 7,427,624 | B2 | 9/2008 | Chen et al. |
| 7,427,636 | B2 | 9/2008 | Cannizzaro et al. |
| 7,429,564 | B2 | 9/2008 | Arbit et al. |
| 7,429,565 | B2 | 9/2008 | Boojamra et al. |
| 7,432,261 | B2 | 10/2008 | Cannizzaro et al. |
| 7,432,273 | B2 | 10/2008 | Fardis et al. |
| 7,452,901 | B2 | 11/2008 | Boojamra et al. |
| 7,462,608 | B2 | 12/2008 | Chen et al. |
| 7,470,724 | B2 | 12/2008 | Cannizzaro et al. |
| 7,645,747 | B2 | 1/2010 | Boojamra et al. |
| 7,649,015 | B2 | 1/2010 | Arimili et al. |
| 7,871,991 | B2 | 1/2011 | Boojamra et al. |
| 7,871,992 | B2 | 1/2011 | Jomaa et al. |
| 8,022,083 | B2 * | 9/2011 | Boojamra et al. ............ 514/300 |
| 8,318,701 | B2 | 11/2012 | Boojamra et al. |
| 8,329,926 | B2 | 12/2012 | Boojamra et al. |
| 8,658,617 | B2 | 2/2014 | Graetz et al. |
| 2001/0031773 | A1 | 10/2001 | Camden |
| 2002/0051805 | A1 | 5/2002 | Ueki et al. |
| 2002/0103378 | A1 | 8/2002 | Ellis |
| 2002/0119443 | A1 | 8/2002 | Becker et al. |
| 2002/0156133 | A1 | 10/2002 | Bartholomaeus et al. |
| 2003/0045583 | A1 | 3/2003 | Hadfield et al. |
| 2003/0109498 | A1 | 6/2003 | Yuasa et al. |
| 2003/0149044 | A1 | 8/2003 | Quallich et al. |
| 2004/0121316 | A1 | 6/2004 | Birkus et al. |
| 2004/0157793 | A1 | 8/2004 | Stuyver et al. |
| 2004/0167096 | A1 | 8/2004 | Cheng et al. |
| 2005/0037925 | A1 | 2/2005 | Tsukamoto et al. |
| 2005/0171126 | A1 | 8/2005 | Torii et al. |
| 2005/0202054 | A1 | 9/2005 | Faryniarz et al. |
| 2006/0069060 | A1 | 3/2006 | Redkar et al. |
| 2006/0079478 | A1 | 4/2006 | Boojamra et al. |
| 2006/0094870 | A1 | 5/2006 | Torii et al. |
| 2006/0223794 | A1 | 10/2006 | Bourghol Hickey et al. |
| 2006/0223820 | A1 | 10/2006 | Brand et al. |
| 2006/0281759 | A1 | 12/2006 | de Diego et al. |
| 2007/0049754 | A1 | 3/2007 | Boojamra et al. |
| 2007/0149479 | A1 | 6/2007 | Fischer et al. |
| 2007/0149552 | A1 | 6/2007 | Ku et al. |
| 2007/0191482 | A1 | 8/2007 | Choi et al. |
| 2007/0225249 | A1 | 9/2007 | Shi |
| 2008/0207620 | A1 | 8/2008 | Desai et al. |
| 2008/0221213 | A1 | 9/2008 | Christgau |
| 2008/0226731 | A1 | 9/2008 | Vasanthavada et al. |
| 2008/0279932 | A1 | 11/2008 | Reber et al. |
| 2009/0012037 | A1 | 1/2009 | Boojamra et al. |
| 2009/0163449 | A1 | 6/2009 | Wempe |
| 2009/0202470 | A1 | 8/2009 | Boojamra et al. |
| 2009/0275535 | A1 | 11/2009 | Boojamra et al. |
| 2010/0093667 | A1 | 4/2010 | Graetz et al. |
| 2011/0288053 | A1 | 11/2011 | Boojamra et al. |
| 2013/0090299 | A1 | 4/2013 | Boojamra et al. |
| 2013/0090302 | A1 | 4/2013 | Boojamra et al. |
| 2013/0316969 | A1 | 11/2013 | Boojamra et al. |

FOREIGN PATENT DOCUMENTS

| | | | |
|---|---|---|---|
| DE | 41 38 584 | A1 | 5/1993 |
| EA | 014685 | B1 | 12/2010 |
| EP | 0 267 050 | A2 | 5/1988 |
| EP | 0 347 852 | A2 | 12/1989 |
| EP | 0 369 409 | A1 | 5/1990 |
| EP | 0 441 192 | A2 | 8/1991 |
| EP | 0 465 297 | A1 | 1/1992 |
| EP | 0 468 119 | A1 | 1/1992 |
| EP | 0 468 866 | A1 | 1/1992 |
| EP | 0 531 597 | A1 | 3/1993 |
| EP | 0 632 048 | A1 | 1/1995 |
| EP | 0 786 455 | A1 | 7/1997 |
| EP | 0 852 233 | A1 | 7/1998 |
| EP | 0 919 562 | A1 | 6/1999 |
| EP | 1 295 879 | A1 | 3/2003 |
| EP | 1 832 582 | A1 | 9/2007 |
| EP | 1 778 249 | B1 | 5/2010 |
| EP | 2 305 680 | A2 | 4/2011 |
| JP | H-02-178295 | A | 7/1990 |
| JP | H-03-5439 | A | 1/1991 |
| JP | H-04-330086 | A | 11/1992 |
| JP | 2007-502329 | A | 2/2007 |
| RU | 2 106 353 | C | 3/1998 |
| RU | 2 188 203 | C | 8/2002 |
| WO | WO-88/06158 | A1 | 8/1988 |
| WO | WO-91/19721 | A1 | 12/1991 |
| WO | WO-92/00988 | A1 | 1/1992 |
| WO | WO-92/03452 | A1 | 3/1992 |
| WO | WO-92/13869 | A1 | 8/1992 |
| WO | WO-92/18520 | A1 | 10/1992 |
| WO | WO-93/12123 | A1 | 6/1993 |
| WO | WO-93/24510 | A1 | 12/1993 |
| WO | WO-94/21604 | A1 | 9/1994 |
| WO | WO-95/07920 | A1 | 3/1995 |
| WO | WO-96/14314 | A2 | 5/1996 |
| WO | WO-96/15111 | A1 | 5/1996 |
| WO | WO-96/40156 | A1 | 12/1996 |
| WO | WO-97/01558 | A1 | 1/1997 |
| WO | WO-98/04569 | A1 | 2/1998 |
| WO | WO-98/11906 | A1 | 3/1998 |
| WO | WO-98/15563 | A1 | 4/1998 |
| WO | WO-99/29702 | A2 | 6/1999 |
| WO | WO-99/33815 | A1 | 7/1999 |
| WO | WO-99/62921 | A1 | 12/1999 |
| WO | WO-00/04033 | A1 | 1/2000 |
| WO | WO-00/52015 | A2 | 9/2000 |

(56) References Cited

FOREIGN PATENT DOCUMENTS

| | | | |
|---|---|---|---|
| WO | WO-00/52015 | A3 | 9/2000 |
| WO | WO-00/56734 | A1 | 9/2000 |
| WO | WO-01/13957 | A2 | 3/2001 |
| WO | WO-01/13957 | A3 | 3/2001 |
| WO | WO-01/17982 | A1 | 3/2001 |
| WO | WO-01/19320 | A2 | 3/2001 |
| WO | WO-01/19320 | A3 | 3/2001 |
| WO | WO-01/39724 | A2 | 6/2001 |
| WO | WO-01/39724 | A3 | 6/2001 |
| WO | WO-01/46204 | A1 | 6/2001 |
| WO | WO-01/64693 | A1 | 9/2001 |
| WO | WO-01/96329 | A1 | 12/2001 |
| WO | WO-01/96354 | A1 | 12/2001 |
| WO | WO-02/03997 | A1 | 1/2002 |
| WO | WO-02/06292 | A1 | 1/2002 |
| WO | WO-02/08241 | A | 1/2002 |
| WO | WO-02/14344 | A2 | 2/2002 |
| WO | WO-02/48165 | A2 | 6/2002 |
| WO | WO-02/48165 | A3 | 6/2002 |
| WO | WO-02/057425 | A2 | 7/2002 |
| WO | WO-02/057425 | A3 | 7/2002 |
| WO | WO-02/100415 | A2 | 12/2002 |
| WO | WO-02/100415 | A3 | 12/2002 |
| WO | WO-02/103008 | A2 | 12/2002 |
| WO | WO-02/103008 | A3 | 12/2002 |
| WO | WO-03/028737 | A1 | 4/2003 |
| WO | WO-03/050129 | A1 | 6/2003 |
| WO | WO-03/059255 | A2 | 7/2003 |
| WO | WO-03/059255 | A3 | 7/2003 |
| WO | WO-03/064383 | A2 | 8/2003 |
| WO | WO-03/064383 | A3 | 8/2003 |
| WO | WO-03/066005 | A2 | 8/2003 |
| WO | WO-03/066005 | A3 | 8/2003 |
| WO | WO-03/080078 | A1 | 10/2003 |
| WO | WO-03/090690 | A2 | 11/2003 |
| WO | WO-03/090690 | A3 | 11/2003 |
| WO | WO-03/090691 | A2 | 11/2003 |
| WO | WO-03/090691 | A3 | 11/2003 |
| WO | WO-03/091264 | A | 11/2003 |
| WO | WO-2004/096233 | A | 11/2004 |
| WO | WO-2004/096234 | A2 | 11/2004 |
| WO | WO-2004/096235 | A2 | 11/2004 |
| WO | WO-2004/096236 | A2 | 11/2004 |
| WO | WO-2004/096237 | A2 | 11/2004 |
| WO | WO-2004/096285 | A2 | 11/2004 |
| WO | WO-2004/096286 | A2 | 11/2004 |
| WO | WO-2004/096286 | A3 | 11/2004 |
| WO | WO-2004/096287 | A2 | 11/2004 |
| WO | WO-2004/096287 | A3 | 11/2004 |
| WO | WO-2004/096818 | A2 | 11/2004 |
| WO | WO-2004/096818 | A3 | 11/2004 |
| WO | WO-2004/100960 | A2 | 11/2004 |
| WO | WO-2005/000786 | A1 | 1/2005 |
| WO | WO-2005/002626 | A2 | 1/2005 |
| WO | WO-2005/011709 | A1 | 2/2005 |
| WO | WO-2005/012324 | A2 | 2/2005 |
| WO | WO-2005/039552 | A2 | 5/2005 |
| WO | WO-2005/039552 | A3 | 5/2005 |
| WO | WO-2005/042772 | A1 | 5/2005 |
| WO | WO-2005/042773 | A1 | 5/2005 |
| WO | WO-2005/044279 | A1 | 5/2005 |
| WO | WO-2005/044308 | A1 | 5/2005 |
| WO | WO-2005/047898 | A2 | 5/2005 |
| WO | WO-2005/047898 | A3 | 5/2005 |
| WO | WO-2005/063258 | A1 | 7/2005 |
| WO | WO-2005/063751 | A1 | 7/2005 |
| WO | WO-2005/064008 | A1 | 7/2005 |
| WO | WO-2006/015261 | A2 | 2/2006 |
| WO | WO-2006/015261 | A3 | 2/2006 |
| WO | WO-2006/015262 | A2 | 2/2006 |
| WO | WO-2006/015262 | A3 | 2/2006 |
| WO | WO-2006/051261 | A1 | 5/2006 |
| WO | WO-2006/110157 | A2 | 10/2006 |
| WO | WO-2006/110157 | A3 | 10/2006 |
| WO | WO-2010/005986 | A1 | 1/2010 |
| WO | WO-2014/055603 | A1 | 4/2014 |
| WO | WO-2014/055618 | A1 | 4/2014 |

OTHER PUBLICATIONS

Alexander, J. et al. (Jan. 19, 1996). "Investigation of (Oxodioxolenyl)Methyl Carbamates as Nonchiral Bioreversible Prodrug Moieties for Chiral Amines," *J. Med. Chem.* 39(2):480-486.

Allen, L.F. et al. (Oct. 2003). "CI-1040 (PDI84352), a Targeted Signal Transduction Inhibitor of MEK (MAPKK)," in *Seminars in Oncology*, Elsevier Inc., 30(5):105-116.

Anan'eva, L.G. et al. (1983). "(2-Iodoethl) Phosphonic Derivatives," *J. Gen. Chem. USSR* 53(3):480-483.

Anderson, R.C. et al. (1984). "2-Chloro-4(R), 5(R)-Dimethyl-2-Oxo-1,3,2-Dioxaphospholane, a New Chiral Derivatizing Agent," *J. Org. Chem.* 49:1304-1305.

Anonymous. (Oct. 31, 2006). CAS Registry No. 182550-46-5, Search Date: Apr. 20, 2011.

Anonymous. (Oct. 31, 2006). CAS Registry No. 182550-51-2, Search Date: Apr. 20, 2011.

Asante-Appiah, E. et al. (1999). "HIV-1 Integrase: Structural Organization, Conformational Changes, and Catalysis," *Advances in Virus Research* 52:351-363.

Avert. (2010). "HIV and AIDS Vaccine," located at <http://www.avert.org/aids-vaccine.htm>, last visited on Sep. 16, 2013, 8 pages.

Balsiger, R.W. et al. (1959). "Synthesis of Potential Anticancer Agents. XVIII. Analogs of Carbamoyl Phosphate," *J. Org. Chem.* 24:434-436.

Balthazor, T.M. et al. (1980). "Nickel-Catalyzed Arbuzov Reaction: Mechanistic Observations," *J. Org. Chem.* 45:5425-5426.

Bantia, S. et al. (2001). "Purine Nucleoside Phosphorylase Inhibitor BCX-1777 (Immucillin-H)—A Novel Potent and Orally Active Immunosuppressive Agent," in *International Immunopharmacology*, Elsevier Science B.V., pp. 1199-1210.

Barre-Sinoussi, F. (1996). "HIV as the Cause of AIDS," *Lancet* 348:31-35.

Beauchamp, L.M. et al. (1996). "Guanine, Pyrazolo[3,4-d]pyrimidine, and Triazolo[4,5-d]pyrimidine(8-Azaguanine) Phosphonate Acyclic Derivatives as Inhibitors of Purine Nucleoside Phosphorylase," in *Journal of Medicinal Chemistry*, American Chemical Society, pp. 949-956.

Benzaria, S. et al. (1996). "Synthesis, in Vitro Antiviral Evaluation, and Stability Studies of Bis(S-acyl-2-thioethyl) Ester Derivatives of 9-[2.-(Phosphonomethoxy)ethyl]adenine (PMEA) as Potential PMEA Prodrugs with Improved Oral Bioavailabitity," *J. Med. Chem.* 39:4958-4965.

Berge, S.M. et al. (1977). "Pharmaceutical Salts," *J. of Pharm. Sciences* 66(1):1-19.

Beusen, D.D. et al. (1995). "Solid-State Nuclear Magnetic Resonance Analysis of the Conformation of an Inhibitor Bound to Thermolysin," *J. Med. Chem.* 38(14):2742-2747.

Birkus et al. (2007). "Cathepsin A is the Major Hydrolase Catalyzing the Intracellular Hydrolysis of the Antiretroviral Nucleotide Phosphonoamidate Prodrugs GS-7340 and GS-9131," *Antimicrob. Agents Chemother.* 51(2):543-550.

Borhani, D.W. et al. (2004). "A-420983: A Potent, Orally Active Inhibitor of Ick With Efficacy in a Model of Transplant Rejection," *Bioorganic & Medicinal Chemistry Letters* 14:2613-2616.

Bowker, M.J. (2002). "A Procedure for Salt Selection and Optimization," Chapter 7 in Handbook of Pharmaceutical Salts: Properties, Selection, and Use, pp. 161-189.

Bundgaard, H. (1985). *Design of Prodrugs*, Elsevier Science Ltd, pp. 70-74.

Bundgaard, H. et al. (1991). "Design and Application of Prodrugs," in Drug Design and Development, pp. 113-191.

Burger, A. et al. (1957). "Monoesters and Ester-Amidates of Aromatic Phosphonic Acids," *J. Am. Chem. Society* 79:3575-3579.

Bzowska, A. et al. (2000). "Purine Nucleoside Phosphorylases: Properties, Functions, and Clinical Aspects," in *Pharmacology & Therapeutics*, vol. 88, Elsevier Science, Inc., pp. 349-425.

(56) References Cited

OTHER PUBLICATIONS

Campagne, J. et al. (1993). "Synthesis of Mixed Phosphonate Diester Analogues of Dipeptides Using BOP or PyBOP Reagents," *Tetrahedron Letters* 34(42):6743-6744.
Campagne, J. et al. (1995). "(1H-Benzotriazol-1-yloxy)tris(dimethylamino)phosphonium Hexafluorophosphate- and (1H-Benzotriazol-1-yloxy)tripyrrolidinophosphonium Hexafluorophosphate-Mediated Activation," *J. Org. Chem.* 60(16):5214-5223.
Campbell, D. (1992). "The Synthesis of Phosphonate Esters, an Extension of the Mitsunobu Reaction," *J. Org. Chem.* 57:6331-6335.
Carter, H.E. et al. (1965). "Carbobenzoxy Chloride and Derivatives," *Org. Synth. Coll.* 3:167-169.
Casara, P.J. et al. (1992). "Synthesis of Acid Stable 5'-0-Fluoromethyl Phosphonates of Nucleosides, Evaluation as Inhibitors of Reverse Transcriptase," *Bioorg. Med. Chem. Letters* 2(2):145-148.
Casteel, D.A. et al. (Sep. 1991). "Steric and Electronic Effects in the Aryl Phosphate to Arylphosphonate Rearrangement," *Synthesis* 691-693.
Cavalier, J. et al. (Jan. 1998). "New Highly Diastereoselective Synthesis of Phosphoramidates. A Route to Chiral Methyl *p*-Nitrophenyl Alkyphosphonates," *Synlett* 1:73-75.
CDC: Centers for Disease Control and Prevention: Pre-Exposure Prophylaxis (PrEP). (2013), located at <http://www.cdc.gov/hiv/prep/>, last visited on Sep. 15, 2013, 4 pages.
Chapman, H. et al. (2001). "Practical Synthesis, Separation, and Stereochemical Assignment of the PMPA Pro-Drug GS-7340," in *Nucleosides, Nucleotides & Nucleic Acids*, vol. 20, No. 4-7, Marcel Dekker, Inc., pp. 621-628.
Chen, S. et al. (1997). "Design, Synthesis, and Biochemical Evaluation of Phosphonate and Phosphonamidate Analogs of Glutathionylspermidine as Inhibitors of Glutathionylspermidine Synthetase/Amidase from *Escherlchia coli,*" *J. Med. Chem.* 40(23):3842-3850.
Chong, Y. et al. (2004). "Effects of Fluorine Substitution of Cytosine Analogues on the Binding Affinity to HIV-1 Reverse Transcriptase," *Bioorganic & Medicinal Chemistry Letters* 14(2):437-440.
Chong, Y. et al. (2002). "Stereoselective Synthesis and Antiviral Activity of D-2',3'-Didehydro-2', 3'-Dideoxy-2'-Fluoro-4'-Thionucleosides," *J. Med. Chem.* 45:4888-4898.
Chong, Y. et al. (May-Aug. 2003). "2'-Fluoro-4'-thio-2',3'-unsaturated nucleosides: anti-HIV activity, resistance profile, and molecular modeling studies," *Nucleosides, Nucleotides & Nucleic Acids* 22(5-8):611-615.
Choo, H. et al. (Jan. 30, 2003). "Synthesis, Anti-HIV Activity, and Molecular Mechanism of Drug Resistance of L-2',3'-Didehydro-2',3'-Dideoxy-2'-Fluoro-4'-Thionucleosides," *J. Med. Chem.* 46(3):389-398.
Clark, J.L. et al. "Mycophenolic Acid Analogues as Potential Agents Against West Nile Virus Infection."
Coe, D.M. et al. (1991). "Synthesis of Some Mimics of Nucleoside Triphosphates," *J. Chem. Soc., Chem. Commun.* 312-314.
Coleman, R. et al. (1992). "Synthesis of the Aziridino [1,2-a] Pyrrolidine Substructure of the Antitumor Agents Azinomycin A and B," *J. Org. Chem.* 57(22):5813-5815.
Conklyn, M. et al. (Dec. 2004, e-pub. Sep. 15, 2004). "The JAK3 Inhibitor CP-690550 Selectively Reduces NK and CDS+ Cell Numbers in Cynomolgus Monkey Blood Following Chronic Oral Dosing," *Journal of Leukocyte Biology* 76(6):1248-1255.
Corey, E.J. et al. (1973). "Selective Cleavage of Allyl Ethers Under Mild Conditions by Transition Metal Reagents," *J. Org. Chem.* 38(18):3224.
D'Addona, D. et al. (2001). "Preparation of Carbamates from Amines and Alcohols Under Mild Conditions," *Tetrahedron Letters* 42:5227-5229.
Davies, L.C. et al. (1988). "Dinucleotide Analogues as Inhibitors of Thymidine Kinase, Thymidylate Kinase, and Ribonucleotide Reductase," *J. Med. Chem.* 31:1305-1308.
De Clercq, E. (1994). "New Developments in the Chemotherapy of Lentivirus (Human Immunodeficiency Virus) Infections: Sensitivity/Resistance of HIV-1 to Non-Nucleoside HIV-1-Specific Inhibitors," *Annals of the NY Academy of Sciences* 724:438-456.
De Clercq, E. (2002). "Highlights in the Development of New Antiviral Agents," in *Mini Reviews in Medicinal Chemistry*, Bentham Science Publishers, Ltd. 2(2):163-175.
De Clercq, E. (2001). "New Developments in Anti-HIV Chemotherapy," *Current Medicinal Chemistry* 8(13):1543-1572.
De Lombaert, S. et al. (1994). "*N*-Phosphonomethyl Dipeptides and Their Phosphonate Prodrugs, a New Generation of Neutral Endopeptidase (NEP, EC 3.4.24.11) Inhibitors," *J. Med. Chem.* 37:498-511.
Dvorakova, H. (Aug. 16, 1996). "Synthesis of 2'-Aminomethyl Derivatives of N-(2-(Phosphonomethoxy)ethyl) Nucleotide Analogues as Potential Antiviral Agents," *J. Med. Chem.* 39(17):3263-3268.
Effenberger, F. et al. (1985). "2(1 *H*)-Pyridon als Austrittsgruppe bei Acylierungsreaktionen Anwendungen in der Peptidchemie," *Chem. Ber.* 118:468-482.
Efimov, V.A. et al. (1998). "Synthesis of DNA Analogues with Novel Carboxamidomethyl Phosphonamide and Glycinamide internucleoside Linkages," *Bioorganic & Medicinal Chemistry Letters* 8:1013-1018.
Eisenberg, E. J. et al. (Apr.-Jul. 2001). "Metabolism of GS-7340, A Novel Phenyl Monophosphoramidate Intracellular Prodrug of PMPA, in Blood," *Nucleosides, Nucleotides and Nucleic Acids*, 20(4-7):1091-1098.
Esposito, D. et al. (1999). "HIV Integrase Structure and Function," *Advances in Virus Research* 52:319-333.
Evans, G.B. (Jul. 17, 2003). "Exploring Structure—Activity Relationships of Transition State Analogues of Human Purine Nucleoside Phosphorylase," *J. Med. Chem.* 46(15):3412-3423.
Farquhar, D. et al. (1983) "Biologically Reversible Phosphate-Protective Groups," *J. Pharm. Sci.* 72:324-325.
Frankel, A. et al. (1998). "HIV-1 Fifteen Proteins and an RNA," *Annu. Rev. Biochem.* 67:1-25.
Freeman, S. et al. (1997). "3 Prodrug Design for Phosphates and Phosphonates," *Progress in Medicinal Chemistry* 34:112-147.
Galeotti, N. et al. (1996). "A Straightforward Synthesis of Alpha—Amino Phosphonate Monoesters Using BroP or TPyCIU," *Tetrahedron Letters* 37(23):3997-3998.
Griffin, B. et al. (1956). "D-Glucopyranose 6-Deoxy-6-phosphonic Acid," *J. Am. Chem. Society* 78(10):2336-2338.
Gobec, S. et al. (Jul. 5, 2004). "Phosphonate inhibitors of Antiget 85C, a Crucial Enzyme Involved in the Biosynthesis of the *Mycobacterium tuberculosis* Cell Wall," *Bioorganic and Medicinal Chemistry Letters* 14(13):3559-3562.
Gumina, G. et al. (2001). "Advances in Antiviral Agents for Hepatitis B Virus," *Antiviral Chemistry & Chemotherapy* 12(Suppl. 1):93-117.
Hakimelahi, G. et al. (1995). "Design, Synthesis, and Structure-Activity Relationship of Novel Dinucleotide Analogs as Agents Against Herpes and Human," *J. Med. Chem.* 38:4648-4659.
Hanaoka, K. et al. (Jul. 19, 1999). "Antitumor Activity and Novel DNA-Self-Strand-Breaking Mechanism of CNDAC (1-(2-C-Cyano-2-Deoxy-β-D-Arabino-Pentofuranosyl) Cytosine) and its N4-Palmitoyl Derivative (CS-682)," *Int. J. Cancer* 82(2):226-236.
Hansen, J. et al. (1982). "Partially Protected Polyamines," *Synthesis* 404-405.
Hartmann, K. et al. (Sep. 1997). "Toxicity Associated With High Dosage 9-[(2R,5R-2,5-Dihydro-5-Phosphonomethoxy)-2-Furanyl]adenine Therapy Off Attempts to Abort Early FIV Infection," *Antiviral Res.* 36(1):11-25.
Hegedus, L.S. et al. (Nov. 26, 2004). "Synthesis of 4'-Methyl and 4'-cyano Carbocyclic 2',3'-Didehydro Nucleoside Analogues Via 1 ,4-Addition to Substituted Cyclopentenones," *J. Org. Chem.* 69(24):8492-8495.
Herczegh, P. et al. (May 23, 2002). "Osteoadsorptive Bisphosphonate Derivatives of Fluoroquinolone Antibacterials," *J. Med. Chem.* 45(11):2338-2341.
Herdewijn, P. et al. (1987). "3'-Substituted 2', 3'-Dideoxynucleoside Analogues as Potential Anti-HIV (HTLV-III/LAV) Agents," *J. Med. Chem.* 30:1270-1278.

(56) References Cited

OTHER PUBLICATIONS

Hildebrand, C. et al. (1992). "Sodium Salt Glycosylation in the Synthesis of Purine 2'-Deoxyribonucleosides; Studies of Isomer Distribution," *J. Org. Chem.* 57:1808-1813.
Hirabayashi, H. et al. (2003). "Bone-Specific Drug Delivery Systems: Approaches Via Chemical Modification of Bone-Seeking Agents," *Clinical Pharmacokinet.* 42(15):1319-1330.
Holy, A. et al. (1989). "Synthesis ofN-(2-Phosphonylmethoxyethyl) Derivatives of Heterocyclic Bases" *Collect. Czech. Chem. Commun.* 54: 2190-2210.
Hostetler. (1997). "Nucleotides for Topical Treatment of Psoriasis," *CAS* 127:185859, 2 pages (Chemical abstract).
Hottiger, M. et al. (1996). "Human Immunodeficiency Virus Type 1 Reverse Transcriptase," *Biol. Chem.* 377:97-120.
Howell, H. et al. (1988). "Antiviral Nucleosides, A Stereospecific, Total Synthesis of 2'-Fluoro-2'-deoxy-beta-D-Arabinoturanosyl Nucleosides," *J. Org. Chem.* 53:85-88.
Jacob III, P. (1982). "Resolution of (Racemic)-5-Bromonornicotine. Synthesis of (R)- and (S)-Nornicotine of High Enantiomeric Purity," *J. Org. Chem.* 47:4165-4167.
Jain, J. et al. (Sep. 2002). "Characterization of Pharmacological Efficacy of VX-148, a New, Potent Immunosuppressive Inosine 5'-Monophosphate Dehydrogenase Inhibitor," *Journal of Pharmacology and Experimental Therapeutics* 302(3) :1272-1277.
Jahne, G. et al. (1992). "Preparation of Carbocyclic Phosphonate Nucleosides," *Tetrahedron Letters* 33(37):5335-5338.
Jeong, L.S. et al. (Jan. 16, 2003). "Design, Synthesis, and Biological Evaluation of Fluoroneplanocin A as the Novel Mechanism-Based Inhibitor of S-Adenosylhomocysteine Hydrolase," *J. Med. Chem.* 46(2):201-203.
Karpenko, I.L. et al. (Mar. 2003). "Synthesis and Antitherpetic Activity of Acyclovir Phosphonates," *Nucleosides, Nucleotides & Nucleic Acids* 22(3):319-328.
Kato, K. et al. (1999). "Stereoselective Synthesis of 4'-.α.-Alkycicarbovir Derivatives Based on an Asymmetric Synthesis or Chemo-Enzymatic Procedure," in *Chemical & Pharmaceutical Bulletin*, Pharmaceutical Society of Japan 49(9):1256-1264.
Kato, K. et al. (1998). "Enantio- and Diastereoselective Syntheis of 4'-a-Substituted Carbocyclic Nucleosides,"*Asymmetry* 9:911-914.
Katz, R. et al. (1994). "The Retroviral Enzymes," *Annu. Rev. Biochem.* 63:133-173.
Kazimierczuk, Z. et al. (1984). "Synthesis of 2'-Deoxytubercidin, 2'-Deoxyadenosine, and Related 2'-Deoxynucleosides via a Novel Direct Stereospecific Sodium Salt Glycosylation Procedure," *J. Am. Chem. Soc.* 106:6379-6382.
Khamnei, S. et al. (1996). "Neighboring Group Catalysis in the Design of Nucleotide Prodrugs," *J. Med. Chem.* 39:4109-4115.
Khandazhinskaya, A.L. et al. (2002). "Carbocyclic Dinucleoside Polyphosphonates: Interactions with HIV Reverse Transcriptase and Antiviral Activity," *J. Med. Chem.*45:1284-1291.
Kilpatrick, J.M. et al. (Apr. 2003). "Intravenous and Oral Pharmacokinetic Study of BCX-1777, A Novel Purine Nucleoside Phosphorylase Transition-State Inhibitor, in Vivo Effects on Blood 2'-Deoxyguanosine in Primates," *International Immunopharmacology* 3(4):541-548.
Kim, C.U.N. et al. (1991). "Regiospecific and Highly Stereoselective Electrophilic Addition to Furanoid Glycals: Synthesis of Phosphonate Nucleotide Analogues with Potent Activity against HIV," *J. Org. Chem.* 56(8):2642-2647.
Kinsky, S.C. et al. (Feb. 14, 1987). "Inhibition of Cell Proliferation by Putative Metabolites and Nondegradable Analogs of Methotrexate-γ-Dimyristoylphosphatidylethanolamine," *Biochimica et Biphysica Acta* 917(2):211-218.
Kinsky, S.C. et al. (Feb. 21, 1986). "Effect of Liposomes Sentitized with Methotrexate-γ-Dimyristoylphosphatidylethanolamine on Cells that are Resistant to Methotrexate," *Biochimica et Biophysica Acta* 885(2):129-135.
Kinsky, S.C. et al. (Sep. 4, 1987). "Circumvention of the Methotrexate Transport System by Methotrexate-Phosphatidylethanolamine Derivatives Effect of Fatty Acid Chain Length," *Biochimica et Biophysica Acta* 921(1):96-103.
Ko, O.H. et al. (2002). "Efficient Synthesis of Novel Carbocyclic Nucleosides Via Sequential Claisen Rearrangement and Ring-Closing Metathesis," *Tetrahedron Letters* 43: 6399-6402.
Kojima, T. et al. (Apr. 2006). "Crystalline Form Information From Multiwell Plate Salt Screening by Use of Raman Microscopy," *Pharm. Res.* 23(4):806-812.
Konakahara, T. et al. (Jan. 1993). "A Convenient Method for the Synthesis of Activated *N*-Methylcarbamates," *Synthesis* 103-106.
Krayevsky, A.A. et al. (1992). "5'Hydrogenphosphonates and 5'-Methylphosphonates of Sugarmodified Pyrimidine Nucleosides as Potential Anti-HIV-I Agents", Nucleosides, Nucleotides & Nucleic Acids 11(2-4):177-196.
Krówczyński, L. (1982). "Drug Interaction," Chapter 17 in *Outline of Clinical Pharmacy*, pp. 323-342.
Krówczyński, L. (1977). "Excipients for Manufacturing of Drug Forms," Chapter 4 in *Outline of Drug Form Technology: A Textbook for Pharmacy Students*. $3^{rd}$ Edition.
Kumamoto, H. et al. (May 31, 2002). "Simple Entry to 3'-Substituted Analogues of Anti-HIV Agent Stavudine Based on an Anionic O → C Stannyl Migration," *J. Org. Chem.* 67(11):3541-3547.
Kunz, H. et al. (1985). "71. Synthesis of the Glycopeptide Partial Sequence $A^{80}$-$A^{84}$ of Human Fibroblast Interferon," *Helvetica Chimica Acta* 68:618-622.
Lee, K. et al. (Apr. 8, 1999). "Synthesis and Anti-HIV and Anti-HBV Activities of 2'-Fluoro-2',3'-Unsaturated L-Nucleosides," *J. Med. Chem.* 42(7):1320-1328.
Lee, K. et al. (Mar. 14, 2002). "Structure-Activity Relationships of 2'-Fiuoro-2',3'-unsaturated D-Nucleosides as Anti-HIV-1 Agents," *J. Med. Chem.* 45(6):1313-1320.
Lee, S. et al. (2002). "Large-Scale Aspects of Salt Formation: Processing of Intermediates and Final Products," Chapter 8 in *Handbook of Pharmaceutical Salts: Properties, Selection, and Use*, pp. 191-220.
Leff et al. (2002). "Antidiabetic PPAR-γ. Ligands: An Update on Compunds in Development," *Curr. Med. Chem. Imun. Endoc. & Metab. Agents* 2(1):33-47.
Lewandowicz, A. et al. (Aug. 22, 2003). "Achieving the Ultimate Physiological Goal in Transition State Analogue Inhibitors for Purine Nucleoside Phosphorylase," *The Journal of Biological Chemistry* 278(34):31465-31468.
Lochmuller, C.H. et al. (1975). "Chromatographic Resolution of Enantiomers Selective Review," *Journal of Chromatography* 113:283-302.
Lu, X. et al. (1987). "Palladium-Catalyzed Reaction of Aryl Polyfluoroalkanesulfonates with O, O-Dialkyl Phosphonates," *Synthesis* 726-727.
Ma, T. et al. (1997). "Synthesis and Anti-Hepatitis B Virus Activity of 9-(2-Deoxy-2-fluoro-Beta-L-arabinofuranosyl)purine Nucleosides," *J. Med. Chem.* 40:2750-2754.
Mackman et al. (2010). "Discovery of GS-9131: Design, Synthesis and Optimization of Amidate Prodrugs of the Novel Nucleoside Phosphonate HIV Reverse Transcriptase (RT) Inhibitor GS-9148," *Bioorganic & Medicinal Chemistry* 18:3606-3617.
Maffre-Lafon, D. et al. (1994). "Solid Phase Synthesis of Phosphonopeptides from Fmoc Phoaphonodipeptides," *Tetrahedron* Letters 35(24):4097-4098.
Margolin et al. (1994). "AMP Deaminase as a Novel Practical Catalyst in the Synthesis of 6-Oxopurine Ribosomes and Their Analogs," *Journal of Organic Chemistry* 59(24):7214-7218.
Marquez, V.E. et al. (1990). "Acid-Stable 2'-Fluoro Purine Dideoxynucleosides as Active Agents against HIV," *J. Med. Chem.* 33:978-985.
Maynard, J. A. et al. (1963). "Organophosphorus Compounds II. Preparation of Phosphonic Acid Esters Using the Dicyclohexylcarbodi-imide Reagent," *Aust. J.*Chem. 16:609-612.
McKenna, C. et al. (1979). "Functional Selectivity in Phosphonate Ester Dealkylation with Bromotrimethylsilane," *J.C.S. Chem. Comm.* 739.

(56) References Cited

OTHER PUBLICATIONS

Melvin, L.S. (1981). "An Efficient Synthesis of 2-Hydroxyphenylphosphonates," *Tetrahedron Letters* 22(35):3375-3376.

Menendez-Arias, L. (Aug. 2002). "Targeting HIV: Antiretroviral Therapy and Development of Drug Resistance," *Trends in Pharmacological Sciences* 23(8):381-388.

Mikhailopulo, I.A. et al. (2000). "Pyrophosphoryl Derivatives of 1-(2-Deoxy-3-O-Phosphonomethyl-Beta- and -Alpha-D-erythro-Pentofuranosyl)Thyrnine: Synthesis and Substrate Properties Towards Some DNA Polymerases," *Nucleosides, Nucleotides, and Nucleic Acids* 19(10-12)1885-1909.

Mikhailopulo, I.A. et al. (Jul. 25, 2003). "2'-Chloro-2',3'-Dideoxy-3'-Fluoro-d-Ribonucleosides: Synthesis, Stereospecificity, Some Chemical Transformations, and Conformational Analysis," *J. Org. Chem.* 68(15):5897-5908.

Mikhailopulo, I.A. et al. (May 12, 1993, e-pub. Jan. 25, 2006). "Synthesis of 2'-Azido-2',3'-Didehydro-2',3'-Dideoxythymidine," *Liebigs Annalen der Chemie* 5:513-519.

Mitchell, A. et al. (1992). "Bioreversible Protection for the Phospho Group: Bioactivation of the Di(4 acyloxybenzyl) Phosphoesters," *J. Chem. Soc. Perkin Trans* 1:2345-2353.

Mitsunobu, O. (1981). "The Use of Diethyl Azodicarboxylate and Triphenylphosphine in Synthesis and Transformation of Natural Products," *Synthesis* 1-28.

Moon, H.R. et al. (2002). "Synthesis of 2',3'-Didehydro-2',3'-Dideoxy-2'-Fluoro Apionnucleosidesas Potential Antiviral Agents," *J. Chem. Soc. Perkin Trans.* 1:1800-1804.

Morgan, B. et al. (1994). "Structure-Based Design of an Inhibitor of the Zinc Peptidase Thermolysin," *J. Am. Chem. Soc.* 116(8):3251-3260.

Morgans et al. (1995). "5-Substituted Derivatives of Mycophenolic Acid," *CAS* 124:86709 (Chemical abstract).

Morr, M. at al (2001). "Formation of Phostonic Acids During the Reduction of Azidonucleosidephosphonic Acids," *Tetrahedron Letters* 42:8841-8843.

Muesing, M. et al (Feb. 1985). "Nucleic Acid Structure and Expression of the Human AIDS/Lymphadenopathy Retrovirus," *Nature* 313(7):450-458.

Musiol, H. et al. (1994). "On the Synthesis of Phosphonamidate Peptides," *J. Org. Chem.* 59(21):6144-6146.

Ohashi, K. et al. (1988). "Synthesis of Phosphonosphingoglycolipid Found in Marine Snail Turbo Cornutus," *Tetrahedron Letters* 29(10):1189-1192.

Okamoto, Y. et al. (1990). "Optical Resolution of DIhydropyridine Enantiomers by High-Performance Liquid Chromatography Using Phenylcarbamates," *Journal of Chromatography* 513:375-378.

Pankiewicz, K.W. (Jan. 31, 2002). "Novel Mycophenolic Adenine Bis(phosphonate) Analogues As Potential Differentiation Agents against Human Leukemia," *J. Med. Chem.* 45(3):703-712.

Paquet, a. (1982). "Introduction of 9-Fluorenylmethyloxycarbonyl, Trichloroethoxycarbonyl, and Benzyloxycarbonyl Amine Protecting Groups Into O-Unprotected Hydroxyamino Acids Using Succinimidyl Carbonates," *Can. J. Chem.* 60:976-960.

Ono-Nita, S.K. et al. (Aug. 2002). "Novel Nucleoside Analogue MCC-478 (LY582563) Is Effective against Wild-Type or Lamivudine-Resistant Hepatitis B Virus," *Antimicrobial Agents and Chemotherapy* 46(8):2602-2605.

Parang, K. et al. (Oct. 2000). "Novel Approaches for Designing 5'-0-Ester Prodrugs of 3'-Azido-2', 3'-dideoxythymidine (AZT)," *Current Medicinal Chemistry* 7(10):995-1039.

Patois, C. et al. (1990). "2-Alkyl-5, 5-Dimethyl-1,3,2-Dioxephosphorinan-2-Ones α-Lithiated Carbanions. Synthesis, Stability, and Conformation," *J. Chem. Soc. Perkin Trans.* (1)1577-1581.

Pauwels et al. (1988). "Investigations on the Anti-HIV Activity of 2', 3'-Dideoxyadenosine Analogues with Modifications in Either the Pentose or Purine Moiety," *Biochem. Pharmacology* 37(7):1317-1325.

Petrakis, K. et al. (1987). "Palladium-Catalyzed Substitutions of Triflates Derived from Tyrosine-Containing Peptides and Simpler Hydroxyarenes Forming," *J. Am. Chem. Soc.* 109:2831-2833.

Porche, D. J. (1999). "State of the Art: Antiretroviral and Prophylactic Treatments in HIV/AIDS," *Nursing Clinics of North America* 34:95-112.

Prashad, M. et al. (Sep. 20, 2002). "An Efficient and Large-Scale Enantioselective Synthesis of PNP405: A Purine Nucleoside Phosphorylase Inhibitor," *J. Org. Chem.* 67(19):6612-6617.

Puech, F. et al. (1993). "Intracellular Delivery of Nucleoside Monophosphates through a Reductase-Mediated Activation Process," *Antiviral Research* 22:155-174.

Pungente, M. et al. (2001). "Synthesis and Stereochemical Elucidation of a 14-Membered Ring Phosphonate," *Organic Letters* 3(5):643-646.

Quast, H. et al. (1974). "Herstellung Von Methylphosphonsaure-Dichlorid," *Synthesis* 490.

Ray, A.S. et al. (Apr. 2004). Role of Purine Nucleoside Phosphorylase in Interactions between 2', 3'-Dideoxyinosine and Allopurinal, Ganciclovir, or Tenofovir, Antimicrobial Agents and Chemotherapy 48(4):1089-1095.

Ray, A.S. et al. (2008). "Intracellular Metabolism of the Nucleotide Prodrug GS-9131, a Potent Anti-Human Immunodeficiency Virus Agent," *Antimicrob. Agents Chemother.* 52(2):648-654.

Redmore, D. (1970). "Phosphorus Derivatives of Nitrogen Heterocycles. 2. Pyridinephosphonic Acid Derivatives," *J. Org. Chem.* 35(12):4114-4117.

Roach et al. (1987). "Fluorescence Detection of Alkylphosphonic Acids Using p-(9-Anthroyloxy)phenacyl Bromide," *Analytical Chem.* 59:1056-1059.

Roberts, S.M. (Dec. 1998). "Development of the Route to the New Anti-AIDS Drug Abacavir: A Highlight of Academic/Industry Laison," *IDrugs* 1(8):896-899.

Rosenberg, I. et al. (1987). "Synthesis of Potential Prodrugs and Metabolites of 9-(S)-(3-Hydroxy-2-Phosphonylmethoxypropyl) Adenine," *Collect. Czech. Chem. Commun.* 52:2792-2800.

Rosowsky, A. et al. (Oct. 1, 1986). "Methotrexate Analogues-27. Dual Inhibition of Dihydrofolate Reductase and Folylpolyglutamate Synthetase by Methotrexate and Aminopterin Analogues with a γ-Phosphonate Group in the Side Chain," *Biochemical Pharmacology* 35(19):3327-3333.

Rosowsky, A. et al. (Jul. 1988). "Methotrexate Analogues. 32. Chain Extension, α-Carboxyl Deletion, and γ-Carboxyl Replacement by Sulfonate and Phosphonate: Effect on Enzyme Binding and Cell-Growth Inhibition," *J. Med. Chem.* 31(7):1326-1331.

Saady, M. et al. (1995) "Selective Monodeprotection of Phosphate, Phosphite, Phosphonate, and Phosphoramide Benzyl Esters," *J. Org. Chem.* 60:2946-2947.

Sasaki, T. et al. (1971). "Chemistry of Cyanoacetylenes. Part X. Further Studies on the Reactions of Cyano-Ynamines with Hydrogen Halides and Bromine," *J. Chem. Soc. C.* 18:3056-3060.

Schon, I. et al. (1986) "9-Fluorenylmethyl Pentafluorophenyl Carbonate as a Useful Reagent for the Preparation of N-9-Fluorenylmethyloxycarbonylamino," Synthesis 303-305.

Schultz, C. (Mar. 20, 2003). "Prodrugs of Biologically Active Phosphate Esters," *Bioorganic & Medicinal Chemistry* 11(6):885-898.

Sekiya, K. et al. (Jul. 4, 2002). "2-Amino-6-arylthio-9-[2-(phosphonomethoxy) ethyl) purine Bis(2,2,2-Trifluoroethyl) Esters as Novel HBV-Specific Antiviral Reagents," *Journal of Medicinal Chemistry* 45(14):3138-3142.

Serafinowska, H. et al. (1995). "Synthesis and in Vivo Evaluation of Prodrugs of 9-[2-(Phosphonomethoxy)ethoxy]adenine," *J. Med. Chem.* 38:1372-1379.

Sharma, S. et al. (1989). "Spermexatin and Spermaxatol: New Synthetic Spermidine-Based Siderophore Analogues," *J. Med. Chem.* 32:357-367.

Shi, W. et al. (Apr. 30, 2004, e-pub. Feb. 23, 2004). "*Plasmodium falciparum* Purine Nucleoside Phosphorylase: Crystal Structures, Immucillin Inhibitors, and Dual Catalytic Function," *Journal of Biological Chemistry* 279(18):18103-18106.

Shirokova, E. A. (2003). "New Lipophilic Derivatives of AZT and d4T 5'-Phosphonates," Nucleosides, Nucleotides and Nucleic Acids, 22(5-8):981-985.

(56) References Cited

OTHER PUBLICATIONS

Siddiqui, A. Q. et al. (Feb. 11, 1999). "The Presence of Substituents on the Aryl Moiety of the Aryl Phosphoramidate Derivative of D4T Enhances Anti-HIV Efficacy in Cell Culture: A Structure Activity Relationship," *J. Med. Chem.* 42(3):393-399.
Silverberg, L. et al. (1996). "A Simple, Rapid and Efficient Protocol for the Selective Phosphorylation of Phenols with Dibenzyl Phosphite," *Tetrahedron Letters* 37(6):771-774.
Smith, M. et al. (1994). "Development and Significance of Nucleoside Drug Resistance in Infection Caused by the Human Immunodeficiency Virus Type 1," *Clin. Invest. Med.* 17(3):226-243.
Smith, R. et al. (2003). "A Novel MyD-1 (S1RP-1) Signaling Pathway that Inhibits LPS-Induced TNF Production by Monocytes," *Blood* 102(7):2532-2540.
Sintchak, M.D. et al. (May 2000). "The Structure of Inosine 5'-Monophosphate Dehydrogenase and the Design of Novel Inhibitors," Immunopharmacology 47(2-3):163-184.
Squires, K.E. (2001). "An Introduction to Nucleoside and Nucleotide Analogues," *Antiviral Therapy* 6(Suppl.3):1-14.
Srinivas, R.V. et al. (1993). "Metabolism and in Vitro Antiretroviral Activities of Bis(Pivaloyloxymethyl) Prodrugs of Acyclic Nucleoside Phosphonates," *Antimicrobial Agents and Chemotherapy* 37(10): 2247-2250.
Stahl, P.H. (2002). "Appendix," in *Handbook of Pharmaceutical Salts: Properties, Selection, and Use*, pp. 329-350.
Stahl, P.H. et al. (2002). "Monographs on Acids and Bases," Chapter 12 in *Handbook of Pharmaceutical Salts: Properties, Selection, and Use*, pp. 265-327.
Stamm, H. et al. (1980). "Reactions with Aziridines XXI The (Michaelis-) Arbuson Reaction with *N-Acyl Aziridines and Other Amidoethylations at Phosphorus," Tetrahedron Letters* 21:1623-1626.
Sturtz, G. et al. (1990). "Su rune nouvelle approche de pharmacomodulation du methotrexate: synthese d'analogues gem-diphosphoniques d'amethopterine et de la N-10 deaza amethopterine," in *Medicinal Chemistry*, C. R. Academie Des Sciences, Paris, 10(2): 739-742. (English abstract available).
Sturtz, G. et al. (1984). "Analogues Phosphonoglutamiques D'amethopterine (methotrexate)," *Eur. J. Med. Chem.* 19(3):267-273 (English summary available).
Sturtz, G. et al. (1993). "Synthesis of Gem-Bisphosphonic Methotrexate Conjugates and their Biological Response Towards Walker's Osteosarcoma," *Eur. J. Med. Chem.* 28:899-903.
Sturtz, G. et al. (1992). "A Study of the Delivery-Targeting Concept Applied to Antineoplasic Drugs Active on Human Osteosarcoma, I. Synthesis and Biological Activity in Nude Mice Carrying Human Osteosarcoma Xenografts of Gem-Bisphosphonic Methotrexate Analogues," *Eur J. Med. Chem.* 27(8):825-833.
Sturtz et al. (1984). "Amethopterine (methotrexate) Phosphonoglutamic Acid Analogs. Part II. Dihydrofolate Reductase Inhinition," *CAS* 101:143560 (Chemical abstract).
Sun, C. et al. (2002). "A General Synthesis of Diozolenone Prodrug Moieties," *Tetrahedron Letters* 43:1161-1164.
Szabo, T. et al. (1995). "Solid Phase Synthesis of 5'-Methylenephosphonate DNA" *Nucls. & Nucli.* 14(3-5):871-874.
Tang, T. et al. (1999). "The Tert-Butanesulfinyl Group: An Ideal Chiral Directing Group and Boc-Surrogate for the Asymmetric Synthesis and Applications of β-Amino Acids," *J. Org. Chem.* 64:12-13.
Tarrago-Litvak, L. et al. (1994). "The Reverse Transcriptase of HIV-1: From Enzymology to Therapeutic Intervention," *The FASEB Journal* 8:497-503.
Thomson, W. et al. (1993). "Synthesis and Bioactivation of Bis(aroyloxymethyl) and Mono(aroyloxymethyl) Esters of Benzylphosphonate," *J. Chem. Soc. Perkin Trans.* 19:2303-2308.
Toyota, A. et al. (Jun. 25, 1998). "α-Fluorination of 6-Phenylsulfinyl-2-Azabicyclo[2.2.1]heptan-3-One and Synthesis of 2'-Fluoro Substituted Carbovir," *Tetrahedron Letters* 39(26):4687-4690.
Truvada® Label Revision Approved on Jul. 16, 2012, NDA No. 021752, Reference ID 3159758, 38 pages.
Van Der Laan, A.C. et al. (1996). "An Approach Towards the Synthesis of Oligomers Containing a N-2 Hydroxyethyl-aminomethylphosphonate Backbone: A Novel PNA Analogue," *Tetrahedron Letters* 37(43):7857-7860.
Van Der Laan, A.C. et al. (1998). "Optimization of the Binding Properties of PNA-(5')-DNA Chimerae," *Bioorg. Med. Chem. Letters* 8:663-668.
Vieira De Almeida, M. et al. (1999). "Synthesis of Deoxy Phosphatidylinositol Analogues and Phosphonate Isosters of Ins(1,4,5)P3," *Tetrahedron Letters* 55:12997-13010.
Vielhaber, B. (2000). "Bericht Vom 3rd International Workshop on Salvage Therapy for HIV Infection," in *Deutsche Aids—Hilfe e.V. FaxReport zu HIV and AIDS*, pp. 12-14.
Von Der Helm, K. (1996). "Retroviral Proteases: Structure, Function and Inhibition From a Non-Anticipated Viral Enzyme to the Target of a Most Promising HIV Therapy," *Biol.* Chem. 377:765-774.
Waegell W. et al. (2002). "A420983, a Novel, Small Molecule Inhibitor of LCK Prevents Allograft Rejection," *Transplantation Proceedings* 34:1411-1417.
Watanabe, Y. et al. (1988). "Dibenzyl Phosphorofluoridate, A New Phosphorylating Agent," *Tetrahedron Letters* 29(45):5763-5764.
Wermuth, C.G. et al. (2002). "Selected Procedures for the Preparation of Pharmeaceutically Acceptable Salts," Chapter 11 in *Handbook of Pharmaceutical Salts: Properties, Selection, and Use*, pp. 249-263.
Wessig, P. et al. (1997). "A Convenient One-Pot Conversion of N-Boc-β-Aminoalcohols into N-Boc-Aziridines," *Synlett* 8:893-894.
West. (1984). "Solid-State Chemistry and its Application," John Wiley & Sons, 3 pages.
Wissner, A. et al. (1992). "Analogues of Platelet Activating Factor. 6 Mono- and Bis-Aryt Phosphate Antagonists of Platelet Activating Factor," *J. Med. Chem.* 35:1650-1662.
Woltermann, C.J. et al. (Apr. 5, 2004). "A Stereoselective Synthesis of 9-(3-*O*-benzyl-5-*O*-Tetrahydropyranyl-β-D-Arabinofuranosyl)Adenine, a Potentially Useful Intermediate for Ribonucleoside Synthesis," *Tetrahedron* 60(15):3445-3449.
Wroblewski, A. et al. (2004). "Synthesis of (1R,2S)- and (1 S,2S)-3-(4-Carbamoyl-1 ,2,3-Triazol-1-yl)-1,2-Dihydroxypropylphosphonates," *Tetrahedron: Asymmetry* 15:1457-1464.
Yamada, K. et al. (2002). "Reactions of 1-Methoxy-3-(2-nitrovinyl)indole with Nucleophiles: An Interesting Solvent Effect and a Novel Preparation of 3-Substituted 1-Methoxyindoles," *Heterocycles* 57(7):1231-1234.
Yamauchi, K. et al. (1984). "Synthesis of Peptides Analogues Containing (2-Aminoethyl)phosphonic Acid(ciliatine)," *J. Org. Chem.* 49(7):1158-1163.
Zemlicka, J. et al. (1972). "Nucleosides, XV. Decarboxylative Elimination of 2'-Deoxynudeodise Uronic Acids," *J. Am. Chem. Soc.* 94(9):3213-3218.
Zhou, W. et al. (Jun. 17, 2004). "Synthesis, Structure-Activity Relationships, and Drug Resistance of Beta-D-3'-Fluoro-2', 3'-Unsaturated Nucleosides as Anti-HIV Agents," *J. Med. Chem.* 47(13) :3399-3408.
U.S. Final Office Action mailed on Mar. 28, 2013, for U.S. Appl. No. 12/999,441, filed Jul. 7, 2009, 16 pages.
U.S. Non-Final Office Action mailed on Aug. 28, 2012, for U.S. Appl. No. 12/999,441, filed Jul. 7, 2009, 16 pages.
U.S. Final Office Action mailed on Dec. 15, 2011, for U.S. Appl. No. 11/658,628, filed Sep. 25, 2012, 6 pages.
U.S. Non-Final Office Action mailed on Jun. 20, 2014, for U.S. Appl. No. 14/150,677, filed Jan. 8, 2014, 5 pages.
U.S. Non-Final Office Action mailed on Apr. 28, 2011, for U.S. Appl. No. 11/658,628, filed Sep. 25, 2012, 12 pages.
U.S. Non-Final Office Action mailed on Sep. 24, 2012, for U.S. Appl. No. 13/187,293, filed Jul. 20, 2011, 7 pages.
U.S. Non-Final Office Action mailed on Oct. 9, 2013, for U.S. Appl. No. 13/848,593, filed Mar. 21, 2013, 7 pages.
U.S. Non-Final Office Action mailed on Feb. 27, 2014, for U.S. Appl. No. 13/653,982, filed Oct. 17, 2012, 6 pages.
Notice of Allowance mailed on Mar. 18, 2014, for U.S. Appl. No. 13/848,593, filed Mar. 21, 2013, 7 pages.

(56) References Cited

OTHER PUBLICATIONS

Notice of Allowance mailed on Oct. 8, 2013, for U.S. Appl. No. 12/999,441, filed Jul. 7, 2009, 7 pages.
African Regional Office Action mailed on Mar. 14, 2014, for African Regional Patent Application No. AP/P/2010/005509, filed Jul. 7, 2009, 5 pages.
African Search Report mailed on Sep. 27, 2011, for African Patent No. AP-2629, issued on Mar. 28, 2013, 1 page.
Chinese Office Action mailed on Mar. 17, 2013 for Chinese Patent Application No. 200980126248.X filed on Jul. 7, 2009, 7 pages.
Chilean Office Action mailed on Jul. 14, 2014, for Chilean Patent Application No. 14-2011 filed on Jul. 7, 2009, 5 pages.
Eurasian Office Action mailed on Aug. 24, 2011, for Eurasian Patent Application No. 200700363 filed Jul. 26, 2005, 2 pages.
European Office Action mailed on Mar. 8, 2011, for European Patent Application No. 09790117.7, filed Jul. 7, 2009, 2 pages.
Indian Office Action mailed on Jan. 12, 2012, for Indian Patent Application No. 1211/DELNP/2007, filed Jul. 27, 2005, 5 pages.
Israeli Official Notification mailed on Jan. 26, 2011, for Israeli Patent Application No. 180758, filed Jul. 27, 2005, 3 pages.
Israeli Official Notification mailed on May 5, 2012, for Israeli Patent Application No. 210006, filed Jul. 7, 2009.
Japanese Office Action mailed on Dec. 3, 2010, for Japanese Patent Application No. 2007-523866, filed Jul. 27, 2005, 2 pages.
Japanese Office Action mailed on Dec. 18, 2013, for Japanese Patent Application No. 2011-517525, filed Jul. 7, 2009, 4 pages.
Mexican Office Action mailed on May 22, 2012 for Mexican Patent Application No. MX/a/2011/000306 filed on Jul. 7, 2009, 5 pages.
Mexican Office Action mailed on Feb. 16, 2012 for Mexican Patent Application No. MX/a/2010/007924 filed on Jul. 27, 2005, 10 pages.
New Zealand Office Action mailed on May 20, 2011, for New Zealand Patent Application No. 590075, filed Jul. 7, 2009, 2 pages.
Peruvian Office Action mailed on Jul. 4, 2012, for Peruvian Patent Application No. 6.2011 filed on Jul. 7, 2009, 14 pages.
Polish Office Action mailed on Oct. 5, 2011 for Polish Patent Application No. P382843 filed Jul. 27, 2005, 5 pages.
Polish Office Action mailed on Oct. 22, 2013, for Polish Patent Application No. P382843, filed on Jul. 27, 2005, 1 page.
Taiwanese Office Action mailed on Jul. 8, 2011, for Taiwanese Patent Application No. 094125503.
Vietnamese Office Action mailed on Jul. 5, 2011, for Vietnamese Patent Application No. 1-2011-00030, filed Jul. 7, 2009, 2 pages.
Vietnamese Office Action mailed on Mar. 14, 2011, for Vietnamese Patent Application No. 1-2011-00030, filed on Jul. 7, 2009, 1 page.
International Search Report mailed on Apr. 13, 2005, for PCT Patent Application No. PCT/US2004/013063 filed on Apr. 26, 2004, 8 pages.
International Search Report mailed on Oct. 8, 2009, for PCT Patent Application No. PCT/US2009/049838, filed on Jul. 7, 2009, 3 pages.
International Search Report and Written Opinion mailed on Sep. 25, 2006 for PCT Patent Application No. PCT/US2005/027088, filed on Jul. 27, 2005, 21 pages.
International Search Report and the Written Opinion mailed on Oct. 30, 2006, for PCT Patent Application No. PCT/US2005/026504, filed on Jul. 26, 2005, 18 pages.
International Preliminary Report on Patentability mailed on Jan. 20, 2011, for PCT Patent Application No. PCT/US2009/049838, filed on Jul. 7, 2009, 7 pages.
International Preliminary Report on Patentability mailed on Jan. 30, 2007, for PCT Patent Application No. PCT/US2005/026504, filed on Jul. 26, 2005, 11 pages.
Written Opinion of the International Searching Authority mailed on Apr. 13, 2005, for PCT Patent Application No. PCT/US2004/013063 filed on Apr. 26, 2004, 8 pages.
Written Opinion of the International Searching Authority mailed on Oct. 8, 2009, for PCT Patent Application No. PCT/US2009/049838 filed on Jul. 7, 2009, 5 pages.
European Search Report mailed on Mar. 12, 2007, for European Patent Application No. 04750807.2 filed on Apr. 26, 2004, 4 pages.
European Communication mailed on Mar. 16, 2007, for European Patent Application No. 04750807.2 filed on Apr. 26, 2004, 6 pages.
European Communication mailed on May 7, 2008, for European Patent Application No. 04750807.2 filed on Apr. 26, 2004, 5 pages.
European Communication mailed on Jul. 8, 2009, for European Patent Application No. 04750807.2 filed on Apr. 26, 2004, 6 pages.
European Communication mailed on Jul. 2, 2010, for European Patent Application No. 04750807.2 filed on Apr. 26, 2004, 3 pages.
European Notice of Allowance mailed on Nov. 11, 2010, for European Patent Application No. 04750807.2 filed on Apr. 26, 2004, 4 pages.
Extended European Search Report mailed on Jul. 19, 2011, for European Patent Application No. 10184722.6 filed on Apr. 26, 2004, 11 pages.
European Search Report mailed on Nov. 2, 2010, for European Patent Application No. 10178348.8 filed on Jul. 26, 2005, 9 pages.
Eurasian Patent Application No. EA-2005-01677.

* cited by examiner

ANTIVIRAL PHOSPHONATE ANALOGS

PRIORITY OF INVENTION

This application is a continuation of U.S. patent application Ser. No. 13/848,593 filed on Mar. 21, 2013, which is a continuation of U.S. patent application Ser. No. 13/187,293 filed on Jul. 20, 2011, now abandoned, which is a divisional of U.S. patent application Ser. No. 12/166,076 filed on Jul. 1, 2008, now U.S. Pat. No. 8,022,083, which is a divisional of U.S. patent application Ser. No. 10/832,815 filed on Apr. 26, 2004, now U.S. Pat. No. 7,429,565, and also claims the benefit of priority under 35 U.S.C. §119(e) to U.S. Provisional Patent Application Ser. Nos. 60/465630, 60/465400, 60/465587, 60/465463, 60/465602, 60/465598, 60/465633, 60/465550,60/465610, 60/465720, 60/465,634, 60/465537, 60/465698, 60/465667, 60/465554, 60/465553, 60/465561 , 60/465548, 60/465696, 60/465347, 60/465289, 60/465478, 60/465600, 60/465591, 60/465684, 60/465821 , 60/465647, 60/465742, 60/465649, 60/465690, 60/465469, 60/465408, 60/465608, 60/465584, 60/465687, 60/465759, 60/465559, 60/465322, 60/465377, 60/465844, and 60/465544, all filed Apr. 25, 2003; and to U.S. Provisional Patent Application Ser. No. 60/490799, filed Jul. 29, 2003; and to U.S. Provisional Patent Application Ser. Nos. 60/495687, 60/495490, 60/495805, 60/495684, 60/495600, 60/495342, 60/495564, 60/495772, 60/495592, 60/495453, 60/495491 , 60/495964, 60/495317, 60/495696, 60/495760, 60/495334, 60/495671, 60/495349, 60/495273, 60/495763, 60/495345, 60/495602, 60/495343, 60/495344, 60/495278, 60/495277, 60/495275, 60/495630, 60/495485, 60/495430, 60/495388, 60/495341, 60/495631 , 60/495633, 60/495632, 60/495539, 60/495387, 60/495392, 60/495425, 60/495393, and 60/495616, all filed Aug. 15, 2003; and to U.S. Provisional Patent Application Ser. No. 60/510245, filed Oct. 10, 2003; and to U.S. Provisional Patent Application Ser. Nos. 60/514202, 60/513,948, and 60/514258, all filed Oct. 24, 2003; and to U.S Provisional Patent Application Serial No. 60/515266, filed Oct. 29, 2003; and to U.S. Provisional Patent Application Ser. No. 60/519476, filed Nov. 12, 2003; and to U.S. Provisional Patent Application Ser. No. 60/524340, filed Nov. 20, 2003; and U.S. Provisional Patent Application Ser. No. 60/532591, filed Dec. 23, 2003. The entirety of all Applications listed above are incorporated herein by reference.

FIELD OF THE INVENTION

The invention relates generally to phosphonate containing compounds with antiviral activity.

BACKGROUND OF THE INVENTION

Improving the delivery of drugs and other agents to target cells and tissues has been the focus of considerable research for many years. Though many attempts have been made to develop effective methods for importing biologically active molecules into cells, both in vivo and in vitro, none has proved to be entirely satisfactory. Optimizing the association of the inhibitory drug with its intracellular target, while minimizing intercellular redistribution of the drug, e.g., to neighboring cells, is often difficult or inefficient.

Most agents currently administered to a patient parenterally are not targeted, resulting in systemic delivery of the agent to cells and tissues of the body where it is unnecessary, and often undesirable. This may result in adverse drug side effects, and often limits the dose of a drug (e.g., glucocorticoids and other anti-inflammatory drugs) that can be administered. By comparison, although oral administration of drugs is generally recognized as a convenient and economical method of administration, oral administration can result in either (a) uptake of the drug through the cellular and tissue barriers, e.g., blood/brain, epithelial, cell membrane, resulting in undesirable systemic distribution, or (b) temporary residence of the drug within the gastrointestinal tract. Accordingly, a major goal has been to develop methods for specifically targeting agents to cells and tissues. Benefits of such treatment includes avoiding the general physiological effects of inappropriate delivery of such agents to other cells and tissues, such as uninfected cells.

Thus, there is a need for therapeutic antiviral agents with improved pharmacological properties, e.g., drugs having improved antiviral activity and pharmacokinetic properties, including improved oral bioavailability, greater potency and extended effective half-life in vivo.

New antiviral compounds should have fewer side effects, less complicated dosing schedules, and be orally active. In particular, there is a need for a less onerous dosage regimen, such as one pill, once per day.

Assay methods capable of determining the presence, absence or amounts of viral inhibition are of practical utility in the search for antiviral as well as for diagnosing the presence of conditions associated infection.

SUMMARY OF THE INVENTION

Intracellular targeting may be achieved by methods and compositions that allow accumulation or retention of biologically active agents inside cells. The present invention provides novel phosphonate analogs of antiviral compounds. These analogs possess all the utilities of the parent compounds and optionally provide cellular accumulation as set forth below.

In one aspect, the present invention provides novel compounds with activity against infectious viruses. The compounds of the invention may inhibit viral RNA polymerases such as, but not limited to hepatitis B, hepatitis C, Polio, Coxsackie A and B, Rhino, Echo, small pox, Ebola, and West Nile virus polymerases. The compounds of the invention may inhibit retroviral RNA dependent RNA polymerases or reverse transcriptases and thus inhibit the replication of the virus. The compounds of the invention may be useful for treating human patients infected with a human retrovirus, such as hepatitis C.

The present invention relates generally to the accumulation or retention of therapeutic compounds inside cells. More particularly, the invention relates to attaining high concentrations of active metabolite molecules in virally infected cells (e.g. cells infected with HCV or HIV). Such effective targeting may be applicable to a variety of therapeutic formulations and procedures. Accordingly, in one embodiment the invention provides a conjugate comprising an antiviral compound linked to one or more phosphonate groups; or a pharmaceutically acceptable salt or solvate thereof.

In another embodiment, the invention provides a compound of any one of formulae 501-561:

501
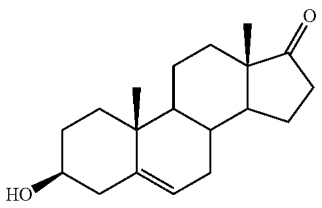
502
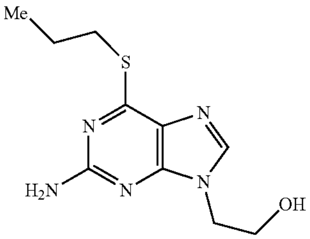
503
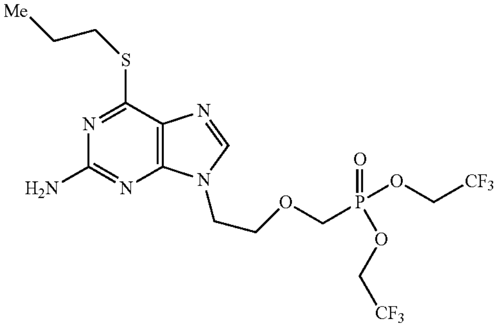
504
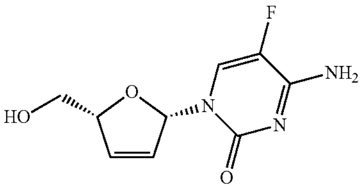
505
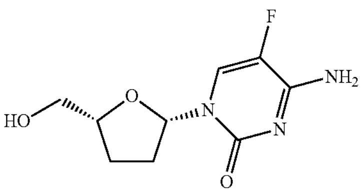
506
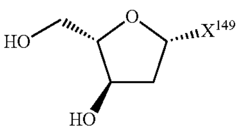
507
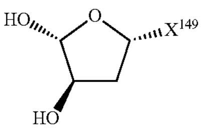
-continued
508
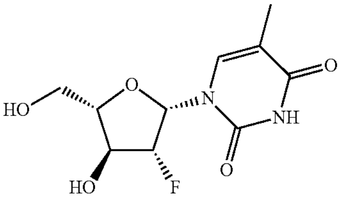
509
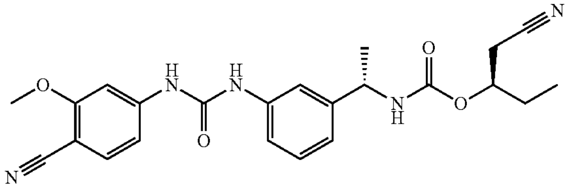
510
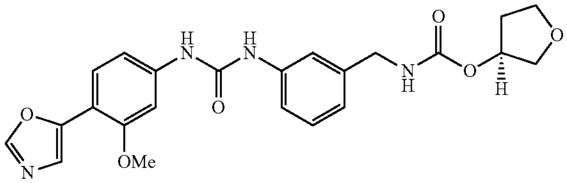
511
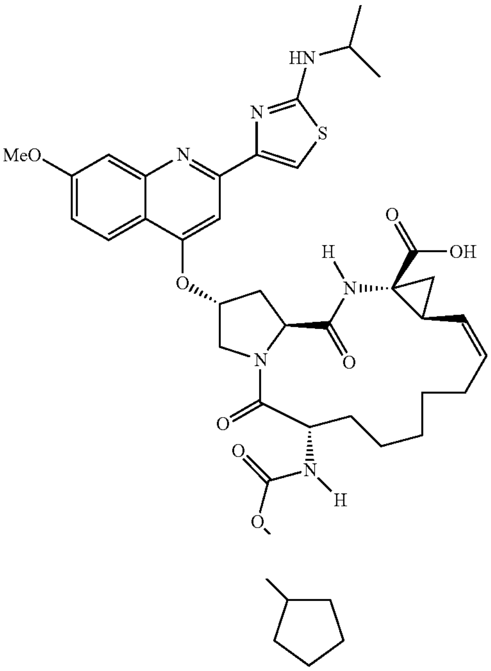
512
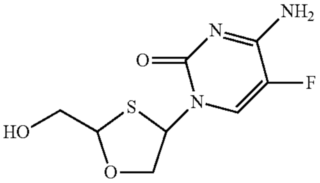

-continued
513
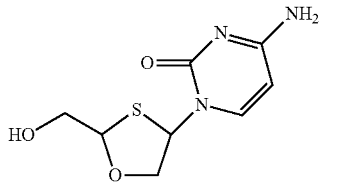
514
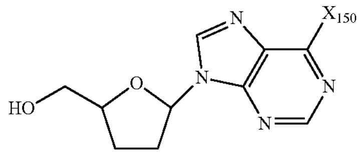
515
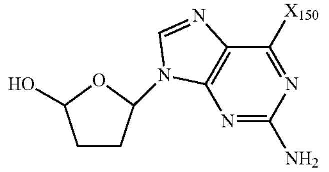
516
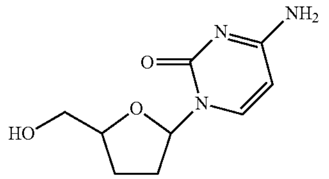
517
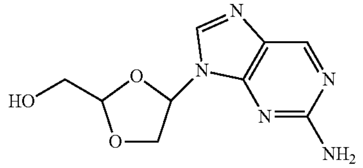
518
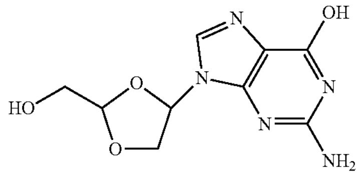
519
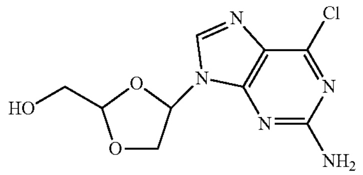
520
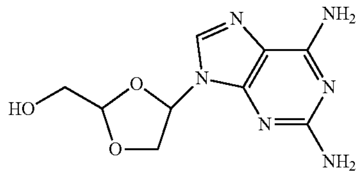
-continued
521
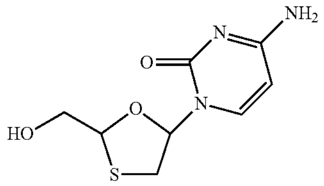
522
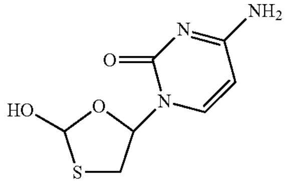
523
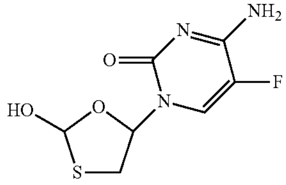
524
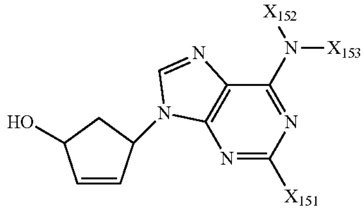
525
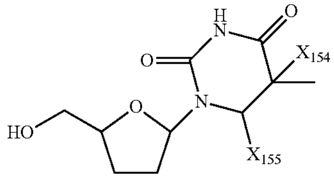
526
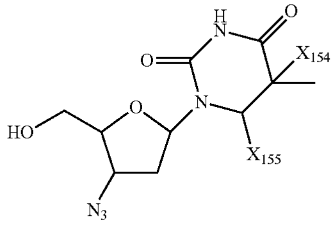
527
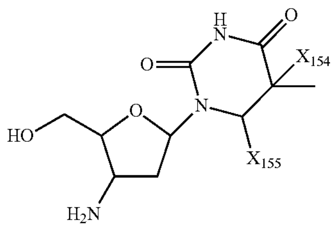

-continued
528
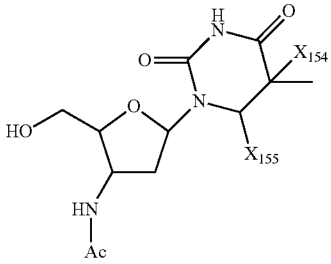
529
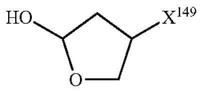
530
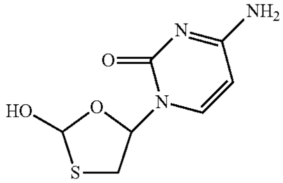
531
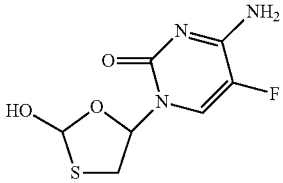
532
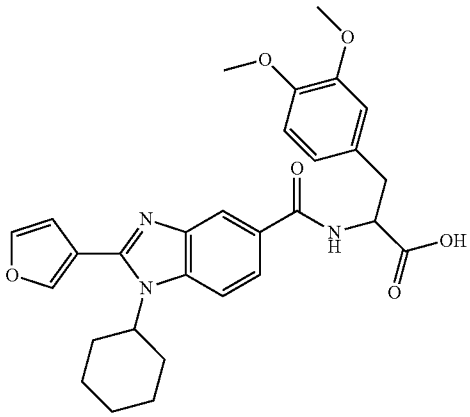
533
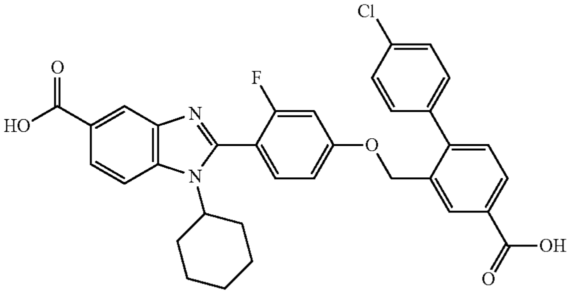
-continued
534
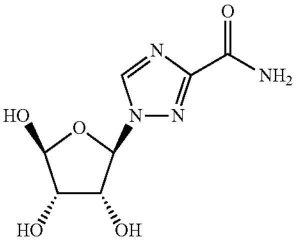
535
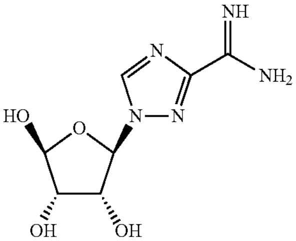
536
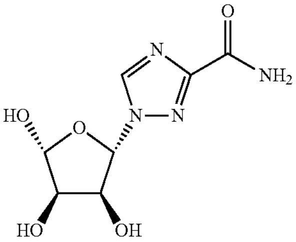
537
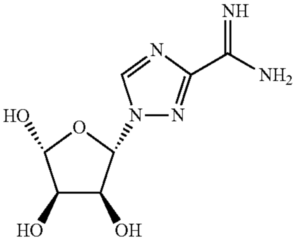
538
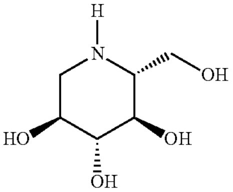
539
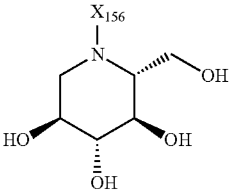
540
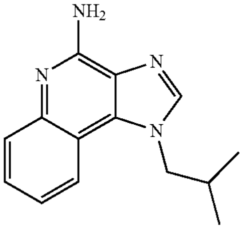

-continued
541
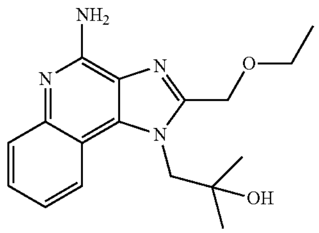
542
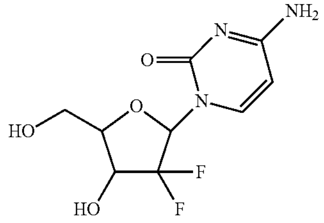
543
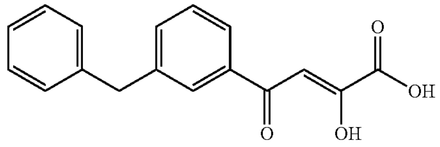
544
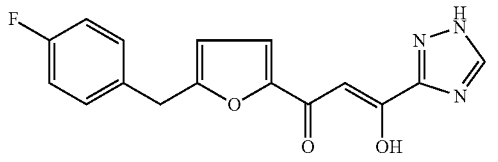
545
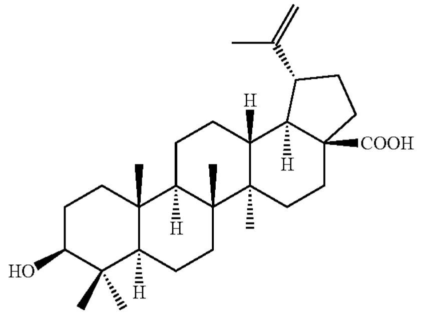
546
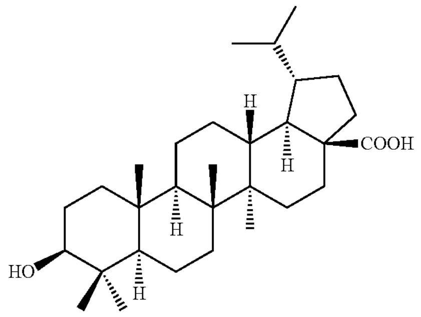
-continued
547
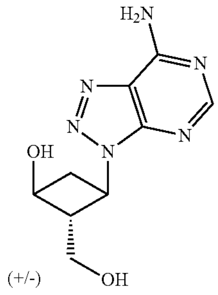
548
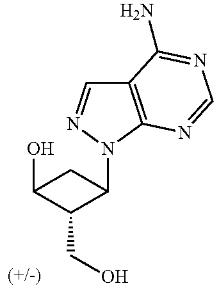
549
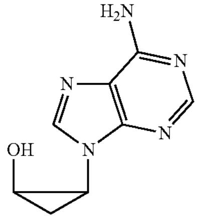
550
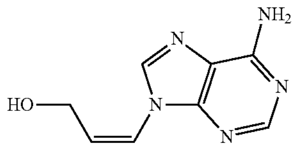
551
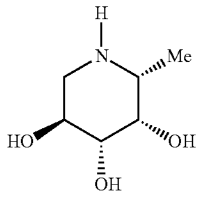
552
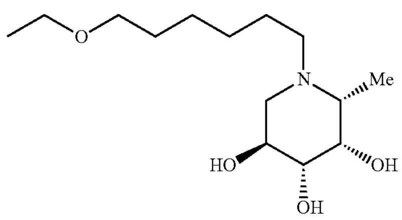
553
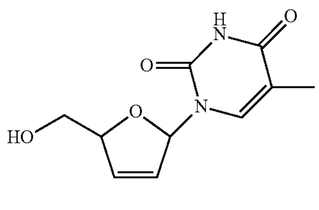

-continued

554

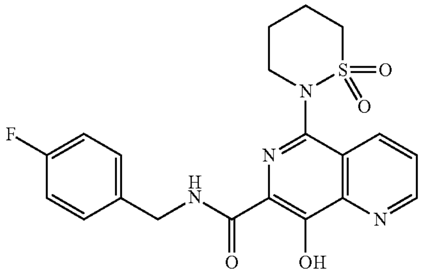

555

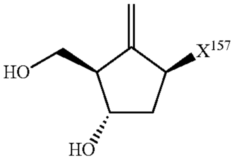

556

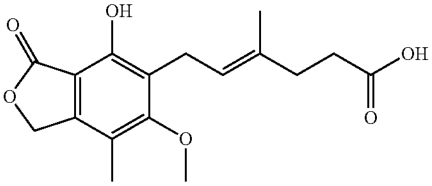

557

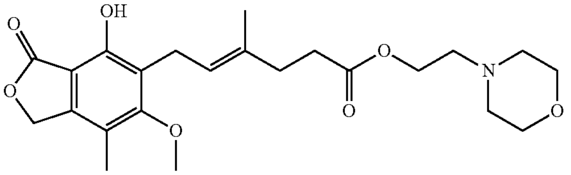

558

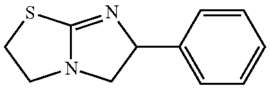

559

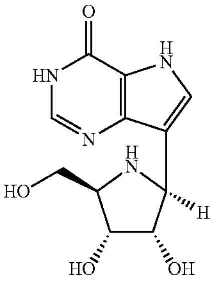

560

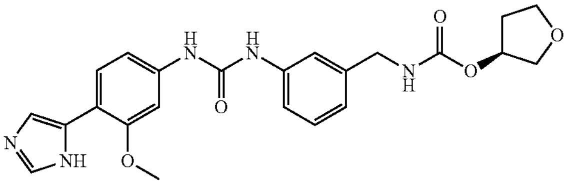

-continued

561

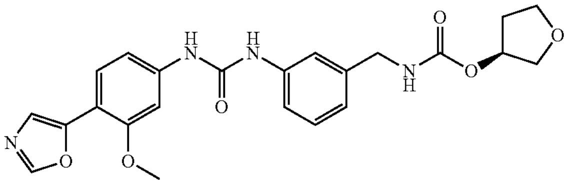

that is substituted with one or more groups $A^0$, wherein:

$A^0$ is $A^1$, $A^2$ or $W^3$ with the proviso that the conjugate includes at least one $A^1$;

$A^1$ is:

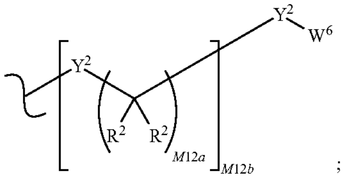

;

$A^2$ is:

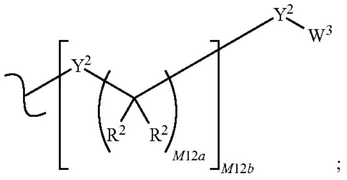

;

$A^3$ is:

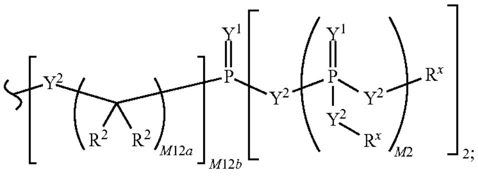

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $—S(O)_{M2}—$, or $—S(O)_{M2}—S(O)_{M2}—$; and when $Y^2$ joins two phosphorous atoms $Y^2$ can also be $C(R^2)(R^2)$;

$R^x$ is independently H, $R^1$, $R^2$, $W^3$, a protecting group, or the formula:

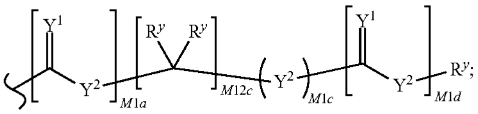

wherein:

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, $N_3$ or —$NO_2$;

$R^{3b}$ is $Y^1$;

$R^{3c}$ is —$R^x$, —$N(R^x)(R^x)$, —$SR^x$, —$S(O)R^x$, —$S(O)_2R^x$, —$S(O)(OR^x)$, —$S(O)_2(OR^x)$, —$OC(Y^1)R^x$, —$OC(Y^1)OR^x$, —$OC(Y^1)(N(R^x)(R^x))$, —$SC(Y^1)R^x$, —$SC(Y^1)OR^x$, —$SC(Y^1)(N(R^x)(R^x))$, —$N(R^x)C(Y^1)R^x$, —$N(R^x)C(Y^1)R^x$, or —$N(R^x)C(Y^1)(N(R^x)(R^x))$;

$R^{3d}$ is —$C(Y^1)R^x$, —$C(Y^1)OR^x$ or —$C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$W^3$ is $W^4$ or $W^5$;

$W^4$ is $R^5$, —$C(Y^1)R^5$, —$C(Y^1)W^5$, —$SO_{M2}R^5$, or —$SO_{M2}W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1;

M12c is 0, 1, 2, 3, 4, 5, 6, 7, 8, 9, 10, 11 or 12;

$X^{149}$ is thymine, adenine, uracil, a 5-halouracil, a 5-alkyluracil, guanine, cytosine, a 5-halo cytosine, 5-alkyl cytosine, or 2,6-diaminopurine;

$X_{150}$ is OH, Cl, $NH_2$, H, Me, or MeO;

$X_{151}$ is H, $NH_2$, or NH-alkyl;

$X_{152}$ and $X_{153}$ are independently H, alkyl, or cyclopropyl;

$X_{154}$ is a halo;

$X_{155}$ is alkoxy, aryloxy, halo-substituted alkoxy, alkenyloxy, or arylalkoxy;

$X_{156}$ is alkyl; and $X^{157}$ is thymine, adenine, guanine, cytosine, uracil, inosine, or diaminopurine.

In another embodiment the invention provides a conjugate which has the formula:

$$[DRUG]\text{-}(A^0)_{nn}$$

wherein:

DRUG is a compound of any one of formulae 501-561;

nn is 1, 2, or 3;

$A^0$ is $A^1$, $A^2$ or $W^3$ with the proviso that the conjugate includes at least one $A^1$;

$A^1$ is:

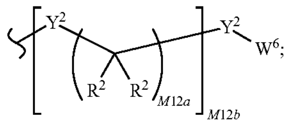

$A^2$ is:

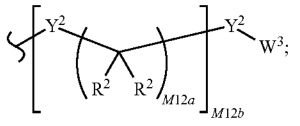

$A^3$ is:

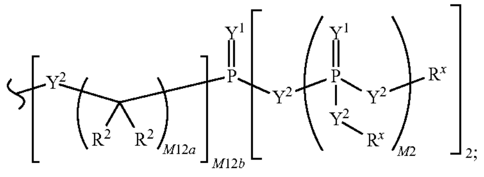

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, —$S(O)_{M2}$—, or —$S(O)_{M2}$—$S(O)_{M2}$—; and when $Y^2$ joins two phosphorous atoms $Y^2$ can also be $C(R^2)(R^2)$;

$R^x$ is independently H, $R^1$, $R^2$, $W^3$, a protecting group, or the formula:

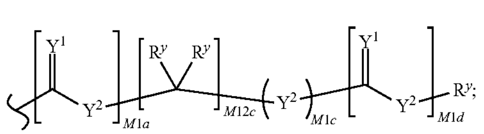

wherein:

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, $N_3$ or —$NO_2$;

$R^{3b}$ is $Y^1$;

$R^{3c}$ is —$R^x$, —$N(R^x)(R^x)$, —$SR^x$, —$S(O)R^x$, —$S(O)_2R^x$, —$S(O)(OR^x)$, —$S(O)_2(OR^x)$, —$OC(Y^1)R^x$, —$OC(Y^1)OR^x$, —$OC(Y^1)(N(R^x)(R^x))$—, —$SC(Y^1)R^x$, —$SC(Y^1)OR^x$, —$SC(Y^1)(N(R^x)(R^x))$, —$N(R^x)C(Y^1)R^x$, —$N(R^x)C(Y^1)OR^x$, or —$N(R^x)C(Y^1)(N(R^x)(R^x))$;

$R^{3d}$ is —$C(Y^1)R^x$, —$C(Y^1)OR^x$ or $C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$W^3$ is $W^4$ or $W^5$;

$W^4$ is $R^5$, —$C(Y^1)R^5$, —$C(Y^1)W^5$, —$SO_{M2}R^5$, or —$SO_{M2}W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1;

M12c is 0, 1, 2, 3, 4, 5, 6, 7, 8, 9, 10, 11 or 12;

$X^{149}$ is thymine, adenine, uracil, a 5-halouracil, a 5-alkyluracil, guanine, cytosine, a 5-halo cytosine, 5-alkyl cytosine, or 2,6-diaminopurine;

$X_{150}$ is OH, Cl, $NH_2$, H, Me, or MeO;

$X_{151}$ is H, $NH_2$, or NH-alkyl;

$X_{152}$ and $X_{153}$ are independently H, alkyl, or cyclopropyl;

$X_{154}$ is a halo;

$X_{155}$ is alkoxy, aryloxy, halo-substituted alkoxy, alkenyloxy, or arylalkoxy;

$X_{156}$ is alkyl; and $X^{157}$ is thymine, adenine, guanine, cytosine, uracil, inosine, or diaminopurine.

In another embodiment, the invention provides a conjugate of any one of formulae 1-108:

1

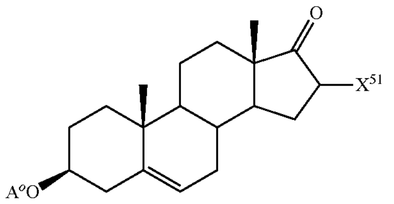

2

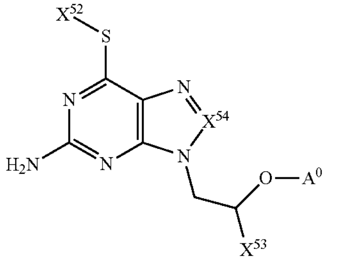

3

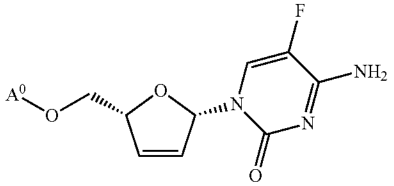

4

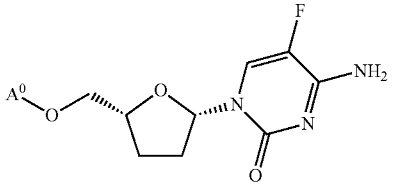

5

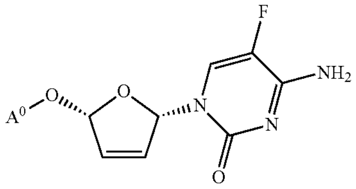

6

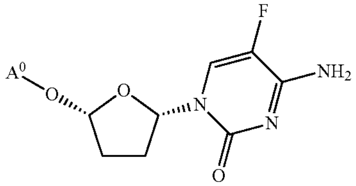

-continued

7

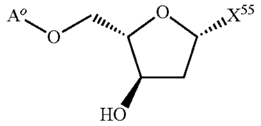

8

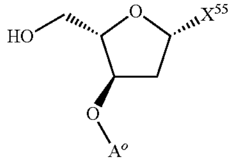

9

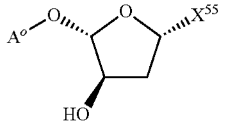

10

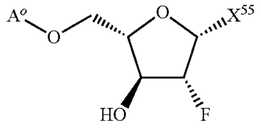

11

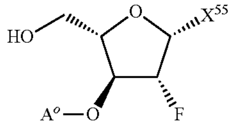

12

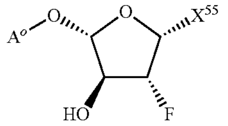

13

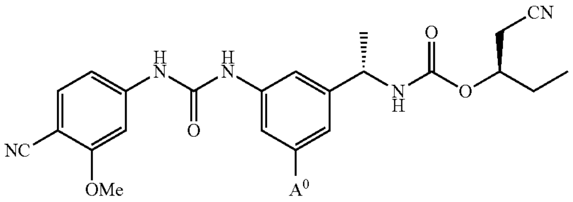

14

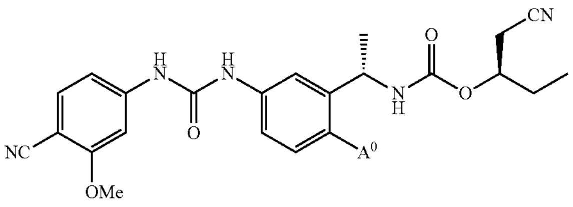

15

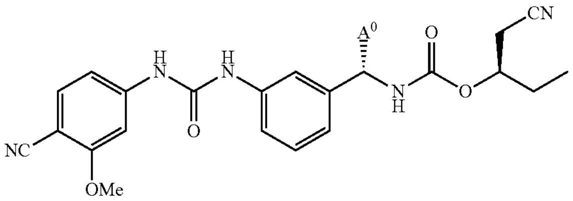

-continued
16
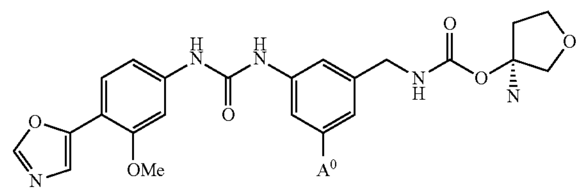
17
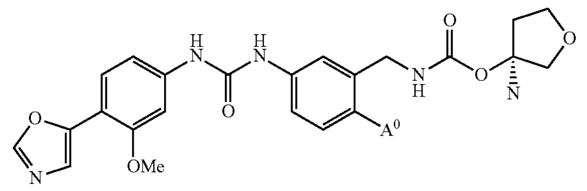
18
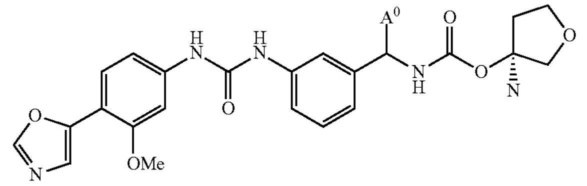
19
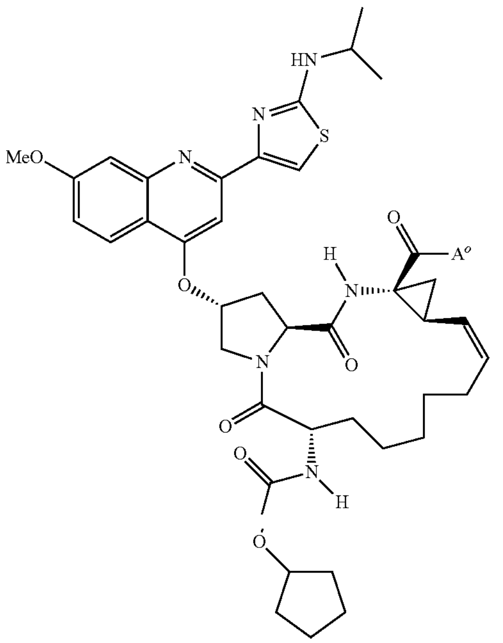
-continued
20
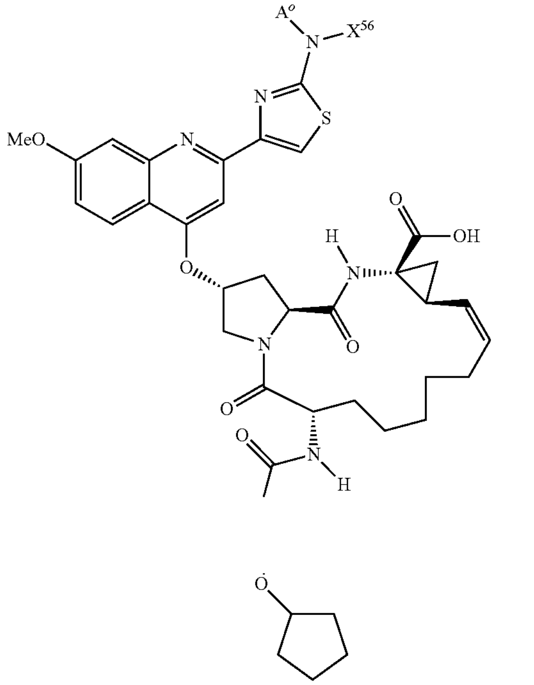
21
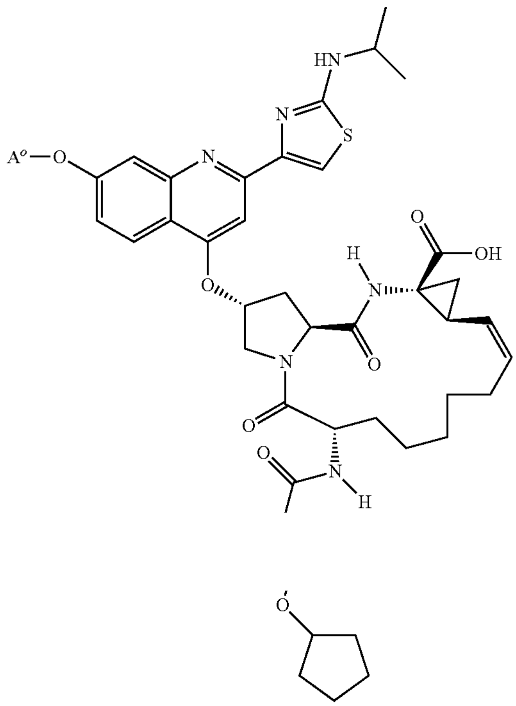

-continued
22
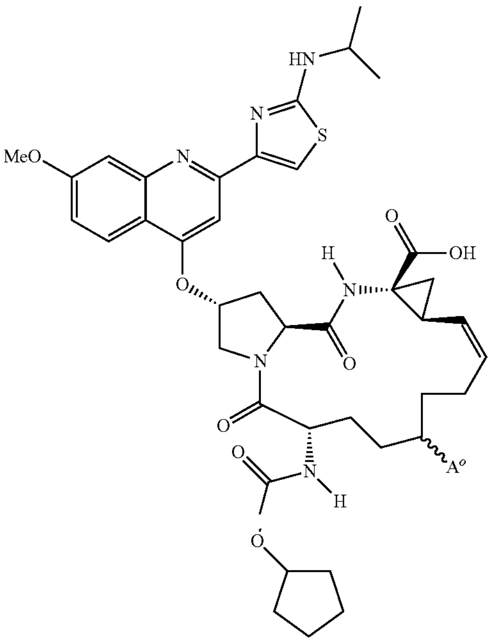
23
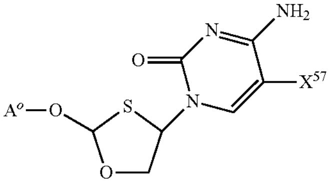
24
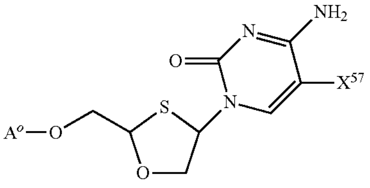
25
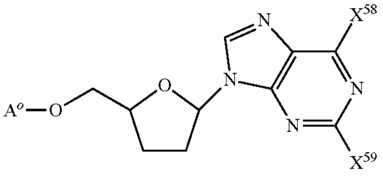
26
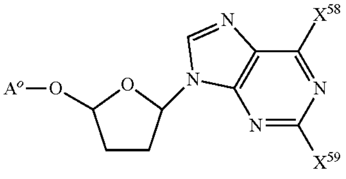
27
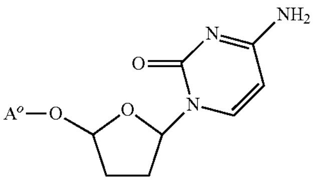
-continued
28
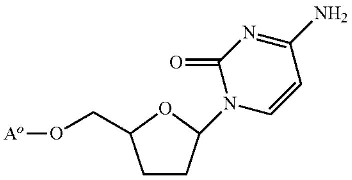
29
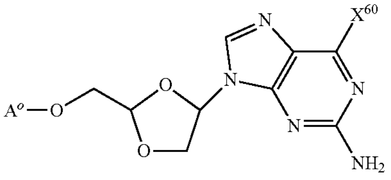
30
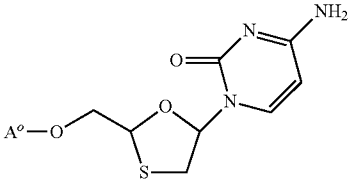
31
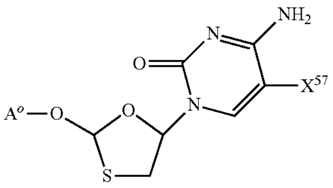
32
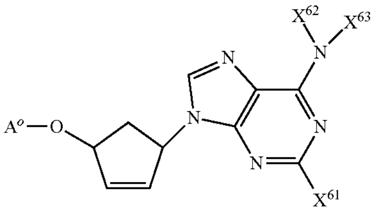
33
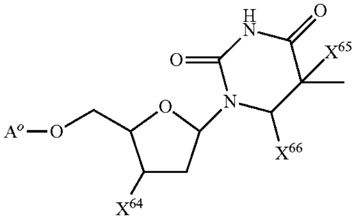
34
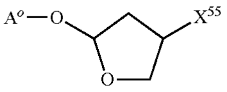
35
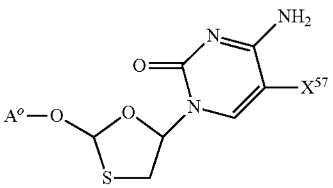

-continued
36
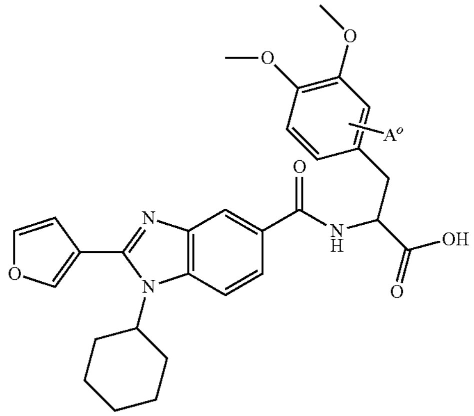
37
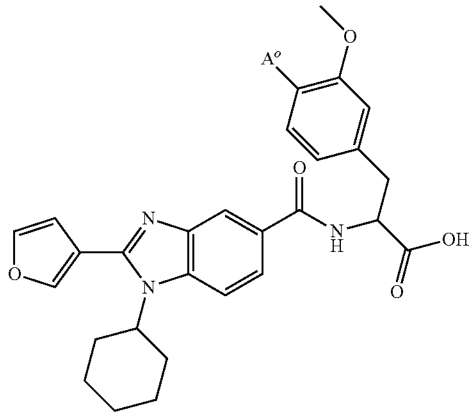
38
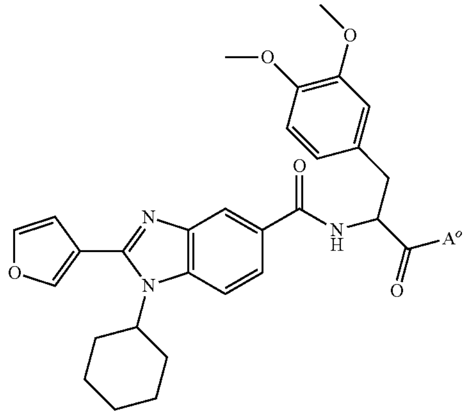
39
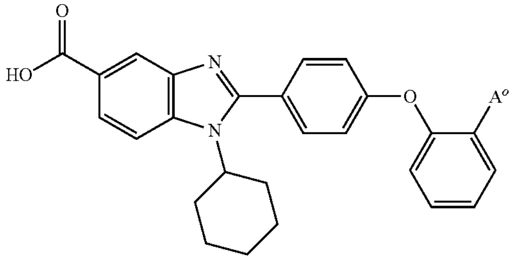
-continued
40
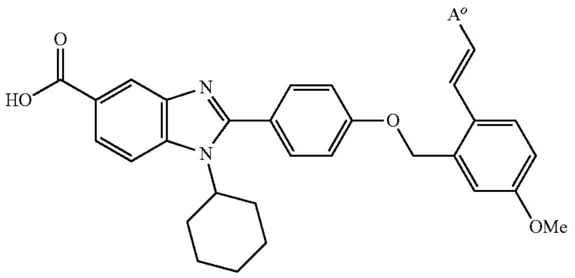
41
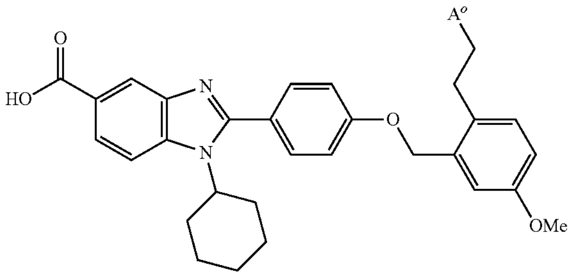
42
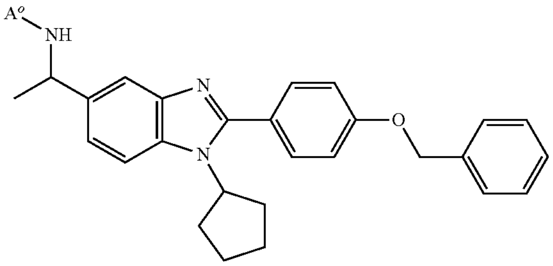
43
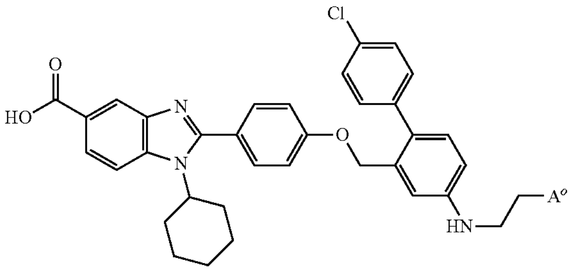
44
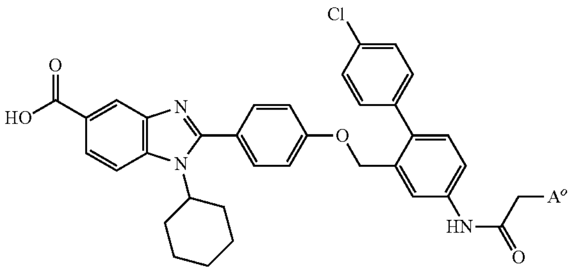

-continued
45
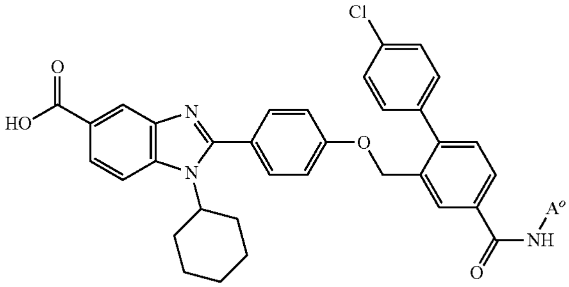
46
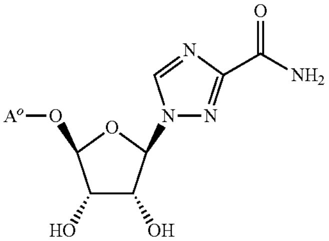
47
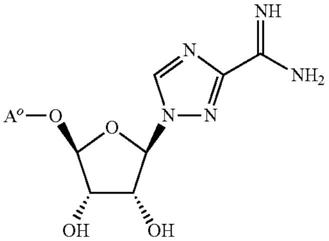
48
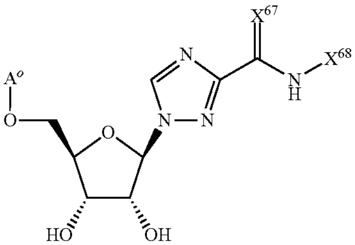
49
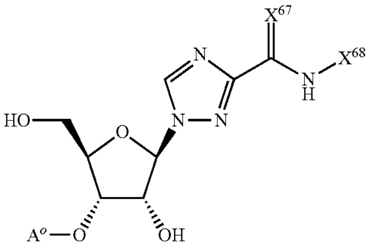
50
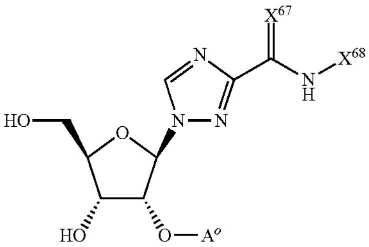
-continued
51
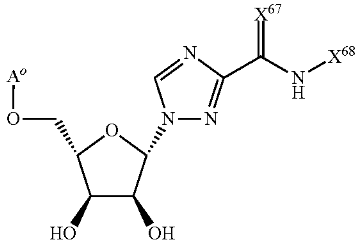
52
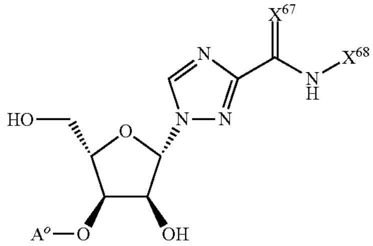
53
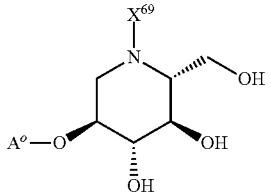
54
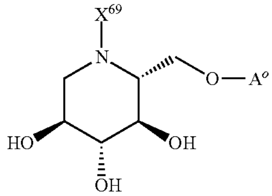
55
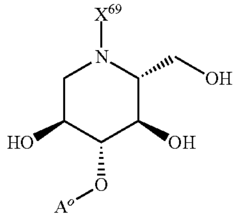
56
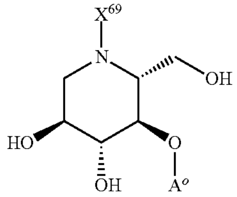
57
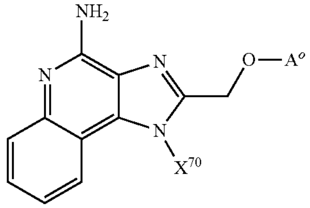

-continued
58
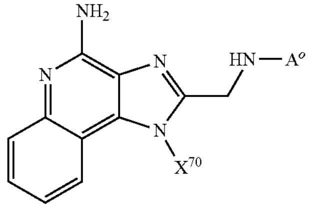
59
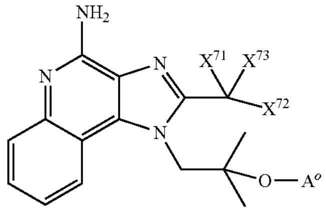
60
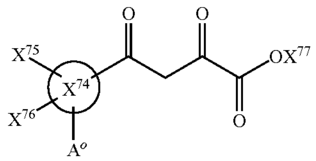
or a tautomer thereof
61
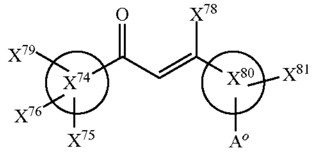
or a tautomer thereof
62
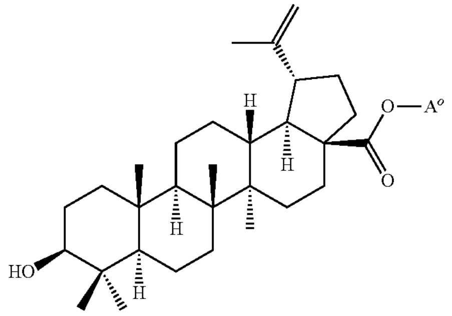
63
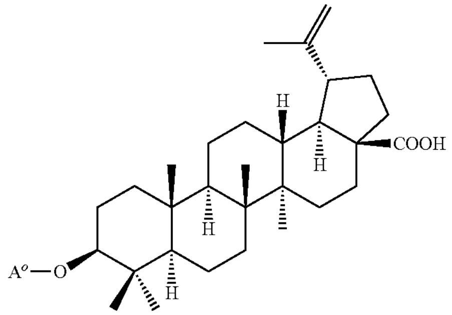
-continued
64
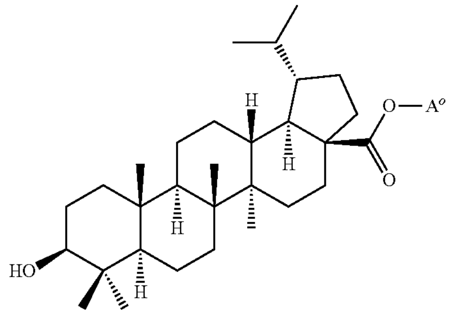
65
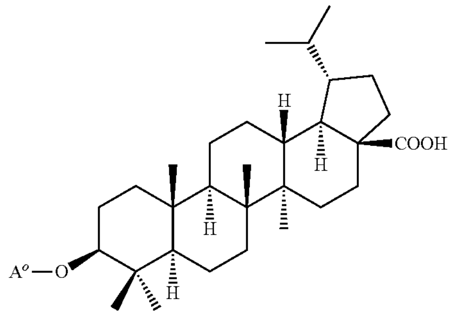
66
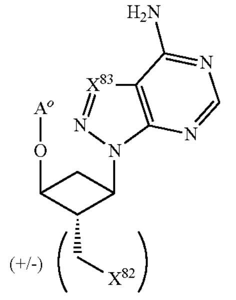
67
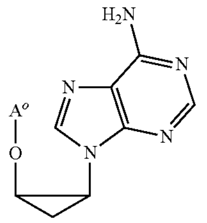
68
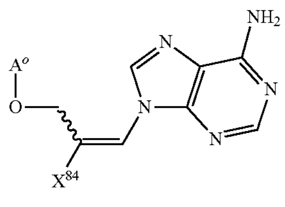
69
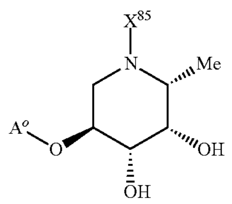

-continued
70
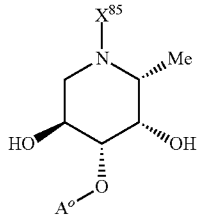
71
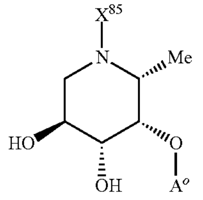
72
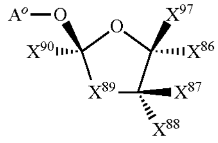
73
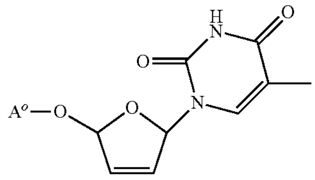
74
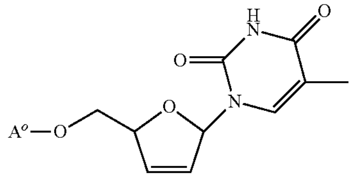
75
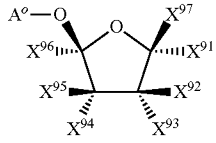
76
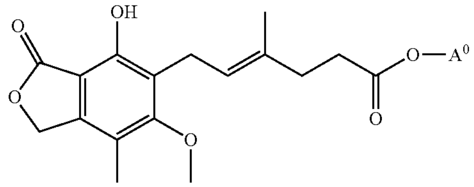
77
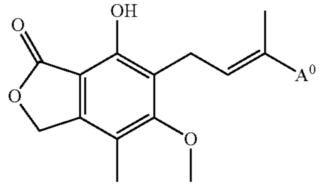
-continued
78
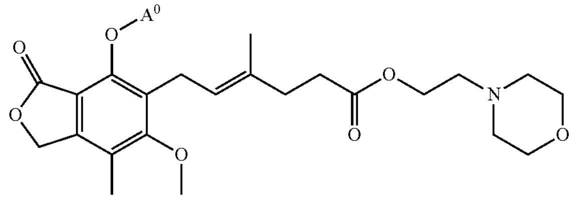
79
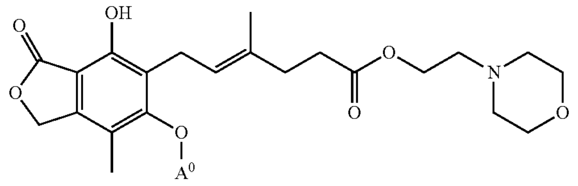
80
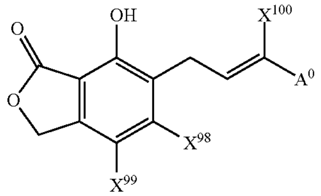
81
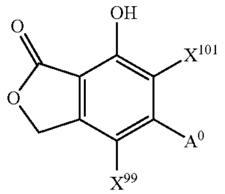
82
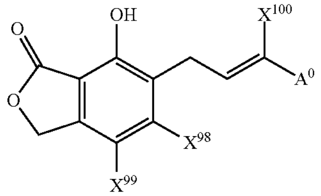
83
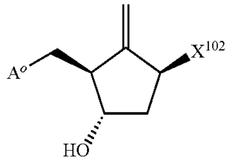
84
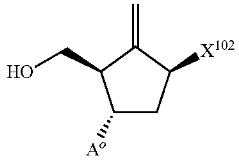

-continued
85
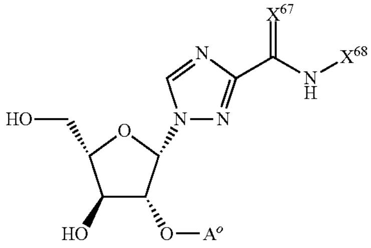
86
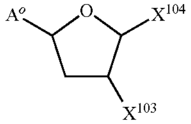
87
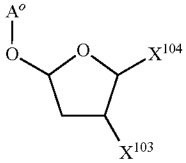
88
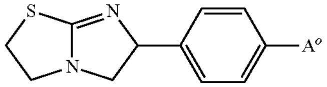
89
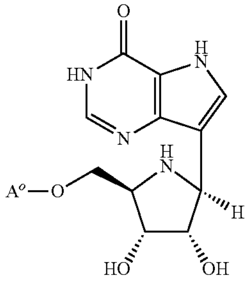
90
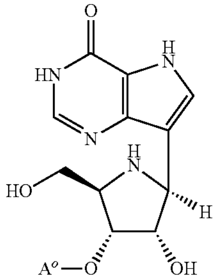
91
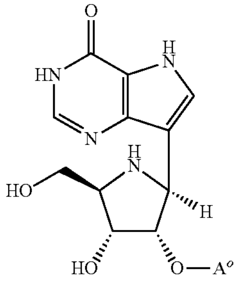
-continued
92
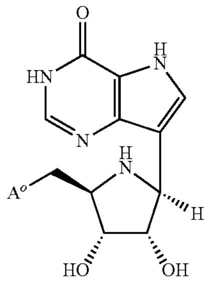
93
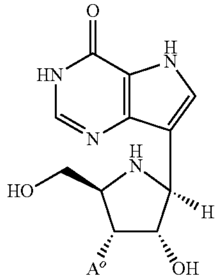
94
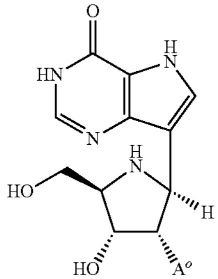
95
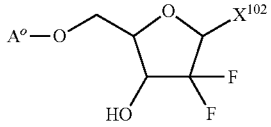
96
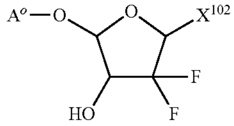
97
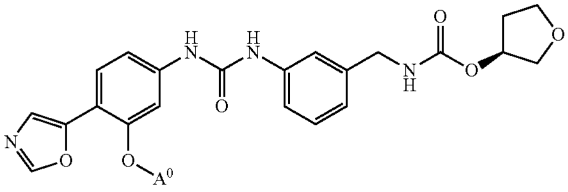
98
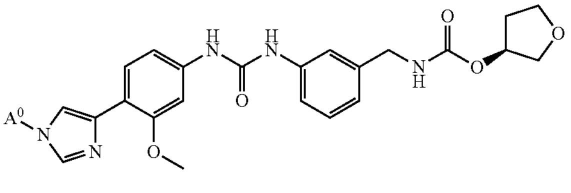

-continued

99

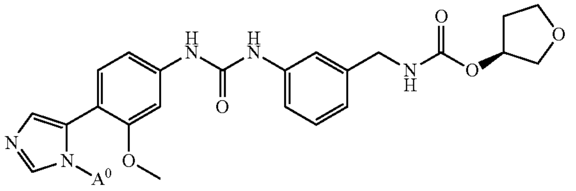

100

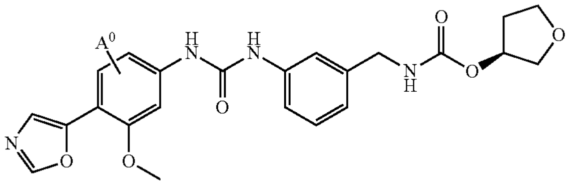

101

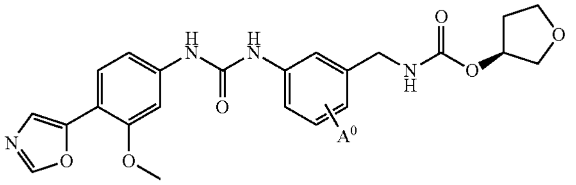

102

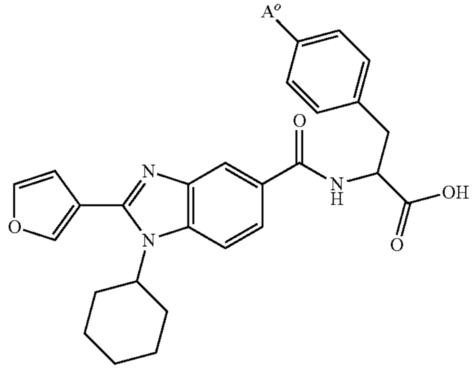

103

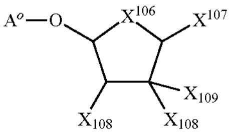

104

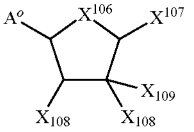

105

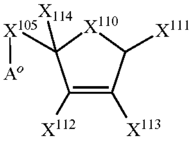

106

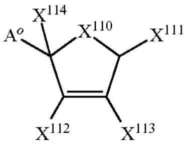

-continued

107

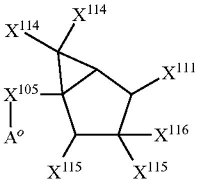

108

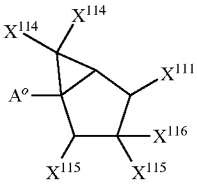

wherein:

$A^0$ is $A^1$;

$A^1$ is:

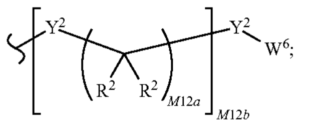

$A^3$ is:

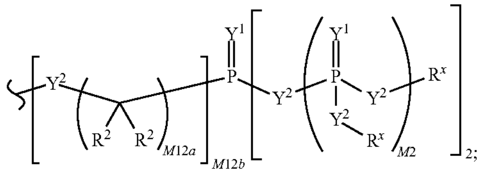

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $—S(O)_{M2}—$, or $—S(O)_{M2}—S(O)_{M2}—$; and when $Y^2$ joins two phosphorous atoms $Y^2$ can also be $C(R^2)(R^2)$;

$R^x$ is independently H, $R^2$, $W^3$, a protecting group, or the formula:

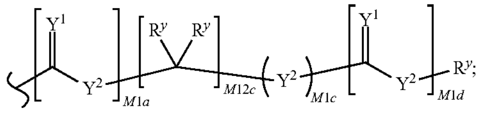

$R^y$ is independently H, $W^3$, $R^2$ or a protecting group;

$R^1$ is independently H or alkyl of 1 to 18 carbon atoms;

$R^2$ is independently H, $R^3$ or $R^4$ wherein each $R^4$ is independently substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, $N_3$ or $—NO_2$;

$R^{3b}$ is $Y^1$;

$R^{3c}$ is $—R^x$, $—N(R^x)(R^x)$, $—SR^x$, $—S(O)R^x$, $—S(O)_2R^x$, $—S(O)(OR^x)$, $—S(O)_2(OR^x)$, $—OC(Y^1)R^x$, $—OC(Y^1)OR^x$, $—OC(Y^1)(N(R^x)(R^x))$, $—SC(Y^1)R^x$, $—SC(Y^1)OR^x$, $—SC(Y^1)(N(R^x)(R^x))$, $—N(R^x)C(Y^1)R^x$, $—N(R^x)C(Y^1)OR^x$, or $—N(R^x)C(Y^1)(N(R^x)(R^x))$;

$R^{3d}$ is —$C(Y^1)R^x$, —$C(Y^1)OR^x$ or —$C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;

$W^3$ is $W^4$ or $W^5$;

$W^4$ is $R^5$, —$C(Y^1)R^5$, —$C(Y^1)W^5$, —$SO_2R^5$, or —$SO_2W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1;

M12c is 0, 1, 2, 3, 4, 5, 6, 7, 8, 9, 10, 11 or 12;

$X^{51}$ is H, α-Br, or β-Br;

$X^{52}$ is $C_1$-$C_5$ alkyl or $C_7$-$C_{10}$ arylalkyl group;

$X^{53}$ is H, alkyl or substituted alkyl;

$X^{54}$ is CH or N;

$X^{55}$ is thymine, adenine, uracil, a 5-halouracil, a 5-alkyluracil, guanine, cytosine, a 5-halo cytosine, a 5-alkyl cytosine, or 2,6-diaminopurine;

$X^{56}$ is H, Me, Et, or i-Pr;

$X^{57}$ is H or F;

$X^{58}$ is OH, Cl, $NH_2$, H, Me, or MeO;

$X^{59}$ is H or $NH_2$;

$X^{60}$ is OH, Cl, $NH_2$, or H;

$X^{61}$ is H, $NH_2$, or NH-alkyl;

$X^{62}$ and $X^{63}$ are independently H, alkyl, or cyclopropyl;

$X^{64}$ is H, $N_3$, $NH_2$, or NHAc;

$X^{65}$ is a halo;

$X^{66}$ is alkoxy, aryloxy, halo-substituted alkoxy, alkenyloxy, arylalkoxy;

$X^{67}$ is O or NH;

$X^{68}$ is H, acetate, benzyl, benzyloxycarbonyl, or an amino protecting group;

$X^{69}$ is H or alkyl;

$X^{70}$ is H; alkyl; alkyl substituted with cycloalkyl containing three to about six carbon atoms that is optionally substituted with one or more alkyl; alkenyl; alkenyl substituted with cycloalkyl containing three to about six carbon atoms that is optionally substituted with one or more alkyl; hydroxyl-substituted alkyl; alkoxy-substituted alkyl; acyloxy-substituted alkyl; aryl; substituted aryl; arylalkyl; or (substituted aryl) alkyl;

$X^{71}$ and $X^{72}$ are each independently hydrogen, alkyl, phenyl, or substituted phenyl;

$X^{73}$ is alkoxy, substituted alkyl, alkylamido amino, monoalkylamino, dialkylamino, azido, chloro, hydroxy, 1-morpholino, 1-pyrrolidino, and alkylthio;

$X^{74}$ is aryl, substituted aryl, heteroaryl, or substituted heteroaryl;

$X^{75}$ and $X^{76}$ attached to nitrogen or carbon in $X^{74}$ wherein $X^{75}$ is H, halo, nitro, $C_1$-$C_6$alkyl, $C_1$-$C_6$alkoxy, (fluoro-substituted)$C_1$-$C_6$alkyl, (fluoro-substituted)$C_1$-$C_6$alkoxy, $C_2$-$C_8$alkoxyalkyl, (fluoro-substituted)$C_2$-$C_8$alkoxyalkyl, $N(R^a)(R^b)$, $(CH_2)_{1-3}N(R^a)(R^b)$, $(CH_2)_{0-3}R^c$, or $O(CH_2)_{0-3}R^c$; and $X^{76}$ is H, halo, nitro, $C_{1-6}$alkyl, $C_{1-6}$alkoxy, (fluoro-substituted)$C_{1-6}$ alkyl, (fluoro-substituted)$C_{1-6}$ alkoxy, $C_{2-8}$alkoxyalkyl, (fluoro-substituted)$C_{2-8}$alkoxyalkyl, $N(R^a)(R^b)$, $(CH_2)_{1-3}N(R^a)(R^b)$, $(CH_2)_{0-3}R^c$, $O(CH_2)_{0-3}R^c$, $(CH_2)_{0-3}$ $R^d$, $O(CH_2)_{0-3}R^d$, $C(=O)CH_2C(=O)R^e$, or $R^f$; $R^a$ and $R^b$ are each independently H, $C_1$-$C_6$ alkyl, or (fluoro-substituted)$C_1$-$C_6$ alkyl; $R^c$ is aryl, or substituted aryl; $R^d$ is heterocycle, or substituted heterocycle; $R^e$ is heteroaryl or substituted heteroaryl; $R^f$ is $X_{120}$—$NH(CH_2)_{1-3}X^{121}$, wherein $X^{120}$ is a 5- or 6-membered monocyclic heterocycle which is saturated or unsaturated and which contains carbon atoms and from 1 to 3 nitrogen atoms and which is unsubstituted or substituted with one or more substituents selected from halo, cyano, OH, $(CH_2)_{1-4}OH$, oxo, $N(R^a)(R^b)$, $C_1$-$C_6$ alkyl, fluorinated $C_1$-$C_6$ alkyl, $C_1$-$C_6$ alkoxy, fluorinated $C_1$-$C_6$ alkoxy, $(CH_2)_{0-4}CO_2R^a$, $(CH_2)_{0-4}C(=O)N(R^a)(R^b)$, $(CH_2)_{0-4}SO_2R^a$, $(CH_2)_{1-4}N(R^a)(R^b)$, $(CH_2)_{0-4}N(R^a)C(=O)R^b$, $(CH_2)_{0-4}SO_2N(R^a)(R^b)$, $(CH_2)_{1-4}N(R^x)SO_2R^b$, $C_2$-$C_8$ alkoxyalkyl, and (fluoro-substituted)$C_2$-$C_8$ alkoxyalkyl; and $X^{121}$ is pyrrolidinyl, piperidinyl, piperazinyl, or morpholinyl, which is unsubstituted or substituted with one or more substituents selected from halo, cyano, OH, $(CH_2)_{1-4}OH$, oxo, $N(R^a)(R^b)$, $C_1$-$C_6$ alkyl, fluorinated $C_1$-$C_6$ alkyl, $C_1$-$C_6$ alkoxy, fluorinated $C_1$-$C_6$ alkoxy, $(CH_2)_{0-4}CO_2R^a$, $(CH_2)_{0-4}C(=O)N(R^a)(R^b)$, $(CH_2)_{0-4}SO_2R^a$, $(CH_2)_{1-4}N(R^a)(R^b)$, $(CH_2)_{0-4}N(R^a)C(=O)R^b$, $(CH_2)_{0-4}SO_2N(R^a)(R^b)$, $(CH_2)_{1-4}N(R^a)SO_2R^b$, $C_2$-$C_8$ alkoxyalkyl, and (fluoro-substituted)$C_2$-$C_8$ alkoxyalkyl;

$X^{77}$ is H or $C_{1-6}$ alkyl;

$X^{78}$ is OH, protected hydroxyl, or $N(R^a)(R^b)$;

$X^{79}$ is a attached to nitrogen or carbon in $X^{74}$; and $X^{79}$ is H, halo, nitro, oxo, $C_{1-6}$alkyl, $C_{3-7}$cycloalkyl, $C_{3-7}$cycloalkoxy, $C_{1-6}$alkoxy, (fluoro-substituted)$C_{1-6}$ alkyl, (fluoro-substituted)$C_{1-6}$ alkoxy, $C_{2-8}$ alkoxyalkyl, (fluoro-substituted)$C_{2-8}$ alkoxyalkyl, $N(R^a)(R^b)$, $(CH_2)_{1-4}N(R^a)(R^b)$, $C(=O)N(R^a)(R^b)$, $(CH_2)_{1-4}C(=O)$ $N(R^a)(R^b)$, $N(R^a)C(=O)R^b$, $(CH_2)_{1-4}N(R^a)C(=O)R^b$, $SO_2R^a$ $(CH_2)_{1-4}SO_2R^a$, $SO_2N(R^a)(R^b)$, $(CH_2)_{1-4}SO_2N(R^a)(R^b)$, $(CH_2)_{1-4}N(R^a)SO_2R^b$, $(CH_2)_{0-3}R^a$, or $(CH_2)_{0-3}R^g$;

$R^g$ is a 5- or 6-membered monocyclic heterocycle which is saturated or unsaturated and which contains one or more carbon atoms and from 1 to 4 nitrogen atoms, the heterocycle being unsubstituted or substituted with one or more substituents selected from halo, cyano, OH, $(CH_2)_{1-4}OH$, oxo, $N(R^a)(R^b)$, $C_1$-$C_6$alkyl, (fluoro-substituted)$C_1$-$C_6$alkyl, $C_1$-$C_6$alkoxy, (fluoro-substituted)$C_1$-$C_6$ alkoxy, $(CH_2)_{0-4}CO_2R^a$, $(CH_2)_{0-4}C(=O)N(R^a)(R^b)$, $(CH_2)_{0-4}SO_2R^a$, $(CH_2)_{1-4}N(R^a)(R^b)$, $(CH_2)_{0-4}N(R^a)C(=O)R^b$, $(CH_2)_{0-4}SO_2N(R^a)(R^b)$, $(CH_2)_{1-4}N(R^a)SO_2R^b$, $C_2$-$C_8$alkoxyalkyl, (fluoro-substituted)$C_2$-$C_8$alkoxyalkyl, phenyl and benzyl;

$X^{80}$ is (i) a 5- or 6-membered heteroaromatic ring containing from 1 to 4 nitrogen atoms, 0 to 2 sulfur atoms, and at least 1 carbon atom, or (ii) an 8- to 10-membered fused bicyclic heterocycle containing from 1 to 4 nitrogen atoms, 0 to 2 sulfur atoms, and carbon atoms, wherein the ring of the heterocycle attached to the central dione moiety is a 5- or 6 membered heteroaromatic ring containing at least one nitrogen or sulfur atom and the other ring of the heterocycle is a saturated or unsaturated ring; wherein $X^{80}$ is attached to the central propenone moiety via a carbon atom and at least one nitrogen or sulfur atom in $X^{80}$ is adjacent to the point of attachment;

$X^{81}$ is attached to nitrogen or carbon in $X^{80}$, and is independently selected from H, halo, OH, $(CH_2)_{1-4}OH$, $C_1$-$C_6$ alkyl, $C_1$-$C_6$ alkoxy, (fluoro-substituted)$C_1$-$C_6$ alkyl, (fluoro-substituted)$C_1$-$C_6$ alkoxy, $C_1$-$C_8$ alkoxyalkyl, (fluoro-substituted)$C_1$-$C_8$ alkoxyalkyl, $N(R^a)(R^b)$, $(CH_2)_{1-4}N(R^a)$ $(R^b)$, $C(=O)N(R^a)(R^b)$, $(CH_2)_{1-4}C(=O)N(R^a)(R^b)$, $N(R^a)C(=O)R^b$, $(CH_2)_{1-4}N(R^a)C(=O)R^b$, $SO_2R^a$, $(CH_2)_{1-4}SO_2R^a$, $SO_2N(R^a)(R^b)$, $(CH_2)_{1-4}SO_2N(R^a)(R^b)$, $(CH_2)_{1-4}N(R^a)$ $SO_2R^b$, and $(CH_2)_{0-3}R^b$;

$X^{82}$ is OH, F, or cyano;

$X^{83}$ is N or CH;

$X^{84}$ is cis H or trans H;

$X^{85}$ is $C_8$-$C_{16}$ alkyl which can optionally contain one to five oxygen atoms in the chain;

$X^{86}$ is H, methyl, hydroxymethyl, or fluoromethyl;

$X^{87}$ and $X^{88}$ are each independently H or $C_{1-4}$ alkyl, which alkyl is optionally substituted with OH, amino, $C_{1-4}$ alkoxy, $C_{1-4}$ alkylthio, or one to three halogen atoms;

$X^{89}$ is —O— or —S(O)n-, where n is 0, 1, or 2;

$X^{90}$ is H, methyl, hydroxymethyl, or fluoromethyl;

$X^{91}$ is H hydroxy, alkyl, azido, cyano, alkenyl, alkynyl, bromovinyl, —C(O)O(alkyl), —O(acyl), alkoxy, alkenyloxy, chloro, bromo, fluoro, iodo, $NO_2$, $NH_2$, —NH(lower alkyl), —NH(acyl), —N(lower alkyl)$_2$, —N(acyl)$_2$;

$X^{92}$ is H, $C_{2-4}$alkenyl, $C_{2-4}$alkynyl, or $C_{1-4}$ alkyl optionally substituted with amino, hydroxy, or 1 to 3 fluorine atoms;

one of $X^{93}$ and $X^{94}$ is hydroxy or $C_{1-4}$ alkoxy and the other of $X^{93}$ and $X^{94}$ is selected from the group consisting of H; hydroxy; halo; $C_{1-4}$ alkyl optionally substituted with 1 to 3 fluorine atoms; $C_{1-10}$ alkoxy, optionally substituted with $C_{1-3}$ alkoxy or 1 to 3 fluorine atoms; $C_{2-6}$ alkenyloxy; $C_{1-4}$alkylthio; $C_{1-4}$ alkylcarbonyloxy; aryloxycarbonyl; azido; amino; $C_{1-4}$ alkylamino; and di($C_{1-4}$ alkyl)amino; or $X^{93}$ is H, $C_{2-4}$ alkenyl, $C_{2-4}$ alkynyl, or $C_{1-4}$ alkyl optionally substituted with amino, hydroxy, or 1 to 3 fluorine atoms, and one of $X^{92}$ and $X^{94}$ is hydroxy or $C_{1-4}$alkoxy and the other of $X^{92}$ and $X^{94}$ is selected from the group consisting of H; hydroxy; halo; $C_{1-4}$ alkyl optionally substituted with 1 to 3 fluorine atoms; $C_{1-10}$ alkoxy, optionally substituted with $C_{1-3}$ alkoxy or 1 to 3 fluorine atoms; $C_{2-6}$ alkenyloxy; $C_{1-4}$alkylthio; $C_{1-8}$ alkylcarbonyloxy; aryloxycarbonyl; azido; amino; $C_{1-4}$ alkylamino; and di($C_{1-4}$ alkyl)amino; or $X^{92}$ and $X^{93}$ together with the carbon atom to which they are attached form a 3- to 6 membered saturated monocyclic ring system optionally containing a heteroatom selected from O, S, and $NC_{0-4}$ alkyl;

$X^{95}$ is H, OH, SH, $NH_2$, $C_{1-4}$ alkylamino, di($C_{1-4}$alkyl) amino, $C_{3-6}$cycloalkylamino, halo, $C_{1-4}$alkyl, $C_{1-4}$ alkoxy, or $CF_3$; or $X^{92}$ and $X^{95}$ can optionally together be a bond linking the two carbons to which they are attached;

$X^{96}$ is H, methyl, hydroxymethyl, or fluoromethyl;

$X^{97}$ is selected from the group consisting of

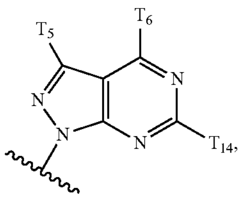

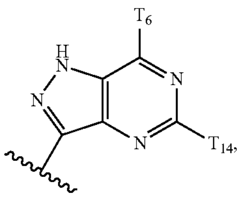

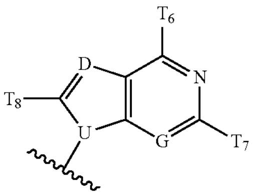

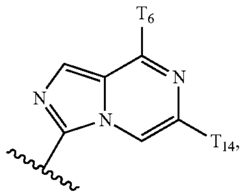

-continued

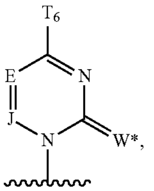

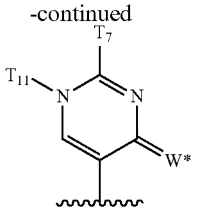

and

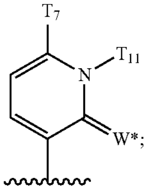

U, G, and J are each independently CH or N;

D is N, CH, C—CN, C—$NO_2$, C—$C_{1-3}$ alkyl, C—NH-$CONH_2$, C—$CONT_{11}T_{11}$, C—$CSNT_{11}T_{11}$, C—$COOT_{11}$, C—C(═NH)$NH_2$, C-hydroxy, C—$C_{1-3}$ alkoxy, C-amino, C—$C_{1-4}$ alkylamino, alkyl)amino, C-halogen, C-(1,3-oxazol-2-yl), C-(1,3 thiazol-2-yl), or C-(imidazol-2-yl); wherein alkyl is unsubstituted or substituted with one to three groups independently selected from halogen, amino, hydroxy, carboxy, and $C_{1-3}$ alkoxy;

E is N or $CT_5$;

$W^a$ is O or S;

$T_1$ is H, $C_{2-4}$alkenyl, $C_{2-4}$alkynyl, or $C_{1-4}$alkyl optionally substituted with amino, hydroxy, or 1 to 3 fluorine atoms and one of $T_2$ and $T_3$ is hydroxy or $C_{1-4}$ alkoxy and the other of $T_2$ and $T_3$ is selected from the group consisting of H; hydroxy; halo; $C_{1-4}$ alkyl optionally substituted with 1 to 3 fluorine atoms; $C_{1-10}$ alkoxy, optionally substituted with $C_{1-3}$ alkoxy or 1 to 3 fluorine atoms; $C_{2-6}$ alkenyloxy; $C_{1-4}$alkylthio; $C_{1-8}$ alkylcarbonyloxy; aryloxycarbonyl; azido; amino; $C_{1-4}$ alkylamino; and di($C_{1-4}$ alkyl)amino; or $T_2$ is H, $C_{2-4}$alkenyl, $C_{2-4}$alkynyl, or $C_{1-4}$alkyl optionally substituted with amino, hydroxy, or 1 to 3 fluorine atoms and one of $T_1$ and $T_3$ is hydroxy or $C_{1-4}$ alkoxy and the other of $T_1$ and $T_3$ is selected from the group consisting of H; hydroxy; halo; $C_{1-4}$ alkyl optionally substituted with 1 to 3 fluorine atoms; $C_{1-10}$ alkoxy, optionally substituted with $C_{1-3}$ alkoxy or 1 to 3 fluorine atoms; $C_{2-6}$ alkenyloxy; $C_1$ alkylthio; $C_{1-8}$ alkylcarbonyloxy; aryloxycarbonyl; azido; amino; $C_{1-4}$ alkylamino; and di($C_{1-4}$ alkyl)amino; or $T_1$ and $T_2$ together with the carbon atom to which they are attached form a 3- to 6 membered saturated monocyclic ring system optionally containing a heteroatom selected from O, S, and $NC_{0-4}$ alkyl;

$T_4$ and $T_6$ are each independently H, OH, SH, $NH_2$, $C_{1-4}$ alkylamino, di($C_{1-4}$ alkyl)amino, $C_{3-6}$cycloalkylamino, halo, $C_{1-4}$ alkyl, $C_{1-4}$ alkoxy, or $CF_3$;

$T_5$ is H, $C_{1-6}$alkyl, $C_{2-6}$alkenyl, $C_{2-6}$alkynyl, $C_1$ alkylamino, $CF_3$, or halogen; $T_{14}$ is H, $CF_3$, $C_{1-4}$ alkyl, amino, $C_{1-4}$alkylamino, $C_{3-6}$cycloalkylamino, or di($C_{1-4}$alkyl) amino;

$T_7$ is H, amino, $C_{1-4}$alkylamino, $C_{3-6}$cycloalkylamino, or di($C_{1-4}$alkyl)amino;

each $T_{11}$ is independently H or $C_{1-6}$ alkyl;

$T_8$ is H, halo, CN, carboxy, $C_{1-4}$ alkyloxycarbonyl, $N_3$, amino, $C_{1-4}$ alkylamino, di($C_{1-4}$ alkyl)amino, hydroxy, $C_{1-6}$ alkoxy, $C_{1-6}$ alkylthio, $C_{1-6}$ alkylsulfonyl, or ($C_{1-4}$ alkyl)$_{0-2}$ aminomethyl;

$X^{98}$ is methoxy, ethoxy, vinyl, ethyl, methyl, cyclopropyl, N-methylamino, or N-formylamino;

$X^{99}$ is methyl, chloro, or trifluoromethyl;

$X^{100}$ is H, methyl, ethyl, cyclopropyl, vinyl, or trifluoromethyl;

$X^{101}$ is H, methyl, ethyl, cyclopropyl, chloro, vinyl, allyl, 3-methyl-1-buten-yl;

$X^{102}$ is thymine, adenine, guanine, cytosine, uracil, inosine, or diaminopurine;

$X^{103}$ is OH, OR, $NR_2$, CN, $NO_2$, F, Cl, Br, or I;

$X^{104}$ is adenine, guanine, cytosine, uracil, thymine, 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, or pyrazolo[3,4-d]pyrimidine;

$X^{105}$ is selected from O, $C(R^y)_2$, $OC(R^y)_2$, NR and S;

$X^{106}$ is selected from O, $C(R^y)_2$, $C{=}C(R^y)_2$, NR and S;

$X^{107}$ is selected from adenine, guanine, cytosine, uracil, thymine, 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^6$-methylthymine, 5,6-dihydrothymine, 5,6-dihydrouracil, 4-methylindole, substituted triazole, and pyrazolo[3,4-D]pyrimidine;

$X^{108}$ is independently selected from H, OH, OR, $NR_2$, CN, $NO_2$, SH, SR, F, Cl, Br, and I;

$X^{109}$ is selected from H, $C_1$-$C_8$alkyl, substituted $C_1$-$C_8$alkyl, $C_1$-$C_8$alkenyl, substituted $C_1$-$C_8$alkenyl, $C_1$-$C_8$alkynyl, and substituted $C_1$-$C_8$alkynyl, $X^{110}$ is independently O, $CR_2$, NR, $^+N(O)(R)$, N(OR), $^+N(O)(OR)$, N—$NR_2$, S, S—S, S(O), or $S(O)_2$;

$X^{111}$ is adenine, guanine, cytosine, uracil, thymine, 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, substituted triazole, or pyrazolo[3,4-D]pyrimidine;

$X^{112}$ is independently selected from H, OH, OR, $NR_2$, CN, $NO_2$, SH, SR, F, Cl, Br, and I;

$X^{113}$ is F;

$X^{114}$ is independently H, F, Cl, Br, I, OH, R, —$C({=}Y^1)R$, —$C({=}Y^1)OR$, —$C({=}Y^1)N(R)_2$, —$N(R)_2$, —$^+N(R)_3$, —SR, —S(O)R, —$S(O)_2R$, —S(O)(OR), —$S(O)_2(OR)$, —$OC({=}Y^1)R$, —$OC({=}Y^1)OR$, —$OC({=}Y^1)(N(R)_2)$, —$SC({=}Y^1)R$, —$SC({=}Y^1)OR$, —$SC({=}Y^1)(N(R)_2)$, —$N(R)C({=}Y^1)R$, —$N(R)C({=}Y^1)OR$, or —$N(R)C({=}Y^1)N(R)_2$, amino (—$NH_2$), ammonium (—$NH_3^+$), alkylamino, dialkylamino, trialkylammonium, $C_1$-$C_8$alkyl, carboxy, sulfate, sulfamate, sulfonate, 5-7 membered ring sultam, $C_1$-$C_8$ alkylsulfonate, 4-dialkylaminopyridinium, hydroxyl-substituted $C_1$-$C_8$alkyl, $C_1$-$C_8$alkylthiol, alkylsulfonyl, arylsulfonyl, arylsulfinyl (—SOAr), arylthio, —$SO_2NR_2$, —SOR, —C(=O)OR, —C(=O)$NR_2$, 5-7 membered ring lactam, 5-7 membered ring lactone, cyano, azido, nitro, $C_1$-$C_8$alkoxy, substituted $C_1$-$C_8$alkyl, $C_1$-$C_8$alkenyl, substituted $C_1$-$C_8$alkenyl, $C_1$-$C_8$alkynyl, substituted $C_1$-$C_8$ alkynyl, aryl, substituted aryl, heterocycle, substituted heterocycle, polyethyleneoxy, a protecting group, or $W^3$; or when taken together, two $R^y$s form a carbocyclic ring of 3 to 7 carbon atoms;

$X^{115}$ is independently selected from H, OH, OR, $NR_2$, CN, $NO_2$, SH, SR, F, Cl, Br, and I; and $X^{116}$ is selected from H, $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, and $C_1$-$C_8$ substituted alkynyl.

The invention provides a pharmaceutical composition comprising an effective amount of a conjugate of the invention, or a pharmaceutically acceptable salt or solvate thereof, and a pharmaceutically acceptable excipient.

This invention pertains to a method of increasing cellular accumulation and retention of an anti-viral compound comprising linking the compound to one or more phosphonate groups.

The invention also provides a method of inhibiting a viral infection in an animal (e.g. a mammal), comprising administering an effective amount a conjugate of the invention to the animal.

The invention also provides a compound of the invention for use in medical therapy (preferably for use in treating a viral infection in an animal), as well as the use of a compound of the invention for the manufacture of a medicament useful for the treatment of a viral infection in an animal (e.g. a mammal).

The invention also provides processes and novel intermediates disclosed herein which are useful for preparing compounds of the invention. Some of the compounds of the invention are useful to prepare other compounds of the invention.

In another embodiment the invention provides a method for inhibiting a viral infection in a sample comprising treating a sample suspected of containing a virus, with a compound or composition of the invention.

DETAILED DESCRIPTION OF EXEMPLARY CLAIMS

Reference will now be made in detail to certain claims of the invention, examples of which are illustrated in the accompanying structures and formulas. While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

Definitions

Unless stated otherwise, the following terms and phrases as used herein are intended to have the following meanings:

When tradenames are used herein, applicants intend to independently include the tradename product and the active pharmaceutical ingredient(s) of the tradename product.

"Bioavailability" is the degree to which the pharmaceutically active agent becomes available to the target tissue after the agent's introduction into the body. Enhancement of the bioavailability of a pharmaceutically active agent can provide a more efficient and effective treatment for patients because, for a given dose, more of the pharmaceutically active agent will be available at the targeted tissue sites.

The terms "phosphonate" and "phosphonate group" include functional groups or moieties within a molecule that comprises a phosphorous that is 1) single-bonded to a carbon, 2) double-bonded to a heteroatom, 3) single-bonded to a heteroatom, and 4) single-bonded to another heteroatom, wherein each heteroatom can be the same or different. The terms "phosphonate" and "phosphonate group" also include functional groups or moieties that comprise a phosphorous in the same oxidation state as the phosphorous described above, as well as functional groups or moieties that comprise a prodrug moiety that can separate from a compound so that the compound retains a phosphorous having the characteriatics described above. For example, the terms "phosphonate" and "phosphonate group" include phosphonic acid, phosphonic monoester, phosphonic diester, phosphonamidate, and phosphonthioate functional groups. In one specific embodiment of the invention, the terms "phosphonate" and "phosphonate group" include functional groups or moieties within a molecule that comprises a phosphorous that is 1) single-bonded to a carbon, 2) double-bonded to an oxygen, 3) single-bonded to an oxygen, and 4) single-bonded to another oxygen, as well as functional groups or moieties that comprise a prodrug moiety that can separate from a compound so that the compound retains a phosphorous having such characteriatics. In another specific embodiment of the invention, the terms "phosphonate" and "phosphonate group" include functional groups or moieties within a molecule that comprises a phosphorous that is 1) single-bonded to a carbon, 2) double-bonded to an oxygen, 3) single-bonded to an oxygen or nitrogen, and 4) single-bonded to another oxygen or nitrogen, as well as functional groups or moieties that comprise a prodrug moiety that can separate from a compound so that the compound retains a phosphorous having such characteristics.

The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically-active compound.

"Prodrug moiety" refers to a labile functional group which separates from the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters $—CH_2OC(=O)R^9$ and acyloxymethyl carbonates $—CH_2OC(=O)OR^9$ where $R^9$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 324; also U.S. Pat. Nos. 4,816,570, 4,968,788, 5,663,159 and 5792756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) $—CH_2OC(=O)C(CH_3)_3$. An exemplary acyloxymethyl carbonate prodrug moiety is pivaloyloxymethylcarbonate (POC) $—CH_2OC(=O)OC(CH_3)_3$.

The phosphonate group may be a phosphonate prodrug moiety. The prodrug moiety may be sensitive to hydrolysis, such as, but not limited to a pivaloyloxymethyl carbonate (POC) or POM group. Alternatively, the prodrug moiety may be sensitive to enzymatic potentiated cleavage, such as a lactate ester or a phosphonamidate-ester group.

Aryl esters of phosphorus groups, especially phenyl esters, are reported to enhance oral bioavailability (De Lombaert et al. (1994) *J. Med. Chem.* 37: 498). Phenyl esters containing a carboxylic ester ortho to the phosphate have also been described (Khamnei and Torrence, (1996) *J. Med. Chem.* 39:4109-4115). Benzyl esters are reported to generate the parent phosphonic acid. In some cases, substituents at the ortho- or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate the phosphoric acid and the quinone methide intermediate. Examples of this class of prodrugs are described by Mitchell et al. (1992) *J. Chem. Soc. Perkin Trans. II* 2345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.,* 22: 155-174; Benzaria et al. (1996) *J. Med. Chem.* 39: 4958). Cyclic phosphonate esters have also been described as prodrugs of phosphorus-containing compounds (Erion et al., U.S. Pat. No. 6,312,662).

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Any reference to any of the compounds of the invention also includes a reference to a physiologically acceptable salt thereof. Examples of physiologically acceptable salts of the compounds of the invention include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of an hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

"Alkyl" is $C_1$-$C_{18}$ hydrocarbon containing normal, secondary, tertiary or cyclic carbon atoms. Examples are methyl (Me, $-CH_3$), ethyl (Et, $-CH_2CH_3$), 1-propyl (n-Pr, n-propyl, $-CH_2CH_2CH_3$), 2-propyl (i-Pr, $-CH(CH_3)_2$), 1-butyl (n-Bu, n-butyl, $-CH_2CH_2CH_2CH_3$), 2-methyl-1-propyl (i-Bu, i-butyl, $-CH_2CH(CH_3)_2$), 2-butyl (s-Bu, s-butyl, $-CH(CH_3)CH_2CH_3$), 2-methyl-2-propyl (t-Bu, t-butyl, $-C(CH_3)_3$), 1-pentyl (n-pentyl, $-CH_2CH_2CH_2CH_2CH_3$), 2-pentyl ($-CH(CH_3)CH_2CH_2CH_3$), 3-pentyl ($-CH(CH_2CH_3)_2$), 2-methyl-2-butyl ($-C(CH_3)_2CH_2CH_3$), 3-methyl-2-butyl ($-CH(CH_3)CH(CH_3)_2$), 3-methyl-1-butyl ($-CH_2CH_2CH(CH_3)_2$), 2-methyl-1-butyl ($-CH_2CH(CH_3)CH_2CH_3$), 1-hexyl ($-CH_2CH_2CH_2CH_2CH_2CH_3$), 2-hexyl ($-CH(CH_3)CH_2CH_2CH_2CH_3$), 3-hexyl ($-CH(CH_2CH_3)(CH_2CH_2CH_3)$), 2-methyl-2-pentyl ($-C(CH_3)_2CH_2CH_2CH_3$), 3-methyl-2-pentyl ($-CH(CH_3)CH(CH_3)CH_2CH_3$), 4-methyl-2-pentyl ($-CH(CH_3)CH_2CH(CH_3)_2$), 3-methyl-3-pentyl ($-C(CH_3)(CH_2CH_3)_2$), 2-methyl-3-pentyl ($-CH(CH_2CH_3)CH(CH_3)_2$), 2,3-dimethyl-2-butyl ($-C(CH_3)_2CH(CH_3)_2$), 3,3-dimethyl-2-butyl ($-CH(CH_3)C(CH_3)_3$.

"Alkenyl" is $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to, ethylene or vinyl ($-CH{=}CH_2$), allyl ($-CH_2CH{=}CH_2$), cyclopentenyl ($-C_5H_7$), and 5-hexenyl ($-CH_2 CH_2CH_2CH_2CH{=}CH_2$).

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to, acetylenic ($-C{\equiv}CH$) and propargyl ($-CH_2C{\equiv}CH$), "Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene ($-CH_2-$) 1,2-ethyl ($-CH_2CH_2-$), 1,3-propyl ($-CH_2CH_2CH_2-$), 1,4-butyl ($-CH_2CH_2CH_2CH_2-$), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to, 1,2-ethylene ($-CH{=}CH-$).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to, acetylene ($-C{\equiv}C-$), propargyl ($-CH_2C{\equiv}C-$), and 4-pentynyl ($-CH_2CH_2CH_2C{\equiv}CH-$).

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or $sp^a$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

"Substituted alkyl", "substituted aryl", and "substituted arylalkyl" mean alkyl, aryl, and arylalkyl respectively, in which one or more hydrogen atoms are each independently replaced with a non-hydrogen substituent. Typical substituents include, but are not limited to, —X, —R, $-O^-$, —OR, —SR, $-S^-$, $-NR_2$, $-NR_3$, =NR, $-CX_3$, —CN, —OCN, —SCN, —N=C=O, —NCS, —NO, $-NO_2$, $=N_2$, $-N_3$, NC(=O)R, —C(=O)R, —C(=O)NRR—$S(=O)_2O^-$, $-S(=O)_2OH$, $-S(=O)_2R$, $-OS(=O)_2OR$, $-S(=O)_2NR$, —S(=O)R, $-OP(=O)O_2RR$, $-P(=O)O_2RR$—$P(=O)(O^-)_2$, $-P(=O)(OH)_2$, —C(=O)R, —C(=O)X, —C(S)R, —C(O)OR, $-C(O)O^-$, —C(S)OR, —C(O)SR, —C(S)SR, —C(O)NRR, —C(S)NRR, —C(NR)NRR, where each X is independently a halogen: F, Cl, Br, or I; and each R is independently —H, alkyl, aryl, heterocycle, protecting group or prodrug moiety. Alkylene, alkenylene, and alkynylene groups may also be similarly substituted.

"Heterocycle" as used herein includes by way of example and not limitation these heterocycles described in Paquette, Leo A.; *Principles of Modern Heterocyclic Chemistry* (W. A. Benjamin, New York, 1968), particularly Chapters 1, 3, 4, 6, 7, and 9*; The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S).

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl,β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

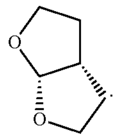

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" refers to a saturated, unsaturated or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl.

"Linker" or "link" refers to a chemical moiety comprising a covalent bond or a chain or group of atoms that covalently attaches a phosphonate group to a drug. Linkers include portions of substituents $A^1$ and $A^3$, which include moieties such as: repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

The phosphonate moieties of the compounds of the invention may or may not be prodrug moieties, i.e. they may or may be susceptible to hydrolytic or enzymatic cleavage or modification. Certain phosphonate moieties are stable under most or nearly all metabolic conditions. For example, a dialkylphosphonate, where the alkyl groups are two or more carbons, may have appreciable stability in vivo due to a slow rate of hydrolysis.

Within the context of phosphonate prodrug moieties, a large number of structurally-diverse prodrugs have been described for phosphonic acids (Freeman and Ross in *Progress in Medicinal Chemistry* 34: 112-147 (1997) and are included within the scope of the present invention. An exemplary phosphonate ester-forming group is the phenyl carbocycle in substructure $A_3$ having the formula:

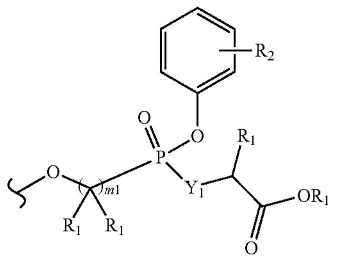

wherein $R_1$ may be H or $C_1$-$C_{12}$ alkyl; m1 is 1, 2, 3, 4, 5, 6, 7 or 8, and the phenyl carbocycle is substituted with 0 to 3 $R_2$ groups. Where $Y_1$ is 0, a lactate ester is formed, and where $Y_1$ is $N(R_2)$, $N(OR_2)$ or $N(N(R_2)_2$, a phosphonamidate ester results.

In its ester-forming role, a protecting group typically is bound to any acidic group such as, by way of example and not limitation, a $—CO_2H$ or —C(S)OH group, thereby resulting in $—CO_2R^x$ where $R^x$ is defined herein. Also, $R^x$ for example includes the enumerated ester groups of WO 95/07920.

Examples of protecting groups include:

$C_3$-$C_{12}$ heterocycle (described above) or aryl. These aromatic groups optionally are polycyclic or monocyclic. Examples include phenyl, spiryl, 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 1-, 2-, 3- and 4-pyridinyl, and 1-, 2-, 4- and 5-pyrimidinyl, $C_3$-$C_{12}$ heterocycle or aryl substituted with halo, $R^1$, $R^1$—O—$C_1$-$C_{12}$ alkylene, $C_1$-$C_{12}$ alkoxy, CN, $NO_2$, OH, carboxy, carboxyester, thiol, thioester, $C_1$-$C_{12}$ haloalkyl (1-6 halogen atoms), $C_2$-$C_{12}$ alkenyl or $C_2$-$C_{12}$ alkynyl. Such groups include 2-, 3- and 4-alkoxyphenyl ($C_1$-$C_{12}$ alkyl), 2-, 3- and 4-methoxyphenyl, 2-, 3- and 4-ethoxyphenyl, 2,3-, 2,4-, 2,5-, 2,6-, 3,4- and 3,5-diethoxyphenyl, 2- and 3-carboethoxy-4-hydroxyphenyl, 2- and 3-ethoxy-4-hydroxyphenyl, 2- and 3-ethoxy-5-hydroxyphenyl, 2- and 3-ethoxy-6-hydroxyphenyl, 2-, 3- and 4-O-acetylphenyl, 2-, 3- and 4-dimethylaminophenyl, 2-, 3- and 4-methylmercaptophenyl, 2-, 3- and 4-halophenyl (including 2-, 3- and 4-fluorophenyl and 2-, 3- and 4-chlorophenyl), 2,3-, 2,4-, 2,5-, 2,6-, 3,4- and 3,5-dimethylphenyl, 2,3-, 2,4-, 2,5-, 2,6-, 3,4- and 3,5-biscarboxyethylphenyl, 2,3-, 2,4-, 2,5-, 2,6-, 3,4- and 3,5-dimethoxyphenyl, 2,3-, 2,4-, 2,5-, 2,6-, 3,4- and 3,5-dihalophenyl (including 2,4-difluorophenyl and 3,5-difluorophenyl), 2-, 3- and 4-haloalkylphenyl (1 to 5 halogen atoms, $C_1$-$C_{12}$ alkyl including 4-trifluoromethylphenyl), 2-, 3- and 4-cyanophenyl, 2-, 3- and 4-nitrophenyl, 2-, 3- and 4-haloalkylbenzyl (1 to 5 halogen atoms, $C_1$-$C_{12}$ alkyl including 4-trifluoromethylbenzyl and 2-, 3- and 4-trichloromethylphenyl and 2-, 3- and 4-trichloromethylphenyl), 4-N-methylpiperidinyl, 3-N-methylpiperidinyl, 1-ethylpiperazinyl, benzyl, alkylsalicylphenyl ($C_1$-$C_4$ alkyl, including 2-, 3- and 4-ethylsalicylphenyl), 2-,3- and 4-acetylphenyl, 1,8-dihydroxynaphthyl ($—C_{10}H_6—OH$) and aryloxy ethyl [$C_6$-$C_9$ aryl (including phenoxy ethyl)], 2,2'-dihydroxybiphenyl, 2-, 3- and 4-N, N-dialkylaminophenol, $—C_6H_4CH_2—N(CH_3)_2$, trimethoxybenzyl, triethoxybenzyl, 2-alkyl pyridinyl ($C_{1-4}$ alkyl);

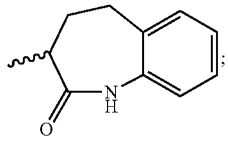 ;

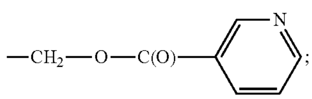 ; 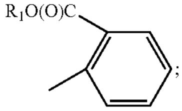 ;

$C_4$-$C_8$ esters of 2-carboxyphenyl; and $C_1$-$C_4$ alkylene-$C_3$-$C_6$ aryl (including benzyl, $—CH_2$-pyrrolyl, $—CH_2$-thienyl, $—CH_2$-imidazolyl, $—CH_2$-oxazolyl, $—CH_2$-isoxazolyl, $—CH_2$-thiazolyl, $—CH_2$-isothiazolyl, $—CH_2$-pyrazolyl, $—CH_2$-pyridinyl and $—CH_2$-pyrimidinyl) substituted in the aryl moiety by 3 to 5 halogen atoms or 1 to 2 atoms or groups selected from halogen, $C_1$-$C_{12}$ alkoxy (including methoxy and ethoxy), cyano, nitro, OH, $C_1$-$C_{12}$ haloalkyl (1 to 6 halogen atoms; including $—CH_2CCl_3$), $C_1$-$C_{12}$ alkyl (including methyl and ethyl), $C_2$-$C_{12}$ alkenyl or $C_2$-$C_{12}$ alkynyl; alkoxy ethyl [$C_1$-$C_6$ alkyl including $—CH_2—CH_2—O—CH_3$ (methoxy ethyl)]; alkyl substituted by any of the groups set forth above for aryl, in particular OH or by 1 to 3 halo atoms (including $—CH_3$, $—CH(CH_3)_2$, $—C(CH_3)_3$, $—CH_2CH_3$, $—(CH_2)_2CH_3$, $—(CH_2)_3CH_3$, $—(CH_2)_4CH_3$, $—(CH_2)_5CH_3$, $—CH_2CH_2F$, $—CH_2CH_2Cl$, $—CH_2CF_3$, and $—CH_2CC_3$);

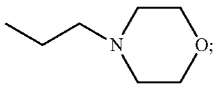

—N-2-propylmorpholino, 2,3-dihydro-6-hydroxyindene, sesamol, catechol monoester, $—CH_2—C(O)—N(R^1)_2$, $—CH_2—S(O)(R^1)$, $—CH_2—S(O)_2(R^1)$, $—CH_2—CH(OC(O)CH_2R^1)—CH_2(OC(O)CH_2R^1)$, cholesteryl, enolpyruvate ($HOOC—C(=CH_2)—$), glycerol;

a 5 or 6 carbon monosaccharide, disaccharide or oligosaccharide (3 to 9 monosaccharide residues);

triglycerides such as α-D-β-diglycerides (wherein the fatty acids composing glyceride lipids generally are naturally occurring saturated or unsaturated $C_{6-26}$, $C_{6-18}$ or $C_{6-10}$ fatty acids such as linoleic, lauric, myristic, palmitic, stearic, oleic, palmitoleic, linolenic and the like fatty acids) linked to acyl of the parental compounds herein through a glyceryl oxygen of the triglyceride;

phospholipids linked to the carboxyl group through the phosphate of the phospholipid;

phthalidyl (shown in FIG. 1 of Clayton et al., *Antimicrob. Agents Chemo.* (1974) 5(6):670-671;

cyclic carbonates such as (5-$R_d$-2-oxo-1,3-dioxolen-4-yl) methyl esters (Sakamoto et al., *Chem. Pharm. Bull.* (1984) 32(6)2241-2248) where $R_d$ is $R_1$, $R_4$ or aryl; and

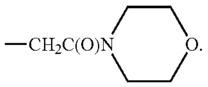

The hydroxyl groups of the compounds of this invention optionally are substituted with one of groups III, IV or V disclosed in WO 94/21604, or with isopropyl.

Table A lists examples of protecting group ester moieties that for example can be bonded via oxygen to —C(O)O— and $—P(O)(O—)_2$ groups. Several amidates also are shown, which are bound directly to —C(O)— or $—P(O)_2$. Esters of structures 1-5, 8-10 and 16, 17, 19-22 are synthesized by reacting the compound herein having a free hydroxyl with the corresponding halide (chloride or acyl chloride and the like) and N,N-dicyclohexyl-N-morpholine carboxamidine (or another base such as DBU, triethylamine, $CsCO_3$, N,N-dimethylaniline and the like) in DMF (or other solvent such as acetonitrile or N-methylpyrrolidone). When the compound to be protected is a phosphonate, the esters of structures 5-7, 11, 12, 21, and 23-26 are synthesized by reaction of the alcohol or alkoxide salt (or the corresponding amines in the case of compounds such as 13, 14 and 15) with the monochlorophosphonate or dichlorophosphonate (or another activated phosphonate).

TABLE A

| | |
|---|---|
| $—CH_2—C(O)—N(R_1)_2$ * | 1. |
| $—CH_2—S(O)(R_1)$ | 2. |
| $—CH_2—S(O)_2(R_1)$ | 3. |
| $—CH_2—O—C(O)—CH_2—C_6H_5$ | 4. |
| 3-cholesteryl | 5. |
| 3-pyridyl | 6. |
| N-ethylmorpholino | 7. |
| $—CH_2—O—C(O)—C_6H_5$ | 8. |
| $—CH_2—O—C(O)—CH_2CH_3$ | 9. |
| $—CH_2—O—C(O)—C(CH_3)_3$ | 10. |
| $—CH_2—CCl_3$ | 11. |
| $—C_6H_5$ | 12. |
| $—NH—CH_2—C(O)O—CH_2CH_3$ | 13. |
| $—N(CH_3)—CH_2—C(O)O—CH_2CH_3$ | 14. |
| $—NHR_1$ | 15. |
| $—CH_2—O—C(O)—C_{10}H_{15}$ | 16. |
| $—CH_2—O—C(O)—CH(CH_3)_2$ | 17. |
| $—CH_2—C$#$H(OC(O)CH_2R_1)—CH_2—(OC(O)CH_2R_1)$* | 18. |
| 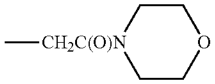 | 19. |
| 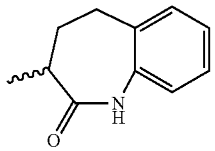 | 20. |
| 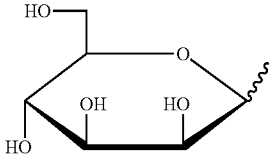 | 21. |
| 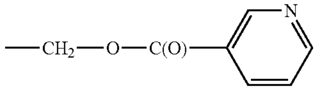 | 22. |
| 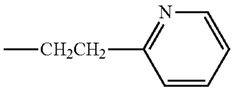 | 23. |
| 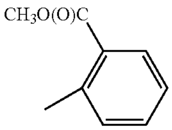 | 24. |
| 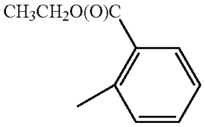 | 25. |
| 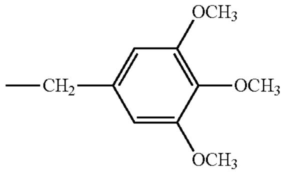 | 26. |

#chiral center is (R), (S) or racemate.

Other esters that are suitable for use herein are described in EP 632048.

Protecting groups also includes "double ester" forming profunctionalities such as $—CH_2OC(O)OCH_3$,

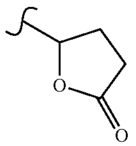

$-CH_2SCOCH_3$, $-CH_2OCON(CH_3)_2$, or alkyl- or aryl-acyloxyalkyl groups of the structure $-CH(R^1$ or $W^5)O((CO)R^{37})$ or $-CH(R^1$ or $W^5)((CO)OR^{38})$ (linked to oxygen of the acidic group) wherein $R^{37}$ and $R^{38}$ are alkyl, aryl, or alkylaryl groups (see U.S. Pat. No. 4,968,788). Frequently $R^{37}$ and $R^{38}$ are bulky groups such as branched alkyl, ortho-substituted aryl, meta-substituted aryl, or combinations thereof, including normal, secondary, iso- and tertiary alkyls of 1-6 carbon atoms. An example is the pivaloyloxymethyl group. These are of particular use with prodrugs for oral administration. Examples of such useful protecting groups are alkylacyloxymethyl esters and their derivatives, including $-CH(CH_2CH_2OCH_3)OC(O)C(CH_3)_3$,

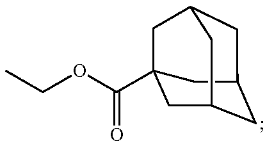

$-CH_2OC(O)C_{10}H_{15}$, $-CH_2OC(O)C(CH_3)_3$, $-CH(CH_2OCH_3)OC(O)C(CH_3)_3$, $-CH(CH(CH_3)_2)OC(O)C(CH_3)_3$, $-CH_2OC(O)CH_2CH(CH_3)_2$, $-CH_2OC(O)C_6H_{11}$, $-CH_2OC(O)C_6H_5$, $-CH_2OC(O)C_{10}H_{15}$, $-CH_2OC(O)CH_2CH_3$, $-CH_2OC(O)CH(CH_3)_2$, $-CH_2OC(O)C(CH_3)_3$ and $-CH_2OC(O)CH_2C_6H_5$.

In some claims the protected acidic group is an ester of the acidic group and is the residue of a hydroxyl-containing functionality. In other claims, an amino compound is used to protect the acid functionality. The residues of suitable hydroxyl or amino-containing functionalities are set forth above or are found in WO 95/07920. Of particular interest are the residues of amino acids, amino acid esters, polypeptides, or aryl alcohols. Typical amino acid, polypeptide and carboxyl-esterified amino acid residues are described on pages 11-18 and related text of WO 95/07920 as groups L1 or L2. WO 95/07920 expressly teaches the amidates of phosphonic acids, but it will be understood that such amidates are formed with any of the acid groups set forth herein and the amino acid residues set forth in WO 95/07920.

Typical esters for protecting acidic functionalities are also described in WO 95/07920, again understanding that the same esters can be formed with the acidic groups herein as with the phosphonate of the '920 publication. Typical ester groups are defined at least on WO 95/07920 pages 89-93 (under $R^{31}$ or $R^{35}$), the table on page 105, and pages 21-23 (as R). Of particular interest are esters of unsubstituted aryl such as phenyl or arylalkyl such benzyl, or hydroxy-, halo-, alkoxy-, carboxy- and/or alkylestercarboxy-substituted aryl or alkylaryl, especially phenyl, ortho-ethoxyphenyl, or $C_1$-$C_4$ alkylestercarboxyphenyl (salicylate $C_1$-$C_{12}$ alkylesters).

The protected acidic groups, particularly when using the esters or amides of WO 95/07920, are useful as prodrugs for oral administration. However, it is not essential that the acidic group be protected in order for the compounds of this invention to be effectively administered by the oral route. When the compounds of the invention having protected groups, in particular amino acid amidates or substituted and unsubstituted aryl esters are administered systemically or orally they are capable of hydrolytic cleavage in vivo to yield the free acid.

One or more of the acidic hydroxyls are protected. If more than one acidic hydroxyl is protected then the same or a different protecting group is employed, e.g., the esters may be different or the same, or a mixed amidate and ester may be used.

Typical hydroxy protecting groups described in Greene (pages 14-118) include substituted methyl and alkyl ethers, substituted benzyl ethers, silyl ethers, esters including sulfonic acid esters, and carbonates. For example:

Ethers (methyl, t-butyl, allyl);

Substituted Methyl Ethers (Methoxymethyl, Methylthiomethyl, t-Butylthiomethyl, (Phenyldimethylsilyl)methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis(2-chloroethoxy)methyl, 2-(Trimethylsilyl)ethoxymethyl, Tetrahydropyranyl, 3-Bromotetrahydropyranyl, Tetrahydropthiopyranyl, 1-Methoxycyclohexyl, 4-Methoxytetrahydropyranyl, 4-Methoxytetrahydrothiopyranyl, 4-Methoxytetrahydropthiopyranyl S,S-Dioxido, 1-[(2-Chloro-4-methyl)phenyl]-4-methoxypiperidin-4-yl, 1,4-Dioxan-2-yl, Tetrahydrofuranyl, Tetrahydrothiofuranyl, 2,3,3a,4,5,6,7,7a-Octahydro-7,8,8-trimethyl-4,7-methanobenzofuran-2-yl));

Substituted Ethyl Ethers (1-Ethoxyethyl, 1-(2-Chloroethoxy)ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl)ethyl, p-Chlorophenyl, p-Methoxyphenyl, 2,4-Dinitrophenyl, Benzyl);

Substituted Benzyl Ethers (p-Methoxybenzyl, 3,4-Dimethoxybenzyl, o-Nitrobenzyl, p-Nitrobenzyl, p-Halobenzyl, 2,6-Dichlorobenzyl, p-Cyanobenzyl, p-Phenylbenzyl, 2- and 4-Picolyl, 3-Methyl-2-picolyl N-Oxido, Diphenylmethyl, p,p'-Dinitrobenzhydryl, 5-Dibenzosuberyl, Triphenylmethyl, α-Naphthyldiphenylmethyl, p-methoxyphenyldiphenylmethyl, Di(p-methoxyphenyl)phenylmethyl, Tri(p-methoxyphenyl)methyl, 4-(4'-Bromophenacyloxy)phenyldiphenylmethyl, 4,4',4"-Tris(4,5-dichlorophthalimidophenyl)methyl, 4,4',4"-Tris(levulinoyloxyphenyl)methyl, 4,4',4"-Tris(benzoyloxyphenyl)methyl, 3-(Imidazol-1-ylmethyl)bis(4',4"-dimethoxyphenyl)methyl, 1,1-Bis(4-methoxyphenyl)-1'-pyrenylmethyl, 9-Anthryl, 9-(9-Phenyl)xanthenyl, 9-(9-Phenyl-10-oxo)anthryl, 1,3-Benzodithiolan-2-yl, Benzisothiazolyl S,S-Dioxido);

Silyl Ethers (Trimethylsilyl, Triethylsilyl, Triisopropylsilyl, Dimethylisopropylsilyl, Diethylisopropylsilyl, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylmethoxyphenylsilyl);

Esters (Formate, Benzoylformate, Acetate, Choroacetate, Dichloroacetate, Trichloroacetate, Trifluoroacetate, Methoxyacetate, Triphenylmethoxyacetate, Phenoxyacetate, p-Chlorophenoxyacetate, p-poly-Phenylacetate, 3-Phenylpropionate, 4-Oxopentanoate (Levulinate), 4,4-(Ethylenedithio)pentanoate, Pivaloate, Adamantoate, Crotonate, 4-Methoxycrotonate, Benzoate, p-Phenylbenzoate, 2,4,6-Trimethylbenzoate (Mesitoate));

Carbonates (Methyl, 9-Fluorenylmethyl, Ethyl, 2,2,2-Trichloroethyl, 2-(Trimethylsilyl)ethyl, 2-(Phenylsulfonyl)ethyl, 2-(Triphenylphosphonio)ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl, S-Benzyl Thiocarbonate, 4-Ethoxy-1-naphthyl, Methyl Dithiocarbonate);

Groups With Assisted Cleavage (2-Iodobenzoate, 4-Azidobutyrate, 4-Nitro-4-methylpentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Miscellaneous Esters (2,6-Dichloro-4-methylphenoxyacetate, 2,6-Dichloro-4-(1,1,3,3 tetramethylbutyl)phenoxyacetate, 2,4-Bis(1,1-dimethylpropyl)phenoxyacetate, Chlorodiphenylacetate, Isobutyrate, Monosuccinate, (E)-2-Methyl-2-butenoate (Tigloate), o-(Methoxycarbonyl)benzoate, p-poly-Benzoate, α-Naphthoate, Nitrate, Alkyl N,N,N',N'-Tetramethylphosphorodiamidate, N-Phenylcarbamate, Borate, Dimethylphosphinothioyl, 2,4-Dinitrophenylsulfenate); and Sulfonates (Sulfate, Methanesulfonate (Mesylate), Benzylsulfonate, Tosylate).

Typical 1,2-diol protecting groups (thus, generally where two OH groups are taken together with the protecting functionality) are described in Greene at pages 118-142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethylidine, 1,2-Dimethoxyethylidene, α-Methoxybenzylidene, 1-(N,N-Dimethylamino)ethylidene Derivative, α-(N,N-Dimethylamino)benzylidene Derivative, 2-Oxacyclopentylidene); Silyl Derivatives (Di-t-butylsilylene Group, 1,3-(1,1,3,3-Tetraisopropyldisiloxanylidene), and Tetra-t-butoxydisiloxane-1,3-diylidene), Cyclic Carbonates, Cyclic Boronates, Ethyl Boronate and Phenyl Boronate.

More typically, 1,2-diol protecting groups include those shown in Table B, still more typically, epoxides, acetonides, cyclic ketals and aryl acetals.

TABLE B

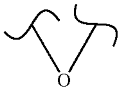

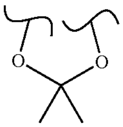

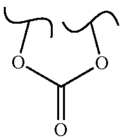

TABLE B-continued

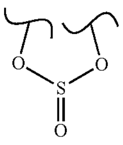

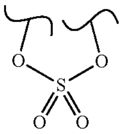

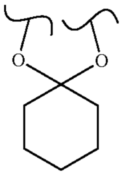

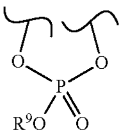

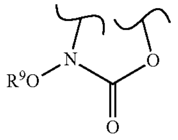

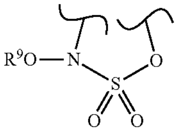

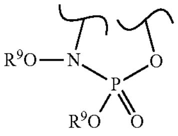

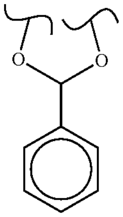

wherein $R^9$ is $C_1$-$C_6$ alkyl.

Amino Protecting Groups

Another set of protecting groups include any of the typical amino protecting groups described by Greene at pages 315-385. They include:

Carbamates: (methyl and ethyl, 9-fluorenylmethyl, 9(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, 4-methoxyphenacyl);

Substituted Ethyl: (2,2,2-trichoroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl, diphenylmethyl);

Groups With Assisted Cleavage: (2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-choro-p-acyloxybenzyl,p-(dihydroxyboryl)benzyl, 5-benzisoxazolylmethyl, 2-(trifluoromethyl)-6-chromonylmethyl);

Groups Capable of Photolytic Cleavage: (m-nitrophenyl, 3,5-dimethoxybenzyl, o-nitrobenzyl, 3,4-dimethoxy-6-nitrobenzyl, phenyl(o-nitrophenyl)methyl); Urea-Type Derivatives (phenothiazinyl-(10)-carbonyl, N'-p-toluenesulfonylaminocarbonyl, N'-phenylaminothiocarbonyl);

Miscellaneous Carbamates: (t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-Iodoethyl, Isobornyl, Isobutyl, Isonicotinyl, p-(p'-Methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, 2,4,6-trimethylbenzyl);

Amides: (N-formyl, N-acetyl, N-choroacetyl, N-trichoroacetyl, N-trifluoroacetyl, N-phenylacetyl, N-3-phenylpropionyl, N-picolinoyl, N-3-pyridylcarboxamide, N-benzoylphenylalanyl, N-benzoyl, N-p-phenylbenzoyl);

Amides With Assisted Cleavage: (N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine, N-o-nitrobenzoyl, N-o-(benzoyloxymethyl)benzoyl, 4,5-diphenyl-3-oxazolin-2-one);

Cyclic Imide Derivatives: (N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3-5-triazacyclohexan-2-one, 1-substituted 3,5-dinitro-4-pyridonyl);

N-Alkyl and N-Aryl Amines: (N-methyl, N-allyl, N-[2-(trimethylsilyl)ethoxy]methyl, N-3-acetoxypropyl, N-(1-isopropyl-4-nitro-2-oxo-3-pyrrolin-3-yl), Quaternary Ammonium Salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, N-2-picolylamine N'-oxide);

Imine Derivatives: (N-1,1-dimethylthiomethylene, N-benzylidene, N-p-methoxybenylidene, N-diphenylmethylene, N-[(2-pyridyl)mesityl]methylene, N,(N',N'-dimethylaminomethylene, N,N'-isopropylidene, N-p-nitrobenzylidene, N-salicylidene, N-5-chlorosalicylidene, N-(5-chloro-2-hydroxyphenyl)phenylmethylene, N-cyclohexylidene);

Enamine Derivatives: (N-(5,5-dimethyl-3-oxo-1-cyclohexenyl));

N-Metal Derivatives (N-borane derivatives, N-diphenylborinic acid derivatives, N-[phenyl(pentacarbonylchromium- or -tungsten)]carbenyl, N-copper or N-zinc chelate);

N—N Derivatives: (N-nitro, N-nitroso, N-oxide);

N—P Derivatives: (N-diphenylphosphinyl, N-dimethylthiophosphinyl, N-diphenylthiophosphinyl, N-dialkyl phosphoryl, N-dibenzyl phosphoryl, N-diphenyl phosphoryl);

N—Si Derivatives, N—S Derivatives, and N-Sulfenyl Derivatives: (N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-3-nitropyridinesulfenyl); and N-sulfonyl Derivatives (N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6,-tetramethyl-4-methoxybenzenesulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N—O-trimethylsilyethanesulfonyl, N-9-anthracenesulfonyl, N-4-(4',8'-dimethoxynaphthylmethyl)benzenesulfonyl, N-benzylsulfonyl, N-trifluoromethylsulfonyl, N-phenacylsulfonyl).

More typically, protected amino groups include carbamates and amides, still more typically, $—NHC(O)R^1$ or $—N{=}CR^1N(R^1)_2$. Another protecting group, also useful as a prodrug for amino or $—NH(R^5)$, is:

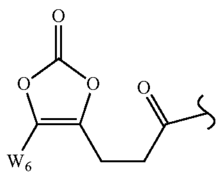

See for example Alexander, J. et al. (1996) *J. Med. Chem.* 39:480-486.

Amino Acid and Polypeptide Protecting Group and Conjugates

An amino acid or polypeptide protecting group of a compound of the invention has the structure $R^{15}NHCH(R^{16})C(O)—$, where $R^{15}$ is H, an amino acid or polypeptide residue, or $R^5$, and $R^{16}$ is defined below.

$R^{16}$ is lower alkyl or lower alkyl ($C_1$-$C_6$) substituted with amino, carboxyl, amide, carboxyl ester, hydroxyl, $C_6$-$C_7$ aryl, guanidinyl, imidazolyl, indolyl, sulfhydryl, sulfoxide, and/or alkylphosphate. $R^{10}$ also is taken together with the amino acid α N to form a proline residue ($R^{10}{=}—CH_2)_3—$). However, $R^{10}$ is generally the side group of a naturally-occurring amino acid such as H, $—CH_3$, $—CH(CH_3)_2$, $—CH_2—CH(CH_3)_2$, $—CHCH_3—CH_2—CH_3$, $—CH_2—C_6H_5$, $—CH_2CH_2—S—$ $CH_3$, $-CH_2OH$, $-CH(OH)-CH_3$, $-CH_2-SH$, $-CH_2-C_6H_4OH$, $-CH_2-CO-NH_2$, $-CH_2-CH_2-CO-NH_2$, $-CH_2-COOH$, $-CH_2-CH_2-COOH$, $-(CH_2)_4-NH_2$ and $-(CH_2)_3-NH-C(NH_2)-NH_2$. $R_{10}$ also includes 1-guanidinoprop-3-yl, benzyl, 4-hydroxybenzyl, imidazol-4-yl, indol-3-yl, methoxyphenyl and ethoxyphenyl.

Another set of protecting groups include the residue of an amino-containing compound, in particular an amino acid, a polypeptide, a protecting group, $-NHSO_2R$, NHC(O)R, $-N(R)_2$, $NH_2$ or —NH(R)(H), whereby for example a carboxylic acid is reacted, i.e. coupled, with the amine to form an amide, as in $C(O)NR_2$. A phosphonic acid may be reacted with the amine to form a phosphonamidate, as in —P(O)(OR)($NR_2$).

In general, amino acids have the structure $R^{17}C(O)CH(R^{16})NH-$, where $R^{17}$ is —OH, —OR, an amino acid or a polypeptide residue. Amino acids are low molecular weight compounds, on the order of less than about 1000 MW and which contain at least one amino or imino group and at least one carboxyl group. Generally the amino acids will be found in nature, i.e., can be detected in biological material such as bacteria or other microbes, plants, animals or man. Suitable amino acids typically are alpha amino acids, i.e. compounds characterized by one amino or imino nitrogen atom separated from the carbon atom of one carboxyl group by a single substituted or unsubstituted alpha carbon atom. Of particular interest are hydrophobic residues such as mono- or di-alkyl or aryl amino acids, cycloalkylamino acids and the like. These residues contribute to cell permeability by increasing the partition coefficient of the parental drug. Typically, the residue does not contain a sulfhydryl or guanidino substituent.

Naturally-occurring amino acid residues are those residues found naturally in plants, animals or microbes, especially proteins thereof. Polypeptides most typically will be substantially composed of such naturally-occurring amino acid residues. These amino acids are glycine, alanine, valine, leucine, isoleucine, serine, threonine, cysteine, methionine, glutamic acid, aspartic acid, lysine, hydroxylysine, arginine, histidine, phenylalanine, tyrosine, tryptophan, proline, asparagine, glutamine and hydroxyproline. Additionally, unnatural amino acids, for example, valanine, phenylglycine and homoarginine are also included. Commonly encountered amino acids that are not gene-encoded may also be used in the present invention. All of the amino acids used in the present invention may be either the D- or L-optical isomer. In addition, other peptidomimetics are also useful in the present invention. For a general review, see Spatola, A. F., in *Chemistry and Biochemistry of Amino Acids, Peptides and Proteins*, B. Weinstein, eds., Marcel Dekker, New York, p. 267 (1983).

When protecting groups are single amino acid residues or polypeptides they optionally are substituted at $R^3$ of substituents $A^1$, $A^2$ or $A^3$ in a compound of the invention. These conjugates are produced by forming an amide bond between a carboxyl group of the amino acid (or C-terminal amino acid of a polypeptide for example). Similarly, conjugates are formed between $R^3$ and an amino group of an amino acid or polypeptide. Generally, only one of any site in the parental molecule is amidated with an amino acid as described herein, although it is within the scope of this invention to introduce amino acids at more than one permitted site. Usually, a carboxyl group of $R^3$ is amidated with an amino acid. In general, the α-amino or α-carboxyl group of the amino acid or the terminal amino or carboxyl group of a polypeptide are bonded to the parental functionalities, i.e., carboxyl or amino groups in the amino acid side chains generally are not used to form the amide bonds with the parental compound (although these groups may need to be protected during synthesis of the conjugates as described further below).

With respect to the carboxyl-containing side chains of amino acids or polypeptides it will be understood that the carboxyl group optionally will be blocked, e.g., by $R^1$, esterified with $R^5$ or amidated. Similarly, the amino side chains $R^{16}$ optionally will be blocked with $R^1$ or substituted with $R^5$.

Such ester or amide bonds with side chain amino or carboxyl groups, like the esters or amides with the parental molecule, optionally are hydrolyzable in vivo or in vitro under acidic (pH<3) or basic (pH>10) conditions. Alternatively, they are substantially stable in the gastrointestinal tract of humans but are hydrolyzed enzymatically in blood or in intracellular environments. The esters or amino acid or polypeptide amidates also are useful as intermediates for the preparation of the parental molecule containing free amino or carboxyl groups. The free acid or base of the parental compound, for example, is readily formed from the esters or amino acid or polypeptide conjugates of this invention by conventional hydrolysis procedures.

When an amino acid residue contains one or more chiral centers, any of the D, L, meso, threo or erythro (as appropriate) racemates, scalemates or mixtures thereof may be used. In general, if the intermediates are to be hydrolyzed non-enzymatically (as would be the case where the amides are used as chemical intermediates for the free acids or free amines), D isomers are useful. On the other hand, L isomers are more versatile since they can be susceptible to both non-enzymatic and enzymatic hydrolysis, and are more efficiently transported by amino acid or dipeptidyl transport systems in the gastrointestinal tract.

Examples of suitable amino acids whose residues are represented by $R^x$ or $R^y$ include the following:

Glycine;

Aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid;

Amino acid amides such as glutamine and asparagine;

Polyamino- or polybasic-monocarboxylic acids such as arginine, lysine, β-aminoalanine, γ-aminobutyrine, ornithine, citruline, homoarginine, homocitrulline, hydroxylysine, allohydroxylsine and diaminobutyric acid;

Other basic amino acid residues such as histidine;

Diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid;

Imino acids such as proline, hydroxyproline, allohydroxyproline, γ-methylproline, pipecolic acid, 5-hydroxypipecolic acid, and azetidine-2-carboxylic acid;

A mono- or di-alkyl (typically $C_1$-$C_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid, isoleucine, alloisoleucine, tert-leucine, β-methyltryptophan and α-amino-β-ethyl-β-phenylpropionic acid;

β-phenylserinyl;

Aliphatic α-amino-β-hydroxy acids such as serine, β-hydroxyleucine, β-hydroxynorleucine, β-hydroxynorvaline, and α-amino-β-hydroxystearic acid;

α-Amino, α-, γ-, β- or ϵ-hydroxy acids such as homoserine, δ-hydroxynorvaline, γ-hydroxynorvaline and ϵ-hydroxynorleucine residues; canavine and canaline; γ-hydroxyornithine;

2-hexosaminic acids such as D-glucosaminic acid or D-galactosaminic acid;

α-Amino-β-thiols such as penicillamine, β-thiolnorvaline or β-thiolbutyrine;

Other sulfur containing amino acid residues including cysteine; homocystine, β-phenylmethionine, methionine, S-allyl-L-cysteine sulfoxide, 2-thiolhistidine, cystathionine, and thiol ethers of cysteine or homocysteine;

Phenylalanine, tryptophan and ring-substituted α-amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dichloro, o-, m- or p-methyl-, 2,4,6-trimethyl-, 2-ethoxy-5-nitro-, 2-hydroxy-5-nitro- and p-nitro-phenylalanine); furyl-, thienyl-, pyridyl-, pyrimidinyl-, purinyl- or naphthyl-alanines; and tryptophan analogues and derivatives including kynurenine, 3-hydroxykynurenine, 2-hydroxytryptophan and 4-carboxytryptophan;

α-Amino substituted amino acids including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acids including serine, threonine, allothreonine, phosphoserine and phosphothreonine.

Polypeptides are polymers of amino acids in which a carboxyl group of one amino acid monomer is bonded to an amino or imino group of the next amino acid monomer by an amide bond. Polypeptides include dipeptides, low molecular weight polypeptides (about 1500-5000 MW) and proteins. Proteins optionally contain 3, 5, 10, 50, 75, 100 or more residues, and suitably are substantially sequence-homologous with human, animal, plant or microbial proteins. They include enzymes (e.g., hydrogen peroxidase) as well as immunogens such as KLH, or antibodies or proteins of any type against which one wishes to raise an immune response. The nature and identity of the polypeptide may vary widely.

The polypeptide amidates are useful as immunogens in raising antibodies against either the polypeptide (if it is not immunogenic in the animal to which it is administered) or against the epitopes on the remainder of the compound of this invention.

Antibodies capable of binding to the parental non-peptidyl compound are used to separate the parental compound from mixtures, for example in diagnosis or manufacturing of the parental compound. The conjugates of parental compound and polypeptide generally are more immunogenic than the polypeptides in closely homologous animals, and therefore make the polypeptide more immunogenic for facilitating raising antibodies against it. Accordingly, the polypeptide or protein may not need to be immunogenic in an animal typically used to raise antibodies, e.g., rabbit, mouse, horse, or rat, but the final product conjugate should be immunogenic in at least one of such animals. The polypeptide optionally contains apeptidolytic enzyme cleavage site at the peptide bond between the first and second residues adjacent to the acidic heteroatom. Such cleavage sites are flanked by enzymatic recognition structures, e.g., a particular sequence of residues recognized by a peptidolytic enzyme.

Peptidolytic enzymes for cleaving the polypeptide conjugates of this invention are well known, and in particular include carboxypeptidases. Carboxypeptidases digest polypeptides by removing C-terminal residues, and are specific in many instances for particular C-terminal sequences. Such enzymes and their substrate requirements in general are well known. For example, a dipeptide (having a given pair of residues and a free carboxyl terminus) is covalently bonded through its α-amino group to the phosphorus or carbon atoms of the compounds herein. In claims where $W_1$ is phosphonate it is expected that this peptide will be cleaved by the appropriate peptidolytic enzyme, leaving the carboxyl of the proximal amino acid residue to autocatalytically cleave the phosphonoamidate bond.

Suitable dipeptidyl groups (designated by their single letter code) are AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, FI, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY and VV.

Tripeptide residues are also useful as protecting groups. When a phosphonate is to be protected, the sequence $-X^{200}$-pro-$X^{201}$- (where $X^{200}$ is any amino acid residue and $X^{201}$ is an amino acid residue, a carboxyl ester of proline, or hydrogen) will be cleaved by luminal carboxypeptidase to yield $X^{200}$ with a free carboxyl, which in turn is expected to autocatalytically cleave the phosphonoamidate bond. The carboxy group of $X^{201}$ optionally is esterified with benzyl.

Dipeptide or tripeptide species can be selected on the basis of known transport properties and/or susceptibility to peptidases that can affect transport to intestinal mucosal or other cell types. Dipeptides and tripeptides lacking an α-amino group are transport substrates for the peptide transporter found in brush border membrane of intestinal mucosal cells (Bai, J. P. F., (1992) *Pharm Res.* 9:969-978). Transport competent peptides can thus be used to enhance bioavailability of the amidate compounds. Di- or tripeptides having one or more amino acids in the D configuration are also compatible with peptide transport and can be utilized in the amidate compounds of this invention. Amino acids in the D configuration can be used to reduce the susceptibility of a di- or tripeptide to hydrolysis by proteases common to the brush border such as aminopeptidase N. In addition, di- or tripeptides alternatively are selected on the basis of their relative resistance to hydrolysis by proteases found in the lumen of the intestine. For example, tripeptides or polypeptides lacking asp and/or glu are poor substrates for aminopeptidase A, di- or tripeptides lacking amino acid residues on the N-terminal side of hydrophobic amino acids (leu, tyr, phe, val, trp) are poor substrates for endopeptidase, and peptides lacking a pro residue at the penultimate position at a free carboxyl terminus are poor substrates for carboxypeptidase P. Similar considerations can also be applied to the selection of peptides that are either relatively resistant or relatively susceptible to hydrolysis by cytosolic, renal, hepatic, serum or other peptidases. Such poorly cleaved polypeptide amidates are immunogens or are useful for bonding to proteins in order to prepare immunogens.

Specific Embodiments of the Invention

Specific values described for radicals, substituents, and ranges, as well as specific embodiments of the invention described herein, are for illustration only; they do not exclude other defined values or other values within defined ranges.

In one specific embodiment of the invention, the conjugate is a compound that is substituted with one or more phosphonate groups either directly or indirectly through a linker; and that is optionally substituted with one or more groups $A^0$; or a pharmaceutically acceptable salt thereof, wherein:

$A^0$ is $A^1$, $A^2$ or $W^3$;

A is:

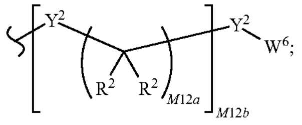

$A^2$ is:

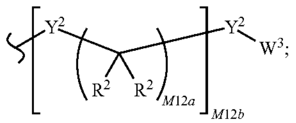

$A^3$ is:

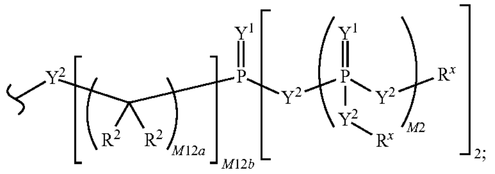

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $—S(O)_{M2}—$, or $—S(O)_{M2}—S(O)_{M2}—$;

$R^x$ is independently H, $R^1$, $W^3$, a protecting group, or the formula:

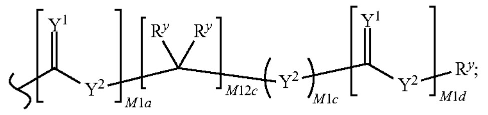

wherein:

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, $N_3$ or $—NO_2$;

$R^{3b}$ is $Y^1$;

$R^{3c}$ is $—R^x$, $—N(R^x)(R^x)$, $—SR^x$, $—S(O)R^x$, $—S(O)_2R^x$, $—S(O)(OR^x)$, $—S(O)_2(OR^x)$, $—OC(Y^1)R^x$, $—OC(Y^1)OR^x$, $—OC(Y^1)(N(R^x)(R^x))$, $—SC(Y^1)R^x$, $—SC(Y^1)OR^x$, $—SC(Y^1)(N(R^x)(R^x))$, $—N(R^x)C(Y^1)R^x$, $—N(R^x)C(Y^1)OR^x$, or $—N(R^x)C(Y^1)(N(R^x)(R^x))$;

$R^{3d}$ is $—C(Y^1)R^x$, $—C(Y^1)OR^x$ or $—C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;

$W^3$ is $W^4$ or $W^5$;

$W^4$ is $R^5$, $—C(Y^1)R^5$, $—C(Y^1)W^5$, $—SO_2R^5$, or $—SO_2W^5$;

$W^6$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and Mid are independently 0 or 1; and

M12c is 0, 1, 2, 3, 4, 5, 6, 7, 8, 9, 10, 11 or 12.

In another specific embodiment of the invention $A^1$ is of the formula:

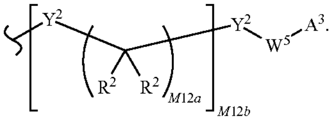

In another specific embodiment of the invention $A^1$ is of the formula:

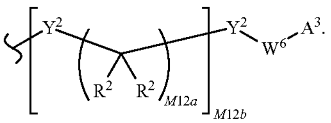

In another specific embodiment of the invention $A^1$ is of the formula:

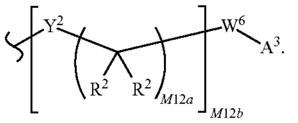

In another specific embodiment of the invention $A^1$ is of the formula:

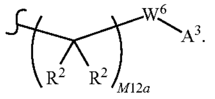

In another specific embodiment of the invention $A^1$ is of the formula:

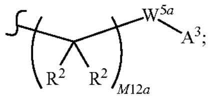

and $W^{5a}$ is a carbocycle or a heterocycle where $W^{5a}$ is independently substituted with 0 or 1 $R^2$ groups. A specific value for M12a is 1.

In another specific embodiment of the invention $A^1$ is of the formula:

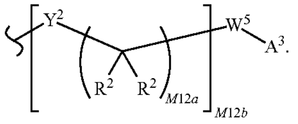

In another specific embodiment of the invention $A^1$ is of the formula:

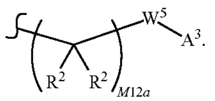

In another specific embodiment of the invention $A^1$ is of the formula:

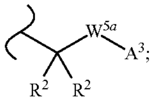

wherein $W^{5a}$ is a carbocycle independently substituted with 0 or 1 $R^2$ groups.

In another specific embodiment of the invention $A^1$ is of the formula:

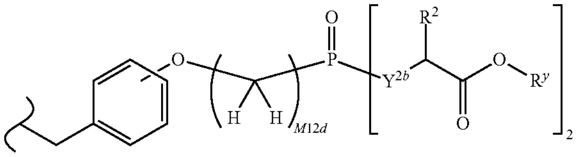

wherein $Y^{2b}$ is O or $N(R^2)$; and M12d is 1, 2, 3, 4, 5, 6, 7 or 8.

In another specific embodiment of the invention $A^1$ is of the formula:

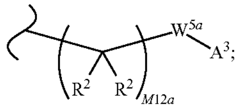

wherein $W^{5a}$ is a carbocycle independently substituted with 0 or 1 $R^2$ groups.

In another specific embodiment of the invention $A^1$ is of the formula:

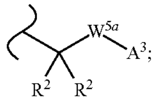

wherein $W^{5a}$ is a carbocycle or heterocycle where $W^{5a}$ is independently substituted with 0 or 1 $R^2$ groups.

In another specific embodiment of the invention $A^1$ is of the formula:

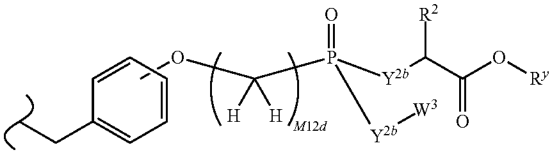

wherein $Y^{2b}$ is O or $N(R^2)$; and M12d is 1, 2, 3, 4, 5, 6, 7 or 8.

In a specific embodiment of the invention $A^2$ is of the formula:

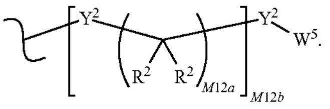

In another specific embodiment of the invention $A^2$ is of the formula:

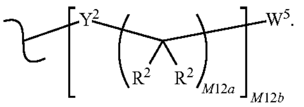

In another specific embodiment of the invention M12b is 1.

In another specific embodiment of the invention e M12b is 0, $Y^2$ is a bond and $W^5$ is a carbocycle or heterocycle where $W^5$ is optionally and independently substituted with 1, 2, or 3 $R^2$ groups.

In another specific embodiment of the invention $A^2$ is of the formula:

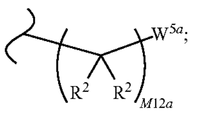

wherein $W^{5a}$ is a carbocycle or heterocycle where $W^{5a}$ is optionally and independently substituted with 1, 2, or 3 $R^2$ groups.

In another specific embodiment of the invention M12a is 1.

In another specific embodiment of the invention $A^2$ is selected from phenyl, substituted phenyl, benzyl, substituted benzyl, pyridyl and substituted pyridyl.

In another specific embodiment of the invention $A^2$ is of the formula:

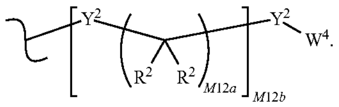

In another specific embodiment of the invention $A^2$ is of the formula:

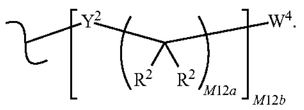

In another specific embodiment of the invention M12b is 1.

In a specific embodiment of the invention $A^3$ is of the formula:

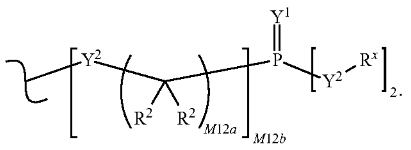

In another specific embodiment of the invention $A^3$ is of the formula:

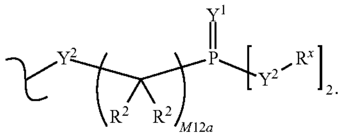

In another specific embodiment of the invention $A^3$ is of the formula:

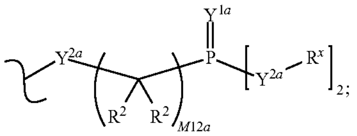

wherein $Y^{1a}$ is O or S; and $Y^{2a}$ is O, $N(R^x)$ or S.

In another specific embodiment of the invention $A^3$ is of the formula:

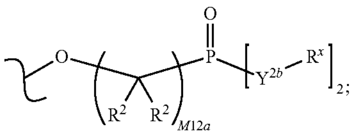

wherein $Y^{2b}$ is O or $N(R^x)$.

In another specific embodiment of the invention $A^3$ is of the formula:

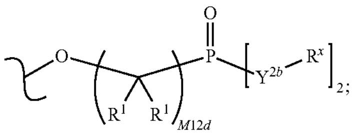

wherein $Y^{2b}$ is O or $N(R^x)$; and M12d is 1, 2, 3, 4, 5, 6, 7 or 8.

In another specific embodiment of the invention $A^3$ is of the formula:

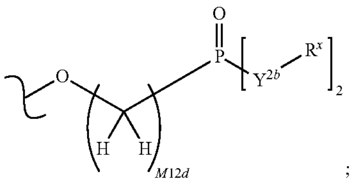

wherein $Y^{2b}$ is O or $N(R^x)$; and M12d is 1, 2, 3, 4, 5, 6, 7 or 8.

In another specific embodiment of the invention M12d is 1.

In another specific embodiment of the invention $A^3$ is of the formula:

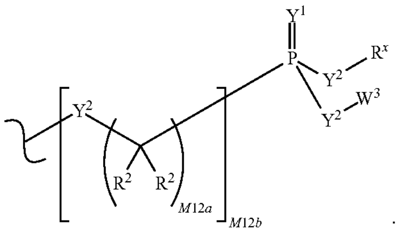

In another specific embodiment of the invention $A^3$ is of the formula:

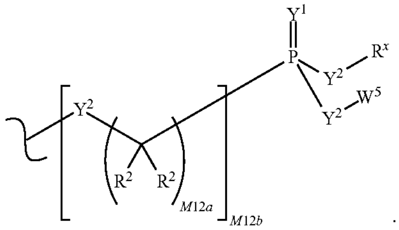

.

In another specific embodiment of the invention $W^5$ is a carbocycle.

In another specific embodiment of the invention $A^3$ is of the formula:

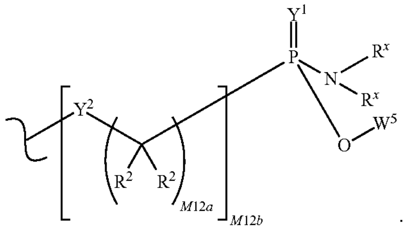

.

In another specific embodiment of the invention $W^5$ is phenyl.

In another specific embodiment of the invention $A^3$ is of the formula:

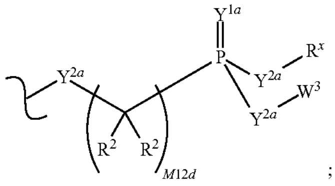

;

wherein $Y^{1a}$ is O or S; and $Y^{2a}$ is O, $N(R^x)$ or S.

In another specific embodiment of the invention $A^3$ is of the formula:

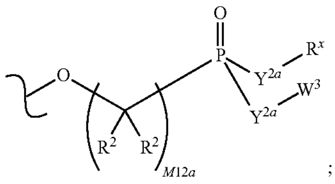

;

wherein $Y^{2b}$ is O or $N(R^x)$.

In another specific embodiment of the invention $A^3$ is of the formula:

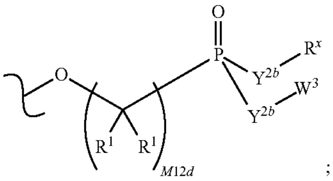

;

wherein $Y^{2b}$ is O or $N(R^x)$; and M12d is 1, 2, 3, 4, 5, 6, 7 or 8.

In another specific embodiment of the invention $R^1$ is H.

In another specific embodiment of the invention $A^3$ is of the formula:

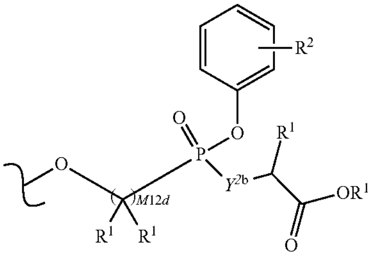

wherein the phenyl carbocycle is substituted with 0, 1, 2, or 3 $R^2$ groups.

In another specific embodiment of the invention $A^3$ is of the formula:

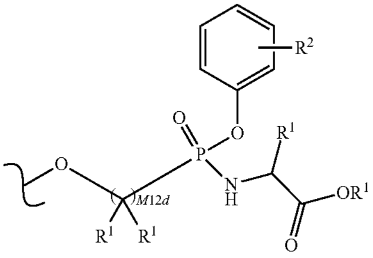

.

In another specific embodiment of the invention $A^3$ is of the formula:

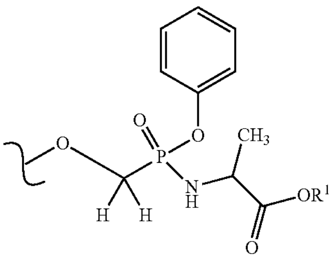

.

In another specific embodiment of the invention $A^3$ is of the formula:

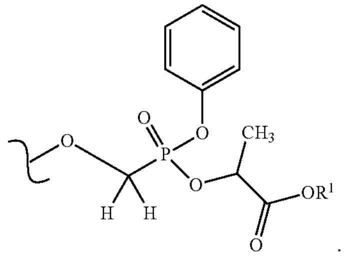

.

In another specific embodiment of the invention $A^3$ is of the formula:

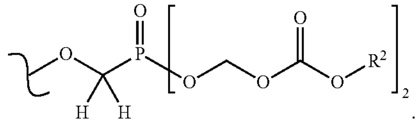

.

In another specific embodiment of the invention $A^3$ is of the formula:

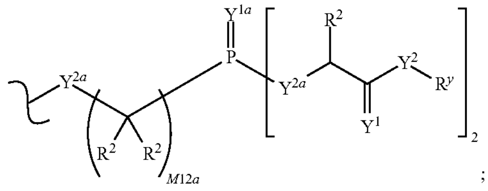

;

wherein $Y^{1a}$ is O or S; and $Y^{2a}$ is O, $N(R^2)$ or S.

In another specific embodiment of the invention $A^3$ is of the formula:

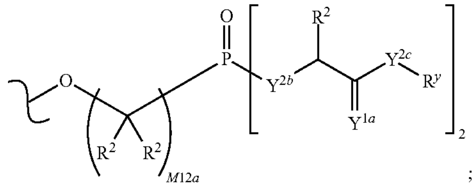

;

wherein $Y^{1a}$ is O or S; $Y^{2b}$ is O or $N(R^2)$; and $Y^{2c}$ is O, $N(R^y)$ or S.

In another specific embodiment of the invention $A^3$ is of the formula:

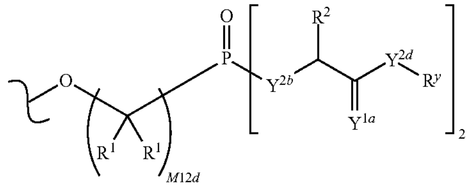

wherein $Y^{1a}$ is O or S; $Y^{2b}$ is O or $N(R^2)$; $Y^{2d}$ is O or $N(R^y)$; and M12d is 1, 2, 3, 4, 5, 6, 7 or 8.

In another specific embodiment of the invention $A^3$ is of the formula:

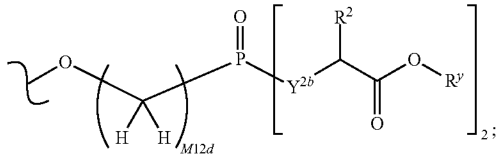

;

wherein $Y^{2b}$ is O or $N(R^2)$; and M12d is 1, 2, 3, 4, 5, 6, 7 or 8.

In another specific embodiment of the invention $A^3$ is of the formula:

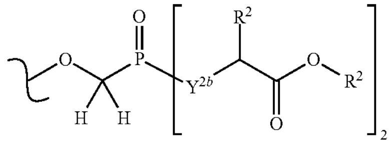

wherein $Y^{2b}$ is O or $N(R^2)$.

In another specific embodiment of the invention $A^3$ is of the formula:

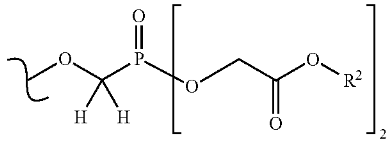

.

In another specific embodiment of the invention $A^3$ is of the formula:

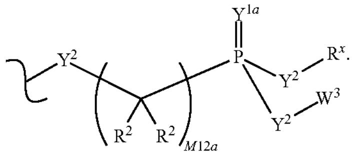

In another specific embodiment of the invention $A^3$ is of the formula:

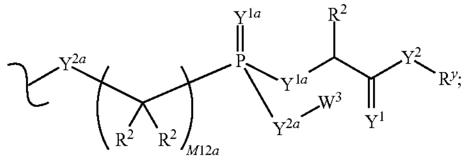

wherein $Y^{1a}$ is O or S; and $Y^{2a}$ is O, $N(R^2)$ or S.

In another specific embodiment of the invention $A^3$ is of the formula:

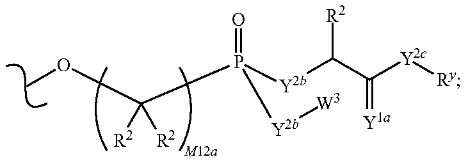

wherein $Y^{1a}$ is O or S; $Y^{2b}$ is O or $N(R^2)$; and $Y^{2c}$ is O, $N(R^y)$ or S.

In another specific embodiment of the invention $A^3$ is of the formula:

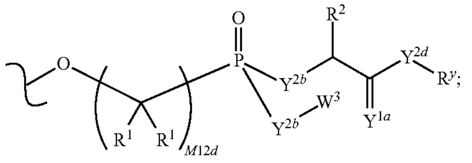

wherein $Y^{1a}$ is O or S; $Y^{2b}$ is O or $N(R^2)$; $Y^{2d}$ is O or $N(R^y)$; and M12d is 1, 2, 3, 4, 5, 6, 7 or 8.

In another specific embodiment of the invention $A^3$ is of the formula:

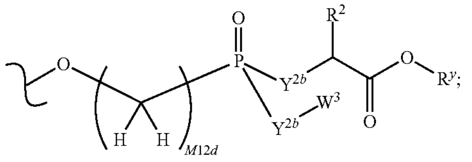

wherein $Y^{2b}$ is O or $N(R^2)$; and M12d is 1, 2, 3, 4, 5, 6, 7 or 8.

In another specific embodiment of the invention $A^3$ is of the formula:

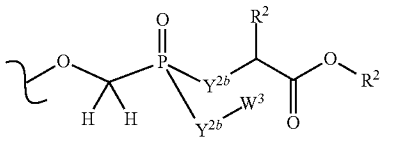

wherein $Y^{2b}$ is O or $N(R^2)$.

In another specific embodiment of the invention $A^3$ is of the formula:

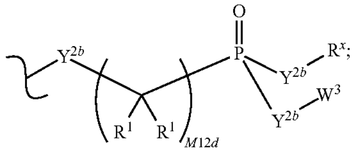

wherein: $Y^{2b}$ is O or $N(R^x)$; and M12d is 1, 2, 3, 4, 5, 6, 7 or 8.

In another specific embodiment of the invention $A^3$ is of the formula:

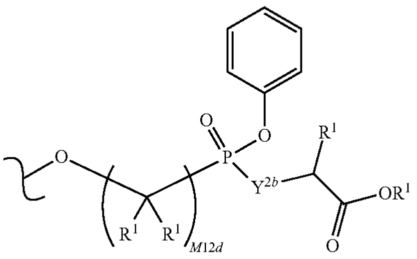

wherein the phenyl carbocycle is substituted with 0, 1, 2, or 3 $R^2$ groups.

In another specific embodiment of the invention $A^3$ is of the formula:

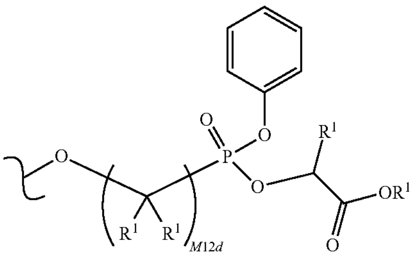

wherein the phenyl carbocycle is substituted with 0, 1, 2, or 3 $R^2$ groups.

In another specific embodiment of the invention $A^3$ is of the formula:

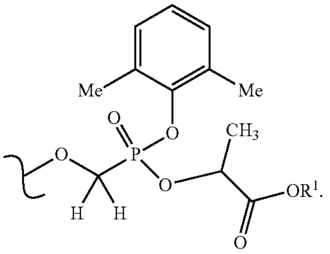

In a specific embodiment of the invention $A^0$ is of the formula:

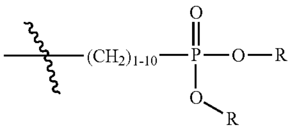

wherein each R is independently $(C_1$-$C_6)$alkyl.

In a specific embodiment of the invention $R^x$ is independently H, $R^1$, $W^3$, a protecting group, or the formula:

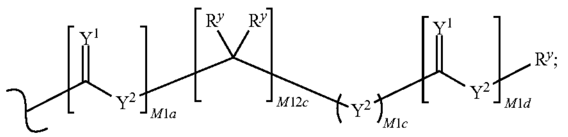

wherein:

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups.

In a specific embodiment of the invention $R^x$ is of the formula:

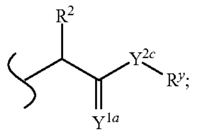

wherein $Y^{1a}$ is O or S; and $Y^{2c}$ is O, $N(R^y)$ or S.

In a specific embodiment of the invention $R^x$ is of the formula:

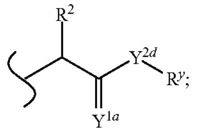

wherein $Y^{1a}$ is O or S; and $Y^{2d}$ is O or $N(R^y)$.

In a specific embodiment of the invention $R^x$ is of the formula:

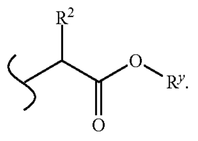

In a specific embodiment of the invention $R^y$ is hydrogen or alkyl of 1 to 10 carbons:

In a specific embodiment of the invention $R^x$ is of the formula:

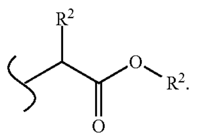

In a specific embodiment of the invention $R^x$ is of the formula:

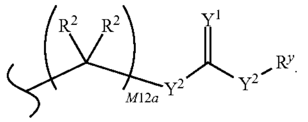

In a specific embodiment of the invention $R^x$ is of the formula:

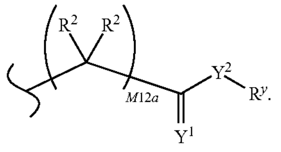

In a specific embodiment of the invention $Y^1$ is O or S.

In a specific embodiment of the invention $Y^2$ is O, $N(R^y)$ or S.

In one specific embodiment of the invention $R^x$ is a group of the formula:

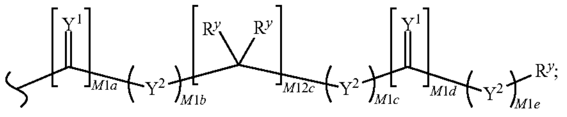

wherein:

m1a, m1b, m1c, m1d and m1e are independently 0 or 1;

m12c is 0, 1, 2, 3, 4, 5, 6, 7, 8, 9, 10, 11 or 12;

$R^y$ is H, $W^3$, $R^2$ or a protecting group;

provided that:

if m1a, m12c, and m1d are 0, then m1b, m1c and m1e are 0;

if m1a and m12c are 0 and m1d is not 0, then m1b and m1c are 0;

if m1a and m1d are 0 and m12c is not 0, then m1b and at least one of m1c and m1e are 0;

if m1a is 0 and m12c and m1d are not 0, then m1b is 0;

if m12c and m1d are 0 and m1a is not 0, then at least two of m1b, m1c and m1e are 0;

if m12c is 0 and m1a and m1d are not 0, then at least one of m1b and m1c are 0; and if m1d is 0 and m1a and m12c are not 0, then at least one of m1c and m1e are 0.

In another specific embodiment, the invention provides a compound of the formula:

$[DRUG]-(A^0)_{nn}$ or a pharmaceutically acceptable salt thereof wherein,

DRUG is a compound of any one of formulae 501-569 nn is 1, 2, or 3;

$A^0$ is $A^1$, $A^2$ or $W^3$ with the proviso that the compound includes at least one $A^1$;

$A^1$ is:

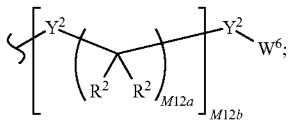

$A^2$ is:

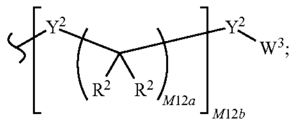

$A^3$ is:

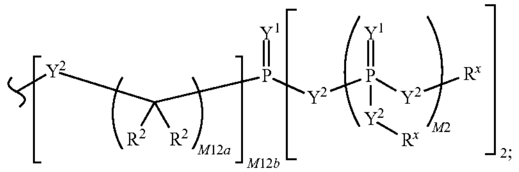

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $—S(O)_{M2}—$, or $—S(O)_{M2}—S(O)_{M2}—$;

$R^x$ is independently H, $R^1$, $W^3$, a protecting group, or the formula:

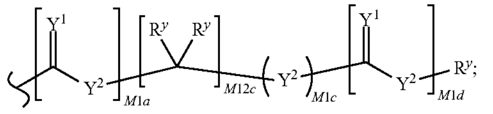

wherein:

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, $N_3$ or $—NO_2$;

$R^{3b}$ is $Y^1$;

$R^{3c}$ is $—R^x$, $—N(R^x)(R^x)$, $—SR^x$, $—S(O)R^x$, $—S(O)_2R^x$, $—S(O)(OR^x)$, $—S(O)_2(OR^x)$, $—OC(Y^1)R^x$, $—OC(Y^1)OR^x$, $—OC(Y^1)(N(R^x)(R^x))$, $—SC(Y^1)R^x$, $—SC(Y^1)OR^x$, $—SC(Y^1)(N(R^x)(R^x))$, $—N(R^x)C(Y^1)R^x$, $—N(R^x)C(Y^1)OR^x$, or $—N(R^x)C(Y^1)(N(R^x)(R^x))$;

$R^{3d}$ is $—C(Y^1)R^x$, $—C(Y^1)OR^x$ or $—C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted' with 0-3 $R^3$ groups;

$W^3$ is $W^4$ or $W^5$;

$W^4$ is $R^5$, $—C(Y^1)R^5$, $—C(Y^1)W^5$, $—SO_2R^5$, or $—SO_2W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

In another specific embodiment the invention provides a compound of any one of formulae 1-108 wherein:

$A^0$ is $A^1$;

$A^1$ is:

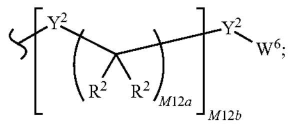

$A^3$ is:

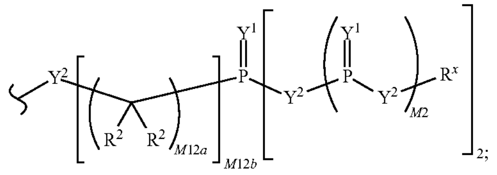

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(In)$, $—S(O)_{M2}—$, or $—S(O)_{M2}—S(O)_{M2}—$;

$R^x$ is independently H, $W^3$, a protecting group, or the formula:

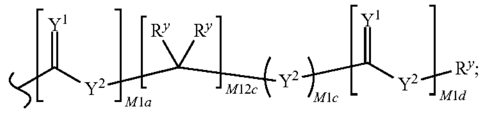

$R^y$ is independently H, $W^3$, $R^2$ or a protecting group;

$R^1$ is independently H or alkyl of 1 to 18 carbon atoms;

$R^2$ is independently H, $R^3$ or $R^4$ wherein each $R^4$ is independently substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, $N_3$ or $—NO_2$;

$R^{3b}$ is $Y^1$;

$R^{3c}$ is $—R^x$, $—N(R^x)(R^x)$, $—SR^x$, $—S(O)R^x$, $—S(O)_2R^x$, $—S(O)(OR^x)$, $—S(O)_2(OR^x)$, $—OC(Y^1)R^x$, $—OC(Y^1)OR^x$, $—OC(Y^1)(N(R^x)(R^x))$, $—SC(Y^1)R^x$, $—SC(Y^1)OR^x$, $—SC(Y^1)(N(R^x)(R^x))$, $—N(R^x)C(Y^1)R^x$, $—N(R^x)C(Y^1)OR^x$, or $—N(R^x)C(Y^1)(N(R^x)(R^x))$;

$R^{3d}$ is $—C(Y^1)R^x$; $—C(Y^1)OR^x$ or $—C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;

$W^3$ is $W^4$ or $W^5$;

$W^4$ is $R^5$, —$C(Y^1)R^5$, —$C(Y^1)W^5$, —$SO_2R^5$, or —$SO_2W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

In another specific embodiment, the invention provides a compound of the formula:

$[DRUG]\text{-}[L\text{-}P(=Y^1)—Y^2—R^x]_{nn}$ or a pharmaceutically acceptable salt thereof wherein, DRUG is a compound of any one of 501-569;

$Y^1$ is independently O, S, $N(R^x)$, $N(O)(R^x)$, $N(OR^x)$, $N(O)(OR^x)$, or $N(N(Rx)(R^x))$;

$Y^2$ is independently a bond, O, $N(R^x)$, $N(O)(R^x)$, $N(OR^x)$, $N(O)(OR^x)$, $N(N(R^x)(R^x))$, —$S(O)_{M2}$—, or —$S(O)_{M2}$—$S(O)_{M2}$—;

$R^x$ is independently H, $W^3$, a protecting group, or the formula:

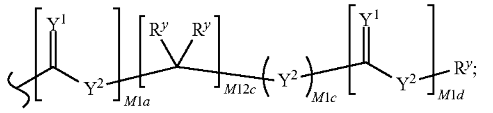

$R^y$ is independently H, $W^3$, $R^2$ or a protecting group;

$R^2$ is independently H, $R^3$ or $R^4$ wherein each $R^4$ is independently substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, $N_3$ or —$NO_2$;

$R^{3b}$ is $Y^1$;

$R^{3c}$ is —$R^x$, —$N(R^x)(R^x)$, —$SR^x$, —$S(O)R^x$, —$S(O)_2R^x$, —$S(O)(OR^x)$, —$S(O)_2(OR^x)$, —$OC(Y^1)R^x$, —$OC(Y^1)R^x$, —$OC(Y^1)(N(R^x)(R^x))$, —$SC(Y^1)R^x$, —$SC(Y^1)OR^x$, —$SC(Y^1)(N(R^x)(R^x))$, —$N(R^x)C(Y^1)R^x$, —$N(R^x)C(Y^1)OR^x$, or —$N(R^x)C(Y^1)(N(R^x)(R^x))$;

$R^{3d}$ is —$C(Y^1)R^x$, —$C(Y^1)OR^x$ or —$C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$W^3$ is $W^4$ or $W^5$;

$W^4$ is $R^5$, —$C(Y^1)R^5$, —$C(Y^1)W^5$, —$SO_2R^5$, or —$SO_2W^5$;

$W^5$ is carbocycle or heterocycle wherein $W^5$ is independently substituted with 0 to 3 $R^2$ groups;

M2 is 1, 2, or 3;

M1a, M1c, and M1d are independently 0 or 1;

M12c is 0, 1, 2, 3, 4, 5, 6, 7, 8, 9, 10, 11 or 12;

nn is 1, 2, or 3; and

L is a linking group.

In another specific embodiment, the invention provides a compound of which is a compound of the formula:

$[DRUG]\text{-}(A^0)_{nn}$ or a pharmaceutically acceptable salt thereof wherein, DRUG is a compound of any one of formulae 501-569;

nn is 1, 2, or 3;

$A^0$ is $A^1$, $A^2$, or $W^3$ with the proviso that the compound includes at least one $A^1$;

$A^1$ is:

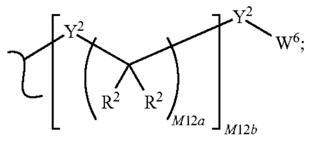

$A^2$ is:

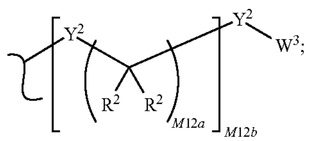

$A^3$ is:

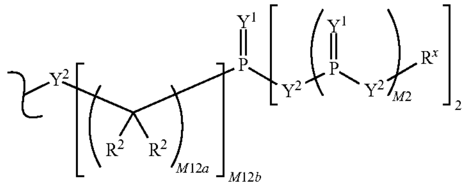

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, —$S(O)_{M2}$—, or —$S(O)_{M2}$—$S(O)_{M2}$—;

$R^x$ is independently H. $W^3$, a protecting group, or the formula:

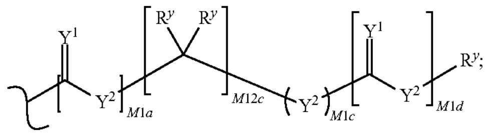

$R^y$ is independently H, $W^3$, $R^2$ or a protecting group;

$R^2$ is independently H, $R^3$ or $R^4$ wherein each $R^4$ is independently substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, $N_3$ or —$NO_2$;

$R^{3b}$ is $Y^1$;

$R^{3c}$ is —$R^x$, —$N(R^x)(R^x)$, —$SR^x$, —$S(O)R^x$, —$S(O)_2R^x$, —$S(O)(OR^x)$, —$S(O)_2(OR^x)$, —$OC(Y^1)R^x$, —$OC(Y^1)OR^x$, —$OC(Y^1)(N(R^x)(R^x))$, —$SC(Y^1)R^x$, —$SC(Y^1)OR^x$, —$SC(Y^1)(N(R^x)(R^x))$, —$N(Rx)C(Y^1)R^x$, —$N(R^x)C(Y^1)OR^x$, or —$N(R^x)C(Y^1)(N(R^x)(R^x))$;

$R^{3d}$ is —$C(Y^1)R^x$, —$C(Y^1)OR^x$ or —$C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$W^3$ is $W^4$ or $W^5$;

$W^4$ is $R^5$, —$C(Y^1)R^5$, —$C(Y^1)W^5$, —$SO_2R^5$, or —$SO_2W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and Mid are independently 0 or 1; and

M12c is 0, 1, 2, 3, 4, 5, 6, 7, 8, 9, 10, 11 or 12.

In compounds of the invention $W^5$ carbocycles and $W^5$ heterocycles may be independently substituted with 0 to 3 $R^2$ groups. $W^5$ may be a saturated, unsaturated or aromatic ring comprising a mono- or bicyclic carbocycle or heterocycle. $W^5$ may have 3 to 10 ring atoms, e.g., 3 to 7 ring atoms. The $W^5$ rings are saturated when containing 3 ring atoms, saturated or mono-unsaturated when containing 4 ring atoms, saturated, or mono- or di-unsaturated when containing 5 ring atoms, and saturated, mono- or di-unsaturated, or aromatic when containing 6 ring atoms.

A $W^5$ heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). $W^5$ heterocyclic monocycles may have 3 to 6 ring atoms (2 to 5 carbon atoms and 1 to 2 heteroatoms selected from N, O, and S); or 5 or 6 ring atoms (3 to 5 carbon atoms and 1 to 2 heteroatoms selected from N and S). $W^5$ heterocyclic bicycles have 7 to 10 ring atoms (6 to 9 carbon atoms and 1 to 2 heteroatoms selected from N, O, and S) arranged as a bicyclo[4,5], [5,5], [5,6], or [6,6] system; or 9 to 10 ring atoms (8 to 9 carbon atoms and 1 to 2 hetero atoms selected from N and S) arranged as a bicyclo[5,6] or [6,6] system. The $W^5$ heterocycle may be bonded to $Y^2$ through a carbon, nitrogen, sulfur or other atom by a stable covalent bond.

$W^5$ heterocycles include for example, pyridyl, dihydropyridyl isomers, piperidine, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl. $W^5$ also includes, but is not limited to, examples such as:

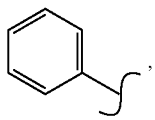, 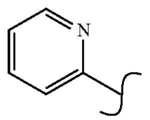, 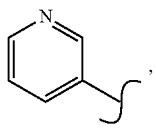,

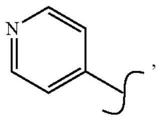, 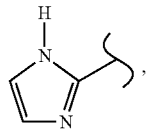, 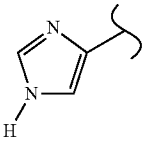,

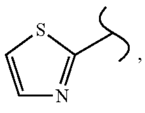, 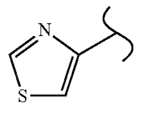, and 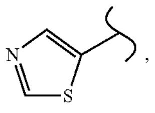, $W^5$ carbocycles and heterocycles may be independently substituted with 0 to 3 $R^2$ groups, as defined above. For example, substituted $W^5$ carbocycles include:

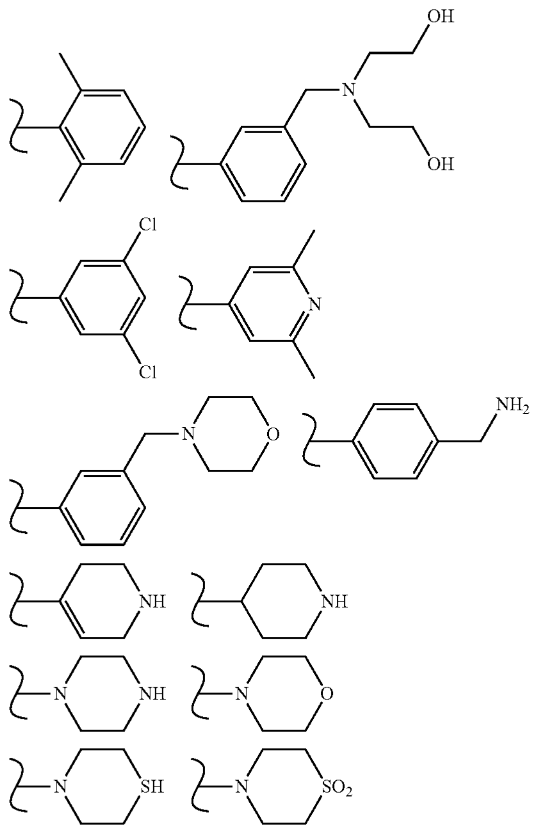

Examples of substituted phenyl carbocycles include:

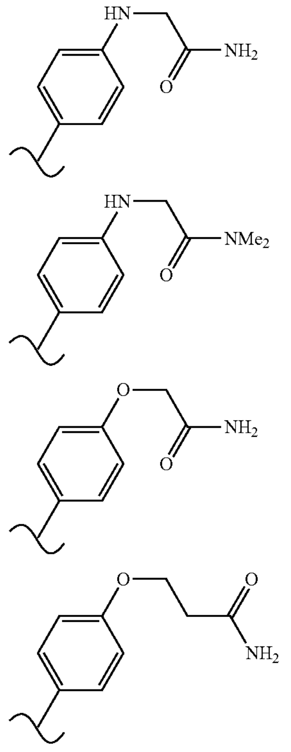

-continued

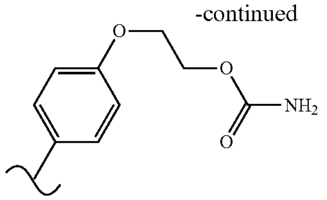

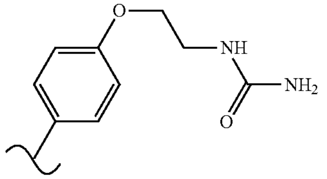

Conjugates of Formula I

In one embodiment, the invention provides a conjugate of Formula I:

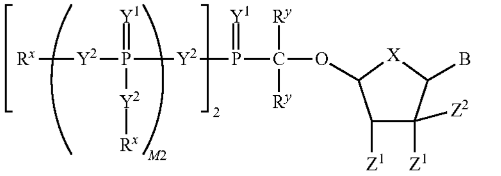

I or a pharmaceutically acceptable salt or solvate thereof; wherein:

B is selected from adenine, guanine, cytosine, uracil, thymine, 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, substituted triazole, and pyrazolo [3,4-D]pyrimidine;

X is selected from 0, $C(R^y)_2$, $C{=}C(R^y)_2$, NR and S;

$Z^1$ is independently selected from H, OH, OR, $NR_2$, CN, $NO_2$, SH, SR, F, Cl, Br, and I;

$Z^2$ is selected from H, $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, and $C_1$-$C_8$ substituted alkynyl, $Y^1$ is independently O, S, NR, $^+N(O)(R)$, N(OR), $^+N(O)(OR)$, or N—$NR_2$;

$Y^2$ is independently a bond, O, $CR_2$, NR, $^+N(O)(R)$, N(OR), $^+N(O)(OR)$, N—$NR_2$, S, S—S, S(O), or $S(O)_2$;

M2 is 0, 1 or 2;

$R^y$ is independently H, F, Cl, Br, I, OH, R, —C(=$Y^1$)R, —C(=$Y^1$)OR, —C(=$Y^1$)N$(R)_2$, —N$(R)_2$, —$^+N(R)_3$, —SR, —S(O)R, —$S(O)_2$R, —S(O)(OR), —$S(O)_2$(OR), —OC(=$Y^1$)R, —OC(=$Y^1$)OR, —OC(=$Y^1$)(N$(R)_2$), —SC(=$Y^1$)R, —SC(=$Y^1$)OR, —SC(=$Y^1$)(N$(R)_2$), —N(R)C(=$Y^1$)R, —N(R)C(=$Y^1$)OR, or —N(R)C(=$Y^1$) N$(R)_2$, amino (—$NH_2$), ammonium (—$NH_3^+$), alkylamino, dialkylamino, trialkylammonium, $C_1$-$C_8$ alkyl, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, alkylsulfone (—$SO_2$R), arylsulfone (—$SO_2$Ar), arylsulfoxide (—SOAr), arylthio (—SAr), sulfonamide (—$SO_2NR_2$), alkylsulfoxide (—SOR), ester (—C(=O)OR), amido (—C(=O)$NR_2$), 5-7 membered ring lactam, 5-7 membered ring lactone, nitrile (—CN), azido (—$N_3$), nitro (—$NO_2$), $C_1$-$C_8$ alkoxy (—OR), $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, polyethyleneoxy, a protecting group (PG), or $W^3$; or when taken together, $R^y$ forms a carbocyclic ring of 3 to 7 carbon atoms;

$R^x$ is independently $R^y$, a protecting group, or the formula:

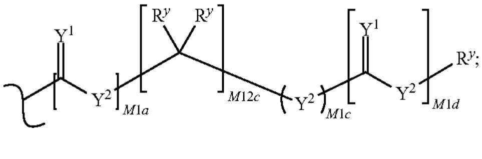

wherein:

M1a, M1c, and Mid are independently 0 or 1;

M12c is 0, 1, 2, 3, 4, 5, 6, 7, 8, 9, 10, 11 or 12; and

R is $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, or a protecting group; and $W^3$ is $W^4$ or $W^5$, where $W^4$ is R, —C($Y^1$)$R^y$, —C($Y^1$)$W^5$, —$SO_2R^y$, or —$SO_2W^5$; and $W^5$ is a carbocycle or a heterocycle wherein $W^5$ is independently substituted with 0 to 3 $R^y$ groups.

For a conjugate of Formula I, in one specific embodiment, $C_1$-$C_8$ substituted alkyl, $C_1$-$C_8$ substituted alkenyl, $C_1$-$C_8$ substituted alkynyl, $C_6$-$C_{20}$ substituted aryl, and $C_2$-$C_{20}$ substituted heterocycle are independently substituted with one or more substituents selected from F, Cl, Br, I, OH, —$NH_2$, —$NH_3^+$, —NHR, —$NR_2$, —$NR_3^+$, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, —$SO_2$R, —$SO_2$Ar, —SOAr, —SAr, —$SO_2NR_2$, —SOR, —$CO_2$R, —C(=O)$NR_2$, 5-7 membered ring lactam, 5-7 membered ring lactone, —CN, —$N_3$, —$NO_2$, $C_1$-$C_8$ alkoxy, $C_1$-$C_8$ trifluoroalkyl, $C_1$-$C_8$ alkyl, $C_3$-$C_{12}$ carbocycle, $C_6$-$C_{20}$ aryl, $C_2$-$C_{20}$ heterocycle, polyethyleneoxy, phosphonate, phosphate, and a prodrug moiety.

For a conjugate of Formula I, in one specific embodiment, "protecting group" is selected from a carboxyl ester, a carboxamide, an aryl ether, an alkyl ether, a trialkylsilyl ether, a sulfonic acid ester, a carbonate, and a carbamate.

For a conjugate of Formula I, in one specific embodiment, $W^5$ is selected from the structures:

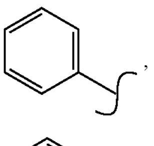,
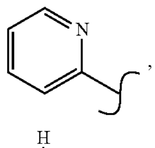,
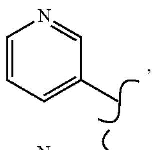,

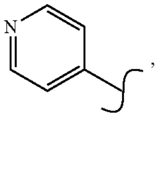,
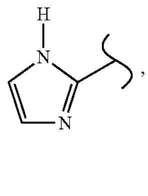,
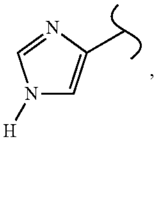,

-continued

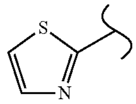, 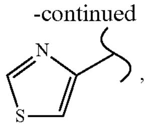, and 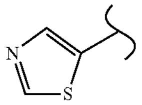.

For a conjugate of Formula I, in one specific embodiment, X is O and $R^y$ is H.

For a conjugate of Formula I, in one specific embodiment, X is C$=$$CH_2$ and $R^y$ is H.

For a conjugate of Formula I, in one specific embodiment, $Z^1$ is OH.

For a conjugate of Formula I, in one specific embodiment, $Z^2$ is $C_1$-$C_8$ alkyl or $C_1$-$C_8$ substituted alkyl.

For a conjugate of Formula I, in one specific embodiment, $Z^2$ is $CH_3$.

In one specific embodiment, the conjugate of formula I has the following formula:

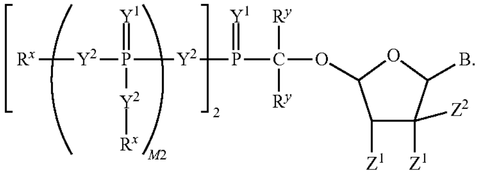

In one specific embodiment, the conjugate of formula I has the following formula:

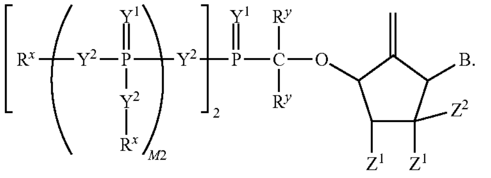

In one specific embodiment, the conjugate of formula I has the following formula:

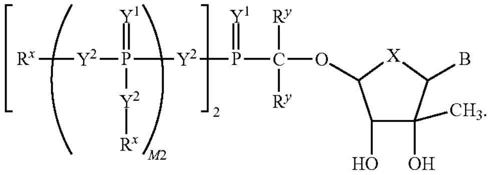

In one specific embodiment, the conjugate of formula I has the following formula:

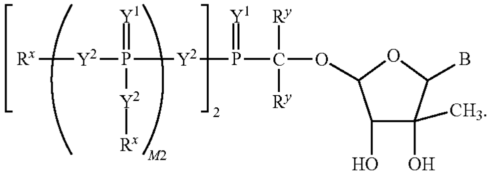

In one specific embodiment, the conjugate of formula I has the following formula:

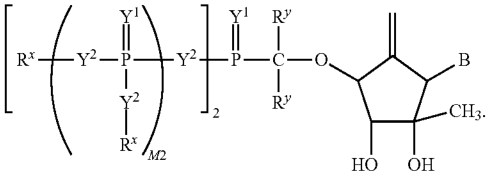

In one specific embodiment, the conjugate of formula I has the following formula:

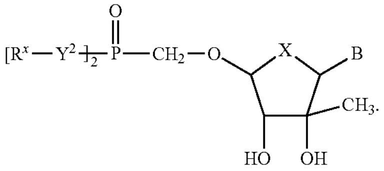

In one specific embodiment, the conjugate of formula I has the following formula:

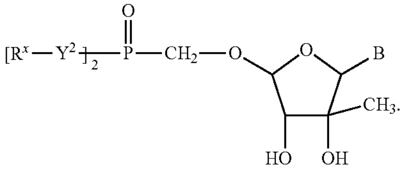

In one specific embodiment, the conjugate of formula I has the following formula:

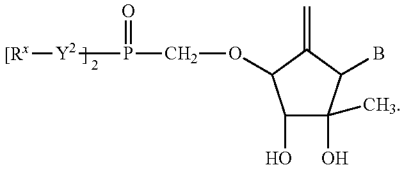

In one specific embodiment, the conjugate of formula I has the following formula:

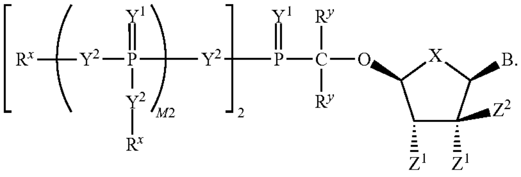

wherein, in a more specific embodiment, $Z^1$ is OH; $Z^2$ is $C_1$-$C_8$ alkyl or $C_1$-$C_8$ substituted alkyl; and $Z^2$ is $CH_3$.

In one specific embodiment, the conjugate of formula I has the following formula:

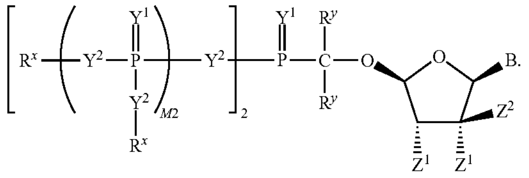

In one specific embodiment, the conjugate of formula I has the following formula:

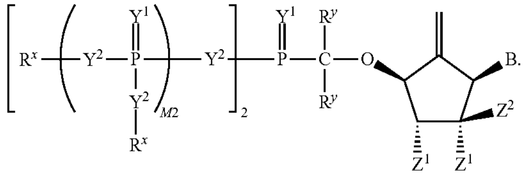

In one specific embodiment, the conjugate of formula I has the following formula:

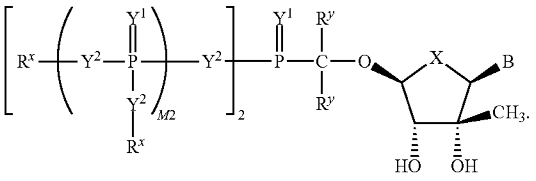

In one specific embodiment, the conjugate of formula I has the following formula:

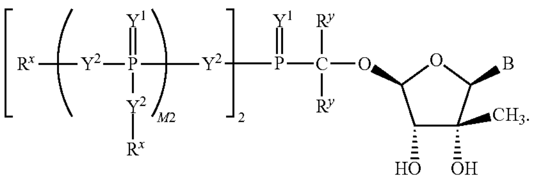

In one specific embodiment, the conjugate of formula I has the following formula:

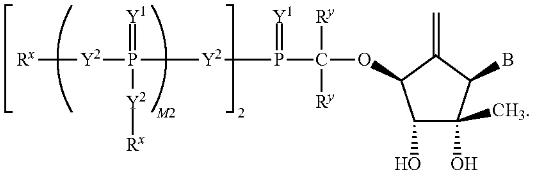

In one specific embodiment, the conjugate of formula I has the following formula:

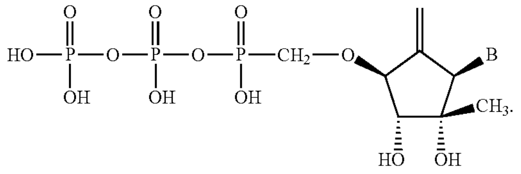

In one specific embodiment, the conjugate of formula I has the following formula:

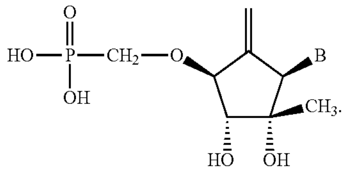

In one specific embodiment, the conjugate of formula I has the following formula:

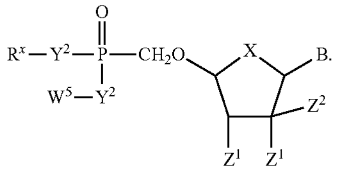

In one specific embodiment, the conjugate of formula I has the following formula:

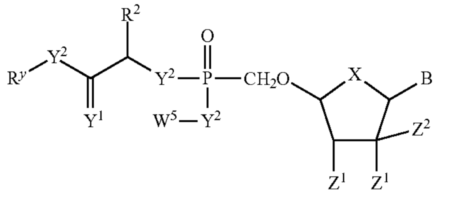

wherein $R^2$ is H or $C_1$-$C_8$ alkyl.

In one specific embodiment, the conjugate of formula I has the following formula:

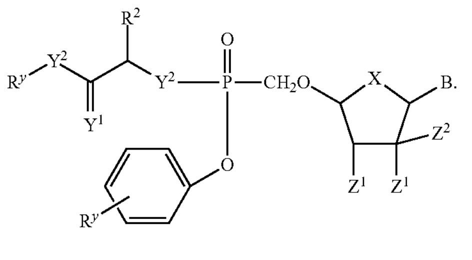

In one specific embodiment, the conjugate of formula I has the following formula:

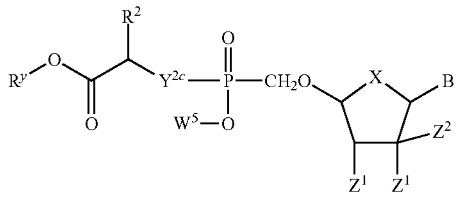

wherein $Y^{2c}$ is O, $N(R^y)$ or S.

In one specific embodiment, the conjugate of formula I has the following formula:

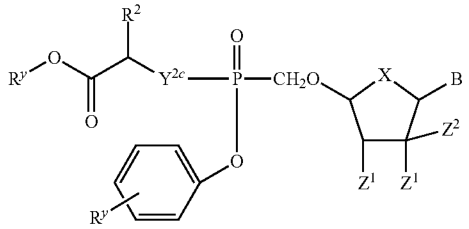

wherein, in a more specific embodiment, $Y^{2c}$ is O; $Y^{2c}$ is $N(CH_3)$; and $R^y$ is H or $C_1$-$C_8$ alkyl.

For a conjugate of Formula I, in one specific embodiment, the substituted triazole has the structure:

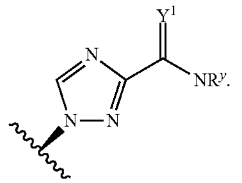

In one specific embodiment, the conjugate of Formula I is a conjugate of the following formula:

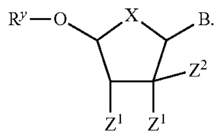

or a pharmaceutically acceptable salt or solvate thereof; wherein:

B is selected from adenine, guanine, cytosine, uracil, thymine, 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^6$-methylthymine, 5,6-dihydrothymine, 5,6-dihydrouracil, 4-methylindole, substituted triazole, and pyrazolo [3,4-D]pyrimidine;

$Z^1$ is independently selected from H, OH, OR, $NR_2$, CN, $NO_2$, SH, SR, F, Cl, Br, and I;

$Z^2$ is selected from H, $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, and $C_1$-$C_8$ substituted alkynyl, $R^y$ is independently H, F, Cl, Br, I, OH, R, $-C(=Y^1)R$, $-C(=Y^1)OR$, $-C(=Y^1)N(R)_2$, $-N(R)_2$, $-^+N(R)_3$, $-SR$, $-S(O)R$, $-S(O)_2R$, $-S(O)(OR)$, $-S(O)_2(OR)$, $-OC(=Y^1)R$, $-OC(=Y^1)OR$, $-OC(=Y^1)(N(R)_2)$, $-SC(=Y^1)R$, $-SC(=Y^1)OR$, $-SC(=Y^1)(N(R)_2)$, $-N(R)C(=Y^1)R$, $-N(R)C(=Y^1)OR$, or $-N(R)C(=Y^1)N(R)_2$, amino ($-NH_2$), ammonium ($-NH_3^+$), alkylamino, dialkylamino, trialkylammonium, $C_1$-$C_8$ alkyl, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, alkylsulfone ($-SO_2R$), arylsulfone ($-SO_2Ar$), arylsulfoxide ($-SOAr$), arylthio ($-SAr$), sulfonamide ($-SO_2NR_2$), alkylsulfoxide ($-SOR$), ester ($-C(=O)OR$), amido ($-C(=O)NR_2$), 5-7 membered ring lactam, 5-7 membered ring lactone, nitrile ($-CN$), azido ($-N_3$), nitro ($-NO_2$), $C_1$-$C_8$ alkoxy ($-OR$), $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, polyethyleneoxy, a protecting group (PG), or $W^3$; or when taken together, $R^y$ forms a carbocyclic ring of 3 to 7 carbon atoms;

R is $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, or a protecting group; and $W^3$ is $W^4$ or $W^5$, where $W^4$ is R, $-C(Y^1)R^y$, $-C(Y^1)W^5$, $-SO_2R^y$, or $-SO_2W^5$; and $W^5$ is a carbocycle or a heterocycle wherein $W^5$ is independently substituted with 0 to 3 $R^y$ groups.

In one specific embodiment, the conjugate of Formula I has the following formula:

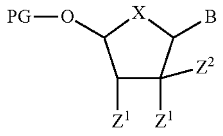

wherein PG is a protecting group selected from an ether-forming group, a thioether-forming group, an ester-forming group, a thioester-forming group, a silyl-ether forming group, an amide-forming group, an acetal-forming group, a ketal-forming group, a carbonate-forming group, a carbamate-forming group, a urea-forming group, an amino acid conjugate, and a polypeptide conjugate.

In one specific embodiment, the invention provides a conjugate of Formula I having one of the following formulae:

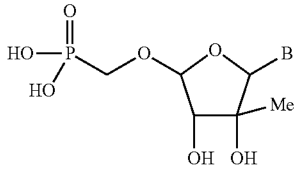

-continued

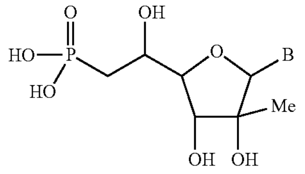

or a pharmaceutically acceptable salt or solvate thereof; wherein B is adenine, guanine, cytosine, uracil, thymine, 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, substituted triazole, or pyrazolo[3,4-D]pyrimidine. In an additional embodiment, the compound is isolated and purified.

In one specific embodiment, the invention provides a conjugate of Formula I having one of the following formulae:

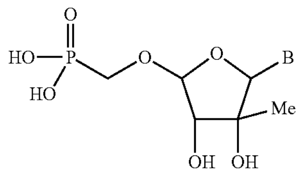

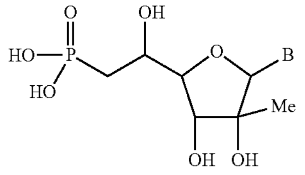

or a pharmaceutically acceptable salt or solvate thereof; wherein B is adenine, guanine, cytosine, uracil, thymine, 7-deazaadenine, 2,6-diaminopurine, 5-fluorocytosine, or c-propyl-2,6-diaminopurine. In an additional embodiment, the compound is isolated and purified.

In one specific embodiment, the invention provides a conjugate of Formula I having one of the following formulae:

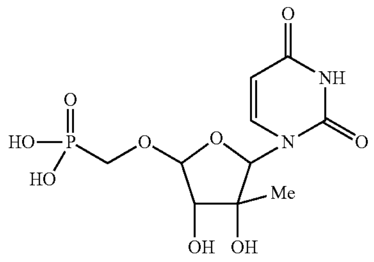

-continued

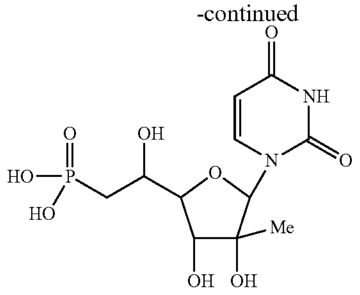

or a pharmaceutically acceptable salt or solvate thereof. In an additional embodiment, the compound is isolated and purified.

In one specific embodiment, the invention provides a conjugate of Formula I having one of the following formulae:

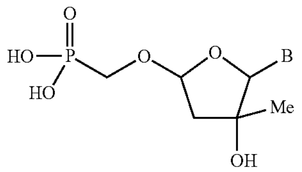

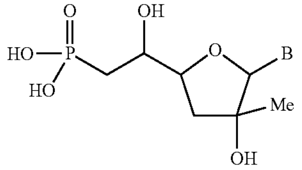

or a pharmaceutically acceptable salt or solvate thereof; wherein B is adenine, guanine, cytosine, uracil, thymine, 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, substituted triazole, or pyrazolo[3,4-D]pyrimidine. In an additional embodiment, the compound is isolated and purified.

In one specific embodiment, the invention provides a conjugate of Formula I having one of the following formulae:

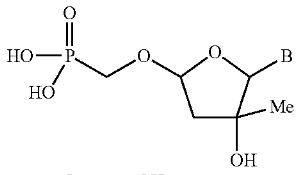

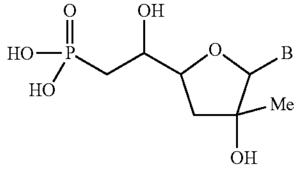

or a pharmaceutically acceptable salt or solvate thereof; wherein B is adenine, guanine, cytosine, uracil, thymine, 7-deazaadenine, 2,6-diaminopurine, 5-fluorocytosine, or c-propyl-2,6-diaminopurine. In an additional embodiment, the compound is isolated and purified.

In one specific embodiment, the invention provides a conjugate of Formula I having one of the following formulae:

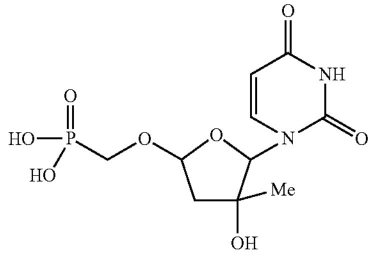

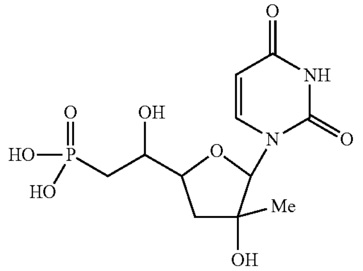

or a pharmaceutically acceptable salt or solvate thereof. In an additional embodiment, the compound is isolated and purified.

In one embodiment, the invention also provides a method for the treatment or prevention of the symptoms or effects of HCV infection in an infected animal comprising administering to said animal, a pharmaceutical composition or formulation comprising an effective amount of a conjugate of formula I, or a pharmaceutically acceptable salt or solvate thereof.

In one embodiment, the invention also provides a method for the treatment or prevention of the symptoms or effects of HCV infection in an infected animal comprising administering to said animal a pharmaceutical composition or formulation comprising a conjugate of formula I, or a pharmaceutically acceptable salt or solvate thereof.

In one embodiment, the invention also provides a method for the treatment or prevention of the symptoms or effects of HCV infection in an infected animal comprising administering said animal with a pharmaceutical combination composition or formulation comprising an effective amount of a conjugate of formula I, or a pharmaceutically acceptable salt or solvate thereof, and a second compound having anti-HCV properties.

In one embodiment, the invention also provides a a pharmaceutical composition comprising an effective amount of a conjugate of formula I, or a pharmaceutically acceptable salt or solvate thereof, and a pharmaceutically acceptable excipient.

In one embodiment, the invention also provides a method of inhibiting a viral enzyme comprising the step of contacting a sample suspected of containing viral infected cells or tissues with a a conjugate of formula I, or a pharmaceutically acceptable salt or solvate thereof.

In one embodiment, the invention also provides a method for the treatment or prevention of the symptoms or effects of a viral infection in an animal which comprises administering to said animal a formulation comprising a therapeutically effective amount of a conjugate of formula I, or a pharmaceutically acceptable salt or solvate thereof.

In one embodiment, the invention also provides the use of a conjugate of formula I, or a pharmaceutically acceptable salt or solvate thereof to prepare a medicament for treatment of HCV.

In one embodiment, the invention also provides a conjugate of formula I, or a pharmaceutically acceptable salt or solvate thereof, which is capable of accumulating in human PBMC.

In one embodiment, the invention also provides a conjugate wherein the bioavailability of the conjugate or an intracellular metabolite of the conjugate in human PBMC is improved compared to the corresponding analog lacking the phosphonate group. For example, in one embodiment, the half-life is improved by at least about 50%; in another embodiment, the half-life is improved by at least about 100%; and in another embodiment, the half-life is improved by greater than 100%.

In one embodiment, the invention also provides a pharmaceutical composition comprising an effective amount of a conjugate of formula I, or a pharmaceutically acceptable salt or solvate thereof; a pharmaceutically acceptable excipient; and a therapeutically effective amount of an AIDS treatment agent selected from an HIV inhibitor agent, an anti-infective agent, and an immunomodulator.

In one embodiment, the invention also provides a pharmaceutical composition comprising an effective amount of a conjugate of Formula I, or a pharmaceutically acceptable salt or solvate thereof; a pharmaceutically acceptable excipient; and a therapeutically effective amount of an HIV-protease inhibitor.

In one embodiment, the invention also provides a pharmaceutical composition comprising an effective amount of a conjugate of Formula I, or a pharmaceutically acceptable salt or solvate thereof; a pharmaceutically acceptable excipient; and a therapeutically effective amount of a reverse transcriptase inhibitor.

In one embodiment, the invention also provides a pharmaceutical composition comprising an effective amount of a conjugate of Formula I, or a pharmaceutically acceptable salt or solvate thereof; a pharmaceutically acceptable excipient; and a therapeutically effective amount of a non-nucleoside reverse transcriptase inhibitor.

In one embodiment, the invention also provides a pharmaceutical composition comprising an effective amount of a conjugate of Formula I, or a pharmaceutically acceptable salt or solvate thereof; a pharmaceutically acceptable excipient; and a therapeutically effective amount of an HIV integrase inhibitor.

In one embodiment, the invention also provides a process for making a pharmaceutical composition comprising combining a conjugate of formula I, or a pharmaceutically acceptable salt or solvate thereof, and a pharmaceutically acceptable excipient.

In one embodiment, the invention also provides a method of inhibiting RNA-dependent RNA polymerase comprising administering to a mammal in need of such treatment, a therapeutically effective amount of a conjugate of Formula I, or a pharmaceutically acceptable salt or solvate thereof.

In one embodiment, the invention also provides a method of treating an HCV infection comprising administering to a mammal in need of such treatment a therapeutically effective amount of a conjugate of formula I, or a pharmaceutically acceptable salt or solvate thereof In one embodiment, the invention also provides a method of treating a disorder affecting white blood cells comprising:

administering a conjugate of Formula I, or a pharmaceutically acceptable salt or solvate thereof to a patient in need of white-blood-cell targeting.

In one embodiment, the invention also provides a method of manufacturing an HCV inhibitor conjugate having both selectivity for white blood cells and a desired pharmaceutical activity, comprising: chemically synthesizing a conjugate of Formula I (as described herein), wherein said conjugate differs from a second structure of a compound known to have said desired pharmaceutical activity by having at least one hydrogen atom of said second structure replaced by an organic substituent comprising a prodrug moiety or incipient prodrug moiety.

In one embodiment, the invention also provides a method of accumulating an RNA-dependent RNA polymerase inhibitor compound inside a white blood cell, comprising administering to a sample, a composition comprising a conjugate of formula I, or a pharmaceutically acceptable salt or solvate thereof. In one specific embodiment, said sample is a patient.

Conjugates of Formula II

In one embodiment, the invention provides a conjugate of Formula II:

II

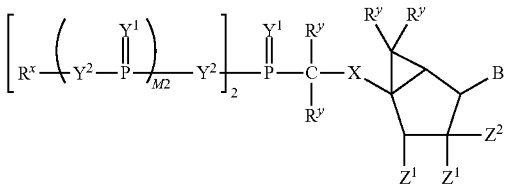

or a pharmaceutically acceptable salt or solvate thereof; wherein:

B is selected from adenine, guanine, cytosine, uracil, thymine, 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, substituted triazole, and pyrazolo [3,4-D]pyrimidine;

X is selected from 0, $C(R^y)_2$, $OC(R^y)_2$, NR and S;

$Z^1$ is independently selected from H, OH, OR, $NR_2$, CN, $NO_2$, SH, SR, F, Cl, Br, and I;

$Z^2$ is selected from H, $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, and $C_1$-$C_8$ substituted alkynyl, $Y^1$ is independently O, S, NR, $^+N(O)(R)$, N(OR), $^+N(O)(OR)$, or N—$NR_2$;

$Y^2$ is independently a bond, O, $CR_2$, NR, $^+N(O)(R)$, N(OR), $^+N(O)(OR)$, N—$NR_2$, S, S—S, S(O), or $S(O)_2$;

M2 is 0, 1 or 2;

$R^y$ is independently H, F, Cl, Br, I, OH, R, —C(=$Y^1$)R, —C(=$Y^1$)OR, —C(=$Y^1$)$N(R)_2$, —$N(R)_2$, —$^+N(R)_3$, —SR, —S(O)R, —$S(O)_2R$, —S(O)(OR), —$S(O)_2(OR)$, —OC(=$Y^1$)R, —OC(=$Y^1$)OR, —OC(=$Y^1$)($N(R)_2$), —SC(=$Y^1$)R, —SC(=$Y^1$)OR, —SC(=$Y^1$)($N(R)_2$), —N(R)C(=$Y^1$)R, —N(R)C(=$Y^1$)OR, or —N(R)C(=$Y^1$) $N(R)_2$, amino (—$NH_2$), ammonium (—$NH_3^+$), alkylamino, dialkylamino, trialkylammonium, $C_1$-$C_8$ alkyl, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, alkylsulfone (—$SO_2R$), arylsulfone (—$SO_2Ar$), arylsulfoxide (—SOAr), arylthio (—SAr), sulfonamide (—$SO_2NR_2$), alkylsulfoxide (—SOR), ester (—C(=O)OR), amido (—C(=O)$NR_2$), 5-7 membered ring lactam, 5-7 membered ring lactone, nitrile (—CN), azido (—$N_3$), nitro (—$NO_2$), $C_1$-$C_8$ alkoxy (—OR), $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, polyethyleneoxy, a protecting group, or $W^3$; or when taken together, $R^y$ forms a carbocyclic ring of 3 to 7 carbon atoms;

$R^x$ is independently $R^y$, a protecting group, or the formula:

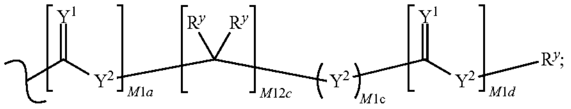

wherein:

M1a, M1c, and M1d are independently 0 or 1;

M12c is 0, 1, 2, 3, 4, 5, 6, 7, 8, 9, 10, 11 or 12; and

R is $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, or a protecting group; and $W^3$ is $W^4$ or $W^5$, where $W^4$ is R, —C($Y^1$)$R^y$, —C($Y^1$)$W^5$, —$SO_2R^y$, or —$SO_2W^5$; and $W^5$ is a carbocycle or a heterocycle wherein $W^5$ is independently substituted with 0 to 3 $R^y$ groups.

For a conjugate of Formula II, in one specific embodiment, $C_1$-$C_8$ substituted alkyl, $C_1$-$C_8$ substituted alkenyl, $C_1$-$C_8$ substituted alkynyl, $C_6$-$C_{20}$ substituted aryl, and $C_2$-$C_{20}$ substituted heterocycle are independently substituted with one or more substituents selected from F, Cl, Br, I, OH, —$NH_2$, —$NH_3^+$, —NHR, —$NR_2$, —$NR_3^+$, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, —$SO_2R$, —$SO_2Ar$, —SOAr, —SAr, —$SO_2NR_2$, —SOR, —$CO_2R$, —C(=O)$NR_2$,5-7 membered ring lactam, 5-7 membered ring lactone, —CN, —$N_3$, —$NO_2$, $C_1$-$C_8$ alkoxy, $C_1$-$C_8$ trifluoroalkyl, $C_1$-$C_8$ alkyl, $C_3$-$C_{12}$ carbocycle, $C_6$-$C_{20}$ aryl, $C_2$-$C_{20}$ heterocycle, polyethyleneoxy, phosphonate, phosphate, and a prodrug moiety.

For a conjugate of Formula II, in one specific embodiment, "protecting group" is selected from a carboxyl ester, a carboxamide, an aryl ether, an alkyl ether, a trialkylsilyl ether, a sulfonic acid ester, a carbonate, and a carbamate.

For a conjugate of Formula II, in one specific embodiment, $W^5$ is selected from the structures:

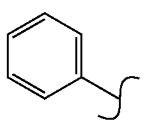, 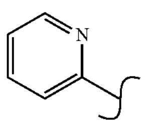, 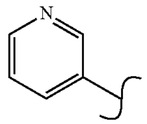,

-continued

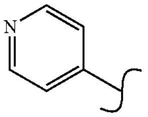,
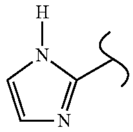,
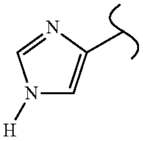,
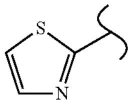,
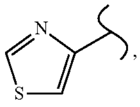, and
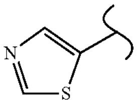.

For a conjugate of Formula II, in one specific embodiment, X is O and $R^y$ is H.

In one specific embodiment, the conjugate of Formula II has the following formula:

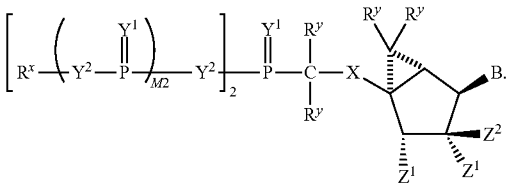

In one specific embodiment, the conjugate of Formula II has the following formula:

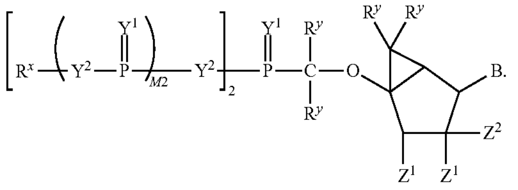

wherein, in a more specific embodiment, $Z^1$ is OH; and $Z^2$ is $CH_3$.

In one specific embodiment, the conjugate of Formula II has the following formula:

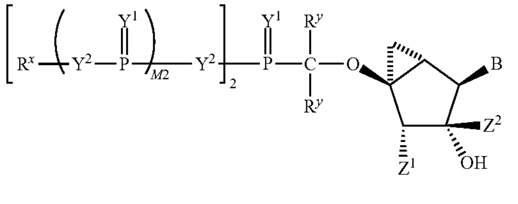

wherein, in a more specific embodiment, $Z^2$ is $C_1$-$C_8$ alkyl or $C_1$-$C_8$ substituted alkyl.

In one specific embodiment, the conjugate of Formula II has the following formula:

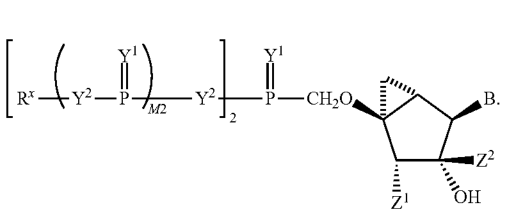

In one specific embodiment, the conjugate of Formula II has the following formula:

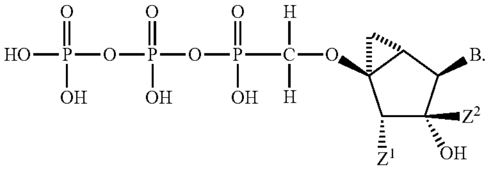

In one specific embodiment, the conjugate of Formula II has the following formula:

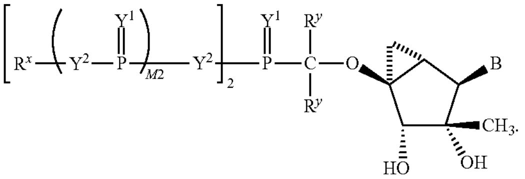

In one specific embodiment; the conjugate of Formula II has the following formula:

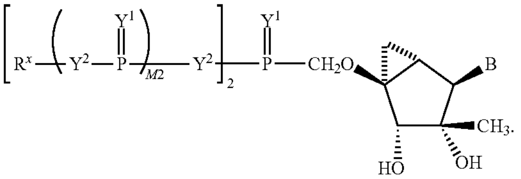

In one specific embodiment, the conjugate of Formula II has the following formula:

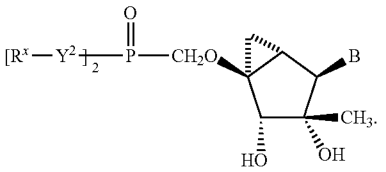

In one specific embodiment, the conjugate of Formula II has the following formula:

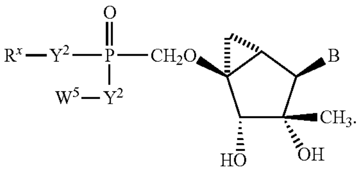

In one specific embodiment, the conjugate of Formula II has the following formula:

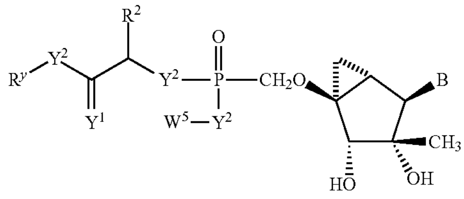

wherein $R^2$ is H or $C_1$-$C_8$ alkyl.

In one specific embodiment, the conjugate of Formula II has the following formula:

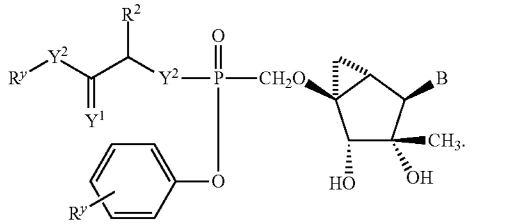

In one specific embodiment, the conjugate of Formula II has the following formula:

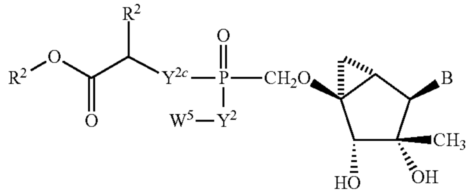

wherein $Y^{2c}$ is O, $N(R^y)$ or S.

In one specific embodiment, the conjugate of Formula II has the following formula:

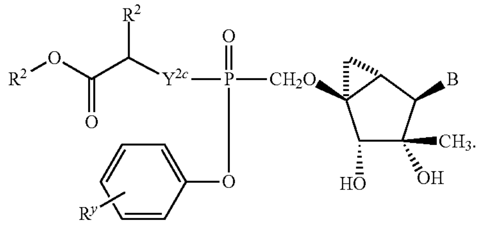

wherein, in a more specific embodiment, $Y^{2c}$ is O; $Y^{2c}$ is $N(CH_3)$.

In one specific embodiment, the substituted triazole has the structure:

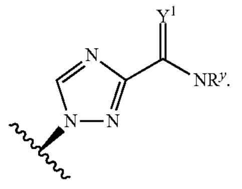

In one specific embodiment, the conjugate of Formula II has the following formula:

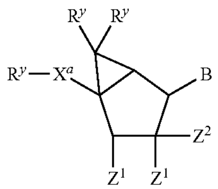

wherein:

B is selected from adenine, guanine, cytosine, uracil, thymine, 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, substituted triazole, and pyrazolo [3,4-D]pyrimidine;

$X^a$ is selected from O, NR and S;

$Z^1$ is independently selected from H, OH, OR, $NR_2$, CN, $NO_2$, SH, SR, F, Cl, Br, and I;

$Z^2$ is selected from H, $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, and $C_1$-$C_8$ substituted alkynyl, $R^y$ is independently H, F, Cl, Br, I, OH, R, $—C(=Y^1)R$, $—C(=Y^1)N(R)_2$, $—N(R)_2$, $—^+N(R)_3$, —SR, —S(O)R, $—S(O)_2R$, —S(O)(OR), $—S(O)_2(OR)$, $—OC(=Y^1)R$, $—OC(=Y^1)OR$, $—OC(=Y^1)(N(R)_2)$, $—SC(=Y^1)R$, $—SC(=Y^1)OR$, $—SC(=Y^1)(N(R)_2)$, $—N(R)C(=Y^1)R$, $—N(R)C(=Y^1)OR$, or $—N(R)C(=Y^1)N(R)_2$, amino ($—NH_2$), ammonium ($—NH_3^+$), alkylamino, dialkylamino, trialkylammonium, $C_1$-$C_8$ alkyl, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, alkylsulfone ($—SO_2R$), arylsulfone ($—SO_2Ar$), arylsulfoxide (—SOAr), arylthio (—SAr), sulfonamide ($—SO_2NR_2$), alkylsulfoxide (—SOR), ester ($—C(=O)OR$), amido ($—C(=O)NR_2$), 5-7 membered ring lactam, 5-7 membered ring lactone, nitrile (—CN), azido ($—N_3$), nitro ($—NO_2$), $C_1$-$C_8$ alkoxy (—OR), $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, polyethyleneoxy, a protecting group, or $W^3$; or when taken together, $R^y$ forms a carbocyclic ring of 3 to 7 carbon atoms;

R is $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, or a protecting group; and $W^3$ is $W^4$ or $W^5$, where $W^4$ is R, $—C(Y^1)R^y$, $—C(Y^1)W^5$, $—SO_2R^y$, or $—SO_2W^5$; and $W^5$ is a carbocycle or a heterocycle wherein $W^5$ is independently substituted with 0 to 3 $R^y$ groups.

In one specific embodiment, the conjugate of Formula II has the following formula:

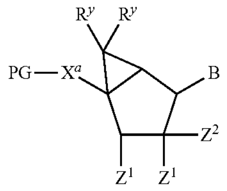

wherein PG is a protecting group selected from an ether-forming group, a thioether-forming group, an ester-forming group, a thioester-forming group, a silyl-ether forming group, an amide-forming group, an acetal-forming group, a ketal-forming group, a carbonate-forming group, a carbamate-forming group, a urea-forming group, an amino acid conjugate, and a polypeptide conjugate.

In one embodiment, the invention also provides a method for the treatment or prevention of the symptoms or effects of HCV infection in an infected animal comprising administering to said animal, a pharmaceutical composition or formulation comprising an effective amount of a conjugate of formula II, or a pharmaceutically acceptable salt or solvate thereof.

In one embodiment, the invention also provides a method for the treatment or prevention of the symptoms or effects of HCV infection in an infected animal comprising administering to said animal a pharmaceutical composition or formulation comprising a conjugate of formula II, or a pharmaceutically acceptable salt or solvate thereof.

In one embodiment, the invention also provides a method for the treatment or prevention of the symptoms or effects of HCV infection in an infected animal comprising administering said animal with a pharmaceutical combination composition or formulation comprising an effective amount of a conjugate of formula II, or a pharmaceutically acceptable salt or solvate thereof, and a second compound having anti-HCV properties.

In one embodiment, the invention also provides a a pharmaceutical composition comprising an effective amount of a conjugate of formula II, or a pharmaceutically acceptable salt or solvate thereof, and a pharmaceutically acceptable excipient.

In one embodiment, the invention also provides a method of inhibiting a viral enzyme comprising the step of contacting a sample suspected of containing viral infected cells or tissues with a a conjugate of formula II, or a pharmaceutically acceptable salt or solvate thereof.

In one embodiment, the invention also provides a method for the treatment or prevention of the symptoms or effects of a viral infection in an animal which comprises administering to said animal a formulation comprising a therapeutically effective amount of a conjugate of formula II, or a pharmaceutically acceptable salt or solvate thereof.

In one embodiment, the invention also provides the use of a conjugate of formula II, or a pharmaceutically acceptable salt or solvate thereof to prepare a medicament for treatment of HCV.

In one embodiment, the invention also provides a conjugate of formula II, or a pharmaceutically acceptable salt or solvate thereof, which is capable of accumulating in human PBMC.

In one embodiment, the invention also provides a conjugate wherein the bioavailability of the conjugate or an intracellular metabolite of the conjugate in human PBMC is improved compared to the corresponding analog lacking the phosphonate group. For example, in one embodiment, the half-life is improved by at least about 50%; in another embodiment, the half-life is improved by at least about 100%; and in another embodiment, the half-life is improved by greater than 100%.

In one embodiment, the invention also provides a pharmaceutical composition comprising an effective amount of a conjugate of formula II, or a pharmaceutically acceptable salt or solvate thereof; a pharmaceutically acceptable excipient; and a therapeutically effective amount of an AIDS treatment agent selected from an HIV inhibitor agent, an anti-infective agent, and an immunomodulator.

In one embodiment, the invention also provides a pharmaceutical composition comprising an effective amount of a conjugate of Formula II, or a pharmaceutically acceptable salt or solvate thereof; a pharmaceutically acceptable excipient; and a therapeutically effective amount of an HIV-protease inhibitor.

In one embodiment, the invention also provides a pharmaceutical composition comprising an effective amount of a conjugate of Formula II, or a pharmaceutically acceptable salt or solvate thereof; a pharmaceutically acceptable excipient; and a therapeutically effective amount of a reverse transcriptase inhibitor.

In one embodiment, the invention also provides a pharmaceutical composition comprising an effective amount of a conjugate of Formula II, or a pharmaceutically acceptable salt or solvate thereof; a pharmaceutically acceptable excipient; and a therapeutically effective amount of a non-nucleoside reverse transcriptase inhibitor.

In one embodiment, the invention also provides a pharmaceutical composition comprising an effective amount of a conjugate of Formula II, or a pharmaceutically acceptable salt or solvate thereof; a pharmaceutically acceptable excipient; and a therapeutically effective amount of an HIV integrase inhibitor.

In one embodiment, the invention also provides a process for making a pharmaceutical composition comprising combining a conjugate of formula II, or a pharmaceutically acceptable salt or solvate thereof, and a pharmaceutically acceptable excipient.

In one embodiment, the invention also provides a method of inhibiting RNA-dependent RNA polymerase comprising administering to a mammal in need of such treatment, a therapeutically effective amount of a conjugate of Formula II, or a pharmaceutically acceptable salt or solvate thereof.

In one embodiment, the invention also provides a method of treating an HCV infection comprising administering to a mammal in need of such treatment a therapeutically effective amount of a conjugate of formula II, or a pharmaceutically acceptable salt or solvate thereof.

In one embodiment, the invention also provides a method of treating a disorder affecting white blood cells comprising: administering a conjugate of Formula II, or a pharmaceutically acceptable salt or solvate thereof to a patient in need of white-blood-cell targeting.

In one embodiment, the invention also provides a method of manufacturing an HCV inhibitor conjugate having both selectivity for white blood cells and a desired pharmaceutical activity, comprising: chemically synthesizing a conjugate of Formula II (as described herein), wherein said conjugate differs from a second structure of a compound known to have said desired pharmaceutical activity by having at least one hydrogen atom of said second structure replaced by an organic substituent comprising a prodrug moiety or incipient prodrug moiety.

In one embodiment, the invention also provides a method of accumulating an RNA-dependent RNA polymerase inhibitor compound inside a white blood cell, comprising administering to a sample, a composition comprising a conjugate of formula II, or a pharmaceutically acceptable salt or solvate thereof. In one specific embodiment, said sample is a patient.

Conjugates of Formula III

In one embodiment, the invention provides a conjugate of Formula III:

III

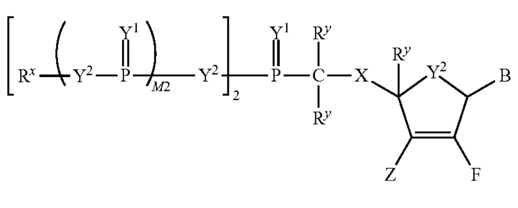

or a pharmaceutically acceptable salt or solvate thereof; wherein:

B is selected from adenine, guanine, cytosine, uracil, thymine, 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, substituted triazole, and pyrazolo [3,4-D]pyrimidine;

X is selected from O, $C(R^y)_2$, $OC(R^y)_2$, NR and S;

Z is independently selected from H, OH, OR, $NR_2$, CN, $NO_2$, SH, SR, F, Cl, Br, and I;

$Y^1$ is independently O, S, NR, $^+N(O)(R)$, N(OR), $^+N(O)(OR)$, or N—$NR_2$;

$Y^2$ is independently O, $CR_2$, NR, $^+N(O)(R)$, N(OR), $^+N(O)(OR)$, N—$NR_2$, S, S—S, S(O), or $S(O)_2$;

M2 is 0, 1 or 2;

$R^y$ is independently H, F, Cl, Br, I, OH, —C(=$Y^1$)R, —C(=$Y^1$)OR, —C(=$Y^1$)N(R)$_2$, —N(R)$_2$, —$^+$N(R)$_3$, —SR, —S(O)R, —S(O)$_2$R, —S(O)(OR), —S(O)$_2$(OR), —OC(=$Y^1$)R, —OC(=$Y^1$)OR, —OC(=$Y^1$)(N(R)$_2$), —SC(=$Y^1$)R, —SC(=$Y^1$)OR, —SC(=$Y^1$)(N(R)$_2$), —N(R)C(=$Y^1$)R, —N(R)C(=$Y^1$)OR, or —N(R)C(=$Y^1$)N(R)$_2$, amino (—$NH_2$), ammonium (—$NH_3^+$), alkylamino, dialkylamino, trialkylammonium, $C_1$-$C_8$ alkyl, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, alkylsulfone (—$SO_2$R), arylsulfone (—$SO_2$Ar), arylsulfoxide (—SOAr), arylthio (—SAr), sulfonamide (—$SO_2NR_2$), alkylsulfoxide (—SOR), ester (—C(=O)OR), amido (—C(=O)$NR_2$), 5-7 membered ring lactam, 5-7 membered ring lactone, nitrite (—CN), azido (—$N_3$), nitro (—$NO_2$), $C_1$-$C_8$ alkoxy (—OR), $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, polyethyleneoxy, or $W^3$; or when taken together, $R^y$ forms a carbocyclic ring of 3 to 7 carbon atoms;

$R^x$ is independently $R_y$, a protecting group, or the formula:

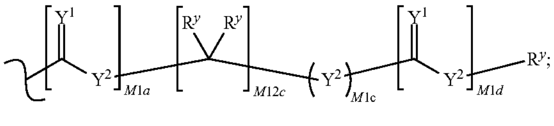

wherein:

M1a, M1c, and Mid are independently 0 or 1;

M12c is 0, 1, 2, 3, 4, 5, 6, 7, 8, 9, 10, 11 or 12; and

R is $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, or a protecting group; and $W^3$ is $W^4$ or $W^5$, where $W^4$ is R, —C($Y^1$)$R^y$, —C($Y^1$)$W^5$, —$SO_2R^y$, or —$SO_2W^5$; and $W^5$ is a carbocycle or a heterocycle wherein $W^5$ is independently substituted with 0 to 3 $R^y$ groups.

For a conjugate of Formula III, in one specific embodiment, $C_1$-$C_8$ substituted alkyl, $C_1$-$C_8$ substituted alkenyl, $C_1$-$C_8$ substituted alkynyl, $C_6$-$C_{20}$ substituted aryl, and $C_2$-$C_{20}$ substituted heterocycle are independently substituted with one or more substituents selected from F, Cl, Br, I, OH, —$NH_2$, —$NH_3^+$, —NHR, —$NR_2$, —$NR_3^+$, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, —$SO_2$R, —$SO_2$Ar, —SOAr, —SAr, —$SO_2NR_2$, —SOR, —$CO_2$R, —C(=O)$NR_2$,5-7 membered ring lactam, 5-7 membered ring lactone, —CN, —$N_3$, —$NO_2$, $C_1$-$C_8$ alkoxy, $C_1$-$C_8$ trifluoroalkyl, $C_1$-$C_8$ alkyl, $C_3$-$C_{12}$ carbocycle, $C_6$-$C_{20}$ aryl, $C_2$-$C_{20}$ heterocycle, polyethyleneoxy, phosphonate, phosphate, and a prodrug moiety.

For a conjugate of Formula III, in one specific embodiment, "protecting group" is selected from a carboxyl ester, a carboxamide, an aryl ether, an alkyl ether, a trialkylsilyl ether, a sulfonic acid ester, a carbonate, and a carbamate.

In one specific embodiment, for a conjugate of Formula III, $W^5$ is selected from the structures:

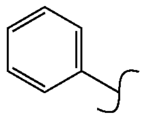, 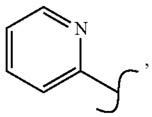, 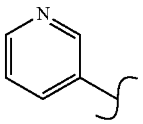,

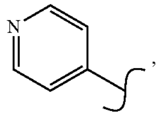, 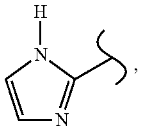, 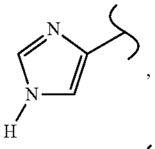,

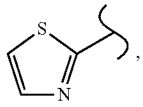, 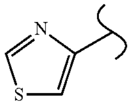, and 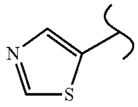.

In one specific embodiment, for a conjugate of Formula III, X is O and each $R^y$ is H.

In one specific embodiment, the conjugate of Formula III is a resolved enantiomer having the structure:

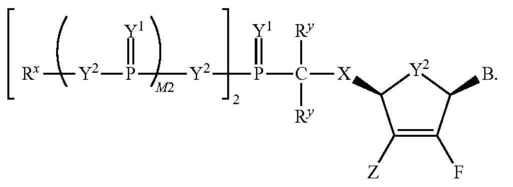

In one specific embodiment, the conjugate of Formula III is a resolved enantiomer having the structure:

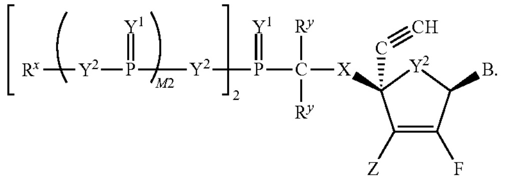

In one specific embodiment, the conjugate of Formula III has the following formula:

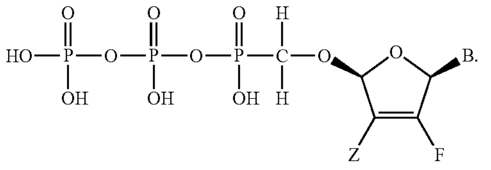

In one specific embodiment, the conjugate of Formula III has the following formula:

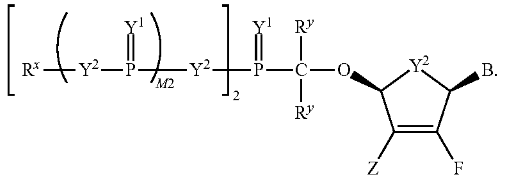

In one specific embodiment, the conjugate of Formula III has the following formula:

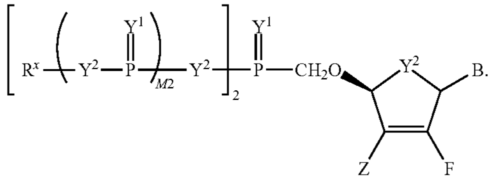

In one specific embodiment, the conjugate of Formula III has the following formula:

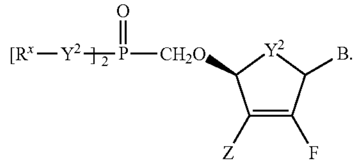

In one specific embodiment, the conjugate of Formula III has the following formula:

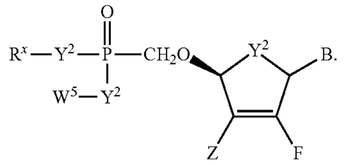

In one specific embodiment, the conjugate of Formula III has the following formula:

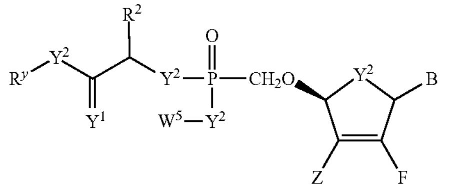

wherein $R^2$ is H or $C_1$-$C_8$ alkyl.

In one specific embodiment, the conjugate of Formula III has the following formula:

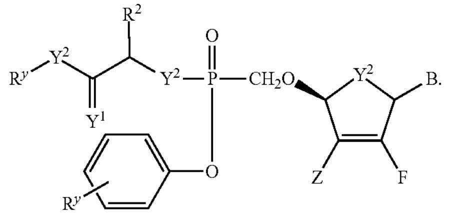

In one specific embodiment, the conjugate of Formula III has the following formula:

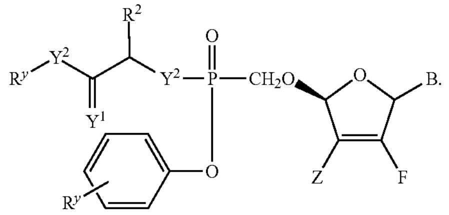

wherein in a more specific embodiment, Z is H and B is adenine.

In one specific embodiment, the conjugate of Formula III has the following formula:

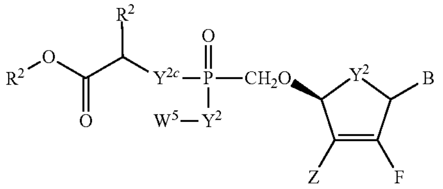

wherein $Y^{2c}$ is O, $N(R^y)$ or S.

In one specific embodiment, the conjugate of Formula III has the following formula:

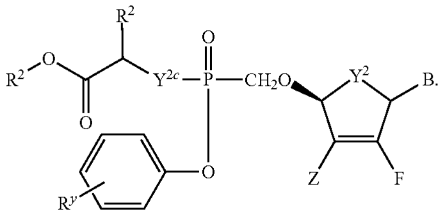

wherein, in a more specific embodiment, $Y^{2c}$ is O or $N(CH_3)$.

In one specific embodiment, for a conjugate of Formula III, substituted triazole has the structure:

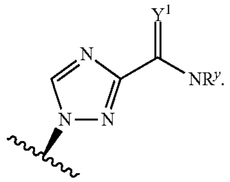

In one specific embodiment, the conjugate of Formula III has the following formula:

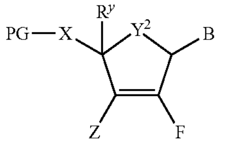

wherein:

B is selected from adenine, guanine, cytosine, uracil, thymine, 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, substituted triazole, and pyrazolo [3,4-D]pyrimidine;

X is selected from O, $C(R^y)_2$, $OC(R^y)_2$, NR and S;

Z is independently selected from H, OH, OR, $NR_2$, CN, $NO_2$, SH, SR, F, Cl, Br, and I;

$Y^2$ is independently O, $CR_2$, NR, $^+N(O)(R)$, N(OR), $^+N(O)(OR)$, N—$NR_2$, S, S—S, S(O), or $S(O)_2$;

$R^y$ is independently H, F, Cl, Br, I, OH, —C(=$Y^1$)R, —C(=$Y^1$)OR, —C(=$Y^1$)N(R)$_2$, —N(R)$_2$, —$^+N(R)_3$, —SR, —S(O)R, —S(O)$_2$R, —S(O)(OR), —S(O)$_2$(OR), —OC(=$Y^1$)R, —OC(=$Y^1$)OR, —OC(=$Y^1$)(N(R)$_2$), —SC(=$Y^1$)R, —SC(=$Y^1$)OR, —SC(=$Y^1$)(N(R)$_2$), —N(R)C(=$Y^1$)R, —N(R)C(=$Y^1$)OR, or —N(R)C(=$Y^1$) N(R)$_2$, amino (—$NH_2$), ammonium (—$NH_3^+$), alkylamino, dialkylamino, trialkylammonium, $C_1$-$C_8$ alkyl, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, alkylsulfone (—$SO_2$R), arylsulfone (—$SO_2$Ar), arylsulfoxide (—SOAr), arylthio (—SAr), sulfonamide (—$SO_2NR_2$), alkylsulfoxide (—SOR), ester (—C(=O)OR), amido (—C(=O)$NR_2$), 5-7 membered ring lactam, 5-7 membered ring lactone, nitrile (—CN), azido (—$N_3$), nitro (—$NO_2$), $C_1$-$C_8$ alkoxy (—OR), $C_1$-$C_8$ alkyl, $C_1$-$C_8$ substituted alkyl, $C_1$-$C_8$ alkenyl, $C_1$-$C_8$ substituted alkenyl, alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, polyethyleneoxy, or $W^3$; or when taken together, $R^y$ forms a carbocyclic ring of 3 to 7 carbon atoms;

R is $C_1$-$C_8$ alkyl, $C_1$-$C_8$ substituted alkyl, $C_1$-$C_8$ alkenyl, $C_1$-$C_8$ substituted alkenyl, $C_1$-$C_8$ alkynyl, $C_1$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, or a protecting group; and PG is a protecting group selected from an ether-forming group, an ester-forming group, a silyl-ether forming group, an amide-forming group, an acetal-forming group, a ketal-forming group, a carbonate-forming group, a carbamate-forming group, an amino acid, and a polypeptide.

In one embodiment, the invention also provides a method for the treatment or prevention of the symptoms or effects of viral infection in an infected animal comprising administering to said animal, a pharmaceutical composition or formulation comprising an effective amount of a conjugate of formula III, or a pharmaceutically acceptable salt or solvate thereof In one embodiment, the invention also provides a method for the treatment or prevention of the symptoms or effects of viral infection in an infected animal comprising administering to said animal a pharmaceutical composition or formulation comprising a conjugate of formula III, or a pharmaceutically acceptable salt or solvate thereof.

In one embodiment, the invention also provides a method for the treatment or prevention of the symptoms or effects of viral infection in an infected animal comprising administering said animal with a pharmaceutical combination composition or formulation comprising an effective amount of a conjugate of formula III, or a pharmaceutically acceptable salt or solvate thereof, and a second compound having antiviral properties.

In one embodiment, the invention also provides a a pharmaceutical composition comprising an effective amount of a conjugate of formula III, or a pharmaceutically acceptable salt or solvate thereof, and a pharmaceutically acceptable excipient.

In one embodiment, the invention also provides a method of inhibiting a viral enzyme comprising the step of contacting a sample suspected of containing viral infected cells or tissues with a a conjugate of formula III, or a pharmaceutically acceptable salt or solvate thereof.

In one embodiment, the invention also provides a method for the treatment or prevention of the symptoms or effects of a viral infection in an animal which comprises administering to said animal a formulation comprising a therapeutically effective amount of a conjugate of formula III, or a pharmaceutically acceptable salt or solvate thereof.

In one embodiment, the invention also provides the use of a conjugate of formula III, or a pharmaceutically acceptable salt or solvate thereof to prepare a medicament for treatment of viral infection.

In one embodiment, the invention also provides a conjugate of formula III, or a pharmaceutically acceptable salt or solvate thereof, which is capable of accumulating in human PBMC.

In one embodiment, the invention also provides a conjugate (e.g. of formula III) wherein the bioavailability of the conjugate or an intracellular metabolite of the conjugate in human PBMC is improved compared to the corresponding analog lacking the phosphonate group. For example, in one embodiment, the half-life is improved by at least about 50%; in another embodiment, the half-life is improved by at least about 100%; and in another embodiment, the half-life is improved by greater than 100%.

In one embodiment, the invention also provides a pharmaceutical composition comprising an effective amount of a conjugate of Formula III, or a pharmaceutically acceptable salt or solvate thereof; a pharmaceutically acceptable excipient; and a therapeutically effective amount of an AIDS treatment agent selected from an HIV inhibitor agent, an anti-infective agent, and an immunomodulator.

In one embodiment, the invention also provides a pharmaceutical composition comprising an effective amount of a conjugate of Formula III, or a pharmaceutically acceptable salt or solvate thereof; a pharmaceutically acceptable excipient; and a therapeutically effective amount of an HIV-protease inhibitor.

In one embodiment, the invention also provides a pharmaceutical composition comprising an effective amount of a conjugate of Formula III, or a pharmaceutically acceptable salt or solvate thereof; a pharmaceutically acceptable excipient; and a therapeutically effective amount of a reverse transcriptase inhibitor.

In one embodiment, the invention also provides a pharmaceutical composition comprising an effective amount of a conjugate of Formula III, or a pharmaceutically acceptable salt or solvate thereof; a pharmaceutically acceptable excipient; and a therapeutically effective amount of a non-nucleoside reverse transcriptase inhibitor.

In one embodiment, the invention also provides a pharmaceutical composition comprising an effective amount of a conjugate of Formula III, or a pharmaceutically acceptable salt or solvate thereof; a pharmaceutically acceptable excipient; and a therapeutically effective amount of an HIV integrase inhibitor.

In one embodiment, the invention also provides a process for making a pharmaceutical composition comprising combining a conjugate of formula III, or a pharmaceutically acceptable salt or solvate thereof, and a pharmaceutically acceptable excipient.

In one embodiment, the invention also provides a method of inhibiting RNA-dependent RNA polymerase comprising administering to a mammal in need of such treatment, a therapeutically effective amount of a conjugate of Formula III, or a pharmaceutically acceptable salt or solvate thereof.

In one embodiment, the invention also provides a method of treating an HCV infection comprising administering to a mammal in need of such treatment a therapeutically effective amount of a conjugate of formula III, or a pharmaceutically acceptable salt or solvate thereof.

In one embodiment, the invention also provides a method of treating a disorder affecting white blood cells comprising: administering a conjugate of Formula III, or a pharmaceutically acceptable salt or solvate thereof to a patient in need of white-blood-cell targeting.

In one embodiment, the invention also provides a method of manufacturing an HCV inhibitor conjugate having both selectivity for white blood cells and a desired pharmaceutical activity, comprising: chemically synthesizing a conjugate of Formula III (as described herein), wherein said conjugate differs from a second structure of a compound known to have said desired pharmaceutical activity by having at least one hydrogen atom of said second structure replaced by an organic substituent comprising a prodrug moiety or incipient prodrug moiety.

In one embodiment, the invention also provides a method of accumulating an RNA-dependent RNA polymerase inhibitor compound inside a white blood cell, comprising administering to a sample, a composition comprising a conjugate of formula III, or a pharmaceutically acceptable salt or solvate thereof. In one specific embodiment, said sample is a patient.

Linking Groups and Linkers

The invention provides conjugates that comprise an antiviral compound that is linked to one or more phosphonate groups either directly (e.g. through a covalent bond) or through a linking group (i.e. a linker) The nature of the linker is not critical provided it does not interfere with the ability of the phosphonate containing compound to function as a therapeutic agent. The phosphonate or the linker can be linked to the compound (e.g. a compound of Formula 501-569) at any synthetically feasible position on the compound by removing a hydrogen or any portion of the compound to provide an open valence for attachment of the phosphonate or the linker.

In one embodiment of the invention the linking group or linker (which can be designated "L") can include all or a portions of the group $A^0$, $A^1$, $A^2$, or $W^3$ described herein.

In another embodiment of the invention the linking group or linker has a molecular weight of from about 20 daltons to about 400 daltons.

In another embodiment of the invention the linking group or linker has a length of about 5 angstroms to about 300 angstroms.

In another embodiment of the invention the linking group or linker separates the DRUG and a $P(=Y^1)$ residue by about 5 angstroms to about 200 angstroms, inclusive, in length.

In another embodiment of the invention the linking group or linker is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from $(C_1$-$C_6)$alkoxy, $(C_3$-$C_6)$cycloalkyl, $(C_1$-$C_6)$alkanoyl, $(C_1$-$C_6)$alkanoyloxy, $(C_1$-$C_6)$alkoxycarbonyl, $(C_1$-$C_6)$alkylthio, azido, cyano, nitro, halo, hydroxy, oxo (=O), carboxy, aryl, aryloxy, heteroaryl, and heteroaryloxy.

In another embodiment of the invention the linking group or linker is of the formula W-A wherein A is $(C_1$-$C_{24})$alkyl, $(C_2$-$C_{24})$alkenyl, $(C_2$-$C_{24})$alkynyl, $(C_3$-$C_8)$cycloalkyl, $(C_6$-$C_{10})$aryl or a combination thereof, wherein W is —N(R)C(=O)—, —C(=O)N(R)—, —OC(=O)—, —C(=O)O—, —O—, —S—, —S(O)—, $—S(O)_2—$, —N(R)—, —C(=O)—, or a direct bond; wherein each R is independently H or $(C_1$-$C_6)$alkyl.

In another embodiment of the invention the linking group or linker is a divalent radical formed from a peptide.

In another embodiment of the invention the linking group or linker is a divalent radical formed from an amino acid.

In another embodiment of the invention the linking group or linker is a divalent radical formed from poly-L-glutamic acid, poly-L-aspartic acid, poly-L-histidine, poly-L-ornithine, poly-L-serine, poly-L-threonine, poly-L-tyrosine, poly-L-leucine, poly-L-lysine-L-phenylalanine, poly-L-lysine or poly-L-lysine-L-tyrosine.

In another embodiment of the invention the linking group or linker is of the formula W—$(CH_2)_n$, wherein, n is between about 1 and about 10; and W is —N(R)C(═O)—, —C(═O)N(R)—, —OC(═O)—, —C(═O)O—, —O—, —S—, —S(O)—, —$S(O)_2$—, —C(═O)—, —N(R)—, or a direct bond; wherein each R is independently H or $(C_1\text{-}C_6)$alkyl.

In another embodiment of the invention the linking group or linker is methylene, ethylene, or propylene.

In another embodiment of the invention the linking group or linker is attached to the phosphonate group through a carbon atom of the linker.

Intracellular Targeting

The phosphonate group of the compounds of the invention may cleave in vivo in stages after they have reached the desired site of action, i.e. inside a cell. One mechanism of action inside a cell may entail a first cleavage, e.g. by esterase, to provide a negatively-charged "locked-in" intermediate. Cleavage of a terminal ester grouping in a compound of the invention thus affords an unstable intermediate which releases a negatively charged "locked in" intermediate.

After passage inside a cell, intracellular enzymatic cleavage or modification of the phosphonate or prodrug compound may result in an intracellular accumulation of the cleaved or modified compound by a "trapping" mechanism. The cleaved or modified compound may then be "locked-in" the cell by a significant change in charge, polarity, or other physical property change which decreases the rate at which the cleaved or modified compound can exit the cell, relative to the rate at which it entered as the phosphonate prodrug. Other mechanisms by which a therapeutic effect are achieved may be operative as well. Enzymes which are capable of an enzymatic activation mechanism with the phosphonate prodrug compounds of the invention include, but are not limited to, amidases, esterases, microbial enzymes, phospholipases, cholinesterases, and phosphatases.

In selected instances in which the drug is of the nucleoside type, such as is the case of zidovudine and numerous other antiretroviral agents, it is known that the drug is activated in vivo by phosphorylation. Such activation may occur in the present system by enzymatic conversion of the "locked-in" intermediate with phosphokinase to the active phosphonate diphosphate and/or by phosphorylation of the drug itself after its release from the "locked-in" intermediate as described above. In either case, the original nucleoside-type drug will be convened, via the derivatives of this invention, to the active phosphorylated species.

From the foregoing, it will be apparent that many different drugs can be derivatized in accord with the present invention. Numerous such drugs are specifically mentioned herein. However, it should be understood that the discussion of drug families and their specific members for derivatization according to this invention is not intended to be exhaustive, but merely illustrative.

Antiviral Compounds

The compounds of the invention include those with antiviral activity. The compounds of the inventions bear one or more (e.g., 1, 2, 3, or 4) phosphonate groups, which may be a prodrug moiety.

The term "antiviral compound" includes those compounds with antiviral activity. In particular, the compounds include Dehydroepiandrosterone, LY-582563, L-Fd4C, L-FddC, telbivudine, clevudine, macrocyclic protease inhibitors, dOTCP, dOTC, DDL DDLP, ddcP, ddC, DADP, DAPD, d4TP, D4T, 3TC, 3TCP FTCP, ABCP, AZT, IsoddAP, FTC, HCV polymerase inhibitors, ribavirin, viramidine, L-enantiomers of ribavirin and viramidine, levovirin, alkovirs, imiquimod, resquimod, 4-(3-benzyl-phenyl)-2-hydroxy-4-oxo-but-2-enoic acid, propenone derivatives having HIV inhibiting activities, aza, polyazanaphthalenyl carboxamides, betulinic acid, dihydrobetulinic acid, isodd a, UT-231B, VX-148, gemcitabine, merimepodib, levamisole, mycophenolate, entecavir, foscarnet, carbovir, abacavir, and BCX-1777.

Typically, compounds of the invention have a molecular weight of from about 400 amu to about 10,000 amu; in a specific embodiment of the invention, compounds have a molecular weight of less than about 5000 amu; in another specific embodiment of the invention, compounds have a molecular weight of less than about 2500 amu; in another specific embodiment of the invention, compounds have a molecular weight of less than about 1000 amu; in another specific embodiment of the invention, compounds have a molecular weight of less than about 800 amu; in another specific embodiment of the invention, compounds have a molecular weight of less than about 600 amu; and in another specific embodiment of the invention, compounds have a molecular weight of less than about 600 amu and a molecular weight of greater than about 400 amu.

The compounds of the invention also typically have a log D (polarity) less than about 5. In one embodiment the invention provides compounds having a log D less than about 4; in another one embodiment the invention provides compounds having a log D less than about 3; in another one embodiment the invention provides compounds having a log D greater than about −5; in another one embodiment the invention provides compounds having a log D greater than about −3; and in another one embodiment the invention provides compounds having a log D greater than about 0 and less than about 3.

In one specific embodiment the invention provides compounds that may fall within the generic definition of the term antiviral compound but which further comprise a phosphonate group, e.g., a phosphonate diester, phosphonamidate-ester prodrug, or a phosphondiamidate-ester (Jiang et al., US 2002/0173490 A1).

Selected substituents within the compounds of the invention are present to a recursive degree. In this context, "recursive substituent" means that a substituent may recite another instance of itself. Because of the recursive nature of such substituents, theoretically, a large number may be present in any given claim. For example, $R^x$ contains a $R^y$ substituent. $R^y$ can be $R^2$, which in turn can be $R^3$. If $R^3$ is selected to be $R^{3c}$, then a second instance of $R^x$ can be selected. One of ordinary skill in the art of medicinal chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

By way of example and not limitation, $W^3$, $R^y$ and $R^3$ are all recursive substituents in certain claims. Typically, each of these may independently occur 20, 19, 18, 17, 16, 15, 14, 13, 12, 11, 10, 9, 8, 7, 6, 5, 4, 3, 2, 1, or 0, times in a given claim. More typically, each of these may independently occur 12 or fewer times in a given claim. More typically yet, $W^3$ will occur 0 to 8 times, $R^y$ will occur 0 to 6 times and $R^3$ will occur 0 to 10 times in a given claim. Even more typically, $W^3$ will occur 0 to 6 times, $R^y$ will occur 0 to 4 times and $R^3$ will occur 0 to 8 times in a given claim.

Recursive substituents are an intended aspect of the invention. One of ordinary skill in the art of medicinal chemistry understands the versatility of such substituents. To the degree that recursive substituents are present in an claim of the invention, the total number will be determined as set forth above.

Whenever a compound described herein is substituted with more than one of the same designated group, e.g., "$R^1$" or "$R^{6a}$", then it will be understood that the groups may be the same or different, i.e., each group is independently selected. Wavy lines indicate the site of covalent bond attachments to the adjoining groups, moieties, or atoms.

The phosphonate group may be a phosphonate prodrug moiety. The prodrug moiety may be sensitive to hydrolysis, such as, but not limited to, a pivaloyloxymethyl carbonate (POC) or POM group. Alternatively, the prodrug moiety may be sensitive to enzymatic potentiated cleavage, such as a lactate ester or a phosphonamidate-ester group.

In one embodiment of the invention the compound is not an anti-inflammatory compound; in another embodiment the compound is not an anti-infective; in another embodiment the compound is not a compound that is active against immune-mediated conditions; in another embodiment the compound is not an anti-cancer compound; in another embodiment the compound is not a compound that is active against metabolic diseases; in another embodiment the compound is not a nucleoside; in another embodiment the compound is not a IMPDH inhibitor; in another embodiment the compound is not an antimetabolite; in another embodiment the compound is not a PNP inhibitor; in another embodiment the compound is not a substituted compound of any one of formulae 509-510, 556-557, and 559-562; and in another embodiment the compound is not a compound of any one of formulae 13-18, 72, 77-83, and 90-102.

In one embodiment of the invention, the compound is in an isolated and purified form. Generally, the term "isolated and purified" means that the compound is substantially free from biological materials (e.g. blood, tissue, cells, etc.). In one specific embodiment of the invention, the term means that the compound or conjugate of the invention is at least about 50 wt. % free from biological materials; in another specific embodiment, the term means that the compound or conjugate of the invention is at least about 75 wt. % free from biological materials; in another specific embodiment, the term means that the compound or conjugate of the invention is at least about 90 wt. % free from biological materials; in another specific embodiment, the term means that the compound or conjugate of the invention is at least about 98 wt. % free from biological materials; and in another embodiment, the term means that the compound or conjugate of the invention is at least about 99 wt. % free from biological materials. In another specific embodiment, the invention provides a compound or conjugate of the invention that has been synthetically prepared (e.g., ex vivo).

Cellular Accumulation

In one embodiment, the invention is provides compounds capable of accumulating in human PBMC (peripheral blood mononuclear cells). PBMC refer to blood cells having round lymphocytes and monocytes. Physiologically, PBMC are critical components of the mechanism against infection. PBMC may be isolated from heparinized whole blood of normal healthy donors or buffy coats, by standard density gradient centrifugation and harvested from the interface, washed (e.g. phosphate-buffered saline) and stored in freezing medium. PBMC may be cultured in multi-well plates. At various times of culture, supernatant may be either removed for assessment, or cells may be harvested and analyzed (Smith R. et al (2003) *Blood* 102(7):2532-2540). The compounds of this claim may further comprise a phosphonate or phosphonate prodrug. More typically, the phosphonate or phosphonate prodrug can have the structure $A^3$ as described herein.

Typically, compounds of the invention demonstrate improved intracellular half-life of the compounds or intracellular metabolites of the compounds in human PBMC when compared to analogs of the compounds not having the phosphonate or phosphonate prodrug. Typically, the half-life is improved by at least about 50%, more typically at least in the range 50-100%, still more typically at least about 100%, more typically yet greater than about 100%.

In one embodiment of the invention the intracellular half-life of a metabolite of the compound in human PBMCs is improved when compared to an analog of the compound not having the phosphonate or phosphonate prodrug. In such claims, the metabolite may be generated intracellularly, e.g. generated within human PBMC. The metabolite may be a product of the cleavage of a phosphonate prodrug within human PBMCs. The phosphonate prodrug may be cleaved to form a metabolite having at least one negative charge at physiological pH. The phosphonate prodrug may be enzymatically cleaved within human PBMC to form a phosphonate having at least one active hydrogen atom of the form P—OH.

Stereoisomers

The compounds of the invention may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. All though only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Salts and Hydrates

The compositions of this invention optionally comprise salts of the compounds herein, especially pharmaceutically acceptable non-toxic salts containing, for example, $Na^+$, $Li^+$, $K^+$, $Ca^{+2}$ and $Mg^{+2}$. Such salts may include those derived by combination of appropriate cations such as alkali and alkaline earth metal ions or ammonium and quaternary amino ions with an acid anion moiety, typically a carboxylic acid. Monovalent salts are preferred if a water soluble salt is desired.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the amino acids described above are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Methods of Inhibition of Viral Infections

Another aspect of the invention relates to methods of inhibiting viral infections, comprising the step of treating a sample or subject suspected of needing such inhibition with a composition of the invention.

Compositions of the invention may act as inhibitors of viral infections, or as intermediates for such inhibitors or have other utilities as described below. The inhibitors will bind to locations on the surface or in a cavity of a cell having a unique geometry. Compositions binding a cell may bind with varying degrees of reversibility. Those compounds binding substantially irreversibly are ideal candidates for use in this method of the invention. Once labeled, the substantially irreversibly binding compositions are useful as probes for the detection of viruses. Accordingly, the invention relates to methods of detecting viruses in a sample or subject suspected of containing a virus, comprising the steps of: treating such a sample or subject with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl or amino.

Within the context of the invention samples suspected of containing a virus include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which induces a viral infection, frequently a pathogenic organism such as an tumor virus. Samples can be contained in any medium including water and organic solvent\water mixtures. Samples include living organisms such as humans, and man made materials such as cell cultures.

The treating step of the invention comprises adding the composition of the invention to the sample or it comprises adding a precursor of the composition to the sample. The addition step comprises any method of administration as described above.

If desired, the anti-virus activity of a compound of the invention after application of the composition can be observed by any method including direct and indirect methods of detecting such activity. Quantitative, qualitative, and semiquantitative methods of determining such activity are all contemplated. Typically one of the screening methods described above are applied, however, any other method such as observation of the physiological properties of a living organism are also applicable.

Screens for Antiviral Compounds

Compositions of the invention are screened for antiviral activity by any of the conventional techniques for evaluating enzyme activity. Within the context of the invention, typically compositions are first screened for inhibitory activity in vitro and compositions showing inhibitory activity are then screened for activity in vivo. Compositions having in vitro Ki (inhibitory constants) of less then about $5\times10^{-6}$ M, typically less than about $1\times10^{-7}$ M and preferably less than about $5\times10^{-8}$ M are preferred for in vivo use.

Useful in vitro screens have been described in detail and will not be elaborated here.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or *acacia*; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions.

Such excipients include a suspending agent, such as sodium carboxymethylcellulose, methylcellulose, hydroxypropyl methylcelluose, sodium alginate, polyvinylpyrrolidone, gum tragacanth and gum *acacia*, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as *arachis* oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or *arachis* oil, a mineral oil, such as liquid paraffin, or a mixture of these. Suitable emulsifying agents include naturally-occurring gums, such as gum *acacia* and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and *acacia* or tragacanth; pastilles comprising the active ingredient in an inert basis such as gelatin and glycerin, or sucrose and *acacia*; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of viral infections as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

Active ingredients of the invention are also used in combination with other active ingredients. Such combinations are selected based on the condition to be treated, cross-reactivities of ingredients and pharmaco-properties of the combination. For example, when treating a viral infection the compositions of the invention can be combined with other agents that are effective to treat a viral infection (such as other antiviral agents).

It is also possible to combine any compound of the invention with one or more other active ingredients in a unitary dosage form for simultaneous or sequential administration to a patient. The combination therapy may be administered as a simultaneous or sequential regimen. When administered sequentially, the combination may be administered in two or more administrations.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no antiviral activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The phosphonate prodrugs of the invention typically will be stable in the digestive system but are substantially hydrolyzed to the parental drug in the digestive lumen, liver or other metabolic organ, or within cells in general.

Antiviral Activity

The antiviral activity of a compound of the invention can be measured using standard screening protocols that are known. For example, the antiviral activity of a compound can be measured in a cell culture assay using the following general protocol.

Antiviral Cell Culture Assay

The assay is based on quantification of the antiviral effect by a colorimetric detection of the viability of virus-infected cells in the presence or absence of tested inhibitors. The compound-induced cell death is determined using a metabolic substrate 2,3-bis(2-methoxy-4-nitro-5-sulfophenyl)-2H-tetrazolium-5-carboxanilide (XTT) which is converted only by intact cells into a product with specific absorption characteristics as described by Weislow O S, Kiser R, Fine D L, Bader J, Shoemaker R H and Boyd M R (1989) *J Natl Cancer Inst* 81, 577.

Assay Protocol for Determination of EC50:

1. Maintain MT2 cells in RPMI-1640 medium supplemented with 5% fetal bovine serum and antibiotics.
2. Infect the cells with the viral agent for 3 hours at 37° C. using the virus inoculum corresponding to a multiplicity of infection equal to 0.01.
3. Distribute the infected cells into a 96-well plate (20,000 cells in 100 μl/well) and add various concentrations of the tested inhibitor in triplicate (100 μl/well in culture media). Include untreated infected and untreated mock-infected control cells.
4. Incubate the cells for 5 days at 37° C.
5. Prepare a compound solution (6 ml per assay plate) at a concentration of 2 mg/ml in a phosphate-buffered saline pH 7.4. Heat the solution in water-bath for 5 min at 55° C. Add 50 μl of N-methylphenazonium methasulfate (5 μg/ml) per 6 ml of XTT solution.
6. Remove 100 μl media from each well on the assay plate.
7. Add 100 μl of the XTT substrate solution per well and incubate at 37° C. for 45 to 60 min in a $CO_2$ incubator.
8. Add 20 μl of 2% Triton X-100 per well to inactivate the virus.
9. Read the absorbance at 450 nm with subtracting off the background absorbance at 650 nm.
10. Plot the percentage absorbance relative to untreated control and estimate the EC50 value as drug concentration resulting in a 50% protection of the infected cells.

The cytotoxicity of a compound of the invention can be determined using the following general protocol.

Cytotoxicity Cell Culture Assay (Determination of CC50):

The assay is based on the evaluation of cytotoxic effect of tested compounds using a metabolic substrate.

Assay Protocol for Determination of CC50:

1. Maintain MT-2 cells in RPMI-1640 medium supplemented with 5% fetal bovine serum and antibiotics.
2. Distribute the cells into a 96-well plate (20,000 cell in 100 μl media per well) and add various concentrations of the tested compound in triplicate (100 μl/well). Include untreated control.
3. Incubate the cells for 5 days at 37° C.
4. Prepare XTT solution (6 ml per assay plate) in dark at a concentration of 2 mg/ml in a phosphate-buffered saline pH 7.4. Heat the solution in a water-bath at 55° C. for 5 min. Add 50 μl of N-methylphenazonium methasulfate (5 μg/ml) per 6 ml of XTT solution.

5. Remove 100 μl media from each well on the assay plate and add 100 μl of the XTT substrate solution per well. Incubate at 37° C. for 45 to 60 min, in a $CO_2$ incubator.
6. Add 20 μl of 2% Triton X-100 per well to stop the metabolic conversion of XTT.
7. Read the absorbance at 450 nm with subtracting off the background at 650 nm.
8. Plot the percentage absorbance relative to untreated control and estimate the CC50 value as drug concentration resulting in a 50% inhibition of the cell growth. Consider the absorbance being directly proportional to the cell growth.

Exemplary Methods of Making the Compounds of the Invention.

The invention also relates to methods of making the compositions of the invention. The compositions are prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., *Advanced Organic Chemistry, Third Edition*, (John Wiley & Sons, New York, 1985), *Comprehensive Organic Synthesis. Selectivity, Strategy & Efficiency in Modern Organic Chemistry*. In 9 *Volumes*, Barry M. Trost, Editor-in-Chief (Pergamon Press, New York, 1993 printing).

A number of exemplary methods for the preparation of the compositions of the invention are provided below. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g., inert gas environments) are common in the art and will be applied when applicable.

Schemes and Examples

General aspects of these exemplary methods are described below and in the Examples. Each of the products of the following processes is optionally separated, isolated, and/or purified prior to its use in subsequent processes.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g., inert gas environments) are common in the art and will be applied when applicable.

The terms "treated", "treating", "treatment", and the like, when used in connection with a chemical synthetic operation, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two. For example, treating indicates the reasonable and usual manner in which organic chemicals are allowed to react. Normal concentrations (0.01 M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes and in the examples (hereafter "exemplary schemes") leads to various analogs of the specific exemplary materials produce. The above-cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as formation of diastereomers using optically active resolving agents (*Stereochemistry of Carbon Compounds*, (1962) by E. L. Eliel, McGraw Hill; Lochmuller, C. H., (1975) *J. Chromatogr.,* 113:(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) *Stereochemistry of Organic Compounds*, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (*Chiral Liquid Chromatography* (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

Examples General Section

A number of exemplary methods for the preparation of compounds of the invention are provided herein, for example, in the Examples hereinbelow. These methods are intended to illustrate the nature of such preparations are not intended to limit the scope of applicable methods. Certain compounds of the invention can be used as intermediates for the preparation of other compounds of the invention. For example, the interconversion of various phosphonate compounds of the invention is illustrated below.

Interconversions of the Phosphonates R-LINK-P(O)($OR^1$)$_2$, R-LINK-P(O)($OR^1$)(OH) AND R-LINK-P(O)(OH)$_2$.

The following schemes 32-38 described the preparation of phosphonate esters of the general structure R-link-P(O)($OR^1$)$_2$, in which the groups $R^1$ may be the same or different. The $R^1$ groups attached to a phosphonate ester, or to precursors thereto, may be changed using established chemical transformations. The interconversion reactions of phosphonates are illustrated in Scheme S32. The group R in Scheme 32 represents the substructure, i.e. the drug "scaffold, to which the substituent link-P(O)($OR^1$)$_2$ is attached, either in the compounds of the invention, or in precursors thereto. At the point in the synthetic route of conducting a phosphonate interconversion, certain functional groups in R may be protected. The methods employed for a given phosphonate transformation depend on the nature of the substituent $R^1$, and of the substrate to which the phosphonate group is attached. The preparation and hydrolysis of phosphonate esters is described in *Organic Phosphorus Compounds*, G. M. Kosolapoff, L. Maeir, eds, Wiley, 1976, p. 9ff.

In general, synthesis of phosphonate esters is achieved by coupling a nucleophile amine or alcohol with the corresponding activated phosphonate electrophilic precursor. For example, chlorophosphonate addition on to 5'-hydroxy of nucleoside is a well known method for preparation of nucleoside phosphate monoesters. The activated precursor can be prepared by several well known methods. Chlorophosphonates useful for synthesis of the prodrugs are prepared from the substituted-1,3-propanediol (Wissner, et al, (1992) *J. Med Chem.* 35:1650). Chlorophosphonates are made by oxidation of the corresponding chlorophospholanes (Anderson, et al, (1984) *J. Org. Chem.* 49:1304) which are obtained by reaction of the substituted diol with phosphorus trichloride. Alternatively, the chlorophosphonate agent is made by treating substituted-1,3-diols with phosphorusoxychloride (Patois, et al, (1990) *J. Chem. Soc. Perkin Trans. I,* 1577). Chlorophosphonate species may also be generated in situ from corresponding cyclic phosphites (Silverburg, et al., (1996) *Tetrahedron lett.,* 37:771-774), which in turn can be either made from chlorophospholane or phosphoramidate intermediate. Phosphoroflouridate intermediate prepared either from pyrophosphate or phosphoric acid may also act as precursor in preparation of cyclic prodrugs (Watanabe et al., (1988) *Tetrahedron lett.,* 29:5763-66).

Phosphonate prodrugs of the present invention may also be prepared from the free acid by Mitsunobu reactions (Mitsunobu, (1981) *Synthesis,* 1; Campbell, (1992) *J. Org. Chem.* 57:6331), and other acid coupling reagents including, but not limited to, carbodiimides (Alexander, et al, (1994) *Collect. Czech. Chem. Commun.* 59:1853; Casara et al, (1992) *Bioorg. Med. Chem. Lett.* 2:145; Ohashi et al, (1988) *Tetrahedron Lett.,* 29:1189), and benzotriazolyloxytris-(dimethylamino) phosphonium salts (Campagne et al (1993) *Tetrahedron Lett.* 34:6743).

Aryl halides undergo $Ni^{+2}$ catalyzed reaction with phosphite derivatives to give aryl phosphonate containing compounds (Balthazar, et al (1980) *J. Org. Chem.* 45:5425). Phosphonates may also be prepared from the chlorophosphonate in the presence of a palladium catalyst using aromatic triflates (Petrakis et al (1987) *J. Am. Chem. Soc.* 109:2831; Lu et al (1987) *Synthesis* 726). In another method, aryl phosphonate esters are prepared from aryl phosphates under anionic rearrangement conditions (Melvin (1981) *Tetrahedron Lett.* 22:3375; Casteel et al (1991) *Synthesis,* 691). N-Alkoxy aryl salts with alkali metal derivatives of cyclic alkyl phosphonate provide general synthesis for heteroaryl-2-phosphonate linkers (Redmore (1970) *J. Org. Chem.* 35:4114). These above mentioned methods can also be extended to compounds where the $W^5$ group is a heterocycle. Cyclic-1,3-propanyl prodrugs of phosphonates are also synthesized from phosphonic diacids and substituted propane-1,3-diols using a coupling reagent such as 1,3-dicyclohexylcarbodiimide (DCC) in presence of a base (e.g., pyridine). Other carbodiimide based coupling agents like 1,3-disopropylcarbodiimide or water soluble reagent, 1-(3-dimethylaminopropyl)-3-ethylcarbodiimide hydrochloride (EDCI) can also be utilized for the synthesis of cyclic phosphonate prodrugs.

The conversion of a phosphonate diester S32.1 into the corresponding phosphonate monoester S32.2 (Scheme 32, Reaction 1) is accomplished by a number of methods. For example, the ester S32.1 in which $R^1$ is an aralkyl group such as benzyl, is converted into the monoester compound S32.2 by reaction with a tertiary organic base such as diazabicyclooctane (DABCO) or quinuclidine, as described in *J. Org. Chem.* (1995) 60:2946. The reaction is performed in an inert hydrocarbon solvent such as toluene or xylene, at about 110° C. The conversion of the diester S32.1 in which $R^1$ is an aryl group such as phenyl, or an alkenyl group such as allyl, into the monoester S32.2 is effected by treatment of the ester S32.1 with a base such as aqueous sodium hydroxide in acetonitrile or lithium hydroxide in aqueous tetrahydrofuran. Phosphonate diesters S32.1 in which one of the groups $R^1$ is aralkyl, such as benzyl, and the other is alkyl, is converted into the monoesters S32.2 in which $R^1$ is alkyl by hydrogenation, for example using a palladium on carbon catalyst. Phosphonate diesters in which both of the groups $R^1$ are alkenyl, such as allyl, is converted into the monoester S32.2 in which $R^1$ isalkenyl, by treatment with chlorotris(triphenylphosphine) rhodium (Wilkinson's catalyst) in aqueous ethanol at reflux, optionally in the presence of diazabicyclooctane, for example by using the procedure described in *J. Org. Chem.* (1973) 38:3224, for the cleavage of allyl carboxylates.

The conversion of a phosphonate diester S32.1 or a phosphonate monoester S32.2 into the corresponding phosphonic acid S32.3 (Scheme 32, Reactions 2 and 3) can be effected by reaction of the diester or the monoester with trimethylsilyl bromide, as described in *J. Chem. Soc., Chem. Comm.*, (1979) 739. The reaction is conducted in an inert solvent such as, for example, dichloromethane, optionally in the presence of a silylating agent such as bis(trimethylsilyl)trifluoroacetamide, at ambient temperature. A phosphonate monoester S32.2 in which $R^1$ isaralkyl such as benzyl, is converted into the corresponding phosphonic acid S32.3 by hydrogenation over a palladium catalyst, or by treatment with hydrogen chloride in an ethereal solvent such as dioxane. A phosphonate monoester S32.2 in which $R^1$ is alkenyl such as, for example, allyl, is converted into the phosphonic acid S32.3 by reaction with Wilkinson's catalyst in an aqueous organic solvent, for example in 15% aqueous acetonitrile, or in aqueous ethanol, for example using the procedure described in *Helv. Chim. Acta.* (1985) 68:618. Palladium catalyzed hydrogenolysis of phosphonate esters S32.1 in which $R^1$ is benzyl is described in *J. Org. Chem.* (1959) 24:434. Platinum-catalyzed hydrogenolysis of phosphonate esters S32.1 in which $R^1$ is phenyl is described in *J. Am. Chem. Soc.* (1956) 78:2336.

The conversion of a phosphonate monoester S32.2 into a phosphonate diester S32.1 (Scheme 32, Reaction 4) in which the newly introduced $R^1$ group is alkyl, aralkyl, haloalkyl such as chloroethyl, or aralkyl is effected by a number of reactions in which the substrate S32.2 is reacted with a hydroxy compound $R^1$ OH, in the presence of a coupling agent. Typically, the second phosphonate ester group is different than the first introduced phosphonate ester group, i.e. $R^1$ is followed by the introduction of $R^2$ where each of $R^1$ and $R^2$ is alkyl, aralkyl, haloalkyl such as chloroethyl, or aralkyl (Scheme 32, Reaction 4a) whereby S32.2 is converted to S32.1a. Suitable coupling agents are those employed for the preparation of carboxylate esters, and include a carbodiimide such as dicyclohexylcarbodiimide, in which case the reaction is preferably conducted in a basic organic solvent such as pyridine, or (benzotriazol-1-yloxy)tripyrrolidinophosphonium hexafluorophosphate (PYBOP, Sigma), in which case the reaction is performed in a polar solvent such as dimethylformamide, in the presence of a tertiary organic base such as diisopropylethylamine, or Aldrithiol-2 (Aldrich) in which case the reaction is conducted in a basic solvent such as pyridine, in the presence of a triaryl phosphine such as triphenylphosphine. Alternatively, the conversion of the phosphonate monoester S32.2 to the diester S32.1 is effected by the use of the Mitsunobu reaction, as described above (Scheme 7). The substrate is reacted with the hydroxy compound $R^1$ OH, in the presence of diethyl azodicarboxylate and a triarylphosphine such as triphenyl phosphine. Alternatively, the phosphonate monoester S32.2 is transformed into the phosphonate diester S32.1, in which the introduced $R^1$ group is alkenyl or aralkyl, by reaction of the monoester with the halide $R^1$Br, in which $R^1$ is as alkenyl or aralkyl. The alkylation reaction is conducted in a polar organic solvent such as dimethylformamide or acetonitrile, in the presence of a base such as cesium carbonate. Alternatively, the phosphonate monoester is transformed into the phosphonate diester in a two step procedure. In the first step, the phosphonate monoester S32.2 is transformed into the chloro analog RP(O)($OR^1$)Cl by reaction with thionyl chloride or oxalyl chloride and the like, as described in *Organic Phosphorus Compounds*, G. M. Kosolapoff, L. Maeir, eds, Wiley, 1976, p. 17, and the thus-obtained product RP(O)($OR^1$)Cl is then reacted with the hydroxy compound $R^1$ OH, in the presence of a base such as triethylamine, to afford the phosphonate diester S32.1.

A phosphonic acid R-link-P(O)$(OH)_2$ is transformed into a phosphonate monoester RP(O)($OR^1$)(OH) (Scheme 32, Reaction 5) by means of the methods described above of for the preparation of the phosphonate diester R-link-P(O)$(OR^1)_2$ S32.1, except that only one molar proportion of the component $R^1$ OH or $R^1$Br is employed. Dialkyl phosphonates may be prepared according to the methods of: Quast et al (1974) *Synthesis* 490; Stowell et al (1990) *Tetrahedron Lett.* 3261; U.S. Pat. No. 5,663,159.

A phosphonic acid R-link-P(O)$(OH)_2$ S32.3 is transformed into a phosphonate diester R-link-P(O)$(OR^1)_2$ S32.1 (Scheme 32, Reaction 6) by a coupling reaction with the hydroxy compound $R^1$ OH, in the presence of a coupling agent such as Aldrithiol-2 (Aldrich) and triphenylphosphine. The reaction is conducted in a basic solvent such as pyridine. Alternatively, phosphonic acids S32.3 are transformed into phosphonic esters S32.1 in which $R^1$ is aryl, by means of a coupling reaction employing, for example, dicyclohexylcarbodiimide in pyridine at ca 70° C. Alternatively, phosphonic acids S32.3 are transformed into phosphonic esters S32.1 in which $R^1$ is alkenyl, by means of an alkylation reaction. The phosphonic acid is reacted with the alkenyl bromide $R^1$ Br in a polar organic solvent such as acetonitrile solution at reflux temperature, the presence of a base such as cesium carbonate, to afford the phosphonic ester S32.1.

Scheme 32

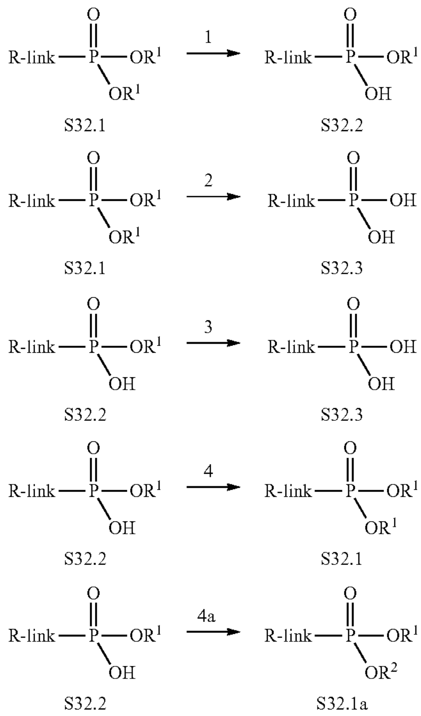

S32.1 S32.2
S32.1 S32.3
S32.2 S32.3
S32.2 S32.1
S32.2 S32.1a

-continued

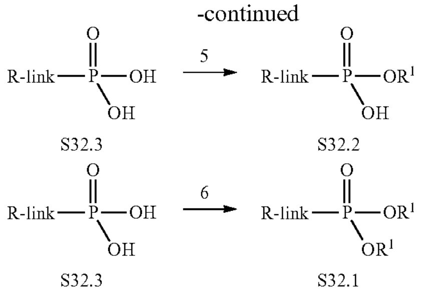

S32.3 S32.2
S32.3 S32.1

Preparation of Phosphonate Carbamates.

Phosphonate esters may contain a carbamate linkage. The preparation of carbamates is described in *Comprehensive Organic Functional Group Transformations*, A. R. Katritzky, ed., Pergamon, 1995, Vol. 6, p. 416ff, and in *Organic Functional Group Preparations*, by S. R. Sandler and W. Karo, Academic Press, 1986, p. 260ff. The carbamoyl group may be formed by reaction of a hydroxy group according to the methods known in the art, including the teachings of Ellis, US 2002/0103378 A1 and Hajima, U.S. Pat. No. 6,018,049.

Scheme 33 illustrates various methods by which the carbamate linkage is synthesized. As shown in Scheme 33, in the general reaction generating carbamates, an alcohol S33.1, is converted into the activated derivative S33.2 in which Lv is a leaving group such as halo, imidazolyl, benztriazolyl and the like, as described herein. The activated derivative S33.2 is then reacted with an amine S33.3, to afford the carbamate product 533.4. Examples 1-7 in Scheme 33 depict methods by which the general reaction is effected. Examples 8-10 illustrate alternative methods for the preparation of carbamates.

Scheme 33, Example 1 illustrates the preparation of carbamates employing a chloroforrnyl derivative of the alcohol S33.5. In this procedure, the alcohol 533.5 is reacted with phosgene, in an inert solvent such as toluene, at about 0° C., as described in *Org. Syn. Coll. Vol.* 3, 167, 1965, or with an equivalent reagent such as trichloromethoxy chloroformate, as described in *Org. Syn. Coll. Vol.* 6, 715, 1988, to afford the chloroformate S33.6. The latter compound is then reacted with the amine component S33.3, in the presence of an organic or inorganic base, to afford the carbamate S33.7. For example, the chloroformyl compound S33.6 is reacted with the amine S33.3 in a water-miscible solvent such as tetrahydrofuran, in the presence of aqueous sodium hydroxide, as described in *Org. Syn. Coll. Vol.* 3, 167, 1965, to yield the carbamate S33.7. Alternatively, the reaction is performed in dichloromethane in the presence of an organic base such as diisopropylethylamine or dimethylaminopyridine.

Scheme 33, Example 2 depicts the reaction of the chloroformate compound S33.6 with imidazole to produce the imidazolide S33.8. The imidazolide product is then reacted with the amine S33.3 to yield the carbamate S33.7. The preparation of the imidazolide is performed in an aprotic solvent such as dichloromethane at 0°, and the preparation of the carbamate is conducted in a similar solvent at ambient temperature, optionally in the presence of a base such as dimethylaminopyridine, as described in *J. Med. Chem.,* 1989, 32, 357.

Scheme 33 Example 3, depicts the reaction of the chloroformate S33.6 with an activated hydroxyl compound $R^x$OH, to yield the mixed carbonate ester S33.10. The reaction is conducted in an inert organic solvent such as ether or dichloromethane, in the presence of a base such as dicyclohexyamine or triethylamine. The hydroxyl component R"OH is selected from the group of compounds S33.19-S33.24 shown in Scheme 33, and similar compounds. For example, if the component R"OH is hydroxybenztriazole S33.19, N-hydroxysuccinimide S33.20, or pentachlorophenol, S33.21, the mixed carbonate S33.10 is obtained by the reaction of the chloroformate with the hydroxyl compound in an ethereal solvent in the presence of dicyclohexylamine, as described in *Can. J. Chem.*, 1982, 60, 976. A similar reaction in which the component R"OH is pentafluorophenol S33.22 or 2-hydroxypyridine S33.23 is performed in an ethereal solvent in the presence of triethylamine, as described in *Syn.*, 1986, 303, and *Chem. Ber.* 118, 468, 1985.

Scheme 33 Example 4 illustrates the preparation of carbamates in which an alkyloxycarbonylimidazole S33.8 is employed. In this procedure, an alcohol S33.5 is reacted with an equimolar amount of carbonyl diimidazole S33.11 to prepare the intermediate S33.8. The reaction is conducted in an aprotic organic solvent such as dichloromethane or tetrahydrofuran. The acyloxyimidazole S33.8 is then reacted with an equimolar amount of the amine $R'NH_2$ to afford the carbamate S33.7. The reaction is performed in an aprotic organic solvent such as dichloromethane, as described in *Tet. Lett.*, 42, 2001, 5227, to afford the carbamate S33.7.

Scheme 33, Example 5 illustrates the preparation of carbamates by means of an intermediate alkoxycarbonylbenztriazole S33.13. In this procedure, an alcohol ROH is reacted at ambient temperature with an equimolar amount of benztriazole carbonyl chloride S33.12, to afford the alkoxycarbonyl product S33.13. The reaction is performed in an organic solvent such as benzene or toluene, in the presence of a tertiary organic amine such as triethylamine, as described in *Synthesis.*, 1977, 704. The product is then reacted with the amine $R'NH_2$ to afford the carbamate S33.7. The reaction is conducted in toluene or ethanol, at from ambient temperature to about 80° C. as described in *Synthesis.*, 1977, 704.

Scheme 33, Example 6 illustrates the preparation of carbamates in which a carbonate $(R''O)_2CO$, S33.14, is reacted with an alcohol S33.5 to afford the intermediate alkyloxycarbonyl intermediate S33.15. The latter reagent is then reacted with the amine $R'NH_2$ to afford the carbamate S33.7. The procedure in which the reagent S33.15 is derived from hydroxybenztriazole S33.19 is described in *Synthesis,* 1993, 908; the procedure in which the reagent S33.15 is derived from N-hydroxysuccinimide S33.20 is described in *Tet. Lett.*, 1992, 2781; the procedure in which the reagent S33.15 is derived from 2-hydroxypyridine S33.23 is described in *Tet. Lett.*, 1991, 4251; the procedure in which the reagent S33.15 is derived from 4-nitrophenol S33.24 is described in *Synthesis.* 1993, 103. The reaction between equimolar amounts of the alcohol ROH and the carbonate S33.14 is conducted in an inert organic solvent at ambient temperature.

Scheme 33, Example 7 illustrates the preparation of carbamates from alkoxycarbonyl azides S33.16. In this procedure, an alkyl chloroformate S33.6 is reacted with an azide, for example sodium azide, to afford the alkoxycarbonyl azide S33.16. The latter compound is then reacted with an equimolar amount of the amine $R'NH_2$ to afford the carbamate S33.7. The reaction is conducted at ambient temperature in a polar aprotic solvent such as dimethylsulfoxide, for example as described in *Synthesis.*, 1982, 404.

Scheme 33, Example 8 illustrates the preparation of carbamates by means of the reaction between an alcohol ROH and the chloroformyl derivative of an amine S33.17. In this procedure, which is described in *Synthetic Organic Chemistry*, R. B. Wagner, H. D. Zook, Wiley, 1953, p. 647, the reactants are combined at ambient temperature in an aprotic solvent such as acetonitrile, in the presence of a base such as triethylamine, to afford the carbamate S33.7.

Scheme 33, Example 9 illustrates the preparation of carbamates by means of the reaction between an alcohol ROH and an isocyanate S33.18. In this procedure, which is described in *Synthetic Organic Chemistry*, R. B. Wagner, H. D. Zook, Wiley, 1953, p. 645, the reactants are combined at ambient temperature in an aprotic solvent such as ether or dichloromethane and the like, to afford the carbamate S33.7.

Scheme 33, Example 10 illustrates the preparation of carbamates by means of the reaction between an alcohol ROH and an amine $R'NH_2$. In this procedure, which is described in *Chem. Lett.* 1972, 373, the reactants are combined at ambient temperature in an aprotic organic solvent such as tetrahydrofuran, in the presence of a tertiary base such as triethylamine, and selenium. Carbon monoxide is passed through the solution and the reaction proceeds to afford the carbamate S33.7.

Scheme 33. Preparation of carbamates.

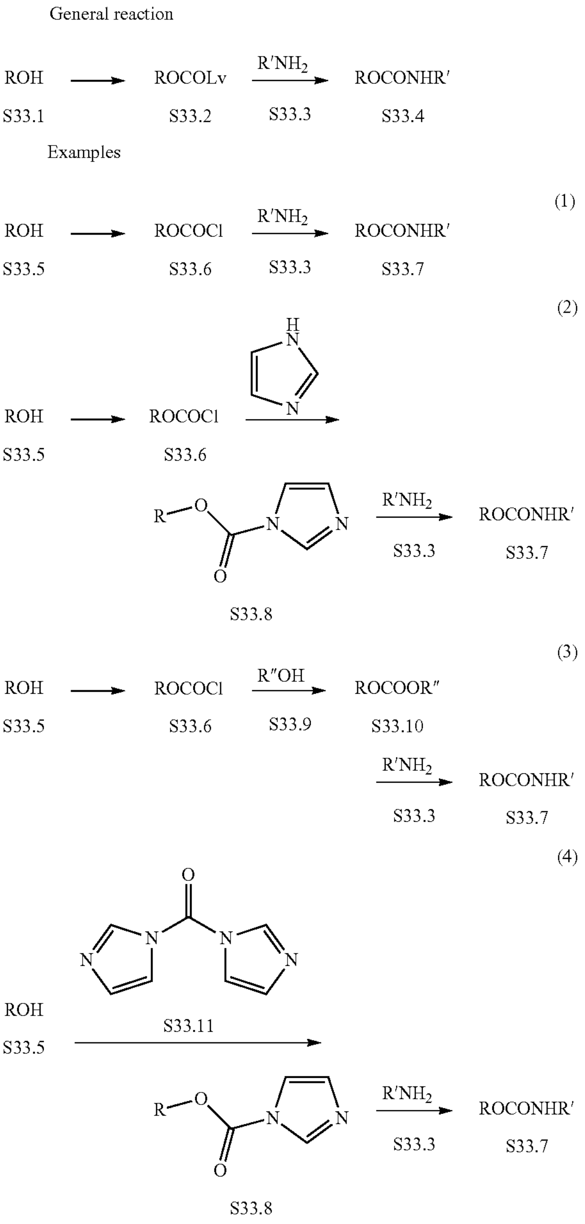

-continued (5)

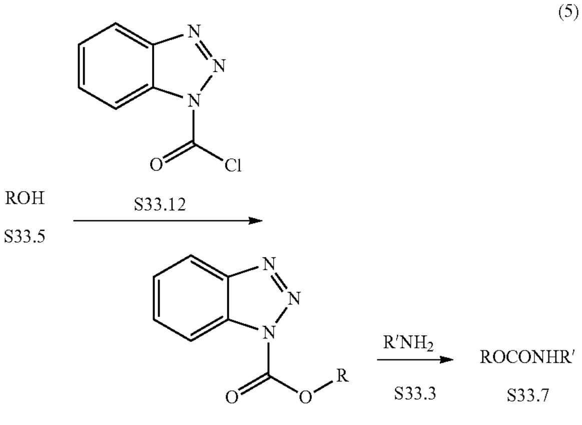

S33.13

(6)

ROH $(R''O_2)C{=}O$ ROCOR'' $R'NH_2$ ROCONHR'

S33.5 S33.14 S33.15 S33.3 S33.7

(7)

ROH ROCOCl $ROCON_3$

S33.5 S33.6 S33.16

$R'NH_2$ ROCONHR'

S33.3 S33.7

(8)

ROH R'NHCOCl ROCONHR'

S33.5 S33.17 S33.7

(9)

ROH R'NCO ROCONHR'

S33.5 S33.18 S33.7

(10)

ROH $R'NH_2$ ROCONHR'

S33.5 S33.3 S33.7

R''OH =

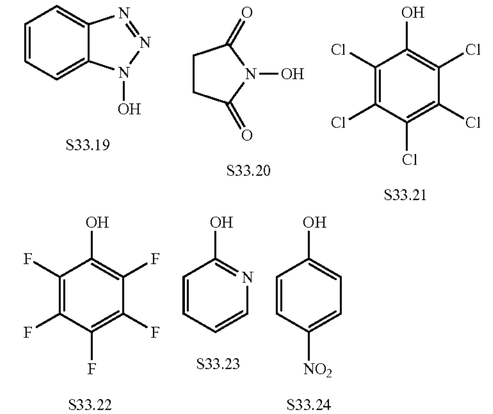

S33.19 S33.20 S33.21

S33.22 S33.23 S33.24

Preparation of Carboalkoxy-Substituted Phosphonate Bisamidates, Monoamidates, Diesters and Monoesters.

A number of methods are available for the conversion of phosphonic acids into amidates and esters. In one group of methods, the phosphonic acid is either converted into an isolated activated intermediate such as a phosphoryl chloride, or the phosphonic acid is activated in situ for reaction with an amine or a hydroxy compound.

The conversion of phosphonic acids into phosphoryl chlorides is accomplished by reaction with thionyl chloride, for example as described in *J. Gen. Chem. USSR,* 1983, 53, 480, *Zh. Obschei Khim.,* 1958, 28, 1063, or *J. Org. Chem.,* 1994, 59, 6144, or by reaction with oxalyl chloride, as described in *J. Am. Chem. Soc.,* 1994, 116, 3251, or *J. Org. Chem.,* 1994, 59, 6144, or by reaction with phosphorus pentachloride, as described in *J. Org. Chem.,* 2001, 66, 329, or in *J. Med. Chem.,* 1995, 38, 1372. The resultant phosphoryl chlorides are then reacted with amines or hydroxy compounds in the presence of a base to afford the amidate or ester products.

Phosphonic acids are converted into activated imidazolyl derivatives by reaction with carbonyl diimidazole, as described in *J. Chem. Soc., Chem. Comm.* (1991) 312, or *Nucleosides & Nucleotides* (2000) 19:1885. Activated sulfonyloxy derivatives are obtained by the reaction of phosphonic acids with trichloromethylsulfonyl chloride or with triisopropylbenzenesulfonyl chloride, as described in *Tet. Lett.* (1996) 7857, or *Bioorg. Med. Chem. Lett.* (1998) 8:663. The activated sulfonyloxy derivatives are then reacted with amines or hydroxy compounds to afford amidates or esters.

Alternatively, the phosphonic acid and the amine or hydroxy reactant are combined in the presence of a diimide coupling agent. The preparation of phosphonic amidates and esters by means of coupling reactions in the presence of dicyclohexyl carbodiimide is described, for example, in *J. Chem. Soc., Chem. Comm.* (1991) 312 or *Coll. Czech. Chem. Comm.* (1987) 52:2792. The use of ethyl dimethylaminopropyl carbodiimide for activation and coupling of phosphonic acids is described in *Tet. Lett.,* (2001) 42:8841, or *Nucleosides & Nucleotides* (2000) 19:1885.

A number of additional coupling reagents have been described for the preparation of amidates and esters from phosphonic acids. The agents include Aldrithiol-2, and PYBOP and BOP, as described in *J. Org. Chem.,* 1995, 60, 5214, and *J. Med. Chem.* (1997) 40:3842, mesitylene-2-sulfonyl-3-nitro-1,2,4-triazole (MSNT), as described in *J. Med. Chem.* (1996) 39:4958, diphenylphosphoryl azide, as described in *J. Org. Chem.* (1984) 49:1158, 1-(2,4,6-triisopropylbenzenesulfonyl-3-nitro-1,2,4-triazole (TPSNT) as described in *Bioorg. Med. Chem. Lett.* (1998) 8:1013, bromotris(dimethylamino)phosphonium hexafluorophosphate (BroP), as described in *Tet. Lett.,* (1996) 37:3997, 2-chloro-5,5-dimethyl-2-oxo-1,3,2-dioxaphosphinane, as described in *Nucleosides Nucleotides* 1995, 14, 871, and diphenyl chlorophosphate, as described in *J. Med. Chem.,* 1988, 31, 1305.

Phosphonic acids are converted into amidates and esters by means of the Mitsunobu reaction, in which the phosphonic acid and the amine or hydroxy reactant are combined in the presence of a triaryl phosphine and a dialkyl azodicarboxylate. The procedure is described in *Org. Lett.,* 2001, 3, 643, or *J. Med. Chem.,* 1997, 40, 3842.

Phosphonic esters are also obtained by the reaction between phosphonic acids and halo compounds, in the presence of a suitable base. The method is described, for example, in *Anal. Chem.,* 1987, 59, 1056, or *J. Chem. Soc. Perkin Trans., I,* 1993, 19, 2303, or *J. Med. Chem.,* 1995, 38, 1372, or *Tet. Lett.,* 2002, 43, 1161.

Schemes 34-37 illustrate the conversion of phosphonate esters and phosphonic acids into carboalkoxy-substituted phosphonbisamidates (Scheme 34), phosphonamidates (Scheme 35), phosphonate monoesters (Scheme 36) and phosphonate diesters, (Scheme 37). Scheme 38 illustrates synthesis of gem-dialkyl amino phosphonate reagents.

Scheme 34 illustrates various methods for the conversion of phosphonate diesters S34.1 into phosphonbisamidates S34.5. The diester S34.1, prepared as described previously, is hydrolyzed, either to the monoester S34.2 or to the phosphonic acid S34.6. The methods employed for these transformations are described above. The monoester S34.2 is converted into the monoamidate S34.3 by reaction with an aminoester S34.9, in which the group $R^2$ is H or alkyl; the group $R^{4b}$ is a divalent alkylene moiety such as, for example, $CHCH_3$, $CHCH_2CH_3$, $CH(CH(CH_3)_2)$, $CH(CH_2Ph)$, and the like, or a side chain group present in natural or modified aminoacids; and the group $R^{5b}$ is $C_1$-$C_{12}$ alkyl, such as methyl, ethyl, propyl, isopropyl, or isobutyl; $C_6$-$C_{20}$ aryl, such as phenyl or substituted phenyl; or $C_6$-$C_{20}$ arylalkyl, such as benzyl or benzyhydryl. The reactants are combined in the presence of a coupling agent such as a carbodiimide, for example dicyclohexyl carbodiimide, as described in *J. Am. Chem. Soc.*, (1957) 79:3575, optionally in the presence of an activating agent such as hydroxybenztriazole, to yield the amidate product S34.3. The amidate-forming reaction is also effected in the presence of coupling agents such as BOP, as described in *J. Org. Chem.* (1995) 60:5214, Aldrithiol, PYBOP and similar coupling agents used for the preparation of amides and esters. Alternatively, the reactants S34.2 and S34.9 are transformed into the monoamidate S34.3 by means of a Mitsunobu reaction. The preparation of amidates by means of the Mitsunobu reaction is described in *J. Med. Chem.* (1995) 38:2742. Equimolar amounts of the reactants are combined in an inert solvent such as tetrahydrofuran in the presence of a triaryl phosphine and a dialkyl azodicarboxylate. The thus-obtained monoamidate ester S34.3 is then transformed into amidate phosphonic acid S34.4. The conditions used for the hydrolysis reaction depend on the nature of the $R^1$ group, as described previously. The phosphonic acid amidate S34.4 is then reacted with an aminoester S34.9, as described above, to yield the bisamidate product S34.5, in which the amino substituents are the same or different. Alternatively, the phosphonic acid S34.6 may be treated with two different amino ester reagents simulataneously, i.e. S34.9 where $R^2$, $R^{4b}$ or $R^{5b}$ are different. The resulting mixture of bisamidate products S34.5 may then be separable, e.g. by chromatography.

Scheme 34

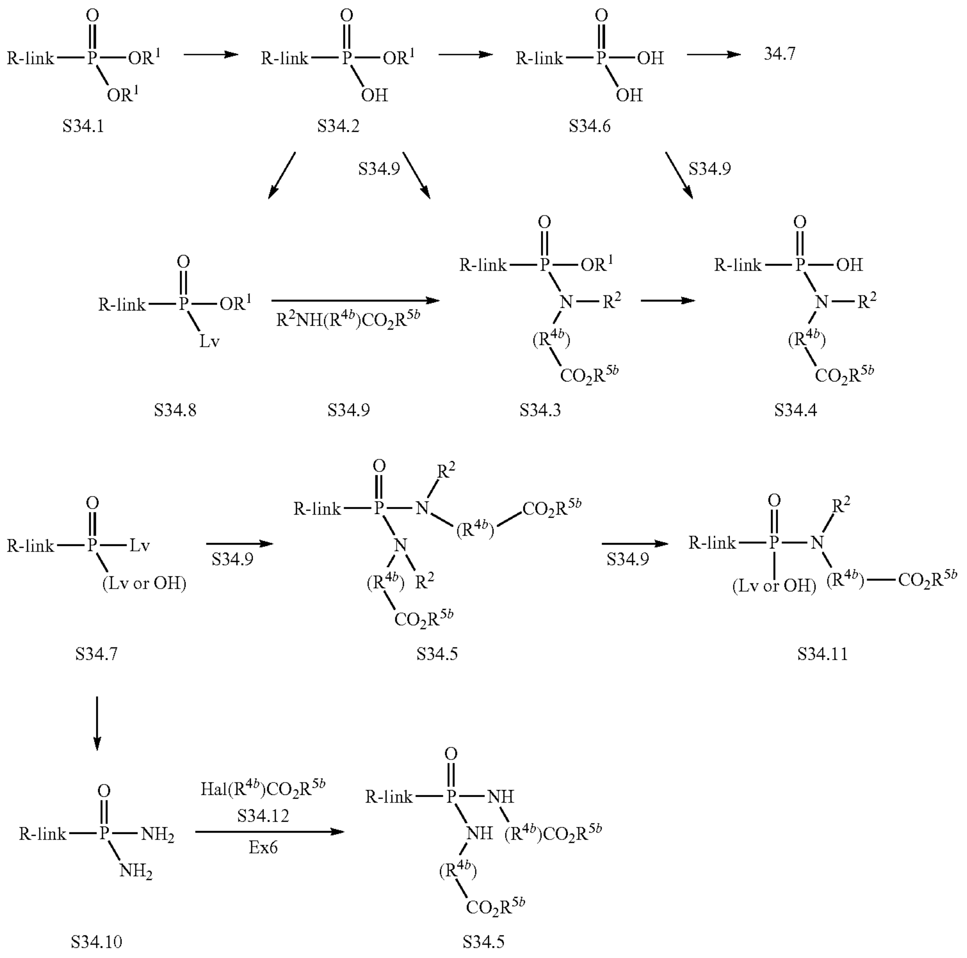

An example of this procedure is shown in Scheme 34, Example 1. In this procedure, a dibenzyl phosphonate S34.14 is reacted with diazabicyclooctane (DABCO) in toluene at reflux, as described in *J. Org. Chem.*, 1995, 60, 2946, to afford the monobenzyl phosphonate S34.15. The product is then reacted with equimolar amounts of ethyl alaninate S34.16 and dicyclohexyl carbodiimide in pyridine, to yield the amidate product S34.17. The benzyl group is then removed, for example by hydrogenolysis over a palladium catalyst, to give the monoacid product S34.18 which may be unstable according to J. Med. Chem. (1997) 40(23):3842. This compound S34.18 is then reacted in a Mitsunobu reaction with ethyl leucinate S34.19, triphenyl phosphine and diethylazodicarboxylate, as described in *J. Med. Chem.*, 1995, 38, 2742, to produce the bisamidate product S34.20.

Using the above procedures, but employing in place of ethyl leucinate S34.19 or ethyl alaninate S34.16, different aminoesters S34.9, the corresponding products S34.5 are obtained.

Alternatively, the phosphonic acid S34.6 is converted into the bisamidate S34.5 by use of the coupling reactions described above. The reaction is performed in one step, in which case the nitrogen-related substituents present in the product S34.5 are the same, or in two steps, in which case the nitrogen-related substituents can be different.

An example of the method is shown in Scheme 34, Example 2. In this procedure, a phosphonic acid S34.6 is reacted in pyridine solution with excess ethyl phenylalaninate S34.21 and dicyclohexylcarbodiimide, for example as described in *J. Chem. Soc., Chem. Comm.,* 1991, 1063, to give the bisamidate product S34.22.

Using the above procedures, but employing, in place of ethyl phenylalaninate, different aminoesters S34.9, the corresponding products S34.5 are obtained.

As a further alternative, the phosphonic acid S34.6 is converted into the mono or bis-activated derivative S34.7, in which Lv is a leaving group such as chloro, imidazolyl, triisopropylbenzenesulfonyloxy etc. The conversion of phosphonic acids into chlorides S34.7 (Lv=Cl) is effected by reaction with thionyl chloride or oxalyl chloride and the like, as described in *Organic Phosphorus Compounds*, G. M. Kosolapoff, L. Maeir, eds, Wiley, 1976, p. 17. The conversion of phosphonic acids into monoimidazolides S34.7 (Lv=imidazolyl) is described in *J. Med. Chem.,* 2002, 45, 1284 and in *J Chem. Soc. Chem. Comm.,* 1991, 312. Alternatively, the phosphonic acid is activated by reaction with triisopropylbenzenesulfonyl chloride, as described in *Nucleosides and Nucleotides,* 2000, 10, 1885. The activated product is then reacted with the aminoester S34.9, in the presence of a base, to give the bisamidate S34.5. The reaction is performed in one step, in which case the nitrogen substituents present in the product S34.5 are the same, or in two steps, via the intermediate S34.11, in which case the nitrogen substituents can be different.

Examples of these methods are shown in Scheme 34, Examples 3 and 5. In the procedure illustrated in Scheme 34, Example 3, a phosphonic acid S34.6 is reacted with ten molar equivalents of thionyl chloride, as described in *Zh. Obschei Khim.,* 1958, 28, 1063, to give the dichloro compound S34.23. The product is then reacted at reflux temperature in a polar aprotic solvent such as acetonitrile, and in the presence of a base such as triethylamine, with butyl serinate S34.24 to afford the bisamidate product S34.25.

Using the above procedures, but employing, in place of butyl serinate S34.24, different aminoesters S34.9, the corresponding products S34.5 are obtained.

In the procedure illustrated in Scheme 34, Example 5, the phosphonic acid S34.6 is reacted, as described in *J. Chem. Soc. Chem. Comm.,* 1991, 312, with carbonyl diimidazole to give the imidazolide S34.S32. The product is then reacted in acetonitrile solution at ambient temperature, with one molar equivalent of ethyl alaninate S34.33 to yield the monodisplacement product S34.S34. The latter compound is then reacted with carbonyl diimidazole to produce the activated intermediate S34.35, and the product is then reacted, under the same conditions, with ethyl N-methylalaninate S34.33a to give the bisamidate product S34.36.

Using the above procedures, but employing, in place of ethyl alaninate S34.33 or ethyl N-methylalaninate S34.33a, different aminoesters S34.9, the corresponding products S34.5 are obtained.

The intermediate monoamidate S34.3 is also prepared from the monoester S34.2 by first converting the monoester into the activated derivative S34.8 in which Lv is a leaving group such as halo, imidazolyl etc, using the procedures described above. The product S34.8 is then reacted with an aminoester S34.9 in the presence of a base such as pyridine, to give an intermediate monoamidate product S34.3. The latter compound is then converted, by removal of the $R^1$ group and coupling of the product with the aminoester S34.9, as described above, into the bisamidate S34.5.

An example of this procedure, in which the phosphonic acid is activated by conversion to the chloro derivative S34.26, is shown in Scheme 34, Example 4. In this procedure, the phosphonic monobenzyl ester S34.15 is reacted, in dichloromethane, with thionyl chloride, as described in *Tet. Letters.,* 1994, 35, 4097, to afford the phosphoryl chloride S34.26. The product is then reacted in acetonitrile solution at ambient temperature with one molar equivalent of ethyl 3-amino-2-methylpropionate S34.27 to yield the monoamidate product S34.28. The latter compound is hydrogenated in ethylacetate over a 5% palladium on carbon catalyst to produce the monoacid product S34.29. The product is subjected to a Mitsunobu coupling procedure, with equimolar amounts of butyl alaninate S34.30, triphenyl phosphine, diethylazodicarboxylate and triethylamine in tetrahydrofuran, to give the bisamidate product S34.31.

Using the above procedures, but employing, in place of ethyl 3-amino-2-methylpropionate S34.27 or butyl alaninate S34.30, different aminoesters S34.9, the corresponding products S34.5 are obtained.

The activated phosphonic acid derivative S34.7 is also converted into the bisamidate S34.5 via the diamino compound S34.10. The conversion of activated phosphonic acid derivatives such as phosphoryl chlorides into the corresponding amino analogs S34.10, by reaction with ammonia, is described in *Organic Phosphorus Compounds*, G. M. Kosolapoff, L. Maeir, eds, Wiley, 1976. The bisamino compound S34.10 is then reacted at elevated temperature with a haloester S34.12 (Hal=halogen, i.e. F, Cl, Br, I), in a polar organic solvent such as dimethylformamide, in the presence of a base such as 4,4-dimethylaminopyridine (DMAP) or potassium carbonate, to yield the bisamidate S34.5. Alternatively, S34.6 may be treated with two different amino ester reagents simulataneously, i.e. S34.12 where $R^{4b}$ or $R^{5b}$ are different. The resulting mixture of bisamidate products S34.5 may then be separable, e.g. by chromatography.

An example of this procedure is shown in Scheme 34, Example 6. In this method, a dichlorophosphonate S34.23 is reacted with ammonia to afford the diamide S34.37. The reaction is performed in aqueous, aqueous alcoholic or alcoholic solution, at reflux temperature. The resulting diamino compound is then reacted with two molar equivalents of ethyl 2-bromo-3-methylbutyrate S34.38, in a polar organic solvent such as N-methylpyrrolidinone at ca. 150° C., in the presence of a base such as potassium carbonate, and optionally in the presence of a catalytic amount of potassium iodide, to afford the bisamidate product S34.39.

Using the above procedures, but employing, in place of ethyl 2-bromo-3-methylbutyrate S34.38, different haloesters S34.12 the corresponding products S34.5 are obtained.

The procedures shown in Scheme 34 are also applicable to the preparation of bisamidates in which the aminoester moiety incorporates different functional groups. Scheme 34, Example 7 illustrates the preparation of bisamidates derived from tyrosine. In this procedure, the monoimidazolide S34.32 is reacted with propyl tyrosinate S34.40, as described in Example 5, to yield the monoamidate S34.41. The product is reacted with carbonyl diimidazole to give the imidazolide S34.42, and this material is reacted with a further molar equivalent of propyl tyrosinate to produce the bisamidate product S34.43.

Using the above procedures, but employing, in place of propyl tyrosinate S34.40, different aminoesters S34.9, the corresponding products S34.5 are obtained. The aminoesters employed in the two stages of the above procedure can be the same or different, so that bisamidates with the same or different amino substituents are prepared.

Scheme 35 illustrates methods for the preparation of phosphonate monoamidates.

In one procedure, a phosphonate monoester S34.1 is converted, as described in Scheme 34, into the activated derivative S34.8. This compound is then reacted, as described above, with an aminoester S34.9, in the presence of a base, to afford the monoamidate product S35.1.

The procedure is illustrated in Scheme 35, Example 1. In this method, a monophenyl phosphonate S35.7 is reacted with, for example, thionyl chloride, as described in *J. Gen. Chem. USSR.,* 1983, 32, 367, to give the chloro product S35.8. The product is then reacted, as described in Scheme 34, with ethyl alaninateS3, to yield the amidate S35.10.

Using the above procedures, but employing, in place of ethyl alaninate S35.9, different aminoesters S34.9, the corresponding products S35.1 are obtained.

Alternatively, the phosphonate monoester S34.1 is coupled, as described in Scheme 34, with an aminoester S34.9 to produce the amidate S335.1. If necessary, the $R^1$ substituent is then altered, by initial cleavage to afford the phosphonic acid S35.2. The procedures for this transformation depend on the nature of the $R^1$ group, and are described above. The phosphonic acid is then transformed into the ester amidate product S35.3, by reaction with the hydroxy compound $R^3OH$, in which the group $R^3$ is aryl, heterocycle, alkyl, cycloalkyl, haloalkyl etc, using the same coupling procedures (carbodiimide, Aldrithiol-2, PYBOP, Mitsunobu reaction etc) described in Scheme 34 for the coupling of amines and phosphonic acids.

Scheme 34 Example 1

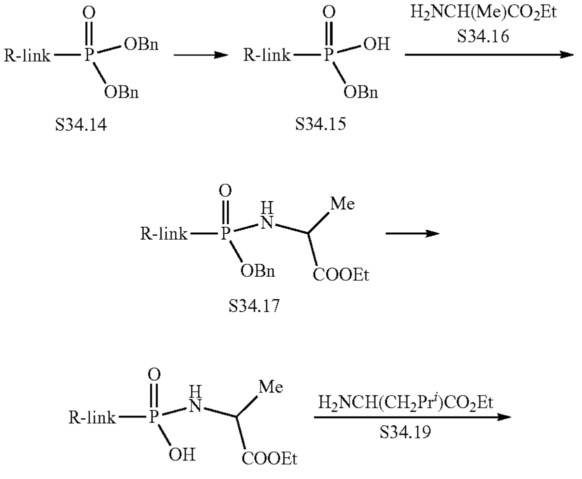

S34.14 S34.15 S34.17 S34.18

-continued

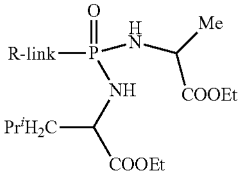

S34.20

Scheme 34 Example 2

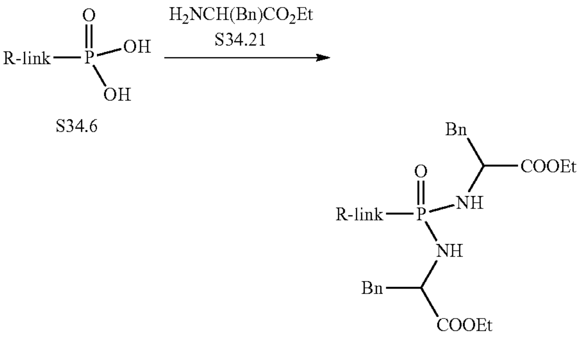

S34.6 S34.22

Scheme 34 Example 3

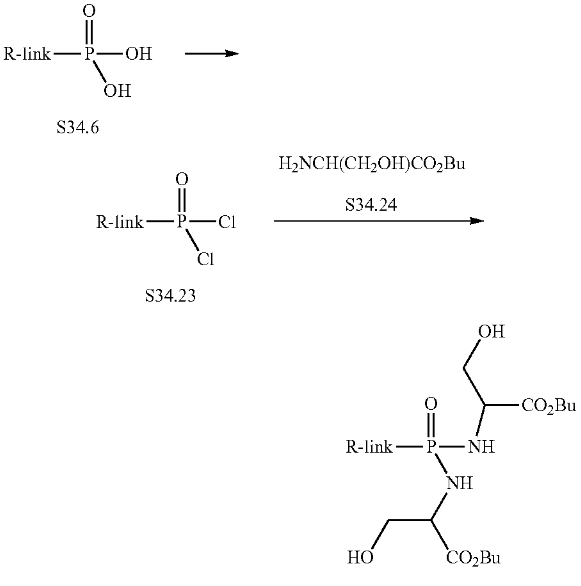

S34.6 S34.23 S34.25

Scheme 34 Example 4

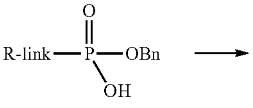

S34.15

-continued
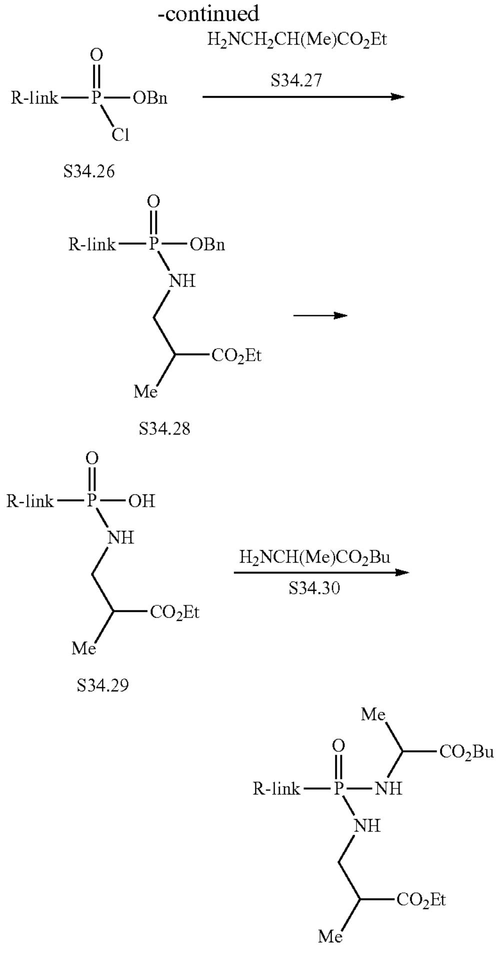
S34.26
S34.28
S34.29
S34.31
Scheme 34 Example 5
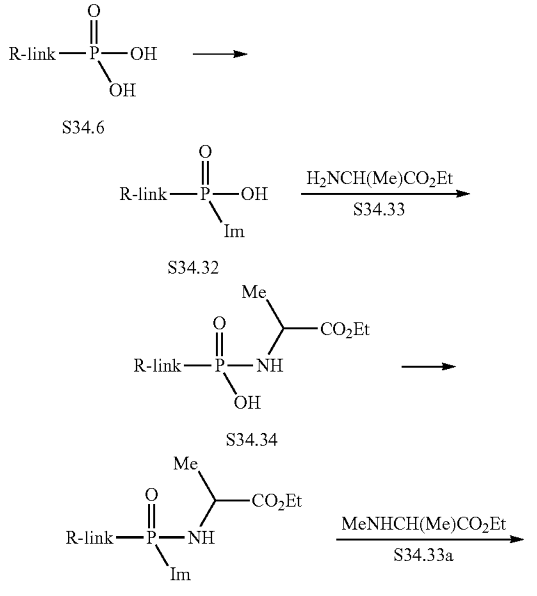
S34.6
S34.32
S34.34
S34.35
-continued
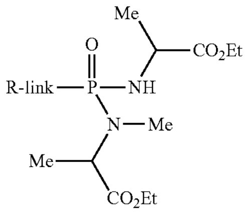
S34.36
Scheme 34 Example 6
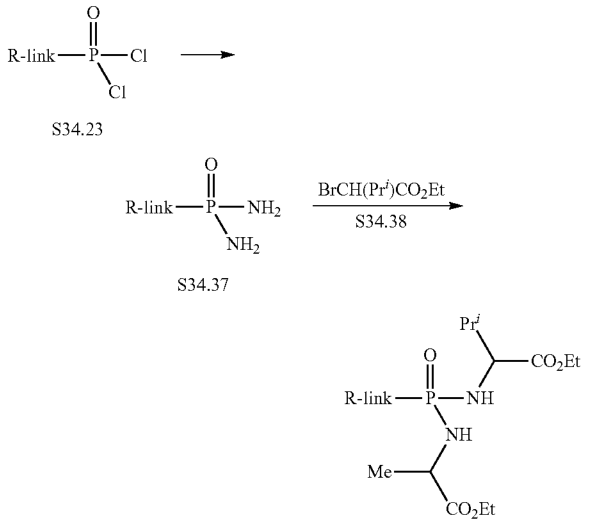
S34.23
S34.37
S34.39
Scheme 34 Example 7
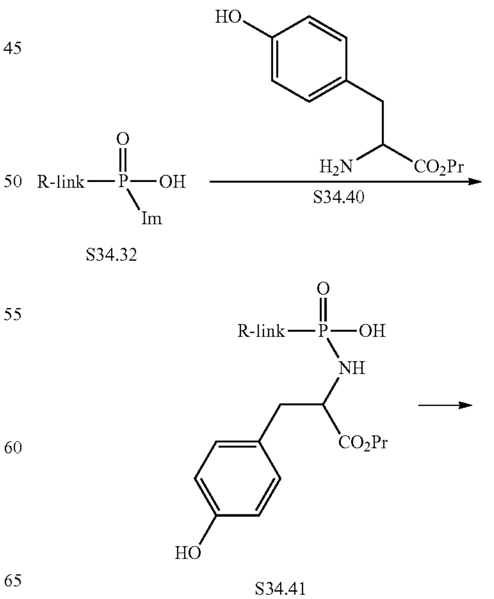
S34.32
S34.41

-continued

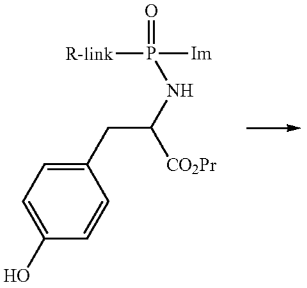

S34.42

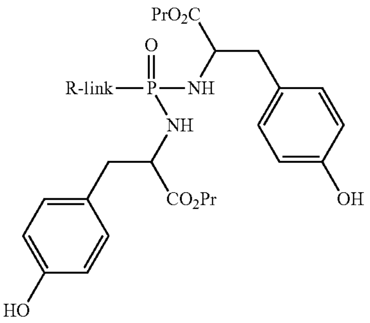

S34.43

Examples of this method are shown in Scheme 35, Examples and 2 and 3. In the sequence shown in Example 2, a monobenzyl phosphonate S35.11 is transformed by reaction with ethyl alaninate, using one of the methods described above, into the monoamidate S35.12. The benzyl group is then removed by catalytic hydrogenation in ethylacetate solution over a 5% palladium on carbon catalyst, to afford the phosphonic acid amidate S35.13. The product is then reacted in dichloromethane solution at ambient temperature with equimolar amounts of 1-(dimethylaminopropyl)-3-ethylcarbodiimide and trifluoroethanol S35.14, for example as described in *Tet. Lett.*, 2001, 42, 8841, to yield the amidate ester S35.15.

In the sequence shown in Scheme 35, Example 3, the monoamidate S35.13 is coupled, in tetrahydrofuran solution at ambient temperature, with equimolar amounts of dicyclohexyl carbodiimide and 4-hydroxy-N-methylpiperidine S35.16, to produce the amidate ester product S35.17.

Using the above procedures, but employing, in place of the ethyl alaninate product S35.12 different monoacids S35.2, and in place of trifluoroethanol S35.14 or 4-hydroxy-N-methylpiperidine S35.16, different hydroxy compounds $R^3OH$, the corresponding products S35.3 are obtained.

Alternatively, the activated phosphonate ester S34.8 is reacted with ammonia to yield the amidate S35.4. The product is then reacted, as described in Scheme 34, with a haloester S35.5, in the presence of a base, to produce the amidate product S35.6. If appropriate, the nature of the $R^1$ group is changed, using the procedures described above, to give the product S35.3. The method is illustrated in Scheme 35, Example 4. In this sequence, the monophenyl phosphoryl chloride S35.18 is reacted, as described in Scheme 34, with ammonia, to yield the amino product S35.19. This material is then reacted in N-methylpyrrolidinone solution at 170° with butyl 2-bromo-3-phenylpropionate S35.20 and potassium carbonate, to afford the amidate product S35.21.

Using these procedures, but employing, in place of butyl 2-bromo-3-phenylpropionate S35.20, different haloesters S35.5, the corresponding products S35.6 are obtained.

The monoamidate products S35.3 are also prepared from the doubly activated phosphonate derivatives S34.7. In this procedure, examples of which are described in *Synlett.*, 1998, 1, 73, the intermediate S34.7 is reacted with a limited amount of the aminoester S34.9 to give the mono-displacement product S34.11. The latter compound is then reacted with the hydroxy compound $R^3OH$ in a polar organic solvent such as dimethylformamide, in the presence of a base such as diisopropylethylamine, to yield the monoamidate ester S35.3.

The method is illustrated in Scheme 35, Example 5. In this method, the phosphoryl dichloride S35.22 is reacted in dichloromethane solution with one molar equivalent of ethyl N-methyl tyrosinate S35.23 and dimethylaminopyridine, to generate the monoamidate S35.24. The product is then reacted with phenol S35.25 in dimethylformamide containing potassium carbonate, to yield the ester amidate product S35.26.

Using these procedures, but employing, in place of ethyl N-methyl tyrosinate S35.23 or phenol S35.25, the aminoesters 34.9 and/or the hydroxy compounds $R^3OH$, the corresponding products S35.3 are obtained.

Scheme 35

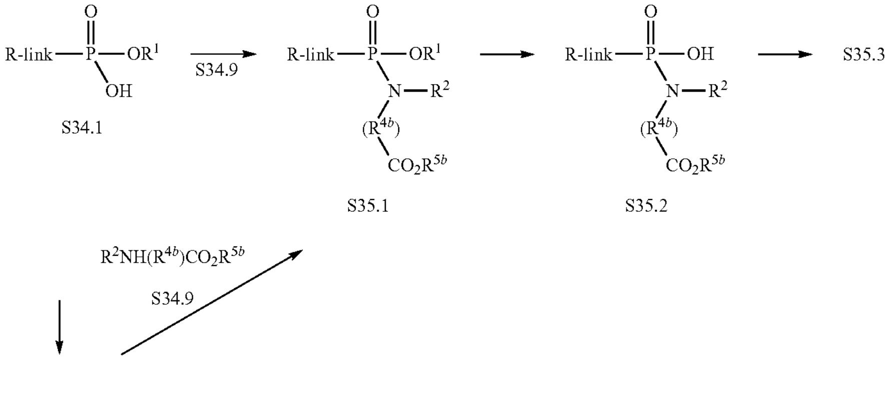

S34.1 S35.1 S35.2 S35.3

-continued
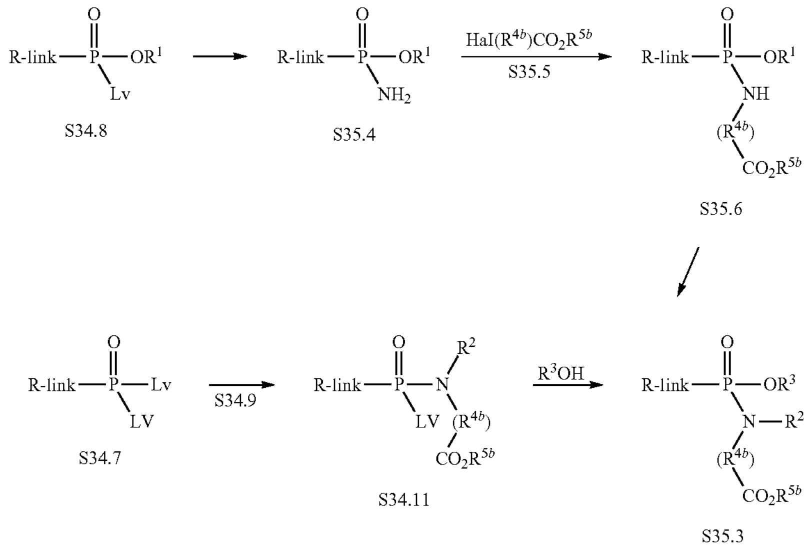
S34.8 S35.4 S35.6 S34.7 S34.11 S35.3
Scheme 35 Example 1
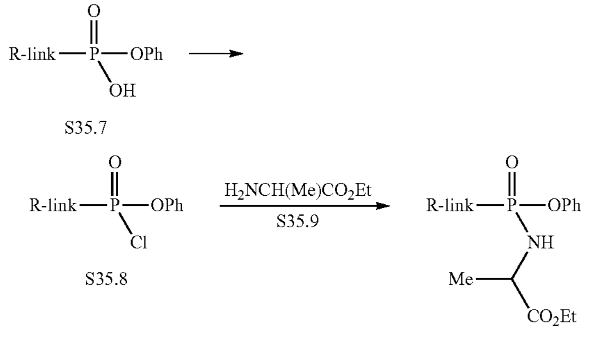
S35.7 S35.8 S35.10
Scheme 35 Example 2
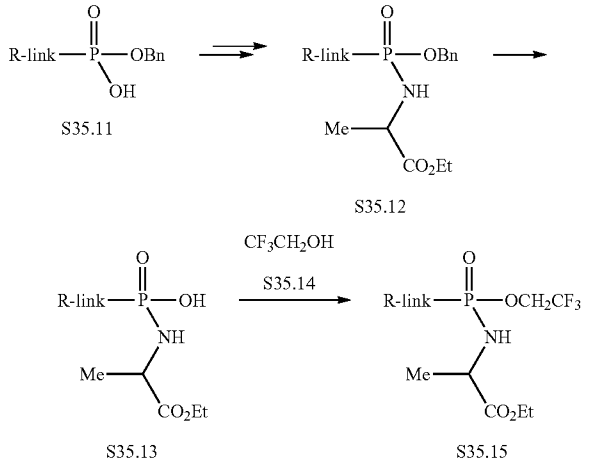
S35.11 S35.12 S35.13 S35.15
Scheme 35 Example 3
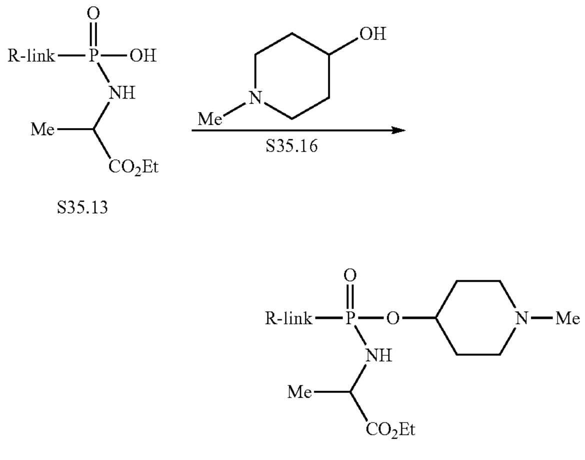
S35.13 S35.17
Scheme 35 Example 4
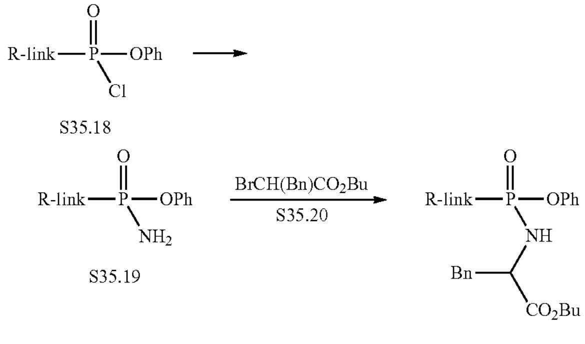
S35.18 S35.19 S35.21

Scheme 35 Example 5

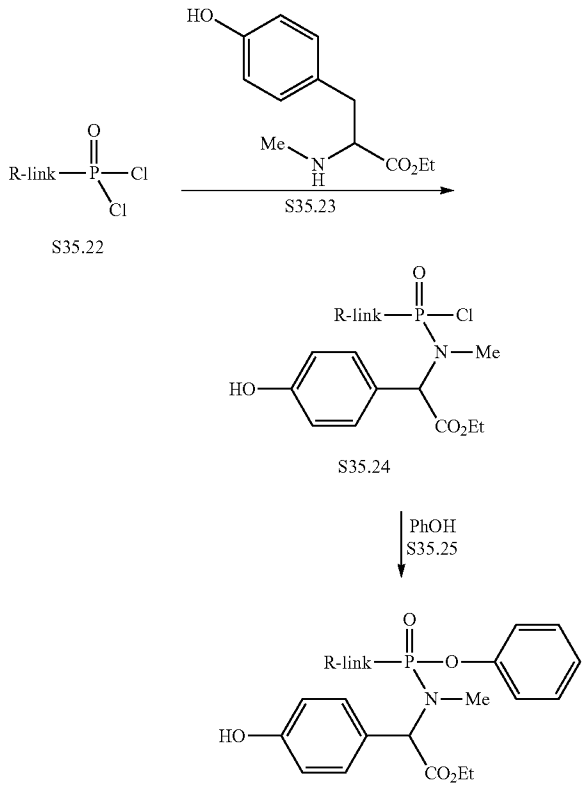

Scheme 36 illustrates methods for the preparation of carboalkoxy-substituted phosphonate diesters in which one of the ester groups incorporates a carboalkoxy substituent.

In one procedure, a phosphonate monoester S34.1, prepared as described above, is coupled, using one of the methods described above, with a hydroxyester S36.1, in which the groups $R^{4b}$ and $R^{5b}$ are as described in Scheme 34. For example, equimolar amounts of the reactants are coupled in the presence of a carbodiimide such as dicyclohexyl carbodiimide, as described in *Aust. J. Chem.*, 1963, 609, optionally in the presence of dimethylaminopyridine, as described in *Tet.*, 1999, 55, 12997. The reaction is conducted in an inert solvent at ambient temperature.

The procedure is illustrated in Scheme 36, Example 1. In this method, a monophenyl phosphonate S36.9 is coupled, in dichloromethane solution in the presence of dicyclohexyl carbodiimide, with ethyl 3-hydroxy-2-methylpropionate S36.10 to yield the phosphonate mixed diester S36.11.

Using this procedure, but employing, in place of ethyl 3-hydroxy-2-methylpropionate S36.10, different hydroxyesters S33.1, the corresponding products S33.2 are obtained.

The conversion of a phosphonate monoester S34.1 into a mixed diester S36.2 is also accomplished by means of a Mitsunobu coupling reaction with the hydroxyester S36.1, as described in *Org. Lett.*, 2001, 643. In this method, the reactants 34.1 and S36.1 are combined in a polar solvent such as tetrahydrofuran, in the presence of a triarylphosphine and a dialkyl azodicarboxylate, to give the mixed diester S36.2. The $R^1$ substituent is varied by cleavage, using the methods described previously, to afford the monoacid product S36.3. The product is then coupled, for example using methods described above, with the hydroxy compound $R^3OH$, to give the diester product S36.4.

The procedure is illustrated in Scheme 36, Example 2. In this method, a monoallyl phosphonate S36.12 is coupled in tetrahydrofuran solution, in the presence of triphenylphosphine and diethylazodicarboxylate, with ethyl lactate S36.13 to give the mixed diester S36.14. The product is reacted with tris(triphenylphosphine) rhodium chloride (Wilkinson catalyst) in acetonitrile, as described previously, to remove the allyl group and produce the monoacid product S36.15. The latter compound is then coupled, in pyridine solution at ambient temperature, in the presence of dicyclohexyl carbodiimide, with one molar equivalent of 3-hydroxypyridine S36.16 to yield the mixed diester S36.17.

Using the above procedures, but employing, in place of the ethyl lactate S36.13 or 3-hydroxypyridine, a different hydroxyester S36.1 and/or a different hydroxy compound $R^3OH$, the corresponding products S36.4 are obtained.

The mixed diesters S36.2 are also obtained from the monoesters S34.1 via the intermediacy of the activated monoesters S36.5. In this procedure, the monoester S34.1 is converted into the activated compound S36.5 by reaction with, for example, phosphorus pentachloride, as described in *J. Org. Chem.*, 2001, 66, 329, or with thionyl chloride or oxalyl chloride (Lv=Cl), or with triisopropylbenzenesulfonyl chloride in pyridine, as described in *Nucleosides and Nucleotides*, 2000, 19, 1885, or with carbonyl diimidazole, as described in *J. Med. Chem.*, 2002, 45, 1284. The resultant activated monoester is then reacted with the hydroxyester S36.1, as described above, to yield the mixed diester S36.2.

The procedure is illustrated in Scheme 36, Example 3. In this sequence, a monophenyl phosphonate S36.9 is reacted, in acetonitrile solution at 70° C., with ten equivalents of thionyl chloride, so as to produce the phosphoryl chloride S36.19. The product is then reacted with ethyl 4-carbamoyl-2-hydroxybutyrate S36.20 in dichloromethane containing triethylamine, to give the mixed diester S36.21.

Using the above procedures, but employing, in place of ethyl 4-carbamoyl-2-hydroxybutyrate S36.20, different hydroxyesters S36.1, the corresponding products S36.2 are obtained.

The mixed phosphonate diesters are also obtained by an alternative route for incorporation of the $R^3O$ group into intermediates S36.3 in which the hydroxyester moiety is already incorporated. In this procedure, the monoacid intermediate S36.3 is converted into the activated derivative S36.6 in which Lv is a leaving group such as chloro, imidazole, and the like, as previously described. The activated intermediate is then reacted with the hydroxy compound $R^3OH$, in the presence of a base, to yield the mixed diester product S36.4.

The method is illustrated in Scheme 36, Example 4. In this sequence, the phosphonate monoacid S36.22 is reacted with trichloromethanesulfonyl chloride in tetrahydrofuran containing collidine, as described in *J. Med. Chem.*, 1995, 38, 4648, to produce the trichloromethanesulfonyloxy product S36.23. This compound is reacted with 3-(morpholinomethyl)phenol S36.24 in dichloromethane containing triethylamine, to yield the mixed diester product S36.25.

Using the above procedures, but employing, in place of with 3-(morpholinomethyl)phenol S36.24, different alcohols $R^3OH$, the corresponding products S36.4 are obtained.

The phosphonate esters S36.4 are also obtained by means of alkylation reactions performed on the monoesters S34.1. The reaction between the monoacid S34.1 and the haloester S36.7 is performed in a polar solvent in the presence of a base such as diisopropylethylamine, as described in *Anal. Chem.*, 1987, 59, 1056, or triethylamine, as described in *J. Med.*

*Chem.*, 1995, 38, 1372, or in a non-polar solvent such as benzene, in the presence of 18-crown-6, as described in *Syn. Comm.*, 1995, 25, 3565.

The method is illustrated in Scheme 36, Example 5. In this procedure, the monoacid S36.26 is reacted with ethyl 2-bromo-3-phenylpropionate S36.27 and diisopropylethylamine in dimethylformamide at 80° C. to afford the mixed diester product S36.28.

Using the above procedure, but employing, in place of ethyl 2-bromo-3-phenylpropionate S36.27, different haloesters S36.7, the corresponding products S36.4 are obtained.

Scheme 36 Example 2

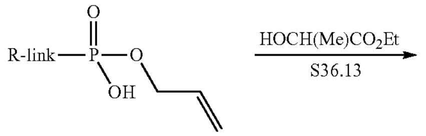

S36.12

Scheme 36

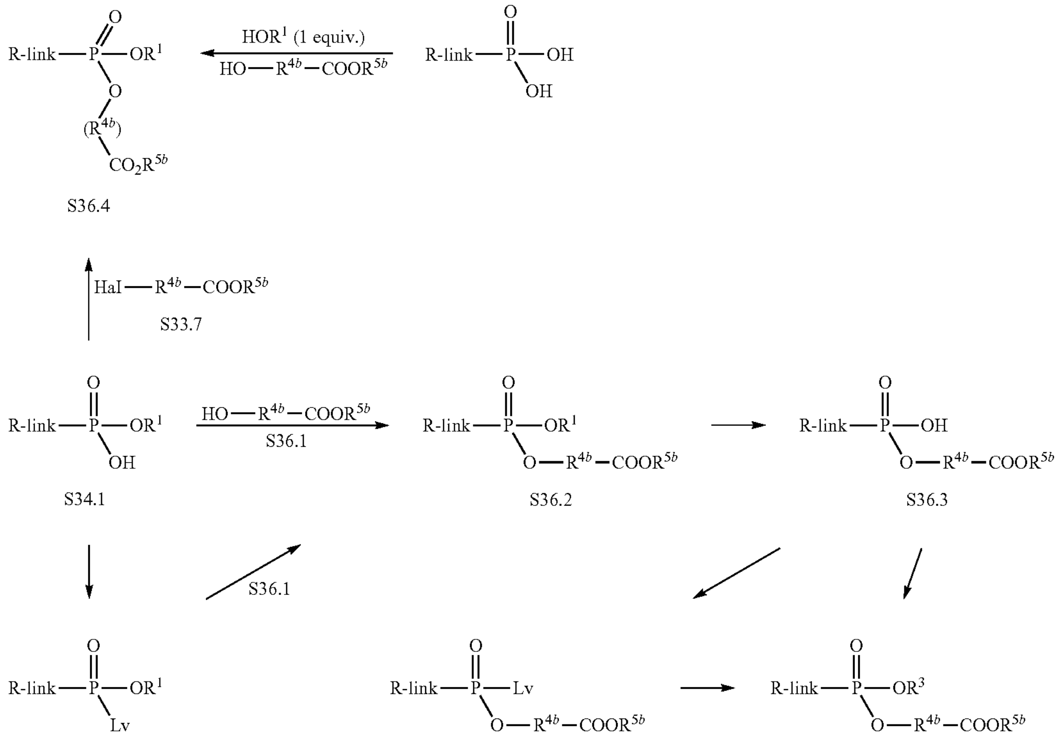

S36.4

S33.7

S34.1 S36.2 S36.3

S36.5 S36.6 S36.4

Scheme 36 Example 1

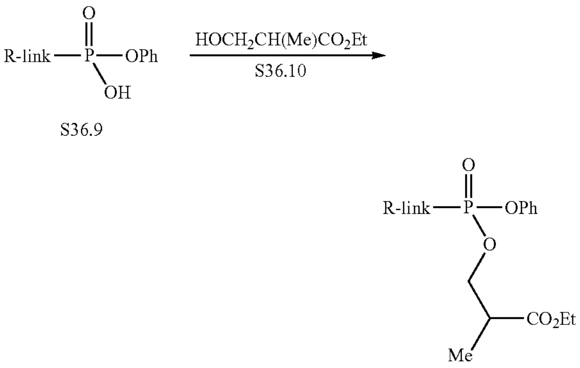

S36.9

S36.11

-continued

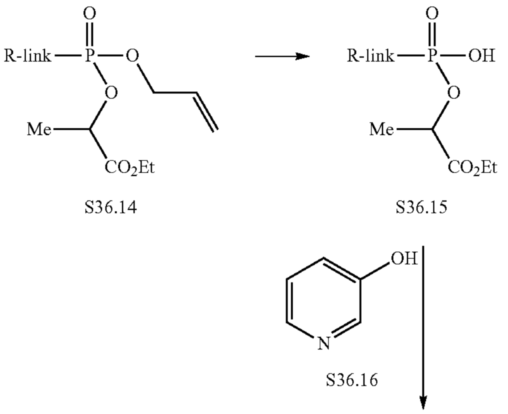

S36.14 S36.15

S36.16

-continued

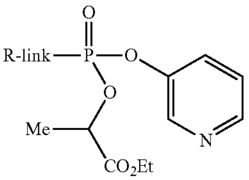

S36.17

Scheme 36 Example 3

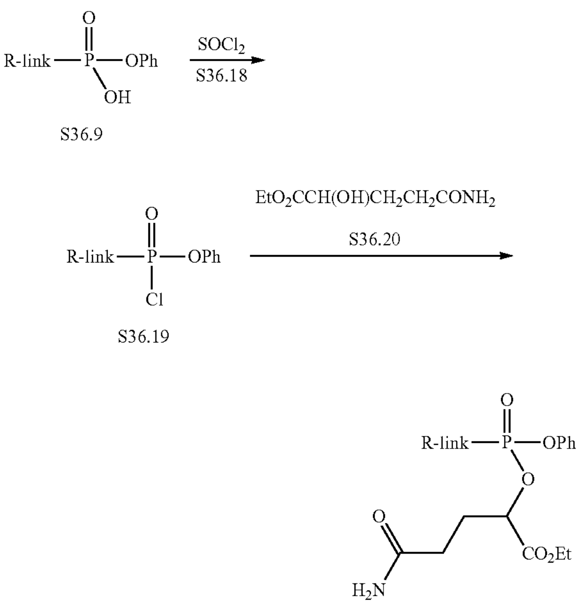

S36.9

S36.19

S36.21

Scheme 36

Example 4

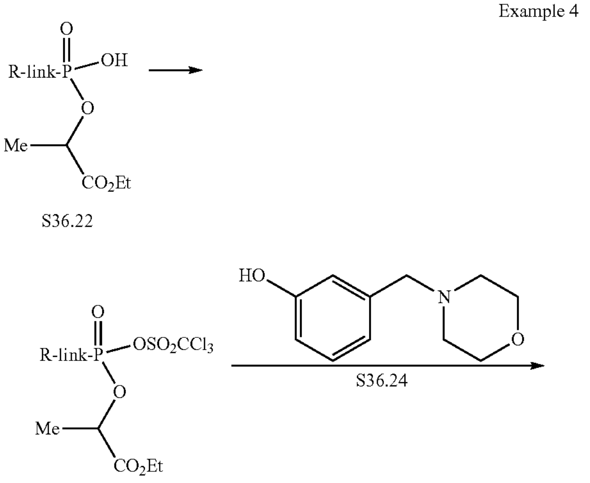

S36.22

S36.23

-continued

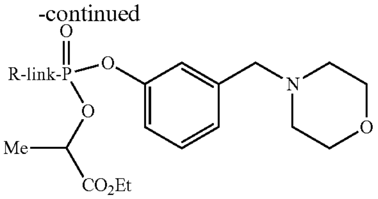

S36.25

Scheme 36

Example 5

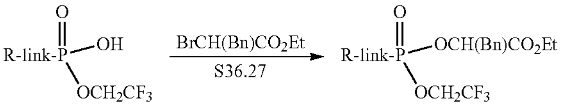

S36.26

S36.28

Scheme 37 illustrates methods for the preparation of phosphonate diesters in which both the ester substituents incorporate carboalkoxy groups.

The compounds are prepared directly or indirectly from the phosphonic acids S34.6. In one alternative, the phosphonic acid is coupled with the hydroxyester S37.2, using the conditions described previously in Schemes 34-36, such as coupling reactions using dicyclohexyl carbodiimide or similar reagents, or under the conditions of the Mitsunobu reaction, to afford the diester product S37.3 in which the ester substituents are identical.

This method is illustrated in Scheme 37, Example 1. In this procedure, the phosphonic acid S34.6 is reacted with three molar equivalents of butyl lactate S37.5 in the presence of Aldrithiol-2 and triphenyl phosphine in pyridine at ca. 70° C., to afford the diester S37.6.

Using the above procedure, but employing, in place of butyl lactate S37.5, different hydroxyesters S37.2, the corresponding products S37.3 are obtained.

Alternatively, the diesters S37.3 are obtained by alkylation of the phosphonic acid S34.6 with a haloester S37.1. The alkylation reaction is performed as described in Scheme 36 for the preparation of the esters S36.4.

This method is illustrated in Scheme 37, Example 2. In this procedure, the phosphonic acid S34.6 is reacted with excess ethyl 3-bromo-2-methylpropionate S37.7 and diisopropylethylamine in dimethylformamide at ca. 80° C., as described in *Anal. Chem.,* 1987, 59, 1056, to produce the diester S37.8.

Using the above procedure, but employing, in place of ethyl 3-bromo-2-methylpropionate S37.7, different haloesters S37.1, the corresponding products S37.3 are obtained.

The diesters S37.3 are also obtained by displacement reactions of activated derivatives S34.7 of the phosphonic acid with the hydroxyesters S37.2. The displacement reaction is performed in a polar solvent in the presence of a suitable base, as described in Scheme 36. The displacement reaction is performed in the presence of an excess of the hydroxyester, to afford the diester product S37.3 in which the ester substituents are identical, or sequentially with limited amounts of different hydroxyesters, to prepare diesters S37.3 in which the ester substituents are different.

The methods are illustrated in Scheme 37, Examples 3 and 4. As shown in Example 3, the phosphoryl dichloride S35.22 is reacted with three molar equivalents of ethyl 3-hydroxy-2-(hydroxymethyl)propionate S37.9 in tetrahydrofuran containing potassium carbonate, to obtain the diester product S37.10.

Using the above procedure, but employing, in place of ethyl 3-hydroxy-2-(hydroxymethyl)propionate S37.9, different hydroxyesters S37.2, the corresponding products S37.3 are obtained.

Scheme 37, Example 4 depicts the displacement reaction between equimolar amounts of the phosphoryl dichloride S35.22 and ethyl 2-methyl-3-hydroxypropionate S37.11, to yield the monoester product S37.12. The reaction is conducted in acetonitrile at 70° in the presence of diisopropylethylamine. The product S37.12 is then reacted, under the same conditions, with one molar equivalent of ethyl lactate S37.13, to give the diester product S37.14.

Using the above procedures, but employing, in place of ethyl 2-methyl-3-hydroxypropionate S37.11 and ethyl lactate S37.13, sequential reactions with different hydroxyesters S37.2, the corresponding products S37.3 are obtained.

Scheme 37

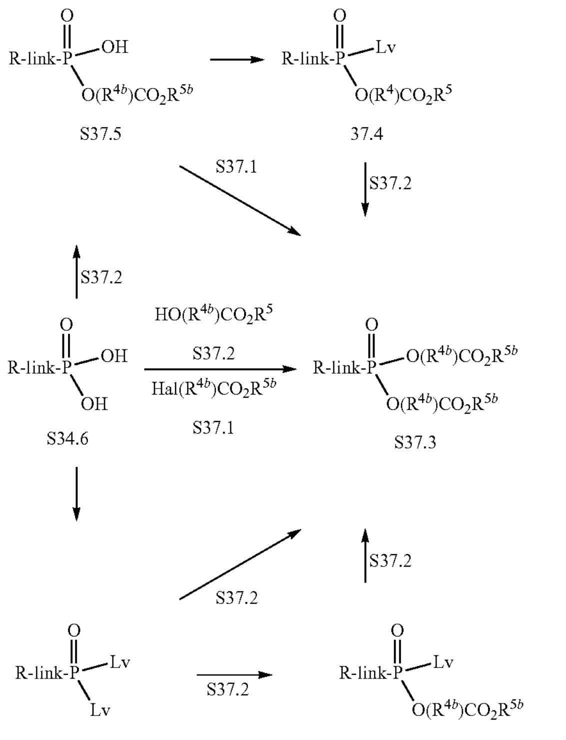

S37.5 37.4 S34.6 S37.3 S34.7 S37.4

Scheme 37

Example 1

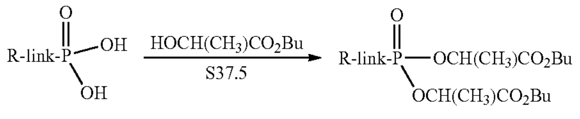

S34.6 S37.6

Scheme 37

Example 2

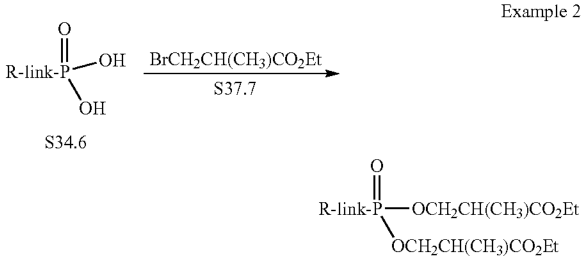

S34.6 S37.8

Scheme 37

Example 3

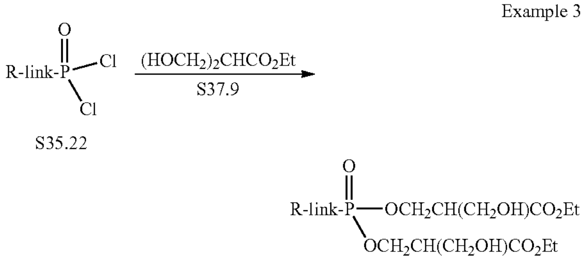

S35.22 S37.10

Scheme 37

Example 4

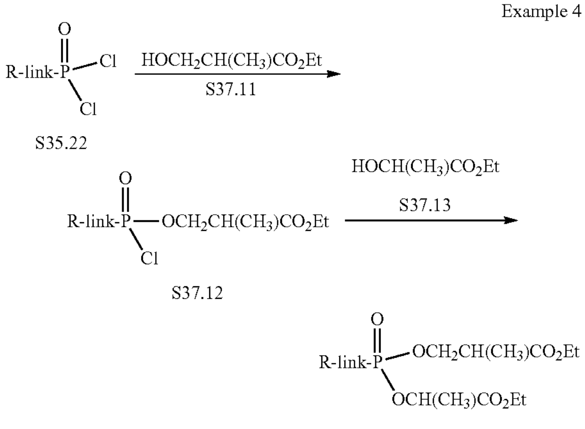

S35.22 S37.12 S37.14

2,2-Dimethyl-2-aminoethylphosphonic acid intermediates can be prepared by the route in Scheme 5. Condensation of 2-methyl-2-propanesulfinamide with acetone give sulfinyl imine S38.11 (*J. Org. Chem.* 1999, 64, 12). Addition of dimethyl methylphosphonate lithium to S38.11 afford S38.12. Acidic methanolysis of S38.12 provide amine S38.13. Protection of amine with Cbz group and removal of methyl groups yield phosphonic acid S38.14, which can be converted to desired S38.15 (Scheme 38a) using methods reported earlier on. An alternative synthesis of compound S38.14 is also shown in Scheme 38b. Commercially available 2-amino-2-methyl-1-propanol is converted to aziridines S38.16 according to literature methods (*J. Org. Chem.* 1992, 57, 5813; *Syn.*

*Lett.* 1997, 8, 893). Aziridine opening with phosphite give S38.17 (*Tetrahedron Lett.* 1980, 21, 1623). Reprotection) of S38.17 affords S38.14.

Scheme 38a

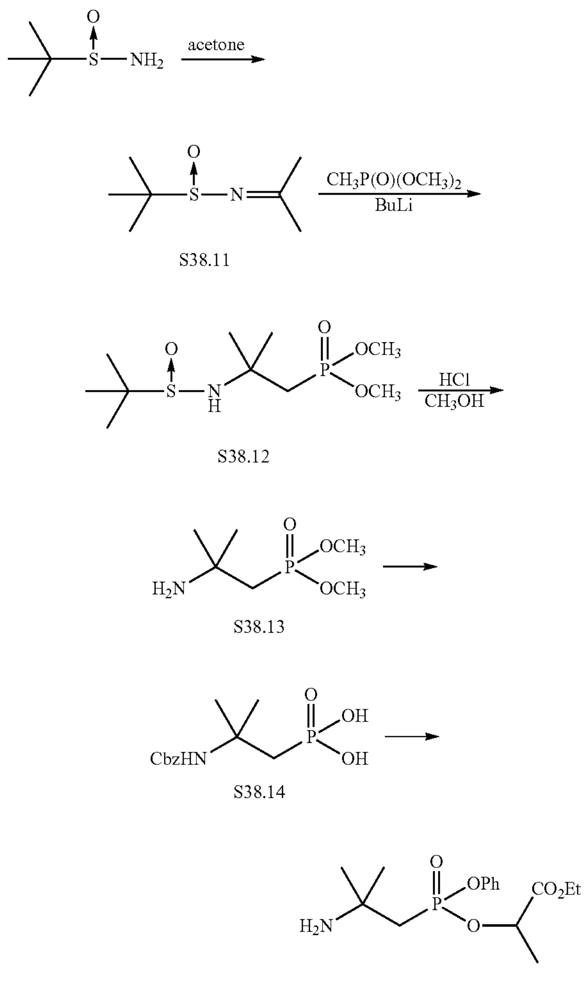

S38.11

S38.12

S38.13

S38.14

S38.15

Scheme 38b

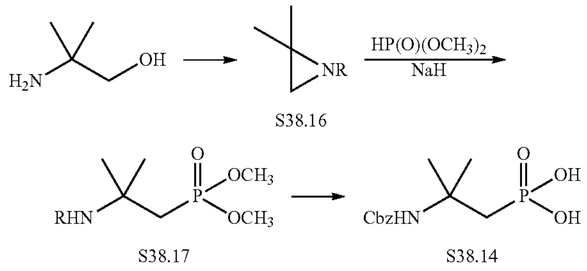

S38.16

S38.17

S38.14

R = Cbz, $R'SO_2$

The invention will now be illustrated by the following non-limiting Examples.

Example 1

Synthesis of Representative Compounds of Formula 1

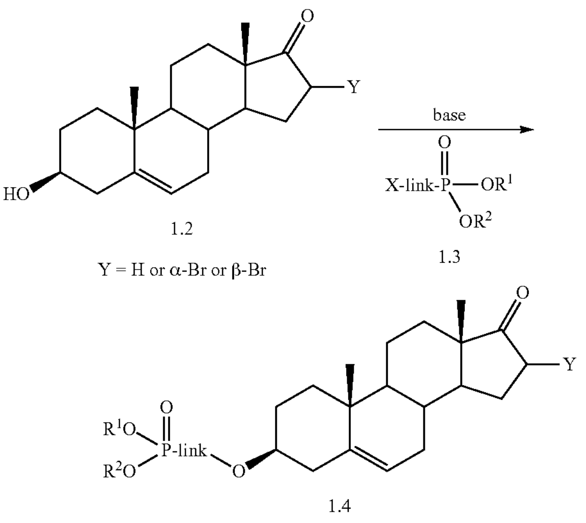

1.2

Y = H or α-Br or β-Br 1.3

1.4

Y = H or α-Br or β-Br

Representative compounds of the invention can be prepared as illustrated above. Dehydroepiandrosterone (purchased from a supplier such as Aldrich), 16-α-bromodehydroepiandrosterone, or 16-β-bromodehydroepiandrosterone (purchased from a supplier such as Steraloids) can be treated with bases such as, but not limited to, $Cs_2CO_3$ or NaH, in an appropriate solvents such as, but not limited to, THF or DMF, in the presence of an alkylating agent of general structure 1.3. Note that X is a leaving group, preferably in this case trifluoromethanesulfonate, but other leaving groups may be used and include bromide, iodide, chloride, p-toluenesulfonate, methanesulfonate, among others. The phosphonate esters of the resulting alkylated product 1.4 can then be converted into the intended final phosphonate functionality.

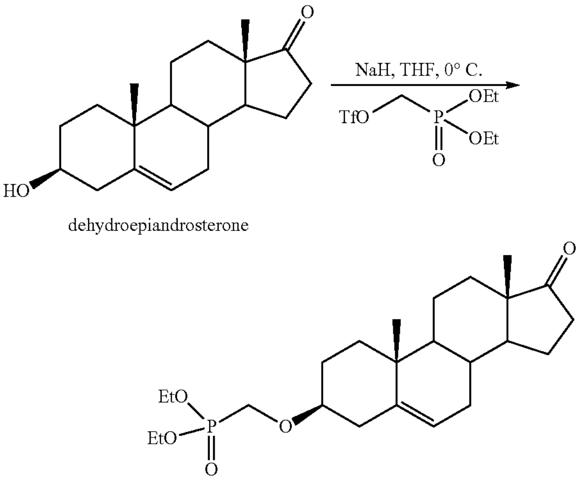

dehydroepiandrosterone 1.5

For instance, dehydroepiandrosterone can be treated in anhydrous THF at 0° C. with NaH. When bubbling ceases, diethyl phosphonomethyltriflate (prepared according to *Tetrahedron Lett.* 1986, 27, 1477) is added yielding intermediate 1.5. The phosphonate esters of 1.5 are then converted into the final desired functionality.

Example 2

Synthesis of Representative Compounds of Formula 2

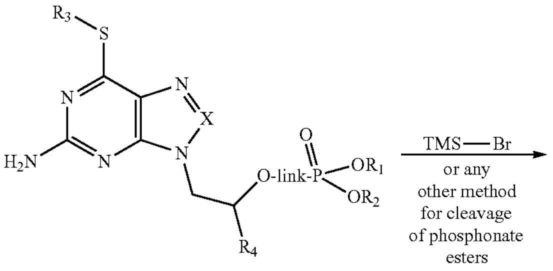

2.2 e.g. $R^1 = R^2 = CH_2CF_3$

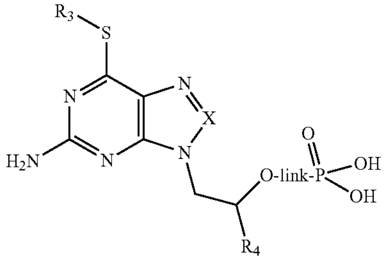

2.3

Representative compounds of the invention can be prepared as illustrated above. Intermediates 2.2 are prepared according to the methods described in U.S. Pat. No. 6,194,398 and any literature cited therein. The phosphonate ester of 2.2 may be converted to the final desired phosphonic acid functionality. Alternatively, phosphonic acids 2.3 may be formed by cleavage of esters 2.2 by treatment with a reagent such as, but not limited to, TMS-bromide in a solvent such as MeCN. Phosphonic acid 2.3 may then be converted to the final desired phosphonic acid functionality.

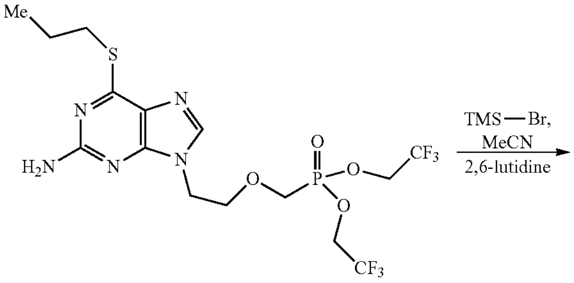

LY-582563

-continued

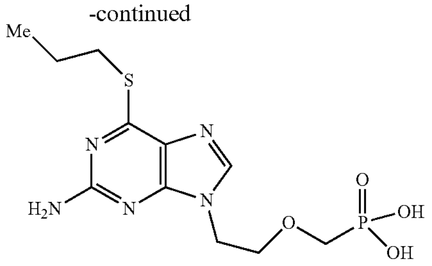

2.4

For instance, LY-582563, prepared as described in U.S. Pat. No. 6,194,398 is treated with TMS-Br and 2,6-lutidine in MeCN to provide phosphonic acid 2.4. Either LY-582563 or 2.4 may then be converted to the final desired phosphonate derivative.

Example 3

Synthesis of Representative Compounds of Formulae 3 and 4

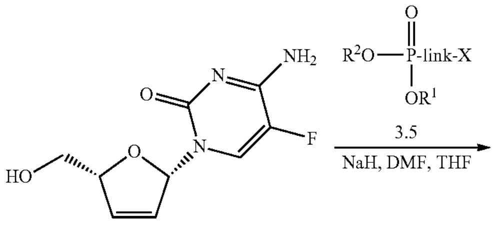

L-Fd4C

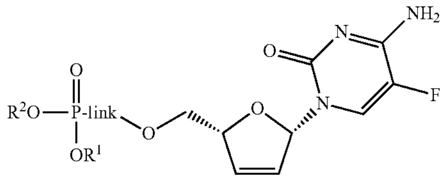

3.6

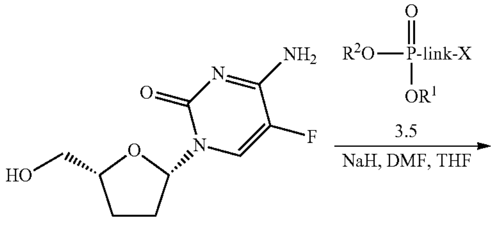

L-FddC

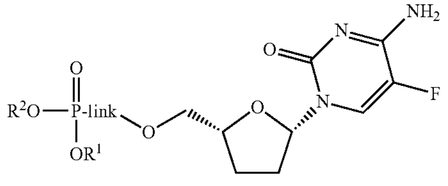

3.7

Representative compounds of the invention can be prepared as illustrated above. L-Fd4C and L-FddC are prepared according to methods in U.S. Pat. No. 5,561,120, U.S. Pat. No. 5,627,160, and U.S. Pat. No. 5,631,239 and any literature references cited therein. Either can be treated with a base such as, but not limited to, NaH or $Cs_2CO_3$, in a solvent such as, but not limited to, THF or DMF, and an alkylating agent of structure 3.5. In compounds 3.5, X is a leaving group such as, but not limited to, bromide, chloride, iodide, p-toluenesulfonate, trifluoromethanesulfonate, or methanesulfonate. It should be noted that cytosine-containing compounds sometimes require protection of the amino group at the 4-position of the base. If necessary, a protecting group may be introduced onto this position before these alkylation reactions are carried out. Introduction of such protecting groups (and their subsequent removal at the end of a synthetic scheme) are processes well known to those skilled in the art of nucleoside and nucleotide synthesis.

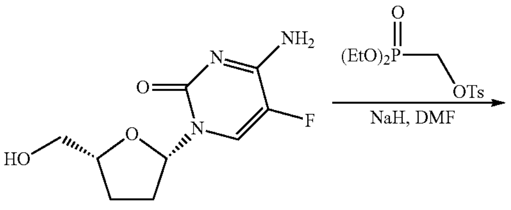

L-FddC

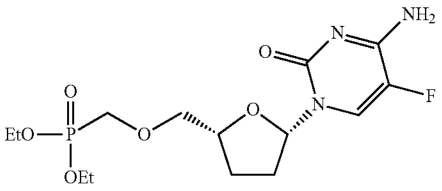

3.8

For instance, L-FddC is treated with NaH in DMF at 0° C. When bubbling has ceased, diethyl phosphonomethyltriflate (prepared according to *Tetrahedron Lett.* 1986, 27, 1477) is added. The resulting product 3.8 is isolated by standard chromatographic means. It may be necessary to protect the amino group at the 4-position of the base before this alkylation is carried out. See the note above regarding such protecting groups.

Example 4

Synthesis of Representative Compounds of Formulae 5 and 6

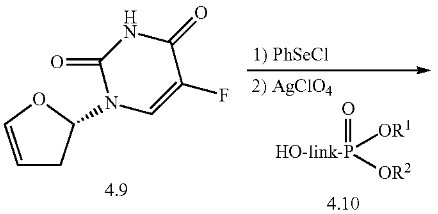

4.9

4.10

-continued

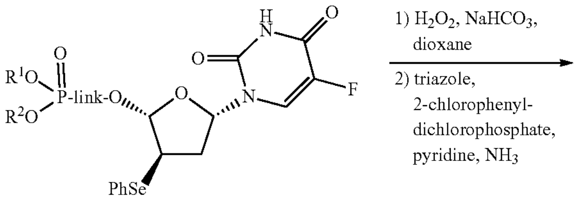

4.11

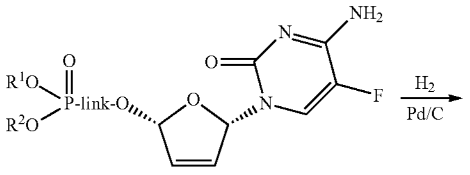

4.12

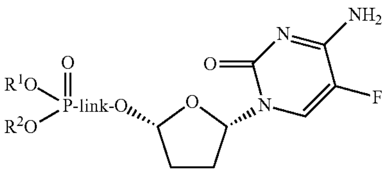

4.13

In Example 4, glycal 4.9 (obtained as described in *J. Am. Chem. Soc.* 1972, 94, 3213) is reacted with phenylselenyl chloride followed by treatment with the respective phosphonate alcohols 4.10 in the presence of silver perchlorate (*J. Org. Chem.* 1991, 56, 2642-2647). Oxidation of the resulting chloride using hydrogen peroxide followed by aminolysis of uracil using triazole, 2-chlorophenyldichlorophosphate, pyridine and ammonia (*Bioorg. Med. Chem. Lett.* 1997, 7, 2567) provides the L-Fd4C phosphonate derivative 4.12. Hydrogenation over 10% Pd/C provides the L-FddC derivative 4.13.

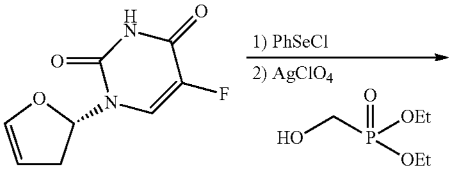

4.9

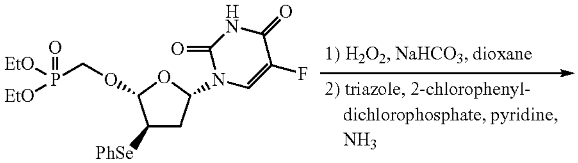

4.14

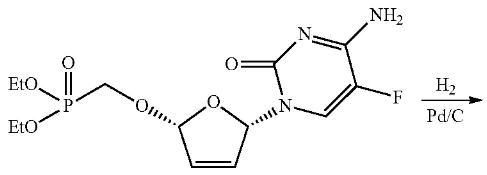

4.15

-continued

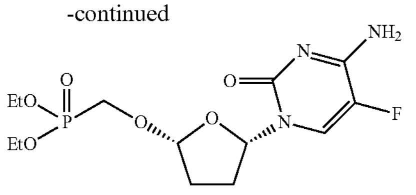

4.16

For instance, glycal 4.9 is reacted with phenylselenyl chloride and then treated with $AgClO_4$ and diethyl phosphonomethanol (available from Aldrich) providing compound 4.14. Treatment of 4.14 with $H_2O_2$ and $NaHCO_3$ in 1,4-dioxane followed by triazole, 2-chlorophenyldichlorophospate, in pyridine with ammonia yields the fluorocytosine derivative 4.15. Hydrogenation at 1 atm, over 10% Pd/C yields derivative 4.16.

Example 5

Synthesis of Representative Compounds of Formula 9

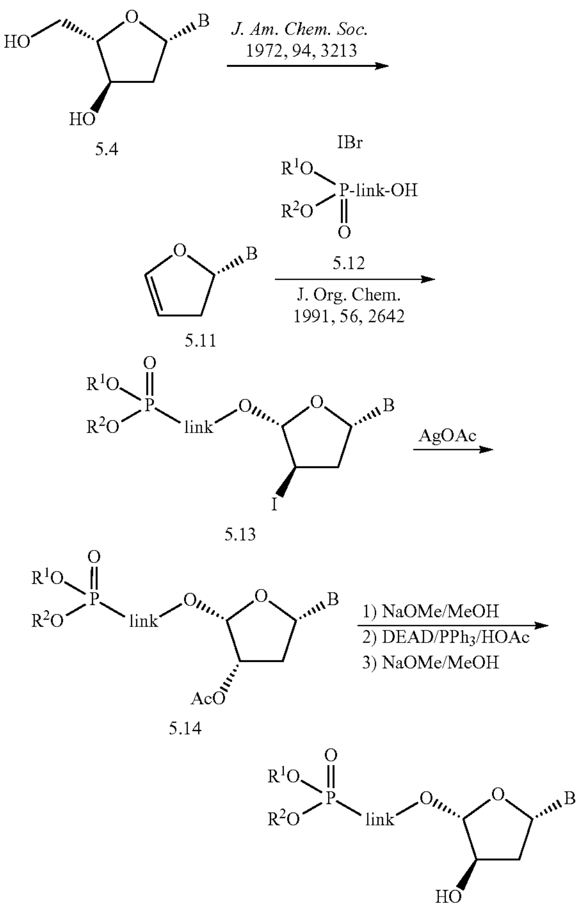

5.4

5.11

5.13

5.14

5.15

Bases such as but not limited to, thymine, adenine, uracil, 5-halouracils, 5-alkyluracils, guanine, cytosine, 5-halo and alkyl cytosines, 2,6 diaminopurine. Bases requiring protecting groups are to be suitably protected using protecting groups and conditions well known to thoses skilled in the art.

Representative compounds of the invention can be prepared as illustrated above. Compounds 5.4, prepared as described in WO 00/09531, U.S. Pat. Nos. 6,395,716, and 6,444,652, can be converted to glycal 5.11 according to the process reported in *J. Am. Chem. Soc.* 1972, 94, 3213. Glycal 5.11 is then treated with IBr in the presence of alcohol 5.12 to provide intermediate 5.13 (see *J. Org. Chem.* 1991, 56, 2642). The iodide of intermediate 5.13 can be treated with AgOAc to provide acetate 5.14, which can be deacetylated in the presence of catalytic sodium methoxide in methanol. Treatment of this product with DEAD and $PPh_3$ in the presence of acetic acid, followed by another deprotection with catalytic sodium methoxide in methanol will provide intermediate 5.15, which is representative of Formula 9. The phosphonates of intermediates 5.15 can be converted into other embodiments of the invention according to procedures know to those of skill in the art.

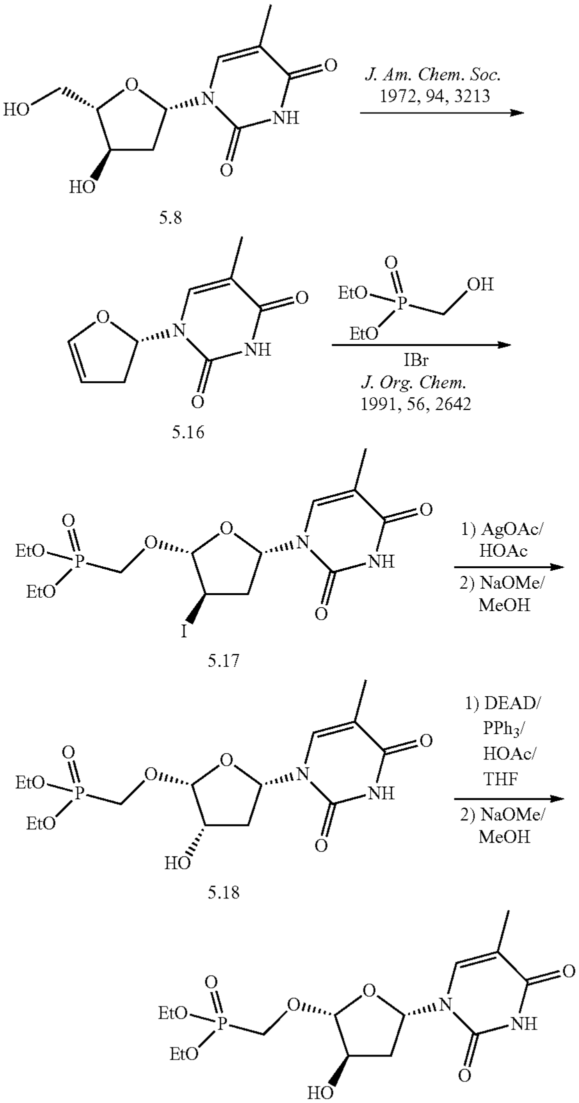

5.8

5.16

5.17

5.18

5.19

For instance, compound 5.8 is converted into glycal 5.16 according to the procedures reported in *J. Am. Chem. Soc.* 1972, 94, 3213. Glycal 5.16 is then treated with IBr in the presence of diethyl phosphonomethanol to provide intermediate 5.17 (see *J. Org. Chem.* 1991, 56, 2642). Intermediate 5.17 is then treated with AgOAc followed by deprotection with catalytic NaOMe in MeOH to provide 5.18. This compound is then converted into epimer 5.19 by a Mitsunobu reaction with DEAD/$PPh_3$ and HOAc in THF, followed by a second catalytic NaOMe/MeOH deprotection. At any point in the synthetic sequence where it is appropriate, the phosphonate group may be converted into a phosphonate with the desired substitution.

Example 6

Synthesis of Representative Compounds of Formulae 10 and 11

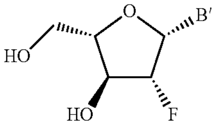
6.6

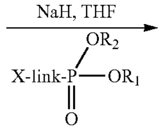

6.7

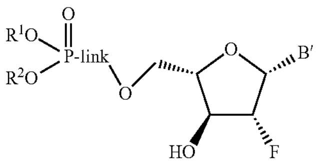
6.8

+

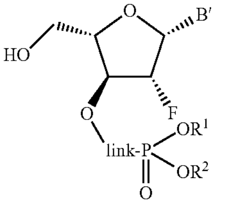
6.9

Representative compounds of the invention can be prepared as illustrated above. The preparation of compounds of structural type 6.6 are described in U.S. Pat. Nos. 5,565,438, 5,567,688, and 5,587,362, and the references cited therein. The compounds are then treated with a limiting amount of NaH in an appropriate solvent such as, but not limited to THF or DMF, and are then treated with an alkylating agent of type 6.7 (X=leaving group such as, but not limited to bromide, chloride, iodide, methanesulfonate, trifluoromethanesulfonate, and p-toluenesulfonate). Intermediates 6.8 and 6.9 result as a mixture and can be separated by chromatographic means that are well known to those skilled in the art. It should be noted that if a base requires a protecting group during this alkylation reaction, suitable protecting groups either will have already been installed throughout the synthetic schemes that provided starting materials 6.6 described in the cited patents, or can be installed prior to the alkylation reaction according to methods well known to chemists skilled in the art. If a protecting group had been added, it may be cleaved at this time according to the methods described in the patents cited above or according to any appropriate method known to those skilled in the art. At this point, the phosphonate esters may be converted to the desired final phosphonate functionality.

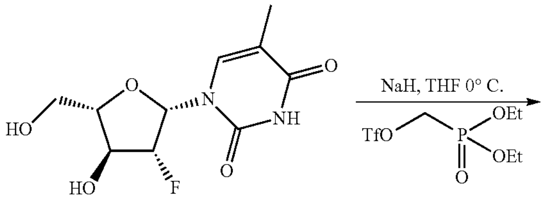

6.2

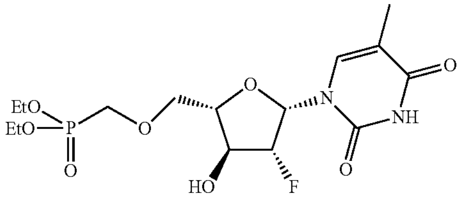
6.10

+

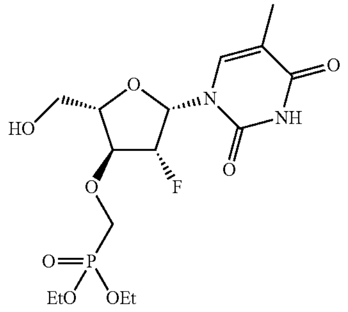
6.11

Clevudine, prepared as described in the patents cited above, is treated in anhydrous THF with NaH at 0° C. When bubbling ceases, diethyl phosphonomethyltriflate (prepared as in *Tetrahedron Lett.* 1986, 27, 1477) is added. The resulting alkylation products 6.10 and 6.11 are isolated after work-up either using silica gel or reversed-phase chromatography. The phosphonates may then be converted to the final desired products.

Example 7

Synthesis of Representative Compounds of Formula 12

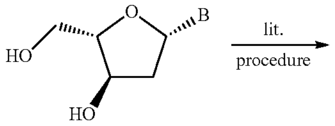

7.12

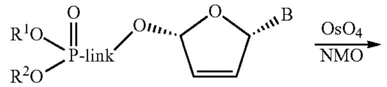

7.13

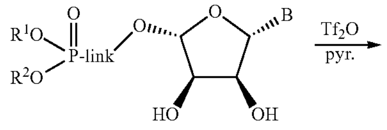

7.14

-continued

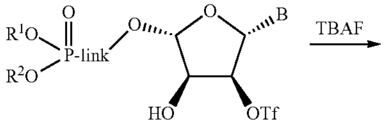

+ isomers 7.15

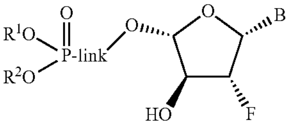

B = Base as defined above, with protecting groups, if necessary, as described above Representative compounds of the invention can be prepared as illustrated above. L-Deoxynucleoside 7.12 is synthesized according to literature procedure (see the methods reported by Holy, *Collect. Czech. Chem. Commun.* 1972, 37, 4072). L-Deoxynucleoside 7.12 is then converted into 7.13 through the procedures reported in *J. Am. Chem. Soc.* 1972, 94, 3213 and *J Org. Chem.* 1991, 56, 2642. Dimethyl phosphonomethanol may be replaced with any alcohol linked to a phosphonate. The double bond of compound 7.13 is then treated with $OsO_4$ and N-methylmorpholine N-oxide to provide the dihydroxylated derivatives 7.14. Triflation of 7.14 results in a mixture of triflates, the desired of which, 7.15, is isolated by the appropriate chromatographic method. The fluoride is installed by treatment of 7.15 with tetra-n-butylammonium fluoride (TBAF) in an appropriate solvent, such as THF, yielding the desired intermediate 7.16.

A specific compound of Formula 12 can be prepared as follows.

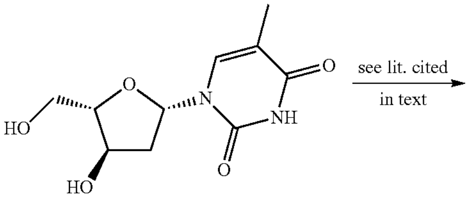

7.17

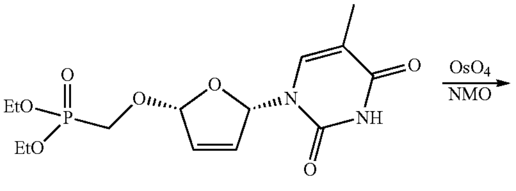

7.18

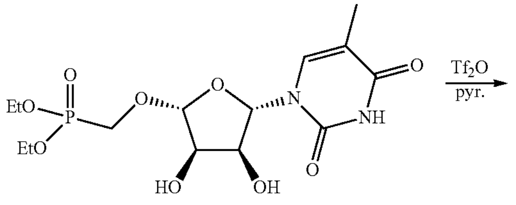

7.19

-continued

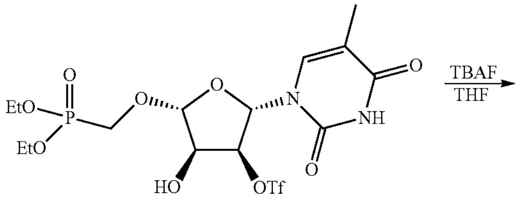

7.20

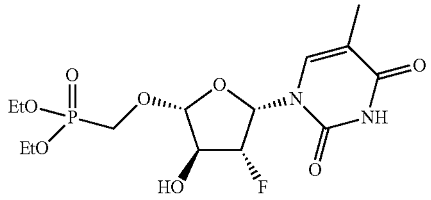

7.21

L-Thymidine 7.17, synthesized by Holy's method, is converted according to the literature procedures cited above to d4 nucleoside derivative 7.18. Compound 7.18 is then treated with $OsO_4$ and NMO to give dihydroxylated product 7.19, which is triflated to provide 7.20 (separated by silica gel chromatography from a mixture of its regioisomers and ditriflated material). Compound 7.20 is then treated with TBAF to convert it to the desired compound 7.21. The diethyl phosphonate may now be converted into any group that is desired according to methods well known to chemists skilled in the art.

Examples 8-13

Synthesis of Representative Compounds of Formulae 13, 14 and 15

Synthetic methodologies and intermediate compounds that can be used to prepare VX-148 analogs of formulae A, B, or C are described in Examples 8-13.

A

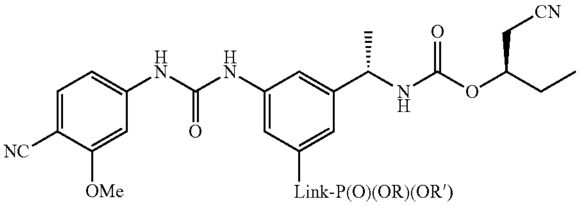

B

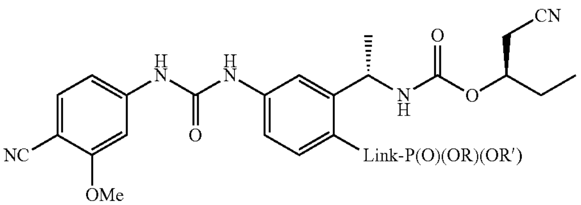

-continued

C

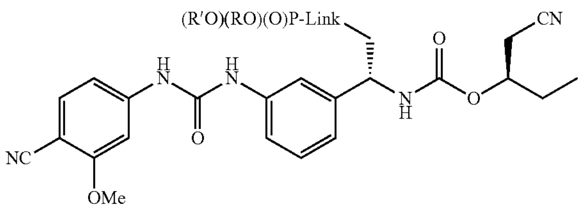

Link includes 0-8 atoms; 2-6 is preferred

Example 8

General Synthesis of Aniline Intermediate Useful for Preparing VX-148 Analogs of Formula A

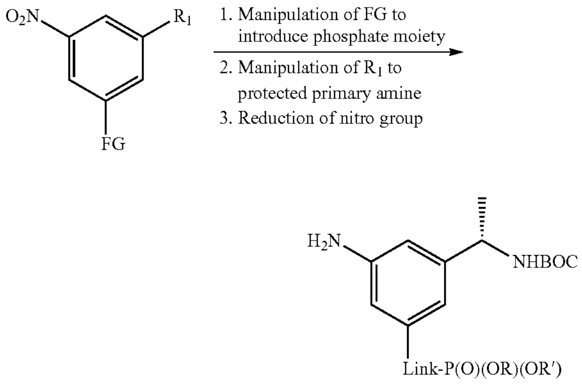

$R_1$ = 1-carbon substituent;
FG = functional group

A general scheme that is useful for converting a 3,5-difunctionalized nitrobenzene derivative to an aniline that can be used to prepare a VX-148 analog of the invention is illustrated above.

Example 9

Synthesis of Aniline Intermediate Useful for Preparing VX-148 Analogs of Formula A

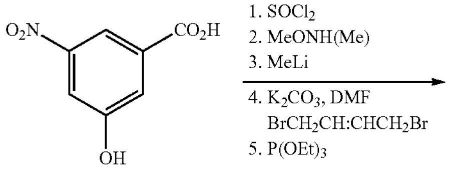

-continued

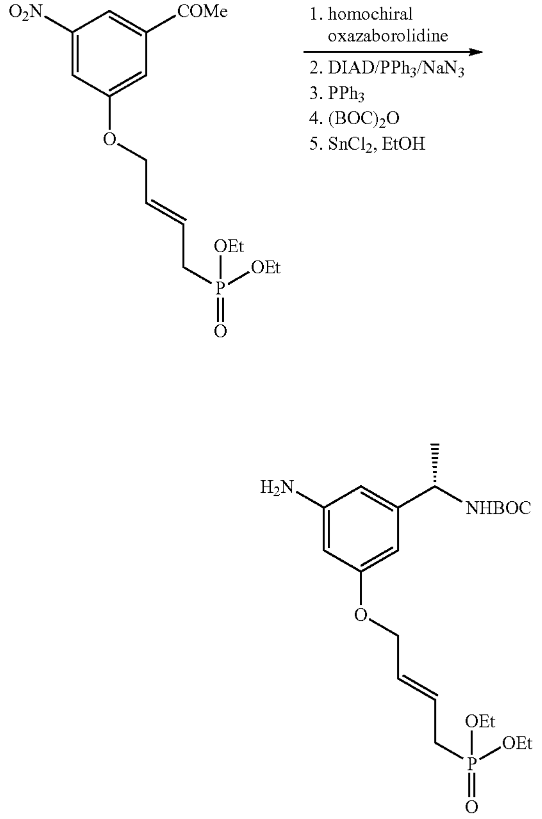

Representative compounds of the invention can be prepared as illustrated above. 3-Hydroxy-5-nitro-benzoic acid is heated briefly in thionyl chloride to generate the acid chloride. This is then condensed with O,N-dimethyl-hydroxylamine in the presence of a base such as triethylamine to produce the Weinreb amide which, upon reaction with methyl lithium, gives the acetophenone derivative. This intermediate is then treated with a base such as potassium carbonate in a dipolar aprotic solvent such as dimethylformamide, in the presence of an excess of E-1,4-dibromobutene. The monobromide is isolated by chromatography and then subjected to treatment with triethylphosphite in a solvent such as toluene (or other Arbuzov reaction conditions: see Engel, R., Synthesis of carbon-phosphorus bonds, CRC press, 1988) to generate the desired phosphonate diethyl ester. Thereafter, the carbonyl of the acetophenone is reduced enantioselectively using an appropriate homochiral oxazaborolidine such as those described by Corey (*J. Am. Chem. Soc.,* 1987, 109, 5551), and the resulting alcohol is displaced by azide using a method such as that described by Mitsunobu (*Bull. Chem. Soc. Japan.,* 1971, 44, 3427). The azide is reduced to the amine under Staudinger conditions (*Helv. Chim. Act.,* 1919, 2, 635) and protected as the t-butyl carbonate. Finally, the desired aniline is generated by tin (II)-mediated reduction of the nitrobenzene. Using coupling reactions similar to those described in U.S. Pat. No. 6,054,472 and U.S. Pat. No. 6,344,465 will give compounds of Formula A.

Example 10

Synthesis of VX-148 Analogs of Formula B

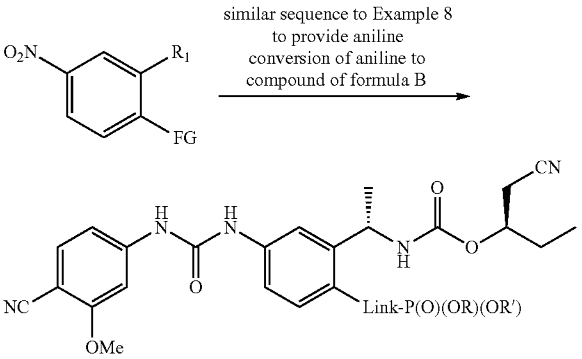

$R_1$ = 1-carbon substituent;
FG = functional group

A general scheme that is useful for converting a 3,4-difunctionalized nitrobenzene derivative to an aniline, which can be converted to a compound of formula B using coupling reactions similar to those described in U.S. Pat. Nos. 6,054,472 and 6,344,465, is illustrated above.

Example 11

General Route to Representative Compounds of Formula C

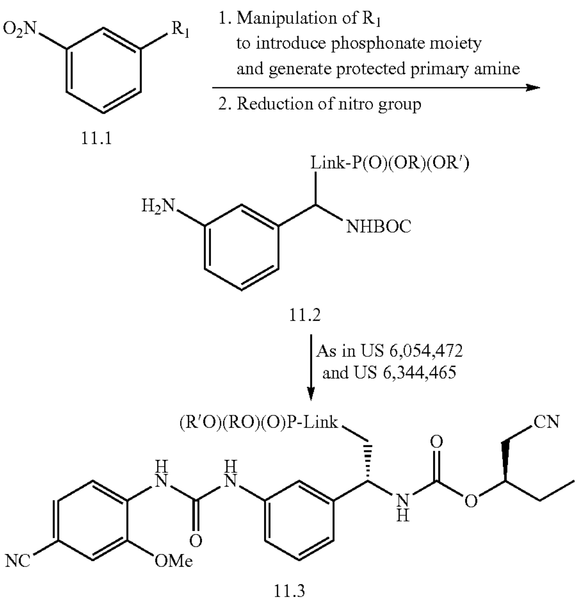

11.1, 11.2, 11.3

$R_1$ = 1-carbon substituent

Manipulation of a 3-substituted nitrobenzene 11.1 provides aniline 11.2, which can be converted to a compound of formula C using coupling reactions similar to those described in U.S. Pat. No. 6,054,472 and. 6,344,465.

Example 12

General Route to Aniline Intermediate Useful for Preparing Representative Compounds of Formula C

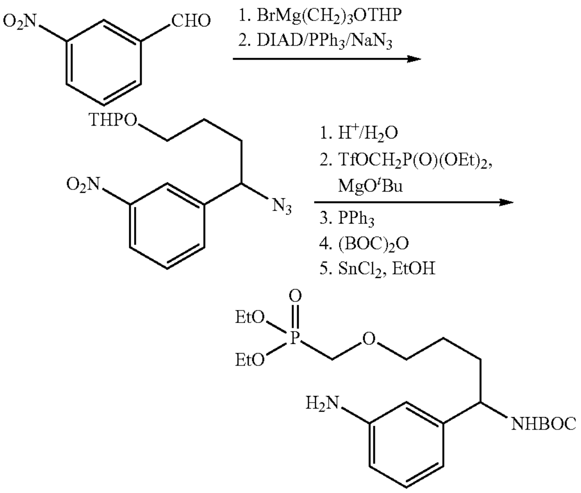

3-Nitrobenzaldehyde reacts with a Grignard reagent to introduce a tether bearing a protected alcohol and simultaneously to generate a benzylic alcohol, as shown. The alcohol is displaced by an azide in a manner similar to that described for Example 9. After deprotection, the liberated alcohol is alkylated with diethyl phosphonomethyltriflate (prepared according to *Tetrahedron Lett.* 1986, 27, 1477) using a base such as magnesium tert-butoxide in a solvent such as tetrahydrofuran. Subsequent transformations of the azide and nitro groups proceed in a fashion similar to that described in Example 9. See Batt et al., *Bioorg. Med. Chem. Lett.* 1995, 5, 1549.

Example 13

General Route to Aniline Intermediate Useful for Preparing Representative Compounds of Formula C

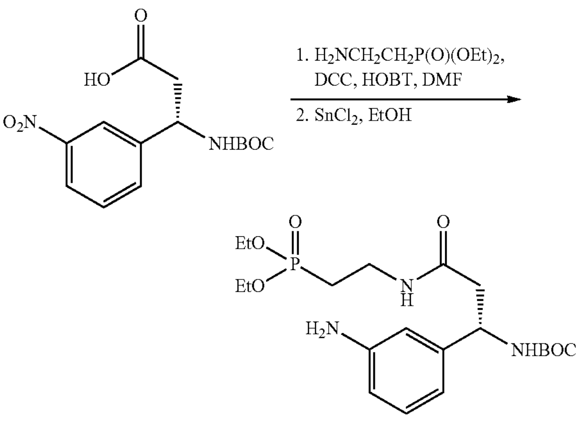

3-tert-Butoxycarbonylamino-3-(3-nitro-phenyl)-propionic acid (commercially available) is coupled with 2-aminoethylphosphonic acid diethyl ester (commercially available) using standard reagents for the formation of a secondary amide such as dicyclohexylcarbodiimide (DCC) and hydroxybenztriazole (HOBT), in a solvent such as dimethylformamide. Subsequent reduction of the nitro group proceeds in a fashion similar to that described in the scheme in Example 9.

Example 14

General Route to Representative Compounds of Formula 16

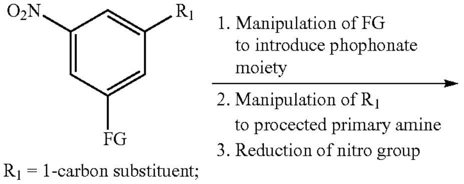

$R_1$ = 1-carbon substituent;
FG = functional group

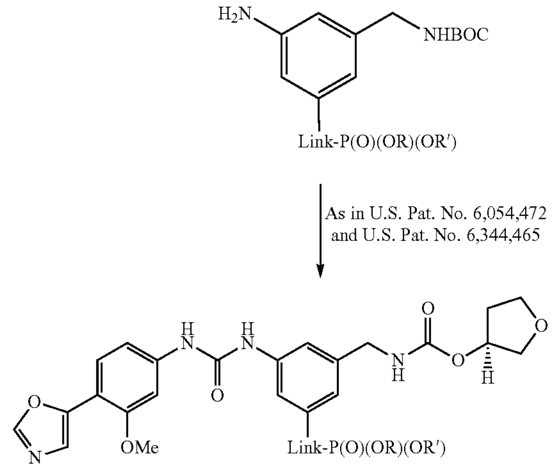

The above scheme illustrates a general route that can be used to prepare compounds of Formula 16.

Example 15

Synthesis of Aniline Intermediate Useful for Preparing Compounds of Formula 16

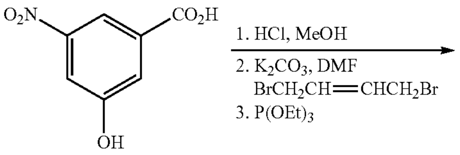

-continued

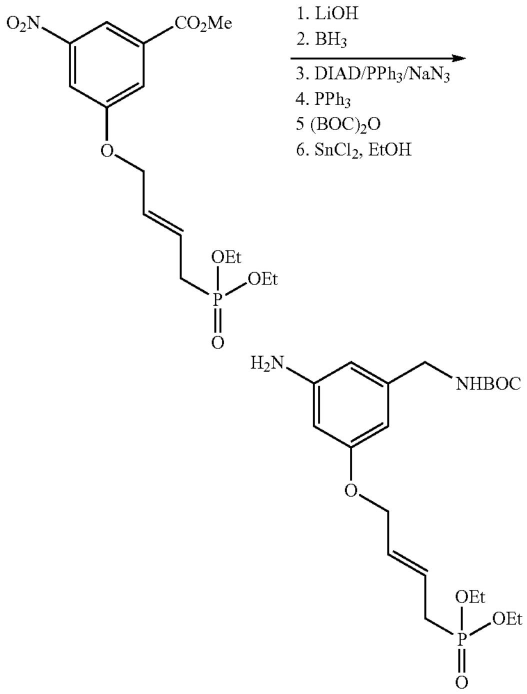

Representative compounds of the invention can be prepared as illustrated above. 3-Hydroxy-5-nitro-benzoic acid is heated briefly in acidic methanol to generate the methyl ester. This is then treated with a base such as potassium carbonate in a dipolar aprotic solvent such as dimethylformamide, in the presence of an excess of E-1,4-dibromobutene. The monobromide is isolated by chromatography and then subjected to treatment with triethylphosphite in a solvent such as toluene (or other Arbuzov reaction conditions: see Engel, R., Synthesis of carbon-phosphorus bonds, CRC press, 1988) to generate the desired phosphonate diethyl ester. Thereafter, the benzoate ester is saponified and reduced, and the resulting alcohol displaced by azide using a method such as that described by Mitsunobu (*Bull. Chem. Soc. Japan.*, 1971, 44, 3427). The azide is reduced to the amine under Staudinger conditions (*Helv. Chim. Acta*, 1919, 2, 635) and protected as the t-butyl carbonate. Finally, the desired aniline is generated by tin (II)-mediated reduction of the nitrobenzene. The aniline is converted to a compound of Formula 16 by the general procedures described in U.S. Pat. Nos. 6,054,472 and 6,344,465 as set forth in Example 10.

Example 16

General Route to Representative Compounds of Formula 17

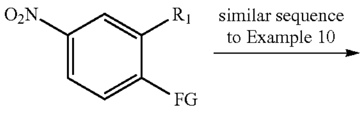

$R_1$ = 1-carbon substituent;
FG = functional group

-continued

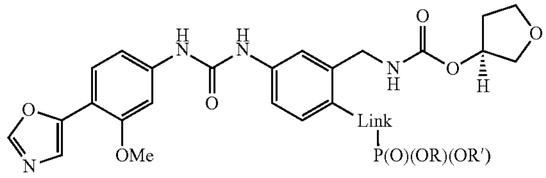

Reagents suitable for use in the synthesis of representative compounds of Formula 17 may be made by routes analogous to that shown in Example 10, starting from 2-hydroxy-5-nitro-benzoic acid.

Example 17

General Route to Representative Compounds of Formula 18

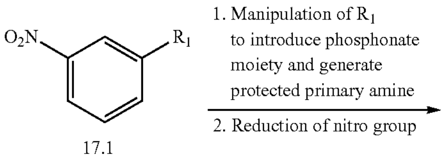

17.1
$R_1$ = 1-carbon substituent

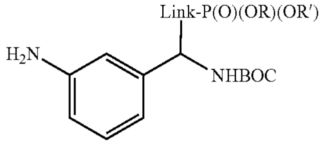

17.2

As in U.S. Pat. No. 6,054,472 and U.S. Pat. No. 6,344,465

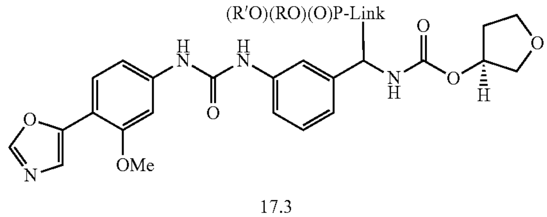

17.3

Representative compounds of Formula 18 can be prepared as illustrated above. The preparation of anilines of formula 17.2 is illustrated in Examples 11-13 above. Anilines of formula 17.2 can be converted to compounds of formula 18 using procedures similar to those described in U.S. Pat. Nos. 6,054,472 and 6,344,465.

Example 18

Synthesis of Representative Compounds of Formula 19

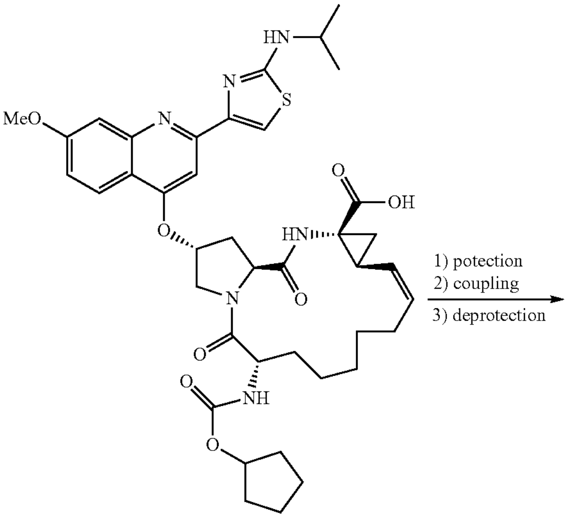

18.1

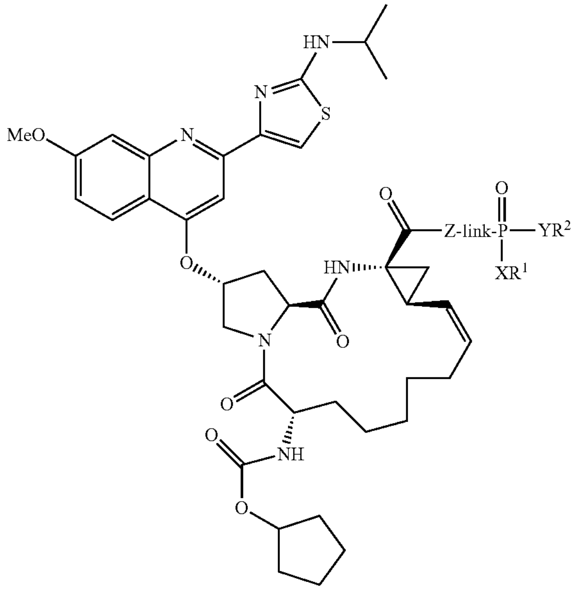

18.2
Z = O, NH

Representative compounds of the invention can be prepared as illustrated above. The phosphorus containing BILN-2061 analog 18.2 is synthesized from the parent compound 18.1 by attachment of phosphorus containing moiety to the carboxylic acid group. Compound 18.1, BILN-2061, is obtained by the procedure as described in WO 00/59929. The secondary amine on the thiazole ring is protected with a suitable protecting group, such as Boc group before the formation of ester or amide as shown above. The protected 18.1 is coupled with a phosphorus containing moiety with a hydroxy group by Mitsunobu reaction using triphenylphosphine and diethyl azadicarboxylate, whereas an amide group is formed using amino group containing phosphonate reagent by suitable coupling reagents, such as EDC-HOBt, BOP reagent etc. Deprotection of the coupled product gives the desired phosphonate of type 18.2.

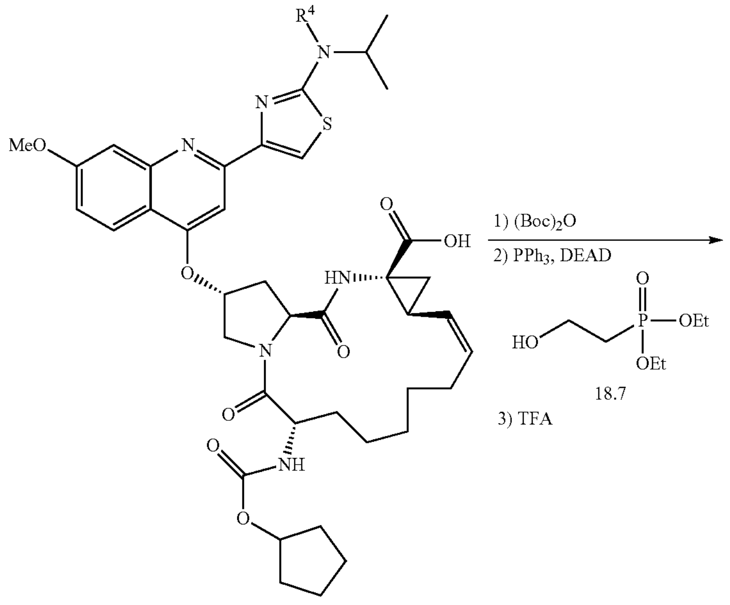
18.1.1 $R^4$ = H, Boc
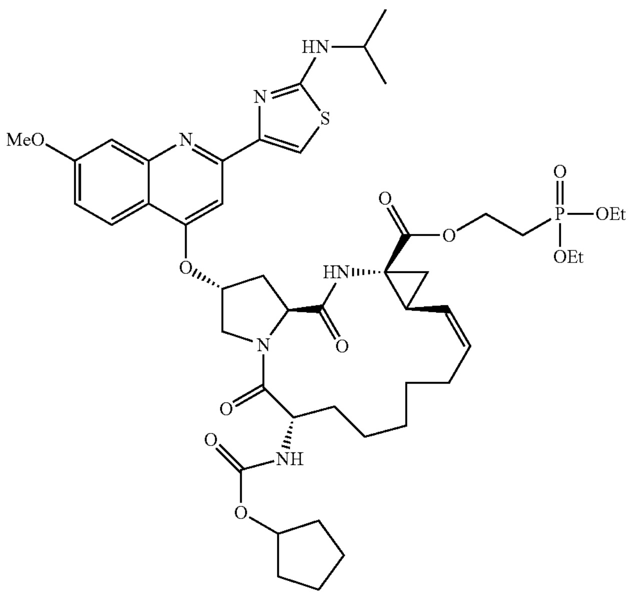
18.8
For instance, 18.1.1 is protected with Boc group using $(Boc)_2O$ and triethylamine and then treated with 2-hydroxyethylphosphonic acid diethyl ester 18.7 in the presence of triphenylphosphine and diethyl azadicarboxylate. The resulting ester is treated with trifluoroacetic acid to obtain analog 18.8, in which the linker is ethylene group.

Example 19

Synthesis of Representative Compounds of Formula 20

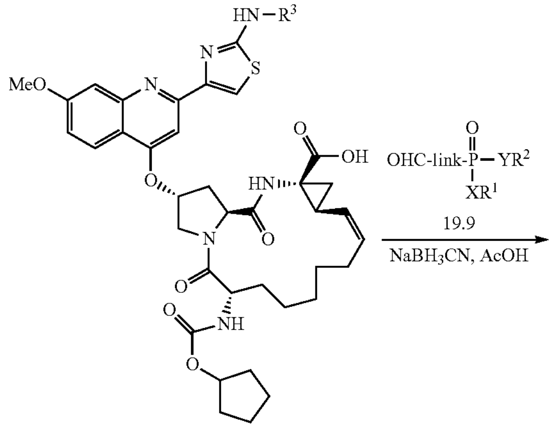

19.1

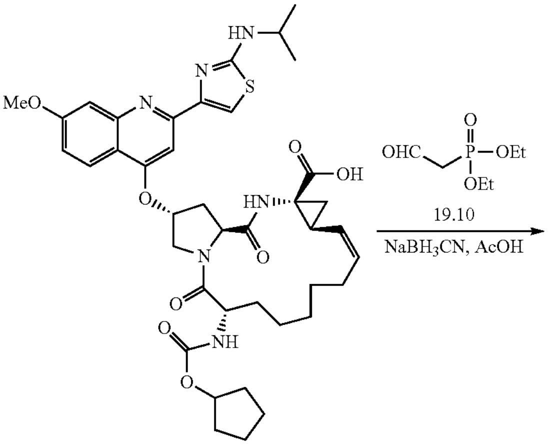

19.1.1

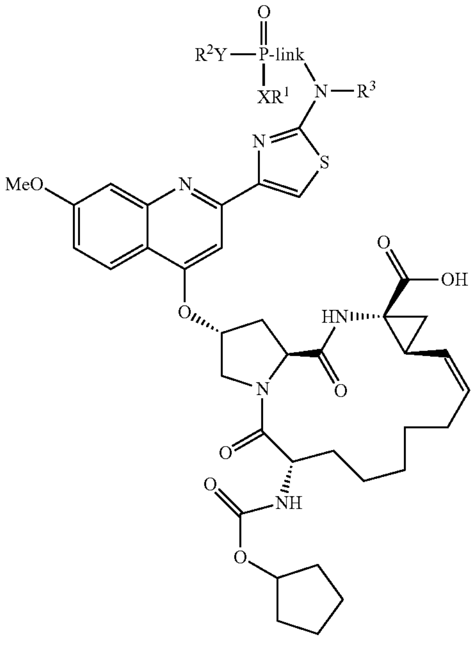

19.3

$R^3$ = H, Me
Et, i-Pr

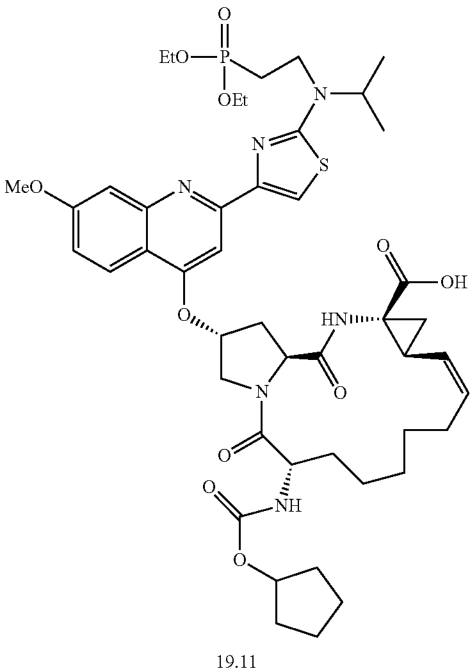

19.11

Synthesis of phosphonate analog of type 19.3 is illustrated above. The phosphonate containing moiety is introduced to compound 19.1, or its analogs ($R^3$=H, Me, Et, i-Pr), which are available by the procedure described in WO 00/59929, by reductive amination using the phosphonate reagent 19.9 bearing aldehyde group.

For instance, compound 19.1.1 is treated with 2-oxoethyl phosphonic acid diethyl ester 19.10 in the presence of sodium cyanoborohydride and acetic acid to provide compound 19.11, in which the linker is ethylene.

Example 20
Synthesis of Representative Compounds of Formula 21
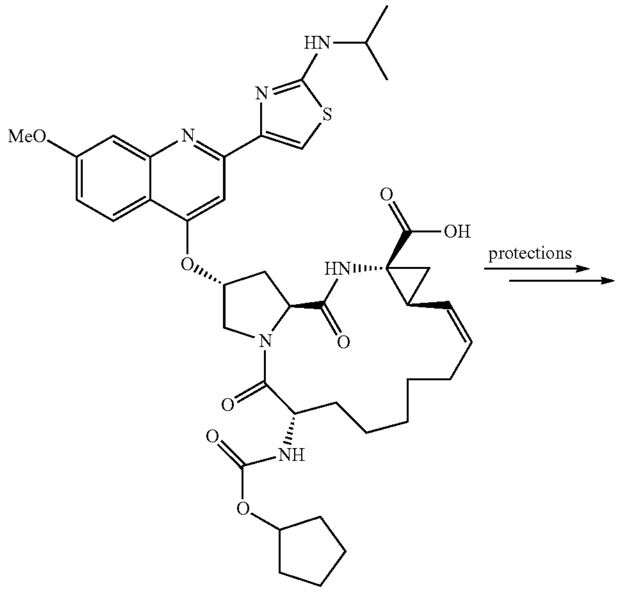
20.1 (BILN2061)
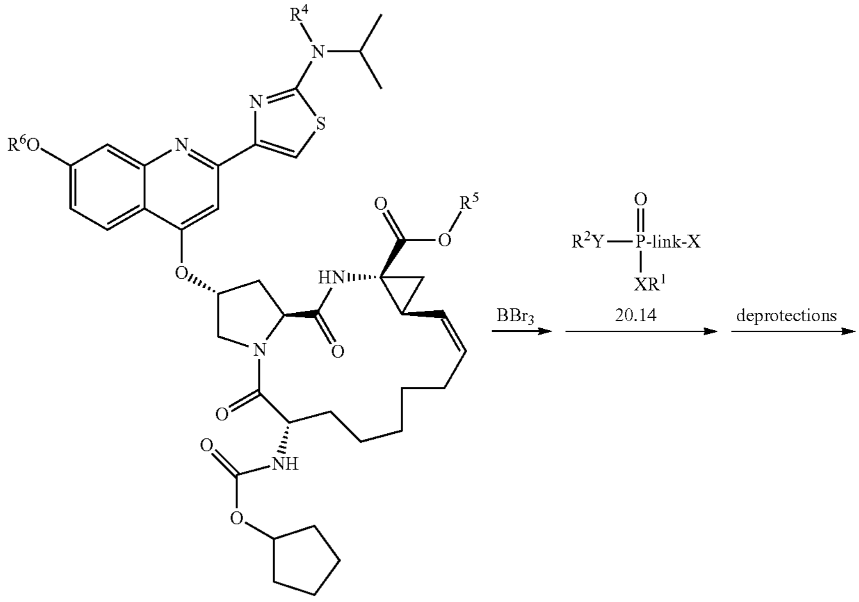
20.12: $R^6$ = OMe
20.13: $R^5$ = H -continued

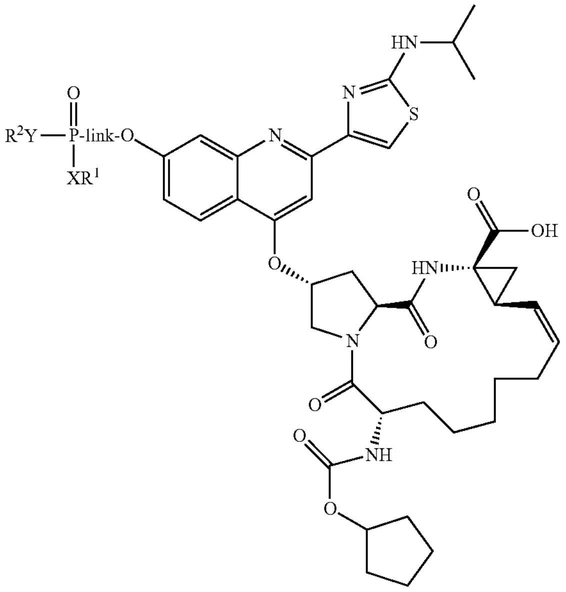

20.4

Example 20 illustrates the preparation of compounds of type 20.4. The secondary amine on the thiazole ring and the carboxylic acid are protected with suitable protecting groups. The methoxy group of the quinoline ring at 7-position is then demethylated using boron tribromide. The phosphonate bearing moiety is then introduced on this hydroxy group in a suitable aprotic solvent such as, DMF, by treating with the phosphonate reagent 20.14, in the presence of a suitable organic or inorganic base. In compounds 20.14, X is a leaving group such as, but not limited to, bromide, chloride, iodide, p-toluenesulfonate, trifluoromethanesulfonate, or methanesulfonate.

The protecting groups are then removed to obtain the analog of type 20.4.

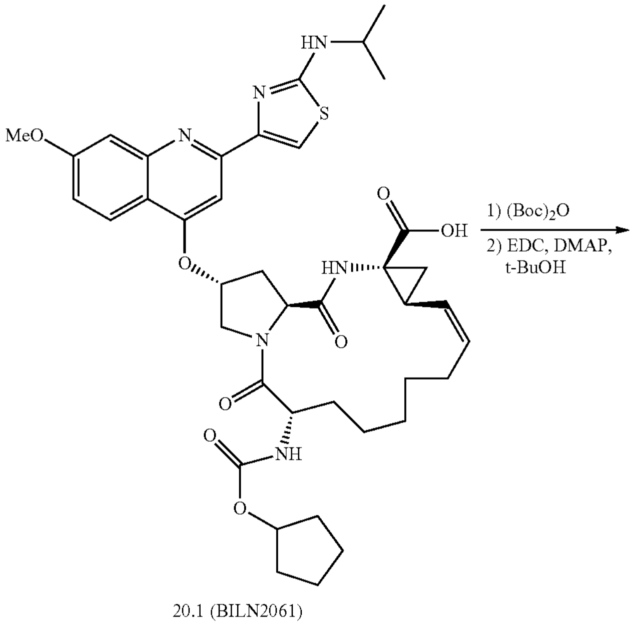

20.1 (BILN2061)

-continued

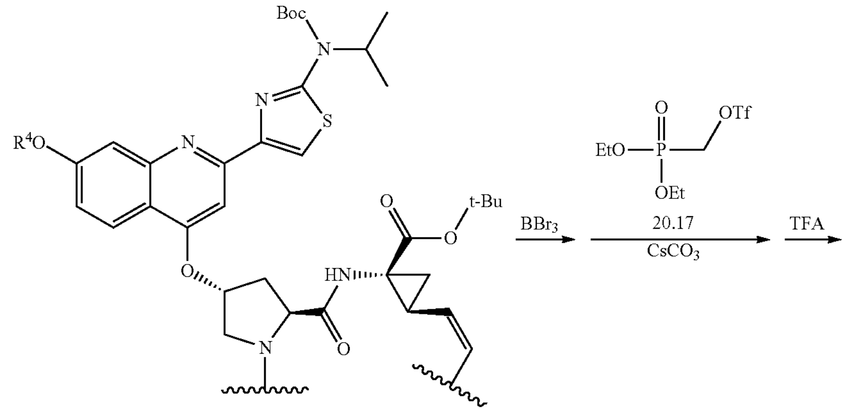

20. 15: $R^4$ = OMe
20. 16: $R^4$ = H

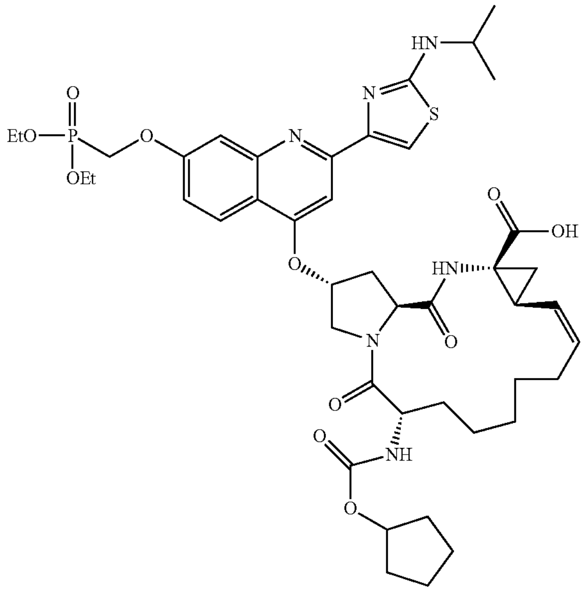

20.18

For instance, the secondary amino group on the thiazole ring of 20.1 is protected with Boc group using $(Boc)_2O$ and triethylamine, and the carboxylic acid is protected with t-butyl group using EDC, DMAP, and t-butyl alcohol, which result 20.15 as shown above. After the resulting 20.15 is demethylated by boron tribromide, the alkylation of 20.16 with cesium carbonate and one equivalent of (trifluoromethanesulfonyloxy)methylphosphonic acid diethyl ester 17, followed by deprotection using trifluoroacetic acid gives 20.18, where the linkage is a methylene group as shown above.

Example 21

Synthesis of Representative Compounds of Formula 22

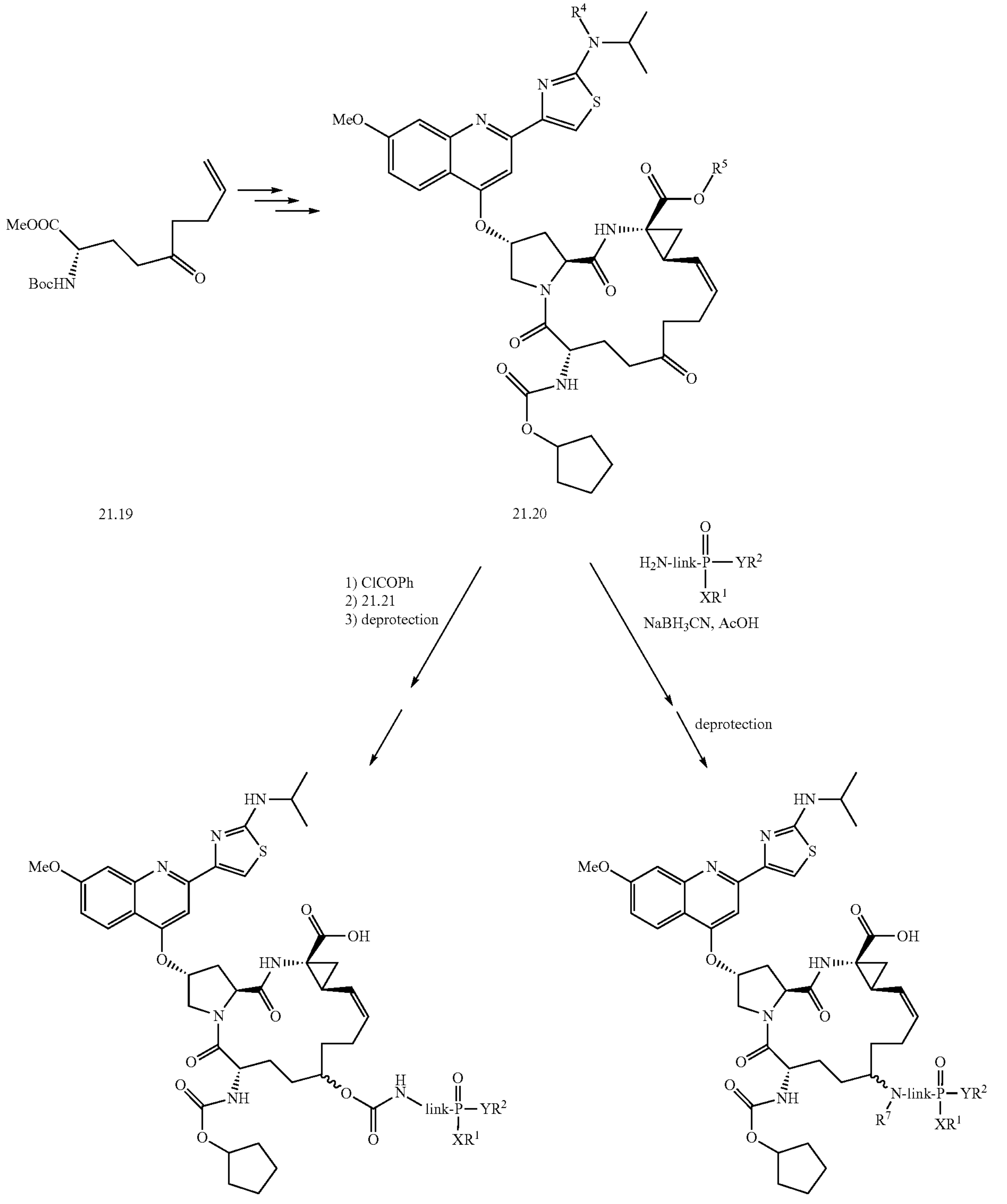

21.19 21.20

21.5.1 21.5.2

Synthesis of analogs 21.5 of BILN-2061 is illustrated above. Compound 21.19 is synthesized by a procedure described in WO 00/59929 based on methodology by T. Tsuda et al. (*J. Am. Chem. Soc.* 1980, 102, 6381). Compound 21.20, containing extra carbonyl group with suitable protecting groups, $R^4$ and $R^5$, is synthesized by the procedure described for the synthesis of 21.1 at WO 00/59929 using compound 21.19. The phosphonate group bearing moiety is attached to the carbonyl group of 21.20 by reductive amination. The obtained secondary amine may be converted to the tertiary amine by repeated reductive amination using formaldehyde or acetaldehyde to provide 21.5.2. The carbonyl group of 21.20 is also reduced to the corresponding alcohol and converted to phenyl carbonate, which is reacted with 21.21 to form compound 21.5.1, where the linkage is a carbamate. After the phosphonate bearing moiety is attached, the protecting groups, $R^4$ and $R^5$, are removed by suitable methods well know to those skilled in the chemical arts.

and followed by EDC, DMAP, and t-butyl alcohol to provide protected compound 21.23, as illustrated above. Compound 21.23 is then treated with 2-aminoethylphosphonic acid diethyl ester 21.24 in the presence of sodium cyanoborohydride and acetic acid, which results in the phosphonate bearing compound 21.25 ($R^7$=H), in which the phosphonate is attached to the structural core through a secondary amine, after deprotection by trifluoroacetic acid. Before deprotection, reductive amination of the secondary amine in the pres-

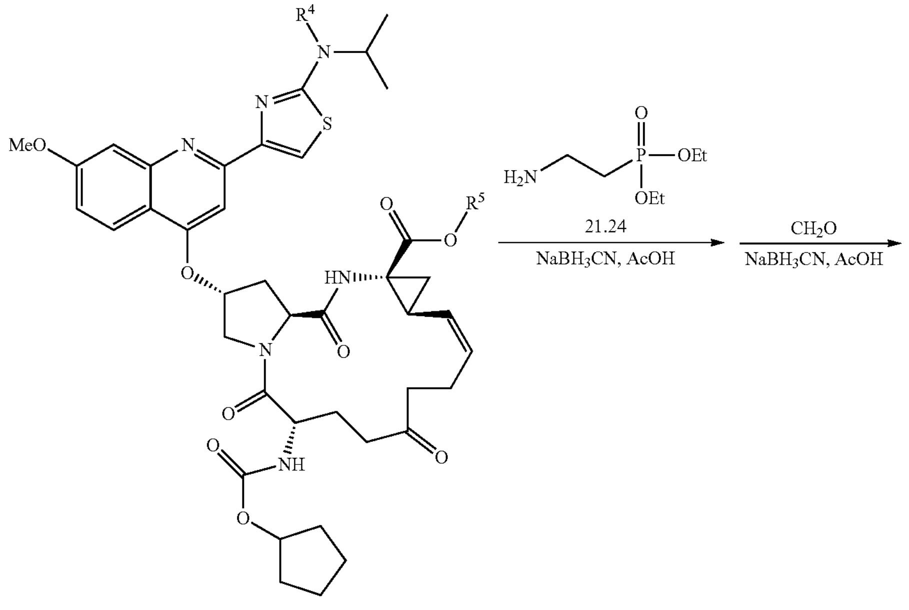

21.22: $R^4$ = H, $R^5$ = H
21.23: $R^4$ = Boc, $R^5$ = t-Bu

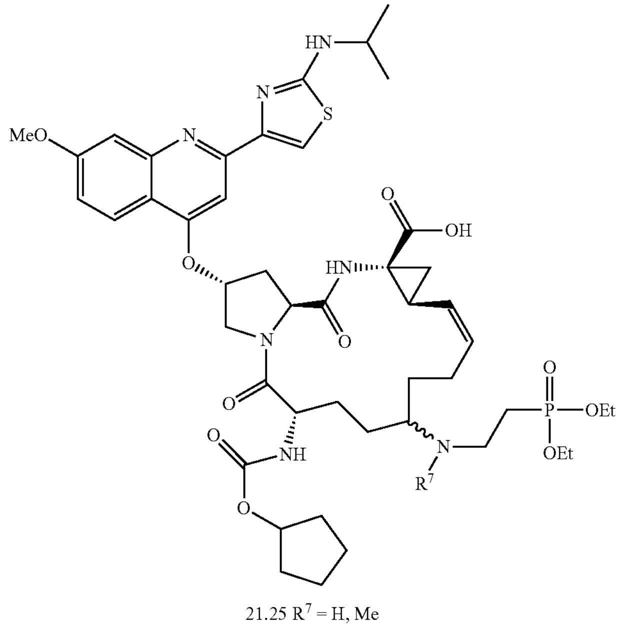

21.25 $R^7$ = H, Me

For instance, compound 21.22, obtained by the procedure of WO 00/59929, is treated with $(Boc)_2O$ and triethylamine ence $CH_2O$ generates the tertiary amine, which is converted to 21.25 ($R^7$=Me) bearing a tertiary amine.

Example 22

Synthesis of Representative Compounds of Formula 23

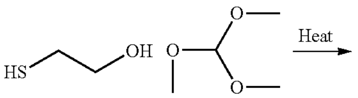

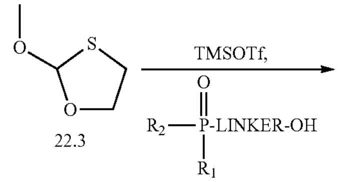

22.3

22.4

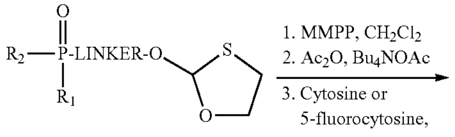

22.5

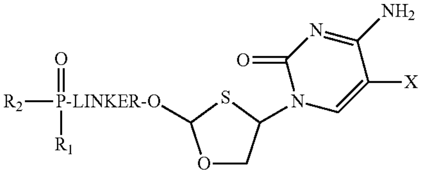

22.2
X = F or H $R_1$ = H, alkyl aryl, haloalkyl, alkenyl, aralyl, aryl
$R_2$ = H, alkyl, aryl, haloalkyl, alkenyl, aralyl, aryl Representative compounds of the invention can be prepared as illustrated above. Condensation of commercially available 2-mercapto-ethanol and trimethoxymethane (*J. Org. Chem. USSR* (*Engl. Transl.*) 1981, 1369-1371) generates heterocycle 22.3. Glycosidation using, for example, trimethylsilyl triflate and the phosphonate substituted alcohol 22.4, provides intermediate 22.5. Oxidation of sulfur to the sulfoxide using monoperoxyphthalic acid, magnesium salt (see U.S. Pat. No. 6,228,860 col. 15 ln. 45-60) followed by a Pummerer rearrangement (see U.S. Pat. No. 6,228,860 col. 16 ln. 25-40) and base introduction (cytosine or 5'-fluoro-cytosine) using conditions as outlined in U.S. Pat. No. 6,228, 860 (col. 17 ln. 15-42) provides the desired phosphonate substituted analogs 22.2.

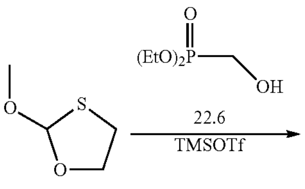

22.3

-continued

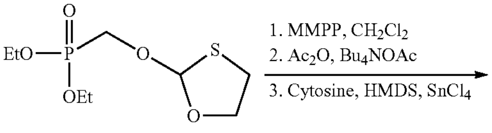

22.7

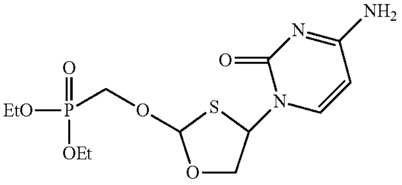

22.8

Specifically, starting with heterocycle 22.3, using the above procedure but using diethyl(hydroxymethyl) phosphonate 22.6, generates 22.7. Introduction of cytosine as outlined above provides the desired product 22.8. Using the above procedure, but employing different phosphonate reagents 22.4 in place of 22.6, the corresponding products 22.2 bearing different linking groups are obtained.

Example 23

Synthesis of Representative Compounds of Formula 24

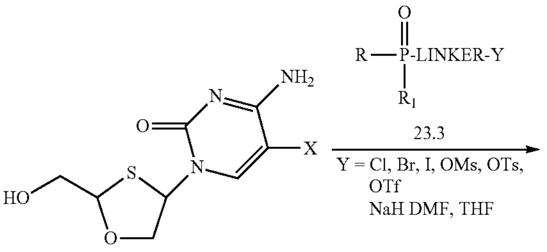

X = F or H
23.1

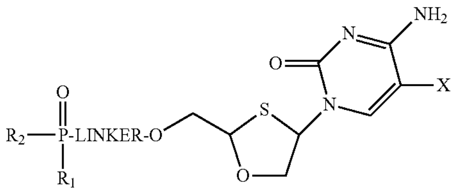

X = F or H
23.2

$R_1$ = H, alkyl, aryl, haloalkyl, alkenyl, aralyl, aryl
$R_2$ = H, alkyl, aryl, haloalkyl, alkenyl, aralyl, aryl Representative compounds of the invention can be prepared by reaction of dOTC analogs of type 23.1 (obtained as described in U.S. Pat. No. 6,228,860 col. 14 line 45 to col. 30 line 50 and references cited therein) with the respective alkylating reagents 23.3. The above scheme shows the preparation of phosphonate linkage to dOTC through the 5' hydroxyl group. Substrate 23.1 (dOTC) is dissolved in a solvent such as, but not limited to, DMF, THF and is treated with a phosphonate reagent bearing a leaving group in the presence of a suitable organic or inorganic base. In compounds 23.3, Y is a leaving group such as, but not limited to, bromide, chloride, iodide, p-toluenesulfonate, trifluoromethanesulfonate, or methanesulfonate.

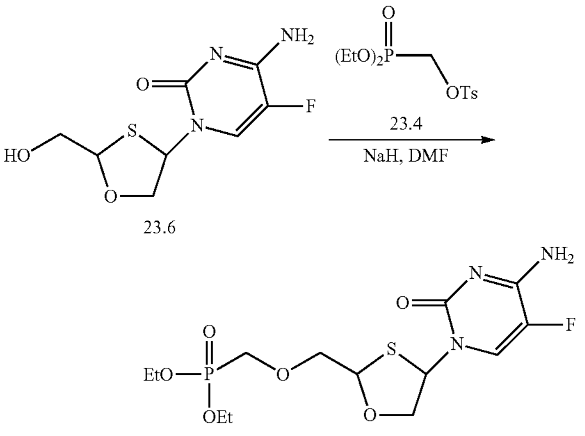

23.6

23.5

For instance, 23.6 dissolved in DMF, is treated with one equivalent of sodium hydride and one equivalent of (toluene-4-sulfonylmethyl)-phosphonic acid diethyl ester 23.4, prepared according to the procedures in *J. Org. Chem.* 1996, 61, 7697, to give fluoro-cytosine phosphonate derivative 5, in which the linkage is a methylene group. Using the above procedure, but employing different phosphonate reagents 23.3 in place of 23.4, the corresponding products 23.2 bearing different linking groups are obtained.

Example 24

Synthesis of Representative Compounds of Formula 25

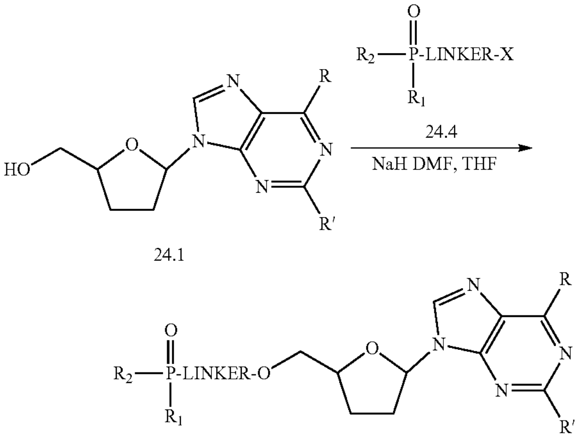

24.1

24.2

For example:
X = Cl, Br, I, OMs, OTs, OTf
R' = $NH_2$, H
R = OH, Cl, $NH_2$, H, OMe, Me
$R_1$ = H, alkyl, aryl, haloalkyl, alkenyl, aralyl
$R_2$ = H, alkyl, aryl, haloalkyl, alkenyl, aralyl Representative compounds of the invention can be prepared as illustrated above. Phosphonate substituted analogs are prepared by reaction of furanoside purine nucleosides, structure 24.1 (obtained as described in U.S. Pat. No. 5,185,437 col. 9 ln. 16 to col. 35 ln. 19 and references cited therein) with the respective alkylating reagents 24.4. Illustrated above is the preparation of the phosphonate linkage to furanoside nucleoside cores through the 5'-hydroxyl group. Parent analog 24.1 is dissolved in a solvent such as, but not limited to, DMF or THF, and is treated with a phosphonate reagent bearing a leaving group in the presence of a suitable organic or inorganic base. In compounds 24.4, X is a leaving group such as, but not limited to, bromide, chloride, iodide, p-toluenesulfonate, trifluoromethanesulfonate, or methanesulfonate.

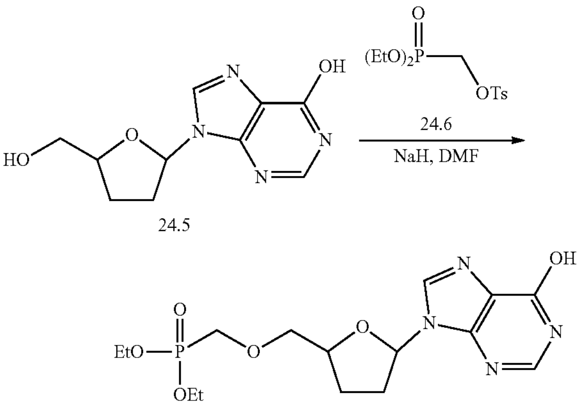

24.5

24.7

For instance, 24.5 (obtained as described in U.S. Pat. No. 5,185,437 col. 9 In. 16 to col. 35 ln. 19 and references cited therein) is dissolved in DMF, is treated with three equivalents of sodium hydride and two equivalents of (toluene-4-sulfonylmethyl)-phosphonic acid diethyl ester 24.6, prepared according to the procedures in 0.1 Org. Chem. 1996, 61, 7697, to give the corresponding phosphonate 24.7, in which the linkage is a methylene group. Using the above procedure, but employing different phosphonate reagents 24.4 in place of 24.6, the corresponding products 24.2 bearing different linking groups are obtained.

Example 25

Synthesis of Representative Compounds of Formula 26

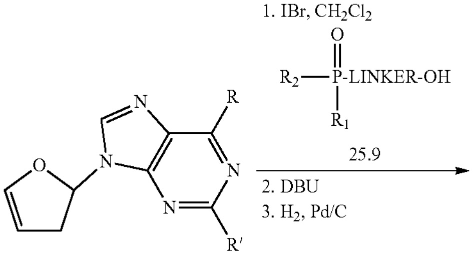

25.8

-continued

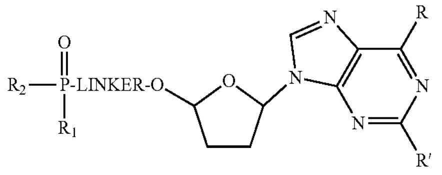

25.3

R = OH, Cl, $NH_2$, H, OMe, Me
R' = $NH_2$, H
$R_1$ = H, alkyl, aryl, haloalkyl, alkenyl, aralyl
$R_2$ = H, alkyl, aryl, haloalkyl, alkenyl, aralyl Representative compounds of the invention can be prepared as illustrated above. Phosphonate substituted analogs 25.3 are prepared by reacting glycal 25.8 (obtained as described in *J. Am. Chem. Soc.* 1972, 94, 3213; in some cases the nucleoside bases may need prior protection) with the respective phosphonate alcohols 25.9, followed by treatment with iodine monobromide (*J. Org. Chem.* 1991, 56, 2642-2647). Elimination of the resulting iodide followed by reduction with palladium on carbon provides the desired product 25.3.

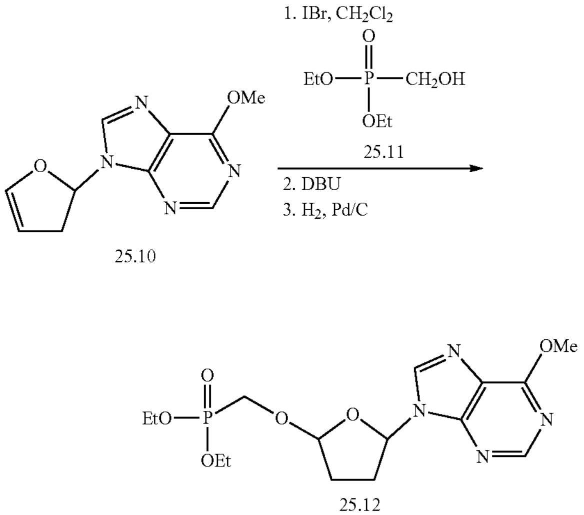

25.10 25.11 25.12

For instance, dihydrofuran 25.10 is dissolved in $CH_2Cl_2$ and is combined with 3.5 equivalents of diethyl(hydroxymethyl) phosphonate. The resulting solution is treated with two equivalents of iodine monobromide at −25° C. The resulting phosphonate-iodide is treated with DBU and reduced under hydrogenation conditions to afford the desired product 25.12. Using the above procedure, but employing different phosphonate reagents 25.9 in place of 25.11, the corresponding products 25.3 bearing different linking groups are obtained.

Example 26

Synthesis of Representative Compounds of Formula 27

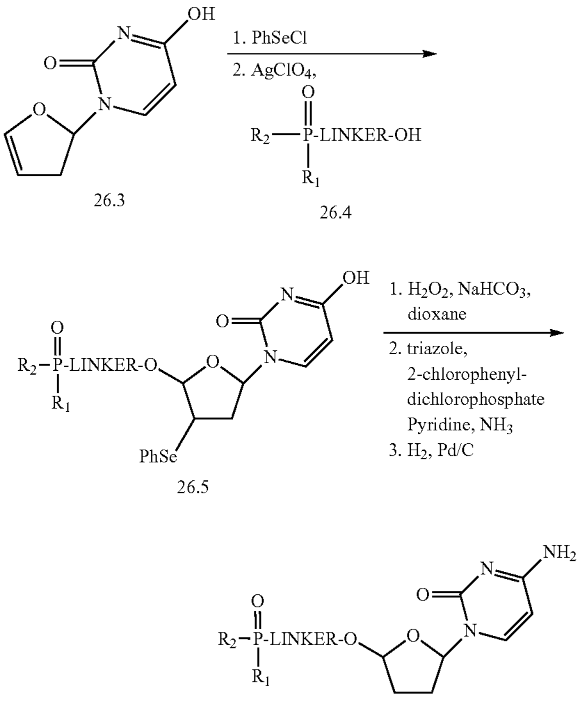

26.3 26.4 26.5 26.2

$R_1$ = H, alkyl, aryl, haloalkyl, alkenyl, aralyl, aryl
$R_2$ = H, alkyl aryl, haloalkyl, alkenyl, aralyl, aryl Representative compounds of the invention can be prepared as illustrated above. Phosphonate substituted analogs 26.2 are prepared by reacting glycal 26.3 (obtained as described in *J. Am. Chem. Soc.* 1972, 94, 3213) with phenylselenyl chloride followed by treatment with the respective phosphonate alcohols 26.4 in the presence of silver perchlorate (*J. Org. Chem.* 1991, 56, 2642-2647). Oxidation of the resulting chloride using hydrogen peroxide, followed by aminolysis treatment of uracil using triazole, 2-chlorophenyldichlorophosphate, pyridine and ammonia (*Bioorg. Med. Chem. Lett.* 1997, 7, 2567) and a palladium on carbon reduction provides the desired product 26.2.

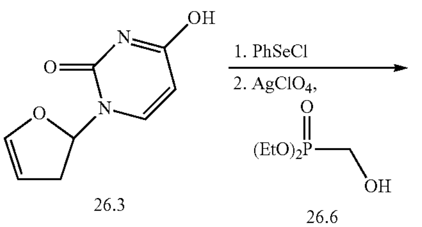

26.3 26.6

-continued

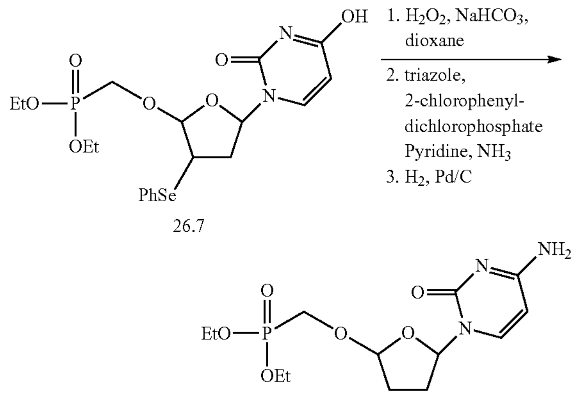

26.7

26.8

For instance, 26.3 dissolved in $CH_2Cl_2$, is treated with one equivalent of phenyl selenyl chloride at −70° C., followed by treatment with silver perchlorate in the presence of diethyl (hydroxymethyl) phosphonate to generate selenide 26.7. The phosphonate is transformed into the d4CP analog by first oxidation with hydrogen peroxide, followed by conversion of the uracil moiety to a cytosine, and finally hydrogenation to the desired product 26.8. Using the above procedure, but employing different phosphonate reagents 26.4 in place of 26.6, the corresponding products 26.2 bearing different linking groups are obtained.

In some cases conversions to desired compounds may require the use of suitable protecting groups for the amino group of cytosine. Similarly, using different natural and unnatural bases with appropriate protecting groups, other analogs containing a variety of bases can be prepared.

Example 27

Synthesis of Representative Compounds of Formula 28

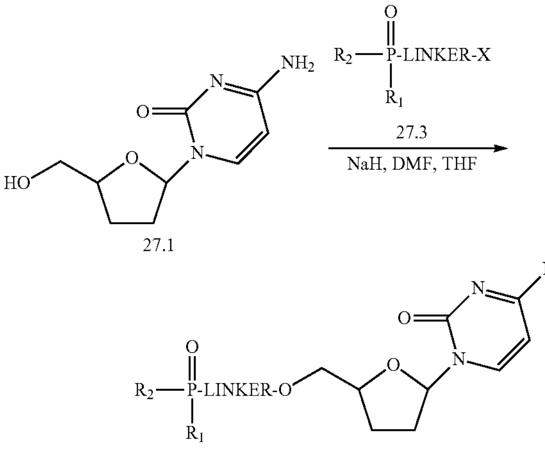

27.1

27.2

For example:
X = Cl, Br, I, OMs, OTs, OTf
$R_1$ = H, alkyl, aryl, haloalkyl, alkenyl, aralyl, aryl
$R_2$ = H, alkyl, aryl, haloalkyl, alkenyl, aralyl, aryl Representative compounds of the invention can be prepared as illustrated above. Phosphonate substituted analogs 27.2 are prepared by reaction of ddC 27.1 (D5782 Sigma-Aldrich, or prepares as described in *J. Org. Chem.* 1967, 32, 817) with the respective alkylating reagents 27.3. The scheme shown above illustrates the preparation of phosphonate linkage to ddC through the 5'-hydroxyl group. Substrate 27.1 (ddC or an analog) is dissolved in a solvent such as, but not limited to, DMF or THF, and is treated with a phosphonate reagent bearing a leaving group, in the presence of a suitable organic or inorganic base. In compounds 27.3, X is a leaving group such as, but not limited to, bromide, chloride, iodide, p-toluenesulfonate, trifluoromethanesulfonate, or methanesulfonate.

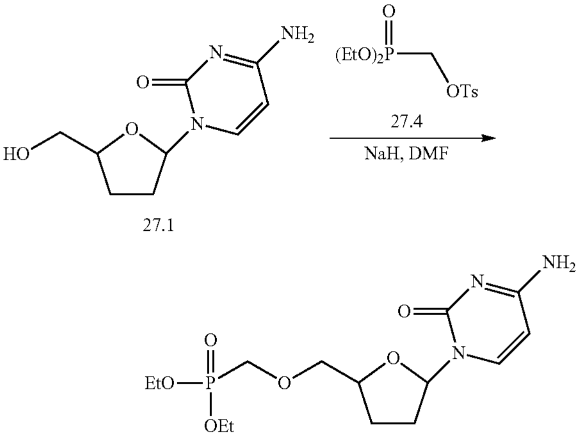

27.1

27.5

For instance, 27.1 dissolved in DMF, is treated with two equivalent of sodium hydride and two equivalent of (toluene-4-sulfonylmethyl)-phosphonic acid diethyl ester 27.4, prepared according to the procedures in *J. Org. Chem.* 1996, 61, 7697, to give ddC phosphonate 27.5 in which the linkage is a methylene group. Using the above procedure, but employing different phosphonate reagents 27.3 in place of 27.4, the corresponding products 27.2 bearing different linking groups are obtained.

Example 28

Synthesis of Representative Compounds of Formula 29

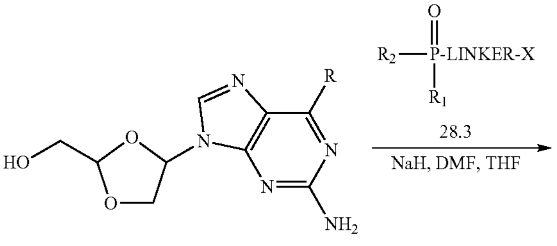

28.1

-continued

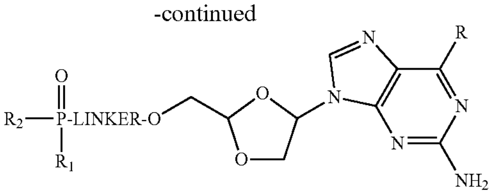

28.2

For example:
X = Cl, Br, I, OMs, OTs, OTf
R = OH, Cl, $NH_2$, H
$R_1$ = H, alkyl, aryl, haloalkyl, alkenyl, aralyl
$R_2$ = H, alkyl, aryl, haloalkyl, alkenyl, aralyl Representative compounds of the invention can be prepared as illustrated above. Phosphonate substituted analogs 28.2 are prepared by reaction of dioxolanyl purine nucleosides, structure 28.1 (obtained as described in U.S. Pat. No. 5,925,643 col. 4 ln. 47 to col. 12 ln. 20 and references therein) with the respective alkylating reagents 28.3. Illustrated above is the preparation of phosphonate linkage to dioxalane nucleoside cores through the 5'-hydroxyl group. Parent analog 28.1 is dissolved in a solvent such as, but not limited to, DMF and/or THF, and is treated with a phosphonate reagent bearing a leaving group, in the presence of a suitable organic or inorganic base. In compounds 28.3, X is a leaving group such as, but not limited to, bromide, chloride, iodide, p-toluenesulfonate, trifluoromethanesulfonate, or methanesulfonate.

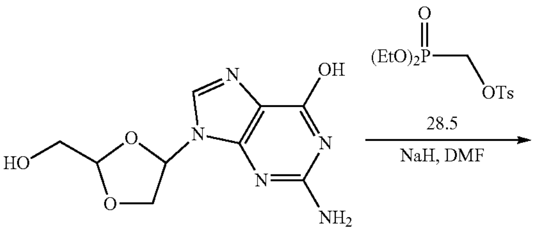

28.4

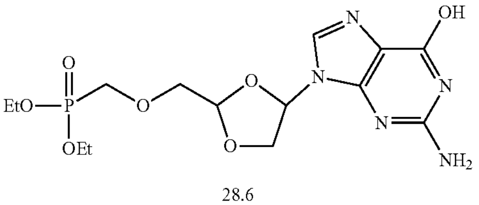

28.6

For instance, 28.4 dissolved in DMF, is treated with five equivalents of sodium hydride and one equivalent of (toluene-4-sulfonylmethyl)-phosphonic acid diethyl ester 28.5, prepared according to the procedures in *J. Org. Chem.* 1996, 61, 7697, to give the corresponding phosphonate 28.6, in which the linkage is a methylene group. Using the above procedure, but employing different phosphonate reagents 28.3 in place of 28.5, the corresponding products 28.2 bearing different linking groups are obtained.

Example 29

Synthesis of Representative Compounds of Formula 30

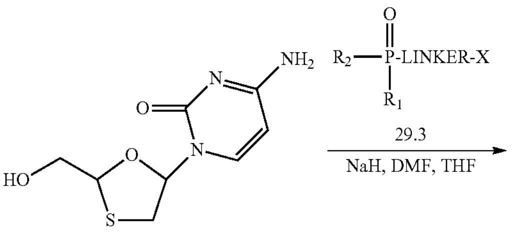

29.1

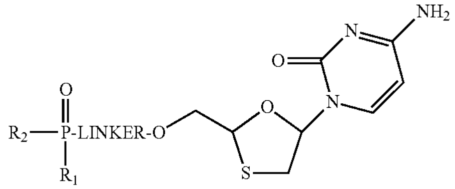

29.2

For example:
X = Cl, Br, I, OMs, OTs, OTf
where $R_1$, $R_2$ = Alkyl, Aryl
$R_1$ = H, alkyl, aryl, haloalkyl, alkenyl, aralyl, aryl
$R_2$ = H, alkyl, aryl, haloalkyl, alkenyl, aralyl, aryl Representative compounds of the invention can be prepared as illustrated above. Phosphonate substituted analogs 29.2 are prepared by reaction of 3TC (29.1) (obtained as described in U.S. Pat. No. 5,047,407 col. 9 line 7 to col. 12 line 30 and references cited therein) with the respective alkylating reagents 29.3. Illustrated above is the preparation of phosphonate linkage to 3TC through the 5'-hydroxyl group. 3TC is dissolved in a solvent such as, but not limited to, DMF and/or THF, and is treated with a phosphonate reagent bearing a leaving group, in the presence of a suitable organic or inorganic base. In compounds 29.3, X is a leaving group such as, but not limited to, bromide, chloride, iodide, p-toluenesulfonate, trifluoromethanesulfonate, or methanesulfonate.

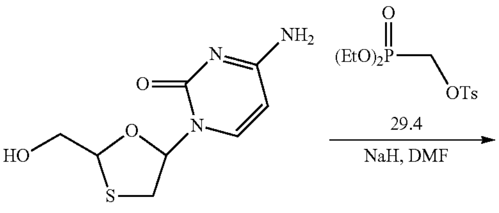

29.1

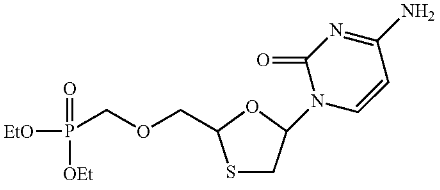

29.5

For instance, 29.1 dissolved in DMF, is treated with one equivalent of sodium hydride and one equivalent of (toluene- 4-sulfonylmethyl)-phosphonic acid diethyl ester 29.4 (prepared according to the procedure in *J. Org. Chem.* 1996, 61, 7697) to give 3TC phosphonate 29.5, in which the linkage is a methylene group. Using the above procedure, but employing different phosphonate reagents 29.3 in place of 29.4, the corresponding products 29.2 bearing different linking groups are obtained.

Example 30

Synthesis of Representative Compounds of Formula 31

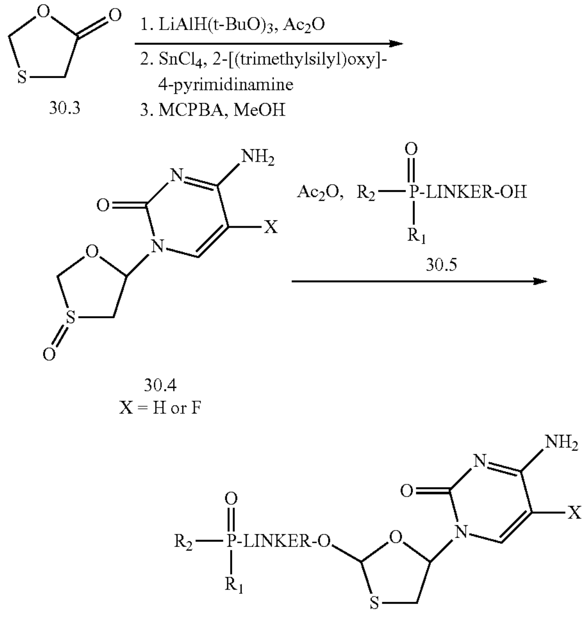

30.3

30.4
X = H or F 30.6
X = H or F $R_1$ = H, alkyl, aryl, haloalkyl, alkenyl, aralyl, aryl
$R_2$ = H, alkyl, aryl, haloalkyl, alkenyl, aralyl, aryl Representative compounds of the invention can be prepared as illustrated above. Starting with the known oxathiolan-5-one (30.3) (*Acta Chem. Scand., Ser. A* 1976, 30, 457), reduction followed by base introduction using the conditions outlined in U.S. Pat. No. 5,914,331 (col. 11 ln. 62 to col. 12 ln. 54) provides the substrate for the Pummerer reaction. Oxidation using m-chloroperbenzoic acid in methanol (U.S. Pat. No. 5,047,407 col. 12 ln. 35 to col. 12 ln. 50) generates sulfoxide 30.4. The Pummerer reaction in the presence of the phosphonate linked alcohol 30.5 and acetic anhydride provides phosphonate 30.6.

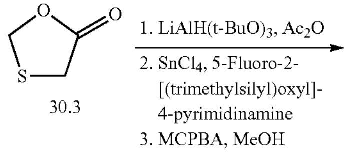

30.3

-continued

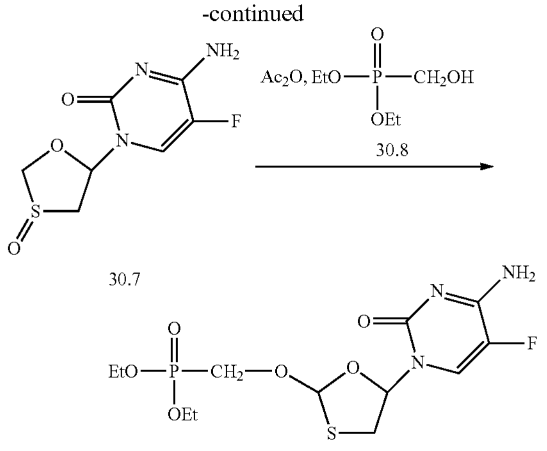

30.7

30.9

As an example, subjecting oxathiolan-5-one to conditions above but using 5-fluoro-2-[(trimethylsilyl)oxy]-4-pyrimidinamine followed by oxidation provides intermediate 30.7. Introduction of phosphonate moiety 30.8, using Pummerer conditions (Org. React. 1991, 40, 157) provides the diethyl phosphonate product 30.9.

Example 31

Synthesis of Representative Compounds of Formula 32

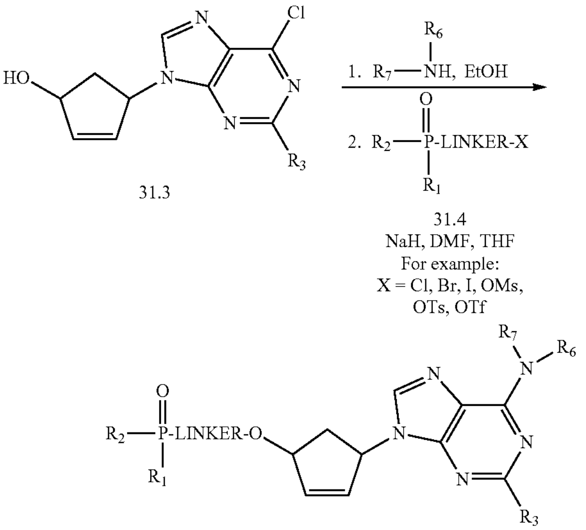

31.3

31.2

$R_1$ = H, alkyl, aryl, haloalkyl, alkenyl, aralyl, aryl
$R_2$ = H, alkyl, aryl, haloalkyl, alkenyl, aralyl, aryl
$R_3$ = H, $NH_2$, NH-alkyl
$R_6$ = H, alkyl, cyclopropyl
$R_7$ = H, alkyl, cyclopropyl Representative compounds of the invention can be prepared as illustrated above. Alcohol 31.3 can be prepared as described in *J. Chem. Soc., Perkin Trans.* 1 1994, 1477. Note that other base derivatives can be prepared in a similar manner starting with their respective bases. Displacement of the chloride of 31.3 with an amine in ethanol under reflux conditions (U.S. Pat. No. 5,034,394, col. 9, ln. 60 to col. 10 ln. 21) provides the key intermediate alcohol. Treatment of this alcohol with the respective alkylating reagents 31.4, provides the desired phosphonate substituted analogs 31.2. In the above compounds, $R_6$ is H, $R_7$ is cyclopropyl, $R_3$ is $NH_2$.

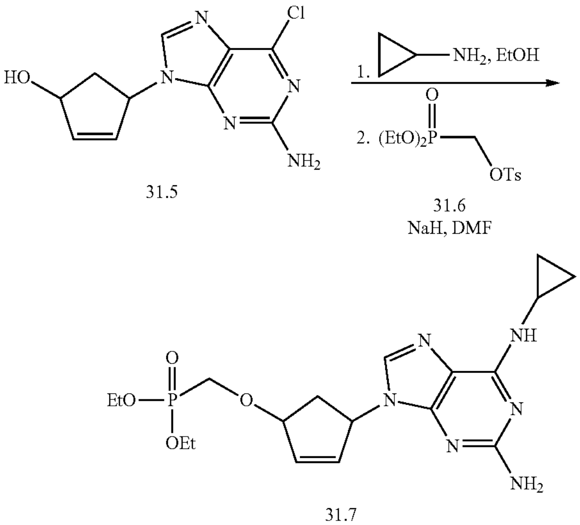

31.5
31.6
31.7

As an example, treatment of the key intermediate alcohol, as described above (*J. Chem. Soc., Perkin Trans.* 1994, 1, 1477), with one equivalent of sodium hydride and one equivalent of (toluene-4-sulfonylmethyl)-phosphonic acid diethyl ester 31.6 (prepared according to the procedures in *J. Org. Chem.* 1996, 61, 7697) affords ABC phosphonate 31.7, in which the linkage is a methylene group. Using the above procedure, but employing different $R_3$, $R_6$, $R_7$ and phosphonate reagents 31.4 in place of 31.6, the corresponding products 31.2 bearing different linking groups are obtained.

Example 32

Synthesis of Representative Compounds of Formula 33

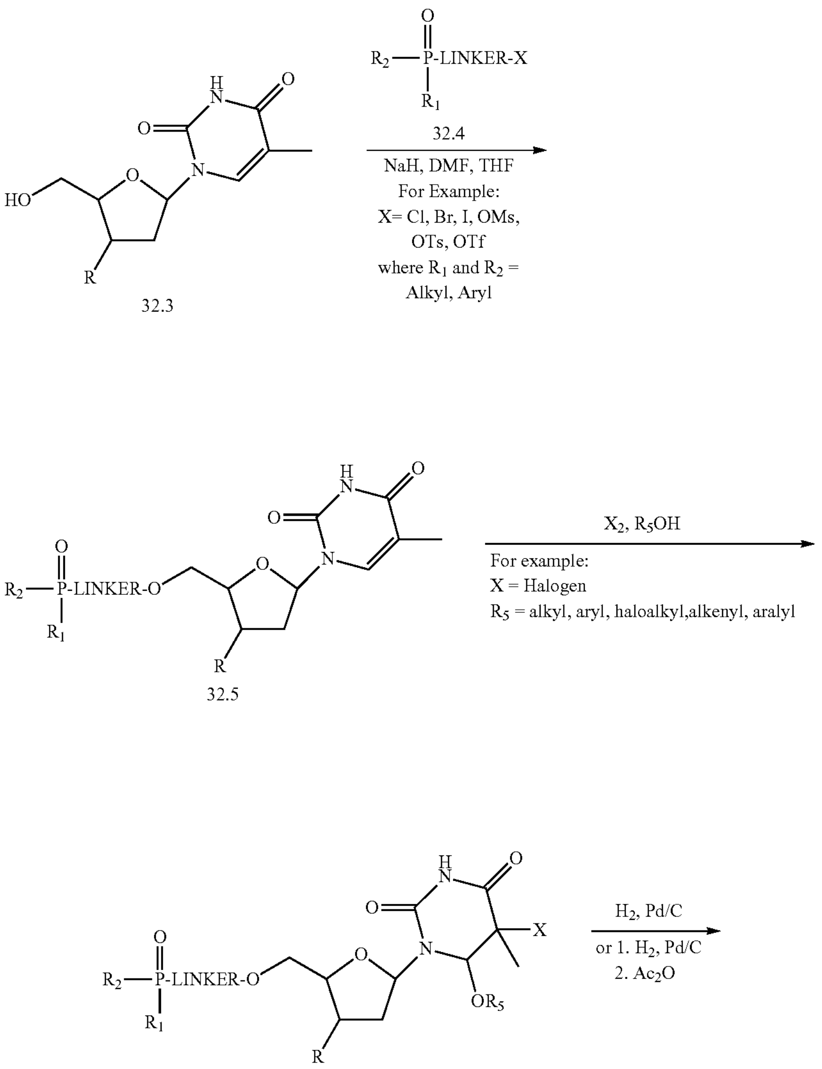

32.3
32.5
32.6

-continued

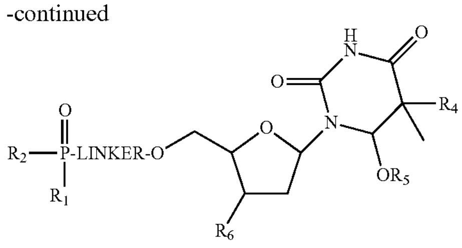

32.7

$R_6 = NH_2$, NHAc

R = H or $N_3$ $R_1$ = H, alkyl, aryl, haloalkyl, alkenyl, aralyl, aryl $R_2$ = H, alkyl, aryl, haloalkyl, alkenyl, aralyl, aryl Representative compounds of the invention can be prepared as illustrated above. Phosphonate substituted analogs 32.5 are prepared by reaction of 32.3 (for example, AZT (A 2169, Sigma Aldrich or obtained as described in U.S. Pat. No. 4,724,232) or 3'-deoxythymidine (D 1138 Sigma Aldrich)) with the respective alkylating reagents 32.4. Further modification of either the base or the 3'-substituent can be carried out as illustrated above. AZT is dissolved in a solvent such as, but not limited to, DMF and/or THF, and is treated with a phosphonate reagent bearing a leaving group, in the presence of a suitable organic or inorganic base. In compounds 32.4, X is a leaving group such as, but not limited to, bromide, chloride, iodide, p-toluenesulfonate, trifluoromethanesulfonate, or methanesulfonate.

Treatment of compound 32.5 with methyl hypobromite provides the 5-bromo-6-alkoxy analog 32.6 (*J. Med. Chem.* 1994, 37, 4297 and US Patent 00/22600). Compound 32.6 can be elaborated by reducing the 3'-azide to the amine and converting the amine to the corresponding acetyl to provide compounds 32.7.

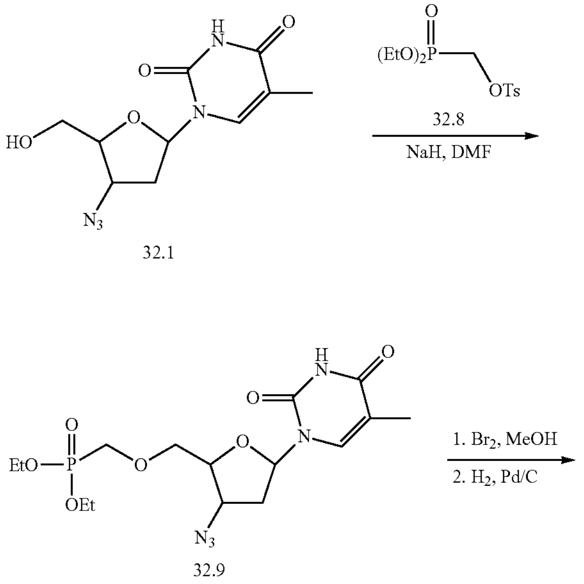

-continued

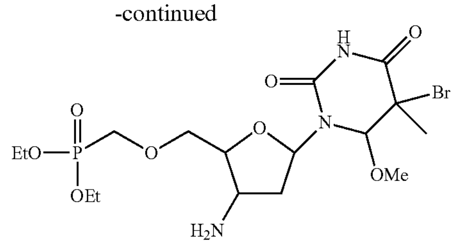

32.10

For instance, 32.1 dissolved in DMF, is treated with one equivalent of sodium hydride and one equivalent of (toluene-4-sulfonylmethyl)-phosphonic acid diethyl ester 32.8 (prepared according to the procedures in *J. Org. Chem.* 1996, 61, 7697) to give AZT phosphonate 32.9, in which the linkage is a methylene group. Treatment with methyl hypobromite followed by hydrogenation provides analog 32.10. Using the above procedure, but employing different phosphonate reagents 32.4 in place of 32.8, the corresponding products 32.2 bearing different linking groups are obtained. Additionally, the $R_3$-$R_5$ groups can be varied to generate other compounds.

Example 33

Synthesis of Representative Compounds of Formula 34

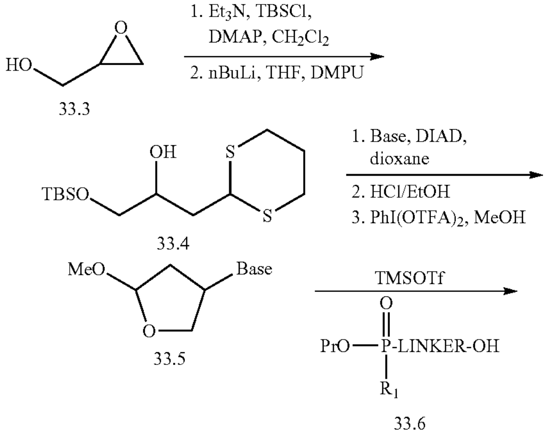

-continued

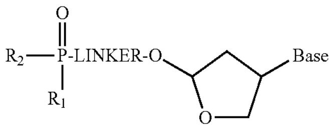

33.2

For example:
Base = adenine, guanasine, thymidine, uracil, cytosine, inosine
$R_1$ = H, alkyl, aryl, haloalkyl, alkenyl, aralyl
$R_2$ = H, alkyl, aryl, haloalkyl, alkenyl, aralyl Representative compounds of the invention can be prepared as illustrated above. Starting with commercially available glycidol, silyl protection of the alcohol followed by a lithium-mediated opening of the epoxide generates alcohol 33.4 (see *Angew. Chem., Int. Ed. Engl.* 1998, 37, 187-192). Introduction of the appropriately protected bases using Mitsunobu reaction conditions (*Tetrahedron Lett.* 1997, 38, 4037-4038; *Tetrahedron* 1996, 52, 13655) followed by acid mediated removal of the silyl protecting group (*J. Org. Chem.* 1980, 45, 4797) and dithiane removal and in situ cyclization (*J. Am. Chem. Soc.* 1990, 112, 5583) produces furanoside 33.5. Introduction of phosphonate linkage using the appropriate alcohol in the presence of TMSOTf (*Synlett* 1998, 177) generates analog 33.2.

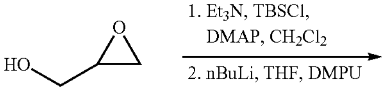

33.3

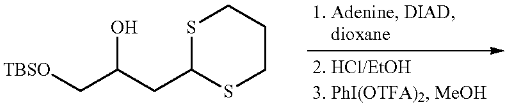

33.4

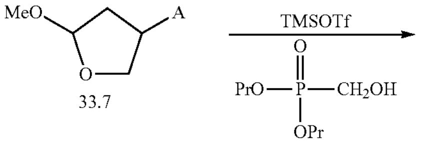

33.7

33.8

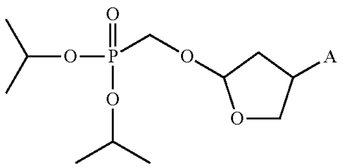

33.9

For instance, 3 equivalents of DIAD (in 3 portions) is added dropwise to a stirred solution of alcohol 33.4 and adenine (3 equivalents) in dioxane. The reaction is stirred for 20 hours. The resulting product is treated with hydrochloric acid in ethanol for 15 hours and filtered. The residue is stirred with [bis(trifluoroacetoxy)iodo]benzene (1.5 equivalents) in methanol to generate 33.7. Lewis acid-mediated reaction (*Synlett* 1998, 177) of diisopropyl hydroxymethylphosphonate 33.8 (*Tetrahedron Lett.* 1986, 27, 1477) produces a diastereomeric mixture of phosphonates 33.9, in which the linkage is a methylene group. Using the above procedure, but employing different appropriately protected bases and phosphonate reagents 33.6 in place of 33.8, the corresponding products 33.2 bearing different linking groups are obtained.

Example 34

Synthesis of Representative Compounds of Formula 35

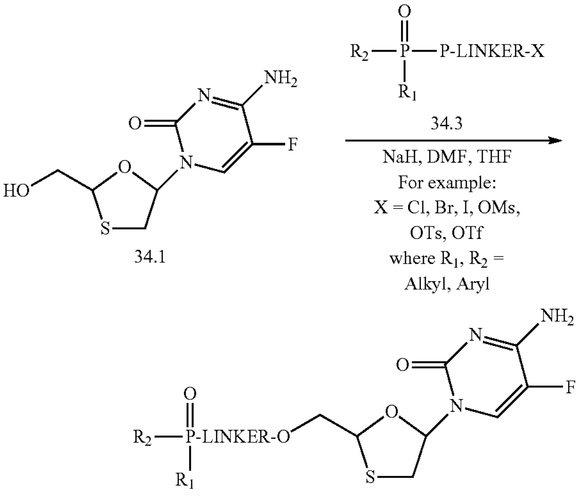

34.1

34.3

34.2

$R_1$ = H, alkyl, aryl, haloalkyl, alkenyl, aralyl, aryl
$R_2$ = H, alkyl, aryl, haloalkyl, alkenyl, aralyl, aryl Representative compounds of the invention can be prepared as illustrated above. Phosphonate substituted analogs 34.2 are prepared by reaction of FTC (34.1) (obtained as described in U.S. Pat. No. 5,914,331 col. 10 line 40 to col. 18 line 15 and references cited therein) with the respective alkylating reagents 34.3. Illustrated above is the preparation of phosphonate linkage to FTC through the 5'-hydroxyl group. FTC is dissolved in a solvent such as, but not limited to, DMF and/or THF, and is treated with a phosphonate reagent bearing a leaving group, in the presence of a suitable organic or inorganic base. In compounds 34.3, X is a leaving group such as, but not limited to, bromide, chloride, iodide, p-toluenesulfonate, trifluoromethanesulfonate, or methanesulfonate.

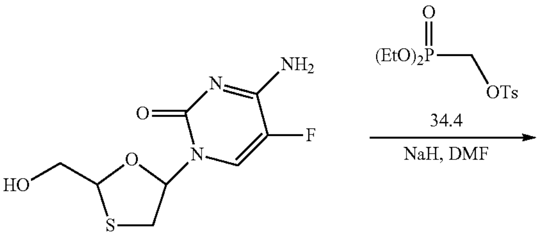

34.4

34.1

-continued

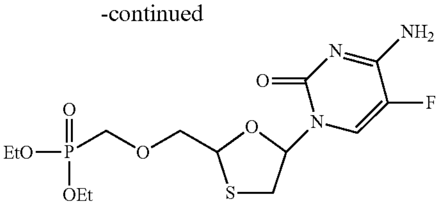

34.5

For instance, 34.1 dissolved in DMF, is treated with one equivalent of sodium hydride and one equivalent of (toluene-4-sulfonylmethyl)-phosphonic acid diethyl ester 34.4 (prepared according to the procedures in *J. Org. Chem.* 1996, 61, 7697) to give FTC phosphonate 34.5 in which the linkage is a methylene group. Using the above procedure but employing different phosphonate reagents 34.3 in place of 34.4, the corresponding products 34.2 bearing different linking groups can be obtained.

Example 35

Synthesis of Representative Compounds of Formula 37

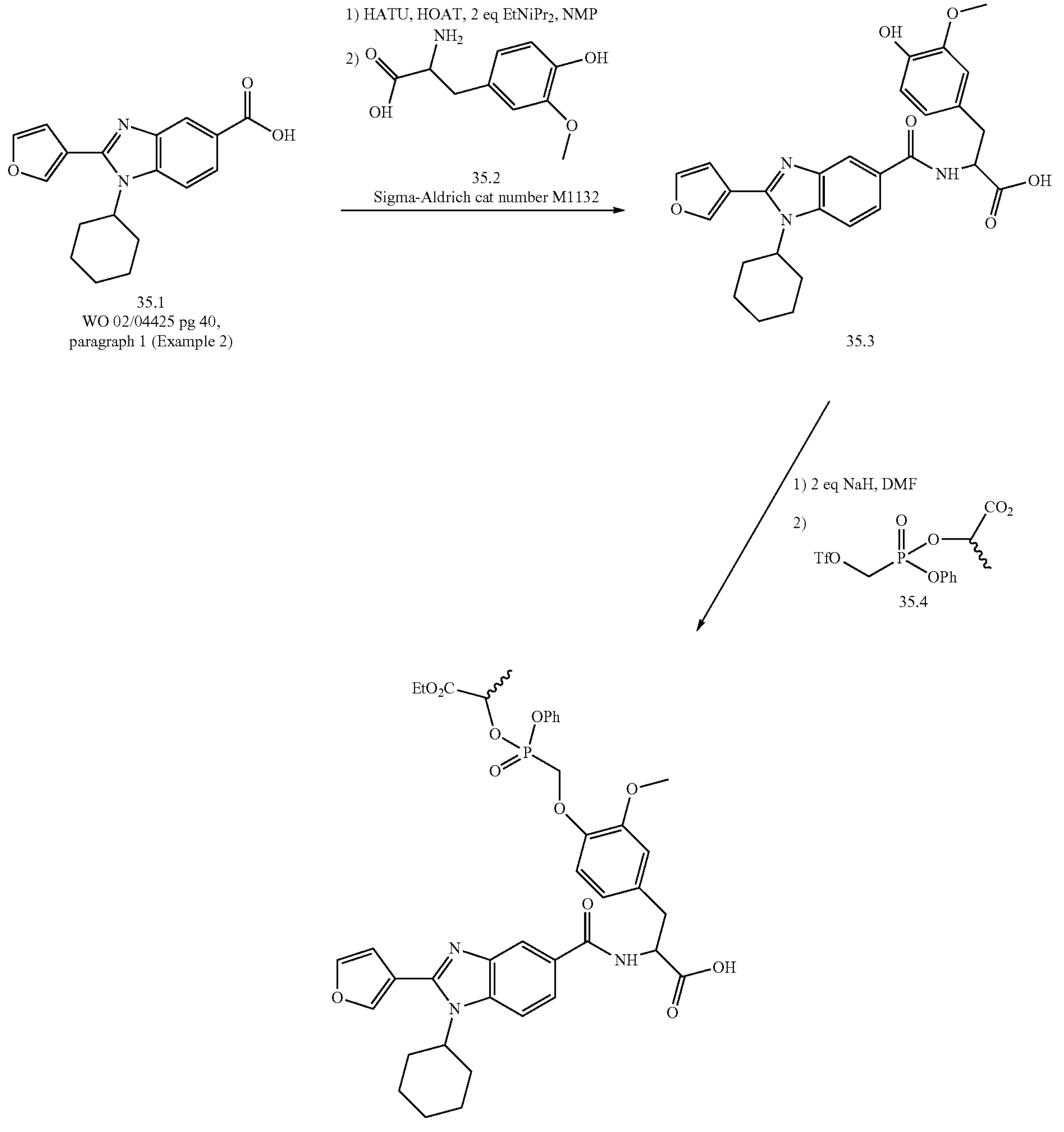

35.1
WO 02/04425 pg 40, paragraph 1 (Example 2)

35.2

35.3

35.4

35.5

Representative compounds of the invention can be prepared as illustrated above. The synthetic scheme above outlines a sequence for producing a phosphonate linked HCV polymerase inhibitor. Compound 35.1 (WO 02/04425 page 40, paragraph 1, Example 2) is reacted with amino acid 35.2 (purchased from a supplier such as Sigma-Aldrich) under standard peptide coupling conditions: 35.1 is combined with, for example, HATU, HOAT, 2 equivalents of EtNiPr2, in NMP, DMF, THF, $CH_2Cl_2$, or DMA for 2 to 60 minutes at room temperature. The resulting mixture is then added to 35.2 for 10 minutes to 5 days at room temperature to 100° C. After standard work-up and purification procedures, compound 35.3 is reacted with 2 equivalents of NaH in anhydrous DMF (NMP, DMSO, or THF) followed by the addition of 35.4 produce substituted phosphonate 35.5 after work-up and purification.

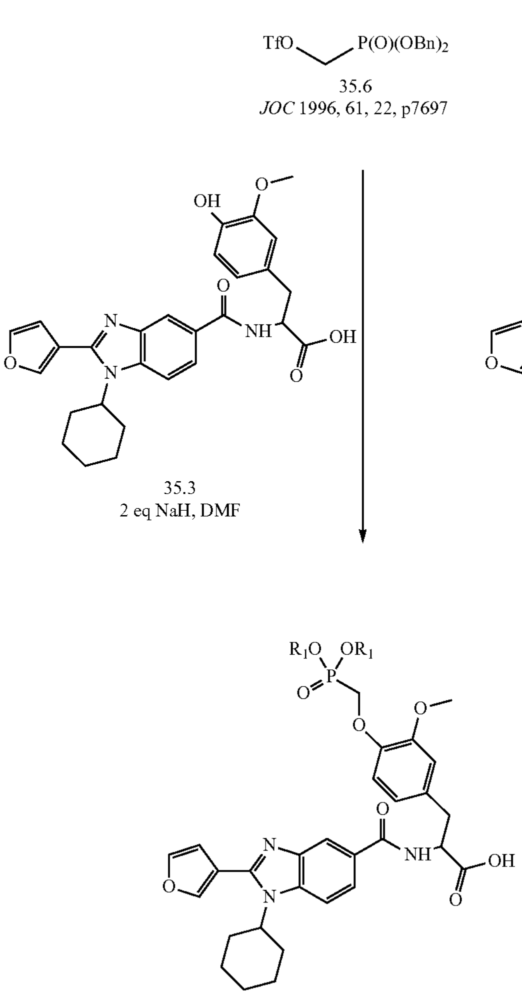
35.9
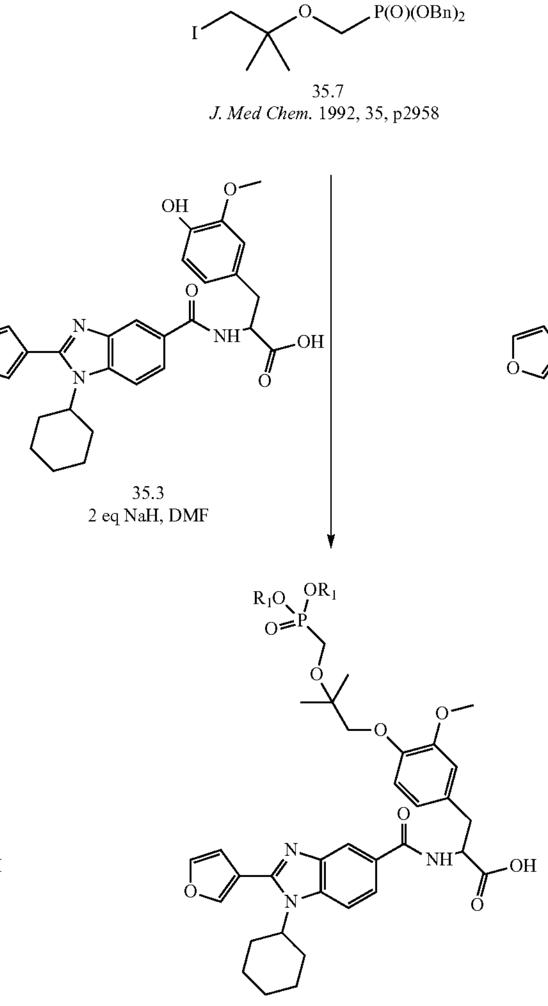
35.10
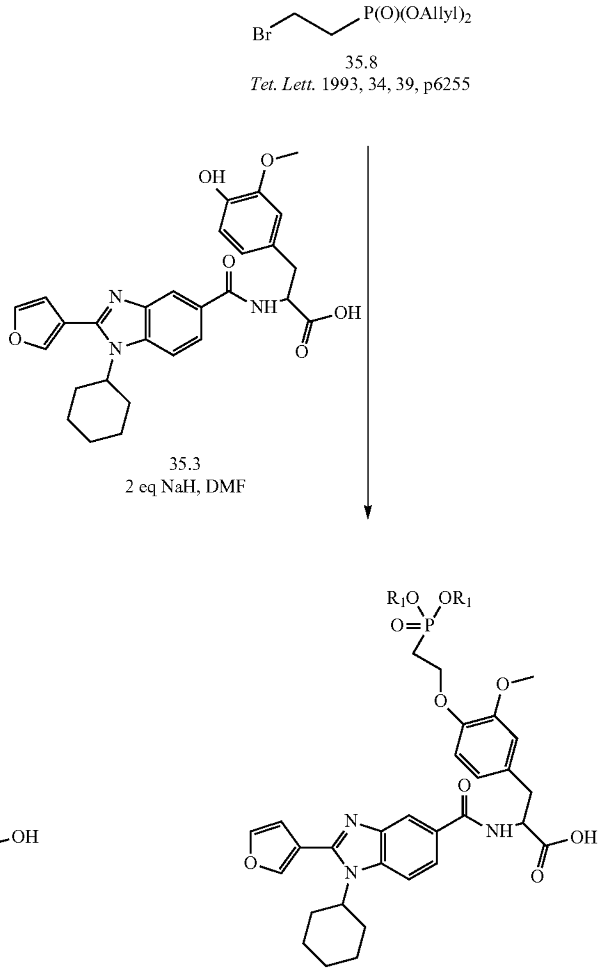
35.11

In an analogous fashion, 35.3 can be converted to 35.9, 35.10, and 35.11 as illustrated above. The $R_1$ groups attached to the phosphonate esters 35.9, 35.10 and 35.11 may be changed using established chemical transformations well know to those of skill in the chemical arts.

Example 36

Synthesis of Representative Compounds of Formula 38

Representative compounds of the invention can be prepared as illustrated above. phosphonate 36.14 is produced from 36.12 (WO 02/04425, page 59, paragraph 1) by the action of HATU/HOAT/EtN(i-Pr)$_2$ on 36.12 and 36.13 using protocols familiar to one skilled in the art in a polar aprotic solvent such as, but not limited to, NMP, DMF, THF, and DMSO.

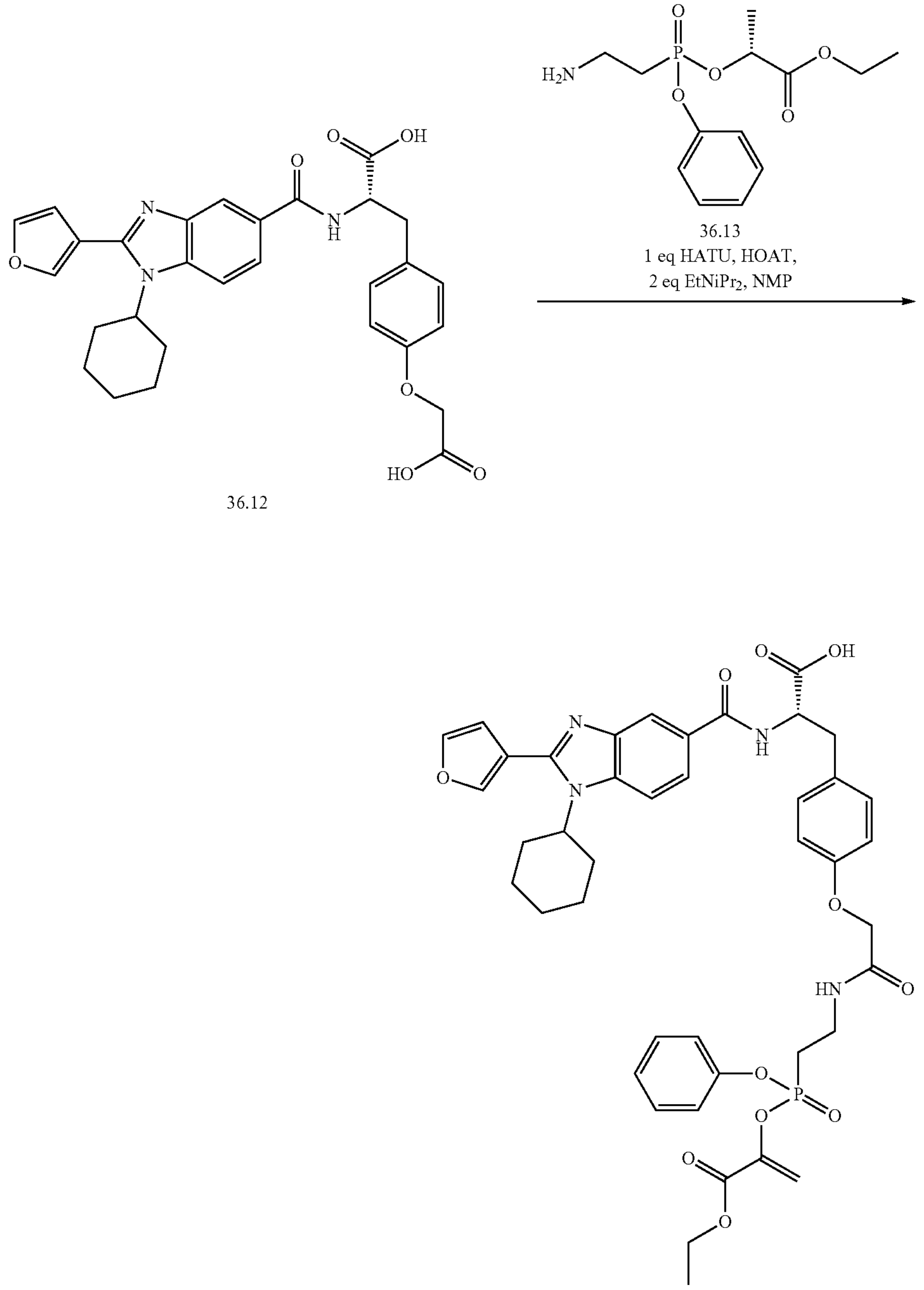

36.12

36.13

36.14

Synthetic methodologies and intermediate compounds that can be used to prepare analogs of Formulae 39-43 are described below in Examples 37-40.

Example 37

General Route to Representative Compounds of Formula 39

This Example describes linkage groups (Linker) that can be used to covalently attach a phosphonate containing group to the compounds described in patent EP1162196A1. This Example also illustrates the chemical reactions that can be used to attach the linker-phosphonate moiety to parent compounds.

amide, sulfonamide, and carboxylic acid. Some representative examples of compounds from JT patent EP 1162196A1 bearing one of the above groups are listed in the following table.

| Group | Example # in JT Patent EP1162196A1 |
|---|---|
| Hydroxyl | 3, 18, 28, 52, 107, 1005, 1026, 1012, 1021, 288, 289, 294, 2231 |
| Amine | 22, 39, 308, 152, 160, 161 |
| Amide | 1260, 1263, 1270, 130, 1280, 162, 190, 195, 205, 225, 1388, 262, 268, 316 |
| Sulfonamide | 41, 42, 57, 1357, 249, 250, 283, 285 |
| Carboxylic acid | 246, 140, 141, 184, 189, 1015, 1020, 1054, 1069, 1084, 255, 260, 292, 293 |

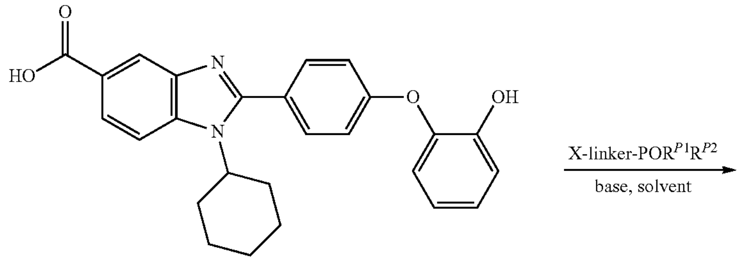

37.2

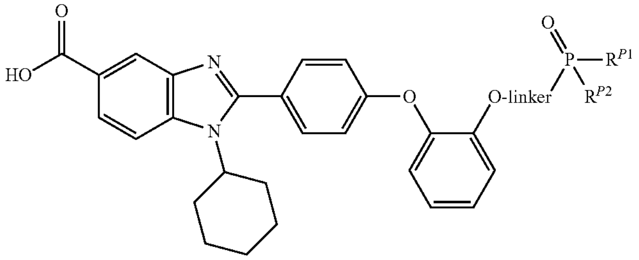

37.3

Representative compounds of the invention can be prepared as illustrated above. Compound 37.2 in an appropriate aprotic solvent can be treated with at least two equivalents of an appropriate organic or inorganic base. An appropriate electrophile bearing a leaving group, such as, but not limited to, diisopropyl bromomethylphosphonate, is added to produce compound 37.3.

Suitable aprotic solvents include, but are not limited to, dimethyl formamide, dimethyl sulfoxide, and N-methylpyrrolidinone. Suitable organic or inorganic base include, but are not limited to, sodium hydride, potassium carbonate, and triethylamine. Suitable leaving groups include, but are not limited to, chlorine, bromine, iodine, p-toluenesulfonate, methanesulfonate, and trifluoromethanesulfonate.

Linker Type I: alkylation of the parent compound 37.2 with an electrophile containing phosphonate. At least five types of functional groups can be directly alkylated. The functional groups include, but are not limited to, hydroxyl, amine, amide, sulfonamide, and carboxylic acid.

Example 38

General Route to Representative Compounds of Formulae 40 and 41

This Example describes linkage groups (Linker) that can be used to covalently attach a phosphonate containing group to the compounds described in patent EP1162196A1. This Example also illustrates the chemical reactions that can be used to attach the linker-phosphonate moiety to parent compounds.

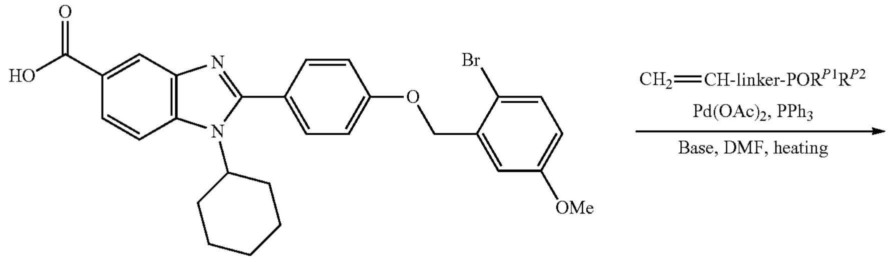

38.4

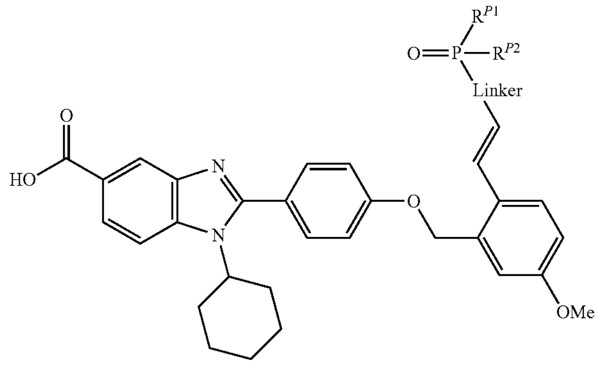

38.5

Representative compounds of the invention can be prepared as illustrated above. Compound 38.4 in an appropriate solvent can be treated with a suitable olefin containing a phosphonate group, catalytic amount of a palladium catalyst, with an optional phosphine ligand, and at least two equivalents of an appropriate base to produce 38.5. Other optional phosphine ligands may be used according to procedures know to those of skill in the art (see *Encyclopedia of Reagents for Organic Synthesis*, Leo A. Paquette Ed.-in-Chief, John Wiley & Sons, Chichester, UK, 1995).

Suitable solvents include, but are not limited to dimethyl formamide, dimethylacetamide, and N-methylpyrrolidinone. Suitable palladium catalysts include, but are not limited to palladium acetate, palladium chloride, and palladium bis (triphenylphosphine) dichloride. Suitable phosphine ligands include, but are not limited to triphenylphosphine, and tri(o-toluyl)phosphine. Suitable bases include, but are not limited to triethylamine, diisopropylethylamine, and tributylamine. Suitable olefins containing a phosphonate group include, but are not limited to esters of vinylphosphonic acid and allylphosphonic acid.

Linker Type II: coupling between an aryl bromide in a parent compound and an olefin containing a phosphonate group. Some representative examples of compounds bearing an aryl bromide are Examples. 1, 2, 4, 7, 244, 180, 1023, 1086, 1087, 1093, 1208, 1220, and 1301, as listed in JT patent EP1162196A1.

Linker Type III: Hydrogenation of Linker Type II.

The following is an example illustrating hydrogenation of Linker Type II.

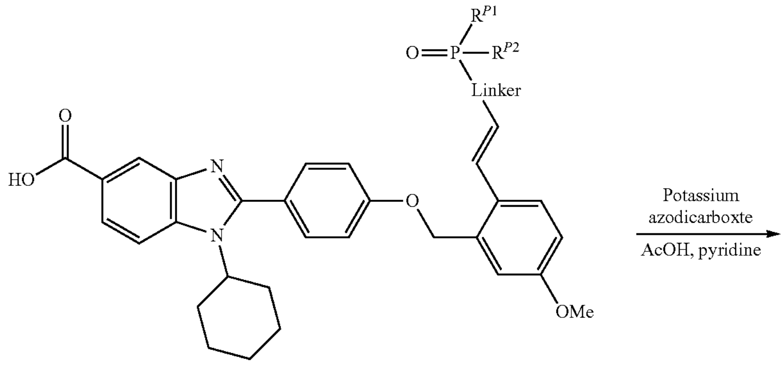

38.5

-continued

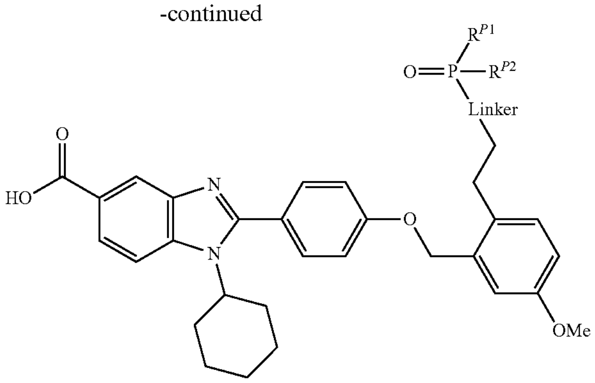

38.6

Compound 38.5 is treated with potassium azodicarboxylate, acetic acid and pyridine (as described in *Liebigs Ann. Chem.* 1984; 98-107) to give 38.6. In cases where the parent structure is stable to hydrogenation using palladium catalyst or Raney nickel, those combination of reagents can also be used to effect the same transformation. Common solvents used for those procedures include, but are not limited to, methanol, ethanol, isopropanol, and acetic acid.

Example 39

General Route to Representative Compounds of Formulae 42 and 43

The following scheme illustrates the reductive amination reaction.

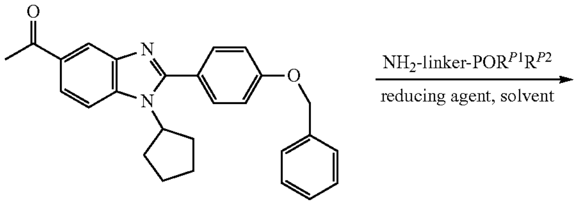

39.7

-continued

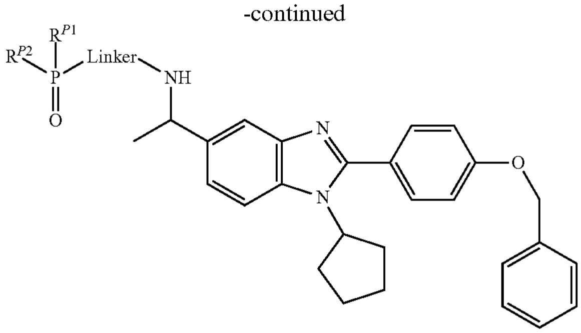

39.8

Representative compounds of the invention can be prepared as illustrated above. Ketone 39.7 in an appropriate solvent can be treated with a suitable amine containing a phosphonate group, and an appropriate reducing agent to produce amine 39.8.

Linker Type IV: Reductive Amination.

Variation 1: coupling between an amine containing a phosphonate group and a parent compound containing an aldehyde or a ketone group. Some representative examples of parent compounds bearing an aldehyde or a ketone group are Examples 36, 1234, 1252, 1256, and 2241 as listed in JT patent EP1162196A1.

Variation 2: Coupling between an aldehyde or ketone containing a phosphonate group and a parent compound containing an amine group. Some representative examples of parent compounds bearing an amino group are Examples 22, 39, 308, 152, 160, and 161 as listed in the JT patent EP1162196A1.

The following is an example illustrating a Variation 2-type of reductive amination reaction.

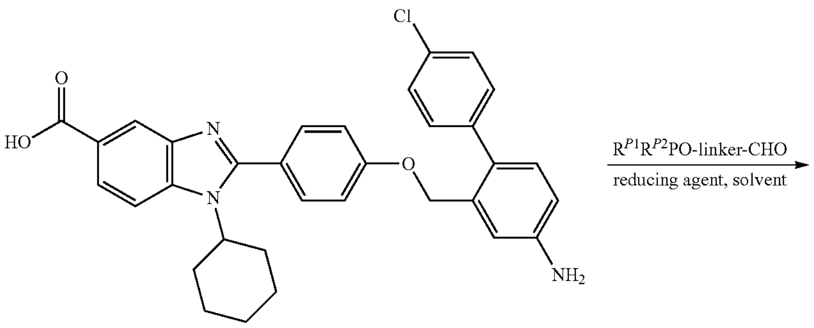

39.9

-continued

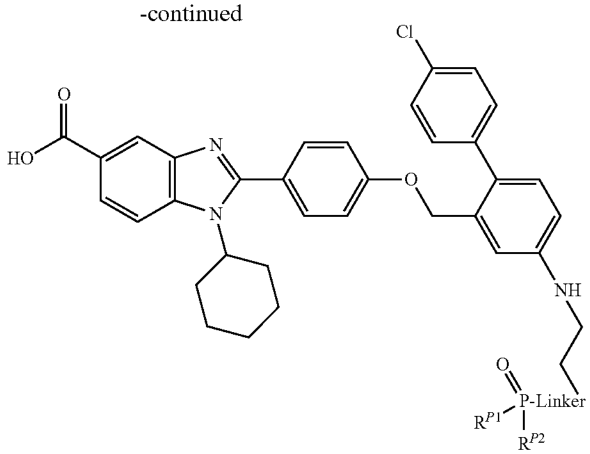

39.10

Aryl amine 39.9 in an appropriate solvent can be treated with a suitable aldehyde or a ketone containing a phosphonate group, and an appropriate reducing agent to produce secondary amine 39.10.

In the above two variations of Linker Type IV, the appropriate reducing agents include, but are not limited to, sodium borohydride, sodium cyanoborohydride, and sodium triacetoxyborohydride. The appropriate solvents include, but are not limited to, methanol, ethanol, and 1,2-dichloromethane.

Example 40

General Route to Representative Compounds of Formulae 44 and 45

The following is an example illustrating an amide formation reaction.

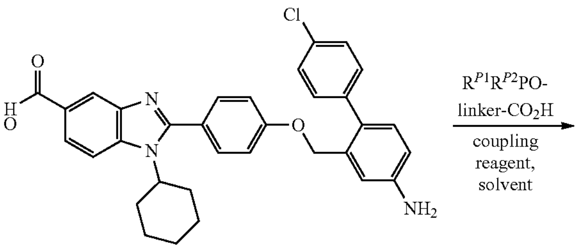

40.11

-continued

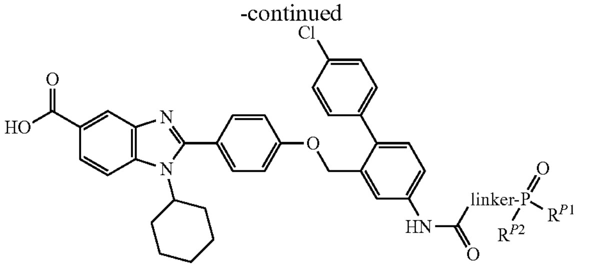

40.12

Representative compounds of the invention can be prepared as illustrated above. Aryl amine 40.11 in an appropriate solvent can be treated with a carboxylic acid containing a phosphonate group and an appropriate coupling reagent to give amide 40.12.

Linker Type V: Amide Formation

Variation 1: amide formation between a carboxylic acid containing a phosphonate group and a parent compound containing an amine group. Some representative examples of parent compounds bearing an amino group are Examples 22, 39, 308, 152, 160, and 161 as listed in JT patent EP1162196A1.

Variation 2: amide formation between an amine containing a phosphonate group and a parent compound containing a carboxylic acid. Some representative examples of parent compounds bearing a carboxylic acid are Examples 246, 184, 189, 1015, 1020, 1054, 255, 260, 292, 295, 305, and 2013 as listed in JT patent EP1162196A1.

The following is an example illustrating this type of amide formation reaction.

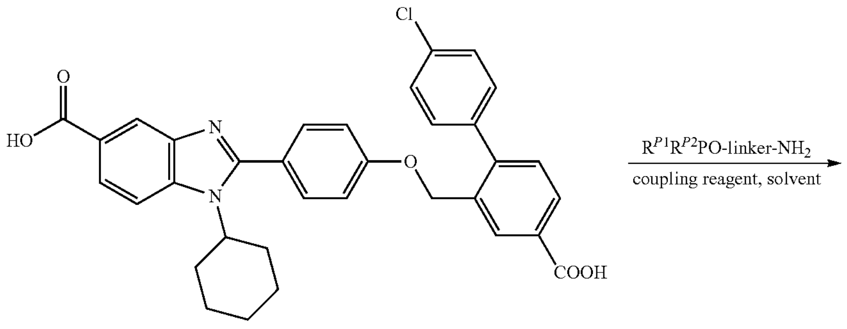

40.13

-continued

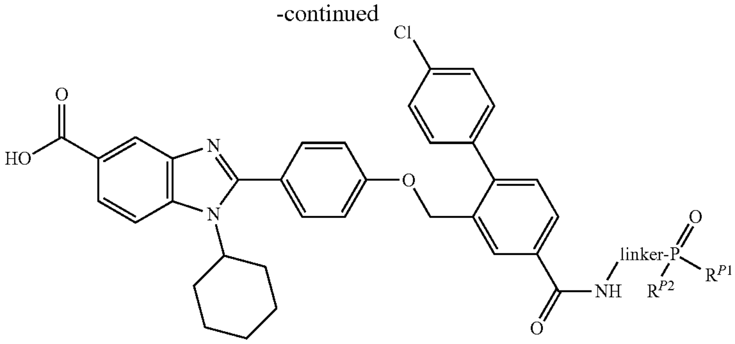

40.14

Representative compounds of the invention can be prepared as illustrated above. Compound 40.13 in an appropriate solvent can be treated with an amine containing a phosphonate group and an appropriate coupling reagent to give 40.14.

In the above two variations of Linker Type 5, the appropriate coupling reagents include, but are not limited to, DCC and EDC. The appropriate solvents include, but are not limited to, dimethylformamide and dichloromethane.

Example 41

Synthesis of Representative Compounds of Formula 46

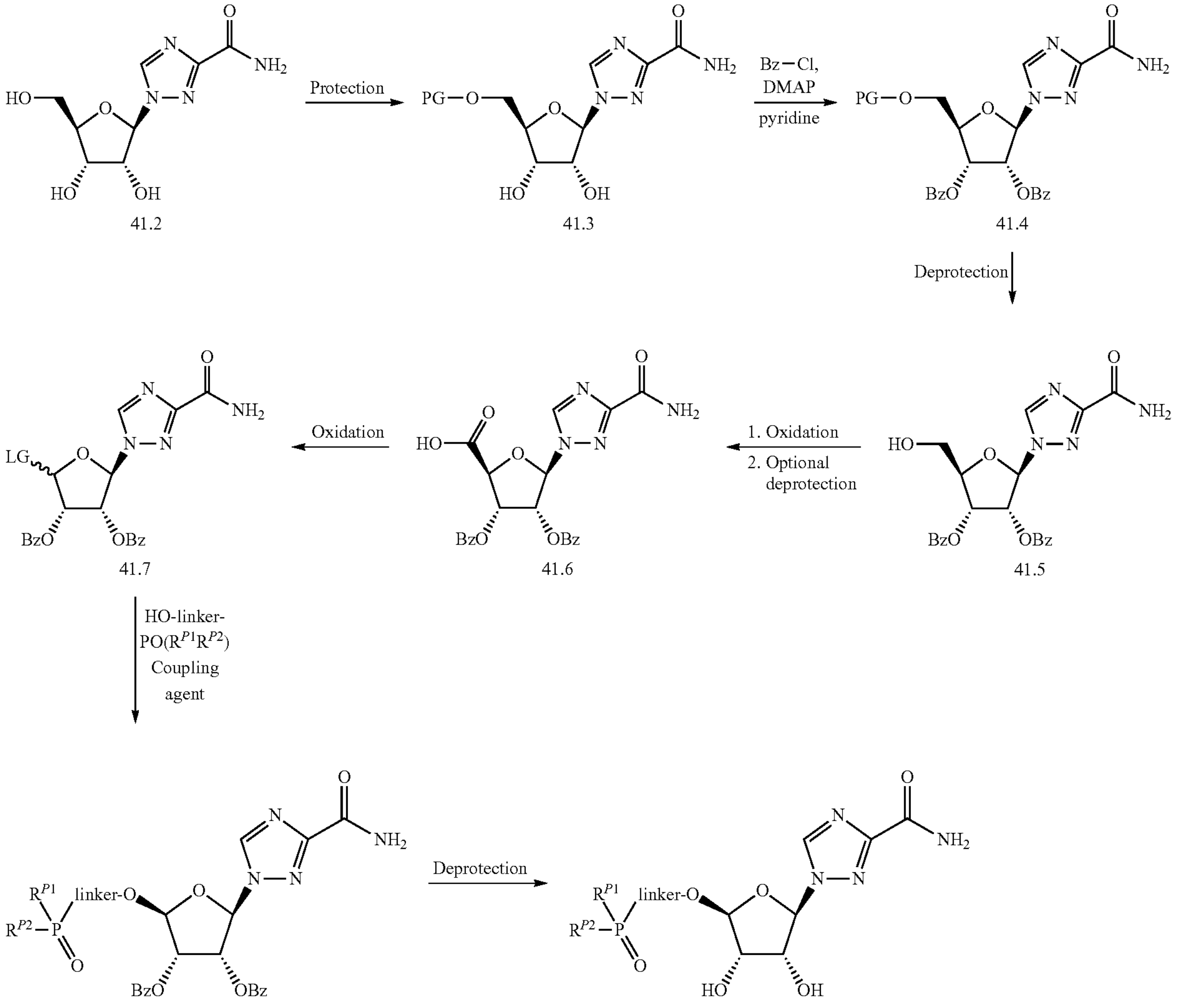

41.2 41.3 41.4 41.5 41.6 41.7 41.8 41.1

Representative compounds of the invention can be prepared as illustrated above. The 5'-hydroxyl group of ribavirin (41.2) can be selectively protected with an appropriate protecting group. The product, 41.3, can be treated with benzoyl chloride, an appropriate base, in the presence of catalytic amount of 4-dimethylaminopyridine, to convert 2'- and 3'-hydroxyl groups to their corresponding benzoyl esters, producing dibenzoate 41.4. The 5'-hydroxyl group can be selectively deprotected to afford alcohol 41.5. Following procedure described for the analogous compound in U.S. Pat. No. 6,087, 482, FIG. 2, dibenzoate 41.4 can be converted to 41.7 in a three-step sequence. Treating electrophile 41.7 with a coupling agent, such as trimethylsilyl trifluoromethanesulfonate, in the presence of an appropriate alcohol containing a phosphonate group can produce phosphonate 41.8. Treating 41.8 with aqueous sodium hydroxide can deprotect the 2'- and 3'-hydroxyl groups to provide diol 41.1. Note that $R^{P1}$ and $R^{P2}$ in 41.8 and 41.1 can be the same or different protecting groups.

Example 42

Synthesis of Representative Compounds of Formula 47

Representative compounds of the invention can be prepared as illustrated above. The synthesis of 3-cyano-1-(2,3,5-tri-O-acetyl-β-D-ribofuranosyl)-1,2,4-triazole (42.2) is described in US 2002/0156030A1, page 6, paragraph 0078 to paragraph 0079. Using this starting material, one can synthesize compound 42.1 using the sequence of chemical transformations outlined above.

Appropriate protection and deportection procedures (see Greene and Wuts, *Protective Groups in Organic Synthesis*, 1999) can be employed to prepare 42.3, in which the 5'-hydroxyl group is protected, while the 2'-, and 3'-hydroxyl groups are not. Subsequent protection, deprotection procedures can introduce protecting groups such as benzoyl group to the 2'- and 3'-hydroxyls, leaving the 5'-hydroxyl group unprotected as in alcohol 42.4. Oxidation can convert the primary alcohol in 42.4 to the corresponding carboxylic acid or its ester. An optional deprotection of the ester can give the acid 42.5 as product. Further oxidation using oxidant such as lead tetraacetate can convert acid 42.5 to electrophile 42.6, in which the leaving group is an acetate. Treating 42.6 with an alcohol containing a phosphonate moiety in the presence of appropriate coupling agent, such as trimethylsilyl trifluoromethanesulfonate, affords phosphonate 42.8. Finally, treating 42.8 with the procedure described in US 2002/0156030 A1, page 6, paragraph 0081, provides phosphonate 42.1. Note that $R^{P1}$ and $R^{P2}$ in 42.7, 42.8 and 42.1 do not need to be the same.

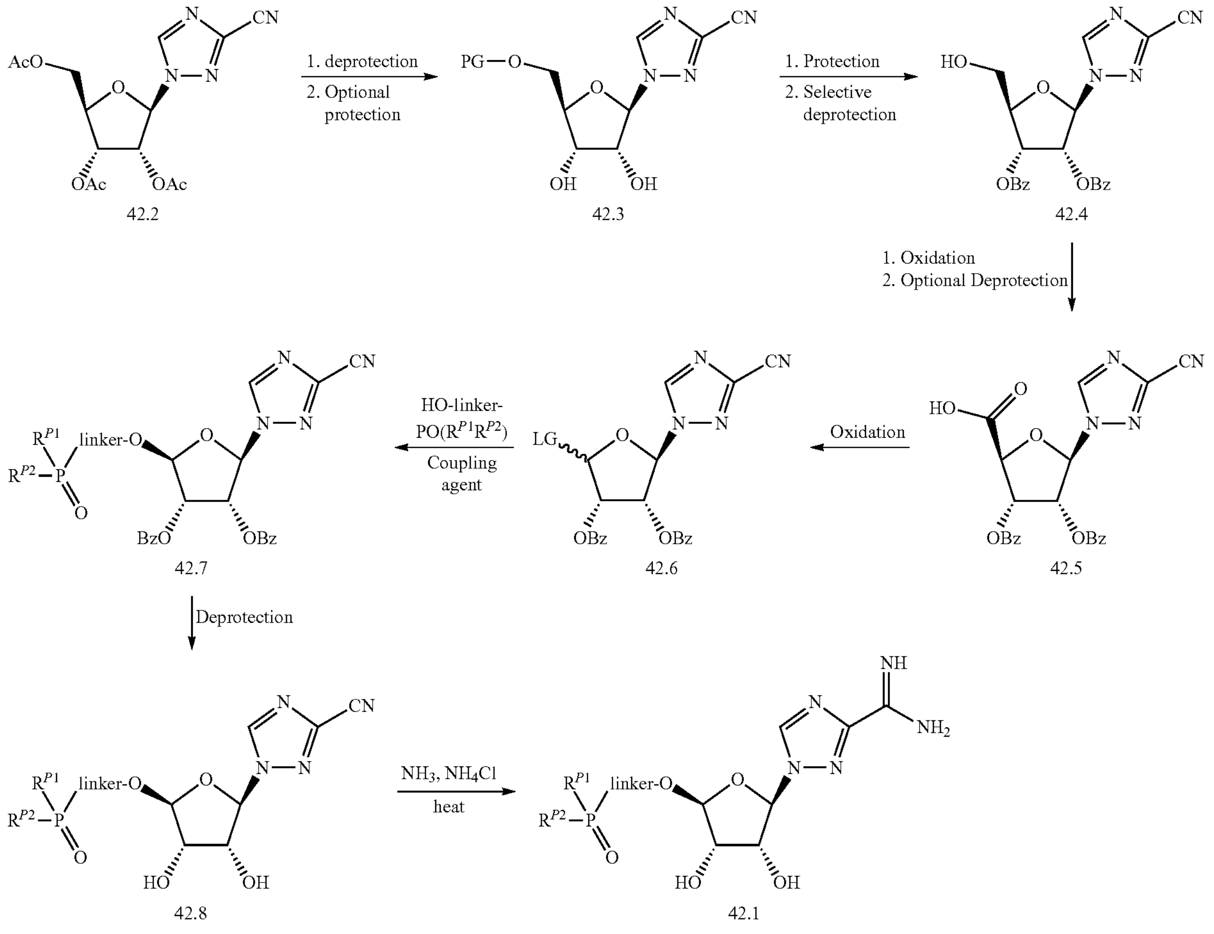

42.2 42.3 42.4

42.7 42.6 42.5

42.8 42.1

Example 43

Synthesis of Representative Compounds of Formula 48

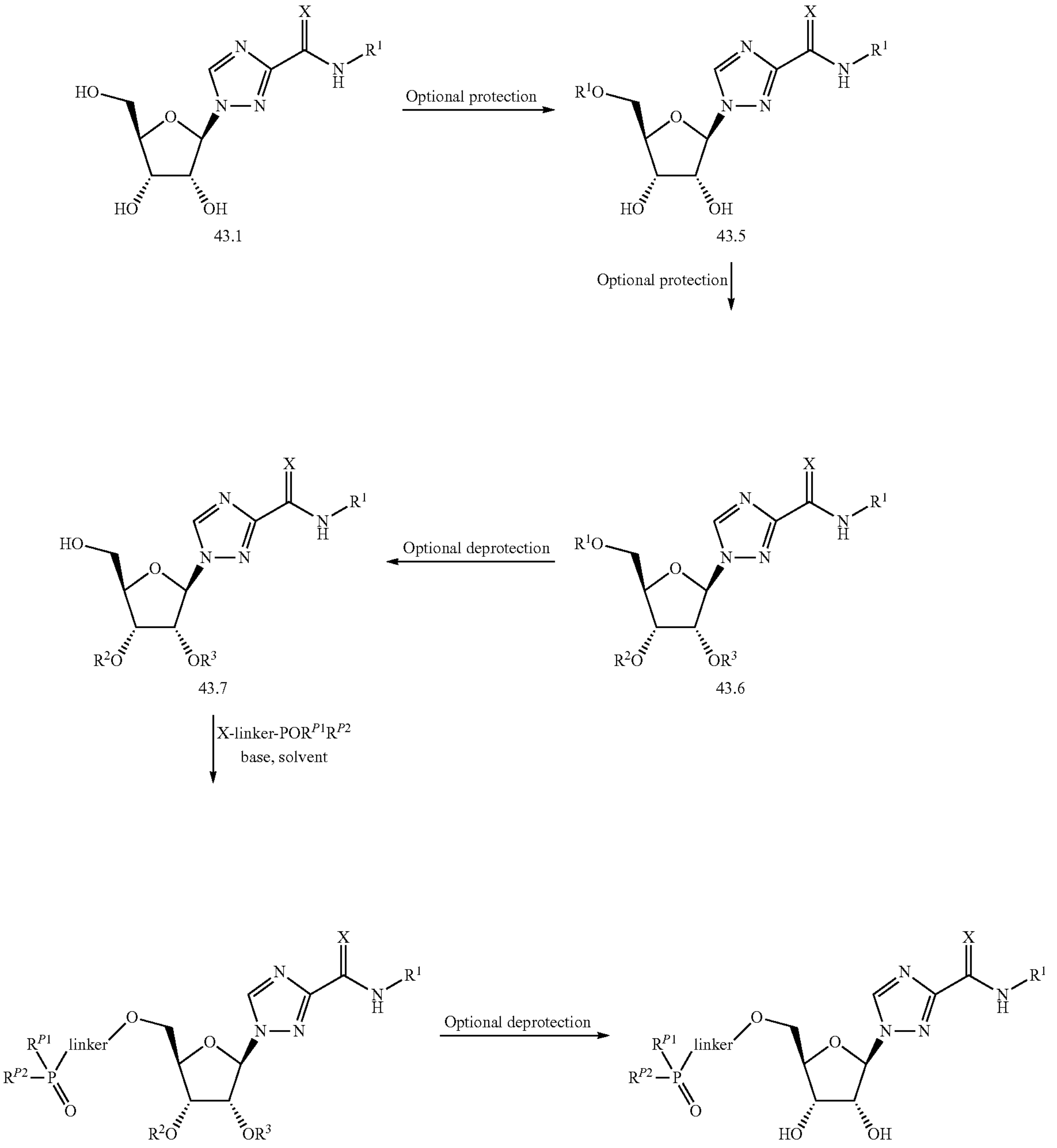

43.1, 43.5, 43.6, 43.7, 43.8, 43.2

Representative compounds of the invention can be prepared as illustrated above. Compound 43.2 can be prepared from 43.1 by a series of selective protections of the 2'-, 3'-, and 5'-hydroxyl groups to give 43.6. The 5'-hydroxyl can then be selectively deprotected to give alcohol 43.7. Compound 43.7 in an appropriate aprotic solvent can be treated with at least two equivalents of an appropriate organic or inorganic base, and an appropriate electrophile bearing a leaving group, as in the structure X-linker-POR$^{P1}$R$^{P2}$, where X is a leaving group, to produce phosphonate 43.8. Appropriate deprotection procedures can be employed to convert 43.8 to diol 43.2. Note that R$^{P1}$ and R$^{P2}$ in 43.8 and 43.2 do not need to be the same.

Suitable aprotic solvents include, but are not limited to dimethyl formamide, dimethyl sulfoxide, and N-methylpyrrolidinone. Suitable organic or inorganic base include, but are not limited to sodium hydride, potassium t-butoxide, and triethylamine. Suitable leaving groups include, but are not limited to, chlorine, bromine, iodine, p-toluenesulfonate, methanesulfonate, and trifluoromethanesulfonate.

Example 44

Synthesis of Representative Compounds of Formulae 49 and 50

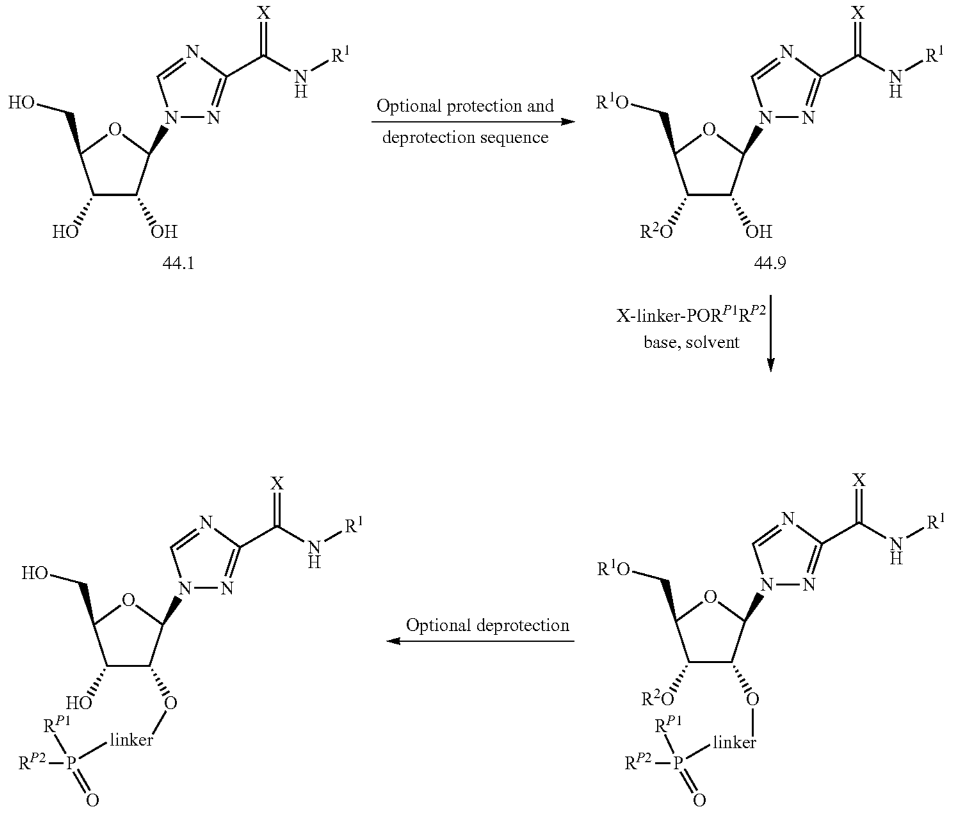

44.1 44.9 44.10 44.3

Representative compounds of the invention can be prepared as illustrated above. Triol 44.1 can be converted to alcohol 44.9, having an unprotected 2'-hydroxyl, by selecting appropriate protecting groups for the 3'- and 5'-hydroxyl groups through a series of protection and deprotection sequences. Alkylation of 44.9 by an electrophile containing a phosphonate as described in Example 43 can produce 44.10. After appropriate deprotection, 44.10 can be converted to phosphonate 44.3.

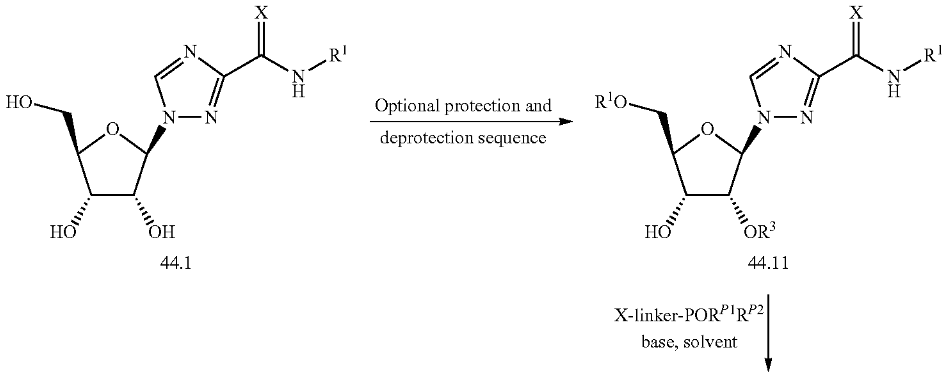

44.1 44.11

-continued

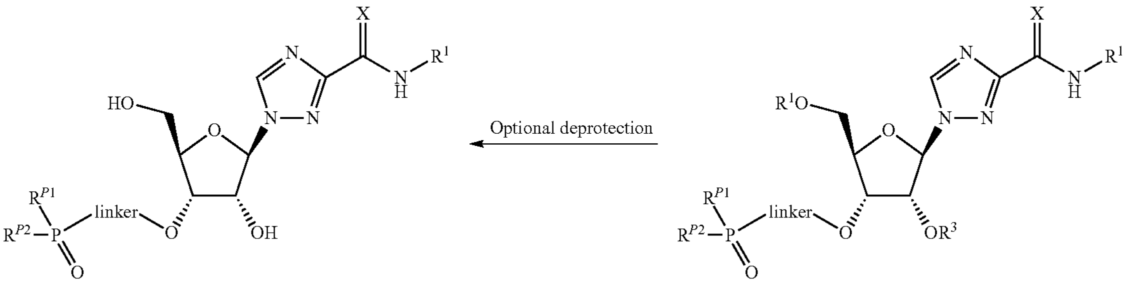

44.3 44.12

The preparation of 44.4 is illustrated above. The reaction sequence and conditions are similar to that of 44.2 and 44.3 described above.

Representative compounds of the invention can also be prepared by following the sequences illustrated in Examples 41-44 using enantiomeric starting materials corresponding to, for example, compounds 41.2 and 42.2 to provide compounds of Formulae 51 and 52, respectively.

Example 45

Synthesis of Representative Compounds of Formula 53

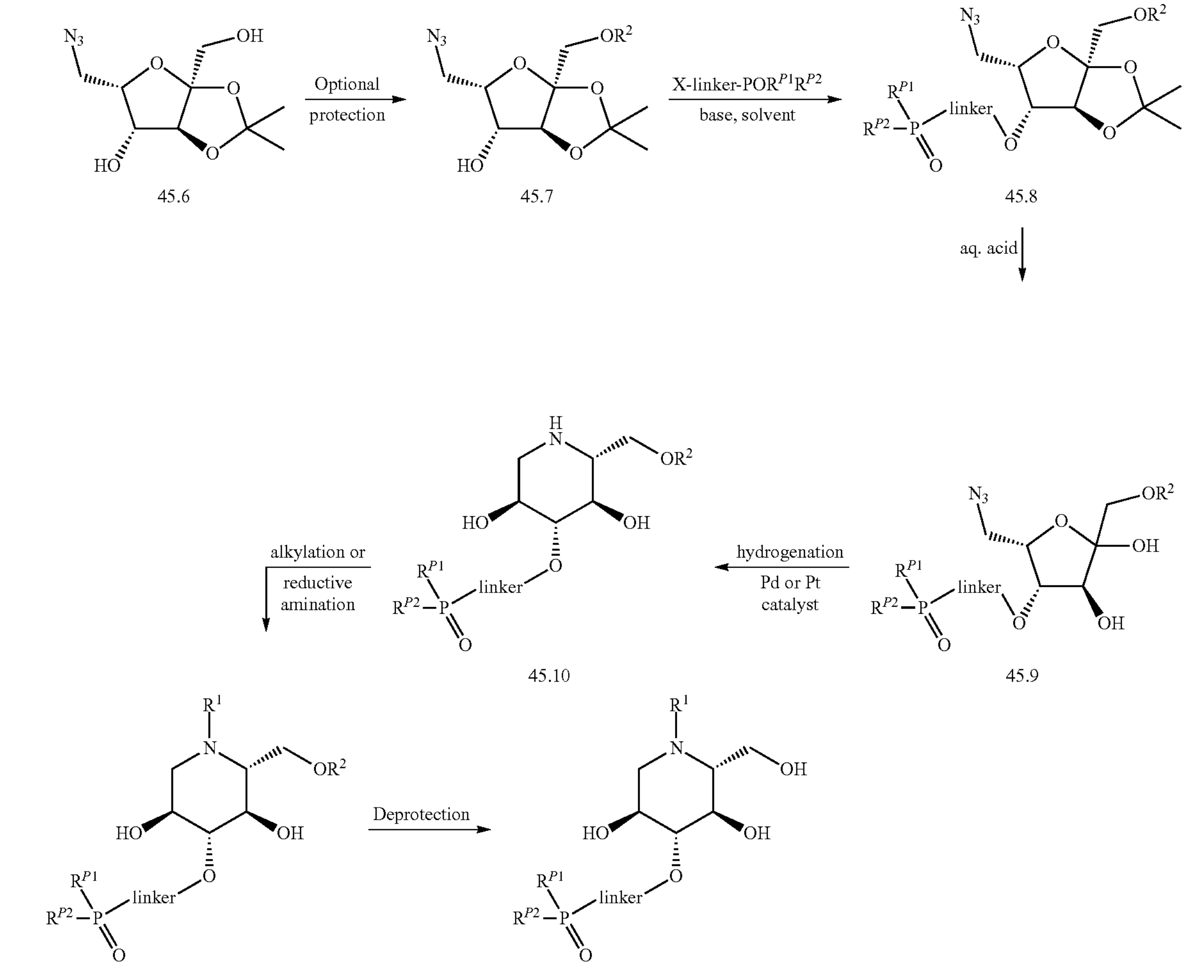

45.6 45.7 45.8 45.9 45.10 45.4

Representative compounds of the invention can be prepared as illustrated above. In *J. Carbohydrate Res.* 1989, 163, the synthesis of azide 45.6 was fully described using L-sorbose as starting material. Preparation of phosphonate 45.4 is outlined above. Selective protection of the primary alcohol in 45.6 gives alcohol 45.7 (see Greene and Wuts, *Protective Groups in Organic Synthesis*, 1999). Compound 45.7 in an appropriate aprotic solvent is treated with at least one equivalents of an appropriate organic or inorganic base. Addition of an appropriate electrophile bearing a leaving group affords compound 45.8.

Transformation of 45.8 to 45.10 is exemplified in *J. Carbohydrate Res.* 1989, 163. $R^1$ can be introduced to the amine nitrogen using an alkylation or reductive amination procedure. Final deprotection of the primary alcohol affords phosphonate 45.4. Note that $R^{P1}$ and $R^{P2}$ in the sequence from 45.8 to 45.4 do not need to be the same.

Suitable aprotic solvents include, but are not limited to dimethyl formamide, dimethyl sulfoxide, and N-methylpyrrolidinone. Suitable organic or inorganic base include, but are not limited to sodium hydride, potassium carbonate, and triethylamine. Suitable leaving groups include, but are not limited to, chlorine, bromine, iodine, p-toluenesulfonate, methanesulfonate, and trifluoromethanesulfonate.

Example 46

Synthesis of Representative Compounds of Formula 53

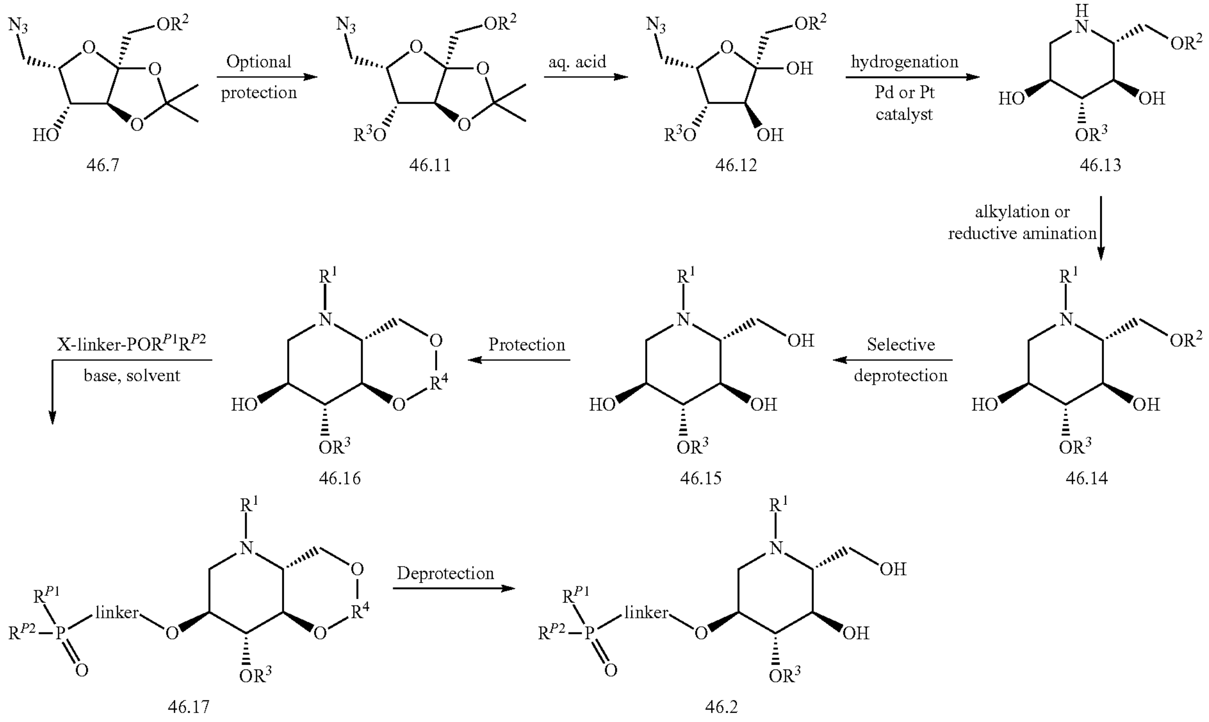

Representative compounds of the invention can be prepared as illustrated above. The details of several individual steps are described above in Example 45. Group $R^4$ is a cyclic protecting group that protects the 1,2-diol in 46.16. Note that $R^{P1}$ and $R^{P2}$ in 46.17 and 46.2 do not need to be the same.

Example 47

Synthesis of Representative Compounds of Formula 54

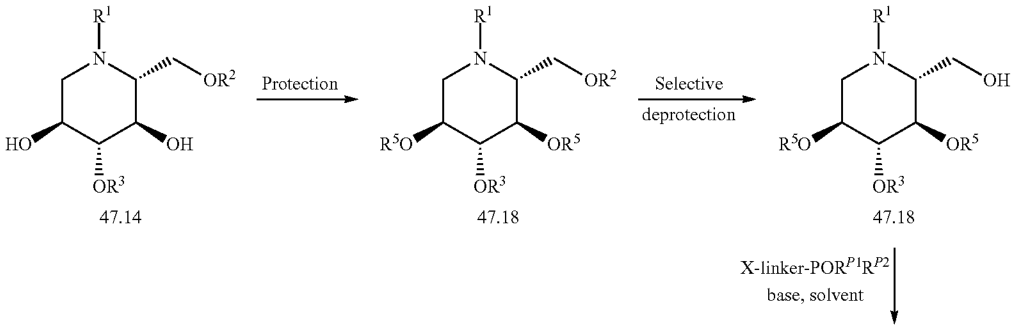

-continued
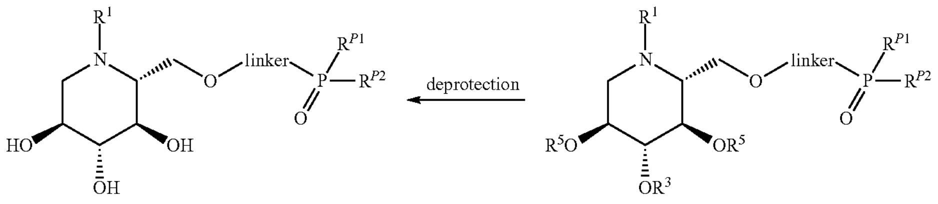
47.3 47.19
Representative compounds of the invention can be prepared as illustrated above. The preparation of 47.3 is outlined above. The details of individual steps are described in Example 45. Note that $R^{P1}$ and $R^{P2}$ in 47.18, 47.19 and 47.3 do not need to be the same.
Example 48
Synthesis of Representative Compounds of Formula 56
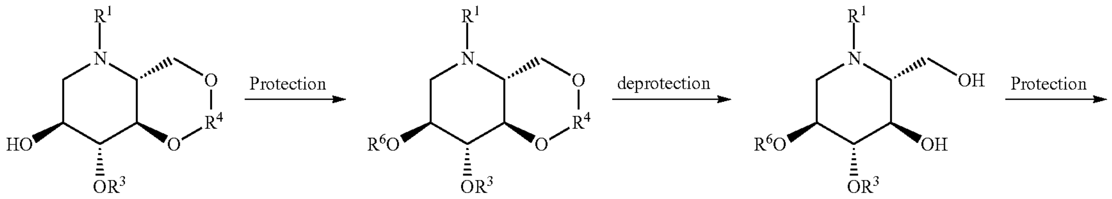
48.16 48.20 48.21
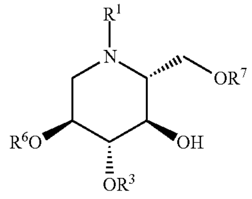
48.22
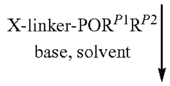
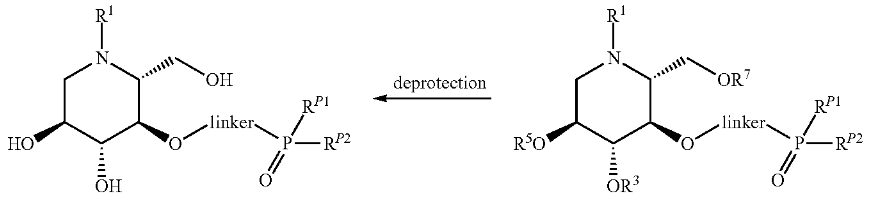
48.5 48.23

Representative compounds of the invention can be prepared as illustrated above. The details of each individual step are outlined in Example 45. Note that $R^{P1}$ and $R^{P2}$ in 48.23 and 48.5 do not need to be the same.

Example 49

Synthesis of Representative Compounds of Formula 57

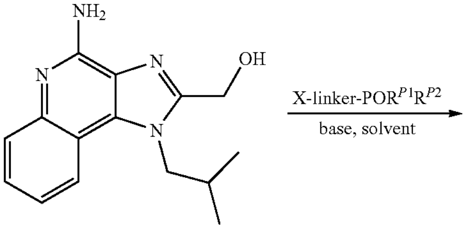

49.5

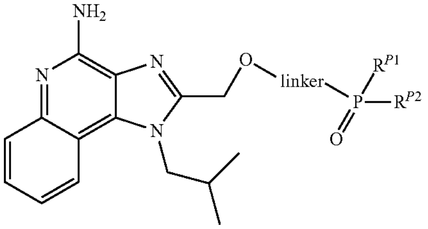

49.6

Representative compounds of the invention can be prepared as illustrated above. The preparation of 49.5 is described in WO 92/15582 A1 page 18 line 30 to page 19 line 14. Compound 49.5 in an appropriate aprotic solvent can be treated with at least one equivalent of an appropriate organic or inorganic base. An appropriate electrophile bearing a leaving group (X) containing a phosphonate, such as diisopropyl bromomethylphosphonate, is added to produce compound 49.6.

Suitable aprotic solvents include, but are not limited to, dimethyl formamide, dimethyl sulfoxide, and N-methylpyrrolidinone. Suitable organic or inorganic base include, but are not limited to, sodium hydride, potassium carbonate, and triethylamine. Suitable leaving groups include, but are not limited to, chlorine, bromine, iodine, p-toluenesulfonate, methanesulfonate, and trifluoromethanesulfonate.

Example 50

Synthesis of Representative Compounds of Formula 58

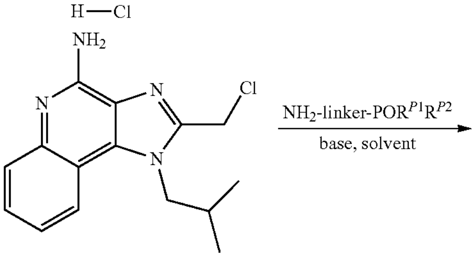

50.7

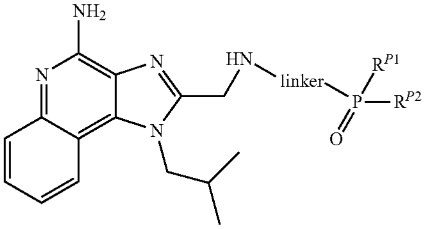

50.8

The preparation of 50.7 is described in WO 92/15582 A1 page 22 line 28 to page 23 line 3. Compound 50.7 in an appropriate solvent can be treated with a suitable amine containing a phosphonate group, and an appropriate base to produce phosphonate 50.8. Suitable bases include, but are not limited to, N-methylmopholine, diisopropylethylamine, and potassium carbonate. Suitable aprotic solvents include, but are not limited to, DMF, DMPU, and NMP.

Example 51

Synthesis of Representative Compounds of Formula 59

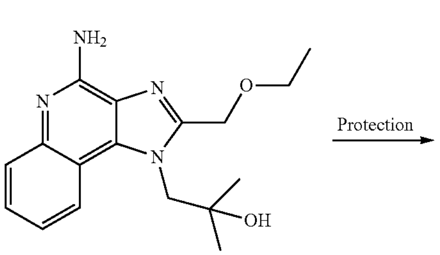

51.1

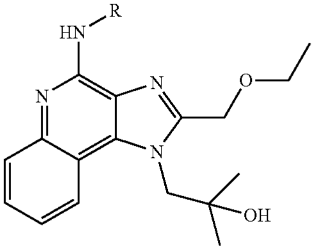

51.9

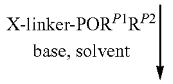

-continued

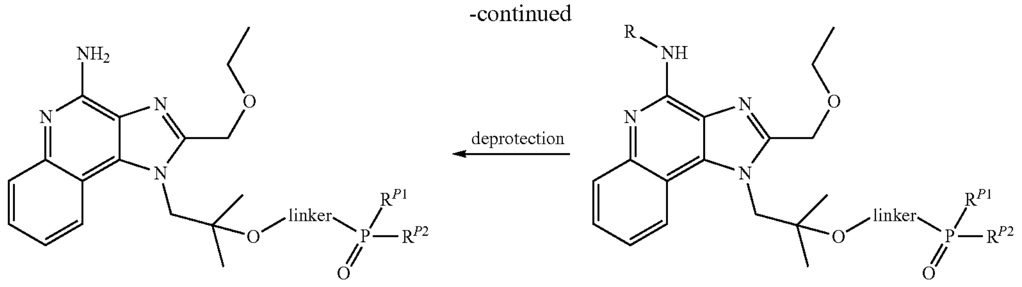

51.11 51.10

Representative compounds of the invention can be prepared as illustrated above. The amino group in 51.1 can be protected with an appropriate protecting group to give 51.9. Compound 51.9 in an appropriate aprotic solvent can be treated with at least one equivalent of an appropriate organic or inorganic base. An appropriate electrophile bearing a leaving group (X) containing a phosphonate, such as diisopropyl bromomethylphosphonate, is added to produce compound 51.10. Appropriate deprotection procedure will convert 51.10 to 51.11.

Suitable aprotic solvents include, but are not limited to, dimethyl formamide, dimethyl sulfoxide, and N-methylpyrrolidinone. Suitable organic or inorganic base include, but are not limited to sodium hydride, potassium carbonate, and triethylamine. Suitable leaving groups include, but are not limited to, chlorine, bromine, iodine, p-toluenesulfonate, methanesulfonate, and trifluoromethanesulfonate.

Example 52

Synthesis of Representative Compounds of Formula 60

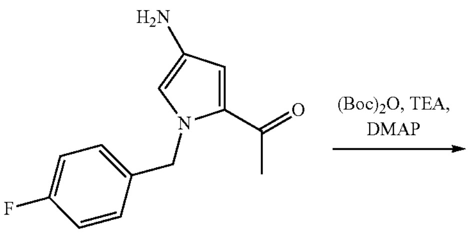

52.1a
(WO99/62513,
page 135, line 15)

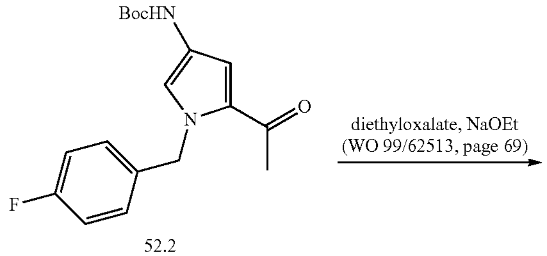

52.2

-continued

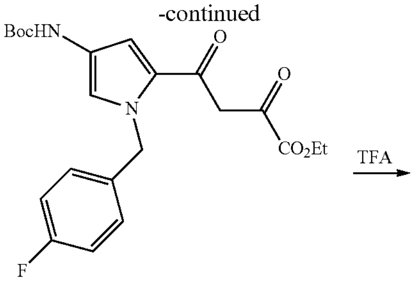

52.3

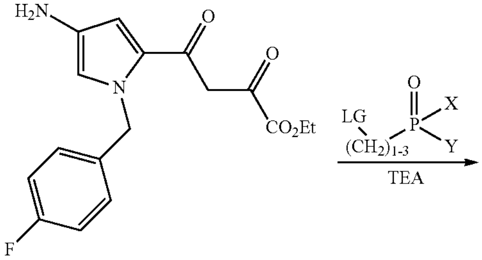

52.4

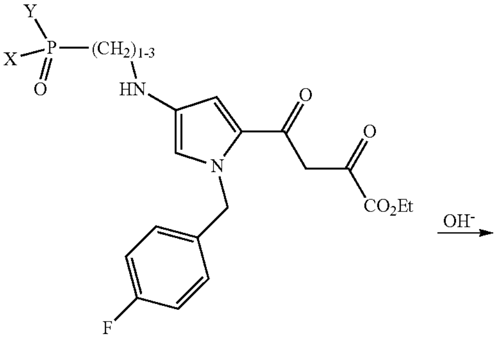

52.5

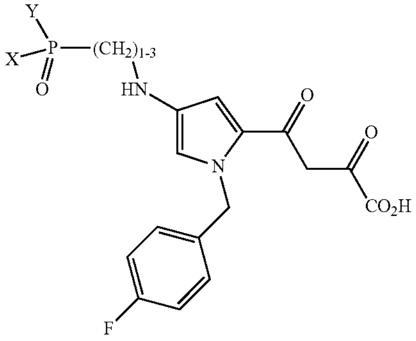

52.1

Representative compounds of the invention can be prepared as illustrated above. The phosphorous-containing compounds can be readily prepared according to conventional synthetic procedures where a phosphonate-containing group may be attached to the starting compound using established chemical processes. The preparations may be carried out from the precursor compounds described in WO 99/62513. The methods for these conversions from precursor compounds to the phosphorous-containing compounds are described in *Comprehensive Organic Transformations*, Richard C. Larock, ed, VCH, 1989*; Comprehensive Organic Synthesis*, Barry M. Trost and Ian Fleming eds., Pergamon Press, 1991. Protection of functional groups during the transformations is described in *Protective Groups in Organic Synthesis*, Theodora W. Greene and Peter G. M. Wuts, eds., Wiley, 1999.

Examples 53-58 illustrate syntheses of Formula 61. The phosphorous-containing compounds of the present invention with formula 61 can be readily prepared according to the conventional synthetic procedures exemplified in Examples 53-58. The preparations may be carried out from the precursor compounds described in WO 00/39085, WO 00/75122, WO 01/00578 and WO 01/95905. The methods for these conversions from precursor compounds to the phosphorous-containing compounds are described in *Comprehensive Organic Transformations*, Richard C. Larock ed., VCH, 1989*; Comprehensive Organic Synthesis*, Barry M. Trost and Ian Fleming eds., Pergamon Press, 1991. Protection of function groups during the transformation is described in *Protective Groups in Organic Synthesis*, Theodora W. Greene and Peter G. M. Wuts, eds., Wiley, 1999. For Examples 53-55: In one embodiment of the invention, Z can be carbon; in another embodiment of the invention, Z can be nitrogen.

Example 53

General Route to Representative Compounds of Formula 61

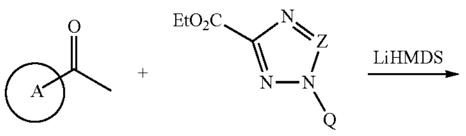

53.1 53.2

(WO 00/75122, page 52, line 7)

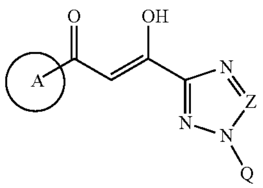

53.3

Representative compounds of the invention can be prepared as illustrated above. Compounds 53.1 and 53.2 can be converted to compound S3.3 under condensation condition in the presence of the base such as lithium bis(trimethylsily) amide (WO 00/75122).

Example 54

General Route to Representative Compounds of Formula 61

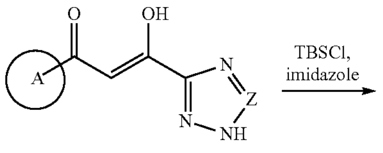

54.1
(WO 00/75122,
page 48 line 15)

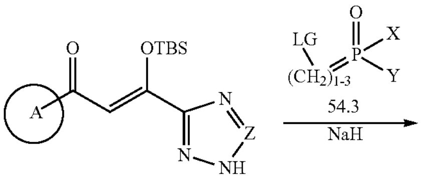

54.3

54.2

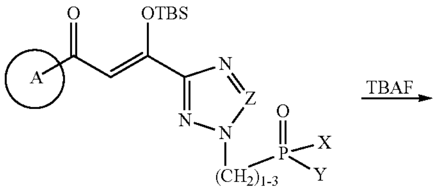

54.4

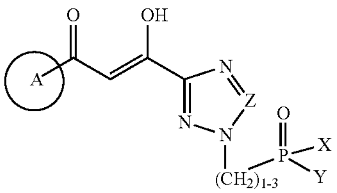

54.5

Representative compounds of the invention can be prepared as illustrated above. Prop-2-enone derivative 54.1 can be protected as a silyl ether such as a TBS ether, as in 54.2. Alkylation of silyl-protected 54.2 with phosphonate 54.3, where LG is OTf, Br, or Cl, is accomplished according to methods described in *J. Heterocyclic Chem.* 1995, 32, 1043-1050 and *Bioorg. Med. Chem. Lett.* 1999, 9, 3075-3080. Phosphonate 54.5 is obtained upon removal of the silyl protection group of 54.4, using a suitable reagent such as tetrabutylammonium fluoride (TBAF).

Example 55

General Route to Representative Compounds of Formula 61

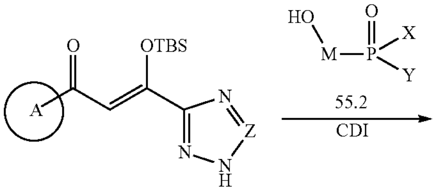

55.1

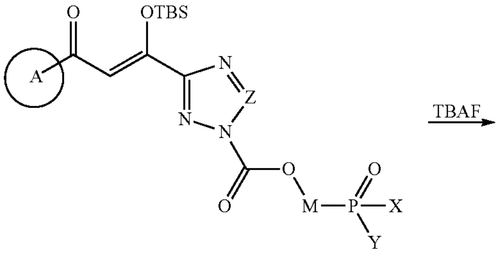

55.3

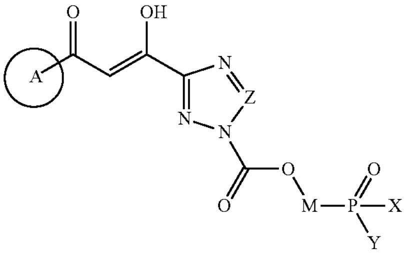

55.4

Representative compounds of the invention can be prepared as illustrated above. A carbamate moiety can be used to connect hydroxy-phosphorous compound 55.2 to heterocycle 55.1. Commonly used reagents such as CDI can are useful in such transformations. Removal of the TBS group of 55.3 provides phosphonate 55.4.

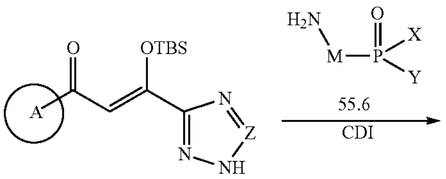

55.5

-continued

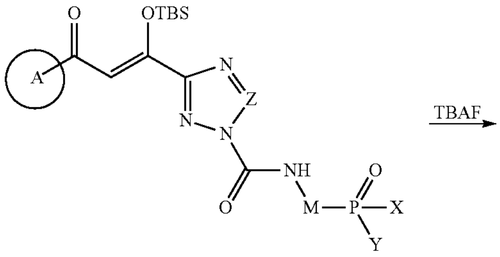

55.7

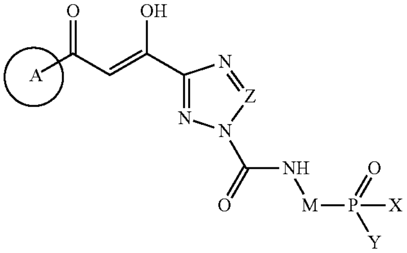

55.8

A urea moiety can be used to connect hydroxy-phosphorous compound 55.6 to heterocycle 55.5. Commonly used reagents such as CDI can are useful in such transformations. Removal of the TBS group of 55.7 provides phosphonate 55.8.

Example 56

General Route to Representative Compounds of Formula 61

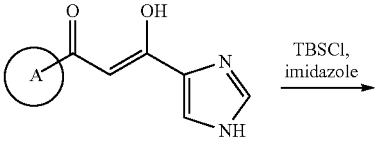

56.1
(WO 01/00578,
page 96, line 15-
page 97, line 19)

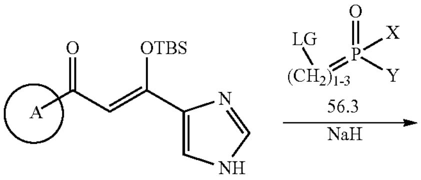

56.2

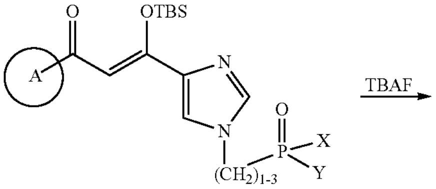

56.4

-continued
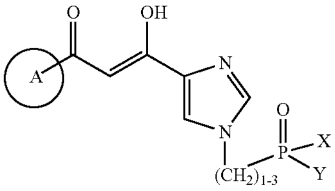
56.5
Representative compounds of the invention can be prepared as illustrated above.
Example 57
Synthesis of Representative Compounds of Formula 61
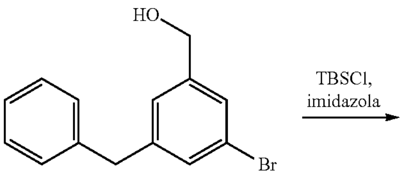
57.1
(WO01/00578,
page 107 line 15-
page 108 line 16)
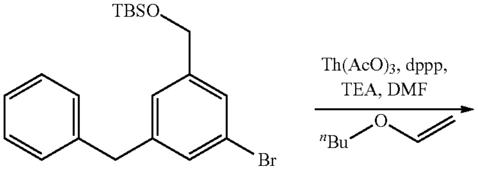
57.2
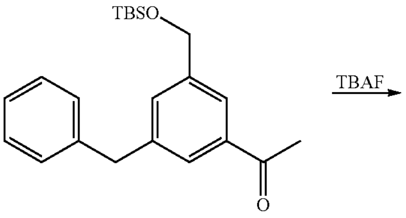
57.3
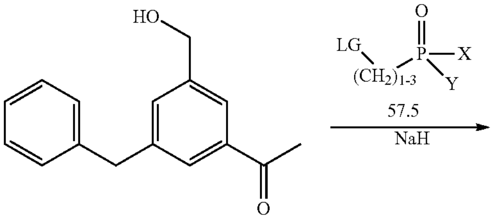
57.4
-continued
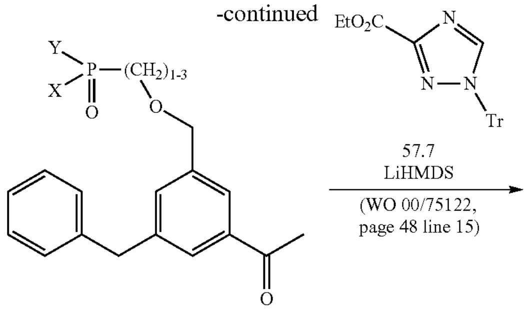
57.6
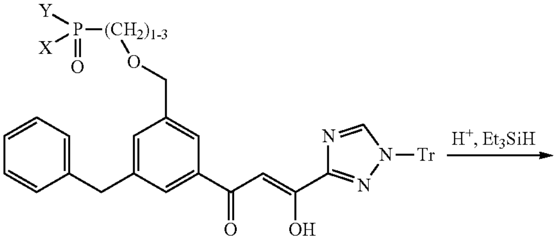
57.8
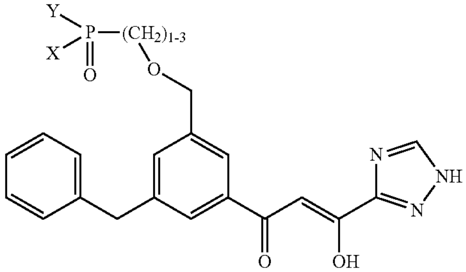
57.9
Representative compounds of the invention can be prepared as illustrated above.
Example 58
Synthesis of Representative Compounds of Formula 61
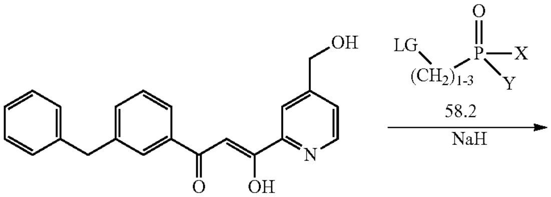
58.1
(WO01/00578,
page 192 line 11)
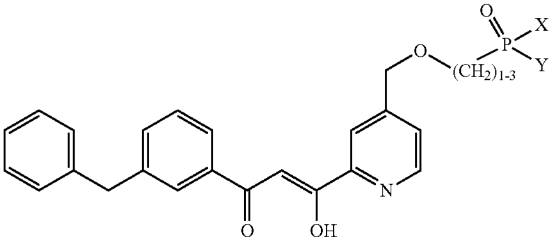
58.3

Representative compounds of the invention can be prepared as illustrated above.

Examples 59 and 60

Synthetic methodologies and intermediate compounds that can be used to prepare analogs of formulae D, E, F and G are described in Examples 59 and 60. These compounds are representative examples of compounds of Formulae 62-65.

D

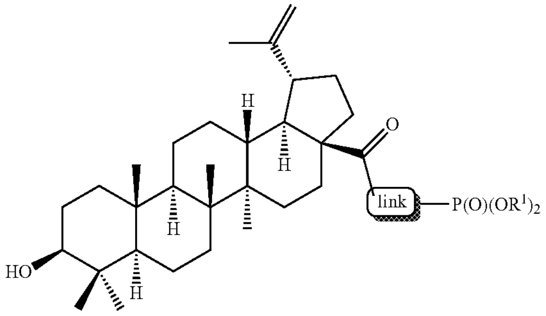

F

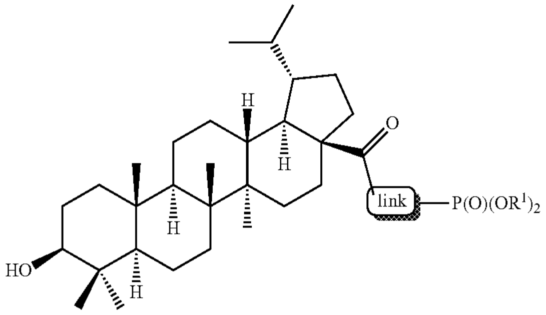

-continued

E

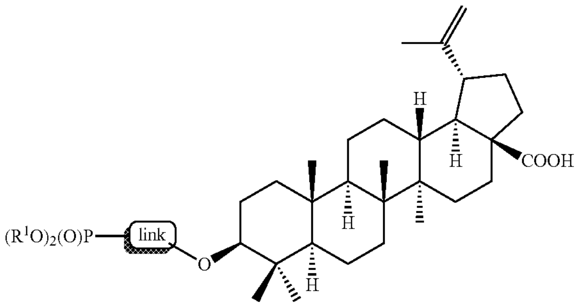

G

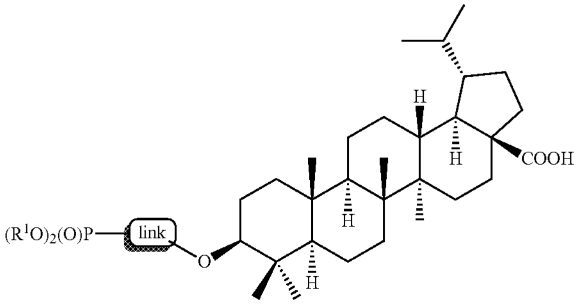

$R^1$ = H, alkyl, aryl, haloalkyl, alkenyl, aralkyl, aryl

Example 59

Synthesis of Representative Compounds of Formulae 62 and 64

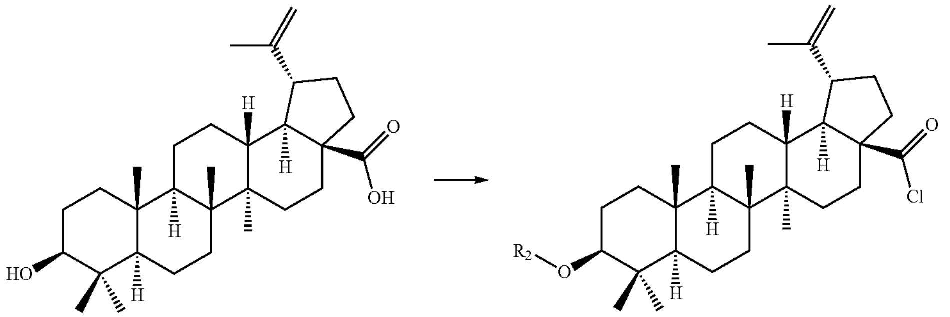

59.1.1

$R_2$ = protection group 59.2

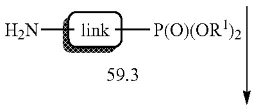

59.3

-continued

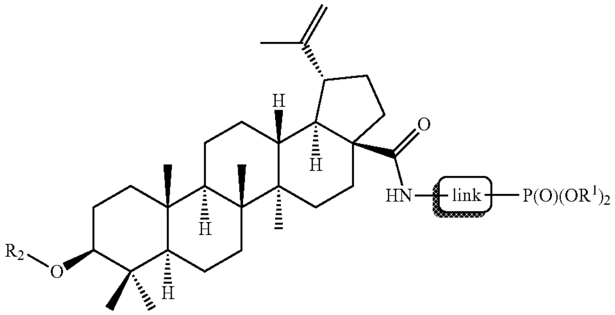

59.4

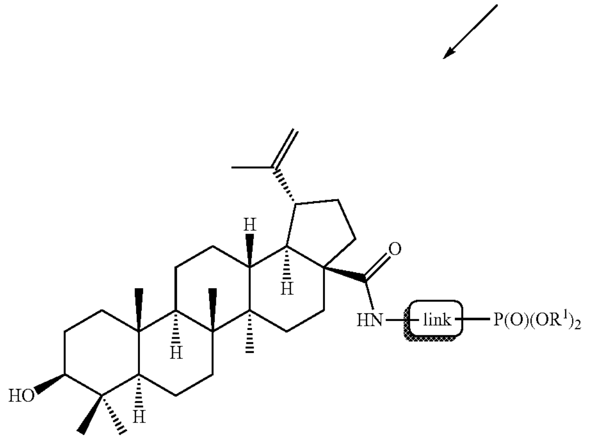

59.1

Representative compounds of the invention can be prepared as illustrated above. Betulinic Acid (59.1.1) may be purchased from Sigma (Cat. No. 85505-7) or alternatively isolated from the stem bark of *Ziziphus mauriitiana* Lam. (Rhamnaceae) as described in WO 02/16395 A1. Dihydrobetulinic acid is obtained by hydrogenation of betulinic acid as described in WO 02/16395 A1. Example 59 illustrates the synthesis of betulinic and diydrobetulinic derivatives D and F.

The hydroxyl group of betulinic acid 59.1.1 is first protected with a suitable protecting group, such as benzyl ether as described in Greene and Wuts, *Protecting Groups in Organic Synthesis*, third edition, John Wiley and Sons, Inc. The protected hydroxyl is then converted into the acid chloride 59.2 which is then treated with an amine phosphonic acid of the general formula 59.3 to form the amide 59.4. Deprotection of the hydroxyl gives products of the general formula 59.1. Dihydrobetulinic acid can be treated in exactly the same manner as 59.1 to give products of the general formula F.

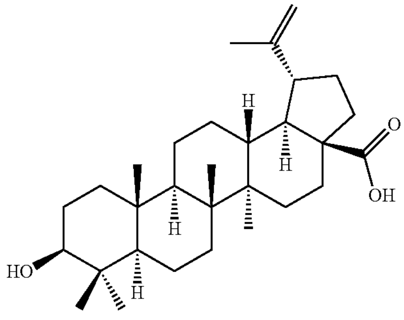

59.1.1

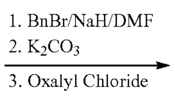

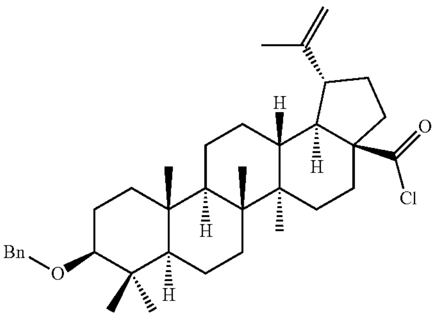

59.5

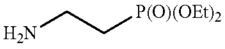

59.6

-continued

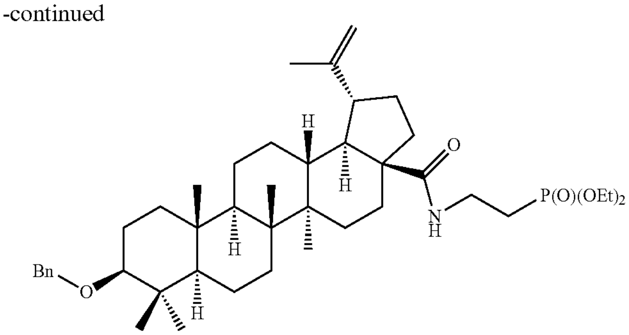

59.7

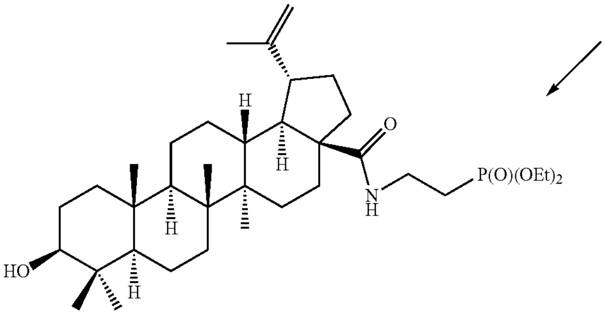

59.8

For instance, betulinic acid is dissolved in a suitable solvent such as, DMF and treated with 2 equivalents of benzyl bromide along with an appropriate base such as NaH. The undesired benzyl protected carboxylate is removed by treatment with aqueous $K_2CO_3$ to give the benzyl ether which is then treated with 4 equivalents of oxalyl chloride in a suitable solvent, such as chloroform or methylene chloride (as described in *J. Med. Chem* 2002, 45, 4271-4275) to give 59.5. Acid chloride 59.5 is then treated with 2 equivalents of diethyl 2-aminoethyl-1-phosphonate 59.6 (prepared as described in *J. Med. Chem.* 1998, 41, 4439-4452), along with 4 equivalents of a tertiary amine such as, for example; triethylamine to give the amide 59.7. Final deprotection of the benzyl ether is achieved by treatment with lithium di-tert-butylbiphenyl in THF at −78° (as described in *J. Am. Chem. Soc.* 1991, 113, 8791-8796) followed by purification using reverse-phase or normal phase chromatography to give 59.8. Using the above procedure, but employing different phosphonate reagents 59.3 in the place of 59.6, the corresponding products of general type D and F bearing different linking groups can be prepared.

Example 60

Synthesis of Representative Compounds of Formulae 63 and 65

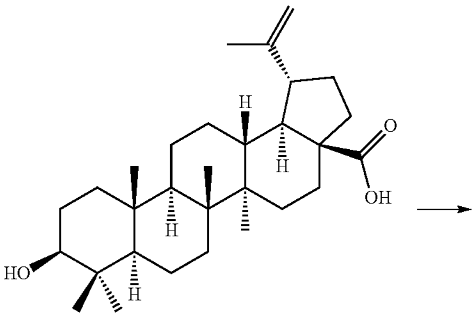

60.1

-continued

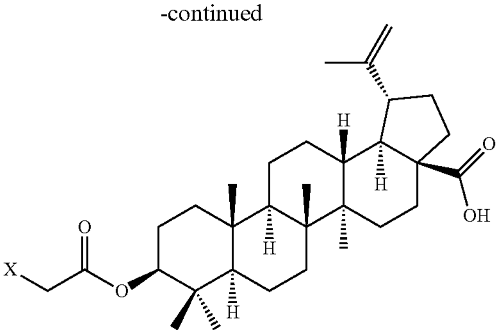

X = I, Br, Cl 60.9

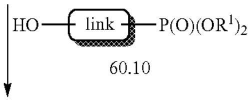

60.10

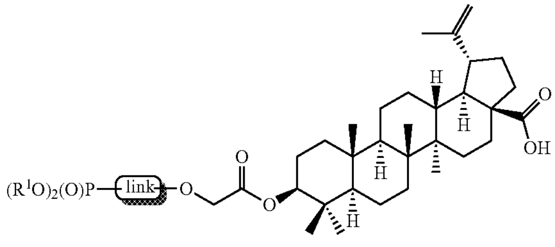

60.11

Representative compounds of the invention can be prepared as illustrated above. Example 60 describes the synthesis of phosphonate derivatives of betulinic and dihydrobetulinic acid of the general formula E and G. Betulinic Acid 60.1 is treated with, for example, an appropriately substituted acid chloride (as described in *Tetrahedron Lett.* 1997, 38, 4277-4280) to form halide derivative 60.9. Halide 60.9 is then treated with a hydroxyl phosphonic acid of the general formula 60.10 along with a suitable base to give compound 60.11. Dihydrobetulinic acid can be treated in exactly the same manner as 60.1 to give products of the general formula G.

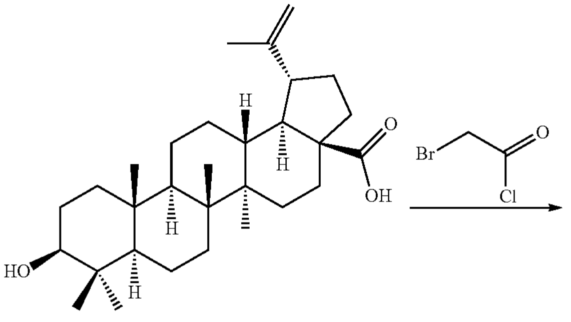

60.1

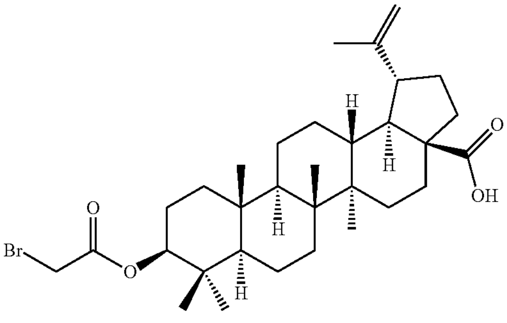

60.12

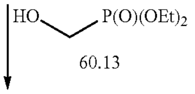

60.13

-continued

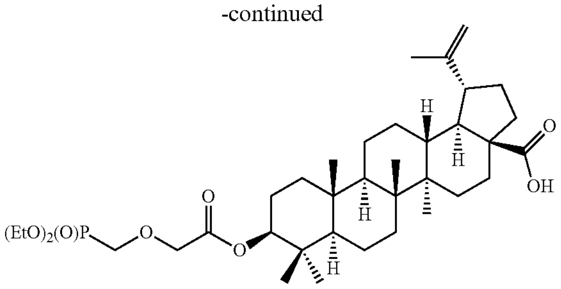

60.14

For instance, 60.1 is dissolved in a suitable solvent such as THF, treated with 2 equivalents of a suitable base, such as triethylamine, and 2 equivalents of bromoacetyl chloride to give compound 60.12. The bromo derivative 60.12 is then treated with diethyl hydroxymethylphosphonate (which can be purchased from Sigma (Cat. No. 39262-6)) along with a suitable base, such as $Cs_2CO_3$ (as described in *Tetrahedron Lett.* 1999, 40, 1843-1846) to give compound 60.14. Dihydrobetulinic acid can be treated in exactly the same manner to give products of the general formula G. Using the above procedure, but employing different phosphonate reagents 60.10 in the place of 60.13, the corresponding products E and G bearing different linking groups can be prepared.

Examples 61-63

The analogs described in Examples 61-63 show a methylene group as the linker. The linker may, however, be any other group described in this specification.

Example 61

General Route to Representative Compounds of Formula 66

Cyclobutanes:

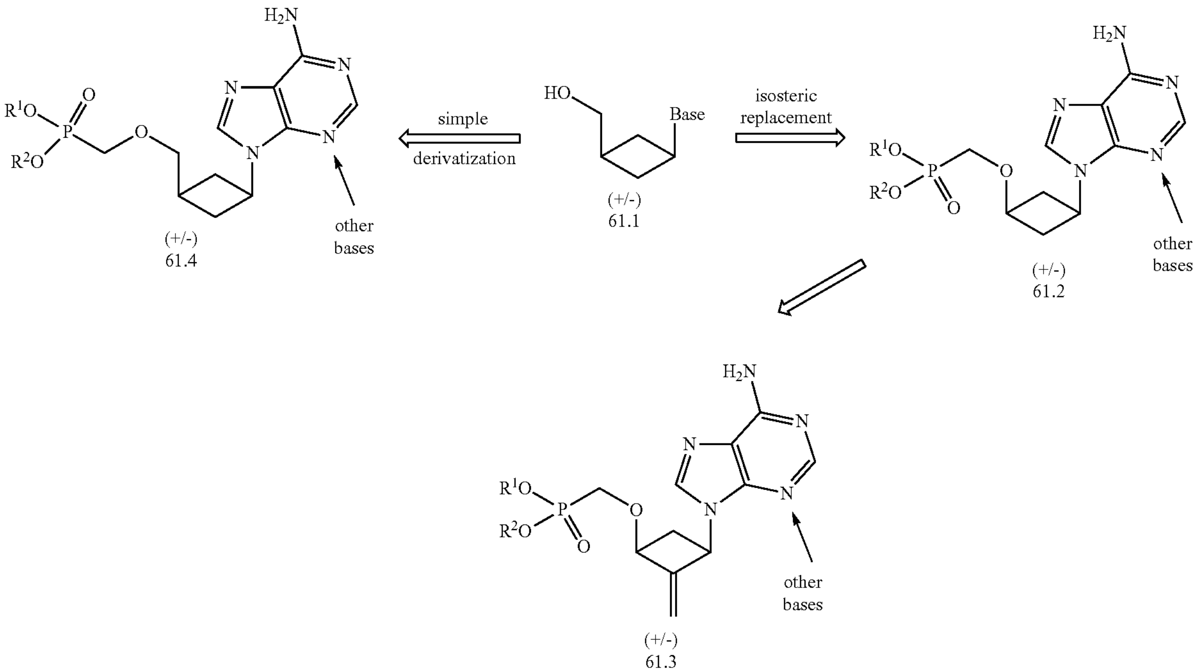

(+/-) 61.4 (+/-) 61.1 (+/-) 61.2 (+/-) 61.3

-continued

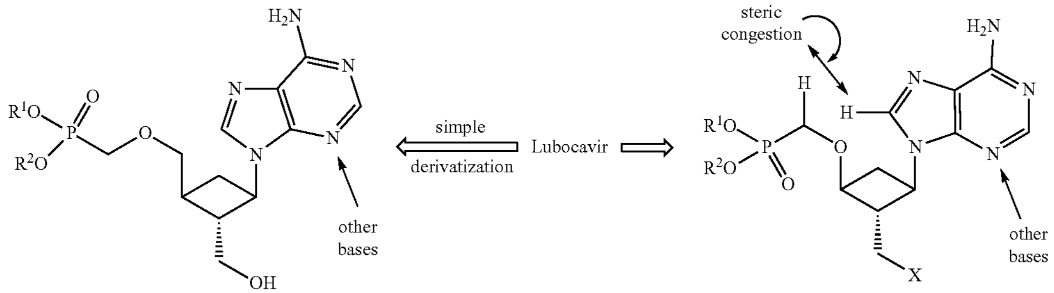

(+/-)
61.5

(+/-)
61:6 X = OH
61.7: X = F or CN

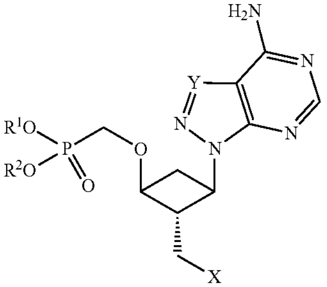

(+/-)
61:8 X = F or CN; Y = CH
61.9: X = F or CN; Y = N

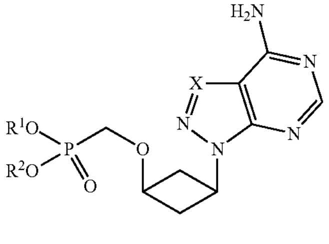

(+/-)
61:10X = CH or N $R^1$ = H, alkyl, aryl, haloalkyl, alkenyl, aralyl, aryl
$R^2$ = H, alkyl, aryl, haloalkyl, alkenyl, aralyl, aryl 4-Membered Ring Nucleoside Series:

Representative compounds of the invention can be prepared as illustrated above. Compound 61.1 (Base=G), described in the literature, was shown to have reasonable anti-HIV activity (50-100 μM, cf. lubocavir 30 μM). Therefore, one target is its isosteric phosphonate derivative 61.2. Also, compound 61.1 can be derivatized to its phosphonate 61.4. In a similar manner, one may add a phosphonate group onto lubocavir to prepare carbocyclic 61.5, or alternatively carbocyclic isostere 61.6. Compounds 61.6 have a hydroxyl group analogous to the 3'-hydroxyl group of natural nucleosides. Such compounds may be incorporated into elongating strands by host DNA polymerases, a phenomenon that may be associated with both carcinogenicity and mitochondrial toxicity. Replacement of hydroxyl groups with fluorine atoms are established in medicinal chemistry. A well-known example is the replacement of the terminal hydroxyl group of the antibiotic chloramphenicol with a fluorine atom, providing the superior drug florfenicol. In the case of 61.6 (or 61.8 and 61.9), the fluorine maintains many beneficial H-bonding interactions with RT that the pseudo-3'-hydroxyl of 61.5 provided, but will not provide a handle for incorporation into nucleic acids.

Considerations in the chemistry of derivatives 61.8/61.9: A protected version of A maybe required (using, e.g., a pivalate) or a masked version of A (methoxy in lieu of aniline). If a masked version of A is required, synthesis of the base will be required. Yields for these processes in the synthesis of cyclobut-A and G derivatives are good-to-excellent. Fluorination reactions in the presence of unprotected A are well precedented to go in good yield (~90%) when pyridine is used as a solvent. Acidic deprotection should not cause de-glycosidation of base since there is no formal glycosidic linkage (O—C—N). Phosphonylation should proceed as for other derivatives in-house. All reactions proceed with useful kinetic diastereoselectivity. In base introduction reactions, equilibration conditions may be used to improve the kinetic diastereoselection ratio. All compound made by this route are racemic. Enantiomerically pure compounds may be prepared by methods known to those of skill in the chemical arts.

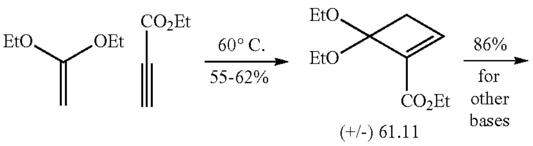

(+/-) 61.11

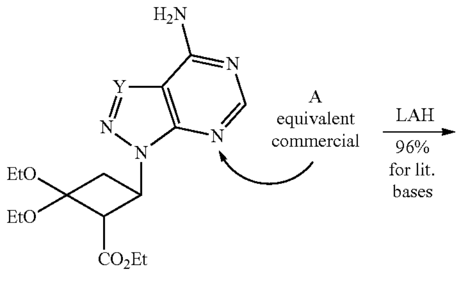

Y = N or CH
61.12

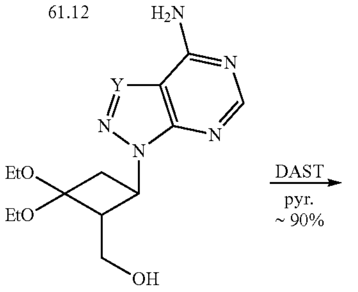

61.13

-continued

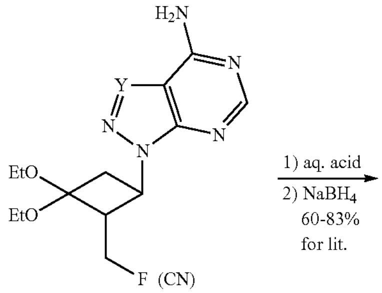

61.14

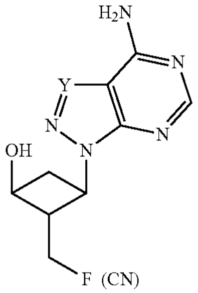

61.15

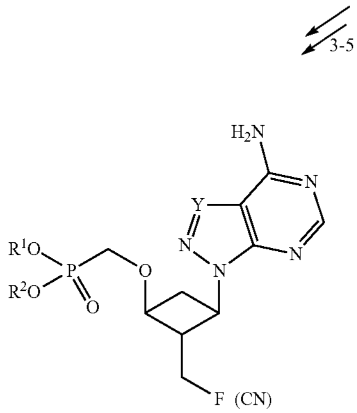

61.16

Illustrated above is a synthetic sequence for the preparation of compound 61.16. Other nucleotide bases may optionally be used in this synthetic sequence.

Example 62

Representative Compounds of Formula 67

Cyclopropyl Nucleoside Series 62.17

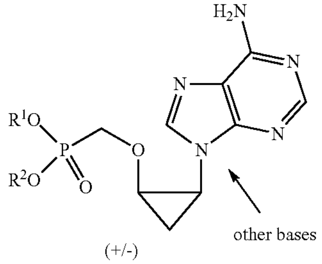

-continued 62.18

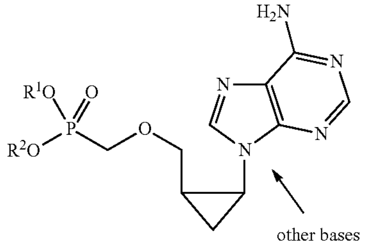

62.19

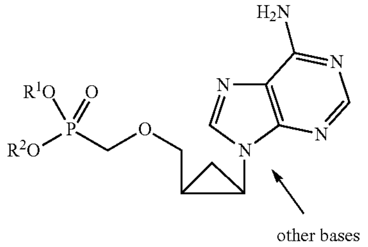

62.20

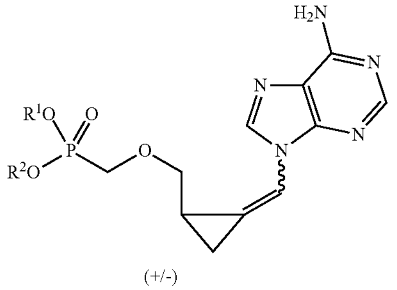

62.21

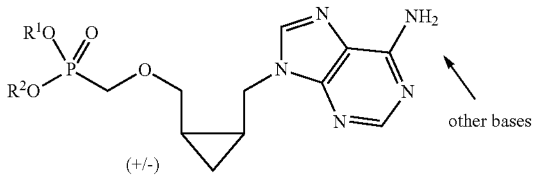

Representative compounds of the invention can be prepared as illustrated above. The synthesis of cyclopropyl nucleosides of type 62.18 and 62.19 is well documented by Chu and coworkers. Additional syntheses are reported by Csuk et al. Synthetic methods allow for the homochiral production of 62.18 and 62.19. Syntheses of compound types 62.17, 62.20, and 62.21 are also reported; these provide for racemic material.

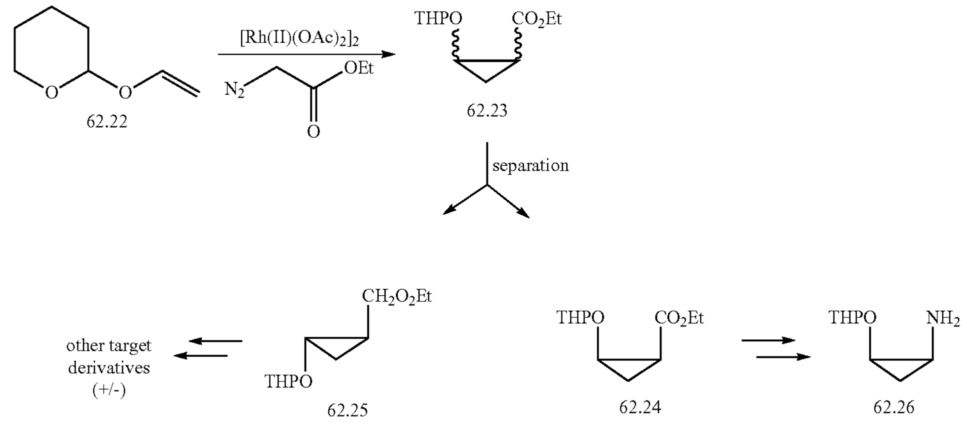

Considerations in the synthesis of 62.17: Literature reports are for industrial processes. Racemic products: diastereomers are produced by a non-stereoselective cyclopropanation reactions and separation of the desired isomer with cis cyclopropyl substituents from that with trans may require rigorous separation techniques or alternate synthetic preparations because of the presence of an additional stereocenter at the THP anomeric position, as shown above in 62.23.

Considerations in the synthesis of 62.18 and 62.19: For the D series (compound 62.18), synthesis of key intermediate 62.29 (see below) can be preformed in 10 steps in 6 pots (24% overall yield from an abundant starting material, 1,2:5,6-di-O-isopropylidine-D-mannitol. Purine bases can be constructed from free amine 62.29. Phosphonate synthesis proceeds well according to known methodology. For the L series, the starting material is vitamin C.

For D product

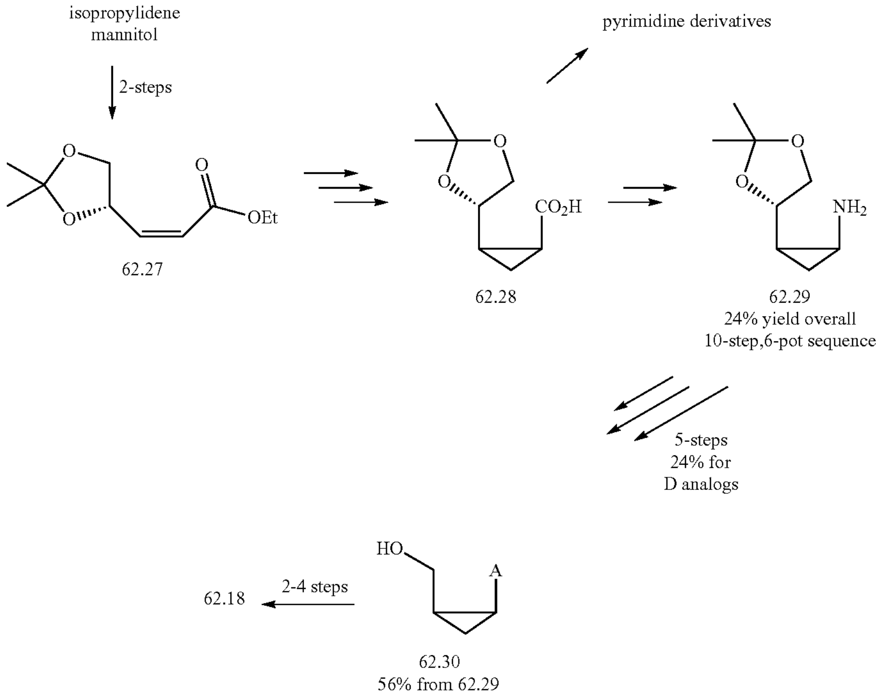

For L Product

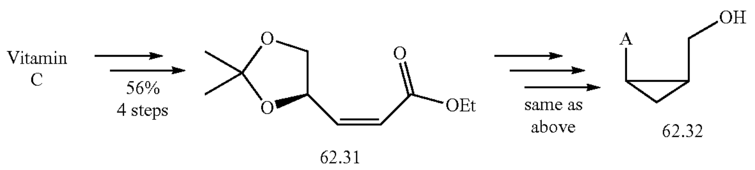

Example 63

Synthesis of Representative Compounds of Formula 68

Vinylic Nucleoside Series

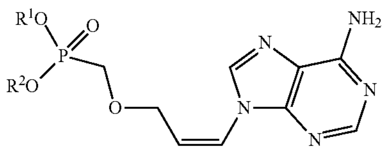

63.33 other bases

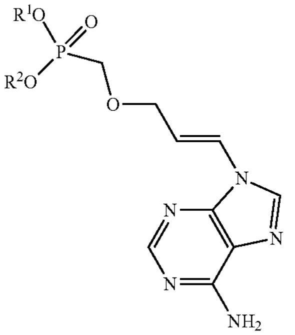

63.34 other bases

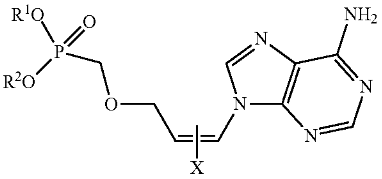

63.35 other bases

Representative compounds of the invention can be prepared as illustrated above. There are only a few reports of compound types 63.33 and 63.34 in the literature. Most reports provide for the syntheses of trans isomers 63.34. The one report that discusses cis isomers 63.33 does not state clear separation conditions from the mixture of cis and trans compounds formed. The cis isomers best resembles the geometry of the nucleoside antiviral agents and are therefore important compounds. Modeling studies indicate that 63.33 will be accommodated by the RT active site. However, when minimized in the RT active site side-by-side with tenofovir, some of the base stacking interactions that provide binding energy between the inhibitor and the template strand may be lost.

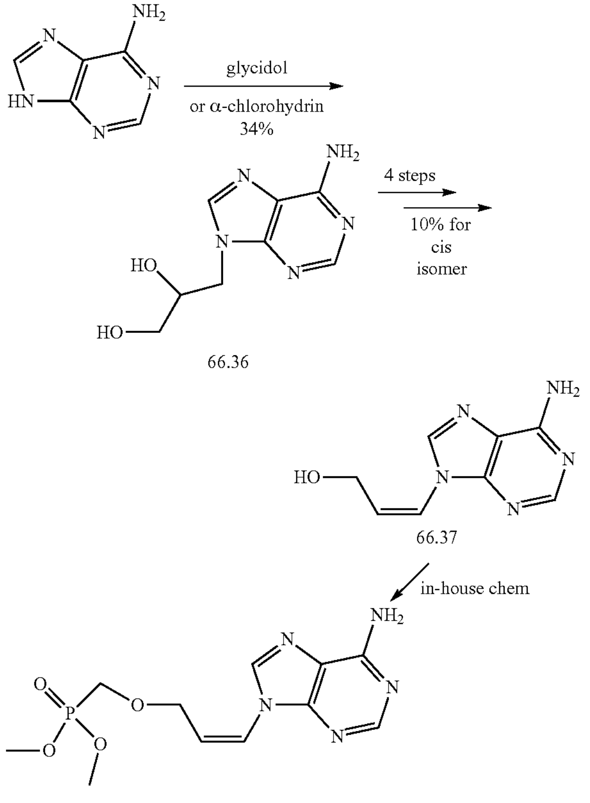

66.36

66.37

66.37

Example 64

Synthesis of Representative Compounds of Formula 69

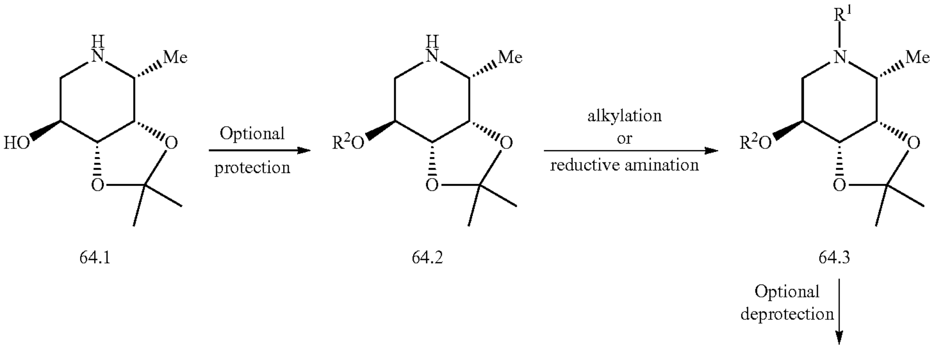

64.1 64.2 64.3

-continued

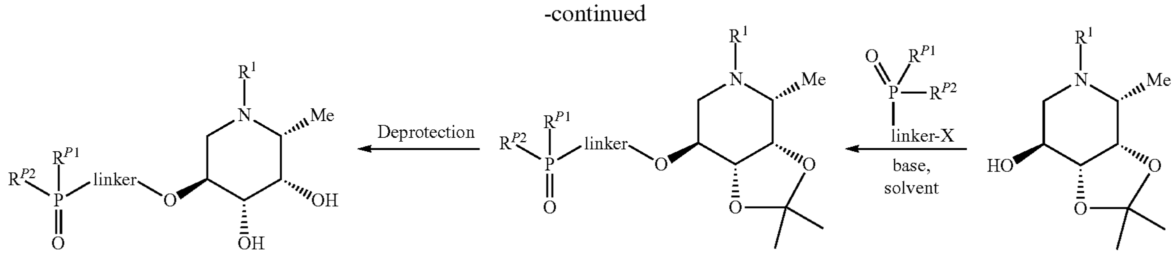

64.6 64.5 64.4

Representative compounds of the invention can be prepared as illustrated above. In WO 01/10429 A2, the synthesis of 64.1 was fully described using D-gulonolactone as the starting material. The secondary alcohol in 64.1 can be optionally protected with an appropriate protecting group (e.g. a silyl protecting group) to give 64.2 (See Greene and Wuts, *Protective Groups in Organic Synthesis*, 1999). Compound 64.3 can be optionally deprotected to give 64.4 containing the secondary alcohol. Compound 64.4 in an appropriate aprotic solvent can be treated with at least one equivalent of an appropriate organic or inorganic base. An appropriate electrophile bearing a leaving group is added to produce compound 64.5. Suitable aprotic solvents include, but are not limited to, dimethyl formamide, dimethyl sulfoxide, and N-methylpyrrolidinone. Suitable organic or inorganic base include, but are not limited to, sodium hydride, potassium carbonate, and triethylamine. Suitable leaving groups include, but are not limited to, chlorine, bromine, iodine, p-toluenesulfonate, methanesulfonate, and trifluoromethanesulfonate.

The isopropylidene group in 64.5 can be removed to provide phosphonate 64.6. Various procedures for the removal of the isopropylidene group are described in Greene and Wuts, *Protective Groups in Organic Synthesis*, 1999. Note that $RP^{P1}$ and $R^{P2}$ in 64.5 and 64.6 do not need to be the same.

A specific preparation of phosphonate 64.6 is illustrated above. The secondary alcohol in 64.7 can be protected with t-butyldimethylsilyl (TBDMS) group to give 64.8 (See Greene and Wuts, *Protective Groups in Organic Synthesis*, 1999). Compound 64.8 can be alkylated by treating a mixture of 64.8 and 64.9 with sodium cyanoborohydride. The aldehyde 64.9 can be prepared using the procedure outlined in below.

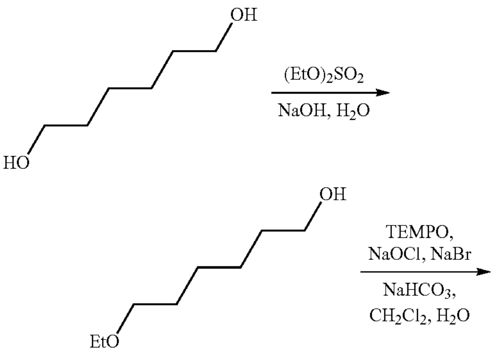

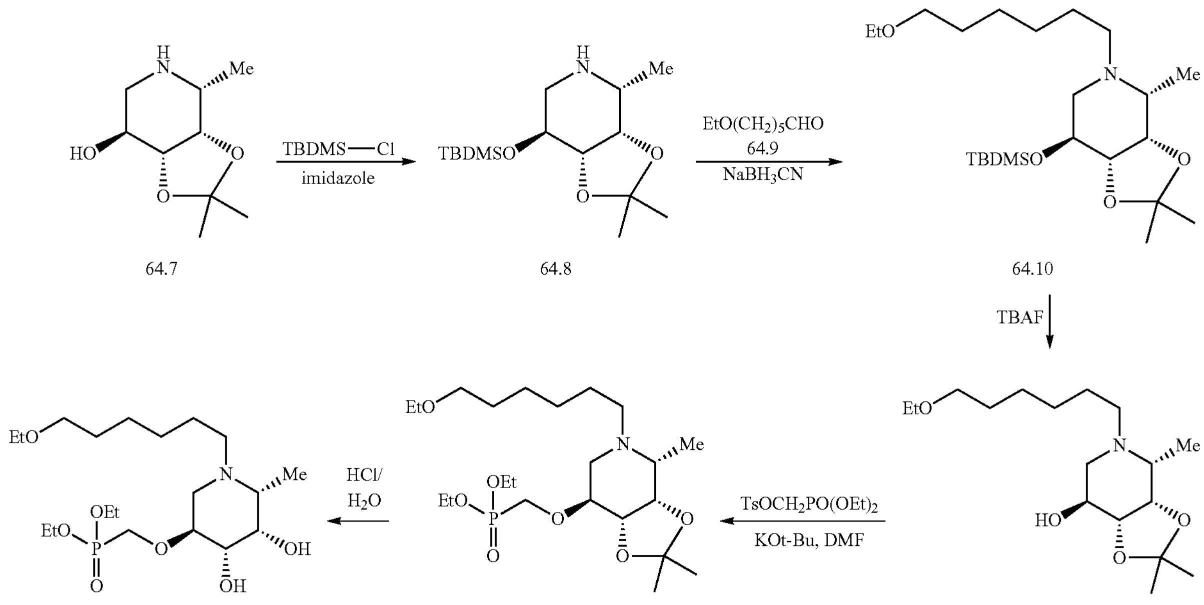

64.7 64.8 64.10

64.13 64.12 64.11

-continued

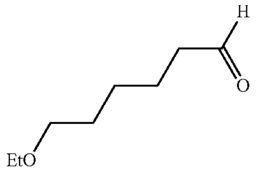

The tertiary amine 64.10 can be treated with tetrabutylammonium fluoride in THF to remove the TBDMS protecting group. Compound 64.11 can be treated with at least one equivalent of potassium tert-butoxide in dimethylformamide. The phosphonate-containing electrophile shown above is added to produce 64.12. The isopropylidene group in 64.12 can be removed by treating 64.12 with an aqueous solution of hydrochloric acid to give 64.13. The para-toluenesulfonate of diethyl hydroxymethylphosphonate can be prepared in a single step from diethyl hydroxymethylphosphonate and para-toluenesulfonyl chloride in pyridine and diethyl ether (see Holy, et al., *Collect. Czech. Chem. Commun.* 1982, 47, 3447-3463).

Example 65

Synthesis of Representative Compounds of Formulae 70 and 71

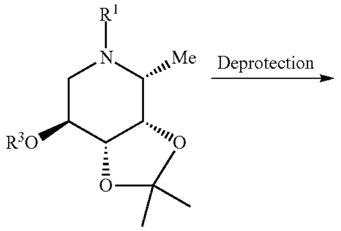

65.1

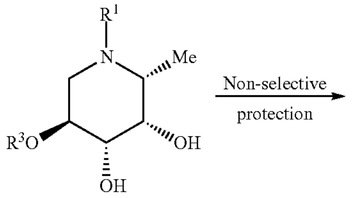

65.2

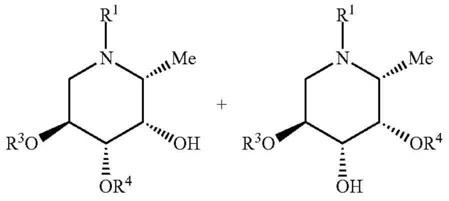

65.3 65.4

65.4 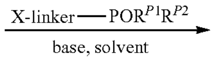

-continued

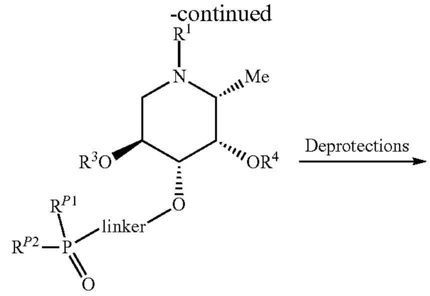

65.5

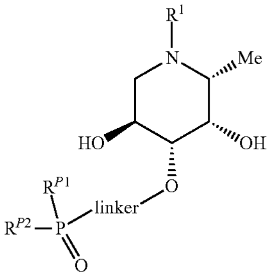

65.6

65.3 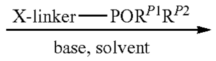

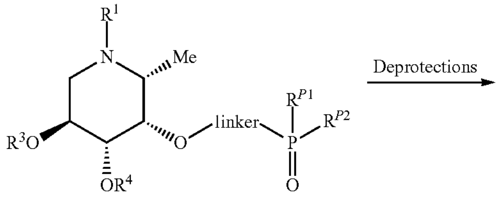

65.7

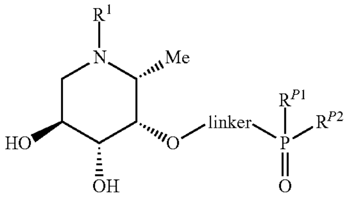

65.8

Representative compounds of the invention can be prepared as illustrated above. The synthesis of 65.1 can be performed as outlined in WO 01/10429 A2, using D-gulonolactone as the starting material. Treating 65.1 with hydrochloric acid can remove the isopropylidene group. The two secondary alcohols in diol 65.2 can be non-selectively protected with an appropriate protecting group to generate a mixture of 65.3 and 65.4. These two products can be converted to 65.6 and 65.8, respectively, using procedures described in Example 64 (from 64.1 to 64.6).

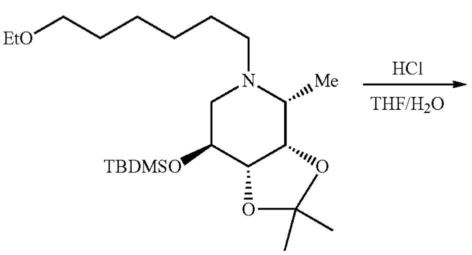

65.9

-continued

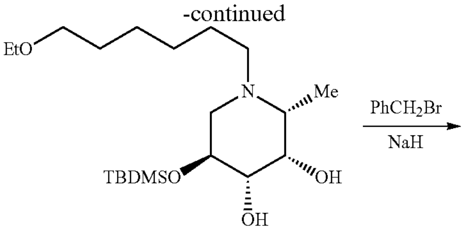

65.10

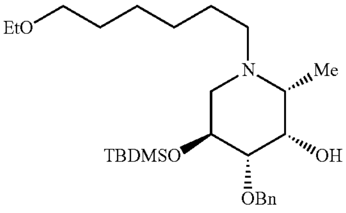

+

65.11

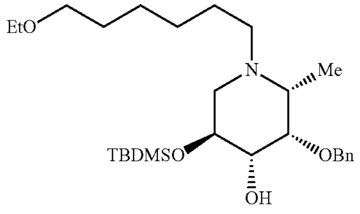

65.12

65.11
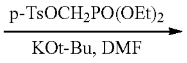

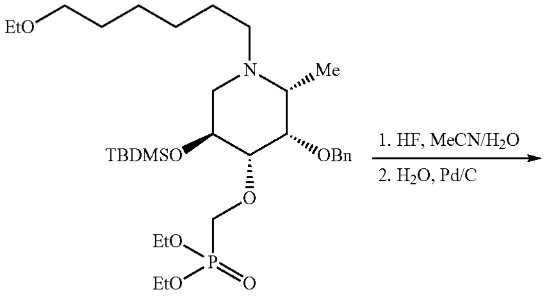

65.13

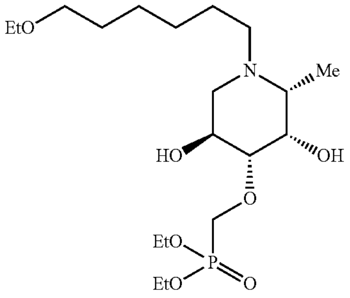

65.14

65.12
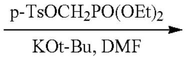

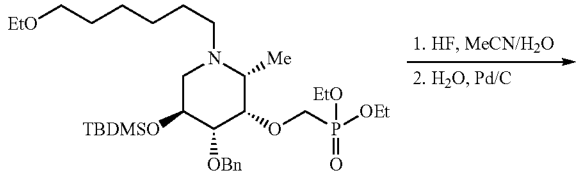

65.15

-continued

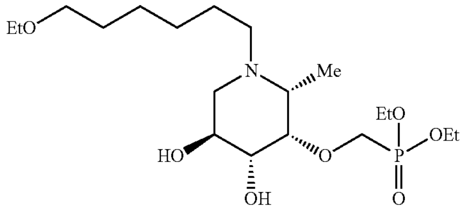

65.16

The preparation of specific examples of Compounds of Formulae 70 and 71 are illustrated above. The details about introducing and removing protecting groups can be found in Greene and Wuts, *Protective Groups in Organic Synthesis*, John Wiley and Sons, Inc., 1999. Other procedures are similar to those described in Example 64.

Example 66

Synthesis of Representative Compounds of Formula 72

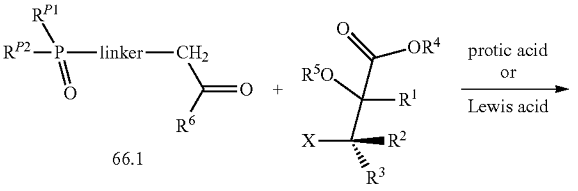

66.1

66.2

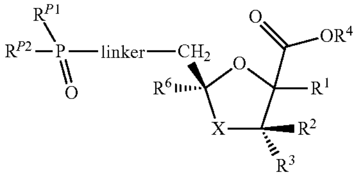

66.3

66.3
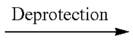

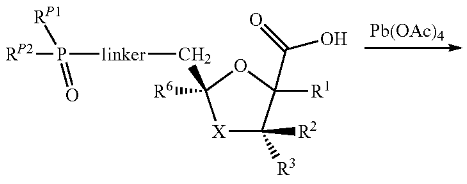

66.4

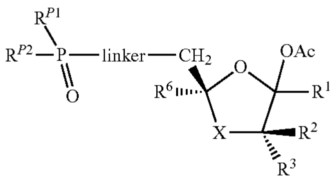

66.5

66.5
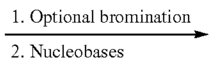

-continued

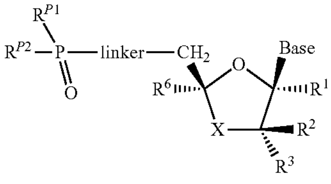

66.6

Representative compounds of the invention can be prepared as illustrated above. In the above scheme, $R^4$ and $R^5$ are appropriate protective groups. Group X is either hydroxyl (or oxygen) or thiol (or sulfur), or appropriately protected hydroxyl or thiol. Additionally, $R^5$ can be a cyclic protecting group for both the hydroxyl and X. The general method for the preparation of intermediates 66.3, 66.4, 66.5, and final product 66.6, are described in WO 03/020222 A2 page 28 line 10 to page 53 line 22, as well as the references cited therein. Additional description is provided in WO 01/32153 A2 page 41 line 3 to page 56 line 29 and references cited therein. Other good sources of information for transformation from 66.5 to 66.6 are Townsend, *Chemistry of Nucleosides and Nucleotides*, Plenum Press, 1994; and Vorbruggen and Ruh-Pohlenz, *Handbook of Nucleoside Synthesis*, John Wiley & Sons, Inc., 2001.

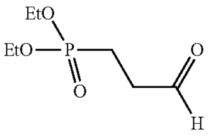

66.2.1

+

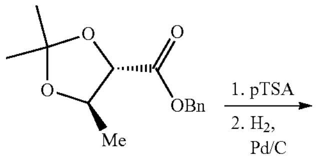

66.2.2

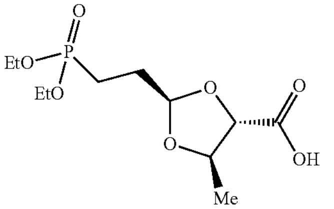

+

66.2.3

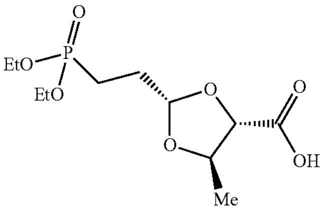

66.2.4

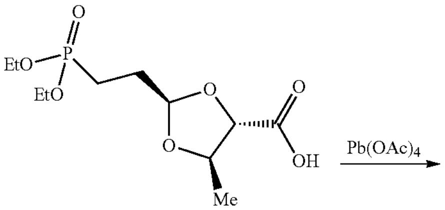

66.2.3

-continued

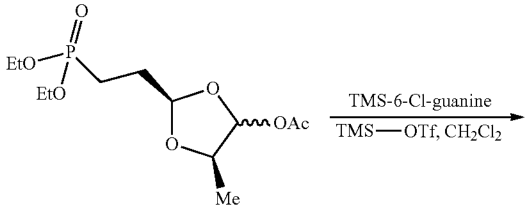

66.2.5

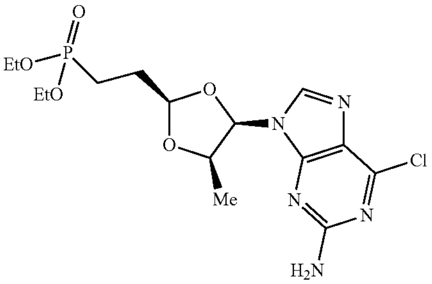

66.2.6

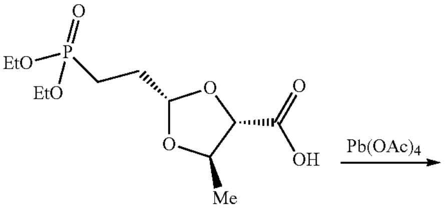

66.2.4

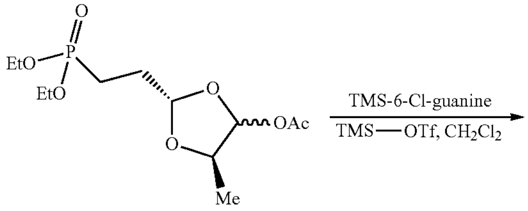

66.2.7

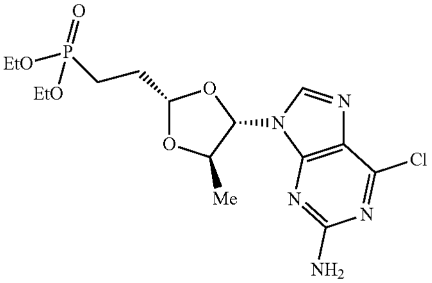

66.2.8

A specific example for the synthesis of a dioxolane nucleoside analog is illustrated above. Treating the mixture of 66.2.1 and 66.2.2 with p-toluenesulfonic acid, followed by removal of the benzyl protecting group on the carboxylic acid produces a mixture of carboxylic acids 66.2.3 and 66.2.4. Treating acid 66.2.3 with lead(IV) tetraacetate gives acetate 66.2.5, which can be converted to nucleoside 66.2.6 under the reaction conditional described above. Treating acid 66.2.4 with same reaction procedures for 66.2.3 to 66.2.6 can generate a different diastereomer 66.2.8, which is an L-nucleoside analog.

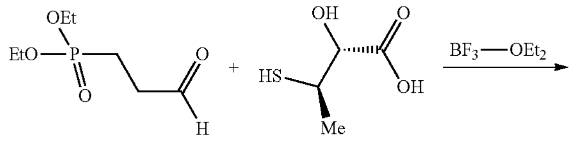

66.3.1 66.3.2

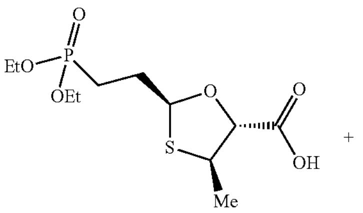

66.3.3

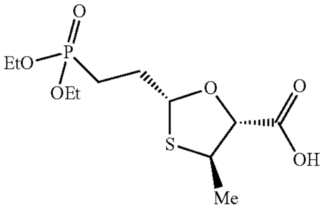

66.3.4

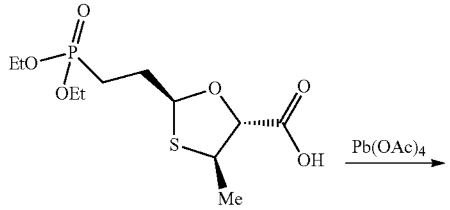

66.3.3

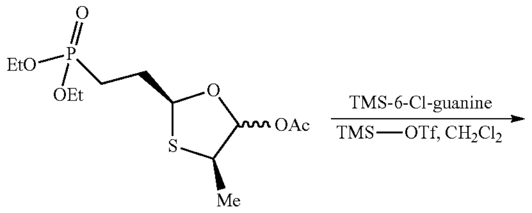

66.3.5

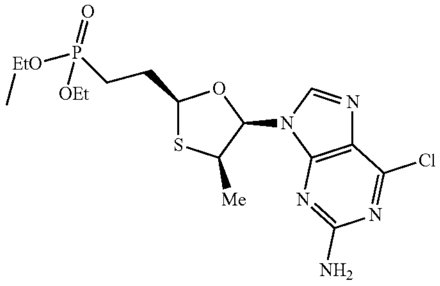

66.3.6

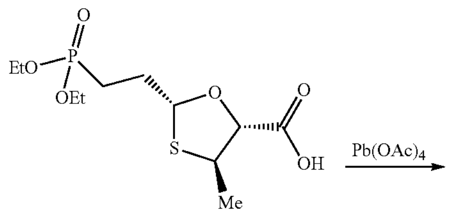

66.3.4

-continued

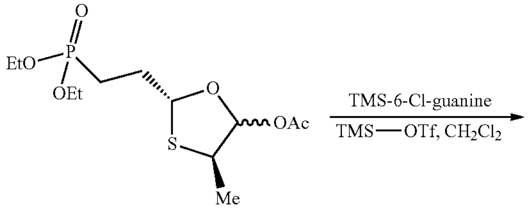

66.3.7

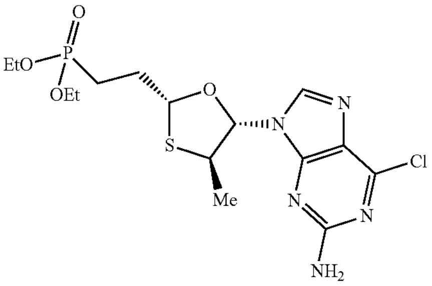

66.3.8

A specific example for the synthesis of a oxathiolane nucleoside analog is illustrated above. The syntheses of 66.3.6 and 66.3.8 are analogous to that of 66.2.6 and 66.2.8 described above.

Preparation and Availability of Starting Materials:

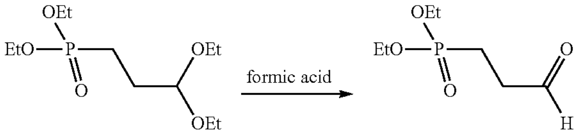

66.4.1 66.2.1

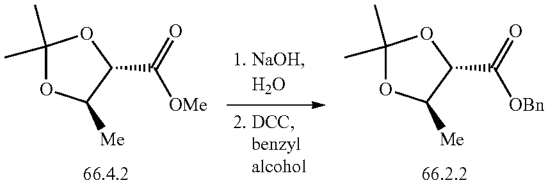

66.4.2 66.2.2

Compound 66.2.1 can be prepared from commercially available starting material 66.4.1 (available from Acros, catalog number 34693-0050 or 34693-0250, or from Epsilon, catalog number 95040) following the method illustrated above. Compound 66.2.2 can be prepared from commercially available starting material 66.4.2 (Fluka, catalog number 59437) following the method illustrated above. The preparation of 66.3.2 was described in WO 03/020222 A2 page 34 line 7 to page 36 line 5, and references cited therein.

Example 67

Synthesis of Representative Compounds of Formula 73

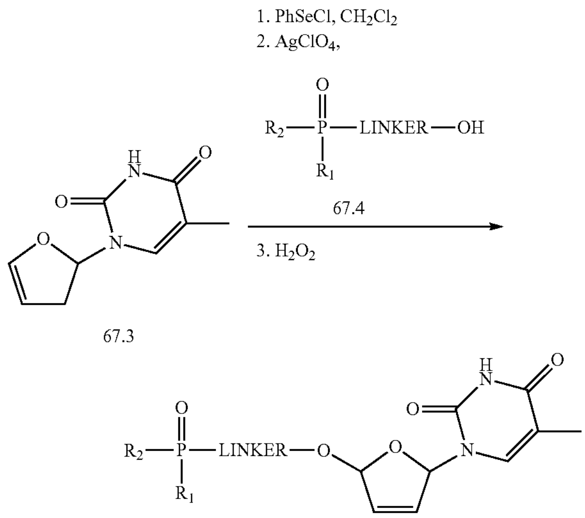

67.3

67.2

$R_1$ = H, alkyl, aryl, haloalkyl, alkenyl, aralyl, aryl
$R_2$ = H, alkyl, aryl, haloalkyl, alkenyl, aralyl, aryl Representative compounds of the invention can be prepared as illustrated above. The desired phosphonate substituted analogs are prepared by first reacting glycal 67.3 (obtained as described in *J. Am. Chem. Soc.* 1972, 94, 3213) with phenylselenyl chloride followed by treatment with the respective phosphonate alcohols 67.4 in the presence of silver perchlorate (*J. Org. Chem.* 1991, 56, 2642-2647). Oxidation of the resulting chloride using hydrogen peroxide provides the desired phosphonate 67.2.

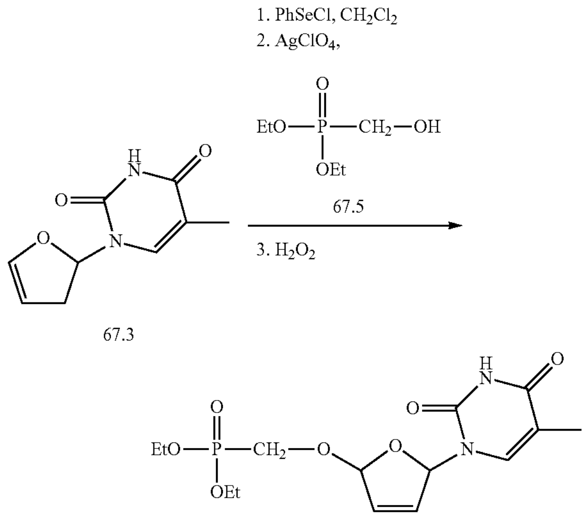

67.3

67.6

For instance, 67.3 dissolved in $CH_2Cl_2$, is treated with one equivalent of phenyl selenyl chloride at −70° C. followed by silver perchlorate in the presence of diethyl(hydroxymethyl) phosphonate (67.5). The phosphonate is transformed into the d4T analog 67.6 by oxidation with hydrogen peroxide. Using the above procedure, but employing different phosphonate reagents 67.4 in place of 67.5, the corresponding products 67.2 bearing different linking groups are obtained. Additionally, analogs containing a variety of bases can be prepared by starting with the appropriately protected glycals (see examples in: *J. Am. Chem. Soc.* 1972, 94, 3213).

Example 68

Synthesis of Representative Compounds of Formula 74

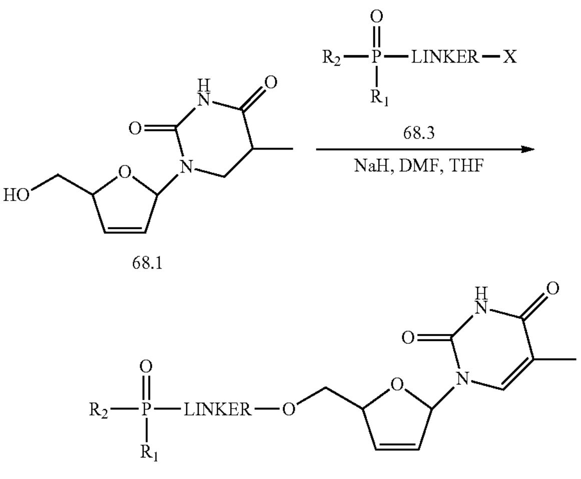

68.1

68.2

For example: X = Cl, Br, I, OMs, OTs, OTf
where $R_1$, $R_2$ = Alkyl, Aryl
$R_1$ = H, alkyl, aryl, haloalkyl, alkenyl, aralyl, aryl
$R_2$ = H, alkyl, aryl, haloalkyl, alkenyl, aralyl, aryl Representative compounds of the invention can be prepared as illustrated above. The desired phosphonate substituted analogs are prepared by reaction of d4T (68.1) (obtained as described in U.S. Pat. No. 4,978,655 col. 2 ln. 46 to col. 3 ln. 47) with the respective alkylating reagents 68.3. Illustrated above is the preparation of phosphonate linkage to d4T through the 5'-hydroxyl group. D4T is dissolved in a solvent such as, but not limited to, DMF or THF, and is treated with a phosphonate reagent bearing a leaving group in the presence of a suitable organic or inorganic base. In compounds 68.3, X is a leaving group such as, but not limited to, bromide, chloride, iodide, p-toluenesulfonate, trifluoromethanesulfonate, or methanesulfonate.

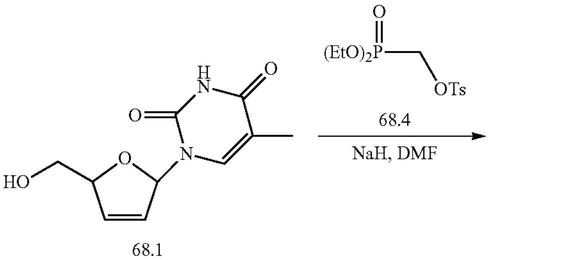

68.1

-continued

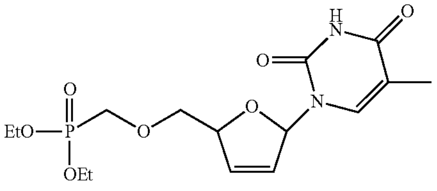

68.5

For instance, 68.1 dissolved in DMF, is treated with one equivalent of sodium hydride and one equivalent of (toluene-4-sulfonylmethyl)-phosphonic acid diethyl ester 68.4 (prepared according to the procedures in *J. Org. Chem.* 1996, 61, 7697) to give d4T phosphonate 68.5, in which the linkage is a methylene group. Using the above procedure, but employing different phosphonate reagents 68.3 in place of 68.4, the corresponding products 68.2 bearing different linking groups are obtained. In a similar manner, using a variety of d4 Ts possessing different natural and non-natural nucleoside bases with the appropriate protecting groups, numerous other valuable analogs can be obtained.

Example 69

Synthesis of Representative Compounds of Formula 75

Representative compounds of the invention can be prepared as illustrated in schemes 69.1-69.12 below.

Scheme 69.1

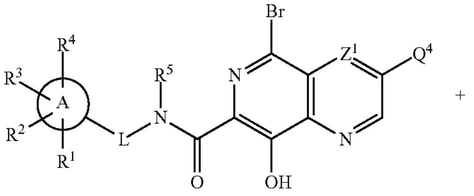

69.1
(WO02/30930,
page 286, lines 5-25)

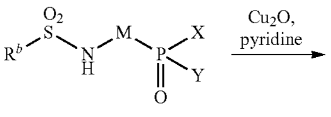

69.2

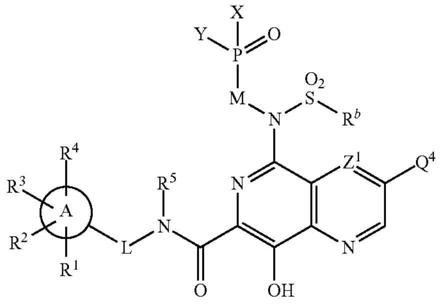

69.3

Scheme 69.2

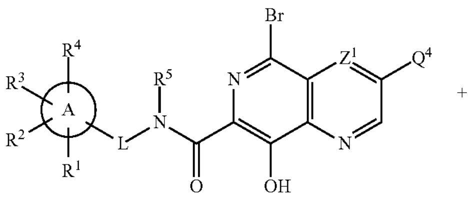

69.4

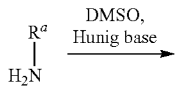

69.5

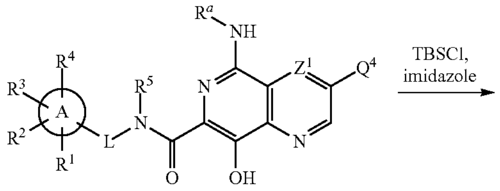

69.6

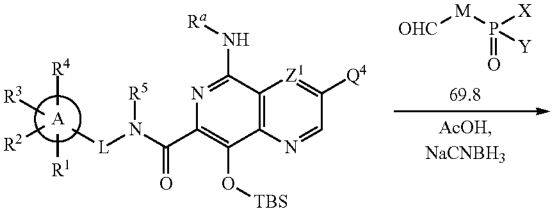

69.7

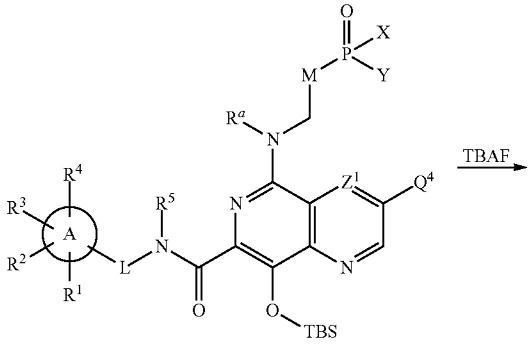

69.9

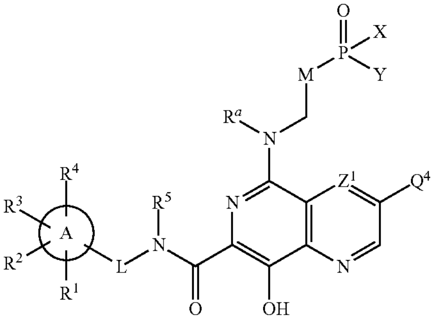

69.10

Scheme 69.3
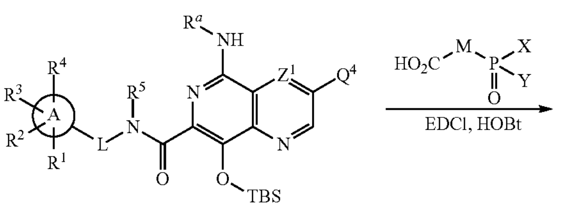
69.11
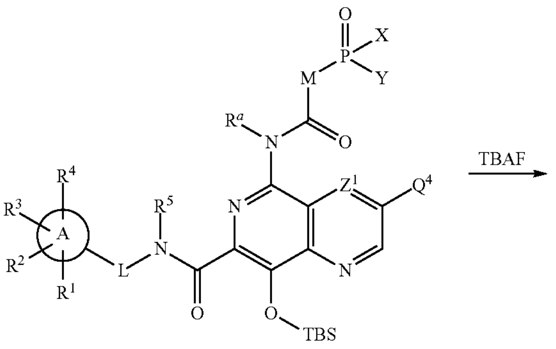
69.12
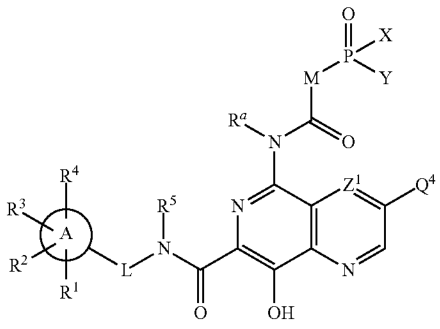
69.13
Scheme 69.4
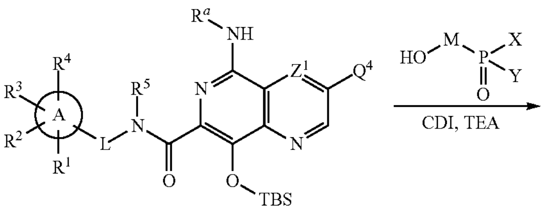
69.14
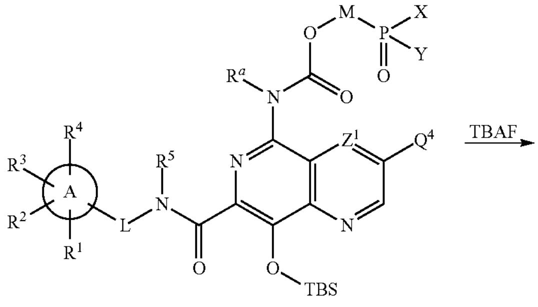
69.15
-continued
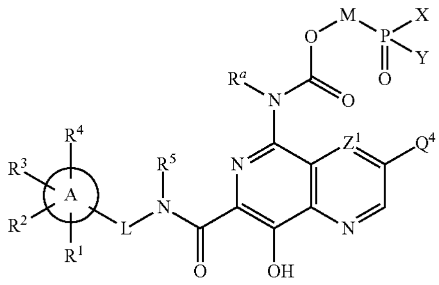
69.16
Scheme 69.5
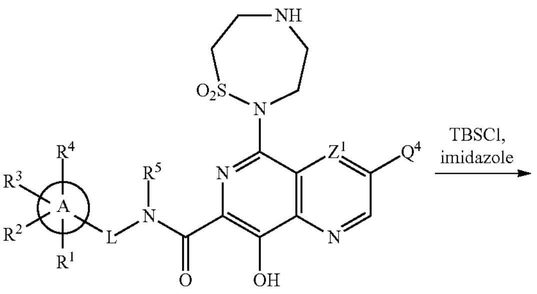
69.17
(WO-02/30931,
page 61, line 3-
page 64, line 28)
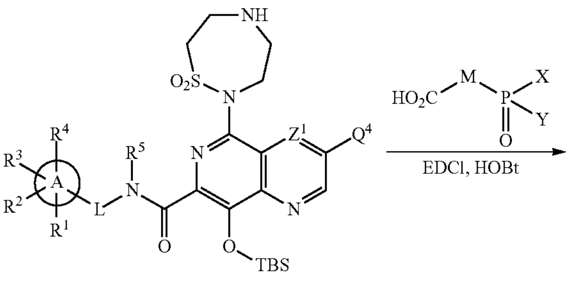
69.18
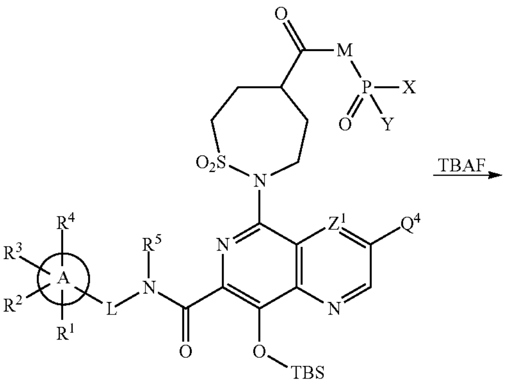
69.19

-continued
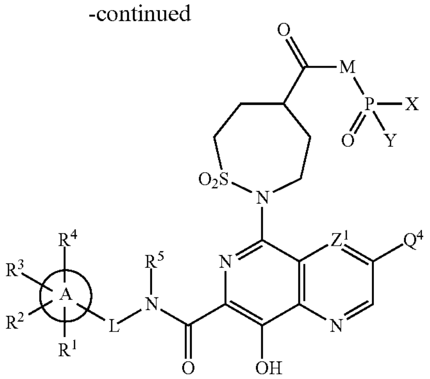
69.20
Scheme 69.6
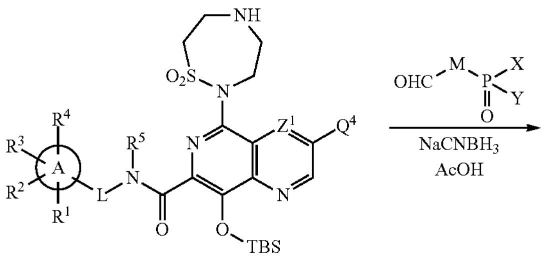
69.21
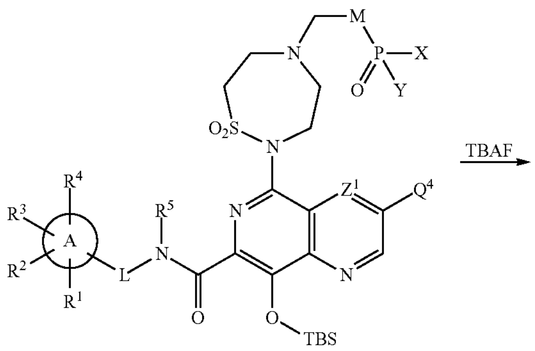
69.22
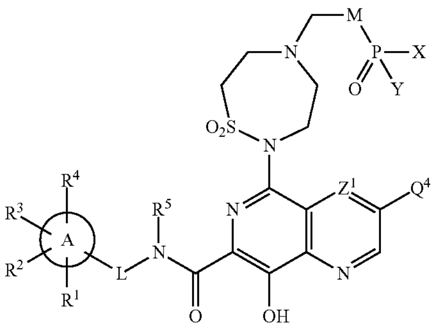
69.23
Scheme 69.7
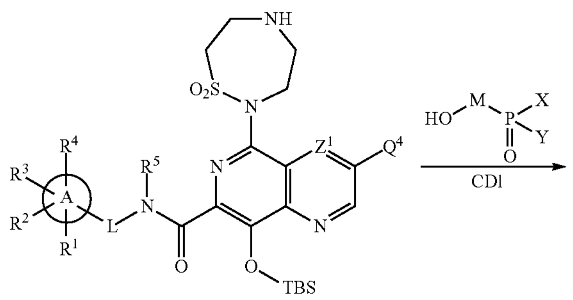
69.24
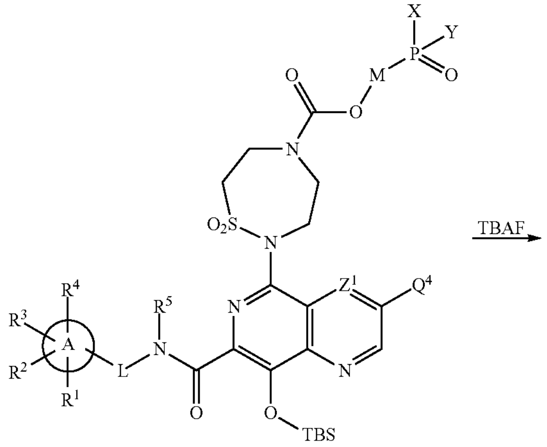
69.25
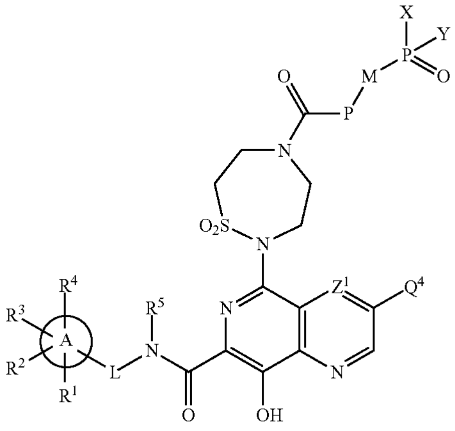
69.26

Scheme 69.8
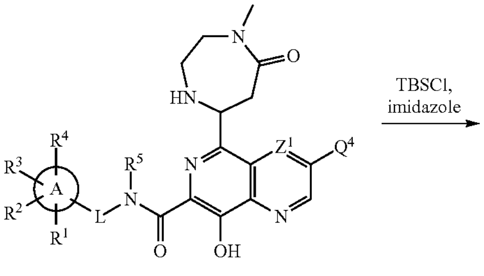
69.27
(WO 02/30930,
page 312, lines 9-28)
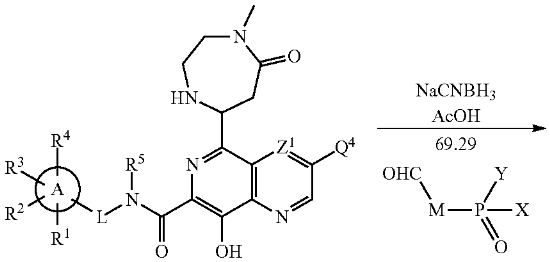
69.28
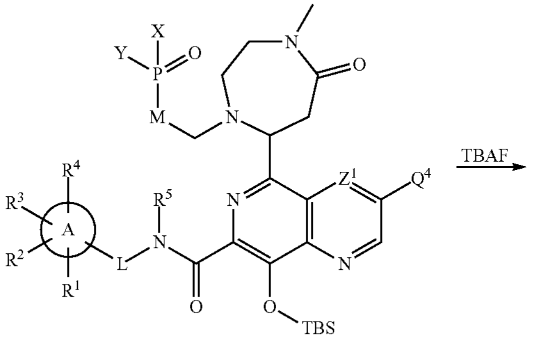
69.30
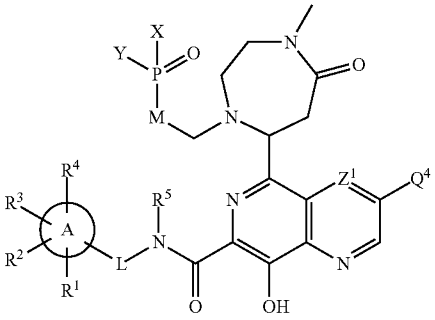
69.31
Scheme 69.9
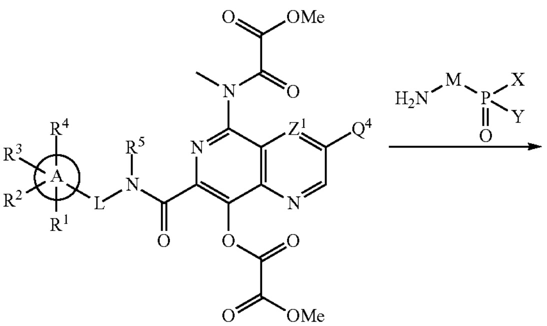
69.32
(WO-02/30930, page 60,
line 22-page 61, line 27)
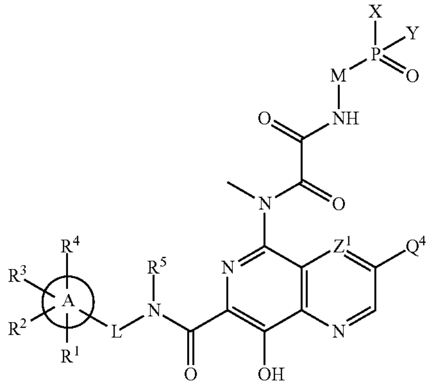
69.33
Scheme 69.10
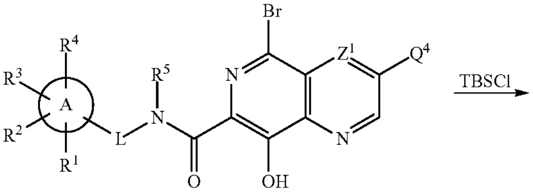
69.34
(WO 02/30930,
p. 286, lines 5-25)
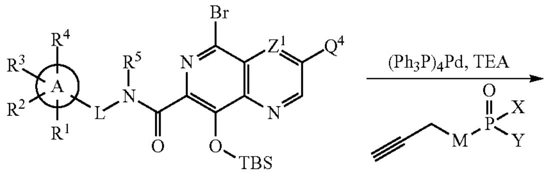
69.35

-continued
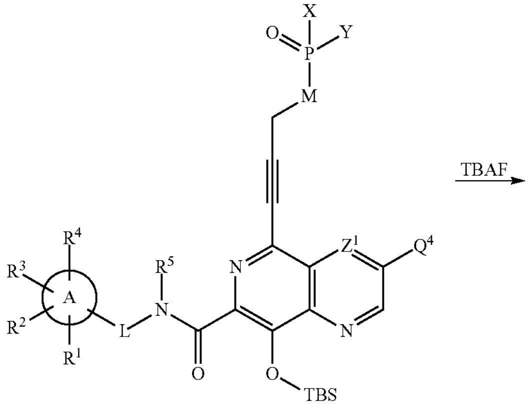
69.36
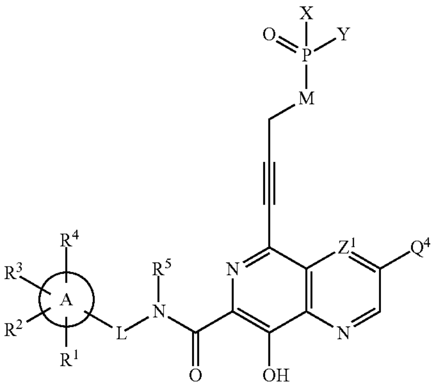
69.37
Scheme 69.11
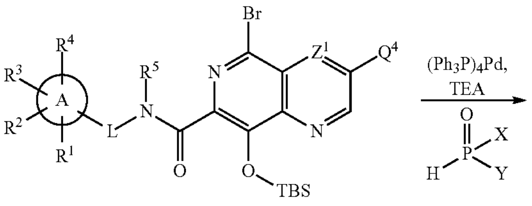
69.38
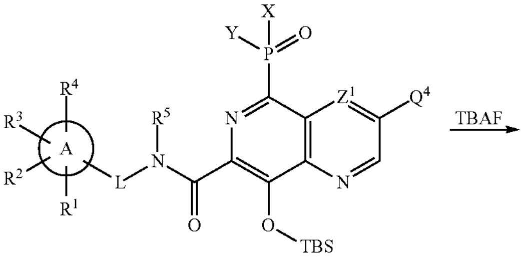
69.40
-continued
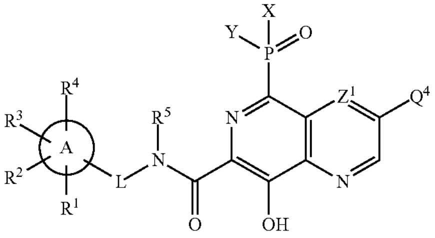
69.41
Scheme 69.12
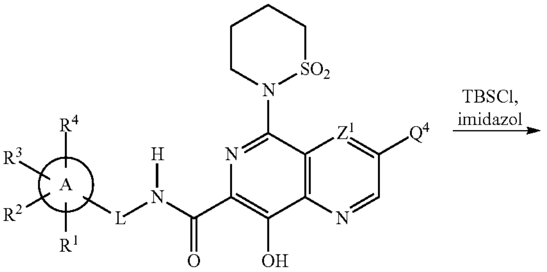
69.42
(WO 02/0230931,
page 71 line 7-page 76, line 13)
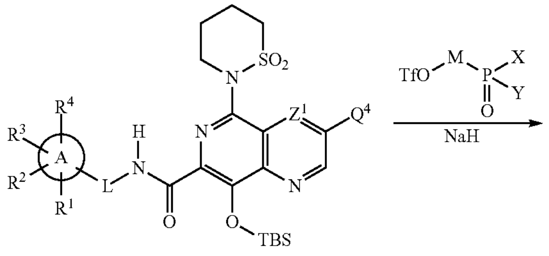
69.43
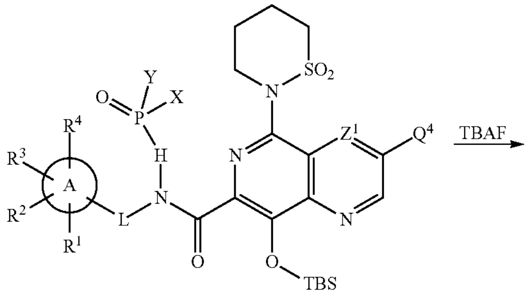
69.44
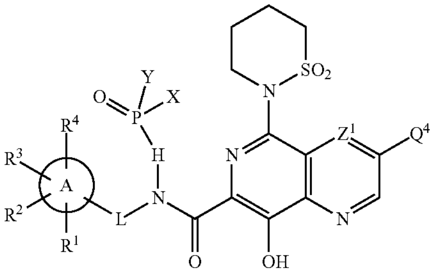
69.45

Representative compounds of the invention can be prepared as illustrated above. The phosphorous-containing compounds of the present invention of Formula 75 can be readily prepared according to the conventional synthetic procedures exemplified in Schemes 69.1-69.12 where a phosphonate-containing moiety may be attached using established chemical processes. The preparations may be carried out from the precursor compounds described in both WO 02/30930 and WO 02/30931. The methods for these conversions from precursor compounds to the phosphorous-containing compounds are described in *Comprehensive Organic Transformations*, Richard C. Larock, ed, VCH, 1989; Comprehensive Organic Synthesis, Barry M. Trost and Ian Fleming eds., Pergamon Press, 1991. Protection of function groups during the transformation is described in *Protective Groups in Organic Synthesis*, Theodora W. Greene and Peter G. M. Wuts, eds., Wiley, 1999.

Example 70

Synthesis of Representative Compounds of Formula 76

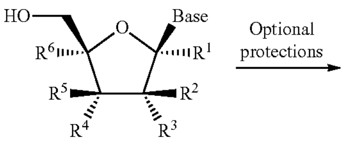

70.1

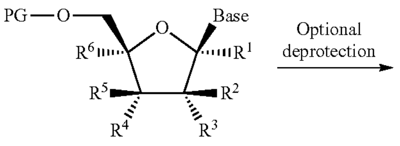

70.2

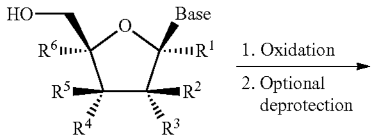

70.3

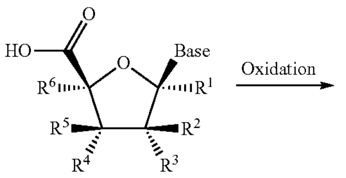

70.4

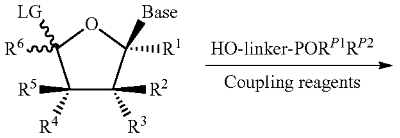

70.5

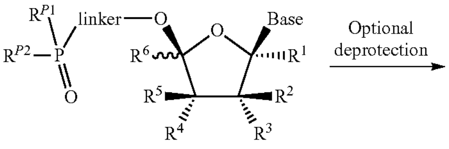

70.6

-continued

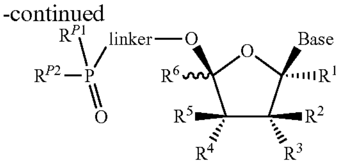

70.7

Representative compounds of the invention can be prepared as illustrated above. The core components of this reaction sequence are the transformations from primary alcohol 70.3 to phosphonate 70.6. Appropriate oxidant(s) can convert the primary alcohol (5'-hydroxy) in 70.3 to a carboxylic acid or its corresponding ester. In the case of an ester, an additional deprotection step will give the carboxylic acid 70.4. A variety of oxidation procedures can be found in the literature and can be utilized here. These include, but are not limited to, the following methods: (i) pyridinium dichromate in $Ac_2O$, t-BuOH, and dichloromethane producing the t-butyl ester, followed by deprotection using a reagent such as trifluoroacetic acid to convert the ester to the corresponding carboxylic acid (see Classon, et al., *Acta Chem. Scand. Ser. B* 1985, 39, 501-504; Cristalli, et al., *J. Med. Chem.* 1988, 31, 1179-1183); (ii) iodobenzene diacetate and 2,2,6,6-tetramethyl-1-piperidinyloxy, free radical (TEMPO) in acetonitrile, producing the carboxylic acid (see Epp, et al., *J. Org. Chem.* 1999, 64, 293-295; Jung et al., *J. Org. Chem.* 2001, 66, 2624-2635); (iii) sodium periodate, ruthenium(III) chloride in chloroform producing the carboxylic acid (see Kim, et al., *J. Med. Chem.* 1994, 37, 4020-4030; Homma, et al., *J. Med. Chem.* 1992, 35, 2881-2890); (iv) chromium trioxide in acetic acid producing the carboxylic acid (see Olsson et al.; *J. Med. Chem.* 1986, 29, 1683-1689; Gallo-Rodriguez et al.; *J. Med. Chem.* 1994, 37, 636-646); (v) potassium permanganate in aqueous potassium hydroxide producing the carboxylic acid (see Ha, et al., *J. Med. Chem.* 1986, 29, 1683-1689; Franchetti, et al., *J. Med. Chem.* 1998, 41, 1708-1715); and (vi) nucleoside oxidase from *S. maltophilia* to give the carboxylic acid (see Mahmoudian, et al., *Tetrahedron* 1998, 54, 8171-8182).

The preparation of 70.5 from 70.4 using lead(IV) tetraacetate (LG=OAc) is described by Teng et al., *J. Org. Chem.* 1994, 59, 278-280 and Schultz, et al; *J. Org. Chem.* 1983, 48; 3408-3412. When lead(IV) tetraacetate is used together with lithium chloride (see Kochi, et al., *J. Am. Chem. Soc.* 1965, 87, 2052), the corresponding chloride is obtained (70.5, LG=Cl). Lead(IV) tetraacetate in combination with N-chlorosuccinimide can produce the same product (70.5, LG=Cl) (see Wang, et al., *Tetrahedron: Asymmetry* 1990, 1, 527; and Wilson et al., *Tetrahedron: Asymmetry* 1990, 1, 525). Alternatively, the acetate leaving group (LG) can also be converted to other leaving group such as bromide by treatment of trimethylsilyl bromide to give 70.5 (see Spencer, et al., *J. Org. Chem.* 1999, 64, 3987-3995).

The coupling of 70.5 (LG=OAc) with a variety of nucleophiles was described by Teng et al., *Synlett* 1996; 346-348 and U.S. Pat. No. 6,087,482; column 54 line 64 to column 55 line 20. Specifically, the coupling between 70.5 and diethyl hydroxymethylphosphonate in the presence of trimethylsilyl trifluoromethanesulfonate (TMS-OTf) is described. Other compounds with the general structure of HO-linker-POR$^{P1}$R$^{P2}$ can also be used so long as the functional groups in these compounds are compatible with the coupling reaction conditions. There are many examples in the published literature describing the coupling of 70.5 (LG=halogen) with a variety of alcohols. The reactions can be facilitated with a number of reagents, such as silver(I) salts (see Kim et al.; *J. Org. Chem.* 1991, 56, 2642-2647; Toikka et al., *J. Chem. Soc. Perkins Trans.* 1, 1999, 13, 1877-1884), mercury(II) salts (see Veeneman et al.; *Rect. Tray. Chim. Pays-Bas.* 1987, 106, 129-131), boron trifluoride diethyl etherate (see Kunz et al., *Hel. Chim Acta* 1985, 68, 283-287), tin(II) chloride (see O'Leary et al., *J. Org. Chem.* 1994, 59, 6629-6636), alkoxide (see Shortnacy-Fowler et al., *Nucleosides Nucleotides* 2001, 20, 1583-1598), and iodine (see Kartha et al., *J. Chem. Soc. Perkins Trans.* 1, 2001, 770-772). These methods can be selectively used in conjunction with different methods in forming 70.5 with various leaving groups (LG) to produce 70.6.

The introduction and removal of protecting groups is commonly practiced in the art of organic synthesis. Many sources of information on transformations involving protecting groups are available in the published literature, e.g. Greene and Wuts, *Protecting Groups in Organic Synthesis,* 3rd Ed., John Wiley & Sons, Inc., 1999. The main purpose is to temporarily transform a functional group so that it will survive a set of subsequent reaction procedures. Afterward, the original functional group can be restored by a preconceived deprotection procedure. Therefore, the transformations from 70.1 to 70.2, from 70.2 to 70.3, and from 70.6 to 70.7 are intended to allow important transformations (e.g., from 70.3 to 70.6) to occur while preserving the functional groups that already exist in the core structures.

It should be understood that in the transformation 70.6 to 70.7, $R^{P1}$ and $R^{P2}$ need not remain unchanged. The final form of $R^{P1}$ and $R^{P2}$ can be selected from a variety of possible structures.

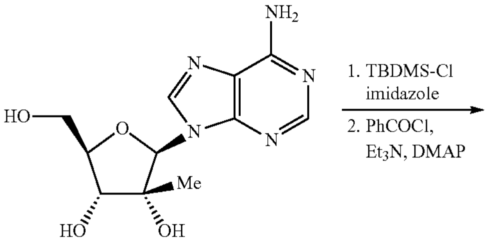

70.2.1

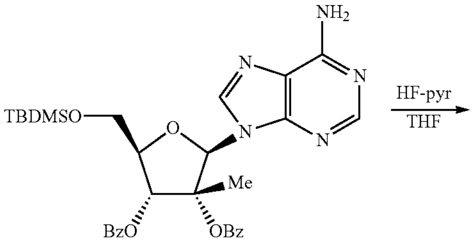

70.2.2

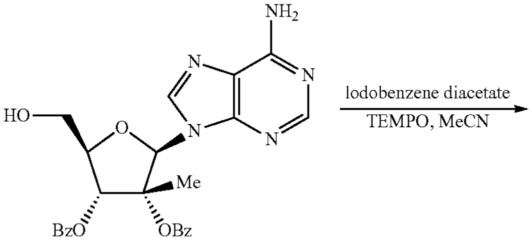

70.2.3

-continued

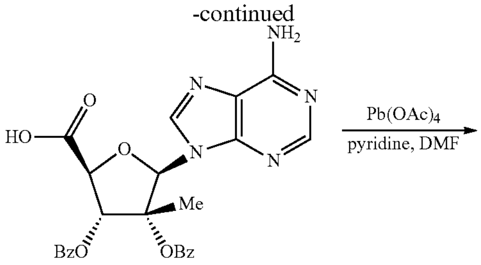

70.2.4

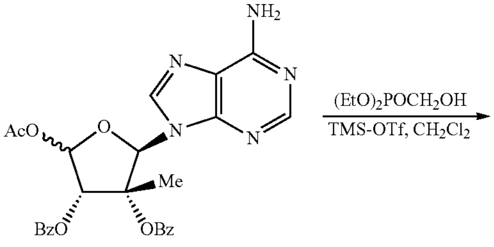

70.2.5

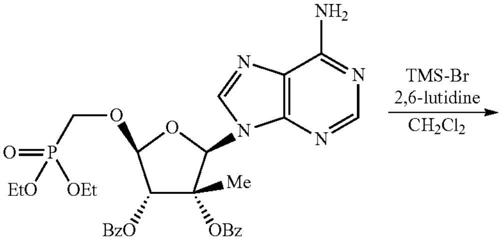

70.2.6

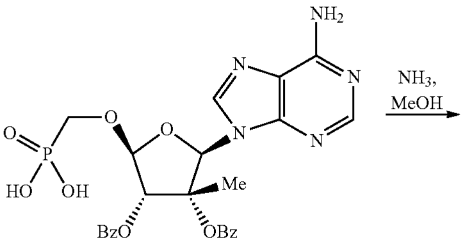

70.2.7

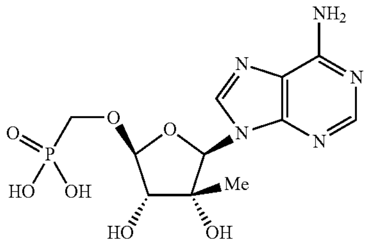

70.2.8

The scheme shown above provides a specific example for the general scheme discussed above. Compound 70.2.1 is prepared using method described in the patent filing WO 01/90121 (page 115). The 5'-hydroxyl in 70.2.1 is protected as a t-butyldimethylsilyl (TBDMS) ether. The 2'- and 3'-hydroxyl groups can be protected as benzoyl (Bz) esters to give 70.2.2. The 5'-hydroxyl can then be deprotected to give 70.2.3. Oxidation using iodobenzene diacetate and 2,2,6,6-tetramethyl-1-piperidinyloxy, free radical (TEMPO) converts the primary alcohol to the corresponding acid 70.2.4. Further oxidation of 70.2.4 using lead tetraacetate can produce 70.2.5. Coupling between 70.2.5 and diethyl hydroxymethylphosphonate (available from Sigma-Aldrich, Cat. No. 39,262-6) effected by TMS-OTf can afford 70.2.6. Treating 70.2.6 with TMS-Br converts the phosphodiester to the corresponding phosphonic acid 70.2.7. Deprotection of the 2'- and 3'-hydroxyl gives 70.2.8 as an example of the generic structure 76, where Base is an adenine, $R^1$, $R^5$, and $R^6$ are hydrogen, $R^2$ is methyl group, $R^3$ and $R^4$ are hydroxyl groups, linker is a methylene group, and $R^{P1}$ and $R^{P2}$ are both hydroxyl groups.

The phosphonic acids in 70.2.7 and 70.2.8 are illustrative examples. Other forms of phosphonates can be accessed via the phosphonic acid, or other forms, such as the corresponding diesters.

Preparation and Availability of Starting Materials for Examples 70-153

A variety of compounds of the general structure 70.1 can either be prepared using procedures described in the literature, or be purchased from commercial sources. The following are good sources for information on the art of preparing a variety of compounds of the general structure 70.1: Townsend, *Chemistry of Nucleosides and Nucleotides*, Plenum Press, 1994; and Vorbruggen and Ruh-Pohlenz, *Handbook of Nucleoside Synthesis*, John Wiley & Sons, Inc., 2001.

There are limited number of common precursors that were used to prepare the structures 70.1 in the examples that follow. Many of them are described in the various patents listed at the beginning of this document and the references cited therein. The following is a list of these common precursors and their commercial sources or method of preparation.

70.3.1

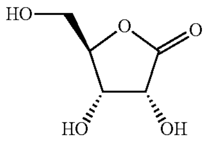

Available from Aldrich Cat. No. 85729-7

70.3.2

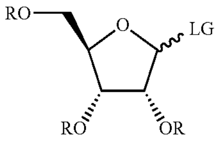

LG = OH, Aldrich Cat. No. R175-7
LG = OAc, R = Benzoyl, Aldrich Cat. No. 15, 901-8

70.3.2

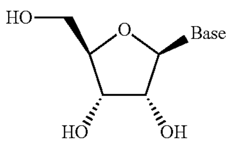

Examples 71-153

Examples 71-153 employ the reaction conditions described above in Example 70. It should be understood that specific reagents, solvents, and reaction conditions used can be substituted by one skilled in the art to accommodate the structure and reactivity requirements of the starting materials. Alternative methods including, but not limited to, those discussed in Example 70 can be applied as needed. Alternative protection and deprotection procedures are also likely to be devised and adapted as needed.

Example 71

Synthesis of Representative Compounds of Formula 76

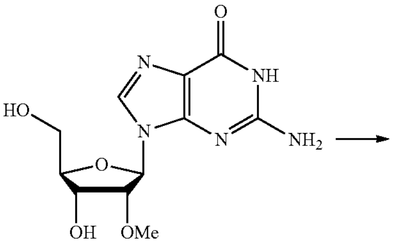

Commercially available from Berry & Assoc. (Cat. No. PR3760).

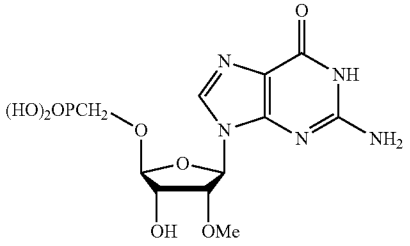

Example 72

Synthesis of Representative Compounds of Formula 76

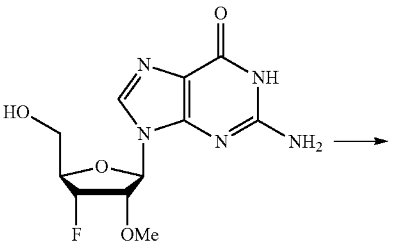

*J. Med. Chem.* 1991, 34, 2195.

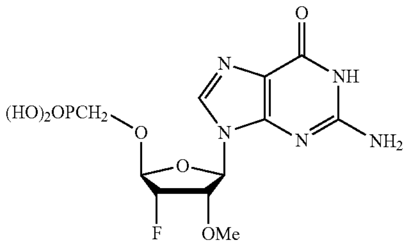

Example 73
Synthesis of Representative Compounds of Formula 76
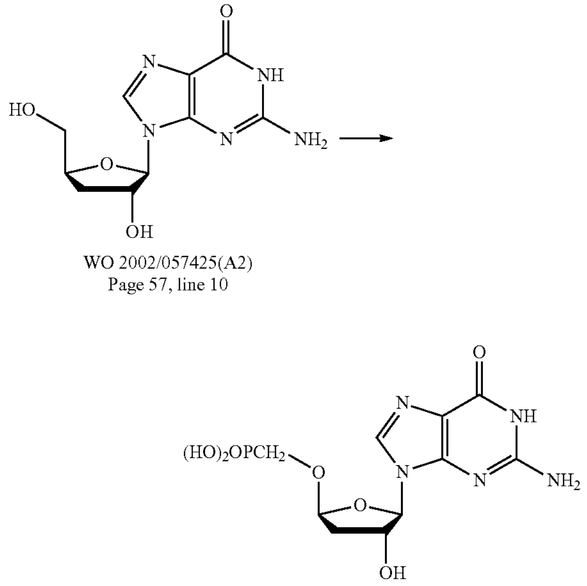
Example 74
Synthesis of Representative Compounds of Formula 76
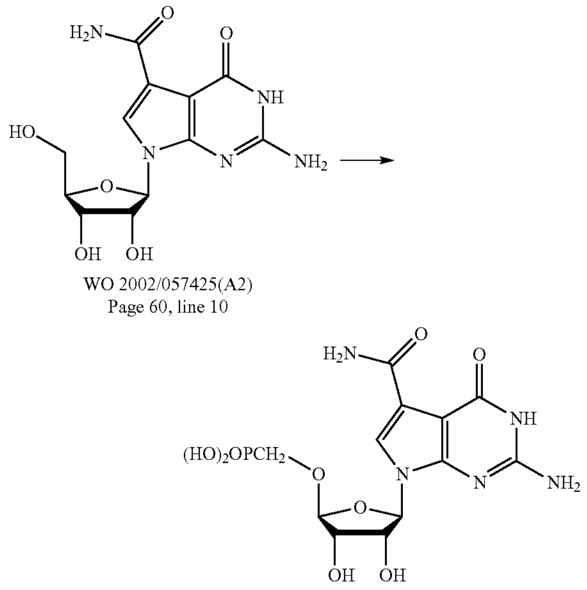
Example 75
Synthesis of Representative Compounds of Formula 76
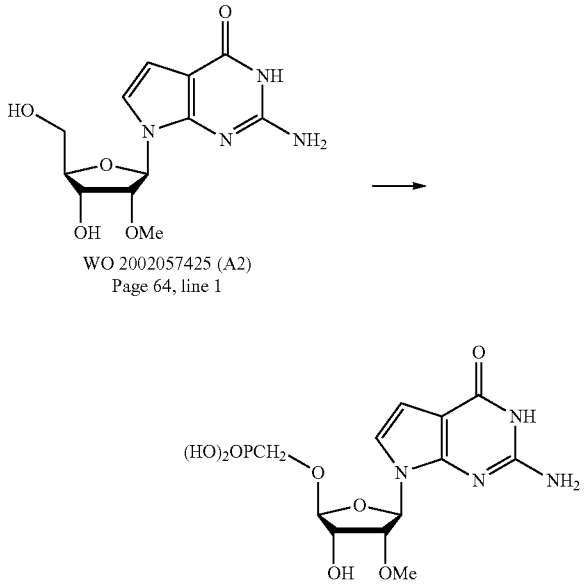
Example 76
Synthesis of Representative Compounds of Formula 76
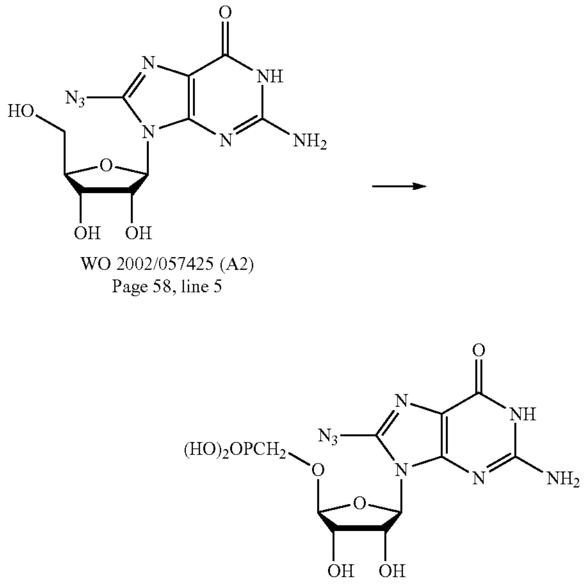

Example 77
Synthesis of Representative Compounds of Formula 76
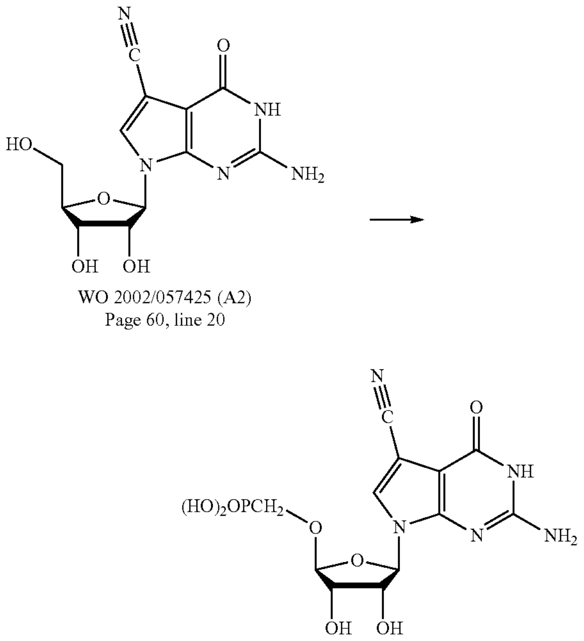
Example 78
Synthesis of Representative Compounds of Formula 76
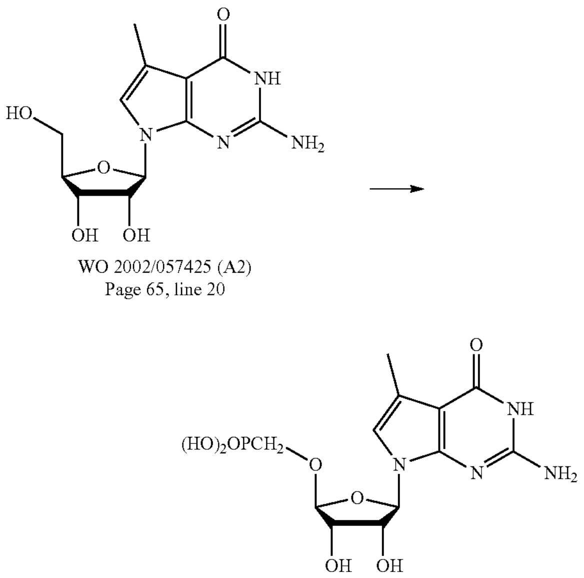
Example 79
Synthesis of Representative Compounds of Formula 76
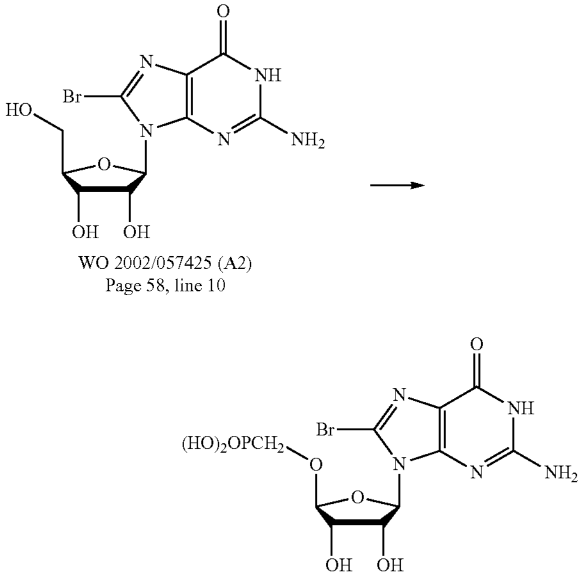
Example 80
Synthesis of Representative Compounds of Formula 76
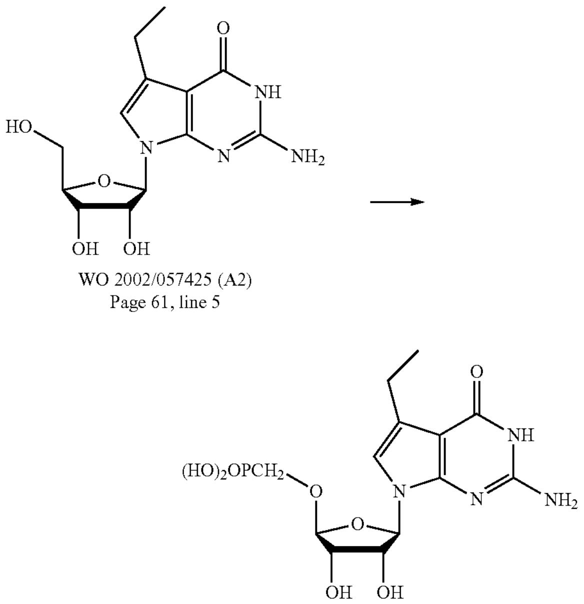

Example 81
Synthesis of Representative Compounds of Formula 76
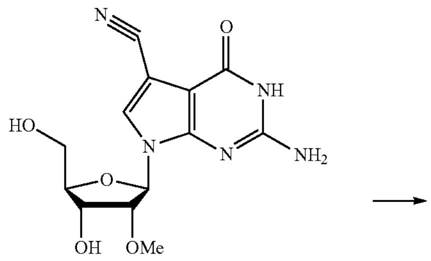
WO 2002/057425 (A2)
Page 67, line 1
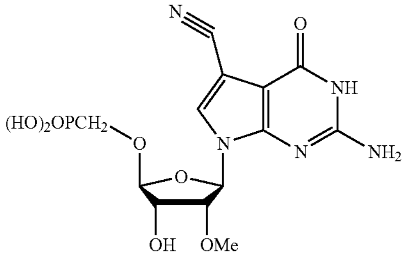
Example 82
Synthesis of Representative Compounds of Formula 76
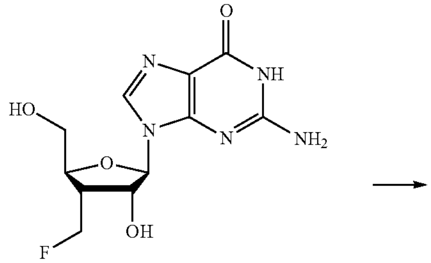
WO 2002/057425 (A2)
Page 59, line 5
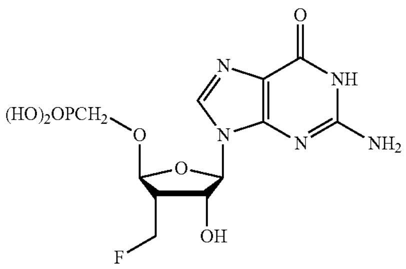
Example 83
Synthesis of Representative Compounds of Formula 76
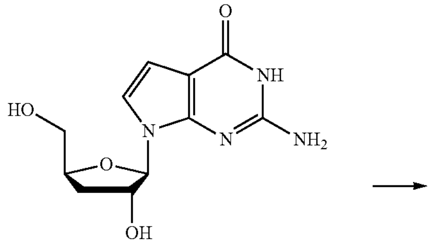
WO 2002/057425 (A2)
Page 60, line 20
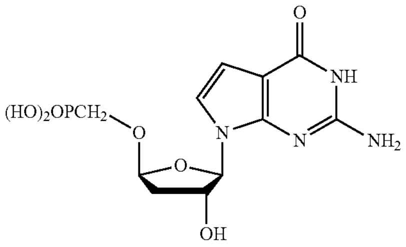
Example 84
Synthesis of Representative Compounds of Formula 76
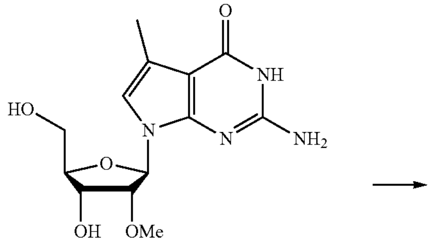
WO 2002/057425 (A2)
Page 69, line 1
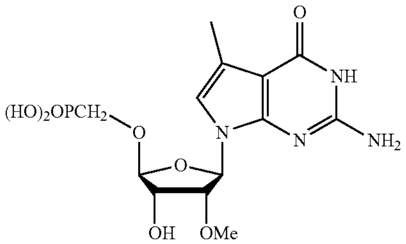

Example 85
Synthesis of Representative Compounds of Formula 76
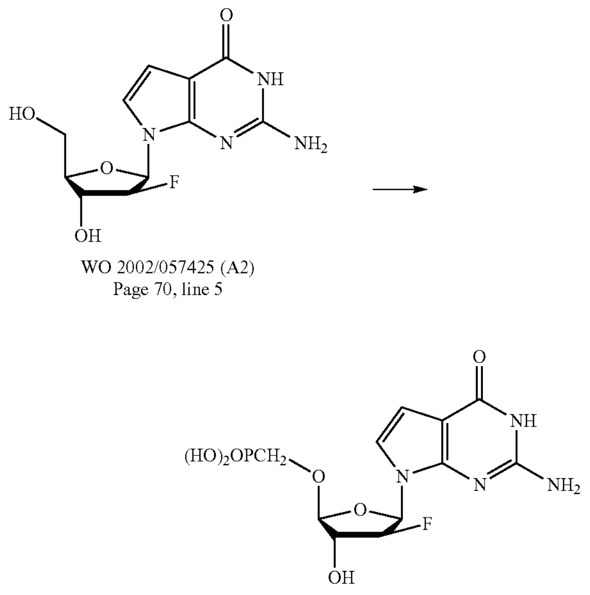
Example 86
Synthesis of Representative Compounds of Formula 76
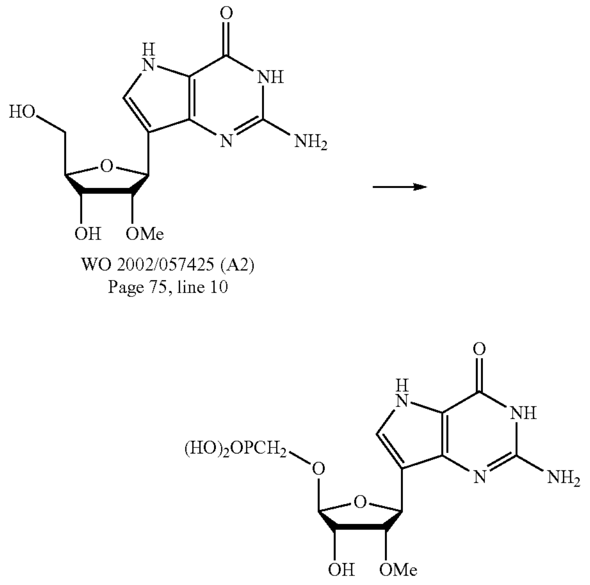
Example 87
Synthesis of Representative Compounds of Formula 76
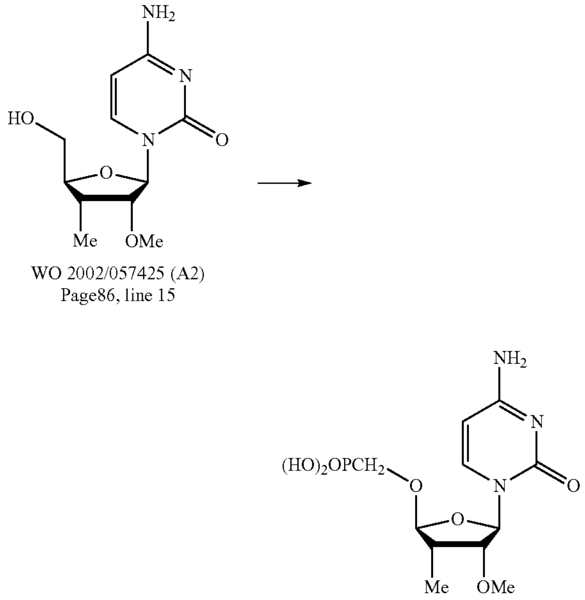
Example 88
Synthesis of Representative Compounds of Formula 76
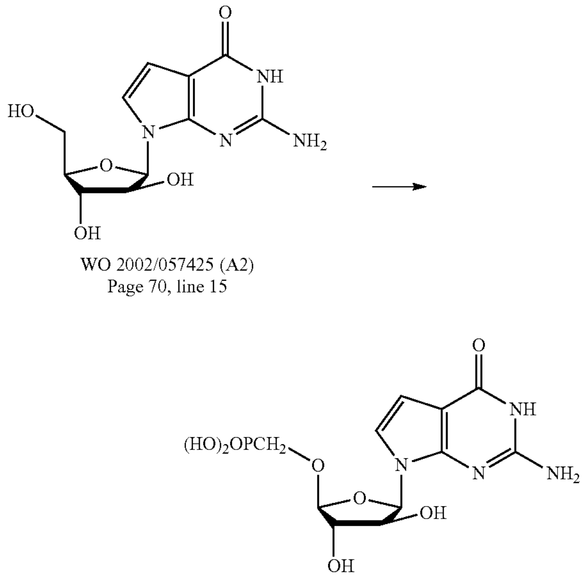

Example 89
Synthesis of Representative Compounds of Formula 76
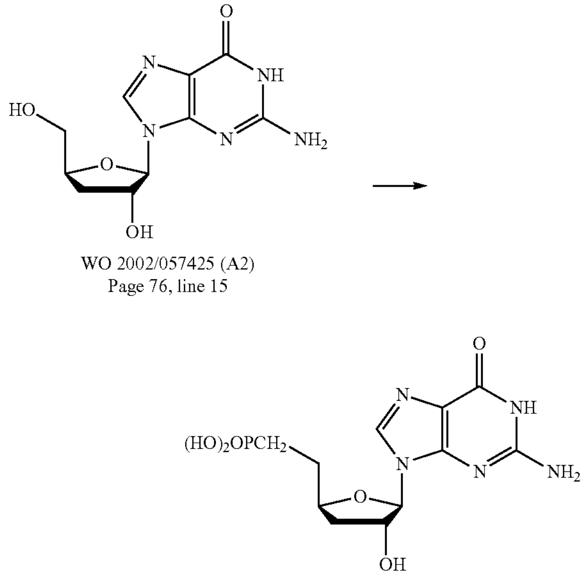
Example 90
Synthesis of Representative Compounds of Formula 76
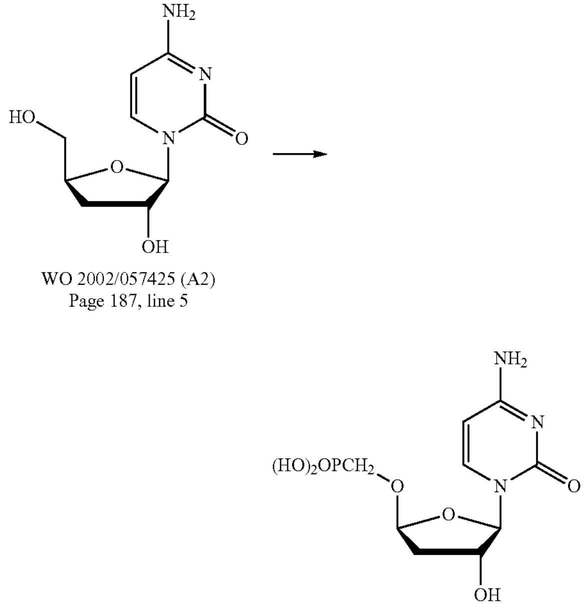
Example 91
Synthesis of Representative Compounds of Formula 76
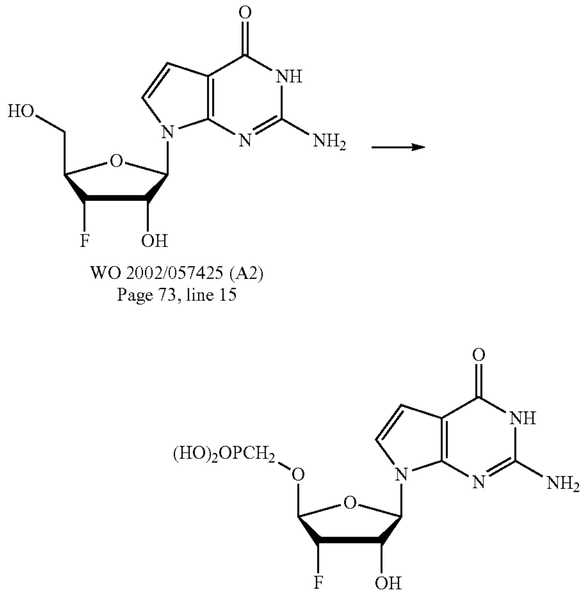
Example 92
Synthesis of Representative Compounds of Formula 76
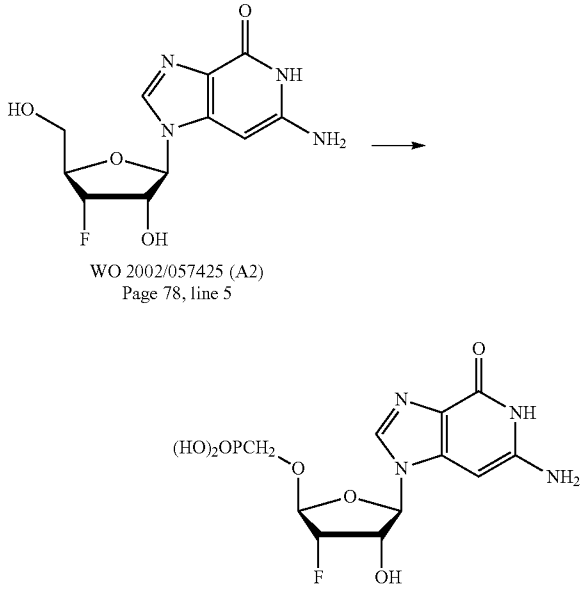

Example 93
Synthesis of Representative Compounds of Formula 76
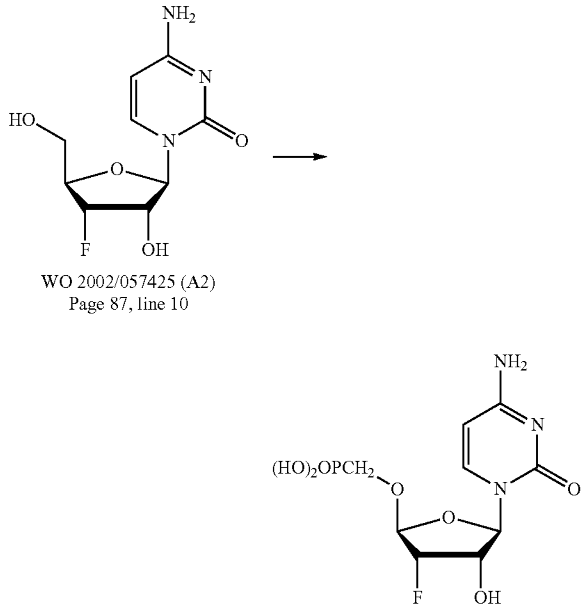
Example 94
Synthesis of Representative Compounds of Formula 76
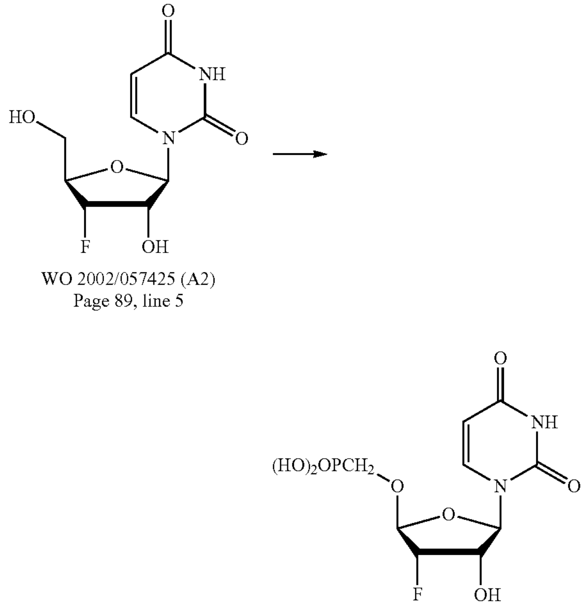
Example 95
Synthesis of Representative Compounds of Formula 76
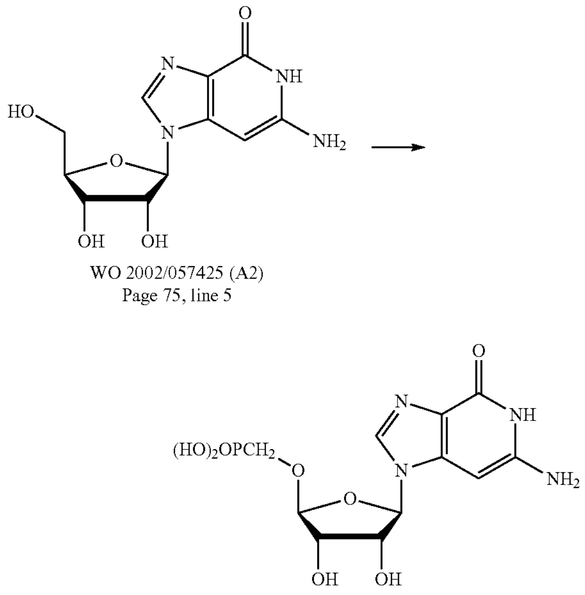
Example 96
Synthesis of Representative Compounds of Formula 76
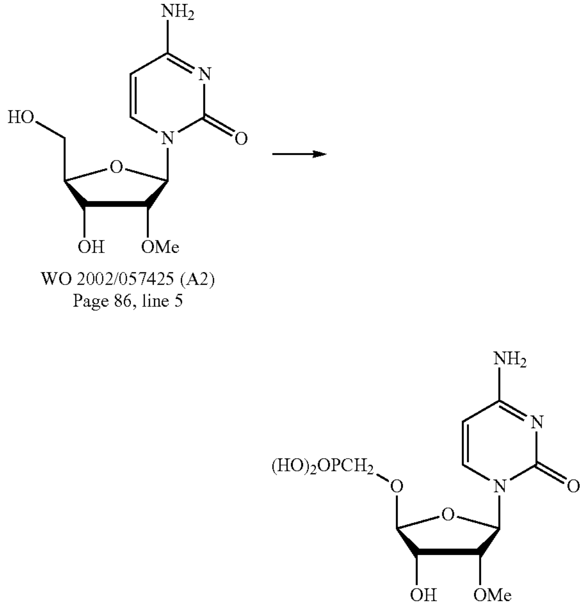

Example 97
Synthesis of Representative Compounds of Formula 76
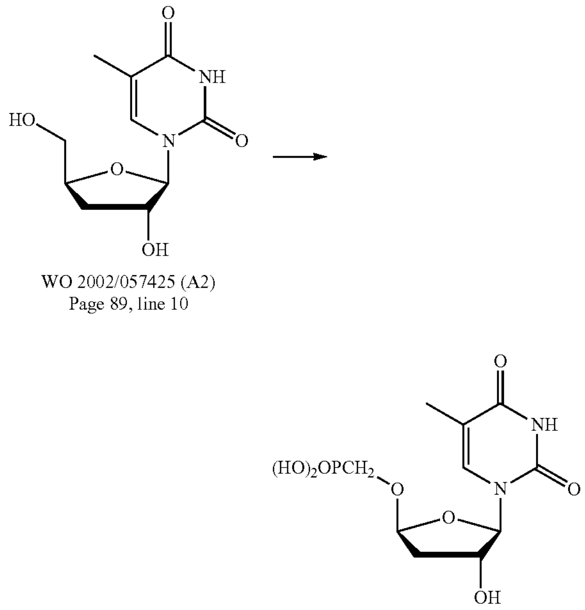
Example 98
Synthesis of Representative Compounds of Formula 76
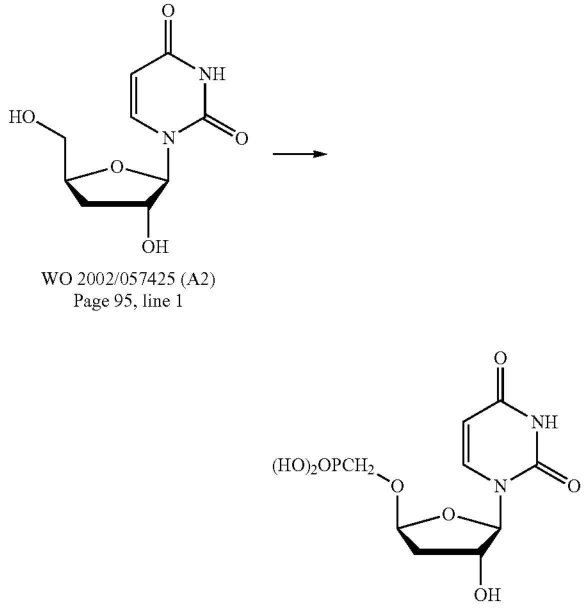
Example 99
Synthesis of Representative Compounds of Formula 76
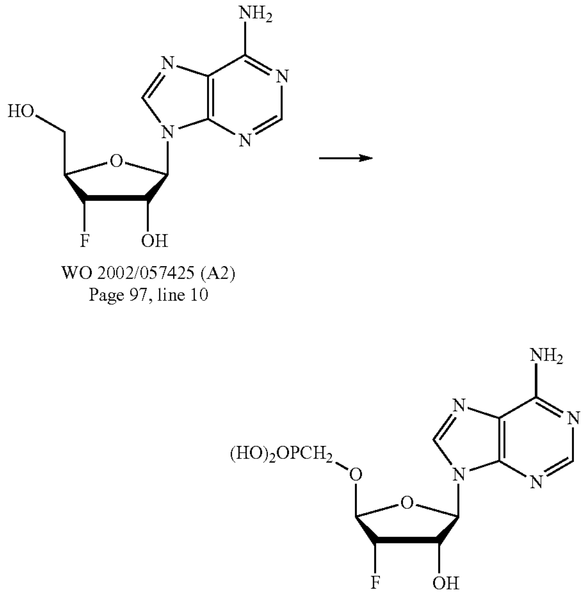
Example 100
Synthesis of Representative Compounds of Formula 76
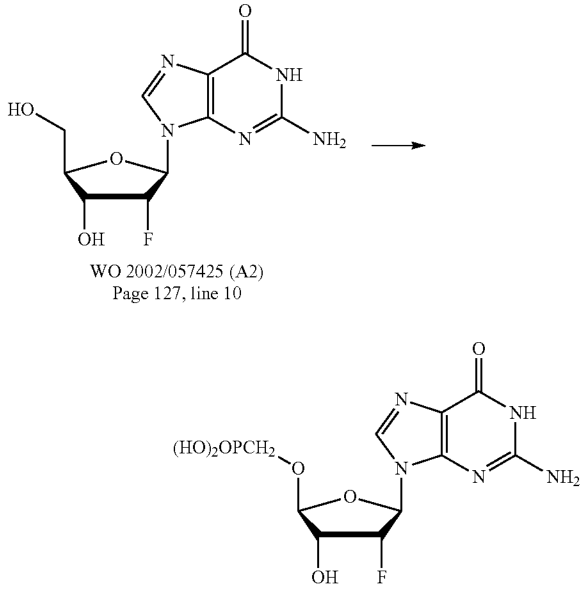

Example 101
Synthesis of Representative Compounds of Formula 76
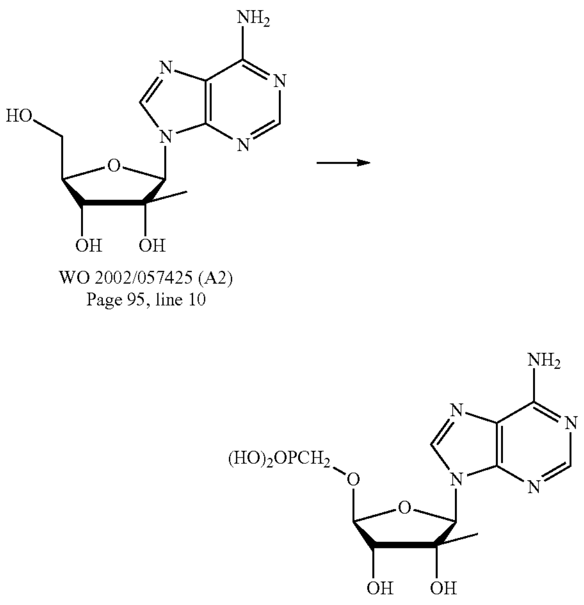
Example 102
Synthesis of Representative Compounds of Formula 76
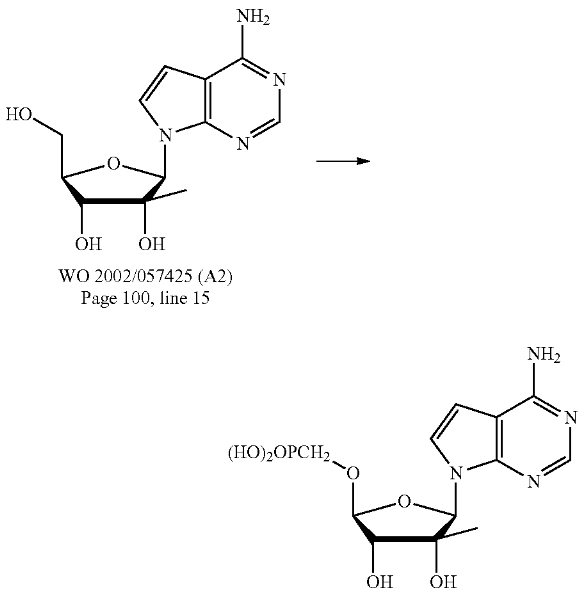
Example 103
Synthesis of Representative Compounds of Formula 76
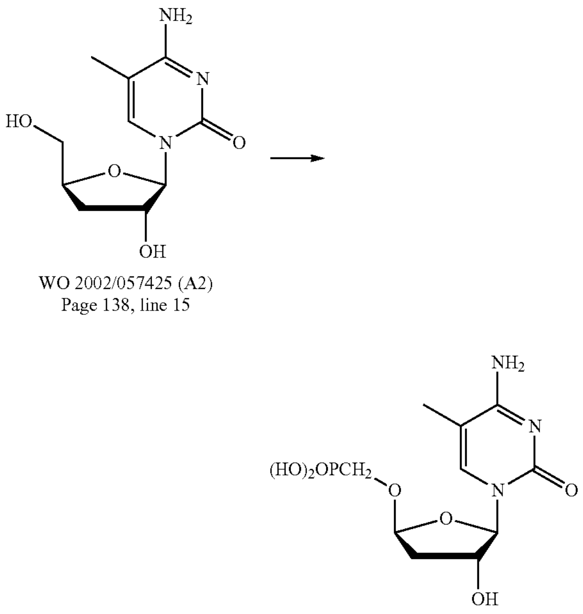
Example 104
Synthesis of Representative Compounds of Formula 76
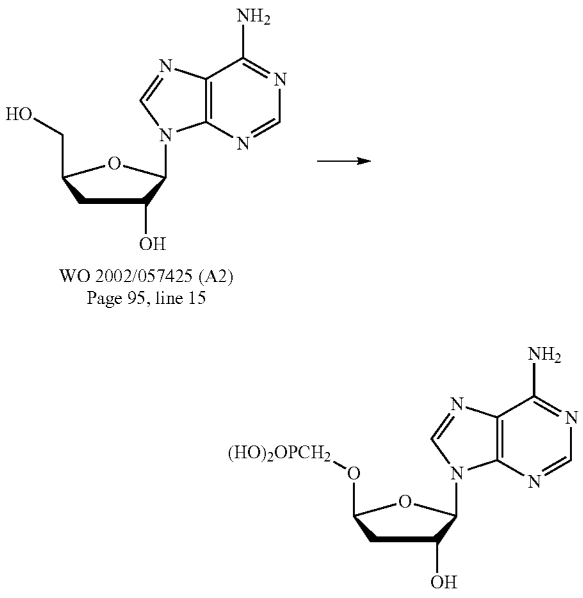

Example 105
Synthesis of Representative Compounds of Formula 76
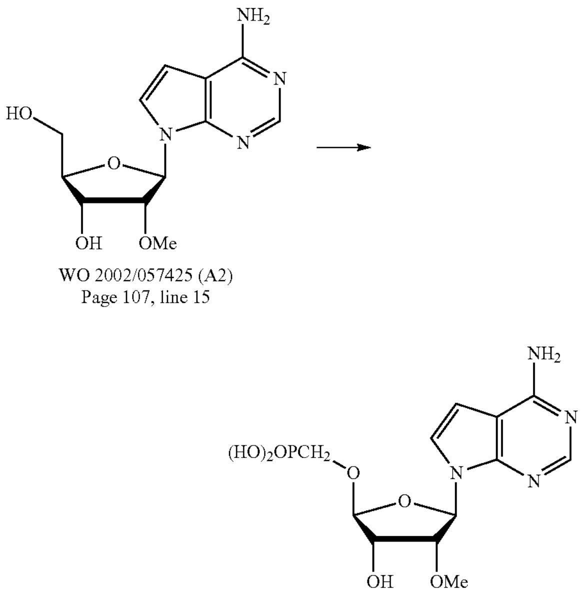
Example 106
Synthesis of Representative Compounds of Formula 76
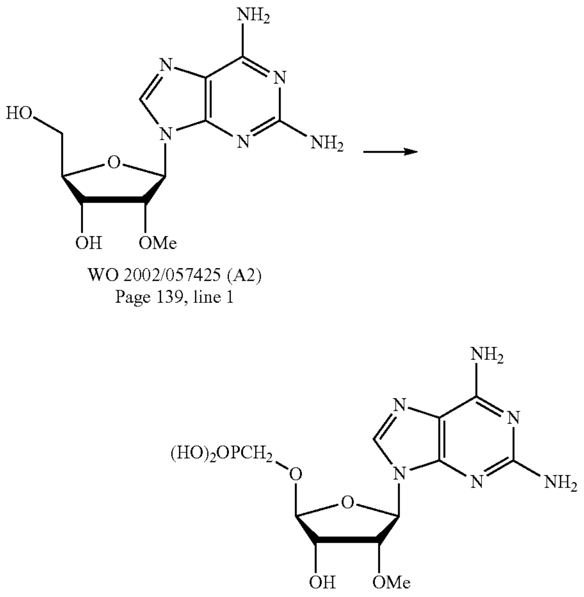
Example 107
Synthesis of Representative Compounds of Formula 76
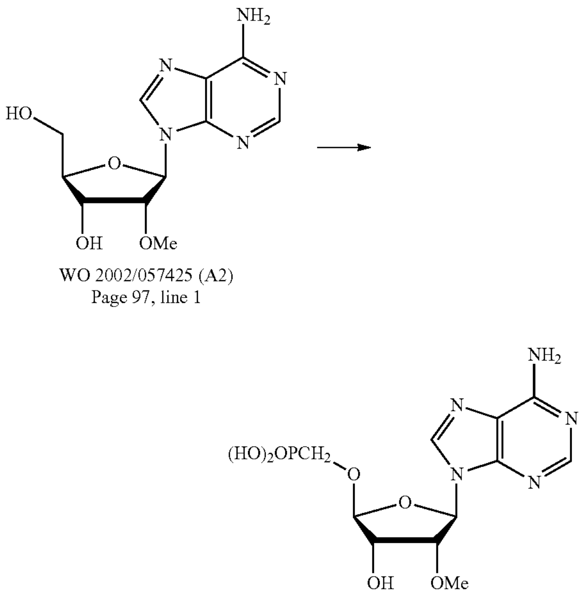
Example 108
Synthesis of Representative Compounds of Formula 76
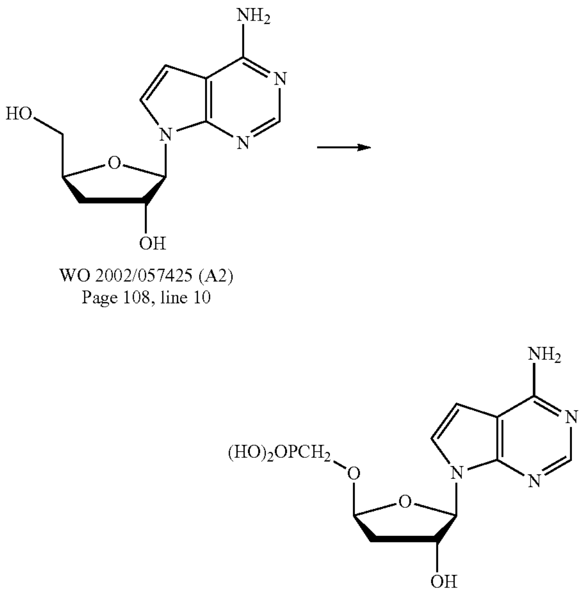

Example 109
Synthesis of Representative Compounds of Formula 76
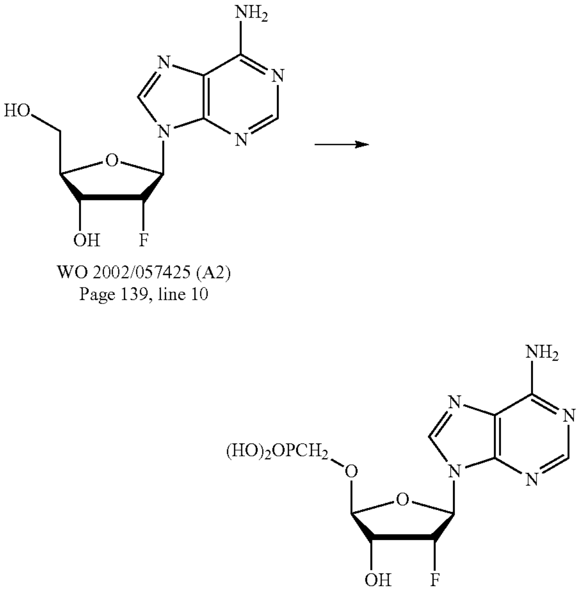
Example 110
Synthesis of Representative Compounds of Formula 76
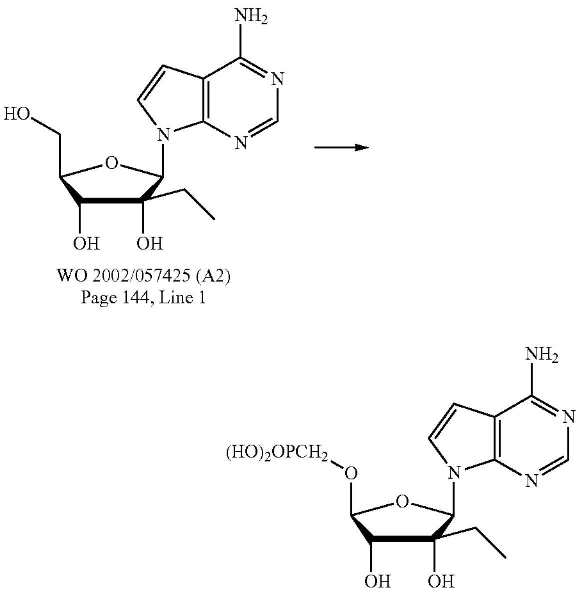
Example 111
Synthesis of Representative Compounds of Formula 76
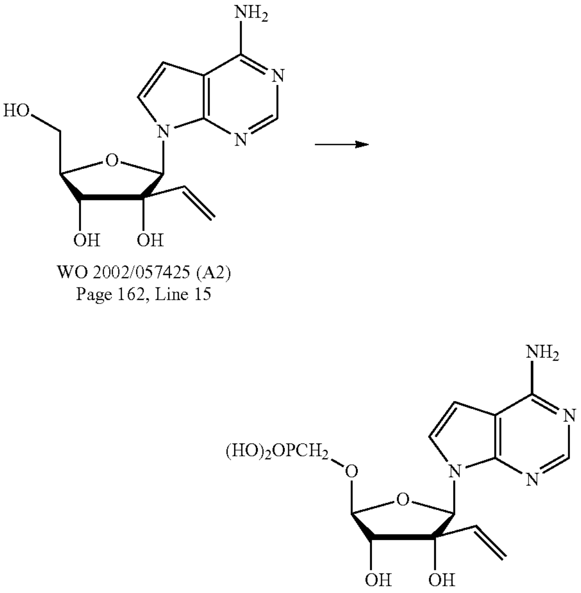
Example 112
Synthesis of Representative Compounds of Formula 76
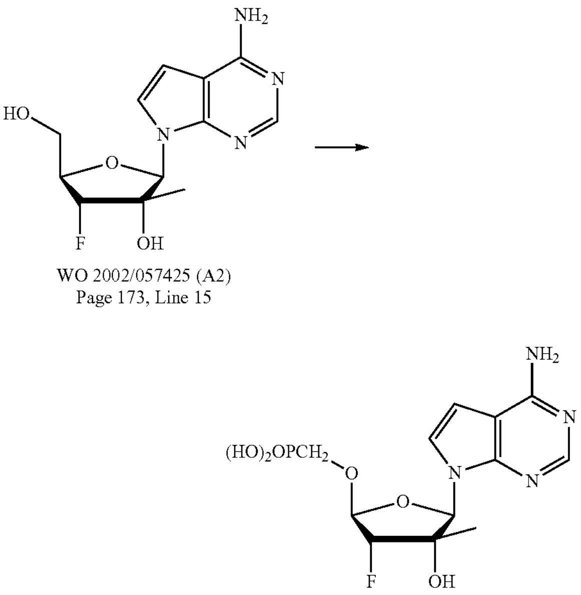

Example 113

Synthesis of Representative Compounds of Formula 76

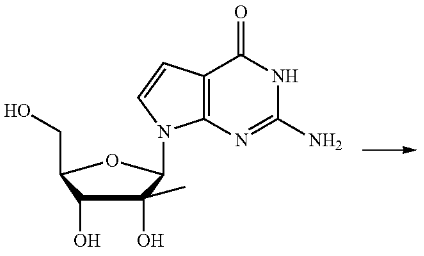

WO 2002/057425 (A2)
Page 145, line 25

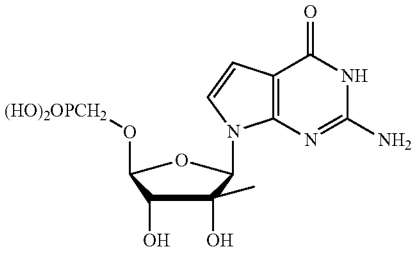

Example 114

Synthesis of Representative Compounds of Formula 76

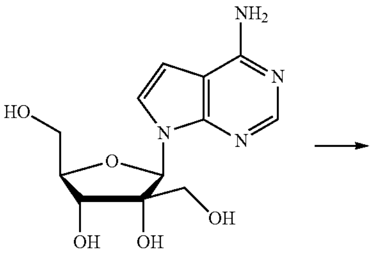

WO 2002/057425 (A2)
Page 165, Line 1

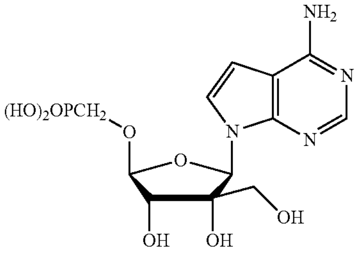

Note: one equivalent of TBDMS-Cl can be used in the protection of the 5'-hydroxyl. The mixture of two TBDMS ethers of the two primary alcohols can be separated, and the 5'-hydroxyl protected ether can be used in subsequent reactions.

Example 115

Synthesis of Representative Compounds of Formula 76

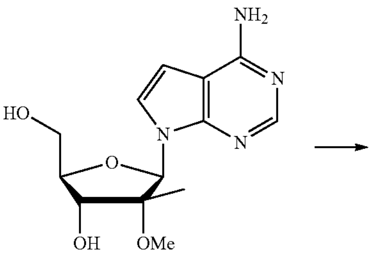

WO 2002/057425 (A2)
Page 176, Line 15

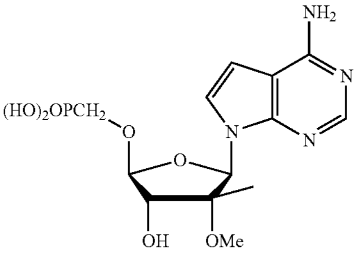

Example 116

Synthesis of Representative Compounds of Formula 76

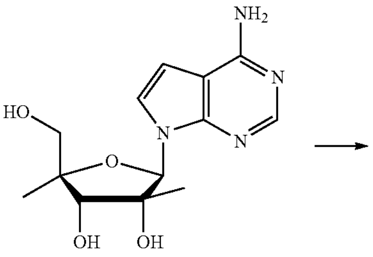

WO 2002/057425 (A2)
Page 170, Line 25

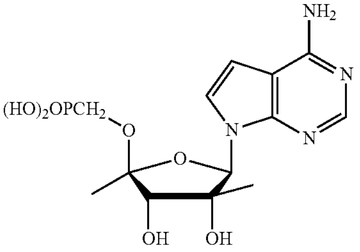

Example 117
Synthesis of Representative Compounds of Formula 76
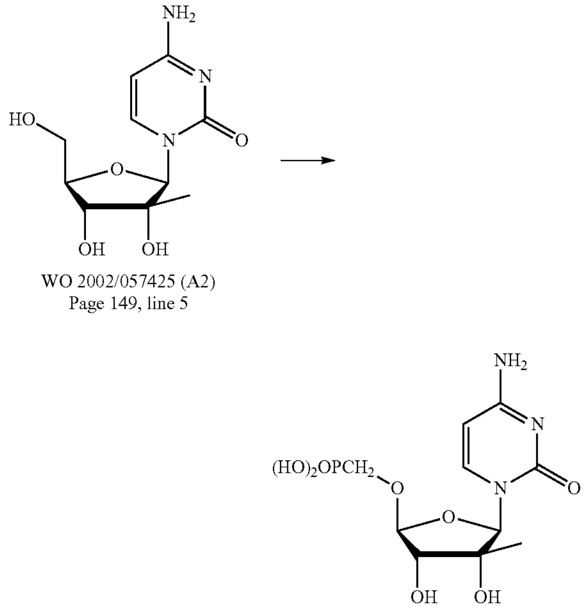
Example 118
Synthesis of Representative Compounds of Formula 76
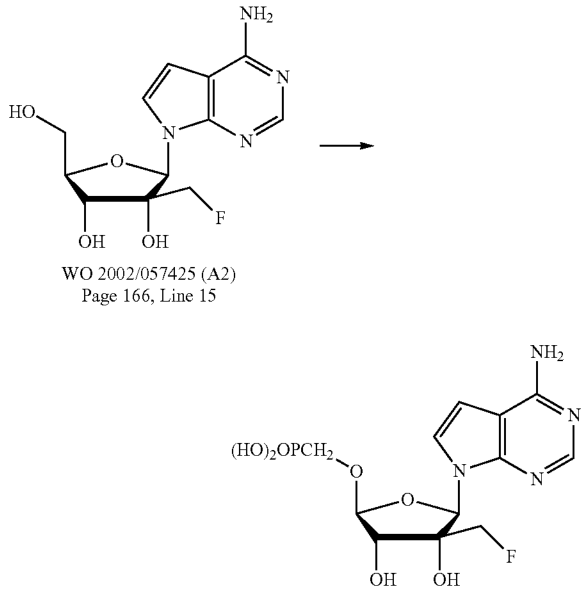
Example 119
Synthesis of Representative Compounds of Formula 76
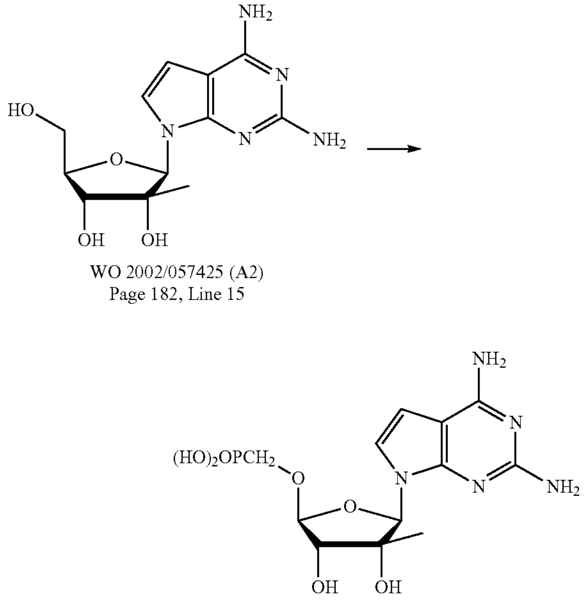
Example 120
Synthesis of Representative Compounds of Formula 76
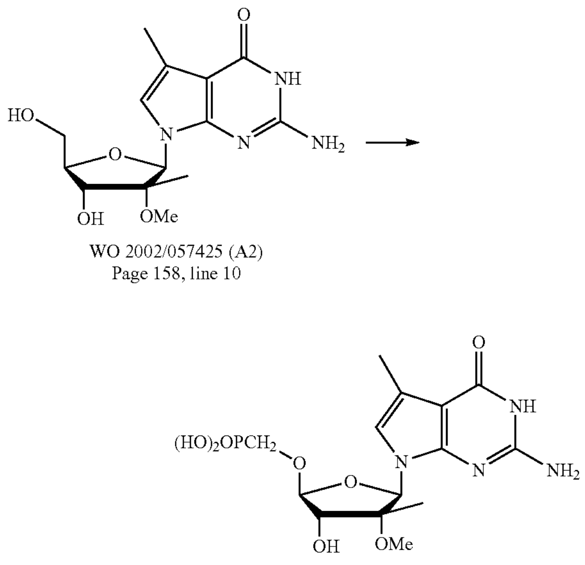

Example 121
Synthesis of Representative Compounds of Formula 76
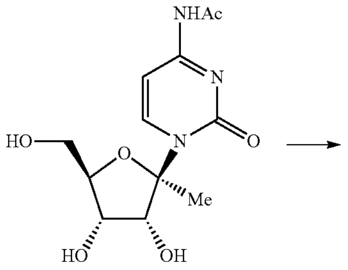
WO 01/90121 (page 89, table)
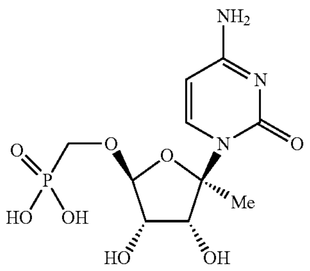
Example 122
Synthesis of Representative Compounds of Formula 76
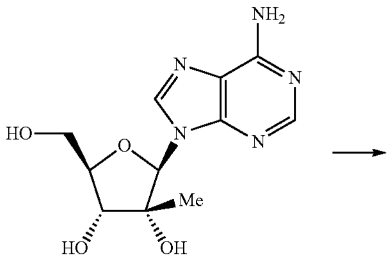
WO 01/90121 (page 115, table)
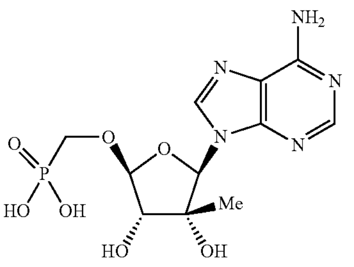
Example 123
Synthesis of Representative Compounds of Formula 76
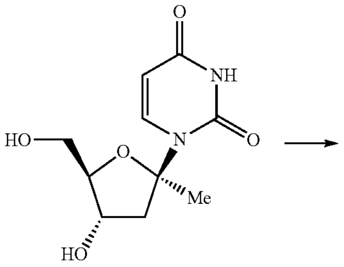
WO 01/90121 (page 102, table)
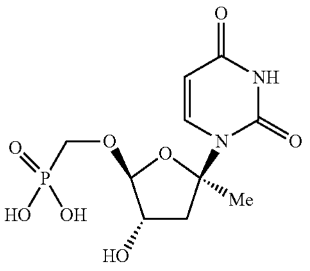
Example 124
Synthesis of Representative Compounds of Formula 76
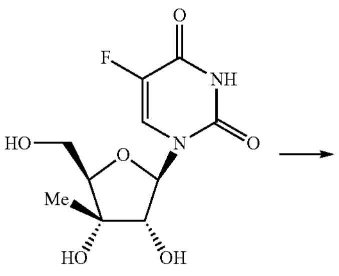
WO 01/90121 (page 167, table)
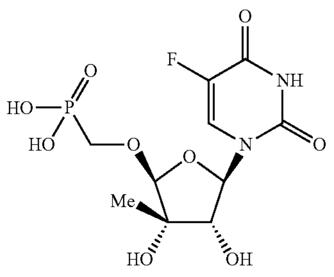

Example 125

Synthesis of Representative Compounds of Formula 76

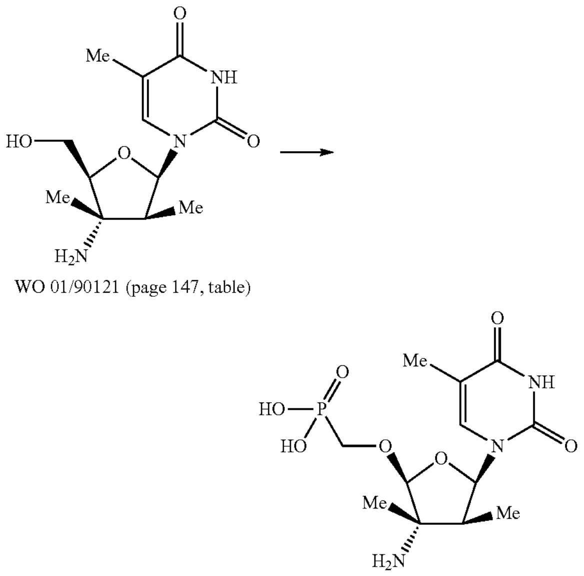

Note: Several options exist for the protection of the amine in the starting material. It can be protected as its corresponding benzyl carbamate, allyl carbamate, trifluoroacetamide, or N-diphenylmethyleneamine derivative.

Example 126

Synthesis of Representative Compounds of Formula 76

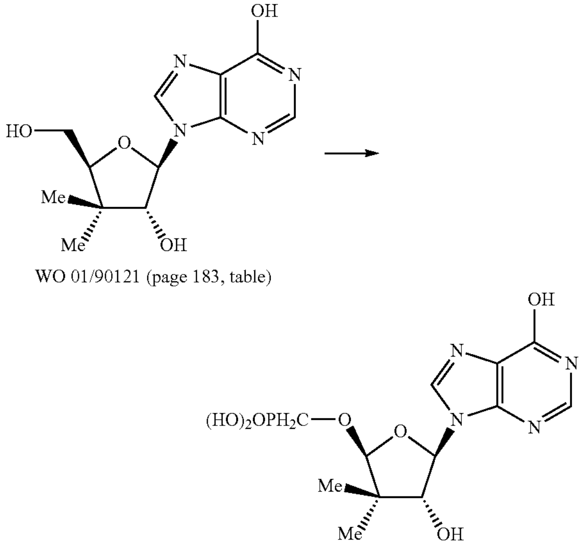

Example 127

Synthesis of Representative Compounds of Formula 76

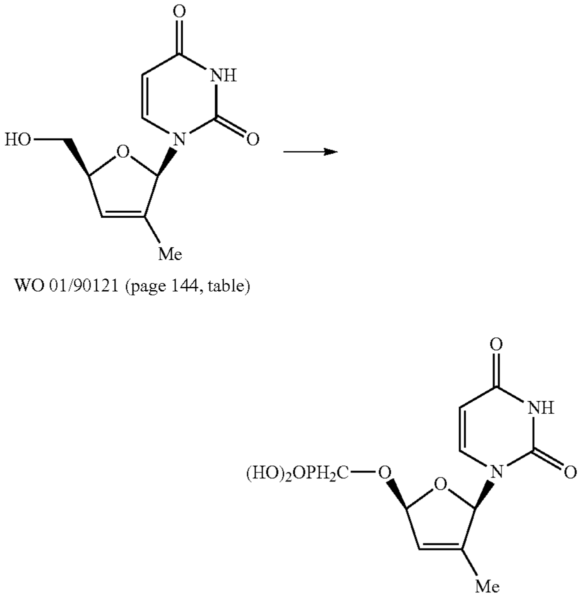

Example 128

Synthesis of Representative Compounds of Formula 76

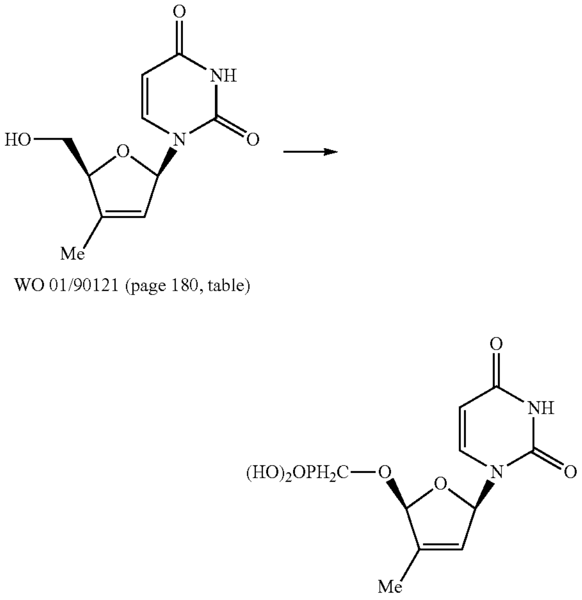

Example 129
Synthesis of Representative Compounds of Formula 76
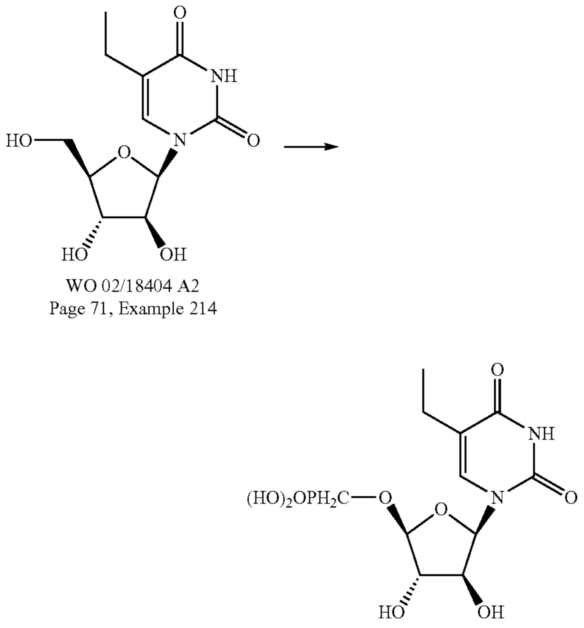
Example 130
Synthesis of Representative Compounds of Formula 76
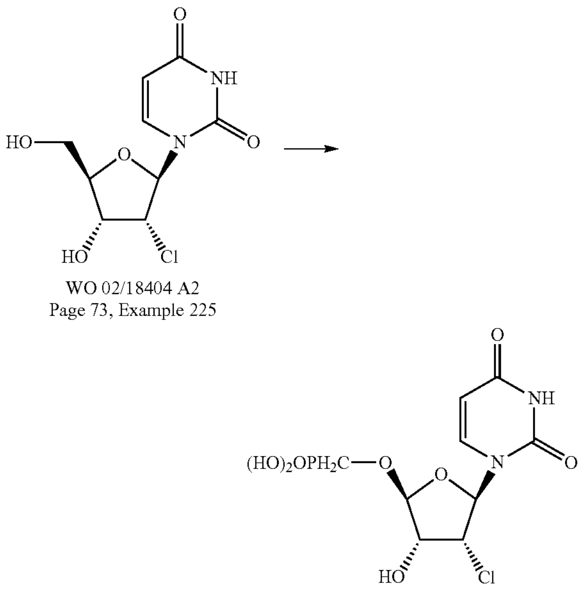
Example 131
Synthesis of Representative Compounds of Formula 76
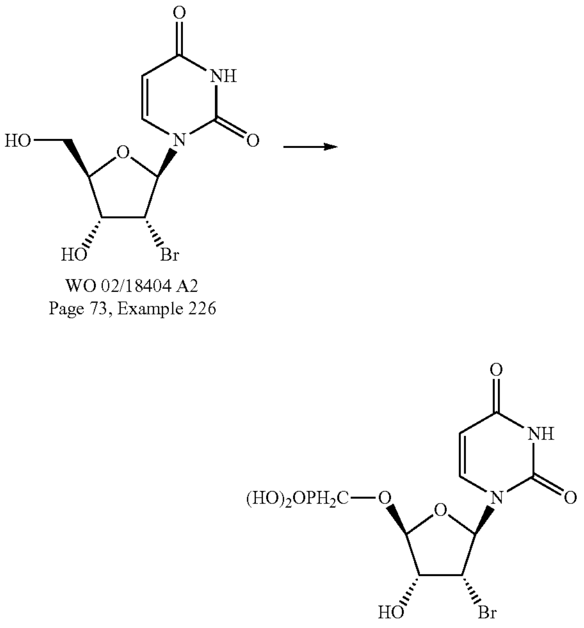
Example 132
Synthesis of Representative Compounds of Formula 76
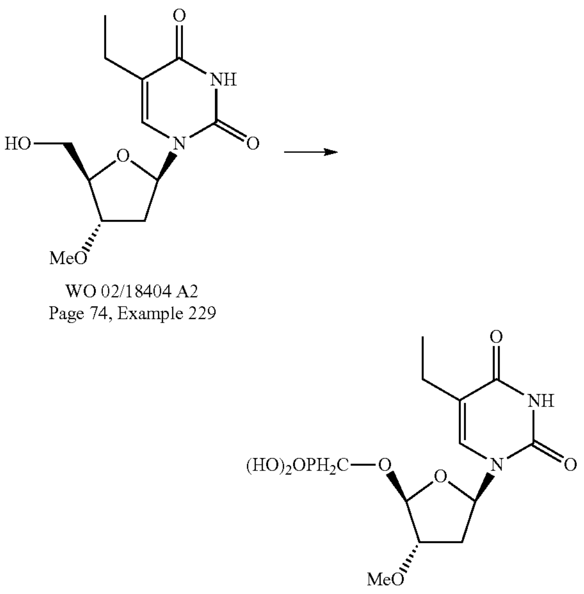

Example 133
Synthesis of Representative Compounds of Formula 76
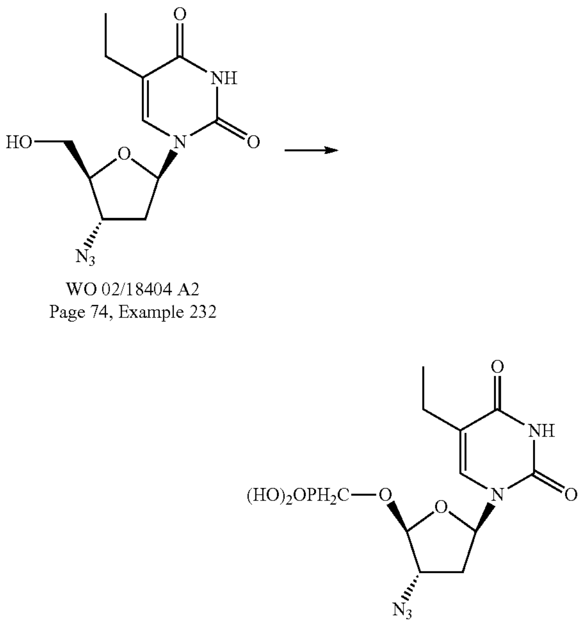
Example 134
Synthesis of Representative Compounds of Formula 76
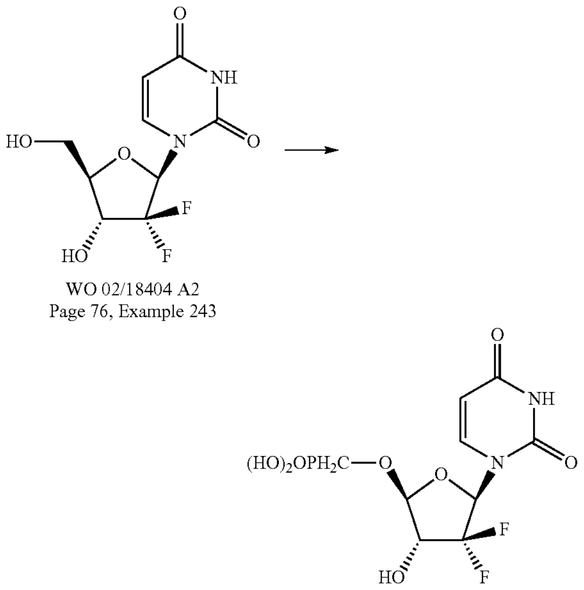
Example 135
Synthesis of Representative Compounds of Formula 76
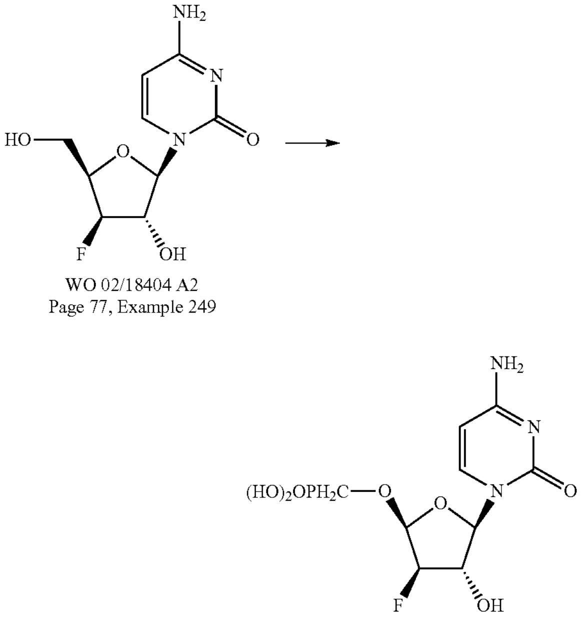
Example 136
Synthesis of Representative Compounds of Formula 76
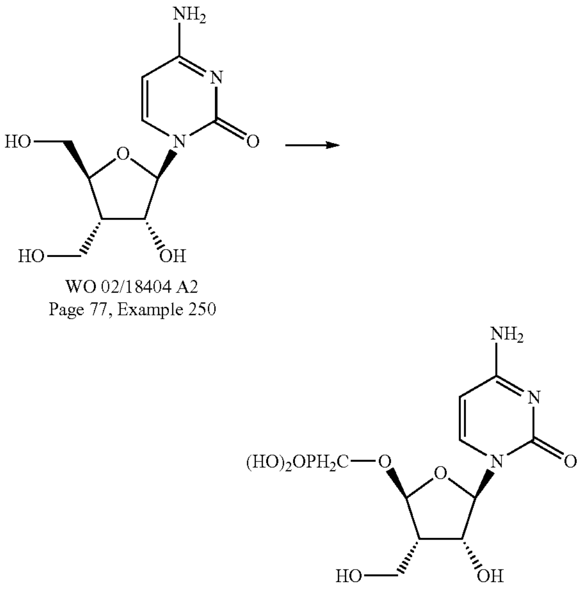

Example 137
Synthesis of Representative Compounds of Formula 76
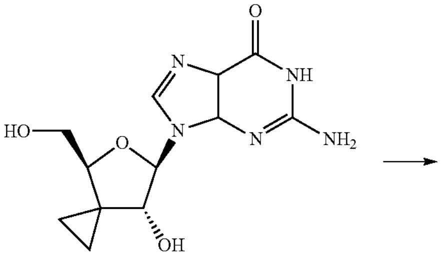
WO 01/60315 A2
Page 20, Compound 33
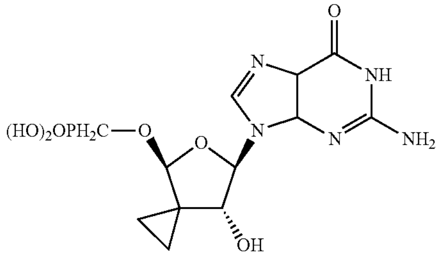
Example 138
Synthesis of Representative Compounds of Formula 76
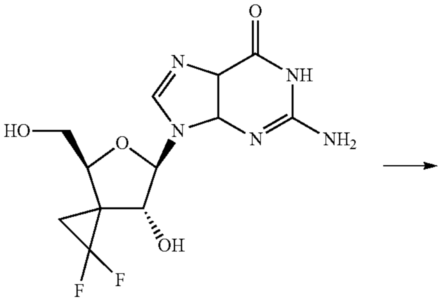
WO 01/60315 A2
Page 20, Compound 35
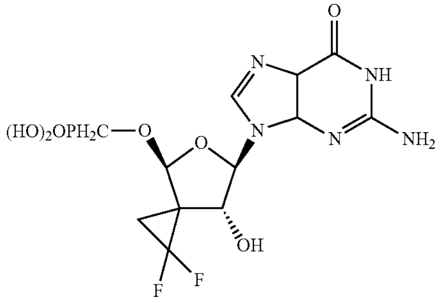
Example 139
Synthesis of Representative Compounds of Formula 76
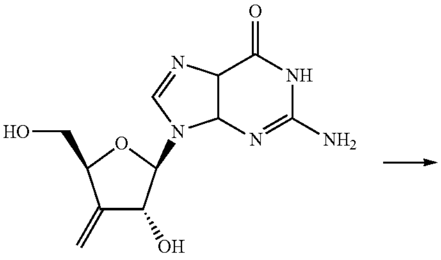
WO 01/60315 A2
Page 21, Compound 37
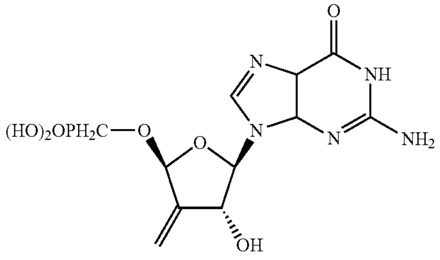
Example 140
Synthesis of Representative Compounds of Formula 76
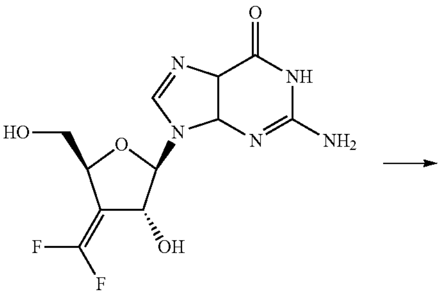
WO 01/60315 A2
Page 21, Compound 39
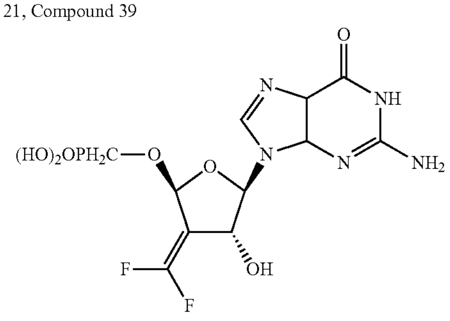

Example 141
Synthesis of Representative Compounds of Formula 76
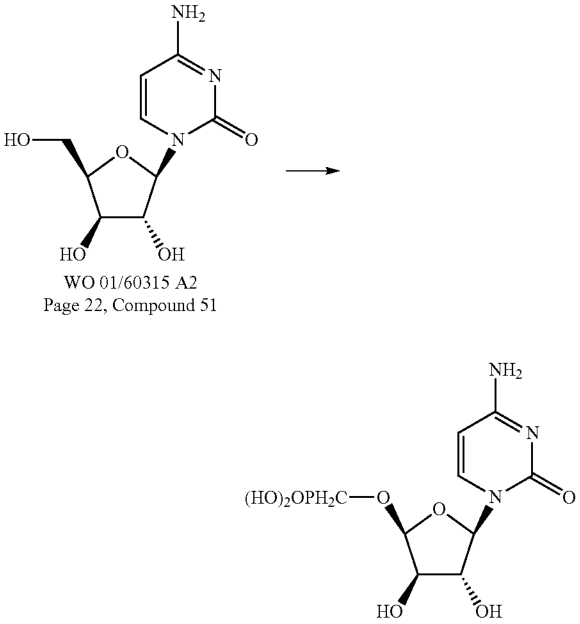
Example 142
Synthesis of Representative Compounds of Formula 76
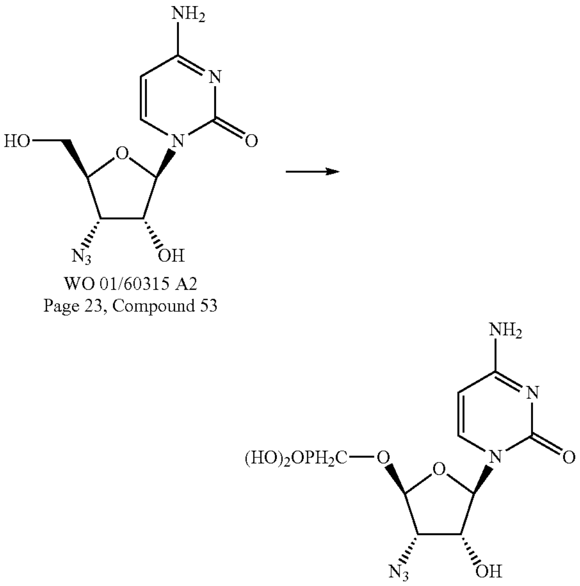
Example 143
Synthesis of Representative Compounds of Formula 76
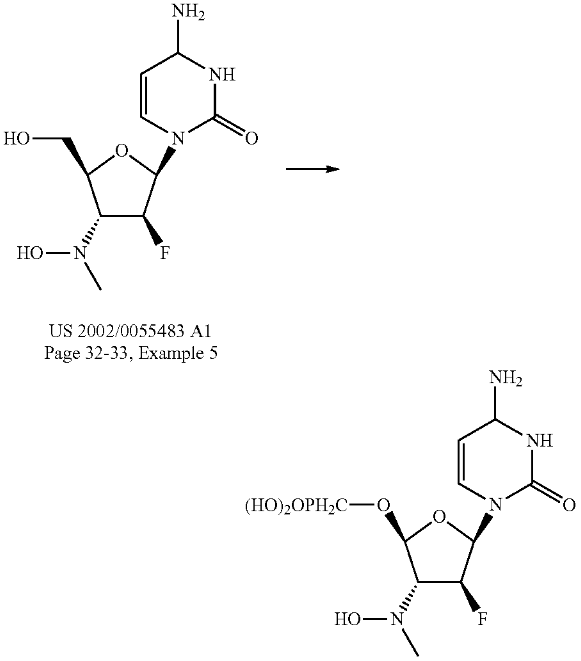
Example 144
Synthesis of Representative Compounds of Formula 76
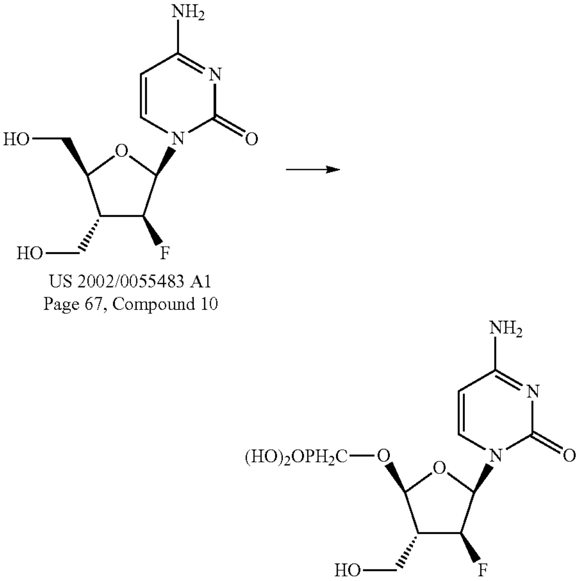
Note: one equivalent of TBDMS-Cl can be used in the protection of the 5'-hydroxyl. The mixture of two TBDMS ethers of the two primary alcohols can be separated, and the 5'-hydroxyl protected ether can be used in subsequent reactions.

Example 145

Synthesis of Representative Compounds of Formula 76

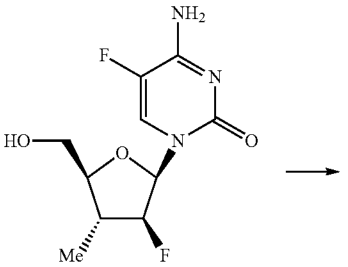

US 2002/0055483 A1
Page 68, Compound 21

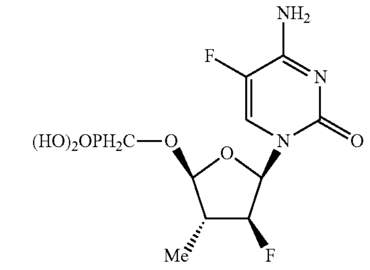

Example 146

Synthesis of Representative Compounds of Formula 76

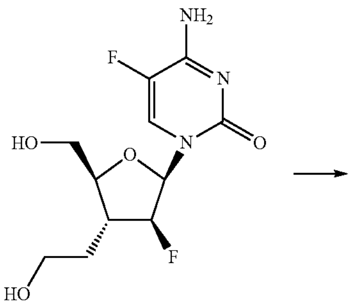

US 2002/0055483 A1
Page 68, Compound 28

-continued

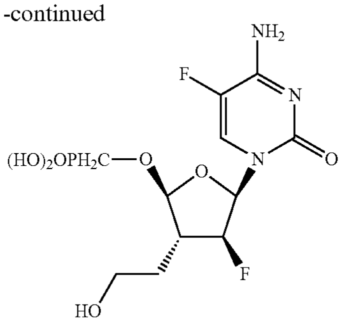

Note: one equivalent of TBDMS-Cl can be used in the protection of the 5'-hydroxyl. The mixture of two TBDMS ethers of the two primary alcohols can be separated, and the 5'-hydroxyl protected ether can be used in subsequent reactions.

Example 147

Synthesis of Representative Compounds of Formula 76

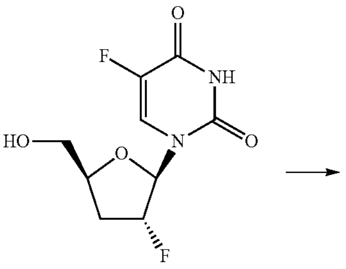

US 6, 348, 587 B1
Column 34, Lines 46-58

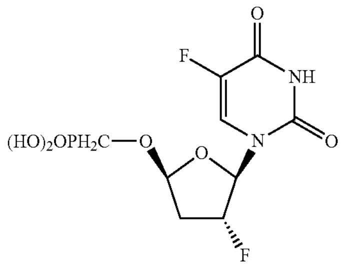

Example 148

Synthesis of Representative Compounds of Formula 76

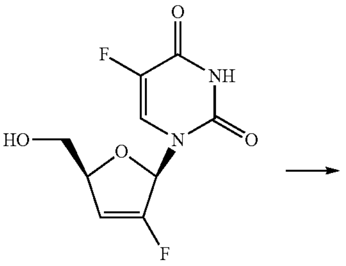

US 6, 348, 587 B1
Column 26, Compound 30

-continued
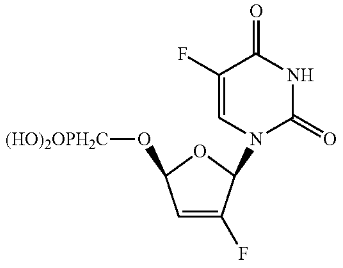
Example 149
Synthesis of Representative Compounds of Formula 76
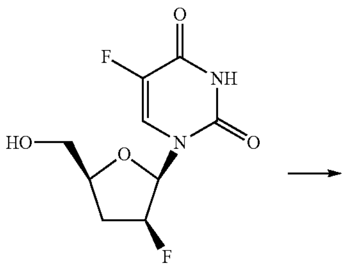
US 6, 348, 587 B1
Column 26, Compound 31
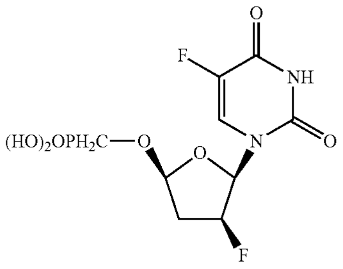
Example 150
Synthesis of Representative Compounds of Formula 76
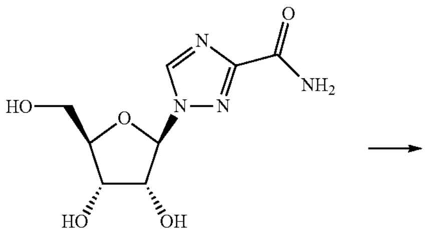
Ribavirin, available from ICN, Cat. No. 196066
-continued
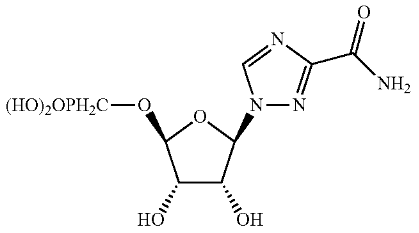
Example 151
Synthesis of Representative Compounds of Formula 76
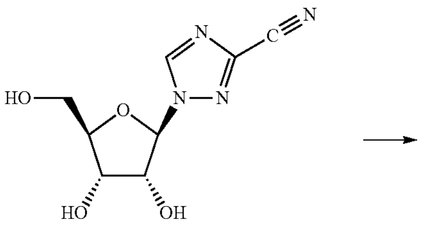
*J. Med. Chem.* 1990, 33, 44-48.
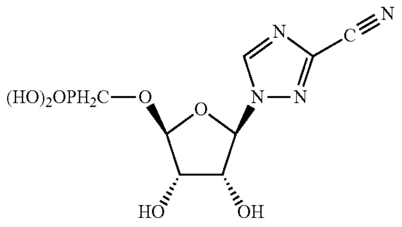
Example 152
Synthesis of Representative Compounds of Formula 76
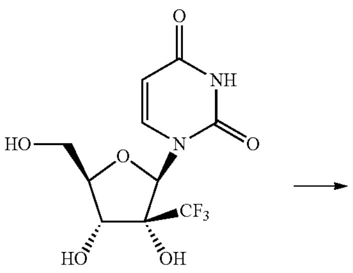
*Org. Lett.* 2001, 3, 1025-1028.

-continued

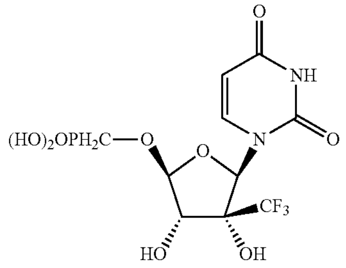

Example 153

Synthesis of Representative Compounds of Formula 76

L-Nucleoside Analogs

Many compounds of Formula 76 with a sugar moiety in its L-configuration are either commercially available or can be prepared by procedures described in the published literature. Many of the compounds illustrated in Examples 71-153 can be prepared from one of the precursors described in Example 70 (see section: *Preparation And Availability Of Starting Materials*). The enantiomers of other nucleoside analogs (the L-nucleosides) can be prepared from enantiomers of the precursors of 70.3.1, 70.3.2, and 70.3.3. This Example describes a preparation of the enantiomers of 70.3.1, 70.3.2, and 70.3.3.

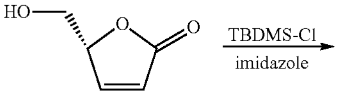

Fluka Cat. No. 55673
153.4.1

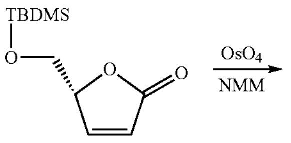

153.4.2

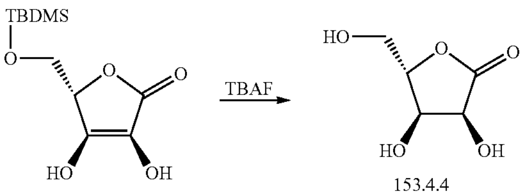

153.4.3

153.4.4
Enantiomer of 70.3.1

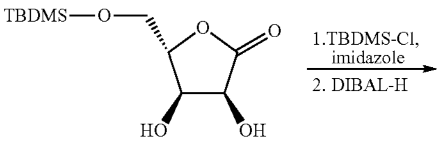

153.4.3

-continued

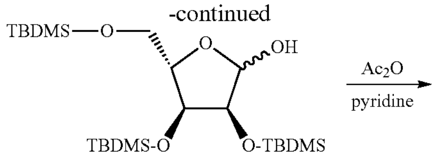

153.4.5
Enantiomer of 70.3.2
(LG = OH, R = TBDMS)

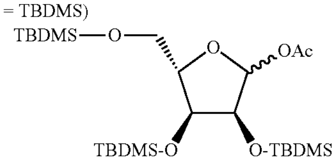

153.4.6
Enantiomer of 70.3.2
(LG = OAc, R = TBDMS)

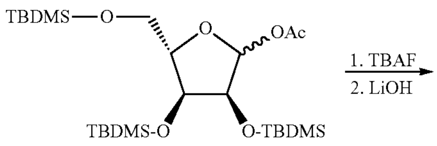

153.4.6

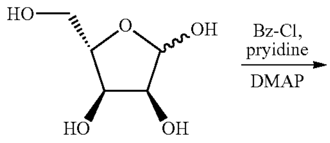

153.4.7

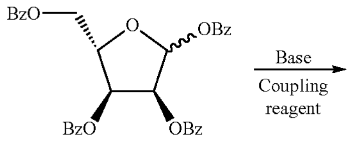

153.4.8

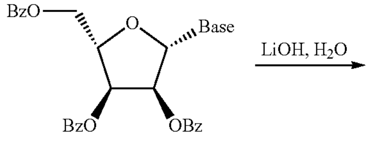

153.4.9

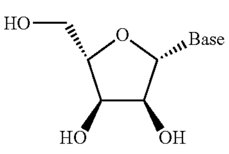

153.4.10
Enantiomer of 70.3.3

The commercially available starting material 153.4.1 can be converted to 153.4.4, which is the enantiomer of 70.3.1, using the sequence of reactions outlined above. The osmium tetroxide catalyzed dihydroxylation introduces the diol selectively to the face opposite of the tert-butyldimethylsilyl (TBDMS) ether of the hydroxymethyl group.

The diol in intermediate 153.4.3 can be protected as its TBDMS ether. Diisobutylaluminum hydride reduction of the lactone at low temperature produces 153.4.5, which can be converted to 153.4.6 by acetylation.

Deprotection of 153.4.6 produces L-ribose (153.4.7). Acylation converts all hydroxyl groups in 153.4.7 to the corresponding benzoyl esters. Standard coupling reactions with a variety of nucleobases produces 153.4.10, which is the enantiomer of 70.3.3.

From 70.3.1, 70.3.2, and 70.3.3, L-nucleosides can be prepared using known procedures, many of which are discussed in previous sections, in the patents cited, and in the published literature.

Many compounds in Examples 70-153 have their corresponding L-analog starting materials described in the same patent. These L-nucleosides can then be used in the same reaction sequences to produce the phosphonate analogs of the L-nucleosides.

Example 154

Synthesis of Representative Compounds of Formulae 84 and 85

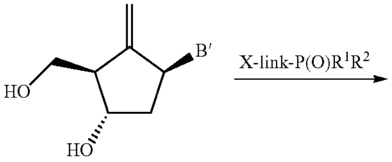

154.5

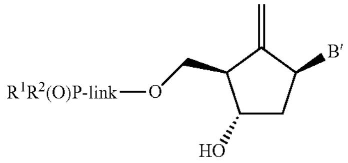

154.2

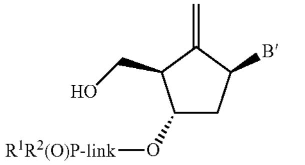

154.3

Representative compounds of the invention can be prepared as illustrated above. Direct alkylation of entecavir derivative 154.5 with a phosphonate attached to a leaving group can be performed in the presence of a suitable organic or inorganic base to obtain analogs of the types 154.2 and 154.3. Compound 154.5 is prepared from protected or deprotected intermediates described in U.S. Pat. Nos. 5,206,244 and 5,340,816. After reaction, a mixture of compounds 154.2 and 154.3 is furnished, which are separated by the appropriate chromatographic method.

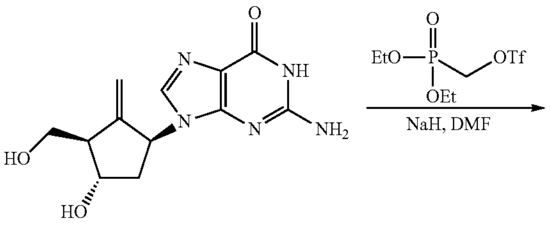

154.1

-continued

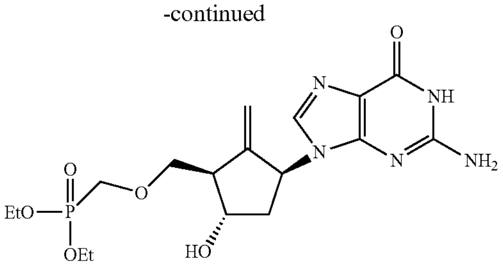

154.6

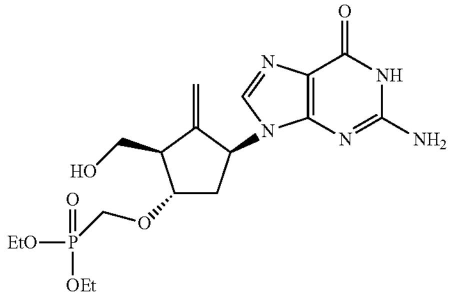

154.7

For instance, entecavir (154.1) is treated with sodium hydroxide and reacted with diethyl phosphomethyltriflate to afford a mixture of 154.6 and 154.7 as illustrated above. Silica gel chromatography is employed to give pure samples of the separated products.

Example 155

Synthesis of Representative Compounds of Formulae 84 and 85

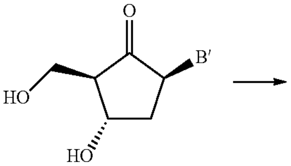

155.8

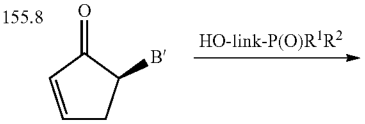

155.9

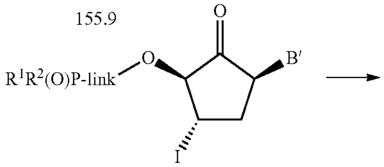

155.10

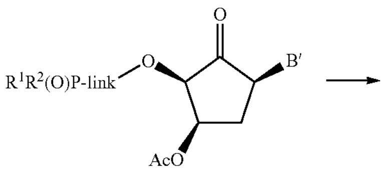

155.11

-continued

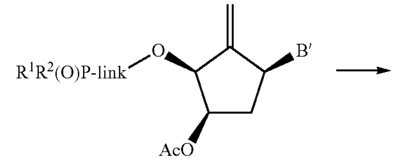

155.12

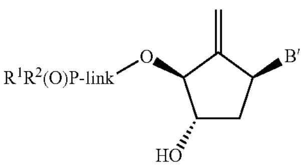

155.4

Representative compounds of the invention can be prepared as illustrated above. Compounds having the structure 155.4 are prepared from intermediate 155.8, which is derived from deprotected intermediates described in U.S. Pat. Nos. 5,206,244 and 5,340,816. Diol 155.8 is converted to glycal 155.9 through published procedures. Upon treatment with IBr in the presence of the appropriate phosphonate alcohol, glycal 155.9 is converted to iodide 155.10. Nysted methylenation provides alkene 155.12, whose hydroxy stereocenter is then inverted to give the final compound 155.4.

For instance, intermediate 155.13 is converted to glycal 155.14 (see *J. Am. Chem. Soc.* 1972, 94, 3213) and then treated with IBr and diethyl phosphomethanol to furnish iodide 155.15 (see *J. Org. Chem.* 1991, 56, 2642). Nucleophilic substitution of the iodide using AgOAc affords acetate 155.16. After methylenation using the procedure of Nysted (U.S. Pat. No. 3,865,848; *Aldrichim. Acta* 1993, 26, 14), the acetate group is removed using sodium methoxide in methanol. The resulting alcohol is inverted by the Mitsunobo protocol, and a second acetate deprotection produces the desired compound 155.18.

Example 156

Preparation of Representative Compounds of Formula 78

Representative compounds of the invention can be prepared as illustrated below.

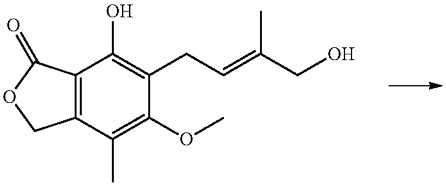

156A

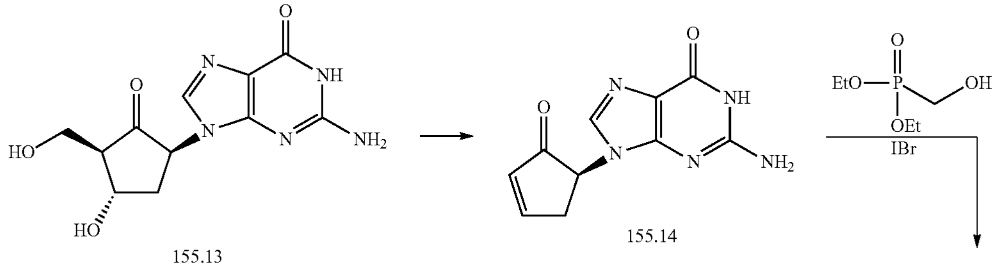

155.13

155.14

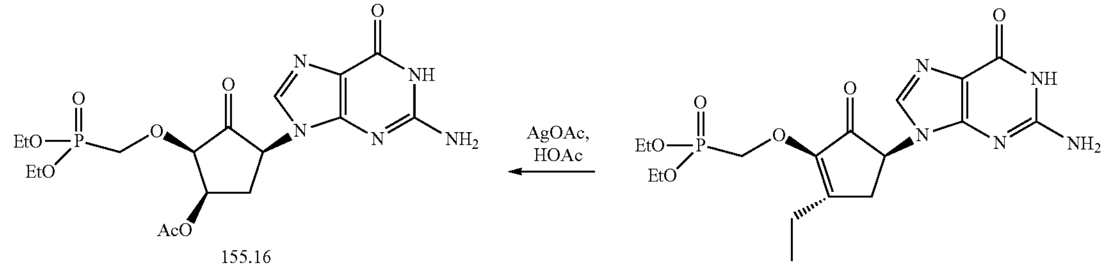

155.16

155.15

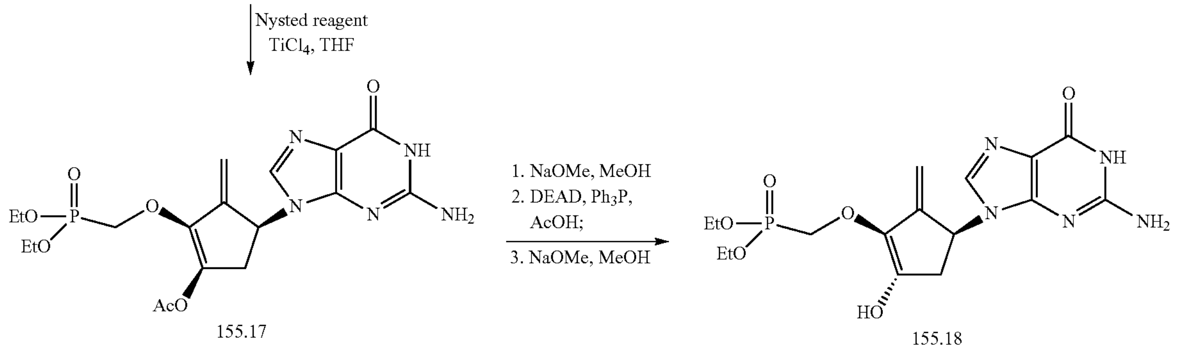

155.17

155.18

-continued

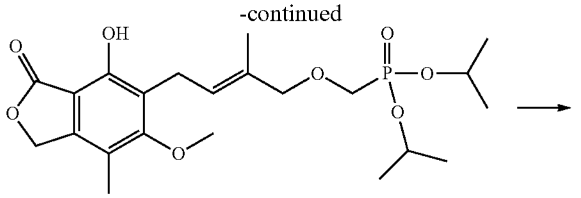

156B

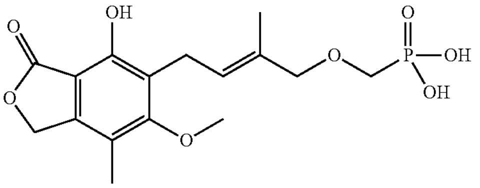

+

156C

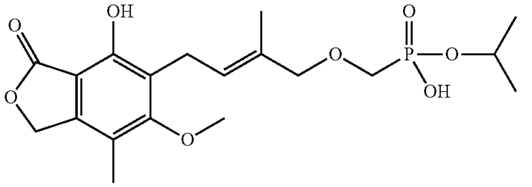

156D

[4-(4-Hydroxy-6-methoxy-7-methyl-3-oxo-1,3-dihydro-isobenzofuran-5-yl)-2-methyl-but-2-enyloxymethyl]-phosphonic acid diisopropyl ester A mixture of 7-hydroxy-6-(4-hydroxy-3-methyl-but-2-enyl)-5-methoxy-4-methyl-3H-isobenzofuran-1-one 156A (50 mg, 0.18 mmol, Pankiewicz et al., *J. Med. Chem.,* 45, 703), diisopropyl bromomethylphosphonate (93 mg, 0.36 mmol) and lithium t-butoxide (1M in THF, 0.54 mL) in DMF (3 mL) was heated at 70° C. for 5 hours. The reaction was quenched with 1N HCl. The mixture was poured into 5% aqueous lithium chloride, extracted with ethyl acetate, and concentrated. The residue was purified by chromatography on silica gel, affording [4-(4-hydroxy-6-methoxy-7-methyl-3-oxo-1,3-dihydro-isobenzofuran-5-yl)-2-methyl-but-2-enyloxymethyl]-phosphonic acid diisopropyl ester 156B (25 mg, 32%); $^1$H NMR (300 MHz, $CDCl_3$) δ 1.25 (m, 12H), 1.79 (s, 3H), 2.05 (s, 3H), 3.37 (d, J=6.6 Hz, 2H), 3.58 (d, 2H), 3.77 (s, 3H), 3.97 (m, 2H), 4.68 (m, 2H), 5.19 (s, 2H), 5.45 (t, J=6.6 Hz, 1H), 7.83 (s, 1H) ppm.

[4-(4-Hydroxy-6-methoxy-7-methyl-3-oxo-1,3-dihydro-isobenzofuran-5-yl)-2-methyl-but-2-enyloxymethyl]-phosphonic acid and [4-(4-Hydroxy-6-methoxy-7-methyl-3-oxo-1,3-dihydro-isobenzofuran-5-yl)-2-methyl-but-2-enyloxymethyl]-phosphonic acid monoisopropyl ester To a solution of [4-(4-hydroxy-6-methoxy-7-methyl-3-oxo-1,3-dihydro-isobenzofuran-5-yl)-2-methyl-but-2-enyloxymethyl]-phosphonic acid diisopropyl ester 156B (25 mg, 0.055 mmol) and 2,6-lutidine (0.18 mL, 1.65 mmol) in acetonitrile was added trimethylsilyl bromide (0.126 mL, 1.1 mmol) at 0° C. The mixture was allowed to warm to room temperature and stirred for 4 hours. The reaction was quenched with methanol at 0° C., and the resulting mixture was concentrated. The residue was purified by preparative reverse-phase HPLC to afford, after removal of the solvent, [4-(4-hydroxy-6-methoxy-7-methyl-3-oxo-1,3-dihydro-isobenzofuran-5-yl)-2-methyl-but-2-enyloxymethyl]-phosphonic acid 156C as an oil (17 mg, 83%); $^1$H NMR (300 MHz, $CD_3OD$) δ 1.81 (s, 3H), 2.06 (s, 3H), 3.40 (d, J=6.6 Hz, 2H), 3.50 (d, 2H), 3.77 (s, 3H), 3.97 (s, 2H), 5.20 (s, 2H), 5.47 (t, J=6.6 Hz, 1H) and [4-(4-hydroxy-6-methoxy-7-methyl-3-oxo-1,3-dihydro-isobenzofuran-5-yl)-2-methyl-but-2-enyloxymethyl]-phosphonic acid monoisopropyl ester 156D as an oil (2 mg, 7%); $^1$H NMR (300 MHz, $CD_3OD$) δ 1.23 (d, 6H), 1.81 (s, 3H), 2.08 (s, 3H), 3.40 (d, J=6.6 Hz, 2H), 3.50 (d, 2H), 3.77 (s, 3H), 3.90 (s, 2H), 4.50 (m, 1H), 5.20 (s, 2H), 5.47 (t, J=6.6 Hz, 1H) ppm.

Example 157

Preparation of Representative Compounds of Formula 78

Representative compounds of the invention can be prepared as illustrated below.

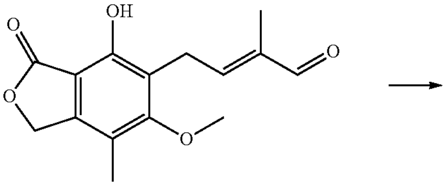

157A

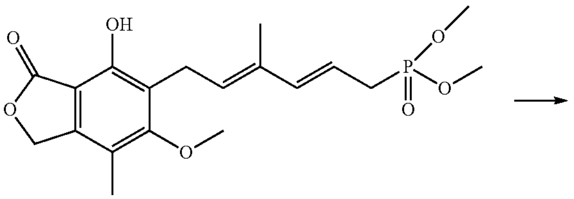

157B

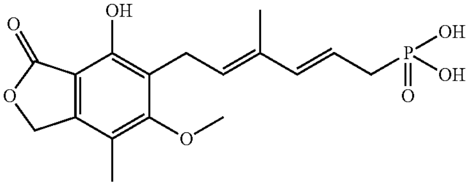

157C

[5-(4-Hydroxy-6-methoxy-7-methyl-3-oxo-1,3-dihydro-isobenzofuran-5-yl)-3-methyl-penta-1,3-dienyl]-phosphonic acid dimethyl ester To a solution of tetramethylmethylene diphosphonate (102 mg, 0.44 mmol) in THF (2.5 mL) was added a THF solution of sodium bis(trimethysilyl)amide (1.0 M, 0.44 mL). After stirring for 30 minutes, a solution of 4-(4-hydroxy-6-methoxy-7-methyl-3-oxo-1,3-dihydro-isobenzofuran-5-yl)-2-methyl-but-2-enal 157A (30 mg, 0.11 mmol, Pankiewicz et al., *J. Med. Chem.,* 45, 703) in THF (2.5 mL) was added and stirring was continued for an additional 15 minutes. The reaction was quenched with saturated aqueous ammonium chloride. The mixture was extracted with ethyl acetate. After evaporation of solvent, the residue was purified by chromatography on silica gel eluting with ethyl acetate (50% to 100%)/hexanes, affording [5-(4-hydroxy-6-methoxy-7-methyl-3-oxo-1,3-dihydro-isobenzofuran-5-yl)-3-methylpenta-1,3-dienyl]-phosphonic acid dimethyl ester 157B (30 mg, 71%) as an oil; $^{1}$H NMR (300 MHz, $CDCl_3$) δ 1.80 (s, 3H), 2.04 (s, 3H), 3.45 (d, J=6.6 Hz, 2H), 3.76 (s, 3H), 3.88 (d, 6H), 5.20 (s, 3H), 5.55 (m, 1H), 5.95 (m, 1H), 7.05 (m, 1H), 7.65 (s, 1H) ppm.

[5-(4-Hydroxy-6-methoxy-7-methyl-3-oxo-1,3-dihydro-isobenzofuran-5-yl)-3-methyl-penta-1,3-dienyl]-phosphonic acid To a solution of [5-(4-hydroxy-6-methoxy-7-methyl-3-oxo-1,3-dihydro-isobenzofuran-5-yl)-3-methyl-penta-1,3-dienyl]-phosphonic acid dimethyl ester 157B (22 mg, 0.057 mmol) and 2,6-lutidine (0.22 mL, 1.71 mmol) in acetonitrile was added trimethylsilyl bromide (0.183 mL, 1.71 mmol) at 0° C. The mixture was allowed to warm to room temperature and stirred for 1 hour. The reaction was quenched with methanol at 0° C., and the resulting mixture was concentrated. The residue was purified by preparative reverse-phase HPLC to afford, after removal of the solvent, [5-(4-hydroxy-6-methoxy-7-methyl-3-oxo-1,3-dihydro-isobenzofuran-5-yl)-3-methyl-penta-1,3-dienyl]-phosphonic acid 157C as a solid (13 mg, 65%); $^{1}$H NMR (300 MHz, $CD_3OD$) δ 1.91 (s, 3H), 2.10 (s, 3H), 3.55 (d, J=6.6 Hz, 2H), 3.75 (s, 3H), 5.2 (s, 2H), 5.6-5.8 (m, 2H), 6.9 (m, 1H) ppm.

Example 158

Preparation of Representative Compounds of Formula 78

Representative compounds of the invention can be prepared as illustrated below.

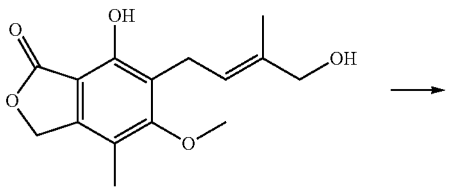

158A

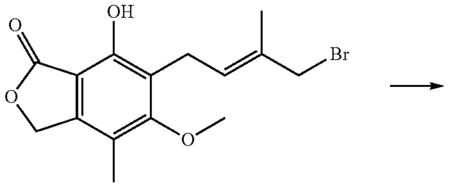

158B

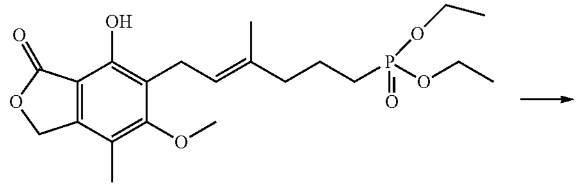

158C

-continued

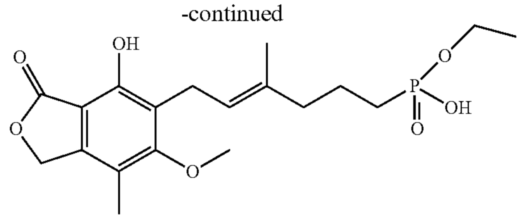

158D

6-(4-Bromo-3-methyl-but-2-enyl)-7-hydroxy-5-methoxy-4-methyl-3H-isobenzofuran-1-one Polymer-supported triphenylphosphine (3 mmol/g, 0.5 g) was soaked in dichloromethane (10 mL) for 1 hour. 7-Hydroxy-6-(4-hydroxy-3-methyl-but-2-enyl)-5-methoxy-4-methyl-3H-isobenzofuran-1-one 158A (100 mg, 0.36 mmol) and carbon tetrabromide (143 mg, 0.43 mmol) were sequentially added and the mixture was shaken for 1 h at room temperature. More carbon tetrabromide (143 mg, 0.43 mmol) was added and the mixture was shaken further for 1 hour. The mixture was filtered and the filtrate was concentrated. The residue was chromatographed on silica gel (0% to 60% ethyl acetate/hexanes) to afford 6-(4-bromo-3-methyl-but-2-enyl)-7-hydroxy-5-methoxy-4-methyl-3H-isobenzofuran-1-one 158B as an oil (52 mg, 42%); $^{1}$H NMR (300 MHz, $CDCl_3$) δ 1.95 (s, 3H), 2.16 (s, 3H), 3.44 (d, J=7.2 Hz, 2H), 3.78 (s, 3H), 3.98 (s, 2H), 5.21 (s, 2H), 5.68 (t, J=7.2 Hz, 1H), 7.71 (brs, 1H) ppm.

[5-(4-Hydroxy-6-methoxy-7-methyl-3-oxo-1,3-dihydro-isobenzofuran-5-yl)-3-methyl-pent-3-enyl]-phosphonic acid diethyl ester n-Butyl lithium (1.6 M in hexanes, 1 mL) was added to an equal volume of THF at −20° C. A solution of diethyl methylphosphonate (220 mg, 1.45 mmol) in THF (1 mL) was then added dropwise and the solution was stirred for 30 minutes. After cooling at −60° C., the solution was transferred via a cannula to a vial containing copper (I) iodide (276 mg, 1.45 mmol), and the resulting mixture was stirred for 1 h at −30° C. A solution of 6-(4-bromo-3-methyl-but-2-enyl)-7-hydroxy-5-methoxy-4-methyl-3H-isobenzofuran-1-one 158B (50 mg, 0.15 mmol) in THF (1 mL) was added and the mixture was allowed to warm to 0° C. for 2 h before saturated aqueous ammonium chloride was added. The reaction mixture was acidified with 2 N HCl and extracted with ethyl acetate. The ethyl acetate extract was concentrated and the residue was chromatographed on silica gel (40% to 100% ethyl acetate/hexanes), affording [5-(4-hydroxy-6-methoxy-7-methyl-3-oxo-1,3-dihydro-isobenzofuran-5-yl)-3-methyl-pent-3-enyl]-phosphonic acid diethyl ester 158C as an oil (27 mg, contaminated with the starting diethyl methylphosphonate); $^{1}$H NMR (300 MHz, $CDCl_3$) δ 1.32 (m, 6H), 1.8-1.9 (m, 5H), 2.18 (s, 3H), 2.25 (m, 2H), 3.42 (d, J=7.2 Hz, 2H), 3.78 (s, 3H), 4.15 (m, 4H), 5.21 (s, 2H), 5.24 (t, J=7.2 Hz, 1H), 7.65 (s, 1H) ppm.

[5-(4-Hydroxy-6-methoxy-7-methyl-3-oxo-1,3-dihydro-isobenzofuran-5-yl)-3-methyl-pent-3-enyl]-phosphonic acid monoethyl ester A mixture of [5-(4-hydroxy-6-methoxy-7-methyl-3-oxo-1,3-dihydro-isobenzofuran-5-yl)-3-methyl-pent-3-enyl]-phosphonic acid diethyl ester 158C (27 mg, 0.066 mmol), LiOH (200 mg), MeOH (3 mL) and water (1 mL) was stirred at 70° C. for 4 hours. After cooling, the reaction solution was acidified with 2 N HCl, mixed with brine, and extracted with ethyl acetate/acetonitrle. The organic extract was concentrated and the residue was purified by preparative reverse-phase HPLC (acetonitrile and 0.1% aqueous $CF_3COOH$), affording [5-(4-hydroxy-6-methoxy-7-methyl-3-oxo-1,3-dihydro-isobenzofuran-5-yl)-3-methyl-pent-3-enyl]-phosphonic acid monoethyl ester 158D (7 mg, 28%); $^1H$ NMR (300 MHz, $CD_3OD$) δ 1.28 (t, J=6.9 Hz, 3H), 1.7-1.9 (m, 5H), 2.20 (s, 3H), 2.2-2.3 (m, 2H), 3.41 (d, J=6.6 Hz, 2H), 3.80 (s, 3H), 4.02 (m, 2H), 5.2-5.3 (m, 3H) ppm.

Compound 158E can be prepared as illustrated below.

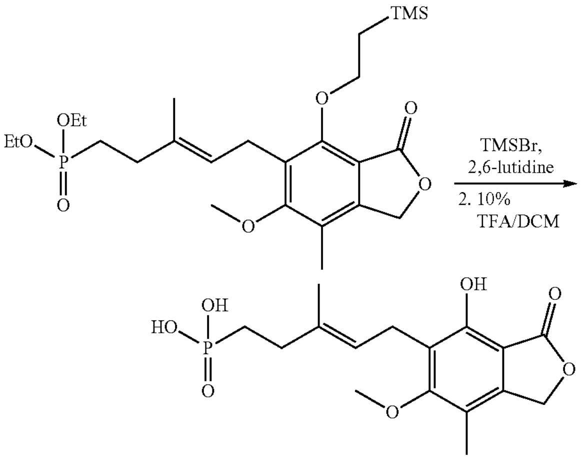

158E

[5-(4-Hydroxy-6-methoxy-7-methyl-3-oxo-1,3-dihydro-isobenzofuran-5-yl)-3-methyl-pent-3-enyl]-phosphonic acid To a solution of {5-[6-Methoxy-7-methyl-3-oxo-4-(2-trimethylsilanyl-ethoxy)-1,3-dihydro-isobenzofuran-5-yl]-3-methyl-pent-3-enyl}-phosphonic acid diethyl ester (20 mg, 0.039 mmol) in DMF (0.5 mL) and DCM (0.5 mL) was added TMSBr (50.5 μL, 0.39 mmol) followed by 2,6-lutidine (45.3 μL, 0.39 mmol). The reaction was allowed to proceed for one hour when it was complete, as judged by LCMS. The reaction mixture was quenched with MeOH and concentrated to dryness. The residue was purified by preparative reverse-phase HPLC. The fraction containing the desired product was concentrated and treated with 10% TFA/DCM for 5 minutes. After concentration, the residue was purified by preparative reverse-phase HPLC to provide 7 mg (50%) of [5-(4-Hydroxy-6-methoxy-7-methyl-3-oxo-1,3-dihydro-isobenzofuran-5-yl)-3-methyl-pent-3-enyl]-phosphonic acid as a solid. $^1H$ NMR (300 MHz, $CD_3OD$) δ 1.66-1.78 (m, 5H), 2.10 (s, 3H), 2.16-2.22 (m, 2H), 3.34 (d, J=7.2 Hz, 2H), 3.72 (s, 3H), 5.16 (s, 2H), 5.20 (t, J=7.2 Hz, 1H) ppm; $^{31}P$ (121.4 MHz, $CD_3OD$) δ 31.57 ppm; MS (m/z) 355 $[M-H]^-$, 357 $[M+H]^+$.

Example 159

Preparation of Representative Compounds of the Invention

Representative compounds of the invention can be prepared as illustrated below.

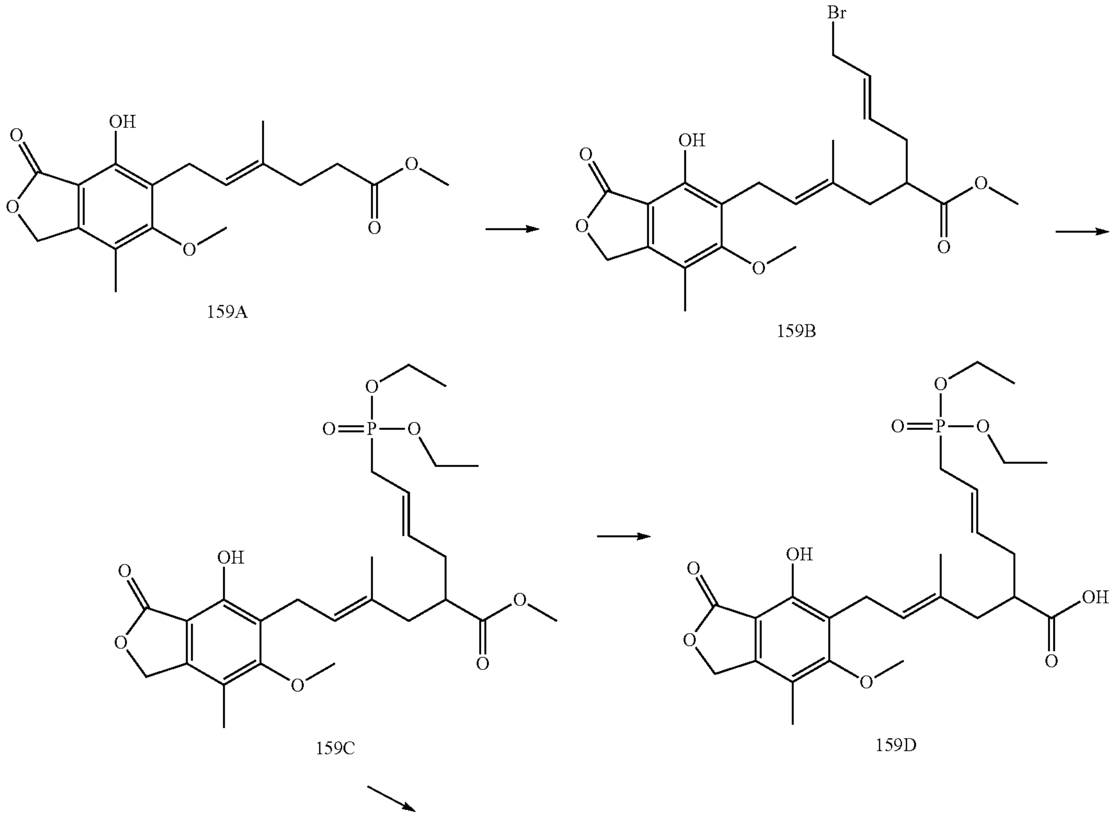

159A

159B

159C

159D

-continued

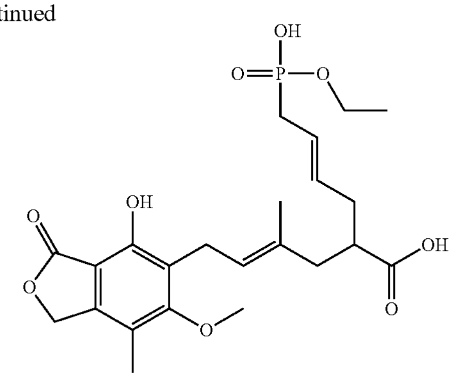

159E 2-(4-Bromo-but-2-enyl)-6-(4-hydroxy-6-methoxy-7-methyl-3-oxo-1,3-dihydro-isobenzofuran-5-yl)-4-methyl-hex-4-enoic acid methyl ester To a cooled (−78° C.) solution of mycophenolic acid methyl ester 159A (138 mg, 0.41 mmol) in THF (2.5 mL) was added a THF solution of sodium bis(trimethysilyl)amide (1.0 M, 0.98 mL). After stirring for 30 minutes, a solution of 1,4-dibromo-2-butene (950 mg, 4.1 mmol) in THF (2.5 mL) was added and stirring was continued for 10 minutes. The resulting mixture was warmed to −30° C. and stored at this temperature for 16 hours. The reaction was quenched with saturated aqueous ammonium chloride. The mixture was extracted with ethyl acetate to give, after evaporation of the solvent, a residue which was purified by chromatography on silica gel eluting with ethyl acetate (0% to 40%)/hexanes, affording 2-(4-bromo-but-2-enyl)-6-(4-hydroxy-6-methoxy-7-methyl-3-oxo-1,3-dihydro-isobenzofuran-5-yl)-4-methyl-hex-4-enoic acid methyl ester 159B (150 mg, 78%) as an oil; $^1$H NMR (300 MHz, $CDCl_3$) δ 1.75 (s, 3H), 2.0-2.4 (m, 8H), 2.62 (m, 1H), 3.37 (d, J=6.6 Hz, 2H), 3.58 (s, 3H), 3.76 (s, 3H), 3.88 (d, J=4.8 Hz, 2H), 5.1-5.3 (m, 3H), 5.67 (brs, 2H), 7.67 (s, 1H) ppm.

2-[4-(Diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid methyl ester A solution of 2-(4-bromo-but-2-enyl)-6-(4-hydroxy-6-methoxy-7-methyl-3-oxo-1,3-dihydro-isobenzofuran-5-yl)-4-methyl-hex-4-enoic acid methyl ester 159B (140 mg, 0.30 mmol) and triethylphosphite (600 mg, 3.6 mmol) in toluene (30 mL) was stirred at reflux for 20 hours. The mixture was concentrated and chromatographed on silica gel eluting with ethyl acetate (60% to 100%)/hexanes, affording 2-[4-(diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid methyl ester 159C as an oil (70 mg, 43%); $^1$H NMR (300 MHz, $CDCl_3$) δ 1.27 (m, 6H), 1.79 (s, 3H), 2.0-2.7 (m, 8H), 3.37 (d, J=6.6 Hz), 3.52 (s, 3H), 3.75 (s, 3H), 4.08 (m, 4H), 5.20 m, 3H), 5.45 (m, 2H) ppm.

2-[4-(Diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid A mixture of 2-[4-(diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid methyl ester 159C (33 mg, 0.063 mmol) and lithium hydroxide (44 mg) in a mixture of THF (6 mL) and water (1 mL) was stirred at room temperature for 6 hours. The organic solvent was removed and the residue was partitioned between ethyl acetate and 5% aqueous sodium bicarbonate. The aqueous layer was acidified with 2 N HCl and extracted with ethyl acetate. The ethyl acetate extract was concentrated, affording 2-[4-(diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid 159D as an oil (30 mg, 100%); $^1$H NMR (300 MHz, $CDCl_3$) δ 1.27 (m, 6H), 1.79 (s, 3H), 2.0-2.7 (m, 8H), 3.37 (d, J=6.6 Hz), 3.75 (s, 3H), 4.08 (m, 4H), 5.19 (s, 2H), 5.25 (m, 1H), 5.44 (m, 1H), 5.55 (m, 1H), 5.45 (m, 2H) ppm.

2-[4-(Ethoxy-hydroxy-phosphoryl)-but-2-enyl]-6-(4-hydroxy-6-methoxy-7-methyl-3-oxo-1,3-dihydro-isobenzofuran-5-yl)-4-methyl-hex-4-enoic acid A mixture of 2-[4-(diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid methyl ester 159C (25 mg, 0.048 mmol) and lithium hydroxide (200 mg) in a mixture of methanol (3 mL) and water (1 mL) was stirred at 70° C. for 2 hours. The organic solvent was evaporated and the residue acidified with 2N HCl and extracted with ethyl acetate/acetonitrile. The organic extract was concentrated and the residue was purified by preparative reverse-phase HPLC (acetonitrile and 0.1% aqueous $CF_3COOH$), affording 2-[4-(ethoxy-hydroxy-phosphoryl)-but-2-enyl]-6-(4-hydroxy-6-methoxy-7-methyl-3-oxo-1,3-dihydro-isobenzofuran-5-yl)-4-methyl-hex-4-enoic acid 159E as an oil (15 mg, 89%); $^1$H NMR (300 MHz, $CD_3OD$) δ 1.25 (t, J=6.9 Hz, 3H), 1.81 (s, 3H), 2.1-2.6 (m, 8H), 3.40 (d, J=6.6 Hz, 2H), 3.77 (s, 3H), 3.97 (m, 2H), 5.1-5.3 (m, 3H), 5.67 (brs, 2H) ppm.

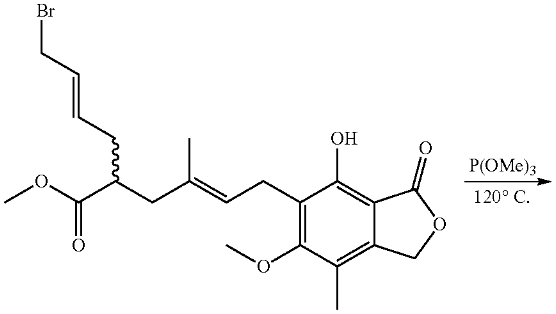

-continued

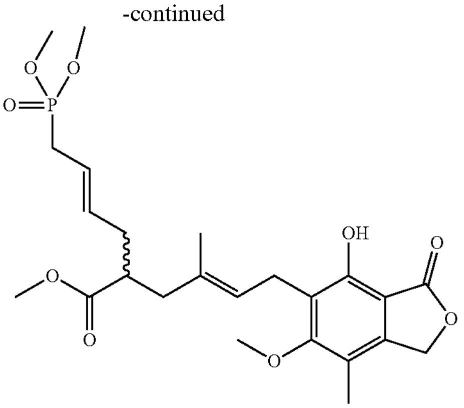

2-[4-(Dimethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid methyl ester Under a $N_2$ atmosphere, a solution of 2-(4-bromo-but-2-enyl)-6-(4-hydroxy-6-methoxy-7-methyl-3-oxo-1,3-dihydro-isobenzofuran-5-yl)-4-methyl-hex-4-enoic acid methyl ester (490 mg, 1.05 mmol) in trimethylphosphite (2.5 mL, 21.1 mmol) was heated at 120° C. for 1 hour. The reaction was allowed to cool to room temperature. The reaction mixture was worked up by removal of the solvent in vacuo followed by chromatography using EtOAc-hexanes to provide 460 mg (88%) of the product as an oil. $^1$H NMR (300 MHz, $CDCl_3$) δ 1.77 (s, 3H), 2.081-2.31 (m, 4H), 2.15 (s, 3H), 2.52 (d, 1H, J=22 Hz), 2.54 (d, 1H, J=22 Hz), 2.55-2.63 (m, 1H), 3.36 (d, 2H, J=7 Hz), 3.57 (s, 3H), 3.72 (d, 6H, J=11 Hz), 3.76 (s, 3H), 5.20 (s, 2H), 5.20-5.26 (m, 1H), 5.36-5.56 (m, 2H), 7.69 (s, 1H) ppm; $^{31}$P (121.4 MHz, $CDCl_3$) δ 30.1 ppm; MS (m/z) 497.2 $[M+H]^+$, 519.2 $[M+Na]^+$.

Compound 159F can be prepared as illustrated below.

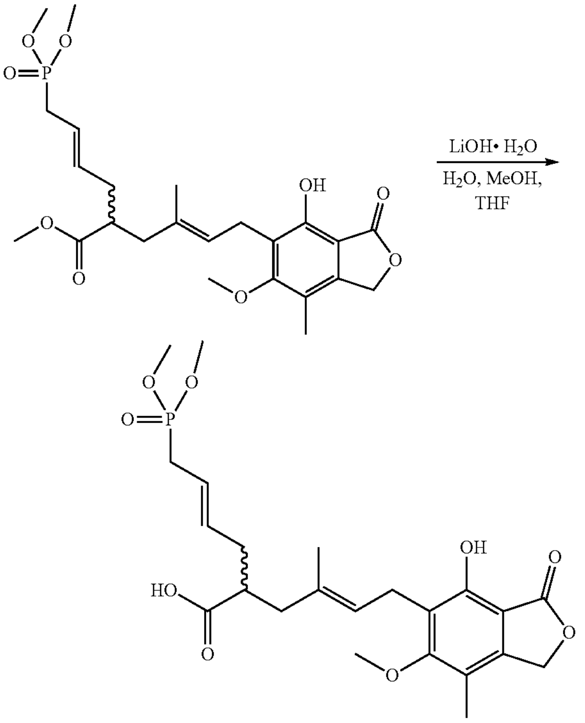

159F

2-[4-(Dimethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid 2-[4-(Dimethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid methyl ester (460 mg, 0.927 mmol) in a solution of 1:1:2 of $H_2O$, MeOH, THF (8 mL) was stirred with LiOH.$H_2O$ (78 mg, 1.86 mmol) at ambient temperature for 12 hours. A second batch of LiOH.$H_2O$ (40 mg, 0.952 mmol) was added. The reaction mixture was stirred at room temperature for another 16 hours, after which no further progress was observed. The reaction was quenched by addition of a saturated aqueous solution of $NH_4Cl$. The organic layer was removed in vacuo and the product was extracted with EtOAc from the aqueous layer, which had been acidified by addition of 5 drops of 2 N HCl. The product was further purified by chromatography to provide the desired product. $^1$H NMR (300 MHz, $CDCl_3$) δ 1.79 (s, 3H), 2.08-2.38 (m, 4H), 2.15 (s, 3H), 2.53 (d, 1H, J=22 Hz), 2.60 (d, 1H, J=22 Hz), 2.57-2.64 (m, 1H), 3.38 (d, 2H, J=7 Hz), 3.72 (d, 6H, J=11 Hz) 3.76 (s, 3H), 5.20 (s, 2H), 5.27 (t, 1H, J=6 Hz), 5.36-5.63 (m, 2H) ppm; $^{31}$P (121.4 MHz, $CDCl_3$) δ 30.5 ppm; MS (m/z) 481.2 $[M-H]^-$.

Compound 159G can be prepared as illustrated below.

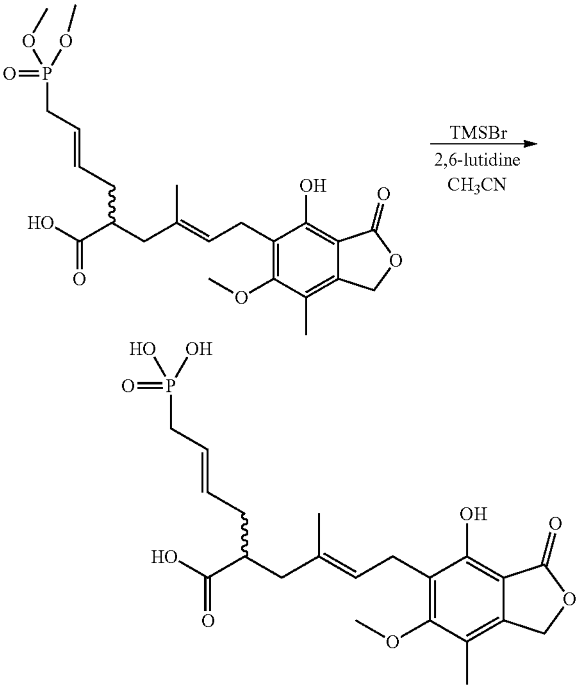

159G

2-[4-(2-[4-(Dihydroxy-phosphoryl)-but-2-enyl]-6-(4-hydroxy-6-methoxy-7-methyl-3-oxo-1,3-dihydro-isobenzofuran-5-yl)-4-methyl-hex-4-enoic acid To a solution of 2-[4-(dimethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid (25 mg, 0.052 mmol) in acetonitrile (2 mL) was added 2,6-lutidine (60 μL, 0.52 mmol) and TMSBr (67 μL, 0.52 mmol). The reaction was allowed to proceed for 45 minutes when it was completed as judged by LCMS. The reaction mixture was concentrated under reduced pressure and quenched with an aqueous NaOH solution (1 mL). The product was purified by RP HPLC (using a C18 column with a gradient of $H_2O$, 0.1% TFA-acetonitrile, 0.1% TFA) to provide 14.2 mg (60%) of the product as a solid. $^1H$ NMR (300 MHz, $CD_3OD$) δ 1.81 (s, 3H), 2.081-2.31 (m, 4H), 2.16 (s, 3H), 2.45 (d, 1H, J=22 Hz), 2.47 (d, 1H, J=22 Hz), 2.55-2.63 (m, 1H), 3.38 (d, 2H, J=7 Hz), 3.77 (s, 3H), 5.25 (s, 2H), 5.20-5.36 (m, 1H), 5.36-5.56 (m, 2H) ppm; $^{31}P$ (121.4 MHz, $CD_3OD$) δ 25.4 ppm; MS (m/z) 453 $[M-H]^-$.

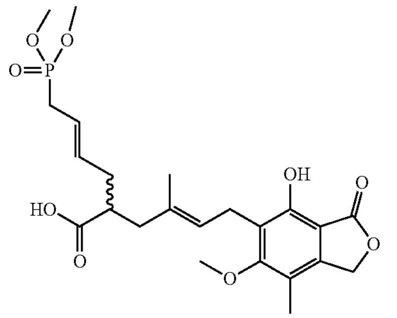

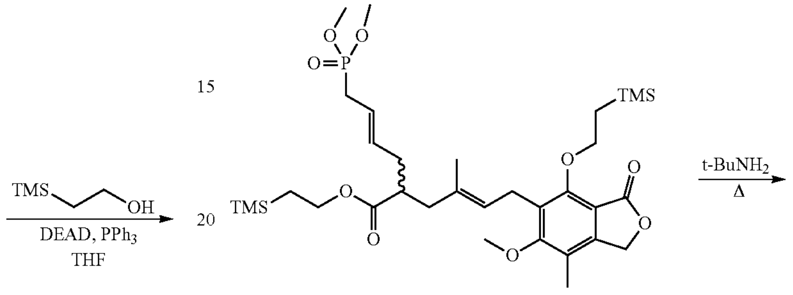

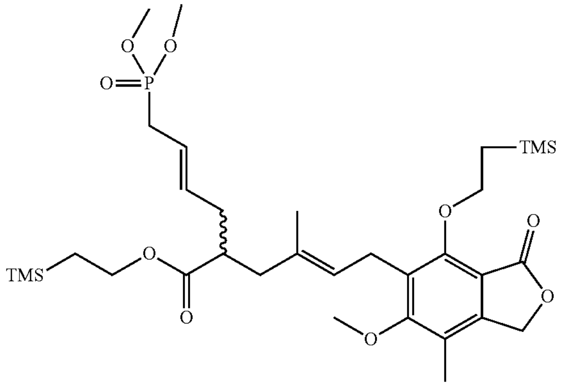

2-[4-(Dimethoxy-phosphoryl)-but-2-enyl]-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester A solution of 2-[4-(dimethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid (160 mg, 0.332 mmol) and trimethylsilylethanol (160 mg, 1.36 mmol) in THF (8.00 mL) was stirred with triphenylphosphine (345 mg, 1.33 mmol). To this solution was added diethyl azodicarboxylate (230 μL, 1.33 mmol) at 0° C. The mixture was allowed to warm to room temperature and stirred for 16 hours. Additional triphenylphosphine (180 mg, 0.692 mmol), trimethylsilylethanol (160 mg, 1.36 mmol), and diethyl azodicarboxylate (115 μL, 0.665 mmol) were added and the reaction mixture was stirred for another 1 day at room temperature. The reaction was worked up by removing the solvents in vacuo and purifying the residue by silica gel chromatography to provide 192 mg (85%) of the product as a clear oil. $^1H$ NMR (300 MHz, $CDCl_3$) δ 0.03 (s, 9H), 0.05 (s, 9H), 0.93-0.96 (m, 2H), 1.20-1.29 (m, 2H), 1.78 (s, 3H), 2.01-2.32 (m, 4H), 2.17 (s, 3H), 2.51 (d, 1H, J=22 Hz), 2.58 (d, 1H, J=22 Hz), 2.50-2.60 (m, 1H), 3.37 (d, 2H, J=7 Hz), 3.72 (d, 6H, J=11 Hz), 3.76 (s, 3H), 4.08 (appt t, 2H, J=8 Hz), 4.30 (appt t, 2H, J=8 Hz), 5.12 (s, 2H), 5.15-5.25 (m, 1H), 5.36-5.63 (m, 2H) ppm; $^{31}P$ (121.4 MHz, $CDCl_3$) δ 29.3 ppm; MS (m/z) 705.3 $[M+Na]^+$.

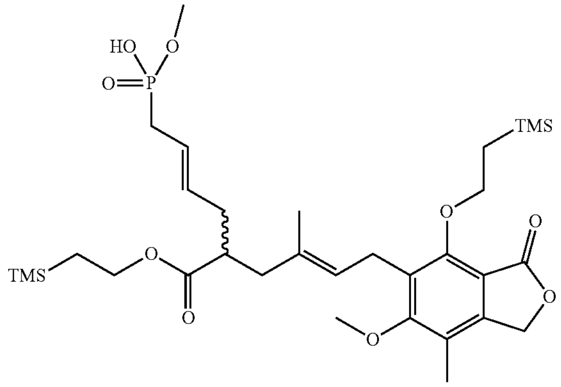

2-[4-(Hydroxy-methoxy-phosphoryl)-but-2-enyl]-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester A mixture of 2-[4-(dimethoxy-phosphoryl)-but-2-enyl]-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (184 mg, 0.270 mmol) in tert-butylamine (2.8 mL, 27 mmol) was heated at 60° C. for 24 hours. The solution was allowed to cool to room temperature and concentrated. The residue was purified by silica gel column chromatography using $MeOH/CH_2Cl_2$ (0-30%) to provide 75 mg of the product as a clear oil. $^1H$ NMR (300 MHz, $CDCl_3$) δ 0.01 (s, 9H), 0.04 (s, 9H), 0.89 (appt t, 2H, J=9 Hz), 1.23 (appt t, 2H, J=9 Hz), 1.77 (s, 3H), 2.01-2.31 (m, 4H), 2.17 (s, 3H), 2.36 (d, 1H, J=22 Hz), 2.38 (d, 1H, J=22 Hz), 2.52 (septet, 1H, J=9 Hz), 3.39 (d, 2H, J=7 Hz), 3.51 (d, 3H, J=11 Hz), 4.01-4.08 (m, 2H), 4.30 (dd, 2H, J=8, 9 Hz), 5.11 (s, 2H), 5.19 (br t, 1H, J=6 Hz), 5.33-5.56 (m, 2H), 8.49 (br s, 1H) ppm; $^{31}P$ (121.4 MHz, $CDCl_3$) δ 22.1 ppm; MS (m/z) 667.4 $[M+Na]^+$.

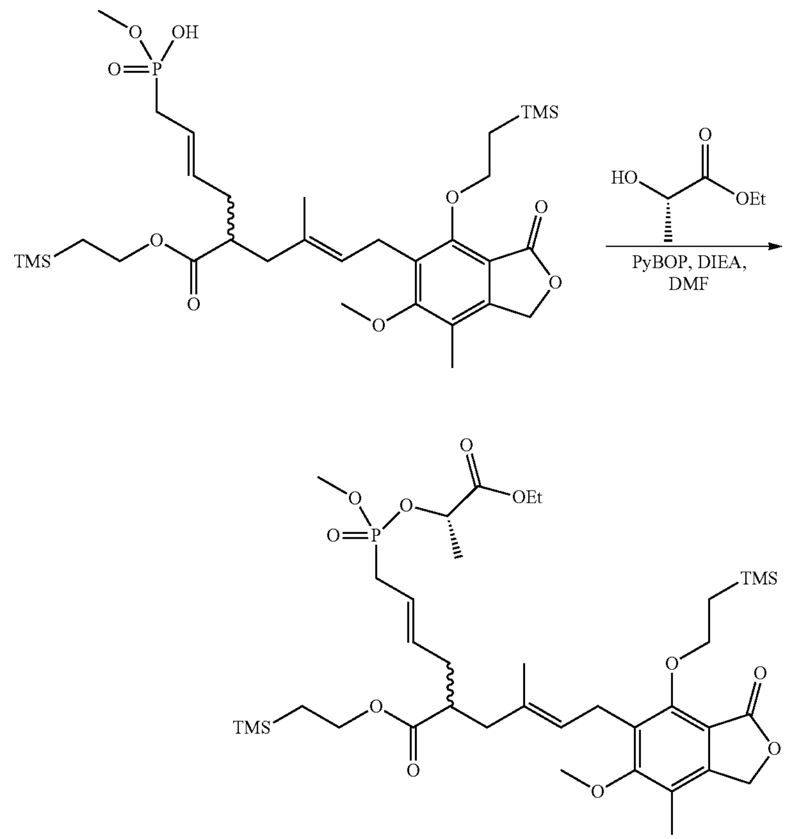

2-{4-[(1-Ethoxycarbonyl-ethoxy)-methoxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester A solution of 2-[4-(hydroxy-methoxy-phosphoryl)-but-2-enyl]-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (67 mg, 0.10 mmol) and PyBOP (234 mg, 0.450 mmol) in DMF (1.5 mL) was stirred with ethyl (S)-(−)-lactate (53 mg, 0.45 mmol) and DIEA (174 μL, 1.00 mmol) at ambient temperature for 1 hour, when complete consumption of the starting materials was observed. The reaction was worked up by addition of saturated aqueous sodium chloride and ethyl acetate. The organic layer was separated and washed with 5% aqueous solution of lithium chloride. The organic layer was dried in vacuo and the residue was purified by silica gel chromatography using MeOH—$CH_2Cl_2$ (0-20%) to provide 57 mg (74%) of the desired product as a clear oil. $^1$H NMR (300 MHz, $CDCl_3$) δ 0.02 (s, 9H), 0.05 (s, 9H), 0.88-0.94 (m, 2H), 1.20-1.30 (m, 2H), 1.29 (t, 3H, J=7 Hz), 1.45 (d, 3H, J=7 Hz), 1.78 (s, 3H), 2.01-2.31 (m, 4H), 2.17 (s, 3H), 2.50-2.58 (m, 1H), 2.65 (d, 1H, J=22 Hz), 2.67 (d, 1H, J=22 Hz), 3.39 (d, 2H, J=7 Hz), 3.69 and 3.77 (d, 3H, J=11 Hz), 3.76 (s, 3H), 4.07 (appt t, 2H, J=7 Hz), 4.20 (dq, 2H, J=3, 7 Hz), 4.29 (appt t, 2H, J=9 Hz), 4.85-4.99 (m, 1H), 5.12 (s, 2H), 5.19 (br t, 1H, J=6 Hz), 5.33-5.61 (m, 2H) ppm; $^{31}$P (121.4 MHz, $CDCl_3$) δ 28.9, 29.9 ppm; MS (m/z) 791.4 $[M+Na]^+$.

Compound 159H can be prepared as illustrated below.

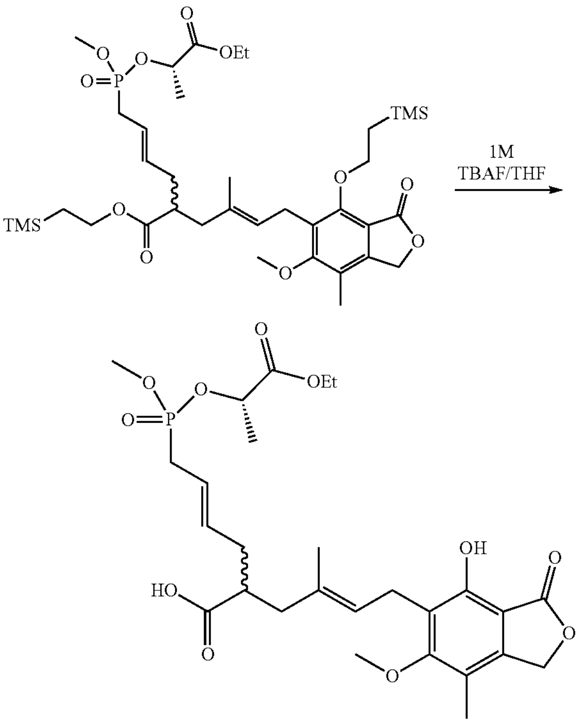

2-{4-[(1-Ethoxycarbonyl-ethoxy)-methoxy-phosphoryl]-but-2-enyl}-6-(4-hydroxy-6-methoxy-7-methyl-3-oxo-1,3-dihydro-isobenzofuran-5-yl)-4-methyl-hex-4-enoic acid A solution of 2-{4-[(1-ethoxycarbonyl-ethoxy)-methoxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (14 mg, 0.018 mmol) in THF (1 mL) was stirred with a 1M solution of TBAF in THF (55 μL, 0.055 mmol) for 1 hour. The reaction mixture was concentrated, acidified with 1N HCl and extracted with EtOAc. The organic layer was washed with brine and dried. The product was purified by silica gel column chromatography EtOH-EtOAc (0-10%). Further purification was performed by dissolving the product in $CH_2Cl_2$ and passing the compound through a 13 mm Acrodisc syringe filter with a 0.45 μm Nylon membrane to provide 8 mg (77%) of the product. $^1$H NMR (300 MHz, $CDCl_3$) δ 0.92 (t, 3H, J=7 Hz), 1.30 (d, 3H, J=8 Hz), 1.79 (s, 3H), 2.10-2.39 (m, 4H), 2.15 (s, 3H), 2.53 (d, 1H, J=8 Hz), 2.65 (d, 1H, J=22 Hz), 2.68 (d, 1H, J=22 Hz), 3.38 (d, 2H, J=7 Hz), 3.70 and 3.74 (d, 3H, J=11 Hz), 3.76 (s, 3H), 4.07 (m, 2H), 4.96 (dq, 1H, J=7 Hz), 5.20 (s, 2H), 5.27 (br t, 1H, J=7 Hz), 5.33-5.55 (m, 2H), 7.51-7.56 (m, 1H), 7.68-7.74 (m, 1H) ppm; $^{31}$P (121.4 MHz, $CDCl_3$) δ 29.0, 30.1 ppm; MS (m/z) 569.2 $[M+H]^+$, 591.3 $[M+Na]^+$.

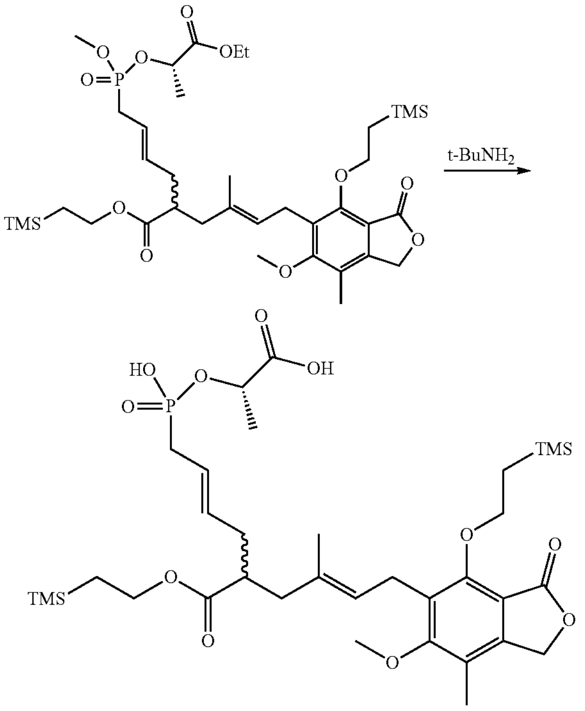

2-{4-[(1-Carboxy-ethoxy)-hydroxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester A solution of 2-{4-[(1-ethoxycarbonyl-ethoxy)-methoxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanylethyl ester (12 mg, 0.016 mmol) in tert-butylamine (1 mL, 9.6 mmol) was heated at 65° C. for 16 hours. The solution was allowed to cool to room temperature and concentrated to provide the crude product as an oil. $^1$H NMR (300 MHz, $CDCl_3$) δ 0.03 (s, 9H), 0.04 (s, 9H), 0.86-0.98 (m, 2H), 1.22-1.33 (m, 2H), 1.50 (d, 3H, J=7 Hz), 1.78 (s, 3H), 2.05-2.30 (m, 4H), 2.10 (s, 3H), 2.48-2.63 (m, 3H), 3.40 (d, 2H, J=7 Hz), 3.76 (s, 3H), 4.08 (appt t, 2H, J=9 Hz), 4.25-4.33 (m, 2H), 4.75-4.84 (m, 1H), 5.13 (s, 2H), 5.15-5.23 (m, 1H), 5.33-5.55 (m, 2H) ppm; $^{31}$P (121.4 MHz, $CDCl_3$) δ 28.9 ppm; MS (m/z) 725.3 $[M-H]^-$.

Compound 159I can be prepared as illustrated below.

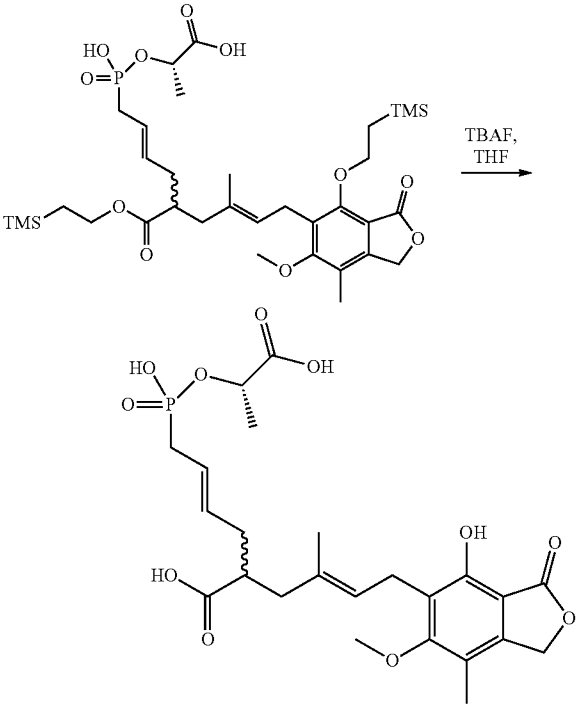

2-{4-[(1-Carboxy-ethoxy)-hydroxy-phosphoryl]-but-2-enyl}-6-(4-hydroxy-6-methoxy-7-methyl-3-oxo-1,3-dihydro-isobenzofuran-5-yl)-4-methyl-hex-4-enoic acid A solution of crude 2-{4-[(1-carboxy-ethoxy)-hydroxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (AC-2101-59) and tetrabutylammonium fluoride in THF (1M, 54 μL, 0.054 mmol) was stirred with THF (1 mL) for 2 hours at ambient temperature, when more tetrabutylammonium fluoride in THF (54 μL, 0.054 mmol) was added. The reaction was stirred for an additional 16 hours, by which time the reaction was complete. The reaction mixture was concentrated in vacuo and the product was purified by RP HPLC using a Phenomenex Synergi 5 μHydro RP 80A column (50×21.2 mm) with eluents of $H_2O$, 0.1% TFA-$CH_3CN$, 0.1% TFA to provide the product (8.0 mg) as a clear oil. $^1$H NMR (300 MHz, $CDCl_3$) δ 1.51 (d, 3H, J=7 Hz), 1.79 (s, 3H), 2.05-2.40 (m, 4H), 2.11 (s, 3H), 2.49-2.71 (m, 3H), 3.38 (d, 2H, J=6 Hz), 3.76 (s, 3H), 4.85 (br s, 1H), 5.20 (s, 2H), 5.21-5.30 (m, 1H), 5.33-5.63 (m, 2H) ppm; $^{31}$P (121.4 MHz, $CDCl_3$) δ 27.7 ppm; MS (m/z) 525.2 $[M-H]^-$.

Compound 159J can be prepared as illustrated below.

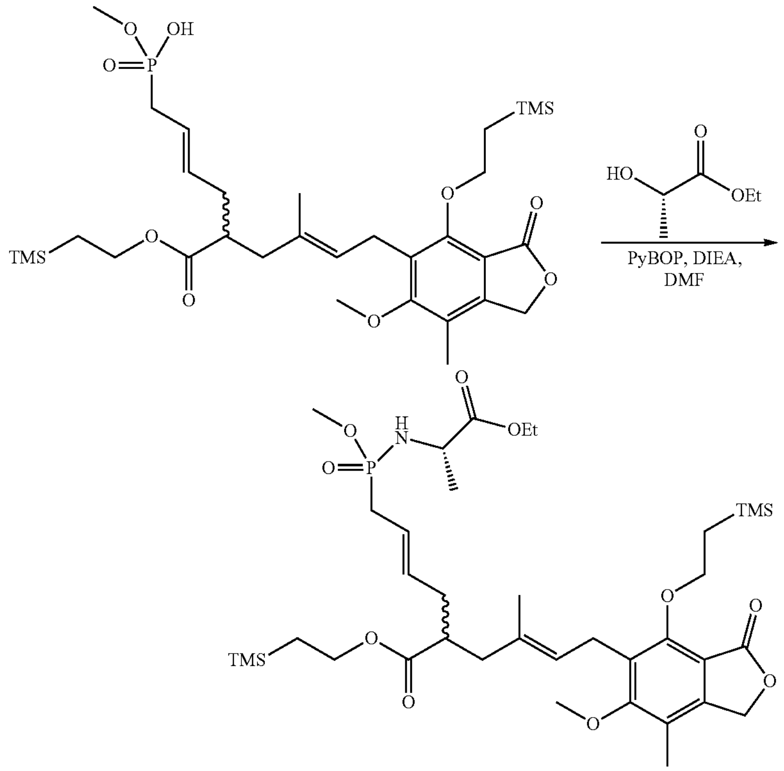

2-{4-[(1-Ethoxycarbonyl-ethylamine)-methoxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester A solution of 2-[4-(hydroxy-methoxy-phosphoryl)-but-2-enyl]-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (20 mg, 0.030 mmol), PyBOP (62.4 mg, 0.120 mmol) in DMF (1.0 mL) was stirred with L-alanine ethyl ester hydrochloride (18 mg, 0.12 mmol) and DIEA (26 μL, 0.15 mmol) at ambient temperature for 1 hour, when complete consumption of the starting materials was observed. The reaction was worked up by addition of water until the reaction solution became cloudy. DMF was added dropwise until the mixture became clear again. The reaction mixture was filtered through Acrodisc (13 mm syringe filter with a 0.45 μm Nylon membrane) and purified by RP HPLC using a Phenomenex Synergi 5 μ Hydro RP 80A column (50×21.2 mm), eluting with water and acetonitrile. The fractions containing the product were pooled together and concentrated in vacuo to remove the acetonitrile. The remaining solution was saturated with sodium chloride and extracted with EtOAc and acetonitrile to provide 7.2 mg of the product. $^1$H NMR (300 MHz, $CDCl_3$) δ 0.03 (s, 9H), 0.05 (s, 9H), 0.923 (appt t, 2H, J=8 Hz), 1.18-1.31 (m, 5H), 1.41 (t, 3H, J=7 Hz), 1.78 (s, 3H), 2.03-2.36 (m, 4H), 2.18 (s, 3H), 2.43-2.63 (m, 3H), 3.10-3.30 (m, 1H), 3.40 (d, 2H, J=7 Hz), 3.62 and 3.65 (d, 3H, J=11 Hz), 3.76 (s, 3H), 4.03-4.12 (m, 2H), 4.20 (dq, 2H, J=2, 7 Hz), 4.29 (appt t, 2H, J=8 Hz), 5.12 (s, 2H), 5.18-5.28 (m, 1H), 5.33-5.67 (m, 2H) ppm; $^{31}$P (121.4 MHz, $CDCl_3$) δ 30.4, 31.2 ppm; MS (m/z) 790.4 $[M+Na]^+$.

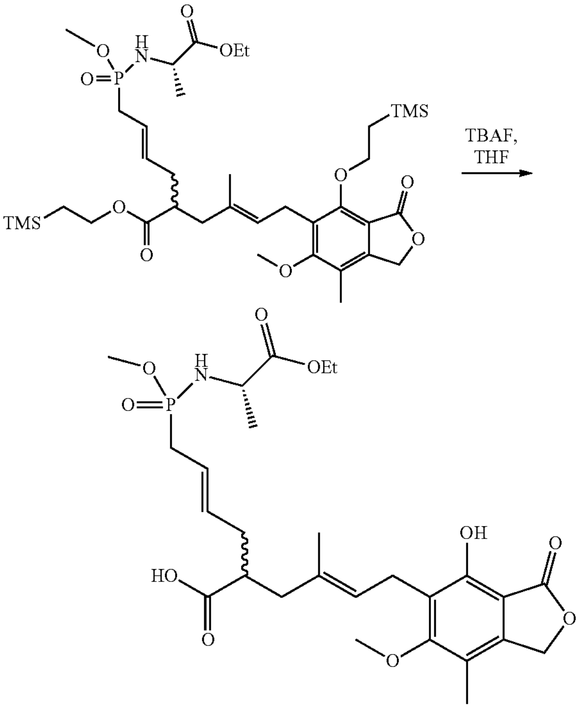

2-{4-[(1-Ethoxycarbonyl-ethylamine)-methoxy-phosphoryl]-but-2-enyl}-6-(4-hydroxy-6-methoxy-7-methyl-3-oxo-1,3-dihydro-isobenzofuran-5-yl)-4-methyl-hex-4-enoic acid To a solution of 2-{4-[(1-ethoxycarbonyl-ethylamine)-methoxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (7.2 mg, 9.38 mmol) in THF (1 mL) was added TBAF (40 μL, 1M solution in THF) at room temperature. The reaction mixture was stirred for 20 minutes, when the starting material was completely converted to the desired product as judged by LCMS. The reaction mixture was dried in vacuo and re-dissolved in DMF. The product was purified by RP HPLC using a Phenomenex Synergi 5 μ Hydro RP 80A column (50×21.2 mm) with eluents of $H_2O$—$CH_3CN$. The fractions containing the desired product were pooled and further purified on Dowex 50WX8-400 packed on a 4.5 cm×2 cm column to elute the sodium salt at $H_2O$— MeOH (1:1), providing 3.2 mg of the desired product. $^1$H NMR (300 MHz, $CD_3OD$) δ 1.26 (dd, 3H, J=4, 7 Hz), 1.37 (t, 3H, J=8 Hz), 1.80 (s, 3H), 2.00-2.22 (m, 4H), 2.10 (s, 3H), 2.25-2.60 (m, 3H), 3.37 (d, 2H, J=7 Hz), 3.60 and 3.65 (d, 3H, J=11 Hz), 3.74 (s, 3H), 3.83-3.96 (m, 1H), 4.18 (q, 2H, J=8 Hz), 5.15 (s, 2H), 5.25-5.42 (m, 2H), 5.55-5.69 (m, 1H) ppm; $^{31}$P (121.4 MHz, $CD_3OD$) δ 33.8, 34.2 ppm; MS (m/z) 568.2 $[M+H]^+$, 590.3 $[M+Na]^+$.

Compound 159K can be prepared as illustrated below.

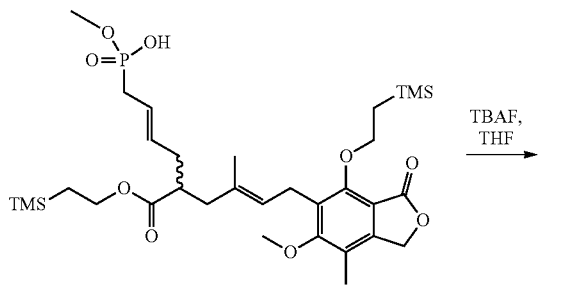

-continued

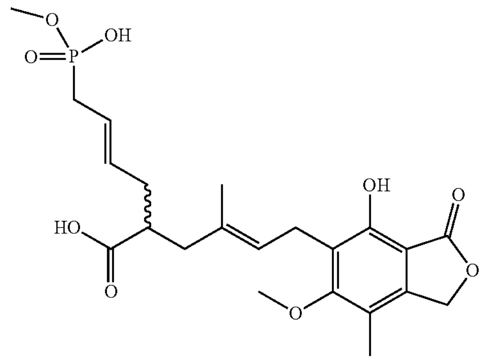

6-(4-Hydroxy-6-methoxy-7-methyl-3-oxo-1,3-dihydro-isobenzofuran-5-yl)-2-[4-(hydroxy-methoxy-phosphoryl)-but-2-enyl]-4-methyl-hex-4-enoic acid To a solution of 2-[4-(hydroxy-methoxy-phosphoryl)-but-2-enyl]-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanylethyl ester (11 mg, 0.016 mmol) in THF (1 mL) was added TBAF (50 μL, 1 M solution in THF) at room temperature. The solution was stirred for 16 hours and concentrated. The solution was dried under reduced pressure and re-suspended in DMF (0.8 mL) and water (0.25 mL). The solution was filtered through Acrodisc (13 mm syringe filter with a 0.45 μm Nylon membrane) and purified by RP HPLC using a Phenomenex Synergi 5 μ Hydro RP 80A column (50×21.2 mm) with eluents of $H_2O$, 0.1% TFA-$CH_3CN$, 0.1% TFA. The product from the column was subjected to ion exchange chromatography (Sodium salt form of Dowex 50WX8-400) using a 2×4.5 cm column eluting with $H_2O$-MeOH (1:1) to provide 7.5 mg of the desired product as an oil. $^1$H NMR (300 MHz, $CDCl_3$) δ 1.80 (s, 3H), 2.01-2.29 (m, 5H), 2.11 (s, 3H), 2.35 (d, 2H, J=22 Hz), 3.38 (d, 2H, J=7 Hz), 3.53 (d, 3H, J=11 Hz), 3.75 (s, 3H), 5.19 (s, 2H), 5.26 (t, 1H, J=6 Hz), 5.43-5.54 (m, 2H) ppm; $^{31}$P (121.4 MHz, $CDCl_3$) δ 23.5 ppm; MS (m/z) 469.2 $[M+H]^+$, 491.3 $[M+Na]^+$.

Example 160

Preparation of Representative Compounds of the Invention

Representative compounds of the invention can be prepared as illustrated below.

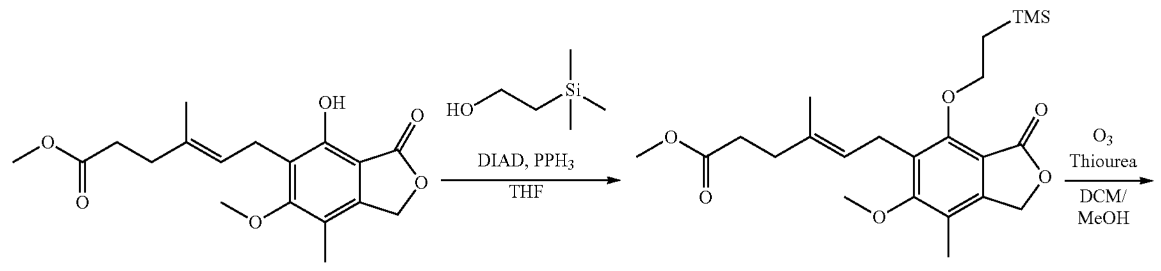

-continued
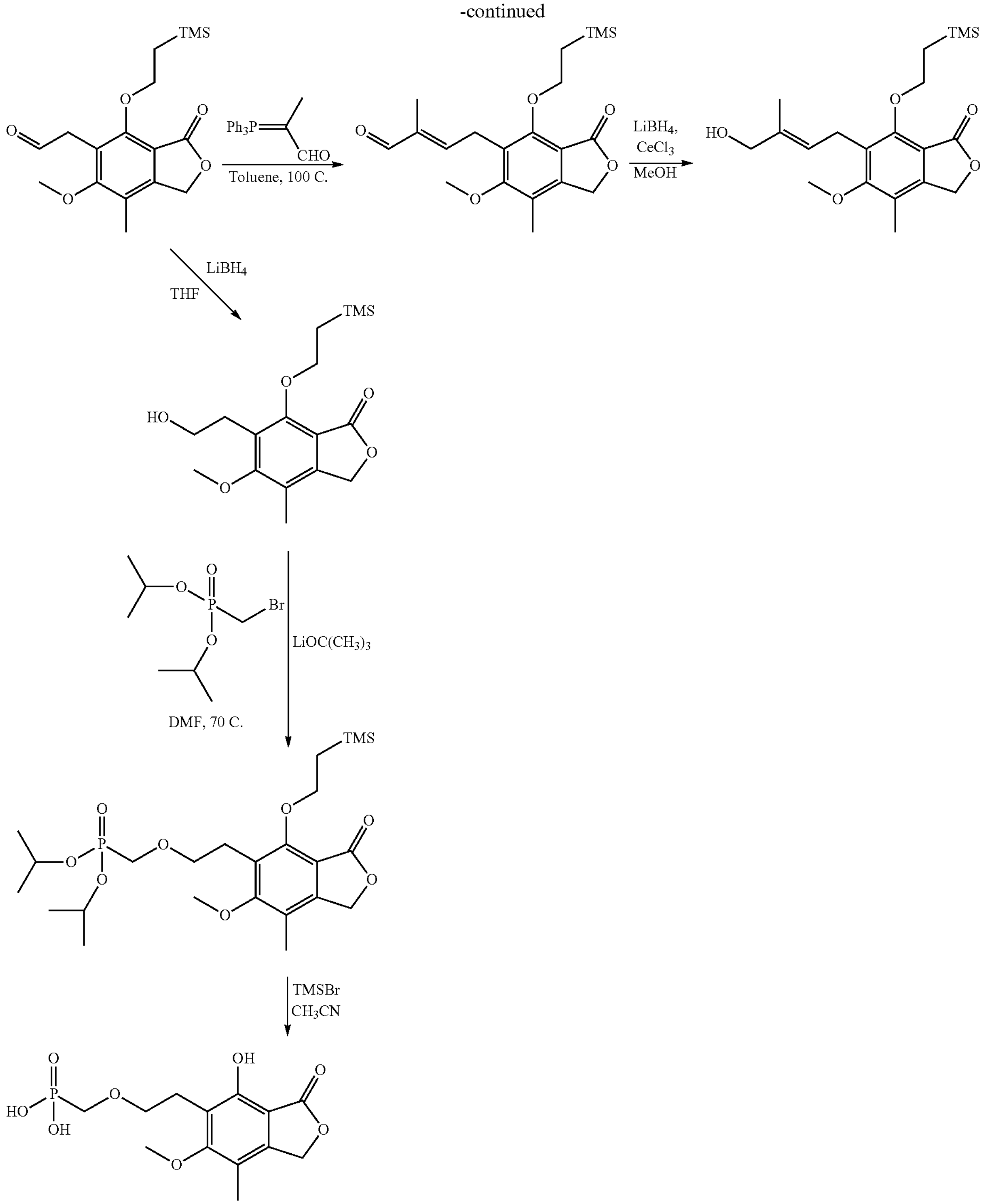
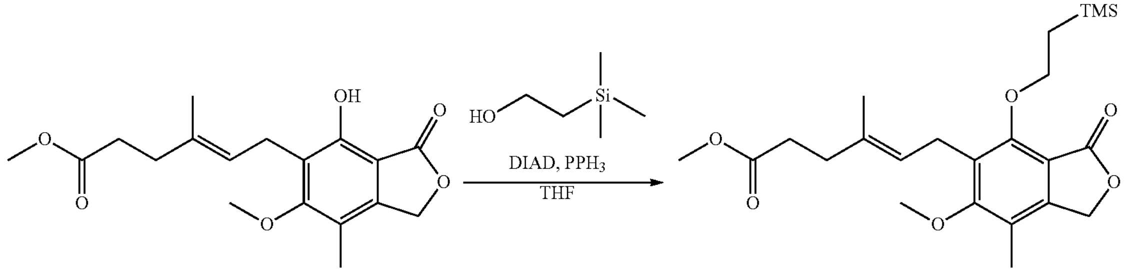

6-[6-Methoxy-7-methyl-3-oxo-4-(2-trimethylsilanyl-ethoxy)-1,3-dihydro-isobenzofuran-5-yl]-4-methyl-hex-4-enoic acid methyl ester To a solution of 6-(4-hydroxy-6-methoxy-7-methyl-3-oxo-1,3-dihydro-isobenzofuran-5-yl)-4-methyl-hex-4-enoic acid methyl ester (222 mg, 0.66 mmol), triphenylphosphine (260 mg, 0.996 mmol), and diethyl azodicarboxylate (173 mg, 0.996 mmol) in THF (3 mL) at 0° C. was added a solution of 2-trimethylsilylethanol (142 μL, 0.996 mmol) in THF (3 mL). The resulting yellow solution was allowed to warm to room temperature and stirred overnight. The reaction was concentrated to dryness and ether and hexanes were added. Triphenyiphosphine oxide was removed by filtration and the filtrate was concentrated and purified by silica gel chromatography to provide 248 mg of the desired product as a colorless oil. $^1$H NMR (300 MHz, $CDCl_3$) δ 0.03 (s, 9H), 1.18-1.30 (m, 2H), 1.81 (s, 3H), 2.18 (s, 3H), 2.25-2.33 (m, 2H), 2.37-2.45 (m, 2H), 3.42 (d, 2H, J=7 Hz), 3.62 (s, 3H), 3.77 (s, 3H), 4.25-4.35 (m, 2H), 5.13 (s, 2H), 5.12-5.22 (m, 1H) ppm.

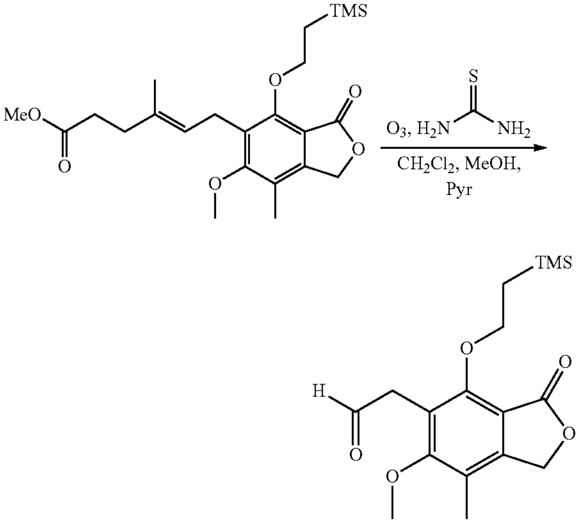

[6-Methoxy-7-methyl-3-oxo-4-(2-trimethylsilanyl-ethoxy)-1,3-dihydro-isobenzofuran-5-yl]-acetaldehyde A solution of 6-[6-methoxy-7-methyl-3-oxo-4-(2-trimethylsilanyl-ethoxy)-1,3-dihydro-isobenzofuran-5-yl]-4-methyl-hex-4-enoic acid methyl ester (618 mg, 1.42 mmol) in MeOH (10 mL), $CH_2Cl_2$ (10 mL) and pyridine (50 μL, 0.618 mmol) was cooled to −70° C. using a dry ice/acetone bath according to the procedure of Smith, D. B. et al., *J. Org. Chem.*, 1996, 61, 6, 2236. A stream of ozone was bubbled through the reaction via a gas dispersion tube until the reaction became blue in color (15 minutes). The ozone line was replaced with a stream of nitrogen and bubbling continued for another 15 minutes, by which time the blue color had disappeared. To this solution at −70° C. was added thiourea (75.7 mg, 0.994 mmol) in one portion, and the cooling bath was removed. The reaction was allowed to warm to room temperature and stirred for 15 hours. The reaction was worked up by filtration to remove solid thiourea S-dioxide, and then partitioned between $CH_2Cl_2$ and water. The organic layer was removed. The aqueous layer was washed with $CH_2Cl_2$ one more time and the organic extracts were combined. The organic layer was washed with aqueous 1N HCl, saturated $NaHCO_3$ and brine. The organic extracts were dried in vacuo and the residue was purified to by silica gel chromatography to afford 357 mg (75%) of the product as a white solid. $^1$H NMR (300 MHz, $CDCl_3$) δ −0.01 (s, 9H), 1.05-1.15 (m, 2H), 2.15 (s, 3H), 3.69 (s, 3H), 3.78 (d, 2H, J=1 Hz), 4.27-4.39 (m, 2H), 5.11 (s, 2H), 9.72 (d, 1H, J=1 Hz) ppm.

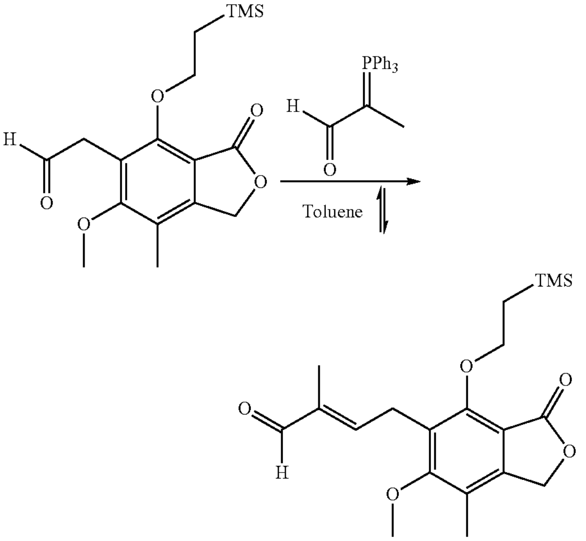

4-[6-Meth oxy-7-methyl-3-oxo-4-(2-trimethylsilanyl-ethoxy)-1,3-dihydro-isobenzofuran-5-yl]-2-methyl-but-2-enal

[6-Methoxy-7-methyl-3-oxo-4-(2-trimethylsilanyl-ethoxy)-1,3-dihydro-isobenzofuran-5-yl]-acetaldehyde (70 mg, 0.21 mmol) in toluene (2 mL) was heated at 100° C. with 2-(triphenyl-phosphanylidene)-propionaldehyde (72.9 mg, 0.23 mmol) overnight. A second portion of 2-(triphenyl-phosphanylidene)-propionaldehyde (33 mg, 0.11 mmol) was added and the reaction mixture was heated for an additional day. After concentration, the residue was purified by silica gel chromatography to provide 54 mg (83%) of the desired product as a pale yellow oil. $^1$H NMR (300 MHz, $CDCl_3$) δ 0.00 (s, 9H), 1.10-1.21 (m, 2H), 1.87 (s, 3H), 2.16 (s, 3H), 3.67-3.76 (m, 2H), 3.74 (s, 3H), 4.27-4.39 (m, 2H), 5.11 (s, 2H), 6.40-6.48 (m, 1H), 9.2 (s, 1H) ppm.

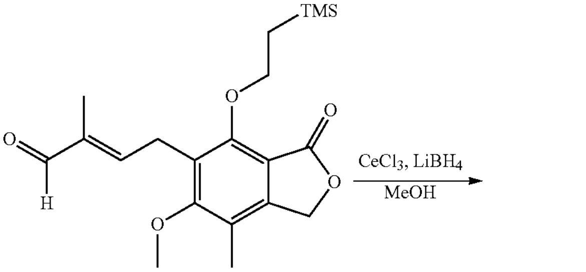

-continued

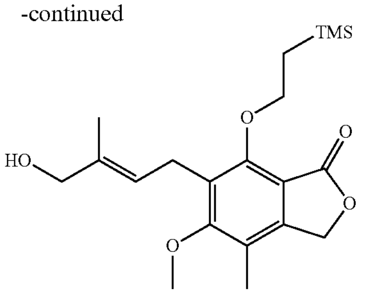

6-(4-Hydroxy-3-methyl-but-2-enyl)-5-methoxy-4-methyl-7-(2-trimethylsilanyl-ethoxy)-3H-isobenzofuran-1-one A solution of 4-[6-methoxy-7-methyl-3-oxo-4-(2-trimethylsilanyl-ethoxy)-1,3-dihydro-isobenzofuran-5-yl]-2-methyl-but-2-enal (103 mg, 0.27 mmol) in methanol (5 mL) was cooled to 0° C. A solution of $CeCl_3$ (0.68 mL, MeOH: $H_2O$, 9:1) was added, followed by $LiBH_4$ (0.14 mL, 0.28 mmol of a 2M solution in THF). The ice bath was removed and the reaction mixture was allowed to warm to room temperature. The reaction mixture was stirred for an additional 40 minutes whereupon TLC indicated complete consumption of starting aldehyde. The reaction was worked up by addition of aqueous 1N HCl (0.5 mL) and the product was extracted with $CH_2Cl_2$. The organic layer was washed with saturated aqueous sodium bicarbonate solution and brine. The organic layer was concentrated under reduced pressure and the residue was purified by silica gel chromatography to provide 100 mg (97%) of the product as a clear liquid. $^1$H NMR (300 MHz, $CDCl_3$) δ 0.00 (s, 9H), 1.20 (dd, 2H, J=7, 8 Hz), 1.81 (s, 3H), 2.13 (s, 3H), 3.38-3.50 (m, 2H), 3.74 (s, 3H), 3.95 (s, 2H), 4.27 (dd, 2H, J=7, 8 Hz), 5.08 (s, 2H), 5.17-5.44 (m, 1H) ppm.

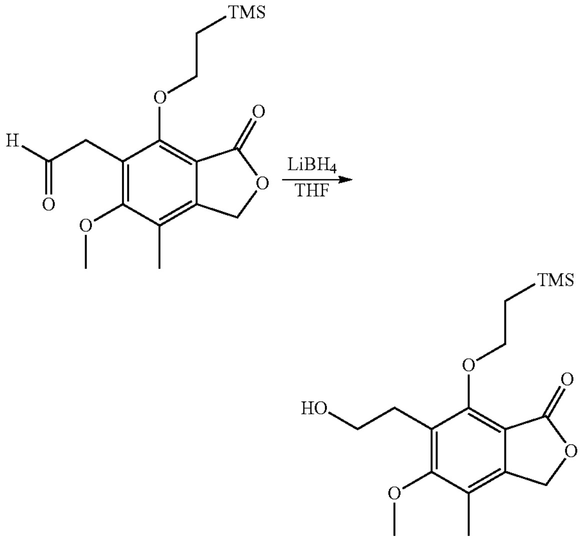

6-(2-Hydroxy-ethyl)-5-methoxy-4-methyl-7-(2-trimethylsilanyl-ethoxy)-3H-isobenzofuran-1-one To a solution of [6-methoxy-7-methyl-3-oxo-4-(2-trimethylsilanyl-ethoxy)-1,3-dihydro-isobenzofuran-5-yl]-acetaldehyde (97 mg, 0.29 mmol) in THF (5 mL) was added an aliquot of a 2 M $LiBH_4$ in THF (150 μL, 0.300 mmol). The reaction mixture was stirred at room temperature for 1 hour when complete consumption of the starting materials was observed by TLC. The reaction mixture was worked up by addition of an aqueous 1N HCl solution and extraction with EtOAc. The organic layer was dried in vacuo and the residue was purified by silica gel chromatography to provide the product. $^1$H NMR (300 MHz, $CDCl_3$) δ 0.00 (s, 9H), 1.20 (dd, 2H, J=7, 9 Hz), 2.07 (br s, 1H), 2.14 (s, 3H), 2.97 (t, 2H, J=6 Hz), 3.76 (t, 2H, J=6 Hz), 3.77 (s, 3H), 4.32 (dd, 2H, J=7, 8 Hz), 5.08 (s, 2H) ppm.

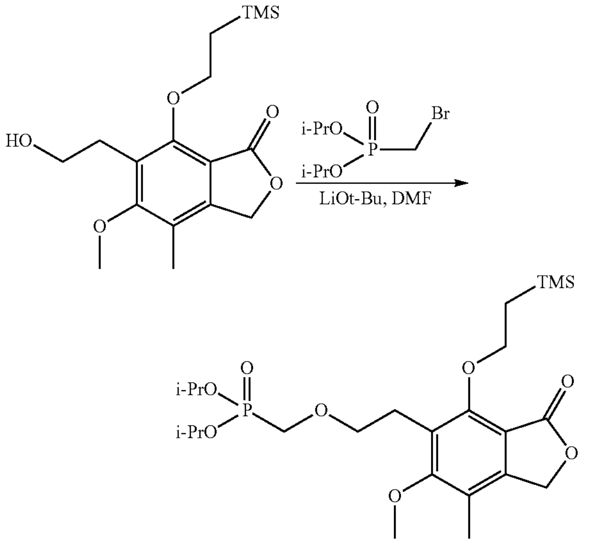

{2-[6-Methoxy-7-methyl-3-oxo-4-(2-trimethylsilanyl-ethoxy)-1,3-dihydro-isobenzofuran-5-yl]-ethoxymethyl}-phosphonic acid diisopropyl ester A mixture of 6-(2-hydroxy-ethyl)-5-methoxy-4-methyl-7-(2-trimethylsilanyl-ethoxy)-3H-isobenzofuran-1-one (79 mg, 0.23 mmol) was heated with bromomethylphosphonic acid diisopropyl ester (120 mg, 0.46 mmol) in the presence of lithium t-butoxide (22 mg, 0.27 mmol) in DMF (2 mL) at 70° C. overnight. The reaction mixture was purified by RP HPLC (acetonitrile and 0.1% aqueous $CF_3COOH$) to provide the desired product. $^1$H NMR (300 MHz, $CDCl_3$) δ 0.00 (s, 9H), 1.13-1.25 (m, 2H), 1.26 (t, 12H, J=6 Hz), 2.12 (s, 3H), 2.98 (t, 2H, J=7 Hz), 3.60-3.73 (m, 4H), 3.77 (s, 3H), 4.05-4.16 (m, 2H), 4.62-4.74 (m, 2H), 5.07 (s, 2H) ppm; MS (m/z) 539 $[M+Na]^+$.

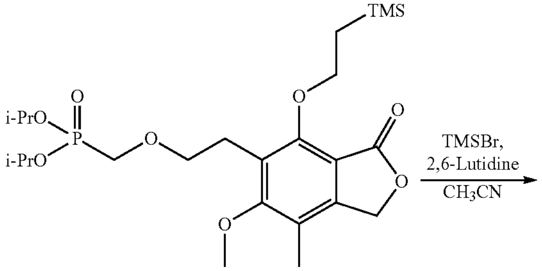

-continued

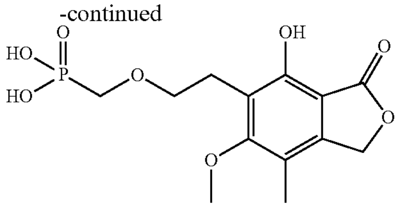

[2-(4-Hydroxy-6-methoxy-7-methyl-3-oxo-1,3-dihydro-isobenzofuran-5-yl)-ethoxymethyl]-phosphonic acid To a solution of {2-[6-methoxy-7-methyl-3-oxo-4-(2-trimethylsilanyl-ethoxy)-1,3-dihydro-isobenzofuran-5-yl]-ethoxymethyl}-phosphonic acid diisopropyl ester (7.5 mg, 0.014 mmol) in acetonitrile (2 mL) and 2,6-lutidine (25 μL, 0.21 mmol) was added trimethylsilyl bromide (27 μL, 0.21 mmol) at room temperature. The reaction was allowed to proceed for 18 hours when completion of the reaction was indicated by LCMS. The reaction was quenched by addition of MeOH and concentration. The residue was purified by RP-HPLC using a C18 column. The collected product was dissolved in a solution of 10% TFA/$CH_2Cl_2$ to assure complete deprotection. The reaction mixture was lyophilized to provide the desired product. $^1$H NMR (300 MHz, $CD_3OD$) δ 2.12 (s, 3H), 2.98 (t, 2H, J=7 Hz), 3.66-3.76 (m, 4H), 3.78 (s, 3H), 5.21 (s, 2H) ppm; MS (m/z) 331 [M−H]$^-$.

Example 161

Preparation of Representative Compounds of Formula 78

Representative compounds of the invention can be prepared as illustrated below.

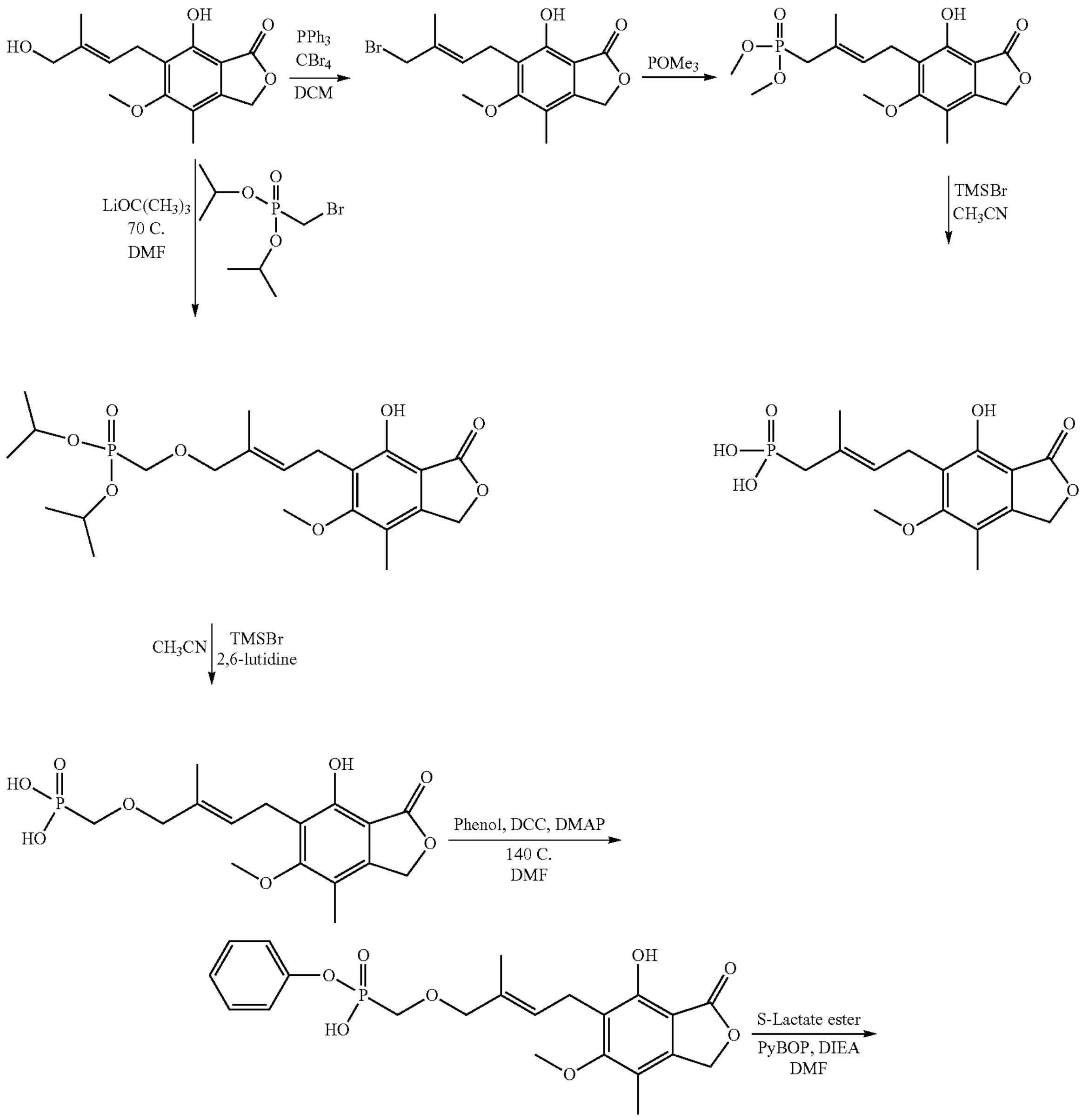

-continued

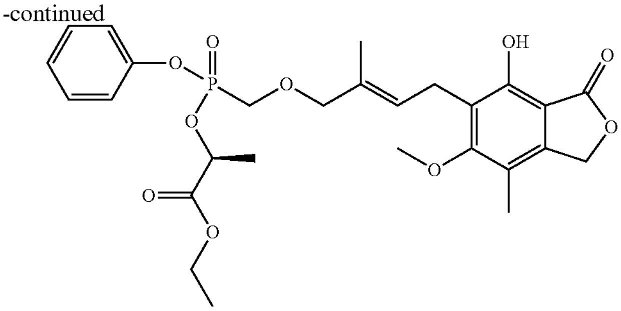

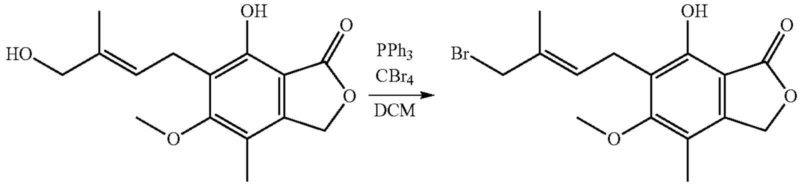 [SMILES: COc1c(C)c2c(c(O)c1C/C=C(\C)CO)C(=O)OC2 ; COc1c(C)c2c(c(O)c1C/C=C(\C)CBr)C(=O)OC2]

6-(4-Bromo-3-methyl-but-2-enyl)-7-hydroxy-5-methoxy-4-methyl-3H-isobenzofuran-1-one Polymer-supported triphenylphosphine (3 mmol/g, 0.5 g) was soaked in dichloromethane (10 mL) for 1 hour. 7-Hydroxy-6-(4-hydroxy-3-methyl-but-2-enyl)-5-methoxy-4-methyl-3H-isobenzofuran-1-one (100 mg, 0.36 mmol) and carbon tetrabromide (143 mg, 0.43 mmol) were added sequentially and the mixture was shaken for 1 hour at room temperature. More carbon tetrabromide (143 mg, 0.43 mmol) was added and the mixture was shaken further for 1 hour. The mixture was filtered and the filtrate was concentrated. The residue was chromatographed on silica gel (0% to 60% ethyl acetate/hexanes) to afford 6-(4-bromo-3-methyl-but-2-enyl)-7-hydroxy-5-methoxy-4-methyl-3H-isobenzofuran-1-one as an oil (52 mg, 42%); $^1$H NMR (300 MHz, $CDCl_3$) δ 1.95 (s, 3H), 2.16 (s, 3H), 3.44 (d, J=7.2, 2H), 3.78 (s, 3H), 3.98 (s, 2H), 5.21 (s, 2H), 5.68 (t, J=7.2 Hz, 1H), 7.71 (brs, 1H) ppm.

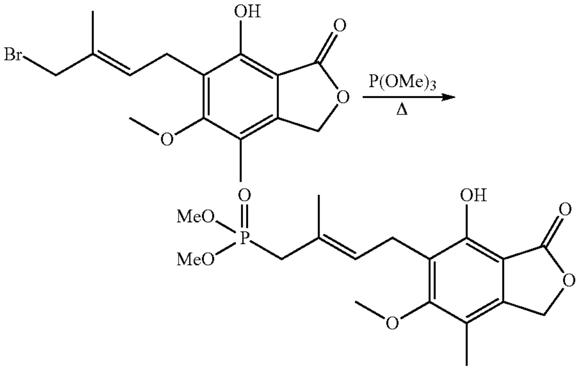

[4-(4-Hydroxy-6-methoxy-7-methyl-3-oxo-1,3-dihydro-isobenzofuran-5-yl)-2-methyl-but-2-enyl]-phosphonic acid dimethyl ester A solution of 6-(4-bromo-3-methyl-but-2-enyl)-7-hydroxy-5-methoxy-4-methyl-3H-isobenzofuran-1-one (33 mg, 0.097 mmol) in trimethylphosphite (1.0 mL, 8.5 mmol) was heated to 100° C. for 1 hour, whereupon complete reaction was indicated by LCMS. The reaction was worked up by removal of the excess reagent under reduced pressure and the residue was purified by silica gel chromatography using EtOAc-hexanes (20-100%) to provide 20 mg (60%) of the desired product. $^1$H NMR (300 MHz, $CDCl_3$) δ 1.90 (s, 3H), 2.09 (s, 3H), 2.48 (d, 2H, J=22 Hz), 3.38 (t, 2H, J=6 Hz), 3.64 (d, 6H, J=11 Hz), 3.72 (s, 3H), 5.14 (s, 2H), 5.33 (q, 1H, J=6 Hz), 7.65 (br s, 1H) ppm; MS (m/z) 371 $[M+H]^+$.

Example 162

Preparation of Representative Compounds of Formula 78

Representative compounds of the invention can be prepared as illustrated below.

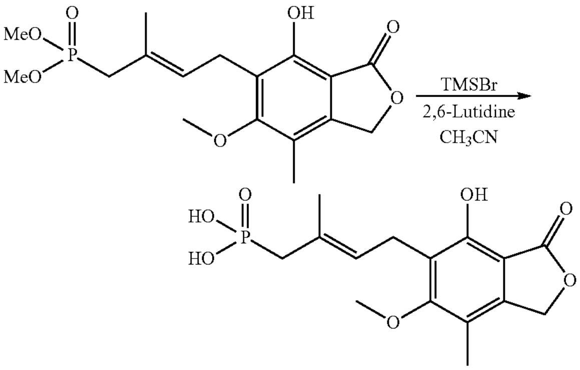

[4-(4-Hydroxy-6-methoxy-7-methyl-3-oxo-1,3-dihydro-isobenzofuran-5-yl)-2-methyl-but-2-enyl]-phosphonic acid To a solution of [4-(4-hydroxy-6-methoxy-7-methyl-3-oxo-1,3-dihydro-isobenzofuran-5-yl)-2-methyl-but-2-enyl]-phosphonic acid dimethyl ester (18 mg, 0.049 mmol) in acetonitrile (2 mL) was added TMSBr (63 μL, 0.49 mmol) and 2,6-lutidine (85 μL, 0.73 mmol) at 0° C. The reaction solution was allowed to warm to room temperature and stirred for 2 hours when completion of the reaction was observed by LCMS. The reaction was cooled to 0° C. and quenched by the addition of MeOH. The reaction mixture was concentrated under reduced pressure and the residue was purified by RP HPLC using a C18 column with a gradient of $H_2O$-acetonitrile (5-0%) over 20 minutes to provide 12.2 mg (73%) of the product. $^1H$ NMR (300 MHz, $CD_3OD$) δ 1.95 (s, 3H), 2.15 (s, 3H), 2.48 (d, 2H, J=22 Hz), 3.44 (t, 2H, J=6 Hz), 3.79 (s, 3H), 5.24 (s, 2H), 5.38 (q, 1H, J=7 Hz), 6.87 (br s, 1H) ppm; MS (m/z) 341 $[M-H]^-$.

Example 163

Preparation of Representative Compounds of Formula 78

Representative compounds of the invention can be prepared as illustrated below.

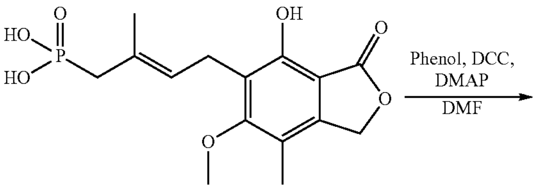

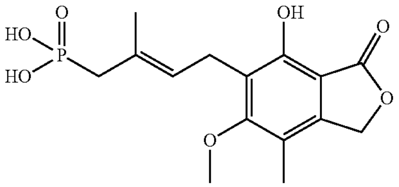

Major

+

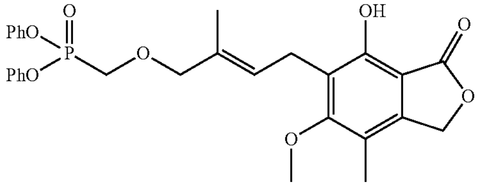

Minor

[4-(4-Hydroxy-6-methoxy-7-methyl-3-oxo-1,3-dihydro-isobenzofuran-5-yl)-2-methyl-but-2-enyloxymethyl]-phosphonic acid monophenyl ester and [4-(4-Hydroxy-6-methoxy-7-methyl-3-oxo-1,3-dihydro-isobenzofuran-5-yl)-2-methyl-but-2-enyloxymethyl]-phosphonic acid diphenyl ester To a solution of [4-(4-hydroxy-6-methoxy-7-methyl-3-oxo-1,3-dihydro-isobenzofuran-5-yl)-2-methyl-but-2-enyloxymethyl]-phosphonic acid (49 mg, 0.13 mmol) in DMF (0.4 mL) and phenol (62 mg, 0.65 mmol) was added dicyclohexyl carbodiimide (107 mg, 0.52 mmol) and DMAP (8 mg, 0.065 mmol) in DMF (0.6 mL), slowly at 0° C. The reaction was allowed to warm to room temperature and heated to 140° C. for 10 hours. After cooling to room temperature the mixture was filtered and extracted with aqueous 1N NaOH solution. The aqueous layer was acidified with aqueous 1N HCl and extracted with EtOAc. The organic layer was dried over $Na_2SO_4$ and concentrated to dryness. The residue was purified by RP HPLC to provide 18.5 mg of [4-(4-hydroxy-6-methoxy-7-methyl-3-oxo-1,3-dihydro-isobenzofuran-5-yl)-2-methyl-but-2-enyloxymethyl]-phosphonic acid monophenyl ester (major product) as a pale yellow solid and 4.1 mg of [4-(4-hydroxy-6-methoxy-7-methyl-3-oxo-1,3-dihydro-isobenzofuran-5-yl)-2-methyl-but-2-enyloxymethyl]-phosphonic acid diphenyl ester (minor product) also as a pale yellow solid. Major product: $^1H$ NMR (300 MHz, $CD_3OD$) δ 1.82 (s, 3H), 2.16 (s, 3H), 3.46 (d, 2H, J=7 Hz), 3.70 (d, 2H, J=8 Hz), 3.77 (s, 3H), 3.96 (s, 2H), 5.25 (s, 2H), 5.52 (t, 1H, J=8 Hz), 7.10-7.21 (m, 3H), 7.30 (t, 2H, J=8 Hz) ppm; $^{31}P$ (121.4 MHz, $CD_3OD$) δ 17.3 ppm; MS (m/z) 449.0 $[M+H]^+$, 471.2 $[M+Na]^+$. Minor product: $^1H$ NMR (300 MHz, $CD_3OD$) δ 1.82 (s, 3H), 2.15 (s, 3H), 3.47 (d, 2H, J=7 Hz), 3.77 (s, 3H), 3.98-4.06 (m, 4H), 5.25 (s, 2H), 5.50-5.61 (m, 1H), 7.10-7.25 (m, 6H), 7.30-7.41 (m, 4H) ppm; $^{31}P$ (121.4 MHz, $CD_3OD$) δ 16.3 ppm; MS (m/z) 525.2 $[M+H]^+$, 547.2 $[M+Na]^+$.

Example 164

Preparation of Representative Compounds of Formula 78

Representative compounds of the invention can be prepared as illustrated below.

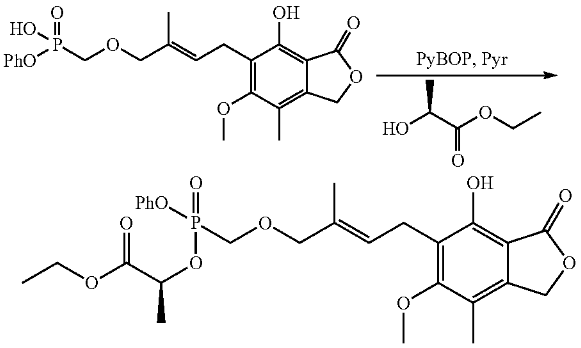

2-{[4-(4-Hydroxy-6-methoxy-7-methyl-3-oxo-1,3-dihydro-isobenzofuran-5-yl)-2-methyl-but-2-enyloxymethyl]-phenoxy-phosphinoyloxy}-propionic acid ethyl ester To a solution of [4-(4-hydroxy-6-methoxy-7-methyl-3-oxo-1,3-dihydro-isobenzofuran-5-yl)-2-methyl-but-2-enyloxymethyl]-phosphonic acid monophenyl ester (18.5 mg, 0.040 mmol) and ethyl (S)-(−)-lactate (47 μL, 0.400 mmol) in pyridine (0.5 mL) was added PyBOP (32 mg, 0.060 mmol). The solution was stirred at room temperature for 1 hour, when an additional portion of PyBOP (21 mg, 0.040 mmol) was added. The solution was stirred for another hour and concentrated. The residue was purified by HPLC to provide 7.5 mg of the desired product as a clear oil. $^1H$ NMR (300 MHz, $CD_3OD$) δ 1.22 and 1.25 (t, 3H, J=7 Hz), 1.42 and 1.50 (d, 3H, J=7 Hz), 1.82 and 1.83 (s, 3H), 2.16 (s, 3H), 3.47 (d, 2H, J=7 Hz), 3.78 (s, 3H), 3.89 (d, 1H, J=8 Hz), 3.93-4.02 (m, 3H), 4.10-4.22 (m, 2H), 4.94-5.08 (m, 1H), 5.25 (s, 2H), 5.50-5.60 (m, 1H), 7.15-7.27 (m, 3H), 7.33-7.41 (m, 2H) ppm; $^{31}P$ (121.4 MHz, $CD_3OD$) δ 18.9, 20.3 ppm (diastereomers at phosphorus); MS (m/z) 549.2 $[M-FH]^+$, 571.3 $[M+Na]^+$.

Example 165

Preparation of Representative Compounds of Formula 78

Representative compounds of the invention can be prepared as illustrated below.

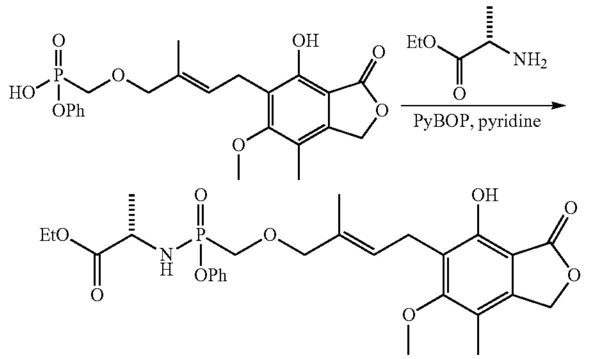

2-{[4-(4-Hydroxy-6-methoxy-7-methyl-3-oxo-1,3-dihydro-isobenzofuran-5-yl)-2-methyl-but-2-eny-loxymethyl]-phenoxy-phosphinoylamino}-propionic acid ethyl ester To a solution of [4-(4-hydroxy-6-methoxy-7-methyl-3-oxo-1,3-dihydro-isobenzofuran-5-yl)-2-methyl-but-2-eny-loxymethyl]-phosphonic acid monophenyl ester (20 mg, 0.045 mmol) and L-alanine ethyl ester hydrochloride (68.5 mg, 0.45 mmol) in pyridine (1.0 mL) was added PyBOP (70 mg, 0.14 mmol). After stirring overnight, the mixture was concentrated and the residue purified by RP HPLC using a C18 column with a gradient of $H_2O$, 0.1% TFA-acetonitrile, 0.1% TFA to provide 3.6 mg of the product as a colorless gel. $^1$H NMR (300 MHz, $CD_3OD$) δ 1.17-1.3 (m, 6H), 1.8-1.9 (m, 3H), 2.16 (s, 3H), 3.17 (m, 1H), 3.47 (d, 2H), 3.72-3.8 (m, 5H), 3.92-4.2 (m, 4H), 5.25 (s, 2H), 5.54 (m, 1H), 7.18 (m, 3H), 7.33 (m, 2H) ppm; $^{31}$P (121.4 MHz, $CD_3OD$) δ 24.1, 25.0 ppm (diastereomers at phosphorus); MS (m/z) 546.2 $[M-H]^+$.

Example 166

Preparation of Representative Compounds of Formula 78

Representative compounds of the invention can be prepared as illustrated below.

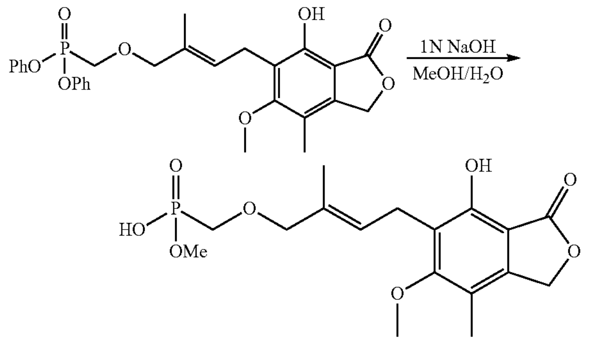

[4-(4-Hydroxy-6-methoxy-7-methyl-3-oxo-1,3-dihydro-isobenzofuran-5-yl)-2-methyl-but-2-enyloxym-ethyl]-phosphonic acid monomethyl ester To a solution of [4-(4-hydroxy-6-methoxy-7-methyl-3-oxo-1,3-dihydro-isobenzofuran-5-yl)-2-methyl-but-2-eny-loxymethyl]-phosphonic acid diphenyl ester (53 mg, 0.1 mmol) in methanol (0.5 mL) was added an aqueous solution of 1N NaOH (300 μL). After stirring overnight, the mixture was concentrated and the residue purified by RP HPLC using a C18 column with a gradient of $H_2O$, 0.1% TFA-acetonitrile, 0.1% TFA to provide 5 mg of the product as a colorless gel, together with the phosphonic acid monophenyl ester (7 mg) and the phosphonic acid dimethyl ester (14.5 mg). $^1$H NMR (300 MHz, $CD_3OD$) δ 1.84 (s, 3H), 2.16 (s, 3H), 3.47 (d, 2H, J=7 Hz), 3.6 (d, 2H, J=12 Hz), 3.75 (d, 3H, J=11 Hz), 3.79 (s, 3H), 3.94 (s, 2H), 5.26 (s, 2H), 5.53 (t, 1H, J=7 Hz) ppm; $^{31}$P (121.4 MHz, $CD_3OD$) δ 21.5 ppm; MS (m/z) 385.2 $[M-H]^+$, 387.1 $[M+H]^+$.

Example 167

Preparation of Representative Compounds of Formula 78

Representative compounds of the invention can be prepared as illustrated below.

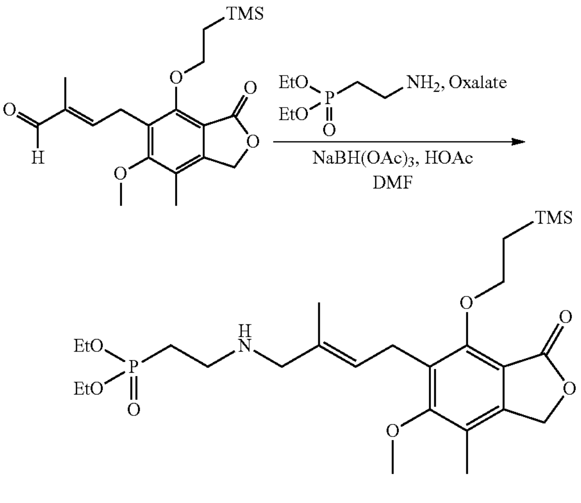

(2-{4-[6-Methoxy-7-methyl-3-oxo-4-(2-trimethylsi-lanyl-ethoxy)-1,3-dihydro-isobenzofuran-5-yl]-2-methyl-but-2-enylamino}-ethyl)-phosphonic acid diethyl ester To a solution of 4-[6-methoxy-7-methyl-3-oxo-4-(2-trim-ethylsilanyl-ethoxy)-1,3-dihydro-isobenzofuran-5-yl]-2-methyl-but-2-enal (84 mg, 0.22 mmol), (2-amino-ethyl)-phosphonic acid diethyl ester oxalate (91 mg, 0.33 mmol), and sodium triacetoxyborohydride (93 mg, 0.44 mmol) in DMF (1.5 mL) was added acetic acid (60 μL, 1.0 mmol) at room temperature. The solution was stirred for 2 days when it was quenched by addition of saturated aqueous sodium bicarbonate solution and EtOAc. The organic layer was separated and concentrated under reduced pressure. The residue was purified by RP HPLC using a C18 column with a gradient of $H_2O$, 0.1% TFA-acetonitrile, 0.1% TFA to provide 115 mg (96%) of the product as an oil. $^1$H NMR (300 MHz, $CDCl_3$) δ 0.04 (s, 9H), 1.16-1.27 (m, 2H), 1.34 (t, 6H, J=7 Hz), 1.94 (s, 3H), 2.18 (s, 3H), 2.20-2.31 (m, 2H), 3.13-3.31 (m, 2H), 3.48 (d, 2H, J=7 Hz), 3.54 (s, 2H), 3.78 (s, 3H), 4.14 (pent, 4H, J=7 Hz), 4.30-4.37 (m, 2H), 5.13 (s, 2H), 5.65 (t, 1H, J=7 Hz), 6.23 (br s, 2H) ppm; $^{31}$P (121.4 MHz, $CDCl_3$) δ 27.8 ppm; MS (m/z) 542.3 $[M+H]^+$, 564.2 $[M+Na]^+$.

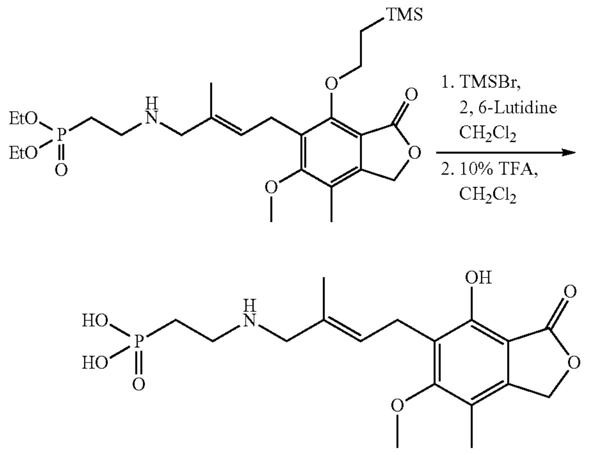

{2-[4-(4-Hydroxy-6-methoxy-7-methyl-3-oxo-1,3-dihydro-isobenzofuran-5-yl)-2-methyl-but-2-enylamino]-ethyl}-phosphonic acid A solution of (2-{4[6-methoxy-7-methyl-3-oxo-4-(2-trimethylsilanyl-ethoxy)-1,3-dihydro-isobenzofuran-5-yl]-2-methyl-but-2-enyl amino}-ethyl)-phosphonic acid diethyl ester (30 mg, 0.055 mmol), TMSBr (72 μL, 0.55 mmol), and 2,6-lutidine (64 μL, 0.55 mmol) was stirred in $CH_2Cl_2$ (1 mL) and DMF (0.5 mL) for 1 hour at ambient temperature. The reaction mixture was purified by RP HPLC using a C18 column with a gradient of $H_2O$, 0.1% TFA-acetonitrile, 0.1% TFA to provide 7.8 mg of the product as a white solid. $^{1}H$ NMR (300 MHz, $CD_3OD$) δ 1.96 (s, 3H), 1.95-2.07 (m, 2H), 2.16 (s, 3H), 3.10-3.24 (m, 2H), 3.51 (d, 2H, J=7 Hz), 3.57 (s, 2H), 3.81 (s, 3H), 5.25 (s, 2H), 5.73 (t, 1H, J=7 Hz) ppm; $^{31}P$ (121.4 MHz, $CD_3OD$) δ 20.2 ppm; $^{19}F$ NMR (282.6 MHz, $CD_3OD$) δ −74.0 ppm; MS (m/z) 386.3 $[M+H]^+$.

Example 168

Preparation of Representative Compounds of Formula 78

Representative compounds of the invention can be prepared as illustrated below.

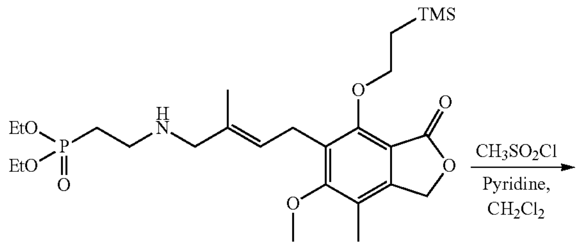

-continued

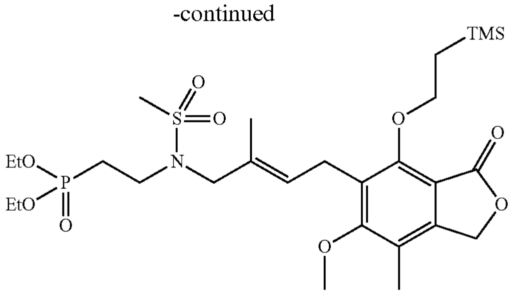

[2-(Methanesulfonyl-{4-[6-methoxy-7-methyl-3-oxo-4-(2-trimethylsilanyl-ethoxy)-1,3-dihydro-isobenzofuran-5-yl]-2-methyl-but-2-enyl}-amino)-ethyl]-phosphonic acid diethyl ester A solution of (2-{4-[6-methoxy-7-methyl-3-oxo-4-(2-trimethylsilanyl-ethoxy)-1,3-dihydro-isobenzofuran-5-yl]-2-methyl-but-2-enylamino}-ethyl)-phosphonic acid diethyl ester (45 mg, 0.092 mmol) in $CH_2Cl_2$ (0.5 mL) was stirred with methanesulfonyl chloride (21 μL, 0.28 mmol) and pyridine (45 μL, 0.55 mmol) at ambient temperature overnight. The reaction was quenched by addition of 2 drops of water. The reaction mixture was concentrated and purified by RP HPLC using a C18 column with a gradient of $H_2O$, 0.1% TFA-acetonitrile, 0.1% TFA to provide 36 mg of the product (63%) as a clear gel. $^{1}H$ NMR (300 MHz, $CDCl_3$) δ 0.05 (s, 9H), 1.18-1.29 (m, 2H), 1.29 (t, 6H, J=7 Hz), 1.85 (s, 3H), 2.00-2.13 (m, 2H), 2.19 (s, 3H), 2.85 (s, 3H), 3.32-3.43 (m, 2H), 3.47 (d, 2H, J=7 Hz), 3.69 (s, 2H), 3.79 (s, 3H), 4.05 (pent, 4H, J=7 Hz), 4.30-4.37 (m, 2H), 5.13 (s, 2H), 5.45 (t, 1H, J=7 Hz) ppm; $^{31}P$ (121.4 MHz, $CD_3Cl$) δ 27.5 ppm; MS (m/z) 642.2 $[M+Na]^+$.

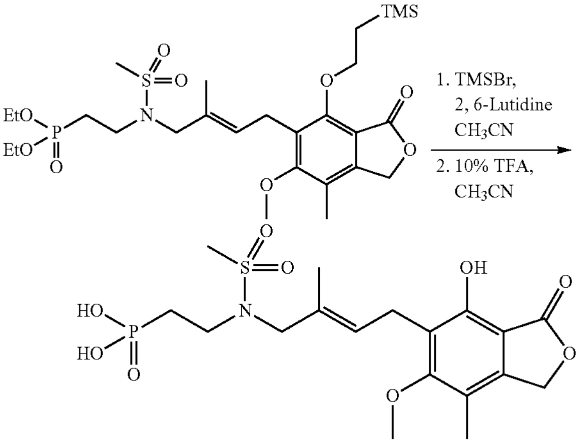

(2-{[4-(4-Hydroxy-6-methoxy-7-methyl-3-oxo-1,3-dihydro-isobenzofuran-5-yl)-2-methyl-but-2-enyl]-methanesulfonyl-amino}-ethyl)-phosphonic acid A solution of [2-(methanesulfonyl-{4-[6-methoxy-7-methyl-3-oxo-4-(2-trimethylsilanyl-ethoxy)-1,3-dihydro-isobenzofuran-5-yl]-2-methyl-but-2-enyl}-amino)-ethyl]-phosphonic acid diethyl ester (18 mg, 0.029 mmol) in acetonitrile (0.5 mL) was stirred with TMSBr (38 μL, 0.29 mmol) and 2,6-lutidine (34 μL, 0.29 mmol) for 2 hours at room temperature. The reaction was worked up by addition of EtOAc and aqueous 1N HCl. The organic layer was washed with brine and the solvent was removed in vacuo. The residue was suspended in a solution of 10% TFA-$CH_2Cl_2$ for 10 minutes before it was dried to provide 9.9 mg of the desired product (73%) as a white solid. $^1$H NMR (300 MHz, DMSO-d6) δ 1.76 (s, 3H), 1.76-1.88 (m, 2H), 2.10 (s, 3H), 2.87 (s, 3H), 3.24-3.35 (m, 2H), 3.39 (d, 2H, J=7 Hz), 3.65 (s, 2H), 3.75 (s, 3H), 5.22 (s, 2H), 5.41-5.48 (m, 1H) ppm; $^{31}$P (121.4 MHz, DMSO-d6) δ 21.4 ppm; MS (m/z) 464.1 [M+H]$^+$.

Example 169

Preparation of Representative Compounds of Formula 78

Representative compounds of the invention can be prepared as illustrated below.

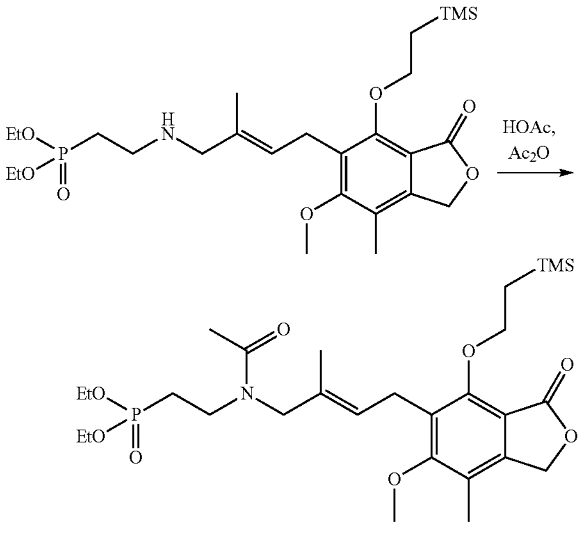

[2-(Acetyl-{4-[6-methoxy-7-methyl-3-oxo-4-(2-trimethylsilanyl-ethoxy)-1,3-dihydro-isobenzofuran-5-yl]-2-methyl-but-2-enyl}-amino)-ethyl]-phosphonic acid diethyl ester To a solution of (2-{4-[6-methoxy-7-methyl-3-oxo-4-(2-trimethylsilanyl-ethoxy)-1,3-dihydro-isobenzofuran-5-yl]-2-methyl-but-2-enylamino}-ethyl)-phosphonic acid diethyl ester (32 mg, 0.059 mmol) in acetic acid (0.5 mL) was added acetic anhydride (0.5 mL). The solution was stirred at room temperature for 90 minutes when it was quenched by addition of 2 drops of water. The solution was dried in vacuo and the residue was purified by RP HPLC using a C18 column with a gradient of $H_2O$, 0.1% TFA-acetonitrile, 0.1% TFA to provide 28 mg of the product (81%) as a clear gel. The NMR data of this compound shows two rotamers in a ratio of 70:30. $^1$H NMR (300 MHz, $CDCl_3$) δ 0.05 (s, 9H), 1.17-1.27 (m, 2H), 1.30 and 1.31 (t, 6H, J=7 Hz), 1.70-1.79 (m, 2H), 1.76 (s, 3H), 2.00 (s, 3H), 2.18 (s, 3H), 3.40-3.52 (m, 2H), 3.46 (d, 2H, 7 Hz), 3.77 (s, 3H), 3.79 and 3.93 (s, 3H), 4.07 (pent, 4H, J=7 Hz), 4.27-4.35 (m, 2H), 5.13 (s, 2H), 5.22-5.30 (m, 1H) ppm; $^{31}$P (121.4 MHz, $CDCl_3$) δ 27.5 and 28.9 ppm; MS (m/z) 584.1 [M+H]$^+$, 606.2 [M+Na]$^+$.

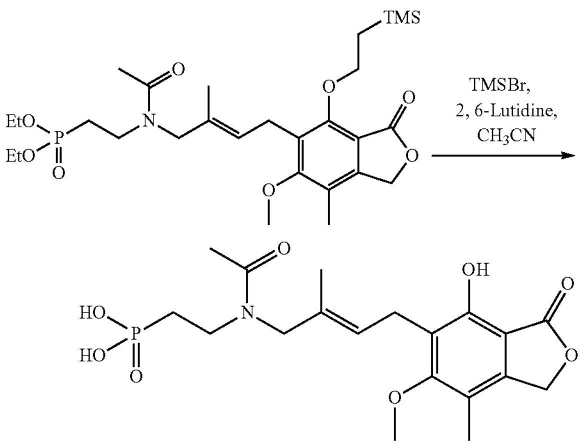

(2-{Acetyl-[4-(4-hydroxy-6-methoxy-7-methyl-3-oxo-1,3-dihydro-isobenzofuran-5-yl)-2-methyl-but-2-enyl]-amino}-ethyl)-phosphonic acid To a solution of [2-(acetyl-{4-[6-methoxy-7-methyl-3-oxo-4-(2-trimethylsilanyl-ethoxy)-1,3-dihydro-isobenzofuran-5-yl]-2-methyl-but-2-enyl}-amino)-ethyl]-phosphonic acid diethyl ester (14 mg, 0.024 mmol) in acetonitrile (0.5 mL) was added TMSBr (31 μL, 0.24 mmol) and 2,6-lutidine (28 μL, 0.24 mmol). The solution was stirred at room temperature for 1 hour. The reaction was quenched by addition of methanol and aqueous 1N HCl. The product was extracted with EtOAc. The combined organic extracts were dried over $Na_2SO_4$ and concentrated in vacuo. The product was purified by RP HPLC using a C18 column with a gradient of $H_2O$, 0.1% TFA-acetonitrile, 0.1% TFA to provide 5.4 mg of the product (53%) as a white solid. The NMR data of this compound shows two rotamers. $^1$H NMR (300 MHz, $CDCl_3$) δ 1.67 and 1.73 (s, 3H), 1.85-2.12 (m, 5H), 2.13 (s, 3H), 3.30-3.61 (m, 4H), 3.75 (s, 3H), 3.76 (br s, 2H), 5.17 (s, 2H), 5.31 (br s, 1H) ppm; $^{31}$P (121.4 MHz, $CDCl_3$) δ 27.5 and 28.8 ppm; MS (m/z) 428.2 [M+H]$^+$, 450.2 [M+Na]$^+$.

Example 170

Preparation of Representative Compounds of Formula 78

Representative compounds of the invention can be prepared as illustrated below.

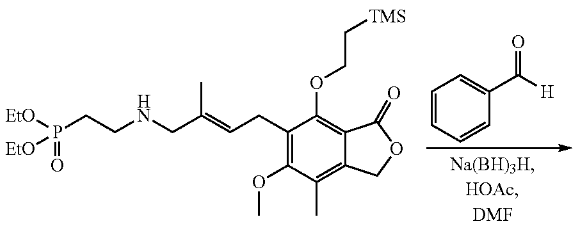

-continued

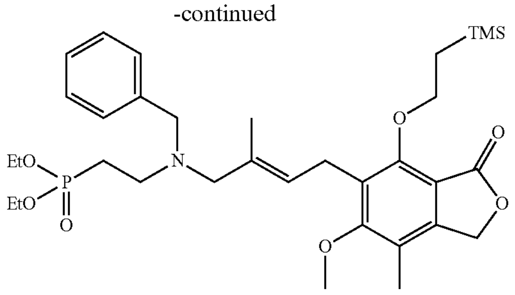

[2-(Benzyl-{4-[6-methoxy-7-methyl-3-oxo-4-(2-trimethylsilanyl-ethoxy)-1,3-dihydro-isobenzofuran-5-yl]-2-methyl-but-2-enyl}-amino)-ethyl]-phosphoric acid diethyl ester A solution of (2-{4-[6-methoxy-7-methyl-3-oxo-4-(2-trimethylsilanyl-ethoxy)-1,3-dihydro-isobenzofuran-5-yl]-2-methyl-but-2-enylamino}-ethyl)-phosphonic acid diethyl ester (30 mg, 0.055 mmol), benzaldehyde (5.6 μL, 0.055 mmol), and sodium triacetoxyborohydride (23 mg, 0.11 mmol) was stirred with acetic acid (15.7 μL, 0.28 mmol) in DMF (0.5 mL) at room temperature over night. The reaction was quenched with a 10% aqueous $Na_2CO_3$ solution and the product was extracted with EtOAc. The organic layer was dried and concentrated under reduced pressure. The product was purified by RP HPLC using a C18 column with a gradient of $H_2O$, 0.1% TFA-acetonitrile, 0.1% TFA to provide 15 mg of the product (43%) as a clear gel. $^1H$ NMR (300 MHz, $CDCl_3$) δ 0.02 (s, 9H), 1.18-1.25 (m, 2H), 1.24 (t, 6H, J=7 Hz), 1.86 (s, 3H), 1.88-2.02 (m, 2H), 2.16 (s, 3H), 2.65-2.74 (m, 2H), 3.93 (s, 2H), 3.46 (br d, 4H, J=7 Hz), 3.76 (s, 3H), 4.00 (pent, 4H, J=7 Hz), 4.25-4.34 (m, 2H), 5.11 (s, 2H), 5.34-5.43 (m, 1H), 7.18-7.33 (m, 5H) ppm; $^{31}P$ (121.4 MHz, $CDCl_3$) δ 30.9 ppm; MS (m/z) 632.4 $[M+H]^+$, 654.3 $[M+Na]^+$.

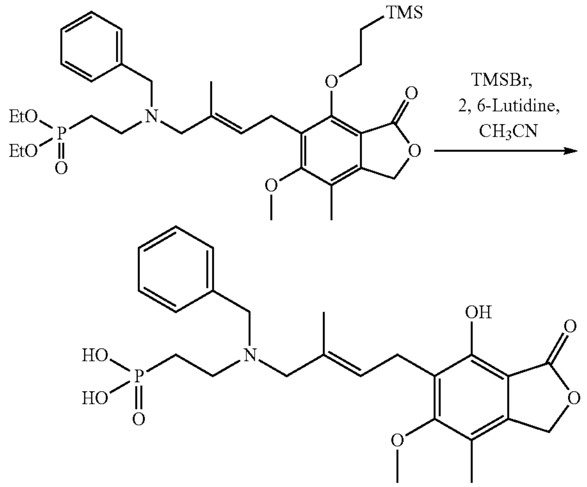

(2-{Benzyl-[4-(4-hydroxy-6-methoxy-7-methyl-3-oxo-1,3-dihydro-isobenzofuran-5-yl)-2-methyl-but-2-enyl]-amino}-ethyl)-phosphonic acid A solution of (2-{4-[6-methoxy-7-methyl-3-oxo-4-(2-trimethylsilanyl-ethoxy)-1,3-dihydro-isobenzofuran-5-yl]-2-methyl-but-2-enylamino}-ethyl)-phosphonic acid diethyl ester (15 mg, 0.024 mmol) in acetonitrile (0.5 mL) was treated with TMSBr (31 μL, 0.24 mmol) and 2,6-lutidine (28 μL, 0.24 mmol). The solution was stirred at ambient temperature for 1 hour, when it was quenched with methanol. The solvent was removed under reduced pressure and the residue was purified by RP HPLC using a C18 column with a gradient of $H_2O$, 0.1% TFA-acetonitrile, 0.1% TFA to provide 11 mg of the product (93%) as a white solid. $^1H$ NMR (300 MHz, $CD_3OD$) δ 1.89 (s, 3H), 2.03-2.15 (m, 2H), 2.14 (s, 3H), 3.30-3.47 (m, 2H), 3.50 (br s, 2H), 3.62 (br s, 2H), 3.79 (s, 3H), 4.28 (s, 2H), 5.23 (s, 2H), 5.76 (br s, 1H), 7.46 (br s, 5H) ppm; $^{31}P$ (121.4 MHz, $CDCl_3$) δ 20.1 ppm; MS (m/z) 476.3 $[M+H]^+$, 498.3 $[M+Na]^+$.

Example 171

Preparation of Representative Compounds of Formula 78

Representative compounds of the invention can be prepared as illustrated below.

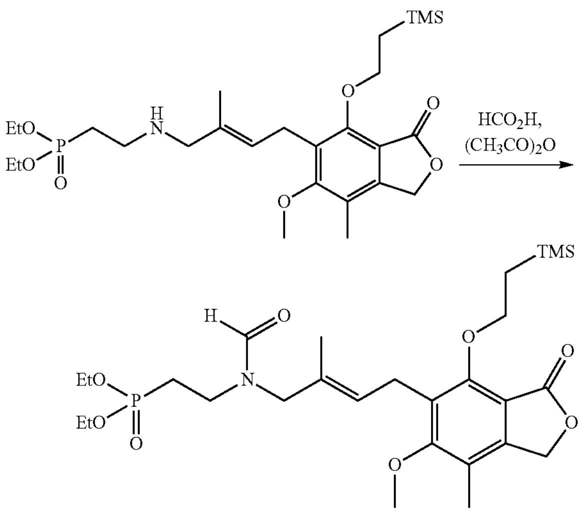

[2-(Formyl-{4-[6-methoxy-7-methyl-3-oxo-4-(2-trimethylsilanyl-ethoxy)-1,3-dihydro-isobenzofuran-5-yl]-2-methyl-but-2-enyl}-amino)-ethyl]-phosphonic acid diethyl ester To a solution of (2-{4-[6-Methoxy-7-methyl-3-oxo-4-(2-trimethylsilanyl-ethoxy)-1,3-dihydro-isobenzofitran-5-yl]-2-methyl-but-2-enylamino}-ethyl)-phosphonic acid diethyl ester (74 mg, 0.14 mmol) in formic acid (1 mL) was added formic anhydride (1 mL) and the solution was stirred at room temperature for 1 hour. The reaction mixture was concentrated and the crude product carried onto the next step. The NMR data of this compound shows two rotamers with the ratio of 70:30. $^1H$ NMR (300 MHz, $CDCl_3$) δ 0.05 (s, 9H), 1.18-1.28 (m, 2H), 1.28 and 1.30 (t, 6H, J=7 Hz), 1.74 (s, 3H), 1.84-2.08 (m, 2H), 2.19 (s, 3H), 3.34-3.45 (m, 2H), 3.47 (d, 2H, J=7 Hz), 3.72 and 3.87 (s, 2H), 3.78 and 3.79 (s, 3H), 4.06 and 4.07 (pent, 4H, J=7 Hz), 4.26-4.37 (m, 2H), 5.13 (s, 2H), 5.30-5.46 (m, 1H), 8.03 and 8.19 (s, 1H) ppm; $^{31}P$ (121.4 MHz, $CDCl_3$) δ 27.5 and 28.1 ppm; MS (m/z) 570.1 $[M+H]^+$, 592.2 $[M+Na]^+$.

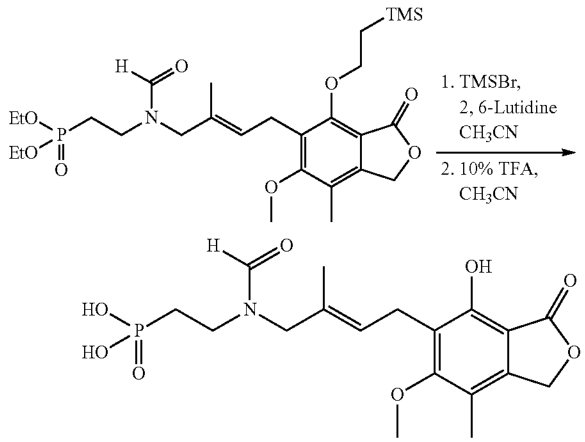

(2-{Formyl-[4-(4-hydroxy-6-methoxy-7-methyl-3-oxo-1,3-dihydro-isobenzofuran-5-yl)-2-methyl-but-2-enyl]-amino}-ethyl)-phosphonic acid To a solution of crude [2-(formyl-{4-[6-methoxy-7-methyl-3-oxo-4-(2-trimethylsilanyl-ethoxy)-1,3-dihydro-isobenzofuran-5-yl]-2-methyl-but-2-enyl}-amino)-ethyl]-phosphonic acid diethyl ester (78 mg, 0.14 mmol) in acetonitrile (1 mL) was added TMSBr (177 μL, 1.4 mmol) and 2,6-lutidine (163 μL, 1.4 mmol). The solution was stirred at room temperature for 1 hour when it was quenched by addition of methanol and 1N aqueous HCl. The product was extracted with EtOAc and purified by RP HPLC using a C18 column with a gradient of $H_2O$, 0.1% TFA-acetonitrile, 0.1% TFA to provide 29 mg of the product as a white solid. The NMR data of this compound shows two rotamers with the ratio of approximately 70:30. $^1H$ NMR (300 MHz, $CD_3OD$) δ 1.62 and 1.64 (s, 3H), 1.83-1.98 (m, 2H), 2.16 (s, 3H), 3.38-3.55 (m, 4H), 3.78 (s, 3H), 3.80 and 3.91 (s, 2H), 5.22 (s, 2H), 5.39-5.52 (m, 1H), 8.03 and 8.18 (s, 1H) ppm; MS (m/z) 414.2 $[M+H]^+$, 436.2 $[M+Na]^+$.

Example 172

Preparation of Representative Compounds of Formula 78

Representative compounds of the invention can be prepared as illustrated below.

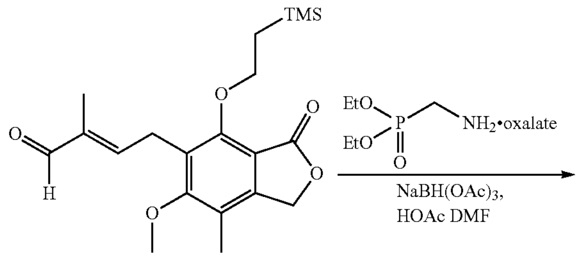

-continued

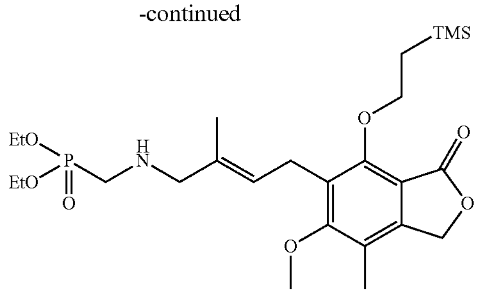

({4-[6-Methoxy-7-methyl-3-oxo-4-(2-trimethylsilanyl-ethoxy)-1,3-dihydro-isobenzofuran-5-yl]-2-methyl-but-2-enylamino}-methyl)-phosphonic acid diethyl ester To a solution of 4-[6-methoxy-7-methyl-3-oxo-4-(2-trimethylsilanyl-ethoxy)-1,3-dihydro-isobenzofuran-5-yl]-2-methyl-but-2-enal (500 mg, 1.33 mmol), (2-aminomethyl) phosphonic acid diethyl ester oxalate (376 mg, 1.46 mmol), sodium triacetoxyborohydride (563 mg, 2.66 mmol) in DMF (10 mL) was added acetic acid (380 μL, 6.65 mmol) at room temperature. The solution was stirred overnight when it was quenched by addition of saturated aqueous sodium bicarbonate solution and EtOAc. The organic layer was separated and concentrated under reduced pressure. The residue was purified by silica gel chromatography to provide 500 mg (71%) of the product as an oil. $^1H$ NMR (300 MHz, $CDCl_3$) δ 0.00 (s, 9H), 1.13-1.23 (m, 2H), 1.25 and 1.27 (t, 6H, J=7 Hz), 1.65-1.75 (m, 2H), 1.77 (s, 3H), 2.13 (s, 3H), 2.80 (s, 1H), 3.14 (s, 2H), 3.41 (d, 2H, J=7 Hz), 3.73 (s, 3H), 4.08 and 4.09 (pent, 4H, J=7 Hz), 4.20-4.30 (m, 2H), 5.08 (s, 2H), 5.30 (t, 1H, J=7 Hz) ppm; $^{31}P$ (121.4 MHz, $CDCl_3$) δ 26.5 ppm; MS (m/z) 528.1 $[M+H]^+$, 550.2 $[M+Na]^+$.

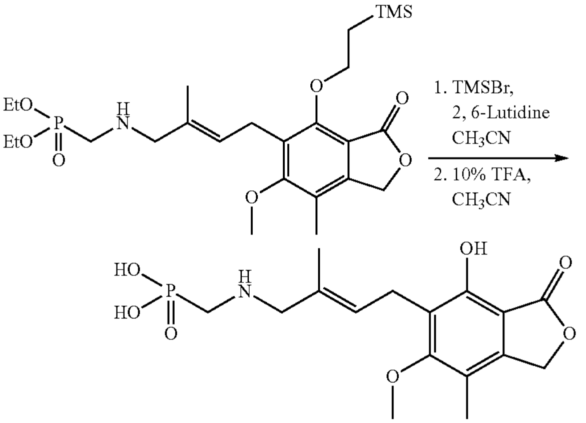

{[4-(4-Hydroxy-6-methoxy-7-methyl-3-oxo-1,3-dihydro-isobenzofuran-5-yl)-2-methyl-but-2-enylamino]-methyl}-phosphonic acid To a solution of ({4-[6-methoxy-7-methyl-3-oxo-4-(2-trimethylsilanyl-ethoxy)-1,3-dihydro-isobenzofuran-5-yl]-2-methyl-but-2-enylamino}-methyl)-phosphonic acid diethyl ester (20 mg, 0.038 mmol) in DMF (0.5 mL) was added TMSBr (49 μL, 0.38 mmol) and 2,6-lutidine (44 μL, 0.38 mmol). The solution was stirred at room temperature for 1 hour when it was quenched by addition of methanol. The product was purified by RP HPLC using a C18 column with a gradient of $H_2O$, 0.1% TFA-acetonitrile, 0.1% TFA to provide 5.6 mg of the product as a white solid. $^1H$ NMR (300 MHz, $CD_3OD$ and $CDCl_3$) δ 1.93 (s, 3H), 2.13 (s, 3H), 2.94 (br d, 2H, J=11 Hz), 3.42-3.53 (m, 2H), 3.60 (s, 2H), 3.78 (s, 3H), 5.22 (s, 2H), 5.71 (br s, 1H) ppm; $^{31}P$ (121.4 MHz, $CDCl_3$) δ 8.5 ppm; MS (m/z) 372.2 $[M+H]^+$, 743.2 $[2M+H]^+$.

Example 173

Preparation of Representative Compounds of Formula 78

Representative compounds of the invention can be prepared as illustrated below.

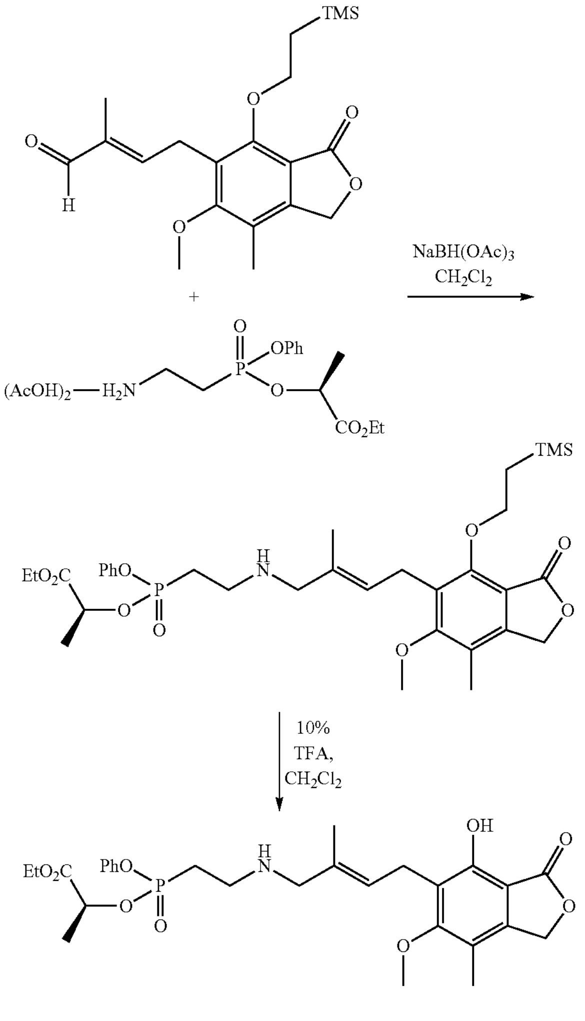

2-({2-[4-(4-Hydroxy-6-methoxy-7-methyl-3-oxo-1,3-dihydro-isobenzofuran-5-yl)-2-methyl-but-2-enylamino]-ethyl}-phenoxy-phosphinoyloxy)-propionic acid ethyl ester A solution of 4-[6-methoxy-7-methyl-3-oxo-4-(2-trimethylsilanyl-ethoxy)-1,3-dihydro-isobenzofuran-5-yl]-2-methyl-but-2-enal (188 mg, 0.5 mmol) was stirred with 2-[(2-aminoethyl)phenoxy-phosphinoyloxy]-propionic acid ethyl ester acetic acid salt (315.8 mg, 0.75 mmol) in $CH_2Cl_2$ (3 mL) for 2 hours at ambient temperature. Sodium triacetoxyborohydride (159 mg, 0.75 mmol) was added to the solution and the reaction was allowed to proceed for 1 hour. The reaction was quenched by addition of a saturated aqueous solution of $NaHCO_3$ and the product was extracted with EtOAc. The organic layer was removed under reduced pressure and the residue was resuspended in a 10% TFA/$CH_2Cl_2$ for 1 hour. The reaction mixture was concentrated and the product was purified by RP HPLC using a C18 column with a gradient of $H_2O$, 0.1% TFA-acetonitrile, 0.1% TFA to provide 198 mg of the product as a white solid. The NMR data of this compound shows two diastereomers at phosphorus in a ratio of approximately 45:55. $^1H$ NMR (300 MHz, $CD_3OD$) δ 1.23 and 1.24 (t, 3H, J=7 Hz), 1.38 and 1.52 (d, 3H, J=7 Hz), 1.97 and 1.98 (s, 3H), 2.14 (s, 3H), 2.44-2.66 (m, 2H), 3.31-3.48 (m, 2H), 3.51 (d, 2H, J=7 Hz), 3.66 (d, 2H, J=5 Hz), 3.80 (s, 3H), 4.10-4.27 (m, 2H), 4.90-5.10 (m, 1H), 5.20 (s, 2H), 5.73-5.82 (m, 1H), 7.15-7.27 (m, 3H), 7.35-7.45 (m, 2H) ppm; $^{31}P$ (121.4 MHz, $CD_3OD$) δ 22.6, 24.3 ppm; MS (m/z) 561.9 $[M+H]^+$.

Example 174

Preparation of Representative Compounds of Formula 78

Representative compounds of the invention can be prepared as illustrated below.

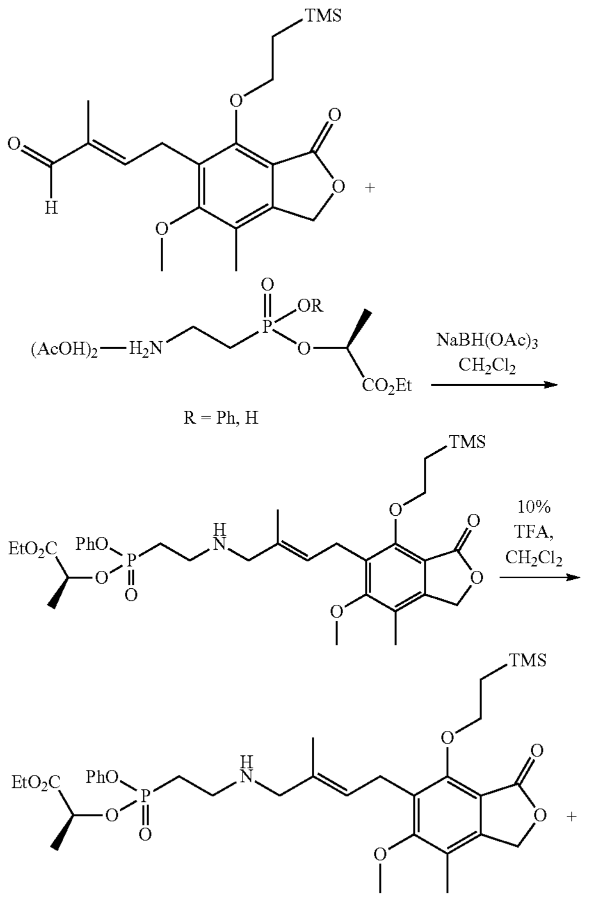

-continued

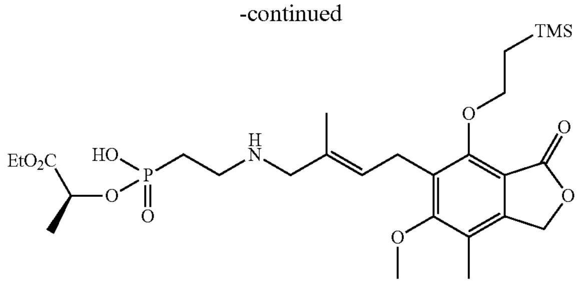

2-[Hydroxy-(2-{4-[6-methoxy-7-methyl-3-oxo-4-(2-trimethylsilanyl-ethoxy)-1,3-dihydro-isobenzofuran-5-yl]-2-methyl-but-2-enylamino}-ethyl)-phosphinoyloxy]-propionic acid ethyl ester A solution of 4-[6-methoxy-7-methyl-3-oxo-4-(2-trimethylsilanyl-ethoxy)-1,3-dihydro-isobenzofuran-5-yl]-2-methyl-but-2-enal (38 mg, 0.1 mmol) was stirred with 2-[(2-aminoethyl)-phenoxy-phosphinoyloxy]-propionic acid ethyl ester acetic acid (63 mg, 0.15 mmol) in $CH_2Cl_2$ (1 mL) for 2 hours at ambient temperature. Sodium triacetoxyborohydride (32 mg, 0.15 mmol) was added to the solution and the reaction was allowed to proceed for 1 hour. The reaction was quenched by addition of a saturated aqueous solution of $NaHCO_3$ and the product was extracted with EtOAc. The organic layer was removed under reduced pressure and the residue was re-suspended in 10% TFA/$CH_2Cl_2$ for 1 hour. The reaction mixture was concentrated and the product was purified by RP HPLC using a C18 column with a gradient of $H_2O$, 0.1% TFA-acetonitrile, 0.1% TFA to provide 15 mg of the product (154-2). $^1H$ NMR (300 MHz, $CDCl_3$) δ 0.04 (s, 9H), 1.15-1.24 (m, 2H), 1.26 (t, 3H, J=7 Hz), 1.48 (d, 3H, J=7 Hz), 1.93 (s, 3H), 2.10-2.25 (m, 2H), 2.18 (s, 3H), 3.10-3.31 (m, 2H), 3.48 (d, 2H, J=7 Hz), 3.48-3.61 (m, 2H), 3.77 (s, 3H), 4.04-4.21 (m, 2H), 4.29-4.40 (m, 2H), 4.81-4.92 (m, 1H), 5.13 (s, 2H), 5.64 (t, 1H, J=7 Hz), 8.70-9.11 (m, 3H) ppm; $^{31}P$ (121.4 MHz, $CDCl_3$) δ 21.9 ppm; MS (m/z) 586.3 $[M+H]^+$, 1171.4 $[2M+H]^+$.

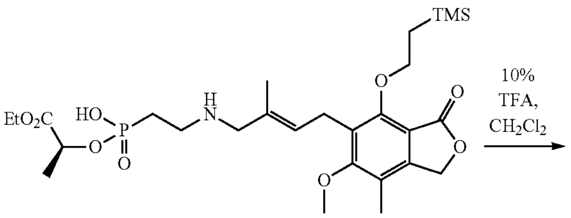

-continued

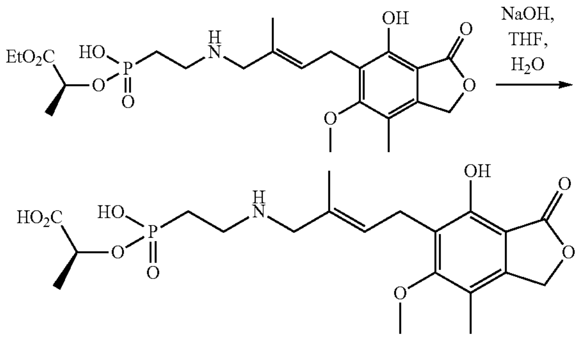

2-(Hydroxy-{2-[4-(4-hydroxy-6-methoxy-7-methyl-3-oxo-1,3-dihydro-isobenzofuran-5-yl)-2-methyl-but-2-enylamino]-ethyl}-phosphinoyloxy)-propionic acid A solution of 2-[hydroxy-(2-{4-[6-methoxy-7-methyl-3-oxo-4-(2-trimethylsilanyl-ethoxy)-1,3-dihydro-isobenzofuran-5-yl]-2-methyl-but-2-enylamino}-ethyl)-phosphinoyloxy]-propionic acid ethyl ester (15 mg, 0.026 mmol) in 10% TFA-$CH_2Cl_2$ (1 mL) was stirred at ambient temperature for 10 minutes. The reaction was worked up by removal of the solvent. The residue was dissolved in THF (0.5 mL) and water (0.4 mL) and 1N aqueous NaOH solution (0.1 mL) was added. The solution was stirred at room temperature for 20 minutes when it was acidified with 1N aqueous HCl solution. The resulting solution was purified by RP HPLC using a C18 column with a gradient of $H_2O$, 0.1% TFA-acetonitrile, 0.1% TFA to provide 6.8 mg of the product as a white solid. $^1H$ NMR (300 MHz, $CDCl_3$) δ 1.38 (d, 3H, J=7 Hz), 1.91 (s, 3H), 2.13 (s, 3H), 2.12-2.28 (m, 2H), 3.12-3.33 (m, 2H), 3.41 (d, 2H, J=6 Hz), 3.56 (br s, 2H), 3.75 (s, 3H), 4.71-4.88 (m, 1H), 5.16 (s, 2H), 5.58-5.71 (m, 1H), 7.88 (br s, 3H), 8.60 (br s, 1H), 8.78 (br s, 1H) ppm; $^{31}P$ (121.4 MHz, $CDCl_3$) δ 22.0 ppm; MS (m/z) 458.3 $[M+H]^+$, 480.3 $[M+Na]^+$.

Example 175

Preparation of Representative Compounds of Formula 78

Representative compounds of the invention can be prepared as illustrated below.

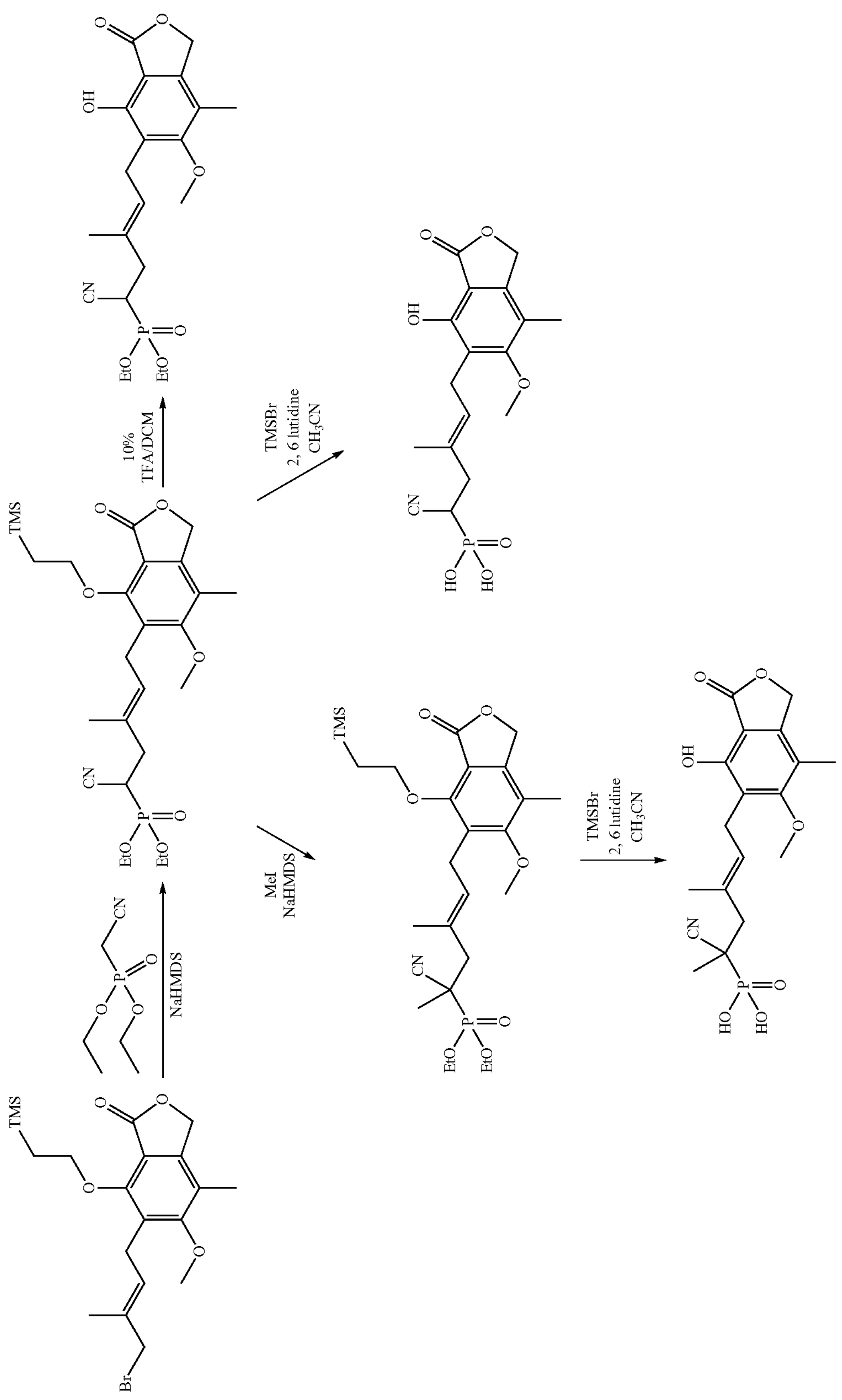
NaHMDS
10%
TFA/DCM
TMSBr
2, 6 lutidine
$CH_3CN$
MeI
NaHMDS
TMSBr
2, 6 lutidine
$CH_3CN$ -continued
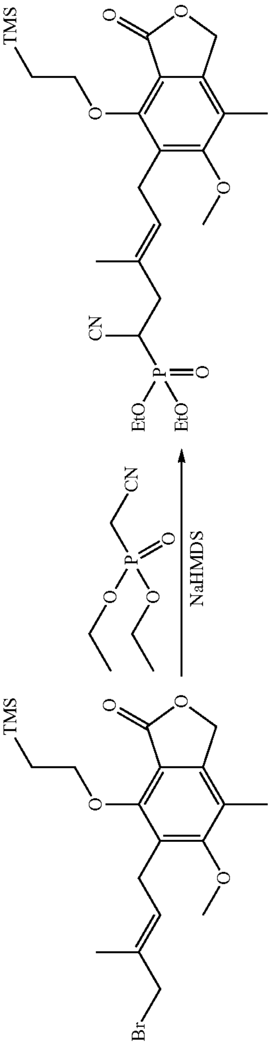

{1-Cyano-5-[6-methoxy-7-methyl-3-oxo-4-(2-trimethylsilanyl-ethoxy)-1,3-dihydro-isobenzofuran-5-yl]-3-methyl-pent-3-enyl}-phosphonic acid diethyl ester To a solution of diethyl cyanomethylphosphonate (241 mg, 1.38 mmol) in THF (1 mL) was added a THF solution of sodium bis(trimethysilyl)amide (1.0 M, 1.13 mL, 1.15 mmol). After stirring for 30 minutes, the solution was added dropwise to a solution of 6-(4-bromo-3-methyl-but-2-enyl)-7-hydroxy-5-methoxy-4-methyl-3H-isobenzofuran-1-one (100 mg, 0.23 mmol) in THF (1 mL). The resulting mixture was allowed to stir at room temperature for one hour before saturated aqueous ammonium chloride was added. The reaction mixture was extracted with ethyl acetate. The organic layer was dried over sodium sulfate and concentrated to dryness. The residue was purified by silica gel column chromatography, affording 110 mg (90%) of the desired product. $^1$H NMR (300 MHz, $CDCl_3$) δ 0.04 (s, 9H), 1.24 (dd, J=7, 8 Hz, 2H), 1.36 (t, 6H), 1.86 (s, 3H), 2.17 (s, 3H), 2.43-2.57 (m, 2H), 3.04-3.17 (m, 1H), 3.47 (d, J=7.2 Hz, 2H), 3.79 (s, 3H), 4.12-4.37 (m, 6H), 5.13 (s, 2H), 5.44 (t, J=7.2 Hz, 1H) ppm; $^{31}$P (121.4 MHz, $CDCl_3$) δ 18.18 ppm; MS (m/z) 560 $[M+Na]^+$.

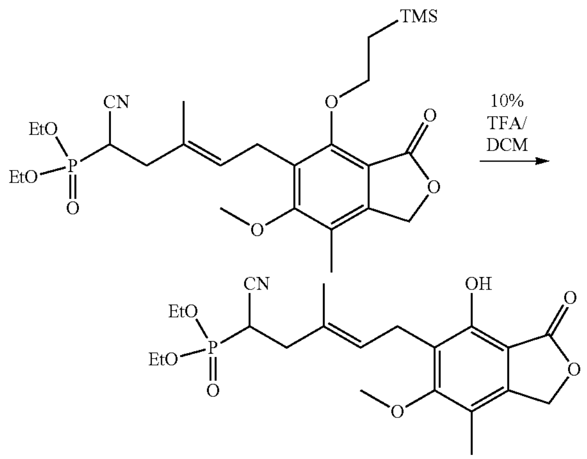

[1-Cyano-5-(4-hydroxy-6-meth oxy-7-methyl-3-oxo-1,3-dihydro-isobenzofuran-5-yl)-3-methyl-pent-3-enyl]-phosphonic acid diethyl ester {1-Cyano-5-[6-methoxy-7-methyl-3-oxo-4-(2-trimethylsilanyl-ethoxy)-1,3-dihydro-isobenzofuran-5-yl]-3-methyl-pent-3-enyl}-phosphonic acid diethyl ester (25 mg, 0.047 mmol) was dissolved in a solution of 10% TFA/$CH_2Cl_2$ (5 mL) and stirred at room temperature for 2 hours. The reaction mixture was dried under reduced pressure and the product was purified by RP-HPLC to provide 16 mg (80%) of the desired product as a white solid. $^1$H NMR (300 MHz, $CDCl_3$) δ 1.38 (t, 6H), 1.86 (s, 3H), 2.15 (s, 3H), 2.40-2.58 (m, 2H), 3.01-3.14 (m, 1H), 3.45 (d, J=7.2 Hz, 2H), 3.79 (s, 3H), 4.18-4.30 (m, 4H), 5.21 (s, 2H), 5.48 (t, J=7.2 Hz, 1H) ppm; $^{31}$P (121.4 MHz, $CDCl_3$) δ 18.09 ppm; MS (m/z) 436 $[M-H]^-$, 438 $[M+H]^+$.

Example 176

Preparation of Representative Compounds of Formula 78

Representative compounds of the invention can be prepared as illustrated below.

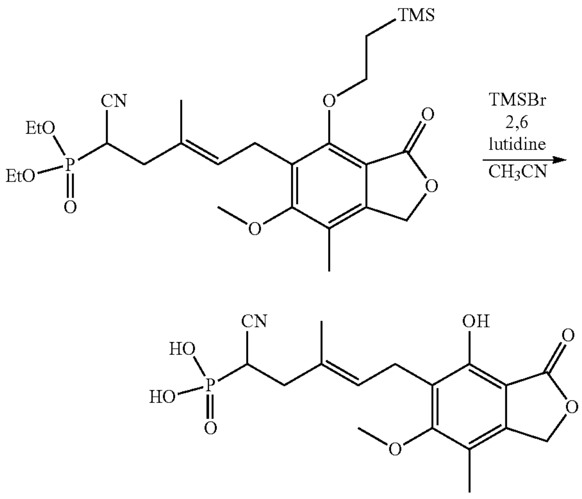

[1-Cyano-5-(4-hydroxy-6-methoxy-7-methyl-3-oxo-1,3-dihydro-isobenzofuran-5-yl)-3-methyl-pent-3-enyl]-phosphonic acid To a solution of {1-cyano-5-[6-methoxy-7-methyl-3-oxo-4-(2-trimethylsilanyl-ethoxy)-1,3-dihydro-isobenzofuran-5-yl]-3-methyl-pent-3-enyl}-phosphonic acid diethyl ester (35 mg, 0.065 mmol) in acetonitrile (2 mL) was added TMSBr (180 μL, 1.38 mmol) and 2,6-lutidine (160 μL, 1.38 mmol). The reaction solution was allowed stir at room temperature for one hour before quenching with MeOH. The reaction mixture was dried under reduced pressure and the residue was purified by RP HPLC using a C18 column with a gradient of $H_2O$, 0.1% TFA-acetonitrile, 0.1% TFA to provide 15 mg (60%) of the desired product. $^1$H NMR (300 MHz, $CD_3OD$) δ 1.86 (s, 3H), 2.15 (s, 3H), 2.38-2.57 (m, 2H), 3.17-3.28 (m, 1H), 3.44 (d, J=7.2 Hz, 2H), 3.80 (s, 3H), 5.25 (s, 2H), 5.47 (t, J=7.2 Hz, 1H) ppm; $^{31}$P (121.4 MHz, $CD_3OD$) δ 15.28 ppm; MS (m/z) 380 $[M-H]^-$, 382 $[M+H]^+$.

Example 177

Preparation of Representative Compounds of Formula 78

Representative compounds of the invention can be prepared as illustrated below.

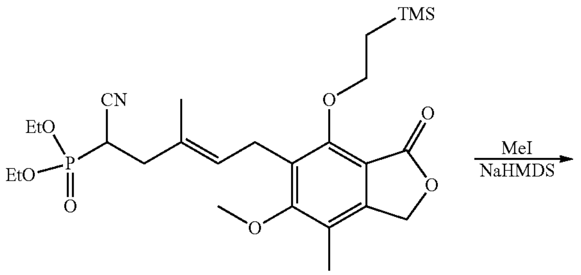

-continued

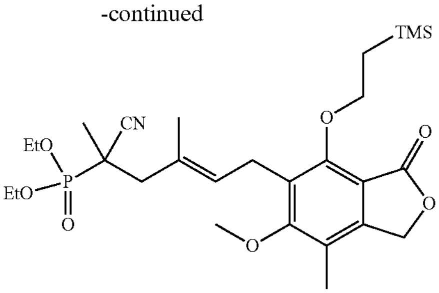

{1-Cyano-5-[6-methoxy-7-methyl-3-oxo-4-(2-trimethylsilanyl-ethoxy)-1,3-dihydro-isobenzofuran-5-yl]-1,3-dimethyl-pent-3-enyl}-phosphonic acid diethyl ester To a solution of {1-cyano-5-[6-methoxy-7-methyl-3-oxo-4-(2-trimethylsilanyl-ethoxy)-1,3-dihydro-isobenzofuran-5-yl]-3-methyl-pent-3-enyl}-phosphonic acid diethyl ester (45 mg, 0.084 mmol) in THF (0.5 mL) was added sodium bis (trimethysilyl)amide (1.0 M, 1.13 mL, 1.15 mmol). After stirring for 20 minutes, iodomethane (52 μL, 0.84 mmol) was added dropwise and the resulting mixture was allowed to stir at room temperature for 2 hours. The reaction mixture was quenched with saturated aqueous ammonium chloride and extracted with ethyl acetate. The organic layer was dried over sodium sulfate and concentrated to dryness. The residue was purified by RP HPLC using a C18 column with a gradient of $H_2O$, 0.1% TFA-acetonitrile, 0.1% TFA to afford 6.6 mg (23%) of the desired product. $^1H$ NMR (300 MHz, $CDCl_3$) δ 0.00 (s, 9H), 1.16 (dd, J=7, 8 Hz, 2H), 1.31 (t, 6H), 1.38 (d, 3H), 1.92 (s, 3H), 2.17 (s, 3H), 2.23 (m, 1H), 2.65 (m, 1H), 3.30-3.42 (m, 2H), 3.73 (s, 3H), 4.14-4.27 (m, 6H), 5.08 (s, 2H), 5.28 (t, J=7.2 Hz, 1H) ppm; $^{31}P$ (121.4 MHz, $CDCl_3$) δ 22.26 ppm; MS (m/z) 574 $[M+Na]^+$.

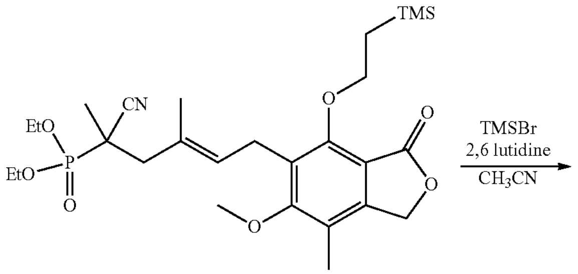

-continued

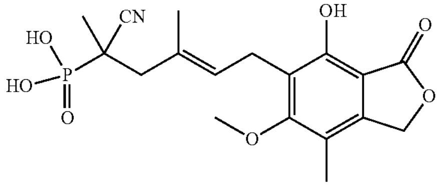

[1-Cyano-5-(4-hydroxy-6-methoxy-7-methyl-3-oxo-1,3-dihydro-isobenzofuran-5-yl)-1,3-dimethyl-pent-3-enyl]-phosphonic acid To a solution of {1-cyano-5-[6-methoxy-7-methyl-3-oxo-4-(2-trimethylsilanyl-ethoxy)-1,3-dihydro-isobenzofuran-5-yl]-1,3-dimethyl-pent-3-enyl}-phosphonic acid diethyl ester (18 mg, 0.04 mmol) in DMF (0.5 mL) and DCM (0.5 mL) was added TMSBr (51 μL, 0.4 mmol) and 2,6-lutidine (46 μL, 0.4 mmol). The reaction solution was allowed stir at room temperature overnight before quenching with MeOH. The reaction mixture was dried under reduced pressure and the residue was purified by RP HPLC using a C18 column with a gradient of $H_2O$, 0.1% TFA-acetonitrile, 0.1% TFA to provide 4.5 mg (33%) of the desired product. $^1H$ NMR (300 MHz, $CD_3OD$) δ 1.37 (d, 3H), 1.87 (s, 3H), 2.13 (s, 3H), 2.26 (m, 1H), 2.64 (m, 1H), 3.39 (m, 2H), 3.75 (s, 3H), 5.18 (s, 2H), 5.34 (m, 1H) ppm; $^{31}P$ (121.4 MHz, $CD_3OD$) δ 21.47 ppm; MS (m/z) 422 $[M-H]^-$, 424 $[M+H]^+$.

Example 178

Preparation of Representative Compounds of Formula 81

Representative compounds of the invention can be prepared as illustrated below.

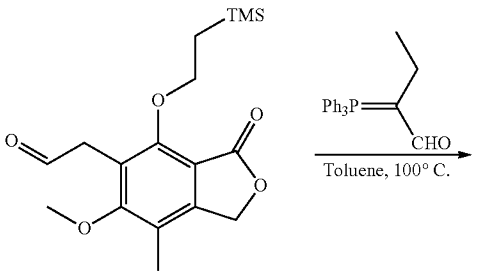

-continued

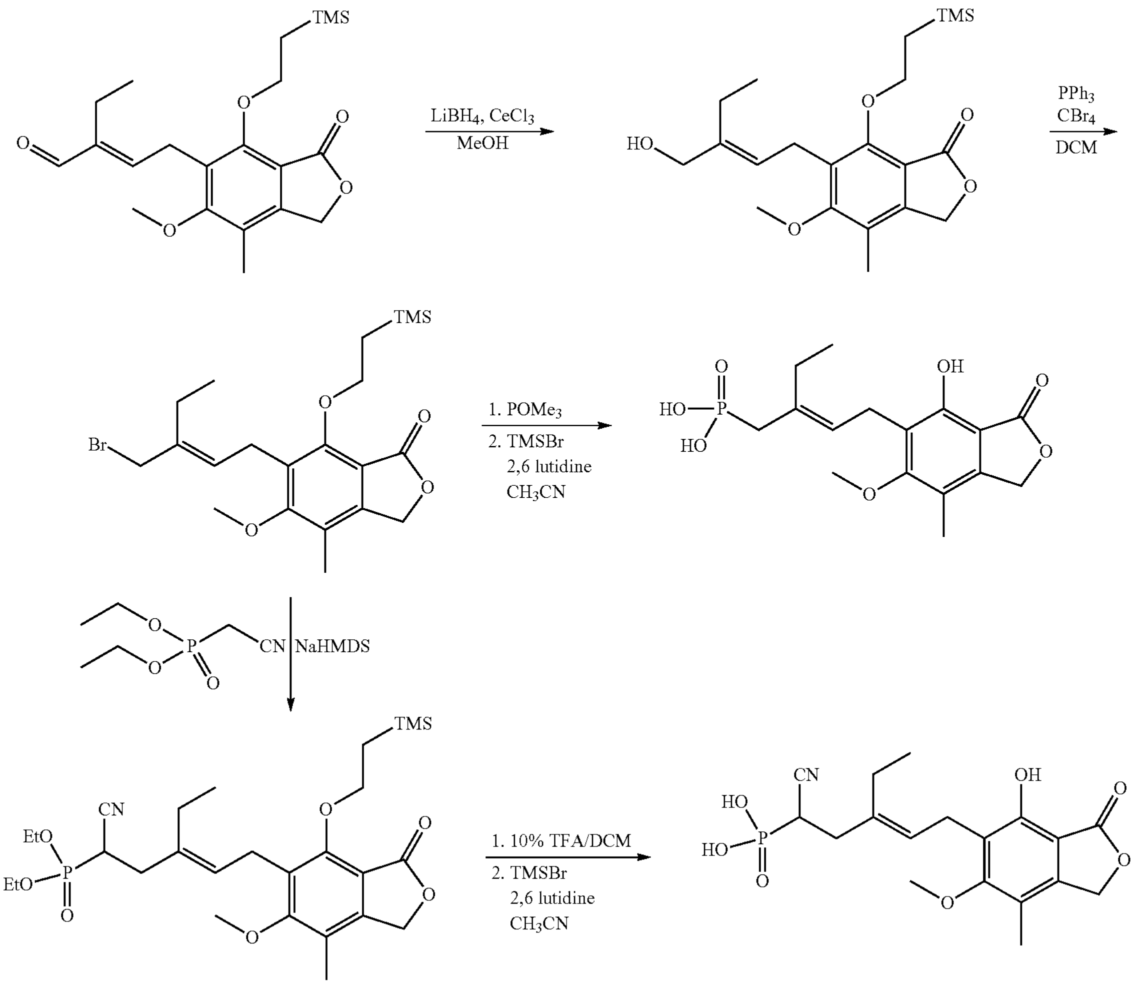

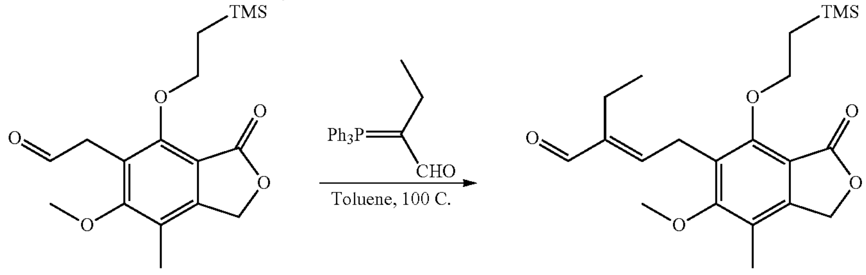

2-Ethyl-4-[6-methoxy-7-methyl-3-oxo-4-(2-trimethylsilanyl-ethoxy)-1,3-dihydro-isobenzofuran-5-yl]-but-2-enal A solution of [6-methoxy-7-methyl-3-oxo-4-(2-trimethylsilanyl-ethoxy)-1,3-dihydro-isobenzofuran-5-yl]-acetaldehyde (1.5 g, 4.46 mmol) in toluene (14 mL) was heated at 100° C. with 2-(triphenyl-phosphanylidene)-butyraldehyde (1.68 g, 5.35 mmol) overnight. A second portion of 2-(triphenyl-phosphanylidene)-butyraldehyde (495 mg, 1.49 mmol) was added and the reaction mixture was heated for an additional day. After concentration, the residue was purified by silica gel chromatography to provide 1.3 g (83%) of the desired product as oil. $^1H$ NMR (300 MHz, $CDCl_3$) δ 0.01 (s, 9H), 1.03 (t, 3H), 1.10-1.21 (m, 2H), 2.15 (s, 3H), 2.15-2.44 (m, 2H), 3.67-3.76 (m, 2H), 3.74 (s, 3H), 4.31-4.36 (m, 2H), 5.10 (s, 2H), 6.34-6.38 (m, 1H), 9.28 (s, 1H) ppm.

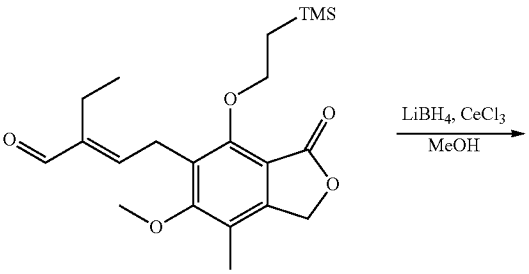

-continued

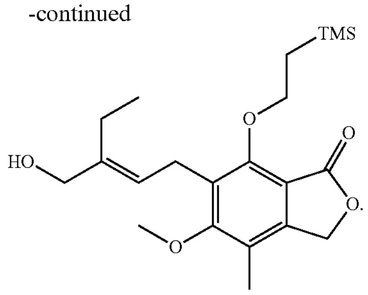

6-(3-Hydroxymethyl-pent-2-enyl)-5-methoxy-4-methyl-7-(2-trimethylsilanyl-ethoxy)-3H-isobenzo-furan-1-one A solution of 2-ethyl-4-[6-methoxy-7-methyl-3-oxo-4-(2-trimethylsilanyl-ethoxy)-1,3-dihydro-isobenzofuran-5-yl]-but-2-enal (1.3 g, 3.30 mmol) in methanol (10 mL) and THF (10 mL) was cooled to 0° C. A solution of $CeCl_3$ (8.25 mL, 0.4M, MeOH: $H_2O$, 9:1) was added, followed by $LiBH_4$ (1.66 mL, 3.30 mmol of a 2M solution in THF). The ice bath was removed and the reaction mixture was allowed to warm to room temperature. The reaction mixture was stirred for an additional 40 minutes whereupon TLC indicated complete consumption of starting aldehyde. The reaction was worked up by addition of aqueous 1N HCl and the product was extracted with EtOAc. The organic layer was washed with saturated aqueous sodium bicarbonate solution and brine. The organic layer was concentrated under reduced pressure and the residue was purified by silica gel chromatography to provide 948 mg (73%) of the product as colorless oil. $^1$H NMR (300 MHz, $CDCl_3$) δ 0.00 (s, 9H), 1.07 (t, 3H), 1.20 (dd, 2H, J=7, 8 Hz), 2.13 (s, 3H), 2.38-2.50 (m, 2H), 3.77 (s, 3H), 3.99 (s, 2H), 4.27 (dd, 2H, J=7, 8 Hz), 5.08 (s, 2H), 5.34 (t, J=7.2 Hz, 1H) ppm.

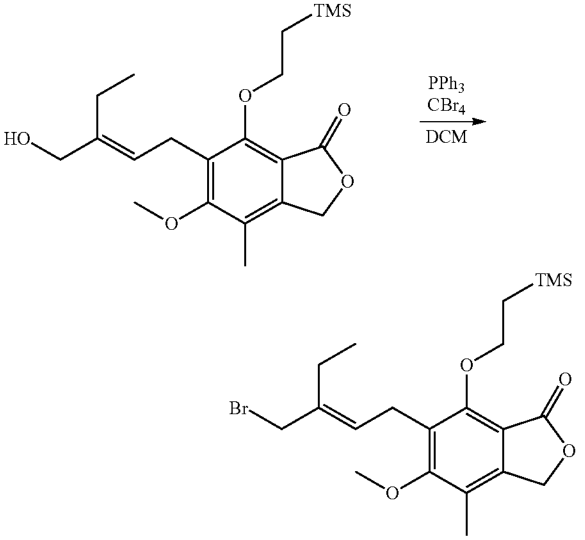

6-(3-Bromomethyl-pent-2-enyl)-5-methoxy-4-methyl-7-(2-trimethylsilanyl-ethoxy)-3H-isobenzofuran-1-one Polymer-supported triphenylphosphine (3 mmol/g, 0.66 g) was soaked in dichloromethane (6 mL) for 1 hour. 6-(3-Hydroxymethyl-pent-2-enyl)-5-methoxy-4-methyl-7-(2-trimethylsilanyl-ethoxy)-3H-isobenzofuran-1-one (260 mg, 0.66 mmol) and carbon tetrabromide (657 mg, 1.98 mmol) were added sequentially and the mixture was shaken for 1 h at room temperature. The mixture was filtered and the filtrate was concentrated. The residue was purified by silica gel chromatography to provide 233 mg (77%) of the product as a white solid. $^1$H NMR (300 MHz, $CDCl_3$) δ 0.00 (s, 9H), 1.08 (t, 3H), 1.20 (dd, 2H, J=7, 8 Hz), 2.14 (s, 3H), 2.35-2.43 (m, 2H), 3.44 (d, J=7.2, 2H), 3.73 (s, 3H), 3.95 (s, 2H), 4.27 (dd, 2H, J=7, 8 Hz), 5.08 (s, 2H), 5.53 (t, J=7.2 Hz, 1H) ppm.

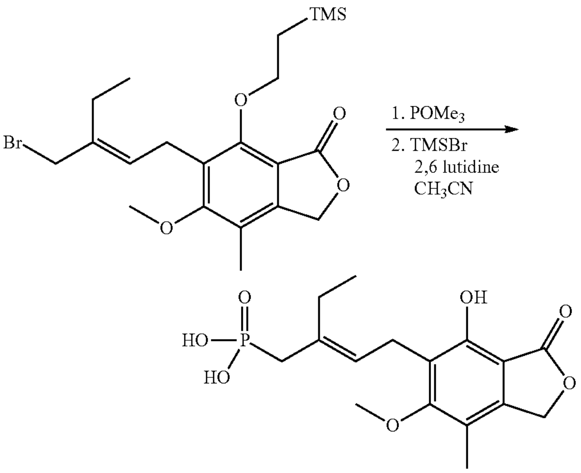

[2-Ethyl-4-(4-hydroxy-6-methoxy-7-methyl-3-oxo-1,3-dihydro-isobenzofuran-5-yl)-but-2-enyl]-phosphonic acid A solution of 6-(3-bromomethyl-pent-2-enyl)-5-methoxy-4-methyl-7-(2-trimethylsilanyl-ethoxy)-3H-isobenzofuran-1-one (230 mg, 0.5 mmol) in trimethylphosphite (1.5 mL, 12.75 mmol) was heated to 100° C. for 4 hours. The reaction was worked up by removal of excess trimethylphosphite under reduced pressure. The residue was dissolved in acetonitrile (1 mL) and TMSBr (646 μL, 5.0 mmol) and 2,6-lutidine (580 μL, 5.0 mmol) were added at 0° C. The reaction solution was allowed to warm to room temperature and stirred for 4 hours. The reaction was cooled to 0° C. and quenched with addition of MeOH. The reaction mixture was dried under reduced pressure and the residue was purified by RP HPLC using a C18 column with a gradient of $H_2O$, 0.1% TFA-acetonitrile, 0.1% TFA to provide 77 mg (58%) of the product. $^1$H NMR (300 MHz, $CD_3OD$) 1.08 (t, 3H), 2.16 (s, 3H), 2.43 (m, 2H), 2.48 (d, 2H, J=22 Hz), 3.46 (t, 2H, J=6 Hz), 3.79 (s, 3H), 5.25 (s, 2H), 5.38 (q, 1H, J=7 Hz) ppm.; $^{31}$P (121.4 MHz, $CD_3OD$) δ 25.65 ppm.; MS (m/z) 355 $[M-H]^-$, 357 $[M+H]^+$.

Example 179

Preparation of Representative Compounds of Formula 81

Representative compounds of the invention can be prepared as illustrated below.

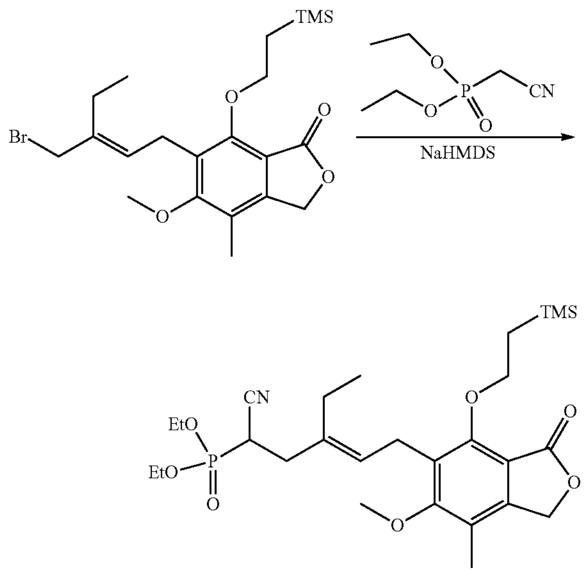

{1-Cyano-3-ethyl-5-[6-methoxy-7-methyl-3-oxo-4-(2-trimethylsilanyl-ethoxy)-1,3-dihydro-isobenzofuran-5-yl]-pent-3-enyl}-phosphonic acid diethyl ester To a solution of diethyl cyanomethylphosphonate (233 mg, 1.32 mmol) in THF (1 mL) was added a THF solution of sodium bis(trimethysilyl)amide (1.0 M, 1.21 mL, 1.21 mmol). After stirring for 30 minutes, the solution was added dropwise to a solution of 6-(3-bromomethyl-pent-2-enyl)-5-methoxy-4-methyl-7-(2-trimethylsilanyl-ethoxy)-3H-isobenzofuran-1-one (100 mg, 0.22 mmol) in THF (1 mL). The resulting mixture was allowed to stir at room temperature overnight before saturated aqueous ammonium chloride was added. The reaction mixture was extracted with ethyl acetate. The organic layer was dried over sodium sulfate and concentrated to dryness. The residue was purified by preparative reverse-phase HPLC, affording 51 mg (42%) of the desired product. $^1$H NMR (300 MHz, $CDCl_3$) δ 0.04 (s, 9H), 1.07 (t, 3H), 1.24 (dd, 2H, J=7, 8 Hz), 1.36 (t, 6H), 2.12 (m, 1H), 2.18 (s, 3H), 2.35-2.47 (m, 2H), 2.67 (m, 1H), 3.00-3.14 (m, 1H), 3.44 (d, J=7.2, 2H), 3.79 (s, 3H), 4.12-4.37 (m, 6H), 5.13 (s, 2H), 5.38 (t, J=7.2 Hz, 1H) ppm; $^{31}$P (121.4 MHz, $CDCl_3$) δ 18.26 ppm; MS (m/z) 574 $[M+Na]^+$.

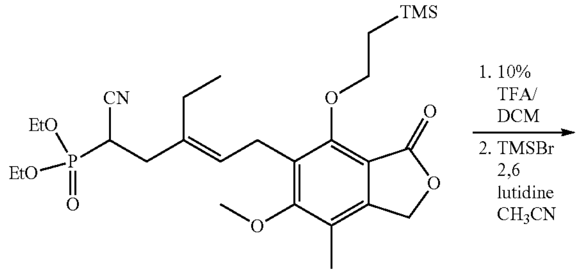

-continued

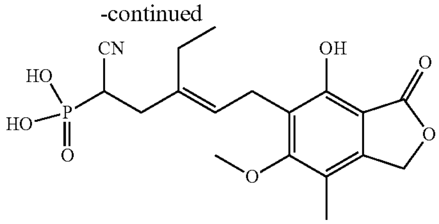

[1-Cyano-3-ethyl-5-(4-hydroxy-6-methoxy-7-methyl-3-oxo-1,3-dihydro-isobenzofuran-5-yl)-pent-3-enyl]-phosphonic acid {1-Cyano-3-ethyl-5-[6-methoxy-7-methyl-3-oxo-4-(2-trimethylsilanyl-ethoxy)-1,3-dihydro-isobenzofuran-5-yl]-pent-3-enyl}-phosphonic acid diethyl ester (19.5 mg, 0.035 mmol) was dissolved in a solution of 10% TFA/$CH_2Cl_2$ (2 mL) and stirred at room temperature for 10 minutes. The reaction mixture was dried under reduced pressure and purified by RP-HPLC to provide 9.5 mg (61%) of the desired product. This material was dissolved in DMF (0.5 mL) and DCM (0.5 mL) and TMSBr (27 μL, 0.2 mmol) and 2,6-lutidine (23 μL, 0.2 mmol) were added. The reaction solution was allowed stir at room temperature overnight before quenching with MeOH. The reaction mixture was dried under reduced pressure and the residue was purified by RP HPLC using a C18 column with a gradient of $H_2O$, 0.1% TFA-acetonitrile, 0.1% TFA to provide 5.1 mg (65%) of the desired product as a white solid. $^1$H NMR (300 MHz, $CD_3OD$) δ 1.10 (t, 3H), 2.16 (s, 3H), 2.23-2.52 (m, 3H), 2.67 (m, 1H), 3.05-3.20 (m, 1H), 3.48 (d, J=7.2, 2H), 3.81 (s, 3H), 5.26 (s, 2H), 5.43 (t, J=7.2 Hz, 1H) ppm; $^{31}$P (121.4 MHz, $CD_3OD$) δ 14.18 ppm; MS (m/z) 394 $[M-H]^-$, 396 $[M+H]^+$.

Example 180

Preparation of Representative Compounds of Formula 81

Representative compounds of the invention can be prepared as illustrated below.

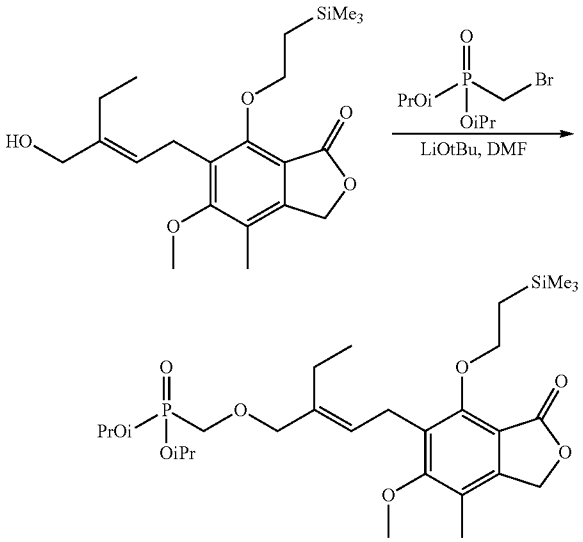

{2-Ethyl-4-[6-methoxy-7-methyl-3-oxo-4-(2-trimethylsilanyl-ethoxy)-1,3-dihydro-isobenzofuran-5-yl]-but-2-enyloxymethyl}-phosphonic acid diisopropyl ester To a solution of bromomethylphosphonate diisopropyl ester (680 mg, 2.62 mmol) and 6-(3-hydroxymethyl-pent-2-enyl)-5-methoxy-4-methyl-7-(2-trimethylsilanyl-ethoxy)-3H-isobenzofuran-1-one (688 mg, 1.75 mmol) in DMF (3 mL) was added lithium t-butoxide (1.0M in THF; 2.6 mL). The reaction was heated at 70° C. for 2 hours. After cooling to ambient temperature, more bromomethylphosphonate diisopropyl ester (680 mg, 2.62 mmol) and lithium t-butoxide (1.0M in THF; 2.6 mL) were added. The reaction mixture was heated at 70° C. for a further hour, cooled, poured into a solution of lithium chloride (5% aqueous) and extracted with ethyl acetate. The organic extract was dried and the product was purified by chromatography on silica gel, eluting with hexane-ethyl acetate to provide 347 mg (35%) of the product as a colorless oil. $^{1}$H NMR (300 MHz, $CDCl_3$) δ 0.04 (s, 9H), 1.09 (t, 3H, J=7.5 Hz), 1.20-1.26 (m, 2H), 1.31 (t, 12H, J=6 Hz), 2.18 (s, 3H), 2.29 (q, 2H, J=7.5 Hz), 3.5 (m, 2H), 3.59 (d, 2H, J=8.7 Hz), 3.78 (s, 3H), 3.98 (s, 2H), 4.28-4.35 (m, 2H), 4.6-4.8 (m, 2H), 5.13 (s, 2H), 5.4 (t, 1H, J=7 Hz) ppm; $^{31}$P (121.4 MHz, $CDCl_3$) δ 20.26 ppm; MS (m/z) 593.3 $[M+Na]^+$.

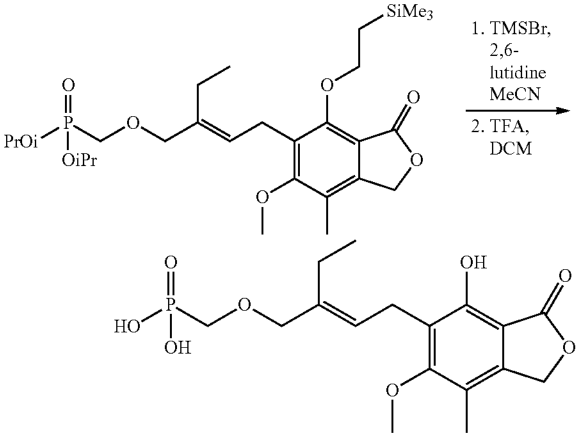

[2-Ethyl-4-(4-hydroxy-6-methoxy-7-methyl-3-oxo-1,3-dihydro-isobenzofuran-5-yl)-but-2-enyloxymethyl]-phosphonic acid To a solution of {2-ethyl-4-[6-methoxy-7-methyl-3-oxo-4-(2-trimethylsilanyl-ethoxy)-1,3-dihydro-isobenzofuran-5-yl]-but-2-enyloxymethyl}-phosphonic acid diisopropyl ester (347 mg, 0.61 mmol) in acetonitrile (5 mL) was added 2,6-lutidine (0.71 mL, 6.1 mmol) and bromotrimethylsilane (0.786 mL, 6.1 mmol). The mixture was stirred at room temperature for 3 hours, quenched with methanol (5 mL), concentrated, and partitioned between ethyl acetate and 1N HCl (aqueous). The organic layer was concentrated to give the free phosphonic acid as a colorless oil (205 mg, 70%). This material (20 mg) was dissolved in a solution of trifluoroacetic acid (0.3 mL) and dichloromethane (2.7 mL) and stirred for 30 minutes at ambient temperature. After concentration, the residue was purified by RP HPLC using a C18 column with a gradient of $H_2O$, 0.1% TFA-acetonitrile, 0.1% TFA to provide the product, after lyophilization, as a white solid (10 mg). $^{1}$H NMR (300 MHz, $CDCl_3$) δ 1.007 (t, 3H, J=7.5 Hz), 2.13 (s, 3H), 2.32 (q, 2H, J=7.5 Hz), 3.41 (d, 2H, J=6.3 Hz), 3.56 (d, 2H, J=9 Hz), 3.75 (s, 3H), 3.95 (s, 2H), 5.16 (s, 2H), 5.43 (t, 1H, J=6.3 Hz) ppm; $^{31}$P (121.4 MHz, $CDCl_3$) δ 22.8 ppm; MS (m/z) 385.2 $[M-H]^+$, 387.1 $[M+H]^+$.

Example 181

Preparation of Representative Compounds of Formula 81

Representative compounds of the invention can be prepared as illustrated below.

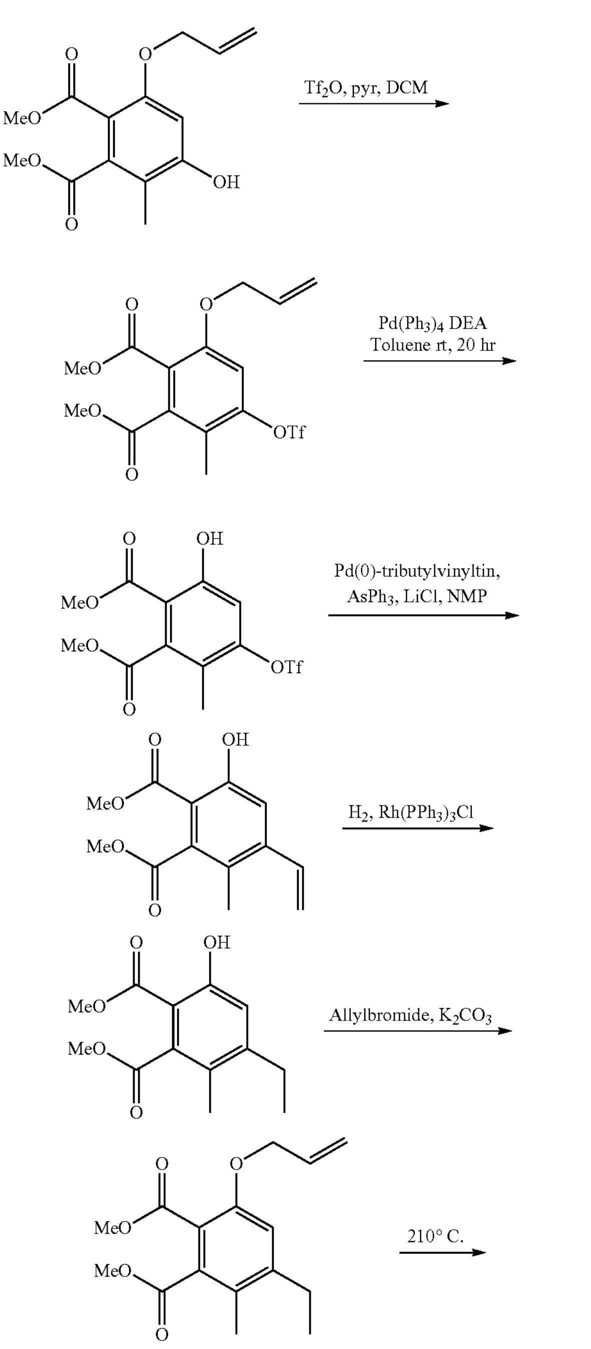

-continued

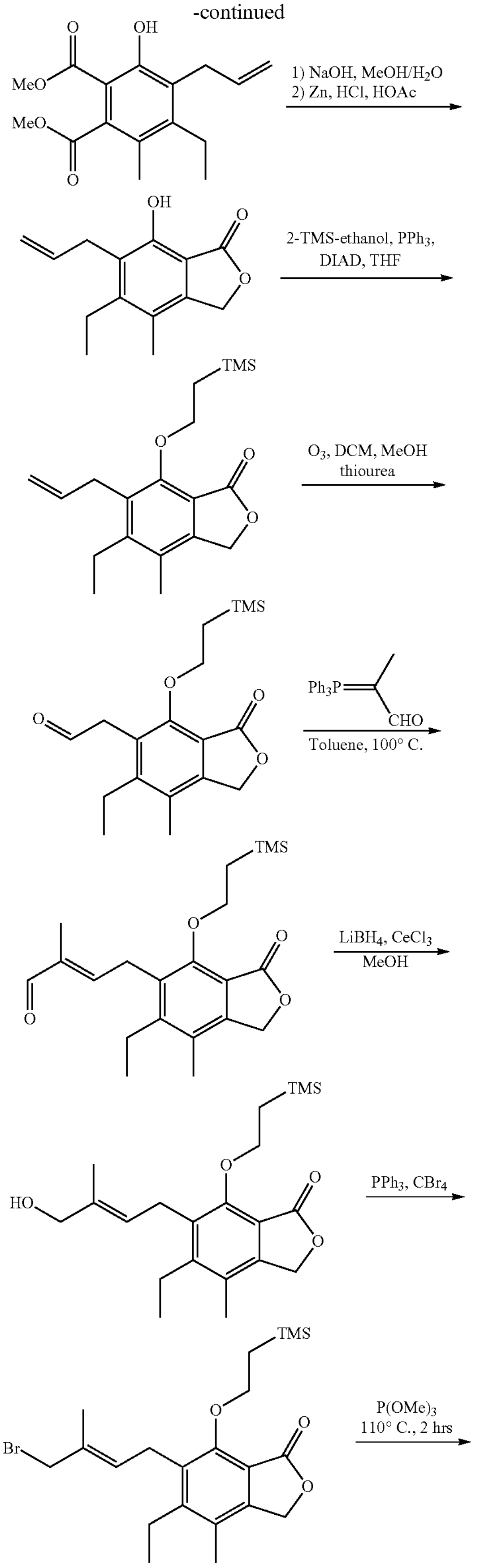

-continued

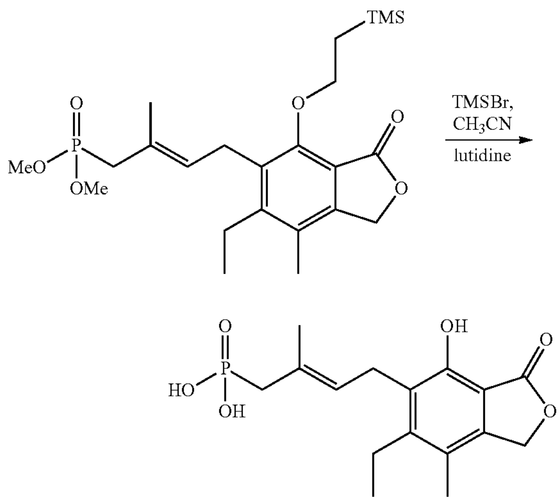

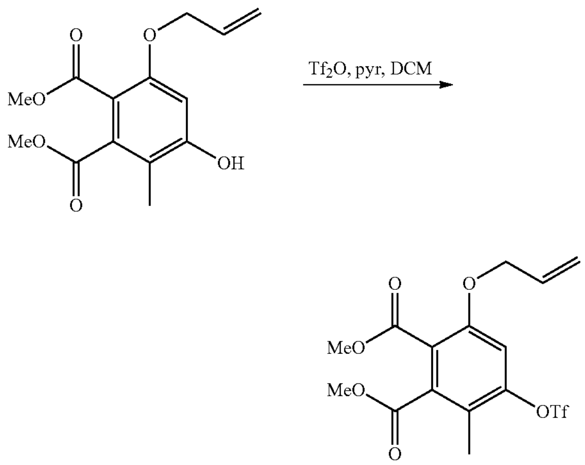

6-Allyloxy-3-methyl-4-trifluoromethanesulfonyloxy-phthalic acid dimethyl ester

To a solution of 6-allyloxy-4-hydroxy-3-methyl-phthalic acid dimethyl ester (8.06 g, 28.8 mmol) [synthesized according to: J. W. Patterson, *Tetrahedron,* 1993, 49, 4789-4798] and pyridine (11.4 g, 144.0 mmol) in dichloromethane (DCM) (20 mL) at 0° C. was added triflic anhydride (12.19 g, 43.2 mmol). The reaction was stirred at 0° C. for 2 hrs after which additional triflic anhydride (3 mL) was added. Stirring at 0° C. was continued for an additional hour. The reaction mixture was poured into a mixture of DCM and HCl (1N). The layers were separated and the aqueous layer was extracted with DCM. The combined organic layers were dried over sodium sulfate. Filtration and evaporation of solvents in vacuo yielded a crude product, which was purified by silica gel chromatography to provide 8.39 g of the product as an oil. $^{1}H$ NMR (300 MHz, $CDCl_3$): δ=2.32 (s, 3H), 3.89 (s, 6H), 4.60 (m, 2H), 5.33 (d, J=9.3 Hz, 1H), 5.41 (d, J=18.6 Hz, 1H), 5.95 (m, 1H), 6.95 (s, 1H) ppm; $^{19}F$ NMR (282 MHz, $CDCl_3$): δ=−74 ppm.

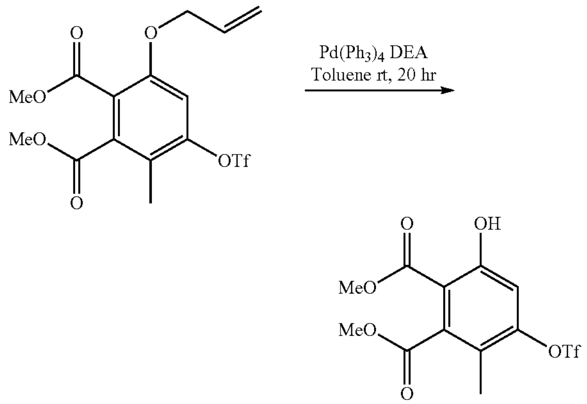

6-Hydroxy-3-methyl-4-trifluoromethanesulfonyloxy-phthalic acid dimethyl ester

To a solution of 6-allyloxy-3-methyl-4-trifluoromethane-sulfonyloxy-phthalic acid dimethyl ester (8.39 g, 20.3 mmol) in toluene (20 mL) was added tetrakistriphenylphosphine palladium (0.47 g, 0.40 mmol) and diethylamine (2.97 g, 40.86 mmol) at room temperature under an atmosphere of nitrogen. Stirring at room temperature was continued until all starting material was consumed. The crude reaction mixture was partitioned between diethyl ether and HCl (0.1 N). The organic layer was washed with brine and dried over sodium sulfate. Filtration and evaporation of solvents in vacuo yielded a crude material, which was purified by silica gel chromatography to provide 4.16 g (55%) of the desired product as an off-white solid. NMR (300 MHz, $CDCl_3$): δ=2.20 (s, 3H), 3.93 (s, 3H), 3.95 (s, 3H), 7.01 (s, 1H) ppm; $^{19}F$ NMR (282 MHz, $CDCl_3$): δ=−74 ppm.

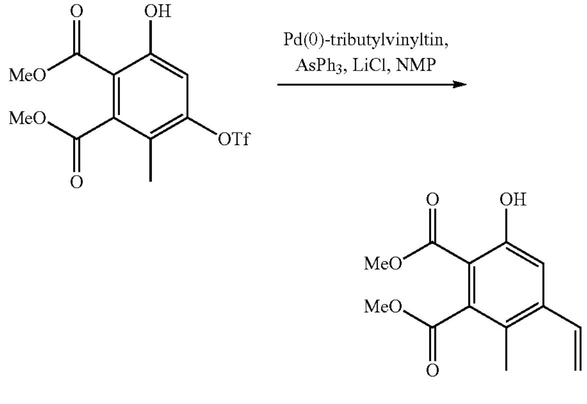

6-Hydroxy-3-methyl-4-vinyl-phthalic acid dimethyl ester

To a solution of 6-hydroxy-3-methyl-4-trifluoromethane-sulfonyloxy-phthalic acid dimethyl ester (2.17 g, 5.85 mmol) in N-methyl pyrolidinone (15 mL) was added lithium chloride (743 mg, 17.5 mmol) and triphenylarsine (179 mg, 0.585 mmol). Tributylvinyltin (2.04 g, 6.43 mmol) was added followed by tris(tribenzylideneacetone)dipalladium(0)-chloroform adduct (90 mg, 0.087 mmol). The reaction was placed under an atmosphere of nitrogen and heated at 60° C. for 18 hrs. The reaction was cooled to room temperature and poured onto a mixture of ice (20 g), EtOAc (40 mL), and potassium fluoride (1 g). Stirring was continued for 1 hr. The aqueous layer was extracted with EtOAc and the organic extracts filtered through Celite. The combined organic layers were washed with water and dried over sodium sulfate. Filtration and evaporation of solvents in vacuo yielded a crude material, which was purified by silica gel chromatography to provide 1.27 g (87%) of the product as an off-white solid. $^1H$ NMR (300 MHz, $CDCl_3$): δ=2.16 (s, 3H), 3.91 (s, 3H), 3.92 (s, 3H), 5.46 (dd, J=11.1, 1.2 Hz, 1H), 5.72 (dd, J=17.1, 0.9 Hz, 1H), 6.86 (dd, J=17.1, 11.1 Hz, 1H), 7.14 (s, 1H), 10.79 (s, 1H) ppm.

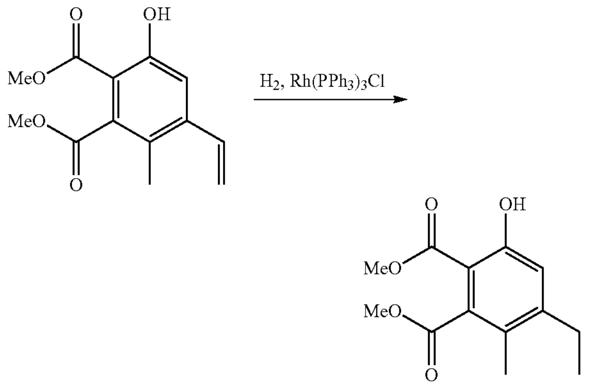

4-Ethyl-6-hydroxy-3-methyl-phthalic acid dimethyl ester

6-Hydroxy-3-methyl-4-vinyl-phthalic acid dimethyl ester (1.27 g, 5.11 mmol) was dissolved in benzene (10 mL) and EtOAc (10 mL). Tristriphenylphosphine rhodium chloride (150 mg) was added and the reaction was placed under an atmosphere of hydrogen. Stirring at room temperature was continued. After 14 hrs, the solvents were removed in vacuo and the crude material was purified by silica gel chromatography to provide 1.14 g (88%) of the desired product as an off-white solid. $^1H$ NMR (300 MHz, $CDCl_3$): δ=1.19 (t, J=7.8 Hz, 3H), 2.10 (s, 3H), 2.60 (q, J=7.8 Hz, 2H), 3.89 (s, 6H), 6.87 (s, 1H), 10.79 (s, 1H) ppm.

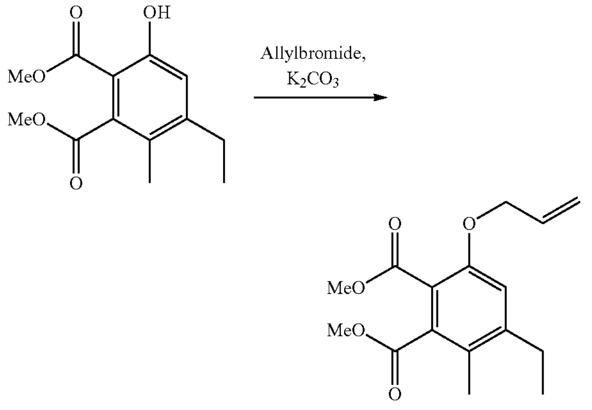

6-Allyloxy-4-ethyl-3-methyl-phthalic acid dimethyl ester

4-Ethyl-6-hydroxy-3-methyl-phthalic acid dimethyl ester (1.01 g, 4.02 mmol) was dissolved in DMF (5 mL). Potassium carbonate (3.33 g, 24.14 mmol) was added, followed by allylbromide (2.92 g, 24.14 mmol). The suspension was heated at 60° C. After 14 hrs, the reaction was cooled to room temperature and filtered. The solvents were removed in vacuo and the crude material was purified by silica gel chromatography to provide 0.976 g (83%) of the desired product as a colorless oil. $^1$H NMR (300 MHz, $CDCl_3$): δ=1.16 (t, J=7.2 Hz, 3H), 2.20 (s, 3H), 2.62 (q, J=7.2 Hz, 2H), 3.83 (s, 3H), 3.84 (s, 3H), 4.57 (m, 2H), 5.26 (dd, J=9.3, 1.5 Hz, 1H), 5.41 (dd, J=13.5, 1.5 Hz, 1H), 5.98 (m, 1H), 6.82 (s, 1H) ppm.

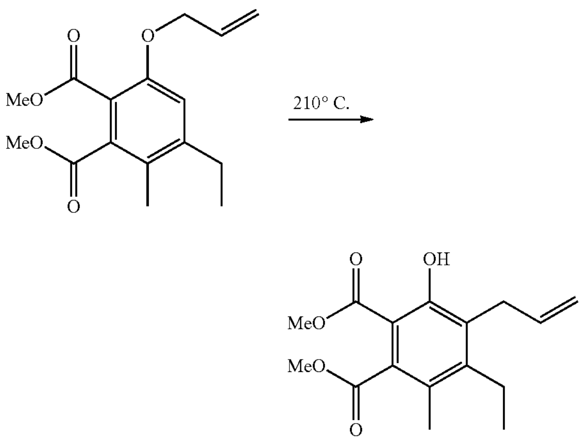

4-Allyl-5-ethyl-3-hydroxy-6-methyl-phthalic acid dimethyl ester

6-Allyloxy-4-ethyl-3-methyl-phthalic acid dimethyl ester (1.25 g, 4.28 mmol) was heated at 210° C. under an atmosphere of nitrogen. After 14 hrs, the reaction was cooled to room temperature. The crude material was purified by silica gel chromatography to provide 0.971 g (77%) of the desired product as a colorless oil. $^1$H NMR (300 MHz, $CDCl_3$): δ=1.14 (t, J=7.8 Hz, 3H), 2.17 (s, 3H), 2.68 (q, J=7.8 Hz, 2H), 3.49 (m, 2H), 3.86 (s, 3H), 3.89 (s, 3H), 4.89-5.01 (m, 2H), 5.93 (m, 1H), 11.22 (s, 1H) ppm.

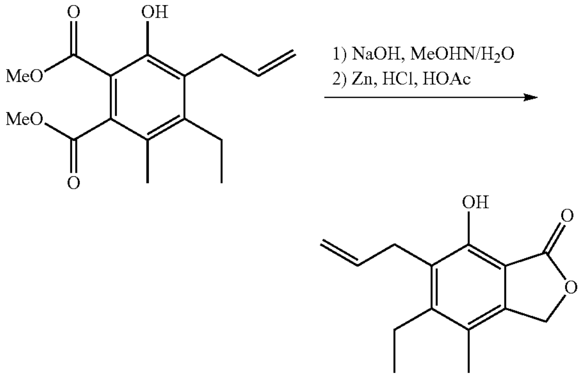

6-Allyl-5-ethyl-7-hydroxy-4-methyl-3H-isobenzofuran-1-one

4-Allyl-5-ethyl-3-hydroxy-6-methyl-phthalic acid dimethyl ester (0.971 g, 3.32 mmol) was dissolved in MeOH (8 mL) at room temperature. A solution of sodium hydroxide (0.798 g, 19.95 mmol) in water (10 mL) was added and the suspension was heated at 55° C. After 16 hrs, the reaction was cooled to room temperature and washed with diethyl ether. The aqueous layer was acidified (1N HCl) and the suspension was extracted with EtOAc. The combined organic layers were dried over sodium sulfate. Filtration and evaporation of solvents in vacuo yielded the desired bis acid as a white solid (0.846 g, 98%, $M^+$=263). The bis acid was dissolved in acetic acid (6 mL) and HCl (conc., 1.5 mL). The reaction was heated at 80° C. Zn dust (0.635 g, 9.72 mmol, each) was added in portions every hour for 7 hours. Stirring at 80° C. was continued for additional 10 hours. The reaction was cooled to room temperature and water was added. The resultant suspension was extracted with EtOAc. The combined organic extracts were washed with sodium bicarbonate solution and dried over sodium sulfate. Filtration and evaporation of solvents in vacuo yielded the crude product, which was purified by silica gel chromatography to provide 0.375 g (50%) of the product as a white solid. $^1$H NMR (300 MHz, $CDCl_3$): δ=1.14 (t, J=7.5 Hz, 3H), 2.18 (s, 3H), 2.71 (q, J=7.5 Hz, 2H), 3.49 (m, 2H), 4.95 (d, J=17.1 Hz, 1H), 5.02 (d, J=10.2 Hz, 1H), 5.23 (s, 2H), 5.98 (m, 1H), 7.66 (s, 1H) ppm.

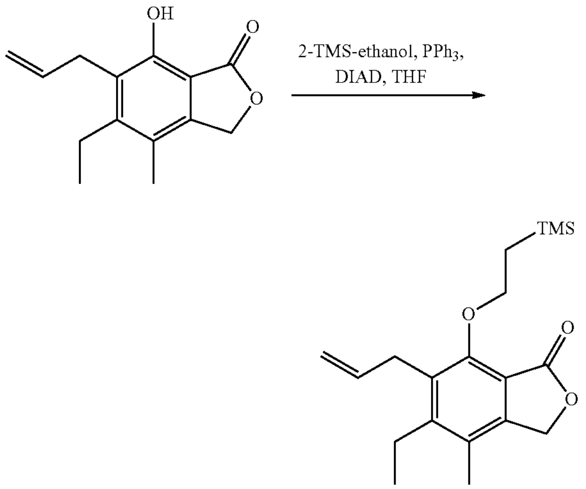

6-Allyl-5-ethyl-4-methyl-7-(2-trimethylsilanyl-ethoxy)-3H-isobenzofuran-1-one

To a solution of 6-allyl-5-ethyl-7-hydroxy-4-methyl-3H-isobenzofuran-1-one (199 mg, 0.857 mmol), $PPh_3$ (337 mg, 1.286 mmol), and 2-trimethylsilylethanol in THF (3 mL) at 0° C. was added diisopropyl azodicarboxylate (259 mg, 1.286 mmol). The resulting yellow solution was allowed to warm to room temperature and stirred for one hour. The solvent was removed in vacuo and the crude material was dissolved in diethyl ether (3 mL). Hexanes (1.5 mL) were added. Triphenylphosphine oxide was removed by filtration and the filtrate was concentrated and purified by silica gel chromatography to provide the desired product (261 mg, 92%) as a clear oil. $^1$H NMR (300 MHz, $CDCl_3$): δ=0.04 (s, 9H), 1.15 (t, J=7.8 Hz, 3H), 1.25 (m, 2H), 2.20 (s, 3H), 2.73 (q, J=7.8 Hz, 2H), 3.54 (m, 2H), 4.28 (m, 2H), 4.95 (d, J=17.1 Hz, 1H), 5.02 (d, J=10.2 Hz, 1H), 5.15 (s, 2H), 5.95 (m, 1H) ppm.

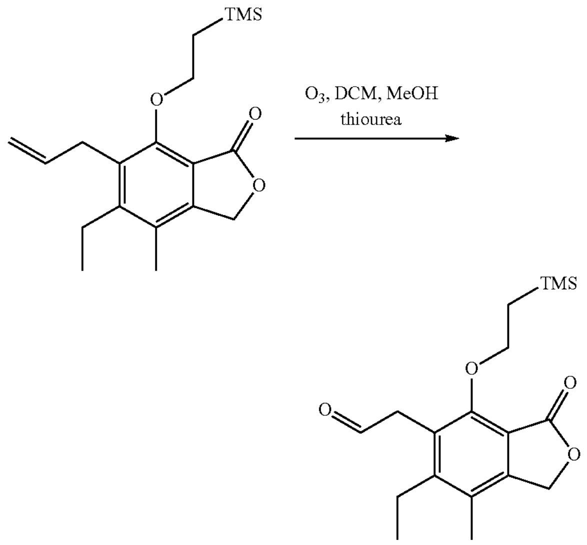

[6-Ethyl-7-methyl-3-oxo-4-(2-trimethylsilanyl-ethoxy)-1,3-dihydro-isobenzofuran-5-yl]-acetaldehyde A solution of 6-allyl-5-ethyl-4-methyl-7-(2-trimethylsilanyl-ethoxy)-3H-isobenzofuran-1-one (261 mg, 0.788 mmol) in MeOH (5 mL), $CH_2Cl_2$ (5 mL) and pyridine (50 μL) was cooled to −78° C. using a dry ice/acetone bath according to the procedure of Smith, D. B. et al., *J. Org. Chem.*, 1996, 61, 6, 2236. A stream of ozone was bubbled through the reaction via a gas dispersion tube until the reaction became blue in color (15 minutes). The ozone line was replaced with a stream of nitrogen and bubbling continued for another 15 minutes, by which time the blue color had disappeared. To this solution at −78° C. was added thiourea (59.9 mg, 0.788 mmol) in one portion, and the cooling bath was removed. The reaction was allowed to warm to room temperature and stirred for 15 hours. The reaction mixture was filtered and then partitioned between $CH_2Cl_2$ and water. The aqueous layer was extracted with $CH_2Cl_2$ one more time and the organic extracts were combined, washed with aqueous 1N HCl, saturated $NaHCO_3$ and brine and dried over sodium sulfate. Filtration and evaporation of solvents in vacuo yielded the crude product, which was purified by silica gel chromatography to afford 181 mg (69%) of the product as a white solid. $^1H$ NMR (300 MHz, $CDCl_3$): δ=0.04 (s, 9H), 1.11 (t, J=7.5 Hz, 3H), 1.19 (m, 2H), 2.21 (s, 3H), 2.66 (q, J=7.5 Hz, 2H), 3.90 (s, 2H), 4.36 (m, 2H), 5.18 (s, 2H), 9.71 (s, 1H) ppm.

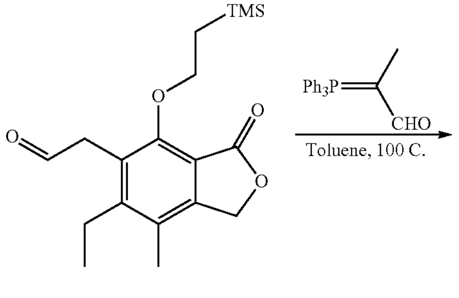

-continued

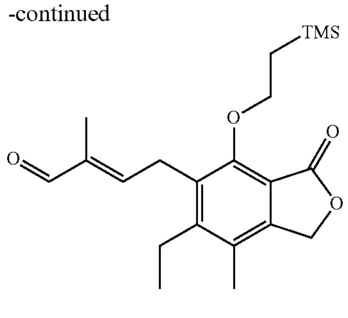

4-[6-Ethyl-7-methyl-3-oxo-4-(2-trimethylsilanyl-ethoxy)-1,3-dihydro-isobenzofuran-5-yl]-2-methyl-but-2-enal

[6-Ethyl-7-methyl-3-oxo-4-(2-trimethylsilanyl-ethoxy)-1,3-dihydro-isobenzofuran-5-yl]-acetaldehyde (90 mg, 0.269 mmol) and 2-(triphenyl-phosphorylidene)-propionaldehyde (72.9 mg, 0.23 mmol) in toluene (3 mL) were heated at 100° C. After 15 hours, a second portion of 2-(triphenyl-phosphanylidene)-propionaldehyde (33 mg, 0.11 mmol) was added and the reaction mixture was heated for additional 9 hours. The toluene was removed in vacuo, and the residue was purified by silica gel chromatography to provide 77.6 mg (77%) of the desired product as a pale yellow oil. $^1H$ NMR (300 MHz, $CDCl_3$): δ=0.03 (s, 9H), 1.15 (t, J=7.5 Hz, 3H), 1.21 (m, 2H), 1.93 (s, 3H), 2.21 (s, 3H), 2.71 (q, J=7.5 Hz, 2H), 3.82 (d, J=6.9 Hz, 2H), 4.34 (m, 2H), 5.18 (s, 2H), 6.38 (m, 1H), 9.35 (s, 1H) ppm.

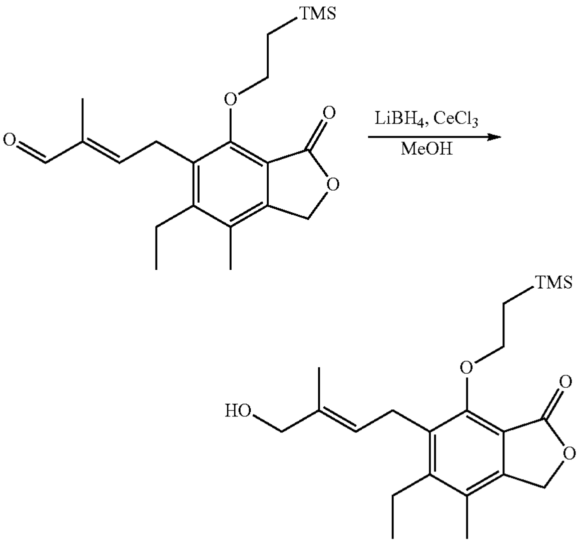

5-Ethyl-6-(4-hydroxy-3-methyl-but-2-enyl)-4-methyl-7-(2-trimethylsilanyl-ethoxy)-3H-isobenzofuran-1-one 4-[6-Ethyl-7-methyl-3-oxo-4-(2-trimethylsilanyl-ethoxy)-1,3-dihydro-isobenzofuran-5-yl]-2-methyl-but-2-enal (77.6 mg, 0.207 mmol) was dissolved in MeOH (4 mL). A solution of $CeCl_3$ (51.1 mg, 0.207 mmol) in MeOH/water (9/1, 0.66 mL) was added and the solution was cooled to 0° C. A solution of lithium borohydride in THF (2M, 0.105 mL) was added dropwise. After 15 minutes, the reaction was quenched with 1N HCl (0.5 mL). The MeOH was removed in vacuo and the crude material was partitioned between DCM and water. The aqueous layer was extracted with DCM and the combined organic layers were washed with sodium bicarbonate solution and dried over sodium sulfate. Filtration and evaporation of solvents yielded a crude oil, which was purified by silica gel chromatography to provide 57.2 mg (73%) of the desired product. $^1$H NMR (300 MHz, $CDCl_3$): δ=0.04 (s, 9H), 1.15 (t, J=7.8 Hz, 3H), 1.26 (m, 2H), 1.86 (s, 3H), 2.19 (s, 3H), 2.72 (q, J=7.8 Hz, 2H), 3.52 (d, J=6.3 Hz, 2H), 3.99 (s, 2H), 4.34 (m, 2H), 5.14 (s, 2H), 5.32 (m, 1H) ppm.

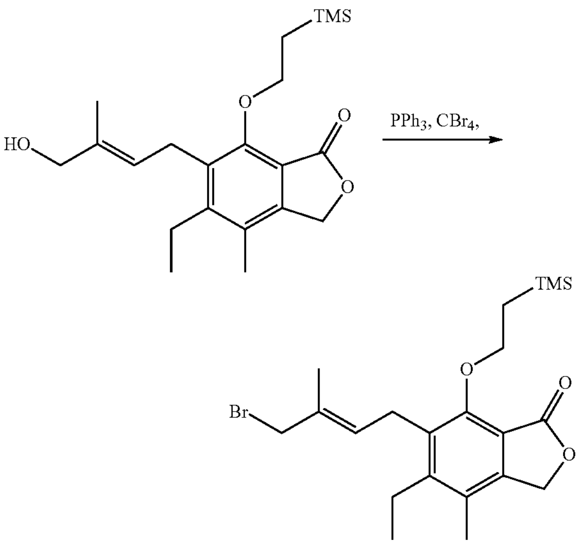

6-(4-Bromo-3-methyl-but-2-enyl)-5-ethyl-4-methyl-7-(2-trimethylsilanyl-ethoxy)-3H-isobenzofuran-1-one 5-Ethyl-6-(4-hydroxy-3-methyl-but-2-enyl)-4-methyl-7-(2-trimethylsilanyl-ethoxy)-3H-isobenzofuran-1-one (57.2 mg, 0.152 mmol) was dissolved in DCM (3.5 mL). Polymer-bound triphenylphosphine (3 mmol/g, 152.1 mg) was added and the mixture was mechanically stirred at room temperature. Carbon tetrabromide (151.3 mg, 0.456 mmol) was added and the solution was stirred at room temperature. After 2 hrs, the reaction was filtered and the solvent was removed in vacuo. The crude material was purified by silica gel chromatography to provide 58.0 mg (87%) of the desired product. $^1$H NMR (300 MHz, $CDCl_3$): δ=0.04 (s, 9H), 1.15 (t, J=7.8 Hz, 3H), 1.25 (m, 2H), 1.95 (s, 3H), 2.20 (s, 3H), 2.70 (q, J=7.8 Hz, 2H), 3.52 (d, J=6.3 Hz, 2H), 3.94 (s, 2H), 4.28 (m, 2H), 5.14 (s, 2H), 5.50 (m, 1H) ppm.

-continued

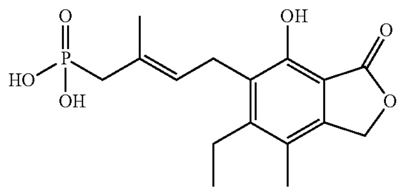

{4-[6-Ethyl-7-methyl-3-oxo-4-hydroxy-1,3-dihydro-isobenzofuran-5-yl]-2-methyl-but-2-enyl}-phosphonic acid A solution of 4-[6'-ethyl-7'-methyl-3'-oxo-4'-(2"-trimethylsilanyl-ethoxy)-1',3'-dihydro-isobenzofuran-5'-yl]-2-methyl-but-2-enyl bromide (58 mg, 0.132 mmol) in trimethylphosphite (0.8 mL) was heated at 110° C. After 2 hrs the reaction was complete. The reaction was cooled to room temperature and the excess trimethylphosphite was removed in vacuo. The crude material was used in the next step without further purification. The crude product of the Arbuzov reaction was dissolved in MeCN (0.8 mL). Trimethylsilyl bromide (202.2 mg, 1.321 mmol) was added and the reaction was stirred at room temperature. After 15 minutes, lutidine (155.7 mg, 1.453 mmol) was added and stirring at room temperature was continued. After 2 hrs additional trimethylsilyl bromide (202.2 mg, 1.321 mmol) was added and stirring at room temperature was continued. After 4 hrs the reaction was quenched with MeOH (2 mL). The solvents were evaporated in vacuo and the crude material was purified by RP-HPLC (eluent: water/MeCN). The product-containing fractions were combined and lyophilized to yield 2.3 mg (5.1%) of the free phosphonic acid. $^1$H NMR (300 MHz, DMSO-d6): δ=1.07 (t, J=7.5 Hz, 3H), 1.84 (s, 3H), 2.14 (s, 3H), 2.64 (q, J=7.5 Hz, 2H), 3.34 (m, 4H), 5.06 (m, 1H), 5.25 (s, 2H) ppm; $^{31}$P NMR (121 MHz, DMSO-d6): δ=22.19 ppm; MS=341 [$M^+$+1].

Example 182

Preparation of Representative Compounds of Formula 81

Representative compounds of the invention can be prepared as illustrated below.

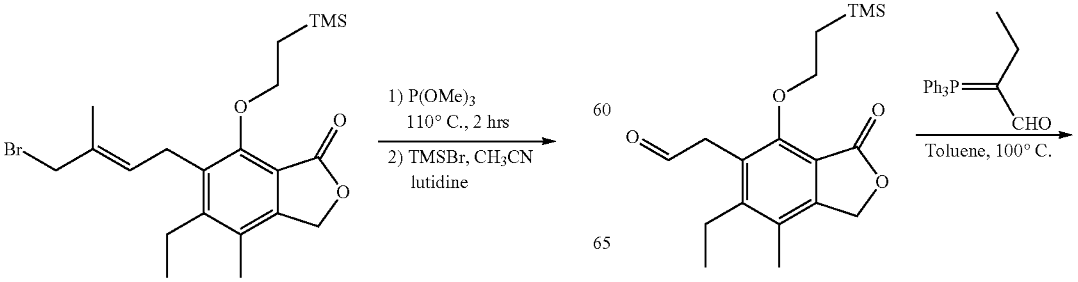

-continued

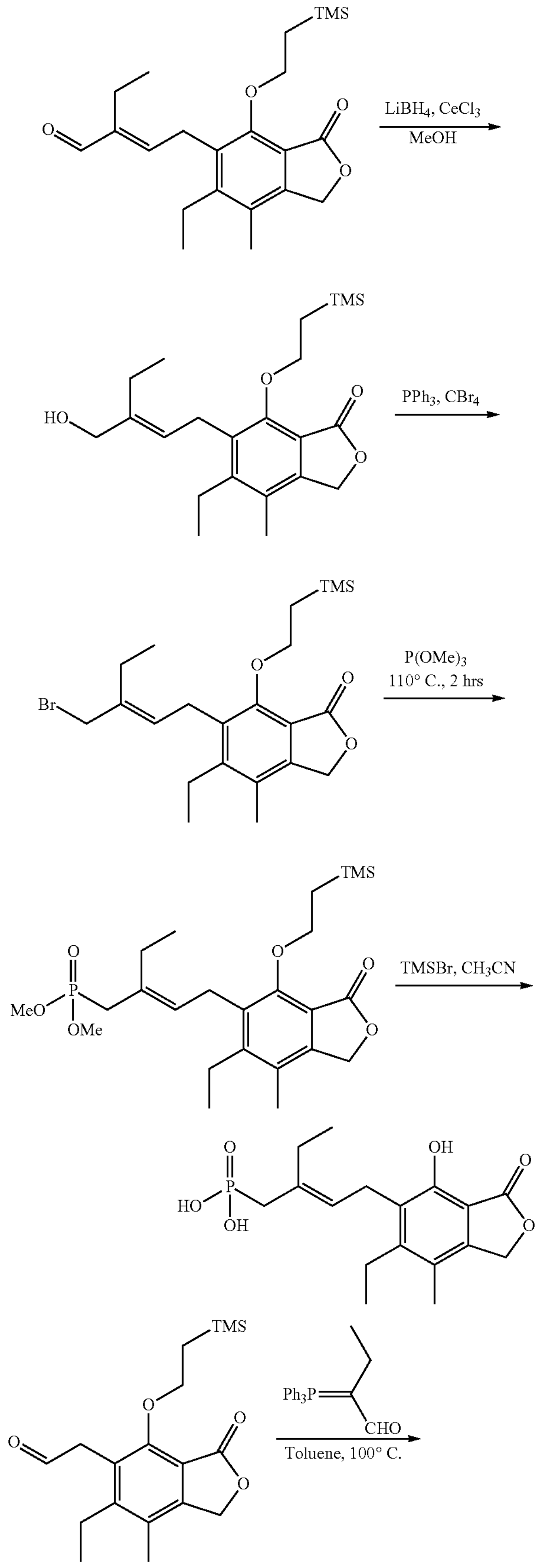

-continued

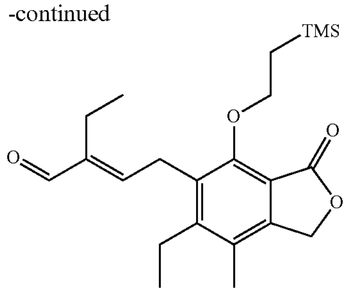

[2-Ethyl-4-[6-ethyl-7-methyl-3-oxo-4-(2-trimethylsilanyl-ethoxy)-1,3-dihydro-isobenzofuran-5-yl]-but-2-enal

[6-Ethyl-7-methyl-3-oxo-4-(2-trimethylsilanyl-ethoxy)-1,3-dihydro-isobenzofuran-5-yl]-acetaldehyde (90 mg, 0.269 mmol) and 2-(triphenyl-phosphorylidene)-butyraldehyde (98.4 mg, 0.296 mmol) in toluene (3 mL) were heated at 100° C. After 15 hours, a second portion of 2-(triphenyl-phosphanylidene)-butyraldehyde (98.4 mg, 0.296 mmol) was added and the reaction mixture was heated for additional 33 hours. After concentration, the residue was purified by silica gel chromatography to provide 50.3 mg (48%) of the desired product as a pale yellow oil.

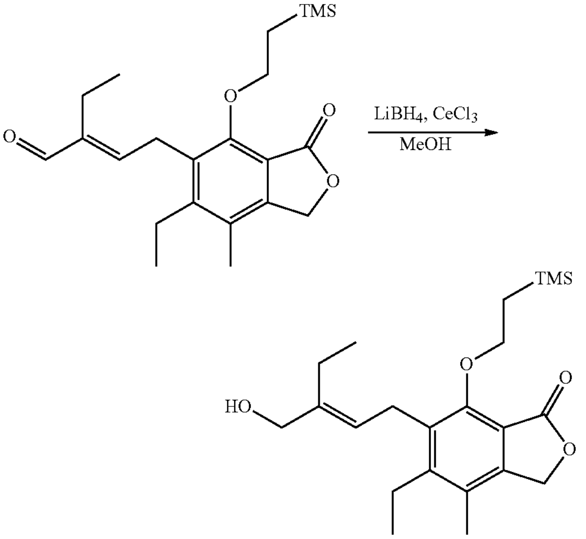

5-Ethyl-6-(3-hydroxymethyl-pent-2-enyl)-4-methyl-7-(2-trimethylsilanyl-ethoxy)-3H-isobenzofuran-1-one 2-Ethyl-4-[6-ethyl-7-methyl-3-oxo-4-(2-trimethylsilanyl-ethoxy)-1,3-dihydro-isobenzofuran-5-yl]-but-2-enal (50.3 mg, 0.129 mmol) was dissolved in MeOH (3 mL). A solution of $CeCl_3$ (31.9 mg, 0.129 mmol) in MeOH/water (9/1, 0.66 mL) was added and the solution was cooled to 0° C. A solution of lithium borohydride in THF (2M, 0.065 mL) was added dropwise. After 10 minutes, the reaction was quenched with 1N HCl (0.5 mL). The methanol was removed in vacuo and the crude material was partitioned between DCM and water. The aqueous layer was extracted with DCM and the combined organic layers were washed with sodium bicarbonate solution and were dried over sodium sulfate. Filtration and evaporation of solvents in vacuo yielded a crude oil, which was purified by silica gel chromatography to provide 35.4 mg (70%) of the desired product. $^1$H NMR (300 MHz, $CDCl_3$): δ=0.04 (s, 9H), 1.10-1.19 (m, 6H), 1.26 (m, 2H), 2.19 (s, 3H), 2.32 (q, J=7.5 Hz, 2H), 2.72 (q, J=7.5 Hz, 2H), 3.54 (d, J=6.6 Hz, 2H), 4.05 (s, 2H), 4.26 (m, 2H), 5.14 (s, 2H), 5.27 (m, 1H) ppm.

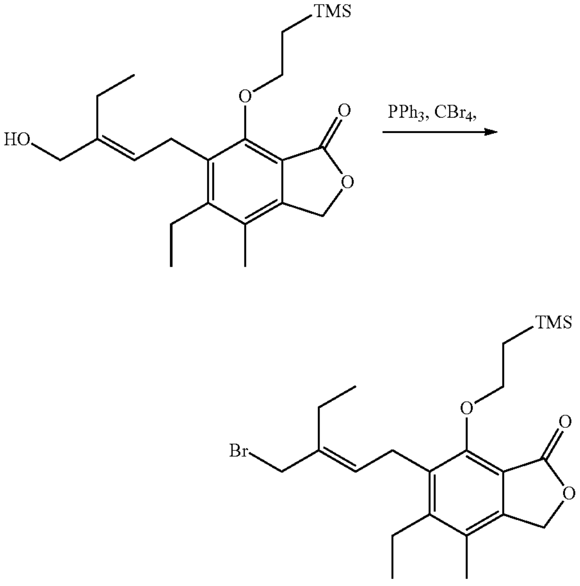

6-(3-Bromomethyl-pent-2-enyl)-5-ethyl-4-methyl-7-(2-trimethylsilanyl-ethoxy)-3H-isobenzofuran-1-one 5-Ethyl-6-(3-hydroxymethyl-pent-2-enyl)-4-methyl-7-(2-trimethylsilanyl-ethoxy)-3H-isobenzofuran-1-one (35.4 mg, 0.090 mmol) was dissolved in DCM (3.0 mL). Polymer-bound triphenylphosphine (3 mmol/g, 90.7 mg) was added and the mixture was mechanically stirred at room temperature. Carbon tetrabromide (90.2 mg, 0.272 mmol) was added and the solution was stirred at room temperature. After 2 hrs, the reaction was filtered and the solvent was removed in vacuo. The crude material was purified by silica gel chromatography to provide 32.0 mg (78%) of the desired product. The material was used in the next step without further characterization.

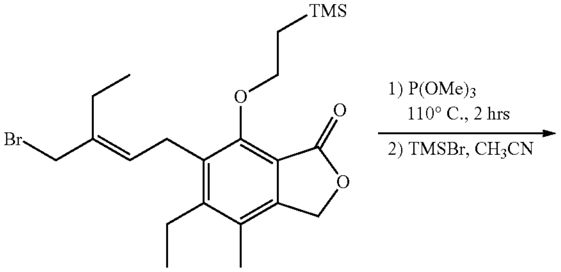

-continued

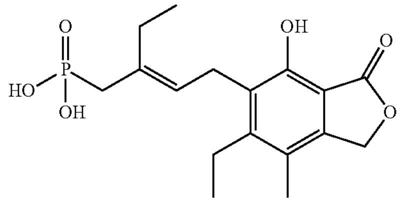

[2-Ethyl-4-(6-ethyl-4-hydroxy-7-methyl-3-oxo-1,3-dihydro-isobenzofuran-5-yl)-but-2-enyl]-phosphonic acid A solution of 6-(3-bromomethyl-pent-2-enyl)-5-ethyl-4-methyl-7-(2-trimethylsilanyl-ethoxy)-3H-isobenzofuran-1-one (32 mg, 0.070 mmol) in trimethylphosphite (0.8 mL) was heated at 110° C. After 2 hrs the reaction was complete. The reaction was cooled to room temperature and the excess trimethylphosphite was removed in vacuo. The crude material was used in the next step without further purification. The crude product of the Arbuzov reaction was dissolved in MeCN (0.8 mL). Trimethylsilyl bromide (108.0 mg, 0.706 mmol) was added and the reaction was stirred at room temperature. After 2 hrs a second batch of trimethysilyl bromide (108.0 mg, 0.706 mmol) was added. After 3 hrs the reaction was quenched with MeOH (2 mL). The solvents were evaporated in vacuo and the crude material was purified by RP-HPLC (eluent: water/MeCN). The product-containing fractions were combined and lyophilized to yield 15.7 mg (63%) of the product. $^1$H NMR (300 MHz, DMSO-d6): δ=0.98-1.09 (m, 6H), 2.10 (s, 3H), 2.30 (m, 2H), 2.64 (q, J=7.5 Hz, 2H), 3.38 (m, 4H), 5.03 (m, 1H), 5.25 (s, 2H) ppm; $^{31}$P NMR (121 MHz, DMSO-d6): δ=22.26 ppm; MS=355 [$M^+$+1].

Example 183

Preparation of Representative Compounds of Formula 81

Representative compounds of the invention can be prepared as illustrated below.

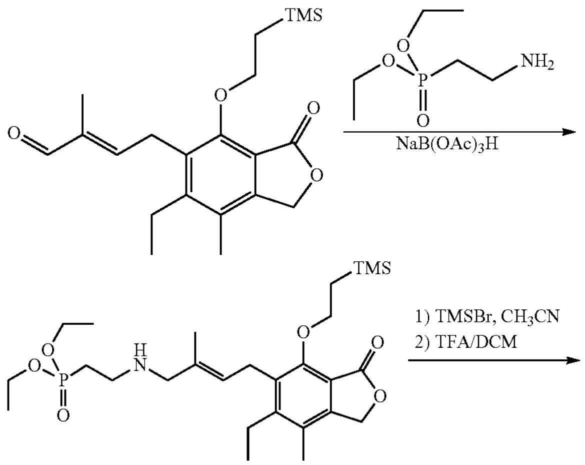

-continued

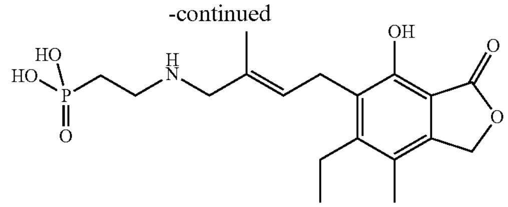

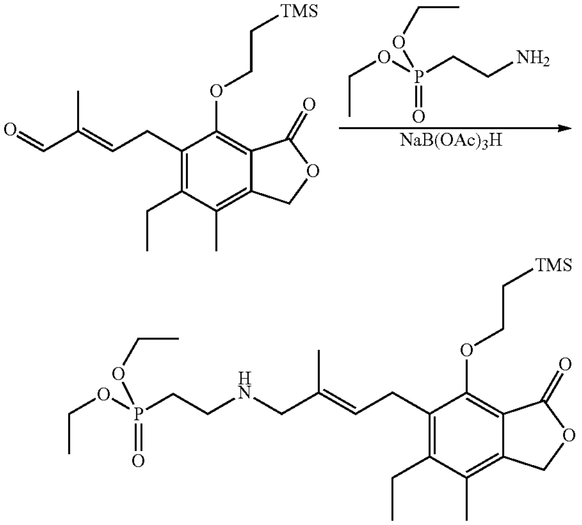

(2-{4-[6-Ethyl-7-methyl-3-oxo-4-(2-trimethylsilanyl-ethoxy)-1,3-dihydro-isobenzofuran-5-yl]-2-methyl-but-2-enylamino}-ethyl)-phosphonic acid diethyl ester 4-[6-Ethyl-7-methyl-3-oxo-4-(2-trimethylsilanyl-ethoxy)-1,3-dihydro-isobenzofuran-5-yl]-2-methyl-but-2-enal (19.7 mg, 0.052 mmol) and aminoethylphosphonic acid diethylester oxalate salt (15.6 mg, 0.057 mmol) were dissolved in DMF (0.5 mL). Acetic acid (15.7 mg, 0.263 mmol) was added, followed by sodium triacetoxyborohydride (22.3 mg, 0.105 mmol). After 4 hrs, the crude reaction mixture was purified by RP-HPLC (eluent: water/MeCN) to provide 27.7 mg (97%) of the desired product after lyophilization. $^1$H NMR (300 MHz, $CDCl_3$): δ=0.04 (s, 9H), 1.14 (t, J=7.5 Hz, 3H), 1.26 (m, 2H), 1.30 (t, J=7.2 Hz, 6H), 1.95 (s, 3H), 2.19 (s, 3H), 2.23 (m, 2H), 2.68 (q, J=7.5 Hz, 2H), 3.18 (m, 2H), 3.53 (s, 2H), 4.13 (m, 4H), 4.28 (m, 2H), 5.15 (s, 2H), 5.51 (m, 1H) ppm; $^{31}$P NMR (121 MHz, $CDCl_3$): δ=27.39 ppm; MS=540 [$M^+$+1].

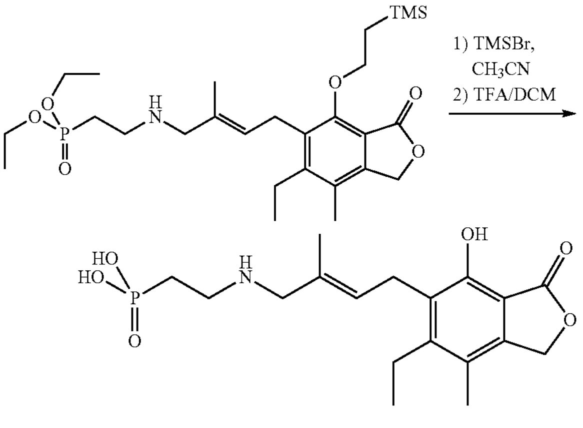

{2-[4-(6-Ethyl-4-hydroxy-7-methyl-3-oxo-1,3-dihydro-isobenzofuran-5-yl)-2-methyl-but-2-enylamino]-ethyl}-phosphonic acid (2-{4-[6-Ethyl-7-methyl-3-oxo-4-(2-trimethylsilanyl-ethoxy)-1,3-dihydro-isobenzofuran-5-yl]-2-methyl-but-2-enylamino}-ethyl)-phosphonic acid diethyl ester (27.7 mg, 0.051 mmol) was dissolved in DMF (0.5 mL) and DCM (0.5 mL). Trimethylsilyl bromide (78.3 mg, 0.512 mmol) was added and the reaction was stirred at room temperature. After 20 hrs the reaction was quenched with MeOH (0.3 mL). The solvents were evaporated in vacuo and the crude material was purified by RP-HPLC (eluent: water/MeCN). The product-containing fractions were combined and lyophilized to yield 14.2 mg (57%) of the free phosphonic acid [MS: 484 $M^+$+1].

The material was dissolved in DCM (0.5 mL). TFA (0.05 mL) was added and stirring at room temperature was continued. After 20 minutes, the solvents were removed in vacuo and the crude material was purified by RP-HPLC (eluent: water/MeCN*0.1% TFA). The product-containing fractions were combined and lyophilized to yield 7.6 mg (52%) of the product as the TFA salt. $^1$H NMR (300 MHz, DMSO-d6): δ=1.07 (t, J=7.5 Hz, 3H), 1.84 (s, 3H), 1.90 (m, 2H), 2.11 (s, 3H), 2.63 (q, J=7.5 Hz, 2H), 2.99 (m, 2H), 3.43 (d, J=6.3 Hz, 2H), 3.51 (s, 2H), 5.26 (s, 2H), 5.45 (m, 1H) ppm; $^{31}$P NMR (121 MHz, DMSO-d6): δ=20.02 ppm; MS=384 [$M^+$+1].

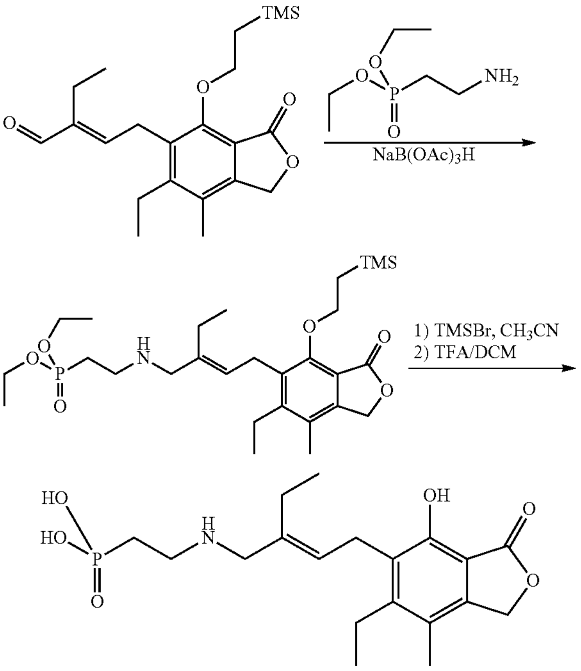

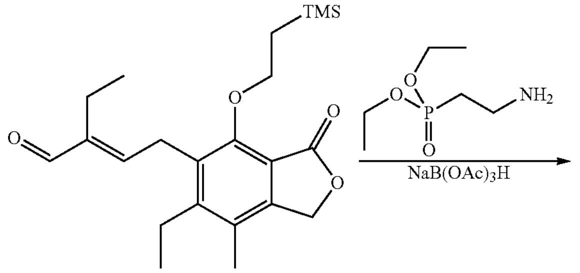

-continued

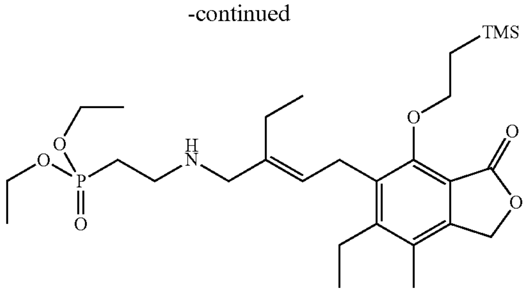

(2-{2-Ethyl-4-[6-ethyl-7-methyl-3-oxo-4-(2-trimethylsilanyl-ethoxy)-1,3-dihydro-isobenzofuran-5-yl]-but-2-enylamino}-ethyl)-phosphonic acid diethyl ester 2-Ethyl-4-[6-ethyl-7-methyl-3-oxo-4-(2-trimethylsilanyl-ethoxy)-1,3-dihydro-isobenzofuran-5-yl]-but-2-enal (26.6 mg, 0.068 mmol) and aminoethylphosphonic acid diethylester oxalate salt (20.4 mg, 0.075 mmol) were dissolved in DMF (0.8 mL). Acetic acid (20.5 mg, 0.342 mmol) was added, followed by sodium triacetoxyborohydride (27.6 mg, 0.137 mmol). After 8 hrs, the crude reaction mixture was purified by RP-HPLC (eluent: water/MeCN) to provide 24.9 mg (65%) of the desired product after lyophilization. $^{1}H$ NMR (300 MHz, $CDCl_3$): δ=0.05 (s, 9H), 1.10-1.24 (m, 8H), 1.35 (t, J=7.5 Hz, 6H), 2.19 (s, 3H), 2.23 (m, 2H), 2.35 (q, J=7.8 Hz, 2H), 2.70 (q, J=7.2 Hz, 2H), 3.25 (m, 2H), 3.56 (m, 4H), 4.15 (m, 4H), 4.29 (m, 2H), 5.15 (s, 2H), 5.47 (m, 1H) ppm; $^{31}P$ NMR (121 MHz, $CDCl_3$): δ=27.71 ppm; MS=554 $[M^{+}+1]$.

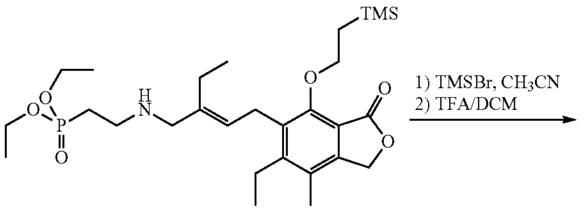

-continued

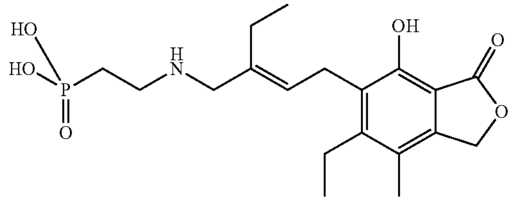

{2-[2-Ethyl-4-(6-ethyl-4-hydroxy-7-methyl-3-oxo-1,3-dihydro-isobenzofuran-5-yl)-but-2-enylamino]-ethyl}-phosphonic acid (2-{2-Ethyl-4-[6-ethyl-7-methyl-3-oxo-4-(2-trimethylsilanyl-ethoxy)-1,3-dihydro-isobenzofuran-5-yl]-but-2-enylamino}-ethyl)-phosphonic acid diethyl ester (24.9 mg, 0.045 mmol) was dissolved in DMF (0.5 mL) and DCM (0.5 mL). Trimethylsilyl bromide (68.7 mg, 0.449 mmol) was added and the reaction was stirred at room temperature. After 20 hrs the reaction was quenched with MeOH (0.15 mL). The solvents were evaporated in vacuo and the crude material was purified by RP-HPLC (eluent: water/MeCN). The product-containing fractions were combined and lyophilized to yield 8.0 mg of the free phosphonic acid [MS: 498 $M^{+}+1$].

This material was dissolved in DCM (0.5 mL). TFA (0.05 mL) was added, and stirring at room temperature was continued. After 20 minutes, the solvents were removed in vacuo and the crude material was purified by RP-HPLC (eluent: water/MeCN*0.1% TFA). The product-containing fractions were combined and lyophilized to yield 4.4 mg (54%) of the product as the TFA salt. $^{1}H$ NMR (300 MHz, DMSO-d6): δ=1.05 (m, 6H), 1.60 (m, 2H), 2.10 (s, 3H), 2.67 (q, J=7.5 Hz, 2H), 2.63 (q, J=6.9 Hz, 2H), 2.93 (m, 2H), 3.45 (m, 4H), 5.24 (s, 2H), 5.36 (m, 1H) ppm.; $^{31}P$ NMR (121 MHz, DMSO-d6): δ=16.93 ppm; MS=398 $[M^{+}+1]$.

Example 184

Preparation of Representative Compounds of 84

Representative compounds of the invention can be prepared as illustrated below.

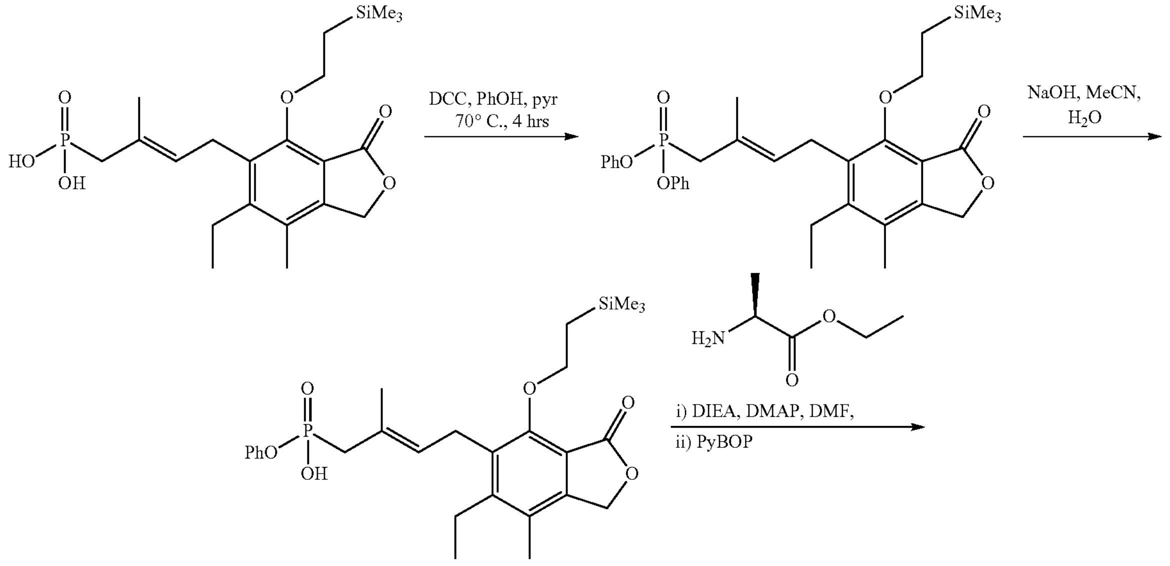

-continued

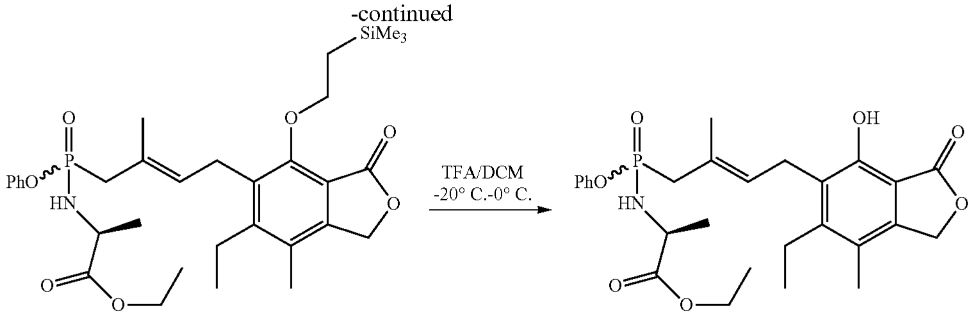

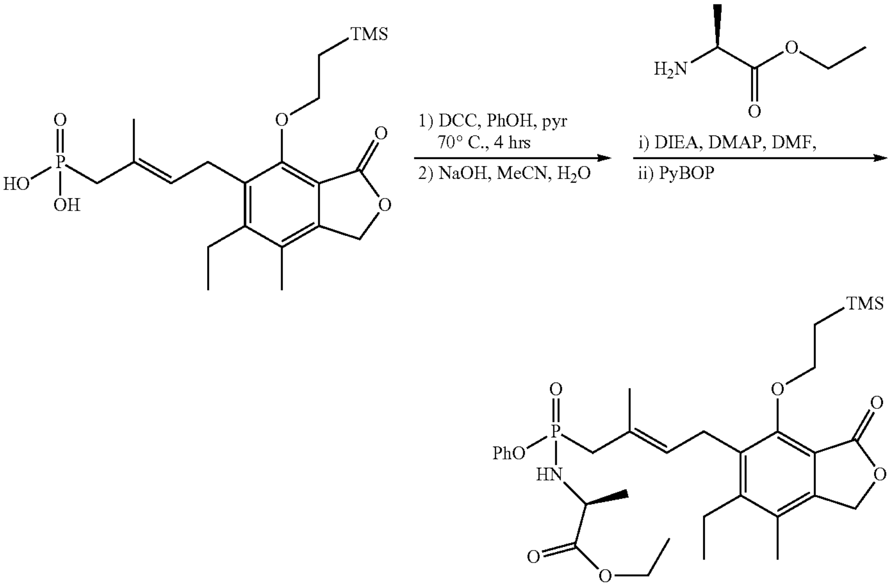

2-({4-[6-Ethyl-7-methyl-3-oxo-4-(2-trimethylsilanyl-ethoxy)-1,3-dihydro-isobenzofuran-5-yl]-2-methyl-but-2-enyl}-phenoxy-phosphinoylamino)-propionic acid ethyl ester 4-[6'-ethyl-7'-methyl-3'-oxo-4'-(2"-trimethylsilanyl-ethoxy)-1',3'-dihydro-isobenzofuran-5'-yl]-2-methyl-but-2-en-phosphonic acid (44.8 mg, 0.101 mmol), dicyclohexylcarbodiimide (52.6 mg, 0.254 mmol), and phenol (95.8 mg, 1.018 mmol) were dissolved in pyridine (0.3 mL) and heated at 70° C. for 4 hrs. The reaction mixture was cooled to room temperature and the pyridine was removed in vacuo. The crude phosphonic acid diphenyl ester material was partitioned between DCM and HCl (0.1N). The aqueous layer was extracted with DCM and the combined organic layers were dried over sodium sulfate. Filtration and evaporation of solvents in vacuo yielded a crude material, which was used in the next step without further purification.

The crude material was dissolved in MeCN (0.8 mL) and water (0.3 mL). Aqueous sodium hydroxide solution (2N, 0.8 mL) was added in portions (0.2 mL). After all starting material was consumed, the organic solvent was removed in vacuo and the crude material was partitioned between chloroform and aqueous HCl (1N). The aqueous layer was extracted with chloroform. The combined organic layers were dried over sodium sulfate. Filtration and evaporation of solvents yielded the crude product as a mixture of mono phenyl ester and the symmetrical anhydride.

The crude material of the previous step and ethyl (L)-alanine hydrochloride salt (78.1 mg, 0.509 mmol) were dissolved in DMF (0.4 mL). DMAP (1.2 mg, catalytic) was added, followed by diisopropylethylamine (131.3 mg, 1.018 mmol). Stirring at room temperature was continued. After 20 minutes complete conversion of the anhydride was observed. After 2 hrs PyBOP (101 mg, 0.202 mmol) was added and stirring at room temperature was continued. The reaction was filtered and the crude reaction solution was purified by RP-HPLC (eluent: water/MeCN). The product-containing fractions were combined and lyophilized to yield the product (15.7 mg, 25% over three steps) as a white powder. $^{1}H$ NMR (300 MHz, $CDCl_3$): δ=0.03 (s, 9H), 1.13-1.28 (m, 8H), 2.03 (s, 3H), 2.19 (s, 3H), 2.62-2.74 (m, 4H), 3.38 (m, 1H), 3.53 (t, J=6.3 Hz, 2H), 4.03 (m, 3H), 4.30 (m, 2H), 5.14 (s, 2H), 5.31 (m, 1H), 7.11-7.17 (m, 3H), 7.25-7.30 (m, 2H) ppm; $^{31}P$ NMR. (121 MHz, $CDCl_3$): δ=27.04, 27.73 ppm; MS=615 $[M^{+}+1]$.

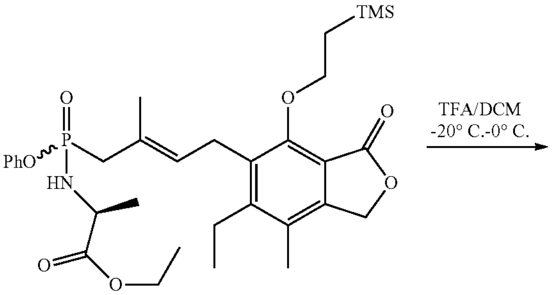

-continued

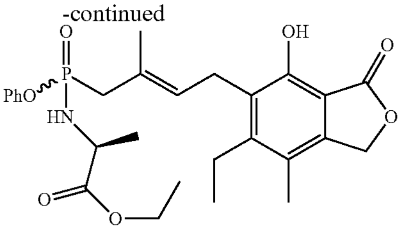

2-{[4-(6-Ethyl-4-hydroxy-7-methyl-3-oxo-1,3-dihydro-isobenzofuran-5-yl)-2-methyl-but-2-enyl]-phenoxy-phosphinoylamino}-propionic acid ethyl ester 2-({4-[6-Ethyl-7-methyl-3-oxo-4-(2-trimethylsilanyl-ethoxy)-1,3-dihydro-isobenzofuran-5-yl]-2-methyl-but-2-enyl}-phenoxy-phosphinoylamino)-propionic acid ethyl ester (7.5 mg, 0.012 mmol) was dissolved in TFA/DCM (10%, 0.3 mL) at −20° C. The reaction mixture was warmed to 0° C. and stirred at this temperature for 45 minutes. Pyridine (0.09 mL) was added the solvents were removed in vacuo. The crude material was purified by RP-HPLC (eluent: water/MeCN). The product-containing fractions were combined and lyophilized, yielding a white powder (5.5 mg, 87%). $^{1}$H NMR (300 MHz, $CDCl_3$): δ=1.12-1.29 (m, 6H), 2.03 (s, 3H), 2.17 (s, 3H), 2.65-2.74 (m, 4H), 3.38 (m, 1H), 3.53 (t, J=6.3 Hz, 2H), 4.03 (m, 3H), 5.22 (s, 2H), 5.36 (m, 1H), 7.11-7.16 (m, 3H), 7.24-7.30 (m, 2H), 7.72 (m, 1H) ppm; $^{31}$P NMR (121 MHz, $CDCl_3$): δ=27.11, 27.57 ppm; MS=515 [$M^{+}$+1].

Example 185

Preparation of Representative Compounds of Formula 81

Representative compounds of the invention can be prepared as illustrated below.

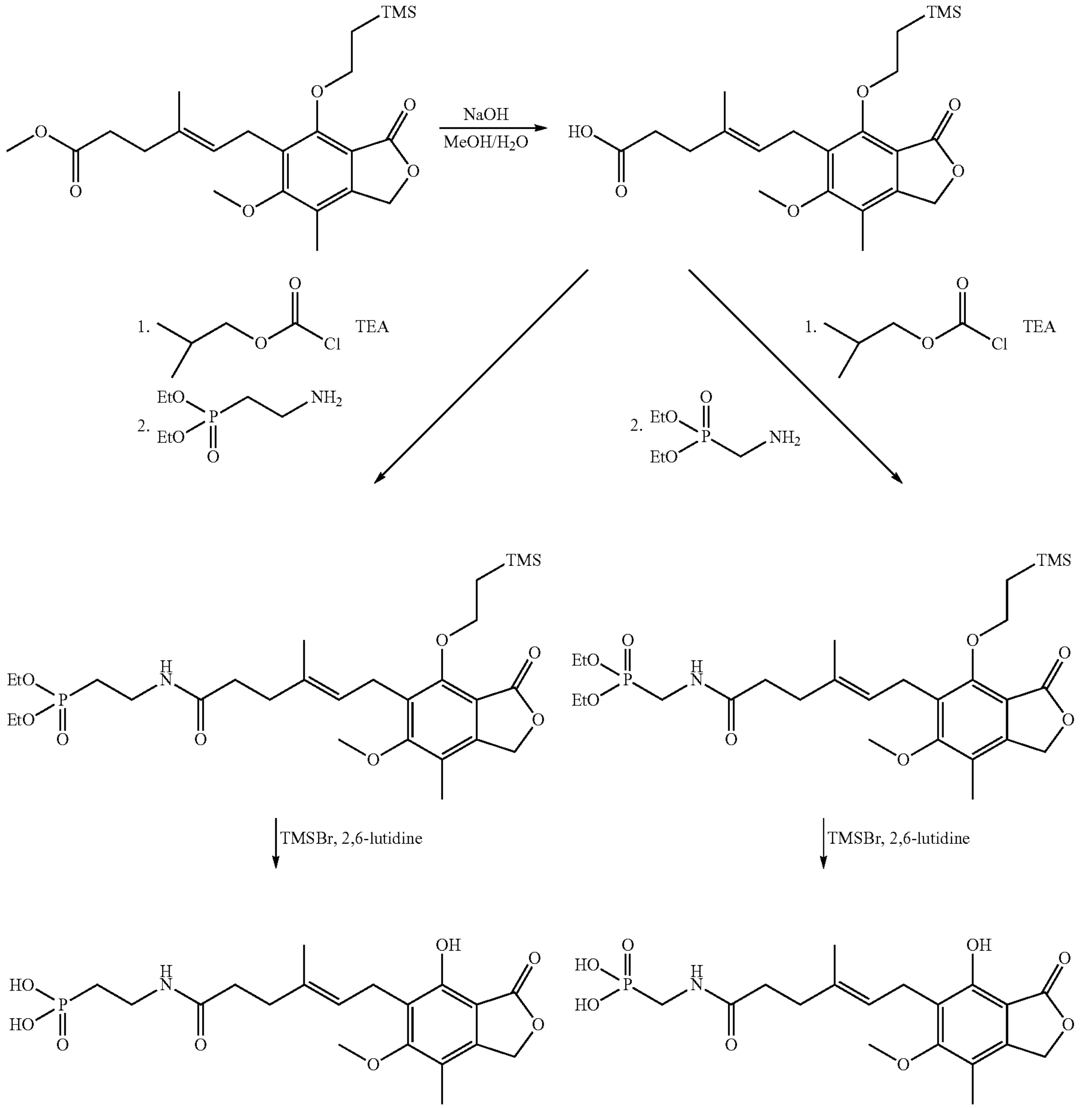

-continued

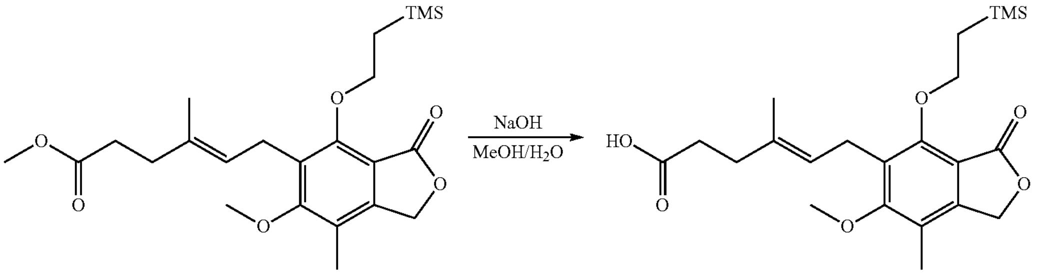

6-[6-Methoxy-7-methyl-3-oxo-4-(2-trimethylsilanyl-ethoxy)-1,3-dihydro-isobenzofuran-5-yl]-4-methyl-hex-4-enoic acid A mixture of 6-[6-methoxy-7-methyl-3-oxo-4-(2-trimethylsilanyl-ethoxy)-1,3-dihydro-isobenzofuran-5-yl]-4-methyl-hex-4-enoic acid methyl ester (1.5 g, 3.45 mmol) and sodium hydroxide (552 mg) in a mixture of methanol (20 mL) and water (7 mL) was stirred at room temperature for one hour. The solution was acidified with 1N HCl. The precipitate was collected by suction filtration and washed with water to give the desired product (1.2 g, 83%). $^1$H NMR (300 MHz, $CDCl_3$) δ 0.02 (s, 9H), 1.15-1.22 (m, 2H), 1.76 (s, 3H), 2.13 (s, 3H), 2.12-2.28 (m, 2H), 2.35-2.41 (m, 2H), 3.37 (d, 2H, J=7 Hz), 3.71 (s, 3H), 4.22-4.28 (m, 2H), 5.07 (s, 2H), 5.13-5.17 (m, 1H) ppm; MS (m/z) 419.3 $[M-H]^-$, 443.2 $[M+Na]^+$.

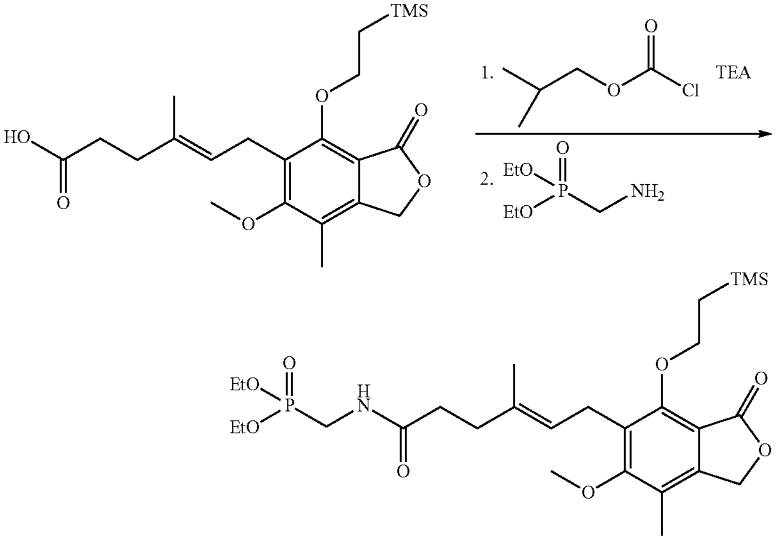

({6-[6-Methoxy-7-methyl-3-oxo-4-(2-trimethylsilanyl-ethoxy)-1,3-dihydro-isobenzofuran-5-yl]-4-methyl-hex-4-enoylamino}-methyl)-phosphonic acid diethyl ester To a solution of 6-[6-methoxy-7-methyl-3-oxo-4-(2-trimethylsilanyl-ethoxy)-1,3-dihydro-isobenzofuran-5-yl]-4-methyl-hex-4-enoic acid (50 mg, 0.12 mmol) in THF (1 mL) was added isobutyl chloroformate (17 μL, 0.13 mmol) and triethylamine (50 μL, 0.36 mmol) at 0° C. After stirring at 0° C. for 2 hours, diethyl (aminomethyl) phosphonate oxalate (62 mg, 0.26 mmol) was added and stirring was continued at room temperature for 20 minutes. After removal of solvent, the residue was purified by preparative reverse-phase HPLC to afford 54.8 mg (81%) of the desired product. $^1$H NMR (300 MHz, $CDCl_3$) δ 0.03 (s, 9H), 1.15-1.22 (m, 2H), 1.31 (t, 6H), 1.81 (s, 3H), 2.18 (s, 3H), 2.30 (m, 4H), 3.41 (d, 2H, J=7 Hz), 3.65 (dd, 2H, J=6, 12 Hz), 3.77 (s, 3H), 3.77-4.16 (m, 4H), 4.26-4.32 (m, 2H), 5.12 (s, 2H), 5.17-5.19 (m, 1H), 5.86 (bs, 1H) ppm; $^{31}$P (121.4 MHz, $CDCl_3$) δ 23.01 ppm; MS (m/z) 568 $[M-H]^-$, 592 $[M+Na]^+$.

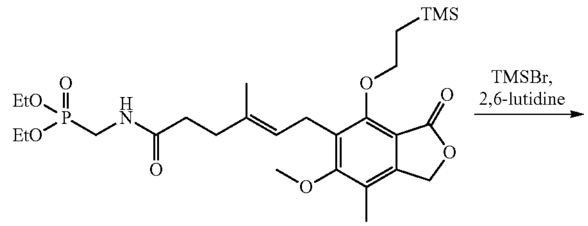

-continued

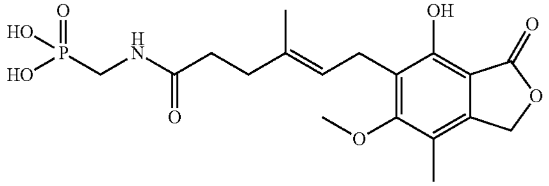

{[6-(4-Hydroxy-6-methoxy-7-methyl-3-oxo-1,3-dihydro-isobenzofuran-5-yl)-4-methyl-hex-4-enoylamino]-methyl}-phosphonic acid To a solution of ({6-[6-methoxy-7-methyl-3-oxo-4-(2-trimethylsilanyl-ethoxy)-1,3-dihydro-isobenzofuran-5-yl]-4-methyl-hex-4-enoylamino}-methyl)-phosphonic acid diethyl ester (40 mg, 0.07 mmol) in acetonitrile (1 mL) was added TMSBr (91 μL, 0.7 mmol) followed by 2,6-lutidine (81.5 μL, 0.7 mmol). The reaction was allowed to proceed overnight when it was completed as judged by LCMS. The reaction mixture was quenched with MeOH and concentrated to dryness. The residue was purified by preparative reverse-phase HPLC to afford 2.6 mg (9%) of desired product as a white solid. $^{1}$H NMR (300 MHz, $CD_3OD$) δ 1.67 (s, 3H), 2.17 (m, 5H), 2.30-2.46 (m, 2H), 2.80-2.86 (m, 2H), 3.55 (m, 2H), 3.82 (s, 3H), 5.26 (s, 3H) ppm; $^{31}$P (121.4 MHz, $CD_3OD$) δ 10.27 ppm; MS (m/z) 412 $[M-H]^-$, 414 $[M+H]^+$.

Example 186

Preparation of Representative Compounds of Formula 81

Representative compounds of the invention can be prepared as illustrated below.

(2-{6-[6-Methoxy-7-methyl-3-oxo-4-(2-trimethylsilanyl-ethoxy)-1,3-dihydro-isobenzofuran-5-yl]-4-methyl-hex-4-enoylamino}-ethyl)-phosphonic acid diethyl ester To a solution of 6-[6-methoxy-7-methyl-3-oxo-4-(2-trimethylsilanyl-ethoxy)-1,3-dihydro-isobenzofuran-5-yl]-4-methyl-hex-4-enoic acid (50 mg, 0.12 mmol) in THF (1 mL) was added isobutyl chloroformate (17 μL, 0.13 mmol) and triethylamine (50 μL, 0.36 mmol) at 0° C. After stirring at 0° C. for 2 hours, diethyl (aminoethyl) phosphonate oxalate (62 mg, 0.26 mmol) was added and stirred at room temperature was continued for one hour. After removal of solvent, the residue was purified by preparative reverse-phase HPLC to afford 37 mg (54%) of the desired product as a white solid. $^{1}$H NMR (300 MHz, $CDCl_3$) δ 0.03 (s, 9H), 1.15-1.22 (m, 2H), 1.31 (t, 6H), 1.81 (s, 3H), 1.85-1.93 (m, 2H), 2.18 (s, 3H), 2.30 (m, 4H), 3.41 (d, 2H, J=7 Hz), 3.48-3.54 (m, 2H), 3.77 (s, 3H), 3.77-4.16 (m, 4H), 4.26-4.32 (m, 2H), 5.12 (s, 2H), 5.17-5.19 (m, 1H), 6.30 (bs, 1H) ppm; $^{31}$P (121.4 MHz, $CDCl_3$) δ 29.91 ppm; MS (m/z) 584 $[M+H]^+$.

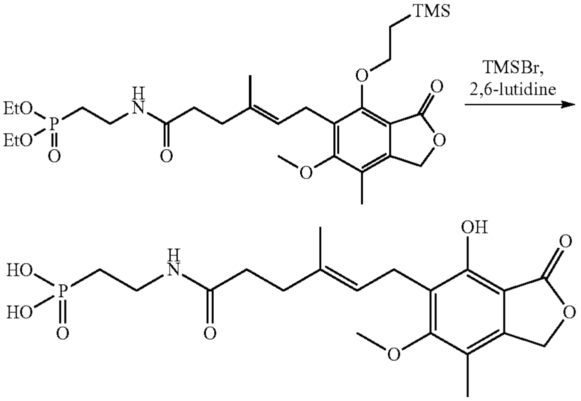

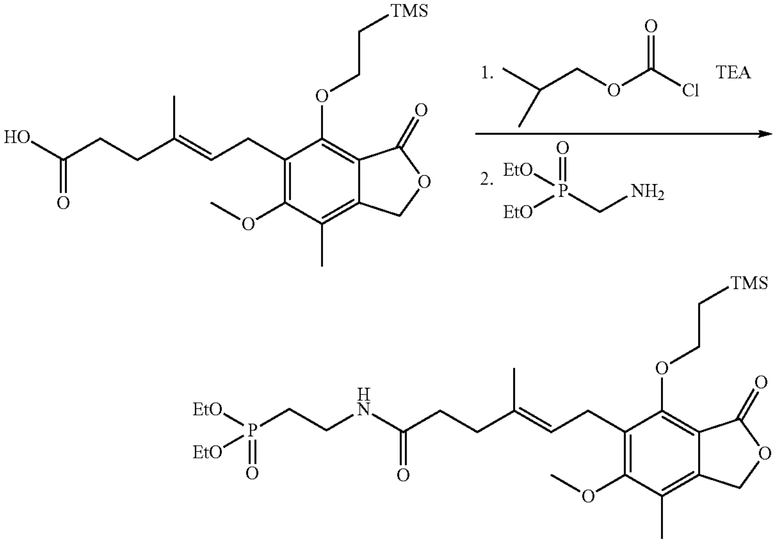

{2-[6-(4-Hydroxy-6-methoxy-7-methyl-3-oxo-1,3-dihydro-isobenzofuran-5-yl)-4-methyl-hex-4-enoylamino]-ethyl}-phosphonic acid To a solution of (2-{6-[6-methoxy-7-methyl-3-oxo-4-(2-trimethylsilanyl-ethoxy)-1,3-dihydro-isobenzofuran-5-yl]-4-methyl-hex-4-enoylamino}-ethyl)-phosphonic acid diethyl ester (36.6 mg, 0.063 mmol) in acetonitrile (1 mL) was added TMSBr (81 μL, 0.63 mmol) followed by 2,6-lutidine (73 μL, 0.63 mmol). The reaction was allowed to proceed overnight when it was completed as judged by LCMS. The reaction mixture was quenched with MeOH and concentrated to dryness. The residue was purified by preparative reverse-phase HPLC to afford 5.8 mg (29%) of desired product as a white solid. $^1$H NMR (300 MHz, $CD_3OD$) δ 1.80 (s, 3H), 2.14 (m, 5H), 2.25 (m, 4H), 3.35 (m, 2H), 3.38-3.38 (m, 2H), 3.75 (s, 3H), 5.23 (s, 3H) ppm; $^{31}$P (121.4 MHz, $CD_3OD$) δ 26.03 ppm; MS (m/z) 426 $[M-H]^-$, 428 $[M+H]^+$.

Example 187

Preparation of Representative Compounds of the Invention

Representative compounds of the invention can be prepared as illustrated below.

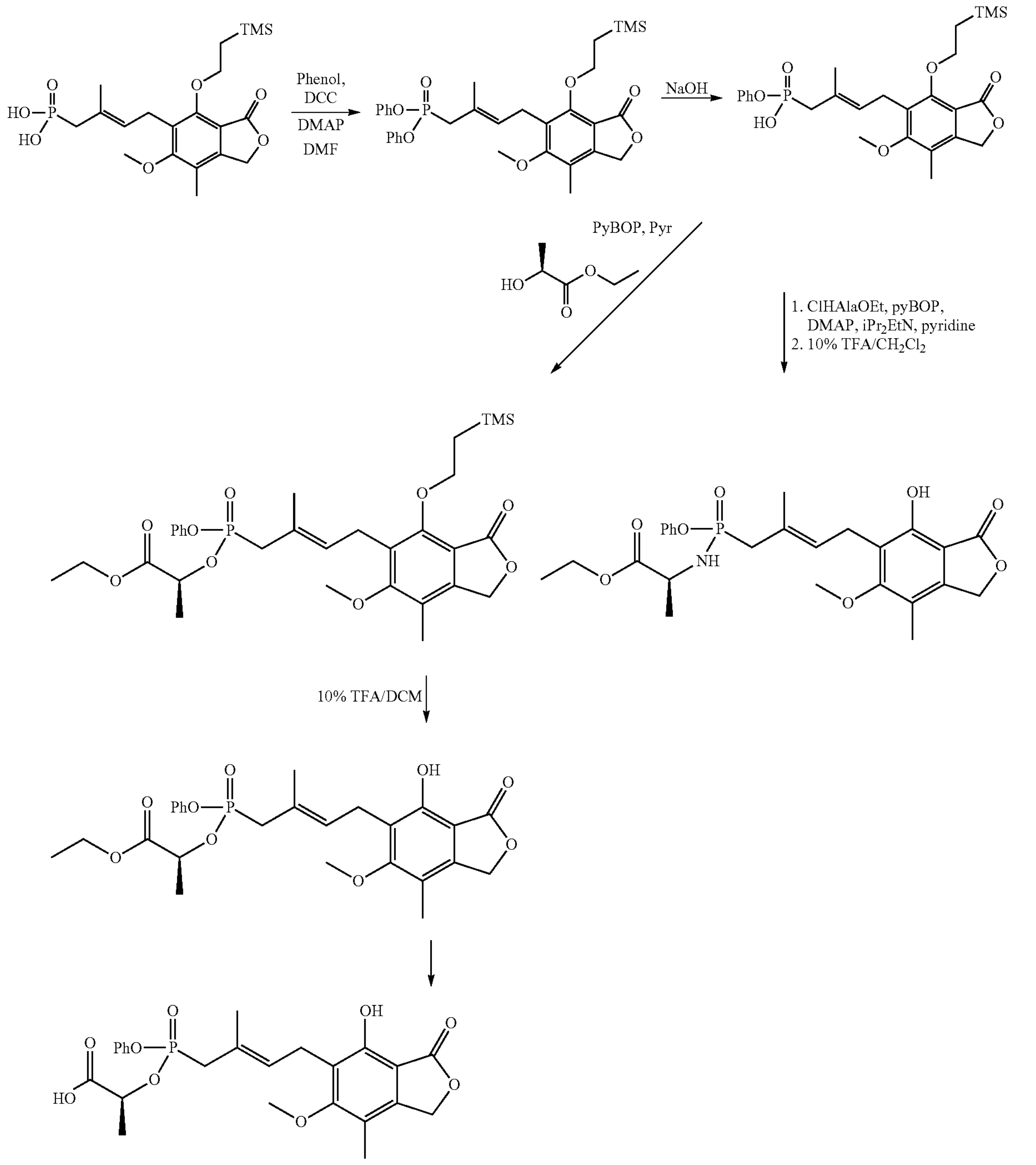

-continued

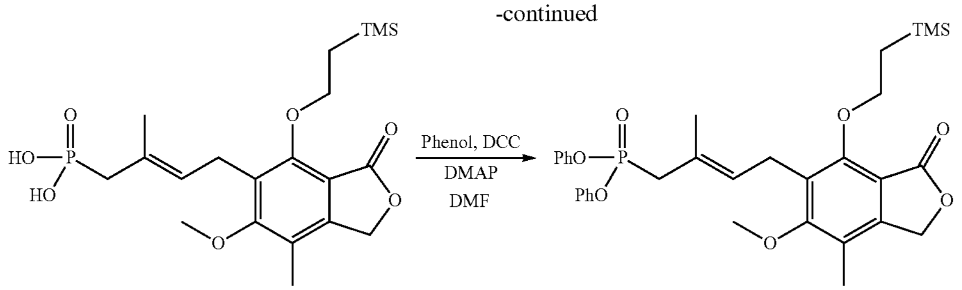

{4-[6-Methoxy-7-methyl-3-oxo-4-(2-trimethylsilanyl-ethoxy)-1,3-dihydro-isobenzofuran-5-yl]-2-methyl-but-2-enyl}-phosphonic acid diphenyl ester To a solution of [{4-[6-methoxy-7-methyl-3-oxo-4-(2-trimethylsilanyl-ethoxy)-1,3-dihydro-isobenzofuran-5-yl]-2-methyl-but-2-enyl}-phosphonic acid (260 mg, 0.59 mmol) in DMF (6 mL) and phenol (555 mg, 5.9 mmol) was added dicyclohexyl carbodiimide (1.21 g, 5.9 mmol) and DMAP (36 mg, 0.295 mmol). The reaction mixture was heated to 140° C. for 30 mins. After cooling to room temperature the mixture was partitioned between EtOAc/Hexane (1:1) and 5% aqueous LiCl solution. The organic layer was washed with 5% aqueous LiCl solution repeatedly, then dried over $Na_2SO_4$. After removal of solvent, the residue was purified by silica gel chromatography to provide 75 mg (21%) of the desired product. MS (m/z) 617 $[M+Na]^+$.

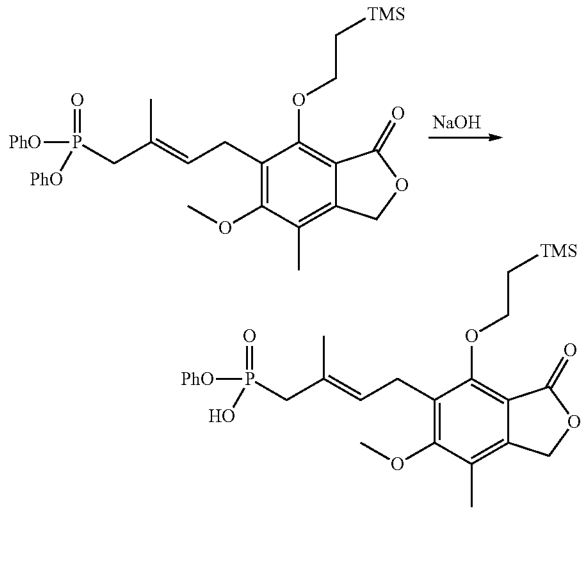

{4-[6-Methoxy-7-methyl-3-oxo-4-(2-trimethylsilanyl-ethoxy)-1,3-dihydro-isobenzofuran-5-yl]-2-methyl-but-2-enyl}-phosphonic acid monophenyl ester To a solution of {4-[6-methoxy-7-methyl-3-oxo-4-(2-trimethylsilanyl-ethoxy)-1,3-dihydro-isobenzofuran-5-yl]-2-methyl-but-2-enyl}-phosphonic acid diphenyl ester (75 mg, 0.126 mmol) in THF (5 mL) was added 1N NaOH (0.1 mL) solution. The mixture was allowed to stir at room temperature for 16 hours. EtOAc was added and the resulting mixture was washed with 1H HCl. The organic layer was concentrated to dryness and the residue was purified by RP HPLC using a C18 column with a gradient of $H_2O$, 0.1% TFA-acetonitrile, 0.1% TFA to provide 24.8 mg (38%) of the desired product. MS (m/z) 517 $[M-H]^-$, 541 $[M+Na]^+$.

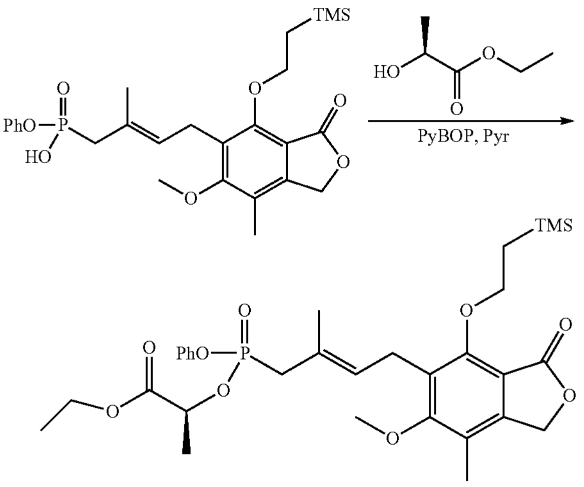

2-({4-[6-Methoxy-7-methyl-3-oxo-4-(2-trimethylsilanyl-ethoxy)-1,3-dihydro-isobenzofuran-5-yl]-2-methyl-but-2-enyl}-phenoxy-phosphinoyloxy)-propionic acid ethyl ester To a solution of {4-[6-methoxy-7-methyl-3-oxo-4-(2-trimethylsilanyl-ethoxy)-1,3-dihydro-isobenzofuran-5-yl]-2-methyl-but-2-enyl}-phosphonic acid monophenyl ester (25 mg, 0.048 mmol) and ethyl (S)-(−)-lactate (34 mg, 0.288 mmol) in pyridine (1 mL) was added PyBOP (125 mg, 0.24 mmol). The solution was stirred at room temperature for 16 hours and concentrated. The residue was purified by RP HPLC using a C18 column with a gradient of $H_2O$, 0.1% TFA-acetonitrile, 0.1% TFA to provide 24 mg (83%) of the desired product. MS (m/z) 641 $[M+Na]^+$.

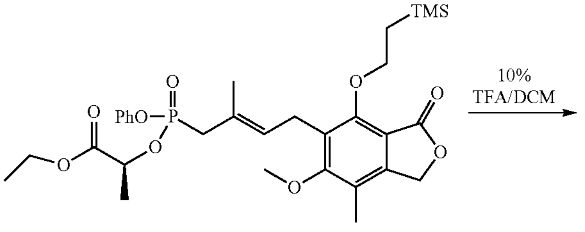

-continued

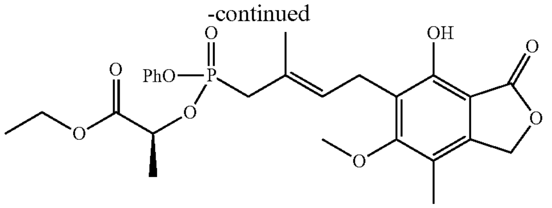

2-{[4-(4-Hydroxy-6-methoxy-7-methyl-3-oxo-1,3-dihydro-isobenzofuran-5-yl)-2-methyl-but-2-enyl]-phenoxy-phosphinoyloxy}-propionic acid ethyl ester To a solution of 2-({4-[6-methoxy-7-methyl-3-oxo-4-(2-trimethylsilanyl-ethoxy)-1,3-dihydro-isobenzofuran-5-yl]-2-methyl-but-2-enyl}-phenoxy-phosphinoyloxy)-propionic acid ethyl ester (24 mg, 0.039 mmol) in DCM (1 mL) was added TFA (0.5 mL) and the mixture was stirred at room temperature for 10 minutes. The reaction mixture was dried under reduced pressure and the residue was purified by RP-HPLC to provide 18 mg (90%) of the desired product as a clear oil. $^{1}H$ NMR (300 MHz, $CDCl_3$) δ 1.18-1.34 (m, 3H), 1.36-1.48 (dd, 3H), 2.02 (m, 3H), 2.17 (s, 3H), 2.78-2.98 (dd, 2H), 3.45 (m, 2H), 3.79 (s, 3H), 4.05-4.25 (m, 2H), 4.97 (m, 1H), 5.21 (s, 2H), 5.48 (t, J=7.2 Hz, 1H), 7.05-7.18 (m, 5H) ppm; $^{31}P$ (121.4 MHz, $CDCl_3$) δ 24.59, 26.13 ppm; MS (m/z) 517 $[M-H]^-$, 519 $[M+H]^+$.

Example 188

Preparation of Representative Compounds of Formula 81

Representative compounds of the invention can be prepared as illustrated below.

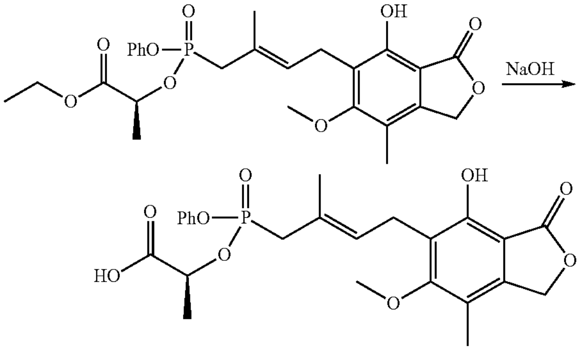

2-{[4-(4-Hydroxy-6-methoxy-7-methyl-3-oxo-1,3-dihydro-isobenzofuran-5-yl)-2-methyl-but-2-enyl]-phenoxy-phosphinoyloxy}-propionic acid To a solution of 2-{[4-(4-hydroxy-6-methoxy-7-methyl-3-oxo-1,3-dihydro-isobenzofuran-5-yl)-2-methyl-but-2-enyl]-phenoxy-phosphinoyloxy}-propionic acid ethyl ester (10 mg, 0.019 mmol) in THF (3 mL) was added 1N NaOH (232 μL) and the mixture was stirred at room temperature for 1 hour. The reaction mixture was dried under reduced pressure and the residue was purified by RP-HPLC to provide 6 mg (77%) of the desired product as a clear oil. $^{1}H$ NMR (300 MHz, $CD_3OD$) δ 1.41 (d, J=7 Hz, 3H), 1.97 (s, 3H), 2.16 (s, 3H), 2.59 (d, J=22 Hz, 2H), 3.45 (m, 2H), 3.79 (s, 3H), 4.83 (m, 1H), 5.26 (s, 2H), 5.43 (t, J=7.2 Hz, 1H) ppm; $^{31}P$ (121.4 MHz, $CD_3OD$) δ 27.02 ppm; MS (m/z) 413 $[M-H]^-$, 415 $[M+H]^+$.

Example 189

Preparation of Representative Compounds of Formula 81

Representative compounds of the invention can be prepared as illustrated below.

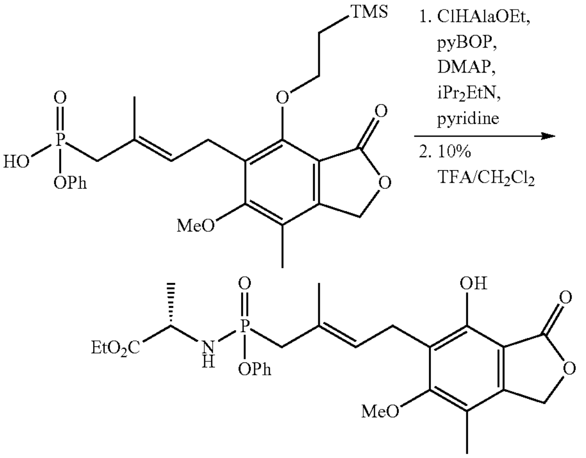

2-{[4-(4-Hydroxy-6-methoxy-7-methyl-3-oxo-1,3-dihydro-isobenzofuran-5-yl)-2-methyl-but-2-enyl]-phenoxy-phosphinoylamino}-propionic acid ethyl ester {4-[6-methoxy-7-methyl-3-oxo-4-(2-trimethylsilanyl-ethoxy)-1,3-dihydro-isobenzofuran-5-yl]-2-methyl-but-2-enyl}-phosphonic acid monophenyl ester (1 g, ~1.9 mmol) was combined with pyBOP (2 g, 4 mmol) and DMAP (120 mg, 0.96 mmol). A solution of L-alanine ethyl ester hydrochloride salt (2.9 g, 19 mmol) and diisopropylethylamine (6.7 mL, 38 mmol) in pyridine (5 mL) was added to the monoacid mixture and the reaction was stirred at room temperature for 12 hours. The reaction mixture was then concentrated and purified twice by column chromatography (1% MeOH/$CH_2Cl_2$ 3% MeOH/$CH_2Cl_2$). The resulting oil was dissolved in a vigorously-stirred solution of 10% TFA/$CH_2Cl_2$ (30 mL) at −40° C. The reaction was gradually warmed to 0° C. After about 3 hours, the reaction was complete. Pyridine (4.5 mL) was added, and the reaction mixture was concentrated. The product was purified by preparative TLC (5% MeOH/$CH_2Cl_2$) and concentrated to give 210 mg (21%) of the desired product as a light yellow oil. $^{1}H$ NMR (300 MHz, $CDCl_3$) δ 7.83-7.70 (m, 1H), 7.30-7.20 (m, 2H), 7.18-7.03 (m, 3H), 5.60-5.35 (m, 1H), 5.21 (s, 2H), 4.17-3.95 (m, 3H), 3.79 (s, 3H), 3.60-3.40 (m, 3H), 2.80-2.60 (m, 2H), 2.17 (m, 3H), 2.01 (m, 3H), 1.30-1.10 (m, 6H) ppm; $^{31}P$ NMR (121 MHz, $CDCl_3$)δ 28.0, 27.5 ppm; MS (m/z) 516 $[M-H]^-$.

Example 190

Preparation of Representative Compounds of Formula 81

Representative compounds of the invention can be prepared as illustrated below.

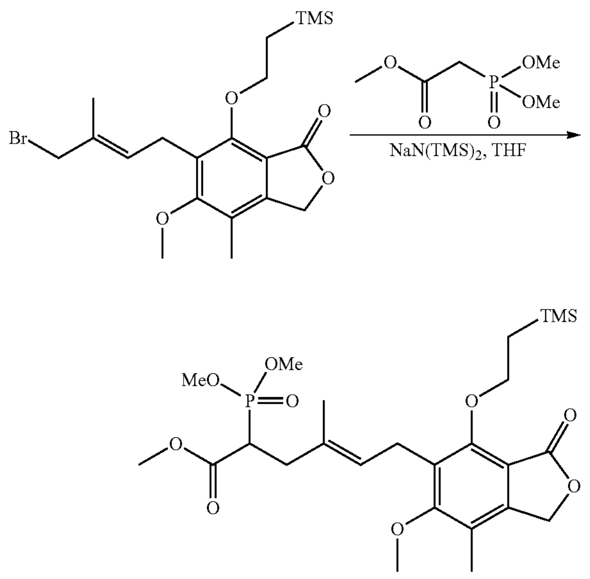

2-(Dimethoxy-phosphoryl)-6-[6-methoxy-7-methyl-3-oxo-4-(2-trimethylsilanyl-ethoxy)-1,3-dihydro-isobenzofuran-5-yl]-4-methyl-hex-4-enoic acid methyl ester To a solution of trimethylphosphonoacetate (63 μL, 0.39 mmol) in THF (1 mL) was added $NaN(TMS)_2$ (0.39 mmol, 0.39 mL) at ambient temperature. After 30 minutes, a solution of 6-(4-bromo-3-methyl-but-2-enyl)-5-methoxy-4-methyl-7-(2-trimethylsilanyl-ethoxy)-3H-isobenzofuran-1-one (69 mg, 0.156 mmol) in THF (1 mL) was added. The reaction mixture was stirred for 2 hours when a precipitate was observed. The reaction mixture was worked up by addition of a saturated aqueous solution of ammonium chloride and extraction of the product with EtOAc. The organic extract was dried and the product was purified using silica gel chromatography with 0-100% EtOAc-Hexanes to provide 40 mg of the desired product as a colorless oil. $^1$H-NMR (300 MHz, $CDCl_3$) δ 0.05 (s, 9H), 1.20-1.26 (m, 2H), 1.79 (s, 3H), 2.17 (s, 3H), 2.42-2.72 (m, 2H), 3.19 (ddd, 1H, J=4, 12, 23 Hz), 3.39 (d, 2H, J=7 Hz), 3.62 (s, 3H), 3.75 (s, 3H), 3.77-3.84 (m, 6H), 4.27-4.34 (m, 2H), 5.12 (s, 2H), 5.24 (t, 1H, J=7 Hz) ppm; $^{31}$P (121.4 MHz, $CDCl_3$) δ 25.1 ppm; MS (m/z) 565.2 $[M+Na]^+$.

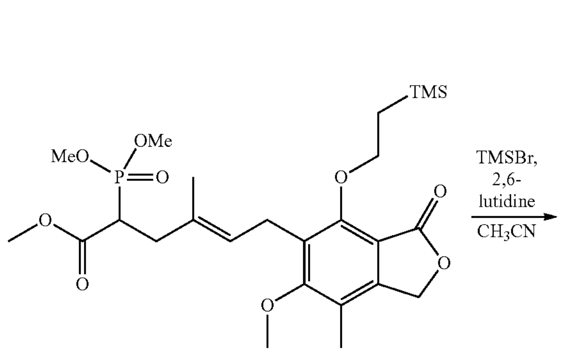

-continued

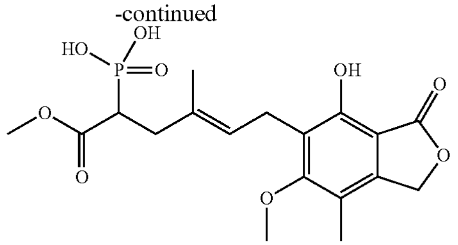

6-(4-Hydroxy-6-methoxy-7-methyl-3-oxo-1,3-dihydro-isobenzofuran-5-yl)-4-methyl-2-phosphono-hex-4-enoic acid methyl ester To a solution of 2-(dimethoxy-phosphoryl)-6-[6-methoxy-7-methyl-3-oxo-4-(2-trimethylsilanyl-ethoxy)-1,3-dihydro-isobenzofuran-5-yl]-4-methyl-hex-4-enoic acid methyl ester (30 mg, 0.055 mmol) in acetonitrile (2 mL) was added trimethylsilyl bromide (0.18 mL). After 10 minutes, 2,6-lutidine (0.16 mL) was added to the reaction at ambient temperature. The reaction was allowed to proceed for 16 hours before it was concentrated to dryness. The residue was resuspended in a solution of DMF:$H_2O$ (8:2, 1 mL) and purified by RP HPLC using a C18 column with a gradient of $H_2O$, 0.1% TFA-acetonitrile, 0.1% TFA to provide 18 mg of the product as a white powder. $^1$H NMR (300 MHz, $CD_3OD$) δ 1.81 (s, 3H), 2.16 (s, 3H), 2.40-2.49 (m, 1H), 2.63 (dt, 1H, J=6, 17 Hz), 3.07 (ddd, 1H, J=4, 12, 23 Hz), 3.38 (3, 2H, J=7 Hz), 3.52 (s, 3H), 3.77 (s, 3H), 5.25 (s, 2H), 5.28 (t, 1H, J=7 Hz) ppm; $^{31}$P (121.4 MHz, $CDCl_3$) δ 19.5 ppm; MS (m/z) 415.2 $[M+H]^+$, 437.2 $[M+Na]^+$.

Example 191

Preparation of Representative Compounds of Formula 81

Representative compounds of the invention can be prepared as illustrated below.

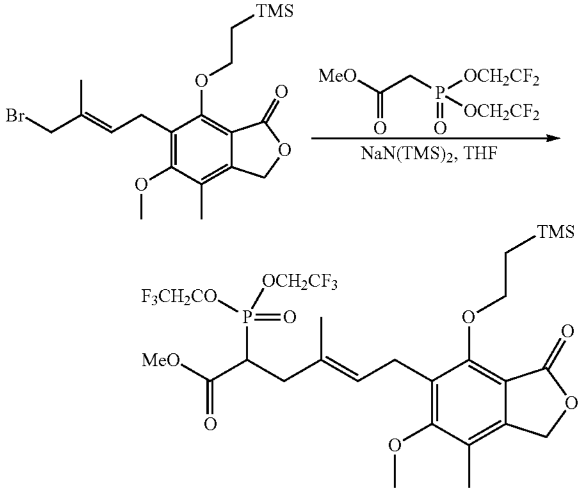

2-(Bis-(2,2,2-trifluoroethoxy)phosphoryl)-6-[6-methoxy-7-methyl-3-oxo-4-(2-trimethylsilanyl-ethoxy)-1,3-dihydro-isobenzofuran-5-yl]-4-methyl-hex-4-enoic acid methyl ester To a solution of [bis-(2,2,2-trifluoro-ethoxy)-phosphoryl]-acetic acid methyl ester (186 μL, 0.88 mmol) in anhydrous THF (2 mL) was added a solution of 1N $NaN(TMS)_2$ in THF (0.88 mL, 0.88 mmol). The solution was stirred at room temperature for 30 minutes, whereupon a solution of 6-(4-bromo-3-methyl-but-2-enyl)-5-methoxy-4-methyl-7-(2-trimethylsilanyl-ethoxy)-3H-isobenzofuran-1-one (98 mg, 0.22 mmol) in THF (1 mL) was added. The reaction mixture was stirred overnight when a precipitate was observed. The reaction mixture was worked up by addition of a saturated aqueous solution of ammonium chloride and extraction of the product with EtOAc. The organic extract was dried and the product was purified by RP HPLC using a C18 column with a gradient of $H_2O$, 0.1% TFA-acetonitrile, 0.1% TFA to provide 72 mg (48%) of the product as a colorless oil. $^1H$ NMR (300 MHz, $CDCl_3$) δ 0.05 (s, 9H), 1.22 (t, 3H, J=7 Hz), 1.81 (s, 3H), 2.18 (s, 3H), 2.5-2.7 (m, 2H), 3.3 (ddd, 1H, J=4, 12, 23 Hz), 3.40 (d, 2H, J=7 Hz), 3.65 (s, 3H), 3.76 (s, 3H), 4.29-5.13 (m, 6H), 5.13 (s, 2H), 5.28 (t, 1H, J=7 Hz) ppm; MS (m/z) 701.2 $[M+Na]^+$.

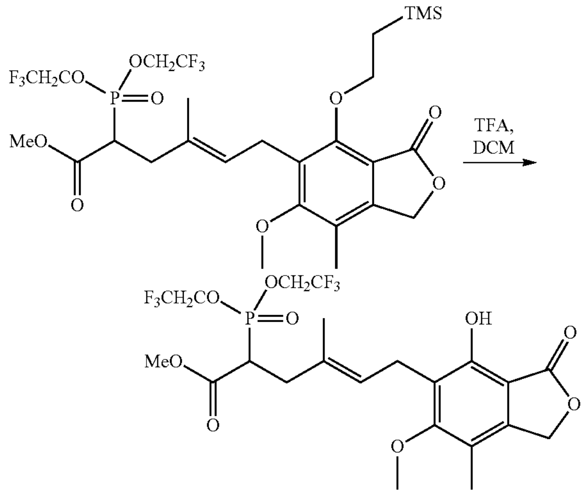

2-(Bis-(2,2,2-trifluoroethoxy)phosphoryl)-6-[6-methoxy-7-methyl-3-oxo-4-(2-hydroxyoxy)-1,3-dihydro-isobenzofuran-5-yl]-4-methyl-hex-4-enoic acid methyl ester

[2-(Bis-(2,2,2-trifluoroethoxy)phosphoryl)-6-[6-methoxy-7-methyl-3-oxo-4-(2-trimethylsilanyl-ethoxy)-1,3-dihydro-isobenzofuran-5-yl]-4-methyl-hex-4-enoic acid methyl ester (70 mg) was dissolved in a solution of 10% trifluoroacetic acid in dichloromethane (5 mL). After 10 minutes the mixture was concentrated and the product was purified by RP HPLC using a C18 column with a gradient of $H_2O$, 0.1% TFA-acetonitrile, 0.1% TFA to provide 45 mg (75%) of the product as a colorless oil. $^1H$ NMR (300 MHz, $CDCl_3$) δ 1.81 (s, 3H), 2.16 (s, 3H), 2.5-2.7 (m, 2H), 3.3 (ddd, 1H), 3.38 (d, 2H, J=7 Hz), 3.65 (s, 3H), 3.77 (s, 3H), 4.33-4.43 (m, 4H), 5.21 (s, 2H), 5.33 (t, 1H, J=7 Hz) ppm; $^{31}P$ (121.4 MHz, $CDCl_3$) δ 25.8 ppm; MS (m/z) 601.2 $[M+Na]^+$.

Example 192

Preparation of Representative Compounds of Formula 81

Representative compounds of the invention can be prepared as illustrated below.

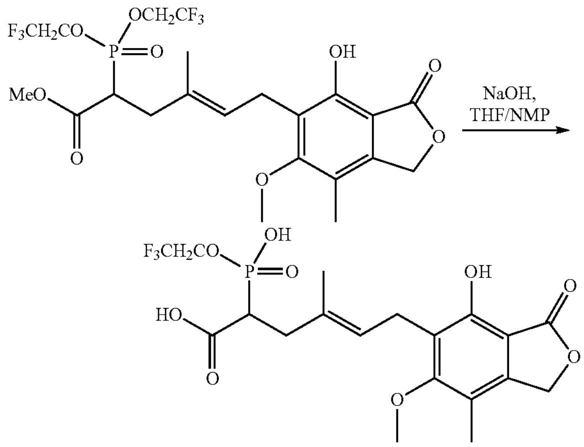

6-(4-Hydroxy-6-methoxy-7-methyl-3-oxo-1,3-dihydro-isobenzofuran-5-yl)-2-[hydroxy-(2,2,2-trifluoro-ethoxy)-phosphoryl]-4-methyl-hex-4-enoic acid To a solution of the bis-(2,2,2-trifluoro-ethoxy)-phosphoryl methyl ester (186 μL, 0.88 mmol) in anhydrous THF (0.5 mL) was added a solution of 1N NaOH (aqueous; 0.06 mL) and N-methylpyrrolidinone (0.2 mL). After 6.5 hours, another aliquot of 1N NaOH (0.06 mL) was added and the mixture was stirred overnight. After concentration, the residue was suspended in DMF (<1 mL), neutralized with a few drops of TFA and purified by RP HPLC using a C18 column with a gradient of $H_2O$, 0.1% TFA-acetonitrile, 0.1% TFA to provide 5.6 mg (72%) of the product as a white powder after lyophilization. NMR (300 MHz, $CD_3OD$) δ 1.83 (s, 3H), 2.16 (s, 3H), 2.43-2.51 (m, 1H), 2.59-2.70 (m, 1H), 3.13 (ddd, 1H), 3.40 (d, 2H), 3.76 (s, 3H), 4.36-4.47 (m, 2H), 5.25 (s, 2H), 5.34 (t, 1H, J=7 Hz) ppm; MS (m/z) 505.2 $[M+Na]^+$.

Example 193

Preparation of Representative Compounds of Formula 81

Representative compounds of the invention can be prepared as illustrated below.

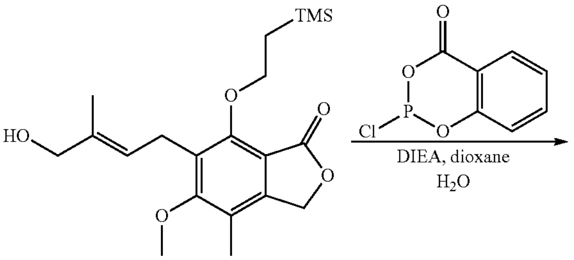

-continued

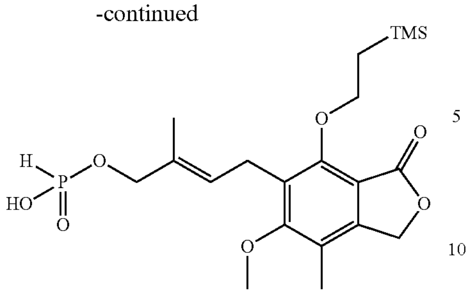

Phosphorous acid mono-{4-[6-methoxy-7-methyl-3-oxo-4-(2-trimethylsilanyl-ethoxy)-1,3-dihydro-isobenzofuran-5-yl]-2-methyl-but-2-enyl}ester To a solution of 6-(4-hydroxy-3-methyl-but-2-enyl)-5-methoxy-4-methyl-7-(2-trimethylsilanyl-ethoxy)-3H-isobenzofuran-1-one (75 mg, 0.20 mmol) and DIEA (49 μL, 0.28 mmol) in dioxane (2 mL) was added 2-chloro-4H-1,3,2-benzodioxaphosphorin-4-one (56.7 mg, 0.28 mmol) according the procedure of Shadid, B. et al., *Tetrahedron,* 1989, 45, 12, 3889. After 10 minutes, another portion of 2-chloro-4H-1,3,2-benzodioxaphosphorin-4-one (40 mg, 0.20 mmol) and DIEA (35 μL, 0.20 mmol) were added. The reaction was allowed to proceed at room temperature for an additional hour, after which it was quenched by the addition of $H_2O$. The solution was stirred for another 10 minutes and concentrated in vacuo to a small volume. The product was triturated with diethyl ether and coevaporated from acetonitrile (4×10 mL) to provide the product. $^1H$ NMR (300 MHz, $CDCl_3$) δ 0.03 (s, 9H), 1.08-1.30 (m, 2H), 1.84 (br s, 3H), 2.17 (s, 3H), 3.46 (br s, 2H), 3.76 (s, 3H), 4.21-4.39 (m, 4H), 5.12 (s, 2H), 5.43-5.60 (m, 1H), 7.83 (br s, 1H); $^{31}P$ (121.4 MHz, $CDCl_3$) δ 7.22; MS (m/z) 441 $[M-H]^-$.

Example 194

Preparation of Representative Compounds of 81

Representative compounds of the invention can be prepared as illustrated below.

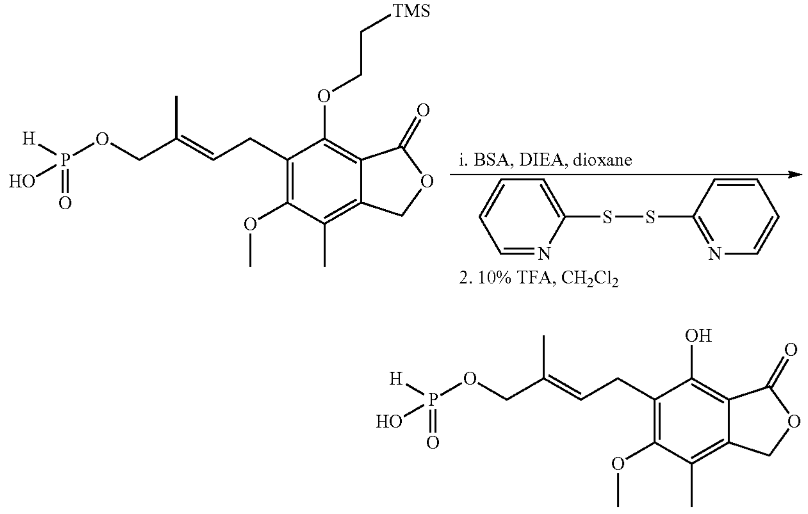

Phosphoric acid mono-{4-[6-methoxy-7-methyl-3-oxo-4-hydroxy-1,3-dihydro-isobenzofuran-5-yl]-2-methyl-but-2-enyl}ester A solution of phosphorous acid mono-{4-[6-methoxy-7-methyl-3-oxo-4-(2-trimethylsilanyl-ethoxy)-1,3-dihydro-isobenzofuran-5-yl]-2-methyl-but-2-enyl}ester (27 mg, 0.06 mmol) in dioxane (1 mL) was stirred with DIEA (21 μL, 0.12 mmol) and N,O-bis(trimethylsilyl)acetamide (29 μL, 0.12 mmol) at room temperature for 3 hours. To the reaction solution was added 2,2'-dipyridyldisulfide (16 mg, 0.072 mmol) and the mixture was allowed to stir for an additional 2 hours at room temperature. The reaction mixture was diluted by addition of $H_2O$ and the solution was stirred for 2 more hours when it was concentrated. The residue was dissolved in a solution of 10% TFA/$CH_2Cl_2$ and stirred at room temperature for 9 hours. The reaction mixture was dried under reduced pressure and the product was purified by reverse-phase HPLC to provide the desired product as a white solid. $^1H$ NMR (300 MHz, $CD_3OD$) δ 1.87 (s, 3H), 2.16 (s, 3H), 3.47 (d, 2H, J=7 Hz), 3.79 (s, 3H), 4.28 (d, 2H, J=6 Hz), 5.26 (s, 2H), 5.50-5.61 (m, 1H); $^{31}P$ (121.4 MHz, $CD_3OD$) δ 0.50; MS (m/z) 357 $[M-H]^-$.

Examples 195-199

Synthetic methodologies and intermediate compounds that can be used to prepare analogs of formulae H, I, J, and K are described in Examples 195-199. These compounds are representative examples of compounds of Formulae 77-80.

H

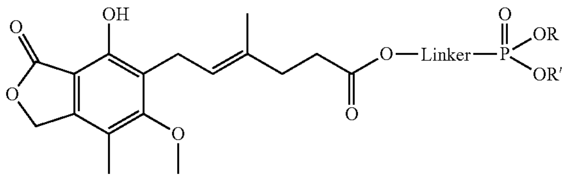

-continued

I

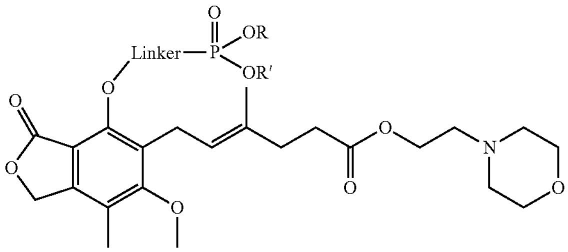

J

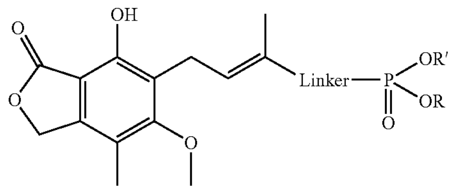

K

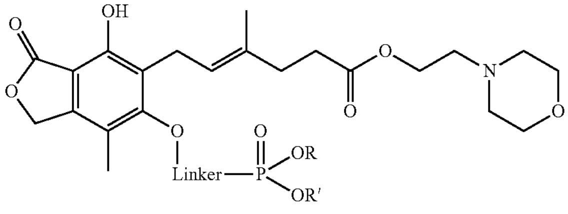

Three regions of mycophenolate mofetil can be utilized for the attachment of the phosphonate prodrug onto mycophenolic acid as demonstrated by compounds H, I, and K shown above. Also, the carbdxylic acid can be replaced with a phosphonic acid that is part of the prodrug moiety as in compound J.

Example 195

Specific Embodiments of the Invention of Formula 81

195.1

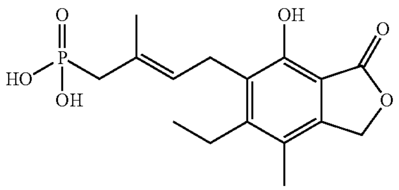

195.2

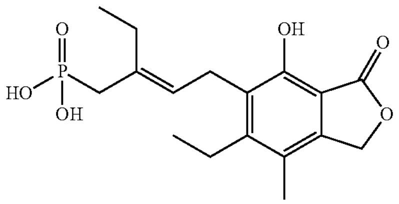

-continued 195.3

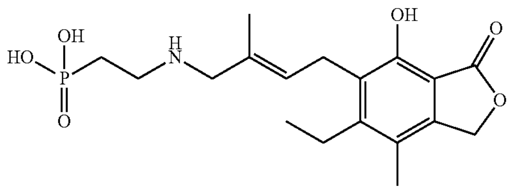

Representative compounds of the invention are illustrated above.

Example 196

General Route to Representative Compounds of Formula 81

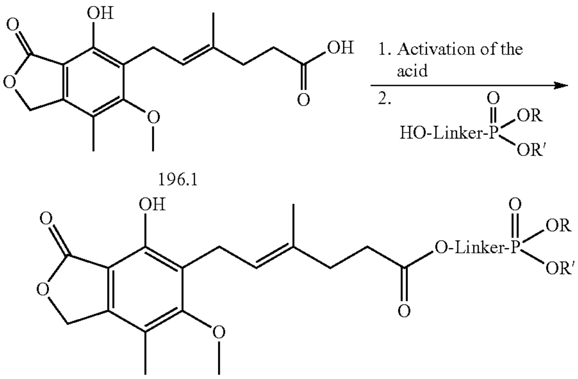

196.1

196.3

Representative compounds of the invention can be prepared as illustrated above. The morpholino ethyl moiety can serve as a prodrug functionality to improve bioavailability and can be replaced with the phosphonate prodrug handle as shown above. Mycophenolic acid is commercially available, e.g., from Sigma Chemical Company, St. Louis, Mo. Activation of the carboxylic acid 196.1 in the presence of the free phenol, followed by addition of an alcohol carrying the phosphonate group, results in the formation of the desired product 196.3 (U.S. Pat. No. 4,786,637).

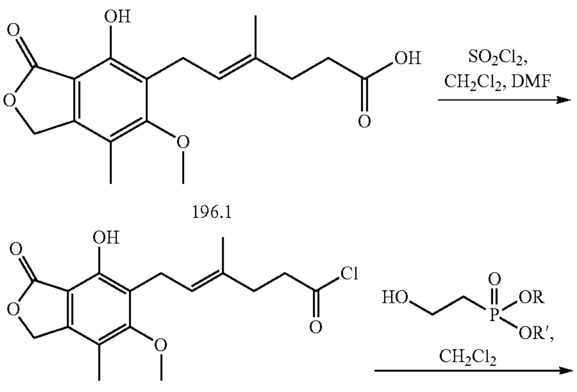

196.1

196.2

-continued

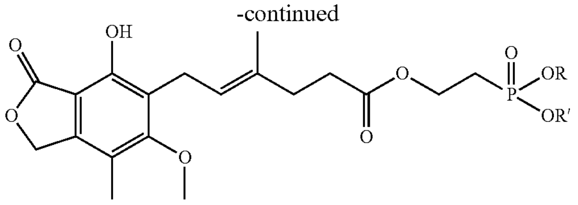

196.4

Specifically, mycophenolic acid 196.1 is dissolved in dichloromethane. Thionyl chloride is added followed by a catalytic amount of DMF. The reaction mixture is stirred at room temperature for 3 hours, after which the volatile components are removed under vacuum. The phosphonate-alcohol is dissolved in dichloromethane and chilled to about 4° C. on an ice bath. The mycophenolic acid chloride 196.2 is dissolved in dichloromethane and added to the chilled solution. After stirring for 90 minutes at about 4° C., the reaction mixture is washed with water and then with aqueous sodium bicarbonate. The organic solution is dried and evaporated to yield the phosphonate prodrug 196.4.

Example 197

Synthesis of Representative Compounds of Formula 79

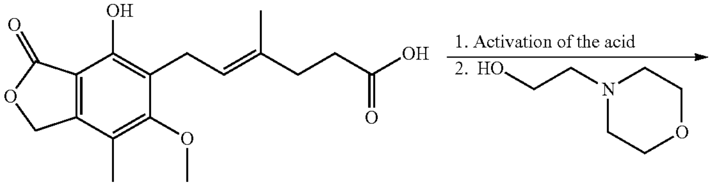

197.1

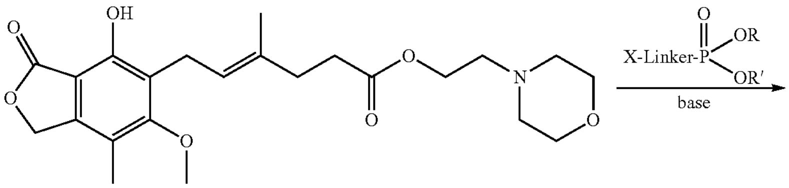

197.2

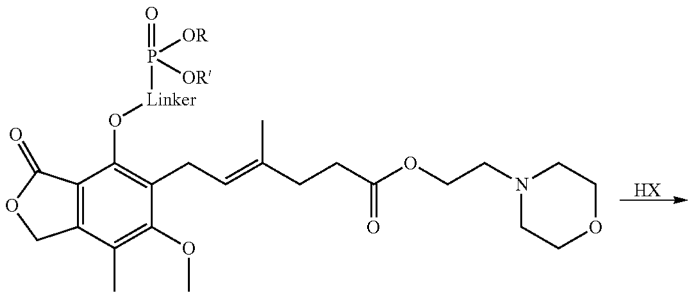

197.3

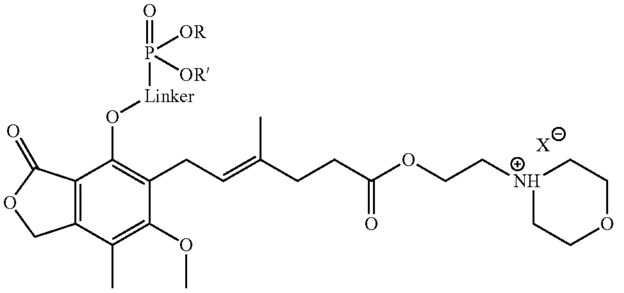

197.4

Representative compounds of the invention can be prepared as illustrated above. The C-4 phenol position provides a reactive handle for further analogs as illustrated above. Once the carboxylic acid of 197.1 is blocked by morpholino ethyl, such as in compound 197.2, or a phosphonate prodrug as in compound 197.3, the phenol can be alkylated under basic conditions. Bases such as pyridine, potassium carbonate, or triethylamine are utilized. Leaving groups such as trifluoromethylsulfonate, mesylate, bromide, or iodide are attached to the phosphonate prodrug subunit and reacted, in the presence of base, with compound 197.2. Compound 197.3 can either be used directly, or in the form of a salt, compound 197.4. Among the large number of salts that can be prepared, chloride and bisulfate salts are of particular utility.

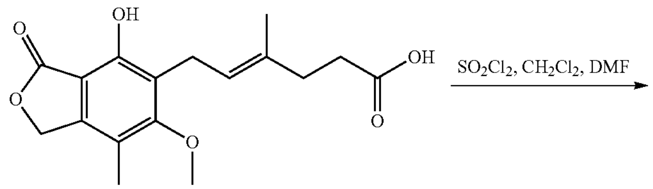

197.1

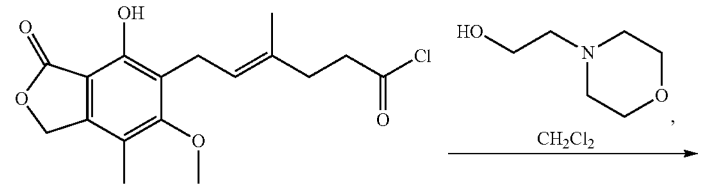

197.1.1

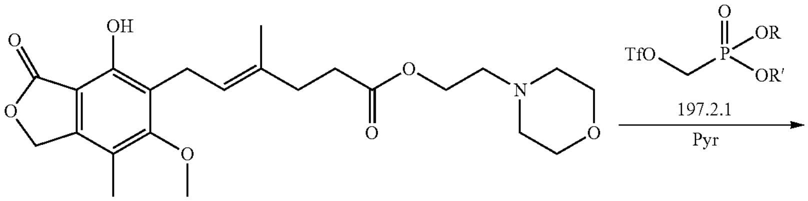

197.2

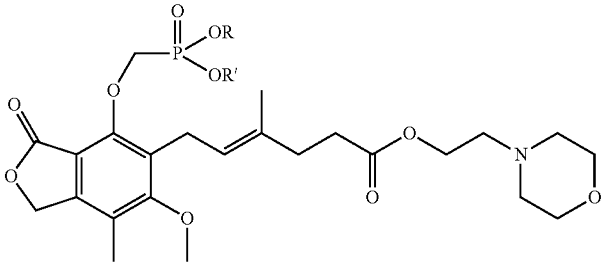

197.3

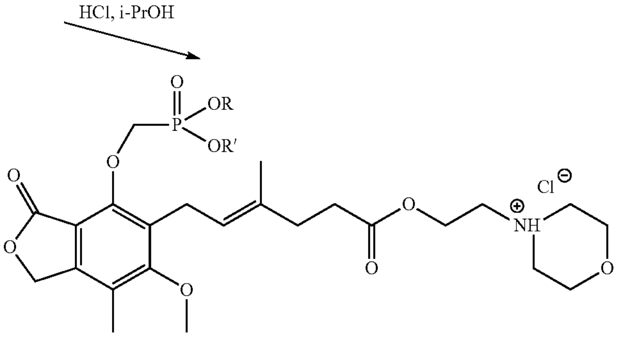

197.4

Preparation of compound 197.4 is outlined in more detail above. Compound 197.2 is prepared similar to compound 196.2 (described in an Example above above). A solution of morpholino ethanol in dichloromethane is cooled to about 4° C. The mycophenolic acid chloride 197.1.1 is dissolved in dichloromethane and added to the cooled solution. Stirring this solution for about 90 minutes gives compound 197.2. The reaction mixture is washed with water and dried with sodium sulfate. Removal of the solvent provides isolated compound 197.2. Alkylation at the phenolic position of 197.2 is achieved by suspending the compound in pyridine. Triflate 197.2.1 is added to the solution and the mixture is stirred at room temperature for about 90 minutes. The reaction mixture is poured into water and the product is extracted with ethyl acetate. Removal of the organic layer provides compound 197.3. Hydrochloride salt of 197.3 can optionally be prepared. Compound 197.3 is dissolved in isopropanol and the solution is added to a mixture of hydrogen chloride in isopropanol. The hydrochloride salt 197.4 is collected by filtration and dried under vacuum.

Example 198

Synthesis of Representative Compounds of Formula 78

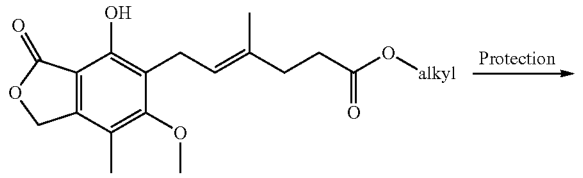

198.1

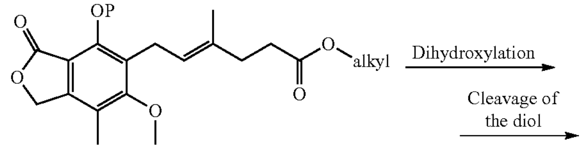

198.2

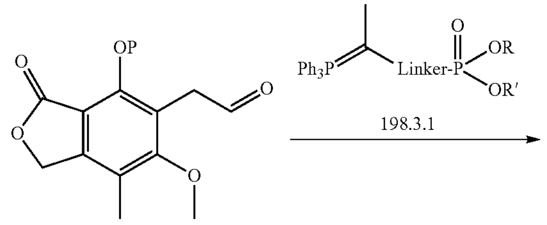

198.3

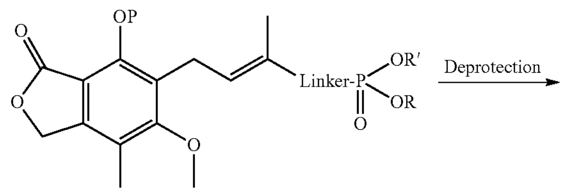

198.4

-continued

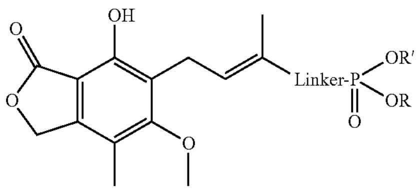

198.5

Representative compounds of the invention can be prepared as illustrated above. The carboxylic acid of mycophenolic acid can be replaced with a phosphonic acid that may also serves as a prodrug handle. In order to remove the carboxylic acid containing side chain, the acid chloride 197.2 (prepared in Example 197) is converted to ester 198.1. Protection of the phenol with a silyl group, followed by dihydroxylation and cleavage of the diol generates aldehyde 198.3 (Pankiewicz, et al., *J. Med. Chem.* 2002, 45, 703), (Patterson et al., U.S. Pat. No. 5,444,072). A Wittig reaction with ylide 198.3.1 carrying an appropriately protected phosphonate provides the desired compound 198.4. Final deprotection yields compound 198.5.

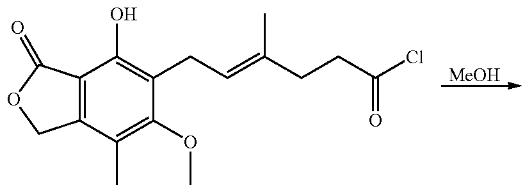

198.1.1

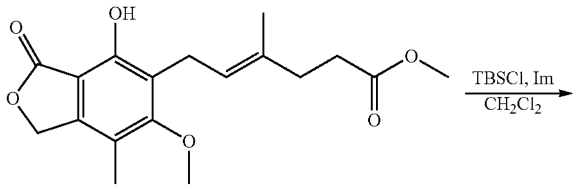

198.1

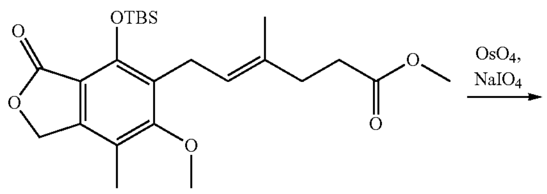

198.2

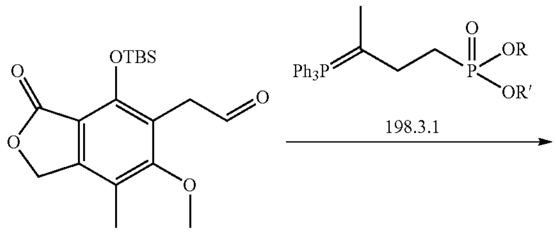

198.3

-continued

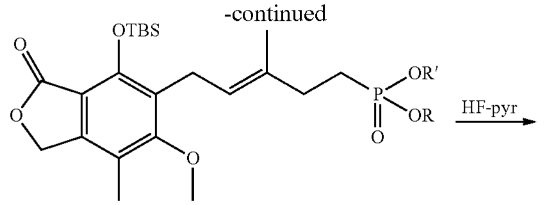

198.4

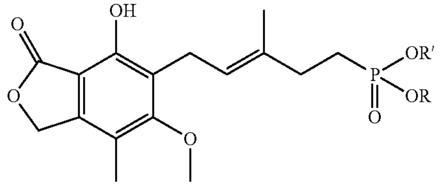

198.5

Mycophenolate ester 198.1 can simply be prepared by stirring the acid chloride 198.1.1 with MeOH. Then, the phenol position of mycophenolate ester is protected by a silyl group such as TBS to provide compound 198.2. Once the phenol position is protected, dihydroxylation using osmium tetraoxide followed by periodinate cleavage provides aldehyde 198.3. Aldehyde 198.3 and excess of the ylide 198.3.1 are heated in benzene at reflux for about 24 hours. The reaction mixture is concentrated and the residue is purified by column chromatography to provide olefin 198.4 (Pankiewics et al., *J. Med. Chem.* 2002, 45, 703). A final deprotection using HF-pyridine yields the final product 198.5.

Example 199

Synthesis of Representative Compounds of Formula 80

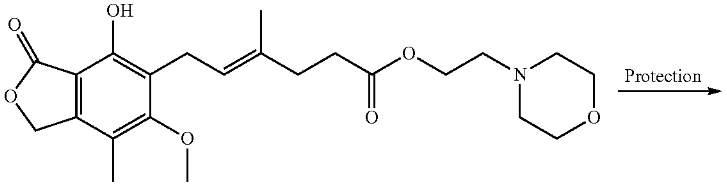

199.1.1

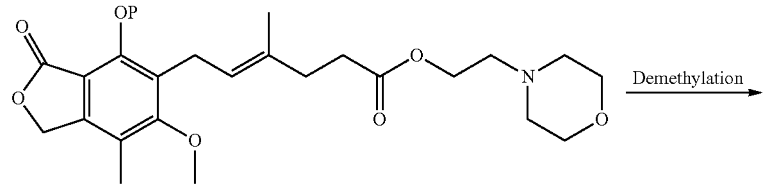

199.1

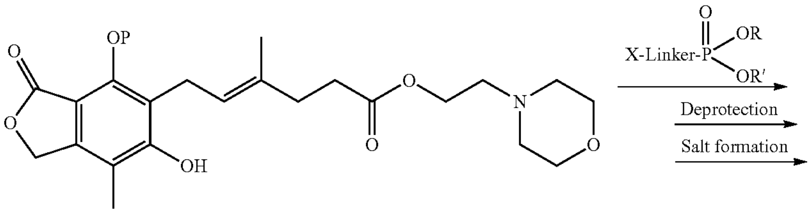

199.2

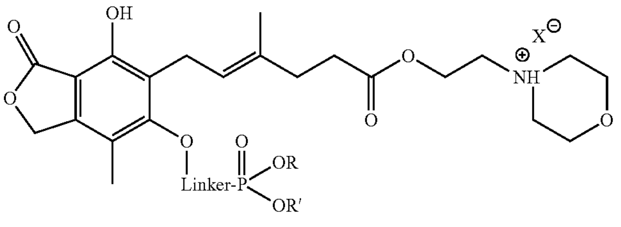

199.4

Representative compounds of the invention can be prepared as illustrated above. A phosphonate-attachment point can be unmasked after demethylation of mycophenolate ester 199.1.1. For this purpose, the 4-OH needs to be masked with a protecting group such as a silyl group. Once the 6-OMe is demethylated and alkylated, the protecting group at position 4 is removed to reveal the final product 199.4. The morphonyl ethanol group is installed early and carried through the alkylation steps. A different protecting group may be installed initially and removed later. In such a synthesis, the last step is the formation of the morpholinoethyl ester compound.

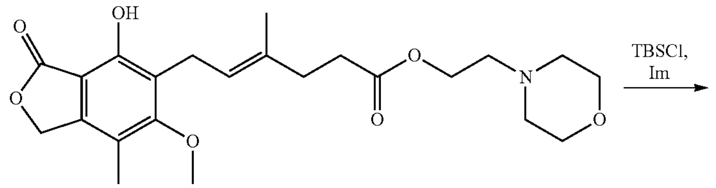

199.1.1

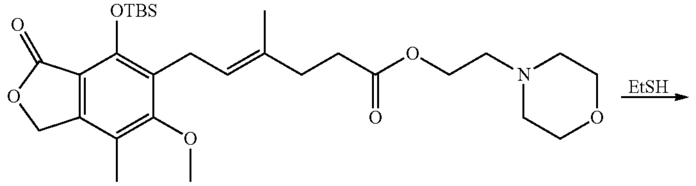

199.5

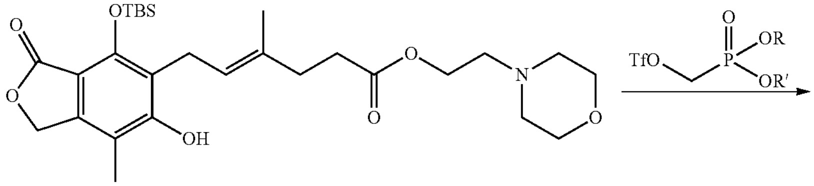

199.6

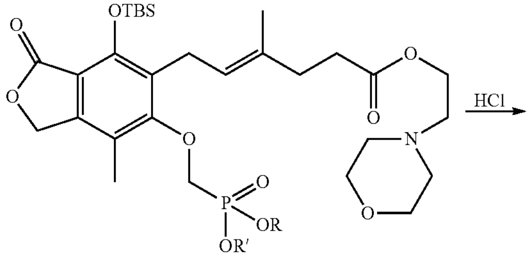

199.7

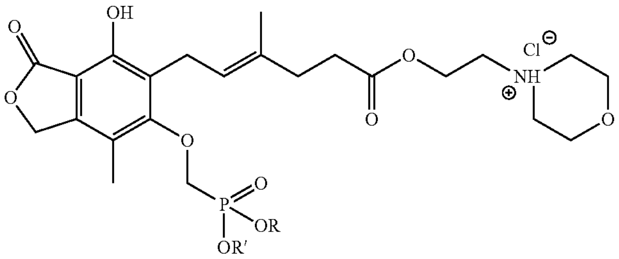

199.4

Synthesis of compound 199.4 is shown above. Phenol 199.1.1 is protected with TBS group in $CH_2Cl_2$ using imidazole as base to yield 199.5. Demethylation is performed using thiolate nucleophiles to generate compound 199.6. A variety of other methods are also available in literature as described in *Protective Groups in Organic Synthesis* by Greene and Wuts. Alklation of the 6-OH using a triflate of the phosphonate prodrug proceeds well using $K_2CO_3$ or TEA to provide 199.7. Final deprotection to remove the TBS group provides product 199.4.

Example 200

Preparation of Representative Compounds of the Invention

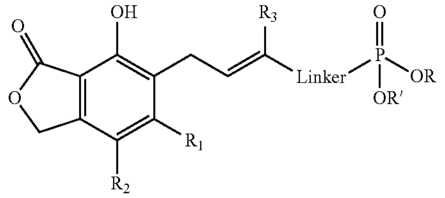

200.1

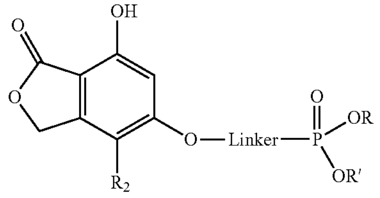

200.2

Linker = 0-8 atoms, preferably 1-6;
$R_1$ = OMe, OEt, vinyl, Et, cyclopropyl, NHMe, NHCHO
$R_2$ = Me, Cl, $CF_3$
$R_3$ = H, Me, cyclopropyl, Et, vinyl, $CF_3$
$R_4$ = H, Cl, Me, Et, cyclopropyl, vinyl, allyl,

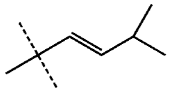

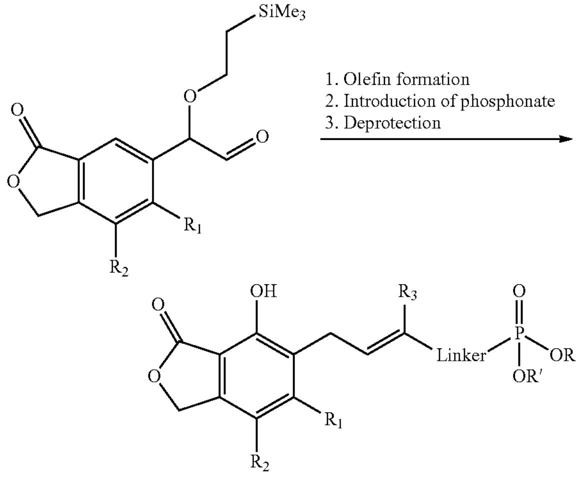

200.1

Representative compounds of the invention can be prepared as illustrated above and in the following schemes.

Synthesis of Phenacetaldehydes with Variants at $R_1$, $R_2$

The parent compound ($R_1$=OMe; $R_2$=Me) is accessible by semi-synthesis from mycophenolic acid as follows:

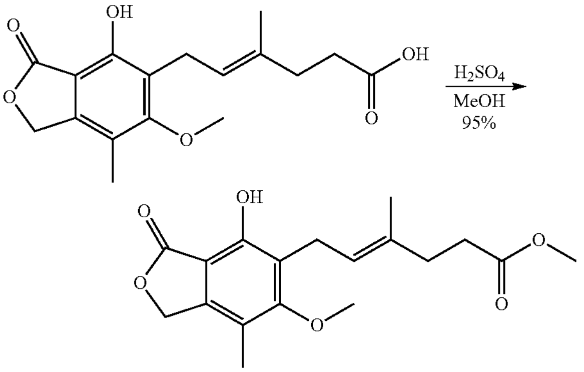

200.3

To a solution of mycophenolic acid (500 g, 1.56 mol) in MeOH (4 L) under nitrogen atmosphere was added sulfuric acid (10 mL) dropwise, and the suspension was stirred at room temperature. After 2 hours the reaction became homogeneous, and soon thereafter a precipitate was formed. The reaction was allowed to stir at room temperature for 10 hours at which time TLC indicated complete reaction. The reaction was cooled in an ice bath to 10° C. and then filtered using a Buchner funnel. The filter cake was washed with ice cold methanol (750 mL) followed by hexanes (750 mL) and then dried to give 497 g (95%) of the desired product 200.3 as a solid: $^1H$ NMR (300 MHz, $CDCl_3$) δ, 1.81 (s, 3H), 2.18 (s, 3H), 2.15 (s, 3H), 2.37-2.50 (m, 4H), 3.38 (d, 2H, J=7 Hz), 3.62 (s, 3H), 3.77 (s, 3H), 5.13 (s, 2H), 5.22 (m, 1H), 7.17 (s, 1H).

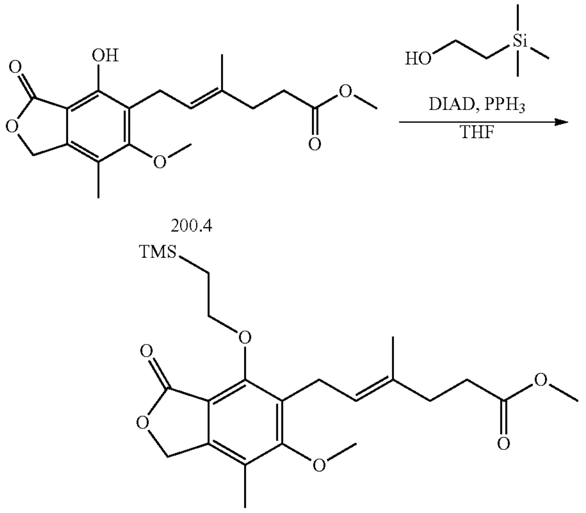

200.4

200.5

To a solution of 200.4 (3.99 g, 11.9 mmol), $PPh_3$ (4.68 g, 17.9 mmol), and diisopropyl azodicarboxylate (3.46 mL, 17.9 mmol) in THF (60 mL) at 0° C. was added a solution of 2-trimethylsilylethanol (2.05 mL, 14.3 mmol) in THF (20 mL). The resulting yellow solution was allowed to warm to room temperature and stirred for 4 hours. The reaction was worked up by concentrating the solution to dryness and addition of ether and hexanes. Triphenylphosphine oxide was removed by filtration and the filtrate was concentrated and purified by silica gel chromatography to provide 4.8 g (100%) of 200.5 as a clear oil: $^1H$ NMR (300 MHz, $CDCl_3$) δ 0.03 (s, 9H), 1.18-1.30 (m, 2H), 1.81 (s, 3H), 2.18 (s, 3H), 2.25-2.33 (m, 2H), 2.37-2.45 (m, 2H), 3.42 (d, 2H, J=7 Hz), 3.62 (s, 3H), 3.77 (s, 3H), 4.25-4.35 (m, 2H), 5.13 (s, 2H), 5.12-5.22 (m, 1H).

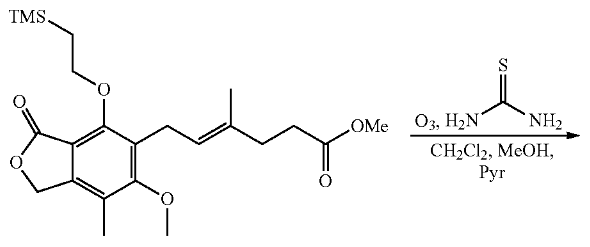

200.5

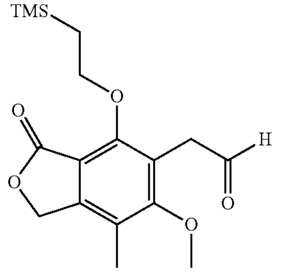

200.6

A solution of 200.5 (9.6 g, 22 mmol) in MeOH (90 mL), $CH_2Cl_2$ (90 mL) and pyridine (0.7 mL) was cooled to −70° C. using a dry ice/acetone bath. A stream of ozone was bubbled through the reaction via a gas dispersion tube until the reaction became blue in color (1.5 hours). The ozone line was replaced with a stream of nitrogen and bubbling continued for another 30 minutes, by which time the blue color had disappeared. To this solution at −70° C. was added thiourea (1.2 g, 15.4 mmol) in one portion, and the cooling bath was removed. The reaction was allowed to warm to room temperature and stirred for 15 hours. The reaction was worked up by filtration to remove solid thiourea S-dioxide, and then partitioned between $CH_2Cl_2$ and water. The organic layer was removed. The aqueous layer was washed with $CH_2Cl_2$ and the organic extracts were combined, washed with aqueous 1N HCl, saturated $NaHCO_3$ and brine, and dried in vacuo. The residue was purified by silica gel chromatography to afford 7.3 g (99%) of 200.6 as a white solid: $^1H$ NMR (300 MHz, $CDCl_3$) δ −0.01 (s, 9H), 1.05-1.15 (m, 2H), 2.15 (s, 3H), 3.69 (s, 3H), 3.78 (d, 2H, J=1 Hz), 4.27-4.39 (m, 2H), 5.11 (s, 2H), 9.72 (d, 1H, J=1 Hz).

Example 201

Preparation of Representative Compounds of the Invention $R_1$ Variants of Example 200:

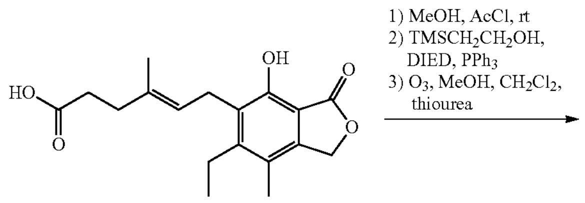

-continued

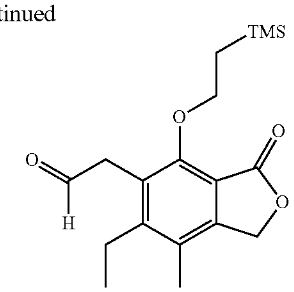

Representative compounds of the invention can be prepared as illustrated above. The starting material, synthesized according to *J. Med. Chem.*, 1996, 39, 4181-4196, is transformed to the desired aldehyde using methods analogous to those described above.

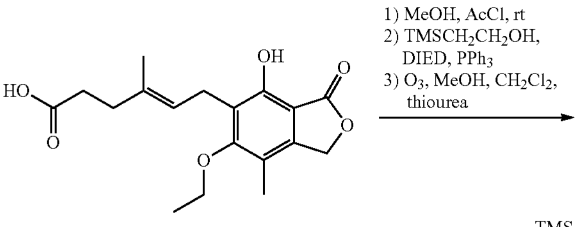

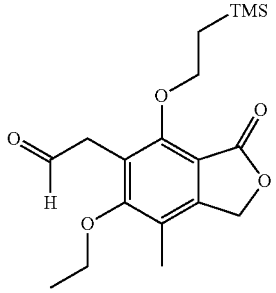

The starting material, synthesized according to *J. Med. Chem.*, 1996, 39, 4181-4196, is transformed to the desired aldehyde using methods analogous to those described above.

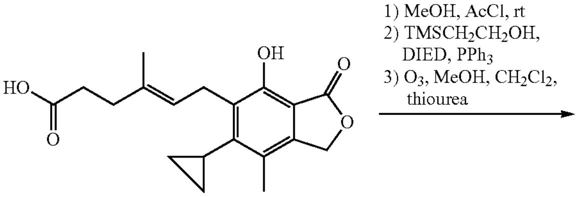

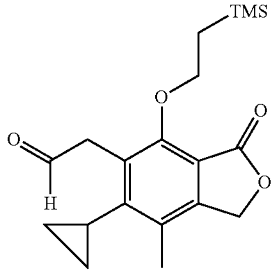

The starting material, synthesized according to *J. Med. Chem.*, 1996, 39, 4181-4196, is transformed to the desired aldehyde using methods analogous to those described above.

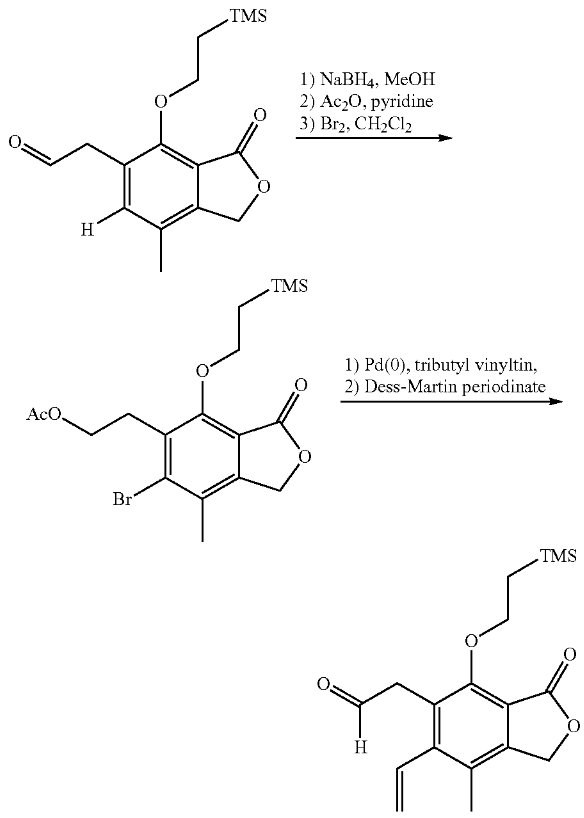

The aldehyde is dissolved in an organic solvent such as methanol and sodium borohydride is added. At the end of the reaction, aqueous HCl solution is added and the solvent is removed in vacuo. Further purification is achieved by chromatography.

The resulting alcohol is dissolved in an organic solvent such as dichloromethane (DCM). Pyridine and acetic anhydride are added and stirring at room temperature is continued. At the end of the reaction additional DCM is added and the solution is washed with aqueous HCl solution, aqueous sodium bicarbonate solution, and dried over sodium sulfate. Filtration and evaporation of the solvent in vacuo gives the crude product. Further purification is achieved by chromatography.

The acetate is dissolved in DCM and bromine is added, according to a procedure from *J. Med. Chem.*, 1996, 39, 4181-4196. At the end of the reaction additional DCM is added and the solution is washed with aqueous sodium thiosulfate solution and brine. The organic layer is dried over sodium sulfate. Filtration and evaporation of solvents yields the crude material. Further purification is achieved by chromatography.

The product of the previous step, lithium chloride, triphenylarsine, tributylvinyltin, and tris(dibenzylideneacetone) dipalladium(0)-chloroform adduct are heated in an organic solvent such as N-methylpyrrolidinone at an elevated temperature of approximately 55° C., according to a procedure from *J. Med. Chem.*, 1996, 39, 4181-4196. At the end of the reaction the mixture is cooled to room temperature and poured into a mixture of ice, potassium fluoride, water, and ethyl acetate. Stirring is continued for one hour. The suspension is filtered through Celite and extracted with ethyl acetate. The combined organic extracts are dried over sodium sulfate. The solvents are removed in vacuo and the crude material is further purified by chromatography.

The product of the previous step is dissolved in an organic solvent such as DCM or THF. 1,1,1-tris(acyloxy)-1,1-dihydro-1,2benziodoxol-3-(1H)-one (Dess-Martin reagent) is added and the solution is stirred at room temperature, according to a procedure from *J. Org. Chem.*, 1984, 48, 4155-4156. At the end of the reaction diethyl ether is added, followed by aqueous sodium hydroxide solution. The layers are separated and the organic layer is washed with aqueous sodium hydroxide solution, water, and dried over sodium sulfate. Filtration and evaporation of solvents yields the crude vinyl product. Further purification is achieved by chromatography.

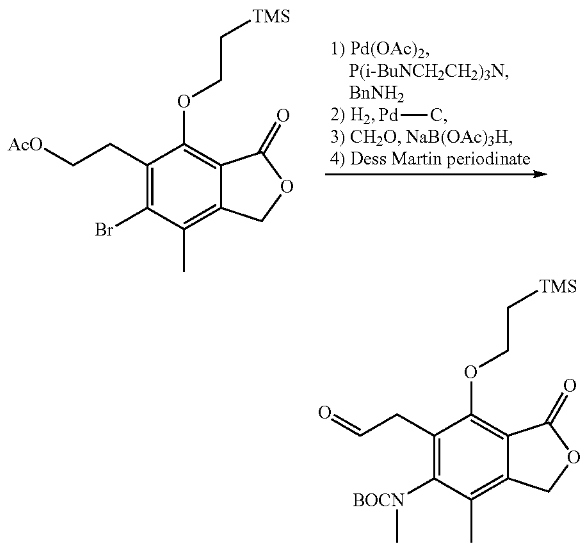

The starting material is dissolved in an organic solvent such as toluene. $P(isobutylNCH_2CH_2)_3N$, palladium(II)acetate, sodium tert-butoxide, and benzylamine are added and the mixture is heated at 80° C., according to a procedure from *J. Org. Chem.*, 2003, 68, 452-459. At the end of the reaction the mixture is cooled to room temperature and the solvents are removed in vacuo. The crude material is purified by chromatography. Any residual acetate is removed by brief treatment with methanolic sodium methoxide.

The benzyl-protected aniline is dissolved in an organic solvent such as DMF. Palladium on carbon is added and the reaction mixture is placed under an atmosphere of hydrogen. At the end of the reaction the mixture is filtered through Celite. The solvents are removed in vacuo. Further purification is achieved by chromatography.

The resulting primary aniline is dissolved in an organic solvent such as THF, acetonitrile, or DMF and is treated with formaldehyde and sodium triacetoxyborohydride as described in *J. Org. Chem*, 1996, 61, 3849-3862. The reaction is quenched with aqueous sodium bicarbonate and the product is extracted with an organic solvent such as ethyl acetate. The crude material is treated with di-t-butyl dicarbonate in an organic solvent such as dimethylformamide and aqueous sodium hydroxide. The resulting carbamate is purified by chromatography.

The primary alcohol product is dissolved in an organic solvent such as DCM or THF. 1,1,1-tris(acyloxy)-1,1-dihydro-1,2-benziodoxol-3-(1H)-one (Dess-Martin reagent) is added and the solution is stirred at room temperature, according to a procedure from *J. Org. Chem.*, 1984, 48, 4155-4156.

At the end of the reaction diethyl ether is added, followed by aqueous sodium hydroxide solution. The layers are separated and the organic layer is washed with aqueous sodium hydroxide solution, water, and dried over sodium sulfate. Filtration and evaporation of solvents yields the crude aldehyde product. Further purification is achieved by chromatography.

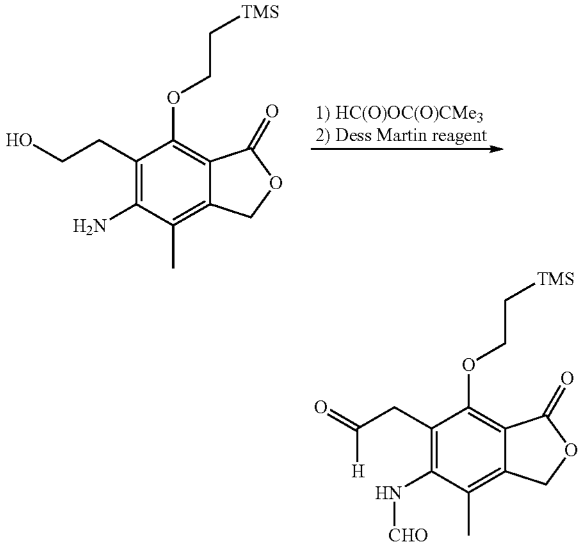

The starting material is dissolved in an organic solvent such as DCM or THF and is treated with the mixed anhydride of formic and pivalic acids, according to a procedure from *Recl. Tray. Chem. Pay-Bas,* 1982, 101, 460. At the end of the reaction, the solvent and all volatiles are removed in vacuo and the crude product is further purified by chromatography.

The product is dissolved in an organic solvent such as DCM or THF. 1,1,1-Tris(acyloxy)-1,1-dihydro-1,2-benziodoxol-3-(1H)-one (Dens-Martin reagent) is added and the solution was stirred at room temperature, according to a procedure from *J. Org. Chem.*, 1984, 48, 4155-4156. At the end of the reaction diethyl ether is added, followed by aqueous sodium hydroxide solution. The layers are separated and the organic layer is washed with aqueous sodium hydroxide solution, water, and dried over sodium sulfate. Filtration and evaporation of solvents yields the crude product. Further purification is achieved by chromatography.

Example 202

Preparation of Representative Compounds of the Invention $R_2$ Variants of Examples 200 and 201:

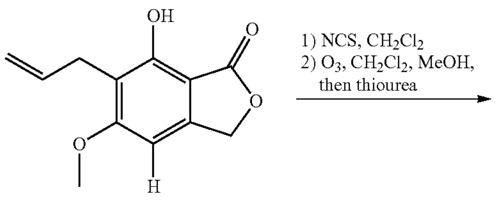

-continued

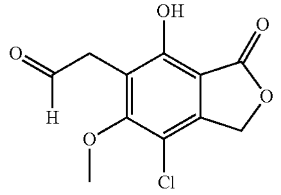

Representative compounds of the invention can be prepared as illustrated above. The starting material is dissolved in an organic solvent such as DMF and reacted with N-chlorosuccinimide, according to a procedure from *J. Med. Chem.*, 1996, 39, 4181-4196. After the starting material is consumed the reaction mixture is poured into water and the product is extracted with diethyl ether. The combined organic layers are dried over sodium sulfate. Filtration and evaporation of the solvent yields a crude reaction product.

The product of step one is dissolved in a mixture of organic solvents such as methanol, DCM, and pyridine. The solution is cooled to −78° C. and ozone is bubbled into the solution until a blue color persists. The excess ozone is removed with a nitrogen stream. The reaction mixture is warmed to room temperature and thiourea is added. Stirring at room temperature is continued. The reaction mixture is filtered and partitioned between DCM and water. The aqueous layer is extracted with DCM and the combined organic layers are washed with HCl (1 N), saturated aqueous sodium bicarbonate solution and brine. The solution is dried over sodium sulfate. Filtration and evaporation of the solvents yields the crude aldehyde. Further purification is achieved by chromatography.

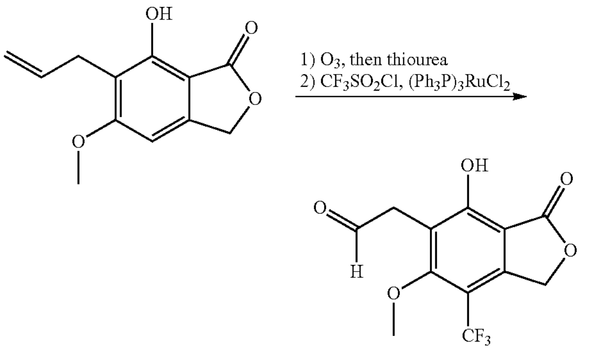

The starting material is dissolved in a mixture of organic solvents such as methanol, DCM, and pyridine. The solution is cooled to −78° C. and ozone is bubbled into the solution until a blue color persists. The excess ozone is removed with a nitrogen stream. The reaction mixture is warmed to room temperature and thiourea is added. Stirring at room temperature is continued. The reaction mixture is filtered and partitioned between DCM and water. The aqueous layer is extracted with DCM and the combined organic layers are washed with HCl (1 N), saturated aqueous sodium bicarbonate solution, and brine. The solution is dried over sodium sulfate. Filtration and evaporation of the solvents yields the crude aldehyde. Further purification is achieved by chromatography.

The product of step one is dissolved in an organic solvent such as benzene. Trifluoromethanesulfonyl chloride and dichlorotris(triphenylphosphine)rhuthenium are added and the solution is degassed. The reaction mixture is heated at 120° C., according to a procedure from *J. Chem. Soc., Perkin Trans.* 1, 1994, 1339-1346. At the end of the reaction the mixture is cooled to room temperature and the solvent is removed in vacuo. Further purification of the trifluoromethyl aldehyde product is achieved by chromatography.

Example 203

Preparation of Representative Compounds of Formula 81

Synthesis of Olefins and Linkers to Phosphonates

Representative compounds of the invention can be prepared as illustrated in the following schemes.

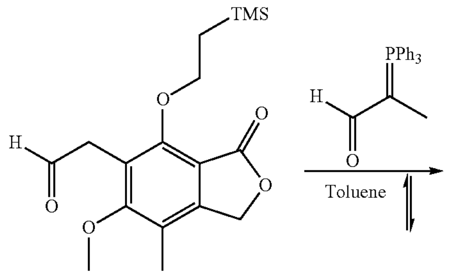

-continued

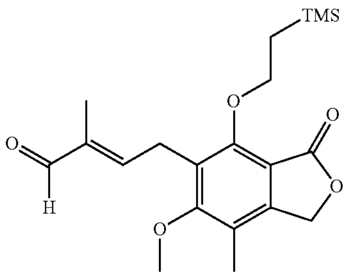

The phenacetaldehyde (5.3 g, 15.8 mmol) in toluene (50 mL) was heated at 100° C. with 2-(triphenyl-phosphanylidene)-propionaldehyde (6.8 g, 20.5 mmol) overnight. After concentration, the residue was purified by silica gel chromatography to provide 4.24 g (72%) of the unsaturated aldehyde as a pale yellow solid. $^1$H NMR (300 MHz, $CDCl_3$) δ 0.00 (s, 9H), 1.10-1.21 (m, 2H), 1.87 (s, 3H), 2.16 (s, 3H), 3.67-3.76 (m, 2H), 3.74 (s, 3H), 4.27-4.39 (m, 2H), 5.11 (s, 2H), 6.40-6.48 (m, 1H), 9.2 (s, 1H).

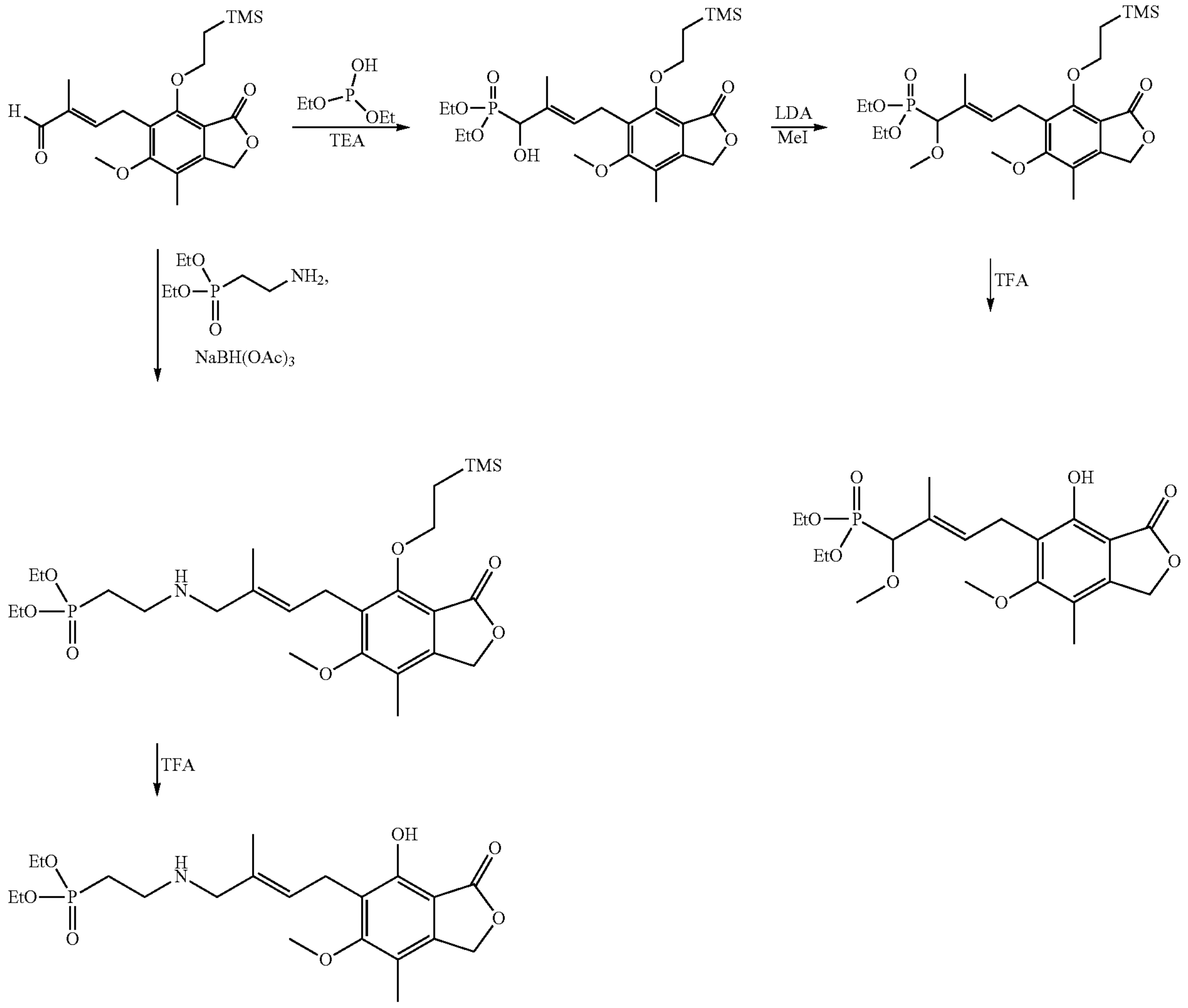

The trimethylsilyethyl protected aldehyde is treated with diethylphosphite in a solvent such as acetonitrile in the presence of a base such as triethylamine to afford the hydroxy phosphonate, according to a procedure such as that reported in *Tetrahedron,* 1995, 51, 2099. The hydroxy phosphonate is O-akylated and then the protecting group is removed by treatment with either trifluoroacetic acid or tetrabutylammonium fluoride to generate the desired methoxy phosphonate analog.

Alternatively, the aldehyde is mixed with diethyl (2-aminoethyl)phosphonate and treated with a reducing agent such as sodium triacetoxyborohydride to generate the amino phosphonate analog.

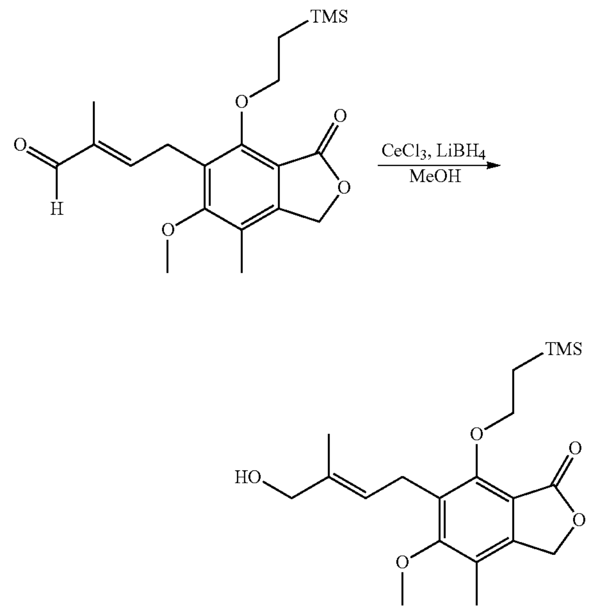

A solution of 4-[6-methoxy-7-methyl-3-oxo-4-(2-trimethylsilanyl-ethoxy)-1,3-dihydro-isobenzofuran-5-yl]-2-methyl-but-2-enal (103 mg, 0.27 mmol) in methanol (5 mL) was cooled to 0° C. A solution of $CeCl_3$ (0.68 mL, MeOH: $H_2O$, 9:1) was added, followed by $LiBH_4$ (0.14 mL, 0.28 mmol of a 2M solution in THF). The ice bath was removed and the reaction mixture was allowed to warm to room temperature. The reaction mixture was stirred for an additional 40 minutes whereupon TLC indicated complete consumption of starting aldehyde. The reaction was worked up by addition of aqueous 1N HCl (0.5 mL) and the product was extracted with $CH_2Cl_2$. The organic layer was washed with saturated aqueous sodium bicarbonate solution and brine. The organic layer was concentrated under reduced pressure and the residue was purified by silica gel chromatography to provide 100 mg (97%) of the product as a clear liquid. $^1H$ NMR (300 MHz, $CDCl_3$) δ 0.00 (s, 9H), 1.20 (dd, 2H, J=7, 8 Hz), 1.81 (s, 3H), 2.13 (s, 3H), 3.38-3.50 (m, 2H), 3.74 (s, 3H), 3.95 (s, 2H), 4.27 (dd, 2H, J=7, 8 Hz), 5.08 (s, 2H), 5.17-5.44 (m, 1H).

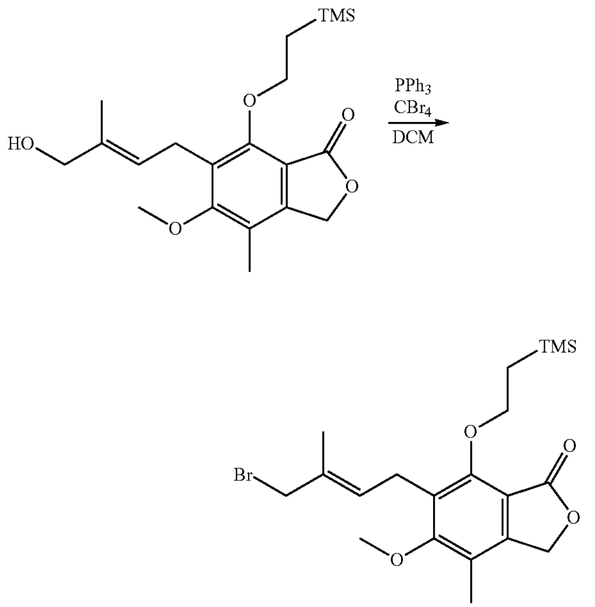

Polymer-supported triphenylphosphine is soaked in DCM for 1 hour. The allylic alcohol and carbon tetrabromide are sequentially added. When the reaction is complete, the mixture is filtered and the filtrate concentrated. The bromide is purified as necessary by chromatography.

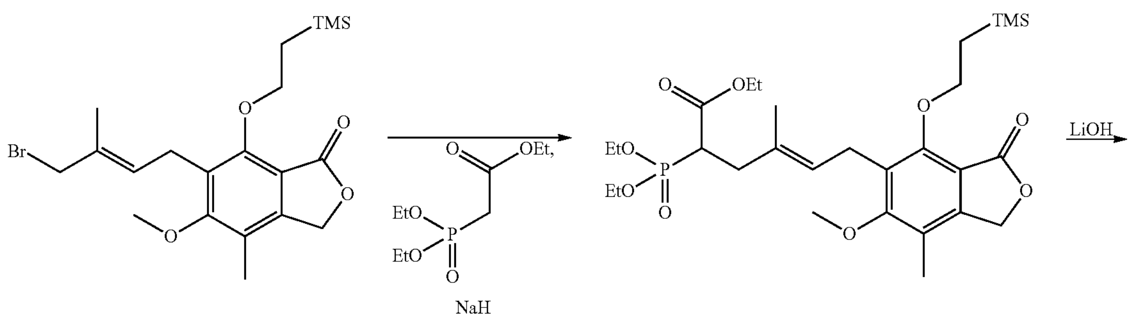

-continued

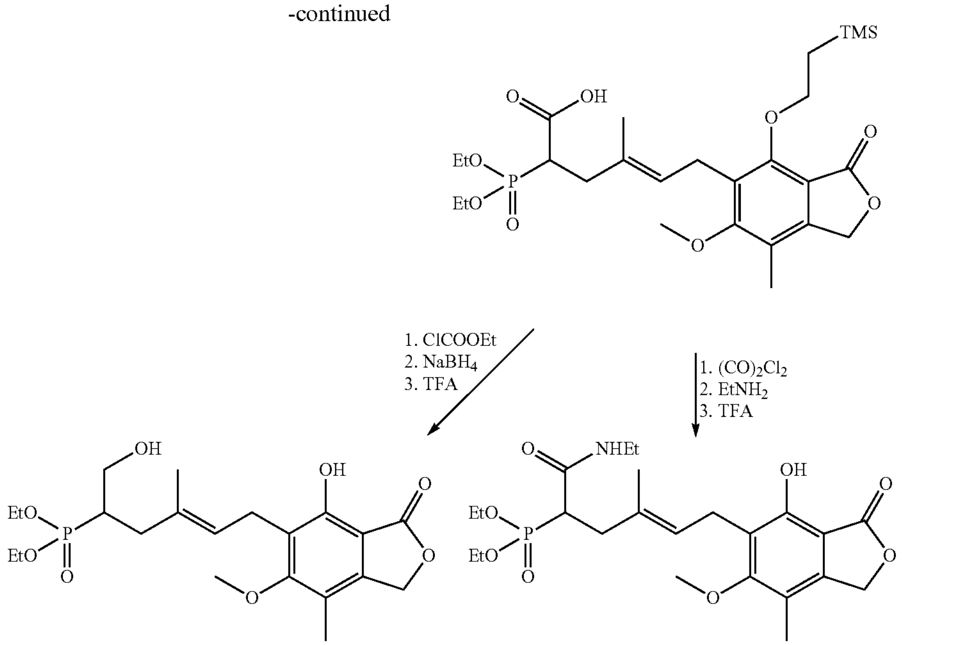

The allylic bromide is treated in an inert organic solvent such as dimethylformamide with an alkali metal salt of ethyl diethoxyphosphorylacetate (prepared by reacting ethyl diethoxyphosphorylacetate with sodium hexamethyldisilazide or sodium hydride) to afford the ethoxycarbonyl phosphonate, according to a procedure such as that described in WO 95/22538. The carboxylic ester group is converted to both the carboxylic amide and the hydroxymethyl groups according to the methods conventionally utilized for amide formations and ester reductions. For example, the carboxylic ester is saponified with aqueous lithium hydroxide. The acid is activated with ethyl chloroformate and reduced with sodium borohydride to generate, after removal of the protecting group, the hydroxymethyl phosphonate analog. The acid is also converted to its acyl chloride and then reacted with ethylamine to afford the amide analog.

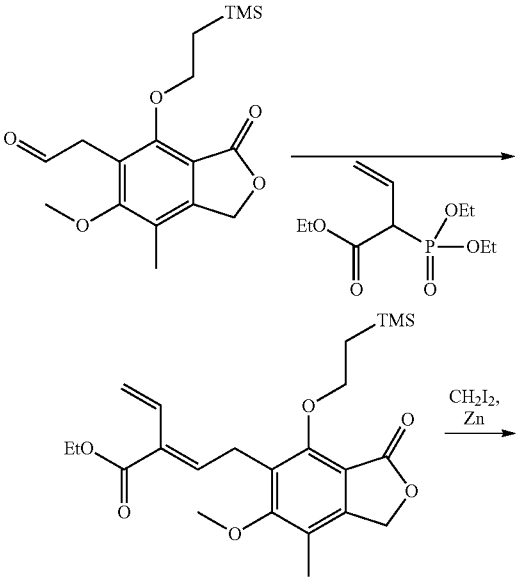

-continued

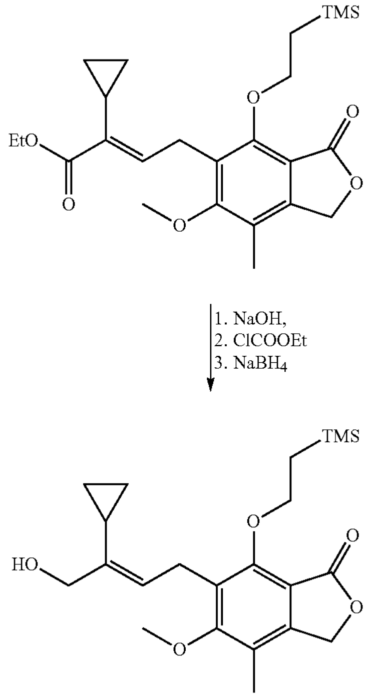

The aryl acetaldehyde is coupled with 2-(diethoxyphosphoryl)-but-3-enoic acid ethyl ester to generate the 2-vinyl substituted ester, according to a procedure such as that reported in *Synthesis,* 1999, 282. The 2-vinyl group is converted to the 2-cyclopropyl group under cyclopropanation conditions such as those described in *Tetrahedron Lett.* 1998, 39, 8621. The ester is converted to the alcohol, which, optionally, can be further subjected to reactions such as that described below to generate various phosphonate-containing mycophenolic acid analogues.

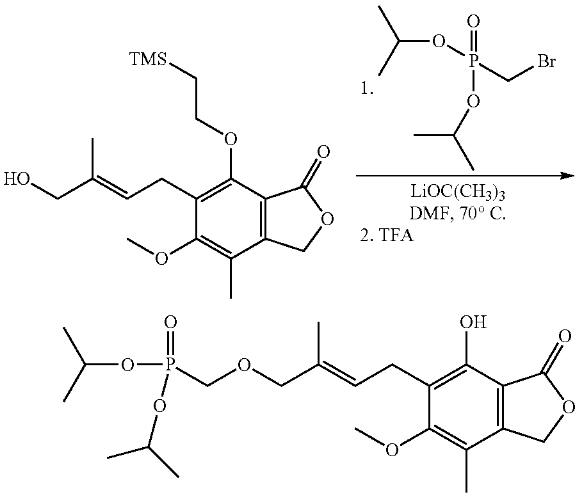

The allylic alcohol is treated with bromomethylphosphonic acid diisopropyl ester in the presence of a base such as lithium t-butoxide in a solvent such as dimethylformamide. The phenol protecting group is then removed by treatment with trifluoroacetic acid.

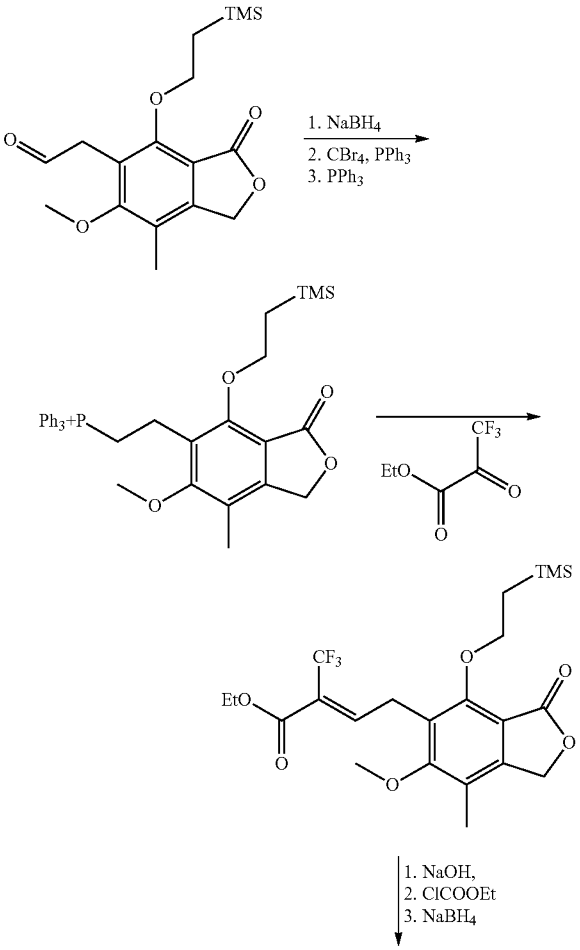

-continued

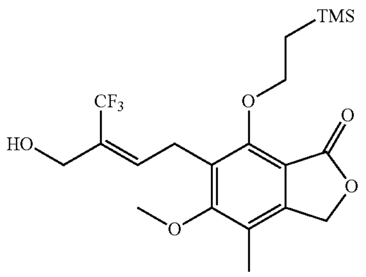

The phenacetaldehyde can alternatively be converted to the allyl phosphonium salt, according to a procedure such as that reported in *J Org. Chem.* 1987, 52, 849. The phosphonium salt is then treated with the commercially available 3,3,3-trifluoro-2-oxo-propionic acid ethyl ester and a base such as sodium hydride to generate the 2-trifluoromethyl substituted ester. The ester is converted to the alcohol, which, optionally, can be further subjected to reactions described earlier to generate mycophenolic acid analogues with various side chains containing the phosphonate group.

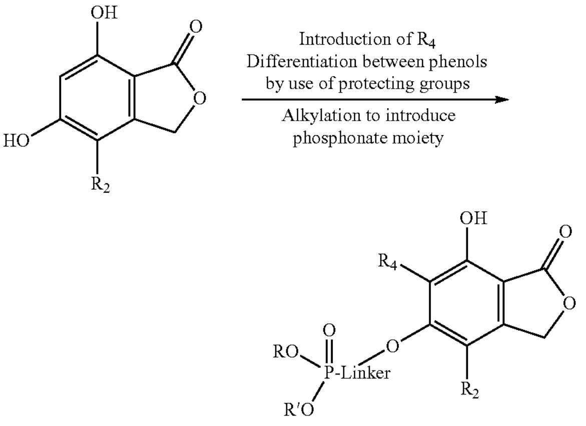

Example 204

Preparation of Representative Compounds of the Invention

Introduction of $R_4$ Variants of Examples 200-203:

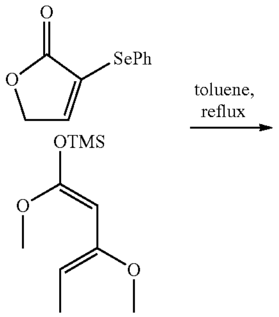

-continued

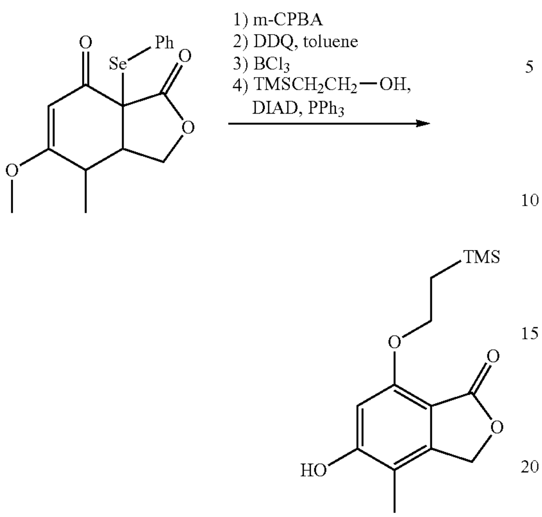

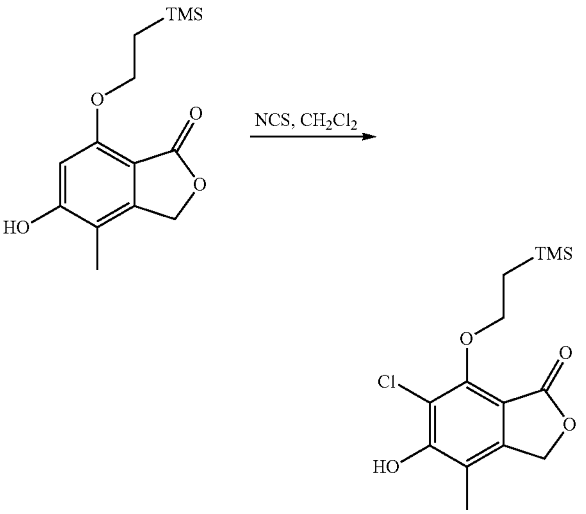

The enone (synthesis reviewed in *Tetrahedron,* 1985, 41, 4881-4889) and the diene (*Chem. Pharm. Bull.,* 1989, 37, 2948-2951) are dissolved in an organic solvent such as toluene, stirred at room temperature for 24 hours and heated to reflux for additional 5 hours, according to a procedure from *J. Med. Chem.,* 1996, 39, 4181-4196. The reaction mixture is cooled to room temperature and the solvent removed in vacuo. The crude reaction product is further purified by chromatography.

The product of step one is dissolved in an organic solvent such as DCM and m-chloroperbenzoic acid is added, according to a procedure from *J. Med. Chem.*, 1996, 39, 4181-4196. At the end of the reaction, the solution is poured into aqueous sodium hydrogen sulfite solution. The organic layer is washed with saturated aqueous sodium bicarbonate solution and is dried over sodium sulfate. Filtration and evaporation of solvents yields the crude product.

The crude product is dissolved in an organic solvent such as toluene and treated with dichlorodicyanoquinone (DDQ), according to a procedure from *J. Med. Chem.*, 1996, 39, 4181-4196. At the end of the reaction the solvent is removed in vacuo and the crude material is further purified by chromatography.

The product is dissolved in an organic solvent such as DCM and treated with boron trichloride at reflux temperature, according to a modified procedure from *J. Med. Chem.*, 1996, 39, 46-55. At the end of the reaction the solution is washed with aqueous HCl solution. The solution is dried over sodium sulfate. Removal of the solvent yields the crude reaction product. Further purification is achieved by chromatography.

The product of the previous step and triphenylphosphine are dissolved in an organic solvent such as tetrahydrofuran (THF). Diisopropylazodicarboxylate (DIAD) is added dropwise at 0° C. Stirring is continued. A solution of 2-trimethylsilyl ethanol in THF is added and stirring is continued. At the end of the reaction the solvent is removed in vacuo. The crude reaction solid is extracted with a mixture of organic solvents such as hexanes and diethylether. The washings are combined and the solvents removed in vacuo. The desired TMS protected product is further purified and separated from the undesired regioisomer by chromatography.

The starting material is dissolved in an organic solvent such as dimethylformamide (DMF) and reacted with N-chlorosuccinimide, according to a procedure from *J. Med. Chem.*, 1996, 39, 4181-4196. After the starting material is consumed the reaction mixture is poured into water and the product is extracted with diethyl ether. The combined organic layers are dried over sodium sulfate. Filtration and evaporation of the solvents yields the crude chloro-substituted product. Further purification is achieved by chromatography.

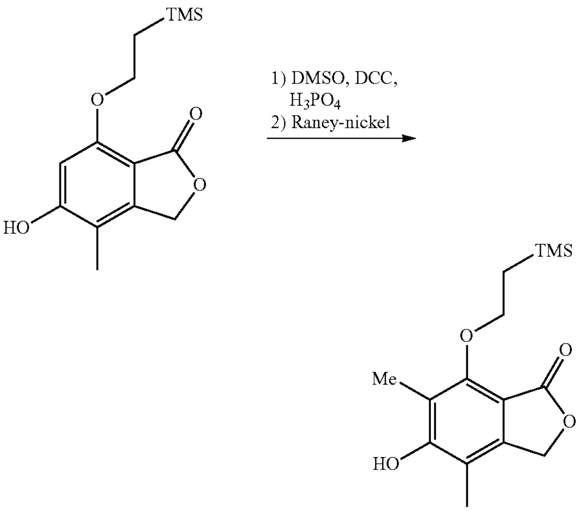

The starting material is dissolved in an organic solvent such as benzene and reacted with dimethyl sulfoxide (DMSO), dicyclohexylcarbodiimide (DCC), and orthophosphoric acid according to a procedure from *J. Am. Chem. Soc.*, 1966, 88, 5855-5866. At the end of the reaction, the suspension is filtered and the organic layer washed with aqueous sodium bicarbonate solution and dried over sodium sulfate. Filtration and evaporation of solvents yields the crude material. Further purification is achieved by chromatography.

The product of step one is dissolved in an organic solvent such as DCM or THF and treated with Raney nickel, according to procedures reviewed in *Chem. Rev.,* 1962, 62, 347-404. When all starting material is consumed, the reaction is filtered and the solvent removed in vacuo. Further purification of the dimethyl substituted product is achieved by chromatography.

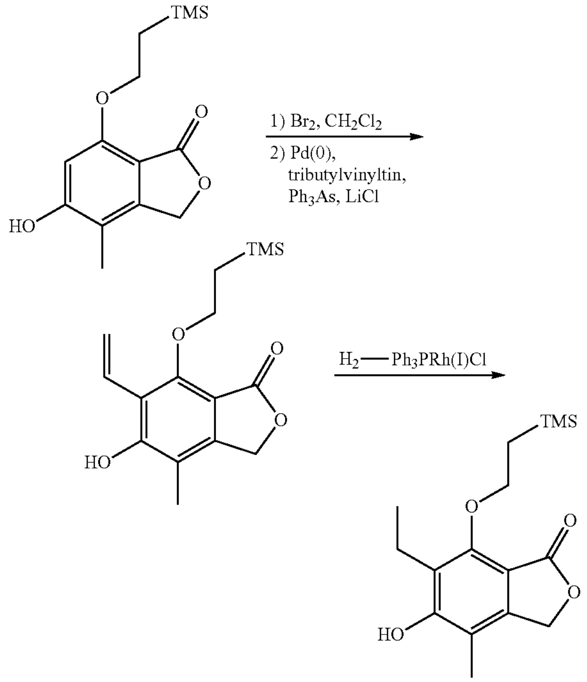

The starting material is dissolved in an organic solvent such as DCM and bromine is added, according to a procedure from *J. Med. Chem.*, 1996, 39, 4181-4196. At the end of the reaction additional DCM is added and the solution washed with aqueous sodium thiosulfate solution and brine. The organic layer is dried over sodium sulfate. Filtration and evaporation of solvents yields the crude material. Further purification is achieved by chromatography on silica gel.

The product of step one, lithium chloride, triphenylarsine, tributylvinyltin, and tris(dibenzylideneacetone)dipalladium (0)-chloroform adduct are heated in an organic solvent such as N-methylpyrrolidinone at an elevated temperature of approximately 55° C., according to a procedure from *J. Med. Chem.*, 1996, 39, 4181-4196. At the end of the reaction the mixture is cooled to room temperature and poured into a mixture of ice, potassium fluoride, water, and ethyl acetate. Stirring is continued for 1 hour. The suspension is filtered through Celite and extracted with ethyl acetate. The combined organic extracts are dried over sodium sulfate. The solvents are removed in vacuo and the crude material is further purified by chromatography.

The product of step two is dissolved in a mixture of organic solvents such as benzene and ethyl acetate. Tris(triphenylphosphine)rhodium(I) chloride is added and the reaction is placed under an atmosphere of hydrogen, according to a procedure from *J. Med. Chem.*, 1996, 39, 4181-4196. The solvents are removed in vacuo and the crude reaction is filtered through silica gel. Further purification of the 6-ethyl substituted compound is achieved by chromatography.

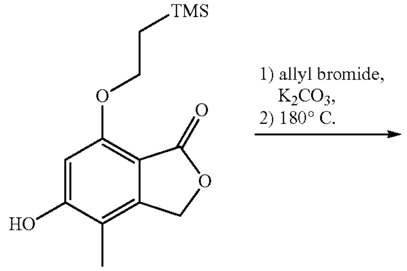

-continued

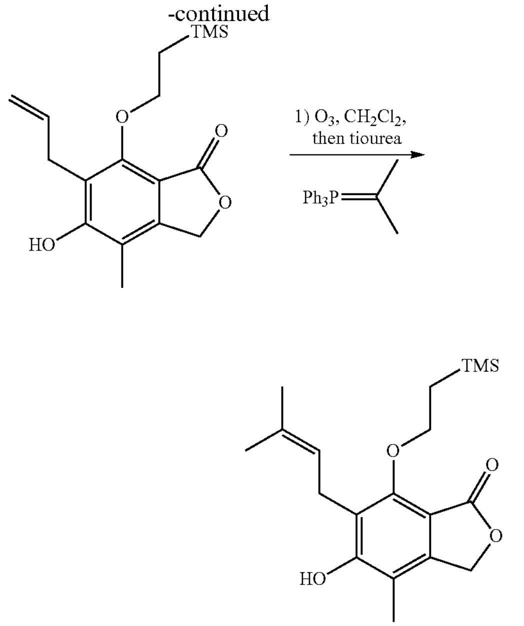

The starting material is dissolved in an organic solvent such as DMF. Potassium carbonate and allyl bromide are added and stirring at room temperature is continued, according to a procedure from *J. Med. Chem.*, 1996, 39, 4181-4196. After all the starting material is consumed, aqueous HCl solution and diethyl ether are added and the organic layer is collected and the solvent is removed in vacuo.

The crude material from step one is dissolved in N,N-diethylaniline and the reaction mixture is heated at an elevated temperature of ca. 180° C. At the end of the reaction the mixture is cooled to room temperature and poured into a mixture of aqueous HCl (2N) and ethyl actetate. The organic layer is washed with aqueous HCl (2N) and dried over sodium sulfate. Filtration and removal of the allyl compound and solvents yields the crude product. Further purification is achieved by chromatography.

The product of step 2 is dissolved in a mixture of organic solvents such as methanol, DCM, and pyridine. The solution is cooled to −78° C. and ozone is bubbled into the solution until a blue color persists. The excess ozone is removed with a nitrogen stream. The reaction mixture is warmed to room temperature and thiourea is added. Stirring at room temperature is continued. The reaction mixture is filtered and partitioned between DCM and water. The aqueous layer is extracted with DCM and the combined organic layers are washed with HCl (1 N), saturated aqueous sodium bicarbonate solution and brine. The solution is dried over sodium sulfate. Filtration and evaporation of the solvents yields the crude aldehyde. Further purification is achieved by chromatography.

The aldehyde is dissolved in an organic solvent such as THF and is reacted with triphenylphosphonium sec-propyl bromide and potassium tert-butoxide, according to procedures reviewed in *Chem. Rev.*, 1989, 89, 863-927. At the end of the reaction the solvent is removed in vacuo and the crude material purified by chromatography to give the 2-methylbut-2-enyl derivative.

Example 205

Preparation of Representative Compounds of Formula

Introduction of Linkers to Phosphonates:

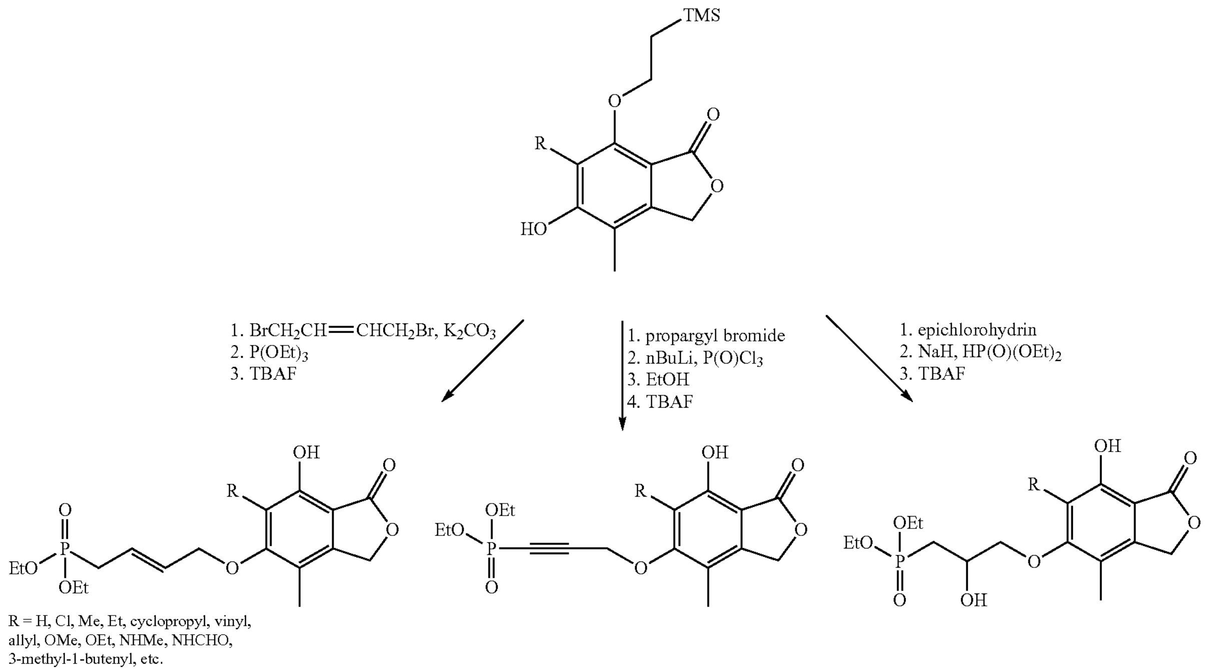

Representative compounds of the invention can be prepared as illustrated above. The phenols shown in herein may optionally be alkylated with the reagent of choice. Optionally, the phosphonate moiety will be part of such a reagent; alternatively it will be introduced in a subsequent step by a variety of means, of which three are illustrated above. For example, an alkyl halide may be heated with triethylphosphite in a solvent such as toluene (or other Arbuzov reaction conditions: see Engel, R., *Synthesis of Carbon-Phosphorus Bonds*, CRC Press, 1988). Alternatively, an epoxide may be reacted with the anion of a dialkyl phosphinate. In a further example, the phosphonate reagent may be the electrophile; for example, an acetylide anion may be condensed with phosphorus oxychloride and the intermediate dichlorophosphonate quenched with ethanol to generate the diethyl ester of the desired phosphonic acid.

Example 206

Preparation of Representative Compounds of Formula 81

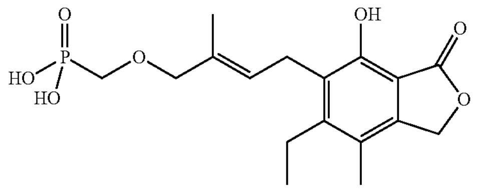 [SMILES: CCc1c(C)c2c(c(O)c1C/C=C(\C)COCP(=O)(O)O)C(=O)OC2]

[4-(6-Ethyl-4-hydroxy-7-methyl-3-oxo-1,3-dihydro-isobenzofuran-5-yl)-2-methyl-but-2-enyloxymethyl]-phosphonic acid this product was prepared using methods similar to those described for. Examples 156 and 181. MS (negative mode): 369.3 [$M^+$−1].

Example 207

Preparation of Representative Compounds of Formula 81

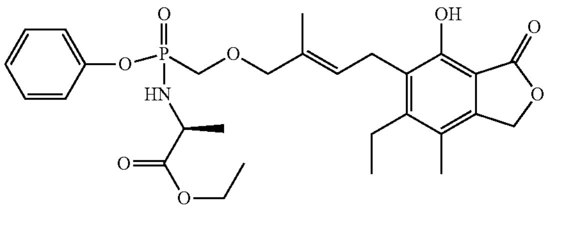 [SMILES: CCOC(=O)[C@H](C)NP(=O)(COC/C(C)=C/Cc1c(O)c2c(c(C)c1CC)COC2=O)Oc1ccccc1]

2-{[4-(6-Ethyl-4-hydroxy-7-methyl-3-oxo-1,3-dihydro-isobenzofuran-5-yl)-2-methyl-but-2-enyloxymethyl]-phenoxy-phosphinoylamino}-propionic acid ethyl ester using methods similar to those described for Example 165, the desired product was prepared starting from material analogous to the compound of Example 193. MS (positive mode): 546.3 [$M^+$+1] & 568.3 [$M^+$+Na]

Example 208

Preparation of Representative Compounds of Formula 81

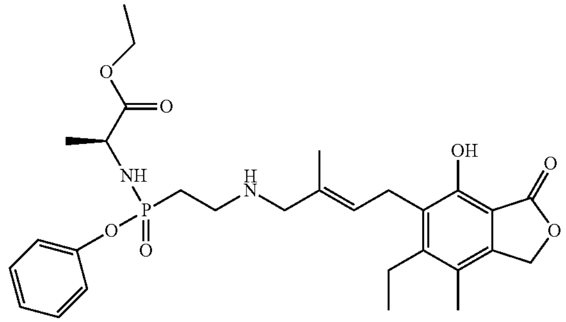 [SMILES: CCOC(=O)[C@H](C)NP(=O)(CCNC/C(C)=C/Cc1c(O)c2c(c(C)c1CC)COC2=O)Oc1ccccc1]

2-({2-[4-(6-Ethyl-4-hydroxy-7-methyl-3-oxo-1,3-dihydro-isobenzofuran-5-yl)-2-methyl-but-2-enylamino]-ethyl}-phenoxy-phosphinoylamino)-propionic acid ethyl ester this product was prepared using methods analogous to those described for Examples 173 and 193, using 2-[(2-amino-ethyl)-phenoxy-phosphinoylamino]-propionic acid ethyl ester in the reductive amination step. MS (positive mode): 559.4 [$M^{+}$+1] & 581.3 [$M^{+}$+Na].

Example 209

Preparation of Representative Compounds of Formula 81

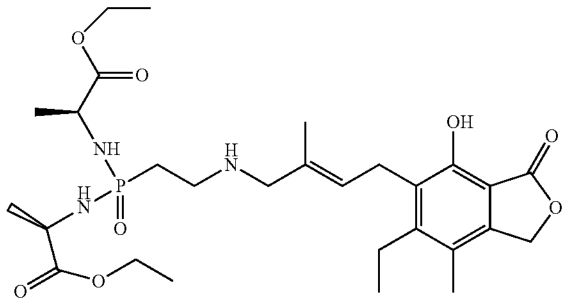 [SMILES: CCOC(=O)[C@H](C)NP(=O)(CCNC/C(C)=C/Cc1c(O)c2c(c(C)c1CC)COC2=O)N[C@H](C)C(=O)OCC]

2-((1-Ethoxycarbonyl-ethylamino)-{2-[4-(6-ethyl-4-hydroxy-7-methyl-3-oxo-1,3-dihydro-isobenzofuran-5-yl)-2-methyl-but-2-enylamino]-ethyl}-phosphinoylamino)-propionic acid ethyl ester this product was prepared by methods analogous to those described for Examples 183, 184, and 187 using 2-[(2-amino ethyl)-(1-ethoxyc arbonyl-ethylam ino)-pho sphinoyl amino]-propionic acid ethyl ester in the reductive amination step. MS (positive mode): 582.4 [$M^{+}$+1] & 604.3 [$M^{+}$+Na].

Example 210

Preparation of Representative Compounds of Formulae 87 and 88

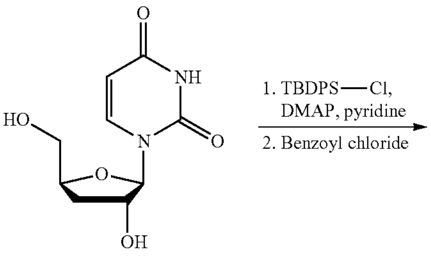

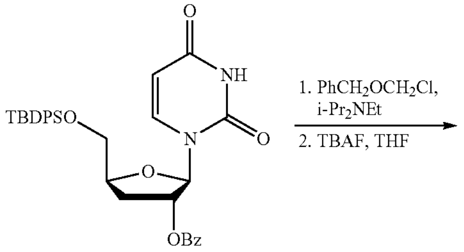

210.1

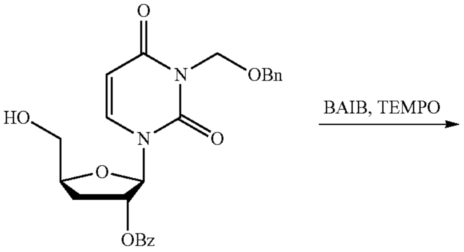

210.2

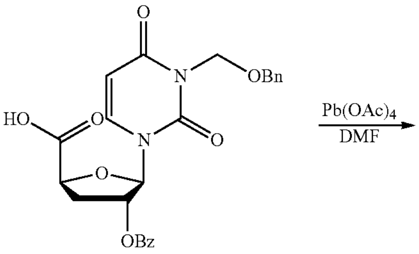

210.3

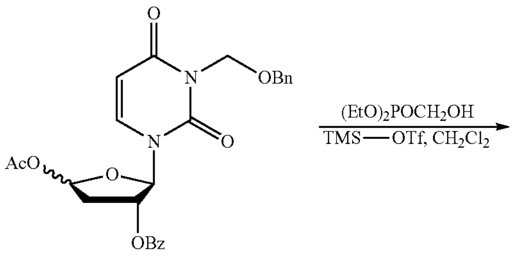

210.4

-continued

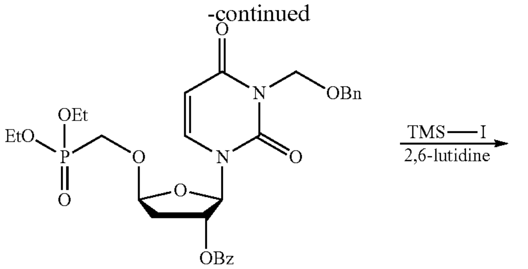

210.5a

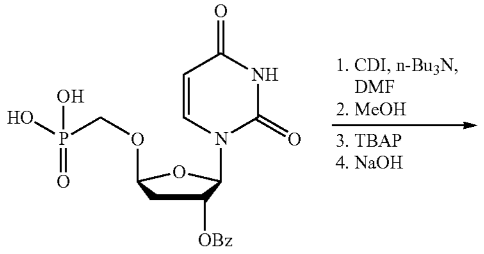

210.6

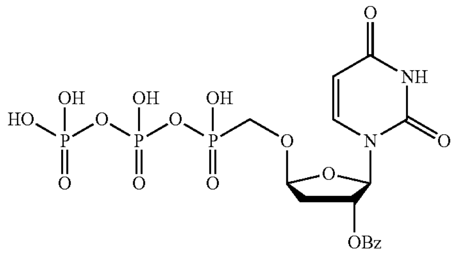

210.7

Compound 210.1

210.1

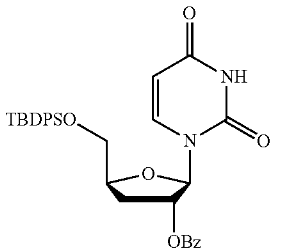

Synthesis of 210.1: To a solution of 3'-deoxyuridine (995 mg, 4.36 mmol) in 8 mL of anhydrous pyridine was added t-butyldiphenylsilyl chloride (TBDPS-Cl, 1.38 g, 5.01 mmol), and 4-dimethylaminopyridine (DMAP, 27 mg, 0.22 mmol). The mixture was stirred at 23° C. for 14 hours and then cooled to 0° C. in a ice-water bath. To this mixture was added benzoyl chloride (735 mg, 0.61 mL, 5.2 mmol). The mixture was warmed to 23° C. and stirred for another 2 hours. The mixture was concentrated in vacuo to give a paste, which was partitioned between water and ethyl acetate. The aqueous later was extracted once with ethyl acetate. The combined ethyl acetate layer was washed sequentially with 1 M aqueous citric acid, saturated sodium bicarbonate, and brine. It was dried over anhydrous sodium sulfate and concentrated in vacuo to give a crude product as a yellow oil. Purification by silica gel chromatography (15-65% ethyl acetate in hexane) gave a colorless oil. Yield 1.35 g (54%). $^1H$ NMR (DMSO-d6): δ 11.38 (s, 1H), 8.01 (d, J=7.9 Hz, 2H), 7.77 (d, J=8.2 Hz, 1H), 7.70-7.40 (m, 13 H), 5.99 (s, 1H), 5.58 (m, 1H), 7.34 (d, J=8.2 Hz, 1H), 4.47 (m, 1H), 4.03 (m, 1H), 3.84 (m, 1H), 2.43 (m, 1H), 2.21 (m, 1H), 1.03 (s, 9H) ppm. MS (m/z) 571.1 ($M+H^+$), 593.3 ($M+Na^+$).

Compound 210.2

210.2

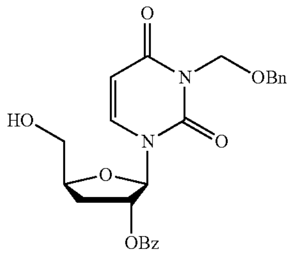

Synthesis of 210.2: To a solution of 210.1 (1.31 g, 2.3 mmol) in 5 mL of anhydrous N,N-dimethylformamide was added benzyl chloromethyl ether (0.54 g, 3.45 mmol), N,N-diisopropylethylamine (446 mg, 0.60 mL, 3.45 mmol). The mixture was stirred at 23° C. for 4 hours. Water was added. The mixture was extracted with ethyl acetate. The organic layer was washed sequentially with 1 M aqueous citric acid, saturated sodium bicarbonate, and brine. It was dried over anhydrous sodium sulfate and concentrated in vacuo to give a crude product as a yellow oil, which was used in the next step without further purification.

The crude product obtained above was dissolved in 9 mL of THF. The solution was cooled to 0° C. A 1 M solution of TBAF (4.6 mL, 4.6 mmol) was added via syringe. The mixture was warmed to 23° C. and stirred for another 2 hours. An additional 2.3 mL of 1 M TBAF was added. The mixture was stirred for another 2 hours at 23° C. Saturated aqueous ammonium chloride was added to the solution. The mixture was evaporated in vacuo to remove most of THF. The aqueous phase was extracted with ethyl acetate. The aqueous layer was washed with brine. It was then dried over anhydrous sodium sulfate and concentrated in vacuo to give a crude product as a yellow oil. Purification by silica gel chromatography (30-80% ethyl acetate in hexane) gave a white solid. Yield of 210.2: 805 mg (77% for two steps). $^1H$ NMR (DMSO-d6): δ 8.04 (m, 3H), 7.67 (t, J=7.3 Hz, 1H), 7.55 (t, J=7.6 Hz, 2H), 7.30 (m, 5H), 5.98 (s, 1H), 5.78 (d, J=7.9 Hz, 1H), 5.55 (m, 1H), 5.31 (s, 2H), 5.22 (m, 1H), 4.57 (s, 2H), 4.41 (m, 1H), 3.80 (m, 1H), 3.60 (m, 1H), 2.31 (m, 1H), 2.15 (m, 1H) ppm. MS (m/z) 453.1 ($M+H^+$), 475.3 ($M+Na^+$).

Compound 210.3

210.3

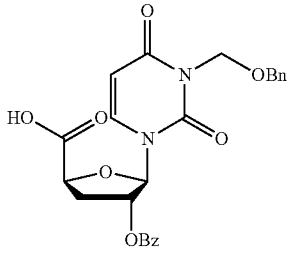

Synthesis of 210.3: To a solution of 210.2 (800 mg, 1.77 mmol) in 3.5 mL of a 1:1 mixture of acetonitrile/water was added iodobenzene diacetate (1.25 g, 3.89 mmol), and TEMPO (55 mg, 0.35 mmol). The mixture was stirred at 23° C. for 14 hours. The mixture was then froze in a −78° C. bath and lyophilized to give a solid residue. This residue was purified by silica gel chromatography (0-15% methanol in dichloromethane). Product 210.3 was obtained as a white solid. Yield: 735 mg (89%). $^{1}$H NMR (DMSO-d6): δ 8.13 (d, J=7.6 Hz, 1H), 8.03 (d, J=7.7 Hz, 2H), 7.68 (m, 1H), 7.58 (t, J=7.0 Hz, 2H), 7.29 (m, 5H), 6.04 (s, 1H), 5.85 (d, J=8.3 Hz, 1H), 5.62 (m, 1H), 5.31 (s, 2H), 4.87 (m, 1H), 4.58 (s, 2H), 2.40-2.20 (m, 2H) ppm. MS (m/z) 467.1 (M+H$^{+}$), 489.3 (M+Na$^{+}$).

Compound 210.4

210.4

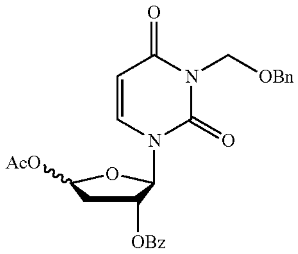

Synthesis of 210.4: To a deoxygenated solution of 210.3 (730 mg, 1.57 mmol) and pyridine (0.51 mL, 6.26 mmol) in 7 mL of anhydrous DMF, was added lead tetraacetate (3.47 g, 7.83 mmol). The mixture was stirred at 23° C. for 14 hours shielded from light. The mixture was diluted with 15 mL of ethyl acetate and 10 mL of water. This mixture filtered through a pad of Celite and separated. The aqueous phase was extracted with another 10 mL of ethyl acetate. The combined ethyl acetate extract was washed with brine, dried over sodium sulfate, and evaporated in vacuo to give the crude product as an oil. The crude product 210.4 was purified by silica gel chromatography (10-50% ethyl acetate in hexane). Products of two diastereomers were obtained as a white foam. Yield: 400 mg (53%). $^{1}$H NMR (DMSO-d6): δ 8.01 (m, 2H), 7.82-7.63 (m, 2H), 7.57 (m, 2H), 7.31 (m, 5H), 6.58 (m, 1H), 6.17 (m, 1H), 5.83 (m, 1H), 5.65 (m, 1H), 5.31 (s, 2H), 4.59 (s, 2H), 2.76 and 2.28 (m, 1H), 2.10 (m, 1H), 2.07 (s, 3H) ppm. MS (m/z) 481.0 (M+H$^{+}$), 503.3 (M+Na$^{+}$).

Compound 210.5a and 210.5b 210.5a

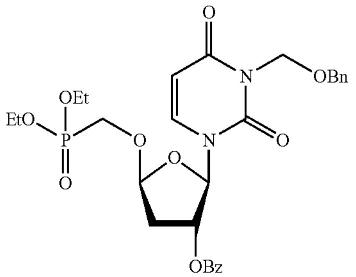

-continued 210.5b

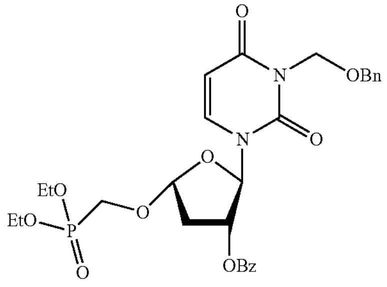

Synthesis of 210.5a: To a solution of 210.4 (300 mg, 0.63 mmol) in 6 mL of anhydrous dichloromethane was added diethyl hydroxymethyl-phosphonate (0.37 mL, 2.5 mmol), followed by trimethylsilyl trifluoromethanesulfonate (0.34 mL, 1.88 mmol). The mixture was stirred at 23° C. for 6 hours. Triethylamine (0.44 mL, 3.15 mmol) was added, followed by water. The mixture was extracted with ethyl acetate. The organic layer was washed with 1 M aqueous citric acid, saturated sodium bicarbonate, and brine. It was then dried over anhydrous sodium sulfate, and evaporated in vacuo to give a residue. This crude product was purified by silica gel chromatography (75-95% ethyl acetate in hexane) to give two products, which were diastereomers of each other shown above (210.5a and 210.5b). Yield of 210.5a: 53 mg (14%). Yield of 210.5b: 129 mg (35%).

Analytical data for 210.5a: $^{1}$H NMR (Acetonitrile-d3): δ 8.04 (d, J=7.0 Hz, 2H), 7.77 (d, J=7.9 Hz, 1H), 7.69 (t, J=7.5 Hz, 1H), 7.53 (m, 2H), 7.33 (m, 5H), 6.38 (d, J=4.0 Hz, 1H), 5.80 (d, J=8.2 Hz, 1H), 5.63 (m, 1H), 5.52 (m, 1H), 5.41 (s, 2H), 4.64 (s, 2H), 4.17 (m, 4H), 4.08 (dd, J=13.8, 10.1 Hz, 1H), 3.92 (dd, J=13.7, 9.5 Hz, 1H), 2.66-2.42 (m, 2H), 1.35 (t, J=7.0 Hz, 6H) ppm. MS (m/z) 589.2 (M+H$^{+}$), 611.3 (M+Na$^{+}$). Stereochemistry of 210.5a was confirmed by additional 2D NMR experiments.

Analytical data for 210.5b: $^{1}$H NMR (Acetonitrile-d3): δ 8.08 (d, J=7.3 Hz, 2H), 7.69 (t, J=7.5 Hz, 1H), 7.55 (m, 2H), 7.43 (d, J=8.2 Hz, 1H), 7.36 (m, 5H), 6.11 (d, J=2.4 Hz, 1H), 5.77 (d, J=8.3 Hz, 1H), 5.57 (m, 2H), 5.41 (s, 2H), 4.66 (s, 2H), 4.12 (m, 5H), 3.88 (dd, J=14.0, 5.2 Hz, 1H), 2.82 (m, 1H), 2.25 (m, 1H), 1.27 (t, J=7.0 Hz, 6H) ppm. MS (m/z) 589.0 (M+H$^{+}$), 611.2 (M+Na$^{+}$).

Compound 210.6

210.6

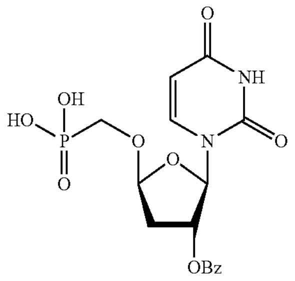

Synthesis of 210.6: To a solution of 210.5a (110 mg, 0.19 mmol) in 3 mL of acetonitrile was added 2,6-lutidine (0.43 mL, 3.74 mmol), followed by iodotrimethylsilane (0.53 mL, 3.74 mmol). After stirring at 23° C. for 30 min, the mixture was heated to 40° C. and stirred at that temperature for another 4 hours. The reaction mixture was cooled to 23° C.

Triethylamine (0.52 mL, 3.74 mmol) was added, followed by water (10 mL). The aqueous mixture was extracted twice with 5 mL of diethyl ether. The resulting aqueous solution was frozen in a −78° C. bath and was lyophilized to give a yellow solid. This crude product was purified by reversed phase HPLC to give 210.6 as a light yellow solid. Yield 26 mg (34%). MS (m/z) 411.3 ($M-H^-$).

Compound 210.7

210.7

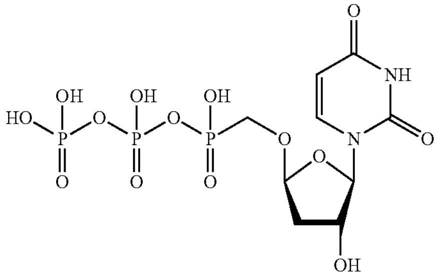

Synthesis of 210.7: Phosphonate 210.6 (12 mg, 0.029 mmol), carbonyldiimidazole (47 mg, 0.29 mmol), and tri-n-butylamine (5.4 mg, 0.029 mmol) were dissolved in 0.3 mL of anhydrous dimethylformamide (DMF). The mixture was stirred at 23° C. for 4 hours. MeOH (0.020 mL) was added and the mixture was stirred for another 30 minutes. A solution of tributylammonium pyrophosphate (159 mg, 0.29 mmol) in 0.63 mL of anhydrous DMF was added. The resulting mixture was stirred at 23° C. for 14 hours. The mixture was evaporated in vacuo to remove most of the DMF. The residue was dissolved in 5 mL of water and was purified by ion-exchange chromatography (DEAE-cellulose resin, 0-50% triethylammonium bicarbonate in water) to give a white solid, which was used directly in the next reaction.

The product obtained above was dissolved in 2 mL of water. A 0.3 mL of a 1 M solution of sodium hydroxide in water was added. The mixture was stirred at 23° C. for 40 min. Acetic acid was added to adjust the pH of the solution to 5. The solution was diluted with water and purified with an ion-exchange column (DEAE-cellulose resin, 0-50% triethylammonium bicarbonate in water) to give diphosphophosphonate 210.7 as a white solid, which is the triethylammonium salt of the structure shown above. Yield 10 mg (45% for two steps). $^1$H NMR ($D_2O$): δ 7.79 (d, J=7.6 Hz, 1H), 5.89 (m, 1H), 5.85 (d, J=7.6 Hz, 1H), 5.41 (m, 1H), 4.49 (m, 1H), 4.02-3.65 (m, 2H), 3.06 (m, 18H), 2.20 (m, 2H), 1.14 (m, 27H) ppm. $^{31}$P NMR ($D_2O$): δ 7.46 (d, 1P), −9.45 (d, 1P), −23.11 (t, 1P) ppm. MS (m/z) 467.0 ($M-H^-$).

Compound 210.8

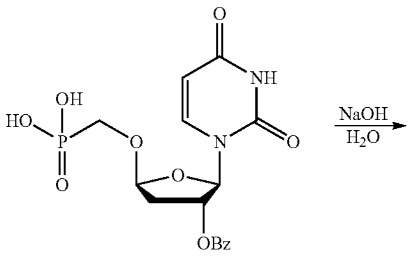

210.6

-continued

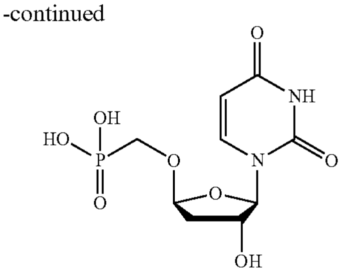

210.8

Synthesis of 210.8: To a solution of 210.6 (16 mg, 0.039 mmol) in 0.4 mL of water was added NaOH (7.8 mg, 0.19 mmol). The solution was stirred at 23° C. for 1 hour. Acetic acid (0.012 mL) was added to the solution. The mixture was then purified by reversed phase HPLC (eluted with 100% water) to give 4.6 mg of 210.8 as a white solid (38% yield). $^1$H NMR ($D_2O$): δ 7.83 (d, J=8.3 Hz, 1H), 5.86 (d, J=3.4 Hz, 1H), 5.82 (d, J=7.9 Hz, 1H), 4.48 (m, 1H), 3.68 (m, 1H), 3.37 (m, 1H), 2.16 (m, 2H) ppm. $^{31}$P NMR ($D_2O$): δ 12.60 (s, 1P) ppm. MS (m/z) 615.1 ($2M-H^-$).

Example 211

Preparation of Representative Compounds of Formula 89

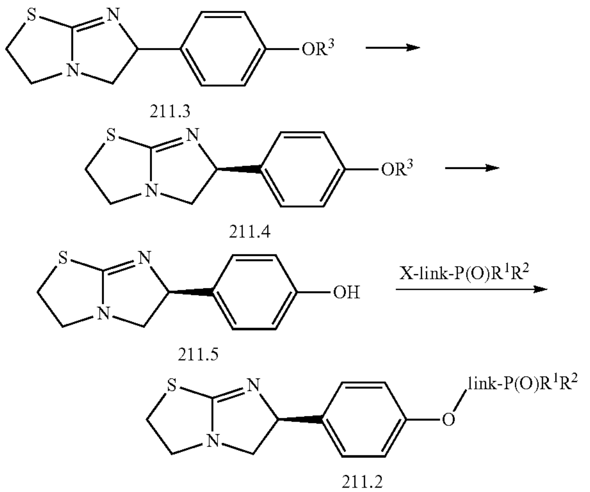

211.3

211.4

211.5

211.2

Representative compounds of the invention can be prepared as illustrated above. Analogs attached to the 4-position of levamisole of the type 211.2 are prepared from the R$^3$-protected starting material 211.3. Following resolution of the enantiomers, the protecting group is cleaved and the appropriate phosphonate is alkylated on to the phenol 211.5.

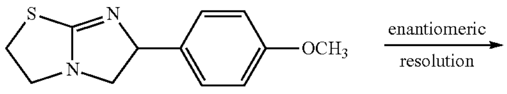

211.6

-continued

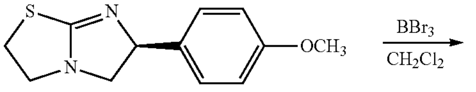

211.7

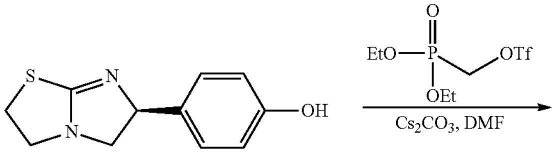

211.5

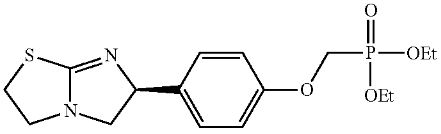

211.8

As an example, the racemic methyl ether 211.6 is synthesized by a published procedure (*J. Med. Chem.* 1966, 9, 545-551). The desired enantiomer 211.7 is resolved between a chiral solid and an achiral supercritical fluid phase (*Tetrahedron: Asymmetry* 1999, 10, 1275-1281). After reaction with $BBr_3$, phenol 211.5 is furnished. Final alkylation with diethyl phosphomethyltriflate affords the desired phophonate 211.8.

Example 212

Preparation of Representative Compounds of Formulae 90 and 93

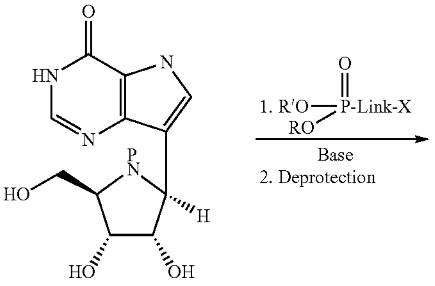

212.2

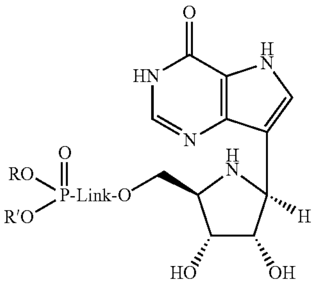

212.1

Representative compounds of the invention can be prepared as illustrated above. Triol 212.2 can be selectively alkylated with an appropriate phosphonate-containing alkylating agent. Deprotection of nitrogen affords phosphonate 212.1.

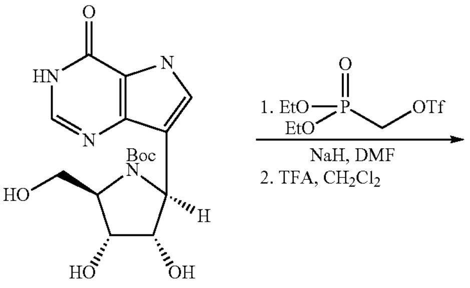

212.3

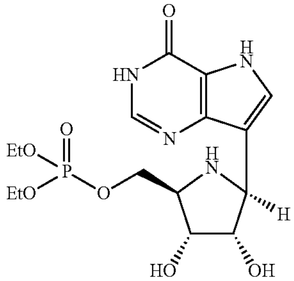

212.4

A specific compound of Formula 90 or 93 can be prepared as illustrated above. The Boc-protected (1S)-1-(9-deazaguanin-9-yl)-1,4-dideoxy-1,4-imino-D-ribitol, compound 212.3, is prepared by stirring the (1 S)-1-(9-deazaguanin-9-yl)-1,4-dideoxy-1,4-imino-D-ribitol (WO 99/19338 and Evans, G. B. et al., *Tetrahedron,* 2000, 56, 3053, also reported in Evans, G. B. et al., *J. Med. Chem.* 2003, 46, 3412) with BOC anhydride as described in Greene, T., *Protective Groups In Organic Synthesis*, Wiley-Interscience, 1999. Compound 212.3 is then treated in a solvent such as tetrahydrofuran or dimethylformamide with a base such as sodium hydride. When bubbling ceases, diethyl phosphonomethyltriflate (prepared according to *Tetrahedron Lett.*, 1986, 27, 1477) is added, yielding the desired phosphonate 212.4 after deprotection of the BOC group using trifluoroacetic acid (TFA).

Example 213

Preparation of Representative Compounds of Formulae 91, 92, 94, and 95

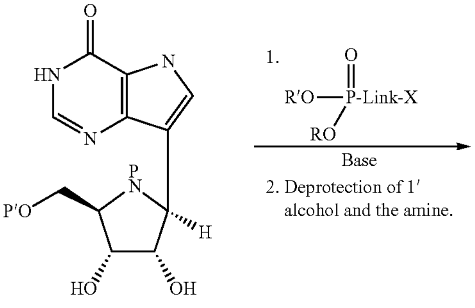

213.1

-continued

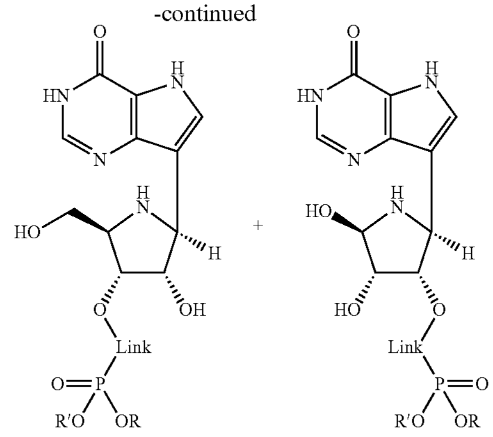

213.2 213.3

Representative compounds of the invention can be prepared as illustrated above. The primary alcohol of triol 213.1 can be selectively alkylated with an appropriate phosphonate-containing alkylating agent. Deprotection of nitrogen affords phosphonates 213.2 and 213.3.

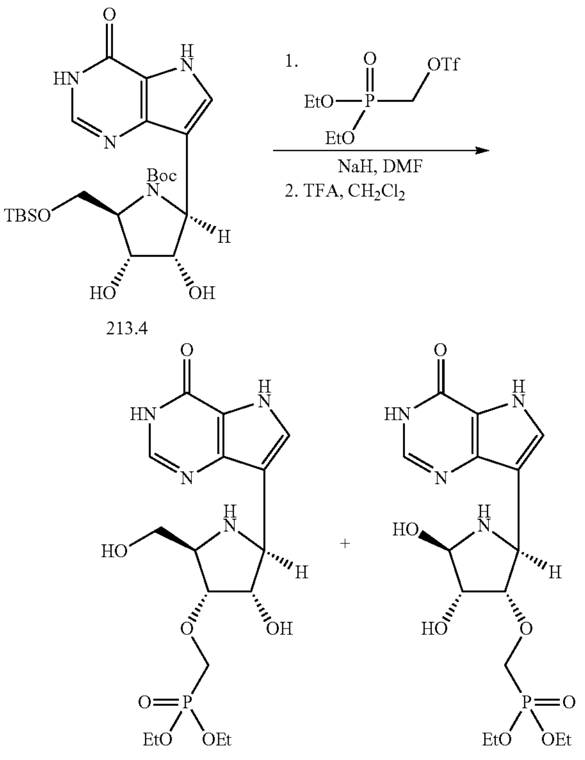

213.4

213.5 213.6

Specific compounds of Formulae 91, 92, 94, and 95 can be prepared as illustrated above. The Boc-protected (1S)-1-(9-deazaguanin-9-yl)-1,4-dideoxy-1,4-imino-D-ribitol, compound 213.4, is prepared by stirring the (1S)-1-(9-deazaguanin-9-yl)-1,4-dideoxy-1,4-imino-D-ribitol (WO 99/19338 and Evans, G. B. et al., *Tetrahedron,* 2000, 56, 3053, also reported in Evans, G. B. et al., *J. Med. Chem.* 2003, 46, 3412) with BOC anhydride as described in Greene, T., *Protective groups in organic synthesis*, Wiley-Interscience, 1999. Subsequent protection of the primary alcohol using a TBS group can be achieved using TBSCl and imidazole in solvents such as $CH_2Cl_2$ as described in Greene, *Protective Groups In Organic Synthesis*, Wiley-Interscience, 1999, to provide compound 213.4. Compound 213.4 is then treated in a solvent such as tetrahydrofuran or dimethylformamide with a base such as sodium hydride. When bubbling ceases, diethyl phosphonomethyltriflate (prepared according to *Tetrahedron Lett.*, 1986, 27, 1477) is added, yielding a mixture of the desired phosphonate diester 213.5 and 213.6 after deprotection of the BOC group using trifluoroacetic acid (TFA). Compounds 213.5 and 213.6 can be also prepared via a more complicated 2'-OH protected analog of 213.4 followed by alkylation using the diethyl phosphonomethyltriflate to provide compound 213.5 exclusively. Compound 213.6 can also be prepared by installation of a different protecting group at the 3'-OH position, followed by deprotection of 2'-OH and alkylation with diethyl phosphonomethyltriflate at the 2'-center followed by global deprotection.

Example 214

Preparation of Representative Compounds of Formula 96

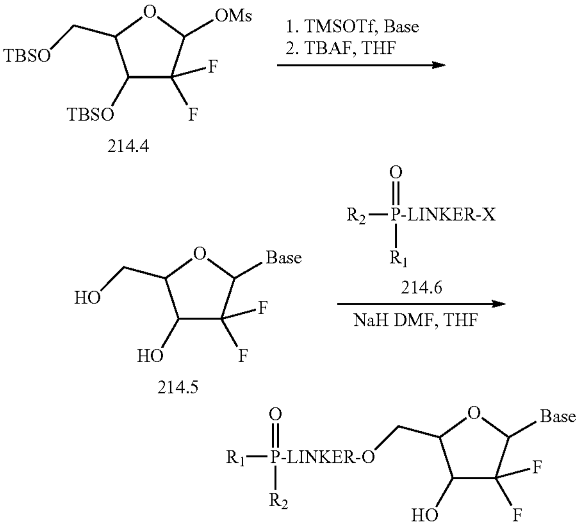

214.4 214.5 214.2

For example:
X = Cl, Br, I, OMs, OTs, OTf
where $R_1$ = Alkyl, Aryl
$R_1$ = H, alkyl, aryl, haloalkyl, alkenyl, aralyl, aryl
$R_2$ = H, alkyl, aryl, haloalkyl, alkenyl, aralyl, aryl
Bases = thymine, adenine, guanine, cytosine, uracil, inosine, diaminopurine.
Bases requiring protecting groups are to be suitably protected using protecting groups and conditions well known to thoses skilled in the art Representative compounds of the invention can be prepared as illustrated above. The desired phosphonate substituted analogs are prepared by reaction of intermediate 214.5 (obtained as described in U.S. Pat. No. 5,464,826) with the respective alkylating reagents 214.6. Illustrated above is the preparation of phosphonate linkage to 2'2'-difluoronucleosides through the 5'-hydroxyl group. The appropriately protected base as described in U.S. Pat. No. 5,464,826 is dissolved in a solvent such as DMF, THF and is treated with a phosphonate reagent bearing a leaving group, for example, bromine, mesyl, tosyl, or trifluoromethanesulfonyl in the presence of a suitable organic or inorganic base.

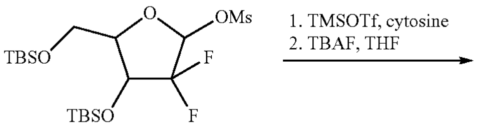

214.4

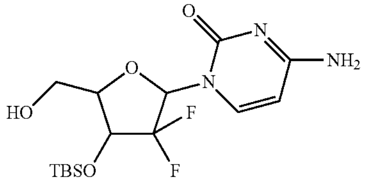

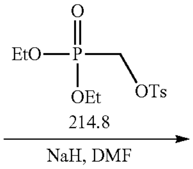

214.8

214.1

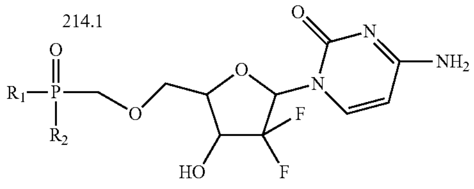

214.9

For instance, 214.1 (obtained as described in U.S. Pat. No. 5,464,826) dissolved in DMF, is treated with two equivalents of sodium hydride and one equivalent of (toluene-4-sulfonyl-methyl)-phosphonic acid diethyl ester 214.8, prepared according to the procedures in *J. Org. Chem.* 1996, 61, 7697, to give the corresponding phosphonate 214.9 in which the linkage is a methylene group. Using the above procedure but employing different phosphonate reagents 214.6 in place of 214.8 the corresponding products 214.2 bearing different linking groups are obtained.

Example 215

Preparation of Representative Compounds of Formula 97

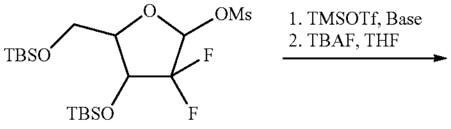

215.4

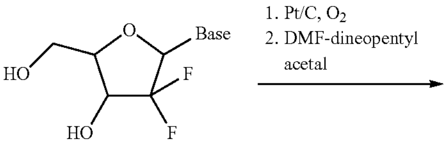

215.5

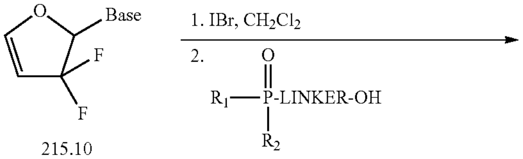

215.10

215.11

$R_1$ = H, alkyl, aryl, haloalkyl, alkenyl, aralyl, aryl $R_2$ = H, alkyl, aryl, haloalkyl, alkenyl, aralyl, aryl -continued

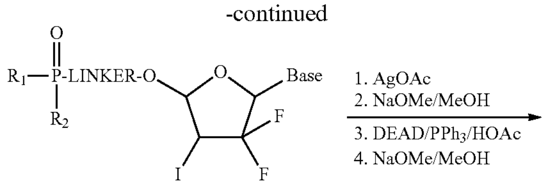

215.12

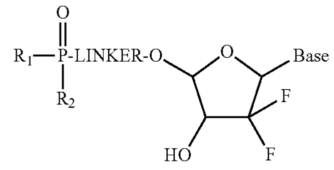

215.3

Representative compounds of the invention can be prepared as illustrated above. Compounds 215.5 containing a variety of suitably protected bases as cited and prepared according to U.S. Pat. No. 5,464,826, can be converted to glycal 215.10 according to the process reported in *J. Am. Chem. Soc.* 1972, 94, 3213. Glycal 215.10 is then treated with IBr in the presence of alcohol 215.11 to provide intermediate 215.12 (see *J. Org. Chem.* 1991, 56, 2642). The iodide of intermediate 215.12 can be treated with AgOAc to provide the corresponding acetate, which is deacetylated in the presence of catalytic sodium methoxide in methanol. Treatment of the resulting alcohol with DEAD and $PPh_3$ in the presence of acetic acid, followed by another deprotection with catalytic sodium methoxide in methanol will provide intermediate 215.3. The phosphonates of intermediates 215.3 can then be converted into their final desired forms.

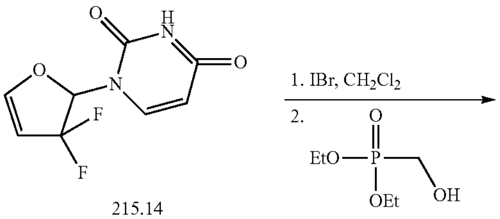

215.14

215.8

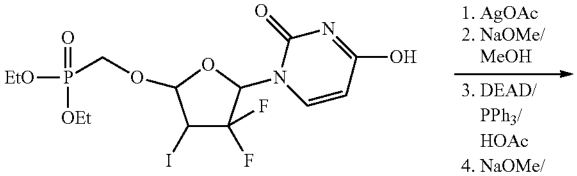

215.15

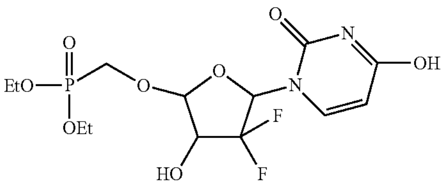

215.16

For instance, glycal 215.14 is prepared according to the procedures cited above (U.S. Pat. No. 5,464,826; *J. Am. Chem. Soc.* 1972, 94, 3213). Glycal 215.14 is then treated with IBr in the presence of diethyl phosphonomethanol, 215.8, to provide intermediate 215.15 (see *J. Org. Chem.* 1991, 56, 2642). Intermediate 215.15 is then treated with AgOAc followed by deprotection with catalytic NaOMe in MeOH. This compound is then converted into 215.16 by a Mitsunobu reaction with DEAD/$PPh_3$ and HOAc in THF, followed by a second catalytic NaOMe/MeOH deprotection. Base conversion of uracil to cytosine is carried out prior to the acetyl deprotection using the procedures in *Bioorg. Med. Lett.* 1997, 7, 2567. At any point in the synthesis sequence where it is appropriate, the phosphonate group may be converted into the phsophonate with the desired substitution. Using the above procedure but employing different phosphonate reagents 215.11 in place of 215.8 the corresponding products 215.3 bearing different linking groups are obtained.

Example 216

Preparation of Representative Compounds of Formula 98 imepodib analog 216.2 is synthesized from parent compounds by alkylation. Merimepodib (216.1) is obtained by the procedure as described in U.S. Pat. No. 6,054,472 and U.S. Pat. No. 6,344,465. Shown above is the procedure for the synthesis of 216.2. Methoxy group of merimepodib (216.1) is demethylated to the phenolic OH using a suitable reagent, such as boron tribromide. The phosphonate moiety is introduced to the phenolic OH in a suitable aprotic solvent such as, DMF by treatment with the phosphonate reagent 216.7, bearing a leaving group, for example, bromine, mesyl, tosyl, or trifluoromethanesulfonyl, in the presence of a suitable organic or inorganic base.

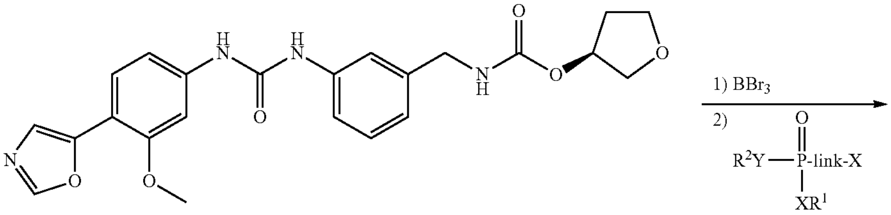

216.1

216.7

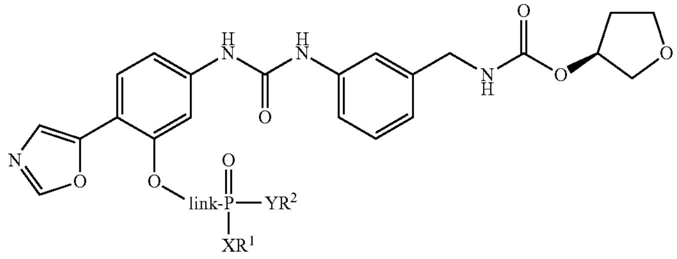

216.2

Representative compounds of the invention can be prepared as illustrated above. The phosphorus containing mer-

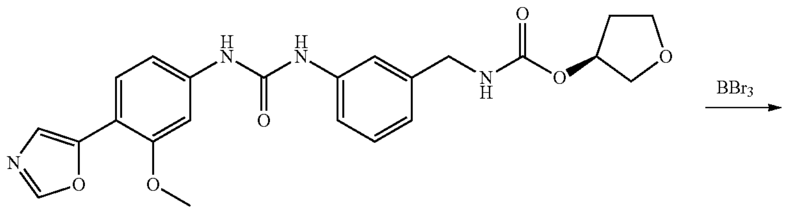

216.1

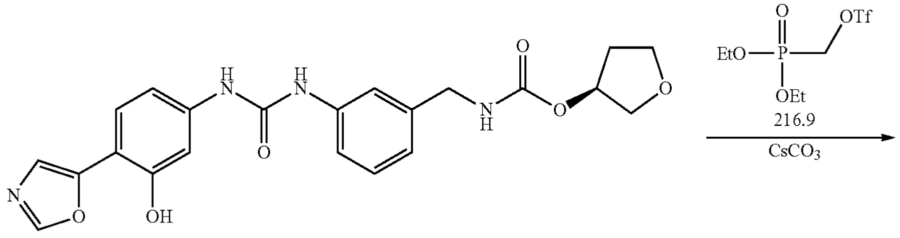

216.8

-continued

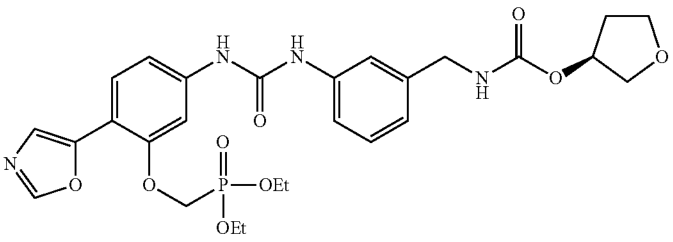

216.10

For instance, a solution of 216.1 in dichloromethane is treated with boron tribromide to obtain the demethylated compound 216.8. Compound 216.8 is then treated with cesium carbonate and one equivalent of (trifluoromethanesulfonyloxy)methylphosphonic acid diethyl ester 216.9 to give merimepodib-phosphonate 216.10 in which the linkage is a methylene group as shown above. Using the above procedure but employing different phosphonate reagents 216.7, the corresponding products 216.2 bearing different linking group can be obtained.

Example 217

Preparation of Representative Compounds of Formulae 99 and 100

Representative compounds of the invention can be prepared as illustrated above. The imidazole containing intermediate 217.13 is synthesized from an aldehyde 217.12 by the procedure of Shih in *Tetrahedron Lett*. 1993, 34, 595. Compound 217.12 is prepared by a two-step procedure described in U.S. Pat. Nos. 5,807,876, 6,054,472, and 6,344,465. The imidazole is protected using suitable reagent, for example 2-(trimethylsilyl)ethyoxymethyl (SEM) chloride, and the compound 217.14 is converted to 217.15 by the similar procedure described for the synthesis of 216.1 in U.S. Pat. Nos. 6,054,472 and 6,344,465. After the protecting group on the imidazole of 217.15 is removed, the phosphonate containing moiety is introduced to the imidazole as shown below.

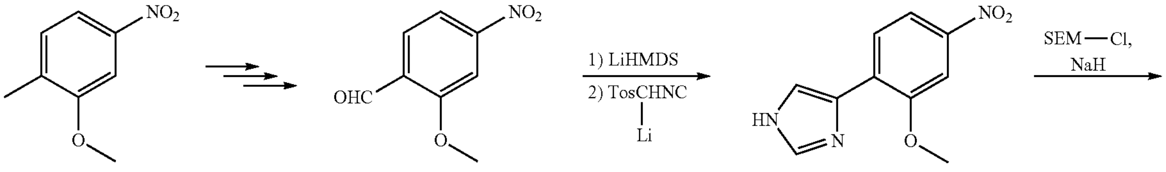

217.11 217.12 217.13

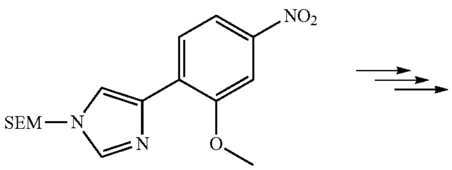

217.14

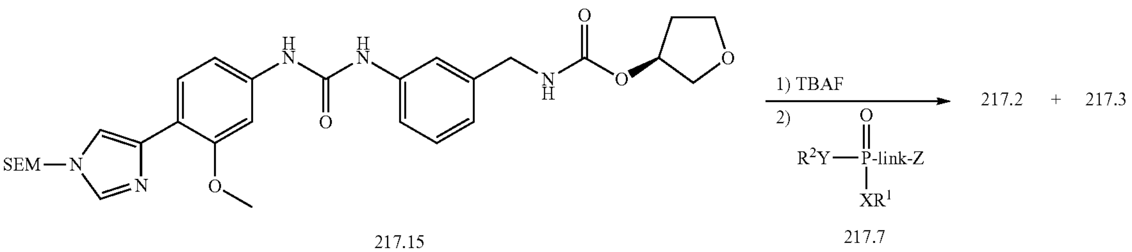

217.15 217.7

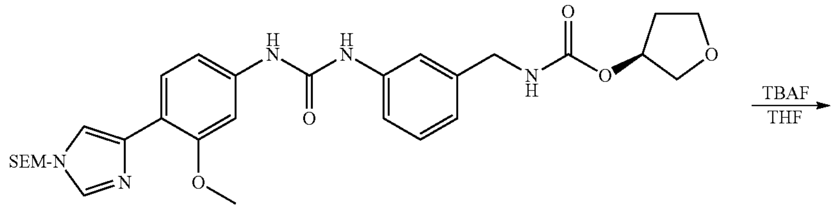
217.15
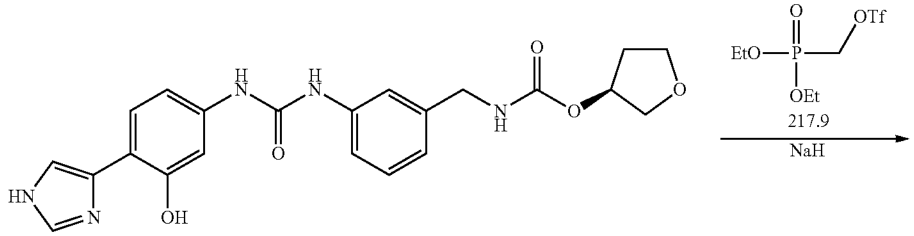
217.16
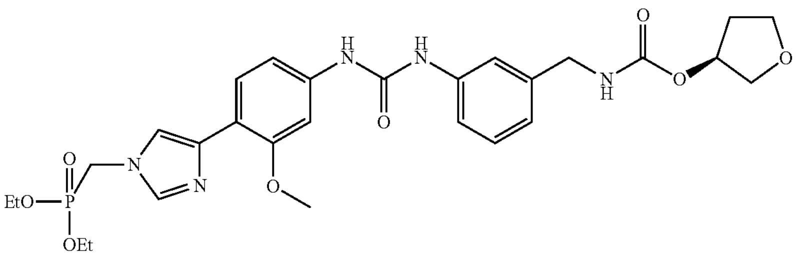
217.17
+
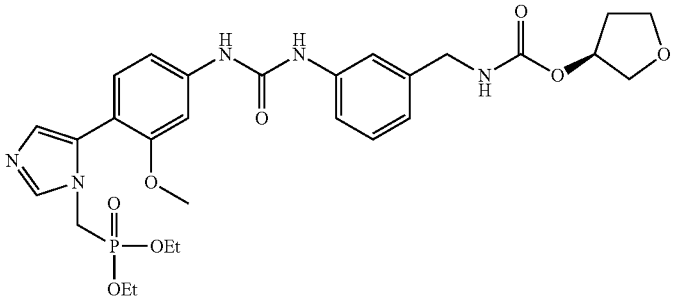
217.18
For example, compound 217.15 is treated with tetrabutylammonium fluoride in THF under refluxing conditions and the resulting 217.16 is alkylated with 217.9 using sodium hydride as a base to obtain the two isomers 217.17 and 217.18, which are separated by chromatography.

Example 218

Preparation of Representative Compounds of Formula 101

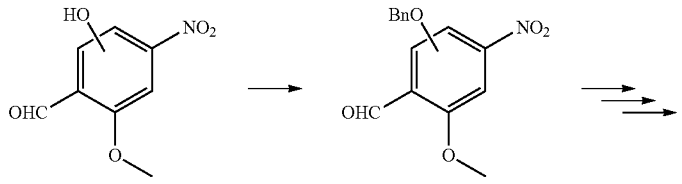

218.19 218.20

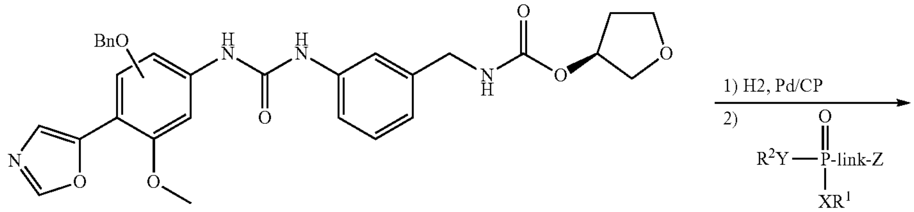

218.21 218.7

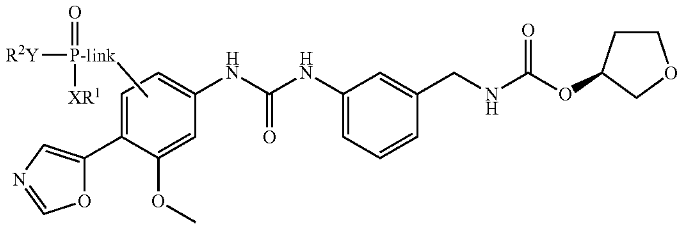

218.5

Representative compounds of the invention can be prepared as illustrated above. Illustrated above is the preparation of merimepodib analog 218.5. Tetrasubstituted benzene derivatives are obtained by literature procedures (Ichikawa and Ichibagase *Yakugaku Zasshi* 1963, 83, 103; Norio, A. et al. *Tetrahedron Lett.* 1992, 33(37), 5403). After the phenolic OH is protected with a suitable protecting group, for example benzyl group, the compound 218.21 is synthesized by the same procedure of the synthesis of 216.1 as described in U.S. Pat. Nos. 6,054,472, and 6,344,465. After the protecting group is removed, the phosphonate containing moiety is introduced to the phenolic OH using the phosphonate reagent 218.7, bearing a suitable leaving group.

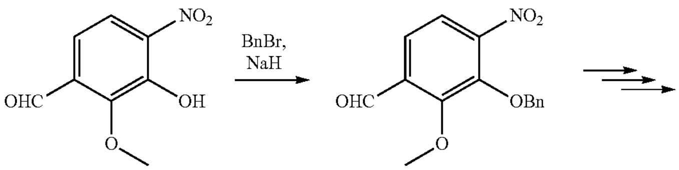

218.22 218.23

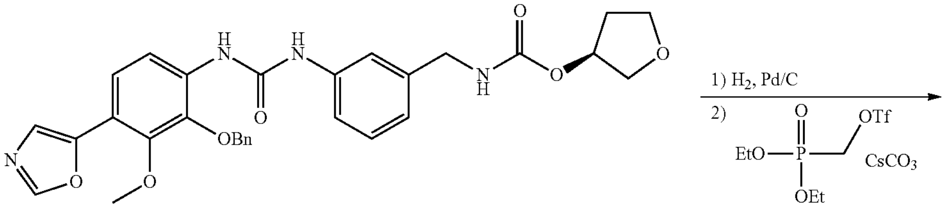

218.24 218.9

-continued

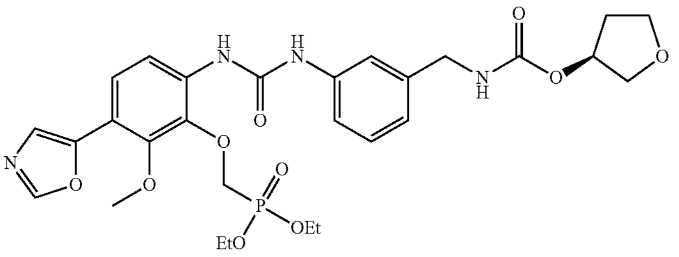

218.25

For example, a solution of 218.22, which is obtained by the procedure of Norio et al. (*Tetrahedron Lett*. 1992, 33(37), 5403), is treated with sodium hydride and one equivalent of benzyl bromide in DMF to get 218.23. Compound 218.23 is converted to 218.24 by a series of steps reported in U.S. Pat. Nos. 6,054,472, and 6,344,465 for the synthesis of 216.1 from 217.12. After the benzyl protecting group of 218.24 is removed by catalytic hydrogenation, a phosphonate bearing moiety is attached by alkylation of the resulting phenol in DMF using sodium hydride and one equivalent of (trifluoromethanesulfonyloxy)methylphosphonic acid diethyl ester 218.7 to give 218.25.

Example 219

Preparation of Representative Compounds of Formula 102

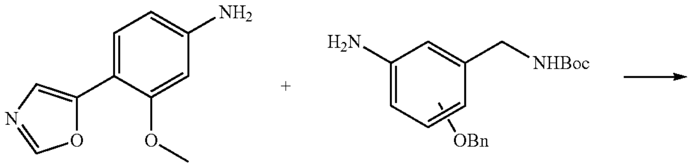

219.26 219.27

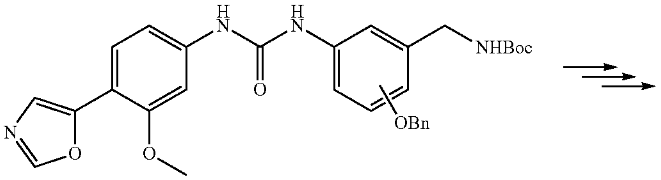

219.28

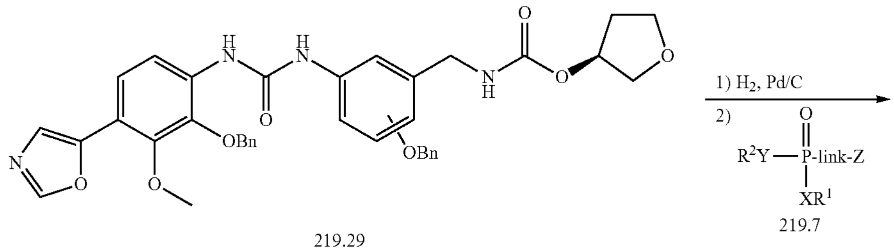

219.29

219.7

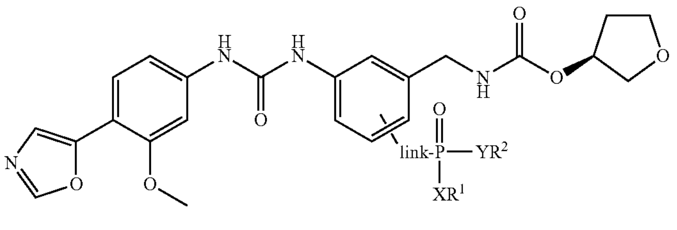

219.6

Representative compounds of the invention can be prepared as illustrated above. Synthesis of merimepodib analog 219.6 is shown above. Compound 219.26, an intermediate in the synthesis of 216.1, is treated with carbonyldiimidazole or triphosgene followed by the compound 219.27, which has an handle to attach phosphonate moiety. Compound 219.27 bearing an extra substituent is synthesized from the tri substituted phenol with cyano and nitro groups, which is either commercially available or can be prepared by literature procedures (Zolfigol, M. A. et. al. *Indian J. Chem. Sect. B* 2001, 40, 1191; De Jongh, R. O. et al. *Recl. Trav. Chim. Pays-Bas* 1968, 87, 1327). The resulting 219.28 is converted to 219.29 using the procedure described in U.S. Pat. No. 6,054,472, and U.S. Pat. No. 6,344,465 for the synthesis of 216.1. The phosphonate moiety of 219.6 is attached after deprotection of the benzyl group of 219.29:

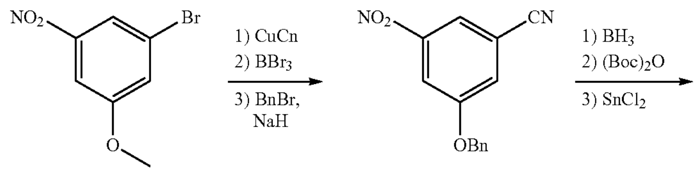

219.30

219.31

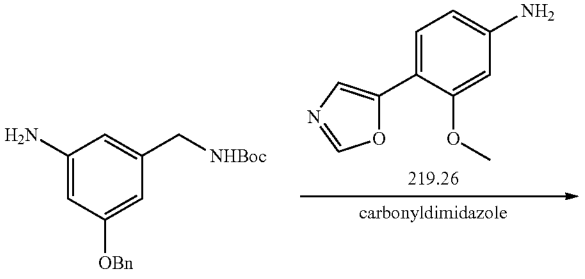

219.32

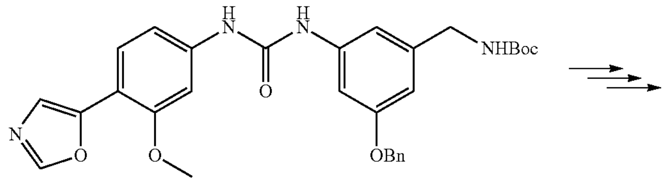

219.33

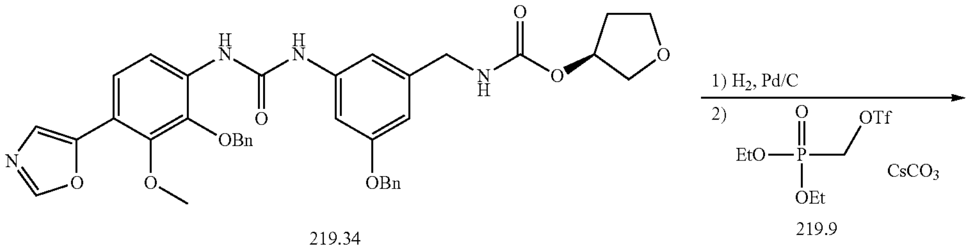

219.34

219.9

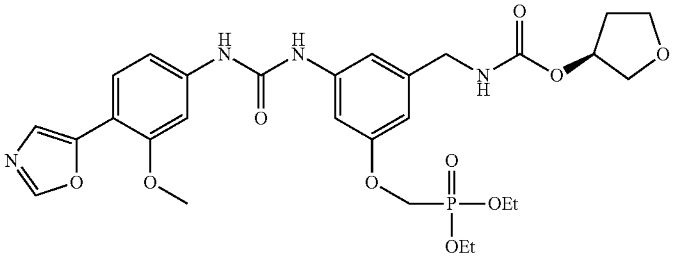

219.35

For example, the bromine substituent of compound 219.30 is substituted with cyano group by the procedure of De Jongh, R. O. et al. (*Recl. Trav. Chim. Pays-Bas* 1968, 87, 1327) and the methoxy group is converted to benzyloxy group as a protecting group, which affords compound 219.31. After selective reduction of cyano to aminomethyl group by borane, the amino group is protected with Boc group and then the reduction of the nitro group using tin (II) chloride generates compound 219.32. This substituted aniline 219.32 is then treated with a reaction mixture of the compound 219.26 and carbonyldiimidazole, as described for the synthesis of 216.1 in U.S. Pat. Nos. 6,054,472, and 6,344,465, to form the urea 219.33. Compound 219.33 is easily converted to 219.34, analog of 216.1 bearing benzyloxy group. Deprotection of the benzyl group using catalytic hydrogenation followed by attachment of a phosphonate moiety using 219.9 in the presence of cesium carbonate produces 219.34.

Example 220

Synthesis of Exemplary Compounds of the Invention

Scheme 518-1

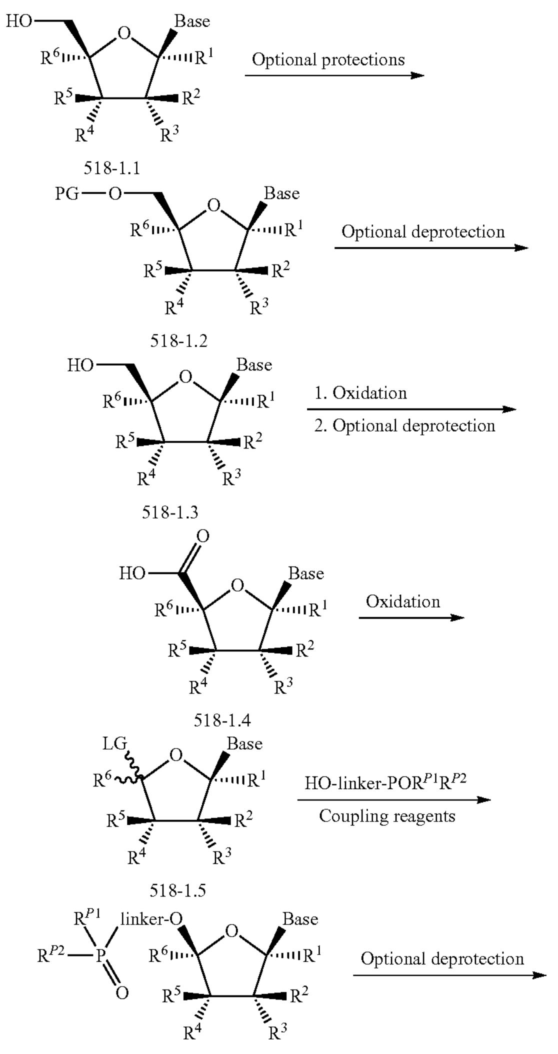

518-1.1

518-1.2

518-1.3

518-1.4

518-1.5

518-1.6

-continued

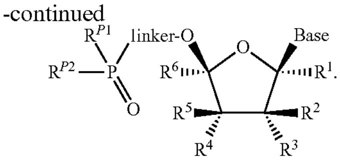

518-A

Appropriate oxidant(s) can convert the primary alcohol (5'-hydroxy) shown in 518-1.3 to a carboxylic acid or its corresponding ester. In the case of an ester, an additional deprotection step will give the carboxylic acid, 518-1.4. A variety of oxidation procedures exist in the literature and can be utilized here. These include but are not limited to the following methods: (i) pyridinium dichromate in $Ac_2O$, t-BuOH, and dichloromethane producing the t-butyl ester, followed by a deprotection using reagent such as trifluoroacetic acid to convert the ester to the corresponding carboxylic acid (see Classon, et al, *Acta Chem. Scand. Ser. B;* 39; 1985; 501-504. Cristalli, et al; *J. Med. Chem.*; 31; 1988; 1179-1183); (ii) iodobenzene diacetate and 2,2,6,6-tetramethyl-1-piperidinyloxy, free radical (TEMPO) in acetonitrile, producing the carboxylic acid (See Epp, et al; *J. Org. Chem.* 64; 1999; 293-295. Jung et al; *J. Org. Chem.*; 66; 2001; 2624-2635); (iii) sodium periodate, ruthenium(III) chloride in chloroform producing the carboxylic acid (see Kim, et al, *J Med. Chem.* 37; 1994; 4020-4030. Homma, et al; *J. Med. Chem.*; 35; 1992; 2881-2890); (iv) chromium trioxide in acetic acid producing the carboxylic acid (see Olsson et al; *J. Med. Chem.*; 29; 1986; 1683-1689. Gallo-Rodriguez et al; *J. Med. Chem.*; 37; 1994; 636-646); (v) potassium permanganate in aqueous potassium hydroxide producing the carboxylic acid (see Ha, et al; *J. Med. Chem.*; 29; 1986; 1683-1689. Franchetti, et al; *J. Med. Chem.*; 41; 1998; 1708-1715.) (vi) nucleoside oxidase from *S. maltophilia* to give the carboxylic acid (see Mahmoudian, et al; *Tetrahedron;* 54; 1998; 8171-8182.)

The preparation of 518-1.5 from 518-1.4 using lead(IV) tetraacetate (LG=OAc) was described by Teng et al; *J. Org. Chem.*; 59; 1994; 278-280 and Schultz, et al; *J. Org. Chem.*; 48; 1983; 3408-3412. When lead(IV) tetraacetate is used together with lithium chloride (see Kochi, et al; *J. Am. Chem. Soc.*; 87; 1965; 2052), the corresponding chloride is obtained (1.5, LG=Cl). Lead(IV) tetraacetate in combination with N-chlorosuccinimide can produce the same product (1.5, LG=Cl) (see Wang, et al; *Tet. Asym.;* 1; 1990; 527 and Wilson et al; *Tet. Asym.;* 1; 1990; 525). Alternatively, the acetate leaving group (LG) can also be converted to other leaving group such as bromide by treatment of trimethylsilyl bromide to give 518-1.5 ((see Spencer, et al; *J. Org. Chem.*; 64; 1999; 3987-3995).

The coupling of 518-1.5 (LG=OAc) with a variety of nucleophiles were described by Teng et al; *Synlett*; 1996; 346-348 and U.S. Pat. No. 6,087,482; Column 54 line 64 to Column 55 line 20. Specifically, the coupling between 518-1.5 and diethyl hydroxymethylphosphonate in the presence of trimethylsilyl trifluoromethanesulfonate (TMS-OTf) was described. It can be envisioned that other compounds with the general structure of HO-linker-POR$^{P1}$R$^{P2}$ can also be used so long as the functional groups in these compounds are compatible with the coupling reaction conditions. There are many examples in the published literature describing the coupling of 518-1.5 (LG=halogen) with a variety of alcohols. The reactions can be facilitated with a number of reagents, such as silver(I) salts (see Kim et al; *J. Org. Chem.*; 56; 1991; 2642-

2647, Toikka et al; *J. Chem. Soc. Perkins Trans*. 1; 13; 1999; 1877-1884), mercury(II) salts (see Veeneman et al; *Recl. Tray. Chim. Pays-Bas;* 106; 1987; 129-131), boron trifluoride diethyl etherate (see Kunz et al; *Hel. Chim Acta;* 68; 1985; 283-287), Tin(II) chloride (see O'Leary et al; *J. Org. Chem*.; 59; 1994; 6629-6636), alkoxide (see Shortnacy-Fowler et al; *Nucleosides Nucleotides*; 20; 2001; 1583-1598), and iodine (see Kartha et al; *J. Chem. Soc. Perkins Trans*. 1; 2001; 770-772). These methods can be selectively used in conjunction with different methods in forming 518-1.5 with various leaving groups (LG) to produce 518-1.6.

The introduction and removal of protecting groups from a compound is a commonly practiced art in organic synthesis. Many sources of information of the art are available in the published literature, e.g. Greene and Wuts, *Protecting Groups in Organic Synthesis,* 3rd Ed., John Wiley & Sons, Inc., 1999. The main purpose is to temporarily transform a functional group so that it will survive a set of subsequent reaction procedures. Afterwards, the original functional group can be restored by a preconceived deprotection procedure. Therefore, the transformations from 518-1.1 to 518-1.2, from 518-1.2 to 518-1.3, and from 518-1.6 to 518-A are intended to allow the core components of the transformations (from 518-1.3 to 518-1.6) to occur while preserving the functional groups already exist in the compound structures.

The 5'-hydroxyl group of ribavirin (518-2) can be selectively protected by an appropriate protecting group. The product, 518-3, can be treated with benzoyl chloride, an appropriate base, in the presence of catalytic amount of 4-dimethylaminopyridine, to convert 2'- and 3'-hydroxyl groups to their corresponding benzoyl esters, 518-4. The 5'-hydroxyl group can be selectively deprotected to give 5. Following procedure described for analogous compound in U.S. Pat. No. 6,087,482, FIG. 2, 518-4 can be converted to 518-7 in a three-step sequence. Treating 518-7 with a coupling agent, such as trimethylsilyl trifluoromethanesulfonate, in the presence of an appropriate alcohol containing a phosphonate group can produce 518-8. Lastly, treating 518-8 with aqueous sodium hydroxide can deprotect the 2'- and 3'-hydroxyl groups to give 518-1. It is important to point out that $R^{P1}$ and $R^{P2}$ in 518-8 and 518-1 do not need to be the same.

A variety of compounds of the general structure 518-1.1 can either be prepared using procedures described in the literature, or be purchased from commercial sources. The following are good sources for information on the art of preparing a variety of compounds of the general structure 518-1.1, Townsend, Chemistry of Nucleosides and Nucleotides, Plenum Press, 1994; and Vorbruggen and Ruh-Pohlenz, *Handbook of Nucleoside Synthesis*, John Wiley & Sons, Inc., 2001. Some exemplary precursors, starting materials and their commercial sources include:

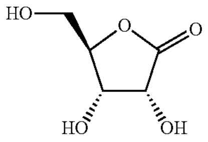

Available from Aldrich Cat. No. 85729-7

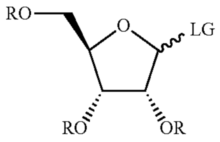

LG = OH, Aldrich Cat. No. R175-7
LG = OAc, R = Benzoyl, Aldrich Cat. No. 15,901-8

-continued

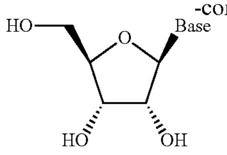

About 300 available from various commercial sources based on ACD search

Compound 518-2.1 in Scheme 518-2 is prepared using method described (WO 01/90121, page 115, table). The 5'-hydroxyl in 518-2.1 is protected as t-butyldimethylsilyl (TBDMS) ether. The 2'- and 3'-hydroxyl groups can be protected as benzoyl (Bz) esters to give 518-2.2. The 5'-hydroxyl can then be deprotected to give 518-2.3. Oxidation using iodobenzene diacetate and 2,2,6,6-tetramethyl-1-piperidinyloxy, free radical (TEMPO) convert the primary alcohol to the corresponding acid S18-2.4. Further oxidation of 518-2.4 using lead tetraacetate can produce 518-2.5. Coupling between 518-2.5 and diethyl hydroxymethylphosphonate (available from Sigma-Aldrich, Cat. No. 39,262-6) effected by TMS-OTf can afford 518-2.6. Treating 518-2.6 with TMS-Br converts the phosphodiester to the corresponding phosphonic acid S18-2.7. Deprotection of the 2'- and 3'-hydroxyl gives 518-2.8 as an example of the generic structure 518-A, where Base is an adenine, $R^1$, $R^5$, and $R^6$ are hydrogen, $R^2$ is methyl group, $R^3$ and $R^4$ are hydroxyl groups, linker is a methylene group, and $R^{P1}$ and $R^{P2}$ are both hydroxyl groups.

Scheme 518-2

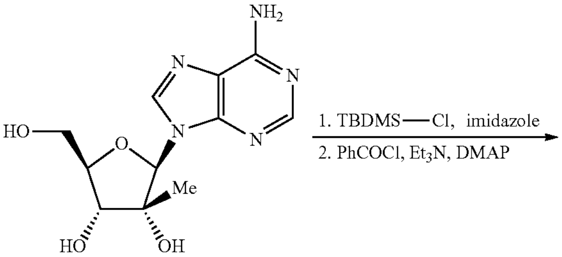

518-2.1

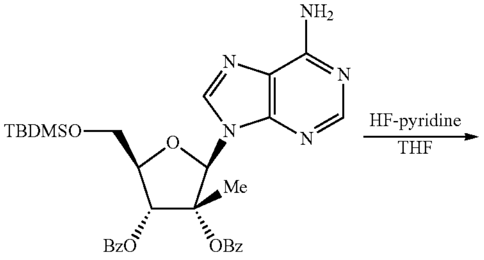

518-2.2

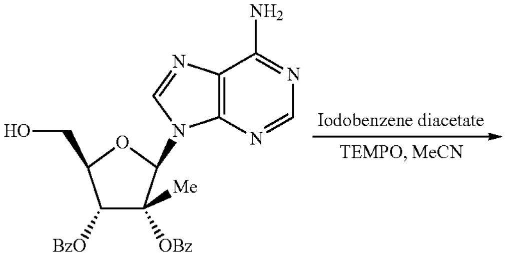

518-2.3

-continued

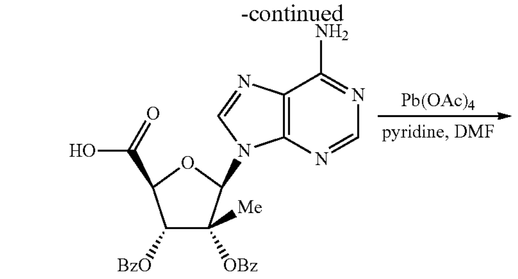

518-2.4

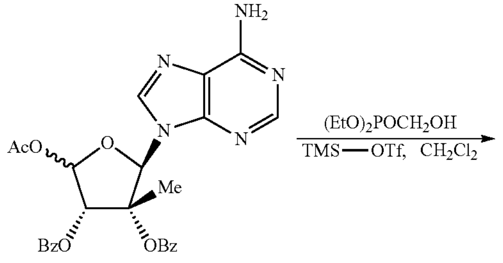

518-2.5

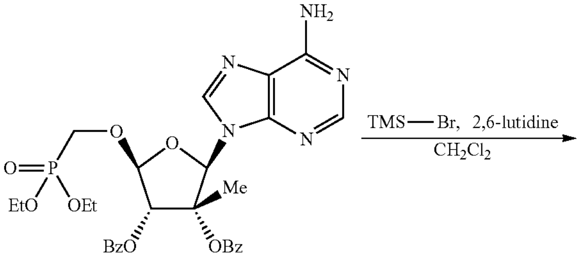

518-2.6

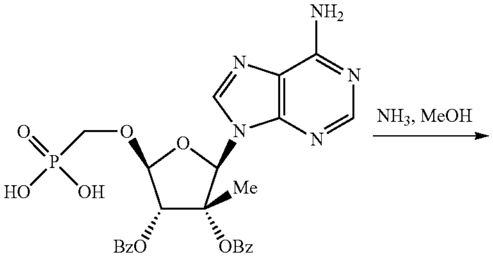

518-2.7

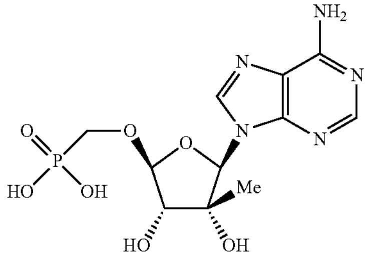

518-2.8

The phosphonic acids in 518-2.7 and 518-2.8 are used as examples for illustration purpose. Other forms of phosphonates can be access via the phosphonic acid, or other forms, such as the corresponding diesters. See section Interconversions of Phosphonates for Details.

Many compounds of the generic structure 518-1.1 with the sugar moiety in its L-configuration are either commercially available or can be prepared by procedures described in the published literature. The opposite D-configuration enantiomers of the L-nucleoside analogs previously discussed can be prepared from the precursors that are the opposite enantiomers of 518-3.1, 518-3.2, and 518-3.3. Scheme 518-3 describes the preparation of the opposite enantiomers of 518-3.1, 518-3.2, and 518-3.3.

Scheme 518-3

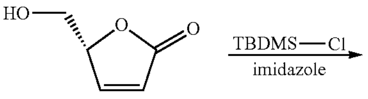

Fluka Cat. No. 55673
518-4.1

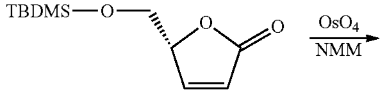

518-4.2

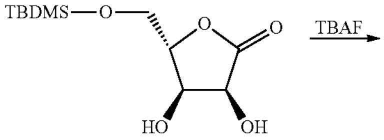

518-4.3

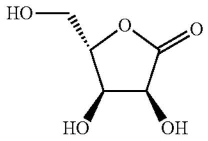

518-4.4
Enantiomer of 3.1

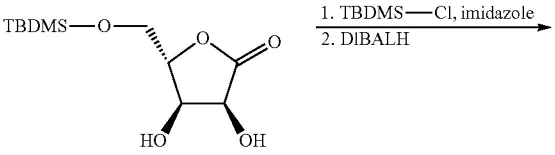

518-4.3

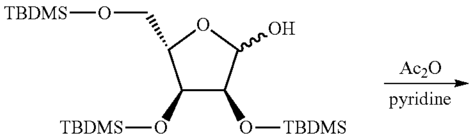

518-4.5
Enantiomer of 3.2
(LG = OH, R = TBDMS)

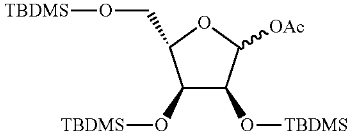

518-4.6
Enantiomer of 3.2
(LG = OAc, R = TBDMS)

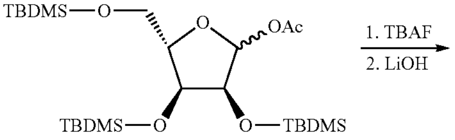

518-4.6

-continued

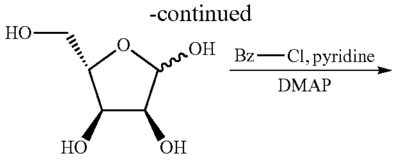

518-4.7

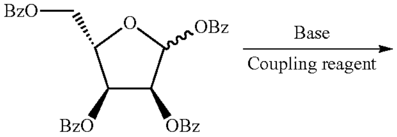

518-4.8

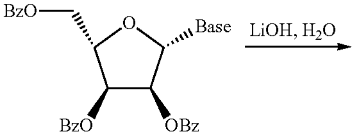

518-4.9

-continued

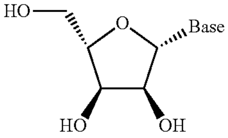

518-4.10

Enantiomer of 3.3

The commercially available starting material 518-4.1 can be converted to 518-4.4, which is the opposite enantiomer of 518-3.1, using the sequence of reactions outlined above in Scheme 518-3. The osmium tetraoxide catalyzed dihydroxylation reaction should introduce the diol selectively in the opposite face to the tert-butyldimethylsilyl (TBDMS) ether of the hydroxymethyl group. The diol in intermediate 518-4.3 can be protected as TBDMS ether. Diisobutylaluminum hydride reduction of the lactone at low temperature should produce 518-4.6, which can be converted to 518-4.6 by acetylation. Deprotection of 518-4.6 should produce L-ribose (518-4.7). Acylation reaction can convert all hydroxyl groups in 518-4.7 to the corresponding benzoyl esters. Standard coupling reactions with a variety of nucleobases should produce 518-4.10, which is the opposite enantiomer of 518-3.3.

Scheme 518-4

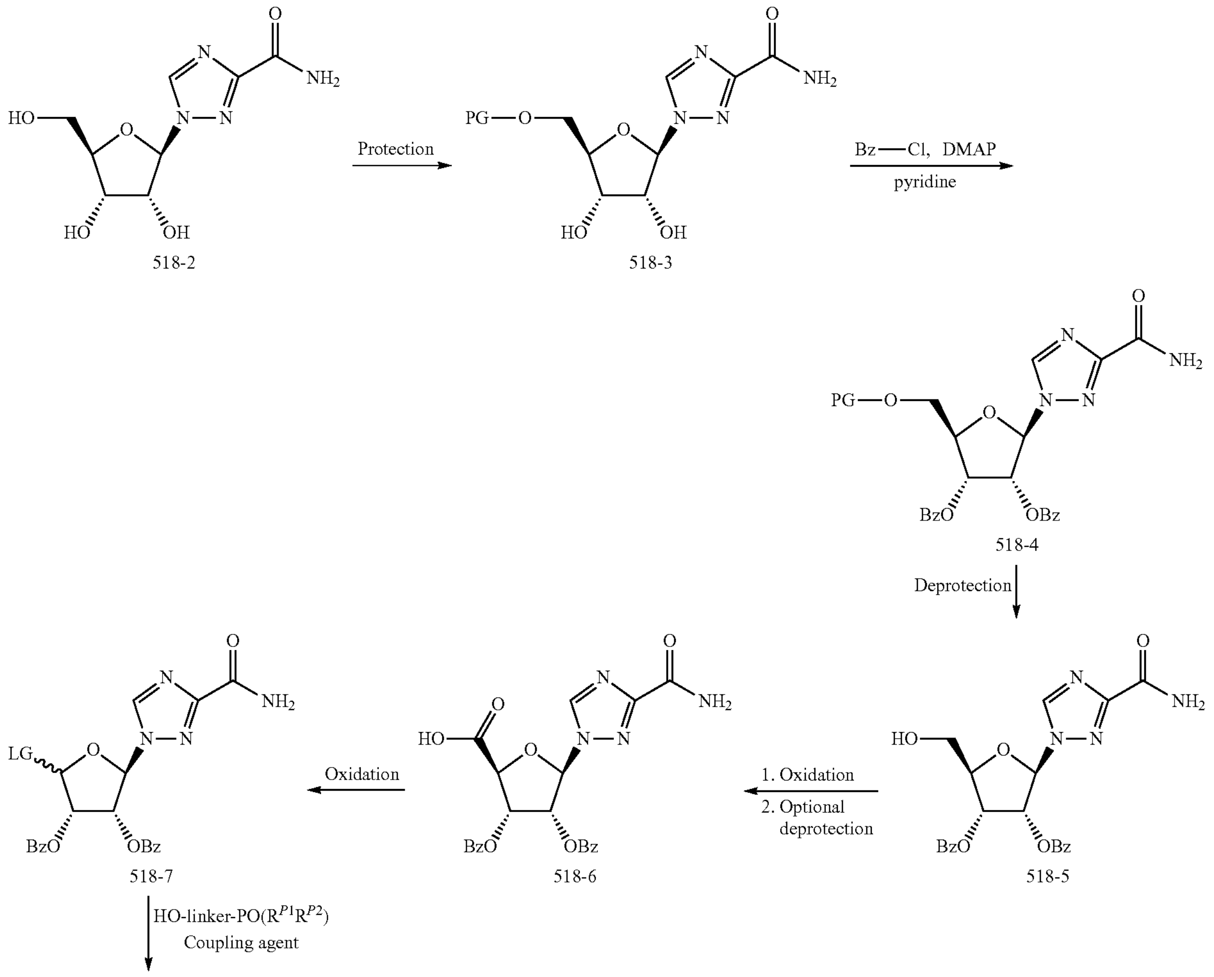

518-2

518-3

518-4

518-5

518-6

518-7

-continued
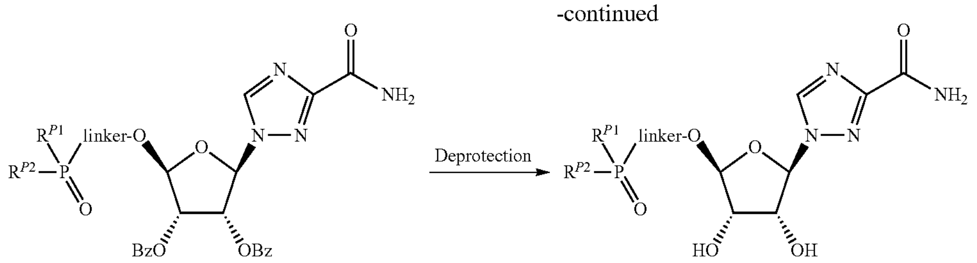
518-8 518-1
The synthesis of 3-cyano-1-(2,3,5-tri-O-acetyl-β-D-ribofuranosyl)-1,2,4-triazole (518-2) is described in US 2002/0156030 A1, page 6, paragraph 0078 to paragraph 0079. Using this starting material, one can synthesize carboxamide compound S18-1 (Scheme 518-4) or formamidine compound S18-1 (Scheme 518-5) using the sequences of chemical transformations outlined in Schemes 518-4 and 518-5, respectively.
Scheme 518-5
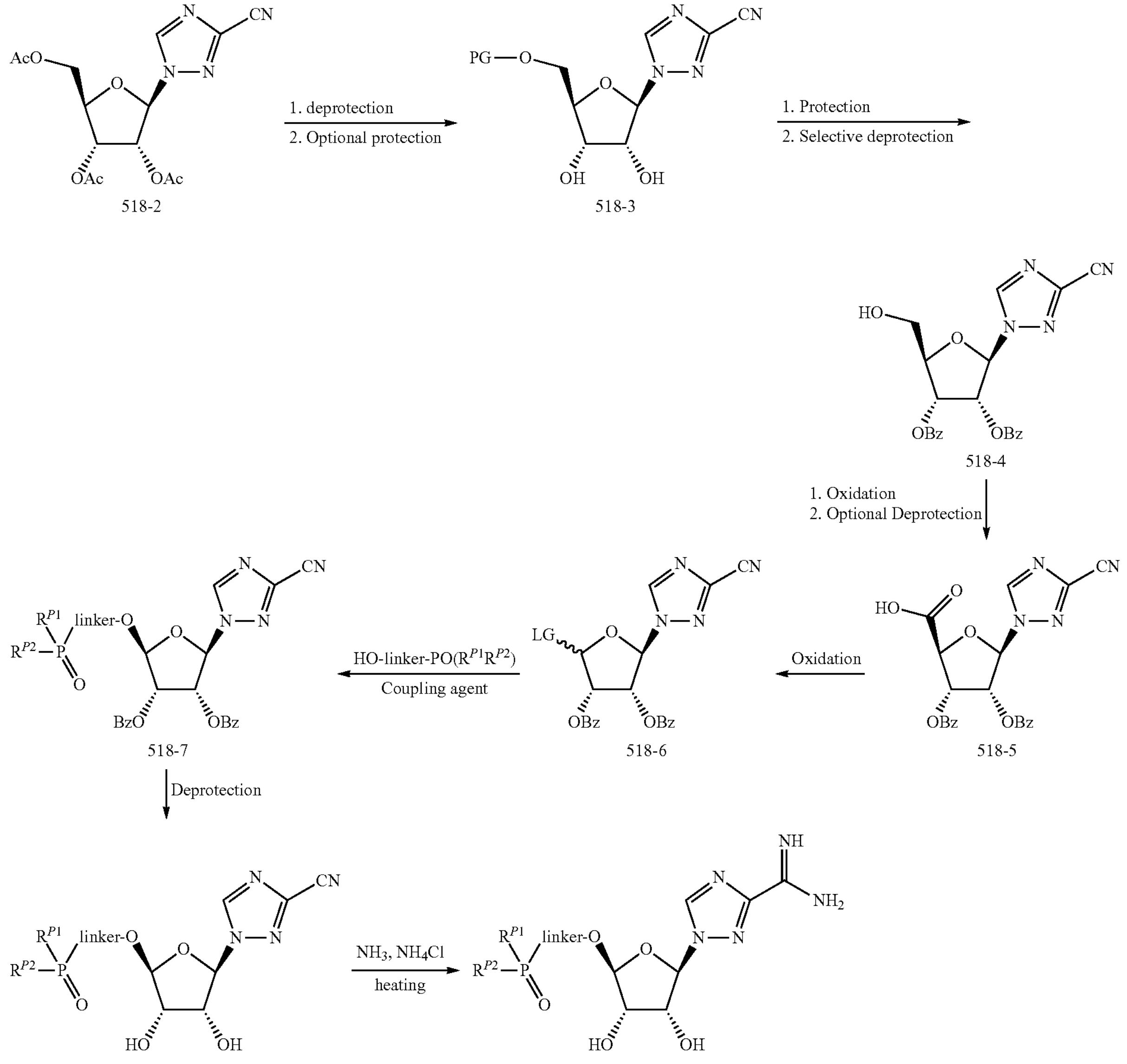
518-2 518-3 518-4 518-5 518-6 518-7 518-8 518-1

Appropriate protection, deprotection procedures (See Greene and Wuts, (1999) *Protective Groups in Organic Synthesis*) can be employed to prepare 518-3, in which the 5'-hydroxyl group is protected, while the 2', and 3'-hydroxyl groups are not (Schemes 518-4 and 518-5). Subsequent protection, depretection procedures can introduce protecting groups such as benzoyl group to the 2'- and 3'-hydroxyl, and leave the 5'-hydroxyl group unprotected as in 518-4. Oxidation can convert the primary alcohol in 518-4 to the corresponding carboxylic acid or its ester. An optional deprotection of the ester can give the acid S18-5 as product. Further oxidation using oxidant such as lead tetraacetate can convert 518-5 to 518-6, in which the leaving group is an acetate. Treating 518-6 with an alcohol containing a phosphonate moiety in the presence of appropriate coupling agent, such as trimethylsilyl trifluoromethanesulfonate, will give 518-8 as product. Finally, treating 518-8 with the procedure described in US 2002/0156030 A1, page 6, paragraph 0081, should give 518-1 as product. It is important to point out that $R^{P1}$ and $R^{P2}$ in 518-7, 518-8 and 518-1 do not need to be the same.

Scheme 518-6

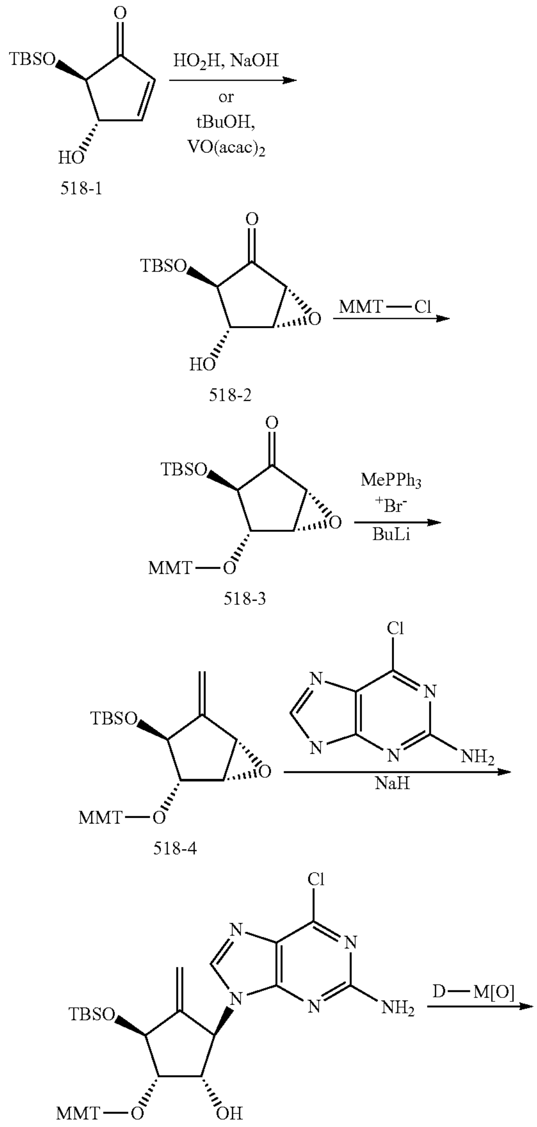

518-1

518-2

518-3

518-4

518-5

-continued

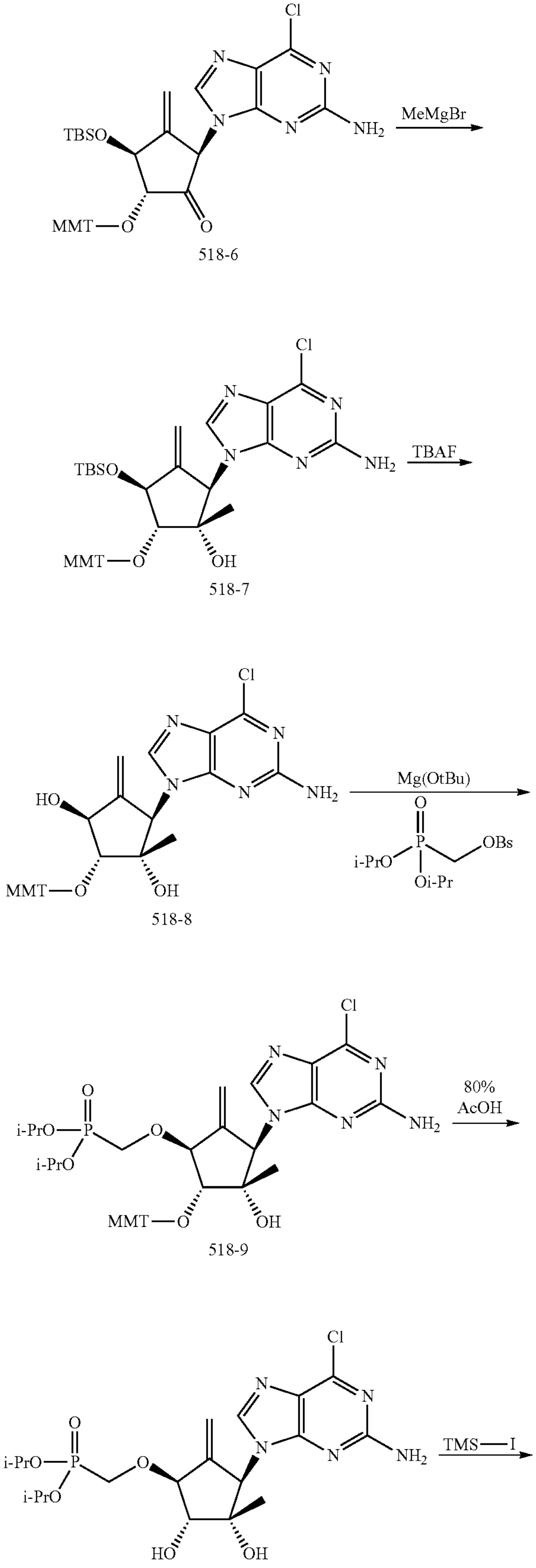

518-6

518-7

518-8

518-9

518-10

-continued

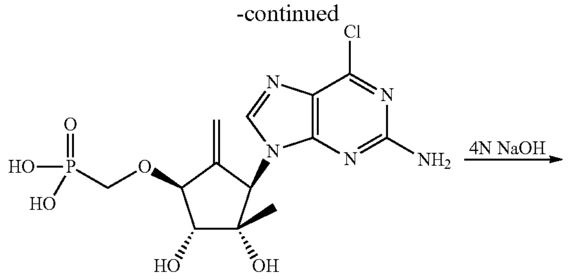

518-11

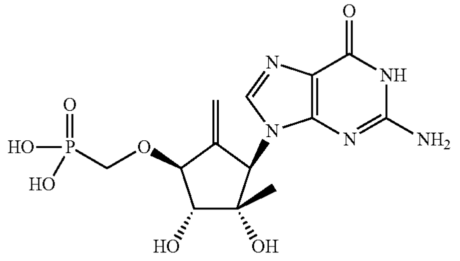

518-12

A solution of tert-butyl hydroperoxide (t-BuOOH) in benzene (68%, 3 eq) is added dropwise to a solution of allylic alcohol 518-1 (synthesized as described in *Tet. Letters* (1997) 38:2355-58) and $VO(acac)_2$ in benzene (final concentration 0.1 M) at room temperature (Scheme 518-6). After 1 h of stirring at room temperature, saturated aqueous $Na_2S_2O_3$ is added to the reaction mixture. The resulting solution is extracted with EtOAc, washed with $H_2O$, and dried over sodium sulfate. After removal of solvent, the crude product 518-2 is purified by column chromatography on silica.

Epoxide 518-2 and p-anisylchlorodiphenylmethane (1.5 eq) is dissolved in anhydrous pyridine (0.17 M) and stirred at 25° C. for 2d. Solvents were removed under reduced pressure and the residue dissolved in EtOAc. The organics were washed with water, saturated aqueous $NaHCO_3$, and dried over sodium sulfate. After removal of solvent, the crude product 518-3 is purified by column chromatography on silica.

To a solution of methyltriphenylphosphonium bromide (2 eq) in anhydrous THF at −78° C. is added n-butyllithium (2.2 eq). The solution is allowed to warm to room temperature and stirred for 20 min. After recooling to −78° C., this solution is added to fully protected epoxide 518-3 in THF (final concentration 0.06 M). The reaction mixture is allowed to warm to room temperature and stirred for 12 h at which point $H_2O$ is added and extracted with diethyl ether. The combined organics were dried over sodium sulfate. After removal of solvent, the crude product 518-4 is purified by column chromatography on silica.

Sodium hydride (1 eq) and 2-amino-4-chloro-7H pyrrolo [2,3-d]pyrimidine (1 eq) were dissolved in anhydrous DMF (0.06 M) and stirred at 120° C. for 10 min. A solution of 518-4 in DMF is then added and the reaction mixture is stirred 12 h at 120° C. at which point the solvents were evaporated under reduced pressure. The residue is dissolved in $CH_2Cl_2$, washed with $H_2O$, and dried over sodium sulfate. After removal of solvent, the crude product 518-5 is purified by column chromatography on silica.

Compound 518-5 is dissolved in dichloromethane and added to a solution of 1,1,1-tris(acetyloxy)-1,1-dihydro-1,2-benziodoxol-3-(1H)-one (Aldrich, Dess-Martin periodinane, 4 eq) in dichloromethane (final concentration 0.06 M). The reaction mixture is stirred at room temperature for 4 d at which point it is diluted with EtOAc and poured into a solution of sodium thiosulfate in saturated aqueous sodium bicarbonate solution. The organic layer is separated and dried over sodium sulfate. After removal of solvent, the crude product 518-6 is purified by column chromatography on silica.

A solution of ketone 518-6 in anhydrous THF is added to a solution of methylmagnesium bromide (4 eq) in anhydrous THF (0.1 M) at −78° C. The reaction mixture is stirred for 12 h at −60° C. at which point the reaction is quenched with saturated aqueous $NH_4Cl$ solution. The mixture is filtered over celite and washed with EtOAc. The combined organics were washed with saturated aqueous $NH_4Cl$, water and dried over sodium sulfate. After removal of solvent, the crude product 7 is purified by column chromatography on silica.

A solution of alcohol 518-7 in anhydrous THF (0.06 M) is treated with a solution of tetrabutylammonium fluoride (1.5 eq) in THF at room temperature. The reaction mixture is stirred for 3 h at which point the solvents were evaporated. The crude desilylated diol 518-8 is purified by column chromatography on silica.

To a solution of diol 518-8 and benzenesulfonic acid diisopropoxy-phosphorylmethyl ester (1.2 eq) in anhydrous DMF (0.1 M) is added magnesium tert-butoxide (1 eq). The reaction mixture is heated to 80° C. for 12 h. After cooling to room temperature, 1 N citric acid is added and extracted with EtOAc. The organics were neutralized with saturated aqueous $NaHCO_3$, washed with saturated aqueous NaCl, and dried over sodium sulfate. After removal of solvent, the crude product 518-9 is purified by column chromatography on silica.

Compound 518-9 is dissolved in 80% acetic acid and stirred 12 h at room temperature. After removal of solvent, the crude product 518-10 is purified by column chromatography on silica.

Phosphonate ester 518-10 and 2,6-lutidine (8 eq) is dissolved in $CH_3CN$ and treated with trimethylsilyliodide (8 eq). After stirring for 3 h at room temperature, triethylamine (8 eq) is added followed by methanol. After removal of solvent, the crude product 518-11 is purified by column chromatography on silica.

Phosphonic diacid S18-11 is dissolved in 1,4-dioxane and treated with 4 N NaOH and heated to 100° C. for 4 h. After cooling to room temperature, the reaction mixture is neutralized with 4N HCl. After removal of solvent, the crude product is purified by column chromatography on silica to provide 518-12.

Scheme 518-7

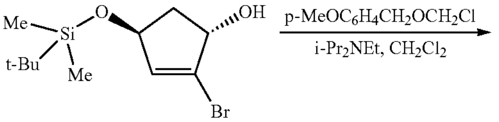

518-13

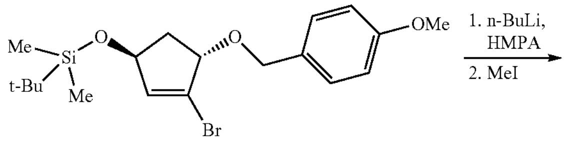

518-14

-continued

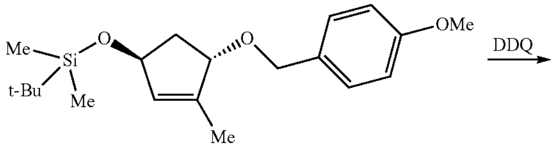

518-15

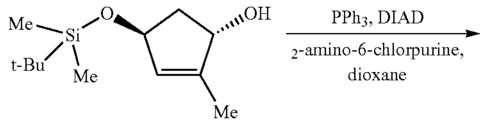

518-16

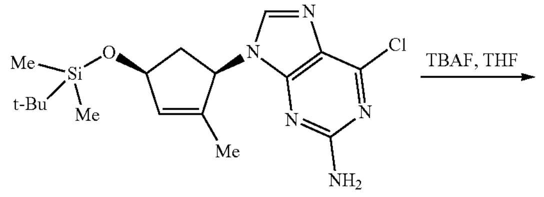

518-17

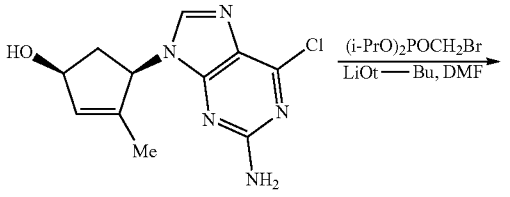

518-18

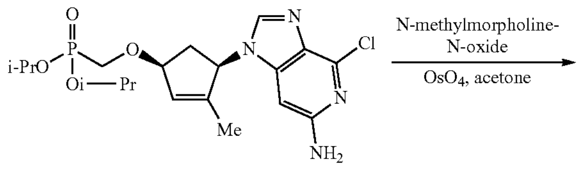

518-19

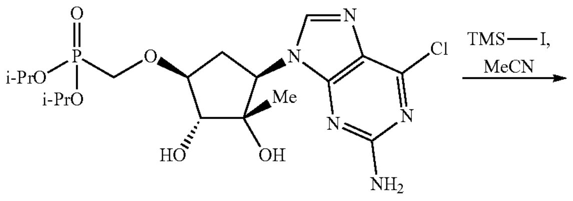

518-20

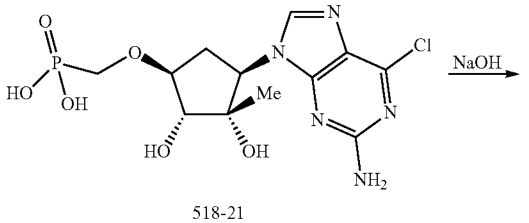

518-21

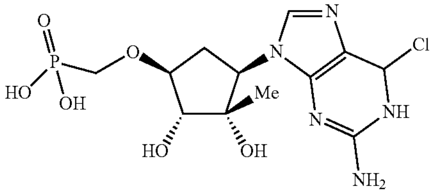

518-22

-continued

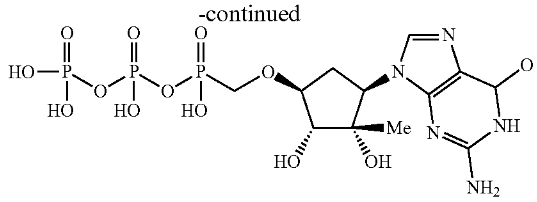

518-23

Compound 518-13 (Paquette et al *J. Org. Chem.* (1997) 62:1730-1736) is treated with p-methoxybenzyl bromide(1.5 eq.), sodium hydride(1.4 eq) in dry DMF at room temperature (Scheme 518-7). The reaction is monitor by TLC for the disappearance of 518-13. The reaction is quenched by the addition of a saturated aqueous solution of ammonium chloride. Extraction by diethyl ether affords a crude product, which can be purified by silica gel chromatography to give 518-14.

A solution of 518-14 in THF is added dropwise to a solution of n-BuLi (1.2 eq) in THF cooled at −78° C. under a nitrogen atmosphere. The solution is stirred for 1 h at −78° C. Excess of HMPA (1.4 eq) is added. After 10 min, a solution of MeI (5 eq) in THF is added. After another 5 h at −78° C., 20% aqueous $NaH_2PO_4$ is added, and the mixture is warmed to room temperature. Extraction with diethyl ether gives a crude product, which is purified by silica gel chromatography to give 518-15.

Dichlorodicyanoquinone (DDQ) is added to a mixture of compound S18-15 in dichloromethane and water. After stirring at room temperature for 2 h. The mixture is extracted with dichloromethane to give a crude product, which is purified by silica gel chromatography to give 518-16.

To a solution of 518-16 in dioxane, is added triphenylphosphine (2 eq.), 2-amino-6-chloropurine (2 eq) at room temperature. Diisopropyl azodicarboxylate (2 eq, DIAD) is added dropwise via syringe. The mixture is stirred at room temperature for another 3 h. Water is added to quench the reaction. Extraction with ethyl acetate gives a crude product, which is purified by silica gel chromatography to give 518-17.

Alternatively, a nucleobase may be added by the methods described in Crimmins, M. T. (1998) *Tetrahedron* 54:9229-9272, such as palladium coupling to a cyclopentyl acetate.

To a solution of compound S18-17 in THF is added a 1 M solution of tetrabutylammonium fluoride (1.2 eq, TBAF) at room temperature. After another few hours, a saturated solution of ammonium chloride is added. Extraction with ethyl acetate gives a crude product, which is purified by silica gel chromatography to give 518-18.

Compound 18, diethyl bromomethylphosphonate (1.5 eq), and lithium t-butoxide (1.5 eq) are added to DMF sequentially. The mixture is stirred at 80° C. for several hours. After the mixture is cooled to room temperature, a 1 M solution of $KH_2PO_4$ is added. Extraction with ethyl acetate gives a crude product, which is purified by silica gel chromatography to give 518-19.

To a solution of 518-19 in acetone, is added N-methylmorpholine N-oxide (2 eq) and osmium tetraoxide (0.2 eq). The mixture is stirred at room temperature for 16 h. A 1 M aqueous solution of sodium sulfite is added. After stirring at room temperature for another hour, the mixture is evaporated to remove most of acetone. The aqueous residue is frozen and lyophilized to give a crude product, which is purified by reversed phase HPLC to give 518-20.

Iodotrimethylsilane (8 eq, TMS-I) is added to a mixture of 518-20, 2,6-lutidine (8 eq) and acetonitrile. After stirring at room temperature for 2 h, the mixture is poured onto ice. The mixture is then frozen and lyophilized to give a residue, which is purified by reversed phase HPLC to give 518-21.

518-21 is dissolved in 4 N aqueous NaOH and refluxed for several hours. The mixture is cooled to room temperature, neutralized with 4 N HCl, and purified with reversed phase HPLC to give 518-22.

Compound 518-22 can be converted to the corresponding diphosphophosphonate 518-23, and prodrugs using known procedures.

Scheme 518-8

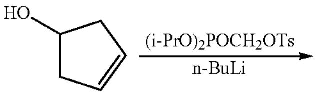

518-24

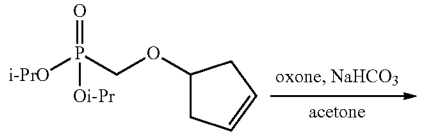

518-25

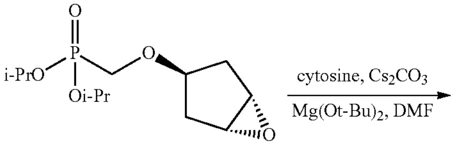

518-26

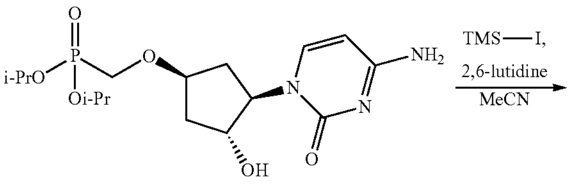

518-27

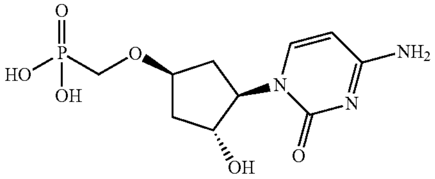

518-28

518-29

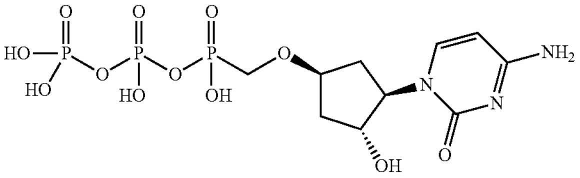

518-30

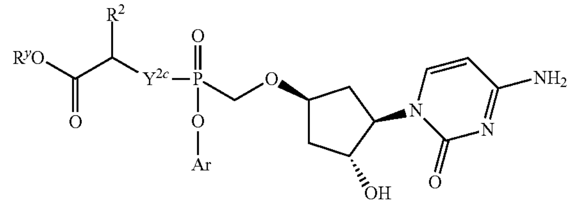

3-Cyclopenten-1-ol 518-24(108 uL, 1.2 mmol, 1.2 eq) is dissolved in 5 mL of dry THF (Scheme 518-8). The solution is cooled to 0° C. A 1.35 M solution of n-BuLi (0.89 mL, 1.2 mmol, 1.2 eq) is added via syringe. After 10 min, diisopropylphosphonomethyl p-toluenesulfonate (350 mg, 1.0 mmol, 1.0 eq) is added. The mixture is stirred in a 45° C. bath for 3.5 h. The reaction is quenched with a pH 7 aqueous phosphate buffer. Extraction with diethyl ether gave a crude product, which is purified by silica gel chromatography (eluted with 45% ethyl acetate in hexane) to give 178 mg of 518-25 (68%).

To a solution of 518-25 (168 mg, 0.69 mmol, 1 eq) in 12 mL of acetone, is added 273 mg of $NaHCO_3$ in 8 mL of water. The mixture is then cooled to 0° C. Oxone (519 mg, 0.85 mmol, 1.3 eq) in 4 mL of water is added over 5 min in portions. The mixture is stirred vigorously for 2.5 h. The mixture is then evaporated in vacuo to remove most of the acetone. The aqueous residue is extracted with ethyl acetate to give a crude product, which is purified by silica gel chromatography to give 518-26 as a clear oil.

To a solution of 518-26 (21 mg, 0.076 mmol, 1.0 eq) in 0.25 mL of DMF, is added cytosine (13 mg, 1.5 eq) and cesium carbonate (6 mg, 0.25 eq) and magnesium t-butoxide. The mixture is heated to 140° C. for several hours. After cooling to room temperature, the reaction mixture is purified by reversed phase HPLC to give 12.5 mg of 518-27 (42%). $^1H$ NMR (CDCl3): δ 9.60 (br s, 1H), 8.96 (br s, 1H), 7.87 (d, 1H), 6.21 (d, 1H), 4.84 (m, 1H), 4.78 (m, 2H), 4.43 (m, 1H), 4.08 (s, 1H), 3.72 (m, 2H), 2.82 (m, 1H), 2.33 (m, 1H), 1.83 (m, 2H), 1.38 (m, 12H) ppm.

Alternatively, the methods in WO 03/105770 can be applied to add a nucleobase with a nucleophilic amine to a cycopentyl epoxide.

The conversion from 518-27 to 518-28 is described in Scheme 518-2 above. The conversion of 518-28 to the corresponding diphosphophosphonate 518-29 and phosphorus prodrugs, e.g. 518-30 can be accomplished using procedures described herein.

Cyclopentyl intermediate 518-31 may be prepared by procedures analogous to those described in U.S. Pat. Nos. 5,206, 244 and 5,340,816 (Scheme 518-4).

Diol 518-31 is converted to cyclopentenone 518-32 and treated with Mr in the presence of the appropriate phosphonate alcohol to give 518-33. Iodide 518-33 is displaced with inversion to give cyclopentanone intermediate 518-34. Nysted methylenation (U.S. Pat. No. 3,865,848; *Aldrichim. Acta* (1993) 26:14) provides exocyclic methylene 518-35, which may be deprotected to give 518-36.

Cyclopentanone 518-34 may be a versatile intermediate to form other compounds of the invention by reduction to cyclopentyl 518-37, or Wittig or Grubb olefination to alkenyl 518-38.

Scheme 518-9

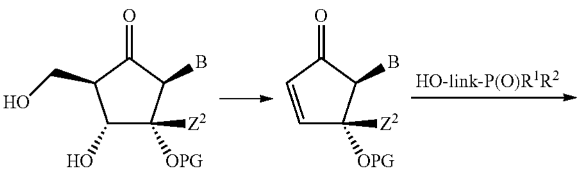

518-31 518-32

-continued

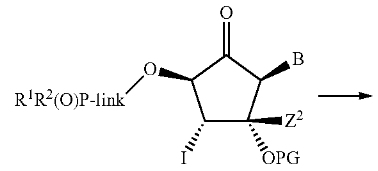

518-33

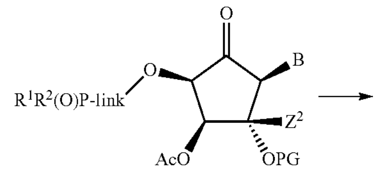

518-34

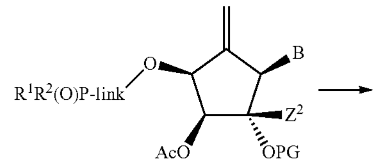

518-35

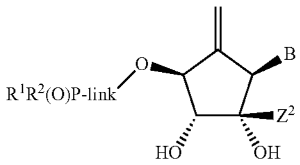

518-36

34 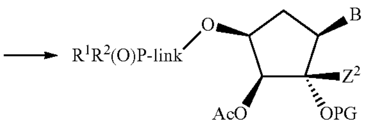

518-37

34 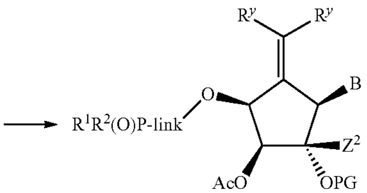

518-38

Scheme 518-10

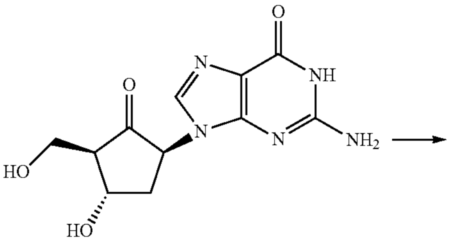

518-39

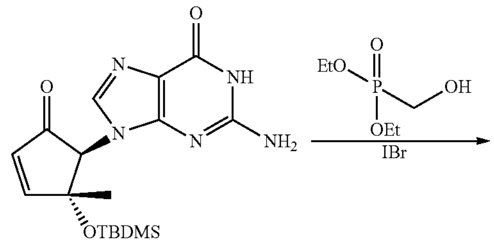

518-40

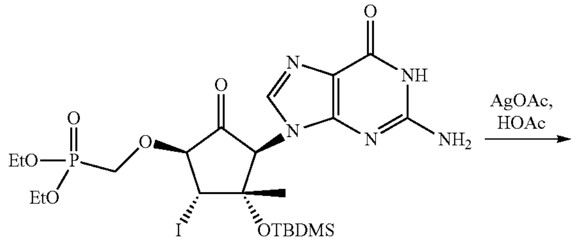

518-41

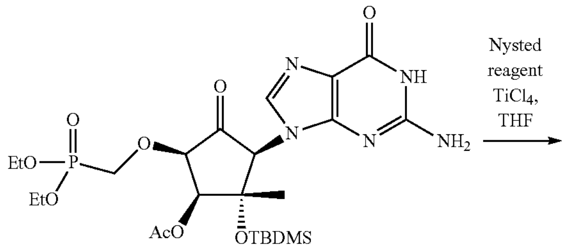

518-42

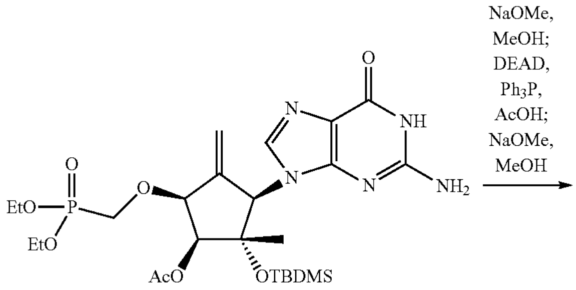

518-43

Scheme 518-10 shows intermediate 518-39 is converted to guanosyl cyclopentenone 518-40 (*J. Am. Chem. Soc.* (1972) 94:3213), then treated with IBr and diethyl phosphomethanol to furnish iodide 518-41 (*J. Org. Chem.* (1991) 56:2642) Nucleophilic substitution with AgOAc affords acetate 518-42. After methylenation using the procedure of Nysted (U.S. Pat. No. 3,865,848; *Aldrichim. Acta* 1993, 26, 14), to give 518-43, the acetate group is removed by the addition of sodium methoxide and the resulting alcohol is inverted by the Mitsunobu protocol, and a second acetate deprotection produces 518-44. Desilylation with tetra-butylammonium fluoride (TBAF) of 518-44 will yield 518-45.

-continued
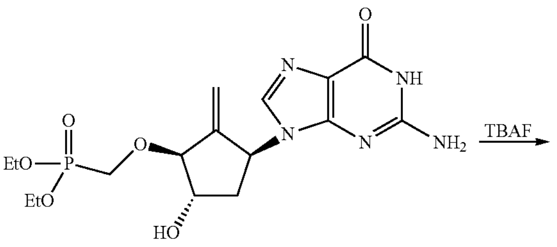
518-44
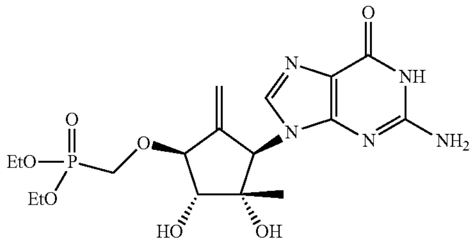
518-45
Specific Embodiments
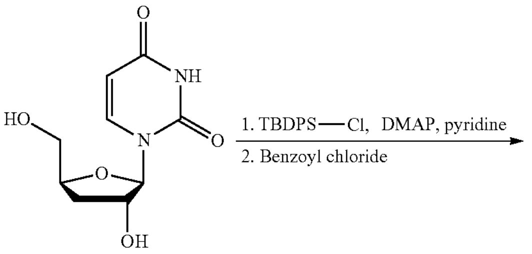
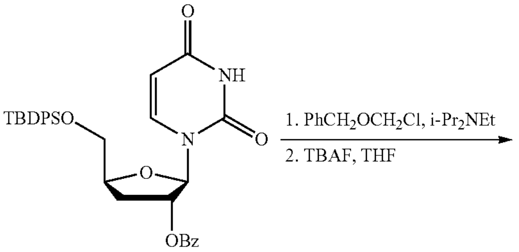
519-1
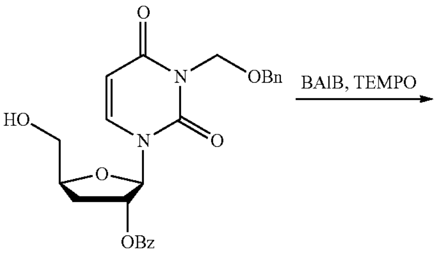
519-2
-continued
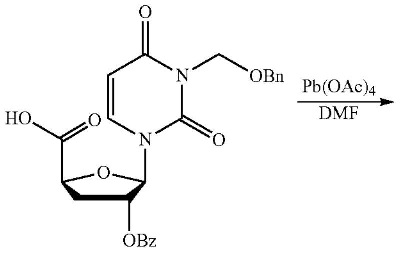
519-3
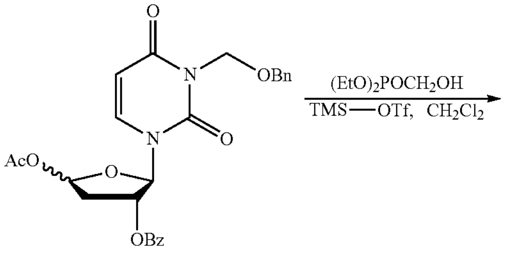
519-4
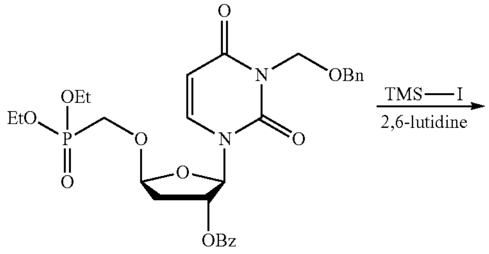
519-5a
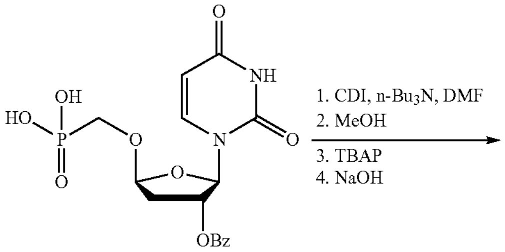
519-6
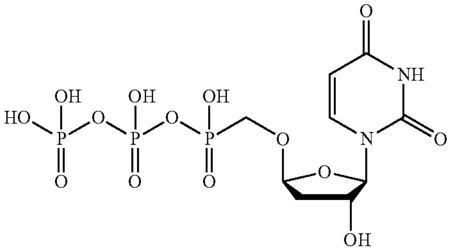
519-7

Example 221

Synthesis of Exemplary Compounds of the Invention 519-1

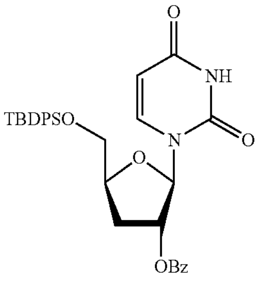

Synthesis of 519-1: To a solution of 3'-deoxyuridine (995 mg, 4.36 mmol) in 8 mL of anhydrous pyridine was added t-butyldiphenylsilyl chloride (TBDPS-Cl, 1.38 g, 5.01 mmol), and 4-dimethylaminopyridine (DMAP, 27 mg, 0.22 mmol). The mixture was stirred at 23 C for 14 h and then cooled to 0 C in a ice-water bath. To this mixture was added benzoyl chloride (735 mg, 0.61 mL, 5.2 mmol). The mixture was warmed to 23° C. and stirred for another 2 h. The mixture was concentrated in vacuo to give a paste, which was partitioned between water and ethyl acetate. The aqueous later was extracted once with ethyl acetate. The combined ethyl acetate layer was washed sequentially with 1 M aqueous citric acid, saturated sodium bicarbonate, and brine. It was dried over anhydrous sodium sulfate and concentrated in vacuo to give a crude product as a yellow oil. Purification by silica gel chromatography (15-65% ethyl acetate in hexane) gave a colorless oil. Yield 1.35 g (54%). $^{1}$H NMR (DMSO-d6): δ 11.38 (s, 1H), 8.01 (d, J=7.9 Hz, 2H), 7.77 (d, J=8.2 Hz, 1H), 7.70-7.40 (m, 13 H), 5.99 (s, 1H), 5.58 (m, 1H), 7.34 (d, J=8.2 Hz, 1H), 4.47 (m, 1H), 4.03 (m, 1H), 3.84 (m, 1H), 2.43 (m, 1H), 2.21 (m, 1H), 1.03 (s, 9H) ppm. MS (m/z) 571.1 (M+H$^{+}$), 593.3 (M+Na$^{+}$).

Example 222

Synthesis of Exemplary Compounds of the Invention 520-2

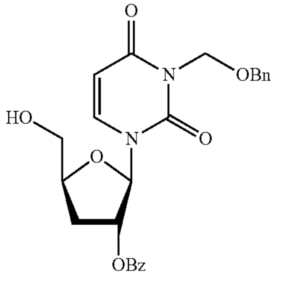

Synthesis of 520-2: To a solution of 519-1 (1.31 g, 2.3 mmol) in 5 mL of anhydrous N,N-dimethylformamide was added benzyl chloromethyl ether (0.54 g, 3.45 mmol), N,N-diisopropylethylamine (446 mg, 0.60 mL, 3.45 mmol). The mixture was stirred at 23° C. for 4 h. Water was added. The mixture was extracted with ethyl acetate. The organic layer was washed sequentially with 1 M aqueous citric acid, saturated sodium bicarbonate, and brine. It was dried over anhydrous sodium sulfate and concentrated in vacuo to give a crude product as a yellow oil, which was used in the next step without further purification.

The crude product obtained above was dissolved in 9 mL of THF. The solution was cooled to 0 C. A 1 M solution of TBAF (4.6 mL, 4.6 mmol) was added via syringe. The mixture was warmed to 23° C. and stirred for another 2 h. An additional 2.3 mL of 1 M TBAF was added. The mixture was stirred for another 2 h at 23 C. Saturated aqueous ammonium chloride was added to the solution. The mixture was evaporated in vacuo to remove most of THF. The aqueous phase was extracted with ethyl acetate. The aqueous layer was washed with brine. It was then dried over anhydrous sodium sulfate and concentrated in vacuo to give a crude product as a yellow oil. Purification by silica gel chromatography (30-80% ethyl acetate in hexane) gave a white solid. Yield of 520-2: 805 mg (77% for two steps). $^{1}$H NMR (DMSO-d6): δ 8.04 (m, 3H), 7.67 (t, J=7.3 Hz, 1H), 7.55 (t, J=7.6 Hz, 2H), 7.30 (m, 5H), 5.98 (s, 1H), 5.78 (d, J=7.9 Hz, 1H), 5.55 (m, 1H), 5.31 (s, 2H), 5.22 (m, 1H), 4.57 (s, 2H), 4.41 (m, 1H), 3.80 (m, 1H), 3.60 (m, 1H), 2.31 (m, 1H), 2.15 (m, 1H) ppm. MS (m/z) 453.1 (M+H$^{+}$), 475.3 (M+Na$^{+}$).

Example 223

Synthesis of Exemplary Compounds of the Invention 521-3

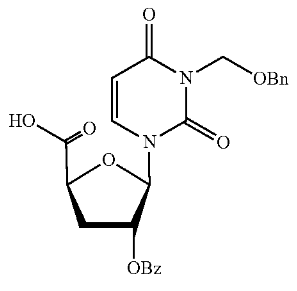

Synthesis of 521-3: To a solution of 520-2 (800 mg, 1.77 mmol) in 3.5 mL of a 1:1 mixture of acetonitrile/water was added iodobenzene diacetate (1.25 g, 3.89 mmol), and TEMPO (55 mg, 0.35 mmol). The mixture was stirred at 23° C. for 14 h. The mixture was then froze in a −78° C. bath and lyophilized to give a solid residue. This residue was purified by silica gel chromatography (0-15% methanol in dichloromethane). Product 521-3 was obtained as a white solid. Yield: 735 mg (89%). $^{1}$H NMR (DMSO-d6): δ 8.13 (d, J=7.6 Hz, 1H), 8.03 (d, J=7.7 Hz, 2H), 7.68 (m, 1H), 7.58 (t, J=7.0 Hz, 2H), 7.29 (m, 5H), 6.04 (s, 1H), 5.85 (d, J=8.3 Hz, 1H), 5.62 (m, 1H), 5.31 (s, 2H), 4.87 (m, 1H), 4.58 (s, 2H), 2.40-2.20 (m, 2H) ppm. MS (m/z) 467.1 ($M+H^+$), 489.3 ($M+Na^+$).

Example 224

Synthesis of Exemplary Compounds of the Invention 522-4

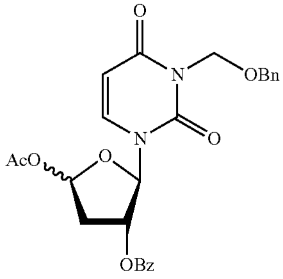

Synthesis of 522-4: To a deoxygenated solution of 521-3 (730 mg, 1.57 mmol) and pyridine (0.51 mL, 6.26 mmol) in 7 mL of anhydrous DMF, was added lead tetraacetate (3.47 g, 7.83 mmol). The mixture was stirred at 23° C. for 14 h shielded from light. The mixture was diluted with 15 mL of ethyl acetate and 10 mL of water. This mixture filtered through a pad of Celite and separated. The aqueous phase was extracted with another 10 mL of ethyl acetate. The combined ethyl acetate extract was washed with brine, dried over sodium sulfate, and evaporated in vacuo to give the crude product as an oil. The crude product 522-4 was purified by silica gel chromatography (10-50% ethyl acetate in hexane). Products of two diastereomers were obtained as a white foam. Yield: 400 mg (53%). $^1$H NMR (DMSO-d6): δ 8.01 (m, 2H), 7.82-7.63 (m, 2H), 7.57 (m, 2H), 7.31 (m, 5H), 6.58 (m, 1H), 6.17 (m, 1H), 5.83 (m, 1H), 5.65 (m, 1H), 5.31 (s, 2H), 4.59 (s, 2H), 2.76 and 2.28 (m, 1H), 2.10 (m, 1H), 2.07 (s, 3H) ppm. MS (m/z) 481.0 ($M+H^+$), 503.3 ($M+Na^+$).

Example 225

Synthesis of Exemplary Compounds of the Invention 523-5a

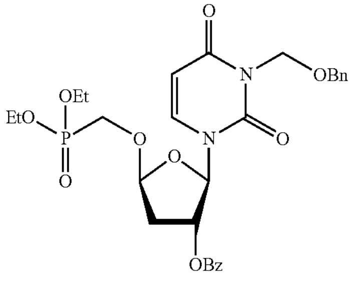

-continued 523-5b

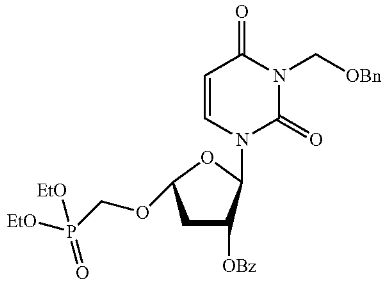

Synthesis of 523-5a: To a solution of 522-4 (300 mg, 0.63 mmol) in 6 mL of anhydrous dichloromethane was added diethyl hydroxymethylphosphonate (0.37 mL, 2.5 mmol), followed by trimethylsilyl trifluoromethanesulfonate (0.34 mL, 1.88 mmol). The mixture was stirred at 23° C. for 6 h. Triethylamine (0.44 mL, 3.15 mmol) was added, followed by water. The mixture was extracted with ethyl acetate. The organic layer was washed with 1 M aqueous citric acid, saturated sodium bicarbonate, and brine. It was then dried over anhydrous sodium sulfate, and evaporated in vacuo to give a residue. This crude product was purified by silica gel chromatography (75-95% ethyl acetate in hexane) to give two products, which were diastereomers of each other shown above (523-5a and 523-5b). Yield of 523-5a: 53 mg (14%). Yield of 523-5b: 129 mg (35%).

Analytical data for 5a: $^1$H NMR (Acetonitrile-d3): δ 8.04 (d, J=7.0 Hz, 2H), 7.77 (d, J=7.9 Hz, 1H), 7.69 (t, J=7.5 Hz, 1H), 7.53 (m, 2H), 7.33 (m, 5H), 6.38 (d, J=4.0 Hz, 1H), 5.80 (d, J=8.2 Hz, 1H), 5.63 (m, 1H), 5.52 (m, 1H), 5.41 (s, 2H), 4.64 (s, 2H), 4.17 (m, 4H), 4.08 (dd, J=13.8, 10.1 Hz, 1H), 3.92 (dd, J=13.7, 9.5 Hz, 1H), 2.66-2.42 (m, 2H), 1.35 (t, J=7.0 Hz, 6H) ppm. MS (m/z) 589.2 ($M+H^+$), 611.3 ($M+Na^+$). Stereochemistry of 523-5a was confirmed by additional 2D NMR experiments.

Analytical data for 523-5b: NMR (Acetonitrile-d3): δ 8.08 (d, J=7.3 Hz, 2H), 7.69 (t, J=7.5 Hz, 1H), 7.55 (m, 2H), 7.43 (d, J=8.2 Hz, 1H), 7.36 (m, 5H), 6.11 (d, J=2.4 Hz, 1H), 5.77 (d, J=8.3 Hz, 1H), 5.57 (m, 2H), 5.41 (s, 2H), 4.66 (s, 2H), 4.12 (m, 5H), 3.88 (dd, J=14.0, 5.2 Hz, 1H), 2.82 (m, 1H), 2.25 (m, 1H), 1.27 (t, J=7.0 Hz, 6H) ppm. MS (m/z) 589.0 ($M+H^+$), 611.2 ($M+Na^+$).

Example 226

Synthesis of Exemplary Compounds of the Invention 524-6

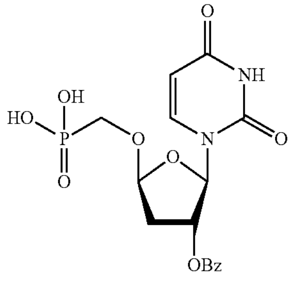

Synthesis of 524-6: To a solution of 523-5a (110 mg, 0.19 mmol) in 3 mL of acetonitrile was added 2,6-lutidine (0.43 mL, 3.74 mmol), followed by iodotrimethylsilane (0.53 mL, 3.74 mmol). After stirring at 23 C for 30 min, the mixture was heated to 40° C. and stirred at that temperature for another 4 h. The reaction mixture was cooled to 23° C. Triethylamine (0.52 mL, 3.74 mmol) was added, followed by water (10 mL). The aqueous mixture was extracted twice with 5 mL of diethyl ether. The resulting aqueous solution was frozen in a −78° C. bath and was lyophilized to give a yellow solid. This crude product was purified by reversed phase HPLC to give 524-6 as a light yellow solid. Yield 26 mg (34%). MS (m/z) 411.3 (M−H$^-$).

Example 227

Synthesis of Exemplary Compounds of the Invention 525-7

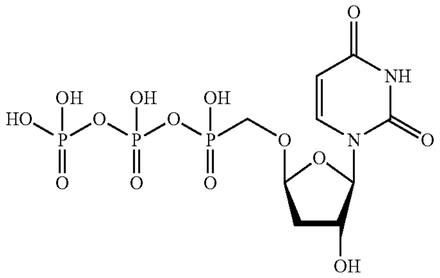

Synthesis of 525-7: Phosphonate 524-6 (12 mg, 0.029 mmol), carbonyldiimidazole (47 mg, 0.29 mmol), and tri-n-butylamine (5.4 mg, 0.029 mmol) were dissolved in 0.3 mL of anhydrous dimethylformamide (DMF). The mixture was stirred at 23° C. for 4 h. MeOH (0.020 mL) was added and the mixture was stirred for another 30 min. A solution of tributylammonium pyrophosphate (159 mg, 0.29 mmol) in 0.63 mL of anhydrous DMF was added. The resulting mixture was stirred at 23° C. for 14 h. The mixture was evaporated in vacuo to remove most of the DMF. The residue was dissolved in 5 mL of water and was purified by ion-exchange chromatography (DEAF-cellulose resin, 0-50% triethylammonium bicarbonate in water) to give a white solid, which was used directly in the next reaction.

The product obtained above was dissolved in 2 mL of water. A 0.3 mL of a 1 M solution of sodium hydroxide in water was added. The mixture was stirred at 23° C. for 40 min. Acetic acid was added to adjust the pH of the solution to 5. The solution was diluted with water and purified with an ion-exchange column (DEAF-cellulose resin, 0-50% triethylammonium bicarbonate in water) to give diphosphophosphonate 525-7 as a white solid, which is the triethylammonium salt of the structure shown above. Yield 10 mg (45% for two steps). $^1$H NMR ($D_2O$): δ 7.79 (d, J=7.6 Hz, 1H), 5.89 (m, 1H), 5.85 (d, J=7.6 Hz, 1H), 5.41 (m, 1H), 4.49 (m, 1H), 4.02-3.65 (m, 2H), 3.06 (m, 18H), 2.20 (m, 2H), 1.14 (m, 27H) ppm. $^{31}$P NMR ($D_2O$): δ 7.46 (d, 1P), −9.45 (d, 1P), −23.11 (t, 1P) ppm. MS (m/z) 467.0 (M−H$^-$).

Example 228

Synthesis of Exemplary Compounds of the Invention

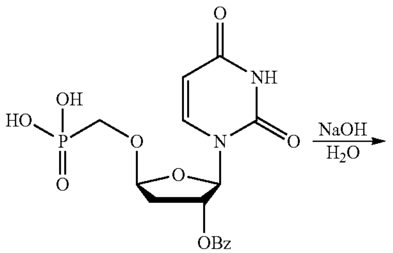

524-6

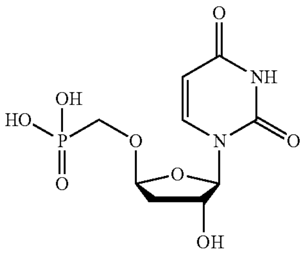

526-8

Synthesis of 526-8: To a solution of 524-6 (16 mg, 0.039 mmol) in 0.4 mL of water was added NaOH (7.8 mg, 0.19 mmol). The solution was stirred at 23° C. for 1 h. Acetic acid (0.012 mL) was added to the solution. The mixture was then purified by reversed phase HPLC (eluted with 100% water) to give 4.6 mg of 526-8 as a white solid (38% yield). $^1$H NMR ($D_2O$): δ 7.83 (d, J=8.3 Hz, 1H), 5.86 (d, J=3.4 Hz, 1H), 5.82 (d, J=7.9 Hz, 1H), 4.48 (m, 1H), 3.68 (m, 1H), 3.37 (m, 1H), 2.16 (m, 2H) ppm. $^{31}$P NMR ($D_2O$): δ 12.60 (s, 1P) ppm. MS (m/z) 615.1 (2M−H$^-$).

Scheme 526-1

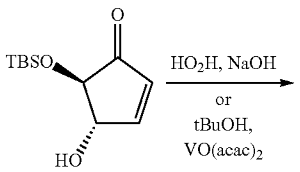

526-1

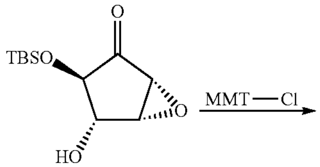

526-2

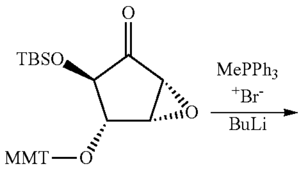

526-3

-continued

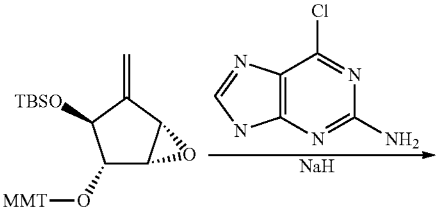

526-4

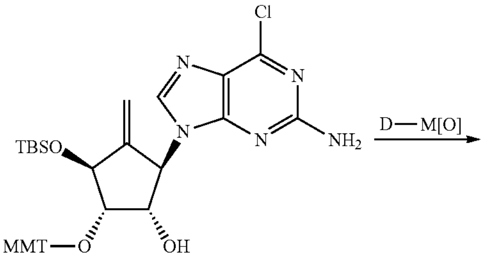

526-5

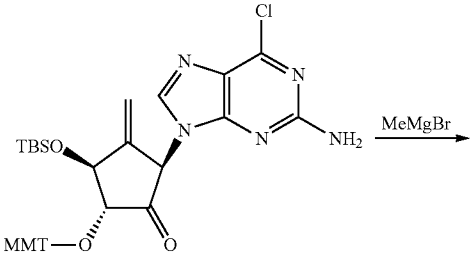

526-6

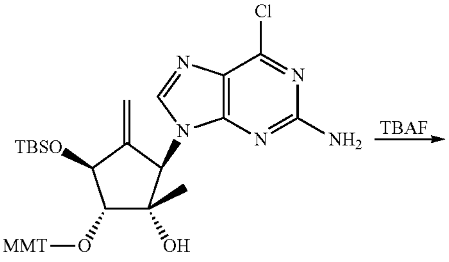

526-7

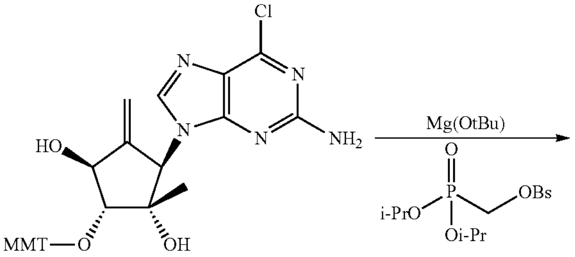

526-8

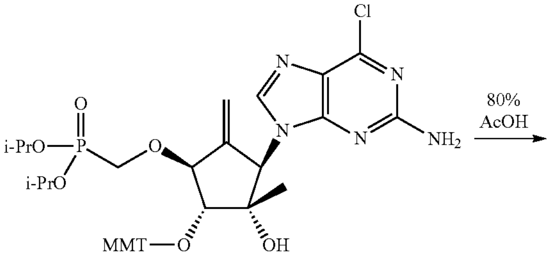

526-9

-continued

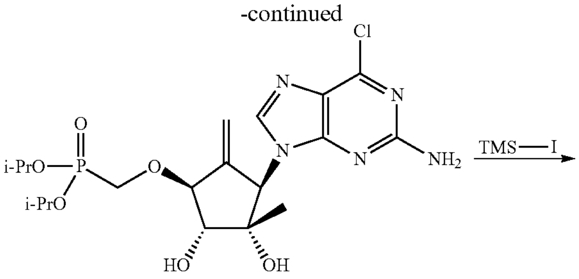

526-10

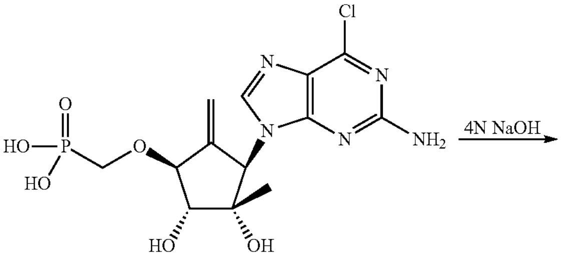

526-11

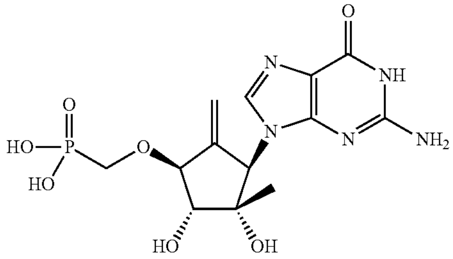

526-12

A solution of tert-butyl hydroperoxide (t-BuOOH) in benzene (68%, 3 eq) is added dropwise to a solution of allylic alcohol 526-1 (synthesized as described in *Tet. Lett.*, 38: 2355 (1997)) and $VO(acac)_2$ in benzene (final concentration 0.1 M) at room temperature (Scheme 526-1). After 1 h of stirring at room temperature, saturated aqueous $Na_2S_2O_3$ is added to the reaction mixture. The resulting solution is extracted with EtOAc, washed with $H_2O$, and dried over sodium sulfate. After removal of solvent, the crude product 526-2 is purified by column chromatography on silica.

Epoxide 526-2 and p-anisylchlorodiphenylmethane (1.5 eq) is dissolved in anhydrous pyridine (0.17 M) and stirred at 25° C. for 2d. Solvents were removed under reduced pressure and the residue dissolved in EtOAc. The organics were washed with water, saturated aqueous $NaHCO_3$, and dried over sodium sulfate. After removal of solvent, the crude product 526-3 is purified by column chromatography on silica.

To a solution of methyltriphenylphosphonium bromide (2 eq) in anhydrous THF at −78° C. is added n-butyllithium (2.2 eq). The solution is allowed to warm to room temperature and stirred for 20 min. After recooling to −78° C., this solution is added to fully protected epoxide 526-3 in THF (final concentration 0.06 M). The reaction mixture is allowed to warm to room temperature and stirred for 12 h at which point $H_2O$ is added and extracted with diethyl ether. The combined organics were dried over sodium sulfate. After removal of solvent, the crude product 526-4 is purified by column chromatography on silica.

Sodium hydride (1 eq) and 2-amino-4-chloro-7H pyrrolo [2,3-d]pyrimidine (1 eq) were dissolved in anhydrous DMF (0.06 M) and stirred at 120° C. for 10 min. A solution of 526-4 in DMF is then added and the reaction mixture is stirred 12 h at 120° C. at which point the solvents were evaporated under reduced pressure. The residue is dissolved in $CH_2Cl_2$, washed with $H_2O$, and dried over sodium sulfate. After removal of solvent, the crude product 526-5 is purified by column chromatography on silica.

Compound 526-5 is dissolved in dichloromethane and added to a solution of 1,1,1-tris(acetyloxy)-1,1-dihydro-1,2-benziodoxol-3-(1H)-one (Aldrich, Dess-Martin periodinane, 4 eq) in dichloromethane (final concentration 0.06 M). The reaction mixture is stirred at room temperature for 4 d at which point it is diluted with EtOAc and poured into a solution of sodium thiosulfate in saturated aqueous sodium bicarbonate solution. The organic layer is separated and dried over sodium sulfate. After removal of solvent, the crude product 6 is purified by column chromatography on silica.

A solution of ketone 526-6 in anhydrous THF is added to a solution of methylmagnesium bromide (4 eq) in anhydrous THF (0.1 M) at −78° C. The reaction mixture is stirred for 12 h at −60° C. at which point the reaction is quenched with saturated aqueous $NH_4Cl$ solution. The mixture is filtered over celite and washed with EtOAc. The combined organics were washed with saturated aqueous $NH_4Cl$, water and dried over sodium sulfate. After removal of solvent, the crude product 526-7 is purified by column chromatography on silica.

A solution of alcohol 7 in anhydrous THF (0.06 M) is treated with a solution of tetrabutylammonium fluoride (1.5 eq) in THF at room temperature. The reaction mixture is stirred for 3 h at which point the solvents were evaporated. The crude desilylated diol 526-8 is purified by column chromatography on silica.

To a solution of diol 526-8 and benzenesulfonic acid diisopropoxy-phosphorylmethyl ester (1.2 eq) in anhydrous DMF (0.1 M) is added magnesium tert-butoxide (1 eq). The reaction mixture is heated to 80° C. for 12 h. After cooling to room temperature, 1 N citric acid is added and extracted with EtOAc. The organics were neutralized with saturated aqueous $NaHCO_3$, washed with saturated aqueous NaCl, and dried over sodium sulfate. After removal of solvent, the crude product 526-9 is purified by column chromatography on silica.

Compound 526-9 is dissolved in 80% acetic acid and stirred 12 h at room temperature. After removal of solvent, the crude product 526-10 is purified by column chromatography on silica.

Phosphonate ester 526-10 and 2,6-lutidine (8 eq) is dissolved in $CH_3CN$ and treated with trimethylsilyliodide (8 eq). After stirring for 3 h at room temperature, triethylamine (8 eq) is added followed by methanol. After removal of solvent, the crude product 526-11 is purified by column chromatography on silica.

Phosphonic diacid S26-11 is dissolved in 1,4-dioxane and treated with 4 N NaOH and heated to 100° C. for 4 h. After cooling to room temperature, the reaction mixture is neutralized with 4N HCl. After removal of solvent, the crude product is purified by column chromatography on silica to provide 526-12.

Scheme 526-2

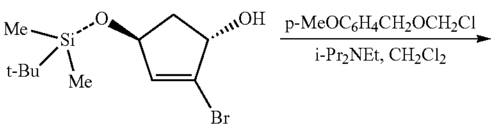

526-13

-continued

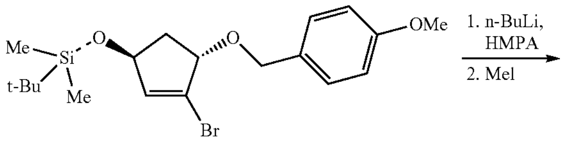

526-14

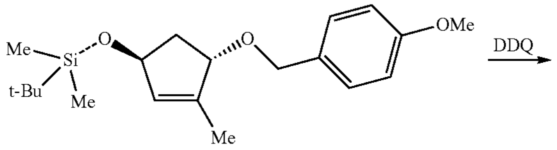

526-15

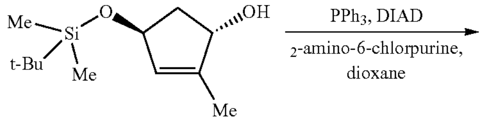

526-16

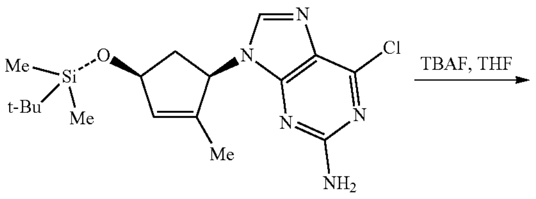

526-17

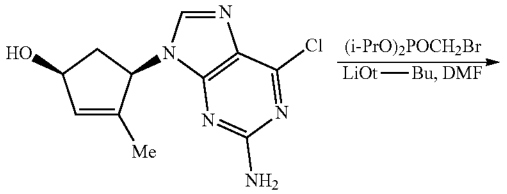

526-18

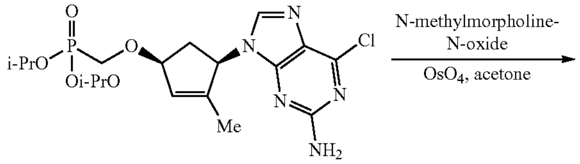

526-19

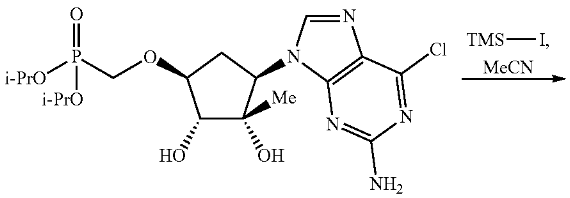

526-20

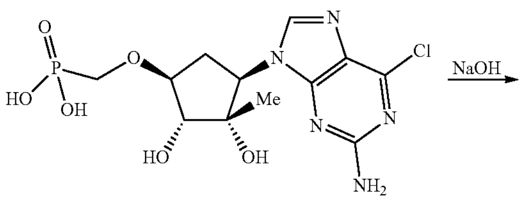

526-21

-continued

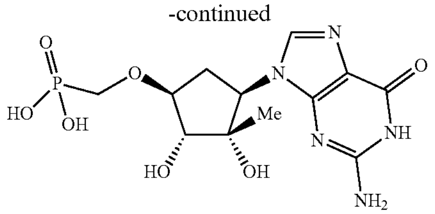

526-22

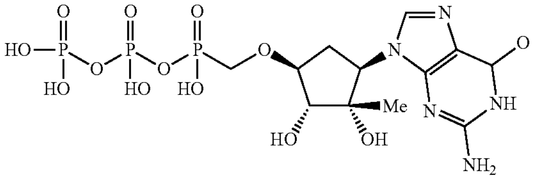

526-23

Compound 526-13 (Paquette et al in *J. Org. Chem.* (1997) 62:1730-1736) is treated with p-methoxybenzyl bromide(1.5 eq.), sodium hydride(1.4 eq) in dry DMF at room temperature (Scheme 526-2). The reaction is monitor by TLC for the disappearance of 526-13. The reaction is quenched by the addition of a saturated aqueous solution of ammonium chloride. Extraction by diethyl ether affords a crude product, which can be purified by silica gel chromatography to give 526-14.

A solution of 526-14 in THF is added dropwise to a solution of n-BuLi (1.2 eq) in THF cooled at −78° C. under a nitrogen atmosphere. The solution is stirred for 1 h at −78° C. Excess of HMPA (1.4 eq) is added. After 10 min, a solution of MeI (5 eq) in THF is added. After another 5 h at −78° C., 20% aqueous $NaH_2PO_4$ is added, and the mixture is warmed to room temperature. Extraction with diethyl ether gives a crude product, which is purified by silica gel chromatography to give 526-15.

Dichlorodicyanoquinone (DDQ) is added to a mixture of compound S26-15 in dichloromethane and water. After stirring at room temperature for 2 h. The mixture is extracted with dichloromethane to give a crude product, which is purified by silica gel chromatography to give 526-16.

To a solution of 526-16 in dioxane, is added triphenylphosphine (2 eq.), 2-amino-6-chloropurine (2 eq) at room temperature. Diisopropyl azodicarboxylate (2 eq, DIAD) is added dropwise via syringe. The mixture is stirred at room temperature for another 3 h. Water is added to quench the reaction. Extraction with ethyl acetate gives a crude product, which is purified by silica gel chromatography to give 526-17.

To a solution of compound S26-17 in THF is added a 1 M solution of tetrabutylammonium fluoride (1.2 eq, TBAF) at room temperature. After another few hours, a saturated solution of ammonium chloride is added. Extraction with ethyl acetate gives a crude product, which is purified by silica gel chromatography to give 526-18.

Compound 526-18, diethyl bromomethylphosphonate (1.5 eq), and lithium t-butoxide (1.5 eq) are added to DMF sequentially. The mixture is stirred at 80° C. for several hours. After the mixture is cooled to room temperature, a 1 M solution of $KH_2PO_4$ is added. Extraction with ethyl acetate gives a crude product, which is purified by silica gel chromatography to give 526-19.

To a solution of 526-19 in acetone, is added N-methylmorpholine N-oxide (2 eq) and osmium tetraoxide (0.2 eq). The mixture is stirred at room temperature for 16 h. A 1 M aqueous solution of sodium sulfite is added. After stirring at room temperature for another hour, the mixture is evaporated to remove most of acetone. The aqueous residue is frozen and lyophilized to give a crude product, which is purified by reversed phase HPLC to give 526-20.

Iodotrimethylsilane (8 eq, TMS-I) is added to a mixture of 526-20, 2,6-lutidine (8 eq) and acetonitrile. After stirring at room temperature for 2 h, the mixture is poured onto ice. The mixture is then frozen and lyophilized to give a residue, which is purified by reversed phase HPLC to give 526-21.

526-21 is dissolved in 4 N aqueous NaOH and refluxed for several hours. The mixture is cooled to room temperature, neutralized with 4 N HCl, and purified with reversed phase HPLC to give 526-22.

Compound 526-22 can be converted to the corresponding diphosphophosphonate 526-23, and prodrugs using known procedures.

Scheme 526-3

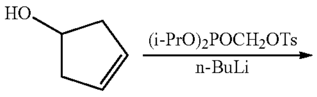

526-24

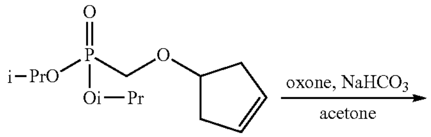

526-25

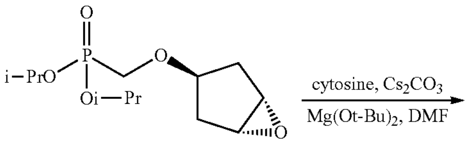

526-26

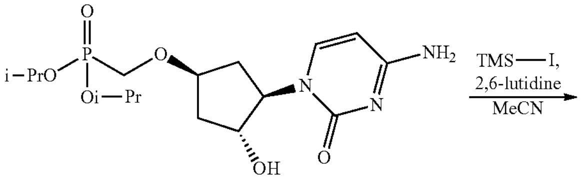

526-27

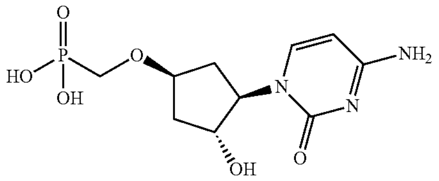

526-28

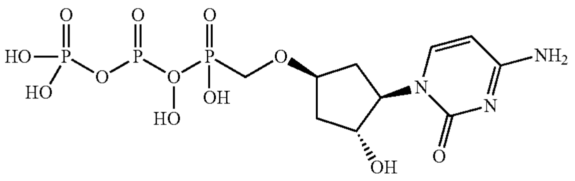

526-29

-continued

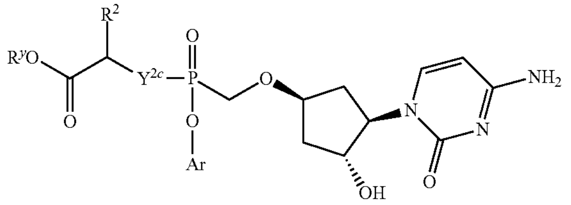

526-30

3-Cyclopenten-1-ol 526-24(108 uL, 1.2 mmol, 1.2 eq) is dissolved in 5 mL of dry THF The solution is cooled to 0° C. A 1.35 M solution of n-BuLi (0.89 mL, 1.2 mmol, 1.2 eq) is added via syringe. After 10 min, diisopropylphosphonomethyl p-toluenesulfonate (350 mg, 1.0 mmol, 1.0 eq) is added. The mixture is stirred in a 45° C. bath for 3.5 h. The reaction is quenched with a pH 7 aqueous phosphate buffer. Extraction with diethyl ether gave a crude product, which is purified by silica gel chromatography (eluted with 45% ethyl acetate in hexane) to give 178 mg of 526-25 (68%).

To a solution of 526-25 (168 mg, 0.69 mmol, 1 eq) in 12 mL of acetone, is added 273 mg of $NaHCO_3$ in 8 mL of water. The mixture is then cooled to 0° C. Oxone (519 mg, 0.85 mmol, 1.3 eq) in 4 mL of water is added over 5 min in portions. The mixture is stirred vigorously for 2.5 h. The mixture is then evaporated in vacuo to remove most of the acetone. The aqueous residue is extracted with ethyl acetate to give a crude product, which is purified by silica gel chromatography to give 526-26 as a clear oil.

To a solution of 526-26 (21 mg, 0.076 mmol, 1.0 eq) in 0.25 mL of DMF, is added cytosine (13 mg, 1.5 eq) and cesium carbonate (6 mg, 0.25 eq) and magnesium t-butoxide. The mixture is heated to 140° C. for several hours. After cooling to room temperature, the reaction mixture is purified by reversed phase HPLC to give 12.5 mg of 526-27 (42%). $^1H$ NMR (CDCl3): δ 9.60 (br s, 1H), 8.96 (br s, 1H), 7.87 (d, 1H), 6.21 (d, 1H), 4.84 (m, 1H), 4.78 (m, 2H), 4.43 (m, 1H), 4.08 (s, 1H), 3.72 (m, 2H), 2.82 (m, 1H), 2.33 (m, 1H), 1.83 (m, 2H), 1.38 (m, 12H) ppm.

The conversion from 526-27 to 526-28 is described in Scheme 526-2 above. The conversion of 526-28 to the corresponding diphosphophosphonate 526-29 and phosphorus prodrugs, e.g. 526-30 can be accomplished using procedures described herein.

Cyclopentyl intermediate 526-31 may be prepared by procedures analogous to those described in U.S. Pat. Nos. 5,206,244 and 5,340,816 (Scheme 526-4). Diol 526-31 is converted to cyclopentenone 526-32 and treated with Mr in the presence of the appropriate phosphonate alcohol to give 526-33. Iodide 526-33 is displaced with inversion to give cyclopentenone intermediate 526-34. Nysted methylenation (U.S. Pat. No. 3,865,848; *Aldrichim. Acta* (1993) 26:14) provides exocyclic methylene 526-35, which may be deprotected to give 526-36.

Cyclopentanone 526-34 may be a versatile intermediate to form other compounds of the invention by reduction to cyclopentyl 526-37, or Wittig or Grubb olefination to alkenyl 526-38.

Scheme 526-4

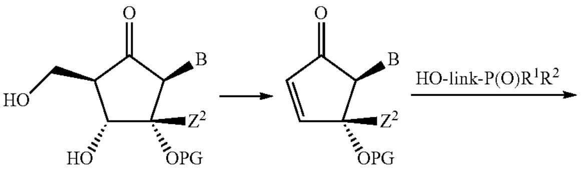

526-31 526-32

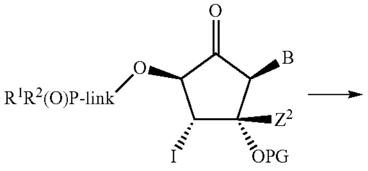

526-33

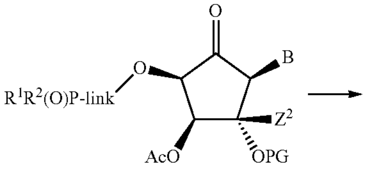

526-34

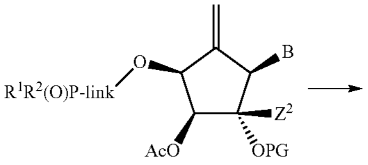

526-35

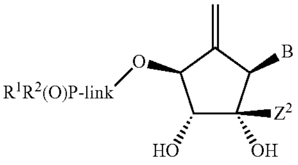

526-36

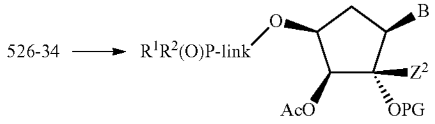

526-37

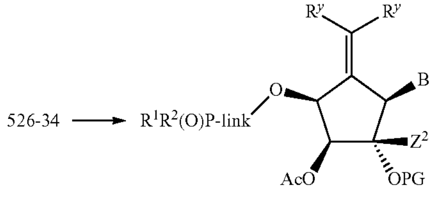

526-38

Scheme 526-5 shows intermediate 526-39 is converted to guanosyl cyclopentenone 526-40 (*J. Am. Chem. Soc.* (1972) 94:3213), then treated with IBr and diethyl phosphomethanol to furnish iodide 526-41 (*J. Org. Chem.* (1991) 56:2642) Nucleophilic substitution with AgOAc affords acetate 526-42. After methylenation using the procedure of Nysted (U.S. Pat. No. 3,865,848; *Aldrichim. Acta* 1993, 26, 14), to give 526-43, the acetate group is removed by the addition of sodium methoxide and the resulting alcohol is inverted by the Mitsunobo protocol, and a second acetate deprotection produces 526-44. Desilylation with tetra-butylammonium fluoride (TBAF) of 526-44 will yield 526-45.

Scheme 526-5
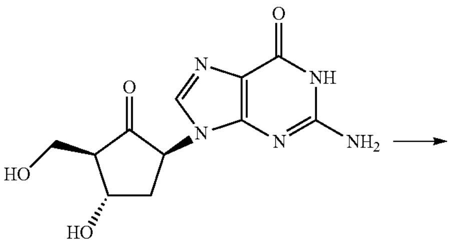
526-39
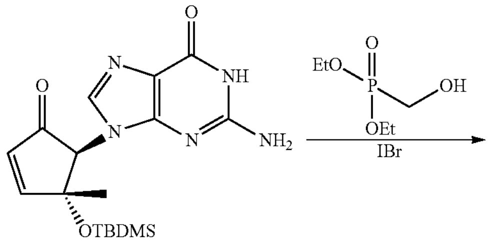
526-40
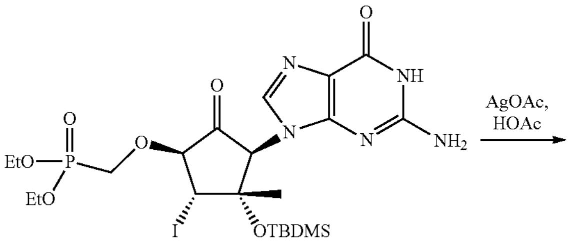
526-41
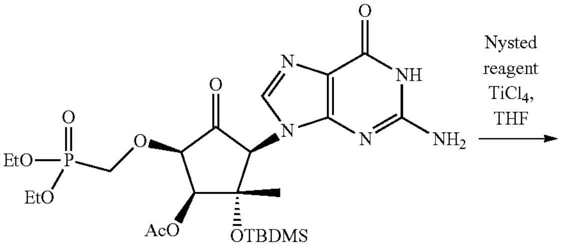
526-42
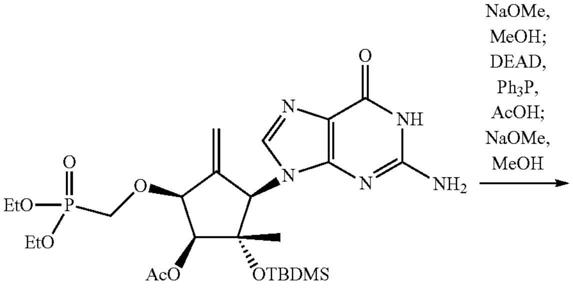
526-43
-continued
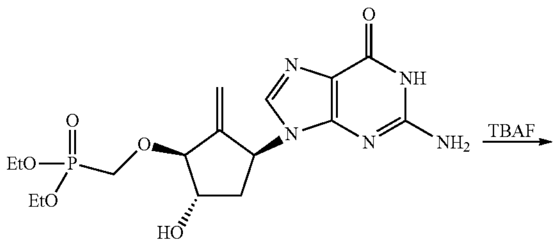
526-44
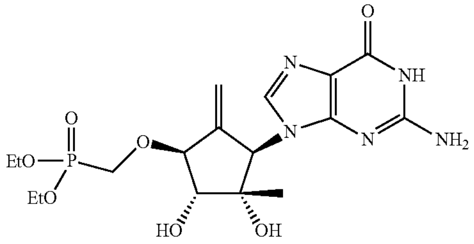
526-45
Synthesis of 2'-C-Me-UP
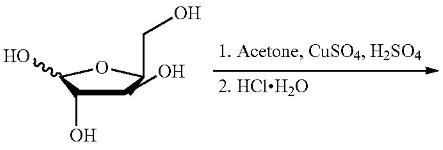
L-Xylose ($4/g)
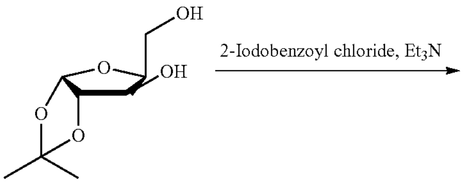
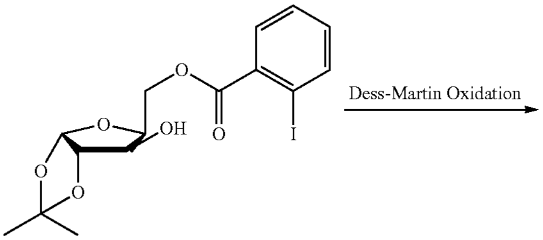
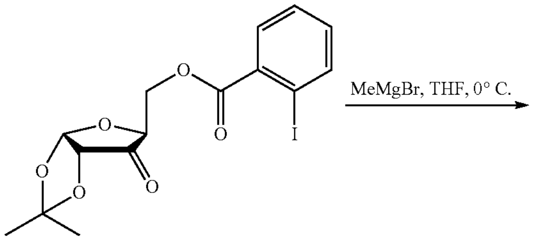

-continued

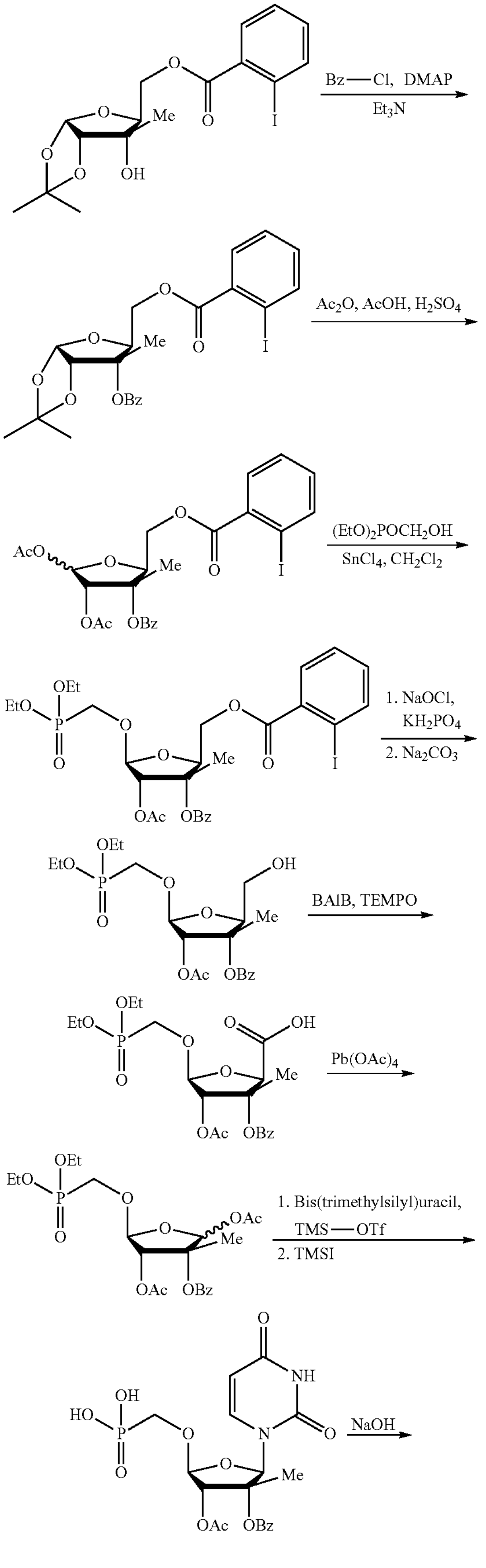

-continued

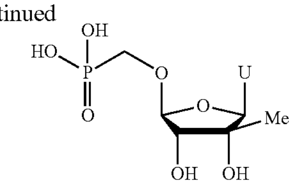

Example 229

Synthesis of Exemplary Compounds of the Invention 527-1

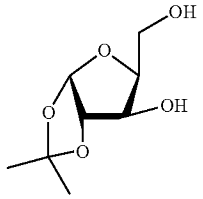

Synthesis of Compound 527-1: L-Xylose (36.2 g) and anhydrous $CuSO_4$ were placed in a 500 mL round bottomed flask. Acetone (220 mL) was added. To this slurry stirred at room temperature was added 3.6 mL of 96% sulfuric acid. The mixture was stirred for another 24 h at room temperature under a nitrogen atmosphere. The mixture is filtered to remove solid material. The solids were washed with 50 mL of acetone. To the combined filtrate was added 25.3 mL of conc. ammonium hydroxide. The precipitates were removed by filtration. The filtrate was evaporated in vacuo to give an oil, which was co-evaporated twice with absolute ethanol to give a yellow oil. The above crude product was stirred with 160 mL of 0.06 M aqueous HCl vigorously at room temperature for 2.5 h. The reaction mixture was homogeneous at the end of the reaction. Solid $NaHCO_3$ (3.26 g) was added in portions. After gas evolution had stopped, the mixture was filtered. The filtrate was frozen and lyophilized overnight to give a syrup, which was dissolved in ethyl acetate and dried over anhydrous Na2SO4 to give the desired diol as a yellow oil. Proton NMR showed the product to be >95% pure. Yield of this crude product: 44.5 g (96%). $^1H$ NMR (DMSO-$d_6$, 300 MHz): δ 5.79 (d, J=3.6 Hz, 1H), 5.13 (d, J=4.9 Hz, 1H), 4.61 (t, J=5.6 Hz, 1H), 4.36 (d, J=3.6 Hz, 1H), 4.10-3.91 (m, 2H), 3.60 (m, 1H), 3.51 (m, 1H), 1.37 (s, 3H), 1.22 (s, 3H) ppm

Example 230

Synthesis of Exemplary Compounds of the Invention 528-2

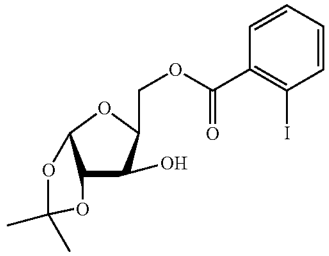

Synthesis of Compound 528-2: 1,2-O-isopropylidene-L-xylose (5 g, 26.3 mmol, 1.0 eq.) and 2-iodobenzoyl chloride (7.01 g, 26.3 mmol) were dissolved in anhydrous dichloromethane (25 mL). The solution was cooled in an ice-water bath. Triethylamine (3.85 mL, 27.6 mmol, 1.05 eq.) was added dropwise via syringe. The mixture was stirred at 0° C. for 30 min and slowly warmed to room temperature over 1 h. Water was added to the reaction mixture. The mixture was washed with 1 M aqueous HCl. The aqueous wash was extracted with 20 mL of dichloromethane. The combined organic extract was washed with a mixture of 20 mL of brine and 5 mL of saturated aqueous sodium bicarbonate. The organic layer was dried over anhydrous $Na_2SO_4$, filtered, and concentrated in vacuo to give a brown oil. This crude product was purified by silica gel chromatography (eluted with 0-50% EtOAc in hexane) to give the desired mono-ester as a yellow oil. Yield: 7.6 g (69%). $^1$H NMR (DMSO-$d_6$, 300 MHz): δ 8.02 (d, J=7.3 Hz, 1H), 7.73 (dd, J=7.8, 1.7 Hz, 1H), 7.52 (t, J=7.3 Hz, 1H), 7.29 (td, J=7.7, 1.8 Hz, 1H), 5.88 (d, J=3.7 Hz, 1H), 5.51 (m, 1H), 4.45 (m, 2H), 4.12 (m, 1H), 1.38 (s, 3H), 1.24 (s, 3H) ppm. MS (m/z): calculated 420.01 (M+H$^+$), 443.00 (M+Na$^+$), found 420.9 (M+H$^+$), 443.0 (M+Na$^+$).

Example 231

Synthesis of Exemplary Compounds of the Invention 529-3

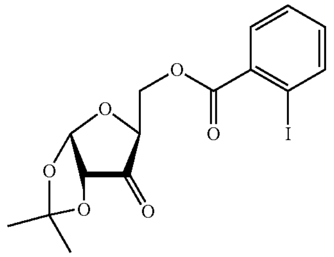

Synthesis of Compound 529-3: The product obtained in the previous step (7.6 g, 18.1 mmol, 1.0 eq.) was dissolved in 35 mL of anhydrous dichloromethane. Dess-Martin periodinane (9.6 g, 22.6 mmol, 1.25 eq.) was added. The mixture was stirred at room temperature for 14 h. A 1 M solution of sodium sulfite (7.5 mL) was added. The resulting mixture was stirred for another 2 h at room temperature. A saturated solution of $NaHCO_3$ was added in portions to adjust the pH of the aqueous phase to 6. The two layers were separated. The aqueous phase was extracted twice with 15 mL of dichloromethane. The combined organic extract was washed with brine, dried over anhydrous $Na_2SO_4$ for 4 h with good stirring. It was then filtered, and dried over excess amount of anhydrous $MgSO_4$ overnight with good stirring. The mixture was filtered and concentrated in vacuo to give a clear oil as product, which was used without further purification in the subsequent step. Yield: 6.7 g (89%). $^1$H NMR (DMSO-$d_6$, 300 MHz): δ 8.02 (d, J=7.9 Hz, 1H), 7.71 (dd, J=7.8, 1.7 Hz, 1H), 7.52 (t, J=7.4 Hz, 1H), 7.29 (td, J=7.6, 1.5 Hz, 1H), 6.16 (d, J=4.6 Hz, 1H), 4.85 (m, 1H), 4.63 (d, J=4.6 Hz, 1H), 4.54 (dd, J=12.2, 2.7 Hz, 1H), 4.42 (dd, J=12.2, 4.3 Hz, 1H), 1.41 (s, 3H), 1.34 (s, 3H) ppm. MS (m/z): calculated 458.99 (M+$H_2O$+Na$^+$), found 459.03 (M+$H_2O$+Na$^+$).

Example 232

Synthesis of Exemplary Compounds of the Invention 530-4

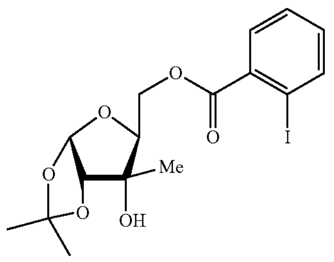

Synthesis of Compound 530-4: The product obtained in the previous step (6.15 g, 14.7 mmol, 1.0 eq.) was dissolved in 29 mL of anhydrous THF. The solution was cooled in an ice-water bath. A 3.0 M solution of methyl magnesium bromide in diethyl ether (5.39 mL, 16.2 mmol, 1.1 eq.) was added dropwise via syringe. The mixture was stirred at 0° C. for 2 h. Aqueous citric acid solution (1 M, 10 mL) was added to the reaction mixture. The resulting mixture was evaporated in vacuo to remove most of THF. The aqueous residue was extracted twice with 10 mL of EtOAc. The organic extract was washed with saturated $NaHCO_3$ and brine. The organic phase was dried over anyhydrous sodium sulfate, filtered, and evaporated in vacuo to give a white solid as product. Yield: 6.11 g (96%). $^1$H NMR (DMSO-$d_6$, 300 MHz): δ 8.01 (dd, J=8.0, 1.0 Hz, 1H), 7.71 (dd, J=7.8, 1.7 Hz, 1H), 7.52 (td, J=7.5, 1.0 Hz, 1H), 7.29 (td, J=7.7, 1.8 Hz, 1H), 5.72 (d, J=3.7 Hz, 1H), 5.13 (s, 1H), 4.46 (dd, J=11.6, 2.3 Hz, 1H), 4.20 (dd, J=11.7, 8.5 Hz, 1H), 4.12 (d, J=3.6 Hz, 1H), 4.08 (dd, J=8.5, 2.1 Hz, 1H), 1.45 (s, 3H), 1.26 (s, 3H), 1.06 (s, 3H) ppm. MS (m/z): calculated 457.01 (M+Na$^+$), found 457.27 (M+Na$^+$).

Example 233

Synthesis of Exemplary Compounds of the Invention 531-5

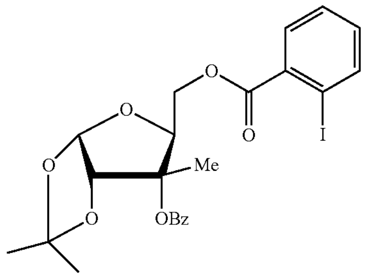

Synthesis of Compound 531-5: To a solution of 530-4 (6.1 g, 14.1 mmol) in 20 mL of anhydrous pyridine, was added triethylamine (3.13 mL, 22.5 mmol), DMAP (0.343 g, 2.8 mmol), followed by benzoyl chloride (2.61 mL, 22.5 mmol). The mixture was stirred at 70 C for 36 h, and then cooled to room temperature. The mixture was evaporated in vacuo to remove most of the pyridine. The residue was acidified with 1 M aqueous citric acid. The resulting mixture was extracted twice with ethyl acetate. The combined organic layer was washed with saturated $NaHCO_3$, and brine, dried over anhydrous $Na_2SO_4$, and evaporated in vacuo to give a crude product. This crude product was purified by silica gel chromatography (0-35% ethyl acetate in hexane) to give 7.0 g (92%) of 5. $^1$H NMR (DMSO-$d_6$, 300 MHz): δ 8.03 (d, J=8.2 Hz, 1H), 7.90 (d, J=7.5 Hz, 2H), 7.79 (d, J=7.7 Hz, 1H), 7.64 (t, J=7.9 Hz, 1H), 7.5 (m, 3H), 7.30 (t, J=7.6 Hz, 1H), 5.92 (d, J=3.7 Hz, 1H), 4.92 (d, J=3.5 Hz, 1H), 4.63 (m, 1H), 4.46 (m, 2H), 1.50 (s, 3H), 1.39 (s, 3H), 1.25 (s, 3H) ppm. MS (m/z) 589.2 ($M+H^+$), 611.3 ($M+Na^+$). MS (m/z): calculated 561.04 ($M+Na^+$), found 561.06 ($M+Na^+$).

Example 234

Synthesis of Exemplary Compounds of the Invention 532-6

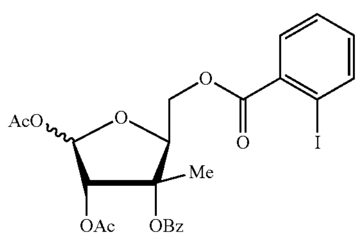

Synthesis of Compound 532-6: To a solution of 531-5 (7.0 g, 13 mmol) in 26 mL of glacial acetic acid, was added acetic anhydride (7.7 mL). The solution was cooled in an ice-water bath. Concentrated sulfuric acid (1.9 mL) was added drop-wise via syringe over 10 min. The cooling bath was removed and the solution was allowed to warm to room temperature and stirred at that temperature for another 20 h. The reaction mixture was poured into a mixture of 75 mL of diethyl ether and 75 g of ice. The layers were separated and the aqueous layer was extracted with 75 mL of diethyl ether. The combined ether extract was stirred with 250 mL of water. Solid NaHCO3 was addedin portions until gas evolution had stopped. The layers were separated. The aqueous layer was extracted with 75 mL of ether. The combined ether extract was washed with brine, dried over anhydrous $MgSO_4$, and concentrated in vacuo to give 6 as a yellow foam. Two diastereomers of the same molecular weight were present in the product mixture, presumably the two anomers. Yield: 6.76 g (89%). This crude product was used without further purification. MS (m/z): calculated 605.03 ($M+Na^+$), found 604.93 ($M+Na^+$).

Example 235

Synthesis of Exemplary Compounds of the Invention 533-7

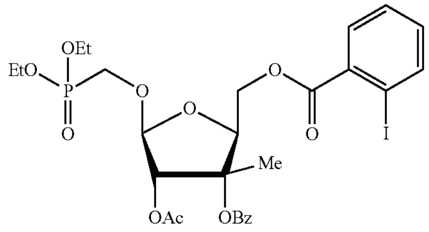

Synthesis of Compound 533-7: 532-6 (6.76 g, 11.6 mmol) was dissolved in 22 mL of dichloromethane. The solution was cooled in an ice-water bath. A solution of $SnCl_4$ in dichloromethane (1.0 M, 29 mL, 29 mmol) was added via syringe. The cooling bath was removed and the mixture was warmed to room temperature and stirred for another hour. The mixture was again cooled to 0° C. Triethylamine (15 mL) was added via syringe. The resulting solution was poured onto a mixture of 75 g of ice and 75 mL of EtOAc. The mixture was filtered through a pad of Celite. The solids were washed thoroughly with EtOAc. The combined filtrate was washed with saturated $NaHCO_3$, brine, dried over $Na_2SO_4$, and concentrated in vacuo to give a crude product, which was purified by silica gel chromatography (25-75% EtOAc in hexane) to give 7 as a light yellow foam. Yield: 6.0 g (75%). $^1$H NMR (DMSO-do, 300 MHz): δ 8.00 (d, J=7.9 Hz, 1H), 7.86 (d, J=8.0 Hz, 2H), 7.79 (d, J=7.9 Hz, 1H), 7.61 (t, J=7.2 Hz, 1H), 7.45 (m, 3H), 7.25 (t, J=7.3 Hz, 1H), 5.28 (s, 1H), 5.07 (s, 1H), 4.65 (m, 2H), 4.49 (m, 1H), 4.10-3.90 (m, 5H), 3.83 (dd, J=13.9, 9.0 Hz, 1H), 1.88 (s, 3H), 1.69 (s, 3H), 1.18 (t, J=6.9 Hz, 6H) ppm. MS (m/z): calculated 713.06 ($M+Na^+$), found 713.08 ($M+Na^+$).

Example 236

Synthesis of Exemplary Compounds of the Invention 534-8

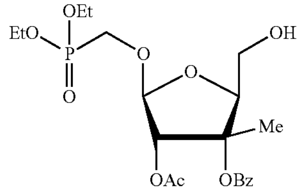

Synthesis of Compound 534-8: To a solution of 533-7 (4.7 g, 6.8 mmol) in 30 mL of dichloromethane was added 27.2 mL of a 1.0 M aqueous solution of $KH_2PO_4$. A 0.8 M solution of NaOCl in water was added. The mixture was stirred at room temperature for 1 h. Methanol (10 mL) was added. Solid K2CO3 was added in portions until the pH of the aqueous phase reached 9-10. The mixture was stirred for another hour at room temperature. An 1 M aqueous solution of $Na_2SO_3$ (10 mL) was added and the mixture was stirred for another 30 min at room temperature. The two layers were separated. The aqueous layer was further extracted with dichloromethane. The combined organic layer was washed with brine, dried over anhydrous Na2SO4, and evaporated in vacuo to give 534-8 as a yellow foam, which was used directly in the next step without further purification. $^1$H NMR (DMSO-$d_6$, 300 MHz): δ 7.94 (d, J=7.8 Hz, 2H), 7.68 (t, J=7.5 Hz, 1H), 7.54 (t, J=7.6 Hz, 2H), 5.28 (d, J=1.0 Hz, 1H), 5.05 (d, J=1.2 Hz, 1H), 4.98 (t, J=5.6 Hz, 1H), 4.34 (dd, J=6.5, 4.6 Hz, 1H), 4.11-3.95 (m, 5H), 3.86 (dd, J=13.7, 8.8 Hz, 1H), 3.76 (m, 1H), 3.63 (m, 1H), 1.93 (s, 3H), 1.64 (s, 3H), 1.25 (t, J=7.0 Hz, 6H) ppm. $^{31}$P NMR (DMSO-$d_6$): δ 20.63 (s, 1P) ppm. MS (m/z): calculated 483.14 ($M+Na^+$), found 483.30 ($M+Na^+$).

Example 237

Synthesis of Exemplary Compounds of the Invention 535-9

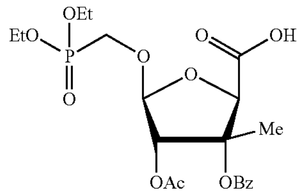

Synthesis of Compound 535-9: To a mixture of 533-8 obtained above and 6.8 mL of acetonitrile and 6.8 mL of water, was added iodobenzene diacetate (4.97 g, 15 mmol), and TEMPO (0.213 g, 1.36 mmol). The mixture was stirred vigorously for 6 h at room temperature. It was then frozen and lyophilized to give a orange colored solid, which was dissolved in dichloromethane and purified by silica gel chromatography (0-10% MeOH in CH2Cl2) to give 534-9 as a light yellow solid. Yield: 2.8 g (87% for two steps). $^{1}$H NMR (DMSO-$d_6$, 300 MHz): δ 13.39 (br s, 1H), 7.97 (d, J=7.8 Hz, 2H), 7.70 (t, J=7.3 Hz, 1H), 7.56 (t, J=7.5 Hz, 2H), 5.35 (s, 1H), 5.16 (s, 1H), 4.89 (s, 1H), 4.18 (dd, J=13.7, 8.8 Hz, 1H), 4.06 (m, 4H), 3.88 (dd, J=13.4, 9.7 Hz, 1H), 1.86 (s, 3H), 1.69 (s, 3H), 1.24 (dt, J=7.0, 2.7 Hz, 6H) ppm. $^{31}$P NMR (DMSO-$d_6$): δ 20.79 (s, 1P) ppm. MS (m/z): calculated 473.12 ($M-H^-$), found 472.95 ($M-H^-$).

Example 238

Synthesis of Exemplary Compounds of the Invention 536-10

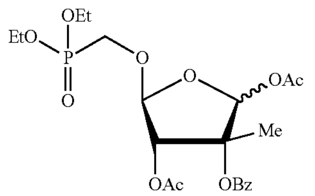

Synthesis of Compound 536-10: To a solution of 535-9 (474 mg, 1.0 mmol) in 2.0 mL of anhydrous DMF, was added pyridine (238 mg, 3.0 mmol), and lead tetraacetate (1.33 g, 3.0 mmol). The mixture was stirred while shielded from light for 7 h at room temperature. It was then poured into a mixture of 10 g of ice and 10 mL of diethyl ether. The mixture was filtered to remove precipitates. The two layers of the filtrate were separated. The aqueous phase was extracted twice with ether. The combined ether extract was washed with 1 M citric acid, saturated $NaHCO_3$, and brine. After drying with anhydrous MgSO4, the ether solution was concentrated in vacuo to give crude 536-10 as a colorless oil, which was used without further purification. Yield: 255 mg (52%). MS (m/z): calculated 511.13 ($M+Na^+$) found 511.11 ($M+Na^+$).

Example 239

Synthesis of Exemplary Compounds of the Invention 537-11

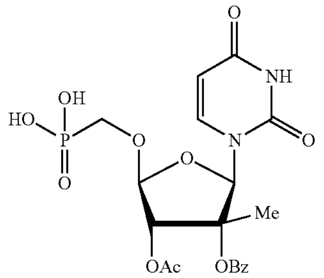

Synthesis of Compound 537-11: To a solution of 536-10 (211 mg, 0.43 mmol) in 2.0 mL of anhydrous acetonitrile, was added O,O-bis(trimethylsilyl)uracil (443 mg, 1.73 mmol), and TMS-OTf (384 mg, 1.73 mmol). The mixture was stirred at room temperature for 3 h. An additional 443 mg of O,O-bis(trimethylsilyl)uracil was added, and the mixture was stirred for another 4 h at room temperature. 2,6-Lutidine (371 mg, 3.46 mmol) was added dropwise via syringe, followed by TMS-I (259 mg, 1.3 mmol). The mixture was stirred for another hour at room temperature and then poured onto 10 g of ice. The mixture frozen and filtered through a pad of Celite. The filtrate was frozen and lyophilized to give a yellow solid, which was dissolved in water and purified by reversed phase HPLC to give 537-11 as a white solid. Yield: 20 mg (10%). MS (m/z): calculated 483.08 ($M-H^-$), found 483.34 ($M-H^-$).

Example 240

Synthesis of Exemplary Compounds of the Invention 538-12

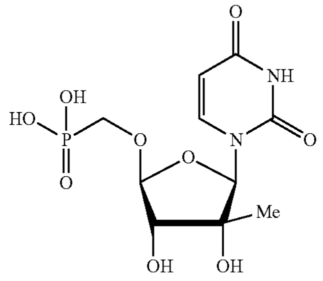

Synthesis of Compound 538-12: To a solution of 537-11 (17 mg, 0.035 mmol) in 0.3 mL water, was added NaOH (4.3 mg, 0.11 mmol). After stirring at room temperature for 2 h, the mixture acidified with trifluoroacetic acid and purified by HPLC to give 538-12 as a white powder. Yiled: 5 mg (42%). $^{1}$H NMR ($D_2O$, 300 MHz): δ 7.74 (d, J=8.2 Hz, 1H), 5.97 (s, 1H), 5.78 (d, J=8.2 Hz, 1H), 5.10 (d, J=4.9 Hz, 1H), 3.86 (dd, J=12.9, 10.0 Hz, 1H), 3.78 (d, J=4.7 Hz, 1H), 3.65 (dd, J=12.7, 9.3 Hz, 1H), 1.10 (s, 3H) ppm. $^{31}$P NMR ($D_2O$): δ 14.60 (s, 1P) ppm. MS (m/z): calculated 337.04 ($M-H^-$), found 337.38 ($M-H^-$).

Example 241

Synthesis of Exemplary Compounds of the Invention

Synthesis of 3'-Deoxy-CP

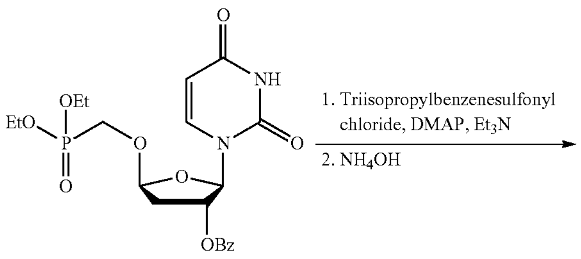

1

-continued

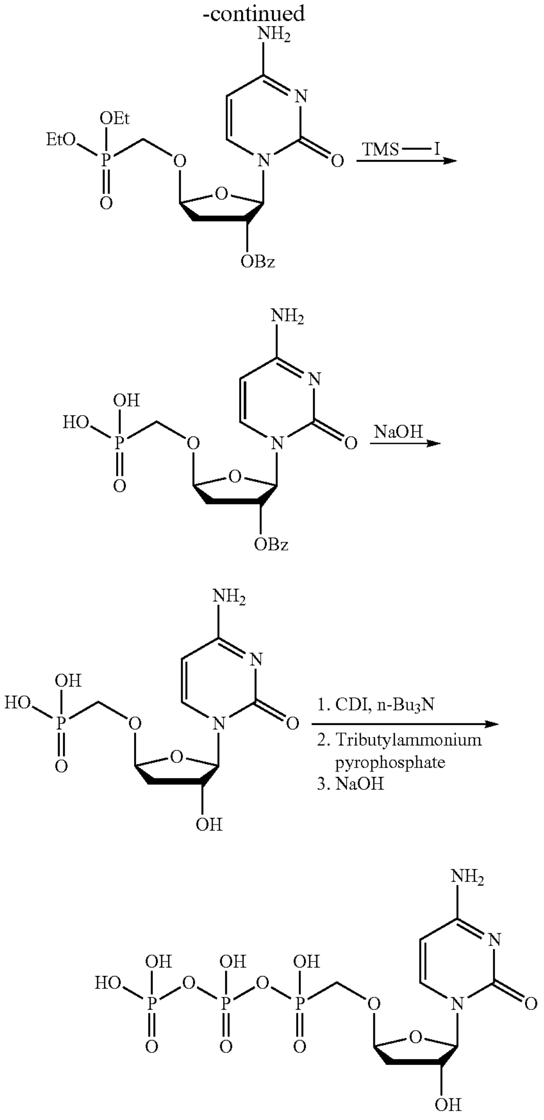

Example 242

Synthesis of Exemplary Compounds of the Invention 540-2

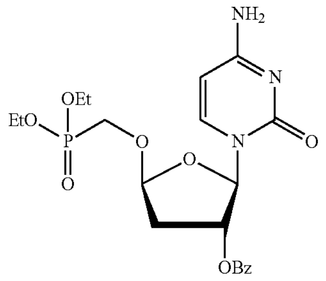

Synthesis of Compound 540-2 To a stirred solution of 527-1 (50 mg, 0.11 mmol) in 1 mL of acetonitrile under nitrogen was added 2,4,6-triisopropylbenzenesulfonyl chloride (65 mg, 0.21 mmol), DMAP (26 mg, 0.21 mmol), and triethylamine (22 mg, 0.21 mmol). The mixture was stirred at room temperature for 4 h. Aqueous ammonia (29%, 1 mL) was added. The mixture was stirred at room temperature for 2 h. Extraction with EtOAc, followed by purification by silica gel chromatography gave 540-2 as a white solid. MS (m/z): calculated 468.15 (M+H$^+$), found 468.0 (M+H$^+$).

Example 243

Synthesis of Exemplary Compounds of the Invention 541-3

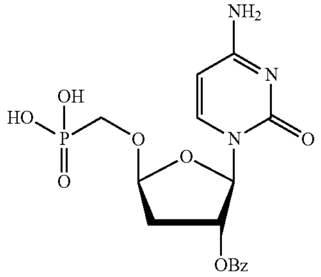

Synthesis of Compound 541-3: To a solution of 540-2 obtained above in acetonitrile was added 2,6-lutidine (118 mg, 1.10 mmol) and TMS-I (165 mg, 0.84 mmol). The mixture was stirred at room temperature for 2 h. Triethylamine was added, followed by water. The mixture was then frozen and lyophilized to give a solid residue. This crude product was purified by reversed phase HPLC to give 541-3 as a white solid. Yiled 44 mg (97% for two steps). MS (m/z): calculated 410.1 (M–H$^-$), found 410.2 (M–H$^-$).

Example 244

Synthesis of Exemplary Compounds of the Invention 542-4

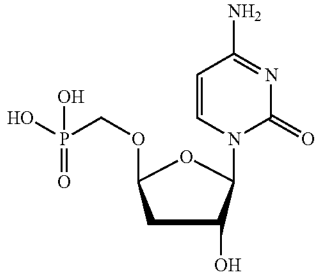

Synthesis of Compound 542-4: To solution of 541-3 (40 mg, 0.097 mmol) in 0.5 mL of water was added NaOH (20 mg, 0.5 mmol). The solution was stirred at room temperature for 30 min. Reversed phase HPLC purification gave 542-4 as a white solid. Yield: 28 mg (94%). $^1$H NMR (D$_2$O, 300 MHz) δ 7.79 (d, J=7.6 Hz, 1H), 5.95 (d, J=7.6 Hz, 1H), 5.88 (d, J=2.8 Hz, 1H), 5.40 (m, 1H), 4.42 (m, 1H), 3.78 (dd, J=12.8, 9.8 Hz, 1H), 3.55 (dd, J=13.1, 9.7 Hz, 1H), 2.20-2.05 (m, 2H) ppm.

$^{31}P$ NMR ($D_2O$, 300 MHz) δ 14.66 ppm. MS (m/z): calculated 306.05 ($M-H^-$), found 305.8 ($M-H^-$).

Example 245

Synthesis of Exemplary Compounds of the Invention 543-5

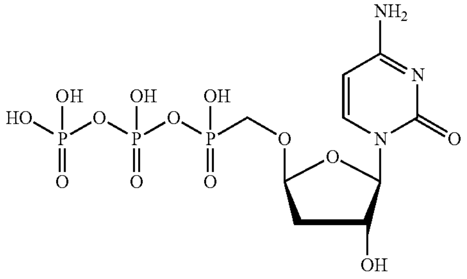

Synthesis of Compound 543-5: To phosphonic diacid S42-4 (9 mg, 0.029 mmol) in 0.25 mL of DMF was added tributylamine (5.4 mg, 0.03 mmol) followed by carbonyldiimidazole (48 mg, 0.3 mmol). Reaction mixture was stirred at room temperature for 4 h at which point MeOH (0.010 mL) was added and stirred for an additional 30 min. Tributyl ammonium pyrophosphate (161 mg, 0.3 mmol) in DMF (0.64 mL) was added the reaction mixture stirred for 14 h. After the solvents were evaporated in vacuo, the crude product was purified by ion exchange HPLC (0-40% TEAB) to give the triethylammonium salt of 543-5 as a white solid. Yield: 3 mg. $^1H$ NMR ($D_2O$, 300 MHz) δ 7.78 (d, J=7.6 Hz, 1H), 6.02 (d, J=7.6 Hz, 1H), 5.88 (d, J=2.9 Hz, 1H), 5.42 (m, 1H), 4.41 (m, 1H), 4.05-3.62 (m, 2H), 3.05 (q, J=7.4 Hz, triethylammonium), 2.23-1.95 (m, 2H), 1.13 (t, J=7.4 Hz, triethylammonium) ppm. $^{31}P$ NMR ($D_2O$, 300 MHz) δ 7.58 (d), −8.34 (d), −22.71 (t) ppm. MS (m/z): calculated 465.98 ($M-H^-$), found 466.16 ($M-H^-$).

Example 246

Synthesis of Exemplary Compounds of the Invention

Synthesis of 3'-Deoxy-CP

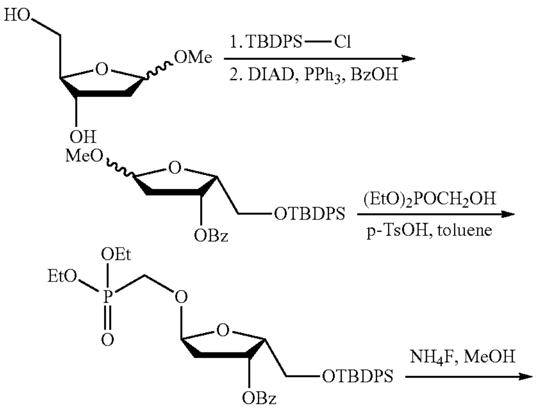

-continued

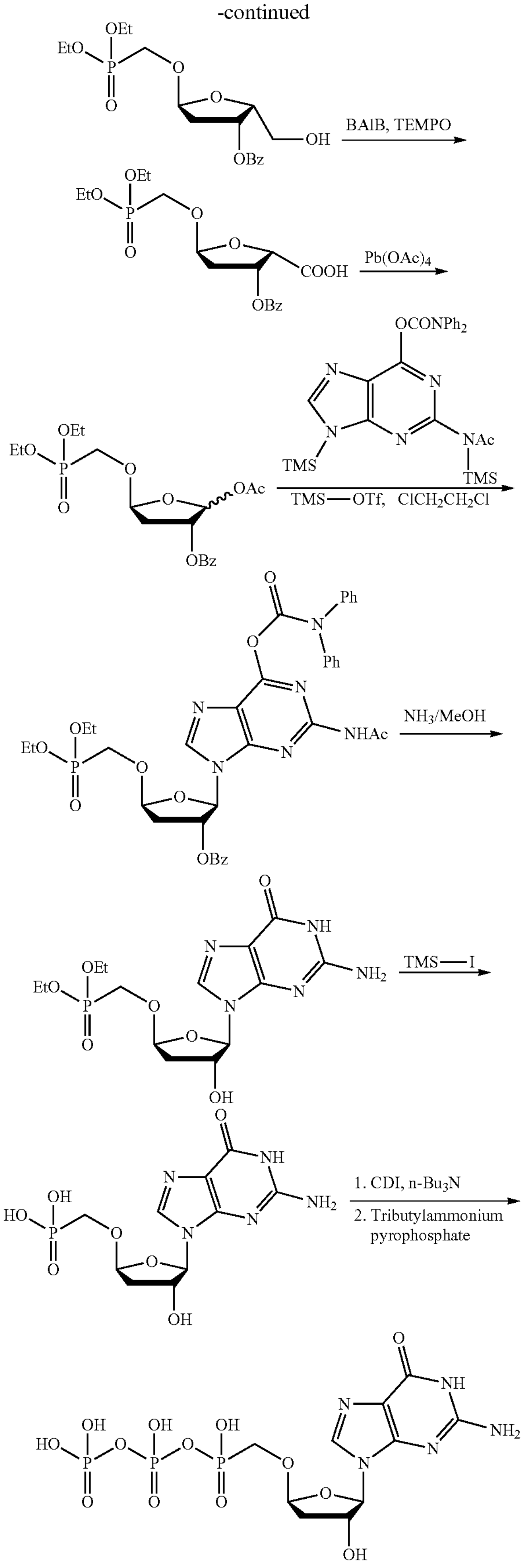

Example 247

Synthesis of Exemplary Compounds of the Invention 545-2

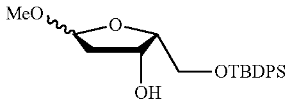

Synthesis of Compound 545-2 To a stirred solution of 1-O-methyl-2'-deoxy-D-ribose (23.9 g, 161.41 mmol) in pyridine under nitrogen was added t-butyldiphenylsilyl chloride (48 mL, 186 mmol) dropwise. When the addition was complete N,N-dimethyl-4-aminopyridine was added as a solid. The reaction was stirred at room temperature for 12 hr. and monitored by TLC. When the reaction was complete by TLC the pyridine was removed under vacuum. The oily residue was suspended in ethyl acetate (150 mL) and a white solid formed. The mixture was filtered and the solid was washed with 50 mL additional ethyl acetate. The solid was then discarded. The organic filtrates were combined and washed with water (2×100 mL), 1N HCl(aq) (2×100 mL) and sodium bicarbonate(sat'd)(2×100 mL). The organic phase was collected and dried over $MgSO_4$(anh). Evaporation and purification by column chromatography provides the desired mixture of diastereomers 545-2: yield 31.15 g (50 0%). $^1$H NMR ($CD_3CN$, 300 MHz): δ 1.08 m, 9H); 1.85 m 1H; 2.27 m 2H; 3.3 s 3H; 3.7 m 2H; 3.90 m 1H; 4.27 m 1H; 5.06 m 1H, 7.45 m 6H; 7.76 m 4H. ppm.

Example 248

Synthesis of Exemplary Compounds of the Invention 546-3

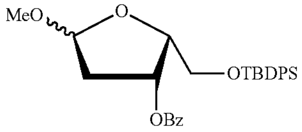

Synthesis of Compound 546-3: The alcohol 545-2 (5.00 g, 12.95 mmol) and triphenylphosphine (6.79 g. 25.9 mmol) were dissolved in anhydrous THF (50 mL) under nitrogen at room temperature. To this stirring solution was added dropwise, a mixture of benzoic acid (3.162 g, 25.9 mmol) and disopropylazodicarboxylate dissolved in anhydrous THF (30 mL). After the addition was complete the reaction was stirred for 12 hr. at room temperature. After the reaction was complete by TLC, the solvent was removed under vacuum. The residue was suspended in diethyl ether (60 mL). Hexane (120 mL) was added and the solid formed was filtered and discarded. The solvents were removed by rotary evaporation and the products 546-3 were purified by column chromatography (2% to 15% EtOAc in hexane): yield 3.074 g (48.4%). $^1$H NMR ($CD_3CN$, 300 MHz): δ 0.98 m 9H; 2.07 m 1H; 2.42 m 2H; 3.35 s 3H; 3.85 m 1H; 3.99 m 1H; 4.4 m 1H; 5.10 m 1H; 5.69 m 1H; 7.30 m 1H; 7.47 m 5H; 7.65 m 6H; 7.80 m 1H; 7.95 m 1H; 8.22 m 1H ppm.

Example 249

Synthesis of Exemplary Compounds of the Invention 547-4

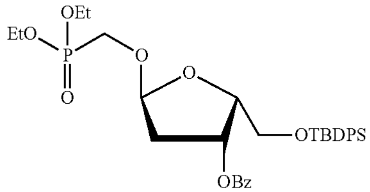

Synthesis of Compound 547-4: The acetal 546-3 (6.88 g, 12.95 mmol) and hydroxymethylphosphonate diethyl ester (7.76 mL, 52.65 mmol) were dissolved in 200 mL of toluene. The toluene was removed by rotary evaporation at 70° C. under vacuum to reduce the reaction volume to approximately 25 mL. The reaction was cooled to room temperature and p-toluene sulfonic acid monohydrate (0.490 g, 2.58 mmol) was added as a solid along with toluene (200 mL). The toluene was removed by rotary evaporation at 70° C. under vacuum to reduce the reaction volume once again to approximately 25 mL. Two additional aliquots of toluene were added and removal by evaporation is repeated each time. The reaction was monitored by TLC and when completed the residue was suspended in ethyl acetate (100 mL) The organic layer was washed with sodium bicarbonate (sat'd), brine and then dried over $MgSO_4$ (anh). The desired phosphonate 547-4 was purified by column chromatography (10% to 90% EtOAc in hexane): yield 2.89 g (33%). $^1$H NMR (DMSO-$d_6$, 300 MHz): δ 0.92 s 9H; 1.25 t 6H; 2.35 t 2H; 3.84 m 4H; 4.05 m 4H; 4.32 q 1H; 5.37 t 1H; 5.62 q 1H; 7.26 t 2H; 7.30-7.55 m 8H; 7.60 d 2H; 7.65 t 1H; 7.82 d 2H ppm.

Example 250

Synthesis of Exemplary Compounds of the Invention 548-5

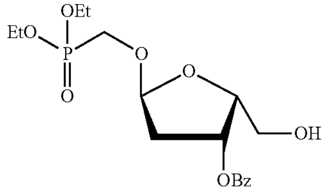

Synthesis of Compound 548-5: The silyl ether 547-4 (2.86 g, 4.57 mmol) was dissolved in a minimal amount of methanol (15 mL) and stirred a room temperature under nitrogen. Ammonium fluoride (1.69 g, 45.7 mmol) was added as a solid and the reaction was stirred at room temperature for 12 hr. The reaction was monitored by TLC and, when complete the methanol was removed under a stream of nitrogen. Add 6 mL of 1N Acetic acid (aq) and extract the aqueous phase with ethyl acetate (2×125 mL). Combine the organic extracts and dried over $Na_2SO_4$(anh). The final product 548-5 was purified by column chromatography (50% to 100% EtOAc in hexane): yield 1.59 g (90%). $^1$H NMR (DMSO-$d_6$, 300 MHz): δ 1.21 t 6H; 2.35 t 2H; 3.62-3.82 m 4H; 4.05 m 4H; 4.12 q 1H; 5.30 t 1H; 5.49 q 1H; 7.47 t 2H; 7.65 t 1H; 7.90 d 2H.

Example 251

Synthesis of Exemplary Compounds of the Invention 549-6

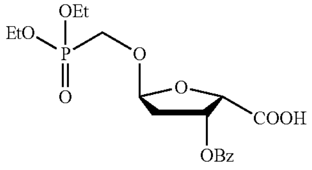

Synthesis of Compound 549-6: The primary alcohol 548-5 (1.43 g, 3.69 mmol) was dissolved in a 1:1 mixture of acetonitrile and water (10 mL) under nitrogen. Bisacetyliodobenzene (2.61 g, 8.12 mmol) was added as a solid along with a catalytic amount of TEMPO (0.115 g, 0.74 mmol). The reaction was stirred at room temperature for 12 hr. and monitored by TLC. When the reaction was complete, it was frozen and lyphilized. The carboxylic acid 549-6 was purified by column chromatography (0% to 10% methanol in dichloromethane): yield 0.750 g (51%). $^1$H NMR ($CD_3CN$, 300 MHz): δ 1.30 t 6H; 2.45 t 2H; 3.84 m 1H; 4.00-4.20 m 5H; 4.82 d 1H; 5.50 t 1H; 5.82 q 1H; 7.54 t 2H; 7.65 t 1H; 7.96 d 2H.

Example 252

Synthesis of Exemplary Compounds of the Invention 550-7

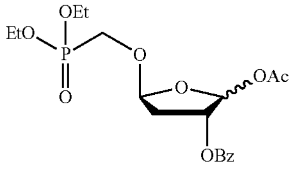

Synthesis of Compound 550-7 To acid S49-6 (88 mg, 0.22 mmol) in DMF (3.1 mL, 0.07 M) was added anhydrous pyridine (0.027 mL, 0.33 mmol) followed by lead tetraacetate (146 mg, 0.33 mmol). After 14 h at room temperature, $Et_2O$/$H_2O$ (1:1, 3 mL) was added. The organics were separated, washed with 1M aqueous citric acid, saturated aqueous $NaHCO_3$, saturated aqueous NaCl and dried over sodium sulfate. After removal of solvent, the crude product 7 (50 mg, 54%) was used directly in the next reaction.

Example 253

Synthesis of Exemplary Compounds of the Invention 551-8

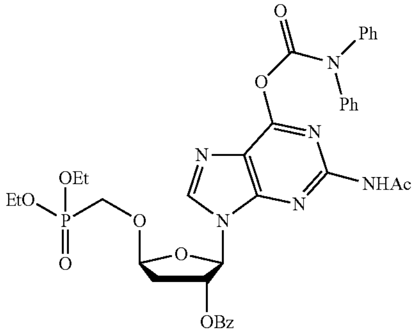

Synthesis of Compound 551-8: N-Acetoxy-diphenylcarbamoyl gaunine (43 mg, 0.11 mmol), synthesized as described in *Can. J. Chem.* 65: 1436 (1987), in dichloroethane (1.1 mL, 0.1 M) was treated with N,O-bis(trimethylsilyl)acetamide (0.054 mL, 0.22 mmol). The reaction mixture was heated to 80° C. for 20 min after which the solvents were removed in vacuo. The crude silylated protected guanine was combined with phosphonate 550-7 (50 mg, 0.12 mmol) in dichloroethane (1.1 mL, 0.1 M) to which TMSOTf (28 μL, 0.153 mmol) was added. The reaction mixture heated to 60° C. for 5 h after with the reaction was quenched with saturated aqueous $NaHCO_3$. The solution was extracted with $CH_2Cl_2$, washed with saturated aqueous $NaHCO_3$, and dried over sodium sulfate. After removal of solvent, the crude product was purified by column chromatography on silica (2% MeOH/$CH_2Cl_2$) to provide the phosphonate diester S51-8 (18 mg, 22%). $^1$H NMR ($CDCl_3$, 300 MHz) δ 8.30 (s, 1H), 8.15 (s, 1H), 8.02 (s, 1H) 8.00 (s, 1H), 7.35-7.62 (m, 12H), 6.43 (d, 1H), 6.02 (m, 1H), 5.65 (m, 1H), 4.18 (q, 4H), 3.78-4.01 (m, 2H), 2.86 (m, 1H), 2.63 (m, 1H), 2.53 (s, 3H), 1.37 (t, 6H) ppm. $^{31}$P NMR ($CDCl_3$, 300 MHz) δ 20.07 (s) ppm. MS (m/z): calculated 744.2 ($M+H^+$), found 744.9 ($M+H^+$).

Example 254

Synthesis of Exemplary Compounds of the Invention 552-9

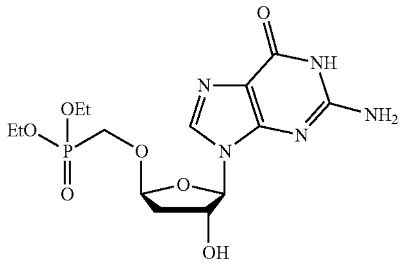

Synthesis of Compound 552-9 Phosphonate ester 551-8 (14 mg, 0.02 mmol) was treated with $NH_3$ in MeOH (2 mL, 2.0 N) at room temperature for 9 h. After solvents were removed in vacuo, the crude product was purified by column chromatography on silica (10% MeOH/$CH_2Cl_2$) to provide 552-9. $^1$H NMR ($CD_3OD$, 300 MHz) δ 7.89 (s, 1H), 5.96 (d, 1H), 5.45 (m, 1H), 4.10-4.21 (q, 4H), 3.84-4.02 (m, 2H), 2.92-2.47 (m, 2H), 1.33 (t, 6H) ppm. $^{31}$P NMR ($CD_3OD$, 300 MHz) δ 21.75 ppm. MS (m/z): calculated 404.1 ($M+H^+$), found 404.2 ($M+H^+$).

Example 255

Synthesis of Exemplary Compounds of the Invention 553-10

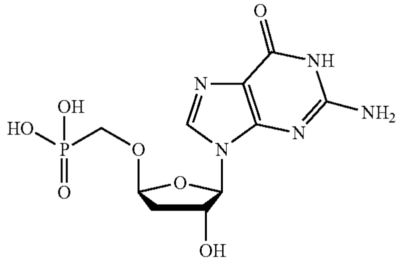

Synthesis of Compound 553-10: To phosphonate ester guanosine derivative 552-9 (5.8 mg, 0.02 mmol) in anhydrous acetonitrile (0.15 mL, 0.1 M) was added 2,6-lutidine (0.014 mL, 0.12 mmol) followed by iodotrimethylsilane (0.016 mL, 0.12 mmol). After stirring for 15 min, triethylamine (0.12 mmol) and methanol (0.020 mL) were added and solvents were removed in vacuo. The crude product was purified by reverse phase column chromatography on C18 (0-10% MeOH/$H_2O$-1% AcOH) to provide the phosphonic diacid S53-10. $^1H$ NMR ($D_2O$, 300 MHz) δ 7.91 (s, 1H), 5.86 (d, 1H), 5.41 (m, 1H), 3.42-3.65 (m, 2H), 2.25-2.36 (m, 2H) ppm. $^{31}P$ NMR ($D_2O$, 300 MHz) δ 15.16 ppm. MS (m/z): calculated 346.1 (M−$H^-$), found 346.3 (M−$H^-$).

Example 256

Synthesis of Exemplary Compounds of the Invention 554-11

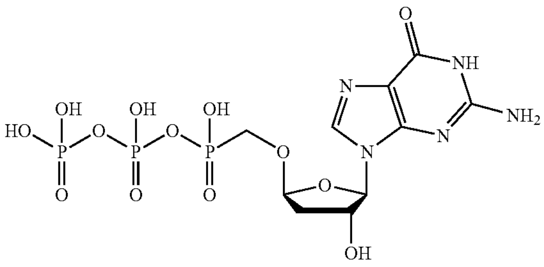

Synthesis of Compound 554-11: To phosphonic diacid S53-10 (2.5 mg, 7.2 μmol) in DMF (144 μL, 0.05 M) was added tributylamine (0.0086 mL, 0.036 mmol) followed by carbonyldiimidazole (12 mg, 0.072 mmol). Reaction was stirred at room temperature for 12 h at which point MeOH (0.005 mL) was added and stirred for an additional 30 min. Tributyl ammonium pyrophosphate (0.040 mg, 72 mmol) in DMF (0.16 mL) was added the reaction mixture stirred for 1 h. After the solvents were evaporated in vacuo, the crude product was purified by ion exchange HPLC (0-60% TEAB) to provide the diphosphophosphonate 554-11. $^1H$ NMR ($D_2O$, 300 MHz) δ 7.94 (s, 1H), 5.85 (d, 1H), 4.47 (m, 1H), 3.71-3.78 (m, 2H), 2.27-2.39 (m, 2H) ppm. $^{31}P$ NMR (D20, 300 MHz) δ 8.09 (d), 7.71 (s), −22.04 (t) ppm. MS (m/z): calculated 505.99 (M−$H^-$), found 506.2 (M−$H^-$).

Example 257

Synthesis of Exemplary Compounds of the Invention

The following Schemes 555-5 to 555-9 describes a general method of preparing the [3.1.0] bicyclo hexane scaffold of the Formula 555-I and 555-II compounds. Exemplary structures, intermediates, substituents, protecting groups, reagents, and synthetic routes chosen for description here are meant to merely illustrate general methods of preparation, and are not intended to any way limit or denote preference to the methods.

The [3.1.0] bicyclo hexane scaffold may be synthesized by intramolecular cyclopropanation of a carbene generated by decomposition of a diazo 1,3-ketoester (Moon et al (2000) *Organic Letters* 2(24):3793-3796). The requisite 1,3-ketoester 555-5.1 may be prepared from acetoacetate ester anion addition to ene-aldehydes, e.g. acrolein (Scheme 555-5a). For example, ethyl acetoacetate treated with 2 equivalents of lithium diisopropylamide at −78° C. and then one equivalent of acrolein gives the 1,3-ketoester 555-5.1 (Yoshimura et al (2002) *Jour. Org. Chem.* 67:5938-5945). Protection of the hydroxyl may be accomplished with phenyldimethylsilyl chloride to give 555-5.2 where PG is phenyldimethylsilyl ($PhMe_2Si$—). Other trialkylsilyl protecting groups may be useful. Diazotization of 2 with p-toluenesulfonyl azide gives 555-5.3. Treatment of 555-5.3 with a carbenoid insertion catalyst, e.g. $CuSO_4$ or $Rh(OAc)_2$, gives 555-5.4 as a mixture of diastereomers.

Scheme 555-5a

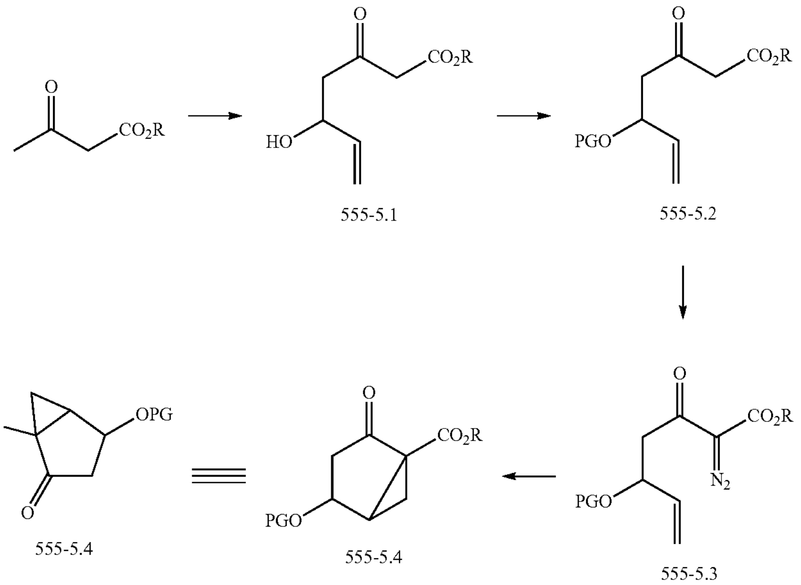

555-5.1

555-5.2

555-5.4

555-5.4

555-5.3

The ester of 555-5.4 may be hydrolyzed to the hydroxymethyl 555-5.5 or saponified directly to carboxylic acid S55-5.6 (Scheme 555-5b). Appropriate oxidant(s) can convert the primary alcohol 555-5.5 to carboxylic acid S55-5.6 or its corresponding ester. In the case of an ester, an additional deprotection step will give the carboxylic acid, 555-5.6. A variety of oxidation procedures exist in the literature and can be utilized here. These include but are not limited to the following methods: (i) pyridinium dichromate in $Ac_2O$, t-BuOH, and dichloromethane producing the t-butyl ester, followed by a deprotection using reagent such as trifluoroacetic acid to convert the ester to the corresponding carboxylic acid (see Classon, et al, *Acta Chem. Scand. Ser. B;* 39; 1985; 501-504. Cristalli, et al; *J. Med. Chem.*; 31; 1988; 1179-1183); (ii) iodobenzene diacetate and 2,2,6,6-tetramethyl-1-piperidinyloxy, free radical (TEMPO) in acetonitrile, producing the carboxylic acid (See Epp, et al; *J. Org. Chem.* 64; 1999; 293-295. Jung et al; *J. Org. Chem.*; 66; 2001; 2624-2635); (iii) sodium periodate, ruthenium(III) chloride in chloroform producing the carboxylic acid (see Kim, et al, *J Med. Chem.* 37; 1994; 4020-4030. Homma, et al; *J. Med. Chem.*; 35; 1992; 2881-2890); (iv) chromium trioxide in acetic acid producing the carboxylic acid (see Olsson et al; *J. Med. Chem.;* 29; 1986; 1683-1689. Gallo-Rodriguez et al; *J. Med. Chem.*; 37; 1994; 636-646); (v) potassium permanganate in aqueous potassium hydroxide producing the carboxylic acid (see Ha, et al; *J. Med. Chem.*; 29; 1986; 1683-1689. Franchetti, et al; *J. Med. Chem.*; 41; 1998; 1708-1715.) (vi) nucleoside oxidase from *S. maltophilia* to give the carboxylic acid (see Mahmoudian, et al; *Tetrahedron;* 54; 1998; 8171-8182.)

Carboxylic acid S55-5.6 may be converted by decarboxylation to acetate 555-5.7 using lead(IV) tetraacetate (Teng et al; (1994) *J. Org. Chem.*; 59:278-280; Schultz, et al; *J. Org. Chem.;* 48; 1983; 3408-3412. When lead(IV) tetraacetate is used together with lithium chloride (see Kochi, et al; *J. Am. Chem. Soc.*; 87; 1965; 2052), the corresponding chloride is obtained 555-5.8. Lead(IV) tetraacetate in combination with N-chlorosuccinimide can also produce 555-5.8 (Wang, et al; *Tet. Asym.;* 1; 1990; 527 and Wilson et al; *Tet. Asym.;* 1; 1990; 525). Alternatively, the acetate can also be converted to other leaving groups such as bromide by treatment of trimethylsilyl bromide (Spencer, et al; *J. Org. Chem.;* 64; 1999; 3987-3995).

Scheme 555-5b

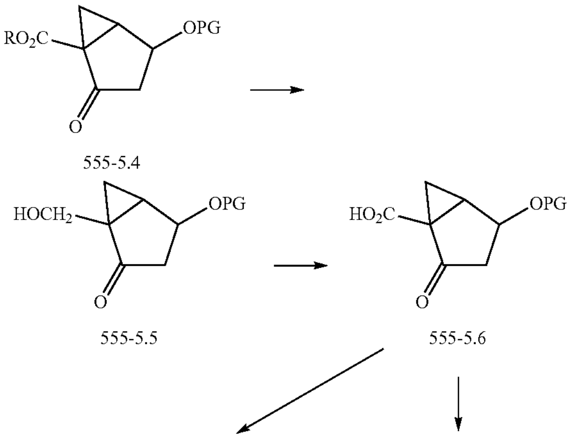

555-5.4

555-5.5

555-5.6

-continued

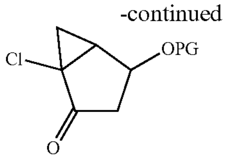

555-5.8

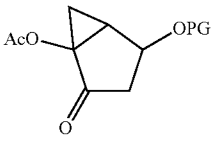

555-5.7

Intermediates 555-5.7 and 555-5.8 may react with a variety of nucleophiles as described by Teng et al; *Synlett*; 1996; 346-348 and U.S. Pat. No. 6,087,482; Column 54 line 64 to Column 55 line 20. Specifically, 555-5.7 may be reacted with diethyl hydroxymethylphosphonate in the presence of trimethylsilyl trifluoromethanesulfonate (TMS-OTf) to give 555-5.9 (Scheme 555-5c). It can be envisioned that other compounds with the general structure of HO-linker-POR$^{P1}$R$^{P2}$ can also be used so long as the functional groups in these compounds are compatible with the coupling reaction conditions. There are many examples in the published literature describing the coupling of 1' acetyl furanosyl compounds with a variety of alcohols. The reactions can be facilitated with a number of reagents, such as silver(I) salts (see Kim et al (1991) *J. Org. Chem.* 56:2642-2647, Toikka et al (1999) *J. Chem. Soc. Perkins Trans.* 1; 13:1877-1884); mercury(II) salts (see Veeneman et al (1987) *Recl. Trav. Chim. Pays-Bas;* 106:129-131); boron trifluoride diethyl etherate (see Kunz et al (1985) *Hel. Chim Acta;* 68:283-287); tin(II) chloride (see O'Leary et al (1994) *J. Org. Chem.* 59:6629-6636); alkoxide (see Shortnacy-Fowler et al (2001) *Nucleosides & Nucleotides*; 20:1583-1598); and iodine (see Kartha et al (2001) *J. Chem. Soc. Perkins Trans.* 1 770-772). These methods can be selectively used in conjunction with different methods in forming intermediates from 555-5.6 with various leaving groups (LG).

Scheme 555-5c

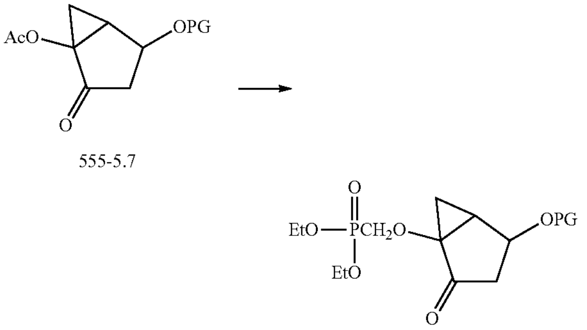

555-5.7

555-5.9

The introduction and removal of protecting groups (represented in the structures herein as PG) from a compound is common practice art in organic synthesis. Many sources of information of the art are available in the published literature, e.g. Greene and Wuts, *Protecting Groups in Organic Synthesis,* 3$^{rd}$ Ed., John Wiley & Sons, Inc., 1999. The main purpose is to temporarily transform a functional group and mask its reactivity so that it will survive a set of subsequent reaction procedures. Afterwards, the original functional group can be restored by a preconceived deprotection procedure. Therefore, the transformations in Schemes 555-(5a-c) are intended to build the [3.1.0] scaffold with the appropriate latent functionality or reactivity components.

The keto group of certain intermediates, e.g. 555-5.4 may be elaborated to ribofuranose-type analogs 555-6.1 where $Z^1$ are for example, each hydroxyl or protected hydroxyl (Scheme 555-6). The hydroxyl groups can be protected as benzoyl (Bz) esters to give 555-6.2. The bridgehead carboxylate ester can then be orthogonally hydrolyzed to give 555-6.3 or reduced to hydroxymethyl 555-6.4. Oxidation of 555-6.4, e.g. using iodobenzene diacetate and 2,2,6,6-tetramethyl-1-piperidinyloxy, free radical (TEMPO), converts the primary alcohol to the corresponding acid 555-6.3. Further oxidation of 555-6.3 using lead tetraacetate can produce acetate 555-6.5. Coupling between 555-6.5 and hydroxyalkyl dialkylphosponate compounds, e.g. diethyl hydroxymethylphosphonate (available from Sigma-Aldrich, Cat. No. 39,262-6) and TMS-OTf can afford 555-6.6. Treating 555-6.6 with TMS-Br converts the phosphodiester to the corresponding phosphonic acid S55-6.7. Deprotection, e.g. $NH_3$ in methanol, of the 2'- and 3'-hydroxyl gives 555-6.8.

Scheme 555-6

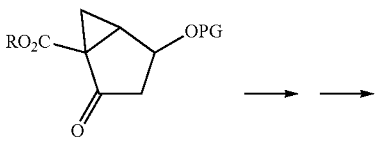

555-5.4

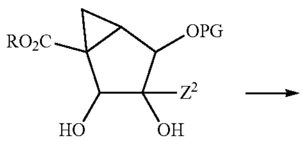

555-6.1

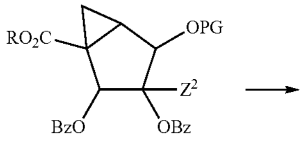

555-6.2

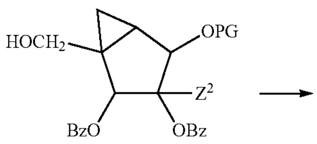

555-6.4

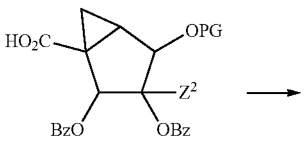

555-6.3

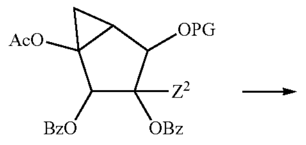

555-6.5

-continued

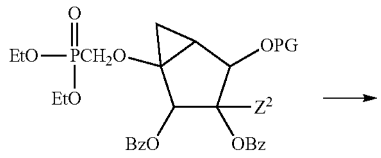

555-6.6

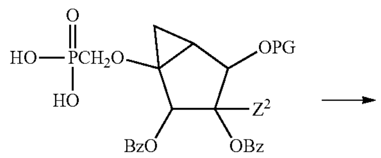

555-6.7

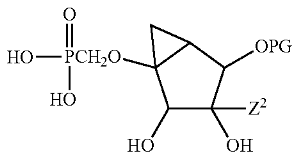

555-6.8

The phosphonic acids in 555-(6.6-6.8) are used as examples for illustration purpose. Other forms of phosphonates can be accessed via the phosphonic acid, or other forms, such as the corresponding diesters. See Schemes 555-A and 555-(1-4) for exemplary interconversions of phosphonate moieties.

Compounds such as 555-6.6 can be further elaborated by selective deprotection of PG and introduction of the nucleobase moiety (B). For example, where PG is trialkylsilyl, e.g. triethylsilyl, t-butyldimethylsilyl, or phenyldimethylsilyl, treatment of 555-6.6 with a fluoride reagent, e.g. tetrabutylammonium fluoride in THF, may selectively remove PG. The resulting hydroxyl may be converted to a leaving group (LG) such as chloro or acetate 555-7.1 under Vorbruggen-type reaction conditions, or the hydroxyl 555-7.2 reacted in situ, e.g. Mitsunobu conditions, to establish the carbon-nitrogen bond with a nucleobase or protected nucleobase reagent to give 555-7.3 (Scheme 555-7). Suitable nucleobase or protected nucleobase reagents (B) include thymidine, cytosine, adenine, guanine, and silylated forms thereof. The resulting covalent attachment may be 9-purinyl or 1-pyrimidinyl. Other positional isomers may result and conventional means of separation may be employed to generate pure 555-7.3 compounds. The 2' and 3' protecting groups (Bz=benzoyl) may be removed from intermediate 555-7.3 with aqueous base to give 555-7.4. The ethyl groups of 555-7.4 may be removed with a dealkylation reagent such as trimethylsilyl bromide to give phosphonic acid S55-7.5 which may be further elaborated according to the reactions shown in Schemes 555-A and 1-4 to other phosphonate moieties, including diphosphophosphonate and phosphophosphonate compounds.

Scheme 555-7

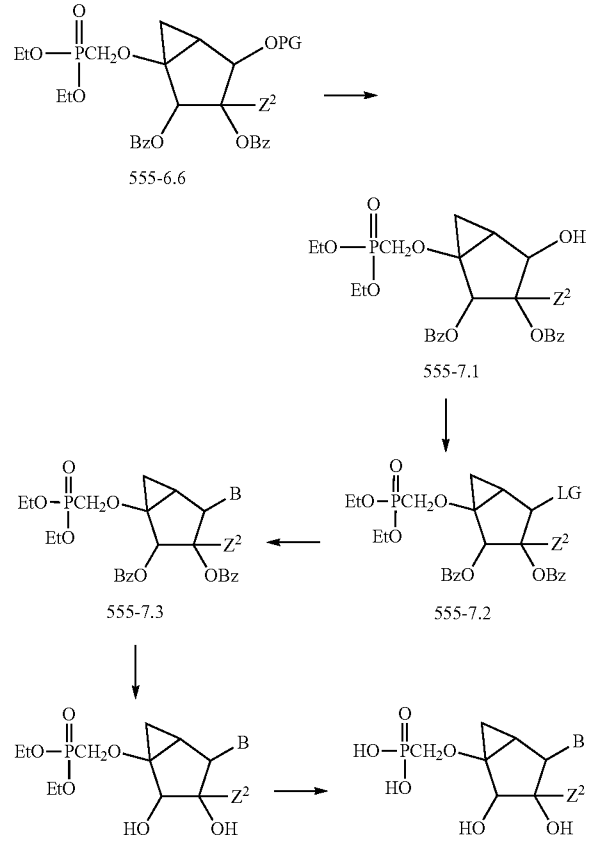

555-6.6

555-7.1

555-7.2

555-7.3

555-7.4

555-7.5

Scheme 555-8 shows an exemplary route to 2'-β-methyl, 2'-3' hydroxyl bicylco adenine compounds. The 3' and 5' hydroxyl groups of [3.1.0] bicyclo analog of adenosine 555-8.1 (Kim, et al (2002) J. Med. Chem. 45:208-218) may be selectively silylated to give 555-8.2. The 2' hydroxyl group may be oxidized under Dess-Martin periodinane conditions to give 555-8.3. The 2' keto of 555-8.3 may be methylenated with a Wittig reagent and desilylated to give 555-8.4. Epoxidation of 555-8.4 gives 555-8.5. Hydride attack on the methylene carbon of the epoxide 555-8.5 gives 555-8.6 with the 2',3'-α-dihydroxy, 2'-β-methyl motif. This synthetic route may be versatile in the preparation of a variety of 2',3'-α-dihydroxy, 2'-β-methyl[3.1.0]bicyclo compounds where B=any protected or unprotected nucleobase.

Scheme 555-8

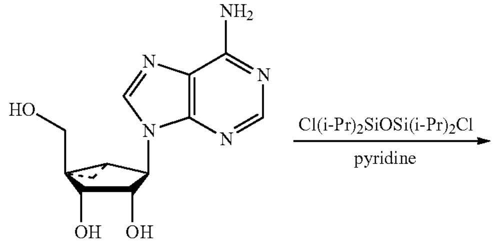

555-8.1

-continued

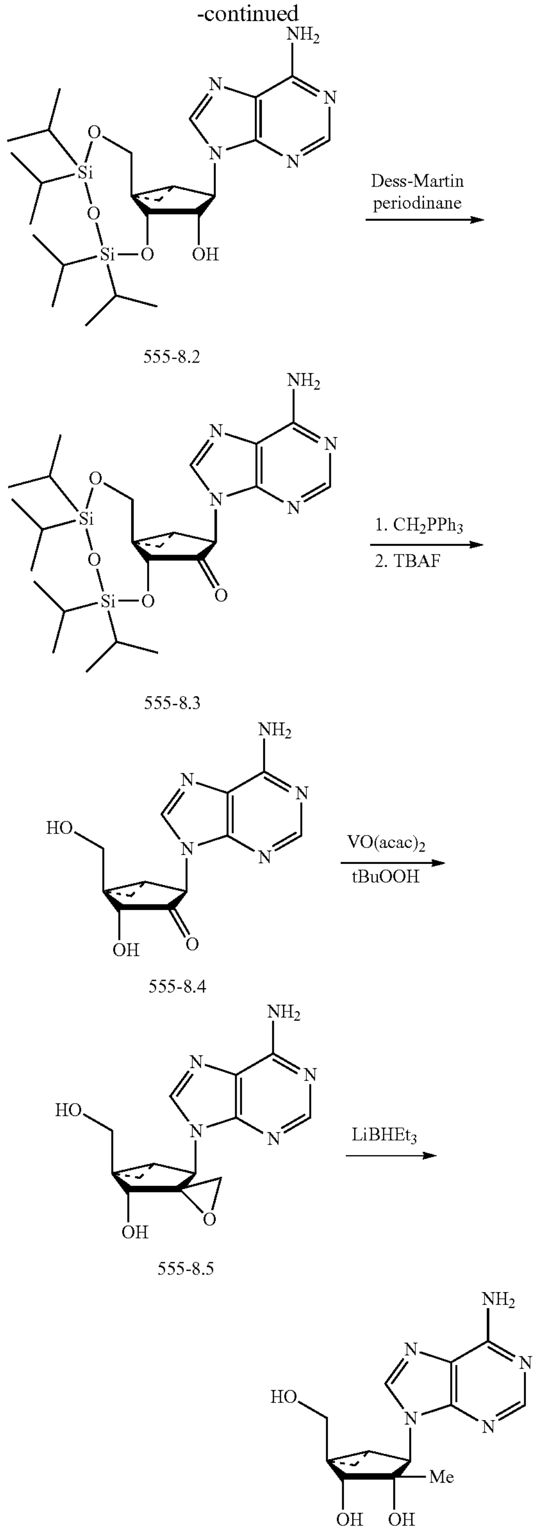

555-8.2

555-8.3

555-8.4

555-8.5

555-8.6

The 5' hydroxymethyl group of 2',3'-α-dihydroxy, 2'-β-methyl[3.1.0]bicyclo compounds, e.g. 555-8.6, may be elaborated by selective reactions such as those shown in Scheme 555-9. The 5' carbon may be removed by an oxidative decarboxylation to allow attachment of a phosphonate moiety through an oxygen atom bound directly to the [3.1.0] scaffold. The 5' hydroxyl group of 555-8.6 may be selectively protected as the 5' tert-butyldiphenylsilyl ether (TBDPS) and then the 2' and 3' hydroxyls may be protected as methoxymethyl ethers to give 555-9.1. The 5' TBDPSi group may be removed with tetra-butyl ammonium fluoride (TBAF) and the resulting hydroxymethyll oxidized with the periodinane reagent, $PhI(OAc)_2$ and TEMPO to the carboxylic acid 555-9.2. Oxidative decarboxylation of 555-9.2 with lead tetracetate and treatment with lithium hydroxide gives 555-9.3. Alkylation of the hydroxyl of 555-9.3 with bromomethyldiethyl phosphonate gives 555-9.4. The phosphonate ethyl groups and the 2',3' methoxymethyl (MOM) protecting groups may be removed with iodotrimethylsilane to give 555-9.5. The phosphonic acid group of 555-9.5 may be activated, for example with carbonyldiimidazole (CDI) and reacted with pyrophosphate anion to give diphosphophosphonate 555-9.6. Other phosphonic acid conversions may be conducted, as described in Schemes 555-A and 555(1-4).

Scheme 555-9

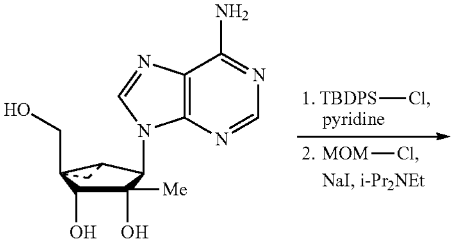

555-8.6

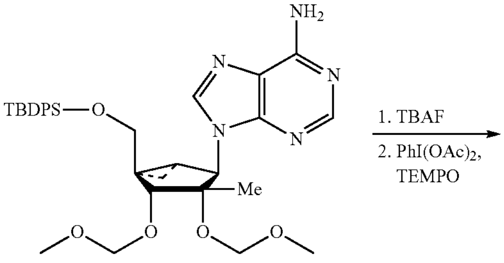

555-9.1

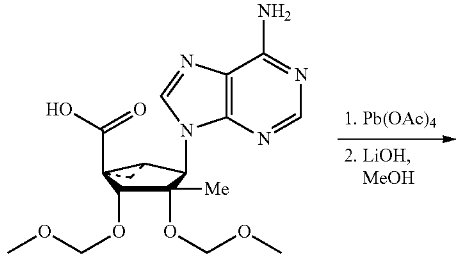

555-9.2

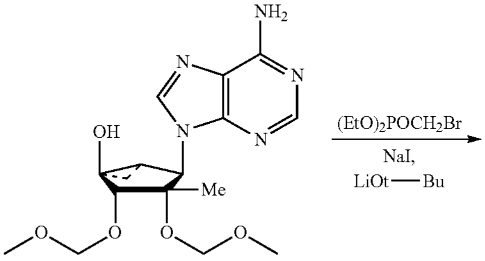

555-9.3

-continued

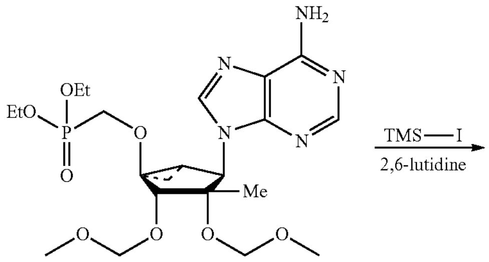

555-9.4

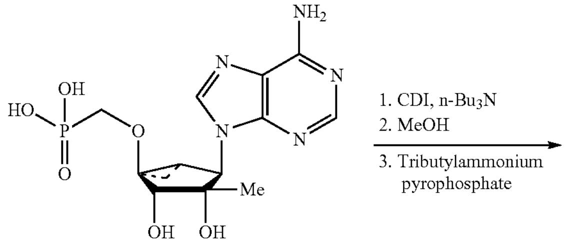

555-9.5

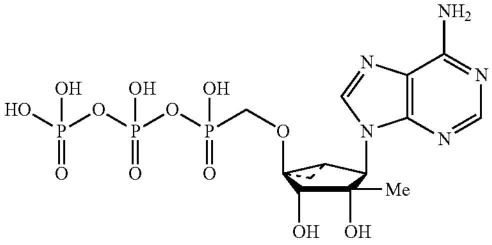

555-9.6

Intermediate 555-8.2 is versatile for the preparation of 2' hydroxyl [3.1.0] bicyclo compounds (Scheme 555-10). Protection of the 2' hydroxyl with para-methoxybenzyl bromide and silyl removal with TBAF gives 555-10.1. The 5' hydroxyl is protected with the TBDPSi group to give 555-10.2. The 3' thioester of 555-10.2 is formed with phenyl chlorothionoformate followed by reduction with tributyl tin hydride with AIBN to give 555-10.3. Desilyation with TBAF and oxidation with BAIB and TEMPO furnishes the carboxylic acid 555-10.4.

Scheme 555-10

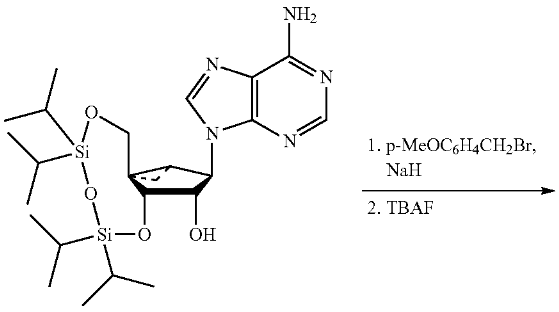

555-8.2

-continued

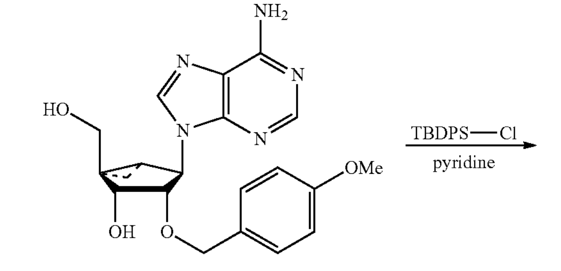

555-10.1

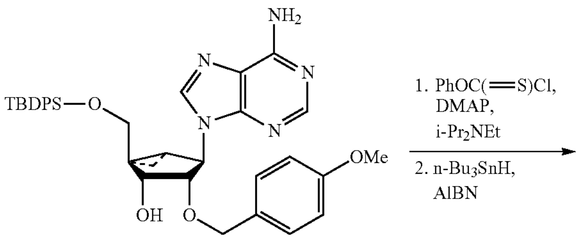

555-10.2

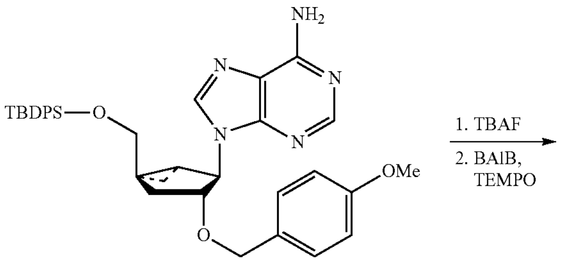

555-10.3

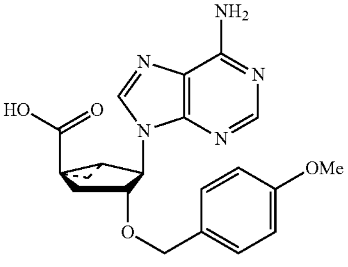

555-10.4

Oxidative decarboxylation of 555-10.4 with lead tetracetate followed by lithium hydroxide treatment gives the hydroxyl 555-11.1 (Scheme 555-11). Alkylation of hydroxyl 555-11.1 with bromomethyl diethyl phosphonate gives 555-11.2. Iodotrimethylsilane cleaves the ethyl groups from the diethylphosphonate and ceric ammonium nitrate deprotects the para-methoxy benzyl group of 555-11.2 to give 555-11.3. Phosphonate activation with CDI and addition of pyrophosphate gives the 2'-hydroxy diphosphophosphonate [3.1.0] compound 555-11.4.

Scheme 555-11

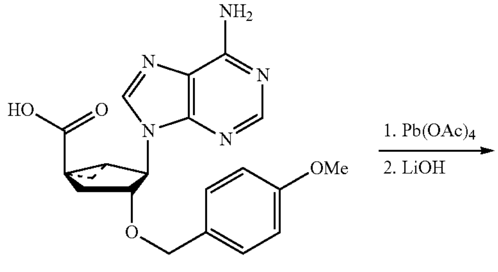

555-10.4

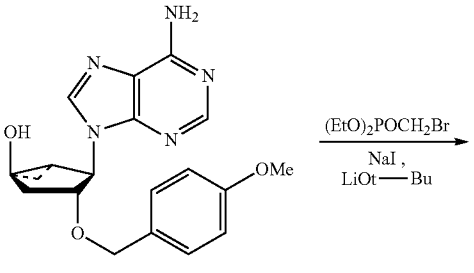

555-11.1

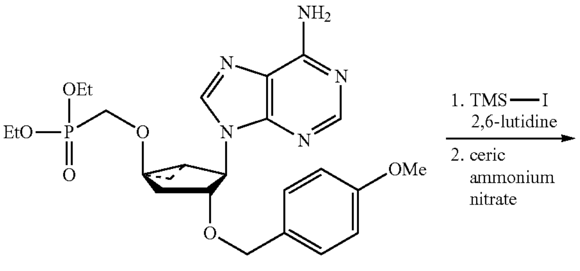

555-11.2

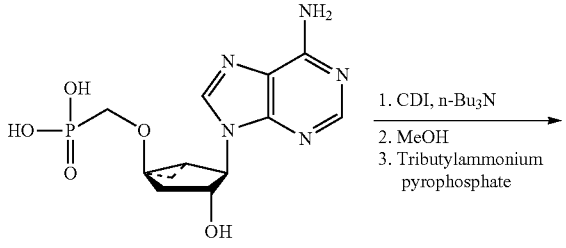

555-11.3

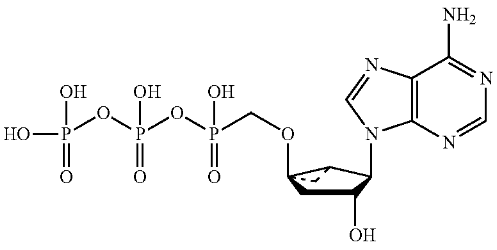

555-11.4

Example 258

Synthesis of Exemplary Compounds of the Invention

The following Schemes describe the general method of preparing the 2' fluoro, 2'-3' didehydro nucleosidescaffold of compounds of the present invention.

Methods of introduction of fluorine at the 2' position of ribonucleosides and nucleoside analogs are described in U.S. Pat. Nos. 5,824,793; 5,859,233; Choo, H. et al *Journal of Medicinal Chemistry* (2003), 46(3), 389-398; Moon, H. et al *Journal of the Chemical Society, Perkin Transactions* 1 (2002), (15), 1800-1804; Lee, Kyeong; Choi, Y. et al *Journal of Medicinal Chemistry* (2002), 45(6), 1313-1320; Lee, Kyeong; Choi, Yongseok; Hong, J. et al *Nucleosides & Nucleotides* (1999), 18(4 & 5), 537-540; Lee, K. et al *Journal of Medicinal Chemistry* (1999), 42(7), 1320-1328; Choi, Y. et al *Tetrahedron Letters* (1998), 39(25), 4437-4440; Chen, Shu-Hui et al *Bioorganic & Medicinal Chemistry Letters* (1998), 8(13), 1589-1594; Siddiqui, Maqbool et al *Tetrahedron Letters* (1998), 39(13), 1657-1660; Nakayama, Toshiaki et al *Nucleic Acids Symposium Series* (1991), 25(Symp. Nucleic Acids Chem., 18th, 1991), 191-2; Huang, Jai Tung et al *Journal of Medicinal Chemistry* (1991), 34(5), 1640-6; Sterzycki, Roman Z et al *Journal of Medicinal Chemistry* (1990), 33(8), 2150-7; Martin, Joseph A et al *Journal of Medicinal Chemistry* (1990), 33(8), 2137-45; Watanabe, Kyoichi et al *Journal of Medicinal Chemistry* (1990), 33(8), 2145-50; Zemlicka et al *Journal of the American Chemical Society* (1972) 94(9):3213-3218.

Schemes 556 (A-F) show the synthetic routes which have been utilized to prepare the exemplary embodiments shown therein.

Scheme 556-B

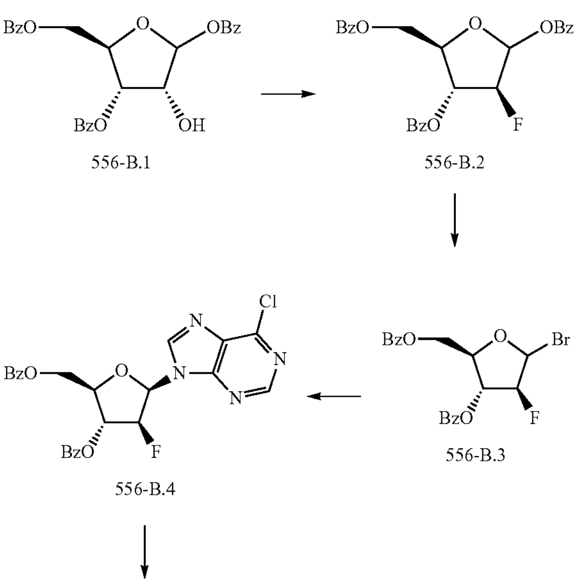

556-B.1

556-B.2

556-B.3

556-B.4

Scheme 556-A

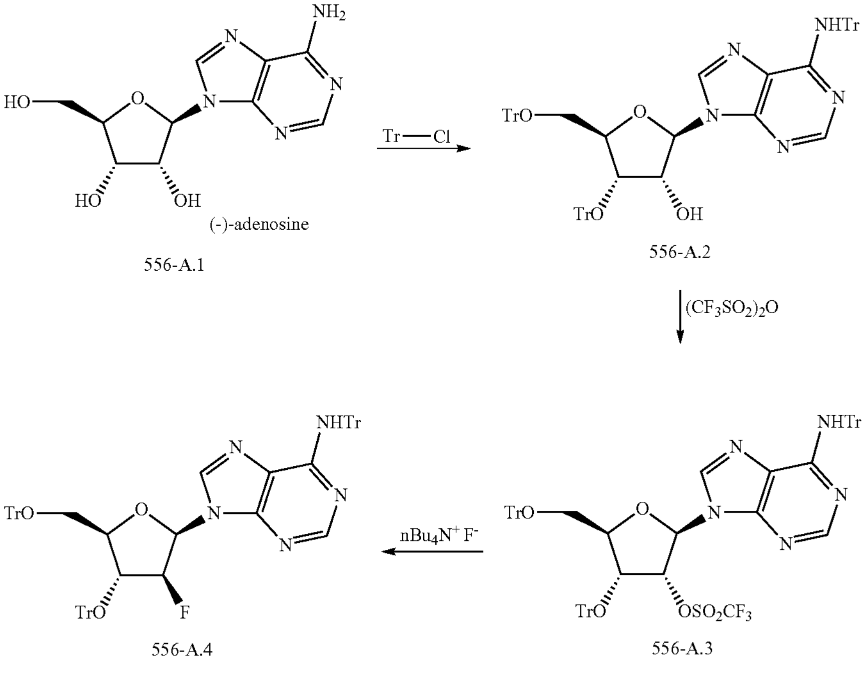

(-)-adenosine

556-A.1

556-A.2

556-A.3

556-A.4

The (−) enantiomer of adenosine 556-A.1 was tritylated at the N-6 of the adenine exocyclic amine and the 5' hydroxyl with an excess of trityl (Tr, triphenylmethyl, $Ph_3C$—) chloride with dimethylaminopyridine in pyridine to give bis-trityl 556-A.2 which was treated with triflic anhydride in dichloromethane and DMAP to give 556-A.3 (Scheme 556-A). The 2' triflate group was displaced by fluoride with tetra-butylammonium fluoride in THF at room temperature to give 556-A.4.

-continued

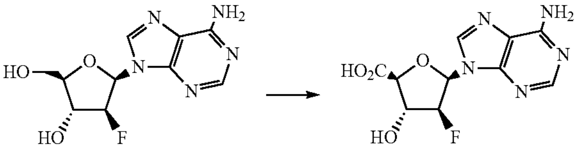

556-B.5

556-B.6

Scheme 556-C
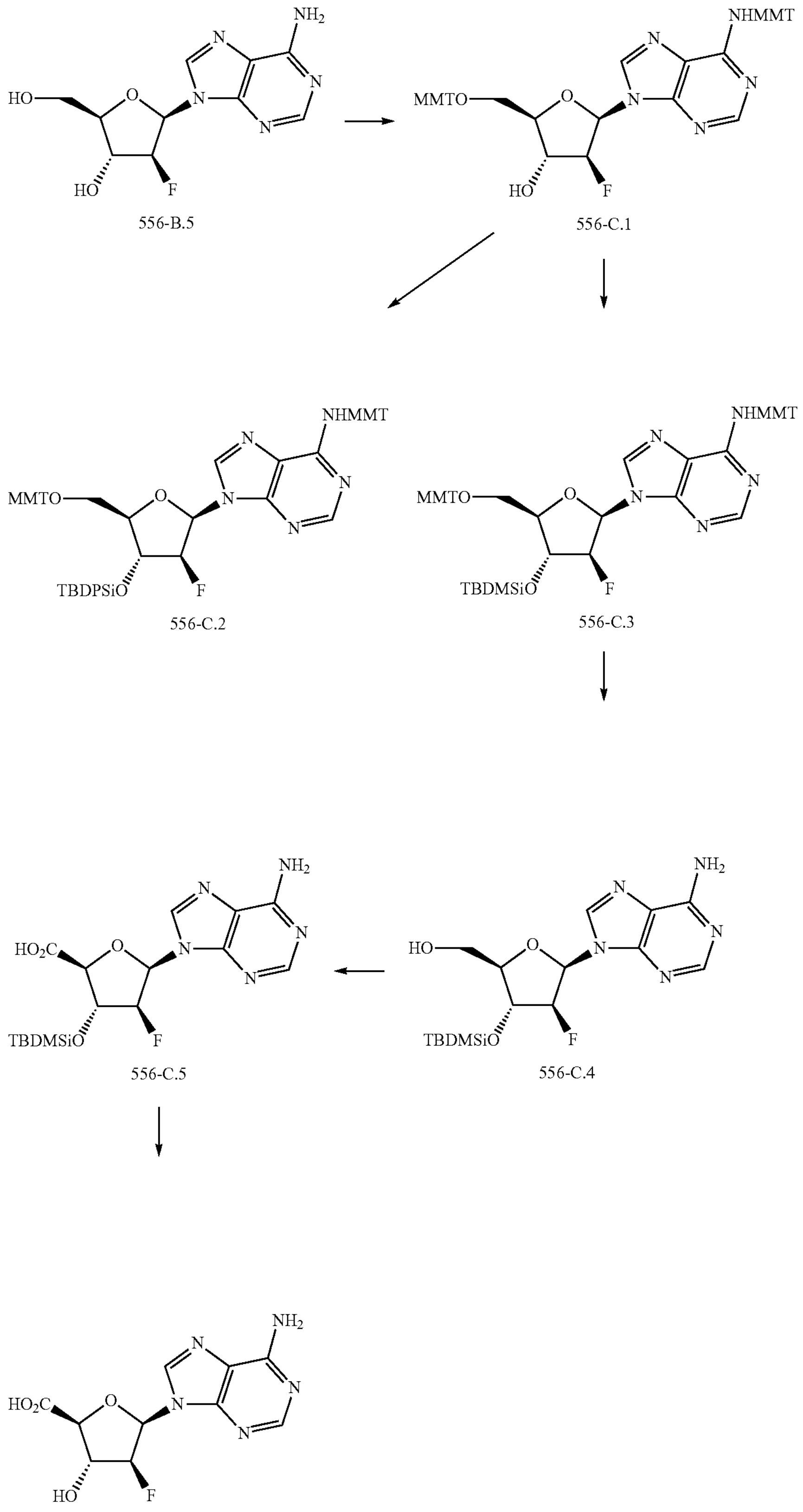
556-B.5
556-C.1
556-C.2
556-C.3
556-C.4
556-C.5
556-C.6

Scheme 556-D
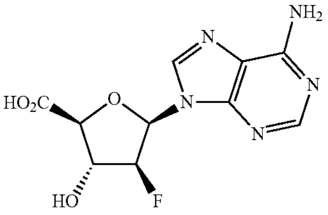
556-C.6
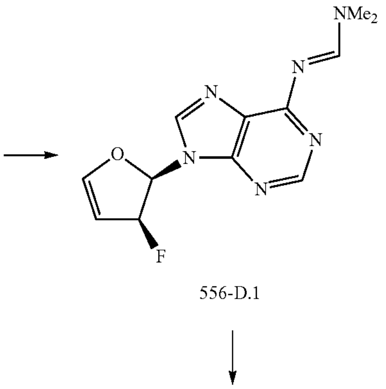
556-D.1
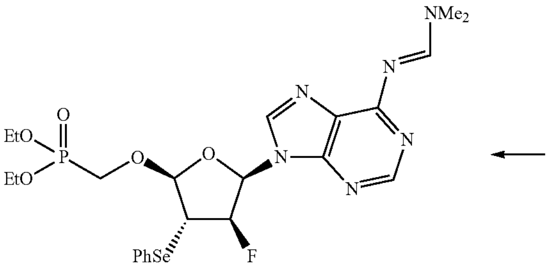
556-D.3
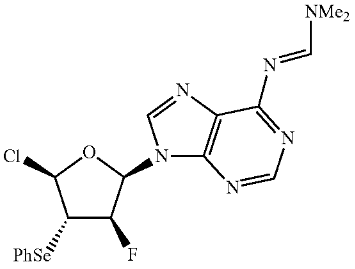
556-D.2
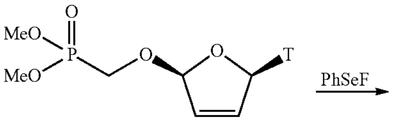
556-D.4
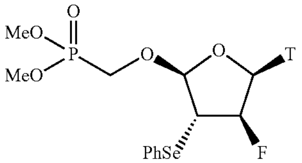
556-D.5
Scheme 556-E
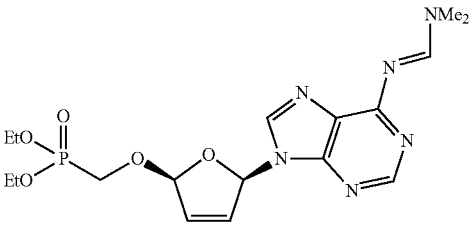
556-E.1

-continued
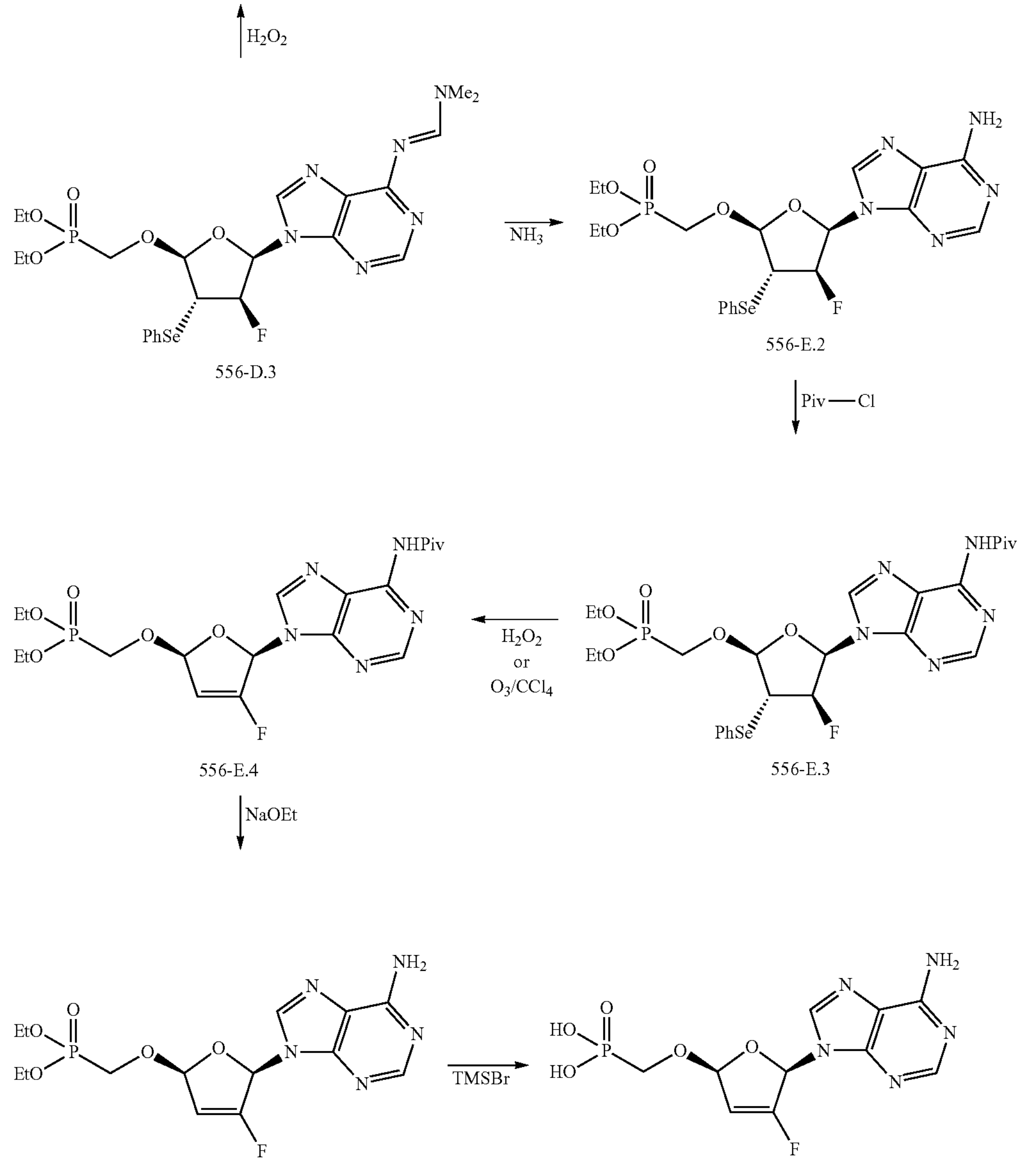
556-D.3, 556-E.2, 556-E.3, 556-E.4, 556-E.5, 556-E.6
Scheme 556-F
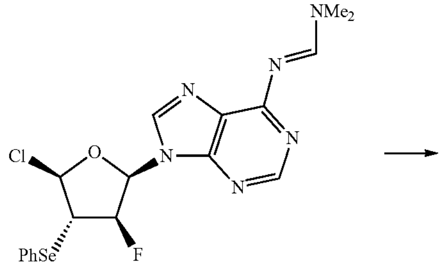
556-D.2
-continued
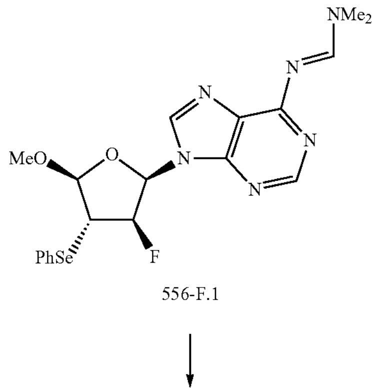
556-F.1

-continued

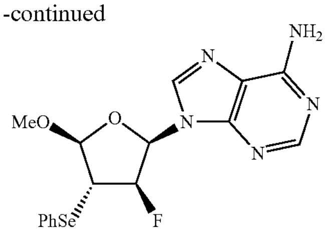

556-F.2

Example 259

By way of example and not limitation, embodiments of the invention are named below in tabular format (Table 100). These embodiments are of the general formula "MBF":

MBF

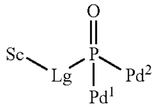

Each embodiment of MBF is depicted as a substituted nucleus (Sc). Sc is described in formula 1-108 herein, wherein $A^0$ is the point of covalent attachment of Sc to Lg, as well as in Tables 1.1 to 1.5 below. For those embodiments described in Table 100, Sc is a nucleus designated by a number and each substituent is designated in order by letter or number. Tables 1.1 to 1.5 are a schedule of nuclei used in forming the embodiments of Table 100. Each nucleus (Sc) is given a number designation from Tables 1.1 to 1.5, and this designation appears first in each embodiment name. Similarly, Tables 10.1 to 10.19 and 20.1 to 20.36 list the selected linking groups (Lg) and prodrug ($Pd^1$ and $Pd^2$) substituents, again by letter or number designation, respectively. Accordingly, a compound of the formula MBF includes compounds having Sc groups based on formula 1-108 herein as well as compounds according to Table 100 below. In all cases, compounds of the formula MBF have groups Lg, $Pd^1$ and $Pd^2$ setforth in the Tables below.

Accordingly, each named embodiment of Table 100 is depicted by a number designating the nucleus from Table 1.1-1.5, followed by a letter designating the linking group (Lg) from Table 10.1-10.19, and two numbers designating the two prodrug groups ($Pd^1$ and $Pd^2$) from Table 20.1-20.36. In graphical tabular form, each embodiment of Table 100 appears as a name having the syntax:

$Sc.Lg.Pd^1.Pd^2$

Each Sc group is shown having a tilda ("~"). The tilda is the point of covalent attachment of Sc to Lg. $Q^1$ and $Q^2$ of the linking groups (Lg), it should be understood, do not represent groups or atoms but are simply connectivity designations. $Q^1$ is the site of the covalent bond to the nucleus (Sc) and $Q^2$ is the site of the covalent bond to the phosphorous atom of formula MBF. Each prodrug group ($Pd^1$ and $Pd^2$) are covalently bonded to the phosphorous atom of MBF at the tilda symbol ("~"). Some embodiments of Tables 10.1-10.19 and 20.1-20.36 may be designated as a combination of letters and numbers (Table 10.1-10.19) or number and letter (Table 20.1-20.36). For example there are Table 10 entries for BJ1 and BJ2. In any event, entries of Table 10.1-10.19 always begin with a letter and those of Table 20.1-20.36 always begin with a number. When a nucleus (Sc) is shown enclosed within square brackets ("[ ]") and a covalent bond extends outside the brackets, the point of covalent attachment of Sc to Lg may be at any substitutable site on SC. Selection of the point of attachment is described herein. By way of example and not limitation, the point of attachment is selected from those depicted in the schemes and examples.

TABLE 1.1

| | |
|---|---|
| 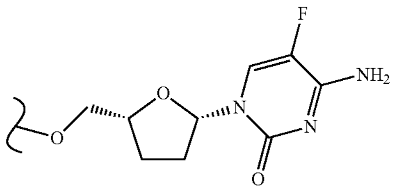 [SMILES: COC[C@H]1CC[C@@H](n2cc(F)c(N)nc2=O)O1] | 1 |
| 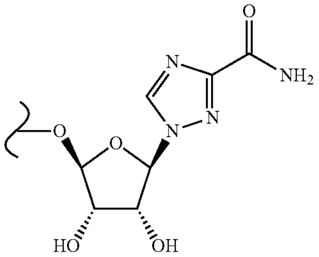 [SMILES: CO[C@H]1O[C@@H](n2cnc(C(N)=O)n2)[C@H](O)[C@@H]1O] | 2 |
| 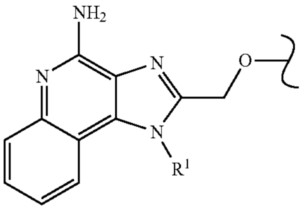 | 3 |
| 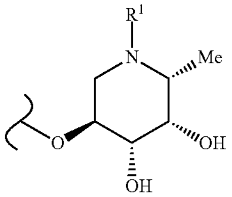 | 4 |

TABLE 1.2

| | |
|---|---|
| 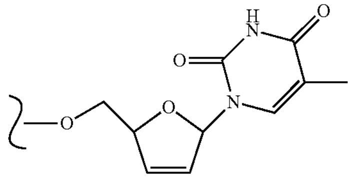 | 5 |
| 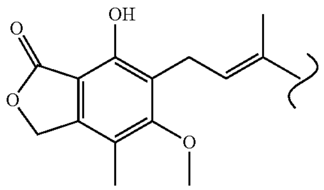 [SMILES: COc1c(C)c2c(c(O)c1CC=C(C)C)C(=O)OC2] | 6 |

TABLE 1.3
| | |
|---|---|
| 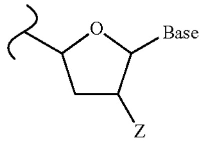 | 7 |
| 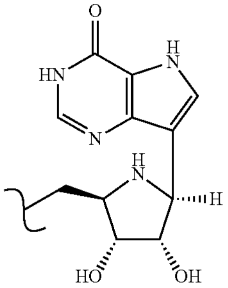 [SMILES: CC[C@H]1N[C@@H](c2c[nH]c3c(=O)[nH]cnc23)[C@H](O)[C@@H]1O] | 8 |
| 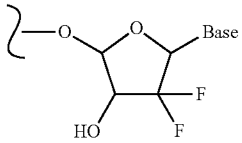 | 9 |
| 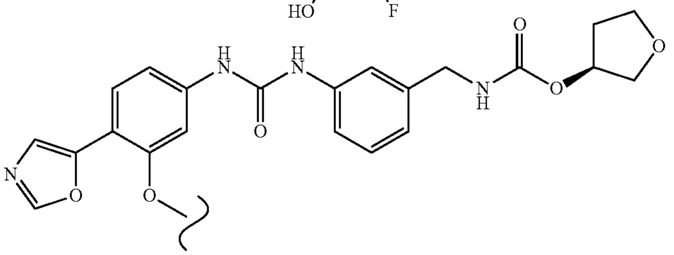 | 10 |
TABLE 1.4
| | |
|---|---|
| 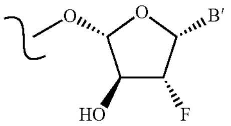 | 11 |
| 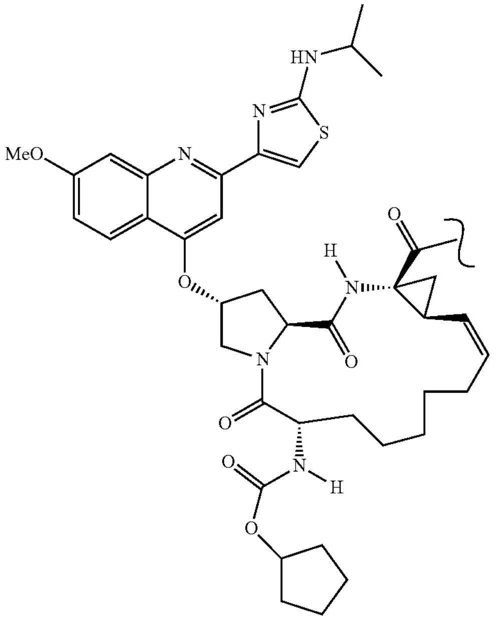 [SMILES: COc1ccc2c(O[C@@H]3C[C@H]4C(=O)N[C@]5(C(C)=O)C[C@H]5/C=C\CCCCC[C@H](NC(=O)OC5CCCC5)C(=O)N4C3)cc(-c3csc(NC(C)C)n3)nc2c1] | 12 |
TABLE 1.5
| | |
|---|---|
| 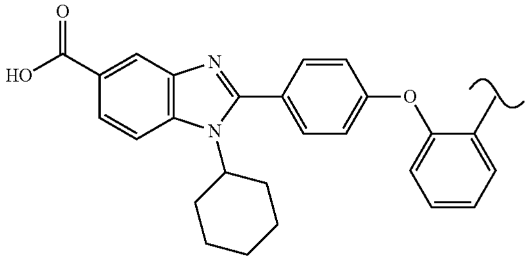 [SMILES: Cc1ccccc1Oc1ccc(-c2nc3cc(C(=O)O)ccc3n2C2CCCCC2)cc1] | 13 |
| 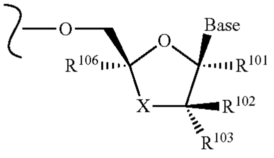 | 14 |
TABLE 10.1
| | |
|---|---|
| 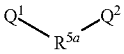 | A |
| $Q^1$—$Q^2$ | B |
| 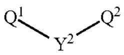 | C |

TABLE 10.1-continued
| | |
|---|---|
| 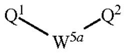 | D |
| 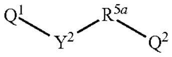 | E |
| 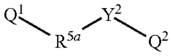 | F |
| 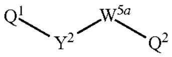 | G |
| 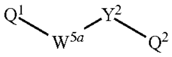 | H |
| 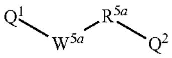 | I |
| 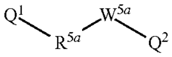 | J |
| 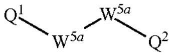 | K |
| 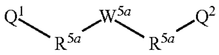 | L |
| 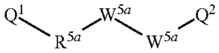 | M |
| 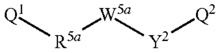 | N |
| 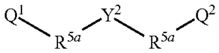 | O |
TABLE 10.2
| | |
|---|---|
| 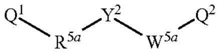 | P |
| 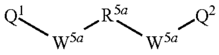 | Q |
| 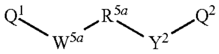 | R |
| 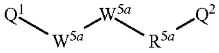 | S |
| 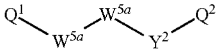 | T |
| 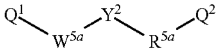 | U |
| 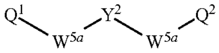 | V |
| 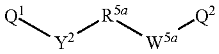 | W |
| 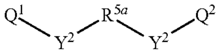 | X |
| 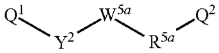 | Y |
TABLE 10.2-continued
| | |
|---|---|
| 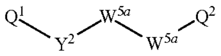 | Z |
| 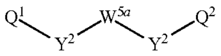 | AA |
TABLE 10.3
| | |
|---|---|
| 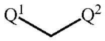 | AB |
| 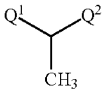 | AC |
| 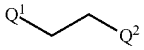 | AD |
| 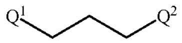 | AE |
| 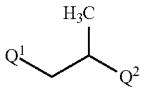 | AF |
| 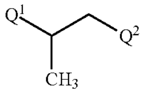 | AG |
| 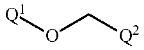 | AH |
| 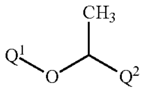 | AI |
| 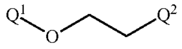 | AJ |
| 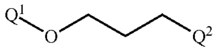 | AK |
| 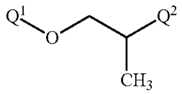 | AL |
| 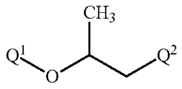 | AM |
TABLE 10.4
| | |
|---|---|
| 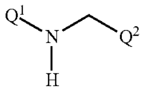 | AN |
| 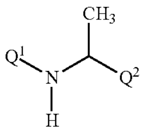 | AO |

TABLE 10.4-continued
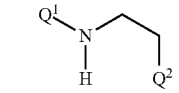 AP
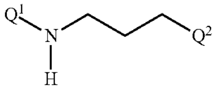 AQ
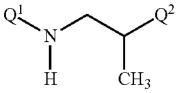 AR
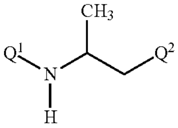 AS
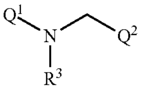 AT
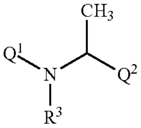 AU
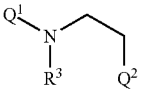 AV
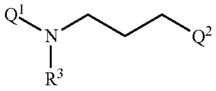 AW
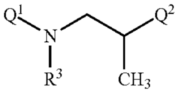 AX
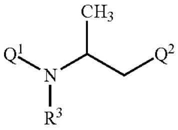 AY
TABLE 10.5
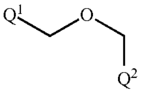 AZ
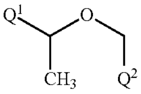 BA
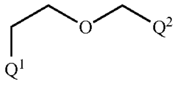 BB
TABLE 10.5-continued
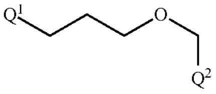 BC
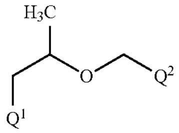 BD
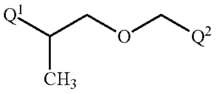 BE
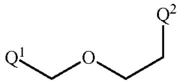 BF
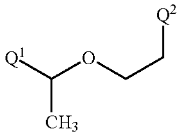 BG
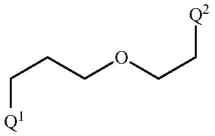 BH
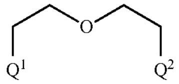 BI
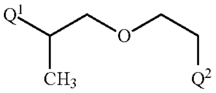 BJ1
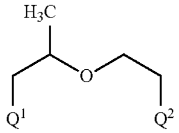 BJ2
TABLE 10.6
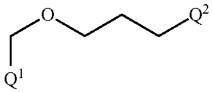 BK
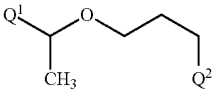 BL
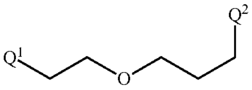 BM
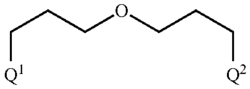 BN TABLE 10.6-continued
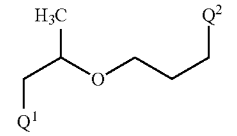
BO
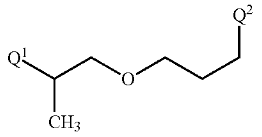
BP
TABLE 10.7
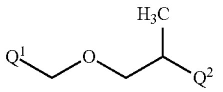
BQ
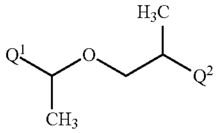
BR
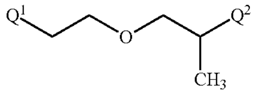
BS
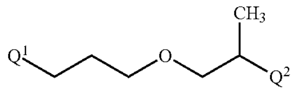
BT
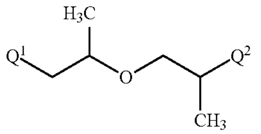
BU
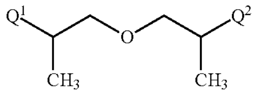
BV
TABLE 10.8
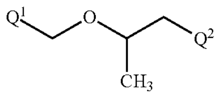
BW
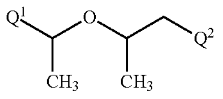
BX
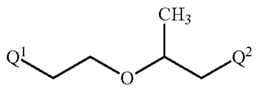
BY
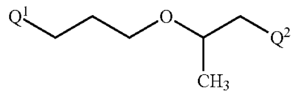
BZ
TABLE 10.8-continued
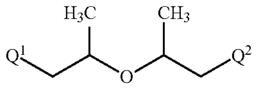
CA
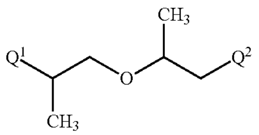
CB
TABLE 10.9
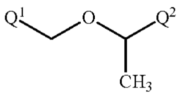
CC
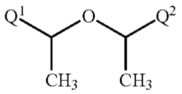
CD
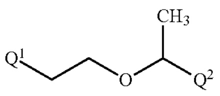
CE
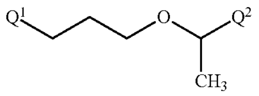
CF
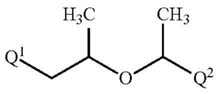
CG
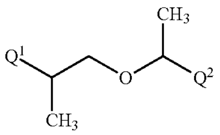
CH
TABLE 10.10
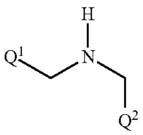
CI
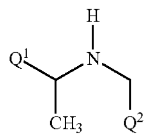
CJ
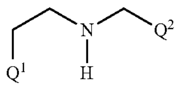
CK
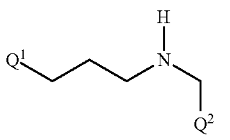
CL TABLE 10.10-continued
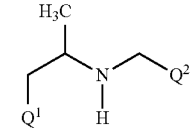
CM
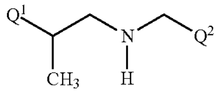
CN
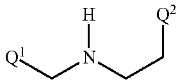
CO
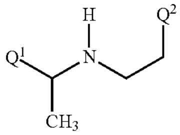
CP
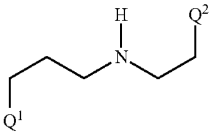
CQ
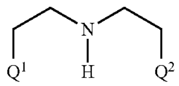
CR
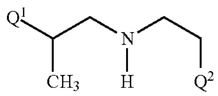
CS
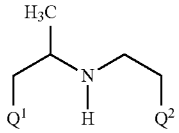
CT
TABLE 10.11
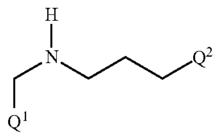
CU
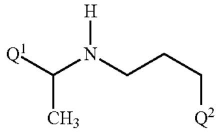
CV
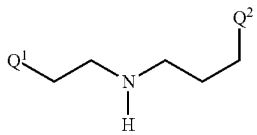
CW
TABLE 10.11-continued
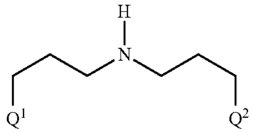
CX
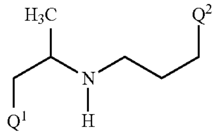
CY
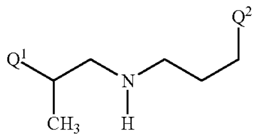
CZ
TABLE 10.12
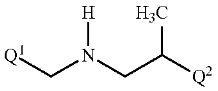
DA
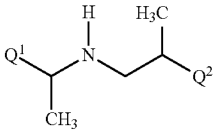
DB
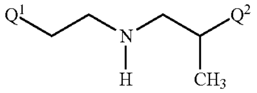
DC
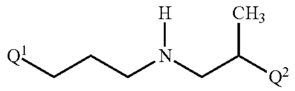
DD
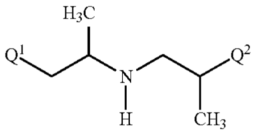
DE
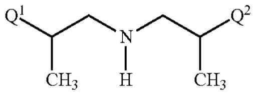
DF
TABLE 10.13
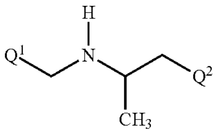
DG
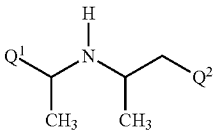
DH TABLE 10.13-continued
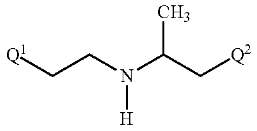
DI
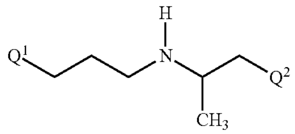
DJ
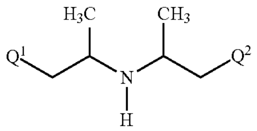
DK
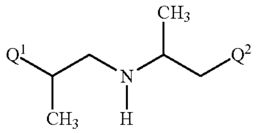
DL
TABLE 10.14
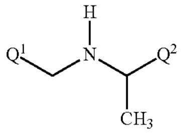
DM
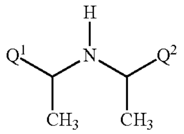
DN
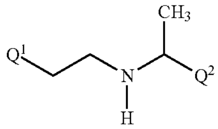
DO
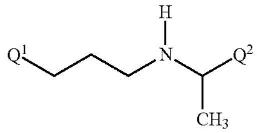
DP
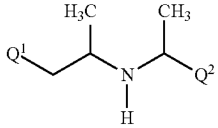
DQ
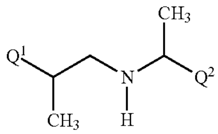
DR
TABLE 10.15
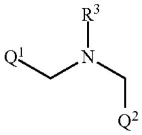
DS
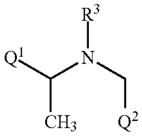
DT
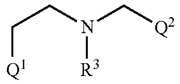
DU
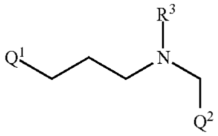
DV
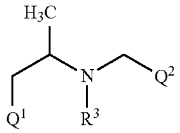
DW
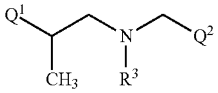
DX
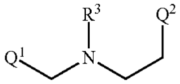
DY
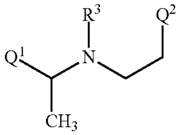
DZ
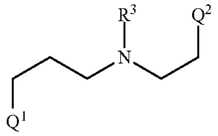
EA
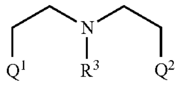
EB
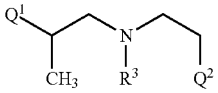
EC
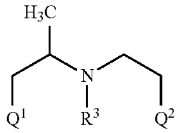
ED TABLE 10.16
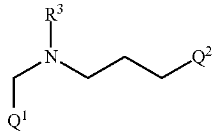
EE
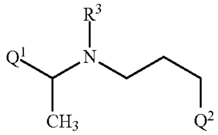
EF
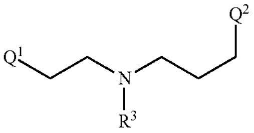
EG
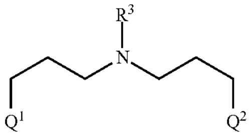
EH
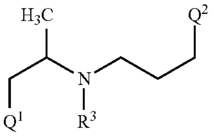
EI
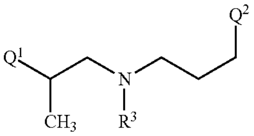
EJ
TABLE 10.17
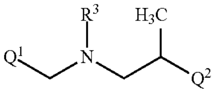
EK
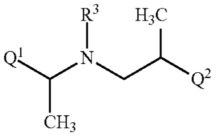
EL
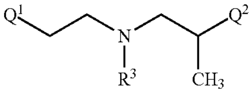
EM
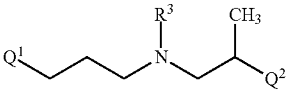
EN
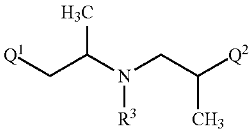
EO
TABLE 10.17-continued
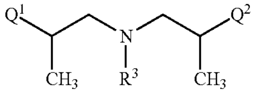
EP
TABLE 10.18
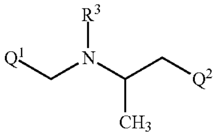
EQ
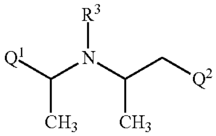
ER
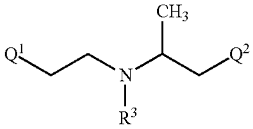
ES
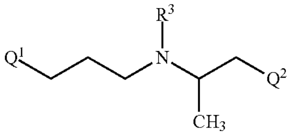
ET
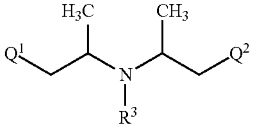
EU
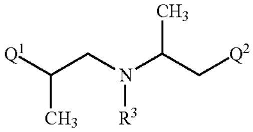
EV
TABLE 10.19
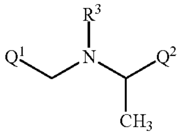
EW
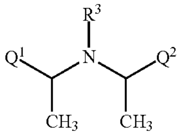
EX
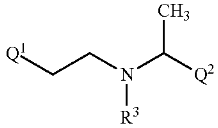
EY TABLE 10.19-continued
| | |
|---|---|
| 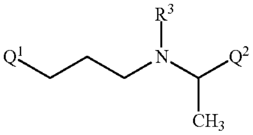 | EZ |
| 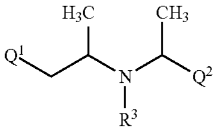 | FA |
| 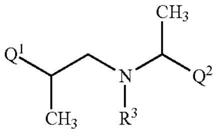 | FB |
TABLE 20.1
| | |
|---|---|
| 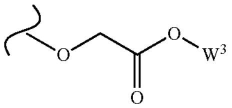 | 1 |
| 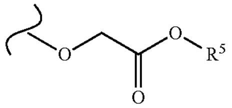 | 2 |
| 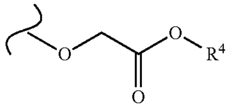 | 3 |
| 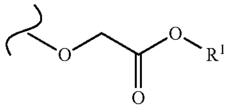 | 4 |
| 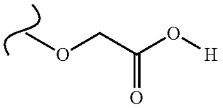 | 5 |
| 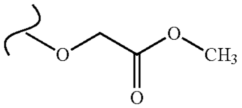 | 6 |
| 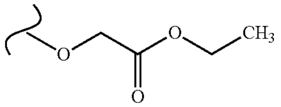 | 7 |
| 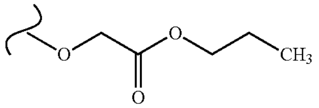 | 8 |
TABLE 20.2
| | |
|---|---|
| 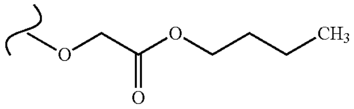 | 9 |
| 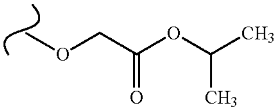 | 10 |
| 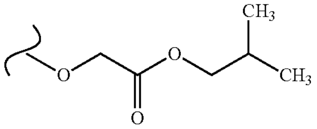 | 11 |
TABLE 20.3
| | |
|---|---|
| 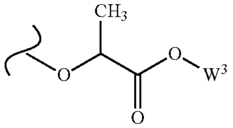 | 12 |
| 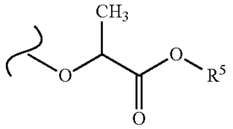 | 13 |
| 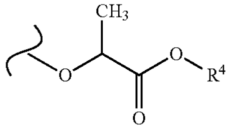 | 14 |
| 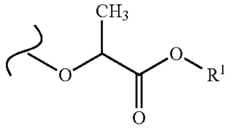 | 15 |
| 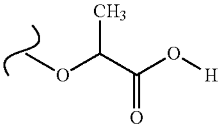 | 16 |
| 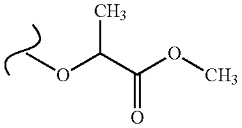 | 17 |
| 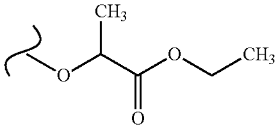 | 18 |
| 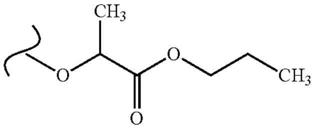 | 19 |

TABLE 20.4
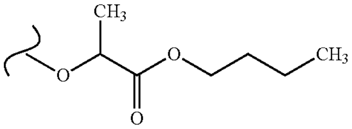 20
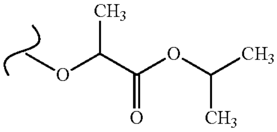 21
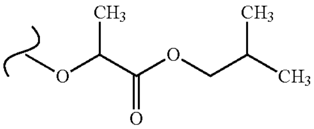 22
TABLE 20.5
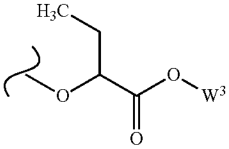 23
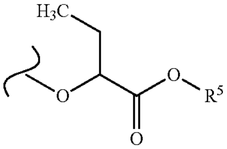 24
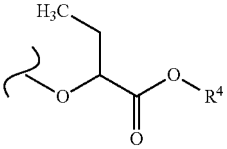 25
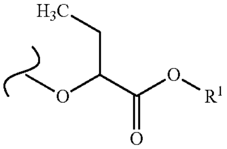 26
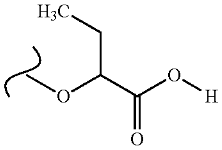 27
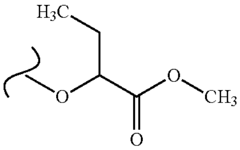 28
TABLE 20.5-continued
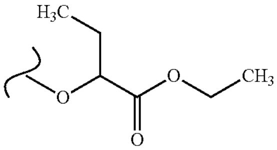 29
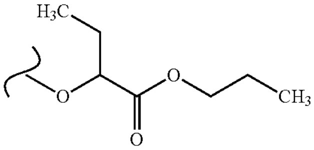 30
TABLE 20.6
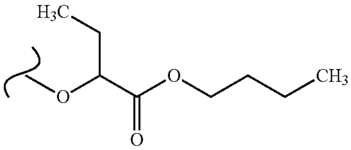 31
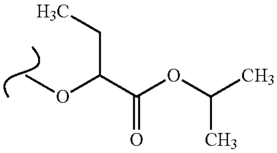 32
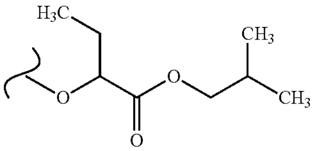 33
TABLE 20.7
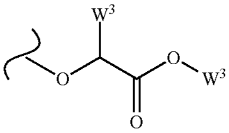 34
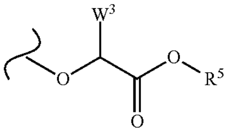 35
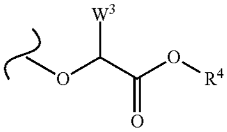 36
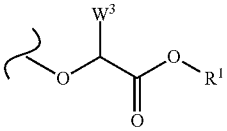 37

TABLE 20.7-continued
38
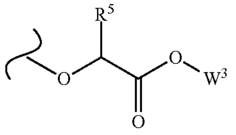
39
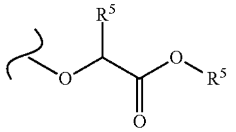
40
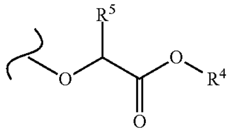
41
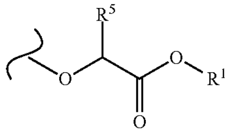
TABLE 20.8
42
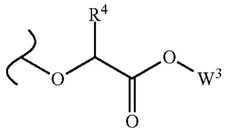
43
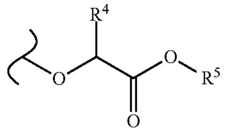
44
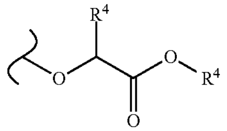
45
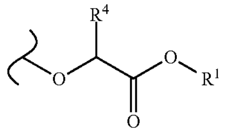
46
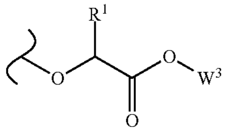
47
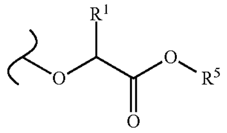
TABLE 20.8-continued
48
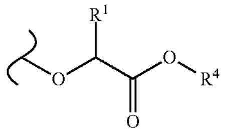
49
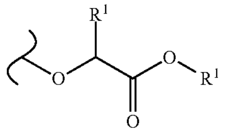
TABLE 20.9
50
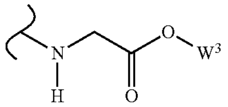
51
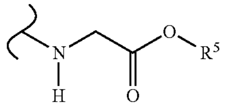
52
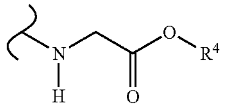
53
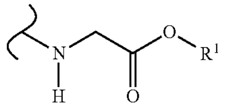
54
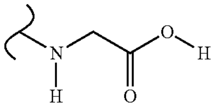
55
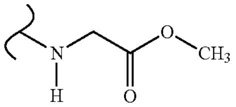
56
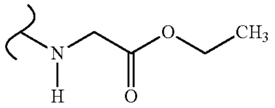
57
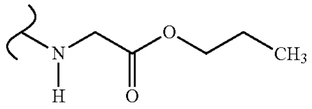
TABLE 20.10
58
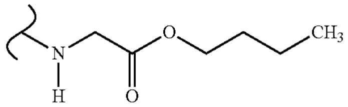

TABLE 20.10-continued
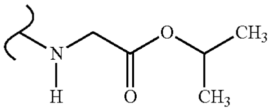
59
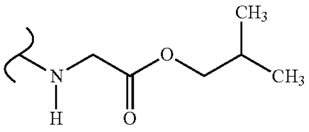
60
TABLE 20.11
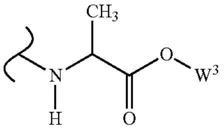
61
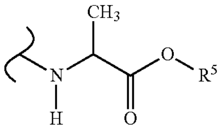
62
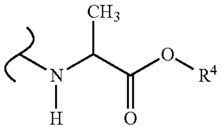
63
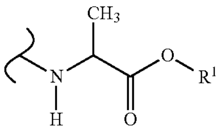
64
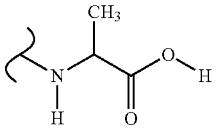
65
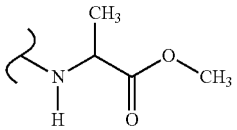
66
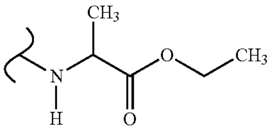
67
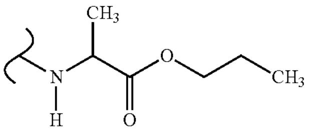
68
TABLE 20.12
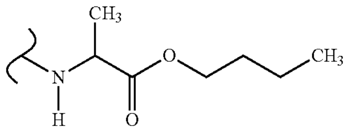
69
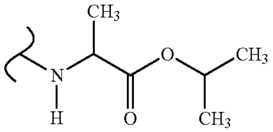
70
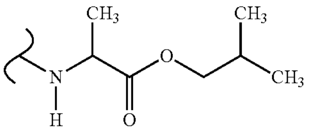
71
TABLE 20.13
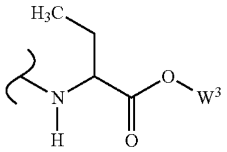
72
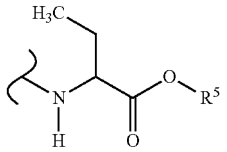
73
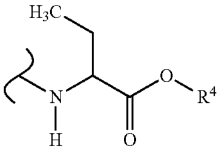
74
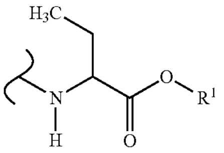
75
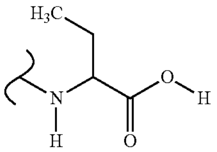
76
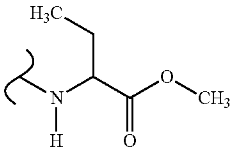
77

TABLE 20.13-continued
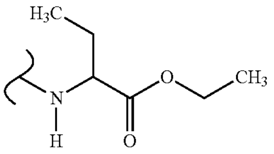
78
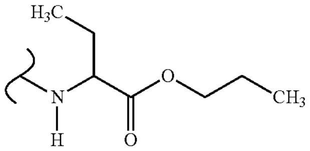
79
TABLE 20.14
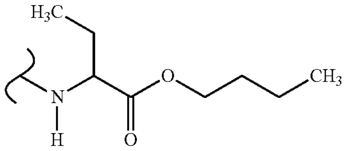
80
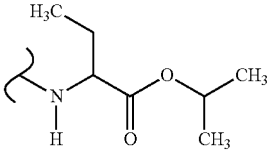
81
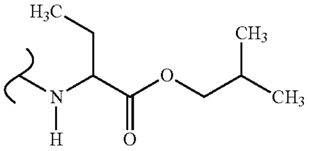
82
TABLE 20.15
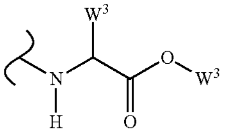
83
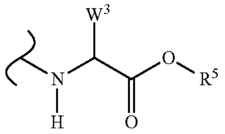
84
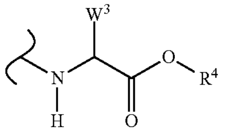
85
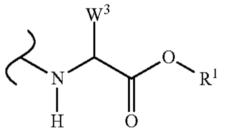
86
TABLE 20.15-continued
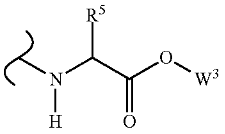
87
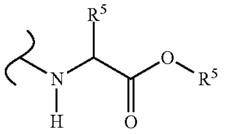
88
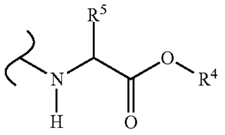
89
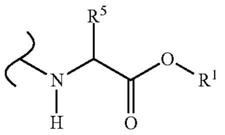
90
TABLE 20.16
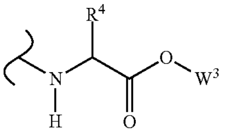
91
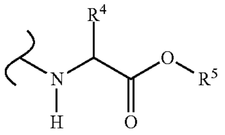
92
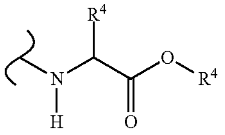
93
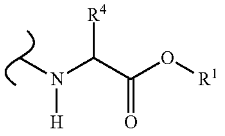
94
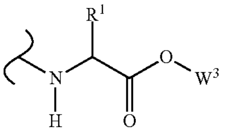
95
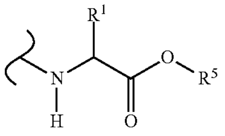
96

TABLE 20.16-continued
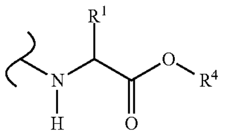
97
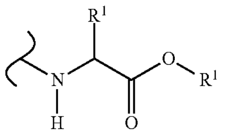
98
TABLE 20.17
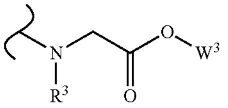
99
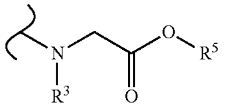
100
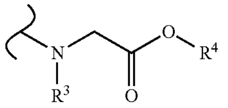
101
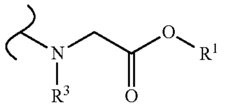
102
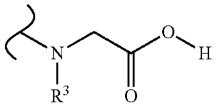
103
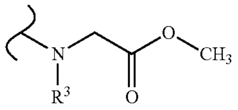
104
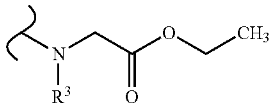
105
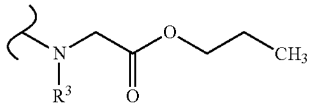
106
TABLE 20.18
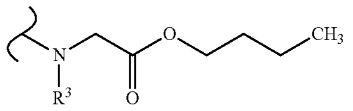
107
TABLE 20.18-continued
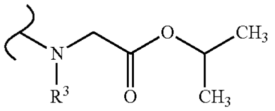
108
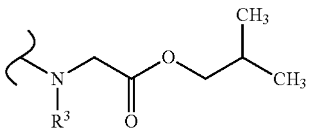
109
TABLE 20.19
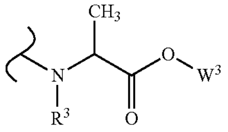
110
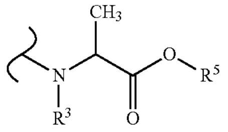
111
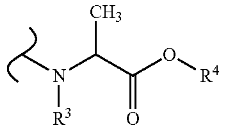
112
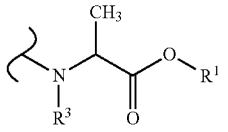
113
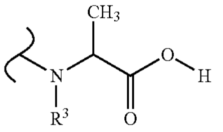
114
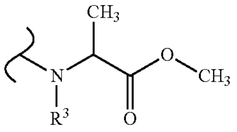
115
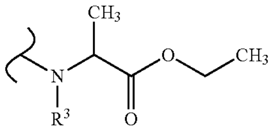
116
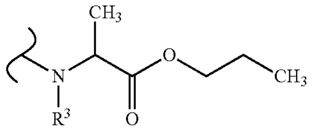
117

TABLE 20.20
| | |
|---|---|
| 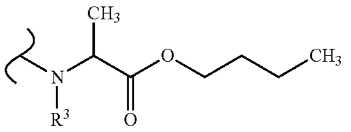 | 118 |
| 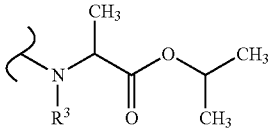 | 119 |
| 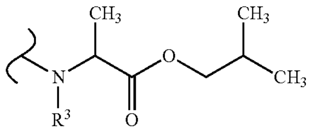 | 120 |
TABLE 20.21
| | |
|---|---|
| 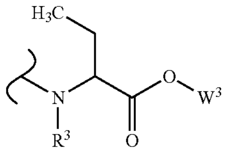 | 121 |
| 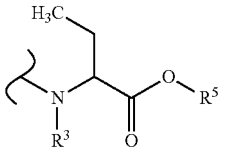 | 122 |
| 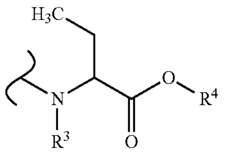 | 123 |
| 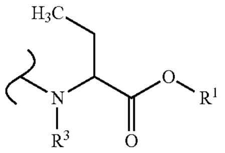 | 124 |
| 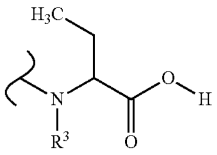 | 125 |
| 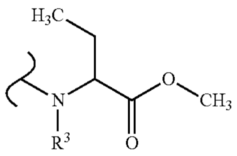 | 126 |
TABLE 20.21-continued
| | |
|---|---|
| 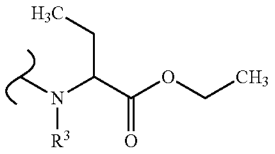 | 127 |
| 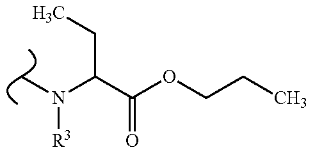 | 128 |
TABLE 20.22
| | |
|---|---|
| 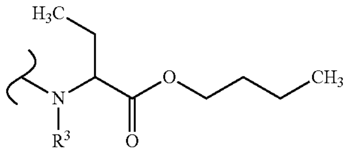 | 129 |
| 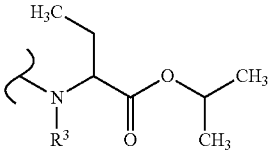 | 130 |
| 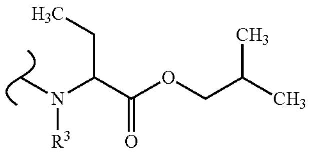 | 131 |
TABLE 20.23
| | |
|---|---|
| 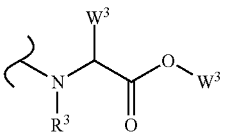 | 132 |
| 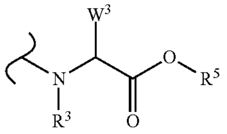 | 133 |
| 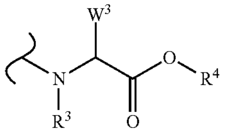 | 134 |
| 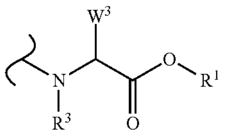 | 135 |

TABLE 20.23-continued
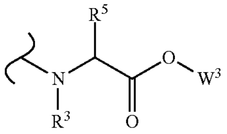 136
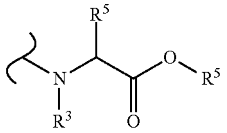 137
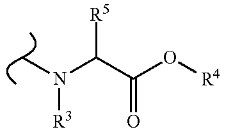 138
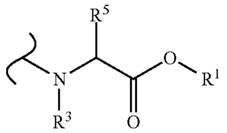 139
TABLE 20.24
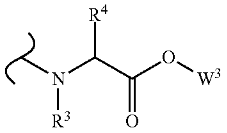 140
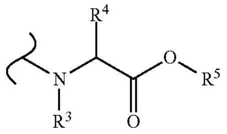 141
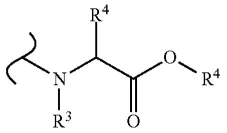 142
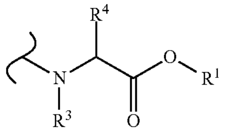 143
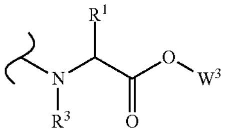 144
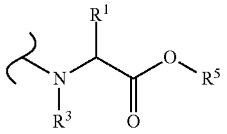 145
TABLE 20.24-continued
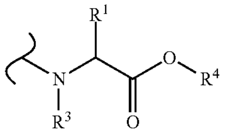 146
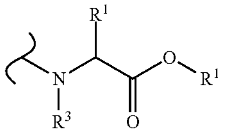 147
TABLE 20.25
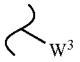 148
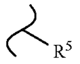 149
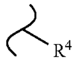 150
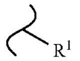 151
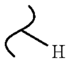 152
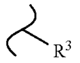 153
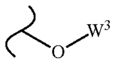 154
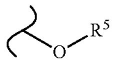 155
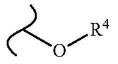 156
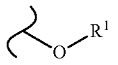 157
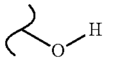 158
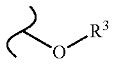 159
TABLE 20.26
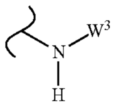 160
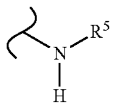 161

TABLE 20.26-continued
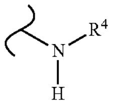 162
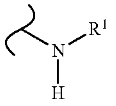 163
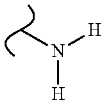 164
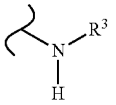 165
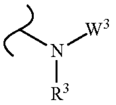 166
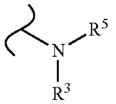 167
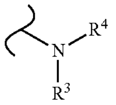 168
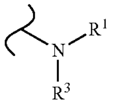 169
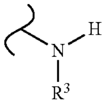 170
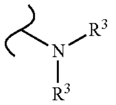 171
TABLE 20.27
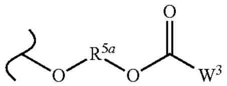 172
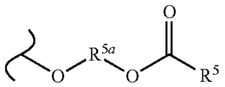 173
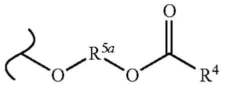 174
TABLE 20.27-continued
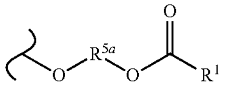 175
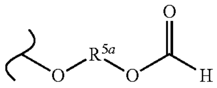 176
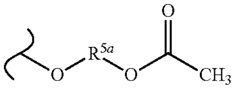 177
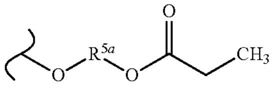 178
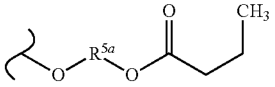 179
TABLE 20.28
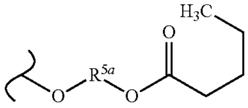 180
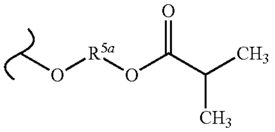 181
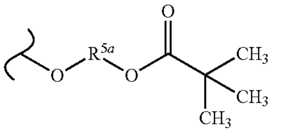 182
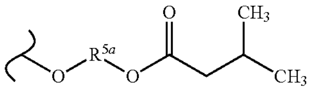 183
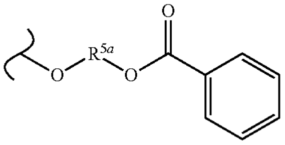 184
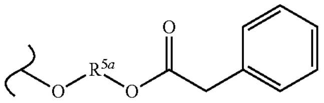 185
TABLE 20.29
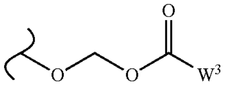 186

TABLE 20.29-continued
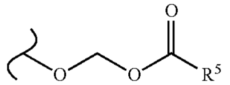
187
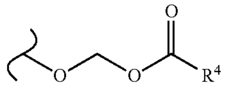
188
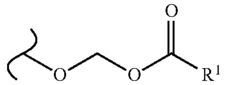
189
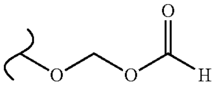
190
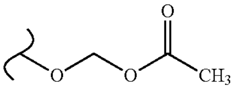
191
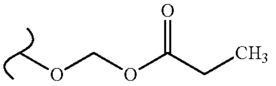
192
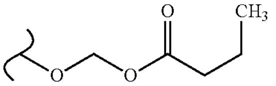
193
TABLE 20.30
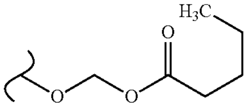
194
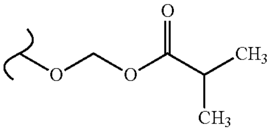
195
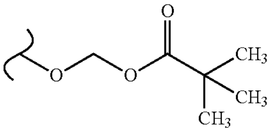
196
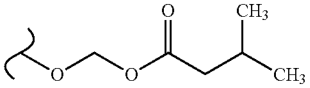
197
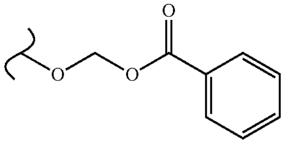
198
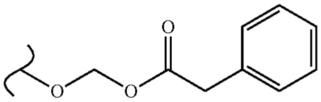
199
TABLE 20.31
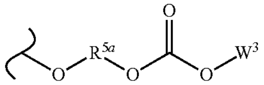
200
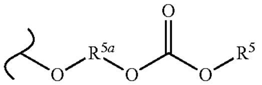
201
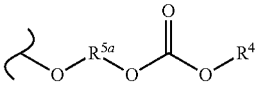
202
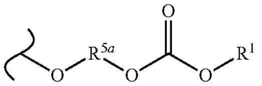
203
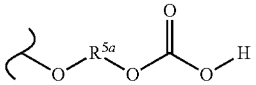
204
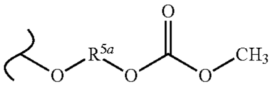
205
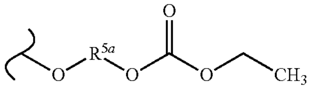
206
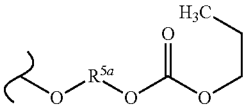
207
TABLE 20.32
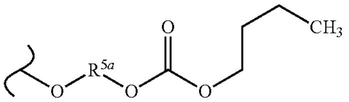
208
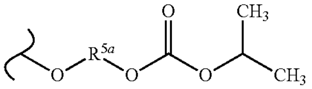
209
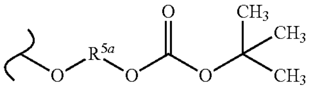
210
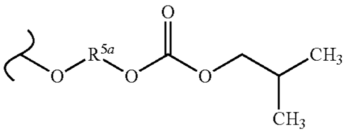
211
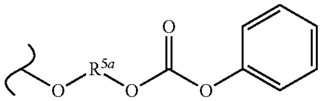
212

TABLE 20.32-continued
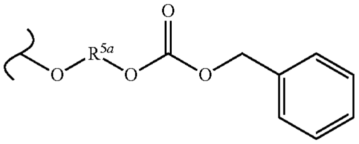
213
TABLE 20.33
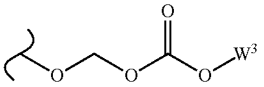
214
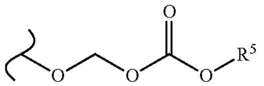
215
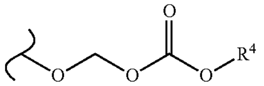
216
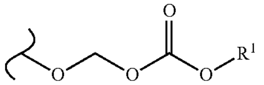
217
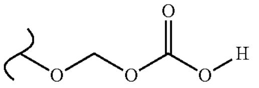
218
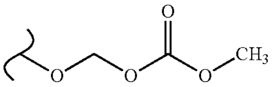
219
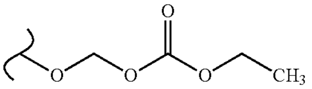
220
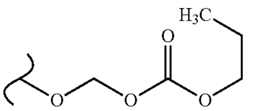
221
TABLE 20.34
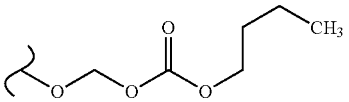
222
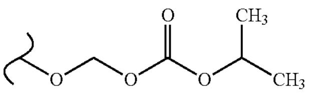
223
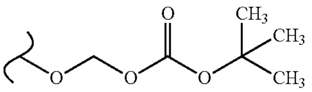
224
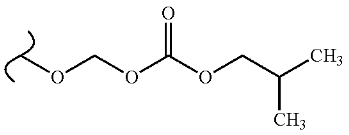
225
TABLE 20.34-continued
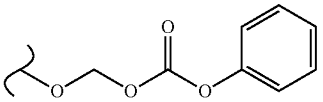
226
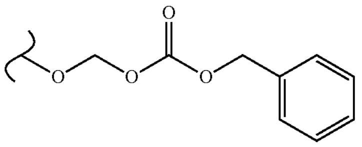
227
TABLE 20.35
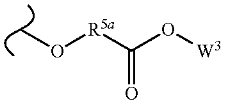
228
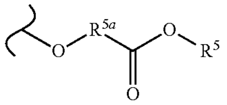
229
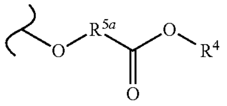
230
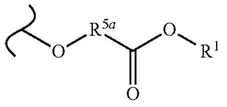
231
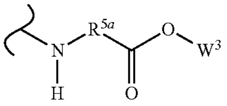
232
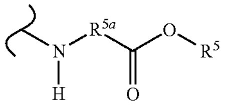
233
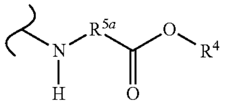
234
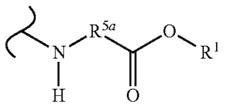
235
TABLE 20.36
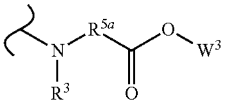
236

TABLE 20.36-continued
| | |
|---|---|
| 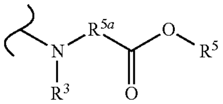 | 237 |
| 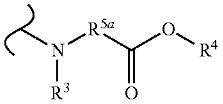 | 238 |
| 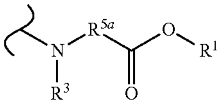 | 239 |
| 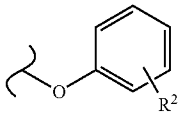 | 240 |
| 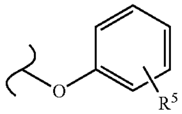 | 241 |
| 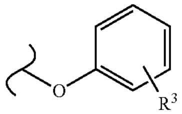 | 242 |
TABLE 20.36-continued
| | |
|---|---|
| 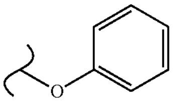 | 243 |
TABLE 20.37
| | |
|---|---|
| 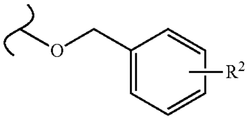 | 244 |
| 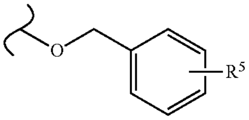 | 245 |
| 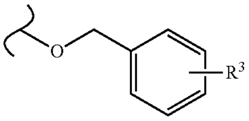 | 246 |
| 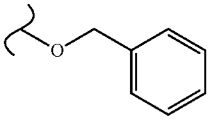 | 247 |
TABLE 100
| Prodrugs of 1.B |
|---|
| 1.B.228.228; 1.B.228.229; 1.B.228.230; 1.B.228.231; 1.B.228.236; 1.B.228.237; 1.B.228.238; 1.B.228.239; 1.B.228.154; 1.B.228.157; 1.B.228.166; 1.B.228.169; 1.B.228.172; 1.B.228.175; 1.B.228.240; 1.B.228.244; 1.B.229.228; 1.B.229.229; 1.B.229.230; 1.B.229.231; 1.B.229.236; 1.B.229.237; 1.B.229.238; 1.B.229.239; 1.B.229.154; 1.B.229.157; 1.B.229.166; 1.B.229.169; 1.B.229.172; 1.B.229.175; 1.B.229.240; 1.B.229.244; 1.B.230.228; 1.B.230.229; 1.B.230.230; 1.B.230.231; 1.B.230.236; 1.B.230.237; 1.B.230.238; 1.B.230.239; 1.B.230.154; 1.B.230.157; 1.B.230.166; 1.B.230.169; 1.B.230.172; 1.B.230.175; 1.B.230.240; 1.B.230.244; 1.B.231.228; 1.B.231.229; 1.B.231.230; 1.B.231.231; 1.B.231.236; 1.B.231.237; 1.B.231.238; 1.B.231.239; 1.B.231.154; 1.B.231.157; 1.B.231.166; 1.B.231.169; 1.B.231.172; 1.B.231.175; 1.B.231.240; 1.B.231.244; 1.B.236.228; 1.B.236.229; 1.B.236.230; 1.B.236.231; 1.B.236.236; 1.B.236.237; 1.B.236.238; 1.B.236.239; 1.B.236.154; 1.B.236.157; 1.B.236.166; 1.B.236.169; 1.B.236.172; 1.B.236.175; 1.B.236.240; 1.B.236.244; 1.B.237.228; 1.B.237.229; 1.B.237.230; 1.B.237.231; 1.B.237.236; 1.B.237.237; 1.B.237.238; 1.B.237.239; 1.B.237.154; 1.B.237.157; 1.B.237.166; 1.B.237.169; 1.B.237.172; 1.B.237.175; 1.B.237.240; 1.B.237.244; 1.B.238.228; 1.B.238.229; 1.B.238.230; 1.B.238.231; 1.B.238.236; 1.B.238.237; 1.B.238.238; 1.B.238.239; 1.B.238.154; 1.B.238.157; 1.B.238.166; 1.B.238.169; 1.B.238.172; 1.B.238.175; 1.B.238.240; 1.B.238.244; 1.B.239.228; 1.B.239.229; 1.B.239.230; 1.B.239.231; 1.B.239.236; 1.B.239.237; 1.B.239.238; 1.B.239.239; 1.B.239.154; 1.B.239.157; 1.B.239.166; 1.B.239.169; 1.B.239.172; 1.B.239.175; 1.B.239.240; 1.B.239.244; 1.B.154.228; 1.B.154.229; 1.B.154.230; 1.B.154.231; 1.B.154.236; 1.B.154.237; 1.B.154.238; 1.B.154.239; 1.B.154.154; 1.B.154.157; 1.B.154.166; 1.B.154.169; 1.B.154.172; 1.B.154.175; 1.B.154.240; 1.B.154.244; 1.B.157.228; 1.B.157.229; 1.B.157.230; 1.B.157.231; 1.B.157.236; 1.B.157.237; 1.B.157.238; 1.B.157.239; 1.B.157.154; 1.B.157.157; 1.B.157.166; 1.B.157.169; 1.B.157.172; 1.B.157.175; 1.B.157.240; 1.B.157.244; 1.B.166.228; 1.B.166.229; 1.B.166.230; 1.B.166.231; 1.B.166.236; 1.B.166.237; 1.B.166.238; 1.B.166.239; 1.B.166.154; 1.B.166.157; 1.B.166.166; 1.B.166.169; 1.B.166.172; 1.B.166.175; 1.B.166.240; 1.B.166.244; 1.B.169.228; 1.B.169.229; 1.B.169.230; 1.B.169.231; 1.B.169.236; 1.B.169.237; 1.B.169.238; 1.B.169.239; 1.B.169.154; 1.B.169.157; 1.B.169.166; 1.B.169.169; 1.B.169.172; 1.B.169.175; 1.B.169.240; 1.B.169.244; 1.B.172.228; 1.B.172.229; 1.B.172.230; 1.B.172.231; 1.B.172.236; 1.B.172.237; 1.B.172.238; 1.B.172.239; 1.B.172.154; 1.B.172.157; 1.B.172.166; 1.B.172.169; 1.B.172.172; 1.B.172.175; 1.B.172.240; 1.B.172.244; 1.B.175.228; 1.B.175.229; 1.B.175.230; 1.B.175.231; 1.B.175.236; 1.B.175.237; 1.B.175.238; 1.B.175.239; 1.B.175.154; 1.B.175.157; 1.B.175.166; 1.B.175.169; 1.B.175.172; |

TABLE 100-continued

| |
|---|
| 1.B.175.175; 1.B.175.240; 1.B.175.244; 1.B.240.228; 1.B.240.229; 1.B.240.230; 1.B.240.231; 1.B.240.236; 1.B.240.237; 1.B.240.238; 1.B.240.239; 1.B.240.154; 1.B.240.157; 1.B.240.166; 1.B.240.169; 1.B.240.172; 1.B.240.175; 1.B.240.240; 1.B.240.244; 1.B.244.228; 1.B.244.229; 1.B.244.230; 1.B.244.231; 1.B.244.236; 1.B.244.237; 1.B.244.238; 1.B.244.239; 1.B.244.154; 1.B.244.157; 1.B.244.166; 1.B.244.169; 1.B.244.172; 1.B.244.175; 1.B.244.240; 1.B.244.244; |
| Prodrugs of 1.D |
| 1.D.228.228; 1.D.228.229; 1.D.228.230; 1.D.228.231; 1.D.228.236; 1.D.228.237; 1.D.228.238; 1.D.228.239; 1.D.228.154; 1.D.228.157; 1.D.228.166; 1.D.228.169; 1.D.228.172; 1.D.228.175; 1.D.228.240; 1.D.228.244; 1.D.229.228; 1.D.229.229; 1.D.229.230; 1.D.229.231; 1.D.229.236; 1.D.229.237; 1.D.229.238; 1.D.229.239; 1.D.229.154; 1.D.229.157; 1.D.229.166; 1.D.229.169; 1.D.229.172; 1.D.229.175; 1.D.229.240; 1.D.229.244; 1.D.230.228; 1.D.230.229; 1.D.230.230; 1.D.230.231; 1.D.230.236; 1.D.230.237; 1.D.230.238; 1.D.230.239; 1.D.230.154; 1.D.230.157; 1.D.230.166; 1.D.230.169; 1.D.230.172; 1.D.230.175; 1.D.230.240; 1.D.230.244; 1.D.231.228; 1.D.231.229; 1.D.231.230; 1.D.231.231; 1.D.231.236; 1.D.231.237; 1.D.231.238; 1.D.231.239; 1.D.231.154; 1.D.231.157; 1.D.231.166; 1.D.231.169; 1.D.231.172; 1.D.231.175; 1.D.231.240; 1.D.231.244; 1.D.236.228; 1.D.236.229; 1.D.236.230; 1.D.236.231; 1.D.236.236; 1.D.236.237; 1.D.236.238; 1.D.236.239; 1.D.236.154; 1.D.236.157; 1.D.236.166; 1.D.236.169; 1.D.236.172; 1.D.236.175; 1.D.236.240; 1.D.236.244; 1.D.237.228; 1.D.237.229; 1.D.237.230; 1.D.237.231; 1.D.237.236; 1.D.237.237; 1.D.237.238; 1.D.237.239; 1.D.237.154; 1.D.237.157; 1.D.237.166; 1.D.237.169; 1.D.237.172; 1.D.237.175; 1.D.237.240; 1.D.237.244; 1.D.238.228; 1.D.238.229; 1.D.238.230; 1.D.238.231; 1.D.238.236; 1.D.238.237; 1.D.238.238; 1.D.238.239; 1.D.238.154; 1.D.238.157; 1.D.238.166; 1.D.238.169; 1.D.238.172; 1.D.238.175; 1.D.238.240; 1.D.238.244; 1.D.239.228; 1.D.239.229; 1.D.239.230; 1.D.239.231; 1.D.239.236; 1.D.239.237; 1.D.239.238; 1.D.239.239; 1.D.239.154; 1.D.239.157; 1.D.239.166; 1.D.239.169; 1.D.239.172; 1.D.239.175; 1.D.239.240; 1.D.239.244; 1.D.154.228; 1.D.154.229; 1.D.154.230; 1.D.154.231; 1.D.154.236; 1.D.154.237; 1.D.154.238; 1.D.154.239; 1.D.154.154; 1.D.154.157; 1.D.154.166; 1.D.154.169; 1.D.154.172; 1.D.154.175; 1.D.154.240; 1.D.154.244; 1.D.157.228; 1.D.157.229; 1.D.157.230; 1.D.157.231; 1.D.157.236; 1.D.157.237; 1.D.157.238; 1.D.157.239; 1.D.157.154; 1.D.157.157; 1.D.157.166; 1.D.157.169; 1.D.157.172; 1.D.157.175; 1.D.157.240; 1.D.157.244; 1.D.166.228; 1.D.166.229; 1.D.166.230; 1.D.166.231; 1.D.166.236; 1.D.166.237; 1.D.166.238; 1.D.166.239; 1.D.166.154; 1.D.166.157; 1.D.166.166; 1.D.166.169; 1.D.166.172; 1.D.166.175; 1.D.166.240; 1.D.166.244; 1.D.169.228; 1.D.169.229; 1.D.169.230; 1.D.169.231; 1.D.169.236; 1.D.169.237; 1.D.169.238; 1.D.169.239; 1.D.169.154; 1.D.169.157; 1.D.169.166; 1.D.169.169; 1.D.169.172; 1.D.169.175; 1.D.169.240; 1.D.169.244; 1.D.172.228; 1.D.172.229; 1.D.172.230; 1.D.172.231; 1.D.172.236; 1.D.172.237; 1.D.172.238; 1.D.172.239; 1.D.172.154; 1.D.172.157; 1.D.172.166; 1.D.172.169; 1.D.172.172; 1.D.172.175; 1.D.172.240; 1.D.172.244; 1.D.175.228; 1.D.175.229; 1.D.175.230; 1.D.175.231; 1.D.175.236; 1.D.175.237; 1.D.175.238; 1.D.175.239; 1.D.175.154; 1.D.175.157; 1.D.175.166; 1.D.175.169; 1.D.175.172; 1.D.175.175; 1.D.175.240; 1.D.175.244; 1.D.240.228; 1.D.240.229; 1.D.240.230; 1.D.240.231; 1.D.240.236; 1.D.240.237; 1.D.240.238; 1.D.240.239; 1.D.240.154; 1.D.240.157; 1.D.240.166; 1.D.240.169; 1.D.240.172; 1.D.240.175; 1.D.240.240; 1.D.240.244; 1.D.244.228; 1.D.244.229; 1.D.244.230; 1.D.244.231; 1.D.244.236; 1.D.244.237; 1.D.244.238; 1.D.244.239; 1.D.244.154; 1.D.244.157; 1.D.244.166; 1.D.244.169; 1.D.244.172; 1.D.244.175; 1.D.244.240; 1.D.244.244; |
| Prodrugs of 1.E |
| 1.E.228.228; 1.E.228.229; 1.E.228.230; 1.E.228.231; 1.E.228.236; 1.E.228.237; 1.E.228.238; 1.E.228.239; 1.E.228.154; 1.E.228.157; 1.E.228.166; 1.E.228.169; 1.E.228.172; 1.E.228.175; 1.E.228.240; 1.E.228.244; 1.E.229.228; 1.E.229.229; 1.E.229.230; 1.E.229.231; 1.E.229.236; 1.E.229.237; 1.E.229.238; 1.E.229.239; 1.E.229.154; 1.E.229.157; 1.E.229.166; 1.E.229.169; 1.E.229.172; 1.E.229.175; 1.E.229.240; 1.E.229.244; 1.E.230.228; 1.E.230.229; 1.E.230.230; 1.E.230.231; 1.E.230.236; 1.E.230.237; 1.E.230.238; 1.E.230.239; 1.E.230.154; 1.E.230.157; 1.E.230.166; 1.E.230.169; 1.E.230.172; 1.E.230.175; 1.E.230.240; 1.E.230.244; 1.E.231.228; 1.E.231.229; 1.E.231.230; 1.E.231.231; 1.E.231.236; 1.E.231.237; 1.E.231.238; 1.E.231.239; 1.E.231.154; 1.E.231.157; 1.E.231.166; 1.E.231.169; 1.E.231.172; 1.E.231.175; 1.E.231.240; 1.E.231.244; 1.E.236.228; 1.E.236.229; 1.E.236.230; 1.E.236.231; 1.E.236.236; 1.E.236.237; 1.E.236.238; 1.E.236.239; 1.E.236.154; 1.E.236.157; 1.E.236.166; 1.E.236.169; 1.E.236.172; 1.E.236.175; 1.E.236.240; 1.E.236.244; 1.E.237.228; 1.E.237.229; 1.E.237.230; 1.E.237.231; 1.E.237.236; 1.E.237.237; 1.E.237.238; 1.E.237.239; 1.E.237.154; 1.E.237.157; 1.E.237.166; 1.E.237.169; 1.E.237.172; 1.E.237.175; 1.E.237.240; 1.E.237.244; 1.E.238.228; 1.E.238.229; 1.E.238.230; 1.E.238.231; 1.E.238.236; 1.E.238.237; 1.E.238.238; 1.E.238.239; 1.E.238.154; 1.E.238.157; 1.E.238.166; 1.E.238.169; 1.E.238.172; 1.E.238.175; 1.E.238.240; 1.E.238.244; 1.E.239.228; |

TABLE 100-continued

| |
|---|
| 1.E.239.229; 1.E.239.230; 1.E.239.231; 1.E.239.236; 1.E.239.237; 1.E.239.238; 1.E.239.239; 1.E.239.154; 1.E.239.157; 1.E.239.166; 1.E.239.169; 1.E.239.172; 1.E.239.175; 1.E.239.240; 1.E.239.244; 1.E.154.228; 1.E.154.229; 1.E.154.230; 1.E.154.231; 1.E.154.236; 1.E.154.237; 1.E.154.238; 1.E.154.239; 1.E.154.154; 1.E.154.157; 1.E.154.166; 1.E.154.169; 1.E.154.172; 1.E.154.175; 1.E.154.240; 1.E.154.244; 1.E.157.228; 1.E.157.229; 1.E.157.230; 1.E.157.231; 1.E.157.236; 1.E.157.237; 1.E.157.238; 1.E.157.239; 1.E.157.154; 1.E.157.157; 1.E.157.166; 1.E.157.169; 1.E.157.172; 1.E.157.175; 1.E.157.240; 1.E.157.244; 1.E.166.228; 1.E.166.229; 1.E.166.230; 1.E.166.231; 1.E.166.236; 1.E.166.237; 1.E.166.238; 1.E.166.239; 1.E.166.154; 1.E.166.157; 1.E.166.166; 1.E.166.169; 1.E.166.172; 1.E.166.175; 1.E.166.240; 1.E.166.244; 1.E.169.228; 1.E.169.229; 1.E.169.230; 1.E.169.231; 1.E.169.236; 1.E.169.237; 1.E.169.238; 1.E.169.239; 1.E.169.154; 1.E.169.157; 1.E.169.166; 1.E.169.169; 1.E.169.172; 1.E.169.175; 1.E.169.240; 1.E.169.244; 1.E.172.228; 1.E.172.229; 1.E.172.230; 1.E.172.231; 1.E.172.236; 1.E.172.237; 1.E.172.238; 1.E.172.239; 1.E.172.154; 1.E.172.157; 1.E.172.166; 1.E.172.169; 1.E.172.172; 1.E.172.175; 1.E.172.240; 1.E.172.244; 1.E.175.228; 1.E.175.229; 1.E.175.230; 1.E.175.231; 1.E.175.236; 1.E.175.237; 1.E.175.238; 1.E.175.239; 1.E.175.154; 1.E.175.157; 1.E.175.166; 1.E.175.169; 1.E.175.172; 1.E.175.175; 1.E.175.240; 1.E.175.244; 1.E.240.228; 1.E.240.229; 1.E.240.230; 1.E.240.231; 1.E.240.236; 1.E.240.237; 1.E.240.238; 1.E.240.239; 1.E.240.154; 1.E.240.157; 1.E.240.166; 1.E.240.169; 1.E.240.172; 1.E.240.175; 1.E.240.240; 1.E.240.244; 1.E.244.228; 1.E.244.229; 1.E.244.230; 1.E.244.231; 1.E.244.236; 1.E.244.237; 1.E.244.238; 1.E.244.239; 1.E.244.154; 1.E.244.157; 1.E.244.166; 1.E.244.169; 1.E.244.172; 1.E.244.175; 1.E.244.240; 1.E.244.244; |
| Prodrugs of 1.G |

1.G.228.228; 1.G.228.229; 1.G.228.230; 1.G.228.231; 1.G.228.236; 1.G.228.237; 1.G.228.238; 1.G.228.239; 1.G.228.154; 1.G.228.157; 1.G.228.166; 1.G.228.169; 1.G.228.172; 1.G.228.175; 1.G.228.240; 1.G.228.244; 1.G.229.228; 1.G.229.229; 1.G.229.230; 1.G.229.231; 1.G.229.236; 1.G.229.237; 1.G.229.238; 1.G.229.239; 1.G.229.154; 1.G.229.157; 1.G.229.166; 1.G.229.169; 1.G.229.172; 1.G.229.175; 1.G.229.240; 1.G.229.244; 1.G.230.228; 1.G.230.229; 1.G.230.230; 1.G.230.231; 1.G.230.236; 1.G.230.237; 1.G.230.238; 1.G.230.239; 1.G.230.154; 1.G.230.157; 1.G.230.166; 1.G.230.169; 1.G.230.172; 1.G.230.175; 1.G.230.240; 1.G.230.244; 1.G.231.228; 1.G.231.229; 1.G.231.230; 1.G.231.231; 1.G.231.236; 1.G.231.237; 1.G.231.238; 1.G.231.239; 1.G.231.154; 1.G.231.157; 1.G.231.166; 1.G.231.169; 1.G.231.172; 1.G.231.175; 1.G.231.240; 1.G.231.244; 1.G.236.228; 1.G.236.229; 1.G.236.230; 1.G.236.231; 1.G.236.236; 1.G.236.237; 1.G.236.238; 1.G.236.239; 1.G.236.154; 1.G.236.157; 1.G.236.166; 1.G.236.169; 1.G.236.172; 1.G.236.175; 1.G.236.240; 1.G.236.244; 1.G.237.228; 1.G.237.229; 1.G.237.230; 1.G.237.231; 1.G.237.236; 1.G.237.237; 1.G.237.238; 1.G.237.239; 1.G.237.154; 1.G.237.157; 1.G.237.166; 1.G.237.169; 1.G.237.172; 1.G.237.175; 1.G.237.240; 1.G.237.244; 1.G.238.228; 1.G.238.229; 1.G.238.230; 1.G.238.231; 1.G.238.236; 1.G.238.237; 1.G.238.238; 1.G.238.239; 1.G.238.154; 1.G.238.157; 1.G.238.166; 1.G.238.169; 1.G.238.172; 1.G.238.175; 1.G.238.240; 1.G.238.244; 1.G.239.228; 1.G.239.229; 1.G.239.230; 1.G.239.231; 1.G.239.236; 1.G.239.237; 1.G.239.238; 1.G.239.239; 1.G.239.154; 1.G.239.157; 1.G.239.166; 1.G.239.169; 1.G.239.172; 1.G.239.175; 1.G.239.240; 1.G.239.244; 1.G.154.228; 1.G.154.229; 1.G.154.230; 1.G.154.231; 1.G.154.236; 1.G.154.237; 1.G.154.238; 1.G.154.239; 1.G.154.154; 1.G.154.157; 1.G.154.166; 1.G.154.169; 1.G.154.172; 1.G.154.175; 1.G.154.240; 1.G.154.244; 1.G.157.228; 1.G.157.229; 1.G.157.230; 1.G.157.231; 1.G.157.236; 1.G.157.237; 1.G.157.238; 1.G.157.239; 1.G.157.154; 1.G.157.157; 1.G.157.166; 1.G.157.169; 1.G.157.172; 1.G.157.175; 1.G.157.240; 1.G.157.244; 1.G.166.228; 1.G.166.229; 1.G.166.230; 1.G.166.231; 1.G.166.236; 1.G.166.237; 1.G.166.238; 1.G.166.239; 1.G.166.154; 1.G.166.157; 1.G.166.166; 1.G.166.169; 1.G.166.172; 1.G.166.175; 1.G.166.240; 1.G.166.244; 1.G.169.228; 1.G.169.229; 1.G.169.230; 1.G.169.231; 1.G.169.236; 1.G.169.237; 1.G.169.238; 1.G.169.239; 1.G.169.154; 1.G.169.157; 1.G.169.166; 1.G.169.169; 1.G.169.172; 1.G.169.175; 1.G.169.240; 1.G.169.244; 1.G.172.228; 1.G.172.229; 1.G.172.230; 1.G.172.231; 1.G.172.236; 1.G.172.237; 1.G.172.238; 1.G.172.239; 1.G.172.154; 1.G.172.157; 1.G.172.166; 1.G.172.169; 1.G.172.172; 1.G.172.175; 1.G.172.240; 1.G.172.244; 1.G.175.228; 1.G.175.229; 1.G.175.230; 1.G.175.231; 1.G.175.236; 1.G.175.237; 1.G.175.238; 1.G.175.239; 1.G.175.154; 1.G.175.157; 1.G.175.166; 1.G.175.169; 1.G.175.172; 1.G.175.175; 1.G.175.240; 1.G.175.244; 1.G.240.228; 1.G.240.229; 1.G.240.230; 1.G.240.231; 1.G.240.236; 1.G.240.237; 1.G.240.238; 1.G.240.239; 1.G.240.154; 1.G.240.157; 1.G.240.166; 1.G.240.169; 1.G.240.172; 1.G.240.175; 1.G.240.240; 1.G.240.244; 1.G.244.228; 1.G.244.229; 1.G.244.230; 1.G.244.231; 1.G.244.236; 1.G.244.237; 1.G.244.238; 1.G.244.239; 1.G.244.154; 1.G.244.157; 1.G.244.166; 1.G.244.169; 1.G.244.172; 1.G.244.175; 1.G.244.240; 1.G.244.244;

TABLE 100-continued

| Prodrugs of 1.I |
|---|
| 1.I.228.228; 1.I.228.229; 1.I.228.230; 1.I.228.231; 1.I.228.236; 1.I.228.237; |
| 1.I.228.238; 1.I.228.239; 1.I.228.154; 1.I.228.157; 1.I.228.166; 1.I.228.169; |
| 1.I.228.172; 1.I.228.175; 1.I.228.240; 1.I.228.244; 1.I.229.228; 1.I.229.229; |
| 1.I.229.230; 1.I.229.231; 1.I.229.236; 1.I.229.237; 1.I.229.238; 1.I.229.239; |
| 1.I.229.154; 1.I.229.157; 1.I.229.166; 1.I.229.169; 1.I.229.172; 1.I.229.175; |
| 1.I.229.240; 1.I.229.244; 1.I.230.228; 1.I.230.229; 1.I.230.230; 1.I.230.231; |
| 1.I.230.236; 1.I.230.237; 1.I.230.238; 1.I.230.239; 1.I.230.154; 1.I.230.157; |
| 1.I.230.166; 1.I.230.169; 1.I.230.172; 1.I.230.175; 1.I.230.240; 1.I.230.244; |
| 1.I.231.228; 1.I.231.229; 1.I.231.230; 1.I.231.231; 1.I.231.236; 1.I.231.237; |
| 1.I.231.238; 1.I.231.239; 1.I.231.154; 1.I.231.157; 1.I.231.166; 1.I.231.169; |
| 1.I.231.172; 1.I.231.175; 1.I.231.240; 1.I.231.244; 1.I.236.228; 1.I.236.229; |
| 1.I.236.230; 1.I.236.231; 1.I.236.236; 1.I.236.237; 1.I.236.238; 1.I.236.239; |
| 1.I.236.154; 1.I.236.157; 1.I.236.166; 1.I.236.169; 1.I.236.172; 1.I.236.175; |
| 1.I.236.240; 1.I.236.244; 1.I.237.228; 1.I.237.229; 1.I.237.230; 1.I.237.231; |
| 1.I.237.236; 1.I.237.237; 1.I.237.238; 1.I.237.239; 1.I.237.154; 1.I.237.157; |
| 1.I.237.166; 1.I.237.169; 1.I.237.172; 1.I.237.175; 1.I.237.240; 1.I.237.244; |
| 1.I.238.228; 1.I.238.229; 1.I.238.230; 1.I.238.231; 1.I.238.236; 1.I.238.237; |
| 1.I.238.238; 1.I.238.239; 1.I.238.154; 1.I.238.157; 1.I.238.166; 1.I.238.169; |
| 1.I.238.172; 1.I.238.175; 1.I.238.240; 1.I.238.244; 1.I.239.228; 1.I.239.229; |
| 1.I.239.230; 1.I.239.231; 1.I.239.236; 1.I.239.237; 1.I.239.238; 1.I.239.239; |
| 1.I.239.154; 1.I.239.157; 1.I.239.166; 1.I.239.169; 1.I.239.172; 1.I.239.175; |
| 1.I.239.240; 1.I.239.244; 1.I.154.228; 1.I.154.229; 1.I.154.230; 1.I.154.231; |
| 1.I.154.236; 1.I.154.237; 1.I.154.238; 1.I.154.239; 1.I.154.154; 1.I.154.157; |
| 1.I.154.166; 1.I.154.169; 1.I.154.172; 1.I.154.175; 1.I.154.240; 1.I.154.244; |
| 1.I.157.228; 1.I.157.229; 1.I.157.230; 1.I.157.231; 1.I.157.236; 1.I.157.237; |
| 1.I.157.238; 1.I.157.239; 1.I.157.154; 1.I.157.157; 1.I.157.166; 1.I.157.169; |
| 1.I.157.172; 1.I.157.175; 1.I.157.240; 1.I.157.244; 1.I.166.228; 1.I.166.229; |
| 1.I.166.230; 1.I.166.231; 1.I.166.236; 1.I.166.237; 1.I.166.238; 1.I.166.239; |
| 1.I.166.154; 1.I.166.157; 1.I.166.166; 1.I.166.169; 1.I.166.172; 1.I.166.175; |
| 1.I.166.240; 1.I.166.244; 1.I.169.228; 1.I.169.229; 1.I.169.230; 1.I.169.231; |
| 1.I.169.236; 1.I.169.237; 1.I.169.238; 1.I.169.239; 1.I.169.154; 1.I.169.157; |
| 1.I.169.166; 1.I.169.169; 1.I.169.172; 1.I.169.175; 1.I.169.240; 1.I.169.244; |
| 1.I.172.228; 1.I.172.229; 1.I.172.230; 1.I.172.231; 1.I.172.236; 1.I.172.237; |
| 1.I.172.238; 1.I.172.239; 1.I.172.154; 1.I.172.157; 1.I.172.166; 1.I.172.169; |
| 1.I.172.172; 1.I.172.175; 1.I.172.240; 1.I.172.244; 1.I.175.228; 1.I.175.229; |
| 1.I.175.230; 1.I.175.231; 1.I.175.236; 1.I.175.237; 1.I.175.238; 1.I.175.239; |
| 1.I.175.154; 1.I.175.157; 1.I.175.166; 1.I.175.169; 1.I.175.172; 1.I.175.175; |
| 1.I.175.240; 1.I.175.244; 1.I.240.228; 1.I.240.229; 1.I.240.230; 1.I.240.231; |
| 1.I.240.236; 1.I.240.237; 1.I.240.238; 1.I.240.239; 1.I.240.154; 1.I.240.157; |
| 1.I.240.166; 1.I.240.169; 1.I.240.172; 1.I.240.175; 1.I.240.240; 1.I.240.244; |
| 1.I.244.228; 1.I.244.229; 1.I.244.230; 1.I.244.231; 1.I.244.236; 1.I.244.237; |
| 1.I.244.238; 1.I.244.239; 1.I.244.154; 1.I.244.157; 1.I.244.166; 1.I.244.169; |
| 1.I.244.172; 1.I.244.175; 1.I.244.240; 1.I.244.244; |
| Prodrugs of 1.J |
| 1.J.228.228; 1.J.228.229; 1.J.228.230; 1.J.228.231; 1.J.228.236; 1.J.228.237; |
| 1.J.228.238; 1.J.228.239; 1.J.228.154; 1.J.228.157; 1.J.228.166; 1.J.228.169; |
| 1.J.228.172; 1.J.228.175; 1.J.228.240; 1.J.228.244; 1.J.229.228; 1.J.229.229; |
| 1.J.229.230; 1.J.229.231; 1.J.229.236; 1.J.229.237; 1.J.229.238; 1.J.229.239; |
| 1.J.229.154; 1.J.229.157; 1.J.229.166; 1.J.229.169; 1.J.229.172; 1.J.229.175; |
| 1.J.229.240; 1.J.229.244; 1.J.230.228; 1.J.230.229; 1.J.230.230; 1.J.230.231; |
| 1.J.230.236; 1.J.230.237; 1.J.230.238; 1.J.230.239; 1.J.230.154; 1.J.230.157; |
| 1.J.230.166; 1.J.230.169; 1.J.230.172; 1.J.230.175; 1.J.230.240; 1.J.230.244; |
| 1.J.231.228; 1.J.231.229; 1.J.231.230; 1.J.231.231; 1.J.231.236; 1.J.231.237; |
| 1.J.231.238; 1.J.231.239; 1.J.231.154; 1.J.231.157; 1.J.231.166; 1.J.231.169; |
| 1.J.231.172; 1.J.231.175; 1.J.231.240; 1.J.231.244; 1.J.236.228; 1.J.236.229; |
| 1.J.236.230; 1.J.236.231; 1.J.236.236; 1.J.236.237; 1.J.236.238; 1.J.236.239; |
| 1.J.236.154; 1.J.236.157; 1.J.236.166; 1.J.236.169; 1.J.236.172; 1.J.236.175; |
| 1.J.236.240; 1.J.236.244; 1.J.237.228; 1.J.237.229; 1.J.237.230; 1.J.237.231; |
| 1.J.237.236; 1.J.237.237; 1.J.237.238; 1.J.237.239; 1.J.237.154; 1.J.237.157; |
| 1.J.237.166; 1.J.237.169; 1.J.237.172; 1.J.237.175; 1.J.237.240; 1.J.237.244; |
| 1.J.238.228; 1.J.238.229; 1.J.238.230; 1.J.238.231; 1.J.238.236; 1.J.238.237; |
| 1.J.238.238; 1.J.238.239; 1.J.238.154; 1.J.238.157; 1.J.238.166; 1.J.238.169; |
| 1.J.238.172; 1.J.238.175; 1.J.238.240; 1.J.238.244; 1.J.239.228; 1.J.239.229; |
| 1.J.239.230; 1.J.239.231; 1.J.239.236; 1.J.239.237; 1.J.239.238; 1.J.239.239; |
| 1.J.239.154; 1.J.239.157; 1.J.239.166; 1.J.239.169; 1.J.239.172; 1.J.239.175; |
| 1.J.239.240; 1.J.239.244; 1.J.154.228; 1.J.154.229; 1.J.154.230; 1.J.154.231; |
| 1.J.154.236; 1.J.154.237; 1.J.154.238; 1.J.154.239; 1.J.154.154; 1.J.154.157; |
| 1.J.154.166; 1.J.154.169; 1.J.154.172; 1.J.154.175; 1.J.154.240; 1.J.154.244; |
| 1.J.157.228; 1.J.157.229; 1.J.157.230; 1.J.157.231; 1.J.157.236; 1.J.157.237; |
| 1.J.157.238; 1.J.157.239; 1.J.157.154; 1.J.157.157; 1.J.157.166; 1.J.157.169; |
| 1.J.157.172; 1.J.157.175; 1.J.157.240; 1.J.157.244; 1.J.166.228; 1.J.166.229; |
| 1.J.166.230; 1.J.166.231; 1.J.166.236; 1.J.166.237; 1.J.166.238; 1.J.166.239; |
| 1.J.166.154; 1.J.166.157; 1.J.166.166; 1.J.166.169; 1.J.166.172; 1.J.166.175; |
| 1.J.166.240; 1.J.166.244; 1.J.169.228; 1.J.169.229; 1.J.169.230; 1.J.169.231; |
| 1.J.169.236; 1.J.169.237; 1.J.169.238; 1.J.169.239; 1.J.169.154; 1.J.169.157; |
| 1.J.169.166; 1.J.169.169; 1.J.169.172; 1.J.169.175; 1.J.169.240; 1.J.169.244; |
| 1.J.172.228; 1.J.172.229; 1.J.172.230; 1.J.172.231; 1.J.172.236; 1.J.172.237; |

TABLE 100-continued

| |
|---|
| 1.J.172.238; 1.J.172.239; 1.J.172.154; 1.J.172.157; 1.J.172.166; 1.J.172.169; 1.J.172.172; 1.J.172.175; 1.J.172.240; 1.J.172.244; 1.J.175.228; 1.J.175.229; 1.J.175.230; 1.J.175.231; 1.J.175.236; 1.J.175.237; 1.J.175.238; 1.J.175.239; 1.J.175.154; 1.J.175.157; 1.J.175.166; 1.J.175.169; 1.J.175.172; 1.J.175.175; 1.J.175.240; 1.J.175.244; 1.J.240.228; 1.J.240.229; 1.J.240.230; 1.J.240.231; 1.J.240.236; 1.J.240.237; 1.J.240.238; 1.J.240.239; 1.J.240.154; 1.J.240.157; 1.J.240.166; 1.J.240.169; 1.J.240.172; 1.J.240.175; 1.J.240.240; 1.J.240.244; 1.J.244.228; 1.J.244.229; 1.J.244.230; 1.J.244.231; 1.J.244.236; 1.J.244.237; 1.J.244.238; 1.J.244.239; 1.J.244.154; 1.J.244.157; 1.J.244.166; 1.J.244.169; 1.J.244.172; 1.J.244.175; 1.J.244.240; 1.J.244.244; |
| Prodrugs of 1.L |
| 1.L.228.228; 1.L.228.229; 1.L.228.230; 1.L.228.231; 1.L.228.236; 1.L.228.237; 1.L.228.238; 1.L.228.239; 1.L.228.154; 1.L.228.157; 1.L.228.166; 1.L.228.169; 1.L.228.172; 1.L.228.175; 1.L.228.240; 1.L.228.244; 1.L.229.228; 1.L.229.229; 1.L.229.230; 1.L.229.231; 1.L.229.236; 1.L.229.237; 1.L.229.238; 1.L.229.239; 1.L.229.154; 1.L.229.157; 1.L.229.166; 1.L.229.169; 1.L.229.172; 1.L.229.175; 1.L.229.240; 1.L.229.244; 1.L.230.228; 1.L.230.229; 1.L.230.230; 1.L.230.231; 1.L.230.236; 1.L.230.237; 1.L.230.238; 1.L.230.239; 1.L.230.154; 1.L.230.157; 1.L.230.166; 1.L.230.169; 1.L.230.172; 1.L.230.175; 1.L.230.240; 1.L.230.244; 1.L.231.228; 1.L.231.229; 1.L.231.230; 1.L.231.231; 1.L.231.236; 1.L.231.237; 1.L.231.238; 1.L.231.239; 1.L.231.154; 1.L.231.157; 1.L.231.166; 1.L.231.169; 1.L.231.172; 1.L.231.175; 1.L.231.240; 1.L.231.244; 1.L.236.228; 1.L.236.229; 1.L.236.230; 1.L.236.231; 1.L.236.236; 1.L.236.237; 1.L.236.238; 1.L.236.239; 1.L.236.154; 1.L.236.157; 1.L.236.166; 1.L.236.169; 1.L.236.172; 1.L.236.175; 1.L.236.240; 1.L.236.244; 1.L.237.228; 1.L.237.229; 1.L.237.230; 1.L.237.231; 1.L.237.236; 1.L.237.237; 1.L.237.238; 1.L.237.239; 1.L.237.154; 1.L.237.157; 1.L.237.166; 1.L.237.169; 1.L.237.172; 1.L.237.175; 1.L.237.240; 1.L.237.244; 1.L.238.228; 1.L.238.229; 1.L.238.230; 1.L.238.231; 1.L.238.236; 1.L.238.237; 1.L.238.238; 1.L.238.239; 1.L.238.154; 1.L.238.157; 1.L.238.166; 1.L.238.169; 1.L.238.172; 1.L.238.175; 1.L.238.240; 1.L.238.244; 1.L.239.228; 1.L.239.229; 1.L.239.230; 1.L.239.231; 1.L.239.236; 1.L.239.237; 1.L.239.238; 1.L.239.239; 1.L.239.154; 1.L.239.157; 1.L.239.166; 1.L.239.169; 1.L.239.172; 1.L.239.175; 1.L.239.240; 1.L.239.244; 1.L.154.228; 1.L.154.229; 1.L.154.230; 1.L.154.231; 1.L.154.236; 1.L.154.237; 1.L.154.238; 1.L.154.239; 1.L.154.154; 1.L.154.157; 1.L.154.166; 1.L.154.169; 1.L.154.172; 1.L.154.175; 1.L.154.240; 1.L.154.244; 1.L.157.228; 1.L.157.229; 1.L.157.230; 1.L.157.231; 1.L.157.236; 1.L.157.237; 1.L.157.238; 1.L.157.239; 1.L.157.154; 1.L.157.157; 1.L.157.166; 1.L.157.169; 1.L.157.172; 1.L.157.175; 1.L.157.240; 1.L.157.244; 1.L.166.228; 1.L.166.229; 1.L.166.230; 1.L.166.231; 1.L.166.236; 1.L.166.237; 1.L.166.238; 1.L.166.239; 1.L.166.154; 1.L.166.157; 1.L.166.166; 1.L.166.169; 1.L.166.172; 1.L.166.175; 1.L.166.240; 1.L.166.244; 1.L.169.228; 1.L.169.229; 1.L.169.230; 1.L.169.231; 1.L.169.236; 1.L.169.237; 1.L.169.238; 1.L.169.239; 1.L.169.154; 1.L.169.157; 1.L.169.166; 1.L.169.169; 1.L.169.172; 1.L.169.175; 1.L.169.240; 1.L.169.244; 1.L.172.228; 1.L.172.229; 1.L.172.230; 1.L.172.231; 1.L.172.236; 1.L.172.237; 1.L.172.238; 1.L.172.239; 1.L.172.154; 1.L.172.157; 1.L.172.166; 1.L.172.169; 1.L.172.172; 1.L.172.175; 1.L.172.240; 1.L.172.244; 1.L.175.228; 1.L.175.229; 1.L.175.230; 1.L.175.231; 1.L.175.236; 1.L.175.237; 1.L.175.238; 1.L.175.239; 1.L.175.154; 1.L.175.157; 1.L.175.166; 1.L.175.169; 1.L.175.172; 1.L.175.175; 1.L.175.240; 1.L.175.244; 1.L.240.228; 1.L.240.229; 1.L.240.230; 1.L.240.231; 1.L.240.236; 1.L.240.237; 1.L.240.238; 1.L.240.239; 1.L.240.154; 1.L.240.157; 1.L.240.166; 1.L.240.169; 1.L.240.172; 1.L.240.175; 1.L.240.240; 1.L.240.244; 1.L.244.228; 1.L.244.229; 1.L.244.230; 1.L.244.231; 1.L.244.236; 1.L.244.237; 1.L.244.238; 1.L.244.239; 1.L.244.154; 1.L.244.157; 1.L.244.166; 1.L.244.169; 1.L.244.172; 1.L.244.175; 1.L.244.240; 1.L.244.244; |
| Prodrugs of 1.O |
| 1.O.228.228; 1.O.228.229; 1.O.228.230; 1.O.228.231; 1.O.228.236; 1.O.228.237; 1.O.228.238; 1.O.228.239; 1.O.228.154; 1.O.228.157; 1.O.228.166; 1.O.228.169; 1.O.228.172; 1.O.228.175; 1.O.228.240; 1.O.228.244; 1.O.229.228; 1.O.229.229; 1.O.229.230; 1.O.229.231; 1.O.229.236; 1.O.229.237; 1.O.229.238; 1.O.229.239; 1.O.229.154; 1.O.229.157; 1.O.229.166; 1.O.229.169; 1.O.229.172; 1.O.229.175; 1.O.229.240; 1.O.229.244; 1.O.230.228; 1.O.230.229; 1.O.230.230; 1.O.230.231; 1.O.230.236; 1.O.230.237; 1.O.230.238; 1.O.230.239; 1.O.230.154; 1.O.230.157; 1.O.230.166; 1.O.230.169; 1.O.230.172; 1.O.230.175; 1.O.230.240; 1.O.230.244; 1.O.231.228; 1.O.231.229; 1.O.231.230; 1.O.231.231; 1.O.231.236; 1.O.231.237; 1.O.231.238; 1.O.231.239; 1.O.231.154; 1.O.231.157; 1.O.231.166; 1.O.231.169; 1.O.231.172; 1.O.231.175; 1.O.231.240; 1.O.231.244; 1.O.236.228; 1.O.236.229; 1.O.236.230; 1.O.236.231; 1.O.236.236; 1.O.236.237; 1.O.236.238; 1.O.236.239; 1.O.236.154; 1.O.236.157; 1.O.236.166; 1.O.236.169; 1.O.236.172; 1.O.236.175; 1.O.236.240; 1.O.236.244; 1.O.237.228; 1.O.237.229; 1.O.237.230; 1.O.237.231; 1.O.237.236; 1.O.237.237; 1.O.237.238; 1.O.237.239; 1.O.237.154; 1.O.237.157; 1.O.237.166; 1.O.237.169; 1.O.237.172; 1.O.237.175; 1.O.237.240; 1.O.237.244; 1.O.238.228; 1.O.238.229; 1.O.238.230; 1.O.238.231; 1.O.238.236; 1.O.238.237; 1.O.238.238; 1.O.238.239; 1.O.238.154; 1.O.238.157; 1.O.238.166; 1.O.238.169; 1.O.238.172; 1.O.238.175; 1.O.238.240; 1.O.238.244; 1.O.239.228; 1.O.239.229; 1.O.239.230; |

TABLE 100-continued

| |
|---|
| 1.O.239.231; 1.O.239.236; 1.O.239.237; 1.O.239.238; 1.O.239.239; 1.O.239.154; 1.O.239.157; 1.O.239.166; 1.O.239.169; 1.O.239.172; 1.O.239.175; 1.O.239.240; 1.O.239.244; 1.O.154.228; 1.O.154.229; 1.O.154.230; 1.O.154.231; 1.O.154.236; 1.O.154.237; 1.O.154.238; 1.O.154.239; 1.O.154.154; 1.O.154.157; 1.O.154.166; 1.O.154.169; 1.O.154.172; 1.O.154.175; 1.O.154.240; 1.O.154.244; 1.O.157.228; 1.O.157.229; 1.O.157.230; 1.O.157.231; 1.O.157.236; 1.O.157.237; 1.O.157.238; 1.O.157.239; 1.O.157.154; 1.O.157.157; 1.O.157.166; 1.O.157.169; 1.O.157.172; 1.O.157.175; 1.O.157.240; 1.O.157.244; 1.O.166.228; 1.O.166.229; 1.O.166.230; 1.O.166.231; 1.O.166.236; 1.O.166.237; 1.O.166.238; 1.O.166.239; 1.O.166.154; 1.O.166.157; 1.O.166.166; 1.O.166.169; 1.O.166.172; 1.O.166.175; 1.O.166.240; 1.O.166.244; 1.O.169.228; 1.O.169.229; 1.O.169.230; 1.O.169.231; 1.O.169.236; 1.O.169.237; 1.O.169.238; 1.O.169.239; 1.O.169.154; 1.O.169.157; 1.O.169.166; 1.O.169.169; 1.O.169.172; 1.O.169.175; 1.O.169.240; 1.O.169.244; 1.O.172.228; 1.O.172.229; 1.O.172.230; 1.O.172.231; 1.O.172.236; 1.O.172.237; 1.O.172.238; 1.O.172.239; 1.O.172.154; 1.O.172.157; 1.O.172.166; 1.O.172.169; 1.O.172.172; 1.O.172.175; 1.O.172.240; 1.O.172.244; 1.O.175.228; 1.O.175.229; 1.O.175.230; 1.O.175.231; 1.O.175.236; 1.O.175.237; 1.O.175.238; 1.O.175.239; 1.O.175.154; 1.O.175.157; 1.O.175.166; 1.O.175.169; 1.O.175.172; 1.O.175.175; 1.O.175.240; 1.O.175.244; 1.O.240.228; 1.O.240.229; 1.O.240.230; 1.O.240.231; 1.O.240.236; 1.O.240.237; 1.O.240.238; 1.O.240.239; 1.O.240.154; 1.O.240.157; 1.O.240.166; 1.O.240.169; 1.O.240.172; 1.O.240.175; 1.O.240.240; 1.O.240.244; 1.O.244.228; 1.O.244.229; 1.O.244.230; 1.O.244.231; 1.O.244.236; 1.O.244.237; 1.O.244.238; 1.O.244.239; 1.O.244.154; 1.O.244.157; 1.O.244.166; 1.O.244.169; 1.O.244.172; 1.O.244.175; 1.O.244.240; 1.O.244.244; |
| Prodrugs of 1.P |
| 1.P.228.228; 1.P.228.229; 1.P.228.230; 1.P.228.231; 1.P.228.236; 1.P.228.237; 1.P.228.238; 1.P.228.239; 1.P.228.154; 1.P.228.157; 1.P.228.166; 1.P.228.169; 1.P.228.172; 1.P.228.175; 1.P.228.240; 1.P.228.244; 1.P.229.228; 1.P.229.229; 1.P.229.230; 1.P.229.231; 1.P.229.236; 1.P.229.237; 1.P.229.238; 1.P.229.239; 1.P.229.154; 1.P.229.157; 1.P.229.166; 1.P.229.169; 1.P.229.172; 1.P.229.175; 1.P.229.240; 1.P.229.244; 1.P.230.228; 1.P.230.229; 1.P.230.230; 1.P.230.231; 1.P.230.236; 1.P.230.237; 1.P.230.238; 1.P.230.239; 1.P.230.154; 1.P.230.157; 1.P.230.166; 1.P.230.169; 1.P.230.172; 1.P.230.175; 1.P.230.240; 1.P.230.244; 1.P.231.228; 1.P.231.229; 1.P.231.230; 1.P.231.231; 1.P.231.236; 1.P.231.237; 1.P.231.238; 1.P.231.239; 1.P.231.154; 1.P.231.157; 1.P.231.166; 1.P.231.169; 1.P.231.172; 1.P.231.175; 1.P.231.240; 1.P.231.244; 1.P.236.228; 1.P.236.229; 1.P.236.230; 1.P.236.231; 1.P.236.236; 1.P.236.237; 1.P.236.238; 1.P.236.239; 1.P.236.154; 1.P.236.157; 1.P.236.166; 1.P.236.169; 1.P.236.172; 1.P.236.175; 1.P.236.240; 1.P.236.244; 1.P.237.228; 1.P.237.229; 1.P.237.230; 1.P.237.231; 1.P.237.236; 1.P.237.237; 1.P.237.238; 1.P.237.239; 1.P.237.154; 1.P.237.157; 1.P.237.166; 1.P.237.169; 1.P.237.172; 1.P.237.175; 1.P.237.240; 1.P.237.244; 1.P.238.228; 1.P.238.229; 1.P.238.230; 1.P.238.231; 1.P.238.236; 1.P.238.237; 1.P.238.238; 1.P.238.239; 1.P.238.154; 1.P.238.157; 1.P.238.166; 1.P.238.169; 1.P.238.172; 1.P.238.175; 1.P.238.240; 1.P.238.244; 1.P.239.228; 1.P.239.229; 1.P.239.230; 1.P.239.231; 1.P.239.236; 1.P.239.237; 1.P.239.238; 1.P.239.239; 1.P.239.154; 1.P.239.157; 1.P.239.166; 1.P.239.169; 1.P.239.172; 1.P.239.175; 1.P.239.240; 1.P.239.244; 1.P.154.228; 1.P.154.229; 1.P.154.230; 1.P.154.231; 1.P.154.236; 1.P.154.237; 1.P.154.238; 1.P.154.239; 1.P.154.154; 1.P.154.157; 1.P.154.166; 1.P.154.169; 1.P.154.172; 1.P.154.175; 1.P.154.240; 1.P.154.244; 1.P.157.228; 1.P.157.229; 1.P.157.230; 1.P.157.231; 1.P.157.236; 1.P.157.237; 1.P.157.238; 1.P.157.239; 1.P.157.154; 1.P.157.157; 1.P.157.166; 1.P.157.169; 1.P.157.172; 1.P.157.175; 1.P.157.240; 1.P.157.244; 1.P.166.228; 1.P.166.229; 1.P.166.230; 1.P.166.231; 1.P.166.236; 1.P.166.237; 1.P.166.238; 1.P.166.239; 1.P.166.154; 1.P.166.157; 1.P.166.166; 1.P.166.169; 1.P.166.172; 1.P.166.175; 1.P.166.240; 1.P.166.244; 1.P.169.228; 1.P.169.229; 1.P.169.230; 1.P.169.231; 1.P.169.236; 1.P.169.237; 1.P.169.238; 1.P.169.239; 1.P.169.154; 1.P.169.157; 1.P.169.166; 1.P.169.169; 1.P.169.172; 1.P.169.175; 1.P.169.240; 1.P.169.244; 1.P.172.228; 1.P.172.229; 1.P.172.230; 1.P.172.231; 1.P.172.236; 1.P.172.237; 1.P.172.238; 1.P.172.239; 1.P.172.154; 1.P.172.157; 1.P.172.166; 1.P.172.169; 1.P.172.172; 1.P.172.175; 1.P.172.240; 1.P.172.244; 1.P.175.228; 1.P.175.229; 1.P.175.230; 1.P.175.231; 1.P.175.236; 1.P.175.237; 1.P.175.238; 1.P.175.239; 1.P.175.154; 1.P.175.157; 1.P.175.166; 1.P.175.169; 1.P.175.172; 1.P.175.175; 1.P.175.240; 1.P.175.244; 1.P.240.228; 1.P.240.229; 1.P.240.230; 1.P.240.231; 1.P.240.236; 1.P.240.237; 1.P.240.238; 1.P.240.239; 1.P.240.154; 1.P.240.157; 1.P.240.166; 1.P.240.169; 1.P.240.172; 1.P.240.175; 1.P.240.240; 1.P.240.244; 1.P.244.228; 1.P.244.229; 1.P.244.230; 1.P.244.231; 1.P.244.236; 1.P.244.237; 1.P.244.238; 1.P.244.239; 1.P.244.154; 1.P.244.157; 1.P.244.166; 1.P.244.169; 1.P.244.172; 1.P.244.175; 1.P.244.240; 1.P.244.244; |
| Prodrugs of 1.U |
| 1.U.228.228; 1.U.228.229; 1.U.228.230; 1.U.228.231; 1.U.228.236; 1.U.228.237; 1.U.228.238; 1.U.228.239; 1.U.228.154; 1.U.228.157; 1.U.228.166; 1.U.228.169; 1.U.228.172; 1.U.228.175; 1.U.228.240; 1.U.228.244; 1.U.229.228; 1.U.229.229; 1.U.229.230; 1.U.229.231; 1.U.229.236; 1.U.229.237; 1.U.229.238; 1.U.229.239; 1.U.229.154; |

TABLE 100-continued

| |
|---|
| 1.U.229.157; 1.U.229.166; 1.U.229.169; 1.U.229.172; 1.U.229.175; 1.U.229.240; 1.U.229.244; 1.U.230.228; 1.U.230.229; 1.U.230.230; 1.U.230.231; 1.U.230.236; 1.U.230.237; 1.U.230.238; 1.U.230.239; 1.U.230.154; 1.U.230.157; 1.U.230.166; 1.U.230.169; 1.U.230.172; 1.U.230.175; 1.U.230.240; 1.U.230.244; 1.U.231.228; 1.U.231.229; 1.U.231.230; 1.U.231.231; 1.U.231.236; 1.U.231.237; 1.U.231.238; 1.U.231.239; 1.U.231.154; 1.U.231.157; 1.U.231.166; 1.U.231.169; 1.U.231.172; 1.U.231.175; 1.U.231.240; 1.U.231.244; 1.U.236.228; 1.U.236.229; 1.U.236.230; 1.U.236.231; 1.U.236.236; 1.U.236.237; 1.U.236.238; 1.U.236.239; 1.U.236.154; 1.U.236.157; 1.U.236.166; 1.U.236.169; 1.U.236.172; 1.U.236.175; 1.U.236.240; 1.U.236.244; 1.U.237.228; 1.U.237.229; 1.U.237.230; 1.U.237.231; 1.U.237.236; 1.U.237.237; 1.U.237.238; 1.U.237.239; 1.U.237.154; 1.U.237.157; 1.U.237.166; 1.U.237.169; 1.U.237.172; 1.U.237.175; 1.U.237.240; 1.U.237.244; 1.U.238.228; 1.U.238.229; 1.U.238.230; 1.U.238.231; 1.U.238.236; 1.U.238.237; 1.U.238.238; 1.U.238.239; 1.U.238.154; 1.U.238.157; 1.U.238.166; 1.U.238.169; 1.U.238.172; 1.U.238.175; 1.U.238.240; 1.U.238.244; 1.U.239.228; 1.U.239.229; 1.U.239.230; 1.U.239.231; 1.U.239.236; 1.U.239.237; 1.U.239.238; 1.U.239.239; 1.U.239.154; 1.U.239.157; 1.U.239.166; 1.U.239.169; 1.U.239.172; 1.U.239.175; 1.U.239.240; 1.U.239.244; 1.U.154.228; 1.U.154.229; 1.U.154.230; 1.U.154.231; 1.U.154.236; 1.U.154.237; 1.U.154.238; 1.U.154.239; 1.U.154.154; 1.U.154.157; 1.U.154.166; 1.U.154.169; 1.U.154.172; 1.U.154.175; 1.U.154.240; 1.U.154.244; 1.U.157.228; 1.U.157.229; 1.U.157.230; 1.U.157.231; 1.U.157.236; 1.U.157.237; 1.U.157.238; 1.U.157.239; 1.U.157.154; 1.U.157.157; 1.U.157.166; 1.U.157.169; 1.U.157.172; 1.U.157.175; 1.U.157.240; 1.U.157.244; 1.U.166.228; 1.U.166.229; 1.U.166.230; 1.U.166.231; 1.U.166.236; 1.U.166.237; 1.U.166.238; 1.U.166.239; 1.U.166.154; 1.U.166.157; 1.U.166.166; 1.U.166.169; 1.U.166.172; 1.U.166.175; 1.U.166.240; 1.U.166.244; 1.U.169.228; 1.U.169.229; 1.U.169.230; 1.U.169.231; 1.U.169.236; 1.U.169.237; 1.U.169.238; 1.U.169.239; 1.U.169.154; 1.U.169.157; 1.U.169.166; 1.U.169.169; 1.U.169.172; 1.U.169.175; 1.U.169.240; 1.U.169.244; 1.U.172.228; 1.U.172.229; 1.U.172.230; 1.U.172.231; 1.U.172.236; 1.U.172.237; 1.U.172.238; 1.U.172.239; 1.U.172.154; 1.U.172.157; 1.U.172.166; 1.U.172.169; 1.U.172.172; 1.U.172.175; 1.U.172.240; 1.U.172.244; 1.U.175.228; 1.U.175.229; 1.U.175.230; 1.U.175.231; 1.U.175.236; 1.U.175.237; 1.U.175.238; 1.U.175.239; 1.U.175.154; 1.U.175.157; 1.U.175.166; 1.U.175.169; 1.U.175.172; 1.U.175.175; 1.U.175.240; 1.U.175.244; 1.U.240.228; 1.U.240.229; 1.U.240.230; 1.U.240.231; 1.U.240.236; 1.U.240.237; 1.U.240.238; 1.U.240.239; 1.U.240.154; 1.U.240.157; 1.U.240.166; 1.U.240.169; 1.U.240.172; 1.U.240.175; 1.U.240.240; 1.U.240.244; 1.U.244.228; 1.U.244.229; 1.U.244.230; 1.U.244.231; 1.U.244.236; 1.U.244.237; 1.U.244.238; 1.U.244.239; 1.U.244.154; 1.U.244.157; 1.U.244.166; 1.U.244.169; 1.U.244.172; 1.U.244.175; 1.U.244.240; 1.U.244.244; |
| Prodrugs of 1.W |
| 1.W.228.228; 1.W.228.229; 1.W.228.230; 1.W.228.231; 1.W.228.236; 1.W.228.237; 1.W.228.238; 1.W.228.239; 1.W.228.154; 1.W.228.157; 1.W.228.166; 1.W.228.169; 1.W.228.172; 1.W.228.175; 1.W.228.240; 1.W.228.244; 1.W.229.228; 1.W.229.229; 1.W.229.230; 1.W.229.231; 1.W.229.236; 1.W.229.237; 1.W.229.238; 1.W.229.239; 1.W.229.154; 1.W.229.157; 1.W.229.166; 1.W.229.169; 1.W.229.172; 1.W.229.175; 1.W.229.240; 1.W.229.244; 1.W.230.228; 1.W.230.229; 1.W.230.230; 1.W.230.231; 1.W.230.236; 1.W.230.237; 1.W.230.238; 1.W.230.239; 1.W.230.154; 1.W.230.157; 1.W.230.166; 1.W.230.169; 1.W.230.172; 1.W.230.175; 1.W.230.240; 1.W.230.244; 1.W.231.228; 1.W.231.229; 1.W.231.230; 1.W.231.231; 1.W.231.236; 1.W.231.237; 1.W.231.238; 1.W.231.239; 1.W.231.154; 1.W.231.157; 1.W.231.166; 1.W.231.169; 1.W.231.172; 1.W.231.175; 1.W.231.240; 1.W.231.244; 1.W.236.228; 1.W.236.229; 1.W.236.230; 1.W.236.231; 1.W.236.236; 1.W.236.237; 1.W.236.238; 1.W.236.239; 1.W.236.154; 1.W.236.157; 1.W.236.166; 1.W.236.169; 1.W.236.172; 1.W.236.175; 1.W.236.240; 1.W.236.244; 1.W.237.228; 1.W.237.229; 1.W.237.230; 1.W.237.231; 1.W.237.236; 1.W.237.237; 1.W.237.238; 1.W.237.239; 1.W.237.154; 1.W.237.157; 1.W.237.166; 1.W.237.169; 1.W.237.172; 1.W.237.175; 1.W.237.240; 1.W.237.244; 1.W.238.228; 1.W.238.229; 1.W.238.230; 1.W.238.231; 1.W.238.236; 1.W.238.237; 1.W.238.238; 1.W.238.239; 1.W.238.154; 1.W.238.157; 1.W.238.166; 1.W.238.169; 1.W.238.172; 1.W.238.175; 1.W.238.240; 1.W.238.244; 1.W.239.228; 1.W.239.229; 1.W.239.230; 1.W.239.231; 1.W.239.236; 1.W.239.237; 1.W.239.238; 1.W.239.239; 1.W.239.154; 1.W.239.157; 1.W.239.166; 1.W.239.169; 1.W.239.172; 1.W.239.175; 1.W.239.240; 1.W.239.244; 1.W.154.228; 1.W.154.229; 1.W.154.230; 1.W.154.231; 1.W.154.236; 1.W.154.237; 1.W.154.238; 1.W.154.239; 1.W.154.154; 1.W.154.157; 1.W.154.166; 1.W.154.169; 1.W.154.172; 1.W.154.175; 1.W.154.240; 1.W.154.244; 1.W.157.228; 1.W.157.229; 1.W.157.230; 1.W.157.231; 1.W.157.236; 1.W.157.237; 1.W.157.238; 1.W.157.239; 1.W.157.154; 1.W.157.157; 1.W.157.166; |

TABLE 100-continued

| |
|---|
| 1.W.157.169; 1.W.157.172; 1.W.157.175; 1.W.157.240; 1.W.157.244; 1.W.166.228; 1.W.166.229; 1.W.166.230; 1.W.166.231; 1.W.166.236; 1.W.166.237; 1.W.166.238; 1.W.166.239; 1.W.166.154; 1.W.166.157; 1.W.166.166; 1.W.166.169; 1.W.166.172; 1.W.166.175; 1.W.166.240; 1.W.166.244; 1.W.169.228; 1.W.169.229; 1.W.169.230; 1.W.169.231; 1.W.169.236; 1.W.169.237; 1.W.169.238; 1.W.169.239; 1.W.169.154; 1.W.169.157; 1.W.169.166; 1.W.169.169; 1.W.169.172; 1.W.169.175; 1.W.169.240; 1.W.169.244; 1.W.172.228; 1.W.172.229; 1.W.172.230; 1.W.172.231; 1.W.172.236; 1.W.172.237; 1.W.172.238; 1.W.172.239; 1.W.172.154; 1.W.172.157; 1.W.172.166; 1.W.172.169; 1.W.172.172; 1.W.172.175; 1.W.172.240; 1.W.172.244; 1.W.175.228; 1.W.175.229; 1.W.175.230; 1.W.175.231; 1.W.175.236; 1.W.175.237; 1.W.175.238; 1.W.175.239; 1.W.175.154; 1.W.175.157; 1.W.175.166; 1.W.175.169; 1.W.175.172; 1.W.175.175; 1.W.175.240; 1.W.175.244; 1.W.240.228; 1.W.240.229; 1.W.240.230; 1.W.240.231; 1.W.240.236; 1.W.240.237; 1.W.240.238; 1.W.240.239; 1.W.240.154; 1.W.240.157; 1.W.240.166; 1.W.240.169; 1.W.240.172; 1.W.240.175; 1.W.240.240; 1.W.240.244; 1.W.244.228; 1.W.244.229; 1.W.244.230; 1.W.244.231; 1.W.244.236; 1.W.244.237; 1.W.244.238; 1.W.244.239; 1.W.244.154; 1.W.244.157; 1.W.244.166; 1.W.244.169; 1.W.244.172; 1.W.244.175; 1.W.244.240; 1.W.244.244; |
| Prodrugs of 1.Y |
| 1.Y.228.228; 1.Y.228.229; 1.Y.228.230; 1.Y.228.231; 1.Y.228.236; 1.Y.228.237; 1.Y.228.238; 1.Y.228.239; 1.Y.228.154; 1.Y.228.157; 1.Y.228.166; 1.Y.228.169; 1.Y.228.172; 1.Y.228.175; 1.Y.228.240; 1.Y.228.244; 1.Y.229.228; 1.Y.229.229; 1.Y.229.230; 1.Y.229.231; 1.Y.229.236; 1.Y.229.237; 1.Y.229.238; 1.Y.229.239; 1.Y.229.154; 1.Y.229.157; 1.Y.229.166; 1.Y.229.169; 1.Y.229.172; 1.Y.229.175; 1.Y.229.240; 1.Y.229.244; 1.Y.230.228; 1.Y.230.229; 1.Y.230.230; 1.Y.230.231; 1.Y.230.236; 1.Y.230.237; 1.Y.230.238; 1.Y.230.239; 1.Y.230.154; 1.Y.230.157; 1.Y.230.166; 1.Y.230.169; 1.Y.230.172; 1.Y.230.175; 1.Y.230.240; 1.Y.230.244; 1.Y.231.228; 1.Y.231.229; 1.Y.231.230; 1.Y.231.231; 1.Y.231.236; 1.Y.231.237; 1.Y.231.238; 1.Y.231.239; 1.Y.231.154; 1.Y.231.157; 1.Y.231.166; 1.Y.231.169; 1.Y.231.172; 1.Y.231.175; 1.Y.231.240; 1.Y.231.244; 1.Y.236.228; 1.Y.236.229; 1.Y.236.230; 1.Y.236.231; 1.Y.236.236; 1.Y.236.237; 1.Y.236.238; 1.Y.236.239; 1.Y.236.154; 1.Y.236.157; 1.Y.236.166; 1.Y.236.169; 1.Y.236.172; 1.Y.236.175; 1.Y.236.240; 1.Y.236.244; 1.Y.237.228; 1.Y.237.229; 1.Y.237.230; 1.Y.237.231; 1.Y.237.236; 1.Y.237.237; 1.Y.237.238; 1.Y.237.239; 1.Y.237.154; 1.Y.237.157; 1.Y.237.166; 1.Y.237.169; 1.Y.237.172; 1.Y.237.175; 1.Y.237.240; 1.Y.237.244; 1.Y.238.228; 1.Y.238.229; 1.Y.238.230; 1.Y.238.231; 1.Y.238.236; 1.Y.238.237; 1.Y.238.238; 1.Y.238.239; 1.Y.238.154; 1.Y.238.157; 1.Y.238.166; 1.Y.238.169; 1.Y.238.172; 1.Y.238.175; 1.Y.238.240; 1.Y.238.244; 1.Y.239.228; 1.Y.239.229; 1.Y.239.230; 1.Y.239.231; 1.Y.239.236; 1.Y.239.237; 1.Y.239.238; 1.Y.239.239; 1.Y.239.154; 1.Y.239.157; 1.Y.239.166; 1.Y.239.169; 1.Y.239.172; 1.Y.239.175; 1.Y.239.240; 1.Y.239.244; 1.Y.154.228; 1.Y.154.229; 1.Y.154.230; 1.Y.154.231; 1.Y.154.236; 1.Y.154.237; 1.Y.154.238; 1.Y.154.239; 1.Y.154.154; 1.Y.154.157; 1.Y.154.166; 1.Y.154.169; 1.Y.154.172; 1.Y.154.175; 1.Y.154.240; 1.Y.154.244; 1.Y.157.228; 1.Y.157.229; 1.Y.157.230; 1.Y.157.231; 1.Y.157.236; 1.Y.157.237; 1.Y.157.238; 1.Y.157.239; 1.Y.157.154; 1.Y.157.157; 1.Y.157.166; 1.Y.157.169; 1.Y.157.172; 1.Y.157.175; 1.Y.157.240; 1.Y.157.244; 1.Y.166.228; 1.Y.166.229; 1.Y.166.230; 1.Y.166.231; 1.Y.166.236; 1.Y.166.237; 1.Y.166.238; 1.Y.166.239; 1.Y.166.154; 1.Y.166.157; 1.Y.166.166; 1.Y.166.169; 1.Y.166.172; 1.Y.166.175; 1.Y.166.240; 1.Y.166.244; 1.Y.169.228; 1.Y.169.229; 1.Y.169.230; 1.Y.169.231; 1.Y.169.236; 1.Y.169.237; 1.Y.169.238; 1.Y.169.239; 1.Y.169.154; 1.Y.169.157; 1.Y.169.166; 1.Y.169.169; 1.Y.169.172; 1.Y.169.175; 1.Y.169.240; 1.Y.169.244; 1.Y.172.228; 1.Y.172.229; 1.Y.172.230; 1.Y.172.231; 1.Y.172.236; 1.Y.172.237; 1.Y.172.238; 1.Y.172.239; 1.Y.172.154; 1.Y.172.157; 1.Y.172.166; 1.Y.172.169; 1.Y.172.172; 1.Y.172.175; 1.Y.172.240; 1.Y.172.244; 1.Y.175.228; 1.Y.175.229; 1.Y.175.230; 1.Y.175.231; 1.Y.175.236; 1.Y.175.237; 1.Y.175.238; 1.Y.175.239; 1.Y.175.154; 1.Y.175.157; 1.Y.175.166; 1.Y.175.169; 1.Y.175.172; 1.Y.175.175; 1.Y.175.240; 1.Y.175.244; 1.Y.240.228; 1.Y.240.229; 1.Y.240.230; 1.Y.240.231; 1.Y.240.236; 1.Y.240.237; 1.Y.240.238; 1.Y.240.239; 1.Y.240.154; 1.Y.240.157; 1.Y.240.166; 1.Y.240.169; 1.Y.240.172; 1.Y.240.175; 1.Y.240.240; 1.Y.240.244; 1.Y.244.228; 1.Y.244.229; 1.Y.244.230; 1.Y.244.231; 1.Y.244.236; 1.Y.244.237; 1.Y.244.238; 1.Y.244.239; 1.Y.244.154; 1.Y.244.157; 1.Y.244.166; 1.Y.244.169; 1.Y.244.172; 1.Y.244.175; 1.Y.244.240; 1.Y.244.244; |
| Prodrugs of 2.B |
| 2.B.228.228; 2.B.228.229; 2.B.228.230; 2.B.228.231; 2.B.228.236; 2.B.228.237; 2.B.228.238; 2.B.228.239; 2.B.228.154; 2.B.228.157; 2.B.228.166; 2.B.228.169; 2.B.228.172; 2.B.228.175; 2.B.228.240; 2.B.228.244; 2.B.229.228; 2.B.229.229; 2.B.229.230; 2.B.229.231; 2.B.229.236; 2.B.229.237; 2.B.229.238; 2.B.229.239; 2.B.229.154; 2.B.229.157; 2.B.229.166; 2.B.229.169; 2.B.229.172; 2.B.229.175; 2.B.229.240; 2.B.229.244; 2.B.230.228; 2.B.230.229; 2.B.230.230; 2.B.230.231; 2.B.230.236; 2.B.230.237; 2.B.230.238; 2.B.230.239; 2.B.230.154; 2.B.230.157; 2.B.230.166; 2.B.230.169; 2.B.230.172; 2.B.230.175; 2.B.230.240; 2.B.230.244; 2.B.231.228; 2.B.231.229; 2.B.231.230; 2.B.231.231; 2.B.231.236; 2.B.231.237; 2.B.231.238; 2.B.231.239; 2.B.231.154; 2.B.231.157; 2.B.231.166; 2.B.231.169; 2.B.231.172; 2.B.231.175; 2.B.231.240; 2.B.231.244; 2.B.236.228; 2.B.236.229; 2.B.236.230; 2.B.236.231; 2.B.236.236; 2.B.236.237; 2.B.236.238; 2.B.236.239; 2.B.236.154; 2.B.236.157; 2.B.236.166; 2.B.236.169; 2.B.236.172; |

TABLE 100-continued

| |
|---|
| 2.B.236.175; 2.B.236.240; 2.B.236.244; 2.B.237.228; 2.B.237.229; 2.B.237.230; 2.B.237.231; 2.B.237.236; 2.B.237.237; 2.B.237.238; 2.B.237.239; 2.B.237.154; 2.B.237.157; 2.B.237.166; 2.B.237.169; 2.B.237.172; 2.B.237.175; 2.B.237.240; 2.B.237.244; 2.B.238.228; 2.B.238.229; 2.B.238.230; 2.B.238.231; 2.B.238.236; 2.B.238.237; 2.B.238.238; 2.B.238.239; 2.B.238.154; 2.B.238.157; 2.B.238.166; 2.B.238.169; 2.B.238.172; 2.B.238.175; 2.B.238.240; 2.B.238.244; 2.B.239.228; 2.B.239.229; 2.B.239.230; 2.B.239.231; 2.B.239.236; 2.B.239.237; 2.B.239.238; 2.B.239.239; 2.B.239.154; 2.B.239.157; 2.B.239.166; 2.B.239.169; 2.B.239.172; 2.B.239.175; 2.B.239.240; 2.B.239.244; 2.B.154.228; 2.B.154.229; 2.B.154.230; 2.B.154.231; 2.B.154.236; 2.B.154.237; 2.B.154.238; 2.B.154.239; 2.B.154.154; 2.B.154.157; 2.B.154.166; 2.B.154.169; 2.B.154.172; 2.B.154.175; 2.B.154.240; 2.B.154.244; 2.B.157.228; 2.B.157.229; 2.B.157.230; 2.B.157.231; 2.B.157.236; 2.B.157.237; 2.B.157.238; 2.B.157.239; 2.B.157.154; 2.B.157.157; 2.B.157.166; 2.B.157.169; 2.B.157.172; 2.B.157.175; 2.B.157.240; 2.B.157.244; 2.B.166.228; 2.B.166.229; 2.B.166.230; 2.B.166.231; 2.B.166.236; 2.B.166.237; 2.B.166.238; 2.B.166.239; 2.B.166.154; 2.B.166.157; 2.B.166.166; 2.B.166.169; 2.B.166.172; 2.B.166.175; 2.B.166.240; 2.B.166.244; 2.B.169.228; 2.B.169.229; 2.B.169.230; 2.B.169.231; 2.B.169.236; 2.B.169.237; 2.B.169.238; 2.B.169.239; 2.B.169.154; 2.B.169.157; 2.B.169.166; 2.B.169.169; 2.B.169.172; 2.B.169.175; 2.B.169.240; 2.B.169.244; 2.B.172.228; 2.B.172.229; 2.B.172.230; 2.B.172.231; 2.B.172.236; 2.B.172.237; 2.B.172.238; 2.B.172.239; 2.B.172.154; 2.B.172.157; 2.B.172.166; 2.B.172.169; 2.B.172.172; 2.B.172.175; 2.B.172.240; 2.B.172.244; 2.B.175.228; 2.B.175.229; 2.B.175.230; 2.B.175.231; 2.B.175.236; 2.B.175.237; 2.B.175.238; 2.B.175.239; 2.B.175.154; 2.B.175.157; 2.B.175.166; 2.B.175.169; 2.B.175.172; 2.B.175.175; 2.B.175.240; 2.B.175.244; 2.B.240.228; 2.B.240.229; 2.B.240.230; 2.B.240.231; 2.B.240.236; 2.B.240.237; 2.B.240.238; 2.B.240.239; 2.B.240.154; 2.B.240.157; 2.B.240.166; 2.B.240.169; 2.B.240.172; 2.B.240.175; 2.B.240.240; 2.B.240.244; 2.B.244.228; 2.B.244.229; 2.B.244.230; 2.B.244.231; 2.B.244.236; 2.B.244.237; 2.B.244.238; 2.B.244.239; 2.B.244.154; 2.B.244.157; 2.B.244.166; 2.B.244.169; 2.B.244.172; 2.B.244.175; 2.B.244.240; 2.B.244.244; |
| Prodrugs of 2.D |
| 2.D.228.228; 2.D.228.229; 2.D.228.230; 2.D.228.231; 2.D.228.236; 2.D.228.237; 2.D.228.238; 2.D.228.239; 2.D.228.154; 2.D.228.157; 2.D.228.166; 2.D.228.169; 2.D.228.172; 2.D.228.175; 2.D.228.240; 2.D.228.244; 2.D.229.228; 2.D.229.229; 2.D.229.230; 2.D.229.231; 2.D.229.236; 2.D.229.237; 2.D.229.238; 2.D.229.239; 2.D.229.154; 2.D.229.157; 2.D.229.166; 2.D.229.169; 2.D.229.172; 2.D.229.175; 2.D.229.240; 2.D.229.244; 2.D.230.228; 2.D.230.229; 2.D.230.230; 2.D.230.231; 2.D.230.236; 2.D.230.237; 2.D.230.238; 2.D.230.239; 2.D.230.154; 2.D.230.157; 2.D.230.166; 2.D.230.169; 2.D.230.172; 2.D.230.175; 2.D.230.240; 2.D.230.244; 2.D.231.228; 2.D.231.229; 2.D.231.230; 2.D.231.231; 2.D.231.236; 2.D.231.237; 2.D.231.238; 2.D.231.239; 2.D.231.154; 2.D.231.157; 2.D.231.166; 2.D.231.169; 2.D.231.172; 2.D.231.175; 2.D.231.240; 2.D.231.244; 2.D.236.228; 2.D.236.229; 2.D.236.230; 2.D.236.231; 2.D.236.236; 2.D.236.237; 2.D.236.238; 2.D.236.239; 2.D.236.154; 2.D.236.157; 2.D.236.166; 2.D.236.169; 2.D.236.172; 2.D.236.175; 2.D.236.240; 2.D.236.244; 2.D.237.228; 2.D.237.229; 2.D.237.230; 2.D.237.231; 2.D.237.236; 2.D.237.237; 2.D.237.238; 2.D.237.239; 2.D.237.154; 2.D.237.157; 2.D.237.166; 2.D.237.169; 2.D.237.172; 2.D.237.175; 2.D.237.240; 2.D.237.244; 2.D.238.228; 2.D.238.229; 2.D.238.230; 2.D.238.231; 2.D.238.236; 2.D.238.237; 2.D.238.238; 2.D.238.239; 2.D.238.154; 2.D.238.157; 2.D.238.166; 2.D.238.169; 2.D.238.172; 2.D.238.175; 2.D.238.240; 2.D.238.244; 2.D.239.228; 2.D.239.229; 2.D.239.230; 2.D.239.231; 2.D.239.236; 2.D.239.237; 2.D.239.238; 2.D.239.239; 2.D.239.154; 2.D.239.157; 2.D.239.166; 2.D.239.169; 2.D.239.172; 2.D.239.175; 2.D.239.240; 2.D.239.244; 2.D.154.228; 2.D.154.229; 2.D.154.230; 2.D.154.231; 2.D.154.236; 2.D.154.237; 2.D.154.238; 2.D.154.239; 2.D.154.154; 2.D.154.157; 2.D.154.166; 2.D.154.169; 2.D.154.172; 2.D.154.175; 2.D.154.240; 2.D.154.244; 2.D.157.228; 2.D.157.229; 2.D.157.230; 2.D.157.231; 2.D.157.236; 2.D.157.237; 2.D.157.238; 2.D.157.239; 2.D.157.154; 2.D.157.157; 2.D.157.166; 2.D.157.169; 2.D.157.172; 2.D.157.175; 2.D.157.240; 2.D.157.244; 2.D.166.228; 2.D.166.229; 2.D.166.230; 2.D.166.231; 2.D.166.236; 2.D.166.237; 2.D.166.238; 2.D.166.239; 2.D.166.154; 2.D.166.157; 2.D.166.166; 2.D.166.169; 2.D.166.172; 2.D.166.175; 2.D.166.240; 2.D.166.244; 2.D.169.228; 2.D.169.229; 2.D.169.230; 2.D.169.231; 2.D.169.236; 2.D.169.237; 2.D.169.238; 2.D.169.239; 2.D.169.154; 2.D.169.157; 2.D.169.166; 2.D.169.169; 2.D.169.172; 2.D.169.175; 2.D.169.240; 2.D.169.244; 2.D.172.228; 2.D.172.229; 2.D.172.230; 2.D.172.231; 2.D.172.236; 2.D.172.237; 2.D.172.238; 2.D.172.239; 2.D.172.154; 2.D.172.157; 2.D.172.166; 2.D.172.169; 2.D.172.172; 2.D.172.175; 2.D.172.240; 2.D.172.244; 2.D.175.228; 2.D.175.229; 2.D.175.230; 2.D.175.231; 2.D.175.236; 2.D.175.237; 2.D.175.238; 2.D.175.239; 2.D.175.154; 2.D.175.157; 2.D.175.166; 2.D.175.169; 2.D.175.172; 2.D.175.175; 2.D.175.240; 2.D.175.244; 2.D.240.228; 2.D.240.229; 2.D.240.230; 2.D.240.231; 2.D.240.236; 2.D.240.237; 2.D.240.238; 2.D.240.239; 2.D.240.154; 2.D.240.157; 2.D.240.166; 2.D.240.169; 2.D.240.172; 2.D.240.175; 2.D.240.240; 2.D.240.244; |

TABLE 100-continued

| |
|---|
| 2.D.244.228; 2.D.244.229; 2.D.244.230; 2.D.244.231; 2.D.244.236; 2.D.244.237; 2.D.244.238; 2.D.244.239; 2.D.244.154; 2.D.244.157; 2.D.244.166; 2.D.244.169; 2.D.244.172; 2.D.244.175; 2.D.244.240; 2.D.244.244; |
| Prodrugs of 2.E |
| 2.E.228.228; 2.E.228.229; 2.E.228.230; 2.E.228.231; 2.E.228.236; 2.E.228.237; 2.E.228.238; 2.E.228.239; 2.E.228.154; 2.E.228.157; 2.E.228.166; 2.E.228.169; 2.E.228.172; 2.E.228.175; 2.E.228.240; 2.E.228.244; 2.E.229.228; 2.E.229.229; 2.E.229.230; 2.E.229.231; 2.E.229.236; 2.E.229.237; 2.E.229.238; 2.E.229.239; 2.E.229.154; 2.E.229.157; 2.E.229.166; 2.E.229.169; 2.E.229.172; 2.E.229.175; 2.E.229.240; 2.E.229.244; 2.E.230.228; 2.E.230.229; 2.E.230.230; 2.E.230.231; 2.E.230.236; 2.E.230.237; 2.E.230.238; 2.E.230.239; 2.E.230.154; 2.E.230.157; 2.E.230.166; 2.E.230.169; 2.E.230.172; 2.E.230.175; 2.E.230.240; 2.E.230.244; 2.E.231.228; 2.E.231.229; 2.E.231.230; 2.E.231.231; 2.E.231.236; 2.E.231.237; 2.E.231.238; 2.E.231.239; 2.E.231.154; 2.E.231.157; 2.E.231.166; 2.E.231.169; 2.E.231.172; 2.E.231.175; 2.E.231.240; 2.E.231.244; 2.E.236.228; 2.E.236.229; 2.E.236.230; 2.E.236.231; 2.E.236.236; 2.E.236.237; 2.E.236.238; 2.E.236.239; 2.E.236.154; 2.E.236.157; 2.E.236.166; 2.E.236.169; 2.E.236.172; 2.E.236.175; 2.E.236.240; 2.E.236.244; 2.E.237.228; 2.E.237.229; 2.E.237.230; 2.E.237.231; 2.E.237.236; 2.E.237.237; 2.E.237.238; 2.E.237.239; 2.E.237.154; 2.E.237.157; 2.E.237.166; 2.E.237.169; 2.E.237.172; 2.E.237.175; 2.E.237.240; 2.E.237.244; 2.E.238.228; 2.E.238.229; 2.E.238.230; 2.E.238.231; 2.E.238.236; 2.E.238.237; 2.E.238.238; 2.E.238.239; 2.E.238.154; 2.E.238.157; 2.E.238.166; 2.E.238.169; 2.E.238.172; 2.E.238.175; 2.E.238.240; 2.E.238.244; 2.E.239.228; 2.E.239.229; 2.E.239.230; 2.E.239.231; 2.E.239.236; 2.E.239.237; 2.E.239.238; 2.E.239.239; 2.E.239.154; 2.E.239.157; 2.E.239.166; 2.E.239.169; 2.E.239.172; 2.E.239.175; 2.E.239.240; 2.E.239.244; 2.E.154.228; 2.E.154.229; 2.E.154.230; 2.E.154.231; 2.E.154.236; 2.E.154.237; 2.E.154.238; 2.E.154.239; 2.E.154.154; 2.E.154.157; 2.E.154.166; 2.E.154.169; 2.E.154.172; 2.E.154.175; 2.E.154.240; 2.E.154.244; 2.E.157.228; 2.E.157.229; 2.E.157.230; 2.E.157.231; 2.E.157.236; 2.E.157.237; 2.E.157.238; 2.E.157.239; 2.E.157.154; 2.E.157.157; 2.E.157.166; 2.E.157.169; 2.E.157.172; 2.E.157.175; 2.E.157.240; 2.E.157.244; 2.E.166.228; 2.E.166.229; 2.E.166.230; 2.E.166.231; 2.E.166.236; 2.E.166.237; 2.E.166.238; 2.E.166.239; 2.E.166.154; 2.E.166.157; 2.E.166.166; 2.E.166.169; 2.E.166.172; 2.E.166.175; 2.E.166.240; 2.E.166.244; 2.E.169.228; 2.E.169.229; 2.E.169.230; 2.E.169.231; 2.E.169.236; 2.E.169.237; 2.E.169.238; 2.E.169.239; 2.E.169.154; 2.E.169.157; 2.E.169.166; 2.E.169.169; 2.E.169.172; 2.E.169.175; 2.E.169.240; 2.E.169.244; 2.E.172.228; 2.E.172.229; 2.E.172.230; 2.E.172.231; 2.E.172.236; 2.E.172.237; 2.E.172.238; 2.E.172.239; 2.E.172.154; 2.E.172.157; 2.E.172.166; 2.E.172.169; 2.E.172.172; 2.E.172.175; 2.E.172.240; 2.E.172.244; 2.E.175.228; 2.E.175.229; 2.E.175.230; 2.E.175.231; 2.E.175.236; 2.E.175.237; 2.E.175.238; 2.E.175.239; 2.E.175.154; 2.E.175.157; 2.E.175.166; 2.E.175.169; 2.E.175.172; 2.E.175.175; 2.E.175.240; 2.E.175.244; 2.E.240.228; 2.E.240.229; 2.E.240.230; 2.E.240.231; 2.E.240.236; 2.E.240.237; 2.E.240.238; 2.E.240.239; 2.E.240.154; 2.E.240.157; 2.E.240.166; 2.E.240.169; 2.E.240.172; 2.E.240.175; 2.E.240.240; 2.E.240.244; 2.E.244.228; 2.E.244.229; 2.E.244.230; 2.E.244.231; 2.E.244.236; 2.E.244.237; 2.E.244.238; 2.E.244.239; 2.E.244.154; 2.E.244.157; 2.E.244.166; 2.E.244.169; 2.E.244.172; 2.E.244.175; 2.E.244.240; 2.E.244.244; |
| Prodrugs of 2.G |
| 2.G.228.228; 2.G.228.229; 2.G.228.230; 2.G.228.231; 2.G.228.236; 2.G.228.237; 2.G.228.238; 2.G.228.239; 2.G.228.154; 2.G.228.157; 2.G.228.166; 2.G.228.169; 2.G.228.172; 2.G.228.175; 2.G.228.240; 2.G.228.244; 2.G.229.228; 2.G.229.229; 2.G.229.230; 2.G.229.231; 2.G.229.236; 2.G.229.237; 2.G.229.238; 2.G.229.239; 2.G.229.154; 2.G.229.157; 2.G.229.166; 2.G.229.169; 2.G.229.172; 2.G.229.175; 2.G.229.240; 2.G.229.244; 2.G.230.228; 2.G.230.229; 2.G.230.230; 2.G.230.231; 2.G.230.236; 2.G.230.237; 2.G.230.238; 2.G.230.239; 2.G.230.154; 2.G.230.157; 2.G.230.166; 2.G.230.169; 2.G.230.172; 2.G.230.175; 2.G.230.240; 2.G.230.244; 2.G.231.228; 2.G.231.229; 2.G.231.230; 2.G.231.231; 2.G.231.236; 2.G.231.237; 2.G.231.238; 2.G.231.239; 2.G.231.154; 2.G.231.157; 2.G.231.166; 2.G.231.169; 2.G.231.172; 2.G.231.175; 2.G.231.240; 2.G.231.244; 2.G.236.228; 2.G.236.229; 2.G.236.230; 2.G.236.231; 2.G.236.236; 2.G.236.237; 2.G.236.238; 2.G.236.239; 2.G.236.154; 2.G.236.157; 2.G.236.166; 2.G.236.169; 2.G.236.172; 2.G.236.175; 2.G.236.240; 2.G.236.244; 2.G.237.228; 2.G.237.229; 2.G.237.230; 2.G.237.231; 2.G.237.236; 2.G.237.237; 2.G.237.238; 2.G.237.239; 2.G.237.154; 2.G.237.157; 2.G.237.166; 2.G.237.169; 2.G.237.172; 2.G.237.175; 2.G.237.240; 2.G.237.244; 2.G.238.228; 2.G.238.229; 2.G.238.230; 2.G.238.231; 2.G.238.236; 2.G.238.237; 2.G.238.238; 2.G.238.239; 2.G.238.154; 2.G.238.157; 2.G.238.166; 2.G.238.169; 2.G.238.172; 2.G.238.175; 2.G.238.240; 2.G.238.244; 2.G.239.228; 2.G.239.229; 2.G.239.230; 2.G.239.231; 2.G.239.236; 2.G.239.237; 2.G.239.238; 2.G.239.239; 2.G.239.154; 2.G.239.157; 2.G.239.166; 2.G.239.169; 2.G.239.172; 2.G.239.175; 2.G.239.240; 2.G.239.244; 2.G.154.228; 2.G.154.229; 2.G.154.230; 2.G.154.231; 2.G.154.236; 2.G.154.237; 2.G.154.238; 2.G.154.239; 2.G.154.154; 2.G.154.157; 2.G.154.166; 2.G.154.169; 2.G.154.172; 2.G.154.175; 2.G.154.240; 2.G.154.244; 2.G.157.228; 2.G.157.229; 2.G.157.230; 2.G.157.231; 2.G.157.236; 2.G.157.237; |

TABLE 100-continued

| |
|---|
| 2.G.157.238; 2.G.157.239; 2.G.157.154; 2.G.157.157; 2.G.157.166; |
| 2.G.157.169; 2.G.157.172; 2.G.157.175; 2.G.157.240; 2.G.157.244; |
| 2.G.166.228; 2.G.166.229; 2.G.166.230; 2.G.166.231; 2.G.166.236; |
| 2.G.166.237; 2.G.166.238; 2.G.166.239; 2.G.166.154; 2.G.166.157; |
| 2.G.166.166; 2.G.166.169; 2.G.166.172; 2.G.166.175; 2.G.166.240; |
| 2.G.166.244; 2.G.169.228; 2.G.169.229; 2.G.169.230; 2.G.169.231; |
| 2.G.169.236; 2.G.169.237; 2.G.169.238; 2.G.169.239; 2.G.169.154; |
| 2.G.169.157; 2.G.169.166; 2.G.169.169; 2.G.169.172; 2.G.169.175; |
| 2.G.169.240; 2.G.169.244; 2.G.172.228; 2.G.172.229; 2.G.172.230; |
| 2.G.172.231; 2.G.172.236; 2.G.172.237; 2.G.172.238; 2.G.172.239; |
| 2.G.172.154; 2.G.172.157; 2.G.172.166; 2.G.172.169; 2.G.172.172; |
| 2.G.172.175; 2.G.172.240; 2.G.172.244; 2.G.175.228; 2.G.175.229; |
| 2.G.175.230; 2.G.175.231; 2.G.175.236; 2.G.175.237; 2.G.175.238; |
| 2.G.175.239; 2.G.175.154; 2.G.175.157; 2.G.175.166; 2.G.175.169; |
| 2.G.175.172; 2.G.175.175; 2.G.175.240; 2.G.175.244; 2.G.240.228; |
| 2.G.240.229; 2.G.240.230; 2.G.240.231; 2.G.240.236; 2.G.240.237; |
| 2.G.240.238; 2.G.240.239; 2.G.240.154; 2.G.240.157; 2.G.240.166; |
| 2.G.240.169; 2.G.240.172; 2.G.240.175; 2.G.240.240; 2.G.240.244; |
| 2.G.244.228; 2.G.244.229; 2.G.244.230; 2.G.244.231; 2.G.244.236; |
| 2.G.244.237; 2.G.244.238; 2.G.244.239; 2.G.244.154; 2.G.244.157; |
| 2.G.244.166; 2.G.244.169; 2.G.244.172; 2.G.244.175; 2.G.244.240; 2.G.244.244; |
| Prodrugs of 2.I |
| 2.I.228.228; 2.I.228.229; 2.I.228.230; 2.I.228.231; 2.I.228.236; 2.I.228.237; |
| 2.I.228.238; 2.I.228.239; 2.I.228.154; 2.I.228.157; 2.I.228.166; 2.I.228.169; |
| 2.I.228.172; 2.I.228.175; 2.I.228.240; 2.I.228.244; 2.I.229.228; 2.I.229.229; |
| 2.I.229.230; 2.I.229.231; 2.I.229.236; 2.I.229.237; 2.I.229.238; 2.I.229.239; |
| 2.I.229.154; 2.I.229.157; 2.I.229.166; 2.I.229.169; 2.I.229.172; 2.I.229.175; |
| 2.I.229.240; 2.I.229.244; 2.I.230.228; 2.I.230.229; 2.I.230.230; 2.I.230.231; |
| 2.I.230.236; 2.I.230.237; 2.I.230.238; 2.I.230.239; 2.I.230.154; 2.I.230.157; |
| 2.I.230.166; 2.I.230.169; 2.I.230.172; 2.I.230.175; 2.I.230.240; 2.I.230.244; |
| 2.I.231.228; 2.I.231.229; 2.I.231.230; 2.I.231.231; 2.I.231.236; 2.I.231.237; |
| 2.I.231.238; 2.I.231.239; 2.I.231.154; 2.I.231.157; 2.I.231.166; 2.I.231.169; |
| 2.I.231.172; 2.I.231.175; 2.I.231.240; 2.I.231.244; 2.I.236.228; 2.I.236.229; |
| 2.I.236.230; 2.I.236.231; 2.I.236.236; 2.I.236.237; 2.I.236.238; 2.I.236.239; |
| 2.I.236.154; 2.I.236.157; 2.I.236.166; 2.I.236.169; 2.I.236.172; 2.I.236.175; |
| 2.I.236.240; 2.I.236.244; 2.I.237.228; 2.I.237.229; 2.I.237.230; 2.I.237.231; |
| 2.I.237.236; 2.I.237.237; 2.I.237.238; 2.I.237.239; 2.I.237.154; 2.I.237.157; |
| 2.I.237.166; 2.I.237.169; 2.I.237.172; 2.I.237.175; 2.I.237.240; 2.I.237.244; |
| 2.I.238.228; 2.I.238.229; 2.I.238.230; 2.I.238.231; 2.I.238.236; 2.I.238.237; |
| 2.I.238.238; 2.I.238.239; 2.I.238.154; 2.I.238.157; 2.I.238.166; 2.I.238.169; |
| 2.I.238.172; 2.I.238.175; 2.I.238.240; 2.I.238.244; 2.I.239.228; 2.I.239.229; |
| 2.I.239.230; 2.I.239.231; 2.I.239.236; 2.I.239.237; 2.I.239.238; 2.I.239.239; |
| 2.I.239.154; 2.I.239.157; 2.I.239.166; 2.I.239.169; 2.I.239.172; 2.I.239.175; |
| 2.I.239.240; 2.I.239.244; 2.I.154.228; 2.I.154.229; 2.I.154.230; 2.I.154.231; |
| 2.I.154.236; 2.I.154.237; 2.I.154.238; 2.I.154.239; 2.I.154.154; 2.I.154.157; |
| 2.I.154.166; 2.I.154.169; 2.I.154.172; 2.I.154.175; 2.I.154.240; 2.I.154.244; |
| 2.I.157.228; 2.I.157.229; 2.I.157.230; 2.I.157.231; 2.I.157.236; 2.I.157.237; |
| 2.I.157.238; 2.I.157.239; 2.I.157.154; 2.I.157.157; 2.I.157.166; 2.I.157.169; |
| 2.I.157.172; 2.I.157.175; 2.I.157.240; 2.I.157.244; 2.I.166.228; 2.I.166.229; |
| 2.I.166.230; 2.I.166.231; 2.I.166.236; 2.I.166.237; 2.I.166.238; 2.I.166.239; |
| 2.I.166.154; 2.I.166.157; 2.I.166.166; 2.I.166.169; 2.I.166.172; 2.I.166.175; |
| 2.I.166.240; 2.I.166.244; 2.I.169.228; 2.I.169.229; 2.I.169.230; 2.I.169.231; |
| 2.I.169.236; 2.I.169.237; 2.I.169.238; 2.I.169.239; 2.I.169.154; 2.I.169.157; |
| 2.I.169.166; 2.I.169.169; 2.I.169.172; 2.I.169.175; 2.I.169.240; 2.I.169.244; |
| 2.I.172.228; 2.I.172.229; 2.I.172.230; 2.I.172.231; 2.I.172.236; 2.I.172.237; |
| 2.I.172.238; 2.I.172.239; 2.I.172.154; 2.I.172.157; 2.I.172.166; 2.I.172.169; |
| 2.I.172.172; 2.I.172.175; 2.I.172.240; 2.I.172.244; 2.I.175.228; 2.I.175.229; |
| 2.I.175.230; 2.I.175.231; 2.I.175.236; 2.I.175.237; 2.I.175.238; 2.I.175.239; |
| 2.I.175.154; 2.I.175.157; 2.I.175.166; 2.I.175.169; 2.I.175.172; 2.I.175.175; |
| 2.I.175.240; 2.I.175.244; 2.I.240.228; 2.I.240.229; 2.I.240.230; 2.I.240.231; |
| 2.I.240.236; 2.I.240.237; 2.I.240.238; 2.I.240.239; 2.I.240.154; 2.I.240.157; |
| 2.I.240.166; 2.I.240.169; 2.I.240.172; 2.I.240.175; 2.I.240.240; 2.I.240.244; |
| 2.I.244.228; 2.I.244.229; 2.I.244.230; 2.I.244.231; 2.I.244.236; 2.I.244.237; |
| 2.I.244.238; 2.I.244.239; 2.I.244.154; 2.I.244.157; 2.I.244.166; 2.I.244.169; |
| 2.I.244.172; 2.I.244.175; 2.I.244.240; 2.I.244.244; |
| Prodrugs of 2.J |
| 2.J.228.228; 2.J.228.229; 2.J.228.230; 2.J.228.231; 2.J.228.236; 2.J.228.237; |
| 2.J.228.238; 2.J.228.239; 2.J.228.154; 2.J.228.157; 2.J.228.166; 2.J.228.169; |
| 2.J.228.172; 2.J.228.175; 2.J.228.240; 2.J.228.244; 2.J.229.228; 2.J.229.229; |
| 2.J.229.230; 2.J.229.231; 2.J.229.236; 2.J.229.237; 2.J.229.238; 2.J.229.239; |
| 2.J.229.154; 2.J.229.157; 2.J.229.166; 2.J.229.169; 2.J.229.172; 2.J.229.175; |
| 2.J.229.240; 2.J.229.244; 2.J.230.228; 2.J.230.229; 2.J.230.230; 2.J.230.231; |
| 2.J.230.236; 2.J.230.237; 2.J.230.238; 2.J.230.239; 2.J.230.154; 2.J.230.157; |
| 2.J.230.166; 2.J.230.169; 2.J.230.172; 2.J.230.175; 2.J.230.240; 2.J.230.244; |
| 2.J.231.228; 2.J.231.229; 2.J.231.230; 2.J.231.231; 2.J.231.236; 2.J.231.237; |
| 2.J.231.238; 2.J.231.239; 2.J.231.154; 2.J.231.157; 2.J.231.166; 2.J.231.169; |
| 2.J.231.172; 2.J.231.175; 2.J.231.240; 2.J.231.244; 2.J.236.228; 2.J.236.229; |
| 2.J.236.230; 2.J.236.231; 2.J.236.236; 2.J.236.237; 2.J.236.238; 2.J.236.239; |

TABLE 100-continued

2.J.236.154; 2.J.236.157; 2.J.236.166; 2.J.236.169; 2.J.236.172; 2.J.236.175; 2.J.236.240; 2.J.236.244; 2.J.237.228; 2.J.237.229; 2.J.237.230; 2.J.237.231; 2.J.237.236; 2.J.237.237; 2.J.237.238; 2.J.237.239; 2.J.237.154; 2.J.237.157; 2.J.237.166; 2.J.237.169; 2.J.237.172; 2.J.237.175; 2.J.237.240; 2.J.237.244; 2.J.238.228; 2.J.238.229; 2.J.238.230; 2.J.238.231; 2.J.238.236; 2.J.238.237; 2.J.238.238; 2.J.238.239; 2.J.238.154; 2.J.238.157; 2.J.238.166; 2.J.238.169; 2.J.238.172; 2.J.238.175; 2.J.238.240; 2.J.238.244; 2.J.239.228; 2.J.239.229; 2.J.239.230; 2.J.239.231; 2.J.239.236; 2.J.239.237; 2.J.239.238; 2.J.239.239; 2.J.239.154; 2.J.239.157; 2.J.239.166; 2.J.239.169; 2.J.239.172; 2.J.239.175; 2.J.239.240; 2.J.239.244; 2.J.154.228; 2.J.154.229; 2.J.154.230; 2.J.154.231; 2.J.154.236; 2.J.154.237; 2.J.154.238; 2.J.154.239; 2.J.154.154; 2.J.154.157; 2.J.154.166; 2.J.154.169; 2.J.154.172; 2.J.154.175; 2.J.154.240; 2.J.154.244; 2.J.157.228; 2.J.157.229; 2.J.157.230; 2.J.157.231; 2.J.157.236; 2.J.157.237; 2.J.157.238; 2.J.157.239; 2.J.157.154; 2.J.157.157; 2.J.157.166; 2.J.157.169; 2.J.157.172; 2.J.157.175; 2.J.157.240; 2.J.157.244; 2.J.166.228; 2.J.166.229; 2.J.166.230; 2.J.166.231; 2.J.166.236; 2.J.166.237; 2.J.166.238; 2.J.166.239; 2.J.166.154; 2.J.166.157; 2.J.166.166; 2.J.166.169; 2.J.166.172; 2.J.166.175; 2.J.166.240; 2.J.166.244; 2.J.169.228; 2.J.169.229; 2.J.169.230; 2.J.169.231; 2.J.169.236; 2.J.169.237; 2.J.169.238; 2.J.169.239; 2.J.169.154; 2.J.169.157; 2.J.169.166; 2.J.169.169; 2.J.169.172; 2.J.169.175; 2.J.169.240; 2.J.169.244; 2.J.172.228; 2.J.172.229; 2.J.172.230; 2.J.172.231; 2.J.172.236; 2.J.172.237; 2.J.172.238; 2.J.172.239; 2.J.172.154; 2.J.172.157; 2.J.172.166; 2.J.172.169; 2.J.172.172; 2.J.172.175; 2.J.172.240; 2.J.172.244; 2.J.175.228; 2.J.175.229; 2.J.175.230; 2.J.175.231; 2.J.175.236; 2.J.175.237; 2.J.175.238; 2.J.175.239; 2.J.175.154; 2.J.175.157; 2.J.175.166; 2.J.175.169; 2.J.175.172; 2.J.175.175; 2.J.175.240; 2.J.175.244; 2.J.240.228; 2.J.240.229; 2.J.240.230; 2.J.240.231; 2.J.240.236; 2.J.240.237; 2.J.240.238; 2.J.240.239; 2.J.240.154; 2.J.240.157; 2.J.240.166; 2.J.240.169; 2.J.240.172; 2.J.240.175; 2.J.240.240; 2.J.240.244; 2.J.244.228; 2.J.244.229; 2.J.244.230; 2.J.244.231; 2.J.244.236; 2.J.244.237; 2.J.244.238; 2.J.244.239; 2.J.244.154; 2.J.244.157; 2.J.244.166; 2.J.244.169; 2.J.244.172; 2.J.244.175; 2.J.244.240; 2.J.244.244;

Prodrugs of 2.L

2.L.228.228; 2.L.228.229; 2.L.228.230; 2.L.228.231; 2.L.228.236; 2.L.228.237; 2.L.228.238; 2.L.228.239; 2.L.228.154; 2.L.228.157; 2.L.228.166; 2.L.228.169; 2.L.228.172; 2.L.228.175; 2.L.228.240; 2.L.228.244; 2.L.229.228; 2.L.229.229; 2.L.229.230; 2.L.229.231; 2.L.229.236; 2.L.229.237; 2.L.229.238; 2.L.229.239; 2.L.229.154; 2.L.229.157; 2.L.229.166; 2.L.229.169; 2.L.229.172; 2.L.229.175; 2.L.229.240; 2.L.229.244; 2.L.230.228; 2.L.230.229; 2.L.230.230; 2.L.230.231; 2.L.230.236; 2.L.230.237; 2.L.230.238; 2.L.230.239; 2.L.230.154; 2.L.230.157; 2.L.230.166; 2.L.230.169; 2.L.230.172; 2.L.230.175; 2.L.230.240; 2.L.230.244; 2.L.231.228; 2.L.231.229; 2.L.231.230; 2.L.231.231; 2.L.231.236; 2.L.231.237; 2.L.231.238; 2.L.231.239; 2.L.231.154; 2.L.231.157; 2.L.231.166; 2.L.231.169; 2.L.231.172; 2.L.231.175; 2.L.231.240; 2.L.231.244; 2.L.236.228; 2.L.236.229; 2.L.236.230; 2.L.236.231; 2.L.236.236; 2.L.236.237; 2.L.236.238; 2.L.236.239; 2.L.236.154; 2.L.236.157; 2.L.236.166; 2.L.236.169; 2.L.236.172; 2.L.236.175; 2.L.236.240; 2.L.236.244; 2.L.237.228; 2.L.237.229; 2.L.237.230; 2.L.237.231; 2.L.237.236; 2.L.237.237; 2.L.237.238; 2.L.237.239; 2.L.237.154; 2.L.237.157; 2.L.237.166; 2.L.237.169; 2.L.237.172; 2.L.237.175; 2.L.237.240; 2.L.237.244; 2.L.238.228; 2.L.238.229; 2.L.238.230; 2.L.238.231; 2.L.238.236; 2.L.238.237; 2.L.238.238; 2.L.238.239; 2.L.238.154; 2.L.238.157; 2.L.238.166; 2.L.238.169; 2.L.238.172; 2.L.238.175; 2.L.238.240; 2.L.238.244; 2.L.239.228; 2.L.239.229; 2.L.239.230; 2.L.239.231; 2.L.239.236; 2.L.239.237; 2.L.239.238; 2.L.239.239; 2.L.239.154; 2.L.239.157; 2.L.239.166; 2.L.239.169; 2.L.239.172; 2.L.239.175; 2.L.239.240; 2.L.239.244; 2.L.154.228; 2.L.154.229; 2.L.154.230; 2.L.154.231; 2.L.154.236; 2.L.154.237; 2.L.154.238; 2.L.154.239; 2.L.154.154; 2.L.154.157; 2.L.154.166; 2.L.154.169; 2.L.154.172; 2.L.154.175; 2.L.154.240; 2.L.154.244; 2.L.157.228; 2.L.157.229; 2.L.157.230; 2.L.157.231; 2.L.157.236; 2.L.157.237; 2.L.157.238; 2.L.157.239; 2.L.157.154; 2.L.157.157; 2.L.157.166; 2.L.157.169; 2.L.157.172; 2.L.157.175; 2.L.157.240; 2.L.157.244; 2.L.166.228; 2.L.166.229; 2.L.166.230; 2.L.166.231; 2.L.166.236; 2.L.166.237; 2.L.166.238; 2.L.166.239; 2.L.166.154; 2.L.166.157; 2.L.166.166; 2.L.166.169; 2.L.166.172; 2.L.166.175; 2.L.166.240; 2.L.166.244; 2.L.169.228; 2.L.169.229; 2.L.169.230; 2.L.169.231; 2.L.169.236; 2.L.169.237; 2.L.169.238; 2.L.169.239; 2.L.169.154; 2.L.169.157; 2.L.169.166; 2.L.169.169; 2.L.169.172; 2.L.169.175; 2.L.169.240; 2.L.169.244; 2.L.172.228; 2.L.172.229; 2.L.172.230; 2.L.172.231; 2.L.172.236; 2.L.172.237; 2.L.172.238; 2.L.172.239; 2.L.172.154; 2.L.172.157; 2.L.172.166; 2.L.172.169; 2.L.172.172; 2.L.172.175; 2.L.172.240; 2.L.172.244; 2.L.175.228; 2.L.175.229; 2.L.175.230; 2.L.175.231; 2.L.175.236; 2.L.175.237; 2.L.175.238; 2.L.175.239; 2.L.175.154; 2.L.175.157; 2.L.175.166; 2.L.175.169; 2.L.175.172; 2.L.175.175; 2.L.175.240; 2.L.175.244; 2.L.240.228; 2.L.240.229; 2.L.240.230; 2.L.240.231; 2.L.240.236; 2.L.240.237; 2.L.240.238; 2.L.240.239; 2.L.240.154; 2.L.240.157; 2.L.240.166; 2.L.240.169; 2.L.240.172; 2.L.240.175; 2.L.240.240; 2.L.240.244; 2.L.244.228; 2.L.244.229; 2.L.244.230; 2.L.244.231; 2.L.244.236; 2.L.244.237; 2.L.244.238; 2.L.244.239; 2.L.244.154; 2.L.244.157; 2.L.244.166; 2.L.244.169; 2.L.244.172; 2.L.244.175; 2.L.244.240; 2.L.244.244;

Prodrugs of 2.O

2.O.228.228; 2.O.228.229; 2.O.228.230; 2.O.228.231; 2.O.228.236; 2.O.228.237; 2.O.228.238; 2.O.228.239; 2.O.228.154; 2.O.228.157;

TABLE 100-continued

2.O.228.166; 2.O.228.169; 2.O.228.172; 2.O.228.175; 2.O.228.240;
2.O.228.244; 2.O.229.228; 2.O.229.229; 2.O.229.230; 2.O.229.231;
2.O.229.236; 2.O.229.237; 2.O.229.238; 2.O.229.239; 2.O.229.154;
2.O.229.157; 2.O.229.166; 2.O.229.169; 2.O.229.172; 2.O.229.175;
2.O.229.240; 2.O.229.244; 2.O.230.228; 2.O.230.229; 2.O.230.230;
2.O.230.231; 2.O.230.236; 2.O.230.237; 2.O.230.238; 2.O.230.239;
2.O.230.154; 2.O.230.157; 2.O.230.166; 2.O.230.169; 2.O.230.172;
2.O.230.175; 2.O.230.240; 2.O.230.244; 2.O.231.228; 2.O.231.229;
2.O.231.230; 2.O.231.231; 2.O.231.236; 2.O.231.237; 2.O.231.238;
2.O.231.239; 2.O.231.154; 2.O.231.157; 2.O.231.166; 2.O.231.169;
2.O.231.172; 2.O.231.175; 2.O.231.240; 2.O.231.244; 2.O.236.228;
2.O.236.229; 2.O.236.230; 2.O.236.231; 2.O.236.236; 2.O.236.237;
2.O.236.238; 2.O.236.239; 2.O.236.154; 2.O.236.157; 2.O.236.166;
2.O.236.169; 2.O.236.172; 2.O.236.175; 2.O.236.240; 2.O.236.244;
2.O.237.228; 2.O.237.229; 2.O.237.230; 2.O.237.231; 2.O.237.236;
2.O.237.237; 2.O.237.238; 2.O.237.239; 2.O.237.154; 2.O.237.157;
2.O.237.166; 2.O.237.169; 2.O.237.172; 2.O.237.175; 2.O.237.240;
2.O.237.244; 2.O.238.228; 2.O.238.229; 2.O.238.230; 2.O.238.231;
2.O.238.236; 2.O.238.237; 2.O.238.238; 2.O.238.239; 2.O.238.154;
2.O.238.157; 2.O.238.166; 2.O.238.169; 2.O.238.172; 2.O.238.175;
2.O.238.240; 2.O.238.244; 2.O.239.228; 2.O.239.229; 2.O.239.230;
2.O.239.231; 2.O.239.236; 2.O.239.237; 2.O.239.238; 2.O.239.239;
2.O.239.154; 2.O.239.157; 2.O.239.166; 2.O.239.169; 2.O.239.172;
2.O.239.175; 2.O.239.240; 2.O.239.244; 2.O.154.228; 2.O.154.229;
2.O.154.230; 2.O.154.231; 2.O.154.236; 2.O.154.237; 2.O.154.238;
2.O.154.239; 2.O.154.154; 2.O.154.157; 2.O.154.166; 2.O.154.169;
2.O.154.172; 2.O.154.175; 2.O.154.240; 2.O.154.244; 2.O.157.228;
2.O.157.229; 2.O.157.230; 2.O.157.231; 2.O.157.236; 2.O.157.237;
2.O.157.238; 2.O.157.239; 2.O.157.154; 2.O.157.157; 2.O.157.166;
2.O.157.169; 2.O.157.172; 2.O.157.175; 2.O.157.240; 2.O.157.244;
2.O.166.228; 2.O.166.229; 2.O.166.230; 2.O.166.231; 2.O.166.236;
2.O.166.237; 2.O.166.238; 2.O.166.239; 2.O.166.154; 2.O.166.157;
2.O.166.166; 2.O.166.169; 2.O.166.172; 2.O.166.175; 2.O.166.240;
2.O.166.244; 2.O.169.228; 2.O.169.229; 2.O.169.230; 2.O.169.231;
2.O.169.236; 2.O.169.237; 2.O.169.238; 2.O.169.239; 2.O.169.154;
2.O.169.157; 2.O.169.166; 2.O.169.169; 2.O.169.172; 2.O.169.175;
2.O.169.240; 2.O.169.244; 2.O.172.228; 2.O.172.229; 2.O.172.230;
2.O.172.231; 2.O.172.236; 2.O.172.237; 2.O.172.238; 2.O.172.239;
2.O.172.154; 2.O.172.157; 2.O.172.166; 2.O.172.169; 2.O.172.172;
2.O.172.175; 2.O.172.240; 2.O.172.244; 2.O.175.228; 2.O.175.229;
2.O.175.230; 2.O.175.231; 2.O.175.236; 2.O.175.237; 2.O.175.238;
2.O.175.239; 2.O.175.154; 2.O.175.157; 2.O.175.166; 2.O.175.169;
2.O.175.172; 2.O.175.175; 2.O.175.240; 2.O.175.244; 2.O.240.228;
2.O.240.229; 2.O.240.230; 2.O.240.231; 2.O.240.236; 2.O.240.237;
2.O.240.238; 2.O.240.239; 2.O.240.154; 2.O.240.157; 2.O.240.166;
2.O.240.169; 2.O.240.172; 2.O.240.175; 2.O.240.240; 2.O.240.244;
2.O.244.228; 2.O.244.229; 2.O.244.230; 2.O.244.231; 2.O.244.236;
2.O.244.237; 2.O.244.238; 2.O.244.239; 2.O.244.154; 2.O.244.157;
2.O.244.166; 2.O.244.169; 2.O.244.172; 2.O.244.175; 2.O.244.240; 2.O.244.244;

Prodrugs of 2.P

2.P.228.228; 2.P.228.229; 2.P.228.230; 2.P.228.231; 2.P.228.236;
2.P.228.237; 2.P.228.238; 2.P.228.239; 2.P.228.154; 2.P.228.157; 2.P.228.166;
2.P.228.169; 2.P.228.172; 2.P.228.175; 2.P.228.240; 2.P.228.244; 2.P.229.228;
2.P.229.229; 2.P.229.230; 2.P.229.231; 2.P.229.236; 2.P.229.237; 2.P.229.238;
2.P.229.239; 2.P.229.154; 2.P.229.157; 2.P.229.166; 2.P.229.169; 2.P.229.172;
2.P.229.175; 2.P.229.240; 2.P.229.244; 2.P.230.228; 2.P.230.229; 2.P.230.230;
2.P.230.231; 2.P.230.236; 2.P.230.237; 2.P.230.238; 2.P.230.239; 2.P.230.154;
2.P.230.157; 2.P.230.166; 2.P.230.169; 2.P.230.172; 2.P.230.175; 2.P.230.240;
2.P.230.244; 2.P.231.228; 2.P.231.229; 2.P.231.230; 2.P.231.231; 2.P.231.236;
2.P.231.237; 2.P.231.238; 2.P.231.239; 2.P.231.154; 2.P.231.157; 2.P.231.166;
2.P.231.169; 2.P.231.172; 2.P.231.175; 2.P.231.240; 2.P.231.244; 2.P.236.228;
2.P.236.229; 2.P.236.230; 2.P.236.231; 2.P.236.236; 2.P.236.237; 2.P.236.238;
2.P.236.239; 2.P.236.154; 2.P.236.157; 2.P.236.166; 2.P.236.169; 2.P.236.172;
2.P.236.175; 2.P.236.240; 2.P.236.244; 2.P.237.228; 2.P.237.229; 2.P.237.230;
2.P.237.231; 2.P.237.236; 2.P.237.237; 2.P.237.238; 2.P.237.239; 2.P.237.154;
2.P.237.157; 2.P.237.166; 2.P.237.169; 2.P.237.172; 2.P.237.175; 2.P.237.240;
2.P.237.244; 2.P.238.228; 2.P.238.229; 2.P.238.230; 2.P.238.231; 2.P.238.236;
2.P.238.237; 2.P.238.238; 2.P.238.239; 2.P.238.154; 2.P.238.157; 2.P.238.166;
2.P.238.169; 2.P.238.172; 2.P.238.175; 2.P.238.240; 2.P.238.244; 2.P.239.228;
2.P.239.229; 2.P.239.230; 2.P.239.231; 2.P.239.236; 2.P.239.237; 2.P.239.238;
2.P.239.239; 2.P.239.154; 2.P.239.157; 2.P.239.166; 2.P.239.169; 2.P.239.172;
2.P.239.175; 2.P.239.240; 2.P.239.244; 2.P.154.228; 2.P.154.229; 2.P.154.230;
2.P.154.231; 2.P.154.236; 2.P.154.237; 2.P.154.238; 2.P.154.239; 2.P.154.154;
2.P.154.157; 2.P.154.166; 2.P.154.169; 2.P.154.172; 2.P.154.175; 2.P.154.240;
2.P.154.244; 2.P.157.228; 2.P.157.229; 2.P.157.230; 2.P.157.231; 2.P.157.236;
2.P.157.237; 2.P.157.238; 2.P.157.239; 2.P.157.154; 2.P.157.157; 2.P.157.166;
2.P.157.169; 2.P.157.172; 2.P.157.175; 2.P.157.240; 2.P.157.244; 2.P.166.228;
2.P.166.229; 2.P.166.230; 2.P.166.231; 2.P.166.236; 2.P.166.237; 2.P.166.238;
2.P.166.239; 2.P.166.154; 2.P.166.157; 2.P.166.166; 2.P.166.169; 2.P.166.172;

TABLE 100-continued

| |
|---|
| 2.P.166.175; 2.P.166.240; 2.P.166.244; 2.P.169.228; 2.P.169.229; 2.P.169.230; 2.P.169.231; 2.P.169.236; 2.P.169.237; 2.P.169.238; 2.P.169.239; 2.P.169.154; 2.P.169.157; 2.P.169.166; 2.P.169.169; 2.P.169.172; 2.P.169.175; 2.P.169.240; 2.P.169.244; 2.P.172.228; 2.P.172.229; 2.P.172.230; 2.P.172.231; 2.P.172.236; 2.P.172.237; 2.P.172.238; 2.P.172.239; 2.P.172.154; 2.P.172.157; 2.P.172.166; 2.P.172.169; 2.P.172.172; 2.P.172.175; 2.P.172.240; 2.P.172.244; 2.P.175.228; 2.P.175.229; 2.P.175.230; 2.P.175.231; 2.P.175.236; 2.P.175.237; 2.P.175.238; 2.P.175.239; 2.P.175.154; 2.P.175.157; 2.P.175.166; 2.P.175.169; 2.P.175.172; 2.P.175.175; 2.P.175.240; 2.P.175.244; 2.P.240.228; 2.P.240.229; 2.P.240.230; 2.P.240.231; 2.P.240.236; 2.P.240.237; 2.P.240.238; 2.P.240.239; 2.P.240.154; 2.P.240.157; 2.P.240.166; 2.P.240.169; 2.P.240.172; 2.P.240.175; 2.P.240.240; 2.P.240.244; 2.P.244.228; 2.P.244.229; 2.P.244.230; 2.P.244.231; 2.P.244.236; 2.P.244.237; 2.P.244.238; 2.P.244.239; 2.P.244.154; 2.P.244.157; 2.P.244.166; 2.P.244.169; 2.P.244.172; 2.P.244.175; 2.P.244.240; 2.P.244.244; |
| Prodrugs of 2.U |
| 2.U.228.228; 2.U.228.229; 2.U.228.230; 2.U.228.231; 2.U.228.236; 2.U.228.237; 2.U.228.238; 2.U.228.239; 2.U.228.154; 2.U.228.157; 2.U.228.166; 2.U.228.169; 2.U.228.172; 2.U.228.175; 2.U.228.240; 2.U.228.244; 2.U.229.228; 2.U.229.229; 2.U.229.230; 2.U.229.231; 2.U.229.236; 2.U.229.237; 2.U.229.238; 2.U.229.239; 2.U.229.154; 2.U.229.157; 2.U.229.166; 2.U.229.169; 2.U.229.172; 2.U.229.175; 2.U.229.240; 2.U.229.244; 2.U.230.228; 2.U.230.229; 2.U.230.230; 2.U.230.231; 2.U.230.236; 2.U.230.237; 2.U.230.238; 2.U.230.239; 2.U.230.154; 2.U.230.157; 2.U.230.166; 2.U.230.169; 2.U.230.172; 2.U.230.175; 2.U.230.240; 2.U.230.244; 2.U.231.228; 2.U.231.229; 2.U.231.230; 2.U.231.231; 2.U.231.236; 2.U.231.237; 2.U.231.238; 2.U.231.239; 2.U.231.154; 2.U.231.157; 2.U.231.166; 2.U.231.169; 2.U.231.172; 2.U.231.175; 2.U.231.240; 2.U.231.244; 2.U.236.228; 2.U.236.229; 2.U.236.230; 2.U.236.231; 2.U.236.236; 2.U.236.237; 2.U.236.238; 2.U.236.239; 2.U.236.154; 2.U.236.157; 2.U.236.166; 2.U.236.169; 2.U.236.172; 2.U.236.175; 2.U.236.240; 2.U.236.244; 2.U.237.228; 2.U.237.229; 2.U.237.230; 2.U.237.231; 2.U.237.236; 2.U.237.237; 2.U.237.238; 2.U.237.239; 2.U.237.154; 2.U.237.157; 2.U.237.166; 2.U.237.169; 2.U.237.172; 2.U.237.175; 2.U.237.240; 2.U.237.244; 2.U.238.228; 2.U.238.229; 2.U.238.230; 2.U.238.231; 2.U.238.236; 2.U.238.237; 2.U.238.238; 2.U.238.239; 2.U.238.154; 2.U.238.157; 2.U.238.166; 2.U.238.169; 2.U.238.172; 2.U.238.175; 2.U.238.240; 2.U.238.244; 2.U.239.228; 2.U.239.229; 2.U.239.230; 2.U.239.231; 2.U.239.236; 2.U.239.237; 2.U.239.238; 2.U.239.239; 2.U.239.154; 2.U.239.157; 2.U.239.166; 2.U.239.169; 2.U.239.172; 2.U.239.175; 2.U.239.240; 2.U.239.244; 2.U.154.228; 2.U.154.229; 2.U.154.230; 2.U.154.231; 2.U.154.236; 2.U.154.237; 2.U.154.238; 2.U.154.239; 2.U.154.154; 2.U.154.157; 2.U.154.166; 2.U.154.169; 2.U.154.172; 2.U.154.175; 2.U.154.240; 2.U.154.244; 2.U.157.228; 2.U.157.229; 2.U.157.230; 2.U.157.231; 2.U.157.236; 2.U.157.237; 2.U.157.238; 2.U.157.239; 2.U.157.154; 2.U.157.157; 2.U.157.166; 2.U.157.169; 2.U.157.172; 2.U.157.175; 2.U.157.240; 2.U.157.244; 2.U.166.228; 2.U.166.229; 2.U.166.230; 2.U.166.231; 2.U.166.236; 2.U.166.237; 2.U.166.238; 2.U.166.239; 2.U.166.154; 2.U.166.157; 2.U.166.166; 2.U.166.169; 2.U.166.172; 2.U.166.175; 2.U.166.240; 2.U.166.244; 2.U.169.228; 2.U.169.229; 2.U.169.230; 2.U.169.231; 2.U.169.236; 2.U.169.237; 2.U.169.238; 2.U.169.239; 2.U.169.154; 2.U.169.157; 2.U.169.166; 2.U.169.169; 2.U.169.172; 2.U.169.175; 2.U.169.240; 2.U.169.244; 2.U.172.228; 2.U.172.229; 2.U.172.230; 2.U.172.231; 2.U.172.236; 2.U.172.237; 2.U.172.238; 2.U.172.239; 2.U.172.154; 2.U.172.157; 2.U.172.166; 2.U.172.169; 2.U.172.172; 2.U.172.175; 2.U.172.240; 2.U.172.244; 2.U.175.228; 2.U.175.229; 2.U.175.230; 2.U.175.231; 2.U.175.236; 2.U.175.237; 2.U.175.238; 2.U.175.239; 2.U.175.154; 2.U.175.157; 2.U.175.166; 2.U.175.169; 2.U.175.172; 2.U.175.175; 2.U.175.240; 2.U.175.244; 2.U.240.228; 2.U.240.229; 2.U.240.230; 2.U.240.231; 2.U.240.236; 2.U.240.237; 2.U.240.238; 2.U.240.239; 2.U.240.154; 2.U.240.157; 2.U.240.166; 2.U.240.169; 2.U.240.172; 2.U.240.175; 2.U.240.240; 2.U.240.244; 2.U.244.228; 2.U.244.229; 2.U.244.230; 2.U.244.231; 2.U.244.236; 2.U.244.237; 2.U.244.238; 2.U.244.239; 2.U.244.154; 2.U.244.157; 2.U.244.166; 2.U.244.169; 2.U.244.172; 2.U.244.175; 2.U.244.240; 2.U.244.244; |
| Prodrugs of 2.W |
| 2.W.228.228; 2.W.228.229; 2.W.228.230; 2.W.228.231; 2.W.228.236; 2.W.228.237; 2.W.228.238; 2.W.228.239; 2.W.228.154; 2.W.228.157; 2.W.228.166; 2.W.228.169; 2.W.228.172; 2.W.228.175; 2.W.228.240; 2.W.228.244; 2.W.229.228; 2.W.229.229; 2.W.229.230; 2.W.229.231; 2.W.229.236; 2.W.229.237; 2.W.229.238; 2.W.229.239; 2.W.229.154; 2.W.229.157; 2.W.229.166; 2.W.229.169; 2.W.229.172; 2.W.229.175; 2.W.229.240; 2.W.229.244; 2.W.230.228; 2.W.230.229; 2.W.230.230; 2.W.230.231; 2.W.230.236; 2.W.230.237; 2.W.230.238; 2.W.230.239; 2.W.230.154; 2.W.230.157; 2.W.230.166; 2.W.230.169; 2.W.230.172; 2.W.230.175; 2.W.230.240; 2.W.230.244; 2.W.231.228; 2.W.231.229; 2.W.231.230; 2.W.231.231; 2.W.231.236; 2.W.231.237; 2.W.231.238; |

TABLE 100-continued

| |
|---|
| 2.W.231.239; 2.W.231.154; 2.W.231.157; 2.W.231.166; 2.W.231.169; 2.W.231.172; 2.W.231.175; 2.W.231.240; 2.W.231.244; 2.W.236.228; 2.W.236.229; 2.W.236.230; 2.W.236.231; 2.W.236.236; 2.W.236.237; 2.W.236.238; 2.W.236.239; 2.W.236.154; 2.W.236.157; 2.W.236.166; 2.W.236.169; 2.W.236.172; 2.W.236.175; 2.W.236.240; 2.W.236.244; 2.W.237.228; 2.W.237.229; 2.W.237.230; 2.W.237.231; 2.W.237.236; 2.W.237.237; 2.W.237.238; 2.W.237.239; 2.W.237.154; 2.W.237.157; 2.W.237.166; 2.W.237.169; 2.W.237.172; 2.W.237.175; 2.W.237.240; 2.W.237.244; 2.W.238.228; 2.W.238.229; 2.W.238.230; 2.W.238.231; 2.W.238.236; 2.W.238.237; 2.W.238.238; 2.W.238.239; 2.W.238.154; 2.W.238.157; 2.W.238.166; 2.W.238.169; 2.W.238.172; 2.W.238.175; 2.W.238.240; 2.W.238.244; 2.W.239.228; 2.W.239.229; 2.W.239.230; 2.W.239.231; 2.W.239.236; 2.W.239.237; 2.W.239.238; 2.W.239.239; 2.W.239.154; 2.W.239.157; 2.W.239.166; 2.W.239.169; 2.W.239.172; 2.W.239.175; 2.W.239.240; 2.W.239.244; 2.W.154.228; 2.W.154.229; 2.W.154.230; 2.W.154.231; 2.W.154.236; 2.W.154.237; 2.W.154.238; 2.W.154.239; 2.W.154.154; 2.W.154.157; 2.W.154.166; 2.W.154.169; 2.W.154.172; 2.W.154.175; 2.W.154.240; 2.W.154.244; 2.W.157.228; 2.W.157.229; 2.W.157.230; 2.W.157.231; 2.W.157.236; 2.W.157.237; 2.W.157.238; 2.W.157.239; 2.W.157.154; 2.W.157.157; 2.W.157.166; 2.W.157.169; 2.W.157.172; 2.W.157.175; 2.W.157.240; 2.W.157.244; 2.W.166.228; 2.W.166.229; 2.W.166.230; 2.W.166.231; 2.W.166.236; 2.W.166.237; 2.W.166.238; 2.W.166.239; 2.W.166.154; 2.W.166.157; 2.W.166.166; 2.W.166.169; 2.W.166.172; 2.W.166.175; 2.W.166.240; 2.W.166.244; 2.W.169.228; 2.W.169.229; 2.W.169.230; 2.W.169.231; 2.W.169.236; 2.W.169.237; 2.W.169.238; 2.W.169.239; 2.W.169.154; 2.W.169.157; 2.W.169.166; 2.W.169.169; 2.W.169.172; 2.W.169.175; 2.W.169.240; 2.W.169.244; 2.W.172.228; 2.W.172.229; 2.W.172.230; 2.W.172.231; 2.W.172.236; 2.W.172.237; 2.W.172.238; 2.W.172.239; 2.W.172.154; 2.W.172.157; 2.W.172.166; 2.W.172.169; 2.W.172.172; 2.W.172.175; 2.W.172.240; 2.W.172.244; 2.W.175.228; 2.W.175.229; 2.W.175.230; 2.W.175.231; 2.W.175.236; 2.W.175.237; 2.W.175.238; 2.W.175.239; 2.W.175.154; 2.W.175.157; 2.W.175.166; 2.W.175.169; 2.W.175.172; 2.W.175.175; 2.W.175.240; 2.W.175.244; 2.W.240.228; 2.W.240.229; 2.W.240.230; 2.W.240.231; 2.W.240.236; 2.W.240.237; 2.W.240.238; 2.W.240.239; 2.W.240.154; 2.W.240.157; 2.W.240.166; 2.W.240.169; 2.W.240.172; 2.W.240.175; 2.W.240.240; 2.W.240.244; 2.W.244.228; 2.W.244.229; 2.W.244.230; 2.W.244.231; 2.W.244.236; 2.W.244.237; 2.W.244.238; 2.W.244.239; 2.W.244.154; 2.W.244.157; 2.W.244.166; 2.W.244.169; 2.W.244.172; 2.W.244.175; 2.W.244.240; 2.W.244.244; |
| Prodrugs of 2.Y |
| 2.Y.228.228; 2.Y.228.229; 2.Y.228.230; 2.Y.228.231; 2.Y.228.236; 2.Y.228.237; 2.Y.228.238; 2.Y.228.239; 2.Y.228.154; 2.Y.228.157; 2.Y.228.166; 2.Y.228.169; 2.Y.228.172; 2.Y.228.175; 2.Y.228.240; 2.Y.228.244; 2.Y.229.228; 2.Y.229.229; 2.Y.229.230; 2.Y.229.231; 2.Y.229.236; 2.Y.229.237; 2.Y.229.238; 2.Y.229.239; 2.Y.229.154; 2.Y.229.157; 2.Y.229.166; 2.Y.229.169; 2.Y.229.172; 2.Y.229.175; 2.Y.229.240; 2.Y.229.244; 2.Y.230.228; 2.Y.230.229; 2.Y.230.230; 2.Y.230.231; 2.Y.230.236; 2.Y.230.237; 2.Y.230.238; 2.Y.230.239; 2.Y.230.154; 2.Y.230.157; 2.Y.230.166; 2.Y.230.169; 2.Y.230.172; 2.Y.230.175; 2.Y.230.240; 2.Y.230.244; 2.Y.231.228; 2.Y.231.229; 2.Y.231.230; 2.Y.231.231; 2.Y.231.236; 2.Y.231.237; 2.Y.231.238; 2.Y.231.239; 2.Y.231.154; 2.Y.231.157; 2.Y.231.166; 2.Y.231.169; 2.Y.231.172; 2.Y.231.175; 2.Y.231.240; 2.Y.231.244; 2.Y.236.228; 2.Y.236.229; 2.Y.236.230; 2.Y.236.231; 2.Y.236.236; 2.Y.236.237; 2.Y.236.238; 2.Y.236.239; 2.Y.236.154; 2.Y.236.157; 2.Y.236.166; 2.Y.236.169; 2.Y.236.172; 2.Y.236.175; 2.Y.236.240; 2.Y.236.244; 2.Y.237.228; 2.Y.237.229; 2.Y.237.230; 2.Y.237.231; 2.Y.237.236; 2.Y.237.237; 2.Y.237.238; 2.Y.237.239; 2.Y.237.154; 2.Y.237.157; 2.Y.237.166; 2.Y.237.169; 2.Y.237.172; 2.Y.237.175; 2.Y.237.240; 2.Y.237.244; 2.Y.238.228; 2.Y.238.229; 2.Y.238.230; 2.Y.238.231; 2.Y.238.236; 2.Y.238.237; 2.Y.238.238; 2.Y.238.239; 2.Y.238.154; 2.Y.238.157; 2.Y.238.166; 2.Y.238.169; 2.Y.238.172; 2.Y.238.175; 2.Y.238.240; 2.Y.238.244; 2.Y.239.228; 2.Y.239.229; 2.Y.239.230; 2.Y.239.231; 2.Y.239.236; 2.Y.239.237; 2.Y.239.238; 2.Y.239.239; 2.Y.239.154; 2.Y.239.157; 2.Y.239.166; 2.Y.239.169; 2.Y.239.172; 2.Y.239.175; 2.Y.239.240; 2.Y.239.244; 2.Y.154.228; 2.Y.154.229; 2.Y.154.230; 2.Y.154.231; 2.Y.154.236; 2.Y.154.237; 2.Y.154.238; 2.Y.154.239; 2.Y.154.154; 2.Y.154.157; 2.Y.154.166; 2.Y.154.169; 2.Y.154.172; 2.Y.154.175; 2.Y.154.240; 2.Y.154.244; 2.Y.157.228; 2.Y.157.229; 2.Y.157.230; 2.Y.157.231; 2.Y.157.236; 2.Y.157.237; 2.Y.157.238; 2.Y.157.239; 2.Y.157.154; 2.Y.157.157; 2.Y.157.166; 2.Y.157.169; 2.Y.157.172; 2.Y.157.175; 2.Y.157.240; 2.Y.157.244; 2.Y.166.228; 2.Y.166.229; 2.Y.166.230; 2.Y.166.231; 2.Y.166.236; 2.Y.166.237; 2.Y.166.238; 2.Y.166.239; 2.Y.166.154; 2.Y.166.157; 2.Y.166.166; 2.Y.166.169; 2.Y.166.172; 2.Y.166.175; 2.Y.166.240; 2.Y.166.244; 2.Y.169.228; 2.Y.169.229; 2.Y.169.230; 2.Y.169.231; 2.Y.169.236; 2.Y.169.237; 2.Y.169.238; 2.Y.169.239; 2.Y.169.154; 2.Y.169.157; 2.Y.169.166; 2.Y.169.169; 2.Y.169.172; 2.Y.169.175; 2.Y.169.240; 2.Y.169.244; 2.Y.172.228; 2.Y.172.229; 2.Y.172.230; 2.Y.172.231; 2.Y.172.236; 2.Y.172.237; 2.Y.172.238; 2.Y.172.239; 2.Y.172.154; 2.Y.172.157; 2.Y.172.166; 2.Y.172.169; 2.Y.172.172; 2.Y.172.175; 2.Y.172.240; 2.Y.172.244; 2.Y.175.228; 2.Y.175.229; 2.Y.175.230; 2.Y.175.231; 2.Y.175.236; 2.Y.175.237; 2.Y.175.238; 2.Y.175.239; 2.Y.175.154; 2.Y.175.157; 2.Y.175.166; 2.Y.175.169; 2.Y.175.172; 2.Y.175.175; 2.Y.175.240; 2.Y.175.244; 2.Y.240.228; 2.Y.240.229; 2.Y.240.230; |

TABLE 100-continued

| |
|---|
| 2.Y.240.231; 2.Y.240.236; 2.Y.240.237; 2.Y.240.238; 2.Y.240.239; 2.Y.240.154; 2.Y.240.157; 2.Y.240.166; 2.Y.240.169; 2.Y.240.172; 2.Y.240.175; 2.Y.240.240; 2.Y.240.244; 2.Y.244.228; 2.Y.244.229; 2.Y.244.230; 2.Y.244.231; 2.Y.244.236; 2.Y.244.237; 2.Y.244.238; 2.Y.244.239; 2.Y.244.154; 2.Y.244.157; 2.Y.244.166; 2.Y.244.169; 2.Y.244.172; 2.Y.244.175; 2.Y.244.240; 2.Y.244.244; |
| Prodrugs of 3.B |
| 3.B.228.228; 3.B.228.229; 3.B.228.230; 3.B.228.231; 3.B.228.236; 3.B.228.237; 3.B.228.238; 3.B.228.239; 3.B.228.154; 3.B.228.157; 3.B.228.166; 3.B.228.169; 3.B.228.172; 3.B.228.175; 3.B.228.240; 3.B.228.244; 3.B.229.228; 3.B.229.229; 3.B.229.230; 3.B.229.231; 3.B.229.236; 3.B.229.237; 3.B.229.238; 3.B.229.239; 3.B.229.154; 3.B.229.157; 3.B.229.166; 3.B.229.169; 3.B.229.172; 3.B.229.175; 3.B.229.240; 3.B.229.244; 3.B.230.228; 3.B.230.229; 3.B.230.230; 3.B.230.231; 3.B.230.236; 3.B.230.237; 3.B.230.238; 3.B.230.239; 3.B.230.154; 3.B.230.157; 3.B.230.166; 3.B.230.169; 3.B.230.172; 3.B.230.175; 3.B.230.240; 3.B.230.244; 3.B.231.228; 3.B.231.229; 3.B.231.230; 3.B.231.231; 3.B.231.236; 3.B.231.237; 3.B.231.238; 3.B.231.239; 3.B.231.154; 3.B.231.157; 3.B.231.166; 3.B.231.169; 3.B.231.172; 3.B.231.175; 3.B.231.240; 3.B.231.244; 3.B.236.228; 3.B.236.229; 3.B.236.230; 3.B.236.231; 3.B.236.236; 3.B.236.237; 3.B.236.238; 3.B.236.239; 3.B.236.154; 3.B.236.157; 3.B.236.166; 3.B.236.169; 3.B.236.172; 3.B.236.175; 3.B.236.240; 3.B.236.244; 3.B.237.228; 3.B.237.229; 3.B.237.230; 3.B.237.231; 3.B.237.236; 3.B.237.237; 3.B.237.238; 3.B.237.239; 3.B.237.154; 3.B.237.157; 3.B.237.166; 3.B.237.169; 3.B.237.172; 3.B.237.175; 3.B.237.240; 3.B.237.244; 3.B.238.228; 3.B.238.229; 3.B.238.230; 3.B.238.231; 3.B.238.236; 3.B.238.237; 3.B.238.238; 3.B.238.239; 3.B.238.154; 3.B.238.157; 3.B.238.166; 3.B.238.169; 3.B.238.172; 3.B.238.175; 3.B.238.240; 3.B.238.244; 3.B.239.228; 3.B.239.229; 3.B.239.230; 3.B.239.231; 3.B.239.236; 3.B.239.237; 3.B.239.238; 3.B.239.239; 3.B.239.154; 3.B.239.157; 3.B.239.166; 3.B.239.169; 3.B.239.172; 3.B.239.175; 3.B.239.240; 3.B.239.244; 3.B.154.228; 3.B.154.229; 3.B.154.230; 3.B.154.231; 3.B.154.236; 3.B.154.237; 3.B.154.238; 3.B.154.239; 3.B.154.154; 3.B.154.157; 3.B.154.166; 3.B.154.169; 3.B.154.172; 3.B.154.175; 3.B.154.240; 3.B.154.244; 3.B.157.228; 3.B.157.229; 3.B.157.230; 3.B.157.231; 3.B.157.236; 3.B.157.237; 3.B.157.238; 3.B.157.239; 3.B.157.154; 3.B.157.157; 3.B.157.166; 3.B.157.169; 3.B.157.172; 3.B.157.175; 3.B.157.240; 3.B.157.244; 3.B.166.228; 3.B.166.229; 3.B.166.230; 3.B.166.231; 3.B.166.236; 3.B.166.237; 3.B.166.238; 3.B.166.239; 3.B.166.154; 3.B.166.157; 3.B.166.166; 3.B.166.169; 3.B.166.172; 3.B.166.175; 3.B.166.240; 3.B.166.244; 3.B.169.228; 3.B.169.229; 3.B.169.230; 3.B.169.231; 3.B.169.236; 3.B.169.237; 3.B.169.238; 3.B.169.239; 3.B.169.154; 3.B.169.157; 3.B.169.166; 3.B.169.169; 3.B.169.172; 3.B.169.175; 3.B.169.240; 3.B.169.244; 3.B.172.228; 3.B.172.229; 3.B.172.230; 3.B.172.231; 3.B.172.236; 3.B.172.237; 3.B.172.238; 3.B.172.239; 3.B.172.154; 3.B.172.157; 3.B.172.166; 3.B.172.169; 3.B.172.172; 3.B.172.175; 3.B.172.240; 3.B.172.244; 3.B.175.228; 3.B.175.229; 3.B.175.230; 3.B.175.231; 3.B.175.236; 3.B.175.237; 3.B.175.238; 3.B.175.239; 3.B.175.154; 3.B.175.157; 3.B.175.166; 3.B.175.169; 3.B.175.172; 3.B.175.175; 3.B.175.240; 3.B.175.244; 3.B.240.228; 3.B.240.229; 3.B.240.230; 3.B.240.231; 3.B.240.236; 3.B.240.237; 3.B.240.238; 3.B.240.239; 3.B.240.154; 3.B.240.157; 3.B.240.166; 3.B.240.169; 3.B.240.172; 3.B.240.175; 3.B.240.240; 3.B.240.244; 3.B.244.228; 3.B.244.229; 3.B.244.230; 3.B.244.231; 3.B.244.236; 3.B.244.237; 3.B.244.238; 3.B.244.239; 3.B.244.154; 3.B.244.157; 3.B.244.166; 3.B.244.169; 3.B.244.172; 3.B.244.175; 3.B.244.240; 3.B.244.244; |
| Prodrugs of 3.D |
| 3.D.228.228; 3.D.228.229; 3.D.228.230; 3.D.228.231; 3.D.228.236; 3.D.228.237; 3.D.228.238; 3.D.228.239; 3.D.228.154; 3.D.228.157; 3.D.228.166; 3.D.228.169; 3.D.228.172; 3.D.228.175; 3.D.228.240; 3.D.228.244; 3.D.229.228; 3.D.229.229; 3.D.229.230; 3.D.229.231; 3.D.229.236; 3.D.229.237; 3.D.229.238; 3.D.229.239; 3.D.229.154; 3.D.229.157; 3.D.229.166; 3.D.229.169; 3.D.229.172; 3.D.229.175; 3.D.229.240; 3.D.229.244; 3.D.230.228; 3.D.230.229; 3.D.230.230; 3.D.230.231; 3.D.230.236; 3.D.230.237; 3.D.230.238; 3.D.230.239; 3.D.230.154; 3.D.230.157; 3.D.230.166; 3.D.230.169; 3.D.230.172; 3.D.230.175; 3.D.230.240; 3.D.230.244; 3.D.231.228; 3.D.231.229; 3.D.231.230; 3.D.231.231; 3.D.231.236; 3.D.231.237; 3.D.231.238; 3.D.231.239; 3.D.231.154; 3.D.231.157; 3.D.231.166; 3.D.231.169; 3.D.231.172; 3.D.231.175; 3.D.231.240; 3.D.231.244; 3.D.236.228; 3.D.236.229; 3.D.236.230; 3.D.236.231; 3.D.236.236; 3.D.236.237; 3.D.236.238; 3.D.236.239; 3.D.236.154; 3.D.236.157; 3.D.236.166; 3.D.236.169; 3.D.236.172; 3.D.236.175; 3.D.236.240; 3.D.236.244; 3.D.237.228; 3.D.237.229; 3.D.237.230; 3.D.237.231; 3.D.237.236; 3.D.237.237; 3.D.237.238; 3.D.237.239; 3.D.237.154; 3.D.237.157; 3.D.237.166; 3.D.237.169; 3.D.237.172; 3.D.237.175; 3.D.237.240; 3.D.237.244; 3.D.238.228; 3.D.238.229; 3.D.238.230; 3.D.238.231; 3.D.238.236; 3.D.238.237; 3.D.238.238; 3.D.238.239; 3.D.238.154; 3.D.238.157; 3.D.238.166; 3.D.238.169; 3.D.238.172; 3.D.238.175; 3.D.238.240; 3.D.238.244; 3.D.239.228; 3.D.239.229; 3.D.239.230; 3.D.239.231; 3.D.239.236; 3.D.239.237; 3.D.239.238; 3.D.239.239; 3.D.239.154; 3.D.239.157; 3.D.239.166; 3.D.239.169; 3.D.239.172; 3.D.239.175; 3.D.239.240; 3.D.239.244; 3.D.154.228; 3.D.154.229; 3.D.154.230; 3.D.154.231; 3.D.154.236; 3.D.154.237; 3.D.154.238; 3.D.154.239; 3.D.154.154; 3.D.154.157; 3.D.154.166; 3.D.154.169; |

TABLE 100-continued

| |
|---|
| 3.D.154.172; 3.D.154.175; 3.D.154.240; 3.D.154.244; 3.D.157.228; 3.D.157.229; 3.D.157.230; 3.D.157.231; 3.D.157.236; 3.D.157.237; 3.D.157.238; 3.D.157.239; 3.D.157.154; 3.D.157.157; 3.D.157.166; 3.D.157.169; 3.D.157.172; 3.D.157.175; 3.D.157.240; 3.D.157.244; 3.D.166.228; 3.D.166.229; 3.D.166.230; 3.D.166.231; 3.D.166.236; 3.D.166.237; 3.D.166.238; 3.D.166.239; 3.D.166.154; 3.D.166.157; 3.D.166.166; 3.D.166.169; 3.D.166.172; 3.D.166.175; 3.D.166.240; 3.D.166.244; 3.D.169.228; 3.D.169.229; 3.D.169.230; 3.D.169.231; 3.D.169.236; 3.D.169.237; 3.D.169.238; 3.D.169.239; 3.D.169.154; 3.D.169.157; 3.D.169.166; 3.D.169.169; 3.D.169.172; 3.D.169.175; 3.D.169.240; 3.D.169.244; 3.D.172.228; 3.D.172.229; 3.D.172.230; 3.D.172.231; 3.D.172.236; 3.D.172.237; 3.D.172.238; 3.D.172.239; 3.D.172.154; 3.D.172.157; 3.D.172.166; 3.D.172.169; 3.D.172.172; 3.D.172.175; 3.D.172.240; 3.D.172.244; 3.D.175.228; 3.D.175.229; 3.D.175.230; 3.D.175.231; 3.D.175.236; 3.D.175.237; 3.D.175.238; 3.D.175.239; 3.D.175.154; 3.D.175.157; 3.D.175.166; 3.D.175.169; 3.D.175.172; 3.D.175.175; 3.D.175.240; 3.D.175.244; 3.D.240.228; 3.D.240.229; 3.D.240.230; 3.D.240.231; 3.D.240.236; 3.D.240.237; 3.D.240.238; 3.D.240.239; 3.D.240.154; 3.D.240.157; 3.D.240.166; 3.D.240.169; 3.D.240.172; 3.D.240.175; 3.D.240.240; 3.D.240.244; 3.D.244.228; 3.D.244.229; 3.D.244.230; 3.D.244.231; 3.D.244.236; 3.D.244.237; 3.D.244.238; 3.D.244.239; 3.D.244.154; 3.D.244.157; 3.D.244.166; 3.D.244.169; 3.D.244.172; 3.D.244.175; 3.D.244.240; 3.D.244.244; |
| Prodrugs of 3.E |
| 3.E.228.228; 3.E.228.229; 3.E.228.230; 3.E.228.231; 3.E.228.236; 3.E.228.237; 3.E.228.238; 3.E.228.239; 3.E.228.154; 3.E.228.157; 3.E.228.166; 3.E.228.169; 3.E.228.172; 3.E.228.175; 3.E.228.240; 3.E.228.244; 3.E.229.228; 3.E.229.229; 3.E.229.230; 3.E.229.231; 3.E.229.236; 3.E.229.237; 3.E.229.238; 3.E.229.239; 3.E.229.154; 3.E.229.157; 3.E.229.166; 3.E.229.169; 3.E.229.172; 3.E.229.175; 3.E.229.240; 3.E.229.244; 3.E.230.228; 3.E.230.229; 3.E.230.230; 3.E.230.231; 3.E.230.236; 3.E.230.237; 3.E.230.238; 3.E.230.239; 3.E.230.154; 3.E.230.157; 3.E.230.166; 3.E.230.169; 3.E.230.172; 3.E.230.175; 3.E.230.240; 3.E.230.244; 3.E.231.228; 3.E.231.229; 3.E.231.230; 3.E.231.231; 3.E.231.236; 3.E.231.237; 3.E.231.238; 3.E.231.239; 3.E.231.154; 3.E.231.157; 3.E.231.166; 3.E.231.169; 3.E.231.172; 3.E.231.175; 3.E.231.240; 3.E.231.244; 3.E.236.228; 3.E.236.229; 3.E.236.230; 3.E.236.231; 3.E.236.236; 3.E.236.237; 3.E.236.238; 3.E.236.239; 3.E.236.154; 3.E.236.157; 3.E.236.166; 3.E.236.169; 3.E.236.172; 3.E.236.175; 3.E.236.240; 3.E.236.244; 3.E.237.228; 3.E.237.229; 3.E.237.230; 3.E.237.231; 3.E.237.236; 3.E.237.237; 3.E.237.238; 3.E.237.239; 3.E.237.154; 3.E.237.157; 3.E.237.166; 3.E.237.169; 3.E.237.172; 3.E.237.175; 3.E.237.240; 3.E.237.244; 3.E.238.228; 3.E.238.229; 3.E.238.230; 3.E.238.231; 3.E.238.236; 3.E.238.237; 3.E.238.238; 3.E.238.239; 3.E.238.154; 3.E.238.157; 3.E.238.166; 3.E.238.169; 3.E.238.172; 3.E.238.175; 3.E.238.240; 3.E.238.244; 3.E.239.228; 3.E.239.229; 3.E.239.230; 3.E.239.231; 3.E.239.236; 3.E.239.237; 3.E.239.238; 3.E.239.239; 3.E.239.154; 3.E.239.157; 3.E.239.166; 3.E.239.169; 3.E.239.172; 3.E.239.175; 3.E.239.240; 3.E.239.244; 3.E.154.228; 3.E.154.229; 3.E.154.230; 3.E.154.231; 3.E.154.236; 3.E.154.237; 3.E.154.238; 3.E.154.239; 3.E.154.154; 3.E.154.157; 3.E.154.166; 3.E.154.169; 3.E.154.172; 3.E.154.175; 3.E.154.240; 3.E.154.244; 3.E.157.228; 3.E.157.229; 3.E.157.230; 3.E.157.231; 3.E.157.236; 3.E.157.237; 3.E.157.238; 3.E.157.239; 3.E.157.154; 3.E.157.157; 3.E.157.166; 3.E.157.169; 3.E.157.172; 3.E.157.175; 3.E.157.240; 3.E.157.244; 3.E.166.228; 3.E.166.229; 3.E.166.230; 3.E.166.231; 3.E.166.236; 3.E.166.237; 3.E.166.238; 3.E.166.239; 3.E.166.154; 3.E.166.157; 3.E.166.166; 3.E.166.169; 3.E.166.172; 3.E.166.175; 3.E.166.240; 3.E.166.244; 3.E.169.228; 3.E.169.229; 3.E.169.230; 3.E.169.231; 3.E.169.236; 3.E.169.237; 3.E.169.238; 3.E.169.239; 3.E.169.154; 3.E.169.157; 3.E.169.166; 3.E.169.169; 3.E.169.172; 3.E.169.175; 3.E.169.240; 3.E.169.244; 3.E.172.228; 3.E.172.229; 3.E.172.230; 3.E.172.231; 3.E.172.236; 3.E.172.237; 3.E.172.238; 3.E.172.239; 3.E.172.154; 3.E.172.157; 3.E.172.166; 3.E.172.169; 3.E.172.172; 3.E.172.175; 3.E.172.240; 3.E.172.244; 3.E.175.228; 3.E.175.229; 3.E.175.230; 3.E.175.231; 3.E.175.236; 3.E.175.237; 3.E.175.238; 3.E.175.239; 3.E.175.154; 3.E.175.157; 3.E.175.166; 3.E.175.169; 3.E.175.172; 3.E.175.175; 3.E.175.240; 3.E.175.244; 3.E.240.228; 3.E.240.229; 3.E.240.230; 3.E.240.231; 3.E.240.236; 3.E.240.237; 3.E.240.238; 3.E.240.239; 3.E.240.154; 3.E.240.157; 3.E.240.166; 3.E.240.169; 3.E.240.172; 3.E.240.175; 3.E.240.240; 3.E.240.244; 3.E.244.228; 3.E.244.229; 3.E.244.230; 3.E.244.231; 3.E.244.236; 3.E.244.237; 3.E.244.238; 3.E.244.239; 3.E.244.154; 3.E.244.157; 3.E.244.166; 3.E.244.169; 3.E.244.172; 3.E.244.175; 3.E.244.240; 3.E.244.244; |
| Prodrugs of 3.G |
| 3.G.228.228; 3.G.228.229; 3.G.228.230; 3.G.228.231; 3.G.228.236; 3.G.228.237; 3.G.228.238; 3.G.228.239; 3.G.228.154; 3.G.228.157; 3.G.228.166; 3.G.228.169; 3.G.228.172; 3.G.228.175; 3.G.228.240; 3.G.228.244; 3.G.229.228; 3.G.229.229; 3.G.229.230; 3.G.229.231; 3.G.229.236; 3.G.229.237; 3.G.229.238; 3.G.229.239; 3.G.229.154; 3.G.229.157; 3.G.229.166; 3.G.229.169; 3.G.229.172; 3.G.229.175; 3.G.229.240; 3.G.229.244; 3.G.230.228; 3.G.230.229; 3.G.230.230; 3.G.230.231; 3.G.230.236; 3.G.230.237; 3.G.230.238; 3.G.230.239; 3.G.230.154; 3.G.230.157; 3.G.230.166; 3.G.230.169; 3.G.230.172; 3.G.230.175; 3.G.230.240; 3.G.230.244; 3.G.231.228; 3.G.231.229; |

TABLE 100-continued

| |
|---|
| 3.G.231.230; 3.G.231.231; 3.G.231.236; 3.G.231.237; 3.G.231.238; 3.G.231.239; 3.G.231.154; 3.G.231.157; 3.G.231.166; 3.G.231.169; 3.G.231.172; 3.G.231.175; 3.G.231.240; 3.G.231.244; 3.G.236.228; 3.G.236.229; 3.G.236.230; 3.G.236.231; 3.G.236.236; 3.G.236.237; 3.G.236.238; 3.G.236.239; 3.G.236.154; 3.G.236.157; 3.G.236.166; 3.G.236.169; 3.G.236.172; 3.G.236.175; 3.G.236.240; 3.G.236.244; 3.G.237.228; 3.G.237.229; 3.G.237.230; 3.G.237.231; 3.G.237.236; 3.G.237.237; 3.G.237.238; 3.G.237.239; 3.G.237.154; 3.G.237.157; 3.G.237.166; 3.G.237.169; 3.G.237.172; 3.G.237.175; 3.G.237.240; 3.G.237.244; 3.G.238.228; 3.G.238.229; 3.G.238.230; 3.G.238.231; 3.G.238.236; 3.G.238.237; 3.G.238.238; 3.G.238.239; 3.G.238.154; 3.G.238.157; 3.G.238.166; 3.G.238.169; 3.G.238.172; 3.G.238.175; 3.G.238.240; 3.G.238.244; 3.G.239.228; 3.G.239.229; 3.G.239.230; 3.G.239.231; 3.G.239.236; 3.G.239.237; 3.G.239.238; 3.G.239.239; 3.G.239.154; 3.G.239.157; 3.G.239.166; 3.G.239.169; 3.G.239.172; 3.G.239.175; 3.G.239.240; 3.G.239.244; 3.G.154.228; 3.G.154.229; 3.G.154.230; 3.G.154.231; 3.G.154.236; 3.G.154.237; 3.G.154.238; 3.G.154.239; 3.G.154.154; 3.G.154.157; 3.G.154.166; 3.G.154.169; 3.G.154.172; 3.G.154.175; 3.G.154.240; 3.G.154.244; 3.G.157.228; 3.G.157.229; 3.G.157.230; 3.G.157.231; 3.G.157.236; 3.G.157.237; 3.G.157.238; 3.G.157.239; 3.G.157.154; 3.G.157.157; 3.G.157.166; 3.G.157.169; 3.G.157.172; 3.G.157.175; 3.G.157.240; 3.G.157.244; 3.G.166.228; 3.G.166.229; 3.G.166.230; 3.G.166.231; 3.G.166.236; 3.G.166.237; 3.G.166.238; 3.G.166.239; 3.G.166.154; 3.G.166.157; 3.G.166.166; 3.G.166.169; 3.G.166.172; 3.G.166.175; 3.G.166.240; 3.G.166.244; 3.G.169.228; 3.G.169.229; 3.G.169.230; 3.G.169.231; 3.G.169.236; 3.G.169.237; 3.G.169.238; 3.G.169.239; 3.G.169.154; 3.G.169.157; 3.G.169.166; 3.G.169.169; 3.G.169.172; 3.G.169.175; 3.G.169.240; 3.G.169.244; 3.G.172.228; 3.G.172.229; 3.G.172.230; 3.G.172.231; 3.G.172.236; 3.G.172.237; 3.G.172.238; 3.G.172.239; 3.G.172.154; 3.G.172.157; 3.G.172.166; 3.G.172.169; 3.G.172.172; 3.G.172.175; 3.G.172.240; 3.G.172.244; 3.G.175.228; 3.G.175.229; 3.G.175.230; 3.G.175.231; 3.G.175.236; 3.G.175.237; 3.G.175.238; 3.G.175.239; 3.G.175.154; 3.G.175.157; 3.G.175.166; 3.G.175.169; 3.G.175.172; 3.G.175.175; 3.G.175.240; 3.G.175.244; 3.G.240.228; 3.G.240.229; 3.G.240.230; 3.G.240.231; 3.G.240.236; 3.G.240.237; 3.G.240.238; 3.G.240.239; 3.G.240.154; 3.G.240.157; 3.G.240.166; 3.G.240.169; 3.G.240.172; 3.G.240.175; 3.G.240.240; 3.G.240.244; 3.G.244.228; 3.G.244.229; 3.G.244.230; 3.G.244.231; 3.G.244.236; 3.G.244.237; 3.G.244.238; 3.G.244.239; 3.G.244.154; 3.G.244.157; 3.G.244.166; 3.G.244.169; 3.G.244.172; 3.G.244.175; 3.G.244.240; 3.G.244.244; |
| Prodrugs of 3.I |
| 3.I.228.228; 3.I.228.229; 3.I.228.230; 3.I.228.231; 3.I.228.236; 3.I.228.237; 3.I.228.238; 3.I.228.239; 3.I.228.154; 3.I.228.157; 3.I.228.166; 3.I.228.169; 3.I.228.172; 3.I.228.175; 3.I.228.240; 3.I.228.244; 3.I.229.228; 3.I.229.229; 3.I.229.230; 3.I.229.231; 3.I.229.236; 3.I.229.237; 3.I.229.238; 3.I.229.239; 3.I.229.154; 3.I.229.157; 3.I.229.166; 3.I.229.169; 3.I.229.172; 3.I.229.175; 3.I.229.240; 3.I.229.244; 3.I.230.228; 3.I.230.229; 3.I.230.230; 3.I.230.231; 3.I.230.236; 3.I.230.237; 3.I.230.238; 3.I.230.239; 3.I.230.154; 3.I.230.157; 3.I.230.166; 3.I.230.169; 3.I.230.172; 3.I.230.175; 3.I.230.240; 3.I.230.244; 3.I.231.228; 3.I.231.229; 3.I.231.230; 3.I.231.231; 3.I.231.236; 3.I.231.237; 3.I.231.238; 3.I.231.239; 3.I.231.154; 3.I.231.157; 3.I.231.166; 3.I.231.169; 3.I.231.172; 3.I.231.175; 3.I.231.240; 3.I.231.244; 3.I.236.228; 3.I.236.229; 3.I.236.230; 3.I.236.231; 3.I.236.236; 3.I.236.237; 3.I.236.238; 3.I.236.239; 3.I.236.154; 3.I.236.157; 3.I.236.166; 3.I.236.169; 3.I.236.172; 3.I.236.175; 3.I.236.240; 3.I.236.244; 3.I.237.228; 3.I.237.229; 3.I.237.230; 3.I.237.231; 3.I.237.236; 3.I.237.237; 3.I.237.238; 3.I.237.239; 3.I.237.154; 3.I.237.157; 3.I.237.166; 3.I.237.169; 3.I.237.172; 3.I.237.175; 3.I.237.240; 3.I.237.244; 3.I.238.228; 3.I.238.229; 3.I.238.230; 3.I.238.231; 3.I.238.236; 3.I.238.237; 3.I.238.238; 3.I.238.239; 3.I.238.154; 3.I.238.157; 3.I.238.166; 3.I.238.169; 3.I.238.172; 3.I.238.175; 3.I.238.240; 3.I.238.244; 3.I.239.228; 3.I.239.229; 3.I.239.230; 3.I.239.231; 3.I.239.236; 3.I.239.237; 3.I.239.238; 3.I.239.239; 3.I.239.154; 3.I.239.157; 3.I.239.166; 3.I.239.169; 3.I.239.172; 3.I.239.175; 3.I.239.240; 3.I.239.244; 3.I.154.228; 3.I.154.229; 3.I.154.230; 3.I.154.231; 3.I.154.236; 3.I.154.237; 3.I.154.238; 3.I.154.239; 3.I.154.154; 3.I.154.157; 3.I.154.166; 3.I.154.169; 3.I.154.172; 3.I.154.175; 3.I.154.240; 3.I.154.244; 3.I.157.228; 3.I.157.229; 3.I.157.230; 3.I.157.231; 3.I.157.236; 3.I.157.237; 3.I.157.238; 3.I.157.239; 3.I.157.154; 3.I.157.157; 3.I.157.166; 3.I.157.169; 3.I.157.172; 3.I.157.175; 3.I.157.240; 3.I.157.244; 3.I.166.228; 3.I.166.229; 3.I.166.230; 3.I.166.231; 3.I.166.236; 3.I.166.237; 3.I.166.238; 3.I.166.239; 3.I.166.154; 3.I.166.157; 3.I.166.166; 3.I.166.169; 3.I.166.172; 3.I.166.175; 3.I.166.240; 3.I.166.244; 3.I.169.228; 3.I.169.229; 3.I.169.230; 3.I.169.231; 3.I.169.236; 3.I.169.237; 3.I.169.238; 3.I.169.239; 3.I.169.154; 3.I.169.157; 3.I.169.166; 3.I.169.169; 3.I.169.172; 3.I.169.175; 3.I.169.240; 3.I.169.244; 3.I.172.228; 3.I.172.229; 3.I.172.230; 3.I.172.231; 3.I.172.236; 3.I.172.237; 3.I.172.238; 3.I.172.239; 3.I.172.154; 3.I.172.157; 3.I.172.166; 3.I.172.169; 3.I.172.172; 3.I.172.175; 3.I.172.240; 3.I.172.244; 3.I.175.228; 3.I.175.229; 3.I.175.230; 3.I.175.231; 3.I.175.236; 3.I.175.237; 3.I.175.238; 3.I.175.239; 3.I.175.154; 3.I.175.157; 3.I.175.166; 3.I.175.169; 3.I.175.172; 3.I.175.175; |

TABLE 100-continued

3.I.175.240; 3.I.175.244; 3.I.240.228; 3.I.240.229; 3.I.240.230; 3.I.240.231; 3.I.240.236; 3.I.240.237; 3.I.240.238; 3.I.240.239; 3.I.240.154; 3.I.240.157; 3.I.240.166; 3.I.240.169; 3.I.240.172; 3.I.240.175; 3.I.240.240; 3.I.240.244; 3.I.244.228; 3.I.244.229; 3.I.244.230; 3.I.244.231; 3.I.244.236; 3.I.244.237; 3.I.244.238; 3.I.244.239; 3.I.244.154; 3.I.244.157; 3.I.244.166; 3.I.244.169; 3.I.244.172; 3.I.244.175; 3.I.244.240; 3.I.244.244;

Prodrugs of 3.J

3.J.228.228; 3.J.228.229; 3.J.228.230; 3.J.228.231; 3.J.228.236; 3.J.228.237; 3.J.228.238; 3.J.228.239; 3.J.228.154; 3.J.228.157; 3.J.228.166; 3.J.228.169; 3.J.228.172; 3.J.228.175; 3.J.228.240; 3.J.228.244; 3.J.229.228; 3.J.229.229; 3.J.229.230; 3.J.229.231; 3.J.229.236; 3.J.229.237; 3.J.229.238; 3.J.229.239; 3.J.229.154; 3.J.229.157; 3.J.229.166; 3.J.229.169; 3.J.229.172; 3.J.229.175; 3.J.229.240; 3.J.229.244; 3.J.230.228; 3.J.230.229; 3.J.230.230; 3.J.230.231; 3.J.230.236; 3.J.230.237; 3.J.230.238; 3.J.230.239; 3.J.230.154; 3.J.230.157; 3.J.230.166; 3.J.230.169; 3.J.230.172; 3.J.230.175; 3.J.230.240; 3.J.230.244; 3.J.231.228; 3.J.231.229; 3.J.231.230; 3.J.231.231; 3.J.231.236; 3.J.231.237; 3.J.231.238; 3.J.231.239; 3.J.231.154; 3.J.231.157; 3.J.231.166; 3.J.231.169; 3.J.231.172; 3.J.231.175; 3.J.231.240; 3.J.231.244; 3.J.236.228; 3.J.236.229; 3.J.236.230; 3.J.236.231; 3.J.236.236; 3.J.236.237; 3.J.236.238; 3.J.236.239; 3.J.236.154; 3.J.236.157; 3.J.236.166; 3.J.236.169; 3.J.236.172; 3.J.236.175; 3.J.236.240; 3.J.236.244; 3.J.237.228; 3.J.237.229; 3.J.237.230; 3.J.237.231; 3.J.237.236; 3.J.237.237; 3.J.237.238; 3.J.237.239; 3.J.237.154; 3.J.237.157; 3.J.237.166; 3.J.237.169; 3.J.237.172; 3.J.237.175; 3.J.237.240; 3.J.237.244; 3.J.238.228; 3.J.238.229; 3.J.238.230; 3.J.238.231; 3.J.238.236; 3.J.238.237; 3.J.238.238; 3.J.238.239; 3.J.238.154; 3.J.238.157; 3.J.238.166; 3.J.238.169; 3.J.238.172; 3.J.238.175; 3.J.238.240; 3.J.238.244; 3.J.239.228; 3.J.239.229; 3.J.239.230; 3.J.239.231; 3.J.239.236; 3.J.239.237; 3.J.239.238; 3.J.239.239; 3.J.239.154; 3.J.239.157; 3.J.239.166; 3.J.239.169; 3.J.239.172; 3.J.239.175; 3.J.239.240; 3.J.239.244; 3.J.154.228; 3.J.154.229; 3.J.154.230; 3.J.154.231; 3.J.154.236; 3.J.154.237; 3.J.154.238; 3.J.154.239; 3.J.154.154; 3.J.154.157; 3.J.154.166; 3.J.154.169; 3.J.154.172; 3.J.154.175; 3.J.154.240; 3.J.154.244; 3.J.157.228; 3.J.157.229; 3.J.157.230; 3.J.157.231; 3.J.157.236; 3.J.157.237; 3.J.157.238; 3.J.157.239; 3.J.157.154; 3.J.157.157; 3.J.157.166; 3.J.157.169; 3.J.157.172; 3.J.157.175; 3.J.157.240; 3.J.157.244; 3.J.166.228; 3.J.166.229; 3.J.166.230; 3.J.166.231; 3.J.166.236; 3.J.166.237; 3.J.166.238; 3.J.166.239; 3.J.166.154; 3.J.166.157; 3.J.166.166; 3.J.166.169; 3.J.166.172; 3.J.166.175; 3.J.166.240; 3.J.166.244; 3.J.169.228; 3.J.169.229; 3.J.169.230; 3.J.169.231; 3.J.169.236; 3.J.169.237; 3.J.169.238; 3.J.169.239; 3.J.169.154; 3.J.169.157; 3.J.169.166; 3.J.169.169; 3.J.169.172; 3.J.169.175; 3.J.169.240; 3.J.169.244; 3.J.172.228; 3.J.172.229; 3.J.172.230; 3.J.172.231; 3.J.172.236; 3.J.172.237; 3.J.172.238; 3.J.172.239; 3.J.172.154; 3.J.172.157; 3.J.172.166; 3.J.172.169; 3.J.172.172; 3.J.172.175; 3.J.172.240; 3.J.172.244; 3.J.175.228; 3.J.175.229; 3.J.175.230; 3.J.175.231; 3.J.175.236; 3.J.175.237; 3.J.175.238; 3.J.175.239; 3.J.175.154; 3.J.175.157; 3.J.175.166; 3.J.175.169; 3.J.175.172; 3.J.175.175; 3.J.175.240; 3.J.175.244; 3.J.240.228; 3.J.240.229; 3.J.240.230; 3.J.240.231; 3.J.240.236; 3.J.240.237; 3.J.240.238; 3.J.240.239; 3.J.240.154; 3.J.240.157; 3.J.240.166; 3.J.240.169; 3.J.240.172; 3.J.240.175; 3.J.240.240; 3.J.240.244; 3.J.244.228; 3.J.244.229; 3.J.244.230; 3.J.244.231; 3.J.244.236; 3.J.244.237; 3.J.244.238; 3.J.244.239; 3.J.244.154; 3.J.244.157; 3.J.244.166; 3.J.244.169; 3.J.244.172; 3.J.244.175; 3.J.244.240; 3.J.244.244;

Prodrugs of 3.L

3.L.228.228; 3.L.228.229; 3.L.228.230; 3.L.228.231; 3.L.228.236; 3.L.228.237; 3.L.228.238; 3.L.228.239; 3.L.228.154; 3.L.228.157; 3.L.228.166; 3.L.228.169; 3.L.228.172; 3.L.228.175; 3.L.228.240; 3.L.228.244; 3.L.229.228; 3.L.229.229; 3.L.229.230; 3.L.229.231; 3.L.229.236; 3.L.229.237; 3.L.229.238; 3.L.229.239; 3.L.229.154; 3.L.229.157; 3.L.229.166; 3.L.229.169; 3.L.229.172; 3.L.229.175; 3.L.229.240; 3.L.229.244; 3.L.230.228; 3.L.230.229; 3.L.230.230; 3.L.230.231; 3.L.230.236; 3.L.230.237; 3.L.230.238; 3.L.230.239; 3.L.230.154; 3.L.230.157; 3.L.230.166; 3.L.230.169; 3.L.230.172; 3.L.230.175; 3.L.230.240; 3.L.230.244; 3.L.231.228; 3.L.231.229; 3.L.231.230; 3.L.231.231; 3.L.231.236; 3.L.231.237; 3.L.231.238; 3.L.231.239; 3.L.231.154; 3.L.231.157; 3.L.231.166; 3.L.231.169; 3.L.231.172; 3.L.231.175; 3.L.231.240; 3.L.231.244; 3.L.236.228; 3.L.236.229; 3.L.236.230; 3.L.236.231; 3.L.236.236; 3.L.236.237; 3.L.236.238; 3.L.236.239; 3.L.236.154; 3.L.236.157; 3.L.236.166; 3.L.236.169; 3.L.236.172; 3.L.236.175; 3.L.236.240; 3.L.236.244; 3.L.237.228; 3.L.237.229; 3.L.237.230; 3.L.237.231; 3.L.237.236; 3.L.237.237; 3.L.237.238; 3.L.237.239; 3.L.237.154; 3.L.237.157; 3.L.237.166; 3.L.237.169; 3.L.237.172; 3.L.237.175; 3.L.237.240; 3.L.237.244; 3.L.238.228; 3.L.238.229; 3.L.238.230; 3.L.238.231; 3.L.238.236; 3.L.238.237; 3.L.238.238; 3.L.238.239; 3.L.238.154; 3.L.238.157; 3.L.238.166; 3.L.238.169; 3.L.238.172; 3.L.238.175; 3.L.238.240; 3.L.238.244; 3.L.239.228; 3.L.239.229; 3.L.239.230; 3.L.239.231; 3.L.239.236; 3.L.239.237; 3.L.239.238; 3.L.239.239; 3.L.239.154; 3.L.239.157; 3.L.239.166; 3.L.239.169; 3.L.239.172; 3.L.239.175; 3.L.239.240; 3.L.239.244; 3.L.154.228; 3.L.154.229; 3.L.154.230; 3.L.154.231; 3.L.154.236; 3.L.154.237; 3.L.154.238; 3.L.154.239; 3.L.154.154; 3.L.154.157; 3.L.154.166; 3.L.154.169; 3.L.154.172; 3.L.154.175; 3.L.154.240; 3.L.154.244; 3.L.157.228; 3.L.157.229; 3.L.157.230; 3.L.157.231; 3.L.157.236; 3.L.157.237; 3.L.157.238; 3.L.157.239; 3.L.157.154; 3.L.157.157; 3.L.157.166; 3.L.157.169; 3.L.157.172; 3.L.157.175; 3.L.157.240; 3.L.157.244; 3.L.166.228;

TABLE 100-continued

| |
|---|
| 3.L.166.229; 3.L.166.230; 3.L.166.231; 3.L.166.236; 3.L.166.237; 3.L.166.238; 3.L.166.239; 3.L.166.154; 3.L.166.157; 3.L.166.166; 3.L.166.169; 3.L.166.172; 3.L.166.175; 3.L.166.240; 3.L.166.244; 3.L.169.228; 3.L.169.229; 3.L.169.230; 3.L.169.231; 3.L.169.236; 3.L.169.237; 3.L.169.238; 3.L.169.239; 3.L.169.154; 3.L.169.157; 3.L.169.166; 3.L.169.169; 3.L.169.172; 3.L.169.175; 3.L.169.240; 3.L.169.244; 3.L.172.228; 3.L.172.229; 3.L.172.230; 3.L.172.231; 3.L.172.236; 3.L.172.237; 3.L.172.238; 3.L.172.239; 3.L.172.154; 3.L.172.157; 3.L.172.166; 3.L.172.169; 3.L.172.172; 3.L.172.175; 3.L.172.240; 3.L.172.244; 3.L.175.228; 3.L.175.229; 3.L.175.230; 3.L.175.231; 3.L.175.236; 3.L.175.237; 3.L.175.238; 3.L.175.239; 3.L.175.154; 3.L.175.157; 3.L.175.166; 3.L.175.169; 3.L.175.172; 3.L.175.175; 3.L.175.240; 3.L.175.244; 3.L.240.228; 3.L.240.229; 3.L.240.230; 3.L.240.231; 3.L.240.236; 3.L.240.237; 3.L.240.238; 3.L.240.239; 3.L.240.154; 3.L.240.157; 3.L.240.166; 3.L.240.169; 3.L.240.172; 3.L.240.175; 3.L.240.240; 3.L.240.244; 3.L.244.228; 3.L.244.229; 3.L.244.230; 3.L.244.231; 3.L.244.236; 3.L.244.237; 3.L.244.238; 3.L.244.239; 3.L.244.154; 3.L.244.157; 3.L.244.166; 3.L.244.169; 3.L.244.172; 3.L.244.175; 3.L.244.240; 3.L.244.244; |
| Prodrugs of 3.O |
| 3.O.228.228; 3.O.228.229; 3.O.228.230; 3.O.228.231; 3.O.228.236; 3.O.228.237; 3.O.228.238; 3.O.228.239; 3.O.228.154; 3.O.228.157; 3.O.228.166; 3.O.228.169; 3.O.228.172; 3.O.228.175; 3.O.228.240; 3.O.228.244; 3.O.229.228; 3.O.229.229; 3.O.229.230; 3.O.229.231; 3.O.229.236; 3.O.229.237; 3.O.229.238; 3.O.229.239; 3.O.229.154; 3.O.229.157; 3.O.229.166; 3.O.229.169; 3.O.229.172; 3.O.229.175; 3.O.229.240; 3.O.229.244; 3.O.230.228; 3.O.230.229; 3.O.230.230; 3.O.230.231; 3.O.230.236; 3.O.230.237; 3.O.230.238; 3.O.230.239; 3.O.230.154; 3.O.230.157; 3.O.230.166; 3.O.230.169; 3.O.230.172; 3.O.230.175; 3.O.230.240; 3.O.230.244; 3.O.231.228; 3.O.231.229; 3.O.231.230; 3.O.231.231; 3.O.231.236; 3.O.231.237; 3.O.231.238; 3.O.231.239; 3.O.231.154; 3.O.231.157; 3.O.231.166; 3.O.231.169; 3.O.231.172; 3.O.231.175; 3.O.231.240; 3.O.231.244; 3.O.236.228; 3.O.236.229; 3.O.236.230; 3.O.236.231; 3.O.236.236; 3.O.236.237; 3.O.236.238; 3.O.236.239; 3.O.236.154; 3.O.236.157; 3.O.236.166; 3.O.236.169; 3.O.236.172; 3.O.236.175; 3.O.236.240; 3.O.236.244; 3.O.237.228; 3.O.237.229; 3.O.237.230; 3.O.237.231; 3.O.237.236; 3.O.237.237; 3.O.237.238; 3.O.237.239; 3.O.237.154; 3.O.237.157; 3.O.237.166; 3.O.237.169; 3.O.237.172; 3.O.237.175; 3.O.237.240; 3.O.237.244; 3.O.238.228; 3.O.238.229; 3.O.238.230; 3.O.238.231; 3.O.238.236; 3.O.238.237; 3.O.238.238; 3.O.238.239; 3.O.238.154; 3.O.238.157; 3.O.238.166; 3.O.238.169; 3.O.238.172; 3.O.238.175; 3.O.238.240; 3.O.238.244; 3.O.239.228; 3.O.239.229; 3.O.239.230; 3.O.239.231; 3.O.239.236; 3.O.239.237; 3.O.239.238; 3.O.239.239; 3.O.239.154; 3.O.239.157; 3.O.239.166; 3.O.239.169; 3.O.239.172; 3.O.239.175; 3.O.239.240; 3.O.239.244; 3.O.154.228; 3.O.154.229; 3.O.154.230; 3.O.154.231; 3.O.154.236; 3.O.154.237; 3.O.154.238; 3.O.154.239; 3.O.154.154; 3.O.154.157; 3.O.154.166; 3.O.154.169; 3.O.154.172; 3.O.154.175; 3.O.154.240; 3.O.154.244; 3.O.157.228; 3.O.157.229; 3.O.157.230; 3.O.157.231; 3.O.157.236; 3.O.157.237; 3.O.157.238; 3.O.157.239; 3.O.157.154; 3.O.157.157; 3.O.157.166; 3.O.157.169; 3.O.157.172; 3.O.157.175; 3.O.157.240; 3.O.157.244; 3.O.166.228; 3.O.166.229; 3.O.166.230; 3.O.166.231; 3.O.166.236; 3.O.166.237; 3.O.166.238; 3.O.166.239; 3.O.166.154; 3.O.166.157; 3.O.166.166; 3.O.166.169; 3.O.166.172; 3.O.166.175; 3.O.166.240; 3.O.166.244; 3.O.169.228; 3.O.169.229; 3.O.169.230; 3.O.169.231; 3.O.169.236; 3.O.169.237; 3.O.169.238; 3.O.169.239; 3.O.169.154; 3.O.169.157; 3.O.169.166; 3.O.169.169; 3.O.169.172; 3.O.169.175; 3.O.169.240; 3.O.169.244; 3.O.172.228; 3.O.172.229; 3.O.172.230; 3.O.172.231; 3.O.172.236; 3.O.172.237; 3.O.172.238; 3.O.172.239; 3.O.172.154; 3.O.172.157; 3.O.172.166; 3.O.172.169; 3.O.172.172; 3.O.172.175; 3.O.172.240; 3.O.172.244; 3.O.175.228; 3.O.175.229; 3.O.175.230; 3.O.175.231; 3.O.175.236; 3.O.175.237; 3.O.175.238; 3.O.175.239; 3.O.175.154; 3.O.175.157; 3.O.175.166; 3.O.175.169; 3.O.175.172; 3.O.175.175; 3.O.175.240; 3.O.175.244; 3.O.240.228; 3.O.240.229; 3.O.240.230; 3.O.240.231; 3.O.240.236; 3.O.240.237; 3.O.240.238; 3.O.240.239; 3.O.240.154; 3.O.240.157; 3.O.240.166; 3.O.240.169; 3.O.240.172; 3.O.240.175; 3.O.240.240; 3.O.240.244; 3.O.244.228; 3.O.244.229; 3.O.244.230; 3.O.244.231; 3.O.244.236; 3.O.244.237; 3.O.244.238; 3.O.244.239; 3.O.244.154; 3.O.244.157; 3.O.244.166; 3.O.244.169; 3.O.244.172; 3.O.244.175; 3.O.244.240; 3.O.244.244; |
| Prodrugs of 3.P |
| 3.P.228.228; 3.P.228.229; 3.P.228.230; 3.P.228.231; 3.P.228.236; 3.P.228.237; 3.P.228.238; 3.P.228.239; 3.P.228.154; 3.P.228.157; 3.P.228.166; 3.P.228.169; 3.P.228.172; 3.P.228.175; 3.P.228.240; 3.P.228.244; 3.P.229.228; 3.P.229.229; 3.P.229.230; 3.P.229.231; 3.P.229.236; 3.P.229.237; 3.P.229.238; 3.P.229.239; 3.P.229.154; 3.P.229.157; 3.P.229.166; 3.P.229.169; 3.P.229.172; 3.P.229.175; 3.P.229.240; 3.P.229.244; 3.P.230.228; 3.P.230.229; 3.P.230.230; 3.P.230.231; 3.P.230.236; 3.P.230.237; 3.P.230.238; 3.P.230.239; 3.P.230.154; 3.P.230.157; 3.P.230.166; 3.P.230.169; 3.P.230.172; 3.P.230.175; 3.P.230.240; 3.P.230.244; 3.P.231.228; 3.P.231.229; 3.P.231.230; 3.P.231.231; 3.P.231.236; |

TABLE 100-continued

| |
|---|
| 3.P.231.237; 3.P.231.238; 3.P.231.239; 3.P.231.154; 3.P.231.157; 3.P.231.166; |
| 3.P.231.169; 3.P.231.172; 3.P.231.175; 3.P.231.240; 3.P.231.244; 3.P.236.228; |
| 3.P.236.229; 3.P.236.230; 3.P.236.231; 3.P.236.236; 3.P.236.237; 3.P.236.238; |
| 3.P.236.239; 3.P.236.154; 3.P.236.157; 3.P.236.166; 3.P.236.169; 3.P.236.172; |
| 3.P.236.175; 3.P.236.240; 3.P.236.244; 3.P.237.228; 3.P.237.229; 3.P.237.230; |
| 3.P.237.231; 3.P.237.236; 3.P.237.237; 3.P.237.238; 3.P.237.239; 3.P.237.154; |
| 3.P.237.157; 3.P.237.166; 3.P.237.169; 3.P.237.172; 3.P.237.175; 3.P.237.240; |
| 3.P.237.244; 3.P.238.228; 3.P.238.229; 3.P.238.230; 3.P.238.231; 3.P.238.236; |
| 3.P.238.237; 3.P.238.238; 3.P.238.239; 3.P.238.154; 3.P.238.157; 3.P.238.166; |
| 3.P.238.169; 3.P.238.172; 3.P.238.175; 3.P.238.240; 3.P.238.244; 3.P.239.228; |
| 3.P.239.229; 3.P.239.230; 3.P.239.231; 3.P.239.236; 3.P.239.237; 3.P.239.238; |
| 3.P.239.239; 3.P.239.154; 3.P.239.157; 3.P.239.166; 3.P.239.169; 3.P.239.172; |
| 3.P.239.175; 3.P.239.240; 3.P.239.244; 3.P.154.228; 3.P.154.229; 3.P.154.230; |
| 3.P.154.231; 3.P.154.236; 3.P.154.237; 3.P.154.238; 3.P.154.239; 3.P.154.154; |
| 3.P.154.157; 3.P.154.166; 3.P.154.169; 3.P.154.172; 3.P.154.175; 3.P.154.240; |
| 3.P.154.244; 3.P.157.228; 3.P.157.229; 3.P.157.230; 3.P.157.231; 3.P.157.236; |
| 3.P.157.237; 3.P.157.238; 3.P.157.239; 3.P.157.154; 3.P.157.157; 3.P.157.166; |
| 3.P.157.169; 3.P.157.172; 3.P.157.175; 3.P.157.240; 3.P.157.244; 3.P.166.228; |
| 3.P.166.229; 3.P.166.230; 3.P.166.231; 3.P.166.236; 3.P.166.237; 3.P.166.238; |
| 3.P.166.239; 3.P.166.154; 3.P.166.157; 3.P.166.166; 3.P.166.169; 3.P.166.172; |
| 3.P.166.175; 3.P.166.240; 3.P.166.244; 3.P.169.228; 3.P.169.229; 3.P.169.230; |
| 3.P.169.231; 3.P.169.236; 3.P.169.237; 3.P.169.238; 3.P.169.239; 3.P.169.154; |
| 3.P.169.157; 3.P.169.166; 3.P.169.169; 3.P.169.172; 3.P.169.175; 3.P.169.240; |
| 3.P.169.244; 3.P.172.228; 3.P.172.229; 3.P.172.230; 3.P.172.231; 3.P.172.236; |
| 3.P.172.237; 3.P.172.238; 3.P.172.239; 3.P.172.154; 3.P.172.157; 3.P.172.166; |
| 3.P.172.169; 3.P.172.172; 3.P.172.175; 3.P.172.240; 3.P.172.244; 3.P.175.228; |
| 3.P.175.229; 3.P.175.230; 3.P.175.231; 3.P.175.236; 3.P.175.237; 3.P.175.238; |
| 3.P.175.239; 3.P.175.154; 3.P.175.157; 3.P.175.166; 3.P.175.169; 3.P.175.172; |
| 3.P.175.175; 3.P.175.240; 3.P.175.244; 3.P.240.228; 3.P.240.229; 3.P.240.230; |
| 3.P.240.231; 3.P.240.236; 3.P.240.237; 3.P.240.238; 3.P.240.239; 3.P.240.154; |
| 3.P.240.157; 3.P.240.166; 3.P.240.169; 3.P.240.172; 3.P.240.175; 3.P.240.240; |
| 3.P.240.244; 3.P.244.228; 3.P.244.229; 3.P.244.230; 3.P.244.231; 3.P.244.236; |
| 3.P.244.237; 3.P.244.238; 3.P.244.239; 3.P.244.154; 3.P.244.157; 3.P.244.166; |
| 3.P.244.169; 3.P.244.172; 3.P.244.175; 3.P.244.240; 3.P.244.244; |
| Prodrugs of 3.U |
| 3.U.228.228; 3.U.228.229; 3.U.228.230; 3.U.228.231; 3.U.228.236; |
| 3.U.228.237; 3.U.228.238; 3.U.228.239; 3.U.228.154; 3.U.228.157; |
| 3.U.228.166; 3.U.228.169; 3.U.228.172; 3.U.228.175; 3.U.228.240; |
| 3.U.228.244; 3.U.229.228; 3.U.229.229; 3.U.229.230; 3.U.229.231; |
| 3.U.229.236; 3.U.229.237; 3.U.229.238; 3.U.229.239; 3.U.229.154; |
| 3.U.229.157; 3.U.229.166; 3.U.229.169; 3.U.229.172; 3.U.229.175; |
| 3.U.229.240; 3.U.229.244; 3.U.230.228; 3.U.230.229; 3.U.230.230; |
| 3.U.230.231; 3.U.230.236; 3.U.230.237; 3.U.230.238; 3.U.230.239; |
| 3.U.230.154; 3.U.230.157; 3.U.230.166; 3.U.230.169; 3.U.230.172; |
| 3.U.230.175; 3.U.230.240; 3.U.230.244; 3.U.231.228; 3.U.231.229; |
| 3.U.231.230; 3.U.231.231; 3.U.231.236; 3.U.231.237; 3.U.231.238; |
| 3.U.231.239; 3.U.231.154; 3.U.231.157; 3.U.231.166; 3.U.231.169; |
| 3.U.231.172; 3.U.231.175; 3.U.231.240; 3.U.231.244; 3.U.236.228; |
| 3.U.236.229; 3.U.236.230; 3.U.236.231; 3.U.236.236; 3.U.236.237; |
| 3.U.236.238; 3.U.236.239; 3.U.236.154; 3.U.236.157; 3.U.236.166; |
| 3.U.236.169; 3.U.236.172; 3.U.236.175; 3.U.236.240; 3.U.236.244; |
| 3.U.237.228; 3.U.237.229; 3.U.237.230; 3.U.237.231; 3.U.237.236; |
| 3.U.237.237; 3.U.237.238; 3.U.237.239; 3.U.237.154; 3.U.237.157; |
| 3.U.237.166; 3.U.237.169; 3.U.237.172; 3.U.237.175; 3.U.237.240; |
| 3.U.237.244; 3.U.238.228; 3.U.238.229; 3.U.238.230; 3.U.238.231; |
| 3.U.238.236; 3.U.238.237; 3.U.238.238; 3.U.238.239; 3.U.238.154; |
| 3.U.238.157; 3.U.238.166; 3.U.238.169; 3.U.238.172; 3.U.238.175; |
| 3.U.238.240; 3.U.238.244; 3.U.239.228; 3.U.239.229; 3.U.239.230; |
| 3.U.239.231; 3.U.239.236; 3.U.239.237; 3.U.239.238; 3.U.239.239; |
| 3.U.239.154; 3.U.239.157; 3.U.239.166; 3.U.239.169; 3.U.239.172; |
| 3.U.239.175; 3.U.239.240; 3.U.239.244; 3.U.154.228; 3.U.154.229; |
| 3.U.154.230; 3.U.154.231; 3.U.154.236; 3.U.154.237; 3.U.154.238; |
| 3.U.154.239; 3.U.154.154; 3.U.154.157; 3.U.154.166; 3.U.154.169; |
| 3.U.154.172; 3.U.154.175; 3.U.154.240; 3.U.154.244; 3.U.157.228; |
| 3.U.157.229; 3.U.157.230; 3.U.157.231; 3.U.157.236; 3.U.157.237; |
| 3.U.157.238; 3.U.157.239; 3.U.157.154; 3.U.157.157; 3.U.157.166; |
| 3.U.157.169; 3.U.157.172; 3.U.157.175; 3.U.157.240; 3.U.157.244; |
| 3.U.166.228; 3.U.166.229; 3.U.166.230; 3.U.166.231; 3.U.166.236; |
| 3.U.166.237; 3.U.166.238; 3.U.166.239; 3.U.166.154; 3.U.166.157; |
| 3.U.166.166; 3.U.166.169; 3.U.166.172; 3.U.166.175; 3.U.166.240; |
| 3.U.166.244; 3.U.169.228; 3.U.169.229; 3.U.169.230; 3.U.169.231; |
| 3.U.169.236; 3.U.169.237; 3.U.169.238; 3.U.169.239; 3.U.169.154; |
| 3.U.169.157; 3.U.169.166; 3.U.169.169; 3.U.169.172; 3.U.169.175; |
| 3.U.169.240; 3.U.169.244; 3.U.172.228; 3.U.172.229; 3.U.172.230; |
| 3.U.172.231; 3.U.172.236; 3.U.172.237; 3.U.172.238; 3.U.172.239; |
| 3.U.172.154; 3.U.172.157; 3.U.172.166; 3.U.172.169; 3.U.172.172; |
| 3.U.172.175; 3.U.172.240; 3.U.172.244; 3.U.175.228; 3.U.175.229; |
| 3.U.175.230; 3.U.175.231; 3.U.175.236; 3.U.175.237; 3.U.175.238; |
| 3.U.175.239; 3.U.175.154; 3.U.175.157; 3.U.175.166; 3.U.175.169; |

TABLE 100-continued

| |
|---|
| 3.U.175.172; 3.U.175.175; 3.U.175.240; 3.U.175.244; 3.U.240.228; 3.U.240.229; 3.U.240.230; 3.U.240.231; 3.U.240.236; 3.U.240.237; 3.U.240.238; 3.U.240.239; 3.U.240.154; 3.U.240.157; 3.U.240.166; 3.U.240.169; 3.U.240.172; 3.U.240.175; 3.U.240.240; 3.U.240.244; 3.U.244.228; 3.U.244.229; 3.U.244.230; 3.U.244.231; 3.U.244.236; 3.U.244.237; 3.U.244.238; 3.U.244.239; 3.U.244.154; 3.U.244.157; 3.U.244.166; 3.U.244.169; 3.U.244.172; 3.U.244.175; 3.U.244.240; 3.U.244.244; |
| Prodrugs of 3.W |
| 3.W.228.228; 3.W.228.229; 3.W.228.230; 3.W.228.231; 3.W.228.236; 3.W.228.237; 3.W.228.238; 3.W.228.239; 3.W.228.154; 3.W.228.157; 3.W.228.166; 3.W.228.169; 3.W.228.172; 3.W.228.175; 3.W.228.240; 3.W.228.244; 3.W.229.228; 3.W.229.229; 3.W.229.230; 3.W.229.231; 3.W.229.236; 3.W.229.237; 3.W.229.238; 3.W.229.239; 3.W.229.154; 3.W.229.157; 3.W.229.166; 3.W.229.169; 3.W.229.172; 3.W.229.175; 3.W.229.240; 3.W.229.244; 3.W.230.228; 3.W.230.229; 3.W.230.230; 3.W.230.231; 3.W.230.236; 3.W.230.237; 3.W.230.238; 3.W.230.239; 3.W.230.154; 3.W.230.157; 3.W.230.166; 3.W.230.169; 3.W.230.172; 3.W.230.175; 3.W.230.240; 3.W.230.244; 3.W.231.228; 3.W.231.229; 3.W.231.230; 3.W.231.231; 3.W.231.236; 3.W.231.237; 3.W.231.238; 3.W.231.239; 3.W.231.154; 3.W.231.157; 3.W.231.166; 3.W.231.169; 3.W.231.172; 3.W.231.175; 3.W.231.240; 3.W.231.244; 3.W.236.228; 3.W.236.229; 3.W.236.230; 3.W.236.231; 3.W.236.236; 3.W.236.237; 3.W.236.238; 3.W.236.239; 3.W.236.154; 3.W.236.157; 3.W.236.166; 3.W.236.169; 3.W.236.172; 3.W.236.175; 3.W.236.240; 3.W.236.244; 3.W.237.228; 3.W.237.229; 3.W.237.230; 3.W.237.231; 3.W.237.236; 3.W.237.237; 3.W.237.238; 3.W.237.239; 3.W.237.154; 3.W.237.157; 3.W.237.166; 3.W.237.169; 3.W.237.172; 3.W.237.175; 3.W.237.240; 3.W.237.244; 3.W.238.228; 3.W.238.229; 3.W.238.230; 3.W.238.231; 3.W.238.236; 3.W.238.237; 3.W.238.238; 3.W.238.239; 3.W.238.154; 3.W.238.157; 3.W.238.166; 3.W.238.169; 3.W.238.172; 3.W.238.175; 3.W.238.240; 3.W.238.244; 3.W.239.228; 3.W.239.229; 3.W.239.230; 3.W.239.231; 3.W.239.236; 3.W.239.237; 3.W.239.238; 3.W.239.239; 3.W.239.154; 3.W.239.157; 3.W.239.166; 3.W.239.169; 3.W.239.172; 3.W.239.175; 3.W.239.240; 3.W.239.244; 3.W.154.228; 3.W.154.229; 3.W.154.230; 3.W.154.231; 3.W.154.236; 3.W.154.237; 3.W.154.238; 3.W.154.239; 3.W.154.154; 3.W.154.157; 3.W.154.166; 3.W.154.169; 3.W.154.172; 3.W.154.175; 3.W.154.240; 3.W.154.244; 3.W.157.228; 3.W.157.229; 3.W.157.230; 3.W.157.231; 3.W.157.236; 3.W.157.237; 3.W.157.238; 3.W.157.239; 3.W.157.154; 3.W.157.157; 3.W.157.166; 3.W.157.169; 3.W.157.172; 3.W.157.175; 3.W.157.240; 3.W.157.244; 3.W.166.228; 3.W.166.229; 3.W.166.230; 3.W.166.231; 3.W.166.236; 3.W.166.237; 3.W.166.238; 3.W.166.239; 3.W.166.154; 3.W.166.157; 3.W.166.166; 3.W.166.169; 3.W.166.172; 3.W.166.175; 3.W.166.240; 3.W.166.244; 3.W.169.228; 3.W.169.229; 3.W.169.230; 3.W.169.231; 3.W.169.236; 3.W.169.237; 3.W.169.238; 3.W.169.239; 3.W.169.154; 3.W.169.157; 3.W.169.166; 3.W.169.169; 3.W.169.172; 3.W.169.175; 3.W.169.240; 3.W.169.244; 3.W.172.228; 3.W.172.229; 3.W.172.230; 3.W.172.231; 3.W.172.236; 3.W.172.237; 3.W.172.238; 3.W.172.239; 3.W.172.154; 3.W.172.157; 3.W.172.166; 3.W.172.169; 3.W.172.172; 3.W.172.175; 3.W.172.240; 3.W.172.244; 3.W.175.228; 3.W.175.229; 3.W.175.230; 3.W.175.231; 3.W.175.236; 3.W.175.237; 3.W.175.238; 3.W.175.239; 3.W.175.154; 3.W.175.157; 3.W.175.166; 3.W.175.169; 3.W.175.172; 3.W.175.175; 3.W.175.240; 3.W.175.244; 3.W.240.228; 3.W.240.229; 3.W.240.230; 3.W.240.231; 3.W.240.236; 3.W.240.237; 3.W.240.238; 3.W.240.239; 3.W.240.154; 3.W.240.157; 3.W.240.166; 3.W.240.169; 3.W.240.172; 3.W.240.175; 3.W.240.240; 3.W.240.244; 3.W.244.228; 3.W.244.229; 3.W.244.230; 3.W.244.231; 3.W.244.236; 3.W.244.237; 3.W.244.238; 3.W.244.239; 3.W.244.154; 3.W.244.157; 3.W.244.166; 3.W.244.169; 3.W.244.172; 3.W.244.175; 3.W.244.240; 3.W.244.244; |
| Prodrugs of 3.Y |
| 3.Y.228.228; 3.Y.228.229; 3.Y.228.230; 3.Y.228.231; 3.Y.228.236; 3.Y.228.237; 3.Y.228.238; 3.Y.228.239; 3.Y.228.154; 3.Y.228.157; 3.Y.228.166; 3.Y.228.169; 3.Y.228.172; 3.Y.228.175; 3.Y.228.240; 3.Y.228.244; 3.Y.229.228; 3.Y.229.229; 3.Y.229.230; 3.Y.229.231; 3.Y.229.236; 3.Y.229.237; 3.Y.229.238; 3.Y.229.239; 3.Y.229.154; 3.Y.229.157; 3.Y.229.166; 3.Y.229.169; 3.Y.229.172; 3.Y.229.175; 3.Y.229.240; 3.Y.229.244; 3.Y.230.228; 3.Y.230.229; 3.Y.230.230; 3.Y.230.231; 3.Y.230.236; 3.Y.230.237; 3.Y.230.238; 3.Y.230.239; 3.Y.230.154; 3.Y.230.157; 3.Y.230.166; 3.Y.230.169; 3.Y.230.172; 3.Y.230.175; 3.Y.230.240; 3.Y.230.244; 3.Y.231.228; 3.Y.231.229; 3.Y.231.230; 3.Y.231.231; 3.Y.231.236; 3.Y.231.237; 3.Y.231.238; 3.Y.231.239; 3.Y.231.154; 3.Y.231.157; 3.Y.231.166; 3.Y.231.169; 3.Y.231.172; 3.Y.231.175; 3.Y.231.240; 3.Y.231.244; 3.Y.236.228; 3.Y.236.229; 3.Y.236.230; 3.Y.236.231; 3.Y.236.236; 3.Y.236.237; 3.Y.236.238; 3.Y.236.239; 3.Y.236.154; 3.Y.236.157; 3.Y.236.166; 3.Y.236.169; 3.Y.236.172; 3.Y.236.175; 3.Y.236.240; 3.Y.236.244; 3.Y.237.228; 3.Y.237.229; 3.Y.237.230; 3.Y.237.231; 3.Y.237.236; 3.Y.237.237; 3.Y.237.238; 3.Y.237.239; 3.Y.237.154; 3.Y.237.157; 3.Y.237.166; 3.Y.237.169; 3.Y.237.172; 3.Y.237.175; 3.Y.237.240; 3.Y.237.244; 3.Y.238.228; 3.Y.238.229; 3.Y.238.230; 3.Y.238.231; 3.Y.238.236; 3.Y.238.237; 3.Y.238.238; 3.Y.238.239; 3.Y.238.154; 3.Y.238.157; 3.Y.238.166; |

TABLE 100-continued

3.Y.238.169; 3.Y.238.172; 3.Y.238.175; 3.Y.238.240; 3.Y.238.244; 3.Y.239.228; 3.Y.239.229; 3.Y.239.230; 3.Y.239.231; 3.Y.239.236; 3.Y.239.237; 3.Y.239.238; 3.Y.239.239; 3.Y.239.154; 3.Y.239.157; 3.Y.239.166; 3.Y.239.169; 3.Y.239.172; 3.Y.239.175; 3.Y.239.240; 3.Y.239.244; 3.Y.154.228; 3.Y.154.229; 3.Y.154.230; 3.Y.154.231; 3.Y.154.236; 3.Y.154.237; 3.Y.154.238; 3.Y.154.239; 3.Y.154.154; 3.Y.154.157; 3.Y.154.166; 3.Y.154.169; 3.Y.154.172; 3.Y.154.175; 3.Y.154.240; 3.Y.154.244; 3.Y.157.228; 3.Y.157.229; 3.Y.157.230; 3.Y.157.231; 3.Y.157.236; 3.Y.157.237; 3.Y.157.238; 3.Y.157.239; 3.Y.157.154; 3.Y.157.157; 3.Y.157.166; 3.Y.157.169; 3.Y.157.172; 3.Y.157.175; 3.Y.157.240; 3.Y.157.244; 3.Y.166.228; 3.Y.166.229; 3.Y.166.230; 3.Y.166.231; 3.Y.166.236; 3.Y.166.237; 3.Y.166.238; 3.Y.166.239; 3.Y.166.154; 3.Y.166.157; 3.Y.166.166; 3.Y.166.169; 3.Y.166.172; 3.Y.166.175; 3.Y.166.240; 3.Y.166.244; 3.Y.169.228; 3.Y.169.229; 3.Y.169.230; 3.Y.169.231; 3.Y.169.236; 3.Y.169.237; 3.Y.169.238; 3.Y.169.239; 3.Y.169.154; 3.Y.169.157; 3.Y.169.166; 3.Y.169.169; 3.Y.169.172; 3.Y.169.175; 3.Y.169.240; 3.Y.169.244; 3.Y.172.228; 3.Y.172.229; 3.Y.172.230; 3.Y.172.231; 3.Y.172.236; 3.Y.172.237; 3.Y.172.238; 3.Y.172.239; 3.Y.172.154; 3.Y.172.157; 3.Y.172.166; 3.Y.172.169; 3.Y.172.172; 3.Y.172.175; 3.Y.172.240; 3.Y.172.244; 3.Y.175.228; 3.Y.175.229; 3.Y.175.230; 3.Y.175.231; 3.Y.175.236; 3.Y.175.237; 3.Y.175.238; 3.Y.175.239; 3.Y.175.154; 3.Y.175.157; 3.Y.175.166; 3.Y.175.169; 3.Y.175.172; 3.Y.175.175; 3.Y.175.240; 3.Y.175.244; 3.Y.240.228; 3.Y.240.229; 3.Y.240.230; 3.Y.240.231; 3.Y.240.236; 3.Y.240.237; 3.Y.240.238; 3.Y.240.239; 3.Y.240.154; 3.Y.240.157; 3.Y.240.166; 3.Y.240.169; 3.Y.240.172; 3.Y.240.175; 3.Y.240.240; 3.Y.240.244; 3.Y.244.228; 3.Y.244.229; 3.Y.244.230; 3.Y.244.231; 3.Y.244.236; 3.Y.244.237; 3.Y.244.238; 3.Y.244.239; 3.Y.244.154; 3.Y.244.157; 3.Y.244.166; 3.Y.244.169; 3.Y.244.172; 3.Y.244.175; 3.Y.244.240; 3.Y.244.244;

Prodrugs of 4.B

4.B.228.228; 4.B.228.229; 4.B.228.230; 4.B.228.231; 4.B.228.236; 4.B.228.237; 4.B.228.238; 4.B.228.239; 4.B.228.154; 4.B.228.157; 4.B.228.166; 4.B.228.169; 4.B.228.172; 4.B.228.175; 4.B.228.240; 4.B.228.244; 4.B.229.228; 4.B.229.229; 4.B.229.230; 4.B.229.231; 4.B.229.236; 4.B.229.237; 4.B.229.238; 4.B.229.239; 4.B.229.154; 4.B.229.157; 4.B.229.166; 4.B.229.169; 4.B.229.172; 4.B.229.175; 4.B.229.240; 4.B.229.244; 4.B.230.228; 4.B.230.229; 4.B.230.230; 4.B.230.231; 4.B.230.236; 4.B.230.237; 4.B.230.238; 4.B.230.239; 4.B.230.154; 4.B.230.157; 4.B.230.166; 4.B.230.169; 4.B.230.172; 4.B.230.175; 4.B.230.240; 4.B.230.244; 4.B.231.228; 4.B.231.229; 4.B.231.230; 4.B.231.231; 4.B.231.236; 4.B.231.237; 4.B.231.238; 4.B.231.239; 4.B.231.154; 4.B.231.157; 4.B.231.166; 4.B.231.169; 4.B.231.172; 4.B.231.175; 4.B.231.240; 4.B.231.244; 4.B.236.228; 4.B.236.229; 4.B.236.230; 4.B.236.231; 4.B.236.236; 4.B.236.237; 4.B.236.238; 4.B.236.239; 4.B.236.154; 4.B.236.157; 4.B.236.166; 4.B.236.169; 4.B.236.172; 4.B.236.175; 4.B.236.240; 4.B.236.244; 4.B.237.228; 4.B.237.229; 4.B.237.230; 4.B.237.231; 4.B.237.236; 4.B.237.237; 4.B.237.238; 4.B.237.239; 4.B.237.154; 4.B.237.157; 4.B.237.166; 4.B.237.169; 4.B.237.172; 4.B.237.175; 4.B.237.240; 4.B.237.244; 4.B.238.228; 4.B.238.229; 4.B.238.230; 4.B.238.231; 4.B.238.236; 4.B.238.237; 4.B.238.238; 4.B.238.239; 4.B.238.154; 4.B.238.157; 4.B.238.166; 4.B.238.169; 4.B.238.172; 4.B.238.175; 4.B.238.240; 4.B.238.244; 4.B.239.228; 4.B.239.229; 4.B.239.230; 4.B.239.231; 4.B.239.236; 4.B.239.237; 4.B.239.238; 4.B.239.239; 4.B.239.154; 4.B.239.157; 4.B.239.166; 4.B.239.169; 4.B.239.172; 4.B.239.175; 4.B.239.240; 4.B.239.244; 4.B.154.228; 4.B.154.229; 4.B.154.230; 4.B.154.231; 4.B.154.236; 4.B.154.237; 4.B.154.238; 4.B.154.239; 4.B.154.154; 4.B.154.157; 4.B.154.166; 4.B.154.169; 4.B.154.172; 4.B.154.175; 4.B.154.240; 4.B.154.244; 4.B.157.228; 4.B.157.229; 4.B.157.230; 4.B.157.231; 4.B.157.236; 4.B.157.237; 4.B.157.238; 4.B.157.239; 4.B.157.154; 4.B.157.157; 4.B.157.166; 4.B.157.169; 4.B.157.172; 4.B.157.175; 4.B.157.240; 4.B.157.244; 4.B.166.228; 4.B.166.229; 4.B.166.230; 4.B.166.231; 4.B.166.236; 4.B.166.237; 4.B.166.238; 4.B.166.239; 4.B.166.154; 4.B.166.157; 4.B.166.166; 4.B.166.169; 4.B.166.172; 4.B.166.175; 4.B.166.240; 4.B.166.244; 4.B.169.228; 4.B.169.229; 4.B.169.230; 4.B.169.231; 4.B.169.236; 4.B.169.237; 4.B.169.238; 4.B.169.239; 4.B.169.154; 4.B.169.157; 4.B.169.166; 4.B.169.169; 4.B.169.172; 4.B.169.175; 4.B.169.240; 4.B.169.244; 4.B.172.228; 4.B.172.229; 4.B.172.230; 4.B.172.231; 4.B.172.236; 4.B.172.237; 4.B.172.238; 4.B.172.239; 4.B.172.154; 4.B.172.157; 4.B.172.166; 4.B.172.169; 4.B.172.172; 4.B.172.175; 4.B.172.240; 4.B.172.244; 4.B.175.228; 4.B.175.229; 4.B.175.230; 4.B.175.231; 4.B.175.236; 4.B.175.237; 4.B.175.238; 4.B.175.239; 4.B.175.154; 4.B.175.157; 4.B.175.166; 4.B.175.169; 4.B.175.172; 4.B.175.175; 4.B.175.240; 4.B.175.244; 4.B.240.228; 4.B.240.229; 4.B.240.230; 4.B.240.231; 4.B.240.236; 4.B.240.237; 4.B.240.238; 4.B.240.239; 4.B.240.154; 4.B.240.157; 4.B.240.166; 4.B.240.169; 4.B.240.172; 4.B.240.175; 4.B.240.240; 4.B.240.244; 4.B.244.228; 4.B.244.229; 4.B.244.230; 4.B.244.231; 4.B.244.236; 4.B.244.237; 4.B.244.238; 4.B.244.239; 4.B.244.154; 4.B.244.157; 4.B.244.166; 4.B.244.169; 4.B.244.172; 4.B.244.175; 4.B.244.240; 4.B.244.244;

Prodrugs of 4.D

4.D.228.228; 4.D.228.229; 4.D.228.230; 4.D.228.231; 4.D.228.236; 4.D.228.237; 4.D.228.238; 4.D.228.239; 4.D.228.154; 4.D.228.157; 4.D.228.166; 4.D.228.169; 4.D.228.172; 4.D.228.175; 4.D.228.240; 4.D.228.244; 4.D.229.228; 4.D.229.229; 4.D.229.230; 4.D.229.231; 4.D.229.236; 4.D.229.237; 4.D.229.238; 4.D.229.239; 4.D.229.154; 4.D.229.157; 4.D.229.166; 4.D.229.169; 4.D.229.172; 4.D.229.175; 4.D.229.240; 4.D.229.244; 4.D.230.228; 4.D.230.229; 4.D.230.230; 4.D.230.231; 4.D.230.236; 4.D.230.237; 4.D.230.238; 4.D.230.239;

TABLE 100-continued

| |
|---|
| 4.D.230.154; 4.D.230.157; 4.D.230.166; 4.D.230.169; 4.D.230.172; 4.D.230.175; 4.D.230.240; 4.D.230.244; 4.D.231.228; 4.D.231.229; 4.D.231.230; 4.D.231.231; 4.D.231.236; 4.D.231.237; 4.D.231.238; 4.D.231.239; 4.D.231.154; 4.D.231.157; 4.D.231.166; 4.D.231.169; 4.D.231.172; 4.D.231.175; 4.D.231.240; 4.D.231.244; 4.D.236.228; 4.D.236.229; 4.D.236.230; 4.D.236.231; 4.D.236.236; 4.D.236.237; 4.D.236.238; 4.D.236.239; 4.D.236.154; 4.D.236.157; 4.D.236.166; 4.D.236.169; 4.D.236.172; 4.D.236.175; 4.D.236.240; 4.D.236.244; 4.D.237.228; 4.D.237.229; 4.D.237.230; 4.D.237.231; 4.D.237.236; 4.D.237.237; 4.D.237.238; 4.D.237.239; 4.D.237.154; 4.D.237.157; 4.D.237.166; 4.D.237.169; 4.D.237.172; 4.D.237.175; 4.D.237.240; 4.D.237.244; 4.D.238.228; 4.D.238.229; 4.D.238.230; 4.D.238.231; 4.D.238.236; 4.D.238.237; 4.D.238.238; 4.D.238.239; 4.D.238.154; 4.D.238.157; 4.D.238.166; 4.D.238.169; 4.D.238.172; 4.D.238.175; 4.D.238.240; 4.D.238.244; 4.D.239.228; 4.D.239.229; 4.D.239.230; 4.D.239.231; 4.D.239.236; 4.D.239.237; 4.D.239.238; 4.D.239.239; 4.D.239.154; 4.D.239.157; 4.D.239.166; 4.D.239.169; 4.D.239.172; 4.D.239.175; 4.D.239.240; 4.D.239.244; 4.D.154.228; 4.D.154.229; 4.D.154.230; 4.D.154.231; 4.D.154.236; 4.D.154.237; 4.D.154.238; 4.D.154.239; 4.D.154.154; 4.D.154.157; 4.D.154.166; 4.D.154.169; 4.D.154.172; 4.D.154.175; 4.D.154.240; 4.D.154.244; 4.D.157.228; 4.D.157.229; 4.D.157.230; 4.D.157.231; 4.D.157.236; 4.D.157.237; 4.D.157.238; 4.D.157.239; 4.D.157.154; 4.D.157.157; 4.D.157.166; 4.D.157.169; 4.D.157.172; 4.D.157.175; 4.D.157.240; 4.D.157.244; 4.D.166.228; 4.D.166.229; 4.D.166.230; 4.D.166.231; 4.D.166.236; 4.D.166.237; 4.D.166.238; 4.D.166.239; 4.D.166.154; 4.D.166.157; 4.D.166.166; 4.D.166.169; 4.D.166.172; 4.D.166.175; 4.D.166.240; 4.D.166.244; 4.D.169.228; 4.D.169.229; 4.D.169.230; 4.D.169.231; 4.D.169.236; 4.D.169.237; 4.D.169.238; 4.D.169.239; 4.D.169.154; 4.D.169.157; 4.D.169.166; 4.D.169.169; 4.D.169.172; 4.D.169.175; 4.D.169.240; 4.D.169.244; 4.D.172.228; 4.D.172.229; 4.D.172.230; 4.D.172.231; 4.D.172.236; 4.D.172.237; 4.D.172.238; 4.D.172.239; 4.D.172.154; 4.D.172.157; 4.D.172.166; 4.D.172.169; 4.D.172.172; 4.D.172.175; 4.D.172.240; 4.D.172.244; 4.D.175.228; 4.D.175.229; 4.D.175.230; 4.D.175.231; 4.D.175.236; 4.D.175.237; 4.D.175.238; 4.D.175.239; 4.D.175.154; 4.D.175.157; 4.D.175.166; 4.D.175.169; 4.D.175.172; 4.D.175.175; 4.D.175.240; 4.D.175.244; 4.D.240.228; 4.D.240.229; 4.D.240.230; 4.D.240.231; 4.D.240.236; 4.D.240.237; 4.D.240.238; 4.D.240.239; 4.D.240.154; 4.D.240.157; 4.D.240.166; 4.D.240.169; 4.D.240.172; 4.D.240.175; 4.D.240.240; 4.D.240.244; 4.D.244.228; 4.D.244.229; 4.D.244.230; 4.D.244.231; 4.D.244.236; 4.D.244.237; 4.D.244.238; 4.D.244.239; 4.D.244.154; 4.D.244.157; 4.D.244.166; 4.D.244.169; 4.D.244.172; 4.D.244.175; 4.D.244.240; 4.D.244.244; |
| Prodrugs of 4.E |
| 4.E.228.228; 4.E.228.229; 4.E.228.230; 4.E.228.231; 4.E.228.236; 4.E.228.237; 4.E.228.238; 4.E.228.239; 4.E.228.154; 4.E.228.157; 4.E.228.166; 4.E.228.169; 4.E.228.172; 4.E.228.175; 4.E.228.240; 4.E.228.244; 4.E.229.228; 4.E.229.229; 4.E.229.230; 4.E.229.231; 4.E.229.236; 4.E.229.237; 4.E.229.238; 4.E.229.239; 4.E.229.154; 4.E.229.157; 4.E.229.166; 4.E.229.169; 4.E.229.172; 4.E.229.175; 4.E.229.240; 4.E.229.244; 4.E.230.228; 4.E.230.229; 4.E.230.230; 4.E.230.231; 4.E.230.236; 4.E.230.237; 4.E.230.238; 4.E.230.239; 4.E.230.154; 4.E.230.157; 4.E.230.166; 4.E.230.169; 4.E.230.172; 4.E.230.175; 4.E.230.240; 4.E.230.244; 4.E.231.228; 4.E.231.229; 4.E.231.230; 4.E.231.231; 4.E.231.236; 4.E.231.237; 4.E.231.238; 4.E.231.239; 4.E.231.154; 4.E.231.157; 4.E.231.166; 4.E.231.169; 4.E.231.172; 4.E.231.175; 4.E.231.240; 4.E.231.244; 4.E.236.228; 4.E.236.229; 4.E.236.230; 4.E.236.231; 4.E.236.236; 4.E.236.237; 4.E.236.238; 4.E.236.239; 4.E.236.154; 4.E.236.157; 4.E.236.166; 4.E.236.169; 4.E.236.172; 4.E.236.175; 4.E.236.240; 4.E.236.244; 4.E.237.228; 4.E.237.229; 4.E.237.230; 4.E.237.231; 4.E.237.236; 4.E.237.237; 4.E.237.238; 4.E.237.239; 4.E.237.154; 4.E.237.157; 4.E.237.166; 4.E.237.169; 4.E.237.172; 4.E.237.175; 4.E.237.240; 4.E.237.244; 4.E.238.228; 4.E.238.229; 4.E.238.230; 4.E.238.231; 4.E.238.236; 4.E.238.237; 4.E.238.238; 4.E.238.239; 4.E.238.154; 4.E.238.157; 4.E.238.166; 4.E.238.169; 4.E.238.172; 4.E.238.175; 4.E.238.240; 4.E.238.244; 4.E.239.228; 4.E.239.229; 4.E.239.230; 4.E.239.231; 4.E.239.236; 4.E.239.237; 4.E.239.238; 4.E.239.239; 4.E.239.154; 4.E.239.157; 4.E.239.166; 4.E.239.169; 4.E.239.172; 4.E.239.175; 4.E.239.240; 4.E.239.244; 4.E.154.228; 4.E.154.229; 4.E.154.230; 4.E.154.231; 4.E.154.236; 4.E.154.237; 4.E.154.238; 4.E.154.239; 4.E.154.154; 4.E.154.157; 4.E.154.166; 4.E.154.169; 4.E.154.172; 4.E.154.175; 4.E.154.240; 4.E.154.244; 4.E.157.228; 4.E.157.229; 4.E.157.230; 4.E.157.231; 4.E.157.236; 4.E.157.237; 4.E.157.238; 4.E.157.239; 4.E.157.154; 4.E.157.157; 4.E.157.166; 4.E.157.169; 4.E.157.172; 4.E.157.175; 4.E.157.240; 4.E.157.244; 4.E.166.228; 4.E.166.229; 4.E.166.230; 4.E.166.231; 4.E.166.236; 4.E.166.237; 4.E.166.238; 4.E.166.239; 4.E.166.154; 4.E.166.157; 4.E.166.166; 4.E.166.169; 4.E.166.172; 4.E.166.175; 4.E.166.240; 4.E.166.244; 4.E.169.228; 4.E.169.229; 4.E.169.230; 4.E.169.231; 4.E.169.236; 4.E.169.237; 4.E.169.238; 4.E.169.239; 4.E.169.154; 4.E.169.157; 4.E.169.166; 4.E.169.169; 4.E.169.172; 4.E.169.175; 4.E.169.240; 4.E.169.244; 4.E.172.228; 4.E.172.229; 4.E.172.230; 4.E.172.231; 4.E.172.236; 4.E.172.237; 4.E.172.238; 4.E.172.239; 4.E.172.154; 4.E.172.157; 4.E.172.166; 4.E.172.169; 4.E.172.172; 4.E.172.175; 4.E.172.240; 4.E.172.244; 4.E.175.228; |

TABLE 100-continued

| |
|---|
| 4.E.175.229; 4.E.175.230; 4.E.175.231; 4.E.175.236; 4.E.175.237; 4.E.175.238; |
| 4.E.175.239; 4.E.175.154; 4.E.175.157; 4.E.175.166; 4.E.175.169; 4.E.175.172; |
| 4.E.175.175; 4.E.175.240; 4.E.175.244; 4.E.240.228; 4.E.240.229; 4.E.240.230; |
| 4.E.240.231; 4.E.240.236; 4.E.240.237; 4.E.240.238; 4.E.240.239; 4.E.240.154; |
| 4.E.240.157; 4.E.240.166; 4.E.240.169; 4.E.240.172; 4.E.240.175; 4.E.240.240; |
| 4.E.240.244; 4.E.244.228; 4.E.244.229; 4.E.244.230; 4.E.244.231; 4.E.244.236; |
| 4.E.244.237; 4.E.244.238; 4.E.244.239; 4.E.244.154; 4.E.244.157; 4.E.244.166; |
| 4.E.244.169; 4.E.244.172; 4.E.244.175; 4.E.244.240; 4.E.244.244; |
| Prodrugs of 4.G |
| 4.G.228.228; 4.G.228.229; 4.G.228.230; 4.G.228.231; 4.G.228.236; |
| 4.G.228.237; 4.G.228.238; 4.G.228.239; 4.G.228.154; 4.G.228.157; |
| 4.G.228.166; 4.G.228.169; 4.G.228.172; 4.G.228.175; 4.G.228.240; |
| 4.G.228.244; 4.G.229.228; 4.G.229.229; 4.G.229.230; 4.G.229.231; |
| 4.G.229.236; 4.G.229.237; 4.G.229.238; 4.G.229.239; 4.G.229.154; |
| 4.G.229.157; 4.G.229.166; 4.G.229.169; 4.G.229.172; 4.G.229.175; |
| 4.G.229.240; 4.G.229.244; 4.G.230.228; 4.G.230.229; 4.G.230.230; |
| 4.G.230.231; 4.G.230.236; 4.G.230.237; 4.G.230.238; 4.G.230.239; |
| 4.G.230.154; 4.G.230.157; 4.G.230.166; 4.G.230.169; 4.G.230.172; |
| 4.G.230.175; 4.G.230.240; 4.G.230.244; 4.G.231.228; 4.G.231.229; |
| 4.G.231.230; 4.G.231.231; 4.G.231.236; 4.G.231.237; 4.G.231.238; |
| 4.G.231.239; 4.G.231.154; 4.G.231.157; 4.G.231.166; 4.G.231.169; |
| 4.G.231.172; 4.G.231.175; 4.G.231.240; 4.G.231.244; 4.G.236.228; |
| 4.G.236.229; 4.G.236.230; 4.G.236.231; 4.G.236.236; 4.G.236.237; |
| 4.G.236.238; 4.G.236.239; 4.G.236.154; 4.G.236.157; 4.G.236.166; |
| 4.G.236.169; 4.G.236.172; 4.G.236.175; 4.G.236.240; 4.G.236.244; |
| 4.G.237.228; 4.G.237.229; 4.G.237.230; 4.G.237.231; 4.G.237.236; |
| 4.G.237.237; 4.G.237.238; 4.G.237.239; 4.G.237.154; 4.G.237.157; |
| 4.G.237.166; 4.G.237.169; 4.G.237.172; 4.G.237.175; 4.G.237.240; |
| 4.G.237.244; 4.G.238.228; 4.G.238.229; 4.G.238.230; 4.G.238.231; |
| 4.G.238.236; 4.G.238.237; 4.G.238.238; 4.G.238.239; 4.G.238.154; |
| 4.G.238.157; 4.G.238.166; 4.G.238.169; 4.G.238.172; 4.G.238.175; |
| 4.G.238.240; 4.G.238.244; 4.G.239.228; 4.G.239.229; 4.G.239.230; |
| 4.G.239.231; 4.G.239.236; 4.G.239.237; 4.G.239.238; 4.G.239.239; |
| 4.G.239.154; 4.G.239.157; 4.G.239.166; 4.G.239.169; 4.G.239.172; |
| 4.G.239.175; 4.G.239.240; 4.G.239.244; 4.G.154.228; 4.G.154.229; |
| 4.G.154.230; 4.G.154.231; 4.G.154.236; 4.G.154.237; 4.G.154.238; |
| 4.G.154.239; 4.G.154.154; 4.G.154.157; 4.G.154.166; 4.G.154.169; |
| 4.G.154.172; 4.G.154.175; 4.G.154.240; 4.G.154.244; 4.G.157.228; |
| 4.G.157.229; 4.G.157.230; 4.G.157.231; 4.G.157.236; 4.G.157.237; |
| 4.G.157.238; 4.G.157.239; 4.G.157.154; 4.G.157.157; 4.G.157.166; |
| 4.G.157.169; 4.G.157.172; 4.G.157.175; 4.G.157.240; 4.G.157.244; |
| 4.G.166.228; 4.G.166.229; 4.G.166.230; 4.G.166.231; 4.G.166.236; |
| 4.G.166.237; 4.G.166.238; 4.G.166.239; 4.G.166.154; 4.G.166.157; |
| 4.G.166.166; 4.G.166.169; 4.G.166.172; 4.G.166.175; 4.G.166.240; |
| 4.G.166.244; 4.G.169.228; 4.G.169.229; 4.G.169.230; 4.G.169.231; |
| 4.G.169.236; 4.G.169.237; 4.G.169.238; 4.G.169.239; 4.G.169.154; |
| 4.G.169.157; 4.G.169.166; 4.G.169.169; 4.G.169.172; 4.G.169.175; |
| 4.G.169.240; 4.G.169.244; 4.G.172.228; 4.G.172.229; 4.G.172.230; |
| 4.G.172.231; 4.G.172.236; 4.G.172.237; 4.G.172.238; 4.G.172.239; |
| 4.G.172.154; 4.G.172.157; 4.G.172.166; 4.G.172.169; 4.G.172.172; |
| 4.G.172.175; 4.G.172.240; 4.G.172.244; 4.G.175.228; 4.G.175.229; |
| 4.G.175.230; 4.G.175.231; 4.G.175.236; 4.G.175.237; 4.G.175.238; |
| 4.G.175.239; 4.G.175.154; 4.G.175.157; 4.G.175.166; 4.G.175.169; |
| 4.G.175.172; 4.G.175.175; 4.G.175.240; 4.G.175.244; 4.G.240.228; |
| 4.G.240.229; 4.G.240.230; 4.G.240.231; 4.G.240.236; 4.G.240.237; |
| 4.G.240.238; 4.G.240.239; 4.G.240.154; 4.G.240.157; 4.G.240.166; |
| 4.G.240.169; 4.G.240.172; 4.G.240.175; 4.G.240.240; 4.G.240.244; |
| 4.G.244.228; 4.G.244.229; 4.G.244.230; 4.G.244.231; 4.G.244.236; |
| 4.G.244.237; 4.G.244.238; 4.G.244.239; 4.G.244.154; 4.G.244.157; |
| 4.G.244.166; 4.G.244.169; 4.G.244.172; 4.G.244.175; 4.G.244.240; 4.G.244.244; |
| Prodrugs of 4.I |
| 4.I.228.228; 4.I.228.229; 4.I.228.230; 4.I.228.231; 4.I.228.236; 4.I.228.237; |
| 4.I.228.238; 4.I.228.239; 4.I.228.154; 4.I.228.157; 4.I.228.166; 4.I.228.169; |
| 4.I.228.172; 4.I.228.175; 4.I.228.240; 4.I.228.244; 4.I.229.228; 4.I.229.229; |
| 4.I.229.230; 4.I.229.231; 4.I.229.236; 4.I.229.237; 4.I.229.238; 4.I.229.239; |
| 4.I.229.154; 4.I.229.157; 4.I.229.166; 4.I.229.169; 4.I.229.172; 4.I.229.175; |
| 4.I.229.240; 4.I.229.244; 4.I.230.228; 4.I.230.229; 4.I.230.230; 4.I.230.231; |
| 4.I.230.236; 4.I.230.237; 4.I.230.238; 4.I.230.239; 4.I.230.154; 4.I.230.157; |
| 4.I.230.166; 4.I.230.169; 4.I.230.172; 4.I.230.175; 4.I.230.240; 4.I.230.244; |
| 4.I.231.228; 4.I.231.229; 4.I.231.230; 4.I.231.231; 4.I.231.236; 4.I.231.237; |
| 4.I.231.238; 4.I.231.239; 4.I.231.154; 4.I.231.157; 4.I.231.166; 4.I.231.169; |
| 4.I.231.172; 4.I.231.175; 4.I.231.240; 4.I.231.244; 4.I.236.228; 4.I.236.229; |
| 4.I.236.230; 4.I.236.231; 4.I.236.236; 4.I.236.237; 4.I.236.238; 4.I.236.239; |
| 4.I.236.154; 4.I.236.157; 4.I.236.166; 4.I.236.169; 4.I.236.172; 4.I.236.175; |
| 4.I.236.240; 4.I.236.244; 4.I.237.228; 4.I.237.229; 4.I.237.230; 4.I.237.231; |
| 4.I.237.236; 4.I.237.237; 4.I.237.238; 4.I.237.239; 4.I.237.154; 4.I.237.157; |
| 4.I.237.166; 4.I.237.169; 4.I.237.172; 4.I.237.175; 4.I.237.240; 4.I.237.244; |
| 4.I.238.228; 4.I.238.229; 4.I.238.230; 4.I.238.231; 4.I.238.236; 4.I.238.237; |

TABLE 100-continued

4.I.238.238; 4.I.238.239; 4.I.238.154; 4.I.238.157; 4.I.238.166; 4.I.238.169; 4.I.238.172; 4.I.238.175; 4.I.238.240; 4.I.238.244; 4.I.239.228; 4.I.239.229; 4.I.239.230; 4.I.239.231; 4.I.239.236; 4.I.239.237; 4.I.239.238; 4.I.239.239; 4.I.239.154; 4.I.239.157; 4.I.239.166; 4.I.239.169; 4.I.239.172; 4.I.239.175; 4.I.239.240; 4.I.239.244; 4.I.154.228; 4.I.154.229; 4.I.154.230; 4.I.154.231; 4.I.154.236; 4.I.154.237; 4.I.154.238; 4.I.154.239; 4.I.154.154; 4.I.154.157; 4.I.154.166; 4.I.154.169; 4.I.154.172; 4.I.154.175; 4.I.154.240; 4.I.154.244; 4.I.157.228; 4.I.157.229; 4.I.157.230; 4.I.157.231; 4.I.157.236; 4.I.157.237; 4.I.157.238; 4.I.157.239; 4.I.157.154; 4.I.157.157; 4.I.157.166; 4.I.157.169; 4.I.157.172; 4.I.157.175; 4.I.157.240; 4.I.157.244; 4.I.166.228; 4.I.166.229; 4.I.166.230; 4.I.166.231; 4.I.166.236; 4.I.166.237; 4.I.166.238; 4.I.166.239; 4.I.166.154; 4.I.166.157; 4.I.166.166; 4.I.166.169; 4.I.166.172; 4.I.166.175; 4.I.166.240; 4.I.166.244; 4.I.169.228; 4.I.169.229; 4.I.169.230; 4.I.169.231; 4.I.169.236; 4.I.169.237; 4.I.169.238; 4.I.169.239; 4.I.169.154; 4.I.169.157; 4.I.169.166; 4.I.169.169; 4.I.169.172; 4.I.169.175; 4.I.169.240; 4.I.169.244; 4.I.172.228; 4.I.172.229; 4.I.172.230; 4.I.172.231; 4.I.172.236; 4.I.172.237; 4.I.172.238; 4.I.172.239; 4.I.172.154; 4.I.172.157; 4.I.172.166; 4.I.172.169; 4.I.172.172; 4.I.172.175; 4.I.172.240; 4.I.172.244; 4.I.175.228; 4.I.175.229; 4.I.175.230; 4.I.175.231; 4.I.175.236; 4.I.175.237; 4.I.175.238; 4.I.175.239; 4.I.175.154; 4.I.175.157; 4.I.175.166; 4.I.175.169; 4.I.175.172; 4.I.175.175; 4.I.175.240; 4.I.175.244; 4.I.240.228; 4.I.240.229; 4.I.240.230; 4.I.240.231; 4.I.240.236; 4.I.240.237; 4.I.240.238; 4.I.240.239; 4.I.240.154; 4.I.240.157; 4.I.240.166; 4.I.240.169; 4.I.240.172; 4.I.240.175; 4.I.240.240; 4.I.240.244; 4.I.244.228; 4.I.244.229; 4.I.244.230; 4.I.244.231; 4.I.244.236; 4.I.244.237; 4.I.244.238; 4.I.244.239; 4.I.244.154; 4.I.244.157; 4.I.244.166; 4.I.244.169; 4.I.244.172; 4.I.244.175; 4.I.244.240; 4.I.244.244;

Prodrugs of 4.J

4.J.228.228; 4.J.228.229; 4.J.228.230; 4.J.228.231; 4.J.228.236; 4.J.228.237; 4.J.228.238; 4.J.228.239; 4.J.228.154; 4.J.228.157; 4.J.228.166; 4.J.228.169; 4.J.228.172; 4.J.228.175; 4.J.228.240; 4.J.228.244; 4.J.229.228; 4.J.229.229; 4.J.229.230; 4.J.229.231; 4.J.229.236; 4.J.229.237; 4.J.229.238; 4.J.229.239; 4.J.229.154; 4.J.229.157; 4.J.229.166; 4.J.229.169; 4.J.229.172; 4.J.229.175; 4.J.229.240; 4.J.229.244; 4.J.230.228; 4.J.230.229; 4.J.230.230; 4.J.230.231; 4.J.230.236; 4.J.230.237; 4.J.230.238; 4.J.230.239; 4.J.230.154; 4.J.230.157; 4.J.230.166; 4.J.230.169; 4.J.230.172; 4.J.230.175; 4.J.230.240; 4.J.230.244; 4.J.231.228; 4.J.231.229; 4.J.231.230; 4.J.231.231; 4.J.231.236; 4.J.231.237; 4.J.231.238; 4.J.231.239; 4.J.231.154; 4.J.231.157; 4.J.231.166; 4.J.231.169; 4.J.231.172; 4.J.231.175; 4.J.231.240; 4.J.231.244; 4.J.236.228; 4.J.236.229; 4.J.236.230; 4.J.236.231; 4.J.236.236; 4.J.236.237; 4.J.236.238; 4.J.236.239; 4.J.236.154; 4.J.236.157; 4.J.236.166; 4.J.236.169; 4.J.236.172; 4.J.236.175; 4.J.236.240; 4.J.236.244; 4.J.237.228; 4.J.237.229; 4.J.237.230; 4.J.237.231; 4.J.237.236; 4.J.237.237; 4.J.237.238; 4.J.237.239; 4.J.237.154; 4.J.237.157; 4.J.237.166; 4.J.237.169; 4.J.237.172; 4.J.237.175; 4.J.237.240; 4.J.237.244; 4.J.238.228; 4.J.238.229; 4.J.238.230; 4.J.238.231; 4.J.238.236; 4.J.238.237; 4.J.238.238; 4.J.238.239; 4.J.238.154; 4.J.238.157; 4.J.238.166; 4.J.238.169; 4.J.238.172; 4.J.238.175; 4.J.238.240; 4.J.238.244; 4.J.239.228; 4.J.239.229; 4.J.239.230; 4.J.239.231; 4.J.239.236; 4.J.239.237; 4.J.239.238; 4.J.239.239; 4.J.239.154; 4.J.239.157; 4.J.239.166; 4.J.239.169; 4.J.239.172; 4.J.239.175; 4.J.239.240; 4.J.239.244; 4.J.154.228; 4.J.154.229; 4.J.154.230; 4.J.154.231; 4.J.154.236; 4.J.154.237; 4.J.154.238; 4.J.154.239; 4.J.154.154; 4.J.154.157; 4.J.154.166; 4.J.154.169; 4.J.154.172; 4.J.154.175; 4.J.154.240; 4.J.154.244; 4.J.157.228; 4.J.157.229; 4.J.157.230; 4.J.157.231; 4.J.157.236; 4.J.157.237; 4.J.157.238; 4.J.157.239; 4.J.157.154; 4.J.157.157; 4.J.157.166; 4.J.157.169; 4.J.157.172; 4.J.157.175; 4.J.157.240; 4.J.157.244; 4.J.166.228; 4.J.166.229; 4.J.166.230; 4.J.166.231; 4.J.166.236; 4.J.166.237; 4.J.166.238; 4.J.166.239; 4.J.166.154; 4.J.166.157; 4.J.166.166; 4.J.166.169; 4.J.166.172; 4.J.166.175; 4.J.166.240; 4.J.166.244; 4.J.169.228; 4.J.169.229; 4.J.169.230; 4.J.169.231; 4.J.169.236; 4.J.169.237; 4.J.169.238; 4.J.169.239; 4.J.169.154; 4.J.169.157; 4.J.169.166; 4.J.169.169; 4.J.169.172; 4.J.169.175; 4.J.169.240; 4.J.169.244; 4.J.172.228; 4.J.172.229; 4.J.172.230; 4.J.172.231; 4.J.172.236; 4.J.172.237; 4.J.172.238; 4.J.172.239; 4.J.172.154; 4.J.172.157; 4.J.172.166; 4.J.172.169; 4.J.172.172; 4.J.172.175; 4.J.172.240; 4.J.172.244; 4.J.175.228; 4.J.175.229; 4.J.175.230; 4.J.175.231; 4.J.175.236; 4.J.175.237; 4.J.175.238; 4.J.175.239; 4.J.175.154; 4.J.175.157; 4.J.175.166; 4.J.175.169; 4.J.175.172; 4.J.175.175; 4.J.175.240; 4.J.175.244; 4.J.240.228; 4.J.240.229; 4.J.240.230; 4.J.240.231; 4.J.240.236; 4.J.240.237; 4.J.240.238; 4.J.240.239; 4.J.240.154; 4.J.240.157; 4.J.240.166; 4.J.240.169; 4.J.240.172; 4.J.240.175; 4.J.240.240; 4.J.240.244; 4.J.244.228; 4.J.244.229; 4.J.244.230; 4.J.244.231; 4.J.244.236; 4.J.244.237; 4.J.244.238; 4.J.244.239; 4.J.244.154; 4.J.244.157; 4.J.244.166; 4.J.244.169; 4.J.244.172; 4.J.244.175; 4.J.244.240; 4.J.244.244;

Prodrugs of 4.L

4.L.228.228; 4.L.228.229; 4.L.228.230; 4.L.228.231; 4.L.228.236; 4.L.228.237; 4.L.228.238; 4.L.228.239; 4.L.228.154; 4.L.228.157; 4.L.228.166; 4.L.228.169; 4.L.228.172; 4.L.228.175; 4.L.228.240; 4.L.228.244; 4.L.229.228; 4.L.229.229; 4.L.229.230; 4.L.229.231; 4.L.229.236; 4.L.229.237; 4.L.229.238; 4.L.229.239; 4.L.229.154; 4.L.229.157; 4.L.229.166; 4.L.229.169; 4.L.229.172; 4.L.229.175; 4.L.229.240; 4.L.229.244; 4.L.230.228; 4.L.230.229; 4.L.230.230; 4.L.230.231; 4.L.230.236; 4.L.230.237; 4.L.230.238; 4.L.230.239; 4.L.230.154;

TABLE 100-continued

4.L.230.157; 4.L.230.166; 4.L.230.169; 4.L.230.172; 4.L.230.175; 4.L.230.240;
4.L.230.244; 4.L.231.228; 4.L.231.229; 4.L.231.230; 4.L.231.231; 4.L.231.236;
4.L.231.237; 4.L.231.238; 4.L.231.239; 4.L.231.154; 4.L.231.157; 4.L.231.166;
4.L.231.169; 4.L.231.172; 4.L.231.175; 4.L.231.240; 4.L.231.244; 4.L.236.228;
4.L.236.229; 4.L.236.230; 4.L.236.231; 4.L.236.236; 4.L.236.237; 4.L.236.238;
4.L.236.239; 4.L.236.154; 4.L.236.157; 4.L.236.166; 4.L.236.169; 4.L.236.172;
4.L.236.175; 4.L.236.240; 4.L.236.244; 4.L.237.228; 4.L.237.229; 4.L.237.230;
4.L.237.231; 4.L.237.236; 4.L.237.237; 4.L.237.238; 4.L.237.239; 4.L.237.154;
4.L.237.157; 4.L.237.166; 4.L.237.169; 4.L.237.172; 4.L.237.175; 4.L.237.240;
4.L.237.244; 4.L.238.228; 4.L.238.229; 4.L.238.230; 4.L.238.231; 4.L.238.236;
4.L.238.237; 4.L.238.238; 4.L.238.239; 4.L.238.154; 4.L.238.157; 4.L.238.166;
4.L.238.169; 4.L.238.172; 4.L.238.175; 4.L.238.240; 4.L.238.244; 4.L.239.228;
4.L.239.229; 4.L.239.230; 4.L.239.231; 4.L.239.236; 4.L.239.237; 4.L.239.238;
4.L.239.239; 4.L.239.154; 4.L.239.157; 4.L.239.166; 4.L.239.169; 4.L.239.172;
4.L.239.175; 4.L.239.240; 4.L.239.244; 4.L.154.228; 4.L.154.229; 4.L.154.230;
4.L.154.231; 4.L.154.236; 4.L.154.237; 4.L.154.238; 4.L.154.239; 4.L.154.154;
4.L.154.157; 4.L.154.166; 4.L.154.169; 4.L.154.172; 4.L.154.175; 4.L.154.240;
4.L.154.244; 4.L.157.228; 4.L.157.229; 4.L.157.230; 4.L.157.231; 4.L.157.236;
4.L.157.237; 4.L.157.238; 4.L.157.239; 4.L.157.154; 4.L.157.157; 4.L.157.166;
4.L.157.169; 4.L.157.172; 4.L.157.175; 4.L.157.240; 4.L.157.244; 4.L.166.228;
4.L.166.229; 4.L.166.230; 4.L.166.231; 4.L.166.236; 4.L.166.237; 4.L.166.238;
4.L.166.239; 4.L.166.154; 4.L.166.157; 4.L.166.166; 4.L.166.169; 4.L.166.172;
4.L.166.175; 4.L.166.240; 4.L.166.244; 4.L.169.228; 4.L.169.229; 4.L.169.230;
4.L.169.231; 4.L.169.236; 4.L.169.237; 4.L.169.238; 4.L.169.239; 4.L.169.154;
4.L.169.157; 4.L.169.166; 4.L.169.169; 4.L.169.172; 4.L.169.175; 4.L.169.240;
4.L.169.244; 4.L.172.228; 4.L.172.229; 4.L.172.230; 4.L.172.231; 4.L.172.236;
4.L.172.237; 4.L.172.238; 4.L.172.239; 4.L.172.154; 4.L.172.157; 4.L.172.166;
4.L.172.169; 4.L.172.172; 4.L.172.175; 4.L.172.240; 4.L.172.244; 4.L.175.228;
4.L.175.229; 4.L.175.230; 4.L.175.231; 4.L.175.236; 4.L.175.237; 4.L.175.238;
4.L.175.239; 4.L.175.154; 4.L.175.157; 4.L.175.166; 4.L.175.169; 4.L.175.172;
4.L.175.175; 4.L.175.240; 4.L.175.244; 4.L.240.228; 4.L.240.229; 4.L.240.230;
4.L.240.231; 4.L.240.236; 4.L.240.237; 4.L.240.238; 4.L.240.239; 4.L.240.154;
4.L.240.157; 4.L.240.166; 4.L.240.169; 4.L.240.172; 4.L.240.175; 4.L.240.240;
4.L.240.244; 4.L.244.228; 4.L.244.229; 4.L.244.230; 4.L.244.231; 4.L.244.236;
4.L.244.237; 4.L.244.238; 4.L.244.239; 4.L.244.154; 4.L.244.157; 4.L.244.166;
4.L.244.169; 4.L.244.172; 4.L.244.175; 4.L.244.240; 4.L.244.244;

Prodrugs of 4.O

4.O.228.228; 4.O.228.229; 4.O.228.230; 4.O.228.231; 4.O.228.236;
4.O.228.237; 4.O.228.238; 4.O.228.239; 4.O.228.154; 4.O.228.157;
4.O.228.166; 4.O.228.169; 4.O.228.172; 4.O.228.175; 4.O.228.240;
4.O.228.244; 4.O.229.228; 4.O.229.229; 4.O.229.230; 4.O.229.231;
4.O.229.236; 4.O.229.237; 4.O.229.238; 4.O.229.239; 4.O.229.154;
4.O.229.157; 4.O.229.166; 4.O.229.169; 4.O.229.172; 4.O.229.175;
4.O.229.240; 4.O.229.244; 4.O.230.228; 4.O.230.229; 4.O.230.230;
4.O.230.231; 4.O.230.236; 4.O.230.237; 4.O.230.238; 4.O.230.239;
4.O.230.154; 4.O.230.157; 4.O.230.166; 4.O.230.169; 4.O.230.172;
4.O.230.175; 4.O.230.240; 4.O.230.244; 4.O.231.228; 4.O.231.229;
4.O.231.230; 4.O.231.231; 4.O.231.236; 4.O.231.237; 4.O.231.238;
4.O.231.239; 4.O.231.154; 4.O.231.157; 4.O.231.166; 4.O.231.169;
4.O.231.172; 4.O.231.175; 4.O.231.240; 4.O.231.244; 4.O.236.228;
4.O.236.229; 4.O.236.230; 4.O.236.231; 4.O.236.236; 4.O.236.237;
4.O.236.238; 4.O.236.239; 4.O.236.154; 4.O.236.157; 4.O.236.166;
4.O.236.169; 4.O.236.172; 4.O.236.175; 4.O.236.240; 4.O.236.244;
4.O.237.228; 4.O.237.229; 4.O.237.230; 4.O.237.231; 4.O.237.236;
4.O.237.237; 4.O.237.238; 4.O.237.239; 4.O.237.154; 4.O.237.157;
4.O.237.166; 4.O.237.169; 4.O.237.172; 4.O.237.175; 4.O.237.240;
4.O.237.244; 4.O.238.228; 4.O.238.229; 4.O.238.230; 4.O.238.231;
4.O.238.236; 4.O.238.237; 4.O.238.238; 4.O.238.239; 4.O.238.154;
4.O.238.157; 4.O.238.166; 4.O.238.169; 4.O.238.172; 4.O.238.175;
4.O.238.240; 4.O.238.244; 4.O.239.228; 4.O.239.229; 4.O.239.230;
4.O.239.231; 4.O.239.236; 4.O.239.237; 4.O.239.238; 4.O.239.239;
4.O.239.154; 4.O.239.157; 4.O.239.166; 4.O.239.169; 4.O.239.172;
4.O.239.175; 4.O.239.240; 4.O.239.244; 4.O.154.228; 4.O.154.229;
4.O.154.230; 4.O.154.231; 4.O.154.236; 4.O.154.237; 4.O.154.238;
4.O.154.239; 4.O.154.154; 4.O.154.157; 4.O.154.166; 4.O.154.169;
4.O.154.172; 4.O.154.175; 4.O.154.240; 4.O.154.244; 4.O.157.228;
4.O.157.229; 4.O.157.230; 4.O.157.231; 4.O.157.236; 4.O.157.237;
4.O.157.238; 4.O.157.239; 4.O.157.154; 4.O.157.157; 4.O.157.166;
4.O.157.169; 4.O.157.172; 4.O.157.175; 4.O.157.240; 4.O.157.244;
4.O.166.228; 4.O.166.229; 4.O.166.230; 4.O.166.231; 4.O.166.236;
4.O.166.237; 4.O.166.238; 4.O.166.239; 4.O.166.154; 4.O.166.157;
4.O.166.166; 4.O.166.169; 4.O.166.172; 4.O.166.175; 4.O.166.240;
4.O.166.244; 4.O.169.228; 4.O.169.229; 4.O.169.230; 4.O.169.231;
4.O.169.236; 4.O.169.237; 4.O.169.238; 4.O.169.239; 4.O.169.154;
4.O.169.157; 4.O.169.166; 4.O.169.169; 4.O.169.172; 4.O.169.175;
4.O.169.240; 4.O.169.244; 4.O.172.228; 4.O.172.229; 4.O.172.230;
4.O.172.231; 4.O.172.236; 4.O.172.237; 4.O.172.238; 4.O.172.239;
4.O.172.154; 4.O.172.157; 4.O.172.166; 4.O.172.169; 4.O.172.172;
4.O.172.175; 4.O.172.240; 4.O.172.244; 4.O.175.228; 4.O.175.229;

TABLE 100-continued

| |
|---|
| 4.O.175.230; 4.O.175.231; 4.O.175.236; 4.O.175.237; 4.O.175.238; 4.O.175.239; 4.O.175.154; 4.O.175.157; 4.O.175.166; 4.O.175.169; 4.O.175.172; 4.O.175.175; 4.O.175.240; 4.O.175.244; 4.O.240.228; 4.O.240.229; 4.O.240.230; 4.O.240.231; 4.O.240.236; 4.O.240.237; 4.O.240.238; 4.O.240.239; 4.O.240.154; 4.O.240.157; 4.O.240.166; 4.O.240.169; 4.O.240.172; 4.O.240.175; 4.O.240.240; 4.O.240.244; 4.O.244.228; 4.O.244.229; 4.O.244.230; 4.O.244.231; 4.O.244.236; 4.O.244.237; 4.O.244.238; 4.O.244.239; 4.O.244.154; 4.O.244.157; 4.O.244.166; 4.O.244.169; 4.O.244.172; 4.O.244.175; 4.O.244.240; 4.O.244.244; |
| Prodrugs of 4.P |
| 4.P.228.228; 4.P.228.229; 4.P.228.230; 4.P.228.231; 4.P.228.236; 4.P.228.237; 4.P.228.238; 4.P.228.239; 4.P.228.154; 4.P.228.157; 4.P.228.166; 4.P.228.169; 4.P.228.172; 4.P.228.175; 4.P.228.240; 4.P.228.244; 4.P.229.228; 4.P.229.229; 4.P.229.230; 4.P.229.231; 4.P.229.236; 4.P.229.237; 4.P.229.238; 4.P.229.239; 4.P.229.154; 4.P.229.157; 4.P.229.166; 4.P.229.169; 4.P.229.172; 4.P.229.175; 4.P.229.240; 4.P.229.244; 4.P.230.228; 4.P.230.229; 4.P.230.230; 4.P.230.231; 4.P.230.236; 4.P.230.237; 4.P.230.238; 4.P.230.239; 4.P.230.154; 4.P.230.157; 4.P.230.166; 4.P.230.169; 4.P.230.172; 4.P.230.175; 4.P.230.240; 4.P.230.244; 4.P.231.228; 4.P.231.229; 4.P.231.230; 4.P.231.231; 4.P.231.236; 4.P.231.237; 4.P.231.238; 4.P.231.239; 4.P.231.154; 4.P.231.157; 4.P.231.166; 4.P.231.169; 4.P.231.172; 4.P.231.175; 4.P.231.240; 4.P.231.244; 4.P.236.228; 4.P.236.229; 4.P.236.230; 4.P.236.231; 4.P.236.236; 4.P.236.237; 4.P.236.238; 4.P.236.239; 4.P.236.154; 4.P.236.157; 4.P.236.166; 4.P.236.169; 4.P.236.172; 4.P.236.175; 4.P.236.240; 4.P.236.244; 4.P.237.228; 4.P.237.229; 4.P.237.230; 4.P.237.231; 4.P.237.236; 4.P.237.237; 4.P.237.238; 4.P.237.239; 4.P.237.154; 4.P.237.157; 4.P.237.166; 4.P.237.169; 4.P.237.172; 4.P.237.175; 4.P.237.240; 4.P.237.244; 4.P.238.228; 4.P.238.229; 4.P.238.230; 4.P.238.231; 4.P.238.236; 4.P.238.237; 4.P.238.238; 4.P.238.239; 4.P.238.154; 4.P.238.157; 4.P.238.166; 4.P.238.169; 4.P.238.172; 4.P.238.175; 4.P.238.240; 4.P.238.244; 4.P.239.228; 4.P.239.229; 4.P.239.230; 4.P.239.231; 4.P.239.236; 4.P.239.237; 4.P.239.238; 4.P.239.239; 4.P.239.154; 4.P.239.157; 4.P.239.166; 4.P.239.169; 4.P.239.172; 4.P.239.175; 4.P.239.240; 4.P.239.244; 4.P.154.228; 4.P.154.229; 4.P.154.230; 4.P.154.231; 4.P.154.236; 4.P.154.237; 4.P.154.238; 4.P.154.239; 4.P.154.154; 4.P.154.157; 4.P.154.166; 4.P.154.169; 4.P.154.172; 4.P.154.175; 4.P.154.240; 4.P.154.244; 4.P.157.228; 4.P.157.229; 4.P.157.230; 4.P.157.231; 4.P.157.236; 4.P.157.237; 4.P.157.238; 4.P.157.239; 4.P.157.154; 4.P.157.157; 4.P.157.166; 4.P.157.169; 4.P.157.172; 4.P.157.175; 4.P.157.240; 4.P.157.244; 4.P.166.228; 4.P.166.229; 4.P.166.230; 4.P.166.231; 4.P.166.236; 4.P.166.237; 4.P.166.238; 4.P.166.239; 4.P.166.154; 4.P.166.157; 4.P.166.166; 4.P.166.169; 4.P.166.172; 4.P.166.175; 4.P.166.240; 4.P.166.244; 4.P.169.228; 4.P.169.229; 4.P.169.230; 4.P.169.231; 4.P.169.236; 4.P.169.237; 4.P.169.238; 4.P.169.239; 4.P.169.154; 4.P.169.157; 4.P.169.166; 4.P.169.169; 4.P.169.172; 4.P.169.175; 4.P.169.240; 4.P.169.244; 4.P.172.228; 4.P.172.229; 4.P.172.230; 4.P.172.231; 4.P.172.236; 4.P.172.237; 4.P.172.238; 4.P.172.239; 4.P.172.154; 4.P.172.157; 4.P.172.166; 4.P.172.169; 4.P.172.172; 4.P.172.175; 4.P.172.240; 4.P.172.244; 4.P.175.228; 4.P.175.229; 4.P.175.230; 4.P.175.231; 4.P.175.236; 4.P.175.237; 4.P.175.238; 4.P.175.239; 4.P.175.154; 4.P.175.157; 4.P.175.166; 4.P.175.169; 4.P.175.172; 4.P.175.175; 4.P.175.240; 4.P.175.244; 4.P.240.228; 4.P.240.229; 4.P.240.230; 4.P.240.231; 4.P.240.236; 4.P.240.237; 4.P.240.238; 4.P.240.239; 4.P.240.154; 4.P.240.157; 4.P.240.166; 4.P.240.169; 4.P.240.172; 4.P.240.175; 4.P.240.240; 4.P.240.244; 4.P.244.228; 4.P.244.229; 4.P.244.230; 4.P.244.231; 4.P.244.236; 4.P.244.237; 4.P.244.238; 4.P.244.239; 4.P.244.154; 4.P.244.157; 4.P.244.166; 4.P.244.169; 4.P.244.172; 4.P.244.175; 4.P.244.240; 4.P.244.244; |
| Prodrugs of 4.U |
| 4.U.228.228; 4.U.228.229; 4.U.228.230; 4.U.228.231; 4.U.228.236; 4.U.228.237; 4.U.228.238; 4.U.228.239; 4.U.228.154; 4.U.228.157; 4.U.228.166; 4.U.228.169; 4.U.228.172; 4.U.228.175; 4.U.228.240; 4.U.228.244; 4.U.229.228; 4.U.229.229; 4.U.229.230; 4.U.229.231; 4.U.229.236; 4.U.229.237; 4.U.229.238; 4.U.229.239; 4.U.229.154; 4.U.229.157; 4.U.229.166; 4.U.229.169; 4.U.229.172; 4.U.229.175; 4.U.229.240; 4.U.229.244; 4.U.230.228; 4.U.230.229; 4.U.230.230; 4.U.230.231; 4.U.230.236; 4.U.230.237; 4.U.230.238; 4.U.230.239; 4.U.230.154; 4.U.230.157; 4.U.230.166; 4.U.230.169; 4.U.230.172; 4.U.230.175; 4.U.230.240; 4.U.230.244; 4.U.231.228; 4.U.231.229; 4.U.231.230; 4.U.231.231; 4.U.231.236; 4.U.231.237; 4.U.231.238; 4.U.231.239; 4.U.231.154; 4.U.231.157; 4.U.231.166; 4.U.231.169; 4.U.231.172; 4.U.231.175; 4.U.231.240; 4.U.231.244; 4.U.236.228; 4.U.236.229; 4.U.236.230; 4.U.236.231; 4.U.236.236; 4.U.236.237; 4.U.236.238; 4.U.236.239; 4.U.236.154; 4.U.236.157; 4.U.236.166; 4.U.236.169; 4.U.236.172; 4.U.236.175; 4.U.236.240; 4.U.236.244; 4.U.237.228; 4.U.237.229; 4.U.237.230; 4.U.237.231; 4.U.237.236; 4.U.237.237; 4.U.237.238; 4.U.237.239; 4.U.237.154; 4.U.237.157; 4.U.237.166; 4.U.237.169; 4.U.237.172; 4.U.237.175; 4.U.237.240; 4.U.237.244; 4.U.238.228; 4.U.238.229; 4.U.238.230; 4.U.238.231; 4.U.238.236; 4.U.238.237; 4.U.238.238; 4.U.238.239; 4.U.238.154; 4.U.238.157; 4.U.238.166; 4.U.238.169; 4.U.238.172; 4.U.238.175; 4.U.238.240; 4.U.238.244; 4.U.239.228; 4.U.239.229; 4.U.239.230; 4.U.239.231; 4.U.239.236; 4.U.239.237; 4.U.239.238; 4.U.239.239; |

TABLE 100-continued

4.U.239.154; 4.U.239.157; 4.U.239.166; 4.U.239.169; 4.U.239.172; 4.U.239.175; 4.U.239.240; 4.U.239.244; 4.U.154.228; 4.U.154.229; 4.U.154.230; 4.U.154.231; 4.U.154.236; 4.U.154.237; 4.U.154.238; 4.U.154.239; 4.U.154.154; 4.U.154.157; 4.U.154.166; 4.U.154.169; 4.U.154.172; 4.U.154.175; 4.U.154.240; 4.U.154.244; 4.U.157.228; 4.U.157.229; 4.U.157.230; 4.U.157.231; 4.U.157.236; 4.U.157.237; 4.U.157.238; 4.U.157.239; 4.U.157.154; 4.U.157.157; 4.U.157.166; 4.U.157.169; 4.U.157.172; 4.U.157.175; 4.U.157.240; 4.U.157.244; 4.U.166.228; 4.U.166.229; 4.U.166.230; 4.U.166.231; 4.U.166.236; 4.U.166.237; 4.U.166.238; 4.U.166.239; 4.U.166.154; 4.U.166.157; 4.U.166.166; 4.U.166.169; 4.U.166.172; 4.U.166.175; 4.U.166.240; 4.U.166.244; 4.U.169.228; 4.U.169.229; 4.U.169.230; 4.U.169.231; 4.U.169.236; 4.U.169.237; 4.U.169.238; 4.U.169.239; 4.U.169.154; 4.U.169.157; 4.U.169.166; 4.U.169.169; 4.U.169.172; 4.U.169.175; 4.U.169.240; 4.U.169.244; 4.U.172.228; 4.U.172.229; 4.U.172.230; 4.U.172.231; 4.U.172.236; 4.U.172.237; 4.U.172.238; 4.U.172.239; 4.U.172.154; 4.U.172.157; 4.U.172.166; 4.U.172.169; 4.U.172.172; 4.U.172.175; 4.U.172.240; 4.U.172.244; 4.U.175.228; 4.U.175.229; 4.U.175.230; 4.U.175.231; 4.U.175.236; 4.U.175.237; 4.U.175.238; 4.U.175.239; 4.U.175.154; 4.U.175.157; 4.U.175.166; 4.U.175.169; 4.U.175.172; 4.U.175.175; 4.U.175.240; 4.U.175.244; 4.U.240.228; 4.U.240.229; 4.U.240.230; 4.U.240.231; 4.U.240.236; 4.U.240.237; 4.U.240.238; 4.U.240.239; 4.U.240.154; 4.U.240.157; 4.U.240.166; 4.U.240.169; 4.U.240.172; 4.U.240.175; 4.U.240.240; 4.U.240.244; 4.U.244.228; 4.U.244.229; 4.U.244.230; 4.U.244.231; 4.U.244.236; 4.U.244.237; 4.U.244.238; 4.U.244.239; 4.U.244.154; 4.U.244.157; 4.U.244.166; 4.U.244.169; 4.U.244.172; 4.U.244.175; 4.U.244.240; 4.U.244.244;

Prodrugs of 4.W

4.W.228.228; 4.W.228.229; 4.W.228.230; 4.W.228.231; 4.W.228.236; 4.W.228.237; 4.W.228.238; 4.W.228.239; 4.W.228.154; 4.W.228.157; 4.W.228.166; 4.W.228.169; 4.W.228.172; 4.W.228.175; 4.W.228.240; 4.W.228.244; 4.W.229.228; 4.W.229.229; 4.W.229.230; 4.W.229.231; 4.W.229.236; 4.W.229.237; 4.W.229.238; 4.W.229.239; 4.W.229.154; 4.W.229.157; 4.W.229.166; 4.W.229.169; 4.W.229.172; 4.W.229.175; 4.W.229.240; 4.W.229.244; 4.W.230.228; 4.W.230.229; 4.W.230.230; 4.W.230.231; 4.W.230.236; 4.W.230.237; 4.W.230.238; 4.W.230.239; 4.W.230.154; 4.W.230.157; 4.W.230.166; 4.W.230.169; 4.W.230.172; 4.W.230.175; 4.W.230.240; 4.W.230.244; 4.W.231.228; 4.W.231.229; 4.W.231.230; 4.W.231.231; 4.W.231.236; 4.W.231.237; 4.W.231.238; 4.W.231.239; 4.W.231.154; 4.W.231.157; 4.W.231.166; 4.W.231.169; 4.W.231.172; 4.W.231.175; 4.W.231.240; 4.W.231.244; 4.W.236.228; 4.W.236.229; 4.W.236.230; 4.W.236.231; 4.W.236.236; 4.W.236.237; 4.W.236.238; 4.W.236.239; 4.W.236.154; 4.W.236.157; 4.W.236.166; 4.W.236.169; 4.W.236.172; 4.W.236.175; 4.W.236.240; 4.W.236.244; 4.W.237.228; 4.W.237.229; 4.W.237.230; 4.W.237.231; 4.W.237.236; 4.W.237.237; 4.W.237.238; 4.W.237.239; 4.W.237.154; 4.W.237.157; 4.W.237.166; 4.W.237.169; 4.W.237.172; 4.W.237.175; 4.W.237.240; 4.W.237.244; 4.W.238.228; 4.W.238.229; 4.W.238.230; 4.W.238.231; 4.W.238.236; 4.W.238.237; 4.W.238.238; 4.W.238.239; 4.W.238.154; 4.W.238.157; 4.W.238.166; 4.W.238.169; 4.W.238.172; 4.W.238.175; 4.W.238.240; 4.W.238.244; 4.W.239.228; 4.W.239.229; 4.W.239.230; 4.W.239.231; 4.W.239.236; 4.W.239.237; 4.W.239.238; 4.W.239.239; 4.W.239.154; 4.W.239.157; 4.W.239.166; 4.W.239.169; 4.W.239.172; 4.W.239.175; 4.W.239.240; 4.W.239.244; 4.W.154.228; 4.W.154.229; 4.W.154.230; 4.W.154.231; 4.W.154.236; 4.W.154.237; 4.W.154.238; 4.W.154.239; 4.W.154.154; 4.W.154.157; 4.W.154.166; 4.W.154.169; 4.W.154.172; 4.W.154.175; 4.W.154.240; 4.W.154.244; 4.W.157.228; 4.W.157.229; 4.W.157.230; 4.W.157.231; 4.W.157.236; 4.W.157.237; 4.W.157.238; 4.W.157.239; 4.W.157.154; 4.W.157.157; 4.W.157.166; 4.W.157.169; 4.W.157.172; 4.W.157.175; 4.W.157.240; 4.W.157.244; 4.W.166.228; 4.W.166.229; 4.W.166.230; 4.W.166.231; 4.W.166.236; 4.W.166.237; 4.W.166.238; 4.W.166.239; 4.W.166.154; 4.W.166.157; 4.W.166.166; 4.W.166.169; 4.W.166.172; 4.W.166.175; 4.W.166.240; 4.W.166.244; 4.W.169.228; 4.W.169.229; 4.W.169.230; 4.W.169.231; 4.W.169.236; 4.W.169.237; 4.W.169.238; 4.W.169.239; 4.W.169.154; 4.W.169.157; 4.W.169.166; 4.W.169.169; 4.W.169.172; 4.W.169.175; 4.W.169.240; 4.W.169.244; 4.W.172.228; 4.W.172.229; 4.W.172.230; 4.W.172.231; 4.W.172.236; 4.W.172.237; 4.W.172.238; 4.W.172.239; 4.W.172.154; 4.W.172.157; 4.W.172.166; 4.W.172.169; 4.W.172.172; 4.W.172.175; 4.W.172.240; 4.W.172.244; 4.W.175.228; 4.W.175.229; 4.W.175.230; 4.W.175.231; 4.W.175.236; 4.W.175.237; 4.W.175.238; 4.W.175.239; 4.W.175.154; 4.W.175.157; 4.W.175.166; 4.W.175.169; 4.W.175.172; 4.W.175.175; 4.W.175.240; 4.W.175.244; 4.W.240.228; 4.W.240.229; 4.W.240.230; 4.W.240.231; 4.W.240.236; 4.W.240.237; 4.W.240.238; 4.W.240.239; 4.W.240.154; 4.W.240.157; 4.W.240.166; 4.W.240.169; 4.W.240.172; 4.W.240.175; 4.W.240.240; 4.W.240.244; 4.W.244.228; 4.W.244.229; 4.W.244.230; 4.W.244.231; 4.W.244.236; 4.W.244.237; 4.W.244.238; 4.W.244.239; 4.W.244.154; 4.W.244.157; 4.W.244.166; 4.W.244.169; 4.W.244.172; 4.W.244.175; 4.W.244.240; 4.W.244.244;

TABLE 100-continued

| Prodrugs of 4.Y |
|---|
| 4.Y.228.228; 4.Y.228.229; 4.Y.228.230; 4.Y.228.231; 4.Y.228.236; 4.Y.228.237; 4.Y.228.238; 4.Y.228.239; 4.Y.228.154; 4.Y.228.157; 4.Y.228.166; 4.Y.228.169; 4.Y.228.172; 4.Y.228.175; 4.Y.228.240; 4.Y.228.244; 4.Y.229.228; 4.Y.229.229; 4.Y.229.230; 4.Y.229.231; 4.Y.229.236; 4.Y.229.237; 4.Y.229.238; 4.Y.229.239; 4.Y.229.154; 4.Y.229.157; 4.Y.229.166; 4.Y.229.169; 4.Y.229.172; 4.Y.229.175; 4.Y.229.240; 4.Y.229.244; 4.Y.230.228; 4.Y.230.229; 4.Y.230.230; 4.Y.230.231; 4.Y.230.236; 4.Y.230.237; 4.Y.230.238; 4.Y.230.239; 4.Y.230.154; 4.Y.230.157; 4.Y.230.166; 4.Y.230.169; 4.Y.230.172; 4.Y.230.175; 4.Y.230.240; 4.Y.230.244; 4.Y.231.228; 4.Y.231.229; 4.Y.231.230; 4.Y.231.231; 4.Y.231.236; 4.Y.231.237; 4.Y.231.238; 4.Y.231.239; 4.Y.231.154; 4.Y.231.157; 4.Y.231.166; 4.Y.231.169; 4.Y.231.172; 4.Y.231.175; 4.Y.231.240; 4.Y.231.244; 4.Y.236.228; 4.Y.236.229; 4.Y.236.230; 4.Y.236.231; 4.Y.236.236; 4.Y.236.237; 4.Y.236.238; 4.Y.236.239; 4.Y.236.154; 4.Y.236.157; 4.Y.236.166; 4.Y.236.169; 4.Y.236.172; 4.Y.236.175; 4.Y.236.240; 4.Y.236.244; 4.Y.237.228; 4.Y.237.229; 4.Y.237.230; 4.Y.237.231; 4.Y.237.236; 4.Y.237.237; 4.Y.237.238; 4.Y.237.239; 4.Y.237.154; 4.Y.237.157; 4.Y.237.166; 4.Y.237.169; 4.Y.237.172; 4.Y.237.175; 4.Y.237.240; 4.Y.237.244; 4.Y.238.228; 4.Y.238.229; 4.Y.238.230; 4.Y.238.231; 4.Y.238.236; 4.Y.238.237; 4.Y.238.238; 4.Y.238.239; 4.Y.238.154; 4.Y.238.157; 4.Y.238.166; 4.Y.238.169; 4.Y.238.172; 4.Y.238.175; 4.Y.238.240; 4.Y.238.244; 4.Y.239.228; 4.Y.239.229; 4.Y.239.230; 4.Y.239.231; 4.Y.239.236; 4.Y.239.237; 4.Y.239.238; 4.Y.239.239; 4.Y.239.154; 4.Y.239.157; 4.Y.239.166; 4.Y.239.169; 4.Y.239.172; 4.Y.239.175; 4.Y.239.240; 4.Y.239.244; 4.Y.154.228; 4.Y.154.229; 4.Y.154.230; 4.Y.154.231; 4.Y.154.236; 4.Y.154.237; 4.Y.154.238; 4.Y.154.239; 4.Y.154.154; 4.Y.154.157; 4.Y.154.166; 4.Y.154.169; 4.Y.154.172; 4.Y.154.175; 4.Y.154.240; 4.Y.154.244; 4.Y.157.228; 4.Y.157.229; 4.Y.157.230; 4.Y.157.231; 4.Y.157.236; 4.Y.157.237; 4.Y.157.238; 4.Y.157.239; 4.Y.157.154; 4.Y.157.157; 4.Y.157.166; 4.Y.157.169; 4.Y.157.172; 4.Y.157.175; 4.Y.157.240; 4.Y.157.244; 4.Y.166.228; 4.Y.166.229; 4.Y.166.230; 4.Y.166.231; 4.Y.166.236; 4.Y.166.237; 4.Y.166.238; 4.Y.166.239; 4.Y.166.154; 4.Y.166.157; 4.Y.166.166; 4.Y.166.169; 4.Y.166.172; 4.Y.166.175; 4.Y.166.240; 4.Y.166.244; 4.Y.169.228; 4.Y.169.229; 4.Y.169.230; 4.Y.169.231; 4.Y.169.236; 4.Y.169.237; 4.Y.169.238; 4.Y.169.239; 4.Y.169.154; 4.Y.169.157; 4.Y.169.166; 4.Y.169.169; 4.Y.169.172; 4.Y.169.175; 4.Y.169.240; 4.Y.169.244; 4.Y.172.228; 4.Y.172.229; 4.Y.172.230; 4.Y.172.231; 4.Y.172.236; 4.Y.172.237; 4.Y.172.238; 4.Y.172.239; 4.Y.172.154; 4.Y.172.157; 4.Y.172.166; 4.Y.172.169; 4.Y.172.172; 4.Y.172.175; 4.Y.172.240; 4.Y.172.244; 4.Y.175.228; 4.Y.175.229; 4.Y.175.230; 4.Y.175.231; 4.Y.175.236; 4.Y.175.237; 4.Y.175.238; 4.Y.175.239; 4.Y.175.154; 4.Y.175.157; 4.Y.175.166; 4.Y.175.169; 4.Y.175.172; 4.Y.175.175; 4.Y.175.240; 4.Y.175.244; 4.Y.240.228; 4.Y.240.229; 4.Y.240.230; 4.Y.240.231; 4.Y.240.236; 4.Y.240.237; 4.Y.240.238; 4.Y.240.239; 4.Y.240.154; 4.Y.240.157; 4.Y.240.166; 4.Y.240.169; 4.Y.240.172; 4.Y.240.175; 4.Y.240.240; 4.Y.240.244; 4.Y.244.228; 4.Y.244.229; 4.Y.244.230; 4.Y.244.231; 4.Y.244.236; 4.Y.244.237; 4.Y.244.238; 4.Y.244.239; 4.Y.244.154; 4.Y.244.157; 4.Y.244.166; 4.Y.244.169; 4.Y.244.172; 4.Y.244.175; 4.Y.244.240; 4.Y.244.244; |
| Prodrugs of 5.B |
| 5.B.228.228; 5.B.228.229; 5.B.228.230; 5.B.228.231; 5.B.228.236; 5.B.228.237; 5.B.228.238; 5.B.228.239; 5.B.228.154; 5.B.228.157; 5.B.228.166; 5.B.228.169; 5.B.228.172; 5.B.228.175; 5.B.228.240; 5.B.228.244; 5.B.229.228; 5.B.229.229; 5.B.229.230; 5.B.229.231; 5.B.229.236; 5.B.229.237; 5.B.229.238; 5.B.229.239; 5.B.229.154; 5.B.229.157; 5.B.229.166; 5.B.229.169; 5.B.229.172; 5.B.229.175; 5.B.229.240; 5.B.229.244; 5.B.230.228; 5.B.230.229; 5.B.230.230; 5.B.230.231; 5.B.230.236; 5.B.230.237; 5.B.230.238; 5.B.230.239; 5.B.230.154; 5.B.230.157; 5.B.230.166; 5.B.230.169; 5.B.230.172; 5.B.230.175; 5.B.230.240; 5.B.230.244; 5.B.231.228; 5.B.231.229; 5.B.231.230; 5.B.231.231; 5.B.231.236; 5.B.231.237; 5.B.231.238; 5.B.231.239; 5.B.231.154; 5.B.231.157; 5.B.231.166; 5.B.231.169; 5.B.231.172; 5.B.231.175; 5.B.231.240; 5.B.231.244; 5.B.236.228; 5.B.236.229; 5.B.236.230; 5.B.236.231; 5.B.236.236; 5.B.236.237; 5.B.236.238; 5.B.236.239; 5.B.236.154; 5.B.236.157; 5.B.236.166; 5.B.236.169; 5.B.236.172; 5.B.236.175; 5.B.236.240; 5.B.236.244; 5.B.237.228; 5.B.237.229; 5.B.237.230; 5.B.237.231; 5.B.237.236; 5.B.237.237; 5.B.237.238; 5.B.237.239; 5.B.237.154; 5.B.237.157; 5.B.237.166; 5.B.237.169; 5.B.237.172; 5.B.237.175; 5.B.237.240; 5.B.237.244; 5.B.238.228; 5.B.238.229; 5.B.238.230; 5.B.238.231; 5.B.238.236; 5.B.238.237; 5.B.238.238; 5.B.238.239; 5.B.238.154; 5.B.238.157; 5.B.238.166; 5.B.238.169; 5.B.238.172; 5.B.238.175; 5.B.238.240; 5.B.238.244; 5.B.239.228; 5.B.239.229; 5.B.239.230; 5.B.239.231; 5.B.239.236; 5.B.239.237; 5.B.239.238; 5.B.239.239; 5.B.239.154; 5.B.239.157; 5.B.239.166; 5.B.239.169; 5.B.239.172; 5.B.239.175; 5.B.239.240; 5.B.239.244; 5.B.154.228; 5.B.154.229; 5.B.154.230; 5.B.154.231; 5.B.154.236; 5.B.154.237; 5.B.154.238; 5.B.154.239; 5.B.154.154; 5.B.154.157; 5.B.154.166; 5.B.154.169; 5.B.154.172; 5.B.154.175; 5.B.154.240; 5.B.154.244; 5.B.157.228; 5.B.157.229; 5.B.157.230; 5.B.157.231; 5.B.157.236; 5.B.157.237; 5.B.157.238; 5.B.157.239; 5.B.157.154; 5.B.157.157; 5.B.157.166; 5.B.157.169; 5.B.157.172; 5.B.157.175; 5.B.157.240; 5.B.157.244; 5.B.166.228; 5.B.166.229; 5.B.166.230; 5.B.166.231; 5.B.166.236; 5.B.166.237; 5.B.166.238; 5.B.166.239; 5.B.166.154; 5.B.166.157; 5.B.166.166; 5.B.166.169; 5.B.166.172; 5.B.166.175; 5.B.166.240; 5.B.166.244; 5.B.169.228; 5.B.169.229; 5.B.169.230; 5.B.169.231; 5.B.169.236; 5.B.169.237; 5.B.169.238; 5.B.169.239; 5.B.169.154; 5.B.169.157; 5.B.169.166; 5.B.169.169; 5.B.169.172; 5.B.169.175; 5.B.169.240; 5.B.169.244; 5.B.172.228; 5.B.172.229; 5.B.172.230; 5.B.172.231; 5.B.172.236; |

TABLE 100-continued

| |
|---|
| 5.B.172.237; 5.B.172.238; 5.B.172.239; 5.B.172.154; 5.B.172.157; 5.B.172.166; 5.B.172.169; 5.B.172.172; 5.B.172.175; 5.B.172.240; 5.B.172.244; 5.B.175.228; 5.B.175.229; 5.B.175.230; 5.B.175.231; 5.B.175.236; 5.B.175.237; 5.B.175.238; 5.B.175.239; 5.B.175.154; 5.B.175.157; 5.B.175.166; 5.B.175.169; 5.B.175.172; 5.B.175.175; 5.B.175.240; 5.B.175.244; 5.B.240.228; 5.B.240.229; 5.B.240.230; 5.B.240.231; 5.B.240.236; 5.B.240.237; 5.B.240.238; 5.B.240.239; 5.B.240.154; 5.B.240.157; 5.B.240.166; 5.B.240.169; 5.B.240.172; 5.B.240.175; 5.B.240.240; 5.B.240.244; 5.B.244.228; 5.B.244.229; 5.B.244.230; 5.B.244.231; 5.B.244.236; 5.B.244.237; 5.B.244.238; 5.B.244.239; 5.B.244.154; 5.B.244.157; 5.B.244.166; 5.B.244.169; 5.B.244.172; 5.B.244.175; 5.B.244.240; 5.B.244.244; |
| Prodrugs of 5.D |
| 5.D.228.228; 5.D.228.229; 5.D.228.230; 5.D.228.231; 5.D.228.236; 5.D.228.237; 5.D.228.238; 5.D.228.239; 5.D.228.154; 5.D.228.157; 5.D.228.166; 5.D.228.169; 5.D.228.172; 5.D.228.175; 5.D.228.240; 5.D.228.244; 5.D.229.228; 5.D.229.229; 5.D.229.230; 5.D.229.231; 5.D.229.236; 5.D.229.237; 5.D.229.238; 5.D.229.239; 5.D.229.154; 5.D.229.157; 5.D.229.166; 5.D.229.169; 5.D.229.172; 5.D.229.175; 5.D.229.240; 5.D.229.244; 5.D.230.228; 5.D.230.229; 5.D.230.230; 5.D.230.231; 5.D.230.236; 5.D.230.237; 5.D.230.238; 5.D.230.239; 5.D.230.154; 5.D.230.157; 5.D.230.166; 5.D.230.169; 5.D.230.172; 5.D.230.175; 5.D.230.240; 5.D.230.244; 5.D.231.228; 5.D.231.229; 5.D.231.230; 5.D.231.231; 5.D.231.236; 5.D.231.237; 5.D.231.238; 5.D.231.239; 5.D.231.154; 5.D.231.157; 5.D.231.166; 5.D.231.169; 5.D.231.172; 5.D.231.175; 5.D.231.240; 5.D.231.244; 5.D.236.228; 5.D.236.229; 5.D.236.230; 5.D.236.231; 5.D.236.236; 5.D.236.237; 5.D.236.238; 5.D.236.239; 5.D.236.154; 5.D.236.157; 5.D.236.166; 5.D.236.169; 5.D.236.172; 5.D.236.175; 5.D.236.240; 5.D.236.244; 5.D.237.228; 5.D.237.229; 5.D.237.230; 5.D.237.231; 5.D.237.236; 5.D.237.237; 5.D.237.238; 5.D.237.239; 5.D.237.154; 5.D.237.157; 5.D.237.166; 5.D.237.169; 5.D.237.172; 5.D.237.175; 5.D.237.240; 5.D.237.244; 5.D.238.228; 5.D.238.229; 5.D.238.230; 5.D.238.231; 5.D.238.236; 5.D.238.237; 5.D.238.238; 5.D.238.239; 5.D.238.154; 5.D.238.157; 5.D.238.166; 5.D.238.169; 5.D.238.172; 5.D.238.175; 5.D.238.240; 5.D.238.244; 5.D.239.228; 5.D.239.229; 5.D.239.230; 5.D.239.231; 5.D.239.236; 5.D.239.237; 5.D.239.238; 5.D.239.239; 5.D.239.154; 5.D.239.157; 5.D.239.166; 5.D.239.169; 5.D.239.172; 5.D.239.175; 5.D.239.240; 5.D.239.244; 5.D.154.228; 5.D.154.229; 5.D.154.230; 5.D.154.231; 5.D.154.236; 5.D.154.237; 5.D.154.238; 5.D.154.239; 5.D.154.154; 5.D.154.157; 5.D.154.166; 5.D.154.169; 5.D.154.172; 5.D.154.175; 5.D.154.240; 5.D.154.244; 5.D.157.228; 5.D.157.229; 5.D.157.230; 5.D.157.231; 5.D.157.236; 5.D.157.237; 5.D.157.238; 5.D.157.239; 5.D.157.154; 5.D.157.157; 5.D.157.166; 5.D.157.169; 5.D.157.172; 5.D.157.175; 5.D.157.240; 5.D.157.244; 5.D.166.228; 5.D.166.229; 5.D.166.230; 5.D.166.231; 5.D.166.236; 5.D.166.237; 5.D.166.238; 5.D.166.239; 5.D.166.154; 5.D.166.157; 5.D.166.166; 5.D.166.169; 5.D.166.172; 5.D.166.175; 5.D.166.240; 5.D.166.244; 5.D.169.228; 5.D.169.229; 5.D.169.230; 5.D.169.231; 5.D.169.236; 5.D.169.237; 5.D.169.238; 5.D.169.239; 5.D.169.154; 5.D.169.157; 5.D.169.166; 5.D.169.169; 5.D.169.172; 5.D.169.175; 5.D.169.240; 5.D.169.244; 5.D.172.228; 5.D.172.229; 5.D.172.230; 5.D.172.231; 5.D.172.236; 5.D.172.237; 5.D.172.238; 5.D.172.239; 5.D.172.154; 5.D.172.157; 5.D.172.166; 5.D.172.169; 5.D.172.172; 5.D.172.175; 5.D.172.240; 5.D.172.244; 5.D.175.228; 5.D.175.229; 5.D.175.230; 5.D.175.231; 5.D.175.236; 5.D.175.237; 5.D.175.238; 5.D.175.239; 5.D.175.154; 5.D.175.157; 5.D.175.166; 5.D.175.169; 5.D.175.172; 5.D.175.175; 5.D.175.240; 5.D.175.244; 5.D.240.228; 5.D.240.229; 5.D.240.230; 5.D.240.231; 5.D.240.236; 5.D.240.237; 5.D.240.238; 5.D.240.239; 5.D.240.154; 5.D.240.157; 5.D.240.166; 5.D.240.169; 5.D.240.172; 5.D.240.175; 5.D.240.240; 5.D.240.244; 5.D.244.228; 5.D.244.229; 5.D.244.230; 5.D.244.231; 5.D.244.236; 5.D.244.237; 5.D.244.238; 5.D.244.239; 5.D.244.154; 5.D.244.157; 5.D.244.166; 5.D.244.169; 5.D.244.172; 5.D.244.175; 5.D.244.240; 5.D.244.244; |
| Prodrugs of 5.E |
| 5.E.228.228; 5.E.228.229; 5.E.228.230; 5.E.228.231; 5.E.228.236; 5.E.228.237; 5.E.228.238; 5.E.228.239; 5.E.228.154; 5.E.228.157; 5.E.228.166; 5.E.228.169; 5.E.228.172; 5.E.228.175; 5.E.228.240; 5.E.228.244; 5.E.229.228; 5.E.229.229; 5.E.229.230; 5.E.229.231; 5.E.229.236; 5.E.229.237; 5.E.229.238; 5.E.229.239; 5.E.229.154; 5.E.229.157; 5.E.229.166; 5.E.229.169; 5.E.229.172; 5.E.229.175; 5.E.229.240; 5.E.229.244; 5.E.230.228; 5.E.230.229; 5.E.230.230; 5.E.230.231; 5.E.230.236; 5.E.230.237; 5.E.230.238; 5.E.230.239; 5.E.230.154; 5.E.230.157; 5.E.230.166; 5.E.230.169; 5.E.230.172; 5.E.230.175; 5.E.230.240; 5.E.230.244; 5.E.231.228; 5.E.231.229; 5.E.231.230; 5.E.231.231; 5.E.231.236; 5.E.231.237; 5.E.231.238; 5.E.231.239; 5.E.231.154; 5.E.231.157; 5.E.231.166; 5.E.231.169; 5.E.231.172; 5.E.231.175; 5.E.231.240; 5.E.231.244; 5.E.236.228; 5.E.236.229; 5.E.236.230; 5.E.236.231; 5.E.236.236; 5.E.236.237; 5.E.236.238; 5.E.236.239; 5.E.236.154; 5.E.236.157; 5.E.236.166; 5.E.236.169; 5.E.236.172; 5.E.236.175; 5.E.236.240; 5.E.236.244; 5.E.237.228; 5.E.237.229; 5.E.237.230; 5.E.237.231; 5.E.237.236; 5.E.237.237; 5.E.237.238; 5.E.237.239; 5.E.237.154; |

TABLE 100-continued

| |
|---|
| 5.E.237.157; 5.E.237.166; 5.E.237.169; 5.E.237.172; 5.E.237.175; 5.E.237.240; 5.E.237.244; 5.E.238.228; 5.E.238.229; 5.E.238.230; 5.E.238.231; 5.E.238.236; 5.E.238.237; 5.E.238.238; 5.E.238.239; 5.E.238.154; 5.E.238.157; 5.E.238.166; 5.E.238.169; 5.E.238.172; 5.E.238.175; 5.E.238.240; 5.E.238.244; 5.E.239.228; 5.E.239.229; 5.E.239.230; 5.E.239.231; 5.E.239.236; 5.E.239.237; 5.E.239.238; 5.E.239.239; 5.E.239.154; 5.E.239.157; 5.E.239.166; 5.E.239.169; 5.E.239.172; 5.E.239.175; 5.E.239.240; 5.E.239.244; 5.E.154.228; 5.E.154.229; 5.E.154.230; 5.E.154.231; 5.E.154.236; 5.E.154.237; 5.E.154.238; 5.E.154.239; 5.E.154.154; 5.E.154.157; 5.E.154.166; 5.E.154.169; 5.E.154.172; 5.E.154.175; 5.E.154.240; 5.E.154.244; 5.E.157.228; 5.E.157.229; 5.E.157.230; 5.E.157.231; 5.E.157.236; 5.E.157.237; 5.E.157.238; 5.E.157.239; 5.E.157.154; 5.E.157.157; 5.E.157.166; 5.E.157.169; 5.E.157.172; 5.E.157.175; 5.E.157.240; 5.E.157.244; 5.E.166.228; 5.E.166.229; 5.E.166.230; 5.E.166.231; 5.E.166.236; 5.E.166.237; 5.E.166.238; 5.E.166.239; 5.E.166.154; 5.E.166.157; 5.E.166.166; 5.E.166.169; 5.E.166.172; 5.E.166.175; 5.E.166.240; 5.E.166.244; 5.E.169.228; 5.E.169.229; 5.E.169.230; 5.E.169.231; 5.E.169.236; 5.E.169.237; 5.E.169.238; 5.E.169.239; 5.E.169.154; 5.E.169.157; 5.E.169.166; 5.E.169.169; 5.E.169.172; 5.E.169.175; 5.E.169.240; 5.E.169.244; 5.E.172.228; 5.E.172.229; 5.E.172.230; 5.E.172.231; 5.E.172.236; 5.E.172.237; 5.E.172.238; 5.E.172.239; 5.E.172.154; 5.E.172.157; 5.E.172.166; 5.E.172.169; 5.E.172.172; 5.E.172.175; 5.E.172.240; 5.E.172.244; 5.E.175.228; 5.E.175.229; 5.E.175.230; 5.E.175.231; 5.E.175.236; 5.E.175.237; 5.E.175.238; 5.E.175.239; 5.E.175.154; 5.E.175.157; 5.E.175.166; 5.E.175.169; 5.E.175.172; 5.E.175.175; 5.E.175.240; 5.E.175.244; 5.E.240.228; 5.E.240.229; 5.E.240.230; 5.E.240.231; 5.E.240.236; 5.E.240.237; 5.E.240.238; 5.E.240.239; 5.E.240.154; 5.E.240.157; 5.E.240.166; 5.E.240.169; 5.E.240.172; 5.E.240.175; 5.E.240.240; 5.E.240.244; 5.E.244.228; 5.E.244.229; 5.E.244.230; 5.E.244.231; 5.E.244.236; 5.E.244.237; 5.E.244.238; 5.E.244.239; 5.E.244.154; 5.E.244.157; 5.E.244.166; 5.E.244.169; 5.E.244.172; 5.E.244.175; 5.E.244.240; 5.E.244.244; |
| Prodrugs of 5.G |

5.G.228.228; 5.G.228.229; 5.G.228.230; 5.G.228.231; 5.G.228.236; 5.G.228.237; 5.G.228.238; 5.G.228.239; 5.G.228.154; 5.G.228.157; 5.G.228.166; 5.G.228.169; 5.G.228.172; 5.G.228.175; 5.G.228.240; 5.G.228.244; 5.G.229.228; 5.G.229.229; 5.G.229.230; 5.G.229.231; 5.G.229.236; 5.G.229.237; 5.G.229.238; 5.G.229.239; 5.G.229.154; 5.G.229.157; 5.G.229.166; 5.G.229.169; 5.G.229.172; 5.G.229.175; 5.G.229.240; 5.G.229.244; 5.G.230.228; 5.G.230.229; 5.G.230.230; 5.G.230.231; 5.G.230.236; 5.G.230.237; 5.G.230.238; 5.G.230.239; 5.G.230.154; 5.G.230.157; 5.G.230.166; 5.G.230.169; 5.G.230.172; 5.G.230.175; 5.G.230.240; 5.G.230.244; 5.G.231.228; 5.G.231.229; 5.G.231.230; 5.G.231.231; 5.G.231.236; 5.G.231.237; 5.G.231.238; 5.G.231.239; 5.G.231.154; 5.G.231.157; 5.G.231.166; 5.G.231.169; 5.G.231.172; 5.G.231.175; 5.G.231.240; 5.G.231.244; 5.G.236.228; 5.G.236.229; 5.G.236.230; 5.G.236.231; 5.G.236.236; 5.G.236.237; 5.G.236.238; 5.G.236.239; 5.G.236.154; 5.G.236.157; 5.G.236.166; 5.G.236.169; 5.G.236.172; 5.G.236.175; 5.G.236.240; 5.G.236.244; 5.G.237.228; 5.G.237.229; 5.G.237.230; 5.G.237.231; 5.G.237.236; 5.G.237.237; 5.G.237.238; 5.G.237.239; 5.G.237.154; 5.G.237.157; 5.G.237.166; 5.G.237.169; 5.G.237.172; 5.G.237.175; 5.G.237.240; 5.G.237.244; 5.G.238.228; 5.G.238.229; 5.G.238.230; 5.G.238.231; 5.G.238.236; 5.G.238.237; 5.G.238.238; 5.G.238.239; 5.G.238.154; 5.G.238.157; 5.G.238.166; 5.G.238.169; 5.G.238.172; 5.G.238.175; 5.G.238.240; 5.G.238.244; 5.G.239.228; 5.G.239.229; 5.G.239.230; 5.G.239.231; 5.G.239.236; 5.G.239.237; 5.G.239.238; 5.G.239.239; 5.G.239.154; 5.G.239.157; 5.G.239.166; 5.G.239.169; 5.G.239.172; 5.G.239.175; 5.G.239.240; 5.G.239.244; 5.G.154.228; 5.G.154.229; 5.G.154.230; 5.G.154.231; 5.G.154.236; 5.G.154.237; 5.G.154.238; 5.G.154.239; 5.G.154.154; 5.G.154.157; 5.G.154.166; 5.G.154.169; 5.G.154.172; 5.G.154.175; 5.G.154.240; 5.G.154.244; 5.G.157.228; 5.G.157.229; 5.G.157.230; 5.G.157.231; 5.G.157.236; 5.G.157.237; 5.G.157.238; 5.G.157.239; 5.G.157.154; 5.G.157.157; 5.G.157.166; 5.G.157.169; 5.G.157.172; 5.G.157.175; 5.G.157.240; 5.G.157.244; 5.G.166.228; 5.G.166.229; 5.G.166.230; 5.G.166.231; 5.G.166.236; 5.G.166.237; 5.G.166.238; 5.G.166.239; 5.G.166.154; 5.G.166.157; 5.G.166.166; 5.G.166.169; 5.G.166.172; 5.G.166.175; 5.G.166.240; 5.G.166.244; 5.G.169.228; 5.G.169.229; 5.G.169.230; 5.G.169.231; 5.G.169.236; 5.G.169.237; 5.G.169.238; 5.G.169.239; 5.G.169.154; 5.G.169.157; 5.G.169.166; 5.G.169.169; 5.G.169.172; 5.G.169.175; 5.G.169.240; 5.G.169.244; 5.G.172.228; 5.G.172.229; 5.G.172.230; 5.G.172.231; 5.G.172.236; 5.G.172.237; 5.G.172.238; 5.G.172.239; 5.G.172.154; 5.G.172.157; 5.G.172.166; 5.G.172.169; 5.G.172.172; 5.G.172.175; 5.G.172.240; 5.G.172.244; 5.G.175.228; 5.G.175.229; 5.G.175.230; 5.G.175.231; 5.G.175.236; 5.G.175.237; 5.G.175.238; 5.G.175.239; 5.G.175.154; 5.G.175.157; 5.G.175.166; 5.G.175.169; 5.G.175.172; 5.G.175.175; 5.G.175.240; 5.G.175.244; 5.G.240.228; 5.G.240.229; 5.G.240.230; 5.G.240.231; 5.G.240.236; 5.G.240.237; 5.G.240.238; 5.G.240.239; 5.G.240.154; 5.G.240.157; 5.G.240.166; 5.G.240.169; 5.G.240.172; 5.G.240.175; 5.G.240.240; 5.G.240.244; 5.G.244.228; 5.G.244.229; 5.G.244.230; 5.G.244.231; 5.G.244.236;

TABLE 100-continued

5.G.244.237; 5.G.244.238; 5.G.244.239; 5.G.244.154; 5.G.244.157;
5.G.244.166; 5.G.244.169; 5.G.244.172; 5.G.244.175; 5.G.244.240; 5.G.244.244;

Prodrugs of 5.I

5.I.228.228; 5.I.228.229; 5.I.228.230; 5.I.228.231; 5.I.228.236; 5.I.228.237;
5.I.228.238; 5.I.228.239; 5.I.228.154; 5.I.228.157; 5.I.228.166; 5.I.228.169;
5.I.228.172; 5.I.228.175; 5.I.228.240; 5.I.228.244; 5.I.229.228; 5.I.229.229;
5.I.229.230; 5.I.229.231; 5.I.229.236; 5.I.229.237; 5.I.229.238; 5.I.229.239;
5.I.229.154; 5.I.229.157; 5.I.229.166; 5.I.229.169; 5.I.229.172; 5.I.229.175;
5.I.229.240; 5.I.229.244; 5.I.230.228; 5.I.230.229; 5.I.230.230; 5.I.230.231;
5.I.230.236; 5.I.230.237; 5.I.230.238; 5.I.230.239; 5.I.230.154; 5.I.230.157;
5.I.230.166; 5.I.230.169; 5.I.230.172; 5.I.230.175; 5.I.230.240; 5.I.230.244;
5.I.231.228; 5.I.231.229; 5.I.231.230; 5.I.231.231; 5.I.231.236; 5.I.231.237;
5.I.231.238; 5.I.231.239; 5.I.231.154; 5.I.231.157; 5.I.231.166; 5.I.231.169;
5.I.231.172; 5.I.231.175; 5.I.231.240; 5.I.231.244; 5.I.236.228; 5.I.236.229;
5.I.236.230; 5.I.236.231; 5.I.236.236; 5.I.236.237; 5.I.236.238; 5.I.236.239;
5.I.236.154; 5.I.236.157; 5.I.236.166; 5.I.236.169; 5.I.236.172; 5.I.236.175;
5.I.236.240; 5.I.236.244; 5.I.237.228; 5.I.237.229; 5.I.237.230; 5.I.237.231;
5.I.237.236; 5.I.237.237; 5.I.237.238; 5.I.237.239; 5.I.237.154; 5.I.237.157;
5.I.237.166; 5.I.237.169; 5.I.237.172; 5.I.237.175; 5.I.237.240; 5.I.237.244;
5.I.238.228; 5.I.238.229; 5.I.238.230; 5.I.238.231; 5.I.238.236; 5.I.238.237;
5.I.238.238; 5.I.238.239; 5.I.238.154; 5.I.238.157; 5.I.238.166; 5.I.238.169;
5.I.238.172; 5.I.238.175; 5.I.238.240; 5.I.238.244; 5.I.239.228; 5.I.239.229;
5.I.239.230; 5.I.239.231; 5.I.239.236; 5.I.239.237; 5.I.239.238; 5.I.239.239;
5.I.239.154; 5.I.239.157; 5.I.239.166; 5.I.239.169; 5.I.239.172; 5.I.239.175;
5.I.239.240; 5.I.239.244; 5.I.154.228; 5.I.154.229; 5.I.154.230; 5.I.154.231;
5.I.154.236; 5.I.154.237; 5.I.154.238; 5.I.154.239; 5.I.154.154; 5.I.154.157;
5.I.154.166; 5.I.154.169; 5.I.154.172; 5.I.154.175; 5.I.154.240; 5.I.154.244;
5.I.157.228; 5.I.157.229; 5.I.157.230; 5.I.157.231; 5.I.157.236; 5.I.157.237;
5.I.157.238; 5.I.157.239; 5.I.157.154; 5.I.157.157; 5.I.157.166; 5.I.157.169;
5.I.157.172; 5.I.157.175; 5.I.157.240; 5.I.157.244; 5.I.166.228; 5.I.166.229;
5.I.166.230; 5.I.166.231; 5.I.166.236; 5.I.166.237; 5.I.166.238; 5.I.166.239;
5.I.166.154; 5.I.166.157; 5.I.166.166; 5.I.166.169; 5.I.166.172; 5.I.166.175;
5.I.166.240; 5.I.166.244; 5.I.169.228; 5.I.169.229; 5.I.169.230; 5.I.169.231;
5.I.169.236; 5.I.169.237; 5.I.169.238; 5.I.169.239; 5.I.169.154; 5.I.169.157;
5.I.169.166; 5.I.169.169; 5.I.169.172; 5.I.169.175; 5.I.169.240; 5.I.169.244;
5.I.172.228; 5.I.172.229; 5.I.172.230; 5.I.172.231; 5.I.172.236; 5.I.172.237;
5.I.172.238; 5.I.172.239; 5.I.172.154; 5.I.172.157; 5.I.172.166; 5.I.172.169;
5.I.172.172; 5.I.172.175; 5.I.172.240; 5.I.172.244; 5.I.175.228; 5.I.175.229;
5.I.175.230; 5.I.175.231; 5.I.175.236; 5.I.175.237; 5.I.175.238; 5.I.175.239;
5.I.175.154; 5.I.175.157; 5.I.175.166; 5.I.175.169; 5.I.175.172; 5.I.175.175;
5.I.175.240; 5.I.175.244; 5.I.240.228; 5.I.240.229; 5.I.240.230; 5.I.240.231;
5.I.240.236; 5.I.240.237; 5.I.240.238; 5.I.240.239; 5.I.240.154; 5.I.240.157;
5.I.240.166; 5.I.240.169; 5.I.240.172; 5.I.240.175; 5.I.240.240; 5.I.240.244;
5.I.244.228; 5.I.244.229; 5.I.244.230; 5.I.244.231; 5.I.244.236; 5.I.244.237;
5.I.244.238; 5.I.244.239; 5.I.244.154; 5.I.244.157; 5.I.244.166; 5.I.244.169;
5.I.244.172; 5.I.244.175; 5.I.244.240; 5.I.244.244;

Prodrugs of 5.J

5.J.228.228; 5.J.228.229; 5.J.228.230; 5.J.228.231; 5.J.228.236; 5.J.228.237;
5.J.228.238; 5.J.228.239; 5.J.228.154; 5.J.228.157; 5.J.228.166; 5.J.228.169;
5.J.228.172; 5.J.228.175; 5.J.228.240; 5.J.228.244; 5.J.229.228; 5.J.229.229;
5.J.229.230; 5.J.229.231; 5.J.229.236; 5.J.229.237; 5.J.229.238; 5.J.229.239;
5.J.229.154; 5.J.229.157; 5.J.229.166; 5.J.229.169; 5.J.229.172; 5.J.229.175;
5.J.229.240; 5.J.229.244; 5.J.230.228; 5.J.230.229; 5.J.230.230; 5.J.230.231;
5.J.230.236; 5.J.230.237; 5.J.230.238; 5.J.230.239; 5.J.230.154; 5.J.230.157;
5.J.230.166; 5.J.230.169; 5.J.230.172; 5.J.230.175; 5.J.230.240; 5.J.230.244;
5.J.231.228; 5.J.231.229; 5.J.231.230; 5.J.231.231; 5.J.231.236; 5.J.231.237;
5.J.231.238; 5.J.231.239; 5.J.231.154; 5.J.231.157; 5.J.231.166; 5.J.231.169;
5.J.231.172; 5.J.231.175; 5.J.231.240; 5.J.231.244; 5.J.236.228; 5.J.236.229;
5.J.236.230; 5.J.236.231; 5.J.236.236; 5.J.236.237; 5.J.236.238; 5.J.236.239;
5.J.236.154; 5.J.236.157; 5.J.236.166; 5.J.236.169; 5.J.236.172; 5.J.236.175;
5.J.236.240; 5.J.236.244; 5.J.237.228; 5.J.237.229; 5.J.237.230; 5.J.237.231;
5.J.237.236; 5.J.237.237; 5.J.237.238; 5.J.237.239; 5.J.237.154; 5.J.237.157;
5.J.237.166; 5.J.237.169; 5.J.237.172; 5.J.237.175; 5.J.237.240; 5.J.237.244;
5.J.238.228; 5.J.238.229; 5.J.238.230; 5.J.238.231; 5.J.238.236; 5.J.238.237;
5.J.238.238; 5.J.238.239; 5.J.238.154; 5.J.238.157; 5.J.238.166; 5.J.238.169;
5.J.238.172; 5.J.238.175; 5.J.238.240; 5.J.238.244; 5.J.239.228; 5.J.239.229;
5.J.239.230; 5.J.239.231; 5.J.239.236; 5.J.239.237; 5.J.239.238; 5.J.239.239;
5.J.239.154; 5.J.239.157; 5.J.239.166; 5.J.239.169; 5.J.239.172; 5.J.239.175;
5.J.239.240; 5.J.239.244; 5.J.154.228; 5.J.154.229; 5.J.154.230; 5.J.154.231;
5.J.154.236; 5.J.154.237; 5.J.154.238; 5.J.154.239; 5.J.154.154; 5.J.154.157;
5.J.154.166; 5.J.154.169; 5.J.154.172; 5.J.154.175; 5.J.154.240; 5.J.154.244;
5.J.157.228; 5.J.157.229; 5.J.157.230; 5.J.157.231; 5.J.157.236; 5.J.157.237;
5.J.157.238; 5.J.157.239; 5.J.157.154; 5.J.157.157; 5.J.157.166; 5.J.157.169;
5.J.157.172; 5.J.157.175; 5.J.157.240; 5.J.157.244; 5.J.166.228; 5.J.166.229;
5.J.166.230; 5.J.166.231; 5.J.166.236; 5.J.166.237; 5.J.166.238; 5.J.166.239;
5.J.166.154; 5.J.166.157; 5.J.166.166; 5.J.166.169; 5.J.166.172; 5.J.166.175;
5.J.166.240; 5.J.166.244; 5.J.169.228; 5.J.169.229; 5.J.169.230; 5.J.169.231;
5.J.169.236; 5.J.169.237; 5.J.169.238; 5.J.169.239; 5.J.169.154; 5.J.169.157;

TABLE 100-continued

5.J.169.166; 5.J.169.169; 5.J.169.172; 5.J.169.175; 5.J.169.240; 5.J.169.244; 5.J.172.228; 5.J.172.229; 5.J.172.230; 5.J.172.231; 5.J.172.236; 5.J.172.237; 5.J.172.238; 5.J.172.239; 5.J.172.154; 5.J.172.157; 5.J.172.166; 5.J.172.169; 5.J.172.172; 5.J.172.175; 5.J.172.240; 5.J.172.244; 5.J.175.228; 5.J.175.229; 5.J.175.230; 5.J.175.231; 5.J.175.236; 5.J.175.237; 5.J.175.238; 5.J.175.239; 5.J.175.154; 5.J.175.157; 5.J.175.166; 5.J.175.169; 5.J.175.172; 5.J.175.175; 5.J.175.240; 5.J.175.244; 5.J.240.228; 5.J.240.229; 5.J.240.230; 5.J.240.231; 5.J.240.236; 5.J.240.237; 5.J.240.238; 5.J.240.239; 5.J.240.154; 5.J.240.157; 5.J.240.166; 5.J.240.169; 5.J.240.172; 5.J.240.175; 5.J.240.240; 5.J.240.244; 5.J.244.228; 5.J.244.229; 5.J.244.230; 5.J.244.231; 5.J.244.236; 5.J.244.237; 5.J.244.238; 5.J.244.239; 5.J.244.154; 5.J.244.157; 5.J.244.166; 5.J.244.169; 5.J.244.172; 5.J.244.175; 5.J.244.240; 5.J.244.244;

Prodrugs of 5.L

5.L.228.228; 5.L.228.229; 5.L.228.230; 5.L.228.231; 5.L.228.236; 5.L.228.237; 5.L.228.238; 5.L.228.239; 5.L.228.154; 5.L.228.157; 5.L.228.166; 5.L.228.169; 5.L.228.172; 5.L.228.175; 5.L.228.240; 5.L.228.244; 5.L.229.228; 5.L.229.229; 5.L.229.230; 5.L.229.231; 5.L.229.236; 5.L.229.237; 5.L.229.238; 5.L.229.239; 5.L.229.154; 5.L.229.157; 5.L.229.166; 5.L.229.169; 5.L.229.172; 5.L.229.175; 5.L.229.240; 5.L.229.244; 5.L.230.228; 5.L.230.229; 5.L.230.230; 5.L.230.231; 5.L.230.236; 5.L.230.237; 5.L.230.238; 5.L.230.239; 5.L.230.154; 5.L.230.157; 5.L.230.166; 5.L.230.169; 5.L.230.172; 5.L.230.175; 5.L.230.240; 5.L.230.244; 5.L.231.228; 5.L.231.229; 5.L.231.230; 5.L.231.231; 5.L.231.236; 5.L.231.237; 5.L.231.238; 5.L.231.239; 5.L.231.154; 5.L.231.157; 5.L.231.166; 5.L.231.169; 5.L.231.172; 5.L.231.175; 5.L.231.240; 5.L.231.244; 5.L.236.228; 5.L.236.229; 5.L.236.230; 5.L.236.231; 5.L.236.236; 5.L.236.237; 5.L.236.238; 5.L.236.239; 5.L.236.154; 5.L.236.157; 5.L.236.166; 5.L.236.169; 5.L.236.172; 5.L.236.175; 5.L.236.240; 5.L.236.244; 5.L.237.228; 5.L.237.229; 5.L.237.230; 5.L.237.231; 5.L.237.236; 5.L.237.237; 5.L.237.238; 5.L.237.239; 5.L.237.154; 5.L.237.157; 5.L.237.166; 5.L.237.169; 5.L.237.172; 5.L.237.175; 5.L.237.240; 5.L.237.244; 5.L.238.228; 5.L.238.229; 5.L.238.230; 5.L.238.231; 5.L.238.236; 5.L.238.237; 5.L.238.238; 5.L.238.239; 5.L.238.154; 5.L.238.157; 5.L.238.166; 5.L.238.169; 5.L.238.172; 5.L.238.175; 5.L.238.240; 5.L.238.244; 5.L.239.228; 5.L.239.229; 5.L.239.230; 5.L.239.231; 5.L.239.236; 5.L.239.237; 5.L.239.238; 5.L.239.239; 5.L.239.154; 5.L.239.157; 5.L.239.166; 5.L.239.169; 5.L.239.172; 5.L.239.175; 5.L.239.240; 5.L.239.244; 5.L.154.228; 5.L.154.229; 5.L.154.230; 5.L.154.231; 5.L.154.236; 5.L.154.237; 5.L.154.238; 5.L.154.239; 5.L.154.154; 5.L.154.157; 5.L.154.166; 5.L.154.169; 5.L.154.172; 5.L.154.175; 5.L.154.240; 5.L.154.244; 5.L.157.228; 5.L.157.229; 5.L.157.230; 5.L.157.231; 5.L.157.236; 5.L.157.237; 5.L.157.238; 5.L.157.239; 5.L.157.154; 5.L.157.157; 5.L.157.166; 5.L.157.169; 5.L.157.172; 5.L.157.175; 5.L.157.240; 5.L.157.244; 5.L.166.228; 5.L.166.229; 5.L.166.230; 5.L.166.231; 5.L.166.236; 5.L.166.237; 5.L.166.238; 5.L.166.239; 5.L.166.154; 5.L.166.157; 5.L.166.166; 5.L.166.169; 5.L.166.172; 5.L.166.175; 5.L.166.240; 5.L.166.244; 5.L.169.228; 5.L.169.229; 5.L.169.230; 5.L.169.231; 5.L.169.236; 5.L.169.237; 5.L.169.238; 5.L.169.239; 5.L.169.154; 5.L.169.157; 5.L.169.166; 5.L.169.169; 5.L.169.172; 5.L.169.175; 5.L.169.240; 5.L.169.244; 5.L.172.228; 5.L.172.229; 5.L.172.230; 5.L.172.231; 5.L.172.236; 5.L.172.237; 5.L.172.238; 5.L.172.239; 5.L.172.154; 5.L.172.157; 5.L.172.166; 5.L.172.169; 5.L.172.172; 5.L.172.175; 5.L.172.240; 5.L.172.244; 5.L.175.228; 5.L.175.229; 5.L.175.230; 5.L.175.231; 5.L.175.236; 5.L.175.237; 5.L.175.238; 5.L.175.239; 5.L.175.154; 5.L.175.157; 5.L.175.166; 5.L.175.169; 5.L.175.172; 5.L.175.175; 5.L.175.240; 5.L.175.244; 5.L.240.228; 5.L.240.229; 5.L.240.230; 5.L.240.231; 5.L.240.236; 5.L.240.237; 5.L.240.238; 5.L.240.239; 5.L.240.154; 5.L.240.157; 5.L.240.166; 5.L.240.169; 5.L.240.172; 5.L.240.175; 5.L.240.240; 5.L.240.244; 5.L.244.228; 5.L.244.229; 5.L.244.230; 5.L.244.231; 5.L.244.236; 5.L.244.237; 5.L.244.238; 5.L.244.239; 5.L.244.154; 5.L.244.157; 5.L.244.166; 5.L.244.169; 5.L.244.172; 5.L.244.175; 5.L.244.240; 5.L.244.244;

Prodrugs of 5.O

5.O.228.228; 5.O.228.229; 5.O.228.230; 5.O.228.231; 5.O.228.236; 5.O.228.237; 5.O.228.238; 5.O.228.239; 5.O.228.154; 5.O.228.157; 5.O.228.166; 5.O.228.169; 5.O.228.172; 5.O.228.175; 5.O.228.240; 5.O.228.244; 5.O.229.228; 5.O.229.229; 5.O.229.230; 5.O.229.231; 5.O.229.236; 5.O.229.237; 5.O.229.238; 5.O.229.239; 5.O.229.154; 5.O.229.157; 5.O.229.166; 5.O.229.169; 5.O.229.172; 5.O.229.175; 5.O.229.240; 5.O.229.244; 5.O.230.228; 5.O.230.229; 5.O.230.230; 5.O.230.231; 5.O.230.236; 5.O.230.237; 5.O.230.238; 5.O.230.239; 5.O.230.154; 5.O.230.157; 5.O.230.166; 5.O.230.169; 5.O.230.172; 5.O.230.175; 5.O.230.240; 5.O.230.244; 5.O.231.228; 5.O.231.229; 5.O.231.230; 5.O.231.231; 5.O.231.236; 5.O.231.237; 5.O.231.238; 5.O.231.239; 5.O.231.154; 5.O.231.157; 5.O.231.166; 5.O.231.169; 5.O.231.172; 5.O.231.175; 5.O.231.240; 5.O.231.244; 5.O.236.228; 5.O.236.229; 5.O.236.230; 5.O.236.231; 5.O.236.236; 5.O.236.237; 5.O.236.238; 5.O.236.239; 5.O.236.154; 5.O.236.157; 5.O.236.166; 5.O.236.169; 5.O.236.172; 5.O.236.175; 5.O.236.240; 5.O.236.244; 5.O.237.228; 5.O.237.229; 5.O.237.230; 5.O.237.231; 5.O.237.236; 5.O.237.237; 5.O.237.238; 5.O.237.239; 5.O.237.154; 5.O.237.157; 5.O.237.166; 5.O.237.169; 5.O.237.172; 5.O.237.175; 5.O.237.240; 5.O.237.244; 5.O.238.228; 5.O.238.229; 5.O.238.230; 5.O.238.231; 5.O.238.236; 5.O.238.237; 5.O.238.238; 5.O.238.239; 5.O.238.154;

TABLE 100-continued

| |
|---|
| 5.O.238.157; 5.O.238.166; 5.O.238.169; 5.O.238.172; 5.O.238.175; 5.O.238.240; 5.O.238.244; 5.O.239.228; 5.O.239.229; 5.O.239.230; 5.O.239.231; 5.O.239.236; 5.O.239.237; 5.O.239.238; 5.O.239.239; 5.O.239.154; 5.O.239.157; 5.O.239.166; 5.O.239.169; 5.O.239.172; 5.O.239.175; 5.O.239.240; 5.O.239.244; 5.O.154.228; 5.O.154.229; 5.O.154.230; 5.O.154.231; 5.O.154.236; 5.O.154.237; 5.O.154.238; 5.O.154.239; 5.O.154.154; 5.O.154.157; 5.O.154.166; 5.O.154.169; 5.O.154.172; 5.O.154.175; 5.O.154.240; 5.O.154.244; 5.O.157.228; 5.O.157.229; 5.O.157.230; 5.O.157.231; 5.O.157.236; 5.O.157.237; 5.O.157.238; 5.O.157.239; 5.O.157.154; 5.O.157.157; 5.O.157.166; 5.O.157.169; 5.O.157.172; 5.O.157.175; 5.O.157.240; 5.O.157.244; 5.O.166.228; 5.O.166.229; 5.O.166.230; 5.O.166.231; 5.O.166.236; 5.O.166.237; 5.O.166.238; 5.O.166.239; 5.O.166.154; 5.O.166.157; 5.O.166.166; 5.O.166.169; 5.O.166.172; 5.O.166.175; 5.O.166.240; 5.O.166.244; 5.O.169.228; 5.O.169.229; 5.O.169.230; 5.O.169.231; 5.O.169.236; 5.O.169.237; 5.O.169.238; 5.O.169.239; 5.O.169.154; 5.O.169.157; 5.O.169.166; 5.O.169.169; 5.O.169.172; 5.O.169.175; 5.O.169.240; 5.O.169.244; 5.O.172.228; 5.O.172.229; 5.O.172.230; 5.O.172.231; 5.O.172.236; 5.O.172.237; 5.O.172.238; 5.O.172.239; 5.O.172.154; 5.O.172.157; 5.O.172.166; 5.O.172.169; 5.O.172.172; 5.O.172.175; 5.O.172.240; 5.O.172.244; 5.O.175.228; 5.O.175.229; 5.O.175.230; 5.O.175.231; 5.O.175.236; 5.O.175.237; 5.O.175.238; 5.O.175.239; 5.O.175.154; 5.O.175.157; 5.O.175.166; 5.O.175.169; 5.O.175.172; 5.O.175.175; 5.O.175.240; 5.O.175.244; 5.O.240.228; 5.O.240.229; 5.O.240.230; 5.O.240.231; 5.O.240.236; 5.O.240.237; 5.O.240.238; 5.O.240.239; 5.O.240.154; 5.O.240.157; 5.O.240.166; 5.O.240.169; 5.O.240.172; 5.O.240.175; 5.O.240.240; 5.O.240.244; 5.O.244.228; 5.O.244.229; 5.O.244.230; 5.O.244.231; 5.O.244.236; 5.O.244.237; 5.O.244.238; 5.O.244.239; 5.O.244.154; 5.O.244.157; 5.O.244.166; 5.O.244.169; 5.O.244.172; 5.O.244.175; 5.O.244.240; 5.O.244.244; |
| Prodrugs of 5.P |
| 5.P.228.228; 5.P.228.229; 5.P.228.230; 5.P.228.231; 5.P.228.236; 5.P.228.237; 5.P.228.238; 5.P.228.239; 5.P.228.154; 5.P.228.157; 5.P.228.166; 5.P.228.169; 5.P.228.172; 5.P.228.175; 5.P.228.240; 5.P.228.244; 5.P.229.228; 5.P.229.229; 5.P.229.230; 5.P.229.231; 5.P.229.236; 5.P.229.237; 5.P.229.238; 5.P.229.239; 5.P.229.154; 5.P.229.157; 5.P.229.166; 5.P.229.169; 5.P.229.172; 5.P.229.175; 5.P.229.240; 5.P.229.244; 5.P.230.228; 5.P.230.229; 5.P.230.230; 5.P.230.231; 5.P.230.236; 5.P.230.237; 5.P.230.238; 5.P.230.239; 5.P.230.154; 5.P.230.157; 5.P.230.166; 5.P.230.169; 5.P.230.172; 5.P.230.175; 5.P.230.240; 5.P.230.244; 5.P.231.228; 5.P.231.229; 5.P.231.230; 5.P.231.231; 5.P.231.236; 5.P.231.237; 5.P.231.238; 5.P.231.239; 5.P.231.154; 5.P.231.157; 5.P.231.166; 5.P.231.169; 5.P.231.172; 5.P.231.175; 5.P.231.240; 5.P.231.244; 5.P.236.228; 5.P.236.229; 5.P.236.230; 5.P.236.231; 5.P.236.236; 5.P.236.237; 5.P.236.238; 5.P.236.239; 5.P.236.154; 5.P.236.157; 5.P.236.166; 5.P.236.169; 5.P.236.172; 5.P.236.175; 5.P.236.240; 5.P.236.244; 5.P.237.228; 5.P.237.229; 5.P.237.230; 5.P.237.231; 5.P.237.236; 5.P.237.237; 5.P.237.238; 5.P.237.239; 5.P.237.154; 5.P.237.157; 5.P.237.166; 5.P.237.169; 5.P.237.172; 5.P.237.175; 5.P.237.240; 5.P.237.244; 5.P.238.228; 5.P.238.229; 5.P.238.230; 5.P.238.231; 5.P.238.236; 5.P.238.237; 5.P.238.238; 5.P.238.239; 5.P.238.154; 5.P.238.157; 5.P.238.166; 5.P.238.169; 5.P.238.172; 5.P.238.175; 5.P.238.240; 5.P.238.244; 5.P.239.228; 5.P.239.229; 5.P.239.230; 5.P.239.231; 5.P.239.236; 5.P.239.237; 5.P.239.238; 5.P.239.239; 5.P.239.154; 5.P.239.157; 5.P.239.166; 5.P.239.169; 5.P.239.172; 5.P.239.175; 5.P.239.240; 5.P.239.244; 5.P.154.228; 5.P.154.229; 5.P.154.230; 5.P.154.231; 5.P.154.236; 5.P.154.237; 5.P.154.238; 5.P.154.239; 5.P.154.154; 5.P.154.157; 5.P.154.166; 5.P.154.169; 5.P.154.172; 5.P.154.175; 5.P.154.240; 5.P.154.244; 5.P.157.228; 5.P.157.229; 5.P.157.230; 5.P.157.231; 5.P.157.236; 5.P.157.237; 5.P.157.238; 5.P.157.239; 5.P.157.154; 5.P.157.157; 5.P.157.166; 5.P.157.169; 5.P.157.172; 5.P.157.175; 5.P.157.240; 5.P.157.244; 5.P.166.228; 5.P.166.229; 5.P.166.230; 5.P.166.231; 5.P.166.236; 5.P.166.237; 5.P.166.238; 5.P.166.239; 5.P.166.154; 5.P.166.157; 5.P.166.166; 5.P.166.169; 5.P.166.172; 5.P.166.175; 5.P.166.240; 5.P.166.244; 5.P.169.228; 5.P.169.229; 5.P.169.230; 5.P.169.231; 5.P.169.236; 5.P.169.237; 5.P.169.238; 5.P.169.239; 5.P.169.154; 5.P.169.157; 5.P.169.166; 5.P.169.169; 5.P.169.172; 5.P.169.175; 5.P.169.240; 5.P.169.244; 5.P.172.228; 5.P.172.229; 5.P.172.230; 5.P.172.231; 5.P.172.236; 5.P.172.237; 5.P.172.238; 5.P.172.239; 5.P.172.154; 5.P.172.157; 5.P.172.166; 5.P.172.169; 5.P.172.172; 5.P.172.175; 5.P.172.240; 5.P.172.244; 5.P.175.228; 5.P.175.229; 5.P.175.230; 5.P.175.231; 5.P.175.236; 5.P.175.237; 5.P.175.238; 5.P.175.239; 5.P.175.154; 5.P.175.157; 5.P.175.166; 5.P.175.169; 5.P.175.172; 5.P.175.175; 5.P.175.240; 5.P.175.244; 5.P.240.228; 5.P.240.229; 5.P.240.230; 5.P.240.231; 5.P.240.236; 5.P.240.237; 5.P.240.238; 5.P.240.239; 5.P.240.154; 5.P.240.157; 5.P.240.166; 5.P.240.169; 5.P.240.172; 5.P.240.175; 5.P.240.240; 5.P.240.244; 5.P.244.228; 5.P.244.229; 5.P.244.230; 5.P.244.231; 5.P.244.236; 5.P.244.237; 5.P.244.238; 5.P.244.239; 5.P.244.154; 5.P.244.157; 5.P.244.166; 5.P.244.169; 5.P.244.172; 5.P.244.175; 5.P.244.240; 5.P.244.244; |
| Prodrugs of 5.U |
| 5.U.228.228; 5.U.228.229; 5.U.228.230; 5.U.228.231; 5.U.228.236; 5.U.228.237; 5.U.228.238; 5.U.228.239; 5.U.228.154; 5.U.228.157; 5.U.228.166; 5.U.228.169; 5.U.228.172; 5.U.228.175; 5.U.228.240; |

TABLE 100-continued

| |
|---|
| 5.U.228.244; 5.U.229.228; 5.U.229.229; 5.U.229.230; 5.U.229.231; 5.U.229.236; 5.U.229.237; 5.U.229.238; 5.U.229.239; 5.U.229.154; 5.U.229.157; 5.U.229.166; 5.U.229.169; 5.U.229.172; 5.U.229.175; 5.U.229.240; 5.U.229.244; 5.U.230.228; 5.U.230.229; 5.U.230.230; 5.U.230.231; 5.U.230.236; 5.U.230.237; 5.U.230.238; 5.U.230.239; 5.U.230.154; 5.U.230.157; 5.U.230.166; 5.U.230.169; 5.U.230.172; 5.U.230.175; 5.U.230.240; 5.U.230.244; 5.U.231.228; 5.U.231.229; 5.U.231.230; 5.U.231.231; 5.U.231.236; 5.U.231.237; 5.U.231.238; 5.U.231.239; 5.U.231.154; 5.U.231.157; 5.U.231.166; 5.U.231.169; 5.U.231.172; 5.U.231.175; 5.U.231.240; 5.U.231.244; 5.U.236.228; 5.U.236.229; 5.U.236.230; 5.U.236.231; 5.U.236.236; 5.U.236.237; 5.U.236.238; 5.U.236.239; 5.U.236.154; 5.U.236.157; 5.U.236.166; 5.U.236.169; 5.U.236.172; 5.U.236.175; 5.U.236.240; 5.U.236.244; 5.U.237.228; 5.U.237.229; 5.U.237.230; 5.U.237.231; 5.U.237.236; 5.U.237.237; 5.U.237.238; 5.U.237.239; 5.U.237.154; 5.U.237.157; 5.U.237.166; 5.U.237.169; 5.U.237.172; 5.U.237.175; 5.U.237.240; 5.U.237.244; 5.U.238.228; 5.U.238.229; 5.U.238.230; 5.U.238.231; 5.U.238.236; 5.U.238.237; 5.U.238.238; 5.U.238.239; 5.U.238.154; 5.U.238.157; 5.U.238.166; 5.U.238.169; 5.U.238.172; 5.U.238.175; 5.U.238.240; 5.U.238.244; 5.U.239.228; 5.U.239.229; 5.U.239.230; 5.U.239.231; 5.U.239.236; 5.U.239.237; 5.U.239.238; 5.U.239.239; 5.U.239.154; 5.U.239.157; 5.U.239.166; 5.U.239.169; 5.U.239.172; 5.U.239.175; 5.U.239.240; 5.U.239.244; 5.U.154.228; 5.U.154.229; 5.U.154.230; 5.U.154.231; 5.U.154.236; 5.U.154.237; 5.U.154.238; 5.U.154.239; 5.U.154.154; 5.U.154.157; 5.U.154.166; 5.U.154.169; 5.U.154.172; 5.U.154.175; 5.U.154.240; 5.U.154.244; 5.U.157.228; 5.U.157.229; 5.U.157.230; 5.U.157.231; 5.U.157.236; 5.U.157.237; 5.U.157.238; 5.U.157.239; 5.U.157.154; 5.U.157.157; 5.U.157.166; 5.U.157.169; 5.U.157.172; 5.U.157.175; 5.U.157.240; 5.U.157.244; 5.U.166.228; 5.U.166.229; 5.U.166.230; 5.U.166.231; 5.U.166.236; 5.U.166.237; 5.U.166.238; 5.U.166.239; 5.U.166.154; 5.U.166.157; 5.U.166.166; 5.U.166.169; 5.U.166.172; 5.U.166.175; 5.U.166.240; 5.U.166.244; 5.U.169.228; 5.U.169.229; 5.U.169.230; 5.U.169.231; 5.U.169.236; 5.U.169.237; 5.U.169.238; 5.U.169.239; 5.U.169.154; 5.U.169.157; 5.U.169.166; 5.U.169.169; 5.U.169.172; 5.U.169.175; 5.U.169.240; 5.U.169.244; 5.U.172.228; 5.U.172.229; 5.U.172.230; 5.U.172.231; 5.U.172.236; 5.U.172.237; 5.U.172.238; 5.U.172.239; 5.U.172.154; 5.U.172.157; 5.U.172.166; 5.U.172.169; 5.U.172.172; 5.U.172.175; 5.U.172.240; 5.U.172.244; 5.U.175.228; 5.U.175.229; 5.U.175.230; 5.U.175.231; 5.U.175.236; 5.U.175.237; 5.U.175.238; 5.U.175.239; 5.U.175.154; 5.U.175.157; 5.U.175.166; 5.U.175.169; 5.U.175.172; 5.U.175.175; 5.U.175.240; 5.U.175.244; 5.U.240.228; 5.U.240.229; 5.U.240.230; 5.U.240.231; 5.U.240.236; 5.U.240.237; 5.U.240.238; 5.U.240.239; 5.U.240.154; 5.U.240.157; 5.U.240.166; 5.U.240.169; 5.U.240.172; 5.U.240.175; 5.U.240.240; 5.U.240.244; 5.U.244.228; 5.U.244.229; 5.U.244.230; 5.U.244.231; 5.U.244.236; 5.U.244.237; 5.U.244.238; 5.U.244.239; 5.U.244.154; 5.U.244.157; 5.U.244.166; 5.U.244.169; 5.U.244.172; 5.U.244.175; 5.U.244.240; 5.U.244.244; |
| Prodrugs of 5.W |
| 5.W.228.228; 5.W.228.229; 5.W.228.230; 5.W.228.231; 5.W.228.236; 5.W.228.237; 5.W.228.238; 5.W.228.239; 5.W.228.154; 5.W.228.157; 5.W.228.166; 5.W.228.169; 5.W.228.172; 5.W.228.175; 5.W.228.240; 5.W.228.244; 5.W.229.228; 5.W.229.229; 5.W.229.230; 5.W.229.231; 5.W.229.236; 5.W.229.237; 5.W.229.238; 5.W.229.239; 5.W.229.154; 5.W.229.157; 5.W.229.166; 5.W.229.169; 5.W.229.172; 5.W.229.175; 5.W.229.240; 5.W.229.244; 5.W.230.228; 5.W.230.229; 5.W.230.230; 5.W.230.231; 5.W.230.236; 5.W.230.237; 5.W.230.238; 5.W.230.239; 5.W.230.154; 5.W.230.157; 5.W.230.166; 5.W.230.169; 5.W.230.172; 5.W.230.175; 5.W.230.240; 5.W.230.244; 5.W.231.228; 5.W.231.229; 5.W.231.230; 5.W.231.231; 5.W.231.236; 5.W.231.237; 5.W.231.238; 5.W.231.239; 5.W.231.154; 5.W.231.157; 5.W.231.166; 5.W.231.169; 5.W.231.172; 5.W.231.175; 5.W.231.240; 5.W.231.244; 5.W.236.228; 5.W.236.229; 5.W.236.230; 5.W.236.231; 5.W.236.236; 5.W.236.237; 5.W.236.238; 5.W.236.239; 5.W.236.154; 5.W.236.157; 5.W.236.166; 5.W.236.169; 5.W.236.172; 5.W.236.175; 5.W.236.240; 5.W.236.244; 5.W.237.228; 5.W.237.229; 5.W.237.230; 5.W.237.231; 5.W.237.236; 5.W.237.237; 5.W.237.238; 5.W.237.239; 5.W.237.154; 5.W.237.157; 5.W.237.166; 5.W.237.169; 5.W.237.172; 5.W.237.175; 5.W.237.240; 5.W.237.244; 5.W.238.228; 5.W.238.229; 5.W.238.230; 5.W.238.231; 5.W.238.236; 5.W.238.237; 5.W.238.238; 5.W.238.239; 5.W.238.154; 5.W.238.157; 5.W.238.166; 5.W.238.169; 5.W.238.172; 5.W.238.175; 5.W.238.240; 5.W.238.244; 5.W.239.228; 5.W.239.229; 5.W.239.230; 5.W.239.231; 5.W.239.236; 5.W.239.237; 5.W.239.238; 5.W.239.239; 5.W.239.154; 5.W.239.157; 5.W.239.166; 5.W.239.169; 5.W.239.172; 5.W.239.175; 5.W.239.240; 5.W.239.244; 5.W.154.228; 5.W.154.229; 5.W.154.230; 5.W.154.231; 5.W.154.236; 5.W.154.237; 5.W.154.238; 5.W.154.239; 5.W.154.154; 5.W.154.157; 5.W.154.166; 5.W.154.169; 5.W.154.172; 5.W.154.175; 5.W.154.240; 5.W.154.244; 5.W.157.228; 5.W.157.229; 5.W.157.230; 5.W.157.231; 5.W.157.236; 5.W.157.237; |

TABLE 100-continued

5.W.157.238; 5.W.157.239; 5.W.157.154; 5.W.157.157; 5.W.157.166; 5.W.157.169; 5.W.157.172; 5.W.157.175; 5.W.157.240; 5.W.157.244; 5.W.166.228; 5.W.166.229; 5.W.166.230; 5.W.166.231; 5.W.166.236; 5.W.166.237; 5.W.166.238; 5.W.166.239; 5.W.166.154; 5.W.166.157; 5.W.166.166; 5.W.166.169; 5.W.166.172; 5.W.166.175; 5.W.166.240; 5.W.166.244; 5.W.169.228; 5.W.169.229; 5.W.169.230; 5.W.169.231; 5.W.169.236; 5.W.169.237; 5.W.169.238; 5.W.169.239; 5.W.169.154; 5.W.169.157; 5.W.169.166; 5.W.169.169; 5.W.169.172; 5.W.169.175; 5.W.169.240; 5.W.169.244; 5.W.172.228; 5.W.172.229; 5.W.172.230; 5.W.172.231; 5.W.172.236; 5.W.172.237; 5.W.172.238; 5.W.172.239; 5.W.172.154; 5.W.172.157; 5.W.172.166; 5.W.172.169; 5.W.172.172; 5.W.172.175; 5.W.172.240; 5.W.172.244; 5.W.175.228; 5.W.175.229; 5.W.175.230; 5.W.175.231; 5.W.175.236; 5.W.175.237; 5.W.175.238; 5.W.175.239; 5.W.175.154; 5.W.175.157; 5.W.175.166; 5.W.175.169; 5.W.175.172; 5.W.175.175; 5.W.175.240; 5.W.175.244; 5.W.240.228; 5.W.240.229; 5.W.240.230; 5.W.240.231; 5.W.240.236; 5.W.240.237; 5.W.240.238; 5.W.240.239; 5.W.240.154; 5.W.240.157; 5.W.240.166; 5.W.240.169; 5.W.240.172; 5.W.240.175; 5.W.240.240; 5.W.240.244; 5.W.244.228; 5.W.244.229; 5.W.244.230; 5.W.244.231; 5.W.244.236; 5.W.244.237; 5.W.244.238; 5.W.244.239; 5.W.244.154; 5.W.244.157; 5.W.244.166; 5.W.244.169; 5.W.244.172; 5.W.244.175; 5.W.244.240; 5.W.244.244;

Prodrugs of 5.Y

5.Y.228.228; 5.Y.228.229; 5.Y.228.230; 5.Y.228.231; 5.Y.228.236; 5.Y.228.237; 5.Y.228.238; 5.Y.228.239; 5.Y.228.154; 5.Y.228.157; 5.Y.228.166; 5.Y.228.169; 5.Y.228.172; 5.Y.228.175; 5.Y.228.240; 5.Y.228.244; 5.Y.229.228; 5.Y.229.229; 5.Y.229.230; 5.Y.229.231; 5.Y.229.236; 5.Y.229.237; 5.Y.229.238; 5.Y.229.239; 5.Y.229.154; 5.Y.229.157; 5.Y.229.166; 5.Y.229.169; 5.Y.229.172; 5.Y.229.175; 5.Y.229.240; 5.Y.229.244; 5.Y.230.228; 5.Y.230.229; 5.Y.230.230; 5.Y.230.231; 5.Y.230.236; 5.Y.230.237; 5.Y.230.238; 5.Y.230.239; 5.Y.230.154; 5.Y.230.157; 5.Y.230.166; 5.Y.230.169; 5.Y.230.172; 5.Y.230.175; 5.Y.230.240; 5.Y.230.244; 5.Y.231.228; 5.Y.231.229; 5.Y.231.230; 5.Y.231.231; 5.Y.231.236; 5.Y.231.237; 5.Y.231.238; 5.Y.231.239; 5.Y.231.154; 5.Y.231.157; 5.Y.231.166; 5.Y.231.169; 5.Y.231.172; 5.Y.231.175; 5.Y.231.240; 5.Y.231.244; 5.Y.236.228; 5.Y.236.229; 5.Y.236.230; 5.Y.236.231; 5.Y.236.236; 5.Y.236.237; 5.Y.236.238; 5.Y.236.239; 5.Y.236.154; 5.Y.236.157; 5.Y.236.166; 5.Y.236.169; 5.Y.236.172; 5.Y.236.175; 5.Y.236.240; 5.Y.236.244; 5.Y.237.228; 5.Y.237.229; 5.Y.237.230; 5.Y.237.231; 5.Y.237.236; 5.Y.237.237; 5.Y.237.238; 5.Y.237.239; 5.Y.237.154; 5.Y.237.157; 5.Y.237.166; 5.Y.237.169; 5.Y.237.172; 5.Y.237.175; 5.Y.237.240; 5.Y.237.244; 5.Y.238.228; 5.Y.238.229; 5.Y.238.230; 5.Y.238.231; 5.Y.238.236; 5.Y.238.237; 5.Y.238.238; 5.Y.238.239; 5.Y.238.154; 5.Y.238.157; 5.Y.238.166; 5.Y.238.169; 5.Y.238.172; 5.Y.238.175; 5.Y.238.240; 5.Y.238.244; 5.Y.239.228; 5.Y.239.229; 5.Y.239.230; 5.Y.239.231; 5.Y.239.236; 5.Y.239.237; 5.Y.239.238; 5.Y.239.239; 5.Y.239.154; 5.Y.239.157; 5.Y.239.166; 5.Y.239.169; 5.Y.239.172; 5.Y.239.175; 5.Y.239.240; 5.Y.239.244; 5.Y.154.228; 5.Y.154.229; 5.Y.154.230; 5.Y.154.231; 5.Y.154.236; 5.Y.154.237; 5.Y.154.238; 5.Y.154.239; 5.Y.154.154; 5.Y.154.157; 5.Y.154.166; 5.Y.154.169; 5.Y.154.172; 5.Y.154.175; 5.Y.154.240; 5.Y.154.244; 5.Y.157.228; 5.Y.157.229; 5.Y.157.230; 5.Y.157.231; 5.Y.157.236; 5.Y.157.237; 5.Y.157.238; 5.Y.157.239; 5.Y.157.154; 5.Y.157.157; 5.Y.157.166; 5.Y.157.169; 5.Y.157.172; 5.Y.157.175; 5.Y.157.240; 5.Y.157.244; 5.Y.166.228; 5.Y.166.229; 5.Y.166.230; 5.Y.166.231; 5.Y.166.236; 5.Y.166.237; 5.Y.166.238; 5.Y.166.239; 5.Y.166.154; 5.Y.166.157; 5.Y.166.166; 5.Y.166.169; 5.Y.166.172; 5.Y.166.175; 5.Y.166.240; 5.Y.166.244; 5.Y.169.228; 5.Y.169.229; 5.Y.169.230; 5.Y.169.231; 5.Y.169.236; 5.Y.169.237; 5.Y.169.238; 5.Y.169.239; 5.Y.169.154; 5.Y.169.157; 5.Y.169.166; 5.Y.169.169; 5.Y.169.172; 5.Y.169.175; 5.Y.169.240; 5.Y.169.244; 5.Y.172.228; 5.Y.172.229; 5.Y.172.230; 5.Y.172.231; 5.Y.172.236; 5.Y.172.237; 5.Y.172.238; 5.Y.172.239; 5.Y.172.154; 5.Y.172.157; 5.Y.172.166; 5.Y.172.169; 5.Y.172.172; 5.Y.172.175; 5.Y.172.240; 5.Y.172.244; 5.Y.175.228; 5.Y.175.229; 5.Y.175.230; 5.Y.175.231; 5.Y.175.236; 5.Y.175.237; 5.Y.175.238; 5.Y.175.239; 5.Y.175.154; 5.Y.175.157; 5.Y.175.166; 5.Y.175.169; 5.Y.175.172; 5.Y.175.175; 5.Y.175.240; 5.Y.175.244; 5.Y.240.228; 5.Y.240.229; 5.Y.240.230; 5.Y.240.231; 5.Y.240.236; 5.Y.240.237; 5.Y.240.238; 5.Y.240.239; 5.Y.240.154; 5.Y.240.157; 5.Y.240.166; 5.Y.240.169; 5.Y.240.172; 5.Y.240.175; 5.Y.240.240; 5.Y.240.244; 5.Y.244.228; 5.Y.244.229; 5.Y.244.230; 5.Y.244.231; 5.Y.244.236; 5.Y.244.237; 5.Y.244.238; 5.Y.244.239; 5.Y.244.154; 5.Y.244.157; 5.Y.244.166; 5.Y.244.169; 5.Y.244.172; 5.Y.244.175; 5.Y.244.240; 5.Y.244.244;

Prodrugs of 6.B

6.B.228.228; 6.B.228.229; 6.B.228.230; 6.B.228.231; 6.B.228.236; 6.B.228.237; 6.B.228.238; 6.B.228.239; 6.B.228.154; 6.B.228.157; 6.B.228.166; 6.B.228.169; 6.B.228.172; 6.B.228.175; 6.B.228.240; 6.B.228.244; 6.B.229.228; 6.B.229.229; 6.B.229.230; 6.B.229.231; 6.B.229.236; 6.B.229.237; 6.B.229.238; 6.B.229.239; 6.B.229.154; 6.B.229.157; 6.B.229.166; 6.B.229.169; 6.B.229.172; 6.B.229.175; 6.B.229.240; 6.B.229.244; 6.B.230.228; 6.B.230.229; 6.B.230.230; 6.B.230.231; 6.B.230.236; 6.B.230.237; 6.B.230.238; 6.B.230.239; 6.B.230.154; 6.B.230.157; 6.B.230.166; 6.B.230.169; 6.B.230.172; 6.B.230.175; 6.B.230.240; 6.B.230.244; 6.B.231.228; 6.B.231.229; 6.B.231.230; 6.B.231.231; 6.B.231.236; 6.B.231.237; 6.B.231.238; 6.B.231.239; 6.B.231.154; 6.B.231.157; 6.B.231.166; 6.B.231.169; 6.B.231.172; 6.B.231.175; 6.B.231.240; 6.B.231.244; 6.B.236.228; 6.B.236.229; 6.B.236.230; 6.B.236.231; 6.B.236.236; 6.B.236.237; 6.B.236.238;

TABLE 100-continued

6.B.236.239; 6.B.236.154; 6.B.236.157; 6.B.236.166; 6.B.236.169; 6.B.236.172;
6.B.236.175; 6.B.236.240; 6.B.236.244; 6.B.237.228; 6.B.237.229; 6.B.237.230;
6.B.237.231; 6.B.237.236; 6.B.237.237; 6.B.237.238; 6.B.237.239; 6.B.237.154;
6.B.237.157; 6.B.237.166; 6.B.237.169; 6.B.237.172; 6.B.237.175; 6.B.237.240;
6.B.237.244; 6.B.238.228; 6.B.238.229; 6.B.238.230; 6.B.238.231; 6.B.238.236;
6.B.238.237; 6.B.238.238; 6.B.238.239; 6.B.238.154; 6.B.238.157; 6.B.238.166;
6.B.238.169; 6.B.238.172; 6.B.238.175; 6.B.238.240; 6.B.238.244; 6.B.239.228;
6.B.239.229; 6.B.239.230; 6.B.239.231; 6.B.239.236; 6.B.239.237; 6.B.239.238;
6.B.239.239; 6.B.239.154; 6.B.239.157; 6.B.239.166; 6.B.239.169; 6.B.239.172;
6.B.239.175; 6.B.239.240; 6.B.239.244; 6.B.154.228; 6.B.154.229; 6.B.154.230;
6.B.154.231; 6.B.154.236; 6.B.154.237; 6.B.154.238; 6.B.154.239; 6.B.154.154;
6.B.154.157; 6.B.154.166; 6.B.154.169; 6.B.154.172; 6.B.154.175; 6.B.154.240;
6.B.154.244; 6.B.157.228; 6.B.157.229; 6.B.157.230; 6.B.157.231; 6.B.157.236;
6.B.157.237; 6.B.157.238; 6.B.157.239; 6.B.157.154; 6.B.157.157; 6.B.157.166;
6.B.157.169; 6.B.157.172; 6.B.157.175; 6.B.157.240; 6.B.157.244; 6.B.166.228;
6.B.166.229; 6.B.166.230; 6.B.166.231; 6.B.166.236; 6.B.166.237; 6.B.166.238;
6.B.166.239; 6.B.166.154; 6.B.166.157; 6.B.166.166; 6.B.166.169; 6.B.166.172;
6.B.166.175; 6.B.166.240; 6.B.166.244; 6.B.169.228; 6.B.169.229; 6.B.169.230;
6.B.169.231; 6.B.169.236; 6.B.169.237; 6.B.169.238; 6.B.169.239; 6.B.169.154;
6.B.169.157; 6.B.169.166; 6.B.169.169; 6.B.169.172; 6.B.169.175; 6.B.169.240;
6.B.169.244; 6.B.172.228; 6.B.172.229; 6.B.172.230; 6.B.172.231; 6.B.172.236;
6.B.172.237; 6.B.172.238; 6.B.172.239; 6.B.172.154; 6.B.172.157; 6.B.172.166;
6.B.172.169; 6.B.172.172; 6.B.172.175; 6.B.172.240; 6.B.172.244; 6.B.175.228;
6.B.175.229; 6.B.175.230; 6.B.175.231; 6.B.175.236; 6.B.175.237; 6.B.175.238;
6.B.175.239; 6.B.175.154; 6.B.175.157; 6.B.175.166; 6.B.175.169; 6.B.175.172;
6.B.175.175; 6.B.175.240; 6.B.175.244; 6.B.240.228; 6.B.240.229; 6.B.240.230;
6.B.240.231; 6.B.240.236; 6.B.240.237; 6.B.240.238; 6.B.240.239; 6.B.240.154;
6.B.240.157; 6.B.240.166; 6.B.240.169; 6.B.240.172; 6.B.240.175; 6.B.240.240;
6.B.240.244; 6.B.244.228; 6.B.244.229; 6.B.244.230; 6.B.244.231; 6.B.244.236;
6.B.244.237; 6.B.244.238; 6.B.244.239; 6.B.244.154; 6.B.244.157; 6.B.244.166;
6.B.244.169; 6.B.244.172; 6.B.244.175; 6.B.244.240; 6.B.244.244;

Prodrugs of 6.D

6.D.228.228; 6.D.228.229; 6.D.228.230; 6.D.228.231; 6.D.228.236;
6.D.228.237; 6.D.228.238; 6.D.228.239; 6.D.228.154; 6.D.228.157;
6.D.228.166; 6.D.228.169; 6.D.228.172; 6.D.228.175; 6.D.228.240;
6.D.228.244; 6.D.229.228; 6.D.229.229; 6.D.229.230; 6.D.229.231;
6.D.229.236; 6.D.229.237; 6.D.229.238; 6.D.229.239; 6.D.229.154;
6.D.229.157; 6.D.229.166; 6.D.229.169; 6.D.229.172; 6.D.229.175;
6.D.229.240; 6.D.229.244; 6.D.230.228; 6.D.230.229; 6.D.230.230;
6.D.230.231; 6.D.230.236; 6.D.230.237; 6.D.230.238; 6.D.230.239;
6.D.230.154; 6.D.230.157; 6.D.230.166; 6.D.230.169; 6.D.230.172;
6.D.230.175; 6.D.230.240; 6.D.230.244; 6.D.231.228; 6.D.231.229;
6.D.231.230; 6.D.231.231; 6.D.231.236; 6.D.231.237; 6.D.231.238;
6.D.231.239; 6.D.231.154; 6.D.231.157; 6.D.231.166; 6.D.231.169;
6.D.231.172; 6.D.231.175; 6.D.231.240; 6.D.231.244; 6.D.236.228;
6.D.236.229; 6.D.236.230; 6.D.236.231; 6.D.236.236; 6.D.236.237;
6.D.236.238; 6.D.236.239; 6.D.236.154; 6.D.236.157; 6.D.236.166;
6.D.236.169; 6.D.236.172; 6.D.236.175; 6.D.236.240; 6.D.236.244;
6.D.237.228; 6.D.237.229; 6.D.237.230; 6.D.237.231; 6.D.237.236;
6.D.237.237; 6.D.237.238; 6.D.237.239; 6.D.237.154; 6.D.237.157;
6.D.237.166; 6.D.237.169; 6.D.237.172; 6.D.237.175; 6.D.237.240;
6.D.237.244; 6.D.238.228; 6.D.238.229; 6.D.238.230; 6.D.238.231;
6.D.238.236; 6.D.238.237; 6.D.238.238; 6.D.238.239; 6.D.238.154;
6.D.238.157; 6.D.238.166; 6.D.238.169; 6.D.238.172; 6.D.238.175;
6.D.238.240; 6.D.238.244; 6.D.239.228; 6.D.239.229; 6.D.239.230;
6.D.239.231; 6.D.239.236; 6.D.239.237; 6.D.239.238; 6.D.239.239;
6.D.239.154; 6.D.239.157; 6.D.239.166; 6.D.239.169; 6.D.239.172;
6.D.239.175; 6.D.239.240; 6.D.239.244; 6.D.154.228; 6.D.154.229;
6.D.154.230; 6.D.154.231; 6.D.154.236; 6.D.154.237; 6.D.154.238;
6.D.154.239; 6.D.154.154; 6.D.154.157; 6.D.154.166; 6.D.154.169;
6.D.154.172; 6.D.154.175; 6.D.154.240; 6.D.154.244; 6.D.157.228;
6.D.157.229; 6.D.157.230; 6.D.157.231; 6.D.157.236; 6.D.157.237;
6.D.157.238; 6.D.157.239; 6.D.157.154; 6.D.157.157; 6.D.157.166;
6.D.157.169; 6.D.157.172; 6.D.157.175; 6.D.157.240; 6.D.157.244;
6.D.166.228; 6.D.166.229; 6.D.166.230; 6.D.166.231; 6.D.166.236;
6.D.166.237; 6.D.166.238; 6.D.166.239; 6.D.166.154; 6.D.166.157;
6.D.166.166; 6.D.166.169; 6.D.166.172; 6.D.166.175; 6.D.166.240;
6.D.166.244; 6.D.169.228; 6.D.169.229; 6.D.169.230; 6.D.169.231;
6.D.169.236; 6.D.169.237; 6.D.169.238; 6.D.169.239; 6.D.169.154;
6.D.169.157; 6.D.169.166; 6.D.169.169; 6.D.169.172; 6.D.169.175;
6.D.169.240; 6.D.169.244; 6.D.172.228; 6.D.172.229; 6.D.172.230;
6.D.172.231; 6.D.172.236; 6.D.172.237; 6.D.172.238; 6.D.172.239;
6.D.172.154; 6.D.172.157; 6.D.172.166; 6.D.172.169; 6.D.172.172;
6.D.172.175; 6.D.172.240; 6.D.172.244; 6.D.175.228; 6.D.175.229;
6.D.175.230; 6.D.175.231; 6.D.175.236; 6.D.175.237; 6.D.175.238;
6.D.175.239; 6.D.175.154; 6.D.175.157; 6.D.175.166; 6.D.175.169;
6.D.175.172; 6.D.175.175; 6.D.175.240; 6.D.175.244; 6.D.240.228;
6.D.240.229; 6.D.240.230; 6.D.240.231; 6.D.240.236; 6.D.240.237;
6.D.240.238; 6.D.240.239; 6.D.240.154; 6.D.240.157; 6.D.240.166;

TABLE 100-continued

| |
|---|
| 6.D.240.169; 6.D.240.172; 6.D.240.175; 6.D.240.240; 6.D.240.244; 6.D.244.228; 6.D.244.229; 6.D.244.230; 6.D.244.231; 6.D.244.236; 6.D.244.237; 6.D.244.238; 6.D.244.239; 6.D.244.154; 6.D.244.157; 6.D.244.166; 6.D.244.169; 6.D.244.172; 6.D.244.175; 6.D.244.240; 6.D.244.244; |
| Prodrugs of 6.E |
| 6.E.228.228; 6.E.228.229; 6.E.228.230; 6.E.228.231; 6.E.228.236; 6.E.228.237; 6.E.228.238; 6.E.228.239; 6.E.228.154; 6.E.228.157; 6.E.228.166; 6.E.228.169; 6.E.228.172; 6.E.228.175; 6.E.228.240; 6.E.228.244; 6.E.229.228; 6.E.229.229; 6.E.229.230; 6.E.229.231; 6.E.229.236; 6.E.229.237; 6.E.229.238; 6.E.229.239; 6.E.229.154; 6.E.229.157; 6.E.229.166; 6.E.229.169; 6.E.229.172; 6.E.229.175; 6.E.229.240; 6.E.229.244; 6.E.230.228; 6.E.230.229; 6.E.230.230; 6.E.230.231; 6.E.230.236; 6.E.230.237; 6.E.230.238; 6.E.230.239; 6.E.230.154; 6.E.230.157; 6.E.230.166; 6.E.230.169; 6.E.230.172; 6.E.230.175; 6.E.230.240; 6.E.230.244; 6.E.231.228; 6.E.231.229; 6.E.231.230; 6.E.231.231; 6.E.231.236; 6.E.231.237; 6.E.231.238; 6.E.231.239; 6.E.231.154; 6.E.231.157; 6.E.231.166; 6.E.231.169; 6.E.231.172; 6.E.231.175; 6.E.231.240; 6.E.231.244; 6.E.236.228; 6.E.236.229; 6.E.236.230; 6.E.236.231; 6.E.236.236; 6.E.236.237; 6.E.236.238; 6.E.236.239; 6.E.236.154; 6.E.236.157; 6.E.236.166; 6.E.236.169; 6.E.236.172; 6.E.236.175; 6.E.236.240; 6.E.236.244; 6.E.237.228; 6.E.237.229; 6.E.237.230; 6.E.237.231; 6.E.237.236; 6.E.237.237; 6.E.237.238; 6.E.237.239; 6.E.237.154; 6.E.237.157; 6.E.237.166; 6.E.237.169; 6.E.237.172; 6.E.237.175; 6.E.237.240; 6.E.237.244; 6.E.238.228; 6.E.238.229; 6.E.238.230; 6.E.238.231; 6.E.238.236; 6.E.238.237; 6.E.238.238; 6.E.238.239; 6.E.238.154; 6.E.238.157; 6.E.238.166; 6.E.238.169; 6.E.238.172; 6.E.238.175; 6.E.238.240; 6.E.238.244; 6.E.239.228; 6.E.239.229; 6.E.239.230; 6.E.239.231; 6.E.239.236; 6.E.239.237; 6.E.239.238; 6.E.239.239; 6.E.239.154; 6.E.239.157; 6.E.239.166; 6.E.239.169; 6.E.239.172; 6.E.239.175; 6.E.239.240; 6.E.239.244; 6.E.154.228; 6.E.154.229; 6.E.154.230; 6.E.154.231; 6.E.154.236; 6.E.154.237; 6.E.154.238; 6.E.154.239; 6.E.154.154; 6.E.154.157; 6.E.154.166; 6.E.154.169; 6.E.154.172; 6.E.154.175; 6.E.154.240; 6.E.154.244; 6.E.157.228; 6.E.157.229; 6.E.157.230; 6.E.157.231; 6.E.157.236; 6.E.157.237; 6.E.157.238; 6.E.157.239; 6.E.157.154; 6.E.157.157; 6.E.157.166; 6.E.157.169; 6.E.157.172; 6.E.157.175; 6.E.157.240; 6.E.157.244; 6.E.166.228; 6.E.166.229; 6.E.166.230; 6.E.166.231; 6.E.166.236; 6.E.166.237; 6.E.166.238; 6.E.166.239; 6.E.166.154; 6.E.166.157; 6.E.166.166; 6.E.166.169; 6.E.166.172; 6.E.166.175; 6.E.166.240; 6.E.166.244; 6.E.169.228; 6.E.169.229; 6.E.169.230; 6.E.169.231; 6.E.169.236; 6.E.169.237; 6.E.169.238; 6.E.169.239; 6.E.169.154; 6.E.169.157; 6.E.169.166; 6.E.169.169; 6.E.169.172; 6.E.169.175; 6.E.169.240; 6.E.169.244; 6.E.172.228; 6.E.172.229; 6.E.172.230; 6.E.172.231; 6.E.172.236; 6.E.172.237; 6.E.172.238; 6.E.172.239; 6.E.172.154; 6.E.172.157; 6.E.172.166; 6.E.172.169; 6.E.172.172; 6.E.172.175; 6.E.172.240; 6.E.172.244; 6.E.175.228; 6.E.175.229; 6.E.175.230; 6.E.175.231; 6.E.175.236; 6.E.175.237; 6.E.175.238; 6.E.175.239; 6.E.175.154; 6.E.175.157; 6.E.175.166; 6.E.175.169; 6.E.175.172; 6.E.175.175; 6.E.175.240; 6.E.175.244; 6.E.240.228; 6.E.240.229; 6.E.240.230; 6.E.240.231; 6.E.240.236; 6.E.240.237; 6.E.240.238; 6.E.240.239; 6.E.240.154; 6.E.240.157; 6.E.240.166; 6.E.240.169; 6.E.240.172; 6.E.240.175; 6.E.240.240; 6.E.240.244; 6.E.244.228; 6.E.244.229; 6.E.244.230; 6.E.244.231; 6.E.244.236; 6.E.244.237; 6.E.244.238; 6.E.244.239; 6.E.244.154; 6.E.244.157; 6.E.244.166; 6.E.244.169; 6.E.244.172; 6.E.244.175; 6.E.244.240; 6.E.244.244; |
| Prodrugs of 6.G |
| 6.G.228.228; 6.G.228.229; 6.G.228.230; 6.G.228.231; 6.G.228.236; 6.G.228.237; 6.G.228.238; 6.G.228.239; 6.G.228.154; 6.G.228.157; 6.G.228.166; 6.G.228.169; 6.G.228.172; 6.G.228.175; 6.G.228.240; 6.G.228.244; 6.G.229.228; 6.G.229.229; 6.G.229.230; 6.G.229.231; 6.G.229.236; 6.G.229.237; 6.G.229.238; 6.G.229.239; 6.G.229.154; 6.G.229.157; 6.G.229.166; 6.G.229.169; 6.G.229.172; 6.G.229.175; 6.G.229.240; 6.G.229.244; 6.G.230.228; 6.G.230.229; 6.G.230.230; 6.G.230.231; 6.G.230.236; 6.G.230.237; 6.G.230.238; 6.G.230.239; 6.G.230.154; 6.G.230.157; 6.G.230.166; 6.G.230.169; 6.G.230.172; 6.G.230.175; 6.G.230.240; 6.G.230.244; 6.G.231.228; 6.G.231.229; 6.G.231.230; 6.G.231.231; 6.G.231.236; 6.G.231.237; 6.G.231.238; 6.G.231.239; 6.G.231.154; 6.G.231.157; 6.G.231.166; 6.G.231.169; 6.G.231.172; 6.G.231.175; 6.G.231.240; 6.G.231.244; 6.G.236.228; 6.G.236.229; 6.G.236.230; 6.G.236.231; 6.G.236.236; 6.G.236.237; 6.G.236.238; 6.G.236.239; 6.G.236.154; 6.G.236.157; 6.G.236.166; 6.G.236.169; 6.G.236.172; 6.G.236.175; 6.G.236.240; 6.G.236.244; 6.G.237.228; 6.G.237.229; 6.G.237.230; 6.G.237.231; 6.G.237.236; 6.G.237.237; 6.G.237.238; 6.G.237.239; 6.G.237.154; 6.G.237.157; 6.G.237.166; 6.G.237.169; 6.G.237.172; 6.G.237.175; 6.G.237.240; 6.G.237.244; 6.G.238.228; 6.G.238.229; 6.G.238.230; 6.G.238.231; 6.G.238.236; 6.G.238.237; 6.G.238.238; 6.G.238.239; 6.G.238.154; 6.G.238.157; 6.G.238.166; 6.G.238.169; 6.G.238.172; 6.G.238.175; 6.G.238.240; 6.G.238.244; 6.G.239.228; 6.G.239.229; 6.G.239.230; 6.G.239.231; 6.G.239.236; 6.G.239.237; 6.G.239.238; 6.G.239.239; 6.G.239.154; 6.G.239.157; 6.G.239.166; 6.G.239.169; 6.G.239.172; 6.G.239.175; 6.G.239.240; 6.G.239.244; 6.G.154.228; 6.G.154.229; 6.G.154.230; 6.G.154.231; 6.G.154.236; 6.G.154.237; 6.G.154.238; 6.G.154.239; 6.G.154.154; 6.G.154.157; 6.G.154.166; 6.G.154.169; 6.G.154.172; 6.G.154.175; 6.G.154.240; 6.G.154.244; 6.G.157.228; |

TABLE 100-continued

6.G.157.229; 6.G.157.230; 6.G.157.231; 6.G.157.236; 6.G.157.237;
6.G.157.238; 6.G.157.239; 6.G.157.154; 6.G.157.157; 6.G.157.166;
6.G.157.169; 6.G.157.172; 6.G.157.175; 6.G.157.240; 6.G.157.244;
6.G.166.228; 6.G.166.229; 6.G.166.230; 6.G.166.231; 6.G.166.236;
6.G.166.237; 6.G.166.238; 6.G.166.239; 6.G.166.154; 6.G.166.157;
6.G.166.166; 6.G.166.169; 6.G.166.172; 6.G.166.175; 6.G.166.240;
6.G.166.244; 6.G.169.228; 6.G.169.229; 6.G.169.230; 6.G.169.231;
6.G.169.236; 6.G.169.237; 6.G.169.238; 6.G.169.239; 6.G.169.154;
6.G.169.157; 6.G.169.166; 6.G.169.169; 6.G.169.172; 6.G.169.175;
6.G.169.240; 6.G.169.244; 6.G.172.228; 6.G.172.229; 6.G.172.230;
6.G.172.231; 6.G.172.236; 6.G.172.237; 6.G.172.238; 6.G.172.239;
6.G.172.154; 6.G.172.157; 6.G.172.166; 6.G.172.169; 6.G.172.172;
6.G.172.175; 6.G.172.240; 6.G.172.244; 6.G.175.228; 6.G.175.229;
6.G.175.230; 6.G.175.231; 6.G.175.236; 6.G.175.237; 6.G.175.238;
6.G.175.239; 6.G.175.154; 6.G.175.157; 6.G.175.166; 6.G.175.169;
6.G.175.172; 6.G.175.175; 6.G.175.240; 6.G.175.244; 6.G.240.228;
6.G.240.229; 6.G.240.230; 6.G.240.231; 6.G.240.236; 6.G.240.237;
6.G.240.238; 6.G.240.239; 6.G.240.154; 6.G.240.157; 6.G.240.166;
6.G.240.169; 6.G.240.172; 6.G.240.175; 6.G.240.240; 6.G.240.244;
6.G.244.228; 6.G.244.229; 6.G.244.230; 6.G.244.231; 6.G.244.236;
6.G.244.237; 6.G.244.238; 6.G.244.239; 6.G.244.154; 6.G.244.157;
6.G.244.166; 6.G.244.169; 6.G.244.172; 6.G.244.175; 6.G.244.240; 6.G.244.244;

Prodrugs of 6.I

6.I.228.228; 6.I.228.229; 6.I.228.230; 6.I.228.231; 6.I.228.236; 6.I.228.237;
6.I.228.238; 6.I.228.239; 6.I.228.154; 6.I.228.157; 6.I.228.166; 6.I.228.169;
6.I.228.172; 6.I.228.175; 6.I.228.240; 6.I.228.244; 6.I.229.228; 6.I.229.229;
6.I.229.230; 6.I.229.231; 6.I.229.236; 6.I.229.237; 6.I.229.238; 6.I.229.239;
6.I.229.154; 6.I.229.157; 6.I.229.166; 6.I.229.169; 6.I.229.172; 6.I.229.175;
6.I.229.240; 6.I.229.244; 6.I.230.228; 6.I.230.229; 6.I.230.230; 6.I.230.231;
6.I.230.236; 6.I.230.237; 6.I.230.238; 6.I.230.239; 6.I.230.154; 6.I.230.157;
6.I.230.166; 6.I.230.169; 6.I.230.172; 6.I.230.175; 6.I.230.240; 6.I.230.244;
6.I.231.228; 6.I.231.229; 6.I.231.230; 6.I.231.231; 6.I.231.236; 6.I.231.237;
6.I.231.238; 6.I.231.239; 6.I.231.154; 6.I.231.157; 6.I.231.166; 6.I.231.169;
6.I.231.172; 6.I.231.175; 6.I.231.240; 6.I.231.244; 6.I.236.228; 6.I.236.229;
6.I.236.230; 6.I.236.231; 6.I.236.236; 6.I.236.237; 6.I.236.238; 6.I.236.239;
6.I.236.154; 6.I.236.157; 6.I.236.166; 6.I.236.169; 6.I.236.172; 6.I.236.175;
6.I.236.240; 6.I.236.244; 6.I.237.228; 6.I.237.229; 6.I.237.230; 6.I.237.231;
6.I.237.236; 6.I.237.237; 6.I.237.238; 6.I.237.239; 6.I.237.154; 6.I.237.157;
6.I.237.166; 6.I.237.169; 6.I.237.172; 6.I.237.175; 6.I.237.240; 6.I.237.244;
6.I.238.228; 6.I.238.229; 6.I.238.230; 6.I.238.231; 6.I.238.236; 6.I.238.237;
6.I.238.238; 6.I.238.239; 6.I.238.154; 6.I.238.157; 6.I.238.166; 6.I.238.169;
6.I.238.172; 6.I.238.175; 6.I.238.240; 6.I.238.244; 6.I.239.228; 6.I.239.229;
6.I.239.230; 6.I.239.231; 6.I.239.236; 6.I.239.237; 6.I.239.238; 6.I.239.239;
6.I.239.154; 6.I.239.157; 6.I.239.166; 6.I.239.169; 6.I.239.172; 6.I.239.175;
6.I.239.240; 6.I.239.244; 6.I.154.228; 6.I.154.229; 6.I.154.230; 6.I.154.231;
6.I.154.236; 6.I.154.237; 6.I.154.238; 6.I.154.239; 6.I.154.154; 6.I.154.157;
6.I.154.166; 6.I.154.169; 6.I.154.172; 6.I.154.175; 6.I.154.240; 6.I.154.244;
6.I.157.228; 6.I.157.229; 6.I.157.230; 6.I.157.231; 6.I.157.236; 6.I.157.237;
6.I.157.238; 6.I.157.239; 6.I.157.154; 6.I.157.157; 6.I.157.166; 6.I.157.169;
6.I.157.172; 6.I.157.175; 6.I.157.240; 6.I.157.244; 6.I.166.228; 6.I.166.229;
6.I.166.230; 6.I.166.231; 6.I.166.236; 6.I.166.237; 6.I.166.238; 6.I.166.239;
6.I.166.154; 6.I.166.157; 6.I.166.166; 6.I.166.169; 6.I.166.172; 6.I.166.175;
6.I.166.240; 6.I.166.244; 6.I.169.228; 6.I.169.229; 6.I.169.230; 6.I.169.231;
6.I.169.236; 6.I.169.237; 6.I.169.238; 6.I.169.239; 6.I.169.154; 6.I.169.157;
6.I.169.166; 6.I.169.169; 6.I.169.172; 6.I.169.175; 6.I.169.240; 6.I.169.244;
6.I.172.228; 6.I.172.229; 6.I.172.230; 6.I.172.231; 6.I.172.236; 6.I.172.237;
6.I.172.238; 6.I.172.239; 6.I.172.154; 6.I.172.157; 6.I.172.166; 6.I.172.169;
6.I.172.172; 6.I.172.175; 6.I.172.240; 6.I.172.244; 6.I.175.228; 6.I.175.229;
6.I.175.230; 6.I.175.231; 6.I.175.236; 6.I.175.237; 6.I.175.238; 6.I.175.239;
6.I.175.154; 6.I.175.157; 6.I.175.166; 6.I.175.169; 6.I.175.172; 6.I.175.175;
6.I.175.240; 6.I.175.244; 6.I.240.228; 6.I.240.229; 6.I.240.230; 6.I.240.231;
6.I.240.236; 6.I.240.237; 6.I.240.238; 6.I.240.239; 6.I.240.154; 6.I.240.157;
6.I.240.166; 6.I.240.169; 6.I.240.172; 6.I.240.175; 6.I.240.240; 6.I.240.244;
6.I.244.228; 6.I.244.229; 6.I.244.230; 6.I.244.231; 6.I.244.236; 6.I.244.237;
6.I.244.238; 6.I.244.239; 6.I.244.154; 6.I.244.157; 6.I.244.166; 6.I.244.169;
6.I.244.172; 6.I.244.175; 6.I.244.240; 6.I.244.244;

Prodrugs of 6.J

6.J.228.228; 6.J.228.229; 6.J.228.230; 6.J.228.231; 6.J.228.236; 6.J.228.237;
6.J.228.238; 6.J.228.239; 6.J.228.154; 6.J.228.157; 6.J.228.166; 6.J.228.169;
6.J.228.172; 6.J.228.175; 6.J.228.240; 6.J.228.244; 6.J.229.228; 6.J.229.229;
6.J.229.230; 6.J.229.231; 6.J.229.236; 6.J.229.237; 6.J.229.238; 6.J.229.239;
6.J.229.154; 6.J.229.157; 6.J.229.166; 6.J.229.169; 6.J.229.172; 6.J.229.175;
6.J.229.240; 6.J.229.244; 6.J.230.228; 6.J.230.229; 6.J.230.230; 6.J.230.231;
6.J.230.236; 6.J.230.237; 6.J.230.238; 6.J.230.239; 6.J.230.154; 6.J.230.157;
6.J.230.166; 6.J.230.169; 6.J.230.172; 6.J.230.175; 6.J.230.240; 6.J.230.244;
6.J.231.228; 6.J.231.229; 6.J.231.230; 6.J.231.231; 6.J.231.236; 6.J.231.237;
6.J.231.238; 6.J.231.239; 6.J.231.154; 6.J.231.157; 6.J.231.166; 6.J.231.169;
6.J.231.172; 6.J.231.175; 6.J.231.240; 6.J.231.244; 6.J.236.228; 6.J.236.229;

TABLE 100-continued

| |
|---|
| 6.J.236.230; 6.J.236.231; 6.J.236.236; 6.J.236.237; 6.J.236.238; 6.J.236.239; 6.J.236.154; 6.J.236.157; 6.J.236.166; 6.J.236.169; 6.J.236.172; 6.J.236.175; 6.J.236.240; 6.J.236.244; 6.J.237.228; 6.J.237.229; 6.J.237.230; 6.J.237.231; 6.J.237.236; 6.J.237.237; 6.J.237.238; 6.J.237.239; 6.J.237.154; 6.J.237.157; 6.J.237.166; 6.J.237.169; 6.J.237.172; 6.J.237.175; 6.J.237.240; 6.J.237.244; 6.J.238.228; 6.J.238.229; 6.J.238.230; 6.J.238.231; 6.J.238.236; 6.J.238.237; 6.J.238.238; 6.J.238.239; 6.J.238.154; 6.J.238.157; 6.J.238.166; 6.J.238.169; 6.J.238.172; 6.J.238.175; 6.J.238.240; 6.J.238.244; 6.J.239.228; 6.J.239.229; 6.J.239.230; 6.J.239.231; 6.J.239.236; 6.J.239.237; 6.J.239.238; 6.J.239.239; 6.J.239.154; 6.J.239.157; 6.J.239.166; 6.J.239.169; 6.J.239.172; 6.J.239.175; 6.J.239.240; 6.J.239.244; 6.J.154.228; 6.J.154.229; 6.J.154.230; 6.J.154.231; 6.J.154.236; 6.J.154.237; 6.J.154.238; 6.J.154.239; 6.J.154.154; 6.J.154.157; 6.J.154.166; 6.J.154.169; 6.J.154.172; 6.J.154.175; 6.J.154.240; 6.J.154.244; 6.J.157.228; 6.J.157.229; 6.J.157.230; 6.J.157.231; 6.J.157.236; 6.J.157.237; 6.J.157.238; 6.J.157.239; 6.J.157.154; 6.J.157.157; 6.J.157.166; 6.J.157.169; 6.J.157.172; 6.J.157.175; 6.J.157.240; 6.J.157.244; 6.J.166.228; 6.J.166.229; 6.J.166.230; 6.J.166.231; 6.J.166.236; 6.J.166.237; 6.J.166.238; 6.J.166.239; 6.J.166.154; 6.J.166.157; 6.J.166.166; 6.J.166.169; 6.J.166.172; 6.J.166.175; 6.J.166.240; 6.J.166.244; 6.J.169.228; 6.J.169.229; 6.J.169.230; 6.J.169.231; 6.J.169.236; 6.J.169.237; 6.J.169.238; 6.J.169.239; 6.J.169.154; 6.J.169.157; 6.J.169.166; 6.J.169.169; 6.J.169.172; 6.J.169.175; 6.J.169.240; 6.J.169.244; 6.J.172.228; 6.J.172.229; 6.J.172.230; 6.J.172.231; 6.J.172.236; 6.J.172.237; 6.J.172.238; 6.J.172.239; 6.J.172.154; 6.J.172.157; 6.J.172.166; 6.J.172.169; 6.J.172.172; 6.J.172.175; 6.J.172.240; 6.J.172.244; 6.J.175.228; 6.J.175.229; 6.J.175.230; 6.J.175.231; 6.J.175.236; 6.J.175.237; 6.J.175.238; 6.J.175.239; 6.J.175.154; 6.J.175.157; 6.J.175.166; 6.J.175.169; 6.J.175.172; 6.J.175.175; 6.J.175.240; 6.J.175.244; 6.J.240.228; 6.J.240.229; 6.J.240.230; 6.J.240.231; 6.J.240.236; 6.J.240.237; 6.J.240.238; 6.J.240.239; 6.J.240.154; 6.J.240.157; 6.J.240.166; 6.J.240.169; 6.J.240.172; 6.J.240.175; 6.J.240.240; 6.J.240.244; 6.J.244.228; 6.J.244.229; 6.J.244.230; 6.J.244.231; 6.J.244.236; 6.J.244.237; 6.J.244.238; 6.J.244.239; 6.J.244.154; 6.J.244.157; 6.J.244.166; 6.J.244.169; 6.J.244.172; 6.J.244.175; 6.J.244.240; 6.J.244.244; |
| Prodrugs of 6.L |
| 6.L.228.228; 6.L.228.229; 6.L.228.230; 6.L.228.231; 6.L.228.236; 6.L.228.237; 6.L.228.238; 6.L.228.239; 6.L.228.154; 6.L.228.157; 6.L.228.166; 6.L.228.169; 6.L.228.172; 6.L.228.175; 6.L.228.240; 6.L.228.244; 6.L.229.228; 6.L.229.229; 6.L.229.230; 6.L.229.231; 6.L.229.236; 6.L.229.237; 6.L.229.238; 6.L.229.239; 6.L.229.154; 6.L.229.157; 6.L.229.166; 6.L.229.169; 6.L.229.172; 6.L.229.175; 6.L.229.240; 6.L.229.244; 6.L.230.228; 6.L.230.229; 6.L.230.230; 6.L.230.231; 6.L.230.236; 6.L.230.237; 6.L.230.238; 6.L.230.239; 6.L.230.154; 6.L.230.157; 6.L.230.166; 6.L.230.169; 6.L.230.172; 6.L.230.175; 6.L.230.240; 6.L.230.244; 6.L.231.228; 6.L.231.229; 6.L.231.230; 6.L.231.231; 6.L.231.236; 6.L.231.237; 6.L.231.238; 6.L.231.239; 6.L.231.154; 6.L.231.157; 6.L.231.166; 6.L.231.169; 6.L.231.172; 6.L.231.175; 6.L.231.240; 6.L.231.244; 6.L.236.228; 6.L.236.229; 6.L.236.230; 6.L.236.231; 6.L.236.236; 6.L.236.237; 6.L.236.238; 6.L.236.239; 6.L.236.154; 6.L.236.157; 6.L.236.166; 6.L.236.169; 6.L.236.172; 6.L.236.175; 6.L.236.240; 6.L.236.244; 6.L.237.228; 6.L.237.229; 6.L.237.230; 6.L.237.231; 6.L.237.236; 6.L.237.237; 6.L.237.238; 6.L.237.239; 6.L.237.154; 6.L.237.157; 6.L.237.166; 6.L.237.169; 6.L.237.172; 6.L.237.175; 6.L.237.240; 6.L.237.244; 6.L.238.228; 6.L.238.229; 6.L.238.230; 6.L.238.231; 6.L.238.236; 6.L.238.237; 6.L.238.238; 6.L.238.239; 6.L.238.154; 6.L.238.157; 6.L.238.166; 6.L.238.169; 6.L.238.172; 6.L.238.175; 6.L.238.240; 6.L.238.244; 6.L.239.228; 6.L.239.229; 6.L.239.230; 6.L.239.231; 6.L.239.236; 6.L.239.237; 6.L.239.238; 6.L.239.239; 6.L.239.154; 6.L.239.157; 6.L.239.166; 6.L.239.169; 6.L.239.172; 6.L.239.175; 6.L.239.240; 6.L.239.244; 6.L.154.228; 6.L.154.229; 6.L.154.230; 6.L.154.231; 6.L.154.236; 6.L.154.237; 6.L.154.238; 6.L.154.239; 6.L.154.154; 6.L.154.157; 6.L.154.166; 6.L.154.169; 6.L.154.172; 6.L.154.175; 6.L.154.240; 6.L.154.244; 6.L.157.228; 6.L.157.229; 6.L.157.230; 6.L.157.231; 6.L.157.236; 6.L.157.237; 6.L.157.238; 6.L.157.239; 6.L.157.154; 6.L.157.157; 6.L.157.166; 6.L.157.169; 6.L.157.172; 6.L.157.175; 6.L.157.240; 6.L.157.244; 6.L.166.228; 6.L.166.229; 6.L.166.230; 6.L.166.231; 6.L.166.236; 6.L.166.237; 6.L.166.238; 6.L.166.239; 6.L.166.154; 6.L.166.157; 6.L.166.166; 6.L.166.169; 6.L.166.172; 6.L.166.175; 6.L.166.240; 6.L.166.244; 6.L.169.228; 6.L.169.229; 6.L.169.230; 6.L.169.231; 6.L.169.236; 6.L.169.237; 6.L.169.238; 6.L.169.239; 6.L.169.154; 6.L.169.157; 6.L.169.166; 6.L.169.169; 6.L.169.172; 6.L.169.175; 6.L.169.240; 6.L.169.244; 6.L.172.228; 6.L.172.229; 6.L.172.230; 6.L.172.231; 6.L.172.236; 6.L.172.237; 6.L.172.238; 6.L.172.239; 6.L.172.154; 6.L.172.157; 6.L.172.166; 6.L.172.169; 6.L.172.172; 6.L.172.175; 6.L.172.240; 6.L.172.244; 6.L.175.228; 6.L.175.229; 6.L.175.230; 6.L.175.231; 6.L.175.236; 6.L.175.237; 6.L.175.238; 6.L.175.239; 6.L.175.154; 6.L.175.157; 6.L.175.166; 6.L.175.169; 6.L.175.172; 6.L.175.175; 6.L.175.240; 6.L.175.244; 6.L.240.228; 6.L.240.229; 6.L.240.230; 6.L.240.231; 6.L.240.236; 6.L.240.237; 6.L.240.238; 6.L.240.239; 6.L.240.154; 6.L.240.157; 6.L.240.166; 6.L.240.169; 6.L.240.172; 6.L.240.175; 6.L.240.240; 6.L.240.244; 6.L.244.228; 6.L.244.229; 6.L.244.230; 6.L.244.231; 6.L.244.236; 6.L.244.237; 6.L.244.238; 6.L.244.239; 6.L.244.154; 6.L.244.157; 6.L.244.166; 6.L.244.169; 6.L.244.172; 6.L.244.175; 6.L.244.240; 6.L.244.244; |

TABLE 100-continued

| Prodrugs of 6.O |
| --- |
| 6.O.228.228; 6.O.228.229; 6.O.228.230; 6.O.228.231; 6.O.228.236; 6.O.228.237; 6.O.228.238; 6.O.228.239; 6.O.228.154; 6.O.228.157; 6.O.228.166; 6.O.228.169; 6.O.228.172; 6.O.228.175; 6.O.228.240; 6.O.228.244; 6.O.229.228; 6.O.229.229; 6.O.229.230; 6.O.229.231; 6.O.229.236; 6.O.229.237; 6.O.229.238; 6.O.229.239; 6.O.229.154; 6.O.229.157; 6.O.229.166; 6.O.229.169; 6.O.229.172; 6.O.229.175; 6.O.229.240; 6.O.229.244; 6.O.230.228; 6.O.230.229; 6.O.230.230; 6.O.230.231; 6.O.230.236; 6.O.230.237; 6.O.230.238; 6.O.230.239; 6.O.230.154; 6.O.230.157; 6.O.230.166; 6.O.230.169; 6.O.230.172; 6.O.230.175; 6.O.230.240; 6.O.230.244; 6.O.231.228; 6.O.231.229; 6.O.231.230; 6.O.231.231; 6.O.231.236; 6.O.231.237; 6.O.231.238; 6.O.231.239; 6.O.231.154; 6.O.231.157; 6.O.231.166; 6.O.231.169; 6.O.231.172; 6.O.231.175; 6.O.231.240; 6.O.231.244; 6.O.236.228; 6.O.236.229; 6.O.236.230; 6.O.236.231; 6.O.236.236; 6.O.236.237; 6.O.236.238; 6.O.236.239; 6.O.236.154; 6.O.236.157; 6.O.236.166; 6.O.236.169; 6.O.236.172; 6.O.236.175; 6.O.236.240; 6.O.236.244; 6.O.237.228; 6.O.237.229; 6.O.237.230; 6.O.237.231; 6.O.237.236; 6.O.237.237; 6.O.237.238; 6.O.237.239; 6.O.237.154; 6.O.237.157; 6.O.237.166; 6.O.237.169; 6.O.237.172; 6.O.237.175; 6.O.237.240; 6.O.237.244; 6.O.238.228; 6.O.238.229; 6.O.238.230; 6.O.238.231; 6.O.238.236; 6.O.238.237; 6.O.238.238; 6.O.238.239; 6.O.238.154; 6.O.238.157; 6.O.238.166; 6.O.238.169; 6.O.238.172; 6.O.238.175; 6.O.238.240; 6.O.238.244; 6.O.239.228; 6.O.239.229; 6.O.239.230; 6.O.239.231; 6.O.239.236; 6.O.239.237; 6.O.239.238; 6.O.239.239; 6.O.239.154; 6.O.239.157; 6.O.239.166; 6.O.239.169; 6.O.239.172; 6.O.239.175; 6.O.239.240; 6.O.239.244; 6.O.154.228; 6.O.154.229; 6.O.154.230; 6.O.154.231; 6.O.154.236; 6.O.154.237; 6.O.154.238; 6.O.154.239; 6.O.154.154; 6.O.154.157; 6.O.154.166; 6.O.154.169; 6.O.154.172; 6.O.154.175; 6.O.154.240; 6.O.154.244; 6.O.157.228; 6.O.157.229; 6.O.157.230; 6.O.157.231; 6.O.157.236; 6.O.157.237; 6.O.157.238; 6.O.157.239; 6.O.157.154; 6.O.157.157; 6.O.157.166; 6.O.157.169; 6.O.157.172; 6.O.157.175; 6.O.157.240; 6.O.157.244; 6.O.166.228; 6.O.166.229; 6.O.166.230; 6.O.166.231; 6.O.166.236; 6.O.166.237; 6.O.166.238; 6.O.166.239; 6.O.166.154; 6.O.166.157; 6.O.166.166; 6.O.166.169; 6.O.166.172; 6.O.166.175; 6.O.166.240; 6.O.166.244; 6.O.169.228; 6.O.169.229; 6.O.169.230; 6.O.169.231; 6.O.169.236; 6.O.169.237; 6.O.169.238; 6.O.169.239; 6.O.169.154; 6.O.169.157; 6.O.169.166; 6.O.169.169; 6.O.169.172; 6.O.169.175; 6.O.169.240; 6.O.169.244; 6.O.172.228; 6.O.172.229; 6.O.172.230; 6.O.172.231; 6.O.172.236; 6.O.172.237; 6.O.172.238; 6.O.172.239; 6.O.172.154; 6.O.172.157; 6.O.172.166; 6.O.172.169; 6.O.172.172; 6.O.172.175; 6.O.172.240; 6.O.172.244; 6.O.175.228; 6.O.175.229; 6.O.175.230; 6.O.175.231; 6.O.175.236; 6.O.175.237; 6.O.175.238; 6.O.175.239; 6.O.175.154; 6.O.175.157; 6.O.175.166; 6.O.175.169; 6.O.175.172; 6.O.175.175; 6.O.175.240; 6.O.175.244; 6.O.240.228; 6.O.240.229; 6.O.240.230; 6.O.240.231; 6.O.240.236; 6.O.240.237; 6.O.240.238; 6.O.240.239; 6.O.240.154; 6.O.240.157; 6.O.240.166; 6.O.240.169; 6.O.240.172; 6.O.240.175; 6.O.240.240; 6.O.240.244; 6.O.244.228; 6.O.244.229; 6.O.244.230; 6.O.244.231; 6.O.244.236; 6.O.244.237; 6.O.244.238; 6.O.244.239; 6.O.244.154; 6.O.244.157; 6.O.244.166; 6.O.244.169; 6.O.244.172; 6.O.244.175; 6.O.244.240; 6.O.244.244; |
| Prodrugs of 6.P |
| 6.P.228.228; 6.P.228.229; 6.P.228.230; 6.P.228.231; 6.P.228.236; 6.P.228.237; 6.P.228.238; 6.P.228.239; 6.P.228.154; 6.P.228.157; 6.P.228.166; 6.P.228.169; 6.P.228.172; 6.P.228.175; 6.P.228.240; 6.P.228.244; 6.P.229.228; 6.P.229.229; 6.P.229.230; 6.P.229.231; 6.P.229.236; 6.P.229.237; 6.P.229.238; 6.P.229.239; 6.P.229.154; 6.P.229.157; 6.P.229.166; 6.P.229.169; 6.P.229.172; 6.P.229.175; 6.P.229.240; 6.P.229.244; 6.P.230.228; 6.P.230.229; 6.P.230.230; 6.P.230.231; 6.P.230.236; 6.P.230.237; 6.P.230.238; 6.P.230.239; 6.P.230.154; 6.P.230.157; 6.P.230.166; 6.P.230.169; 6.P.230.172; 6.P.230.175; 6.P.230.240; 6.P.230.244; 6.P.231.228; 6.P.231.229; 6.P.231.230; 6.P.231.231; 6.P.231.236; 6.P.231.237; 6.P.231.238; 6.P.231.239; 6.P.231.154; 6.P.231.157; 6.P.231.166; 6.P.231.169; 6.P.231.172; 6.P.231.175; 6.P.231.240; 6.P.231.244; 6.P.236.228; 6.P.236.229; 6.P.236.230; 6.P.236.231; 6.P.236.236; 6.P.236.237; 6.P.236.238; 6.P.236.239; 6.P.236.154; 6.P.236.157; 6.P.236.166; 6.P.236.169; 6.P.236.172; 6.P.236.175; 6.P.236.240; 6.P.236.244; 6.P.237.228; 6.P.237.229; 6.P.237.230; 6.P.237.231; 6.P.237.236; 6.P.237.237; 6.P.237.238; 6.P.237.239; 6.P.237.154; 6.P.237.157; 6.P.237.166; 6.P.237.169; 6.P.237.172; 6.P.237.175; 6.P.237.240; 6.P.237.244; 6.P.238.228; 6.P.238.229; 6.P.238.230; 6.P.238.231; 6.P.238.236; 6.P.238.237; 6.P.238.238; 6.P.238.239; 6.P.238.154; 6.P.238.157; 6.P.238.166; 6.P.238.169; 6.P.238.172; 6.P.238.175; 6.P.238.240; 6.P.238.244; 6.P.239.228; 6.P.239.229; 6.P.239.230; 6.P.239.231; 6.P.239.236; 6.P.239.237; 6.P.239.238; 6.P.239.239; 6.P.239.154; 6.P.239.157; 6.P.239.166; 6.P.239.169; 6.P.239.172; 6.P.239.175; 6.P.239.240; 6.P.239.244; 6.P.154.228; 6.P.154.229; 6.P.154.230; 6.P.154.231; 6.P.154.236; 6.P.154.237; 6.P.154.238; 6.P.154.239; 6.P.154.154; 6.P.154.157; 6.P.154.166; 6.P.154.169; 6.P.154.172; 6.P.154.175; 6.P.154.240; 6.P.154.244; 6.P.157.228; 6.P.157.229; 6.P.157.230; 6.P.157.231; 6.P.157.236; |

TABLE 100-continued

6.P.157.237; 6.P.157.238; 6.P.157.239; 6.P.157.154; 6.P.157.157; 6.P.157.166; 6.P.157.169; 6.P.157.172; 6.P.157.175; 6.P.157.240; 6.P.157.244; 6.P.166.228; 6.P.166.229; 6.P.166.230; 6.P.166.231; 6.P.166.236; 6.P.166.237; 6.P.166.238; 6.P.166.239; 6.P.166.154; 6.P.166.157; 6.P.166.166; 6.P.166.169; 6.P.166.172; 6.P.166.175; 6.P.166.240; 6.P.166.244; 6.P.169.228; 6.P.169.229; 6.P.169.230; 6.P.169.231; 6.P.169.236; 6.P.169.237; 6.P.169.238; 6.P.169.239; 6.P.169.154; 6.P.169.157; 6.P.169.166; 6.P.169.169; 6.P.169.172; 6.P.169.175; 6.P.169.240; 6.P.169.244; 6.P.172.228; 6.P.172.229; 6.P.172.230; 6.P.172.231; 6.P.172.236; 6.P.172.237; 6.P.172.238; 6.P.172.239; 6.P.172.154; 6.P.172.157; 6.P.172.166; 6.P.172.169; 6.P.172.172; 6.P.172.175; 6.P.172.240; 6.P.172.244; 6.P.175.228; 6.P.175.229; 6.P.175.230; 6.P.175.231; 6.P.175.236; 6.P.175.237; 6.P.175.238; 6.P.175.239; 6.P.175.154; 6.P.175.157; 6.P.175.166; 6.P.175.169; 6.P.175.172; 6.P.175.175; 6.P.175.240; 6.P.175.244; 6.P.240.228; 6.P.240.229; 6.P.240.230; 6.P.240.231; 6.P.240.236; 6.P.240.237; 6.P.240.238; 6.P.240.239; 6.P.240.154; 6.P.240.157; 6.P.240.166; 6.P.240.169; 6.P.240.172; 6.P.240.175; 6.P.240.240; 6.P.240.244; 6.P.244.228; 6.P.244.229; 6.P.244.230; 6.P.244.231; 6.P.244.236; 6.P.244.237; 6.P.244.238; 6.P.244.239; 6.P.244.154; 6.P.244.157; 6.P.244.166; 6.P.244.169; 6.P.244.172; 6.P.244.175; 6.P.244.240; 6.P.244.244;

Prodrugs of 6.U

6.U.228.228; 6.U.228.229; 6.U.228.230; 6.U.228.231; 6.U.228.236; 6.U.228.237; 6.U.228.238; 6.U.228.239; 6.U.228.154; 6.U.228.157; 6.U.228.166; 6.U.228.169; 6.U.228.172; 6.U.228.175; 6.U.228.240; 6.U.228.244; 6.U.229.228; 6.U.229.229; 6.U.229.230; 6.U.229.231; 6.U.229.236; 6.U.229.237; 6.U.229.238; 6.U.229.239; 6.U.229.154; 6.U.229.157; 6.U.229.166; 6.U.229.169; 6.U.229.172; 6.U.229.175; 6.U.229.240; 6.U.229.244; 6.U.230.228; 6.U.230.229; 6.U.230.230; 6.U.230.231; 6.U.230.236; 6.U.230.237; 6.U.230.238; 6.U.230.239; 6.U.230.154; 6.U.230.157; 6.U.230.166; 6.U.230.169; 6.U.230.172; 6.U.230.175; 6.U.230.240; 6.U.230.244; 6.U.231.228; 6.U.231.229; 6.U.231.230; 6.U.231.231; 6.U.231.236; 6.U.231.237; 6.U.231.238; 6.U.231.239; 6.U.231.154; 6.U.231.157; 6.U.231.166; 6.U.231.169; 6.U.231.172; 6.U.231.175; 6.U.231.240; 6.U.231.244; 6.U.236.228; 6.U.236.229; 6.U.236.230; 6.U.236.231; 6.U.236.236; 6.U.236.237; 6.U.236.238; 6.U.236.239; 6.U.236.154; 6.U.236.157; 6.U.236.166; 6.U.236.169; 6.U.236.172; 6.U.236.175; 6.U.236.240; 6.U.236.244; 6.U.237.228; 6.U.237.229; 6.U.237.230; 6.U.237.231; 6.U.237.236; 6.U.237.237; 6.U.237.238; 6.U.237.239; 6.U.237.154; 6.U.237.157; 6.U.237.166; 6.U.237.169; 6.U.237.172; 6.U.237.175; 6.U.237.240; 6.U.237.244; 6.U.238.228; 6.U.238.229; 6.U.238.230; 6.U.238.231; 6.U.238.236; 6.U.238.237; 6.U.238.238; 6.U.238.239; 6.U.238.154; 6.U.238.157; 6.U.238.166; 6.U.238.169; 6.U.238.172; 6.U.238.175; 6.U.238.240; 6.U.238.244; 6.U.239.228; 6.U.239.229; 6.U.239.230; 6.U.239.231; 6.U.239.236; 6.U.239.237; 6.U.239.238; 6.U.239.239; 6.U.239.154; 6.U.239.157; 6.U.239.166; 6.U.239.169; 6.U.239.172; 6.U.239.175; 6.U.239.240; 6.U.239.244; 6.U.154.228; 6.U.154.229; 6.U.154.230; 6.U.154.231; 6.U.154.236; 6.U.154.237; 6.U.154.238; 6.U.154.239; 6.U.154.154; 6.U.154.157; 6.U.154.166; 6.U.154.169; 6.U.154.172; 6.U.154.175; 6.U.154.240; 6.U.154.244; 6.U.157.228; 6.U.157.229; 6.U.157.230; 6.U.157.231; 6.U.157.236; 6.U.157.237; 6.U.157.238; 6.U.157.239; 6.U.157.154; 6.U.157.157; 6.U.157.166; 6.U.157.169; 6.U.157.172; 6.U.157.175; 6.U.157.240; 6.U.157.244; 6.U.166.228; 6.U.166.229; 6.U.166.230; 6.U.166.231; 6.U.166.236; 6.U.166.237; 6.U.166.238; 6.U.166.239; 6.U.166.154; 6.U.166.157; 6.U.166.166; 6.U.166.169; 6.U.166.172; 6.U.166.175; 6.U.166.240; 6.U.166.244; 6.U.169.228; 6.U.169.229; 6.U.169.230; 6.U.169.231; 6.U.169.236; 6.U.169.237; 6.U.169.238; 6.U.169.239; 6.U.169.154; 6.U.169.157; 6.U.169.166; 6.U.169.169; 6.U.169.172; 6.U.169.175; 6.U.169.240; 6.U.169.244; 6.U.172.228; 6.U.172.229; 6.U.172.230; 6.U.172.231; 6.U.172.236; 6.U.172.237; 6.U.172.238; 6.U.172.239; 6.U.172.154; 6.U.172.157; 6.U.172.166; 6.U.172.169; 6.U.172.172; 6.U.172.175; 6.U.172.240; 6.U.172.244; 6.U.175.228; 6.U.175.229; 6.U.175.230; 6.U.175.231; 6.U.175.236; 6.U.175.237; 6.U.175.238; 6.U.175.239; 6.U.175.154; 6.U.175.157; 6.U.175.166; 6.U.175.169; 6.U.175.172; 6.U.175.175; 6.U.175.240; 6.U.175.244; 6.U.240.228; 6.U.240.229; 6.U.240.230; 6.U.240.231; 6.U.240.236; 6.U.240.237; 6.U.240.238; 6.U.240.239; 6.U.240.154; 6.U.240.157; 6.U.240.166; 6.U.240.169; 6.U.240.172; 6.U.240.175; 6.U.240.240; 6.U.240.244; 6.U.244.228; 6.U.244.229; 6.U.244.230; 6.U.244.231; 6.U.244.236; 6.U.244.237; 6.U.244.238; 6.U.244.239; 6.U.244.154; 6.U.244.157; 6.U.244.166; 6.U.244.169; 6.U.244.172; 6.U.244.175; 6.U.244.240; 6.U.244.244;

Prodrugs of 6.W

6.W.228.228; 6.W.228.229; 6.W.228.230; 6.W.228.231; 6.W.228.236; 6.W.228.237; 6.W.228.238; 6.W.228.239; 6.W.228.154; 6.W.228.157; 6.W.228.166; 6.W.228.169; 6.W.228.172; 6.W.228.175; 6.W.228.240; 6.W.228.244; 6.W.229.228; 6.W.229.229; 6.W.229.230; 6.W.229.231; 6.W.229.236; 6.W.229.237; 6.W.229.238; 6.W.229.239; 6.W.229.154; 6.W.229.157; 6.W.229.166; 6.W.229.169; 6.W.229.172; 6.W.229.175; 6.W.229.240; 6.W.229.244; 6.W.230.228; 6.W.230.229; 6.W.230.230;

TABLE 100-continued

| |
|---|
| 6.W.230.231; 6.W.230.236; 6.W.230.237; 6.W.230.238; 6.W.230.239; 6.W.230.154; 6.W.230.157; 6.W.230.166; 6.W.230.169; 6.W.230.172; 6.W.230.175; 6.W.230.240; 6.W.230.244; 6.W.231.228; 6.W.231.229; 6.W.231.230; 6.W.231.231; 6.W.231.236; 6.W.231.237; 6.W.231.238; 6.W.231.239; 6.W.231.154; 6.W.231.157; 6.W.231.166; 6.W.231.169; 6.W.231.172; 6.W.231.175; 6.W.231.240; 6.W.231.244; 6.W.236.228; 6.W.236.229; 6.W.236.230; 6.W.236.231; 6.W.236.236; 6.W.236.237; 6.W.236.238; 6.W.236.239; 6.W.236.154; 6.W.236.157; 6.W.236.166; 6.W.236.169; 6.W.236.172; 6.W.236.175; 6.W.236.240; 6.W.236.244; 6.W.237.228; 6.W.237.229; 6.W.237.230; 6.W.237.231; 6.W.237.236; 6.W.237.237; 6.W.237.238; 6.W.237.239; 6.W.237.154; 6.W.237.157; 6.W.237.166; 6.W.237.169; 6.W.237.172; 6.W.237.175; 6.W.237.240; 6.W.237.244; 6.W.238.228; 6.W.238.229; 6.W.238.230; 6.W.238.231; 6.W.238.236; 6.W.238.237; 6.W.238.238; 6.W.238.239; 6.W.238.154; 6.W.238.157; 6.W.238.166; 6.W.238.169; 6.W.238.172; 6.W.238.175; 6.W.238.240; 6.W.238.244; 6.W.239.228; 6.W.239.229; 6.W.239.230; 6.W.239.231; 6.W.239.236; 6.W.239.237; 6.W.239.238; 6.W.239.239; 6.W.239.154; 6.W.239.157; 6.W.239.166; 6.W.239.169; 6.W.239.172; 6.W.239.175; 6.W.239.240; 6.W.239.244; 6.W.154.228; 6.W.154.229; 6.W.154.230; 6.W.154.231; 6.W.154.236; 6.W.154.237; 6.W.154.238; 6.W.154.239; 6.W.154.154; 6.W.154.157; 6.W.154.166; 6.W.154.169; 6.W.154.172; 6.W.154.175; 6.W.154.240; 6.W.154.244; 6.W.157.228; 6.W.157.229; 6.W.157.230; 6.W.157.231; 6.W.157.236; 6.W.157.237; 6.W.157.238; 6.W.157.239; 6.W.157.154; 6.W.157.157; 6.W.157.166; 6.W.157.169; 6.W.157.172; 6.W.157.175; 6.W.157.240; 6.W.157.244; 6.W.166.228; 6.W.166.229; 6.W.166.230; 6.W.166.231; 6.W.166.236; 6.W.166.237; 6.W.166.238; 6.W.166.239; 6.W.166.154; 6.W.166.157; 6.W.166.166; 6.W.166.169; 6.W.166.172; 6.W.166.175; 6.W.166.240; 6.W.166.244; 6.W.169.228; 6.W.169.229; 6.W.169.230; 6.W.169.231; 6.W.169.236; 6.W.169.237; 6.W.169.238; 6.W.169.239; 6.W.169.154; 6.W.169.157; 6.W.169.166; 6.W.169.169; 6.W.169.172; 6.W.169.175; 6.W.169.240; 6.W.169.244; 6.W.172.228; 6.W.172.229; 6.W.172.230; 6.W.172.231; 6.W.172.236; 6.W.172.237; 6.W.172.238; 6.W.172.239; 6.W.172.154; 6.W.172.157; 6.W.172.166; 6.W.172.169; 6.W.172.172; 6.W.172.175; 6.W.172.240; 6.W.172.244; 6.W.175.228; 6.W.175.229; 6.W.175.230; 6.W.175.231; 6.W.175.236; 6.W.175.237; 6.W.175.238; 6.W.175.239; 6.W.175.154; 6.W.175.157; 6.W.175.166; 6.W.175.169; 6.W.175.172; 6.W.175.175; 6.W.175.240; 6.W.175.244; 6.W.240.228; 6.W.240.229; 6.W.240.230; 6.W.240.231; 6.W.240.236; 6.W.240.237; 6.W.240.238; 6.W.240.239; 6.W.240.154; 6.W.240.157; 6.W.240.166; 6.W.240.169; 6.W.240.172; 6.W.240.175; 6.W.240.240; 6.W.240.244; 6.W.244.228; 6.W.244.229; 6.W.244.230; 6.W.244.231; 6.W.244.236; 6.W.244.237; 6.W.244.238; 6.W.244.239; 6.W.244.154; 6.W.244.157; 6.W.244.166; 6.W.244.169; 6.W.244.172; 6.W.244.175; 6.W.244.240; 6.W.244.244; |
| Prodrugs of 6.Y |
| 6.Y.228.228; 6.Y.228.229; 6.Y.228.230; 6.Y.228.231; 6.Y.228.236; 6.Y.228.237; 6.Y.228.238; 6.Y.228.239; 6.Y.228.154; 6.Y.228.157; 6.Y.228.166; 6.Y.228.169; 6.Y.228.172; 6.Y.228.175; 6.Y.228.240; 6.Y.228.244; 6.Y.229.228; 6.Y.229.229; 6.Y.229.230; 6.Y.229.231; 6.Y.229.236; 6.Y.229.237; 6.Y.229.238; 6.Y.229.239; 6.Y.229.154; 6.Y.229.157; 6.Y.229.166; 6.Y.229.169; 6.Y.229.172; 6.Y.229.175; 6.Y.229.240; 6.Y.229.244; 6.Y.230.228; 6.Y.230.229; 6.Y.230.230; 6.Y.230.231; 6.Y.230.236; 6.Y.230.237; 6.Y.230.238; 6.Y.230.239; 6.Y.230.154; 6.Y.230.157; 6.Y.230.166; 6.Y.230.169; 6.Y.230.172; 6.Y.230.175; 6.Y.230.240; 6.Y.230.244; 6.Y.231.228; 6.Y.231.229; 6.Y.231.230; 6.Y.231.231; 6.Y.231.236; 6.Y.231.237; 6.Y.231.238; 6.Y.231.239; 6.Y.231.154; 6.Y.231.157; 6.Y.231.166; 6.Y.231.169; 6.Y.231.172; 6.Y.231.175; 6.Y.231.240; 6.Y.231.244; 6.Y.236.228; 6.Y.236.229; 6.Y.236.230; 6.Y.236.231; 6.Y.236.236; 6.Y.236.237; 6.Y.236.238; 6.Y.236.239; 6.Y.236.154; 6.Y.236.157; 6.Y.236.166; 6.Y.236.169; 6.Y.236.172; 6.Y.236.175; 6.Y.236.240; 6.Y.236.244; 6.Y.237.228; 6.Y.237.229; 6.Y.237.230; 6.Y.237.231; 6.Y.237.236; 6.Y.237.237; 6.Y.237.238; 6.Y.237.239; 6.Y.237.154; 6.Y.237.157; 6.Y.237.166; 6.Y.237.169; 6.Y.237.172; 6.Y.237.175; 6.Y.237.240; 6.Y.237.244; 6.Y.238.228; 6.Y.238.229; 6.Y.238.230; 6.Y.238.231; 6.Y.238.236; 6.Y.238.237; 6.Y.238.238; 6.Y.238.239; 6.Y.238.154; 6.Y.238.157; 6.Y.238.166; 6.Y.238.169; 6.Y.238.172; 6.Y.238.175; 6.Y.238.240; 6.Y.238.244; 6.Y.239.228; 6.Y.239.229; 6.Y.239.230; 6.Y.239.231; 6.Y.239.236; 6.Y.239.237; 6.Y.239.238; 6.Y.239.239; 6.Y.239.154; 6.Y.239.157; 6.Y.239.166; 6.Y.239.169; 6.Y.239.172; 6.Y.239.175; 6.Y.239.240; 6.Y.239.244; 6.Y.154.228; 6.Y.154.229; 6.Y.154.230; 6.Y.154.231; 6.Y.154.236; 6.Y.154.237; 6.Y.154.238; 6.Y.154.239; 6.Y.154.154; 6.Y.154.157; 6.Y.154.166; 6.Y.154.169; 6.Y.154.172; 6.Y.154.175; 6.Y.154.240; 6.Y.154.244; 6.Y.157.228; 6.Y.157.229; 6.Y.157.230; 6.Y.157.231; 6.Y.157.236; 6.Y.157.237; 6.Y.157.238; 6.Y.157.239; 6.Y.157.154; 6.Y.157.157; 6.Y.157.166; 6.Y.157.169; 6.Y.157.172; 6.Y.157.175; 6.Y.157.240; 6.Y.157.244; 6.Y.166.228; 6.Y.166.229; 6.Y.166.230; 6.Y.166.231; 6.Y.166.236; 6.Y.166.237; 6.Y.166.238; 6.Y.166.239; 6.Y.166.154; 6.Y.166.157; |

TABLE 100-continued

| |
|---|
| 6.Y.166.166; 6.Y.166.169; 6.Y.166.172; 6.Y.166.175; 6.Y.166.240; 6.Y.166.244; 6.Y.169.228; 6.Y.169.229; 6.Y.169.230; 6.Y.169.231; 6.Y.169.236; 6.Y.169.237; 6.Y.169.238; 6.Y.169.239; 6.Y.169.154; 6.Y.169.157; 6.Y.169.166; 6.Y.169.169; 6.Y.169.172; 6.Y.169.175; 6.Y.169.240; 6.Y.169.244; 6.Y.172.228; 6.Y.172.229; 6.Y.172.230; 6.Y.172.231; 6.Y.172.236; 6.Y.172.237; 6.Y.172.238; 6.Y.172.239; 6.Y.172.154; 6.Y.172.157; 6.Y.172.166; 6.Y.172.169; 6.Y.172.172; 6.Y.172.175; 6.Y.172.240; 6.Y.172.244; 6.Y.175.228; 6.Y.175.229; 6.Y.175.230; 6.Y.175.231; 6.Y.175.236; 6.Y.175.237; 6.Y.175.238; 6.Y.175.239; 6.Y.175.154; 6.Y.175.157; 6.Y.175.166; 6.Y.175.169; 6.Y.175.172; 6.Y.175.175; 6.Y.175.240; 6.Y.175.244; 6.Y.240.228; 6.Y.240.229; 6.Y.240.230; 6.Y.240.231; 6.Y.240.236; 6.Y.240.237; 6.Y.240.238; 6.Y.240.239; 6.Y.240.154; 6.Y.240.157; 6.Y.240.166; 6.Y.240.169; 6.Y.240.172; 6.Y.240.175; 6.Y.240.240; 6.Y.240.244; 6.Y.244.228; 6.Y.244.229; 6.Y.244.230; 6.Y.244.231; 6.Y.244.236; 6.Y.244.237; 6.Y.244.238; 6.Y.244.239; 6.Y.244.154; 6.Y.244.157; 6.Y.244.166; 6.Y.244.169; 6.Y.244.172; 6.Y.244.175; 6.Y.244.240; 6.Y.244.244; |
| Prodrugs of 7.AH |
| 7.AH.4.157; 7.AH.4.158; 7.AH.4.196; 7.AH.4.223; 7.AH.4.240; 7.AH.4.244; 7.AH.4.243; 7.AH.4.247; 7.AH.5.157; 7.AH.5.158; 7.AH.5.196; 7.AH.5.223; 7.AH.5.240; 7.AH.5.244; 7.AH.5.243; 7.AH.5.247; 7.AH.7.157; 7.AH.7.158; 7.AH.7.196; 7.AH.7.223; 7.AH.7.240; 7.AH.7.244; 7.AH.7.243; 7.AH.7.247; 7.AH.15.157; 7.AH.15.158; 7.AH.15.196; 7.AH.15.223; 7.AH.15.240; 7.AH.15.244; 7.AH.15.243; 7.AH.15.247; 7.AH.16.157; 7.AH.16.158; 7.AH.16.196; 7.AH.16.223; 7.AH.16.240; 7.AH.16.244; 7.AH.16.243; 7.AH.16.247; 7.AH.18.157; 7.AH.18.158; 7.AH.18.196; 7.AH.18.223; 7.AH.18.240; 7.AH.18.244; 7.AH.18.243; 7.AH.18.247; 7.AH.26.157; 7.AH.26.158; 7.AH.26.196; 7.AH.26.223; 7.AH.26.240; 7.AH.26.244; 7.AH.26.243; 7.AH.26.247; 7.AH.27.157; 7.AH.27.158; 7.AH.27.196; 7.AH.27.223; 7.AH.27.240; 7.AH.27.244; 7.AH.27.243; 7.AH.27.247; 7.AH.29.157; 7.AH.29.158; 7.AH.29.196; 7.AH.29.223; 7.AH.29.240; 7.AH.29.244; 7.AH.29.243; 7.AH.29.247; 7.AH.54.157; 7.AH.54.158; 7.AH.54.196; 7.AH.54.223; 7.AH.54.240; 7.AH.54.244; 7.AH.54.243; 7.AH.54.247; 7.AH.55.157; 7.AH.55.158; 7.AH.55.196; 7.AH.55.223; 7.AH.55.240; 7.AH.55.244; 7.AH.55.243; 7.AH.55.247; 7.AH.56.157; 7.AH.56.158; 7.AH.56.196; 7.AH.56.223; 7.AH.56.240; 7.AH.56.244; 7.AH.56.243; 7.AH.56.247; 7.AH.157.157; 7.AH.157.158; 7.AH.157.196; 7.AH.157.223; 7.AH.157.240; 7.AH.157.244; 7.AH.157.243; 7.AH.157.247; 7.AH.196.157; 7.AH.196.158; 7.AH.196.196; 7.AH.196.223; 7.AH.196.240; 7.AH.196.244; 7.AH.196.243; 7.AH.196.247; 7.AH.223.157; 7.AH.223.158; 7.AH.223.196; 7.AH.223.223; 7.AH.223.240; 7.AH.223.244; 7.AH.223.243; 7.AH.223.247; 7.AH.240.157; 7.AH.240.158; 7.AH.240.196; 7.AH.240.223; 7.AH.240.240; 7.AH.240.244; 7.AH.240.243; 7.AH.240.247; 7.AH.244.157; 7.AH.244.158; 7.AH.244.196; 7.AH.244.223; 7.AH.244.240; 7.AH.244.244; 7.AH.244.243; 7.AH.244.247; 7.AH.247.157; 7.AH.247.158; 7.AH.247.196; 7.AH.247.223; 7.AH.247.240; 7.AH.247.244; 7.AH.247.243; 7.AH.247.247; |
| Prodrugs of 7.AJ |
| 7.AJ.4.157; 7.AJ.4.158; 7.AJ.4.196; 7.AJ.4.223; 7.AJ.4.240; 7.AJ.4.244; 7.AJ.4.243; 7.AJ.4.247; 7.AJ.5.157; 7.AJ.5.158; 7.AJ.5.196; 7.AJ.5.223; 7.AJ.5.240; 7.AJ.5.244; 7.AJ.5.243; 7.AJ.5.247; 7.AJ.7.157; 7.AJ.7.158; 7.AJ.7.196; 7.AJ.7.223; 7.AJ.7.240; 7.AJ.7.244; 7.AJ.7.243; 7.AJ.7.247; 7.AJ.15.157; 7.AJ.15.158; 7.AJ.15.196; 7.AJ.15.223; 7.AJ.15.240; 7.AJ.15.244; 7.AJ.15.243; 7.AJ.15.247; 7.AJ.16.157; 7.AJ.16.158; 7.AJ.16.196; 7.AJ.16.223; 7.AJ.16.240; 7.AJ.16.244; 7.AJ.16.243; 7.AJ.16.247; 7.AJ.18.157; 7.AJ.18.158; 7.AJ.18.196; 7.AJ.18.223; 7.AJ.18.240; 7.AJ.18.244; 7.AJ.18.243; 7.AJ.18.247; 7.AJ.26.157; 7.AJ.26.158; 7.AJ.26.196; 7.AJ.26.223; 7.AJ.26.240; 7.AJ.26.244; 7.AJ.26.243; 7.AJ.26.247; 7.AJ.27.157; 7.AJ.27.158; 7.AJ.27.196; 7.AJ.27.223; 7.AJ.27.240; 7.AJ.27.244; 7.AJ.27.243; 7.AJ.27.247; 7.AJ.29.157; 7.AJ.29.158; 7.AJ.29.196; 7.AJ.29.223; 7.AJ.29.240; 7.AJ.29.244; 7.AJ.29.243; 7.AJ.29.247; 7.AJ.54.157; 7.AJ.54.158; 7.AJ.54.196; 7.AJ.54.223; 7.AJ.54.240; 7.AJ.54.244; 7.AJ.54.243; 7.AJ.54.247; 7.AJ.55.157; 7.AJ.55.158; 7.AJ.55.196; 7.AJ.55.223; 7.AJ.55.240; 7.AJ.55.244; 7.AJ.55.243; 7.AJ.55.247; 7.AJ.56.157; 7.AJ.56.158; 7.AJ.56.196; 7.AJ.56.223; 7.AJ.56.240; 7.AJ.56.244; 7.AJ.56.243; 7.AJ.56.247; 7.AJ.157.157; 7.AJ.157.158; 7.AJ.157.196; 7.AJ.157.223; 7.AJ.157.240; 7.AJ.157.244; 7.AJ.157.243; 7.AJ.157.247; 7.AJ.196.157; 7.AJ.196.158; 7.AJ.196.196; 7.AJ.196.223; 7.AJ.196.240; 7.AJ.196.244; 7.AJ.196.243; 7.AJ.196.247; 7.AJ.223.157; 7.AJ.223.158; 7.AJ.223.196; 7.AJ.223.223; 7.AJ.223.240; 7.AJ.223.244; 7.AJ.223.243; 7.AJ.223.247; 7.AJ.240.157; 7.AJ.240.158; 7.AJ.240.196; 7.AJ.240.223; 7.AJ.240.240; 7.AJ.240.244; 7.AJ.240.243; 7.AJ.240.247; 7.AJ.244.157; 7.AJ.244.158; 7.AJ.244.196; 7.AJ.244.223; 7.AJ.244.240; 7.AJ.244.244; 7.AJ.244.243; 7.AJ.244.247; 7.AJ.247.157; 7.AJ.247.158; 7.AJ.247.196; 7.AJ.247.223; 7.AJ.247.240; 7.AJ.247.244; 7.AJ.247.243; 7.AJ.247.247; |
| Prodrugs of 7.AN |
| 7.AN.4.157; 7.AN.4.158; 7.AN.4.196; 7.AN.4.223; 7.AN.4.240; 7.AN.4.244; 7.AN.4.243; 7.AN.4.247; 7.AN.5.157; 7.AN.5.158; 7.AN.5.196; 7.AN.5.223; 7.AN.5.240; 7.AN.5.244; 7.AN.5.243; 7.AN.5.247; 7.AN.7.157; 7.AN.7.158; |

TABLE 100-continued

| |
|---|
| 7.AN.7.196; 7.AN.7.223; 7.AN.7.240; 7.AN.7.244; 7.AN.7.243; 7.AN.7.247; 7.AN.15.157; 7.AN.15.158; 7.AN.15.196; 7.AN.15.223; 7.AN.15.240; 7.AN.15.244; 7.AN.15.243; 7.AN.15.247; 7.AN.16.157; 7.AN.16.158; 7.AN.16.196; 7.AN.16.223; 7.AN.16.240; 7.AN.16.244; 7.AN.16.243; 7.AN.16.247; 7.AN.18.157; 7.AN.18.158; 7.AN.18.196; 7.AN.18.223; 7.AN.18.240; 7.AN.18.244; 7.AN.18.243; 7.AN.18.247; 7.AN.26.157; 7.AN.26.158; 7.AN.26.196; 7.AN.26.223; 7.AN.26.240; 7.AN.26.244; 7.AN.26.243; 7.AN.26.247; 7.AN.27.157; 7.AN.27.158; 7.AN.27.196; 7.AN.27.223; 7.AN.27.240; 7.AN.27.244; 7.AN.27.243; 7.AN.27.247; 7.AN.29.157; 7.AN.29.158; 7.AN.29.196; 7.AN.29.223; 7.AN.29.240; 7.AN.29.244; 7.AN.29.243; 7.AN.29.247; 7.AN.54.157; 7.AN.54.158; 7.AN.54.196; 7.AN.54.223; 7.AN.54.240; 7.AN.54.244; 7.AN.54.243; 7.AN.54.247; 7.AN.55.157; 7.AN.55.158; 7.AN.55.196; 7.AN.55.223; 7.AN.55.240; 7.AN.55.244; 7.AN.55.243; 7.AN.55.247; 7.AN.56.157; 7.AN.56.158; 7.AN.56.196; 7.AN.56.223; 7.AN.56.240; 7.AN.56.244; 7.AN.56.243; 7.AN.56.247; 7.AN.157.157; 7.AN.157.158; 7.AN.157.196; 7.AN.157.223; 7.AN.157.240; 7.AN.157.244; 7.AN.157.243; 7.AN.157.247; 7.AN.196.157; 7.AN.196.158; 7.AN.196.196; 7.AN.196.223; 7.AN.196.240; 7.AN.196.244; 7.AN.196.243; 7.AN.196.247; 7.AN.223.157; 7.AN.223.158; 7.AN.223.196; 7.AN.223.223; 7.AN.223.240; 7.AN.223.244; 7.AN.223.243; 7.AN.223.247; 7.AN.240.157; 7.AN.240.158; 7.AN.240.196; 7.AN.240.223; 7.AN.240.240; 7.AN.240.244; 7.AN.240.243; 7.AN.240.247; 7.AN.244.157; 7.AN.244.158; 7.AN.244.196; 7.AN.244.223; 7.AN.244.240; 7.AN.244.244; 7.AN.244.243; 7.AN.244.247; 7.AN.247.157; 7.AN.247.158; 7.AN.247.196; 7.AN.247.223; 7.AN.247.240; 7.AN.247.244; 7.AN.247.243; 7.AN.247.247; |
| Prodrugs of 7.AP |
| 7.AP.4.157; 7.AP.4.158; 7.AP.4.196; 7.AP.4.223; 7.AP.4.240; 7.AP.4.244; 7.AP.4.243; 7.AP.4.247; 7.AP.5.157; 7.AP.5.158; 7.AP.5.196; 7.AP.5.223; 7.AP.5.240; 7.AP.5.244; 7.AP.5.243; 7.AP.5.247; 7.AP.7.157; 7.AP.7.158; 7.AP.7.196; 7.AP.7.223; 7.AP.7.240; 7.AP.7.244; 7.AP.7.243; 7.AP.7.247; 7.AP.15.157; 7.AP.15.158; 7.AP.15.196; 7.AP.15.223; 7.AP.15.240; 7.AP.15.244; 7.AP.15.243; 7.AP.15.247; 7.AP.16.157; 7.AP.16.158; 7.AP.16.196; 7.AP.16.223; 7.AP.16.240; 7.AP.16.244; 7.AP.16.243; 7.AP.16.247; 7.AP.18.157; 7.AP.18.158; 7.AP.18.196; 7.AP.18.223; 7.AP.18.240; 7.AP.18.244; 7.AP.18.243; 7.AP.18.247; 7.AP.26.157; 7.AP.26.158; 7.AP.26.196; 7.AP.26.223; 7.AP.26.240; 7.AP.26.244; 7.AP.26.243; 7.AP.26.247; 7.AP.27.157; 7.AP.27.158; 7.AP.27.196; 7.AP.27.223; 7.AP.27.240; 7.AP.27.244; 7.AP.27.243; 7.AP.27.247; 7.AP.29.157; 7.AP.29.158; 7.AP.29.196; 7.AP.29.223; 7.AP.29.240; 7.AP.29.244; 7.AP.29.243; 7.AP.29.247; 7.AP.54.157; 7.AP.54.158; 7.AP.54.196; 7.AP.54.223; 7.AP.54.240; 7.AP.54.244; 7.AP.54.243; 7.AP.54.247; 7.AP.55.157; 7.AP.55.158; 7.AP.55.196; 7.AP.55.223; 7.AP.55.240; 7.AP.55.244; 7.AP.55.243; 7.AP.55.247; 7.AP.56.157; 7.AP.56.158; 7.AP.56.196; 7.AP.56.223; 7.AP.56.240; 7.AP.56.244; 7.AP.56.243; 7.AP.56.247; 7.AP.157.157; 7.AP.157.158; 7.AP.157.196; 7.AP.157.223; 7.AP.157.240; 7.AP.157.244; 7.AP.157.243; 7.AP.157.247; 7.AP.196.157; 7.AP.196.158; 7.AP.196.196; 7.AP.196.223; 7.AP.196.240; 7.AP.196.244; 7.AP.196.243; 7.AP.196.247; 7.AP.223.157; 7.AP.223.158; 7.AP.223.196; 7.AP.223.223; 7.AP.223.240; 7.AP.223.244; 7.AP.223.243; 7.AP.223.247; 7.AP.240.157; 7.AP.240.158; 7.AP.240.196; 7.AP.240.223; 7.AP.240.240; 7.AP.240.244; 7.AP.240.243; 7.AP.240.247; 7.AP.244.157; 7.AP.244.158; 7.AP.244.196; 7.AP.244.223; 7.AP.244.240; 7.AP.244.244; 7.AP.244.243; 7.AP.244.247; 7.AP.247.157; 7.AP.247.158; 7.AP.247.196; 7.AP.247.223; 7.AP.247.240; 7.AP.247.244; 7.AP.247.243; 7.AP.247.247; |
| Prodrugs of 7.AZ |
| 7.AZ.4.157; 7.AZ.4.158; 7.AZ.4.196; 7.AZ.4.223; 7.AZ.4.240; 7.AZ.4.244; 7.AZ.4.243; 7.AZ.4.247; 7.AZ.5.157; 7.AZ.5.158; 7.AZ.5.196; 7.AZ.5.223; 7.AZ.5.240; 7.AZ.5.244; 7.AZ.5.243; 7.AZ.5.247; 7.AZ.7.157; 7.AZ.7.158; 7.AZ.7.196; 7.AZ.7.223; 7.AZ.7.240; 7.AZ.7.244; 7.AZ.7.243; 7.AZ.7.247; 7.AZ.15.157; 7.AZ.15.158; 7.AZ.15.196; 7.AZ.15.223; 7.AZ.15.240; 7.AZ.15.244; 7.AZ.15.243; 7.AZ.15.247; 7.AZ.16.157; 7.AZ.16.158; 7.AZ.16.196; 7.AZ.16.223; 7.AZ.16.240; 7.AZ.16.244; 7.AZ.16.243; 7.AZ.16.247; 7.AZ.18.157; 7.AZ.18.158; 7.AZ.18.196; 7.AZ.18.223; 7.AZ.18.240; 7.AZ.18.244; 7.AZ.18.243; 7.AZ.18.247; 7.AZ.26.157; 7.AZ.26.158; 7.AZ.26.196; 7.AZ.26.223; 7.AZ.26.240; 7.AZ.26.244; 7.AZ.26.243; 7.AZ.26.247; 7.AZ.27.157; 7.AZ.27.158; 7.AZ.27.196; 7.AZ.27.223; 7.AZ.27.240; 7.AZ.27.244; 7.AZ.27.243; 7.AZ.27.247; 7.AZ.29.157; 7.AZ.29.158; 7.AZ.29.196; 7.AZ.29.223; 7.AZ.29.240; 7.AZ.29.244; 7.AZ.29.243; 7.AZ.29.247; 7.AZ.54.157; 7.AZ.54.158; 7.AZ.54.196; 7.AZ.54.223; 7.AZ.54.240; 7.AZ.54.244; 7.AZ.54.243; 7.AZ.54.247; 7.AZ.55.157; 7.AZ.55.158; 7.AZ.55.196; 7.AZ.55.223; 7.AZ.55.240; 7.AZ.55.244; 7.AZ.55.243; 7.AZ.55.247; 7.AZ.56.157; 7.AZ.56.158; 7.AZ.56.196; 7.AZ.56.223; 7.AZ.56.240; 7.AZ.56.244; 7.AZ.56.243; 7.AZ.56.247; 7.AZ.157.157; 7.AZ.157.158; 7.AZ.157.196; 7.AZ.157.223; 7.AZ.157.240; 7.AZ.157.244; 7.AZ.157.243; 7.AZ.157.247; 7.AZ.196.157; 7.AZ.196.158; 7.AZ.196.196; 7.AZ.196.223; 7.AZ.196.240; 7.AZ.196.244; 7.AZ.196.243; 7.AZ.196.247; 7.AZ.223.157; 7.AZ.223.158; 7.AZ.223.196; 7.AZ.223.223; 7.AZ.223.240; 7.AZ.223.244; 7.AZ.223.243; |

TABLE 100-continued

| |
|---|
| 7.AZ.223.247; 7.AZ.240.157; 7.AZ.240.158; 7.AZ.240.196; 7.AZ.240.223; 7.AZ.240.240; 7.AZ.240.244; 7.AZ.240.243; 7.AZ.240.247; 7.AZ.244.157; 7.AZ.244.158; 7.AZ.244.196; 7.AZ.244.223; 7.AZ.244.240; 7.AZ.244.244; 7.AZ.244.243; 7.AZ.244.247; 7.AZ.247.157; 7.AZ.247.158; 7.AZ.247.196; 7.AZ.247.223; 7.AZ.247.240; 7.AZ.247.244; 7.AZ.247.243; 7.AZ.247.247; |
| Prodrugs of 7.BF |
| 7.BF.4.157; 7.BF.4.158; 7.BF.4.196; 7.BF.4.223; 7.BF.4.240; 7.BF.4.244; 7.BF.4.243; 7.BF.4.247; 7.BF.5.157; 7.BF.5.158; 7.BF.5.196; 7.BF.5.223; 7.BF.5.240; 7.BF.5.244; 7.BF.5.243; 7.BF.5.247; 7.BF.7.157; 7.BF.7.158; 7.BF.7.196; 7.BF.7.223; 7.BF.7.240; 7.BF.7.244; 7.BF.7.243; 7.BF.7.247; 7.BF.15.157; 7.BF.15.158; 7.BF.15.196; 7.BF.15.223; 7.BF.15.240; 7.BF.15.244; 7.BF.15.243; 7.BF.15.247; 7.BF.16.157; 7.BF.16.158; 7.BF.16.196; 7.BF.16.223; 7.BF.16.240; 7.BF.16.244; 7.BF.16.243; 7.BF.16.247; 7.BF.18.157; 7.BF.18.158; 7.BF.18.196; 7.BF.18.223; 7.BF.18.240; 7.BF.18.244; 7.BF.18.243; 7.BF.18.247; 7.BF.26.157; 7.BF.26.158; 7.BF.26.196; 7.BF.26.223; 7.BF.26.240; 7.BF.26.244; 7.BF.26.243; 7.BF.26.247; 7.BF.27.157; 7.BF.27.158; 7.BF.27.196; 7.BF.27.223; 7.BF.27.240; 7.BF.27.244; 7.BF.27.243; 7.BF.27.247; 7.BF.29.157; 7.BF.29.158; 7.BF.29.196; 7.BF.29.223; 7.BF.29.240; 7.BF.29.244; 7.BF.29.243; 7.BF.29.247; 7.BF.54.157; 7.BF.54.158; 7.BF.54.196; 7.BF.54.223; 7.BF.54.240; 7.BF.54.244; 7.BF.54.243; 7.BF.54.247; 7.BF.55.157; 7.BF.55.158; 7.BF.55.196; 7.BF.55.223; 7.BF.55.240; 7.BF.55.244; 7.BF.55.243; 7.BF.55.247; 7.BF.56.157; 7.BF.56.158; 7.BF.56.196; 7.BF.56.223; 7.BF.56.240; 7.BF.56.244; 7.BF.56.243; 7.BF.56.247; 7.BF.157.157; 7.BF.157.158; 7.BF.157.196; 7.BF.157.223; 7.BF.157.240; 7.BF.157.244; 7.BF.157.243; 7.BF.157.247; 7.BF.196.157; 7.BF.196.158; 7.BF.196.196; 7.BF.196.223; 7.BF.196.240; 7.BF.196.244; 7.BF.196.243; 7.BF.196.247; 7.BF.223.157; 7.BF.223.158; 7.BF.223.196; 7.BF.223.223; 7.BF.223.240; 7.BF.223.244; 7.BF.223.243; 7.BF.223.247; 7.BF.240.157; 7.BF.240.158; 7.BF.240.196; 7.BF.240.223; 7.BF.240.240; 7.BF.240.244; 7.BF.240.243; 7.BF.240.247; 7.BF.244.157; 7.BF.244.158; 7.BF.244.196; 7.BF.244.223; 7.BF.244.240; 7.BF.244.244; 7.BF.244.243; 7.BF.244.247; 7.BF.247.157; 7.BF.247.158; 7.BF.247.196; 7.BF.247.223; 7.BF.247.240; 7.BF.247.244; 7.BF.247.243; 7.BF.247.247; |
| Prodrugs of 7.CI |
| 7.CI.4.157; 7.CI.4.158; 7.CI.4.196; 7.CI.4.223; 7.CI.4.240; 7.CI.4.244; 7.CI.4.243; 7.CI.4.247; 7.CI.5.157; 7.CI.5.158; 7.CI.5.196; 7.CI.5.223; 7.CI.5.240; 7.CI.5.244; 7.CI.5.243; 7.CI.5.247; 7.CI.7.157; 7.CI.7.158; 7.CI.7.196; 7.CI.7.223; 7.CI.7.240; 7.CI.7.244; 7.CI.7.243; 7.CI.7.247; 7.CI.15.157; 7.CI.15.158; 7.CI.15.196; 7.CI.15.223; 7.CI.15.240; 7.CI.15.244; 7.CI.15.243; 7.CI.15.247; 7.CI.16.157; 7.CI.16.158; 7.CI.16.196; 7.CI.16.223; 7.CI.16.240; 7.CI.16.244; 7.CI.16.243; 7.CI.16.247; 7.CI.18.157; 7.CI.18.158; 7.CI.18.196; 7.CI.18.223; 7.CI.18.240; 7.CI.18.244; 7.CI.18.243; 7.CI.18.247; 7.CI.26.157; 7.CI.26.158; 7.CI.26.196; 7.CI.26.223; 7.CI.26.240; 7.CI.26.244; 7.CI.26.243; 7.CI.26.247; 7.CI.27.157; 7.CI.27.158; 7.CI.27.196; 7.CI.27.223; 7.CI.27.240; 7.CI.27.244; 7.CI.27.243; 7.CI.27.247; 7.CI.29.157; 7.CI.29.158; 7.CI.29.196; 7.CI.29.223; 7.CI.29.240; 7.CI.29.244; 7.CI.29.243; 7.CI.29.247; 7.CI.54.157; 7.CI.54.158; 7.CI.54.196; 7.CI.54.223; 7.CI.54.240; 7.CI.54.244; 7.CI.54.243; 7.CI.54.247; 7.CI.55.157; 7.CI.55.158; 7.CI.55.196; 7.CI.55.223; 7.CI.55.240; 7.CI.55.244; 7.CI.55.243; 7.CI.55.247; 7.CI.56.157; 7.CI.56.158; 7.CI.56.196; 7.CI.56.223; 7.CI.56.240; 7.CI.56.244; 7.CI.56.243; 7.CI.56.247; 7.CI.157.157; 7.CI.157.158; 7.CI.157.196; 7.CI.157.223; 7.CI.157.240; 7.CI.157.244; 7.CI.157.243; 7.CI.157.247; 7.CI.196.157; 7.CI.196.158; 7.CI.196.196; 7.CI.196.223; 7.CI.196.240; 7.CI.196.244; 7.CI.196.243; 7.CI.196.247; 7.CI.223.157; 7.CI.223.158; 7.CI.223.196; 7.CI.223.223; 7.CI.223.240; 7.CI.223.244; 7.CI.223.243; 7.CI.223.247; 7.CI.240.157; 7.CI.240.158; 7.CI.240.196; 7.CI.240.223; 7.CI.240.240; 7.CI.240.244; 7.CI.240.243; 7.CI.240.247; 7.CI.244.157; 7.CI.244.158; 7.CI.244.196; 7.CI.244.223; 7.CI.244.240; 7.CI.244.244; 7.CI.244.243; 7.CI.244.247; 7.CI.247.157; 7.CI.247.158; 7.CI.247.196; 7.CI.247.223; 7.CI.247.240; 7.CI.247.244; 7.CI.247.243; 7.CI.247.247; |
| Prodrugs of 7.CO |
| 7.CO.4.157; 7.CO.4.158; 7.CO.4.196; 7.CO.4.223; 7.CO.4.240; 7.CO.4.244; 7.CO.4.243; 7.CO.4.247; 7.CO.5.157; 7.CO.5.158; 7.CO.5.196; 7.CO.5.223; 7.CO.5.240; 7.CO.5.244; 7.CO.5.243; 7.CO.5.247; 7.CO.7.157; 7.CO.7.158; 7.CO.7.196; 7.CO.7.223; 7.CO.7.240; 7.CO.7.244; 7.CO.7.243; 7.CO.7.247; 7.CO.15.157; 7.CO.15.158; 7.CO.15.196; 7.CO.15.223; 7.CO.15.240; 7.CO.15.244; 7.CO.15.243; 7.CO.15.247; 7.CO.16.157; 7.CO.16.158; 7.CO.16.196; 7.CO.16.223; 7.CO.16.240; 7.CO.16.244; 7.CO.16.243; 7.CO.16.247; 7.CO.18.157; 7.CO.18.158; 7.CO.18.196; 7.CO.18.223; 7.CO.18.240; 7.CO.18.244; 7.CO.18.243; 7.CO.18.247; 7.CO.26.157; 7.CO.26.158; 7.CO.26.196; 7.CO.26.223; 7.CO.26.240; 7.CO.26.244; 7.CO.26.243; 7.CO.26.247; 7.CO.27.157; 7.CO.27.158; 7.CO.27.196; 7.CO.27.223; 7.CO.27.240; 7.CO.27.244; 7.CO.27.243; 7.CO.27.247; 7.CO.29.157; 7.CO.29.158; 7.CO.29.196; 7.CO.29.223; 7.CO.29.240; 7.CO.29.244; 7.CO.29.243; 7.CO.29.247; 7.CO.54.157; 7.CO.54.158; 7.CO.54.196; 7.CO.54.223; 7.CO.54.240; 7.CO.54.244; 7.CO.54.243; |

TABLE 100-continued

| |
|---|
| 7.CO.54.247; 7.CO.55.157; 7.CO.55.158; 7.CO.55.196; 7.CO.55.223; 7.CO.55.240; 7.CO.55.244; 7.CO.55.243; 7.CO.55.247; 7.CO.56.157; 7.CO.56.158; 7.CO.56.196; 7.CO.56.223; 7.CO.56.240; 7.CO.56.244; 7.CO.56.243; 7.CO.56.247; 7.CO.157.157; 7.CO.157.158; 7.CO.157.196; 7.CO.157.223; 7.CO.157.240; 7.CO.157.244; 7.CO.157.243; 7.CO.157.247; 7.CO.196.157; 7.CO.196.158; 7.CO.196.196; 7.CO.196.223; 7.CO.196.240; 7.CO.196.244; 7.CO.196.243; 7.CO.196.247; 7.CO.223.157; 7.CO.223.158; 7.CO.223.196; 7.CO.223.223; 7.CO.223.240; 7.CO.223.244; 7.CO.223.243; 7.CO.223.247; 7.CO.240.157; 7.CO.240.158; 7.CO.240.196; 7.CO.240.223; 7.CO.240.240; 7.CO.240.244; 7.CO.240.243; 7.CO.240.247; 7.CO.244.157; 7.CO.244.158; 7.CO.244.196; 7.CO.244.223; 7.CO.244.240; 7.CO.244.244; 7.CO.244.243; 7.CO.244.247; 7.CO.4.157; 7.CO.4.158; 7.CO.4.196; 7.CO.4.223; 7.CO.4.240; 7.CO.4.244; 7.CO.4.243; 7.CO.4.247; |
| Prodrugs of 8.AH |
| 8.AH.4.157; 8.AH.4.158; 8.AH.4.196; 8.AH.4.223; 8.AH.4.240; 8.AH.4.244; 8.AH.4.243; 8.AH.4.247; 8.AH.5.157; 8.AH.5.158; 8.AH.5.196; 8.AH.5.223; 8.AH.5.240; 8.AH.5.244; 8.AH.5.243; 8.AH.5.247; 8.AH.7.157; 8.AH.7.158; 8.AH.7.196; 8.AH.7.223; 8.AH.7.240; 8.AH.7.244; 8.AH.7.243; 8.AH.7.247; 8.AH.15.157; 8.AH.15.158; 8.AH.15.196; 8.AH.15.223; 8.AH.15.240; 8.AH.15.244; 8.AH.15.243; 8.AH.15.247; 8.AH.16.157; 8.AH.16.158; 8.AH.16.196; 8.AH.16.223; 8.AH.16.240; 8.AH.16.244; 8.AH.16.243; 8.AH.16.247; 8.AH.18.157; 8.AH.18.158; 8.AH.18.196; 8.AH.18.223; 8.AH.18.240; 8.AH.18.244; 8.AH.18.243; 8.AH.18.247; 8.AH.26.157; 8.AH.26.158; 8.AH.26.196; 8.AH.26.223; 8.AH.26.240; 8.AH.26.244; 8.AH.26.243; 8.AH.26.247; 8.AH.27.157; 8.AH.27.158; 8.AH.27.196; 8.AH.27.223; 8.AH.27.240; 8.AH.27.244; 8.AH.27.243; 8.AH.27.247; 8.AH.29.157; 8.AH.29.158; 8.AH.29.196; 8.AH.29.223; 8.AH.29.240; 8.AH.29.244; 8.AH.29.243; 8.AH.29.247; 8.AH.54.157; 8.AH.54.158; 8.AH.54.196; 8.AH.54.223; 8.AH.54.240; 8.AH.54.244; 8.AH.54.243; 8.AH.54.247; 8.AH.55.157; 8.AH.55.158; 8.AH.55.196; 8.AH.55.223; 8.AH.55.240; 8.AH.55.244; 8.AH.55.243; 8.AH.55.247; 8.AH.56.157; 8.AH.56.158; 8.AH.56.196; 8.AH.56.223; 8.AH.56.240; 8.AH.56.244; 8.AH.56.243; 8.AH.56.247; 8.AH.157.157; 8.AH.157.158; 8.AH.157.196; 8.AH.157.223; 8.AH.157.240; 8.AH.157.244; 8.AH.157.243; 8.AH.157.247; 8.AH.196.157; 8.AH.196.158; 8.AH.196.196; 8.AH.196.223; 8.AH.196.240; 8.AH.196.244; 8.AH.196.243; 8.AH.196.247; 8.AH.223.157; 8.AH.223.158; 8.AH.223.196; 8.AH.223.223; 8.AH.223.240; 8.AH.223.244; 8.AH.223.243; 8.AH.223.247; 8.AH.240.157; 8.AH.240.158; 8.AH.240.196; 8.AH.240.223; 8.AH.240.240; 8.AH.240.244; 8.AH.240.243; 8.AH.240.247; 8.AH.244.157; 8.AH.244.158; 8.AH.244.196; 8.AH.244.223; 8.AH.244.240; 8.AH.244.244; 8.AH.244.243; 8.AH.244.247; 8.AH.247.157; 8.AH.247.158; 8.AH.247.196; 8.AH.247.223; 8.AH.247.240; 8.AH.247.244; 8.AH.247.243; 8.AH.247.247; |
| Prodrugs of 8.AJ |
| 8.AJ.4.157; 8.AJ.4.158; 8.AJ.4.196; 8.AJ.4.223; 8.AJ.4.240; 8.AJ.4.244; 8.AJ.4.243; 8.AJ.4.247; 8.AJ.5.157; 8.AJ.5.158; 8.AJ.5.196; 8.AJ.5.223; 8.AJ.5.240; 8.AJ.5.244; 8.AJ.5.243; 8.AJ.5.247; 8.AJ.7.157; 8.AJ.7.158; 8.AJ.7.196; 8.AJ.7.223; 8.AJ.7.240; 8.AJ.7.244; 8.AJ.7.243; 8.AJ.7.247; 8.AJ.15.157; 8.AJ.15.158; 8.AJ.15.196; 8.AJ.15.223; 8.AJ.15.240; 8.AJ.15.244; 8.AJ.15.243; 8.AJ.15.247; 8.AJ.16.157; 8.AJ.16.158; 8.AJ.16.196; 8.AJ.16.223; 8.AJ.16.240; 8.AJ.16.244; 8.AJ.16.243; 8.AJ.16.247; 8.AJ.18.157; 8.AJ.18.158; 8.AJ.18.196; 8.AJ.18.223; 8.AJ.18.240; 8.AJ.18.244; 8.AJ.18.243; 8.AJ.18.247; 8.AJ.26.157; 8.AJ.26.158; 8.AJ.26.196; 8.AJ.26.223; 8.AJ.26.240; 8.AJ.26.244; 8.AJ.26.243; 8.AJ.26.247; 8.AJ.27.157; 8.AJ.27.158; 8.AJ.27.196; 8.AJ.27.223; 8.AJ.27.240; 8.AJ.27.244; 8.AJ.27.243; 8.AJ.27.247; 8.AJ.29.157; 8.AJ.29.158; 8.AJ.29.196; 8.AJ.29.223; 8.AJ.29.240; 8.AJ.29.244; 8.AJ.29.243; 8.AJ.29.247; 8.AJ.54.157; 8.AJ.54.158; 8.AJ.54.196; 8.AJ.54.223; 8.AJ.54.240; 8.AJ.54.244; 8.AJ.54.243; 8.AJ.54.247; 8.AJ.55.157; 8.AJ.55.158; 8.AJ.55.196; 8.AJ.55.223; 8.AJ.55.240; 8.AJ.55.244; 8.AJ.55.243; 8.AJ.55.247; 8.AJ.56.157; 8.AJ.56.158; 8.AJ.56.196; 8.AJ.56.223; 8.AJ.56.240; 8.AJ.56.244; 8.AJ.56.243; 8.AJ.56.247; 8.AJ.157.157; 8.AJ.157.158; 8.AJ.157.196; 8.AJ.157.223; 8.AJ.157.240; 8.AJ.157.244; 8.AJ.157.243; 8.AJ.157.247; 8.AJ.196.157; 8.AJ.196.158; 8.AJ.196.196; 8.AJ.196.223; 8.AJ.196.240; 8.AJ.196.244; 8.AJ.196.243; 8.AJ.196.247; 8.AJ.223.157; 8.AJ.223.158; 8.AJ.223.196; 8.AJ.223.223; 8.AJ.223.240; 8.AJ.223.244; 8.AJ.223.243; 8.AJ.223.247; 8.AJ.240.157; 8.AJ.240.158; 8.AJ.240.196; 8.AJ.240.223; 8.AJ.240.240; 8.AJ.240.244; 8.AJ.240.243; 8.AJ.240.247; 8.AJ.244.157; 8.AJ.244.158; 8.AJ.244.196; 8.AJ.244.223; 8.AJ.244.240; 8.AJ.244.244; 8.AJ.244.243; 8.AJ.244.247; 8.AJ.247.157; 8.AJ.247.158; 8.AJ.247.196; 8.AJ.247.223; 8.AJ.247.240; 8.AJ.247.244; 8.AJ.247.243; 8.AJ.247.247; |
| Prodrugs of 8.AN |
| 8.AN.4.157; 8.AN.4.158; 8.AN.4.196; 8.AN.4.223; 8.AN.4.240; 8.AN.4.244; 8.AN.4.243; 8.AN.4.247; 8.AN.5.157; 8.AN.5.158; 8.AN.5.196; 8.AN.5.223; 8.AN.5.240; 8.AN.5.244; 8.AN.5.243; 8.AN.5.247; 8.AN.7.157; 8.AN.7.158; 8.AN.7.196; 8.AN.7.223; 8.AN.7.240; 8.AN.7.244; 8.AN.7.243; 8.AN.7.247; 8.AN.15.157; 8.AN.15.158; 8.AN.15.196; 8.AN.15.223; 8.AN.15.240; 8.AN.15.244; 8.AN.15.243; 8.AN.15.247; 8.AN.16.157; 8.AN.16.158; 8.AN.16.196; 8.AN.16.223; 8.AN.16.240; 8.AN.16.244; 8.AN.16.243; |

TABLE 100-continued

| |
|---|
| 8.AN.16.247; 8.AN.18.157; 8.AN.18.158; 8.AN.18.196; 8.AN.18.223; 8.AN.18.240; 8.AN.18.244; 8.AN.18.243; 8.AN.18.247; 8.AN.26.157; 8.AN.26.158; 8.AN.26.196; 8.AN.26.223; 8.AN.26.240; 8.AN.26.244; 8.AN.26.243; 8.AN.26.247; 8.AN.27.157; 8.AN.27.158; 8.AN.27.196; 8.AN.27.223; 8.AN.27.240; 8.AN.27.244; 8.AN.27.243; 8.AN.27.247; 8.AN.29.157; 8.AN.29.158; 8.AN.29.196; 8.AN.29.223; 8.AN.29.240; 8.AN.29.244; 8.AN.29.243; 8.AN.29.247; 8.AN.54.157; 8.AN.54.158; 8.AN.54.196; 8.AN.54.223; 8.AN.54.240; 8.AN.54.244; 8.AN.54.243; 8.AN.54.247; 8.AN.55.157; 8.AN.55.158; 8.AN.55.196; 8.AN.55.223; 8.AN.55.240; 8.AN.55.244; 8.AN.55.243; 8.AN.55.247; 8.AN.56.157; 8.AN.56.158; 8.AN.56.196; 8.AN.56.223; 8.AN.56.240; 8.AN.56.244; 8.AN.56.243; 8.AN.56.247; 8.AN.157.157; 8.AN.157.158; 8.AN.157.196; 8.AN.157.223; 8.AN.157.240; 8.AN.157.244; 8.AN.157.243; 8.AN.157.247; 8.AN.196.157; 8.AN.196.158; 8.AN.196.196; 8.AN.196.223; 8.AN.196.240; 8.AN.196.244; 8.AN.196.243; 8.AN.196.247; 8.AN.223.157; 8.AN.223.158; 8.AN.223.196; 8.AN.223.223; 8.AN.223.240; 8.AN.223.244; 8.AN.223.243; 8.AN.223.247; 8.AN.240.157; 8.AN.240.158; 8.AN.240.196; 8.AN.240.223; 8.AN.240.240; 8.AN.240.244; 8.AN.240.243; 8.AN.240.247; 8.AN.244.157; 8.AN.244.158; 8.AN.244.196; 8.AN.244.223; 8.AN.244.240; 8.AN.244.244; 8.AN.244.243; 8.AN.244.247; 8.AN.247.157; 8.AN.247.158; 8.AN.247.196; 8.AN.247.223; 8.AN.247.240; 8.AN.247.244; 8.AN.247.243; 8.AN.247.247; |
| Prodrugs of 8.AP |
| 8.AP.4.157; 8.AP.4.158; 8.AP.4.196; 8.AP.4.223; 8.AP.4.240; 8.AP.4.244; 8.AP.4.243; 8.AP.4.247; 8.AP.5.157; 8.AP.5.158; 8.AP.5.196; 8.AP.5.223; 8.AP.5.240; 8.AP.5.244; 8.AP.5.243; 8.AP.5.247; 8.AP.7.157; 8.AP.7.158; 8.AP.7.196; 8.AP.7.223; 8.AP.7.240; 8.AP.7.244; 8.AP.7.243; 8.AP.7.247; 8.AP.15.157; 8.AP.15.158; 8.AP.15.196; 8.AP.15.223; 8.AP.15.240; 8.AP.15.244; 8.AP.15.243; 8.AP.15.247; 8.AP.16.157; 8.AP.16.158; 8.AP.16.196; 8.AP.16.223; 8.AP.16.240; 8.AP.16.244; 8.AP.16.243; 8.AP.16.247; 8.AP.18.157; 8.AP.18.158; 8.AP.18.196; 8.AP.18.223; 8.AP.18.240; 8.AP.18.244; 8.AP.18.243; 8.AP.18.247; 8.AP.26.157; 8.AP.26.158; 8.AP.26.196; 8.AP.26.223; 8.AP.26.240; 8.AP.26.244; 8.AP.26.243; 8.AP.26.247; 8.AP.27.157; 8.AP.27.158; 8.AP.27.196; 8.AP.27.223; 8.AP.27.240; 8.AP.27.244; 8.AP.27.243; 8.AP.27.247; 8.AP.29.157; 8.AP.29.158; 8.AP.29.196; 8.AP.29.223; 8.AP.29.240; 8.AP.29.244; 8.AP.29.243; 8.AP.29.247; 8.AP.54.157; 8.AP.54.158; 8.AP.54.196; 8.AP.54.223; 8.AP.54.240; 8.AP.54.244; 8.AP.54.243; 8.AP.54.247; 8.AP.55.157; 8.AP.55.158; 8.AP.55.196; 8.AP.55.223; 8.AP.55.240; 8.AP.55.244; 8.AP.55.243; 8.AP.55.247; 8.AP.56.157; 8.AP.56.158; 8.AP.56.196; 8.AP.56.223; 8.AP.56.240; 8.AP.56.244; 8.AP.56.243; 8.AP.56.247; 8.AP.157.157; 8.AP.157.158; 8.AP.157.196; 8.AP.157.223; 8.AP.157.240; 8.AP.157.244; 8.AP.157.243; 8.AP.157.247; 8.AP.196.157; 8.AP.196.158; 8.AP.196.196; 8.AP.196.223; 8.AP.196.240; 8.AP.196.244; 8.AP.196.243; 8.AP.196.247; 8.AP.223.157; 8.AP.223.158; 8.AP.223.196; 8.AP.223.223; 8.AP.223.240; 8.AP.223.244; 8.AP.223.243; 8.AP.223.247; 8.AP.240.157; 8.AP.240.158; 8.AP.240.196; 8.AP.240.223; 8.AP.240.240; 8.AP.240.244; 8.AP.240.243; 8.AP.240.247; 8.AP.244.157; 8.AP.244.158; 8.AP.244.196; 8.AP.244.223; 8.AP.244.240; 8.AP.244.244; 8.AP.244.243; 8.AP.244.247; 8.AP.247.157; 8.AP.247.158; 8.AP.247.196; 8.AP.247.223; 8.AP.247.240; 8.AP.247.244; 8.AP.247.243; 8.AP.247.247; |
| Prodrugs of 8.AZ |
| 8.AZ.4.157; 8.AZ.4.158; 8.AZ.4.196; 8.AZ.4.223; 8.AZ.4.240; 8.AZ.4.244; 8.AZ.4.243; 8.AZ.4.247; 8.AZ.5.157; 8.AZ.5.158; 8.AZ.5.196; 8.AZ.5.223; 8.AZ.5.240; 8.AZ.5.244; 8.AZ.5.243; 8.AZ.5.247; 8.AZ.7.157; 8.AZ.7.158; 8.AZ.7.196; 8.AZ.7.223; 8.AZ.7.240; 8.AZ.7.244; 8.AZ.7.243; 8.AZ.7.247; 8.AZ.15.157; 8.AZ.15.158; 8.AZ.15.196; 8.AZ.15.223; 8.AZ.15.240; 8.AZ.15.244; 8.AZ.15.243; 8.AZ.15.247; 8.AZ.16.157; 8.AZ.16.158; 8.AZ.16.196; 8.AZ.16.223; 8.AZ.16.240; 8.AZ.16.244; 8.AZ.16.243; 8.AZ.16.247; 8.AZ.18.157; 8.AZ.18.158; 8.AZ.18.196; 8.AZ.18.223; 8.AZ.18.240; 8.AZ.18.244; 8.AZ.18.243; 8.AZ.18.247; 8.AZ.26.157; 8.AZ.26.158; 8.AZ.26.196; 8.AZ.26.223; 8.AZ.26.240; 8.AZ.26.244; 8.AZ.26.243; 8.AZ.26.247; 8.AZ.27.157; 8.AZ.27.158; 8.AZ.27.196; 8.AZ.27.223; 8.AZ.27.240; 8.AZ.27.244; 8.AZ.27.243; 8.AZ.27.247; 8.AZ.29.157; 8.AZ.29.158; 8.AZ.29.196; 8.AZ.29.223; 8.AZ.29.240; 8.AZ.29.244; 8.AZ.29.243; 8.AZ.29.247; 8.AZ.54.157; 8.AZ.54.158; 8.AZ.54.196; 8.AZ.54.223; 8.AZ.54.240; 8.AZ.54.244; 8.AZ.54.243; 8.AZ.54.247; 8.AZ.55.157; 8.AZ.55.158; 8.AZ.55.196; 8.AZ.55.223; 8.AZ.55.240; 8.AZ.55.244; 8.AZ.55.243; 8.AZ.55.247; 8.AZ.56.157; 8.AZ.56.158; 8.AZ.56.196; 8.AZ.56.223; 8.AZ.56.240; 8.AZ.56.244; 8.AZ.56.243; 8.AZ.56.247; 8.AZ.157.157; 8.AZ.157.158; 8.AZ.157.196; 8.AZ.157.223; 8.AZ.157.240; 8.AZ.157.244; 8.AZ.157.243; 8.AZ.157.247; 8.AZ.196.157; 8.AZ.196.158; 8.AZ.196.196; 8.AZ.196.223; 8.AZ.196.240; 8.AZ.196.244; 8.AZ.196.243; 8.AZ.196.247; 8.AZ.223.157; 8.AZ.223.158; 8.AZ.223.196; 8.AZ.223.223; 8.AZ.223.240; 8.AZ.223.244; 8.AZ.223.243; 8.AZ.223.247; 8.AZ.240.157; 8.AZ.240.158; 8.AZ.240.196; 8.AZ.240.223; 8.AZ.240.240; 8.AZ.240.244; 8.AZ.240.243; 8.AZ.240.247; 8.AZ.244.157; 8.AZ.244.158; 8.AZ.244.196; 8.AZ.244.223; 8.AZ.244.240; 8.AZ.244.244; |

TABLE 100-continued

| |
|---|
| 8.AZ.244.243; 8.AZ.244.247; 8.AZ.247.157; 8.AZ.247.158; 8.AZ.247.196; 8.AZ.247.223; 8.AZ.247.240; 8.AZ.247.244; 8.AZ.247.243; 8.AZ.247.247; |
| Prodrugs of 8.BF |
| 8.BF.4.157; 8.BF.4.158; 8.BF.4.196; 8.BF.4.223; 8.BF.4.240; 8.BF.4.244; 8.BF.4.243; 8.BF.4.247; 8.BF.5.157; 8.BF.5.158; 8.BF.5.196; 8.BF.5.223; 8.BF.5.240; 8.BF.5.244; 8.BF.5.243; 8.BF.5.247; 8.BF.7.157; 8.BF.7.158; 8.BF.7.196; 8.BF.7.223; 8.BF.7.240; 8.BF.7.244; 8.BF.7.243; 8.BF.7.247; 8.BF.15.157; 8.BF.15.158; 8.BF.15.196; 8.BF.15.223; 8.BF.15.240; 8.BF.15.244; 8.BF.15.243; 8.BF.15.247; 8.BF.16.157; 8.BF.16.158; 8.BF.16.196; 8.BF.16.223; 8.BF.16.240; 8.BF.16.244; 8.BF.16.243; 8.BF.16.247; 8.BF.18.157; 8.BF.18.158; 8.BF.18.196; 8.BF.18.223; 8.BF.18.240; 8.BF.18.244; 8.BF.18.243; 8.BF.18.247; 8.BF.26.157; 8.BF.26.158; 8.BF.26.196; 8.BF.26.223; 8.BF.26.240; 8.BF.26.244; 8.BF.26.243; 8.BF.26.247; 8.BF.27.157; 8.BF.27.158; 8.BF.27.196; 8.BF.27.223; 8.BF.27.240; 8.BF.27.244; 8.BF.27.243; 8.BF.27.247; 8.BF.29.157; 8.BF.29.158; 8.BF.29.196; 8.BF.29.223; 8.BF.29.240; 8.BF.29.244; 8.BF.29.243; 8.BF.29.247; 8.BF.54.157; 8.BF.54.158; 8.BF.54.196; 8.BF.54.223; 8.BF.54.240; 8.BF.54.244; 8.BF.54.243; 8.BF.54.247; 8.BF.55.157; 8.BF.55.158; 8.BF.55.196; 8.BF.55.223; 8.BF.55.240; 8.BF.55.244; 8.BF.55.243; 8.BF.55.247; 8.BF.56.157; 8.BF.56.158; 8.BF.56.196; 8.BF.56.223; 8.BF.56.240; 8.BF.56.244; 8.BF.56.243; 8.BF.56.247; 8.BF.157.157; 8.BF.157.158; 8.BF.157.196; 8.BF.157.223; 8.BF.157.240; 8.BF.157.244; 8.BF.157.243; 8.BF.157.247; 8.BF.196.157; 8.BF.196.158; 8.BF.196.196; 8.BF.196.223; 8.BF.196.240; 8.BF.196.244; 8.BF.196.243; 8.BF.196.247; 8.BF.223.157; 8.BF.223.158; 8.BF.223.196; 8.BF.223.223; 8.BF.223.240; 8.BF.223.244; 8.BF.223.243; 8.BF.223.247; 8.BF.240.157; 8.BF.240.158; 8.BF.240.196; 8.BF.240.223; 8.BF.240.240; 8.BF.240.244; 8.BF.240.243; 8.BF.240.247; 8.BF.244.157; 8.BF.244.158; 8.BF.244.196; 8.BF.244.223; 8.BF.244.240; 8.BF.244.244; 8.BF.244.243; 8.BF.244.247; 8.BF.247.157; 8.BF.247.158; 8.BF.247.196; 8.BF.247.223; 8.BF.247.240; 8.BF.247.244; 8.BF.247.243; 8.BF.247.247; |
| Prodrugs of 8.CI |
| 8.CI.4.157; 8.CI.4.158; 8.CI.4.196; 8.CI.4.223; 8.CI.4.240; 8.CI.4.244; 8.CI.4.243; 8.CI.4.247; 8.CI.5.157; 8.CI.5.158; 8.CI.5.196; 8.CI.5.223; 8.CI.5.240; 8.CI.5.244; 8.CI.5.243; 8.CI.5.247; 8.CI.7.157; 8.CI.7.158; 8.CI.7.196; 8.CI.7.223; 8.CI.7.240; 8.CI.7.244; 8.CI.7.243; 8.CI.7.247; 8.CI.15.157; 8.CI.15.158; 8.CI.15.196; 8.CI.15.223; 8.CI.15.240; 8.CI.15.244; 8.CI.15.243; 8.CI.15.247; 8.CI.16.157; 8.CI.16.158; 8.CI.16.196; 8.CI.16.223; 8.CI.16.240; 8.CI.16.244; 8.CI.16.243; 8.CI.16.247; 8.CI.18.157; 8.CI.18.158; 8.CI.18.196; 8.CI.18.223; 8.CI.18.240; 8.CI.18.244; 8.CI.18.243; 8.CI.18.247; 8.CI.26.157; 8.CI.26.158; 8.CI.26.196; 8.CI.26.223; 8.CI.26.240; 8.CI.26.244; 8.CI.26.243; 8.CI.26.247; 8.CI.27.157; 8.CI.27.158; 8.CI.27.196; 8.CI.27.223; 8.CI.27.240; 8.CI.27.244; 8.CI.27.243; 8.CI.27.247; 8.CI.29.157; 8.CI.29.158; 8.CI.29.196; 8.CI.29.223; 8.CI.29.240; 8.CI.29.244; 8.CI.29.243; 8.CI.29.247; 8.CI.54.157; 8.CI.54.158; 8.CI.54.196; 8.CI.54.223; 8.CI.54.240; 8.CI.54.244; 8.CI.54.243; 8.CI.54.247; 8.CI.55.157; 8.CI.55.158; 8.CI.55.196; 8.CI.55.223; 8.CI.55.240; 8.CI.55.244; 8.CI.55.243; 8.CI.55.247; 8.CI.56.157; 8.CI.56.158; 8.CI.56.196; 8.CI.56.223; 8.CI.56.240; 8.CI.56.244; 8.CI.56.243; 8.CI.56.247; 8.CI.157.157; 8.CI.157.158; 8.CI.157.196; 8.CI.157.223; 8.CI.157.240; 8.CI.157.244; 8.CI.157.243; 8.CI.157.247; 8.CI.196.157; 8.CI.196.158; 8.CI.196.196; 8.CI.196.223; 8.CI.196.240; 8.CI.196.244; 8.CI.196.243; 8.CI.196.247; 8.CI.223.157; 8.CI.223.158; 8.CI.223.196; 8.CI.223.223; 8.CI.223.240; 8.CI.223.244; 8.CI.223.243; 8.CI.223.247; 8.CI.240.157; 8.CI.240.158; 8.CI.240.196; 8.CI.240.223; 8.CI.240.240; 8.CI.240.244; 8.CI.240.243; 8.CI.240.247; 8.CI.244.157; 8.CI.244.158; 8.CI.244.196; 8.CI.244.223; 8.CI.244.240; 8.CI.244.244; 8.CI.244.243; 8.CI.244.247; 8.CI.247.157; 8.CI.247.158; 8.CI.247.196; 8.CI.247.223; 8.CI.247.240; 8.CI.247.244; 8.CI.247.243; 8.CI.247.247; |
| Prodrugs of 8.CO |
| 8.CO.4.157; 8.CO.4.158; 8.CO.4.196; 8.CO.4.223; 8.CO.4.240; 8.CO.4.244; 8.CO.4.243; 8.CO.4.247; 8.CO.5.157; 8.CO.5.158; 8.CO.5.196; 8.CO.5.223; 8.CO.5.240; 8.CO.5.244; 8.CO.5.243; 8.CO.5.247; 8.CO.7.157; 8.CO.7.158; 8.CO.7.196; 8.CO.7.223; 8.CO.7.240; 8.CO.7.244; 8.CO.7.243; 8.CO.7.247; 8.CO.15.157; 8.CO.15.158; 8.CO.15.196; 8.CO.15.223; 8.CO.15.240; 8.CO.15.244; 8.CO.15.243; 8.CO.15.247; 8.CO.16.157; 8.CO.16.158; 8.CO.16.196; 8.CO.16.223; 8.CO.16.240; 8.CO.16.244; 8.CO.16.243; 8.CO.16.247; 8.CO.18.157; 8.CO.18.158; 8.CO.18.196; 8.CO.18.223; 8.CO.18.240; 8.CO.18.244; 8.CO.18.243; 8.CO.18.247; 8.CO.26.157; 8.CO.26.158; 8.CO.26.196; 8.CO.26.223; 8.CO.26.240; 8.CO.26.244; 8.CO.26.243; 8.CO.26.247; 8.CO.27.157; 8.CO.27.158; 8.CO.27.196; 8.CO.27.223; 8.CO.27.240; 8.CO.27.244; 8.CO.27.243; 8.CO.27.247; 8.CO.29.157; 8.CO.29.158; 8.CO.29.196; 8.CO.29.223; 8.CO.29.240; 8.CO.29.244; 8.CO.29.243; 8.CO.29.247; 8.CO.54.157; 8.CO.54.158; 8.CO.54.196; 8.CO.54.223; 8.CO.54.240; 8.CO.54.244; 8.CO.54.243; 8.CO.54.247; 8.CO.55.157; 8.CO.55.158; 8.CO.55.196; 8.CO.55.223; 8.CO.55.240; 8.CO.55.244; 8.CO.55.243; 8.CO.55.247; 8.CO.56.157; 8.CO.56.158; 8.CO.56.196; 8.CO.56.223; 8.CO.56.240; 8.CO.56.244; |

TABLE 100-continued

8.CO.56.243; 8.CO.56.247; 8.CO.157.157; 8.CO.157.158; 8.CO.157.196; 8.CO.157.223; 8.CO.157.240; 8.CO.157.244; 8.CO.157.243; 8.CO.157.247; 8.CO.196.157; 8.CO.196.158; 8.CO.196.196; 8.CO.196.223; 8.CO.196.240; 8.CO.196.244; 8.CO.196.243; 8.CO.196.247; 8.CO.223.157; 8.CO.223.158; 8.CO.223.196; 8.CO.223.223; 8.CO.223.240; 8.CO.223.244; 8.CO.223.243; 8.CO.223.247; 8.CO.240.157; 8.CO.240.158; 8.CO.240.196; 8.CO.240.223; 8.CO.240.240; 8.CO.240.244; 8.CO.240.243; 8.CO.240.247; 8.CO.244.157; 8.CO.244.158; 8.CO.244.196; 8.CO.244.223; 8.CO.244.240; 8.CO.244.244; 8.CO.244.243; 8.CO.244.247; 8.CO.247.157; 8.CO.247.158; 8.CO.247.196; 8.CO.247.223; 8.CO.247.240; 8.CO.247.244; 8.CO.247.243; 8.CO.247.247;

Prodrugs of 9.AH

9.AH.4.157; 9.AH.4.158; 9.AH.4.196; 9.AH.4.223; 9.AH.4.240; 9.AH.4.244; 9.AH.4.243; 9.AH.4.247; 9.AH.5.157; 9.AH.5.158; 9.AH.5.196; 9.AH.5.223; 9.AH.5.240; 9.AH.5.244; 9.AH.5.243; 9.AH.5.247; 9.AH.7.157; 9.AH.7.158; 9.AH.7.196; 9.AH.7.223; 9.AH.7.240; 9.AH.7.244; 9.AH.7.243; 9.AH.7.247; 9.AH.15.157; 9.AH.15.158; 9.AH.15.196; 9.AH.15.223; 9.AH.15.240; 9.AH.15.244; 9.AH.15.243; 9.AH.15.247; 9.AH.16.157; 9.AH.16.158; 9.AH.16.196; 9.AH.16.223; 9.AH.16.240; 9.AH.16.244; 9.AH.16.243; 9.AH.16.247; 9.AH.18.157; 9.AH.18.158; 9.AH.18.196; 9.AH.18.223; 9.AH.18.240; 9.AH.18.244; 9.AH.18.243; 9.AH.18.247; 9.AH.26.157; 9.AH.26.158; 9.AH.26.196; 9.AH.26.223; 9.AH.26.240; 9.AH.26.244; 9.AH.26.243; 9.AH.26.247; 9.AH.27.157; 9.AH.27.158; 9.AH.27.196; 9.AH.27.223; 9.AH.27.240; 9.AH.27.244; 9.AH.27.243; 9.AH.27.247; 9.AH.29.157; 9.AH.29.158; 9.AH.29.196; 9.AH.29.223; 9.AH.29.240; 9.AH.29.244; 9.AH.29.243; 9.AH.29.247; 9.AH.54.157; 9.AH.54.158; 9.AH.54.196; 9.AH.54.223; 9.AH.54.240; 9.AH.54.244; 9.AH.54.243; 9.AH.54.247; 9.AH.55.157; 9.AH.55.158; 9.AH.55.196; 9.AH.55.223; 9.AH.55.240; 9.AH.55.244; 9.AH.55.243; 9.AH.55.247; 9.AH.56.157; 9.AH.56.158; 9.AH.56.196; 9.AH.56.223; 9.AH.56.240; 9.AH.56.244; 9.AH.56.243; 9.AH.56.247; 9.AH.157.157; 9.AH.157.158; 9.AH.157.196; 9.AH.157.223; 9.AH.157.240; 9.AH.157.244; 9.AH.157.243; 9.AH.157.247; 9.AH.196.157; 9.AH.196.158; 9.AH.196.196; 9.AH.196.223; 9.AH.196.240; 9.AH.196.244; 9.AH.196.243; 9.AH.196.247; 9.AH.223.157; 9.AH.223.158; 9.AH.223.196; 9.AH.223.223; 9.AH.223.240; 9.AH.223.244; 9.AH.223.243; 9.AH.223.247; 9.AH.240.157; 9.AH.240.158; 9.AH.240.196; 9.AH.240.223; 9.AH.240.240; 9.AH.240.244; 9.AH.240.243; 9.AH.240.247; 9.AH.244.157; 9.AH.244.158; 9.AH.244.196; 9.AH.244.223; 9.AH.244.240; 9.AH.244.244; 9.AH.244.243; 9.AH.244.247; 9.AH.247.157; 9.AH.247.158; 9.AH.247.196; 9.AH.247.223; 9.AH.247.240; 9.AH.247.244; 9.AH.247.243; 9.AH.247.247;

Prodrugs of 9.AJ

9.AJ.4.157; 9.AJ.4.158; 9.AJ.4.196; 9.AJ.4.223; 9.AJ.4.240; 9.AJ.4.244; 9.AJ.4.243; 9.AJ.4.247; 9.AJ.5.157; 9.AJ.5.158; 9.AJ.5.196; 9.AJ.5.223; 9.AJ.5.240; 9.AJ.5.244; 9.AJ.5.243; 9.AJ.5.247; 9.AJ.7.157; 9.AJ.7.158; 9.AJ.7.196; 9.AJ.7.223; 9.AJ.7.240; 9.AJ.7.244; 9.AJ.7.243; 9.AJ.7.247; 9.AJ.15.157; 9.AJ.15.158; 9.AJ.15.196; 9.AJ.15.223; 9.AJ.15.240; 9.AJ.15.244; 9.AJ.15.243; 9.AJ.15.247; 9.AJ.16.157; 9.AJ.16.158; 9.AJ.16.196; 9.AJ.16.223; 9.AJ.16.240; 9.AJ.16.244; 9.AJ.16.243; 9.AJ.16.247; 9.AJ.18.157; 9.AJ.18.158; 9.AJ.18.196; 9.AJ.18.223; 9.AJ.18.240; 9.AJ.18.244; 9.AJ.18.243; 9.AJ.18.247; 9.AJ.26.157; 9.AJ.26.158; 9.AJ.26.196; 9.AJ.26.223; 9.AJ.26.240; 9.AJ.26.244; 9.AJ.26.243; 9.AJ.26.247; 9.AJ.27.157; 9.AJ.27.158; 9.AJ.27.196; 9.AJ.27.223; 9.AJ.27.240; 9.AJ.27.244; 9.AJ.27.243; 9.AJ.27.247; 9.AJ.29.157; 9.AJ.29.158; 9.AJ.29.196; 9.AJ.29.223; 9.AJ.29.240; 9.AJ.29.244; 9.AJ.29.243; 9.AJ.29.247; 9.AJ.54.157; 9.AJ.54.158; 9.AJ.54.196; 9.AJ.54.223; 9.AJ.54.240; 9.AJ.54.244; 9.AJ.54.243; 9.AJ.54.247; 9.AJ.55.157; 9.AJ.55.158; 9.AJ.55.196; 9.AJ.55.223; 9.AJ.55.240; 9.AJ.55.244; 9.AJ.55.243; 9.AJ.55.247; 9.AJ.56.157; 9.AJ.56.158; 9.AJ.56.196; 9.AJ.56.223; 9.AJ.56.240; 9.AJ.56.244; 9.AJ.56.243; 9.AJ.56.247; 9.AJ.157.157; 9.AJ.157.158; 9.AJ.157.196; 9.AJ.157.223; 9.AJ.157.240; 9.AJ.157.244; 9.AJ.157.243; 9.AJ.157.247; 9.AJ.196.157; 9.AJ.196.158; 9.AJ.196.196; 9.AJ.196.223; 9.AJ.196.240; 9.AJ.196.244; 9.AJ.196.243; 9.AJ.196.247; 9.AJ.223.157; 9.AJ.223.158; 9.AJ.223.196; 9.AJ.223.223; 9.AJ.223.240; 9.AJ.223.244; 9.AJ.223.243; 9.AJ.223.247; 9.AJ.240.157; 9.AJ.240.158; 9.AJ.240.196; 9.AJ.240.223; 9.AJ.240.240; 9.AJ.240.244; 9.AJ.240.243; 9.AJ.240.247; 9.AJ.244.157; 9.AJ.244.158; 9.AJ.244.196; 9.AJ.244.223; 9.AJ.244.240; 9.AJ.244.244; 9.AJ.244.243; 9.AJ.244.247; 9.AJ.247.157; 9.AJ.247.158; 9.AJ.247.196; 9.AJ.247.223; 9.AJ.247.240; 9.AJ.247.244; 9.AJ.247.243; 9.AJ.247.247;

Prodrugs of 9.AN

9.AN.4.157; 9.AN.4.158; 9.AN.4.196; 9.AN.4.223; 9.AN.4.240; 9.AN.4.244; 9.AN.4.243; 9.AN.4.247; 9.AN.5.157; 9.AN.5.158; 9.AN.5.196; 9.AN.5.223; 9.AN.5.240; 9.AN.5.244; 9.AN.5.243; 9.AN.5.247; 9.AN.7.157; 9.AN.7.158; 9.AN.7.196; 9.AN.7.223; 9.AN.7.240; 9.AN.7.244; 9.AN.7.243; 9.AN.7.247; 9.AN.15.157; 9.AN.15.158; 9.AN.15.196; 9.AN.15.223; 9.AN.15.240; 9.AN.15.244; 9.AN.15.243; 9.AN.15.247; 9.AN.16.157; 9.AN.16.158; 9.AN.16.196; 9.AN.16.223; 9.AN.16.240; 9.AN.16.244; 9.AN.16.243; 9.AN.16.247; 9.AN.18.157; 9.AN.18.158; 9.AN.18.196; 9.AN.18.223; 9.AN.18.240; 9.AN.18.244; 9.AN.18.243; 9.AN.18.247; 9.AN.26.157; 9.AN.26.158; 9.AN.26.196; 9.AN.26.223; 9.AN.26.240; 9.AN.26.244;

TABLE 100-continued

| |
|---|
| 9.AN.26.243; 9.AN.26.247; 9.AN.27.157; 9.AN.27.158; 9.AN.27.196; 9.AN.27.223; 9.AN.27.240; 9.AN.27.244; 9.AN.27.243; 9.AN.27.247; 9.AN.29.157; 9.AN.29.158; 9.AN.29.196; 9.AN.29.223; 9.AN.29.240; 9.AN.29.244; 9.AN.29.243; 9.AN.29.247; 9.AN.54.157; 9.AN.54.158; 9.AN.54.196; 9.AN.54.223; 9.AN.54.240; 9.AN.54.244; 9.AN.54.243; 9.AN.54.247; 9.AN.55.157; 9.AN.55.158; 9.AN.55.196; 9.AN.55.223; 9.AN.55.240; 9.AN.55.244; 9.AN.55.243; 9.AN.55.247; 9.AN.56.157; 9.AN.56.158; 9.AN.56.196; 9.AN.56.223; 9.AN.56.240; 9.AN.56.244; 9.AN.56.243; 9.AN.56.247; 9.AN.157.157; 9.AN.157.158; 9.AN.157.196; 9.AN.157.223; 9.AN.157.240; 9.AN.157.244; 9.AN.157.243; 9.AN.157.247; 9.AN.196.157; 9.AN.196.158; 9.AN.196.196; 9.AN.196.223; 9.AN.196.240; 9.AN.196.244; 9.AN.196.243; 9.AN.196.247; 9.AN.223.157; 9.AN.223.158; 9.AN.223.196; 9.AN.223.223; 9.AN.223.240; 9.AN.223.244; 9.AN.223.243; 9.AN.223.247; 9.AN.240.157; 9.AN.240.158; 9.AN.240.196; 9.AN.240.223; 9.AN.240.240; 9.AN.240.244; 9.AN.240.243; 9.AN.240.247; 9.AN.244.157; 9.AN.244.158; 9.AN.244.196; 9.AN.244.223; 9.AN.244.240; 9.AN.244.244; 9.AN.244.243; 9.AN.244.247; 9.AN.247.157; 9.AN.247.158; 9.AN.247.196; 9.AN.247.223; 9.AN.247.240; 9.AN.247.244; 9.AN.247.243; 9.AN.247.247; |
| Prodrugs of 9.AP |
| 9.AP.4.157; 9.AP.4.158; 9.AP.4.196; 9.AP.4.223; 9.AP.4.240; 9.AP.4.244; 9.AP.4.243; 9.AP.4.247; 9.AP.5.157; 9.AP.5.158; 9.AP.5.196; 9.AP.5.223; 9.AP.5.240; 9.AP.5.244; 9.AP.5.243; 9.AP.5.247; 9.AP.7.157; 9.AP.7.158; 9.AP.7.196; 9.AP.7.223; 9.AP.7.240; 9.AP.7.244; 9.AP.7.243; 9.AP.7.247; 9.AP.15.157; 9.AP.15.158; 9.AP.15.196; 9.AP.15.223; 9.AP.15.240; 9.AP.15.244; 9.AP.15.243; 9.AP.15.247; 9.AP.16.157; 9.AP.16.158; 9.AP.16.196; 9.AP.16.223; 9.AP.16.240; 9.AP.16.244; 9.AP.16.243; 9.AP.16.247; 9.AP.18.157; 9.AP.18.158; 9.AP.18.196; 9.AP.18.223; 9.AP.18.240; 9.AP.18.244; 9.AP.18.243; 9.AP.18.247; 9.AP.26.157; 9.AP.26.158; 9.AP.26.196; 9.AP.26.223; 9.AP.26.240; 9.AP.26.244; 9.AP.26.243; 9.AP.26.247; 9.AP.27.157; 9.AP.27.158; 9.AP.27.196; 9.AP.27.223; 9.AP.27.240; 9.AP.27.244; 9.AP.27.243; 9.AP.27.247; 9.AP.29.157; 9.AP.29.158; 9.AP.29.196; 9.AP.29.223; 9.AP.29.240; 9.AP.29.244; 9.AP.29.243; 9.AP.29.247; 9.AP.54.157; 9.AP.54.158; 9.AP.54.196; 9.AP.54.223; 9.AP.54.240; 9.AP.54.244; 9.AP.54.243; 9.AP.54.247; 9.AP.55.157; 9.AP.55.158; 9.AP.55.196; 9.AP.55.223; 9.AP.55.240; 9.AP.55.244; 9.AP.55.243; 9.AP.55.247; 9.AP.56.157; 9.AP.56.158; 9.AP.56.196; 9.AP.56.223; 9.AP.56.240; 9.AP.56.244; 9.AP.56.243; 9.AP.56.247; 9.AP.157.157; 9.AP.157.158; 9.AP.157.196; 9.AP.157.223; 9.AP.157.240; 9.AP.157.244; 9.AP.157.243; 9.AP.157.247; 9.AP.196.157; 9.AP.196.158; 9.AP.196.196; 9.AP.196.223; 9.AP.196.240; 9.AP.196.244; 9.AP.196.243; 9.AP.196.247; 9.AP.223.157; 9.AP.223.158; 9.AP.223.196; 9.AP.223.223; 9.AP.223.240; 9.AP.223.244; 9.AP.223.243; 9.AP.223.247; 9.AP.240.157; 9.AP.240.158; 9.AP.240.196; 9.AP.240.223; 9.AP.240.240; 9.AP.240.244; 9.AP.240.243; 9.AP.240.247; 9.AP.244.157; 9.AP.244.158; 9.AP.244.196; 9.AP.244.223; 9.AP.244.240; 9.AP.244.244; 9.AP.244.243; 9.AP.244.247; 9.AP.247.157; 9.AP.247.158; 9.AP.247.196; 9.AP.247.223; 9.AP.247.240; 9.AP.247.244; 9.AP.247.243; 9.AP.247.247; |
| Prodrugs of 9.AZ |
| 9.AZ.4.157; 9.AZ.4.158; 9.AZ.4.196; 9.AZ.4.223; 9.AZ.4.240; 9.AZ.4.244; 9.AZ.4.243; 9.AZ.4.247; 9.AZ.5.157; 9.AZ.5.158; 9.AZ.5.196; 9.AZ.5.223; 9.AZ.5.240; 9.AZ.5.244; 9.AZ.5.243; 9.AZ.5.247; 9.AZ.7.157; 9.AZ.7.158; 9.AZ.7.196; 9.AZ.7.223; 9.AZ.7.240; 9.AZ.7.244; 9.AZ.7.243; 9.AZ.7.247; 9.AZ.15.157; 9.AZ.15.158; 9.AZ.15.196; 9.AZ.15.223; 9.AZ.15.240; 9.AZ.15.244; 9.AZ.15.243; 9.AZ.15.247; 9.AZ.16.157; 9.AZ.16.158; 9.AZ.16.196; 9.AZ.16.223; 9.AZ.16.240; 9.AZ.16.244; 9.AZ.16.243; 9.AZ.16.247; 9.AZ.18.157; 9.AZ.18.158; 9.AZ.18.196; 9.AZ.18.223; 9.AZ.18.240; 9.AZ.18.244; 9.AZ.18.243; 9.AZ.18.247; 9.AZ.26.157; 9.AZ.26.158; 9.AZ.26.196; 9.AZ.26.223; 9.AZ.26.240; 9.AZ.26.244; 9.AZ.26.243; 9.AZ.26.247; 9.AZ.27.157; 9.AZ.27.158; 9.AZ.27.196; 9.AZ.27.223; 9.AZ.27.240; 9.AZ.27.244; 9.AZ.27.243; 9.AZ.27.247; 9.AZ.29.157; 9.AZ.29.158; 9.AZ.29.196; 9.AZ.29.223; 9.AZ.29.240; 9.AZ.29.244; 9.AZ.29.243; 9.AZ.29.247; 9.AZ.54.157; 9.AZ.54.158; 9.AZ.54.196; 9.AZ.54.223; 9.AZ.54.240; 9.AZ.54.244; 9.AZ.54.243; 9.AZ.54.247; 9.AZ.55.157; 9.AZ.55.158; 9.AZ.55.196; 9.AZ.55.223; 9.AZ.55.240; 9.AZ.55.244; 9.AZ.55.243; 9.AZ.55.247; 9.AZ.56.157; 9.AZ.56.158; 9.AZ.56.196; 9.AZ.56.223; 9.AZ.56.240; 9.AZ.56.244; 9.AZ.56.243; 9.AZ.56.247; 9.AZ.157.157; 9.AZ.157.158; 9.AZ.157.196; 9.AZ.157.223; 9.AZ.157.240; 9.AZ.157.244; 9.AZ.157.243; 9.AZ.157.247; 9.AZ.196.157; 9.AZ.196.158; 9.AZ.196.196; 9.AZ.196.223; 9.AZ.196.240; 9.AZ.196.244; 9.AZ.196.243; 9.AZ.196.247; 9.AZ.223.157; 9.AZ.223.158; 9.AZ.223.196; 9.AZ.223.223; 9.AZ.223.240; 9.AZ.223.244; 9.AZ.223.243; 9.AZ.223.247; 9.AZ.240.157; 9.AZ.240.158; 9.AZ.240.196; 9.AZ.240.223; 9.AZ.240.240; 9.AZ.240.244; 9.AZ.240.243; 9.AZ.240.247; 9.AZ.244.157; 9.AZ.244.158; 9.AZ.244.196; 9.AZ.244.223; 9.AZ.244.240; 9.AZ.244.244; 9.AZ.244.243; 9.AZ.244.247; 9.AZ.247.157; 9.AZ.247.158; 9.AZ.247.196; 9.AZ.247.223; 9.AZ.247.240; 9.AZ.247.244; 9.AZ.247.243; 9.AZ.247.247; |

TABLE 100-continued

| Prodrugs of 9.BF |
|---|
| 9.BF.4.157; 9.BF.4.158; 9.BF.4.196; 9.BF.4.223; 9.BF.4.240; 9.BF.4.244; 9.BF.4.243; 9.BF.4.247; 9.BF.5.157; 9.BF.5.158; 9.BF.5.196; 9.BF.5.223; 9.BF.5.240; 9.BF.5.244; 9.BF.5.243; 9.BF.5.247; 9.BF.7.157; 9.BF.7.158; 9.BF.7.196; 9.BF.7.223; 9.BF.7.240; 9.BF.7.244; 9.BF.7.243; 9.BF.7.247; 9.BF.15.157; 9.BF.15.158; 9.BF.15.196; 9.BF.15.223; 9.BF.15.240; 9.BF.15.244; 9.BF.15.243; 9.BF.15.247; 9.BF.16.157; 9.BF.16.158; 9.BF.16.196; 9.BF.16.223; 9.BF.16.240; 9.BF.16.244; 9.BF.16.243; 9.BF.16.247; 9.BF.18.157; 9.BF.18.158; 9.BF.18.196; 9.BF.18.223; 9.BF.18.240; 9.BF.18.244; 9.BF.18.243; 9.BF.18.247; 9.BF.26.157; 9.BF.26.158; 9.BF.26.196; 9.BF.26.223; 9.BF.26.240; 9.BF.26.244; 9.BF.26.243; 9.BF.26.247; 9.BF.27.157; 9.BF.27.158; 9.BF.27.196; 9.BF.27.223; 9.BF.27.240; 9.BF.27.244; 9.BF.27.243; 9.BF.27.247; 9.BF.29.157; 9.BF.29.158; 9.BF.29.196; 9.BF.29.223; 9.BF.29.240; 9.BF.29.244; 9.BF.29.243; 9.BF.29.247; 9.BF.54.157; 9.BF.54.158; 9.BF.54.196; 9.BF.54.223; 9.BF.54.240; 9.BF.54.244; 9.BF.54.243; 9.BF.54.247; 9.BF.55.157; 9.BF.55.158; 9.BF.55.196; 9.BF.55.223; 9.BF.55.240; 9.BF.55.244; 9.BF.55.243; 9.BF.55.247; 9.BF.56.157; 9.BF.56.158; 9.BF.56.196; 9.BF.56.223; 9.BF.56.240; 9.BF.56.244; 9.BF.56.243; 9.BF.56.247; 9.BF.157.157; 9.BF.157.158; 9.BF.157.196; 9.BF.157.223; 9.BF.157.240; 9.BF.157.244; 9.BF.157.243; 9.BF.157.247; 9.BF.196.157; 9.BF.196.158; 9.BF.196.196; 9.BF.196.223; 9.BF.196.240; 9.BF.196.244; 9.BF.196.243; 9.BF.196.247; 9.BF.223.157; 9.BF.223.158; 9.BF.223.196; 9.BF.223.223; 9.BF.223.240; 9.BF.223.244; 9.BF.223.243; 9.BF.223.247; 9.BF.240.157; 9.BF.240.158; 9.BF.240.196; 9.BF.240.223; 9.BF.240.240; 9.BF.240.244; 9.BF.240.243; 9.BF.240.247; 9.BF.244.157; 9.BF.244.158; 9.BF.244.196; 9.BF.244.223; 9.BF.244.240; 9.BF.244.244; 9.BF.244.243; 9.BF.244.247; 9.BF.247.157; 9.BF.247.158; 9.BF.247.196; 9.BF.247.223; 9.BF.247.240; 9.BF.247.244; 9.BF.247.243; 9.BF.247.247; |
| Prodrugs of 9.CI |
| 9.CI.4.157; 9.CI.4.158; 9.CI.4.196; 9.CI.4.223; 9.CI.4.240; 9.CI.4.244; 9.CI.4.243; 9.CI.4.247; 9.CI.5.157; 9.CI.5.158; 9.CI.5.196; 9.CI.5.223; 9.CI.5.240; 9.CI.5.244; 9.CI.5.243; 9.CI.5.247; 9.CI.7.157; 9.CI.7.158; 9.CI.7.196; 9.CI.7.223; 9.CI.7.240; 9.CI.7.244; 9.CI.7.243; 9.CI.7.247; 9.CI.15.157; 9.CI.15.158; 9.CI.15.196; 9.CI.15.223; 9.CI.15.240; 9.CI.15.244; 9.CI.15.243; 9.CI.15.247; 9.CI.16.157; 9.CI.16.158; 9.CI.16.196; 9.CI.16.223; 9.CI.16.240; 9.CI.16.244; 9.CI.16.243; 9.CI.16.247; 9.CI.18.157; 9.CI.18.158; 9.CI.18.196; 9.CI.18.223; 9.CI.18.240; 9.CI.18.244; 9.CI.18.243; 9.CI.18.247; 9.CI.26.157; 9.CI.26.158; 9.CI.26.196; 9.CI.26.223; 9.CI.26.240; 9.CI.26.244; 9.CI.26.243; 9.CI.26.247; 9.CI.27.157; 9.CI.27.158; 9.CI.27.196; 9.CI.27.223; 9.CI.27.240; 9.CI.27.244; 9.CI.27.243; 9.CI.27.247; 9.CI.29.157; 9.CI.29.158; 9.CI.29.196; 9.CI.29.223; 9.CI.29.240; 9.CI.29.244; 9.CI.29.243; 9.CI.29.247; 9.CI.54.157; 9.CI.54.158; 9.CI.54.196; 9.CI.54.223; 9.CI.54.240; 9.CI.54.244; 9.CI.54.243; 9.CI.54.247; 9.CI.55.157; 9.CI.55.158; 9.CI.55.196; 9.CI.55.223; 9.CI.55.240; 9.CI.55.244; 9.CI.55.243; 9.CI.55.247; 9.CI.56.157; 9.CI.56.158; 9.CI.56.196; 9.CI.56.223; 9.CI.56.240; 9.CI.56.244; 9.CI.56.243; 9.CI.56.247; 9.CI.157.157; 9.CI.157.158; 9.CI.157.196; 9.CI.157.223; 9.CI.157.240; 9.CI.157.244; 9.CI.157.243; 9.CI.157.247; 9.CI.196.157; 9.CI.196.158; 9.CI.196.196; 9.CI.196.223; 9.CI.196.240; 9.CI.196.244; 9.CI.196.243; 9.CI.196.247; 9.CI.223.157; 9.CI.223.158; 9.CI.223.196; 9.CI.223.223; 9.CI.223.240; 9.CI.223.244; 9.CI.223.243; 9.CI.223.247; 9.CI.240.157; 9.CI.240.158; 9.CI.240.196; 9.CI.240.223; 9.CI.240.240; 9.CI.240.244; 9.CI.240.243; 9.CI.240.247; 9.CI.244.157; 9.CI.244.158; 9.CI.244.196; 9.CI.244.223; 9.CI.244.240; 9.CI.244.244; 9.CI.244.243; 9.CI.244.247; 9.CI.247.157; 9.CI.247.158; 9.CI.247.196; 9.CI.247.223; 9.CI.247.240; 9.CI.247.244; 9.CI.247.243; 9.CI.247.247; |
| Prodrugs of 9.CO |
| 9.CO.4.157; 9.CO.4.158; 9.CO.4.196; 9.CO.4.223; 9.CO.4.240; 9.CO.4.244; 9.CO.4.243; 9.CO.4.247; 9.CO.5.157; 9.CO.5.158; 9.CO.5.196; 9.CO.5.223; 9.CO.5.240; 9.CO.5.244; 9.CO.5.243; 9.CO.5.247; 9.CO.7.157; 9.CO.7.158; 9.CO.7.196; 9.CO.7.223; 9.CO.7.240; 9.CO.7.244; 9.CO.7.243; 9.CO.7.247; 9.CO.15.157; 9.CO.15.158; 9.CO.15.196; 9.CO.15.223; 9.CO.15.240; 9.CO.15.244; 9.CO.15.243; 9.CO.15.247; 9.CO.16.157; 9.CO.16.158; 9.CO.16.196; 9.CO.16.223; 9.CO.16.240; 9.CO.16.244; 9.CO.16.243; 9.CO.16.247; 9.CO.18.157; 9.CO.18.158; 9.CO.18.196; 9.CO.18.223; 9.CO.18.240; 9.CO.18.244; 9.CO.18.243; 9.CO.18.247; 9.CO.26.157; 9.CO.26.158; 9.CO.26.196; 9.CO.26.223; 9.CO.26.240; 9.CO.26.244; 9.CO.26.243; 9.CO.26.247; 9.CO.27.157; 9.CO.27.158; 9.CO.27.196; 9.CO.27.223; 9.CO.27.240; 9.CO.27.244; 9.CO.27.243; 9.CO.27.247; 9.CO.29.157; 9.CO.29.158; 9.CO.29.196; 9.CO.29.223; 9.CO.29.240; 9.CO.29.244; 9.CO.29.243; 9.CO.29.247; 9.CO.54.157; 9.CO.54.158; 9.CO.54.196; 9.CO.54.223; 9.CO.54.240; 9.CO.54.244; 9.CO.54.243; 9.CO.54.247; 9.CO.55.157; 9.CO.55.158; 9.CO.55.196; 9.CO.55.223; 9.CO.55.240; 9.CO.55.244; 9.CO.55.243; 9.CO.55.247; 9.CO.56.157; 9.CO.56.158; 9.CO.56.196; 9.CO.56.223; 9.CO.56.240; 9.CO.56.244; 9.CO.56.243; 9.CO.56.247; 9.CO.157.157; 9.CO.157.158; 9.CO.157.196; 9.CO.157.223; 9.CO.157.240; 9.CO.157.244; 9.CO.157.243; 9.CO.157.247; |

TABLE 100-continued

| |
|---|
| 9.CO.196.157; 9.CO.196.158; 9.CO.196.196; 9.CO.196.223; 9.CO.196.240; 9.CO.196.244; 9.CO.196.243; 9.CO.196.247; 9.CO.223.157; 9.CO.223.158; 9.CO.223.196; 9.CO.223.223; 9.CO.223.240; 9.CO.223.244; 9.CO.223.243; 9.CO.223.247; 9.CO.240.157; 9.CO.240.158; 9.CO.240.196; 9.CO.240.223; 9.CO.240.240; 9.CO.240.244; 9.CO.240.243; 9.CO.240.247; 9.CO.244.157; 9.CO.244.158; 9.CO.244.196; 9.CO.244.223; 9.CO.244.240; 9.CO.244.244; 9.CO.244.243; 9.CO.244.247; 9.CO.247.157; 9.CO.247.158; 9.CO.247.196; 9.CO.247.223; 9.CO.247.240; 9.CO.247.244; 9.CO.247.243; 9.CO.247.247; |
| Prodrugs of 10.AH |
| 10.AH.4.157; 10.AH.4.158; 10.AH.4.196; 10.AH.4.223; 10.AH.4.240; 10.AH.4.244; 10.AH.4.243; 10.AH.4.247; 10.AH.5.157; 10.AH.5.158; 10.AH.5.196; 10.AH.5.223; 10.AH.5.240; 10.AH.5.244; 10.AH.5.243; 10.AH.5.247; 10.AH.7.157; 10.AH.7.158; 10.AH.7.196; 10.AH.7.223; 10.AH.7.240; 10.AH.7.244; 10.AH.7.243; 10.AH.7.247; 10.AH.15.157; 10.AH.15.158; 10.AH.15.196; 10.AH.15.223; 10.AH.15.240; 10.AH.15.244; 10.AH.15.243; 10.AH.15.247; 10.AH.16.157; 10.AH.16.158; 10.AH.16.196; 10.AH.16.223; 10.AH.16.240; 10.AH.16.244; 10.AH.16.243; 10.AH.16.247; 10.AH.18.157; 10.AH.18.158; 10.AH.18.196; 10.AH.18.223; 10.AH.18.240; 10.AH.18.244; 10.AH.18.243; 10.AH.18.247; 10.AH.26.157; 10.AH.26.158; 10.AH.26.196; 10.AH.26.223; 10.AH.26.240; 10.AH.26.244; 10.AH.26.243; 10.AH.26.247; 10.AH.27.157; 10.AH.27.158; 10.AH.27.196; 10.AH.27.223; 10.AH.27.240; 10.AH.27.244; 10.AH.27.243; 10.AH.27.247; 10.AH.29.157; 10.AH.29.158; 10.AH.29.196; 10.AH.29.223; 10.AH.29.240; 10.AH.29.244; 10.AH.29.243; 10.AH.29.247; 10.AH.54.157; 10.AH.54.158; 10.AH.54.196; 10.AH.54.223; 10.AH.54.240; 10.AH.54.244; 10.AH.54.243; 10.AH.54.247; 10.AH.55.157; 10.AH.55.158; 10.AH.55.196; 10.AH.55.223; 10.AH.55.240; 10.AH.55.244; 10.AH.55.243; 10.AH.55.247; 10.AH.56.157; 10.AH.56.158; 10.AH.56.196; 10.AH.56.223; 10.AH.56.240; 10.AH.56.244; 10.AH.56.243; 10.AH.56.247; 10.AH.157.157; 10.AH.157.158; 10.AH.157.196; 10.AH.157.223; 10.AH.157.240; 10.AH.157.244; 10.AH.157.243; 10.AH.157.247; 10.AH.196.157; 10.AH.196.158; 10.AH.196.196; 10.AH.196.223; 10.AH.196.240; 10.AH.196.244; 10.AH.196.243; 10.AH.196.247; 10.AH.223.157; 10.AH.223.158; 10.AH.223.196; 10.AH.223.223; 10.AH.223.240; 10.AH.223.244; 10.AH.223.243; 10.AH.223.247; 10.AH.240.157; 10.AH.240.158; 10.AH.240.196; 10.AH.240.223; 10.AH.240.240; 10.AH.240.244; 10.AH.240.243; 10.AH.240.247; 10.AH.244.157; 10.AH.244.158; 10.AH.244.196; 10.AH.244.223; 10.AH.244.240; 10.AH.244.244; 10.AH.244.243; 10.AH.244.247; 10.AH.247.157; 10.AH.247.158; 10.AH.247.196; 10.AH.247.223; 10.AH.247.240; 10.AH.247.244; 10.AH.247.243; 10.AH.247.247; |
| Prodrugs of 10.AJ |
| 10.AJ.4.157; 10.AJ.4.158; 10.AJ.4.196; 10.AJ.4.223; 10.AJ.4.240; 10.AJ.4.244; 10.AJ.4.243; 10.AJ.4.247; 10.AJ.5.157; 10.AJ.5.158; 10.AJ.5.196; 10.AJ.5.223; 10.AJ.5.240; 10.AJ.5.244; 10.AJ.5.243; 10.AJ.5.247; 10.AJ.7.157; 10.AJ.7.158; 10.AJ.7.196; 10.AJ.7.223; 10.AJ.7.240; 10.AJ.7.244; 10.AJ.7.243; 10.AJ.7.247; 10.AJ.15.157; 10.AJ.15.158; 10.AJ.15.196; 10.AJ.15.223; 10.AJ.15.240; 10.AJ.15.244; 10.AJ.15.243; 10.AJ.15.247; 10.AJ.16.157; 10.AJ.16.158; 10.AJ.16.196; 10.AJ.16.223; 10.AJ.16.240; 10.AJ.16.244; 10.AJ.16.243; 10.AJ.16.247; 10.AJ.18.157; 10.AJ.18.158; 10.AJ.18.196; 10.AJ.18.223; 10.AJ.18.240; 10.AJ.18.244; 10.AJ.18.243; 10.AJ.18.247; 10.AJ.26.157; 10.AJ.26.158; 10.AJ.26.196; 10.AJ.26.223; 10.AJ.26.240; 10.AJ.26.244; 10.AJ.26.243; 10.AJ.26.247; 10.AJ.27.157; 10.AJ.27.158; 10.AJ.27.196; 10.AJ.27.223; 10.AJ.27.240; 10.AJ.27.244; 10.AJ.27.243; 10.AJ.27.247; 10.AJ.29.157; 10.AJ.29.158; 10.AJ.29.196; 10.AJ.29.223; 10.AJ.29.240; 10.AJ.29.244; 10.AJ.29.243; 10.AJ.29.247; 10.AJ.54.157; 10.AJ.54.158; 10.AJ.54.196; 10.AJ.54.223; 10.AJ.54.240; 10.AJ.54.244; 10.AJ.54.243; 10.AJ.54.247; 10.AJ.55.157; 10.AJ.55.158; 10.AJ.55.196; 10.AJ.55.223; 10.AJ.55.240; 10.AJ.55.244; 10.AJ.55.243; 10.AJ.55.247; 10.AJ.56.157; 10.AJ.56.158; 10.AJ.56.196; 10.AJ.56.223; 10.AJ.56.240; 10.AJ.56.244; 10.AJ.56.243; 10.AJ.56.247; 10.AJ.157.157; 10.AJ.157.158; 10.AJ.157.196; 10.AJ.157.223; 10.AJ.157.240; 10.AJ.157.244; 10.AJ.157.243; 10.AJ.157.247; 10.AJ.196.157; 10.AJ.196.158; 10.AJ.196.196; 10.AJ.196.223; 10.AJ.196.240; 10.AJ.196.244; 10.AJ.196.243; 10.AJ.196.247; 10.AJ.223.157; 10.AJ.223.158; 10.AJ.223.196; 10.AJ.223.223; 10.AJ.223.240; 10.AJ.223.244; 10.AJ.223.243; 10.AJ.223.247; 10.AJ.240.157; 10.AJ.240.158; 10.AJ.240.196; 10.AJ.240.223; 10.AJ.240.240; 10.AJ.240.244; 10.AJ.240.243; 10.AJ.240.247; 10.AJ.244.157; 10.AJ.244.158; 10.AJ.244.196; 10.AJ.244.223; 10.AJ.244.240; 10.AJ.244.244; 10.AJ.244.243; 10.AJ.244.247; 10.AJ.247.157; 10.AJ.247.158; 10.AJ.247.196; 10.AJ.247.223; 10.AJ.247.240; 10.AJ.247.244; 10.AJ.247.243; 10.AJ.247.247; |
| Prodrugs of 10.AN |
| 10.AN.4.157; 10.AN.4.158; 10.AN.4.196; 10.AN.4.223; 10.AN.4.240; 10.AN.4.244; 10.AN.4.243; 10.AN.4.247; 10.AN.5.157; 10.AN.5.158; 10.AN.5.196; 10.AN.5.223; 10.AN.5.240; 10.AN.5.244; 10.AN.5.243; 10.AN.5.247; 10.AN.7.157; 10.AN.7.158; 10.AN.7.196; 10.AN.7.223; 10.AN.7.240; 10.AN.7.244; 10.AN.7.243; 10.AN.7.247; 10.AN.15.157; |

TABLE 100-continued

10.AN.15.158; 10.AN.15.196; 10.AN.15.223; 10.AN.15.240; 10.AN.15.244; 10.AN.15.243; 10.AN.15.247; 10.AN.16.157; 10.AN.16.158; 10.AN.16.196; 10.AN.16.223; 10.AN.16.240; 10.AN.16.244; 10.AN.16.243; 10.AN.16.247; 10.AN.18.157; 10.AN.18.158; 10.AN.18.196; 10.AN.18.223; 10.AN.18.240; 10.AN.18.244; 10.AN.18.243; 10.AN.18.247; 10.AN.26.157; 10.AN.26.158; 10.AN.26.196; 10.AN.26.223; 10.AN.26.240; 10.AN.26.244; 10.AN.26.243; 10.AN.26.247; 10.AN.27.157; 10.AN.27.158; 10.AN.27.196; 10.AN.27.223; 10.AN.27.240; 10.AN.27.244; 10.AN.27.243; 10.AN.27.247; 10.AN.29.157; 10.AN.29.158; 10.AN.29.196; 10.AN.29.223; 10.AN.29.240; 10.AN.29.244; 10.AN.29.243; 10.AN.29.247; 10.AN.54.157; 10.AN.54.158; 10.AN.54.196; 10.AN.54.223; 10.AN.54.240; 10.AN.54.244; 10.AN.54.243; 10.AN.54.247; 10.AN.55.157; 10.AN.55.158; 10.AN.55.196; 10.AN.55.223; 10.AN.55.240; 10.AN.55.244; 10.AN.55.243; 10.AN.55.247; 10.AN.56.157; 10.AN.56.158; 10.AN.56.196; 10.AN.56.223; 10.AN.56.240; 10.AN.56.244; 10.AN.56.243; 10.AN.56.247; 10.AN.157.157; 10.AN.157.158; 10.AN.157.196; 10.AN.157.223; 10.AN.157.240; 10.AN.157.244; 10.AN.157.243; 10.AN.157.247; 10.AN.196.157; 10.AN.196.158; 10.AN.196.196; 10.AN.196.223; 10.AN.196.240; 10.AN.196.244; 10.AN.196.243; 10.AN.196.247; 10.AN.223.157; 10.AN.223.158; 10.AN.223.196; 10.AN.223.223; 10.AN.223.240; 10.AN.223.244; 10.AN.223.243; 10.AN.223.247; 10.AN.240.157; 10.AN.240.158; 10.AN.240.196; 10.AN.240.223; 10.AN.240.240; 10.AN.240.244; 10.AN.240.243; 10.AN.240.247; 10.AN.244.157; 10.AN.244.158; 10.AN.244.196; 10.AN.244.223; 10.AN.244.240; 10.AN.244.244; 10.AN.244.243; 10.AN.244.247; 10.AN.247.157; 10.AN.247.158; 10.AN.247.196; 10.AN.247.223; 10.AN.247.240; 10.AN.247.244; 10.AN.247.243; 10.AN.247.247;

Prodrugs of 10.AP

10.AP.4.157; 10.AP.4.158; 10.AP.4.196; 10.AP.4.223; 10.AP.4.240; 10.AP.4.244; 10.AP.4.243; 10.AP.4.247; 10.AP.5.157; 10.AP.5.158; 10.AP.5.196; 10.AP.5.223; 10.AP.5.240; 10.AP.5.244; 10.AP.5.243; 10.AP.5.247; 10.AP.7.157; 10.AP.7.158; 10.AP.7.196; 10.AP.7.223; 10.AP.7.240; 10.AP.7.244; 10.AP.7.243; 10.AP.7.247; 10.AP.15.157; 10.AP.15.158; 10.AP.15.196; 10.AP.15.223; 10.AP.15.240; 10.AP.15.244; 10.AP.15.243; 10.AP.15.247; 10.AP.16.157; 10.AP.16.158; 10.AP.16.196; 10.AP.16.223; 10.AP.16.240; 10.AP.16.244; 10.AP.16.243; 10.AP.16.247; 10.AP.18.157; 10.AP.18.158; 10.AP.18.196; 10.AP.18.223; 10.AP.18.240; 10.AP.18.244; 10.AP.18.243; 10.AP.18.247; 10.AP.26.157; 10.AP.26.158; 10.AP.26.196; 10.AP.26.223; 10.AP.26.240; 10.AP.26.244; 10.AP.26.243; 10.AP.26.247; 10.AP.27.157; 10.AP.27.158; 10.AP.27.196; 10.AP.27.223; 10.AP.27.240; 10.AP.27.244; 10.AP.27.243; 10.AP.27.247; 10.AP.29.157; 10.AP.29.158; 10.AP.29.196; 10.AP.29.223; 10.AP.29.240; 10.AP.29.244; 10.AP.29.243; 10.AP.29.247; 10.AP.54.157; 10.AP.54.158; 10.AP.54.196; 10.AP.54.223; 10.AP.54.240; 10.AP.54.244; 10.AP.54.243; 10.AP.54.247; 10.AP.55.157; 10.AP.55.158; 10.AP.55.196; 10.AP.55.223; 10.AP.55.240; 10.AP.55.244; 10.AP.55.243; 10.AP.55.247; 10.AP.56.157; 10.AP.56.158; 10.AP.56.196; 10.AP.56.223; 10.AP.56.240; 10.AP.56.244; 10.AP.56.243; 10.AP.56.247; 10.AP.157.157; 10.AP.157.158; 10.AP.157.196; 10.AP.157.223; 10.AP.157.240; 10.AP.157.244; 10.AP.157.243; 10.AP.157.247; 10.AP.196.157; 10.AP.196.158; 10.AP.196.196; 10.AP.196.223; 10.AP.196.240; 10.AP.196.244; 10.AP.196.243; 10.AP.196.247; 10.AP.223.157; 10.AP.223.158; 10.AP.223.196; 10.AP.223.223; 10.AP.223.240; 10.AP.223.244; 10.AP.223.243; 10.AP.223.247; 10.AP.240.157; 10.AP.240.158; 10.AP.240.196; 10.AP.240.223; 10.AP.240.240; 10.AP.240.244; 10.AP.240.243; 10.AP.240.247; 10.AP.244.157; 10.AP.244.158; 10.AP.244.196; 10.AP.244.223; 10.AP.244.240; 10.AP.244.244; 10.AP.244.243; 10.AP.244.247; 10.AP.247.157; 10.AP.247.158; 10.AP.247.196; 10.AP.247.223; 10.AP.247.240; 10.AP.247.244; 10.AP.247.243; 10.AP.247.247;

Prodrugs of 10.AZ

10.AZ.4.157; 10.AZ.4.158; 10.AZ.4.196; 10.AZ.4.223; 10.AZ.4.240; 10.AZ.4.244; 10.AZ.4.243; 10.AZ.4.247; 10.AZ.5.157; 10.AZ.5.158; 10.AZ.5.196; 10.AZ.5.223; 10.AZ.5.240; 10.AZ.5.244; 10.AZ.5.243; 10.AZ.5.247; 10.AZ.7.157; 10.AZ.7.158; 10.AZ.7.196; 10.AZ.7.223; 10.AZ.7.240; 10.AZ.7.244; 10.AZ.7.243; 10.AZ.7.247; 10.AZ.15.157; 10.AZ.15.158; 10.AZ.15.196; 10.AZ.15.223; 10.AZ.15.240; 10.AZ.15.244; 10.AZ.15.243; 10.AZ.15.247; 10.AZ.16.157; 10.AZ.16.158; 10.AZ.16.196; 10.AZ.16.223; 10.AZ.16.240; 10.AZ.16.244; 10.AZ.16.243; 10.AZ.16.247; 10.AZ.18.157; 10.AZ.18.158; 10.AZ.18.196; 10.AZ.18.223; 10.AZ.18.240; 10.AZ.18.244; 10.AZ.18.243; 10.AZ.18.247; 10.AZ.26.157; 10.AZ.26.158; 10.AZ.26.196; 10.AZ.26.223; 10.AZ.26.240; 10.AZ.26.244; 10.AZ.26.243; 10.AZ.26.247; 10.AZ.27.157; 10.AZ.27.158; 10.AZ.27.196; 10.AZ.27.223; 10.AZ.27.240; 10.AZ.27.244; 10.AZ.27.243; 10.AZ.27.247; 10.AZ.29.157; 10.AZ.29.158; 10.AZ.29.196; 10.AZ.29.223; 10.AZ.29.240; 10.AZ.29.244; 10.AZ.29.243; 10.AZ.29.247; 10.AZ.54.157; 10.AZ.54.158; 10.AZ.54.196; 10.AZ.54.223; 10.AZ.54.240; 10.AZ.54.244; 10.AZ.54.243; 10.AZ.54.247; 10.AZ.55.157; 10.AZ.55.158; 10.AZ.55.196; 10.AZ.55.223; 10.AZ.55.240; 10.AZ.55.244; 10.AZ.55.243; 10.AZ.55.247; 10.AZ.56.157; 10.AZ.56.158; 10.AZ.56.196; 10.AZ.56.223; 10.AZ.56.240; 10.AZ.56.244; 10.AZ.56.243;

TABLE 100-continued

| |
|---|
| 10.AZ.56.247; 10.AZ.157.157; 10.AZ.157.158; 10.AZ.157.196; 10.AZ.157.223; 10.AZ.157.240; 10.AZ.157.244; 10.AZ.157.243; 10.AZ.157.247; 10.AZ.196.157; 10.AZ.196.158; 10.AZ.196.196; 10.AZ.196.223; 10.AZ.196.240; 10.AZ.196.244; 10.AZ.196.243; 10.AZ.196.247; 10.AZ.223.157; 10.AZ.223.158; 10.AZ.223.196; 10.AZ.223.223; 10.AZ.223.240; 10.AZ.223.244; 10.AZ.223.243; 10.AZ.223.247; 10.AZ.240.157; 10.AZ.240.158; 10.AZ.240.196; 10.AZ.240.223; 10.AZ.240.240; 10.AZ.240.244; 10.AZ.240.243; 10.AZ.240.247; 10.AZ.244.157; 10.AZ.244.158; 10.AZ.244.196; 10.AZ.244.223; 10.AZ.244.240; 10.AZ.244.244; 10.AZ.244.243; 10.AZ.244.247; 10.AZ.247.157; 10.AZ.247.158; 10.AZ.247.196; 10.AZ.247.223; 10.AZ.247.240; 10.AZ.247.244; 10.AZ.247.243; 10.AZ.247.247; |
| Prodrugs of 10.BF |
| 10.BF.4.157; 10.BF.4.158; 10.BF.4.196; 10.BF.4.223; 10.BF.4.240; 10.BF.4.244; 10.BF.4.243; 10.BF.4.247; 10.BF.5.157; 10.BF.5.158; 10.BF.5.196; 10.BF.5.223; 10.BF.5.240; 10.BF.5.244; 10.BF.5.243; 10.BF.5.247; 10.BF.7.157; 10.BF.7.158; 10.BF.7.196; 10.BF.7.223; 10.BF.7.240; 10.BF.7.244; 10.BF.7.243; 10.BF.7.247; 10.BF.15.157; 10.BF.15.158; 10.BF.15.196; 10.BF.15.223; 10.BF.15.240; 10.BF.15.244; 10.BF.15.243; 10.BF.15.247; 10.BF.16.157; 10.BF.16.158; 10.BF.16.196; 10.BF.16.223; 10.BF.16.240; 10.BF.16.244; 10.BF.16.243; 10.BF.16.247; 10.BF.18.157; 10.BF.18.158; 10.BF.18.196; 10.BF.18.223; 10.BF.18.240; 10.BF.18.244; 10.BF.18.243; 10.BF.18.247; 10.BF.26.157; 10.BF.26.158; 10.BF.26.196; 10.BF.26.223; 10.BF.26.240; 10.BF.26.244; 10.BF.26.243; 10.BF.26.247; 10.BF.27.157; 10.BF.27.158; 10.BF.27.196; 10.BF.27.223; 10.BF.27.240; 10.BF.27.244; 10.BF.27.243; 10.BF.27.247; 10.BF.29.157; 10.BF.29.158; 10.BF.29.196; 10.BF.29.223; 10.BF.29.240; 10.BF.29.244; 10.BF.29.243; 10.BF.29.247; 10.BF.54.157; 10.BF.54.158; 10.BF.54.196; 10.BF.54.223; 10.BF.54.240; 10.BF.54.244; 10.BF.54.243; 10.BF.54.247; 10.BF.55.157; 10.BF.55.158; 10.BF.55.196; 10.BF.55.223; 10.BF.55.240; 10.BF.55.244; 10.BF.55.243; 10.BF.55.247; 10.BF.56.157; 10.BF.56.158; 10.BF.56.196; 10.BF.56.223; 10.BF.56.240; 10.BF.56.244; 10.BF.56.243; 10.BF.56.247; 10.BF.157.157; 10.BF.157.158; 10.BF.157.196; 10.BF.157.223; 10.BF.157.240; 10.BF.157.244; 10.BF.157.243; 10.BF.157.247; 10.BF.196.157; 10.BF.196.158; 10.BF.196.196; 10.BF.196.223; 10.BF.196.240; 10.BF.196.244; 10.BF.196.243; 10.BF.196.247; 10.BF.223.157; 10.BF.223.158; 10.BF.223.196; 10.BF.223.223; 10.BF.223.240; 10.BF.223.244; 10.BF.223.243; 10.BF.223.247; 10.BF.240.157; 10.BF.240.158; 10.BF.240.196; 10.BF.240.223; 10.BF.240.240; 10.BF.240.244; 10.BF.240.243; 10.BF.240.247; 10.BF.244.157; 10.BF.244.158; 10.BF.244.196; 10.BF.244.223; 10.BF.244.240; 10.BF.244.244; 10.BF.244.243; 10.BF.244.247; 10.BF.247.157; 10.BF.247.158; 10.BF.247.196; 10.BF.247.223; 10.BF.247.240; 10.BF.247.244; 10.BF.247.243; 10.BF.247.247; |
| Prodrugs of 10.CI |
| 10.CI.4.157; 10.CI.4.158; 10.CI.4.196; 10.CI.4.223; 10.CI.4.240; 10.CI.4.244; 10.CI.4.243; 10.CI.4.247; 10.CI.5.157; 10.CI.5.158; 10.CI.5.196; 10.CI.5.223; 10.CI.5.240; 10.CI.5.244; 10.CI.5.243; 10.CI.5.247; 10.CI.7.157; 10.CI.7.158; 10.CI.7.196; 10.CI.7.223; 10.CI.7.240; 10.CI.7.244; 10.CI.7.243; 10.CI.7.247; 10.CI.15.157; 10.CI.15.158; 10.CI.15.196; 10.CI.15.223; 10.CI.15.240; 10.CI.15.244; 10.CI.15.243; 10.CI.15.247; 10.CI.16.157; 10.CI.16.158; 10.CI.16.196; 10.CI.16.223; 10.CI.16.240; 10.CI.16.244; 10.CI.16.243; 10.CI.16.247; 10.CI.18.157; 10.CI.18.158; 10.CI.18.196; 10.CI.18.223; 10.CI.18.240; 10.CI.18.244; 10.CI.18.243; 10.CI.18.247; 10.CI.26.157; 10.CI.26.158; 10.CI.26.196; 10.CI.26.223; 10.CI.26.240; 10.CI.26.244; 10.CI.26.243; 10.CI.26.247; 10.CI.27.157; 10.CI.27.158; 10.CI.27.196; 10.CI.27.223; 10.CI.27.240; 10.CI.27.244; 10.CI.27.243; 10.CI.27.247; 10.CI.29.157; 10.CI.29.158; 10.CI.29.196; 10.CI.29.223; 10.CI.29.240; 10.CI.29.244; 10.CI.29.243; 10.CI.29.247; 10.CI.54.157; 10.CI.54.158; 10.CI.54.196; 10.CI.54.223; 10.CI.54.240; 10.CI.54.244; 10.CI.54.243; 10.CI.54.247; 10.CI.55.157; 10.CI.55.158; 10.CI.55.196; 10.CI.55.223; 10.CI.55.240; 10.CI.55.244; 10.CI.55.243; 10.CI.55.247; 10.CI.56.157; 10.CI.56.158; 10.CI.56.196; 10.CI.56.223; 10.CI.56.240; 10.CI.56.244; 10.CI.56.243; 10.CI.56.247; 10.CI.157.157; 10.CI.157.158; 10.CI.157.196; 10.CI.157.223; 10.CI.157.240; 10.CI.157.244; 10.CI.157.243; 10.CI.157.247; 10.CI.196.157; 10.CI.196.158; 10.CI.196.196; 10.CI.196.223; 10.CI.196.240; 10.CI.196.244; 10.CI.196.243; 10.CI.196.247; 10.CI.223.157; 10.CI.223.158; 10.CI.223.196; 10.CI.223.223; 10.CI.223.240; 10.CI.223.244; 10.CI.223.243; 10.CI.223.247; 10.CI.240.157; 10.CI.240.158; 10.CI.240.196; 10.CI.240.223; 10.CI.240.240; 10.CI.240.244; 10.CI.240.243; 10.CI.240.247; 10.CI.244.157; 10.CI.244.158; 10.CI.244.196; 10.CI.244.223; 10.CI.244.240; 10.CI.244.244; 10.CI.244.243; 10.CI.244.247; 10.CI.247.157; 10.CI.247.158; 10.CI.247.196; 10.CI.247.223; 10.CI.247.240; 10.CI.247.244; 10.CI.247.243; 10.CI.247.247; |
| Prodrugs of 10.CO |
| 10.CO.4.157; 10.CO.4.158; 10.CO.4.196; 10.CO.4.223; 10.CO.4.240; 10.CO.4.244; 10.CO.4.243; 10.CO.4.247; 10.CO.5.157; 10.CO.5.158; 10.CO.5.196; 10.CO.5.223; 10.CO.5.240; 10.CO.5.244; 10.CO.5.243; 10.CO.5.247; 10.CO.7.157; 10.CO.7.158; 10.CO.7.196; 10.CO.7.223; |

TABLE 100-continued

10.CO.7.240; 10.CO.7.244; 10.CO.7.243; 10.CO.7.247; 10.CO.15.157; 10.CO.15.158; 10.CO.15.196; 10.CO.15.223; 10.CO.15.240; 10.CO.15.244; 10.CO.15.243; 10.CO.15.247; 10.CO.16.157; 10.CO.16.158; 10.CO.16.196; 10.CO.16.223; 10.CO.16.240; 10.CO.16.244; 10.CO.16.243; 10.CO.16.247; 10.CO.18.157; 10.CO.18.158; 10.CO.18.196; 10.CO.18.223; 10.CO.18.240; 10.CO.18.244; 10.CO.18.243; 10.CO.18.247; 10.CO.26.157; 10.CO.26.158; 10.CO.26.196; 10.CO.26.223; 10.CO.26.240; 10.CO.26.244; 10.CO.26.243; 10.CO.26.247; 10.CO.27.157; 10.CO.27.158; 10.CO.27.196; 10.CO.27.223; 10.CO.27.240; 10.CO.27.244; 10.CO.27.243; 10.CO.27.247; 10.CO.29.157; 10.CO.29.158; 10.CO.29.196; 10.CO.29.223; 10.CO.29.240; 10.CO.29.244; 10.CO.29.243; 10.CO.29.247; 10.CO.54.157; 10.CO.54.158; 10.CO.54.196; 10.CO.54.223; 10.CO.54.240; 10.CO.54.244; 10.CO.54.243; 10.CO.54.247; 10.CO.55.157; 10.CO.55.158; 10.CO.55.196; 10.CO.55.223; 10.CO.55.240; 10.CO.55.244; 10.CO.55.243; 10.CO.55.247; 10.CO.56.157; 10.CO.56.158; 10.CO.56.196; 10.CO.56.223; 10.CO.56.240; 10.CO.56.244; 10.CO.56.243; 10.CO.56.247; 10.CO.157.157; 10.CO.157.158; 10.CO.157.196; 10.CO.157.223; 10.CO.157.240; 10.CO.157.244; 10.CO.157.243; 10.CO.157.247; 10.CO.196.157; 10.CO.196.158; 10.CO.196.196; 10.CO.196.223; 10.CO.196.240; 10.CO.196.244; 10.CO.196.243; 10.CO.196.247; 10.CO.223.157; 10.CO.223.158; 10.CO.223.196; 10.CO.223.223; 10.CO.223.240; 10.CO.223.244; 10.CO.223.243; 10.CO.223.247; 10.CO.240.157; 10.CO.240.158; 10.CO.240.196; 10.CO.240.223; 10.CO.240.240; 10.CO.240.244; 10.CO.240.243; 10.CO.240.247; 10.CO.244.157; 10.CO.244.158; 10.CO.244.196; 10.CO.244.223; 10.CO.244.240; 10.CO.244.244; 10.CO.244.243; 10.CO.244.247; 10.CO.247.157; 10.CO.247.158; 10.CO.247.196; 10.CO.247.223; 10.CO.247.240; 10.CO.247.244; 10.CO.247.243; 10.CO.247.247;

Prodrugs of 11.AH

11.AH.4.157; 11.AH.4.158; 11.AH.4.196; 11.AH.4.223; 11.AH.4.240; 11.AH.4.244; 11.AH.4.243; 11.AH.4.247; 11.AH.5.157; 11.AH.5.158; 11.AH.5.196; 11.AH.5.223; 11.AH.5.240; 11.AH.5.244; 11.AH.5.243; 11.AH.5.247; 11.AH.7.157; 11.AH.7.158; 11.AH.7.196; 11.AH.7.223; 11.AH.7.240; 11.AH.7.244; 11.AH.7.243; 11.AH.7.247; 11.AH.15.157; 11.AH.15.158; 11.AH.15.196; 11.AH.15.223; 11.AH.15.240; 11.AH.15.244; 11.AH.15.243; 11.AH.15.247; 11.AH.16.157; 11.AH.16.158; 11.AH.16.196; 11.AH.16.223; 11.AH.16.240; 11.AH.16.244; 11.AH.16.243; 11.AH.16.247; 11.AH.18.157; 11.AH.18.158; 11.AH.18.196; 11.AH.18.223; 11.AH.18.240; 11.AH.18.244; 11.AH.18.243; 11.AH.18.247; 11.AH.26.157; 11.AH.26.158; 11.AH.26.196; 11.AH.26.223; 11.AH.26.240; 11.AH.26.244; 11.AH.26.243; 11.AH.26.247; 11.AH.27.157; 11.AH.27.158; 11.AH.27.196; 11.AH.27.223; 11.AH.27.240; 11.AH.27.244; 11.AH.27.243; 11.AH.27.247; 11.AH.29.157; 11.AH.29.158; 11.AH.29.196; 11.AH.29.223; 11.AH.29.240; 11.AH.29.244; 11.AH.29.243; 11.AH.29.247; 11.AH.54.157; 11.AH.54.158; 11.AH.54.196; 11.AH.54.223; 11.AH.54.240; 11.AH.54.244; 11.AH.54.243; 11.AH.54.247; 11.AH.55.157; 11.AH.55.158; 11.AH.55.196; 11.AH.55.223; 11.AH.55.240; 11.AH.55.244; 11.AH.55.243; 11.AH.55.247; 11.AH.56.157; 11.AH.56.158; 11.AH.56.196; 11.AH.56.223; 11.AH.56.240; 11.AH.56.244; 11.AH.56.243; 11.AH.56.247; 11.AH.157.157; 11.AH.157.158; 11.AH.157.196; 11.AH.157.223; 11.AH.157.240; 11.AH.157.244; 11.AH.157.243; 11.AH.157.247; 11.AH.196.157; 11.AH.196.158; 11.AH.196.196; 11.AH.196.223; 11.AH.196.240; 11.AH.196.244; 11.AH.196.243; 11.AH.196.247; 11.AH.223.157; 11.AH.223.158; 11.AH.223.196; 11.AH.223.223; 11.AH.223.240; 11.AH.223.244; 11.AH.223.243; 11.AH.223.247; 11.AH.240.157; 11.AH.240.158; 11.AH.240.196; 11.AH.240.223; 11.AH.240.240; 11.AH.240.244; 11.AH.240.243; 11.AH.240.247; 11.AH.244.157; 11.AH.244.158; 11.AH.244.196; 11.AH.244.223; 11.AH.244.240; 11.AH.244.244; 11.AH.244.243; 11.AH.244.247; 11.AH.247.157; 11.AH.247.158; 11.AH.247.196; 11.AH.247.223; 11.AH.247.240; 11.AH.247.244; 11.AH.247.243; 11.AH.247.247;

Prodrugs of 11.AJ

11.AJ.4.157; 11.AJ.4.158; 11.AJ.4.196; 11.AJ.4.223; 11.AJ.4.240; 11.AJ.4.244; 11.AJ.4.243; 11.AJ.4.247; 11.AJ.5.157; 11.AJ.5.158; 11.AJ.5.196; 11.AJ.5.223; 11.AJ.5.240; 11.AJ.5.244; 11.AJ.5.243; 11.AJ.5.247; 11.AJ.7.157; 11.AJ.7.158; 11.AJ.7.196; 11.AJ.7.223; 11.AJ.7.240; 11.AJ.7.244; 11.AJ.7.243; 11.AJ.7.247; 11.AJ.15.157; 11.AJ.15.158; 11.AJ.15.196; 11.AJ.15.223; 11.AJ.15.240; 11.AJ.15.244; 11.AJ.15.243; 11.AJ.15.247; 11.AJ.16.157; 11.AJ.16.158; 11.AJ.16.196; 11.AJ.16.223; 11.AJ.16.240; 11.AJ.16.244; 11.AJ.16.243; 11.AJ.16.247; 11.AJ.18.157; 11.AJ.18.158; 11.AJ.18.196; 11.AJ.18.223; 11.AJ.18.240; 11.AJ.18.244; 11.AJ.18.243; 11.AJ.18.247; 11.AJ.26.157; 11.AJ.26.158; 11.AJ.26.196; 11.AJ.26.223; 11.AJ.26.240; 11.AJ.26.244; 11.AJ.26.243; 11.AJ.26.247; 11.AJ.27.157; 11.AJ.27.158; 11.AJ.27.196; 11.AJ.27.223; 11.AJ.27.240; 11.AJ.27.244; 11.AJ.27.243; 11.AJ.27.247; 11.AJ.29.157; 11.AJ.29.158; 11.AJ.29.196; 11.AJ.29.223; 11.AJ.29.240; 11.AJ.29.244; 11.AJ.29.243; 11.AJ.29.247; 11.AJ.54.157; 11.AJ.54.158; 11.AJ.54.196; 11.AJ.54.223; 11.AJ.54.240; 11.AJ.54.244; 11.AJ.54.243; 11.AJ.54.247; 11.AJ.55.157; 11.AJ.55.158; 11.AJ.55.196; 11.AJ.55.223; 11.AJ.55.240; 11.AJ.55.244; 11.AJ.55.243; 11.AJ.55.247; 11.AJ.56.157; 11.AJ.56.158; 11.AJ.56.196; 11.AJ.56.223; 11.AJ.56.240;

TABLE 100-continued

| |
|---|
| 11.AJ.56.244; 11.AJ.56.243; 11.AJ.56.247; 11.AJ.157.157; 11.AJ.157.158; 11.AJ.157.196; 11.AJ.157.223; 11.AJ.157.240; 11.AJ.157.244; 11.AJ.157.243; 11.AJ.157.247; 11.AJ.196.157; 11.AJ.196.158; 11.AJ.196.196; 11.AJ.196.223; 11.AJ.196.240; 11.AJ.196.244; 11.AJ.196.243; 11.AJ.196.247; 11.AJ.223.157; 11.AJ.223.158; 11.AJ.223.196; 11.AJ.223.223; 11.AJ.223.240; 11.AJ.223.244; 11.AJ.223.243; 11.AJ.223.247; 11.AJ.240.157; 11.AJ.240.158; 11.AJ.240.196; 11.AJ.240.223; 11.AJ.240.240; 11.AJ.240.244; 11.AJ.240.243; 11.AJ.240.247; 11.AJ.244.157; 11.AJ.244.158; 11.AJ.244.196; 11.AJ.244.223; 11.AJ.244.240; 11.AJ.244.244; 11.AJ.244.243; 11.AJ.244.247; 11.AJ.247.157; 11.AJ.247.158; 11.AJ.247.196; 11.AJ.247.223; 11.AJ.247.240; 11.AJ.247.244; 11.AJ.247.243; 11.AJ.247.247; |
| Prodrugs of 11.AN |
| 11.AN.4.157; 11.AN.4.158; 11.AN.4.196; 11.AN.4.223; 11.AN.4.240; 11.AN.4.244; 11.AN.4.243; 11.AN.4.247; 11.AN.5.157; 11.AN.5.158; 11.AN.5.196; 11.AN.5.223; 11.AN.5.240; 11.AN.5.244; 11.AN.5.243; 11.AN.5.247; 11.AN.7.157; 11.AN.7.158; 11.AN.7.196; 11.AN.7.223; 11.AN.7.240; 11.AN.7.244; 11.AN.7.243; 11.AN.7.247; 11.AN.15.157; 11.AN.15.158; 11.AN.15.196; 11.AN.15.223; 11.AN.15.240; 11.AN.15.244; 11.AN.15.243; 11.AN.15.247; 11.AN.16.157; 11.AN.16.158; 11.AN.16.196; 11.AN.16.223; 11.AN.16.240; 11.AN.16.244; 11.AN.16.243; 11.AN.16.247; 11.AN.18.157; 11.AN.18.158; 11.AN.18.196; 11.AN.18.223; 11.AN.18.240; 11.AN.18.244; 11.AN.18.243; 11.AN.18.247; 11.AN.26.157; 11.AN.26.158; 11.AN.26.196; 11.AN.26.223; 11.AN.26.240; 11.AN.26.244; 11.AN.26.243; 11.AN.26.247; 11.AN.27.157; 11.AN.27.158; 11.AN.27.196; 11.AN.27.223; 11.AN.27.240; 11.AN.27.244; 11.AN.27.243; 11.AN.27.247; 11.AN.29.157; 11.AN.29.158; 11.AN.29.196; 11.AN.29.223; 11.AN.29.240; 11.AN.29.244; 11.AN.29.243; 11.AN.29.247; 11.AN.54.157; 11.AN.54.158; 11.AN.54.196; 11.AN.54.223; 11.AN.54.240; 11.AN.54.244; 11.AN.54.243; 11.AN.54.247; 11.AN.55.157; 11.AN.55.158; 11.AN.55.196; 11.AN.55.223; 11.AN.55.240; 11.AN.55.244; 11.AN.55.243; 11.AN.55.247; 11.AN.56.157; 11.AN.56.158; 11.AN.56.196; 11.AN.56.223; 11.AN.56.240; 11.AN.56.244; 11.AN.56.243; 11.AN.56.247; 11.AN.157.157; 11.AN.157.158; 11.AN.157.196; 11.AN.157.223; 11.AN.157.240; 11.AN.157.244; 11.AN.157.243; 11.AN.157.247; 11.AN.196.157; 11.AN.196.158; 11.AN.196.196; 11.AN.196.223; 11.AN.196.240; 11.AN.196.244; 11.AN.196.243; 11.AN.196.247; 11.AN.223.157; 11.AN.223.158; 11.AN.223.196; 11.AN.223.223; 11.AN.223.240; 11.AN.223.244; 11.AN.223.243; 11.AN.223.247; 11.AN.240.157; 11.AN.240.158; 11.AN.240.196; 11.AN.240.223; 11.AN.240.240; 11.AN.240.244; 11.AN.240.243; 11.AN.240.247; 11.AN.244.157; 11.AN.244.158; 11.AN.244.196; 11.AN.244.223; 11.AN.244.240; 11.AN.244.244; 11.AN.244.243; 11.AN.244.247; 11.AN.247.157; 11.AN.247.158; 11.AN.247.196; 11.AN.247.223; 11.AN.247.240; 11.AN.247.244; 11.AN.247.243; 11.AN.247.247; |
| Prodrugs of 11.AP |
| 11.AP.4.157; 11.AP.4.158; 11.AP.4.196; 11.AP.4.223; 11.AP.4.240; 11.AP.4.244; 11.AP.4.243; 11.AP.4.247; 11.AP.5.157; 11.AP.5.158; 11.AP.5.196; 11.AP.5.223; 11.AP.5.240; 11.AP.5.244; 11.AP.5.243; 11.AP.5.247; 11.AP.7.157; 11.AP.7.158; 11.AP.7.196; 11.AP.7.223; 11.AP.7.240; 11.AP.7.244; 11.AP.7.243; 11.AP.7.247; 11.AP.15.157; 11.AP.15.158; 11.AP.15.196; 11.AP.15.223; 11.AP.15.240; 11.AP.15.244; 11.AP.15.243; 11.AP.15.247; 11.AP.16.157; 11.AP.16.158; 11.AP.16.196; 11.AP.16.223; 11.AP.16.240; 11.AP.16.244; 11.AP.16.243; 11.AP.16.247; 11.AP.18.157; 11.AP.18.158; 11.AP.18.196; 11.AP.18.223; 11.AP.18.240; 11.AP.18.244; 11.AP.18.243; 11.AP.18.247; 11.AP.26.157; 11.AP.26.158; 11.AP.26.196; 11.AP.26.223; 11.AP.26.240; 11.AP.26.244; 11.AP.26.243; 11.AP.26.247; 11.AP.27.157; 11.AP.27.158; 11.AP.27.196; 11.AP.27.223; 11.AP.27.240; 11.AP.27.244; 11.AP.27.243; 11.AP.27.247; 11.AP.29.157; 11.AP.29.158; 11.AP.29.196; 11.AP.29.223; 11.AP.29.240; 11.AP.29.244; 11.AP.29.243; 11.AP.29.247; 11.AP.54.157; 11.AP.54.158; 11.AP.54.196; 11.AP.54.223; 11.AP.54.240; 11.AP.54.244; 11.AP.54.243; 11.AP.54.247; 11.AP.55.157; 11.AP.55.158; 11.AP.55.196; 11.AP.55.223; 11.AP.55.240; 11.AP.55.244; 11.AP.55.243; 11.AP.55.247; 11.AP.56.157; 11.AP.56.158; 11.AP.56.196; 11.AP.56.223; 11.AP.56.240; 11.AP.56.244; 11.AP.56.243; 11.AP.56.247; 11.AP.157.157; 11.AP.157.158; 11.AP.157.196; 11.AP.157.223; 11.AP.157.240; 11.AP.157.244; 11.AP.157.243; 11.AP.157.247; 11.AP.196.157; 11.AP.196.158; 11.AP.196.196; 11.AP.196.223; 11.AP.196.240; 11.AP.196.244; 11.AP.196.243; 11.AP.196.247; 11.AP.223.157; 11.AP.223.158; 11.AP.223.196; 11.AP.223.223; 11.AP.223.240; 11.AP.223.244; 11.AP.223.243; 11.AP.223.247; 11.AP.240.157; 11.AP.240.158; 11.AP.240.196; 11.AP.240.223; 11.AP.240.240; 11.AP.240.244; 11.AP.240.243; 11.AP.240.247; 11.AP.244.157; 11.AP.244.158; 11.AP.244.196; 11.AP.244.223; 11.AP.244.240; 11.AP.244.244; 11.AP.244.243; 11.AP.244.247; 11.AP.247.157; 11.AP.247.158; 11.AP.247.196; 11.AP.247.223; 11.AP.247.240; 11.AP.247.244; 11.AP.247.243; 11.AP.247.247; |

TABLE 100-continued

| Prodrugs of 11.AZ |
|---|
| 11.AZ.4.157; 11.AZ.4.158; 11.AZ.4.196; 11.AZ.4.223; 11.AZ.4.240; 11.AZ.4.244; 11.AZ.4.243; 11.AZ.4.247; 11.AZ.5.157; 11.AZ.5.158; 11.AZ.5.196; 11.AZ.5.223; 11.AZ.5.240; 11.AZ.5.244; 11.AZ.5.243; 11.AZ.5.247; 11.AZ.7.157; 11.AZ.7.158; 11.AZ.7.196; 11.AZ.7.223; 11.AZ.7.240; 11.AZ.7.244; 11.AZ.7.243; 11.AZ.7.247; 11.AZ.15.157; 11.AZ.15.158; 11.AZ.15.196; 11.AZ.15.223; 11.AZ.15.240; 11.AZ.15.244; 11.AZ.15.243; 11.AZ.15.247; 11.AZ.16.157; 11.AZ.16.158; 11.AZ.16.196; 11.AZ.16.223; 11.AZ.16.240; 11.AZ.16.244; 11.AZ.16.243; 11.AZ.16.247; 11.AZ.18.157; 11.AZ.18.158; 11.AZ.18.196; 11.AZ.18.223; 11.AZ.18.240; 11.AZ.18.244; 11.AZ.18.243; 11.AZ.18.247; 11.AZ.26.157; 11.AZ.26.158; 11.AZ.26.196; 11.AZ.26.223; 11.AZ.26.240; 11.AZ.26.244; 11.AZ.26.243; 11.AZ.26.247; 11.AZ.27.157; 11.AZ.27.158; 11.AZ.27.196; 11.AZ.27.223; 11.AZ.27.240; 11.AZ.27.244; 11.AZ.27.243; 11.AZ.27.247; 11.AZ.29.157; 11.AZ.29.158; 11.AZ.29.196; 11.AZ.29.223; 11.AZ.29.240; 11.AZ.29.244; 11.AZ.29.243; 11.AZ.29.247; 11.AZ.54.157; 11.AZ.54.158; 11.AZ.54.196; 11.AZ.54.223; 11.AZ.54.240; 11.AZ.54.244; 11.AZ.54.243; 11.AZ.54.247; 11.AZ.55.157; 11.AZ.55.158; 11.AZ.55.196; 11.AZ.55.223; 11.AZ.55.240; 11.AZ.55.244; 11.AZ.55.243; 11.AZ.55.247; 11.AZ.56.157; 11.AZ.56.158; 11.AZ.56.196; 11.AZ.56.223; 11.AZ.56.240; 11.AZ.56.244; 11.AZ.56.243; 11.AZ.56.247; 11.AZ.157.157; 11.AZ.157.158; 11.AZ.157.196; 11.AZ.157.223; 11.AZ.157.240; 11.AZ.157.244; 11.AZ.157.243; 11.AZ.157.247; 11.AZ.196.157; 11.AZ.196.158; 11.AZ.196.196; 11.AZ.196.223; 11.AZ.196.240; 11.AZ.196.244; 11.AZ.196.243; 11.AZ.196.247; 11.AZ.223.157; 11.AZ.223.158; 11.AZ.223.196; 11.AZ.223.223; 11.AZ.223.240; 11.AZ.223.244; 11.AZ.223.243; 11.AZ.223.247; 11.AZ.240.157; 11.AZ.240.158; 11.AZ.240.196; 11.AZ.240.223; 11.AZ.240.240; 11.AZ.240.244; 11.AZ.240.243; 11.AZ.240.247; 11.AZ.244.157; 11.AZ.244.158; 11.AZ.244.196; 11.AZ.244.223; 11.AZ.244.240; 11.AZ.244.244; 11.AZ.244.243; 11.AZ.244.247; 11.AZ.247.157; 11.AZ.247.158; 11.AZ.247.196; 11.AZ.247.223; 11.AZ.247.240; 11.AZ.247.244; 11.AZ.247.243; 11.AZ.247.247; |
| Prodrugs of 11.BF |
| 11.BF.4.157; 11.BF.4.158; 11.BF.4.196; 11.BF.4.223; 11.BF.4.240; 11.BF.4.244; 11.BF.4.243; 11.BF.4.247; 11.BF.5.157; 11.BF.5.158; 11.BF.5.196; 11.BF.5.223; 11.BF.5.240; 11.BF.5.244; 11.BF.5.243; 11.BF.5.247; 11.BF.7.157; 11.BF.7.158; 11.BF.7.196; 11.BF.7.223; 11.BF.7.240; 11.BF.7.244; 11.BF.7.243; 11.BF.7.247; 11.BF.15.157; 11.BF.15.158; 11.BF.15.196; 11.BF.15.223; 11.BF.15.240; 11.BF.15.244; 11.BF.15.243; 11.BF.15.247; 11.BF.16.157; 11.BF.16.158; 11.BF.16.196; 11.BF.16.223; 11.BF.16.240; 11.BF.16.244; 11.BF.16.243; 11.BF.16.247; 11.BF.18.157; 11.BF.18.158; 11.BF.18.196; 11.BF.18.223; 11.BF.18.240; 11.BF.18.244; 11.BF.18.243; 11.BF.18.247; 11.BF.26.157; 11.BF.26.158; 11.BF.26.196; 11.BF.26.223; 11.BF.26.240; 11.BF.26.244; 11.BF.26.243; 11.BF.26.247; 11.BF.27.157; 11.BF.27.158; 11.BF.27.196; 11.BF.27.223; 11.BF.27.240; 11.BF.27.244; 11.BF.27.243; 11.BF.27.247; 11.BF.29.157; 11.BF.29.158; 11.BF.29.196; 11.BF.29.223; 11.BF.29.240; 11.BF.29.244; 11.BF.29.243; 11.BF.29.247; 11.BF.54.157; 11.BF.54.158; 11.BF.54.196; 11.BF.54.223; 11.BF.54.240; 11.BF.54.244; 11.BF.54.243; 11.BF.54.247; 11.BF.55.157; 11.BF.55.158; 11.BF.55.196; 11.BF.55.223; 11.BF.55.240; 11.BF.55.244; 11.BF.55.243; 11.BF.55.247; 11.BF.56.157; 11.BF.56.158; 11.BF.56.196; 11.BF.56.223; 11.BF.56.240; 11.BF.56.244; 11.BF.56.243; 11.BF.56.247; 11.BF.157.157; 11.BF.157.158; 11.BF.157.196; 11.BF.157.223; 11.BF.157.240; 11.BF.157.244; 11.BF.157.243; 11.BF.157.247; 11.BF.196.157; 11.BF.196.158; 11.BF.196.196; 11.BF.196.223; 11.BF.196.240; 11.BF.196.244; 11.BF.196.243; 11.BF.196.247; 11.BF.223.157; 11.BF.223.158; 11.BF.223.196; 11.BF.223.223; 11.BF.223.240; 11.BF.223.244; 11.BF.223.243; 11.BF.223.247; 11.BF.240.157; 11.BF.240.158; 11.BF.240.196; 11.BF.240.223; 11.BF.240.240; 11.BF.240.244; 11.BF.240.243; 11.BF.240.247; 11.BF.244.157; 11.BF.244.158; 11.BF.244.196; 11.BF.244.223; 11.BF.244.240; 11.BF.244.244; 11.BF.244.243; 11.BF.244.247; 11.BF.247.157; 11.BF.247.158; 11.BF.247.196; 11.BF.247.223; 11.BF.247.240; 11.BF.247.244; 11.BF.247.243; 11.BF.247.247; |
| Prodrugs of 11.CI |
| 11.CI.4.157; 11.CI.4.158; 11.CI.4.196; 11.CI.4.223; 11.CI.4.240; 11.CI.4.244; 11.CI.4.243; 11.CI.4.247; 11.CI.5.157; 11.CI.5.158; 11.CI.5.196; 11.CI.5.223; 11.CI.5.240; 11.CI.5.244; 11.CI.5.243; 11.CI.5.247; 11.CI.7.157; 11.CI.7.158; 11.CI.7.196; 11.CI.7.223; 11.CI.7.240; 11.CI.7.244; 11.CI.7.243; 11.CI.7.247; 11.CI.15.157; 11.CI.15.158; 11.CI.15.196; 11.CI.15.223; 11.CI.15.240; 11.CI.15.244; 11.CI.15.243; 11.CI.15.247; 11.CI.16.157; 11.CI.16.158; 11.CI.16.196; 11.CI.16.223; 11.CI.16.240; 11.CI.16.244; 11.CI.16.243; 11.CI.16.247; 11.CI.18.157; 11.CI.18.158; 11.CI.18.196; 11.CI.18.223; 11.CI.18.240; 11.CI.18.244; 11.CI.18.243; 11.CI.18.247; 11.CI.26.157; 11.CI.26.158; 11.CI.26.196; 11.CI.26.223; 11.CI.26.240; 11.CI.26.244; 11.CI.26.243; 11.CI.26.247; 11.CI.27.157; 11.CI.27.158; 11.CI.27.196; 11.CI.27.223; 11.CI.27.240; 11.CI.27.244; 11.CI.27.243; 11.CI.27.247; 11.CI.29.157; 11.CI.29.158; 11.CI.29.196; 11.CI.29.223; 11.CI.29.240; 11.CI.29.244; 11.CI.29.243; 11.CI.29.247; 11.CI.54.157; |

TABLE 100-continued

| |
|---|
| 11.CI.54.158; 11.CI.54.196; 11.CI.54.223; 11.CI.54.240; 11.CI.54.244; 11.CI.54.243; 11.CI.54.247; 11.CI.55.157; 11.CI.55.158; 11.CI.55.196; 11.CI.55.223; 11.CI.55.240; 11.CI.55.244; 11.CI.55.243; 11.CI.55.247; 11.CI.56.157; 11.CI.56.158; 11.CI.56.196; 11.CI.56.223; 11.CI.56.240; 11.CI.56.244; 11.CI.56.243; 11.CI.56.247; 11.CI.157.157; 11.CI.157.158; 11.CI.157.196; 11.CI.157.223; 11.CI.157.240; 11.CI.157.244; 11.CI.157.243; 11.CI.157.247; 11.CI.196.157; 11.CI.196.158; 11.CI.196.196; 11.CI.196.223; 11.CI.196.240; 11.CI.196.244; 11.CI.196.243; 11.CI.196.247; 11.CI.223.157; 11.CI.223.158; 11.CI.223.196; 11.CI.223.223; 11.CI.223.240; 11.CI.223.244; 11.CI.223.243; 11.CI.223.247; 11.CI.240.157; 11.CI.240.158; 11.CI.240.196; 11.CI.240.223; 11.CI.240.240; 11.CI.240.244; 11.CI.240.243; 11.CI.240.247; 11.CI.244.157; 11.CI.244.158; 11.CI.244.196; 11.CI.244.223; 11.CI.244.240; 11.CI.244.244; 11.CI.244.243; 11.CI.244.247; 11.CI.247.157; 11.CI.247.158; 11.CI.247.196; 11.CI.247.223; 11.CI.247.240; 11.CI.247.244; 11.CI.247.243; 11.CI.247.247; |
| Prodrugs of 11.CO |
| 11.CO.4.157; 11.CO.4.158; 11.CO.4.196; 11.CO.4.223; 11.CO.4.240; 11.CO.4.244; 11.CO.4.243; 11.CO.4.247; 11.CO.5.157; 11.CO.5.158; 11.CO.5.196; 11.CO.5.223; 11.CO.5.240; 11.CO.5.244; 11.CO.5.243; 11.CO.5.247; 11.CO.7.157; 11.CO.7.158; 11.CO.7.196; 11.CO.7.223; 11.CO.7.240; 11.CO.7.244; 11.CO.7.243; 11.CO.7.247; 11.CO.15.157; 11.CO.15.158; 11.CO.15.196; 11.CO.15.223; 11.CO.15.240; 11.CO.15.244; 11.CO.15.243; 11.CO.15.247; 11.CO.16.157; 11.CO.16.158; 11.CO.16.196; 11.CO.16.223; 11.CO.16.240; 11.CO.16.244; 11.CO.16.243; 11.CO.16.247; 11.CO.18.157; 11.CO.18.158; 11.CO.18.196; 11.CO.18.223; 11.CO.18.240; 11.CO.18.244; 11.CO.18.243; 11.CO.18.247; 11.CO.26.157; 11.CO.26.158; 11.CO.26.196; 11.CO.26.223; 11.CO.26.240; 11.CO.26.244; 11.CO.26.243; 11.CO.26.247; 11.CO.27.157; 11.CO.27.158; 11.CO.27.196; 11.CO.27.223; 11.CO.27.240; 11.CO.27.244; 11.CO.27.243; 11.CO.27.247; 11.CO.29.157; 11.CO.29.158; 11.CO.29.196; 11.CO.29.223; 11.CO.29.240; 11.CO.29.244; 11.CO.29.243; 11.CO.29.247; 11.CO.54.157; 11.CO.54.158; 11.CO.54.196; 11.CO.54.223; 11.CO.54.240; 11.CO.54.244; 11.CO.54.243; 11.CO.54.247; 11.CO.55.157; 11.CO.55.158; 11.CO.55.196; 11.CO.55.223; 11.CO.55.240; 11.CO.55.244; 11.CO.55.243; 11.CO.55.247; 11.CO.56.157; 11.CO.56.158; 11.CO.56.196; 11.CO.56.223; 11.CO.56.240; 11.CO.56.244; 11.CO.56.243; 11.CO.56.247; 11.CO.157.157; 11.CO.157.158; 11.CO.157.196; 11.CO.157.223; 11.CO.157.240; 11.CO.157.244; 11.CO.157.243; 11.CO.157.247; 11.CO.196.157; 11.CO.196.158; 11.CO.196.196; 11.CO.196.223; 11.CO.196.240; 11.CO.196.244; 11.CO.196.243; 11.CO.196.247; 11.CO.223.157; 11.CO.223.158; 11.CO.223.196; 11.CO.223.223; 11.CO.223.240; 11.CO.223.244; 11.CO.223.243; 11.CO.223.247; 11.CO.240.157; 11.CO.240.158; 11.CO.240.196; 11.CO.240.223; 11.CO.240.240; 11.CO.240.244; 11.CO.240.243; 11.CO.240.247; 11.CO.244.157; 11.CO.244.158; 11.CO.244.196; 11.CO.244.223; 11.CO.244.240; 11.CO.244.244; 11.CO.244.243; 11.CO.244.247; 11.CO.247.157; 11.CO.247.158; 11.CO.247.196; 11.CO.247.223; 11.CO.247.240; 11.CO.247.244; 11.CO.247.243; 11.CO.247.247; |
| Prodrugs of 12.AH |
| 12.AH.4.157; 12.AH.4.158; 12.AH.4.196; 12.AH.4.223; 12.AH.4.240; 12.AH.4.244; 12.AH.4.243; 12.AH.4.247; 12.AH.5.157; 12.AH.5.158; 12.AH.5.196; 12.AH.5.223; 12.AH.5.240; 12.AH.5.244; 12.AH.5.243; 12.AH.5.247; 12.AH.7.157; 12.AH.7.158; 12.AH.7.196; 12.AH.7.223; 12.AH.7.240; 12.AH.7.244; 12.AH.7.243; 12.AH.7.247; 12.AH.15.157; 12.AH.15.158; 12.AH.15.196; 12.AH.15.223; 12.AH.15.240; 12.AH.15.244; 12.AH.15.243; 12.AH.15.247; 12.AH.16.157; 12.AH.16.158; 12.AH.16.196; 12.AH.16.223; 12.AH.16.240; 12.AH.16.244; 12.AH.16.243; 12.AH.16.247; 12.AH.18.157; 12.AH.18.158; 12.AH.18.196; 12.AH.18.223; 12.AH.18.240; 12.AH.18.244; 12.AH.18.243; 12.AH.18.247; 12.AH.26.157; 12.AH.26.158; 12.AH.26.196; 12.AH.26.223; 12.AH.26.240; 12.AH.26.244; 12.AH.26.243; 12.AH.26.247; 12.AH.27.157; 12.AH.27.158; 12.AH.27.196; 12.AH.27.223; 12.AH.27.240; 12.AH.27.244; 12.AH.27.243; 12.AH.27.247; 12.AH.29.157; 12.AH.29.158; 12.AH.29.196; 12.AH.29.223; 12.AH.29.240; 12.AH.29.244; 12.AH.29.243; 12.AH.29.247; 12.AH.54.157; 12.AH.54.158; 12.AH.54.196; 12.AH.54.223; 12.AH.54.240; 12.AH.54.244; 12.AH.54.243; 12.AH.54.247; 12.AH.55.157; 12.AH.55.158; 12.AH.55.196; 12.AH.55.223; 12.AH.55.240; 12.AH.55.244; 12.AH.55.243; 12.AH.55.247; 12.AH.56.157; 12.AH.56.158; 12.AH.56.196; 12.AH.56.223; 12.AH.56.240; 12.AH.56.244; 12.AH.56.243; 12.AH.56.247; 12.AH.157.157; 12.AH.157.158; 12.AH.157.196; 12.AH.157.223; 12.AH.157.240; 12.AH.157.244; 12.AH.157.243; 12.AH.157.247; 12.AH.196.157; 12.AH.196.158; 12.AH.196.196; 12.AH.196.223; 12.AH.196.240; 12.AH.196.244; 12.AH.196.243; 12.AH.196.247; 12.AH.223.157; 12.AH.223.158; 12.AH.223.196; 12.AH.223.223; 12.AH.223.240; 12.AH.223.244; 12.AH.223.243; 12.AH.223.247; 12.AH.240.157; 12.AH.240.158; 12.AH.240.196; 12.AH.240.223; 12.AH.240.240; 12.AH.240.244; 12.AH.240.243; 12.AH.240.247; 12.AH.244.157; 12.AH.244.158; 12.AH.244.196; 12.AH.244.223; 12.AH.244.240; 12.AH.244.244; 12.AH.244.243; |

TABLE 100-continued

| |
|---|
| 12.AH.244.247; 12.AH.247.157; 12.AH.247.158; 12.AH.247.196; 12.AH.247.223; 12.AH.247.240; 12.AH.247.244; 12.AH.247.243; 12.AH.247.247; |
| Prodrugs of 12.AJ |
| 12.AJ.4.157; 12.AJ.4.158; 12.AJ.4.196; 12.AJ.4.223; 12.AJ.4.240; 12.AJ.4.244; 12.AJ.4.243; 12.AJ.4.247; 12.AJ.5.157; 12.AJ.5.158; 12.AJ.5.196; 12.AJ.5.223; 12.AJ.5.240; 12.AJ.5.244; 12.AJ.5.243; 12.AJ.5.247; 12.AJ.7.157; 12.AJ.7.158; 12.AJ.7.196; 12.AJ.7.223; 12.AJ.7.240; 12.AJ.7.244; 12.AJ.7.243; 12.AJ.7.247; 12.AJ.15.157; 12.AJ.15.158; 12.AJ.15.196; 12.AJ.15.223; 12.AJ.15.240; 12.AJ.15.244; 12.AJ.15.243; 12.AJ.15.247; 12.AJ.16.157; 12.AJ.16.158; 12.AJ.16.196; 12.AJ.16.223; 12.AJ.16.240; 12.AJ.16.244; 12.AJ.16.243; 12.AJ.16.247; 12.AJ.18.157; 12.AJ.18.158; 12.AJ.18.196; 12.AJ.18.223; 12.AJ.18.240; 12.AJ.18.244; 12.AJ.18.243; 12.AJ.18.247; 12.AJ.26.157; 12.AJ.26.158; 12.AJ.26.196; 12.AJ.26.223; 12.AJ.26.240; 12.AJ.26.244; 12.AJ.26.243; 12.AJ.26.247; 12.AJ.27.157; 12.AJ.27.158; 12.AJ.27.196; 12.AJ.27.223; 12.AJ.27.240; 12.AJ.27.244; 12.AJ.27.243; 12.AJ.27.247; 12.AJ.29.157; 12.AJ.29.158; 12.AJ.29.196; 12.AJ.29.223; 12.AJ.29.240; 12.AJ.29.244; 12.AJ.29.243; 12.AJ.29.247; 12.AJ.54.157; 12.AJ.54.158; 12.AJ.54.196; 12.AJ.54.223; 12.AJ.54.240; 12.AJ.54.244; 12.AJ.54.243; 12.AJ.54.247; 12.AJ.55.157; 12.AJ.55.158; 12.AJ.55.196; 12.AJ.55.223; 12.AJ.55.240; 12.AJ.55.244; 12.AJ.55.243; 12.AJ.55.247; 12.AJ.56.157; 12.AJ.56.158; 12.AJ.56.196; 12.AJ.56.223; 12.AJ.56.240; 12.AJ.56.244; 12.AJ.56.243; 12.AJ.56.247; 12.AJ.157.157; 12.AJ.157.158; 12.AJ.157.196; 12.AJ.157.223; 12.AJ.157.240; 12.AJ.157.244; 12.AJ.157.243; 12.AJ.157.247; 12.AJ.196.157; 12.AJ.196.158; 12.AJ.196.196; 12.AJ.196.223; 12.AJ.196.240; 12.AJ.196.244; 12.AJ.196.243; 12.AJ.196.247; 12.AJ.223.157; 12.AJ.223.158; 12.AJ.223.196; 12.AJ.223.223; 12.AJ.223.240; 12.AJ.223.244; 12.AJ.223.243; 12.AJ.223.247; 12.AJ.240.157; 12.AJ.240.158; 12.AJ.240.196; 12.AJ.240.223; 12.AJ.240.240; 12.AJ.240.244; 12.AJ.240.243; 12.AJ.240.247; 12.AJ.244.157; 12.AJ.244.158; 12.AJ.244.196; 12.AJ.244.223; 12.AJ.244.240; 12.AJ.244.244; 12.AJ.244.243; 12.AJ.244.247; 12.AJ.247.157; 12.AJ.247.158; 12.AJ.247.196; 12.AJ.247.223; 12.AJ.247.240; 12.AJ.247.244; 12.AJ.247.243; 12.AJ.247.247; |
| Prodrugs of 12.AN |
| 12.AN.4.157; 12.AN.4.158; 12.AN.4.196; 12.AN.4.223; 12.AN.4.240; 12.AN.4.244; 12.AN.4.243; 12.AN.4.247; 12.AN.5.157; 12.AN.5.158; 12.AN.5.196; 12.AN.5.223; 12.AN.5.240; 12.AN.5.244; 12.AN.5.243; 12.AN.5.247; 12.AN.7.157; 12.AN.7.158; 12.AN.7.196; 12.AN.7.223; 12.AN.7.240; 12.AN.7.244; 12.AN.7.243; 12.AN.7.247; 12.AN.15.157; 12.AN.15.158; 12.AN.15.196; 12.AN.15.223; 12.AN.15.240; 12.AN.15.244; 12.AN.15.243; 12.AN.15.247; 12.AN.16.157; 12.AN.16.158; 12.AN.16.196; 12.AN.16.223; 12.AN.16.240; 12.AN.16.244; 12.AN.16.243; 12.AN.16.247; 12.AN.18.157; 12.AN.18.158; 12.AN.18.196; 12.AN.18.223; 12.AN.18.240; 12.AN.18.244; 12.AN.18.243; 12.AN.18.247; 12.AN.26.157; 12.AN.26.158; 12.AN.26.196; 12.AN.26.223; 12.AN.26.240; 12.AN.26.244; 12.AN.26.243; 12.AN.26.247; 12.AN.27.157; 12.AN.27.158; 12.AN.27.196; 12.AN.27.223; 12.AN.27.240; 12.AN.27.244; 12.AN.27.243; 12.AN.27.247; 12.AN.29.157; 12.AN.29.158; 12.AN.29.196; 12.AN.29.223; 12.AN.29.240; 12.AN.29.244; 12.AN.29.243; 12.AN.29.247; 12.AN.54.157; 12.AN.54.158; 12.AN.54.196; 12.AN.54.223; 12.AN.54.240; 12.AN.54.244; 12.AN.54.243; 12.AN.54.247; 12.AN.55.157; 12.AN.55.158; 12.AN.55.196; 12.AN.55.223; 12.AN.55.240; 12.AN.55.244; 12.AN.55.243; 12.AN.55.247; 12.AN.56.157; 12.AN.56.158; 12.AN.56.196; 12.AN.56.223; 12.AN.56.240; 12.AN.56.244; 12.AN.56.243; 12.AN.56.247; 12.AN.157.157; 12.AN.157.158; 12.AN.157.196; 12.AN.157.223; 12.AN.157.240; 12.AN.157.244; 12.AN.157.243; 12.AN.157.247; 12.AN.196.157; 12.AN.196.158; 12.AN.196.196; 12.AN.196.223; 12.AN.196.240; 12.AN.196.244; 12.AN.196.243; 12.AN.196.247; 12.AN.223.157; 12.AN.223.158; 12.AN.223.196; 12.AN.223.223; 12.AN.223.240; 12.AN.223.244; 12.AN.223.243; 12.AN.223.247; 12.AN.240.157; 12.AN.240.158; 12.AN.240.196; 12.AN.240.223; 12.AN.240.240; 12.AN.240.244; 12.AN.240.243; 12.AN.240.247; 12.AN.244.157; 12.AN.244.158; 12.AN.244.196; 12.AN.244.223; 12.AN.244.240; 12.AN.244.244; 12.AN.244.243; 12.AN.244.247; 12.AN.247.157; 12.AN.247.158; 12.AN.247.196; 12.AN.247.223; 12.AN.247.240; 12.AN.247.244; 12.AN.247.243; 12.AN.247.247; |
| Prodrugs of 12.AP |
| 12.AP.4.157; 12.AP.4.158; 12.AP.4.196; 12.AP.4.223; 12.AP.4.240; 12.AP.4.244; 12.AP.4.243; 12.AP.4.247; 12.AP.5.157; 12.AP.5.158; 12.AP.5.196; 12.AP.5.223; 12.AP.5.240; 12.AP.5.244; 12.AP.5.243; 12.AP.5.247; 12.AP.7.157; 12.AP.7.158; 12.AP.7.196; 12.AP.7.223; 12.AP.7.240; 12.AP.7.244; 12.AP.7.243; 12.AP.7.247; 12.AP.15.157; 12.AP.15.158; 12.AP.15.196; 12.AP.15.223; 12.AP.15.240; 12.AP.15.244; 12.AP.15.243; 12.AP.15.247; 12.AP.16.157; 12.AP.16.158; 12.AP.16.196; 12.AP.16.223; 12.AP.16.240; 12.AP.16.244; 12.AP.16.243; 12.AP.16.247; 12.AP.18.157; 12.AP.18.158; 12.AP.18.196; 12.AP.18.223; 12.AP.18.240; 12.AP.18.244; 12.AP.18.243; 12.AP.18.247; 12.AP.26.157; 12.AP.26.158; 12.AP.26.196; 12.AP.26.223; 12.AP.26.240; 12.AP.26.244; 12.AP.26.243; |

TABLE 100-continued

| |
|---|
| 12.AP.26.247; 12.AP.27.157; 12.AP.27.158; 12.AP.27.196; 12.AP.27.223; 12.AP.27.240; 12.AP.27.244; 12.AP.27.243; 12.AP.27.247; 12.AP.29.157; 12.AP.29.158; 12.AP.29.196; 12.AP.29.223; 12.AP.29.240; 12.AP.29.244; 12.AP.29.243; 12.AP.29.247; 12.AP.54.157; 12.AP.54.158; 12.AP.54.196; 12.AP.54.223; 12.AP.54.240; 12.AP.54.244; 12.AP.54.243; 12.AP.54.247; 12.AP.55.157; 12.AP.55.158; 12.AP.55.196; 12.AP.55.223; 12.AP.55.240; 12.AP.55.244; 12.AP.55.243; 12.AP.55.247; 12.AP.56.157; 12.AP.56.158; 12.AP.56.196; 12.AP.56.223; 12.AP.56.240; 12.AP.56.244; 12.AP.56.243; 12.AP.56.247; 12.AP.157.157; 12.AP.157.158; 12.AP.157.196; 12.AP.157.223; 12.AP.157.240; 12.AP.157.244; 12.AP.157.243; 12.AP.157.247; 12.AP.196.157; 12.AP.196.158; 12.AP.196.196; 12.AP.196.223; 12.AP.196.240; 12.AP.196.244; 12.AP.196.243; 12.AP.196.247; 12.AP.223.157; 12.AP.223.158; 12.AP.223.196; 12.AP.223.223; 12.AP.223.240; 12.AP.223.244; 12.AP.223.243; 12.AP.223.247; 12.AP.240.157; 12.AP.240.158; 12.AP.240.196; 12.AP.240.223; 12.AP.240.240; 12.AP.240.244; 12.AP.240.243; 12.AP.240.247; 12.AP.244.157; 12.AP.244.158; 12.AP.244.196; 12.AP.244.223; 12.AP.244.240; 12.AP.244.244; 12.AP.244.243; 12.AP.244.247; 12.AP.247.157; 12.AP.247.158; 12.AP.247.196; 12.AP.247.223; 12.AP.247.240; 12.AP.247.244; 12.AP.247.243; 12.AP.247.247; |
| Prodrugs of 12.AZ |
| 12.AZ.4.157; 12.AZ.4.158; 12.AZ.4.196; 12.AZ.4.223; 12.AZ.4.240; 12.AZ.4.244; 12.AZ.4.243; 12.AZ.4.247; 12.AZ.5.157; 12.AZ.5.158; 12.AZ.5.196; 12.AZ.5.223; 12.AZ.5.240; 12.AZ.5.244; 12.AZ.5.243; 12.AZ.5.247; 12.AZ.7.157; 12.AZ.7.158; 12.AZ.7.196; 12.AZ.7.223; 12.AZ.7.240; 12.AZ.7.244; 12.AZ.7.243; 12.AZ.7.247; 12.AZ.15.157; 12.AZ.15.158; 12.AZ.15.196; 12.AZ.15.223; 12.AZ.15.240; 12.AZ.15.244; 12.AZ.15.243; 12.AZ.15.247; 12.AZ.16.157; 12.AZ.16.158; 12.AZ.16.196; 12.AZ.16.223; 12.AZ.16.240; 12.AZ.16.244; 12.AZ.16.243; 12.AZ.16.247; 12.AZ.18.157; 12.AZ.18.158; 12.AZ.18.196; 12.AZ.18.223; 12.AZ.18.240; 12.AZ.18.244; 12.AZ.18.243; 12.AZ.18.247; 12.AZ.26.157; 12.AZ.26.158; 12.AZ.26.196; 12.AZ.26.223; 12.AZ.26.240; 12.AZ.26.244; 12.AZ.26.243; 12.AZ.26.247; 12.AZ.27.157; 12.AZ.27.158; 12.AZ.27.196; 12.AZ.27.223; 12.AZ.27.240; 12.AZ.27.244; 12.AZ.27.243; 12.AZ.27.247; 12.AZ.29.157; 12.AZ.29.158; 12.AZ.29.196; 12.AZ.29.223; 12.AZ.29.240; 12.AZ.29.244; 12.AZ.29.243; 12.AZ.29.247; 12.AZ.54.157; 12.AZ.54.158; 12.AZ.54.196; 12.AZ.54.223; 12.AZ.54.240; 12.AZ.54.244; 12.AZ.54.243; 12.AZ.54.247; 12.AZ.55.157; 12.AZ.55.158; 12.AZ.55.196; 12.AZ.55.223; 12.AZ.55.240; 12.AZ.55.244; 12.AZ.55.243; 12.AZ.55.247; 12.AZ.56.157; 12.AZ.56.158; 12.AZ.56.196; 12.AZ.56.223; 12.AZ.56.240; 12.AZ.56.244; 12.AZ.56.243; 12.AZ.56.247; 12.AZ.157.157; 12.AZ.157.158; 12.AZ.157.196; 12.AZ.157.223; 12.AZ.157.240; 12.AZ.157.244; 12.AZ.157.243; 12.AZ.157.247; 12.AZ.196.157; 12.AZ.196.158; 12.AZ.196.196; 12.AZ.196.223; 12.AZ.196.240; 12.AZ.196.244; 12.AZ.196.243; 12.AZ.196.247; 12.AZ.223.157; 12.AZ.223.158; 12.AZ.223.196; 12.AZ.223.223; 12.AZ.223.240; 12.AZ.223.244; 12.AZ.223.243; 12.AZ.223.247; 12.AZ.240.157; 12.AZ.240.158; 12.AZ.240.196; 12.AZ.240.223; 12.AZ.240.240; 12.AZ.240.244; 12.AZ.240.243; 12.AZ.240.247; 12.AZ.244.157; 12.AZ.244.158; 12.AZ.244.196; 12.AZ.244.223; 12.AZ.244.240; 12.AZ.244.244; 12.AZ.244.243; 12.AZ.244.247; 12.AZ.247.157; 12.AZ.247.158; 12.AZ.247.196; 12.AZ.247.223; 12.AZ.247.240; 12.AZ.247.244; 12.AZ.247.243; 12.AZ.247.247; |
| Prodrugs of 12.BF |
| 12.BF.4.157; 12.BF.4.158; 12.BF.4.196; 12.BF.4.223; 12.BF.4.240; 12.BF.4.244; 12.BF.4.243; 12.BF.4.247; 12.BF.5.157; 12.BF.5.158; 12.BF.5.196; 12.BF.5.223; 12.BF.5.240; 12.BF.5.244; 12.BF.5.243; 12.BF.5.247; 12.BF.7.157; 12.BF.7.158; 12.BF.7.196; 12.BF.7.223; 12.BF.7.240; 12.BF.7.244; 12.BF.7.243; 12.BF.7.247; 12.BF.15.157; 12.BF.15.158; 12.BF.15.196; 12.BF.15.223; 12.BF.15.240; 12.BF.15.244; 12.BF.15.243; 12.BF.15.247; 12.BF.16.157; 12.BF.16.158; 12.BF.16.196; 12.BF.16.223; 12.BF.16.240; 12.BF.16.244; 12.BF.16.243; 12.BF.16.247; 12.BF.18.157; 12.BF.18.158; 12.BF.18.196; 12.BF.18.223; 12.BF.18.240; 12.BF.18.244; 12.BF.18.243; 12.BF.18.247; 12.BF.26.157; 12.BF.26.158; 12.BF.26.196; 12.BF.26.223; 12.BF.26.240; 12.BF.26.244; 12.BF.26.243; 12.BF.26.247; 12.BF.27.157; 12.BF.27.158; 12.BF.27.196; 12.BF.27.223; 12.BF.27.240; 12.BF.27.244; 12.BF.27.243; 12.BF.27.247; 12.BF.29.157; 12.BF.29.158; 12.BF.29.196; 12.BF.29.223; 12.BF.29.240; 12.BF.29.244; 12.BF.29.243; 12.BF.29.247; 12.BF.54.157; 12.BF.54.158; 12.BF.54.196; 12.BF.54.223; 12.BF.54.240; 12.BF.54.244; 12.BF.54.243; 12.BF.54.247; 12.BF.55.157; 12.BF.55.158; 12.BF.55.196; 12.BF.55.223; 12.BF.55.240; 12.BF.55.244; 12.BF.55.243; 12.BF.55.247; 12.BF.56.157; 12.BF.56.158; 12.BF.56.196; 12.BF.56.223; 12.BF.56.240; 12.BF.56.244; 12.BF.56.243; 12.BF.56.247; 12.BF.157.157; 12.BF.157.158; 12.BF.157.196; 12.BF.157.223; 12.BF.157.240; 12.BF.157.244; 12.BF.157.243; 12.BF.157.247; 12.BF.196.157; 12.BF.196.158; 12.BF.196.196; 12.BF.196.223; 12.BF.196.240; 12.BF.196.244; 12.BF.196.243; 12.BF.196.247; 12.BF.223.157; 12.BF.223.158; 12.BF.223.196; 12.BF.223.223; 12.BF.223.240; 12.BF.223.244; 12.BF.223.243; 12.BF.223.247; 12.BF.240.157; 12.BF.240.158; 12.BF.240.196; 12.BF.240.223; 12.BF.240.240; |

TABLE 100-continued

12.BF.240.244; 12.BF.240.243; 12.BF.240.247; 12.BF.244.157; 12.BF.244.158; 12.BF.244.196; 12.BF.244.223; 12.BF.244.240; 12.BF.244.244; 12.BF.244.243; 12.BF.244.247; 12.BF.247.157; 12.BF.247.158; 12.BF.247.196; 12.BF.247.223; 12.BF.247.240; 12.BF.247.244; 12.BF.247.243; 12.BF.247.247;

Prodrugs of 12.CI

12.CI.4.157; 12.CI.4.158; 12.CI.4.196; 12.CI.4.223; 12.CI.4.240; 12.CI.4.244; 12.CI.4.243; 12.CI.4.247; 12.CI.5.157; 12.CI.5.158; 12.CI.5.196; 12.CI.5.223; 12.CI.5.240; 12.CI.5.244; 12.CI.5.243; 12.CI.5.247; 12.CI.7.157; 12.CI.7.158; 12.CI.7.196; 12.CI.7.223; 12.CI.7.240; 12.CI.7.244; 12.CI.7.243; 12.CI.7.247; 12.CI.15.157; 12.CI.15.158; 12.CI.15.196; 12.CI.15.223; 12.CI.15.240; 12.CI.15.244; 12.CI.15.243; 12.CI.15.247; 12.CI.16.157; 12.CI.16.158; 12.CI.16.196; 12.CI.16.223; 12.CI.16.240; 12.CI.16.244; 12.CI.16.243; 12.CI.16.247; 12.CI.18.157; 12.CI.18.158; 12.CI.18.196; 12.CI.18.223; 12.CI.18.240; 12.CI.18.244; 12.CI.18.243; 12.CI.18.247; 12.CI.26.157; 12.CI.26.158; 12.CI.26.196; 12.CI.26.223; 12.CI.26.240; 12.CI.26.244; 12.CI.26.243; 12.CI.26.247; 12.CI.27.157; 12.CI.27.158; 12.CI.27.196; 12.CI.27.223; 12.CI.27.240; 12.CI.27.244; 12.CI.27.243; 12.CI.27.247; 12.CI.29.157; 12.CI.29.158; 12.CI.29.196; 12.CI.29.223; 12.CI.29.240; 12.CI.29.244; 12.CI.29.243; 12.CI.29.247; 12.CI.54.157; 12.CI.54.158; 12.CI.54.196; 12.CI.54.223; 12.CI.54.240; 12.CI.54.244; 12.CI.54.243; 12.CI.54.247; 12.CI.55.157; 12.CI.55.158; 12.CI.55.196; 12.CI.55.223; 12.CI.55.240; 12.CI.55.244; 12.CI.55.243; 12.CI.55.247; 12.CI.56.157; 12.CI.56.158; 12.CI.56.196; 12.CI.56.223; 12.CI.56.240; 12.CI.56.244; 12.CI.56.243; 12.CI.56.247; 12.CI.157.157; 12.CI.157.158; 12.CI.157.196; 12.CI.157.223; 12.CI.157.240; 12.CI.157.244; 12.CI.157.243; 12.CI.157.247; 12.CI.196.157; 12.CI.196.158; 12.CI.196.196; 12.CI.196.223; 12.CI.196.240; 12.CI.196.244; 12.CI.196.243; 12.CI.196.247; 12.CI.223.157; 12.CI.223.158; 12.CI.223.196; 12.CI.223.223; 12.CI.223.240; 12.CI.223.244; 12.CI.223.243; 12.CI.223.247; 12.CI.240.157; 12.CI.240.158; 12.CI.240.196; 12.CI.240.223; 12.CI.240.240; 12.CI.240.244; 12.CI.240.243; 12.CI.240.247; 12.CI.244.157; 12.CI.244.158; 12.CI.244.196; 12.CI.244.223; 12.CI.244.240; 12.CI.244.244; 12.CI.244.243; 12.CI.244.247; 12.CI.247.157; 12.CI.247.158; 12.CI.247.196; 12.CI.247.223; 12.CI.247.240; 12.CI.247.244; 12.CI.247.243; 12.CI.247.247;

Prodrugs of 12.CO

12.CO.4.157; 12.CO.4.158; 12.CO.4.196; 12.CO.4.223; 12.CO.4.240; 12.CO.4.244; 12.CO.4.243; 12.CO.4.247; 12.CO.5.157; 12.CO.5.158; 12.CO.5.196; 12.CO.5.223; 12.CO.5.240; 12.CO.5.244; 12.CO.5.243; 12.CO.5.247; 12.CO.7.157; 12.CO.7.158; 12.CO.7.196; 12.CO.7.223; 12.CO.7.240; 12.CO.7.244; 12.CO.7.243; 12.CO.7.247; 12.CO.15.157; 12.CO.15.158; 12.CO.15.196; 12.CO.15.223; 12.CO.15.240; 12.CO.15.244; 12.CO.15.243; 12.CO.15.247; 12.CO.16.157; 12.CO.16.158; 12.CO.16.196; 12.CO.16.223; 12.CO.16.240; 12.CO.16.244; 12.CO.16.243; 12.CO.16.247; 12.CO.18.157; 12.CO.18.158; 12.CO.18.196; 12.CO.18.223; 12.CO.18.240; 12.CO.18.244; 12.CO.18.243; 12.CO.18.247; 12.CO.26.157; 12.CO.26.158; 12.CO.26.196; 12.CO.26.223; 12.CO.26.240; 12.CO.26.244; 12.CO.26.243; 12.CO.26.247; 12.CO.27.157; 12.CO.27.158; 12.CO.27.196; 12.CO.27.223; 12.CO.27.240; 12.CO.27.244; 12.CO.27.243; 12.CO.27.247; 12.CO.29.157; 12.CO.29.158; 12.CO.29.196; 12.CO.29.223; 12.CO.29.240; 12.CO.29.244; 12.CO.29.243; 12.CO.29.247; 12.CO.54.157; 12.CO.54.158; 12.CO.54.196; 12.CO.54.223; 12.CO.54.240; 12.CO.54.244; 12.CO.54.243; 12.CO.54.247; 12.CO.55.157; 12.CO.55.158; 12.CO.55.196; 12.CO.55.223; 12.CO.55.240; 12.CO.55.244; 12.CO.55.243; 12.CO.55.247; 12.CO.56.157; 12.CO.56.158; 12.CO.56.196; 12.CO.56.223; 12.CO.56.240; 12.CO.56.244; 12.CO.56.243; 12.CO.56.247; 12.CO.157.157; 12.CO.157.158; 12.CO.157.196; 12.CO.157.223; 12.CO.157.240; 12.CO.157.244; 12.CO.157.243; 12.CO.157.247; 12.CO.196.157; 12.CO.196.158; 12.CO.196.196; 12.CO.196.223; 12.CO.196.240; 12.CO.196.244; 12.CO.196.243; 12.CO.196.247; 12.CO.223.157; 12.CO.223.158; 12.CO.223.196; 12.CO.223.223; 12.CO.223.240; 12.CO.223.244; 12.CO.223.243; 12.CO.223.247; 12.CO.240.157; 12.CO.240.158; 12.CO.240.196; 12.CO.240.223; 12.CO.240.240; 12.CO.240.244; 12.CO.240.243; 12.CO.240.247; 12.CO.244.157; 12.CO.244.158; 12.CO.244.196; 12.CO.244.223; 12.CO.244.240; 12.CO.244.244; 12.CO.244.243; 12.CO.244.247; 12.CO.247.157; 12.CO.247.158; 12.CO.247.196; 12.CO.247.223; 12.CO.247.240; 12.CO.247.244; 12.CO.247.243; 12.CO.247.247.

Prodrugs of 13.B

13.B.228.228; 13.B.228.229; 13.B.228.230; 13.B.228.231; 13.B.228.236; 13.B.228.237; 13.B.228.238; 13.B.228.239; 13.B.228.154; 13.B.228.157; 13.B.228.166; 13.B.228.169; 13.B.228.172; 13.B.228.175; 13.B.228.240; 13.B.228.244; 13.B.229.228; 13.B.229.229; 13.B.229.230; 13.B.229.231; 13.B.229.236; 13.B.229.237; 13.B.229.238; 13.B.229.239; 13.B.229.154; 13.B.229.157; 13.B.229.166; 13.B.229.169; 13.B.229.172; 13.B.229.175; 13.B.229.240; 13.B.229.244; 13.B.230.228; 13.B.230.229; 13.B.230.230; 13.B.230.231; 13.B.230.236; 13.B.230.237; 13.B.230.238; 13.B.230.239; 13.B.230.154; 13.B.230.157; 13.B.230.166; 13.B.230.169; 13.B.230.172;

TABLE 100-continued

13.B.230.175; 13.B.230.240; 13.B.230.244; 13.B.231.228; 13.B.231.229; 13.B.231.230; 13.B.231.231; 13.B.231.236; 13.B.231.237; 13.B.231.238; 13.B.231.239; 13.B.231.154; 13.B.231.157; 13.B.231.166; 13.B.231.169; 13.B.231.172; 13.B.231.175; 13.B.231.240; 13.B.231.244; 13.B.236.228; 13.B.236.229; 13.B.236.230; 13.B.236.231; 13.B.236.236; 13.B.236.237; 13.B.236.238; 13.B.236.239; 13.B.236.154; 13.B.236.157; 13.B.236.166; 13.B.236.169; 13.B.236.172; 13.B.236.175; 13.B.236.240; 13.B.236.244; 13.B.237.228; 13.B.237.229; 13.B.237.230; 13.B.237.231; 13.B.237.236; 13.B.237.237; 13.B.237.238; 13.B.237.239; 13.B.237.154; 13.B.237.157; 13.B.237.166; 13.B.237.169; 13.B.237.172; 13.B.237.175; 13.B.237.240; 13.B.237.244; 13.B.238.228; 13.B.238.229; 13.B.238.230; 13.B.238.231; 13.B.238.236; 13.B.238.237; 13.B.238.238; 13.B.238.239; 13.B.238.154; 13.B.238.157; 13.B.238.166; 13.B.238.169; 13.B.238.172; 13.B.238.175; 13.B.238.240; 13.B.238.244; 13.B.239.228; 13.B.239.229; 13.B.239.230; 13.B.239.231; 13.B.239.236; 13.B.239.237; 13.B.239.238; 13.B.239.239; 13.B.239.154; 13.B.239.157; 13.B.239.166; 13.B.239.169; 13.B.239.172; 13.B.239.175; 13.B.239.240; 13.B.239.244; 13.B.154.228; 13.B.154.229; 13.B.154.230; 13.B.154.231; 13.B.154.236; 13.B.154.237; 13.B.154.238; 13.B.154.239; 13.B.154.154; 13.B.154.157; 13.B.154.166; 13.B.154.169; 13.B.154.172; 13.B.154.175; 13.B.154.240; 13.B.154.244; 13.B.157.228; 13.B.157.229; 13.B.157.230; 13.B.157.231; 13.B.157.236; 13.B.157.237; 13.B.157.238; 13.B.157.239; 13.B.157.154; 13.B.157.157; 13.B.157.166; 13.B.157.169; 13.B.157.172; 13.B.157.175; 13.B.157.240; 13.B.157.244; 13.B.166.228; 13.B.166.229; 13.B.166.230; 13.B.166.231; 13.B.166.236; 13.B.166.237; 13.B.166.238; 13.B.166.239; 13.B.166.154; 13.B.166.157; 13.B.166.166; 13.B.166.169; 13.B.166.172; 13.B.166.175; 13.B.166.240; 13.B.166.244; 13.B.169.228; 13.B.169.229; 13.B.169.230; 13.B.169.231; 13.B.169.236; 13.B.169.237; 13.B.169.238; 13.B.169.239; 13.B.169.154; 13.B.169.157; 13.B.169.166; 13.B.169.169; 13.B.169.172; 13.B.169.175; 13.B.169.240; 13.B.169.244; 13.B.172.228; 13.B.172.229; 13.B.172.230; 13.B.172.231; 13.B.172.236; 13.B.172.237; 13.B.172.238; 13.B.172.239; 13.B.172.154; 13.B.172.157; 13.B.172.166; 13.B.172.169; 13.B.172.172; 13.B.172.175; 13.B.172.240; 13.B.172.244; 13.B.175.228; 13.B.175.229; 13.B.175.230; 13.B.175.231; 13.B.175.236; 13.B.175.237; 13.B.175.238; 13.B.175.239; 13.B.175.154; 13.B.175.157; 13.B.175.166; 13.B.175.169; 13.B.175.172; 13.B.175.175; 13.B.175.240; 13.B.175.244; 13.B.240.228; 13.B.240.229; 13.B.240.230; 13.B.240.231; 13.B.240.236; 13.B.240.237; 13.B.240.238; 13.B.240.239; 13.B.240.154; 13.B.240.157; 13.B.240.166; 13.B.240.169; 13.B.240.172; 13.B.240.175; 13.B.240.240; 13.B.240.244; 13.B.244.228; 13.B.244.229; 13.B.244.230; 13.B.244.231; 13.B.244.236; 13.B.244.237; 13.B.244.238; 13.B.244.239; 13.B.244.154; 13.B.244.157; 13.B.244.166; 13.B.244.169; 13.B.244.172; 13.B.244.175; 13.B.244.240; 13.B.244.244;

Prodrugs of 13.D

13.D.228.228; 13.D.228.229; 13.D.228.230; 13.D.228.231; 13.D.228.236; 13.D.228.237; 13.D.228.238; 13.D.228.239; 13.D.228.154; 13.D.228.157; 13.D.228.166; 13.D.228.169; 13.D.228.172; 13.D.228.175; 13.D.228.240; 13.D.228.244; 13.D.229.228; 13.D.229.229; 13.D.229.230; 13.D.229.231; 13.D.229.236; 13.D.229.237; 13.D.229.238; 13.D.229.239; 13.D.229.154; 13.D.229.157; 13.D.229.166; 13.D.229.169; 13.D.229.172; 13.D.229.175; 13.D.229.240; 13.D.229.244; 13.D.230.228; 13.D.230.229; 13.D.230.230; 13.D.230.231; 13.D.230.236; 13.D.230.237; 13.D.230.238; 13.D.230.239; 13.D.230.154; 13.D.230.157; 13.D.230.166; 13.D.230.169; 13.D.230.172; 13.D.230.175; 13.D.230.240; 13.D.230.244; 13.D.231.228; 13.D.231.229; 13.D.231.230; 13.D.231.231; 13.D.231.236; 13.D.231.237; 13.D.231.238; 13.D.231.239; 13.D.231.154; 13.D.231.157; 13.D.231.166; 13.D.231.169; 13.D.231.172; 13.D.231.175; 13.D.231.240; 13.D.231.244; 13.D.236.228; 13.D.236.229; 13.D.236.230; 13.D.236.231; 13.D.236.236; 13.D.236.237; 13.D.236.238; 13.D.236.239; 13.D.236.154; 13.D.236.157; 13.D.236.166; 13.D.236.169; 13.D.236.172; 13.D.236.175; 13.D.236.240; 13.D.236.244; 13.D.237.228; 13.D.237.229; 13.D.237.230; 13.D.237.231; 13.D.237.236; 13.D.237.237; 13.D.237.238; 13.D.237.239; 13.D.237.154; 13.D.237.157; 13.D.237.166; 13.D.237.169; 13.D.237.172; 13.D.237.175; 13.D.237.240; 13.D.237.244; 13.D.238.228; 13.D.238.229; 13.D.238.230; 13.D.238.231; 13.D.238.236; 13.D.238.237; 13.D.238.238; 13.D.238.239; 13.D.238.154; 13.D.238.157; 13.D.238.166; 13.D.238.169; 13.D.238.172; 13.D.238.175; 13.D.238.240; 13.D.238.244; 13.D.239.228; 13.D.239.229; 13.D.239.230; 13.D.239.231; 13.D.239.236; 13.D.239.237; 13.D.239.238; 13.D.239.239; 13.D.239.154; 13.D.239.157; 13.D.239.166; 13.D.239.169; 13.D.239.172; 13.D.239.175; 13.D.239.240; 13.D.239.244; 13.D.154.228; 13.D.154.229; 13.D.154.230; 13.D.154.231; 13.D.154.236; 13.D.154.237; 13.D.154.238; 13.D.154.239; 13.D.154.154; 13.D.154.157; 13.D.154.166; 13.D.154.169; 13.D.154.172; 13.D.154.175; 13.D.154.240; 13.D.154.244; 13.D.157.228; 13.D.157.229; 13.D.157.230; 13.D.157.231; 13.D.157.236; 13.D.157.237; 13.D.157.238; 13.D.157.239; 13.D.157.154; 13.D.157.157; 13.D.157.166; 13.D.157.169; 13.D.157.172; 13.D.157.175; 13.D.157.240; 13.D.157.244; 13.D.166.228; 13.D.166.229; 13.D.166.230; 13.D.166.231; 13.D.166.236; 13.D.166.237; 13.D.166.238; 13.D.166.239; 13.D.166.154; 13.D.166.157; 13.D.166.166; 13.D.166.169; 13.D.166.172; 13.D.166.175; 13.D.166.240; 13.D.166.244; 13.D.169.228; 13.D.169.229; 13.D.169.230; 13.D.169.231;

TABLE 100-continued

| |
|---|
| 13.D.169.236; 13.D.169.237; 13.D.169.238; 13.D.169.239; 13.D.169.154; 13.D.169.157; 13.D.169.166; 13.D.169.169; 13.D.169.172; 13.D.169.175; 13.D.169.240; 13.D.169.244; 13.D.172.228; 13.D.172.229; 13.D.172.230; 13.D.172.231; 13.D.172.236; 13.D.172.237; 13.D.172.238; 13.D.172.239; 13.D.172.154; 13.D.172.157; 13.D.172.166; 13.D.172.169; 13.D.172.172; 13.D.172.175; 13.D.172.240; 13.D.172.244; 13.D.175.228; 13.D.175.229; 13.D.175.230; 13.D.175.231; 13.D.175.236; 13.D.175.237; 13.D.175.238; 13.D.175.239; 13.D.175.154; 13.D.175.157; 13.D.175.166; 13.D.175.169; 13.D.175.172; 13.D.175.175; 13.D.175.240; 13.D.175.244; 13.D.240.228; 13.D.240.229; 13.D.240.230; 13.D.240.231; 13.D.240.236; 13.D.240.237; 13.D.240.238; 13.D.240.239; 13.D.240.154; 13.D.240.157; 13.D.240.166; 13.D.240.169; 13.D.240.172; 13.D.240.175; 13.D.240.240; 13.D.240.244; 13.D.244.228; 13.D.244.229; 13.D.244.230; 13.D.244.231; 13.D.244.236; 13.D.244.237; 13.D.244.238; 13.D.244.239; 13.D.244.154; 13.D.244.157; 13.D.244.166; 13.D.244.169; 13.D.244.172; 13.D.244.175; 13.D.244.240; 13.D.244.244; |
| Prodrugs of 13.E |
| 13.E.228.228; 13.E.228.229; 13.E.228.230; 13.E.228.231; 13.E.228.236; 13.E.228.237; 13.E.228.238; 13.E.228.239; 13.E.228.154; 13.E.228.157; 13.E.228.166; 13.E.228.169; 13.E.228.172; 13.E.228.175; 13.E.228.240; 13.E.228.244; 13.E.229.228; 13.E.229.229; 13.E.229.230; 13.E.229.231; 13.E.229.236; 13.E.229.237; 13.E.229.238; 13.E.229.239; 13.E.229.154; 13.E.229.157; 13.E.229.166; 13.E.229.169; 13.E.229.172; 13.E.229.175; 13.E.229.240; 13.E.229.244; 13.E.230.228; 13.E.230.229; 13.E.230.230; 13.E.230.231; 13.E.230.236; 13.E.230.237; 13.E.230.238; 13.E.230.239; 13.E.230.154; 13.E.230.157; 13.E.230.166; 13.E.230.169; 13.E.230.172; 13.E.230.175; 13.E.230.240; 13.E.230.244; 13.E.231.228; 13.E.231.229; 13.E.231.230; 13.E.231.231; 13.E.231.236; 13.E.231.237; 13.E.231.238; 13.E.231.239; 13.E.231.154; 13.E.231.157; 13.E.231.166; 13.E.231.169; 13.E.231.172; 13.E.231.175; 13.E.231.240; 13.E.231.244; 13.E.236.228; 13.E.236.229; 13.E.236.230; 13.E.236.231; 13.E.236.236; 13.E.236.237; 13.E.236.238; 13.E.236.239; 13.E.236.154; 13.E.236.157; 13.E.236.166; 13.E.236.169; 13.E.236.172; 13.E.236.175; 13.E.236.240; 13.E.236.244; 13.E.237.228; 13.E.237.229; 13.E.237.230; 13.E.237.231; 13.E.237.236; 13.E.237.237; 13.E.237.238; 13.E.237.239; 13.E.237.154; 13.E.237.157; 13.E.237.166; 13.E.237.169; 13.E.237.172; 13.E.237.175; 13.E.237.240; 13.E.237.244; 13.E.238.228; 13.E.238.229; 13.E.238.230; 13.E.238.231; 13.E.238.236; 13.E.238.237; 13.E.238.238; 13.E.238.239; 13.E.238.154; 13.E.238.157; 13.E.238.166; 13.E.238.169; 13.E.238.172; 13.E.238.175; 13.E.238.240; 13.E.238.244; 13.E.239.228; 13.E.239.229; 13.E.239.230; 13.E.239.231; 13.E.239.236; 13.E.239.237; 13.E.239.238; 13.E.239.239; 13.E.239.154; 13.E.239.157; 13.E.239.166; 13.E.239.169; 13.E.239.172; 13.E.239.175; 13.E.239.240; 13.E.239.244; 13.E.154.228; 13.E.154.229; 13.E.154.230; 13.E.154.231; 13.E.154.236; 13.E.154.237; 13.E.154.238; 13.E.154.239; 13.E.154.154; 13.E.154.157; 13.E.154.166; 13.E.154.169; 13.E.154.172; 13.E.154.175; 13.E.154.240; 13.E.154.244; 13.E.157.228; 13.E.157.229; 13.E.157.230; 13.E.157.231; 13.E.157.236; 13.E.157.237; 13.E.157.238; 13.E.157.239; 13.E.157.154; 13.E.157.157; 13.E.157.166; 13.E.157.169; 13.E.157.172; 13.E.157.175; 13.E.157.240; 13.E.157.244; 13.E.166.228; 13.E.166.229; 13.E.166.230; 13.E.166.231; 13.E.166.236; 13.E.166.237; 13.E.166.238; 13.E.166.239; 13.E.166.154; 13.E.166.157; 13.E.166.166; 13.E.166.169; 13.E.166.172; 13.E.166.175; 13.E.166.240; 13.E.166.244; 13.E.169.228; 13.E.169.229; 13.E.169.230; 13.E.169.231; 13.E.169.236; 13.E.169.237; 13.E.169.238; 13.E.169.239; 13.E.169.154; 13.E.169.157; 13.E.169.166; 13.E.169.169; 13.E.169.172; 13.E.169.175; 13.E.169.240; 13.E.169.244; 13.E.172.228; 13.E.172.229; 13.E.172.230; 13.E.172.231; 13.E.172.236; 13.E.172.237; 13.E.172.238; 13.E.172.239; 13.E.172.154; 13.E.172.157; 13.E.172.166; 13.E.172.169; 13.E.172.172; 13.E.172.175; 13.E.172.240; 13.E.172.244; 13.E.175.228; 13.E.175.229; 13.E.175.230; 13.E.175.231; 13.E.175.236; 13.E.175.237; 13.E.175.238; 13.E.175.239; 13.E.175.154; 13.E.175.157; 13.E.175.166; 13.E.175.169; 13.E.175.172; 13.E.175.175; 13.E.175.240; 13.E.175.244; 13.E.240.228; 13.E.240.229; 13.E.240.230; 13.E.240.231; 13.E.240.236; 13.E.240.237; 13.E.240.238; 13.E.240.239; 13.E.240.154; 13.E.240.157; 13.E.240.166; 13.E.240.169; 13.E.240.172; 13.E.240.175; 13.E.240.240; 13.E.240.244; 13.E.244.228; 13.E.244.229; 13.E.244.230; 13.E.244.231; 13.E.244.236; 13.E.244.237; 13.E.244.238; 13.E.244.239; 13.E.244.154; 13.E.244.157; 13.E.244.166; 13.E.244.169; 13.E.244.172; 13.E.244.175; 13.E.244.240; 13.E.244.244; |
| Prodrugs of 13.G |
| 13.G.228.228; 13.G.228.229; 13.G.228.230; 13.G.228.231; 13.G.228.236; 13.G.228.237; 13.G.228.238; 13.G.228.239; 13.G.228.154; 13.G.228.157; 13.G.228.166; 13.G.228.169; 13.G.228.172; 13.G.228.175; 13.G.228.240; 13.G.228.244; 13.G.229.228; 13.G.229.229; 13.G.229.230; 13.G.229.231; 13.G.229.236; 13.G.229.237; 13.G.229.238; 13.G.229.239; 13.G.229.154; 13.G.229.157; 13.G.229.166; 13.G.229.169; 13.G.229.172; 13.G.229.175; 13.G.229.240; 13.G.229.244; 13.G.230.228; 13.G.230.229; 13.G.230.230; 13.G.230.231; 13.G.230.236; 13.G.230.237; 13.G.230.238; 13.G.230.239; 13.G.230.154; 13.G.230.157; 13.G.230.166; 13.G.230.169; 13.G.230.172; |

TABLE 100-continued

13.G.230.175; 13.G.230.240; 13.G.230.244; 13.G.231.228; 13.G.231.229;
13.G.231.230; 13.G.231.231; 13.G.231.236; 13.G.231.237; 13.G.231.238;
13.G.231.239; 13.G.231.154; 13.G.231.157; 13.G.231.166; 13.G.231.169;
13.G.231.172; 13.G.231.175; 13.G.231.240; 13.G.231.244; 13.G.236.228;
13.G.236.229; 13.G.236.230; 13.G.236.231; 13.G.236.236; 13.G.236.237;
13.G.236.238; 13.G.236.239; 13.G.236.154; 13.G.236.157; 13.G.236.166;
13.G.236.169; 13.G.236.172; 13.G.236.175; 13.G.236.240; 13.G.236.244;
13.G.237.228; 13.G.237.229; 13.G.237.230; 13.G.237.231; 13.G.237.236;
13.G.237.237; 13.G.237.238; 13.G.237.239; 13.G.237.154; 13.G.237.157;
13.G.237.166; 13.G.237.169; 13.G.237.172; 13.G.237.175; 13.G.237.240;
13.G.237.244; 13.G.238.228; 13.G.238.229; 13.G.238.230; 13.G.238.231;
13.G.238.236; 13.G.238.237; 13.G.238.238; 13.G.238.239; 13.G.238.154;
13.G.238.157; 13.G.238.166; 13.G.238.169; 13.G.238.172; 13.G.238.175;
13.G.238.240; 13.G.238.244; 13.G.239.228; 13.G.239.229; 13.G.239.230;
13.G.239.231; 13.G.239.236; 13.G.239.237; 13.G.239.238; 13.G.239.239;
13.G.239.154; 13.G.239.157; 13.G.239.166; 13.G.239.169; 13.G.239.172;
13.G.239.175; 13.G.239.240; 13.G.239.244; 13.G.154.228; 13.G.154.229;
13.G.154.230; 13.G.154.231; 13.G.154.236; 13.G.154.237; 13.G.154.238;
13.G.154.239; 13.G.154.154; 13.G.154.157; 13.G.154.166; 13.G.154.169;
13.G.154.172; 13.G.154.175; 13.G.154.240; 13.G.154.244; 13.G.157.228;
13.G.157.229; 13.G.157.230; 13.G.157.231; 13.G.157.236; 13.G.157.237;
13.G.157.238; 13.G.157.239; 13.G.157.154; 13.G.157.157; 13.G.157.166;
13.G.157.169; 13.G.157.172; 13.G.157.175; 13.G.157.240; 13.G.157.244;
13.G.166.228; 13.G.166.229; 13.G.166.230; 13.G.166.231; 13.G.166.236;
13.G.166.237; 13.G.166.238; 13.G.166.239; 13.G.166.154; 13.G.166.157;
13.G.166.166; 13.G.166.169; 13.G.166.172; 13.G.166.175; 13.G.166.240;
13.G.166.244; 13.G.169.228; 13.G.169.229; 13.G.169.230; 13.G.169.231;
13.G.169.236; 13.G.169.237; 13.G.169.238; 13.G.169.239; 13.G.169.154;
13.G.169.157; 13.G.169.166; 13.G.169.169; 13.G.169.172; 13.G.169.175;
13.G.169.240; 13.G.169.244; 13.G.172.228; 13.G.172.229; 13.G.172.230;
13.G.172.231; 13.G.172.236; 13.G.172.237; 13.G.172.238; 13.G.172.239;
13.G.172.154; 13.G.172.157; 13.G.172.166; 13.G.172.169; 13.G.172.172;
13.G.172.175; 13.G.172.240; 13.G.172.244; 13.G.175.228; 13.G.175.229;
13.G.175.230; 13.G.175.231; 13.G.175.236; 13.G.175.237; 13.G.175.238;
13.G.175.239; 13.G.175.154; 13.G.175.157; 13.G.175.166; 13.G.175.169;
13.G.175.172; 13.G.175.175; 13.G.175.240; 13.G.175.244; 13.G.240.228;
13.G.240.229; 13.G.240.230; 13.G.240.231; 13.G.240.236; 13.G.240.237;
13.G.240.238; 13.G.240.239; 13.G.240.154; 13.G.240.157; 13.G.240.166;
13.G.240.169; 13.G.240.172; 13.G.240.175; 13.G.240.240; 13.G.240.244;
13.G.244.228; 13.G.244.229; 13.G.244.230; 13.G.244.231; 13.G.244.236;
13.G.244.237; 13.G.244.238; 13.G.244.239; 13.G.244.154; 13.G.244.157;
13.G.244.166; 13.G.244.169; 13.G.244.172; 13.G.244.175; 13.G.244.240; 13.G.244.244;

Prodrugs of 13.I

13.I.228.228; 13.I.228.229; 13.I.228.230; 13.I.228.231; 13.I.228.236;
13.I.228.237; 13.I.228.238; 13.I.228.239; 13.I.228.154; 13.I.228.157;
13.I.228.166; 13.I.228.169; 13.I.228.172; 13.I.228.175; 13.I.228.240;
13.I.228.244; 13.I.229.228; 13.I.229.229; 13.I.229.230; 13.I.229.231;
13.I.229.236; 13.I.229.237; 13.I.229.238; 13.I.229.239; 13.I.229.154;
13.I.229.157; 13.I.229.166; 13.I.229.169; 13.I.229.172; 13.I.229.175;
13.I.229.240; 13.I.229.244; 13.I.230.228; 13.I.230.229; 13.I.230.230;
13.I.230.231; 13.I.230.236; 13.I.230.237; 13.I.230.238; 13.I.230.239;
13.I.230.154; 13.I.230.157; 13.I.230.166; 13.I.230.169; 13.I.230.172;
13.I.230.175; 13.I.230.240; 13.I.230.244; 13.I.231.228; 13.I.231.229;
13.I.231.230; 13.I.231.231; 13.I.231.236; 13.I.231.237; 13.I.231.238;
13.I.231.239; 13.I.231.154; 13.I.231.157; 13.I.231.166; 13.I.231.169;
13.I.231.172; 13.I.231.175; 13.I.231.240; 13.I.231.244; 13.I.236.228;
13.I.236.229; 13.I.236.230; 13.I.236.231; 13.I.236.236; 13.I.236.237;
13.I.236.238; 13.I.236.239; 13.I.236.154; 13.I.236.157; 13.I.236.166;
13.I.236.169; 13.I.236.172; 13.I.236.175; 13.I.236.240; 13.I.236.244;
13.I.237.228; 13.I.237.229; 13.I.237.230; 13.I.237.231; 13.I.237.236;
13.I.237.237; 13.I.237.238; 13.I.237.239; 13.I.237.154; 13.I.237.157;
13.I.237.166; 13.I.237.169; 13.I.237.172; 13.I.237.175; 13.I.237.240;
13.I.237.244; 13.I.238.228; 13.I.238.229; 13.I.238.230; 13.I.238.231;
13.I.238.236; 13.I.238.237; 13.I.238.238; 13.I.238.239; 13.I.238.154;
13.I.238.157; 13.I.238.166; 13.I.238.169; 13.I.238.172; 13.I.238.175;
13.I.238.240; 13.I.238.244; 13.I.239.228; 13.I.239.229; 13.I.239.230;
13.I.239.231; 13.I.239.236; 13.I.239.237; 13.I.239.238; 13.I.239.239;
13.I.239.154; 13.I.239.157; 13.I.239.166; 13.I.239.169; 13.I.239.172;
13.I.239.175; 13.I.239.240; 13.I.239.244; 13.I.154.228; 13.I.154.229;
13.I.154.230; 13.I.154.231; 13.I.154.236; 13.I.154.237; 13.I.154.238;
13.I.154.239; 13.I.154.154; 13.I.154.157; 13.I.154.166; 13.I.154.169;
13.I.154.172; 13.I.154.175; 13.I.154.240; 13.I.154.244; 13.I.157.228;
13.I.157.229; 13.I.157.230; 13.I.157.231; 13.I.157.236; 13.I.157.237;
13.I.157.238; 13.I.157.239; 13.I.157.154; 13.I.157.157; 13.I.157.166;
13.I.157.169; 13.I.157.172; 13.I.157.175; 13.I.157.240; 13.I.157.244;
13.I.166.228; 13.I.166.229; 13.I.166.230; 13.I.166.231; 13.I.166.236;
13.I.166.237; 13.I.166.238; 13.I.166.239; 13.I.166.154; 13.I.166.157;
13.I.166.166; 13.I.166.169; 13.I.166.172; 13.I.166.175; 13.I.166.240;
13.I.166.244; 13.I.169.228; 13.I.169.229; 13.I.169.230; 13.I.169.231;

TABLE 100-continued

| |
|---|
| 13.I.169.236; 13.I.169.237; 13.I.169.238; 13.I.169.239; 13.I.169.154; 13.I.169.157; 13.I.169.166; 13.I.169.169; 13.I.169.172; 13.I.169.175; 13.I.169.240; 13.I.169.244; 13.I.172.228; 13.I.172.229; 13.I.172.230; 13.I.172.231; 13.I.172.236; 13.I.172.237; 13.I.172.238; 13.I.172.239; 13.I.172.154; 13.I.172.157; 13.I.172.166; 13.I.172.169; 13.I.172.172; 13.I.172.175; 13.I.172.240; 13.I.172.244; 13.I.175.228; 13.I.175.229; 13.I.175.230; 13.I.175.231; 13.I.175.236; 13.I.175.237; 13.I.175.238; 13.I.175.239; 13.I.175.154; 13.I.175.157; 13.I.175.166; 13.I.175.169; 13.I.175.172; 13.I.175.175; 13.I.175.240; 13.I.175.244; 13.I.240.228; 13.I.240.229; 13.I.240.230; 13.I.240.231; 13.I.240.236; 13.I.240.237; 13.I.240.238; 13.I.240.239; 13.I.240.154; 13.I.240.157; 13.I.240.166; 13.I.240.169; 13.I.240.172; 13.I.240.175; 13.I.240.240; 13.I.240.244; 13.I.244.228; 13.I.244.229; 13.I.244.230; 13.I.244.231; 13.I.244.236; 13.I.244.237; 13.I.244.238; 13.I.244.239; 13.I.244.154; 13.I.244.157; 13.I.244.166; 13.I.244.169; 13.I.244.172; 13.I.244.175; 13.I.244.240; 13.I.244.244; |
| Prodrugs of 13.J |
| 13.J.228.228; 13.J.228.229; 13.J.228.230; 13.J.228.231; 13.J.228.236; 13.J.228.237; 13.J.228.238; 13.J.228.239; 13.J.228.154; 13.J.228.157; 13.J.228.166; 13.J.228.169; 13.J.228.172; 13.J.228.175; 13.J.228.240; 13.J.228.244; 13.J.229.228; 13.J.229.229; 13.J.229.230; 13.J.229.231; 13.J.229.236; 13.J.229.237; 13.J.229.238; 13.J.229.239; 13.J.229.154; 13.J.229.157; 13.J.229.166; 13.J.229.169; 13.J.229.172; 13.J.229.175; 13.J.229.240; 13.J.229.244; 13.J.230.228; 13.J.230.229; 13.J.230.230; 13.J.230.231; 13.J.230.236; 13.J.230.237; 13.J.230.238; 13.J.230.239; 13.J.230.154; 13.J.230.157; 13.J.230.166; 13.J.230.169; 13.J.230.172; 13.J.230.175; 13.J.230.240; 13.J.230.244; 13.J.231.228; 13.J.231.229; 13.J.231.230; 13.J.231.231; 13.J.231.236; 13.J.231.237; 13.J.231.238; 13.J.231.239; 13.J.231.154; 13.J.231.157; 13.J.231.166; 13.J.231.169; 13.J.231.172; 13.J.231.175; 13.J.231.240; 13.J.231.244; 13.J.236.228; 13.J.236.229; 13.J.236.230; 13.J.236.231; 13.J.236.236; 13.J.236.237; 13.J.236.238; 13.J.236.239; 13.J.236.154; 13.J.236.157; 13.J.236.166; 13.J.236.169; 13.J.236.172; 13.J.236.175; 13.J.236.240; 13.J.236.244; 13.J.237.228; 13.J.237.229; 13.J.237.230; 13.J.237.231; 13.J.237.236; 13.J.237.237; 13.J.237.238; 13.J.237.239; 13.J.237.154; 13.J.237.157; 13.J.237.166; 13.J.237.169; 13.J.237.172; 13.J.237.175; 13.J.237.240; 13.J.237.244; 13.J.238.228; 13.J.238.229; 13.J.238.230; 13.J.238.231; 13.J.238.236; 13.J.238.237; 13.J.238.238; 13.J.238.239; 13.J.238.154; 13.J.238.157; 13.J.238.166; 13.J.238.169; 13.J.238.172; 13.J.238.175; 13.J.238.240; 13.J.238.244; 13.J.239.228; 13.J.239.229; 13.J.239.230; 13.J.239.231; 13.J.239.236; 13.J.239.237; 13.J.239.238; 13.J.239.239; 13.J.239.154; 13.J.239.157; 13.J.239.166; 13.J.239.169; 13.J.239.172; 13.J.239.175; 13.J.239.240; 13.J.239.244; 13.J.154.228; 13.J.154.229; 13.J.154.230; 13.J.154.231; 13.J.154.236; 13.J.154.237; 13.J.154.238; 13.J.154.239; 13.J.154.154; 13.J.154.157; 13.J.154.166; 13.J.154.169; 13.J.154.172; 13.J.154.175; 13.J.154.240; 13.J.154.244; 13.J.157.228; 13.J.157.229; 13.J.157.230; 13.J.157.231; 13.J.157.236; 13.J.157.237; 13.J.157.238; 13.J.157.239; 13.J.157.154; 13.J.157.157; 13.J.157.166; 13.J.157.169; 13.J.157.172; 13.J.157.175; 13.J.157.240; 13.J.157.244; 13.J.166.228; 13.J.166.229; 13.J.166.230; 13.J.166.231; 13.J.166.236; 13.J.166.237; 13.J.166.238; 13.J.166.239; 13.J.166.154; 13.J.166.157; 13.J.166.166; 13.J.166.169; 13.J.166.172; 13.J.166.175; 13.J.166.240; 13.J.166.244; 13.J.169.228; 13.J.169.229; 13.J.169.230; 13.J.169.231; 13.J.169.236; 13.J.169.237; 13.J.169.238; 13.J.169.239; 13.J.169.154; 13.J.169.157; 13.J.169.166; 13.J.169.169; 13.J.169.172; 13.J.169.175; 13.J.169.240; 13.J.169.244; 13.J.172.228; 13.J.172.229; 13.J.172.230; 13.J.172.231; 13.J.172.236; 13.J.172.237; 13.J.172.238; 13.J.172.239; 13.J.172.154; 13.J.172.157; 13.J.172.166; 13.J.172.169; 13.J.172.172; 13.J.172.175; 13.J.172.240; 13.J.172.244; 13.J.175.228; 13.J.175.229; 13.J.175.230; 13.J.175.231; 13.J.175.236; 13.J.175.237; 13.J.175.238; 13.J.175.239; 13.J.175.154; 13.J.175.157; 13.J.175.166; 13.J.175.169; 13.J.175.172; 13.J.175.175; 13.J.175.240; 13.J.175.244; 13.J.240.228; 13.J.240.229; 13.J.240.230; 13.J.240.231; 13.J.240.236; 13.J.240.237; 13.J.240.238; 13.J.240.239; 13.J.240.154; 13.J.240.157; 13.J.240.166; 13.J.240.169; 13.J.240.172; 13.J.240.175; 13.J.240.240; 13.J.240.244; 13.J.244.228; 13.J.244.229; 13.J.244.230; 13.J.244.231; 13.J.244.236; 13.J.244.237; 13.J.244.238; 13.J.244.239; 13.J.244.154; 13.J.244.157; 13.J.244.166; 13.J.244.169; 13.J.244.172; 13.J.244.175; 13.J.244.240; 13.J.244.244; |
| Prodrugs of 13.L |
| 13.L.228.228; 13.L.228.229; 13.L.228.230; 13.L.228.231; 13.L.228.236; 13.L.228.237; 13.L.228.238; 13.L.228.239; 13.L.228.154; 13.L.228.157; 13.L.228.166; 13.L.228.169; 13.L.228.172; 13.L.228.175; 13.L.228.240; 13.L.228.244; 13.L.229.228; 13.L.229.229; 13.L.229.230; 13.L.229.231; 13.L.229.236; 13.L.229.237; 13.L.229.238; 13.L.229.239; 13.L.229.154; 13.L.229.157; 13.L.229.166; 13.L.229.169; 13.L.229.172; 13.L.229.175; 13.L.229.240; 13.L.229.244; 13.L.230.228; 13.L.230.229; 13.L.230.230; 13.L.230.231; 13.L.230.236; 13.L.230.237; 13.L.230.238; 13.L.230.239; |

TABLE 100-continued

| |
|---|
| 13.L.230.154; 13.L.230.157; 13.L.230.166; 13.L.230.169; 13.L.230.172; 13.L.230.175; 13.L.230.240; 13.L.230.244; 13.L.231.228; 13.L.231.229; 13.L.231.230; 13.L.231.231; 13.L.231.236; 13.L.231.237; 13.L.231.238; 13.L.231.239; 13.L.231.154; 13.L.231.157; 13.L.231.166; 13.L.231.169; 13.L.231.172; 13.L.231.175; 13.L.231.240; 13.L.231.244; 13.L.236.228; 13.L.236.229; 13.L.236.230; 13.L.236.231; 13.L.236.236; 13.L.236.237; 13.L.236.238; 13.L.236.239; 13.L.236.154; 13.L.236.157; 13.L.236.166; 13.L.236.169; 13.L.236.172; 13.L.236.175; 13.L.236.240; 13.L.236.244; 13.L.237.228; 13.L.237.229; 13.L.237.230; 13.L.237.231; 13.L.237.236; 13.L.237.237; 13.L.237.238; 13.L.237.239; 13.L.237.154; 13.L.237.157; 13.L.237.166; 13.L.237.169; 13.L.237.172; 13.L.237.175; 13.L.237.240; 13.L.237.244; 13.L.238.228; 13.L.238.229; 13.L.238.230; 13.L.238.231; 13.L.238.236; 13.L.238.237; 13.L.238.238; 13.L.238.239; 13.L.238.154; 13.L.238.157; 13.L.238.166; 13.L.238.169; 13.L.238.172; 13.L.238.175; 13.L.238.240; 13.L.238.244; 13.L.239.228; 13.L.239.229; 13.L.239.230; 13.L.239.231; 13.L.239.236; 13.L.239.237; 13.L.239.238; 13.L.239.239; 13.L.239.154; 13.L.239.157; 13.L.239.166; 13.L.239.169; 13.L.239.172; 13.L.239.175; 13.L.239.240; 13.L.239.244; 13.L.154.228; 13.L.154.229; 13.L.154.230; 13.L.154.231; 13.L.154.236; 13.L.154.237; 13.L.154.238; 13.L.154.239; 13.L.154.154; 13.L.154.157; 13.L.154.166; 13.L.154.169; 13.L.154.172; 13.L.154.175; 13.L.154.240; 13.L.154.244; 13.L.157.228; 13.L.157.229; 13.L.157.230; 13.L.157.231; 13.L.157.236; 13.L.157.237; 13.L.157.238; 13.L.157.239; 13.L.157.154; 13.L.157.157; 13.L.157.166; 13.L.157.169; 13.L.157.172; 13.L.157.175; 13.L.157.240; 13.L.157.244; 13.L.166.228; 13.L.166.229; 13.L.166.230; 13.L.166.231; 13.L.166.236; 13.L.166.237; 13.L.166.238; 13.L.166.239; 13.L.166.154; 13.L.166.157; 13.L.166.166; 13.L.166.169; 13.L.166.172; 13.L.166.175; 13.L.166.240; 13.L.166.244; 13.L.169.228; 13.L.169.229; 13.L.169.230; 13.L.169.231; 13.L.169.236; 13.L.169.237; 13.L.169.238; 13.L.169.239; 13.L.169.154; 13.L.169.157; 13.L.169.166; 13.L.169.169; 13.L.169.172; 13.L.169.175; 13.L.169.240; 13.L.169.244; 13.L.172.228; 13.L.172.229; 13.L.172.230; 13.L.172.231; 13.L.172.236; 13.L.172.237; 13.L.172.238; 13.L.172.239; 13.L.172.154; 13.L.172.157; 13.L.172.166; 13.L.172.169; 13.L.172.172; 13.L.172.175; 13.L.172.240; 13.L.172.244; 13.L.175.228; 13.L.175.229; 13.L.175.230; 13.L.175.231; 13.L.175.236; 13.L.175.237; 13.L.175.238; 13.L.175.239; 13.L.175.154; 13.L.175.157; 13.L.175.166; 13.L.175.169; 13.L.175.172; 13.L.175.175; 13.L.175.240; 13.L.175.244; 13.L.240.228; 13.L.240.229; 13.L.240.230; 13.L.240.231; 13.L.240.236; 13.L.240.237; 13.L.240.238; 13.L.240.239; 13.L.240.154; 13.L.240.157; 13.L.240.166; 13.L.240.169; 13.L.240.172; 13.L.240.175; 13.L.240.240; 13.L.240.244; 13.L.244.228; 13.L.244.229; 13.L.244.230; 13.L.244.231; 13.L.244.236; 13.L.244.237; 13.L.244.238; 13.L.244.239; 13.L.244.154; 13.L.244.157; 13.L.244.166; 13.L.244.169; 13.L.244.172; 13.L.244.175; 13.L.244.240; 13.L.244.244; |
| Prodrugs of 13.O |
| 13.O.228.228; 13.O.228.229; 13.O.228.230; 13.O.228.231; 13.O.228.236; 13.O.228.237; 13.O.228.238; 13.O.228.239; 13.O.228.154; 13.O.228.157; 13.O.228.166; 13.O.228.169; 13.O.228.172; 13.O.228.175; 13.O.228.240; 13.O.228.244; 13.O.229.228; 13.O.229.229; 13.O.229.230; 13.O.229.231; 13.O.229.236; 13.O.229.237; 13.O.229.238; 13.O.229.239; 13.O.229.154; 13.O.229.157; 13.O.229.166; 13.O.229.169; 13.O.229.172; 13.O.229.175; 13.O.229.240; 13.O.229.244; 13.O.230.228; 13.O.230.229; 13.O.230.230; 13.O.230.231; 13.O.230.236; 13.O.230.237; 13.O.230.238; 13.O.230.239; 13.O.230.154; 13.O.230.157; 13.O.230.166; 13.O.230.169; 13.O.230.172; 13.O.230.175; 13.O.230.240; 13.O.230.244; 13.O.231.228; 13.O.231.229; 13.O.231.230; 13.O.231.231; 13.O.231.236; 13.O.231.237; 13.O.231.238; 13.O.231.239; 13.O.231.154; 13.O.231.157; 13.O.231.166; 13.O.231.169; 13.O.231.172; 13.O.231.175; 13.O.231.240; 13.O.231.244; 13.O.236.228; 13.O.236.229; 13.O.236.230; 13.O.236.231; 13.O.236.236; 13.O.236.237; 13.O.236.238; 13.O.236.239; 13.O.236.154; 13.O.236.157; 13.O.236.166; 13.O.236.169; 13.O.236.172; 13.O.236.175; 13.O.236.240; 13.O.236.244; 13.O.237.228; 13.O.237.229; 13.O.237.230; 13.O.237.231; 13.O.237.236; 13.O.237.237; 13.O.237.238; 13.O.237.239; 13.O.237.154; 13.O.237.157; 13.O.237.166; 13.O.237.169; 13.O.237.172; 13.O.237.175; 13.O.237.240; 13.O.237.244; 13.O.238.228; 13.O.238.229; 13.O.238.230; 13.O.238.231; 13.O.238.236; 13.O.238.237; 13.O.238.238; 13.O.238.239; 13.O.238.154; 13.O.238.157; 13.O.238.166; 13.O.238.169; 13.O.238.172; 13.O.238.175; 13.O.238.240; 13.O.238.244; 13.O.239.228; 13.O.239.229; 13.O.239.230; 13.O.239.231; 13.O.239.236; 13.O.239.237; 13.O.239.238; 13.O.239.239; 13.O.239.154; 13.O.239.157; 13.O.239.166; 13.O.239.169; 13.O.239.172; 13.O.239.175; 13.O.239.240; 13.O.239.244; 13.O.154.228; 13.O.154.229; 13.O.154.230; 13.O.154.231; 13.O.154.236; 13.O.154.237; 13.O.154.238; 13.O.154.239; 13.O.154.154; 13.O.154.157; 13.O.154.166; 13.O.154.169; 13.O.154.172; 13.O.154.175; 13.O.154.240; 13.O.154.244; 13.O.157.228; 13.O.157.229; 13.O.157.230; 13.O.157.231; 13.O.157.236; 13.O.157.237; 13.O.157.238; 13.O.157.239; 13.O.157.154; 13.O.157.157; 13.O.157.166; 13.O.157.169; 13.O.157.172; 13.O.157.175; 13.O.157.240; 13.O.157.244; 13.O.166.228; 13.O.166.229; 13.O.166.230; 13.O.166.231; 13.O.166.236; 13.O.166.237; 13.O.166.238; 13.O.166.239; 13.O.166.154; 13.O.166.157; |

TABLE 100-continued

13.O.166.166; 13.O.166.169; 13.O.166.172; 13.O.166.175; 13.O.166.240; 13.O.166.244; 13.O.169.228; 13.O.169.229; 13.O.169.230; 13.O.169.231; 13.O.169.236; 13.O.169.237; 13.O.169.238; 13.O.169.239; 13.O.169.154; 13.O.169.157; 13.O.169.166; 13.O.169.169; 13.O.169.172; 13.O.169.175; 13.O.169.240; 13.O.169.244; 13.O.172.228; 13.O.172.229; 13.O.172.230; 13.O.172.231; 13.O.172.236; 13.O.172.237; 13.O.172.238; 13.O.172.239; 13.O.172.154; 13.O.172.157; 13.O.172.166; 13.O.172.169; 13.O.172.172; 13.O.172.175; 13.O.172.240; 13.O.172.244; 13.O.175.228; 13.O.175.229; 13.O.175.230; 13.O.175.231; 13.O.175.236; 13.O.175.237; 13.O.175.238; 13.O.175.239; 13.O.175.154; 13.O.175.157; 13.O.175.166; 13.O.175.169; 13.O.175.172; 13.O.175.175; 13.O.175.240; 13.O.175.244; 13.O.240.228; 13.O.240.229; 13.O.240.230; 13.O.240.231; 13.O.240.236; 13.O.240.237; 13.O.240.238; 13.O.240.239; 13.O.240.154; 13.O.240.157; 13.O.240.166; 13.O.240.169; 13.O.240.172; 13.O.240.175; 13.O.240.240; 13.O.240.244; 13.O.244.228; 13.O.244.229; 13.O.244.230; 13.O.244.231; 13.O.244.236; 13.O.244.237; 13.O.244.238; 13.O.244.239; 13.O.244.154; 13.O.244.157; 13.O.244.166; 13.O.244.169; 13.O.244.172; 13.O.244.175; 13.O.244.240; 13.O.244.244;

Prodrugs of 13.P

13.P.228.228; 13.P.228.229; 13.P.228.230; 13.P.228.231; 13.P.228.236; 13.P.228.237; 13.P.228.238; 13.P.228.239; 13.P.228.154; 13.P.228.157; 13.P.228.166; 13.P.228.169; 13.P.228.172; 13.P.228.175; 13.P.228.240; 13.P.228.244; 13.P.229.228; 13.P.229.229; 13.P.229.230; 13.P.229.231; 13.P.229.236; 13.P.229.237; 13.P.229.238; 13.P.229.239; 13.P.229.154; 13.P.229.157; 13.P.229.166; 13.P.229.169; 13.P.229.172; 13.P.229.175; 13.P.229.240; 13.P.229.244; 13.P.230.228; 13.P.230.229; 13.P.230.230; 13.P.230.231; 13.P.230.236; 13.P.230.237; 13.P.230.238; 13.P.230.239; 13.P.230.154; 13.P.230.157; 13.P.230.166; 13.P.230.169; 13.P.230.172; 13.P.230.175; 13.P.230.240; 13.P.230.244; 13.P.231.228; 13.P.231.229; 13.P.231.230; 13.P.231.231; 13.P.231.236; 13.P.231.237; 13.P.231.238; 13.P.231.239; 13.P.231.154; 13.P.231.157; 13.P.231.166; 13.P.231.169; 13.P.231.172; 13.P.231.175; 13.P.231.240; 13.P.231.244; 13.P.236.228; 13.P.236.229; 13.P.236.230; 13.P.236.231; 13.P.236.236; 13.P.236.237; 13.P.236.238; 13.P.236.239; 13.P.236.154; 13.P.236.157; 13.P.236.166; 13.P.236.169; 13.P.236.172; 13.P.236.175; 13.P.236.240; 13.P.236.244; 13.P.237.228; 13.P.237.229; 13.P.237.230; 13.P.237.231; 13.P.237.236; 13.P.237.237; 13.P.237.238; 13.P.237.239; 13.P.237.154; 13.P.237.157; 13.P.237.166; 13.P.237.169; 13.P.237.172; 13.P.237.175; 13.P.237.240; 13.P.237.244; 13.P.238.228; 13.P.238.229; 13.P.238.230; 13.P.238.231; 13.P.238.236; 13.P.238.237; 13.P.238.238; 13.P.238.239; 13.P.238.154; 13.P.238.157; 13.P.238.166; 13.P.238.169; 13.P.238.172; 13.P.238.175; 13.P.238.240; 13.P.238.244; 13.P.239.228; 13.P.239.229; 13.P.239.230; 13.P.239.231; 13.P.239.236; 13.P.239.237; 13.P.239.238; 13.P.239.239; 13.P.239.154; 13.P.239.157; 13.P.239.166; 13.P.239.169; 13.P.239.172; 13.P.239.175; 13.P.239.240; 13.P.239.244; 13.P.154.228; 13.P.154.229; 13.P.154.230; 13.P.154.231; 13.P.154.236; 13.P.154.237; 13.P.154.238; 13.P.154.239; 13.P.154.154; 13.P.154.157; 13.P.154.166; 13.P.154.169; 13.P.154.172; 13.P.154.175; 13.P.154.240; 13.P.154.244; 13.P.157.228; 13.P.157.229; 13.P.157.230; 13.P.157.231; 13.P.157.236; 13.P.157.237; 13.P.157.238; 13.P.157.239; 13.P.157.154; 13.P.157.157; 13.P.157.166; 13.P.157.169; 13.P.157.172; 13.P.157.175; 13.P.157.240; 13.P.157.244; 13.P.166.228; 13.P.166.229; 13.P.166.230; 13.P.166.231; 13.P.166.236; 13.P.166.237; 13.P.166.238; 13.P.166.239; 13.P.166.154; 13.P.166.157; 13.P.166.166; 13.P.166.169; 13.P.166.172; 13.P.166.175; 13.P.166.240; 13.P.166.244; 13.P.169.228; 13.P.169.229; 13.P.169.230; 13.P.169.231; 13.P.169.236; 13.P.169.237; 13.P.169.238; 13.P.169.239; 13.P.169.154; 13.P.169.157; 13.P.169.166; 13.P.169.169; 13.P.169.172; 13.P.169.175; 13.P.169.240; 13.P.169.244; 13.P.172.228; 13.P.172.229; 13.P.172.230; 13.P.172.231; 13.P.172.236; 13.P.172.237; 13.P.172.238; 13.P.172.239; 13.P.172.154; 13.P.172.157; 13.P.172.166; 13.P.172.169; 13.P.172.172; 13.P.172.175; 13.P.172.240; 13.P.172.244; 13.P.175.228; 13.P.175.229; 13.P.175.230; 13.P.175.231; 13.P.175.236; 13.P.175.237; 13.P.175.238; 13.P.175.239; 13.P.175.154; 13.P.175.157; 13.P.175.166; 13.P.175.169; 13.P.175.172; 13.P.175.175; 13.P.175.240; 13.P.175.244; 13.P.240.228; 13.P.240.229; 13.P.240.230; 13.P.240.231; 13.P.240.236; 13.P.240.237; 13.P.240.238; 13.P.240.239; 13.P.240.154; 13.P.240.157; 13.P.240.166; 13.P.240.169; 13.P.240.172; 13.P.240.175; 13.P.240.240; 13.P.240.244; 13.P.244.228; 13.P.244.229; 13.P.244.230; 13.P.244.231; 13.P.244.236; 13.P.244.237; 13.P.244.238; 13.P.244.239; 13.P.244.154; 13.P.244.157; 13.P.244.166; 13.P.244.169; 13.P.244.172; 13.P.244.175; 13.P.244.240; 13.P.244.244;

Prodrugs of 13.U

13.U.228.228; 13.U.228.229; 13.U.228.230; 13.U.228.231; 13.U.228.236; 13.U.228.237; 13.U.228.238; 13.U.228.239; 13.U.228.154; 13.U.228.157; 13.U.228.166; 13.U.228.169; 13.U.228.172; 13.U.228.175; 13.U.228.240; 13.U.228.244; 13.U.229.228; 13.U.229.229; 13.U.229.230; 13.U.229.231; 13.U.229.236; 13.U.229.237; 13.U.229.238; 13.U.229.239; 13.U.229.154; 13.U.229.157; 13.U.229.166; 13.U.229.169; 13.U.229.172; 13.U.229.175; 13.U.229.240; 13.U.229.244; 13.U.230.228; 13.U.230.229; 13.U.230.230;

TABLE 100-continued

| |
|---|
| 13.U.230.231; 13.U.230.236; 13.U.230.237; 13.U.230.238; 13.U.230.239; 13.U.230.154; 13.U.230.157; 13.U.230.166; 13.U.230.169; 13.U.230.172; 13.U.230.175; 13.U.230.240; 13.U.230.244; 13.U.231.228; 13.U.231.229; 13.U.231.230; 13.U.231.231; 13.U.231.236; 13.U.231.237; 13.U.231.238; 13.U.231.239; 13.U.231.154; 13.U.231.157; 13.U.231.166; 13.U.231.169; 13.U.231.172; 13.U.231.175; 13.U.231.240; 13.U.231.244; 13.U.236.228; 13.U.236.229; 13.U.236.230; 13.U.236.231; 13.U.236.236; 13.U.236.237; 13.U.236.238; 13.U.236.239; 13.U.236.154; 13.U.236.157; 13.U.236.166; 13.U.236.169; 13.U.236.172; 13.U.236.175; 13.U.236.240; 13.U.236.244; 13.U.237.228; 13.U.237.229; 13.U.237.230; 13.U.237.231; 13.U.237.236; 13.U.237.237; 13.U.237.238; 13.U.237.239; 13.U.237.154; 13.U.237.157; 13.U.237.166; 13.U.237.169; 13.U.237.172; 13.U.237.175; 13.U.237.240; 13.U.237.244; 13.U.238.228; 13.U.238.229; 13.U.238.230; 13.U.238.231; 13.U.238.236; 13.U.238.237; 13.U.238.238; 13.U.238.239; 13.U.238.154; 13.U.238.157; 13.U.238.166; 13.U.238.169; 13.U.238.172; 13.U.238.175; 13.U.238.240; 13.U.238.244; 13.U.239.228; 13.U.239.229; 13.U.239.230; 13.U.239.231; 13.U.239.236; 13.U.239.237; 13.U.239.238; 13.U.239.239; 13.U.239.154; 13.U.239.157; 13.U.239.166; 13.U.239.169; 13.U.239.172; 13.U.239.175; 13.U.239.240; 13.U.239.244; 13.U.154.228; 13.U.154.229; 13.U.154.230; 13.U.154.231; 13.U.154.236; 13.U.154.237; 13.U.154.238; 13.U.154.239; 13.U.154.154; 13.U.154.157; 13.U.154.166; 13.U.154.169; 13.U.154.172; 13.U.154.175; 13.U.154.240; 13.U.154.244; 13.U.157.228; 13.U.157.229; 13.U.157.230; 13.U.157.231; 13.U.157.236; 13.U.157.237; 13.U.157.238; 13.U.157.239; 13.U.157.154; 13.U.157.157; 13.U.157.166; 13.U.157.169; 13.U.157.172; 13.U.157.175; 13.U.157.240; 13.U.157.244; 13.U.166.228; 13.U.166.229; 13.U.166.230; 13.U.166.231; 13.U.166.236; 13.U.166.237; 13.U.166.238; 13.U.166.239; 13.U.166.154; 13.U.166.157; 13.U.166.166; 13.U.166.169; 13.U.166.172; 13.U.166.175; 13.U.166.240; 13.U.166.244; 13.U.169.228; 13.U.169.229; 13.U.169.230; 13.U.169.231; 13.U.169.236; 13.U.169.237; 13.U.169.238; 13.U.169.239; 13.U.169.154; 13.U.169.157; 13.U.169.166; 13.U.169.169; 13.U.169.172; 13.U.169.175; 13.U.169.240; 13.U.169.244; 13.U.172.228; 13.U.172.229; 13.U.172.230; 13.U.172.231; 13.U.172.236; 13.U.172.237; 13.U.172.238; 13.U.172.239; 13.U.172.154; 13.U.172.157; 13.U.172.166; 13.U.172.169; 13.U.172.172; 13.U.172.175; 13.U.172.240; 13.U.172.244; 13.U.175.228; 13.U.175.229; 13.U.175.230; 13.U.175.231; 13.U.175.236; 13.U.175.237; 13.U.175.238; 13.U.175.239; 13.U.175.154; 13.U.175.157; 13.U.175.166; 13.U.175.169; 13.U.175.172; 13.U.175.175; 13.U.175.240; 13.U.175.244; 13.U.240.228; 13.U.240.229; 13.U.240.230; 13.U.240.231; 13.U.240.236; 13.U.240.237; 13.U.240.238; 13.U.240.239; 13.U.240.154; 13.U.240.157; 13.U.240.166; 13.U.240.169; 13.U.240.172; 13.U.240.175; 13.U.240.240; 13.U.240.244; 13.U.244.228; 13.U.244.229; 13.U.244.230; 13.U.244.231; 13.U.244.236; 13.U.244.237; 13.U.244.238; 13.U.244.239; 13.U.244.154; 13.U.244.157; 13.U.244.166; 13.U.244.169; 13.U.244.172; 13.U.244.175; 13.U.244.240; 13.U.244.244; |
| Prodrugs of 13.W |
| 13.W.228.228; 13.W.228.229; 13.W.228.230; 13.W.228.231; 13.W.228.236; 13.W.228.237; 13.W.228.238; 13.W.228.239; 13.W.228.154; 13.W.228.157; 13.W.228.166; 13.W.228.169; 13.W.228.172; 13.W.228.175; 13.W.228.240; 13.W.228.244; 13.W.229.228; 13.W.229.229; 13.W.229.230; 13.W.229.231; 13.W.229.236; 13.W.229.237; 13.W.229.238; 13.W.229.239; 13.W.229.154; 13.W.229.157; 13.W.229.166; 13.W.229.169; 13.W.229.172; 13.W.229.175; 13.W.229.240; 13.W.229.244; 13.W.230.228; 13.W.230.229; 13.W.230.230; 13.W.230.231; 13.W.230.236; 13.W.230.237; 13.W.230.238; 13.W.230.239; 13.W.230.154; 13.W.230.157; 13.W.230.166; 13.W.230.169; 13.W.230.172; 13.W.230.175; 13.W.230.240; 13.W.230.244; 13.W.231.228; 13.W.231.229; 13.W.231.230; 13.W.231.231; 13.W.231.236; 13.W.231.237; 13.W.231.238; 13.W.231.239; 13.W.231.154; 13.W.231.157; 13.W.231.166; 13.W.231.169; 13.W.231.172; 13.W.231.175; 13.W.231.240; 13.W.231.244; 13.W.236.228; 13.W.236.229; 13.W.236.230; 13.W.236.231; 13.W.236.236; 13.W.236.237; 13.W.236.238; 13.W.236.239; 13.W.236.154; 13.W.236.157; 13.W.236.166; 13.W.236.169; 13.W.236.172; 13.W.236.175; 13.W.236.240; 13.W.236.244; 13.W.237.228; 13.W.237.229; 13.W.237.230; 13.W.237.231; 13.W.237.236; 13.W.237.237; 13.W.237.238; 13.W.237.239; 13.W.237.154; 13.W.237.157; 13.W.237.166; 13.W.237.169; 13.W.237.172; 13.W.237.175; 13.W.237.240; 13.W.237.244; 13.W.238.228; 13.W.238.229; 13.W.238.230; 13.W.238.231; 13.W.238.236; 13.W.238.237; 13.W.238.238; 13.W.238.239; 13.W.238.154; 13.W.238.157; 13.W.238.166; 13.W.238.169; 13.W.238.172; 13.W.238.175; 13.W.238.240; 13.W.238.244; 13.W.239.228; 13.W.239.229; 13.W.239.230; 13.W.239.231; 13.W.239.236; 13.W.239.237; 13.W.239.238; 13.W.239.239; 13.W.239.154; 13.W.239.157; 13.W.239.166; 13.W.239.169; 13.W.239.172; 13.W.239.175; 13.W.239.240; 13.W.239.244; 13.W.154.228; 13.W.154.229; 13.W.154.230; 13.W.154.231; 13.W.154.236; 13.W.154.237; 13.W.154.238; 13.W.154.239; 13.W.154.154; 13.W.154.157; 13.W.154.166; 13.W.154.169; 13.W.154.172; 13.W.154.175; 13.W.154.240; 13.W.154.244; 13.W.157.228; 13.W.157.229; 13.W.157.230; 13.W.157.231; 13.W.157.236; 13.W.157.237; 13.W.157.238; 13.W.157.239; 13.W.157.154; 13.W.157.157; 13.W.157.166; 13.W.157.169; 13.W.157.172; 13.W.157.175; 13.W.157.240; 13.W.157.244; 13.W.166.228; 13.W.166.229; 13.W.166.230; 13.W.166.231; 13.W.166.236; |

TABLE 100-continued

| |
|---|
| 13.W.166.237; 13.W.166.238; 13.W.166.239; 13.W.166.154; 13.W.166.157; 13.W.166.166; 13.W.166.169; 13.W.166.172; 13.W.166.175; 13.W.166.240; 13.W.166.244; 13.W.169.228; 13.W.169.229; 13.W.169.230; 13.W.169.231; 13.W.169.236; 13.W.169.237; 13.W.169.238; 13.W.169.239; 13.W.169.154; 13.W.169.157; 13.W.169.166; 13.W.169.169; 13.W.169.172; 13.W.169.175; 13.W.169.240; 13.W.169.244; 13.W.172.228; 13.W.172.229; 13.W.172.230; 13.W.172.231; 13.W.172.236; 13.W.172.237; 13.W.172.238; 13.W.172.239; 13.W.172.154; 13.W.172.157; 13.W.172.166; 13.W.172.169; 13.W.172.172; 13.W.172.175; 13.W.172.240; 13.W.172.244; 13.W.175.228; 13.W.175.229; 13.W.175.230; 13.W.175.231; 13.W.175.236; 13.W.175.237; 13.W.175.238; 13.W.175.239; 13.W.175.154; 13.W.175.157; 13.W.175.166; 13.W.175.169; 13.W.175.172; 13.W.175.175; 13.W.175.240; 13.W.175.244; 13.W.240.228; 13.W.240.229; 13.W.240.230; 13.W.240.231; 13.W.240.236; 13.W.240.237; 13.W.240.238; 13.W.240.239; 13.W.240.154; 13.W.240.157; 13.W.240.166; 13.W.240.169; 13.W.240.172; 13.W.240.175; 13.W.240.240; 13.W.240.244; 13.W.244.228; 13.W.244.229; 13.W.244.230; 13.W.244.231; 13.W.244.236; 13.W.244.237; 13.W.244.238; 13.W.244.239; 13.W.244.154; 13.W.244.157; 13.W.244.166; 13.W.244.169; 13.W.244.172; 13.W.244.175; 13.W.244.240; 13.W.244.244; |
| Prodrugs of 13.Y |
| 13.Y.228.228; 13.Y.228.229; 13.Y.228.230; 13.Y.228.231; 13.Y.228.236; 13.Y.228.237; 13.Y.228.238; 13.Y.228.239; 13.Y.228.154; 13.Y.228.157; 13.Y.228.166; 13.Y.228.169; 13.Y.228.172; 13.Y.228.175; 13.Y.228.240; 13.Y.228.244; 13.Y.229.228; 13.Y.229.229; 13.Y.229.230; 13.Y.229.231; 13.Y.229.236; 13.Y.229.237; 13.Y.229.238; 13.Y.229.239; 13.Y.229.154; 13.Y.229.157; 13.Y.229.166; 13.Y.229.169; 13.Y.229.172; 13.Y.229.175; 13.Y.229.240; 13.Y.229.244; 13.Y.230.228; 13.Y.230.229; 13.Y.230.230; 13.Y.230.231; 13.Y.230.236; 13.Y.230.237; 13.Y.230.238; 13.Y.230.239; 13.Y.230.154; 13.Y.230.157; 13.Y.230.166; 13.Y.230.169; 13.Y.230.172; 13.Y.230.175; 13.Y.230.240; 13.Y.230.244; 13.Y.231.228; 13.Y.231.229; 13.Y.231.230; 13.Y.231.231; 13.Y.231.236; 13.Y.231.237; 13.Y.231.238; 13.Y.231.239; 13.Y.231.154; 13.Y.231.157; 13.Y.231.166; 13.Y.231.169; 13.Y.231.172; 13.Y.231.175; 13.Y.231.240; 13.Y.231.244; 13.Y.236.228; 13.Y.236.229; 13.Y.236.230; 13.Y.236.231; 13.Y.236.236; 13.Y.236.237; 13.Y.236.238; 13.Y.236.239; 13.Y.236.154; 13.Y.236.157; 13.Y.236.166; 13.Y.236.169; 13.Y.236.172; 13.Y.236.175; 13.Y.236.240; 13.Y.236.244; 13.Y.237.228; 13.Y.237.229; 13.Y.237.230; 13.Y.237.231; 13.Y.237.236; 13.Y.237.237; 13.Y.237.238; 13.Y.237.239; 13.Y.237.154; 13.Y.237.157; 13.Y.237.166; 13.Y.237.169; 13.Y.237.172; 13.Y.237.175; 13.Y.237.240; 13.Y.237.244; 13.Y.238.228; 13.Y.238.229; 13.Y.238.230; 13.Y.238.231; 13.Y.238.236; 13.Y.238.237; 13.Y.238.238; 13.Y.238.239; 13.Y.238.154; 13.Y.238.157; 13.Y.238.166; 13.Y.238.169; 13.Y.238.172; 13.Y.238.175; 13.Y.238.240; 13.Y.238.244; 13.Y.239.228; 13.Y.239.229; 13.Y.239.230; 13.Y.239.231; 13.Y.239.236; 13.Y.239.237; 13.Y.239.238; 13.Y.239.239; 13.Y.239.154; 13.Y.239.157; 13.Y.239.166; 13.Y.239.169; 13.Y.239.172; 13.Y.239.175; 13.Y.239.240; 13.Y.239.244; 13.Y.154.228; 13.Y.154.229; 13.Y.154.230; 13.Y.154.231; 13.Y.154.236; 13.Y.154.237; 13.Y.154.238; 13.Y.154.239; 13.Y.154.154; 13.Y.154.157; 13.Y.154.166; 13.Y.154.169; 13.Y.154.172; 13.Y.154.175; 13.Y.154.240; 13.Y.154.244; 13.Y.157.228; 13.Y.157.229; 13.Y.157.230; 13.Y.157.231; 13.Y.157.236; 13.Y.157.237; 13.Y.157.238; 13.Y.157.239; 13.Y.157.154; 13.Y.157.157; 13.Y.157.166; 13.Y.157.169; 13.Y.157.172; 13.Y.157.175; 13.Y.157.240; 13.Y.157.244; 13.Y.166.228; 13.Y.166.229; 13.Y.166.230; 13.Y.166.231; 13.Y.166.236; 13.Y.166.237; 13.Y.166.238; 13.Y.166.239; 13.Y.166.154; 13.Y.166.157; 13.Y.166.166; 13.Y.166.169; 13.Y.166.172; 13.Y.166.175; 13.Y.166.240; 13.Y.166.244; 13.Y.169.228; 13.Y.169.229; 13.Y.169.230; 13.Y.169.231; 13.Y.169.236; 13.Y.169.237; 13.Y.169.238; 13.Y.169.239; 13.Y.169.154; 13.Y.169.157; 13.Y.169.166; 13.Y.169.169; 13.Y.169.172; 13.Y.169.175; 13.Y.169.240; 13.Y.169.244; 13.Y.172.228; 13.Y.172.229; 13.Y.172.230; 13.Y.172.231; 13.Y.172.236; 13.Y.172.237; 13.Y.172.238; 13.Y.172.239; 13.Y.172.154; 13.Y.172.157; 13.Y.172.166; 13.Y.172.169; 13.Y.172.172; 13.Y.172.175; 13.Y.172.240; 13.Y.172.244; 13.Y.175.228; 13.Y.175.229; 13.Y.175.230; 13.Y.175.231; 13.Y.175.236; 13.Y.175.237; 13.Y.175.238; 13.Y.175.239; 13.Y.175.154; 13.Y.175.157; 13.Y.175.166; 13.Y.175.169; 13.Y.175.172; 13.Y.175.175; 13.Y.175.240; 13.Y.175.244; 13.Y.240.228; 13.Y.240.229; 13.Y.240.230; 13.Y.240.231; 13.Y.240.236; 13.Y.240.237; 13.Y.240.238; 13.Y.240.239; 13.Y.240.154; 13.Y.240.157; 13.Y.240.166; 13.Y.240.169; 13.Y.240.172; 13.Y.240.175; 13.Y.240.240; 13.Y.240.244; 13.Y.244.228; 13.Y.244.229; 13.Y.244.230; 13.Y.244.231; 13.Y.244.236; 13.Y.244.237; 13.Y.244.238; 13.Y.244.239; 13.Y.244.154; 13.Y.244.157; 13.Y.244.166; 13.Y.244.169; 13.Y.244.172; 13.Y.244.175; 13.Y.244.240; 13.Y.244.244; |
| Prodrugs of 14.AH |
| 14.AH.4.157; 14.AH.4.158; 14.AH.4.196; 14.AH.4.223; 14.AH.4.240; 14.AH.4.244; 14.AH.4.243; 14.AH.4.247; 14.AH.5.157; 14.AH.5.158; 14.AH.5.196; 14.AH.5.223; 14.AH.5.240; 14.AH.5.244; 14.AH.5.243; 14.AH.5.247; 14.AH.7.157; 14.AH.7.158; 14.AH.7.196; 14.AH.7.223; 14.AH.7.240; 14.AH.7.244; 14.AH.7.243; 14.AH.7.247; 14.AH.15.157; |

TABLE 100-continued

14.AH.15.158; 14.AH.15.196; 14.AH.15.223; 14.AH.15.240; 14.AH.15.244; 14.AH.15.243; 14.AH.15.247; 14.AH.16.157; 14.AH.16.158; 14.AH.16.196; 14.AH.16.223; 14.AH.16.240; 14.AH.16.244; 14.AH.16.243; 14.AH.16.247; 14.AH.18.157; 14.AH.18.158; 14.AH.18.196; 14.AH.18.223; 14.AH.18.240; 14.AH.18.244; 14.AH.18.243; 14.AH.18.247; 14.AH.26.157; 14.AH.26.158; 14.AH.26.196; 14.AH.26.223; 14.AH.26.240; 14.AH.26.244; 14.AH.26.243; 14.AH.26.247; 14.AH.27.157; 14.AH.27.158; 14.AH.27.196; 14.AH.27.223; 14.AH.27.240; 14.AH.27.244; 14.AH.27.243; 14.AH.27.247; 14.AH.29.157; 14.AH.29.158; 14.AH.29.196; 14.AH.29.223; 14.AH.29.240; 14.AH.29.244; 14.AH.29.243; 14.AH.29.247; 14.AH.54.157; 14.AH.54.158; 14.AH.54.196; 14.AH.54.223; 14.AH.54.240; 14.AH.54.244; 14.AH.54.243; 14.AH.54.247; 14.AH.55.157; 14.AH.55.158; 14.AH.55.196; 14.AH.55.223; 14.AH.55.240; 14.AH.55.244; 14.AH.55.243; 14.AH.55.247; 14.AH.56.157; 14.AH.56.158; 14.AH.56.196; 14.AH.56.223; 14.AH.56.240; 14.AH.56.244; 14.AH.56.243; 14.AH.56.247; 14.AH.157.157; 14.AH.157.158; 14.AH.157.196; 14.AH.157.223; 14.AH.157.240; 14.AH.157.244; 14.AH.157.243; 14.AH.157.247; 14.AH.196.157; 14.AH.196.158; 14.AH.196.196; 14.AH.196.223; 14.AH.196.240; 14.AH.196.244; 14.AH.196.243; 14.AH.196.247; 14.AH.223.157; 14.AH.223.158; 14.AH.223.196; 14.AH.223.223; 14.AH.223.240; 14.AH.223.244; 14.AH.223.243; 14.AH.223.247; 14.AH.240.157; 14.AH.240.158; 14.AH.240.196; 14.AH.240.223; 14.AH.240.240; 14.AH.240.244; 14.AH.240.243; 14.AH.240.247; 14.AH.244.157; 14.AH.244.158; 14.AH.244.196; 14.AH.244.223; 14.AH.244.240; 14.AH.244.244; 14.AH.244.243; 14.AH.244.247; 14.AH.247.157; 14.AH.247.158; 14.AH.247.196; 14.AH.247.223; 14.AH.247.240; 14.AH.247.244; 14.AH.247.243; 14.AH.247.247;

Prodrugs of 14.AJ

14.AJ.4.157; 14.AJ.4.158; 14.AJ.4.196; 14.AJ.4.223; 14.AJ.4.240; 14.AJ.4.244; 14.AJ.4.243; 14.AJ.4.247; 14.AJ.5.157; 14.AJ.5.158; 14.AJ.5.196; 14.AJ.5.223; 14.AJ.5.240; 14.AJ.5.244; 14.AJ.5.243; 14.AJ.5.247; 14.AJ.7.157; 14.AJ.7.158; 14.AJ.7.196; 14.AJ.7.223; 14.AJ.7.240; 14.AJ.7.244; 14.AJ.7.243; 14.AJ.7.247; 14.AJ.15.157; 14.AJ.15.158; 14.AJ.15.196; 14.AJ.15.223; 14.AJ.15.240; 14.AJ.15.244; 14.AJ.15.243; 14.AJ.15.247; 14.AJ.16.157; 14.AJ.16.158; 14.AJ.16.196; 14.AJ.16.223; 14.AJ.16.240; 14.AJ.16.244; 14.AJ.16.243; 14.AJ.16.247; 14.AJ.18.157; 14.AJ.18.158; 14.AJ.18.196; 14.AJ.18.223; 14.AJ.18.240; 14.AJ.18.244; 14.AJ.18.243; 14.AJ.18.247; 14.AJ.26.157; 14.AJ.26.158; 14.AJ.26.196; 14.AJ.26.223; 14.AJ.26.240; 14.AJ.26.244; 14.AJ.26.243; 14.AJ.26.247; 14.AJ.27.157; 14.AJ.27.158; 14.AJ.27.196; 14.AJ.27.223; 14.AJ.27.240; 14.AJ.27.244; 14.AJ.27.243; 14.AJ.27.247; 14.AJ.29.157; 14.AJ.29.158; 14.AJ.29.196; 14.AJ.29.223; 14.AJ.29.240; 14.AJ.29.244; 14.AJ.29.243; 14.AJ.29.247; 14.AJ.54.157; 14.AJ.54.158; 14.AJ.54.196; 14.AJ.54.223; 14.AJ.54.240; 14.AJ.54.244; 14.AJ.54.243; 14.AJ.54.247; 14.AJ.55.157; 14.AJ.55.158; 14.AJ.55.196; 14.AJ.55.223; 14.AJ.55.240; 14.AJ.55.244; 14.AJ.55.243; 14.AJ.55.247; 14.AJ.56.157; 14.AJ.56.158; 14.AJ.56.196; 14.AJ.56.223; 14.AJ.56.240; 14.AJ.56.244; 14.AJ.56.243; 14.AJ.56.247; 14.AJ.157.157; 14.AJ.157.158; 14.AJ.157.196; 14.AJ.157.223; 14.AJ.157.240; 14.AJ.157.244; 14.AJ.157.243; 14.AJ.157.247; 14.AJ.196.157; 14.AJ.196.158; 14.AJ.196.196; 14.AJ.196.223; 14.AJ.196.240; 14.AJ.196.244; 14.AJ.196.243; 14.AJ.196.247; 14.AJ.223.157; 14.AJ.223.158; 14.AJ.223.196; 14.AJ.223.223; 14.AJ.223.240; 14.AJ.223.244; 14.AJ.223.243; 14.AJ.223.247; 14.AJ.240.157; 14.AJ.240.158; 14.AJ.240.196; 14.AJ.240.223; 14.AJ.240.240; 14.AJ.240.244; 14.AJ.240.243; 14.AJ.240.247; 14.AJ.244.157; 14.AJ.244.158; 14.AJ.244.196; 14.AJ.244.223; 14.AJ.244.240; 14.AJ.244.244; 14.AJ.244.243; 14.AJ.244.247; 14.AJ.247.157; 14.AJ.247.158; 14.AJ.247.196; 14.AJ.247.223; 14.AJ.247.240; 14.AJ.247.244; 14.AJ.247.243; 14.AJ.247.247;

Prodrugs of 14.AN

14.AN.4.157; 14.AN.4.158; 14.AN.4.196; 14.AN.4.223; 14.AN.4.240; 14.AN.4.244; 14.AN.4.243; 14.AN.4.247; 14.AN.5.157; 14.AN.5.158; 14.AN.5.196; 14.AN.5.223; 14.AN.5.240; 14.AN.5.244; 14.AN.5.243; 14.AN.5.247; 14.AN.7.157; 14.AN.7.158; 14.AN.7.196; 14.AN.7.223; 14.AN.7.240; 14.AN.7.244; 14.AN.7.243; 14.AN.7.247; 14.AN.15.157; 14.AN.15.158; 14.AN.15.196; 14.AN.15.223; 14.AN.15.240; 14.AN.15.244; 14.AN.15.243; 14.AN.15.247; 14.AN.16.157; 14.AN.16.158; 14.AN.16.196; 14.AN.16.223; 14.AN.16.240; 14.AN.16.244; 14.AN.16.243; 14.AN.16.247; 14.AN.18.157; 14.AN.18.158; 14.AN.18.196; 14.AN.18.223; 14.AN.18.240; 14.AN.18.244; 14.AN.18.243; 14.AN.18.247; 14.AN.26.157; 14.AN.26.158; 14.AN.26.196; 14.AN.26.223; 14.AN.26.240; 14.AN.26.244; 14.AN.26.243; 14.AN.26.247; 14.AN.27.157; 14.AN.27.158; 14.AN.27.196; 14.AN.27.223; 14.AN.27.240; 14.AN.27.244; 14.AN.27.243; 14.AN.27.247; 14.AN.29.157; 14.AN.29.158; 14.AN.29.196; 14.AN.29.223; 14.AN.29.240; 14.AN.29.244; 14.AN.29.243; 14.AN.29.247; 14.AN.54.157; 14.AN.54.158; 14.AN.54.196; 14.AN.54.223; 14.AN.54.240; 14.AN.54.244; 14.AN.54.243; 14.AN.54.247; 14.AN.55.157; 14.AN.55.158; 14.AN.55.196; 14.AN.55.223; 14.AN.55.240; 14.AN.55.244; 14.AN.55.243; 14.AN.55.247; 14.AN.56.157; 14.AN.56.158; 14.AN.56.196; 14.AN.56.223; 14.AN.56.240; 14.AN.56.244; 14.AN.56.243; 14.AN.56.247; 14.AN.157.157; 14.AN.157.158; 14.AN.157.196; 14.AN.157.223; 14.AN.157.240; 14.AN.157.244; 14.AN.157.243;

TABLE 100-continued

| |
|---|
| 14.AN.157.247; 14.AN.196.157; 14.AN.196.158; 14.AN.196.196; 14.AN.196.223; 14.AN.196.240; 14.AN.196.244; 14.AN.196.243; 14.AN.196.247; 14.AN.223.157; 14.AN.223.158; 14.AN.223.196; 14.AN.223.223; 14.AN.223.240; 14.AN.223.244; 14.AN.223.243; 14.AN.223.247; 14.AN.240.157; 14.AN.240.158; 14.AN.240.196; 14.AN.240.223; 14.AN.240.240; 14.AN.240.244; 14.AN.240.243; 14.AN.240.247; 14.AN.244.157; 14.AN.244.158; 14.AN.244.196; 14.AN.244.223; 14.AN.244.240; 14.AN.244.244; 14.AN.244.243; 14.AN.244.247; 14.AN.247.157; 14.AN.247.158; 14.AN.247.196; 14.AN.247.223; 14.AN.247.240; 14.AN.247.244; 14.AN.247.243; 14.AN.247.247; |
| Prodrugs of 14.AP |
| 14.AP.4.157; 14.AP.4.158; 14.AP.4.196; 14.AP.4.223; 14.AP.4.240; 14.AP.4.244; 14.AP.4.243; 14.AP.4.247; 14.AP.5.157; 14.AP.5.158; 14.AP.5.196; 14.AP.5.223; 14.AP.5.240; 14.AP.5.244; 14.AP.5.243; 14.AP.5.247; 14.AP.7.157; 14.AP.7.158; 14.AP.7.196; 14.AP.7.223; 14.AP.7.240; 14.AP.7.244; 14.AP.7.243; 14.AP.7.247; 14.AP.15.157; 14.AP.15.158; 14.AP.15.196; 14.AP.15.223; 14.AP.15.240; 14.AP.15.244; 14.AP.15.243; 14.AP.15.247; 14.AP.16.157; 14.AP.16.158; 14.AP.16.196; 14.AP.16.223; 14.AP.16.240; 14.AP.16.244; 14.AP.16.243; 14.AP.16.247; 14.AP.18.157; 14.AP.18.158; 14.AP.18.196; 14.AP.18.223; 14.AP.18.240; 14.AP.18.244; 14.AP.18.243; 14.AP.18.247; 14.AP.26.157; 14.AP.26.158; 14.AP.26.196; 14.AP.26.223; 14.AP.26.240; 14.AP.26.244; 14.AP.26.243; 14.AP.26.247; 14.AP.27.157; 14.AP.27.158; 14.AP.27.196; 14.AP.27.223; 14.AP.27.240; 14.AP.27.244; 14.AP.27.243; 14.AP.27.247; 14.AP.29.157; 14.AP.29.158; 14.AP.29.196; 14.AP.29.223; 14.AP.29.240; 14.AP.29.244; 14.AP.29.243; 14.AP.29.247; 14.AP.54.157; 14.AP.54.158; 14.AP.54.196; 14.AP.54.223; 14.AP.54.240; 14.AP.54.244; 14.AP.54.243; 14.AP.54.247; 14.AP.55.157; 14.AP.55.158; 14.AP.55.196; 14.AP.55.223; 14.AP.55.240; 14.AP.55.244; 14.AP.55.243; 14.AP.55.247; 14.AP.56.157; 14.AP.56.158; 14.AP.56.196; 14.AP.56.223; 14.AP.56.240; 14.AP.56.244; 14.AP.56.243; 14.AP.56.247; 14.AP.157.157; 14.AP.157.158; 14.AP.157.196; 14.AP.157.223; 14.AP.157.240; 14.AP.157.244; 14.AP.157.243; 14.AP.157.247; 14.AP.196.157; 14.AP.196.158; 14.AP.196.196; 14.AP.196.223; 14.AP.196.240; 14.AP.196.244; 14.AP.196.243; 14.AP.196.247; 14.AP.223.157; 14.AP.223.158; 14.AP.223.196; 14.AP.223.223; 14.AP.223.240; 14.AP.223.244; 14.AP.223.243; 14.AP.223.247; 14.AP.240.157; 14.AP.240.158; 14.AP.240.196; 14.AP.240.223; 14.AP.240.240; 14.AP.240.244; 14.AP.240.243; 14.AP.240.247; 14.AP.244.157; 14.AP.244.158; 14.AP.244.196; 14.AP.244.223; 14.AP.244.240; 14.AP.244.244; 14.AP.244.243; 14.AP.244.247; 14.AP.247.157; 14.AP.247.158; 14.AP.247.196; 14.AP.247.223; 14.AP.247.240; 14.AP.247.244; 14.AP.247.243; 14.AP.247.247; |
| Prodrugs of 14.AZ |
| 14.AZ.4.157; 14.AZ.4.158; 14.AZ.4.196; 14.AZ.4.223; 14.AZ.4.240; 14.AZ.4.244; 14.AZ.4.243; 14.AZ.4.247; 14.AZ.5.157; 14.AZ.5.158; 14.AZ.5.196; 14.AZ.5.223; 14.AZ.5.240; 14.AZ.5.244; 14.AZ.5.243; 14.AZ.5.247; 14.AZ.7.157; 14.AZ.7.158; 14.AZ.7.196; 14.AZ.7.223; 14.AZ.7.240; 14.AZ.7.244; 14.AZ.7.243; 14.AZ.7.247; 14.AZ.15.157; 14.AZ.15.158; 14.AZ.15.196; 14.AZ.15.223; 14.AZ.15.240; 14.AZ.15.244; 14.AZ.15.243; 14.AZ.15.247; 14.AZ.16.157; 14.AZ.16.158; 14.AZ.16.196; 14.AZ.16.223; 14.AZ.16.240; 14.AZ.16.244; 14.AZ.16.243; 14.AZ.16.247; 14.AZ.18.157; 14.AZ.18.158; 14.AZ.18.196; 14.AZ.18.223; 14.AZ.18.240; 14.AZ.18.244; 14.AZ.18.243; 14.AZ.18.247; 14.AZ.26.157; 14.AZ.26.158; 14.AZ.26.196; 14.AZ.26.223; 14.AZ.26.240; 14.AZ.26.244; 14.AZ.26.243; 14.AZ.26.247; 14.AZ.27.157; 14.AZ.27.158; 14.AZ.27.196; 14.AZ.27.223; 14.AZ.27.240; 14.AZ.27.244; 14.AZ.27.243; 14.AZ.27.247; 14.AZ.29.157; 14.AZ.29.158; 14.AZ.29.196; 14.AZ.29.223; 14.AZ.29.240; 14.AZ.29.244; 14.AZ.29.243; 14.AZ.29.247; 14.AZ.54.157; 14.AZ.54.158; 14.AZ.54.196; 14.AZ.54.223; 14.AZ.54.240; 14.AZ.54.244; 14.AZ.54.243; 14.AZ.54.247; 14.AZ.55.157; 14.AZ.55.158; 14.AZ.55.196; 14.AZ.55.223; 14.AZ.55.240; 14.AZ.55.244; 14.AZ.55.243; 14.AZ.55.247; 14.AZ.56.157; 14.AZ.56.158; 14.AZ.56.196; 14.AZ.56.223; 14.AZ.56.240; 14.AZ.56.244; 14.AZ.56.243; 14.AZ.56.247; 14.AZ.157.157; 14.AZ.157.158; 14.AZ.157.196; 14.AZ.157.223; 14.AZ.157.240; 14.AZ.157.244; 14.AZ.157.243; 14.AZ.157.247; 14.AZ.196.157; 14.AZ.196.158; 14.AZ.196.196; 14.AZ.196.223; 14.AZ.196.240; 14.AZ.196.244; 14.AZ.196.243; 14.AZ.196.247; 14.AZ.223.157; 14.AZ.223.158; 14.AZ.223.196; 14.AZ.223.223; 14.AZ.223.240; 14.AZ.223.244; 14.AZ.223.243; 14.AZ.223.247; 14.AZ.240.157; 14.AZ.240.158; 14.AZ.240.196; 14.AZ.240.223; 14.AZ.240.240; 14.AZ.240.244; 14.AZ.240.243; 14.AZ.240.247; 14.AZ.244.157; 14.AZ.244.158; 14.AZ.244.196; 14.AZ.244.223; 14.AZ.244.240; 14.AZ.244.244; 14.AZ.244.243; 14.AZ.244.247; 14.AZ.247.157; 14.AZ.247.158; 14.AZ.247.196; 14.AZ.247.223; 14.AZ.247.240; 14.AZ.247.244; 14.AZ.247.243; 14.AZ.247.247; |
| Prodrugs of 14.BF |
| 14.BF.4.157; 14.BF.4.158; 14.BF.4.196; 14.BF.4.223; 14.BF.4.240; 14.BF.4.244; 14.BF.4.243; 14.BF.4.247; 14.BF.5.157; 14.BF.5.158; |

TABLE 100-continued

| |
|---|
| 14.BF.5.196; 14.BF.5.223; 14.BF.5.240; 14.BF.5.244; 14.BF.5.243; 14.BF.5.247; 14.BF.7.157; 14.BF.7.158; 14.BF.7.196; 14.BF.7.223; 14.BF.7.240; 14.BF.7.244; 14.BF.7.243; 14.BF.7.247; 14.BF.15.157; 14.BF.15.158; 14.BF.15.196; 14.BF.15.223; 14.BF.15.240; 14.BF.15.244; 14.BF.15.243; 14.BF.15.247; 14.BF.16.157; 14.BF.16.158; 14.BF.16.196; 14.BF.16.223; 14.BF.16.240; 14.BF.16.244; 14.BF.16.243; 14.BF.16.247; 14.BF.18.157; 14.BF.18.158; 14.BF.18.196; 14.BF.18.223; 14.BF.18.240; 14.BF.18.244; 14.BF.18.243; 14.BF.18.247; 14.BF.26.157; 14.BF.26.158; 14.BF.26.196; 14.BF.26.223; 14.BF.26.240; 14.BF.26.244; 14.BF.26.243; 14.BF.26.247; 14.BF.27.157; 14.BF.27.158; 14.BF.27.196; 14.BF.27.223; 14.BF.27.240; 14.BF.27.244; 14.BF.27.243; 14.BF.27.247; 14.BF.29.157; 14.BF.29.158; 14.BF.29.196; 14.BF.29.223; 14.BF.29.240; 14.BF.29.244; 14.BF.29.243; 14.BF.29.247; 14.BF.54.157; 14.BF.54.158; 14.BF.54.196; 14.BF.54.223; 14.BF.54.240; 14.BF.54.244; 14.BF.54.243; 14.BF.54.247; 14.BF.55.157; 14.BF.55.158; 14.BF.55.196; 14.BF.55.223; 14.BF.55.240; 14.BF.55.244; 14.BF.55.243; 14.BF.55.247; 14.BF.56.157; 14.BF.56.158; 14.BF.56.196; 14.BF.56.223; 14.BF.56.240; 14.BF.56.244; 14.BF.56.243; 14.BF.56.247; 14.BF.157.157; 14.BF.157.158; 14.BF.157.196; 14.BF.157.223; 14.BF.157.240; 14.BF.157.244; 14.BF.157.243; 14.BF.157.247; 14.BF.196.157; 14.BF.196.158; 14.BF.196.196; 14.BF.196.223; 14.BF.196.240; 14.BF.196.244; 14.BF.196.243; 14.BF.196.247; 14.BF.223.157; 14.BF.223.158; 14.BF.223.196; 14.BF.223.223; 14.BF.223.240; 14.BF.223.244; 14.BF.223.243; 14.BF.223.247; 14.BF.240.157; 14.BF.240.158; 14.BF.240.196; 14.BF.240.223; 14.BF.240.240; 14.BF.240.244; 14.BF.240.243; 14.BF.240.247; 14.BF.244.157; 14.BF.244.158; 14.BF.244.196; 14.BF.244.223; 14.BF.244.240; 14.BF.244.244; 14.BF.244.243; 14.BF.244.247; 14.BF.247.157; 14.BF.247.158; 14.BF.247.196; 14.BF.247.223; 14.BF.247.240; 14.BF.247.244; 14.BF.247.243; 14.BF.247.247; |
| Prodrugs of 14.CI |
| 14.CI.4.157; 14.CI.4.158; 14.CI.4.196; 14.CI.4.223; 14.CI.4.240; 14.CI.4.244; 14.CI.4.243; 14.CI.4.247; 14.CI.5.157; 14.CI.5.158; 14.CI.5.196; 14.CI.5.223; 14.CI.5.240; 14.CI.5.244; 14.CI.5.243; 14.CI.5.247; 14.CI.7.157; 14.CI.7.158; 14.CI.7.196; 14.CI.7.223; 14.CI.7.240; 14.CI.7.244; 14.CI.7.243; 14.CI.7.247; 14.CI.15.157; 14.CI.15.158; 14.CI.15.196; 14.CI.15.223; 14.CI.15.240; 14.CI.15.244; 14.CI.15.243; 14.CI.15.247; 14.CI.16.157; 14.CI.16.158; 14.CI.16.196; 14.CI.16.223; 14.CI.16.240; 14.CI.16.244; 14.CI.16.243; 14.CI.16.247; 14.CI.18.157; 14.CI.18.158; 14.CI.18.196; 14.CI.18.223; 14.CI.18.240; 14.CI.18.244; 14.CI.18.243; 14.CI.18.247; 14.CI.26.157; 14.CI.26.158; 14.CI.26.196; 14.CI.26.223; 14.CI.26.240; 14.CI.26.244; 14.CI.26.243; 14.CI.26.247; 14.CI.27.157; 14.CI.27.158; 14.CI.27.196; 14.CI.27.223; 14.CI.27.240; 14.CI.27.244; 14.CI.27.243; 14.CI.27.247; 14.CI.29.157; 14.CI.29.158; 14.CI.29.196; 14.CI.29.223; 14.CI.29.240; 14.CI.29.244; 14.CI.29.243; 14.CI.29.247; 14.CI.54.157; 14.CI.54.158; 14.CI.54.196; 14.CI.54.223; 14.CI.54.240; 14.CI.54.244; 14.CI.54.243; 14.CI.54.247; 14.CI.55.157; 14.CI.55.158; 14.CI.55.196; 14.CI.55.223; 14.CI.55.240; 14.CI.55.244; 14.CI.55.243; 14.CI.55.247; 14.CI.56.157; 14.CI.56.158; 14.CI.56.196; 14.CI.56.223; 14.CI.56.240; 14.CI.56.244; 14.CI.56.243; 14.CI.56.247; 14.CI.157.157; 14.CI.157.158; 14.CI.157.196; 14.CI.157.223; 14.CI.157.240; 14.CI.157.244; 14.CI.157.243; 14.CI.157.247; 14.CI.196.157; 14.CI.196.158; 14.CI.196.196; 14.CI.196.223; 14.CI.196.240; 14.CI.196.244; 14.CI.196.243; 14.CI.196.247; 14.CI.223.157; 14.CI.223.158; 14.CI.223.196; 14.CI.223.223; 14.CI.223.240; 14.CI.223.244; 14.CI.223.243; 14.CI.223.247; 14.CI.240.157; 14.CI.240.158; 14.CI.240.196; 14.CI.240.223; 14.CI.240.240; 14.CI.240.244; 14.CI.240.243; 14.CI.240.247; 14.CI.244.157; 14.CI.244.158; 14.CI.244.196; 14.CI.244.223; 14.CI.244.240; 14.CI.244.244; 14.CI.244.243; 14.CI.244.247; 14.CI.247.157; 14.CI.247.158; 14.CI.247.196; 14.CI.247.223; 14.CI.247.240; 14.CI.247.244; 14.CI.247.243; 14.CI.247.247; |
| Prodrugs of 14.CO |
| 14.CO.4.157; 14.CO.4.158; 14.CO.4.196; 14.CO.4.223; 14.CO.4.240; 14.CO.4.244; 14.CO.4.243; 14.CO.4.247; 14.CO.5.157; 14.CO.5.158; 14.CO.5.196; 14.CO.5.223; 14.CO.5.240; 14.CO.5.244; 14.CO.5.243; 14.CO.5.247; 14.CO.7.157; 14.CO.7.158; 14.CO.7.196; 14.CO.7.223; 14.CO.7.240; 14.CO.7.244; 14.CO.7.243; 14.CO.7.247; 14.CO.15.157; 14.CO.15.158; 14.CO.15.196; 14.CO.15.223; 14.CO.15.240; 14.CO.15.244; 14.CO.15.243; 14.CO.15.247; 14.CO.16.157; 14.CO.16.158; 14.CO.16.196; 14.CO.16.223; 14.CO.16.240; 14.CO.16.244; 14.CO.16.243; 14.CO.16.247; 14.CO.18.157; 14.CO.18.158; 14.CO.18.196; 14.CO.18.223; 14.CO.18.240; 14.CO.18.244; 14.CO.18.243; 14.CO.18.247; 14.CO.26.157; 14.CO.26.158; 14.CO.26.196; 14.CO.26.223; 14.CO.26.240; 14.CO.26.244; 14.CO.26.243; 14.CO.26.247; 14.CO.27.157; 14.CO.27.158; 14.CO.27.196; 14.CO.27.223; 14.CO.27.240; 14.CO.27.244; 14.CO.27.243; 14.CO.27.247; 14.CO.29.157; 14.CO.29.158; 14.CO.29.196; 14.CO.29.223; 14.CO.29.240; 14.CO.29.244; 14.CO.29.243; 14.CO.29.247; 14.CO.54.157; 14.CO.54.158; 14.CO.54.196; 14.CO.54.223; 14.CO.54.240; 14.CO.54.244; 14.CO.54.243; 14.CO.54.247; 14.CO.55.157; 14.CO.55.158; 14.CO.55.196; 14.CO.55.223; 14.CO.55.240; 14.CO.55.244; 14.CO.55.243; 14.CO.55.247; 14.CO.56.157; 14.CO.56.158; 14.CO.56.196; 14.CO.56.223; 14.CO.56.240; 14.CO.56.244; 14.CO.56.243; 14.CO.56.247; 14.CO.157.157; 14.CO.157.158; 14.CO.157.196; |

TABLE 100-continued

| |
|---|
| 14.CO.157.223; 14.CO.157.240; 14.CO.157.244; 14.CO.157.243; |
| 14.CO.157.247; 14.CO.196.157; 14.CO.196.158; 14.CO.196.196; |
| 14.CO.196.223; 14.CO.196.240; 14.CO.196.244; 14.CO.196.243; |
| 14.CO.196.247; 14.CO.223.157; 14.CO.223.158; 14.CO.223.196; |
| 14.CO.223.223; 14.CO.223.240; 14.CO.223.244; 14.CO.223.243; |
| 14.CO.223.247; 14.CO.240.157; 14.CO.240.158; 14.CO.240.196; |
| 14.CO.240.223; 14.CO.240.240; 14.CO.240.244; 14.CO.240.243; |
| 14.CO.240.247; 14.CO.244.157; 14.CO.244.158; 14.CO.244.196; |
| 14.CO.244.223; 14.CO.244.240; 14.CO.244.244; 14.CO.244.243; |
| 14.CO.244.247; 14.CO.4.157; 14.CO.4.158; 14.CO.4.196; 14.CO.4.223; |
| 14.CO.4.240; 14.CO.4.244; 14.CO.4.243; 14.CO.4.247. |

All literature and patent citations above are hereby expressly incorporated by reference at the locations of their citation. Specifically cited sections or pages of the above cited works are incorporated by reference with specificity. The invention has been described in detail sufficient to allow one of ordinary skill in the art to make and use the subject matter of the following Claims. It is apparent that certain modifications of the methods and compositions of the following Claims can be made within the scope and spirit of the invention.

In the claims hereinbelow, the subscript and superscripts of a given variable are distinct. For example, $R_1$ is distinct from $R^1$.

What is claimed is:

1. A compound of formula:

556-E.6

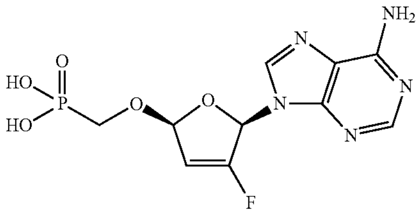

or a pharmaceutically acceptable salt thereof.

2. A compound of formula:

556-E.6

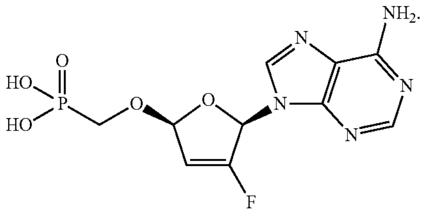

3. A pharmaceutically acceptable salt of a compound of formula:

556-E.6

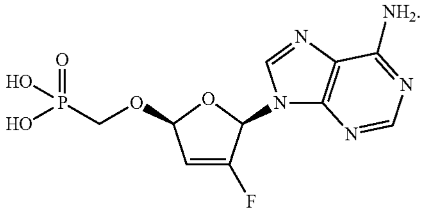

4. A pharmaceutical composition comprising a pharmaceutically acceptable excipient and a compound of formula:

556-E.6

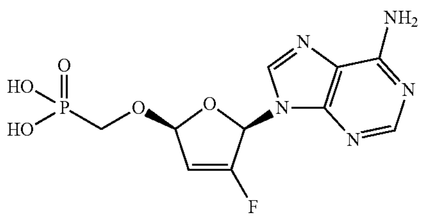

or a pharmaceutically acceptable salt thereof.

5. A pharmaceutical composition comprising a pharmaceutically acceptable excipient and a compound of formula:

556-E.6

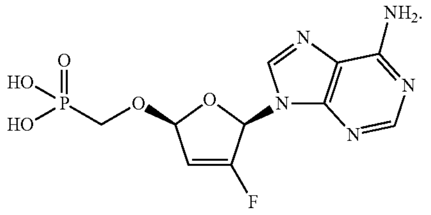

6. A pharmaceutical composition comprising a pharmaceutically acceptable excipient and a pharmaceutically acceptable salt of a compound of formula:

556-E.6

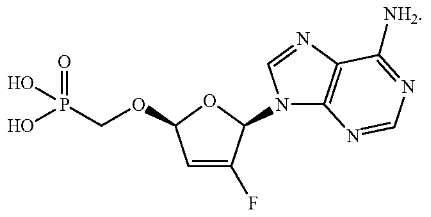

7. A method for promoting an anti-viral effect in vitro or in vivo, comprising contacting a sample in need of such treatment with a compound of formula:

556-E.6

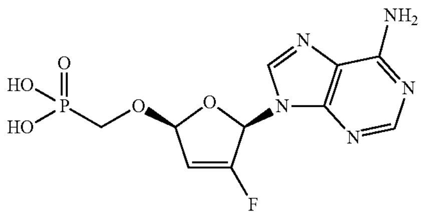

or a pharmaceutically acceptable salt thereof.

8. A method of inhibiting a viral infection in an animal, comprising administering an effective amount of a compound of formula:
556-E.6
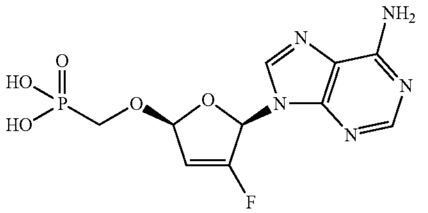
or a pharmaceutically acceptable salt thereof, to the animal.
9. The method of claim 8, wherein the viral infection is an HIV infection.
* * * * *